United States Patent
Taylor et al.

(10) Patent No.: US 11,591,336 B2
(45) Date of Patent: Feb. 28, 2023

(54) SUBSTITUTED PYRAZOLO[3,4-B]PYRAZINES AS SHP2 PHOSPHATASE INHIBITORS

(71) Applicants: Relay Therapeutics, Inc., Cambridge, MA (US); D. E. Shaw Research, LLC, New York, NY (US)

(72) Inventors: Alexander M. Taylor, Cambridge, MA (US); André Lescarbeau, Somerville, MA (US); Elizabeth H. Kelley, Cambridge, MA (US); Kelley C. Shortsleeves, Maynard, MA (US); Lucian V. DiPietro, Gloucester, MA (US); W. Patrick Walters, Westborough, MA (US); Mark Andrew Murcko, Holliston, MA (US); Levi Charles Thomas Pierce, Somerville, MA (US); Yong Tang, West Roxbury, MA (US); Fabrizio Giordanetto, New York, NY (US); Jack Benjamin Greisman, New York, NY (US); Paul Maragakis, New York, NY (US); Sathesh Bhat, Jersey City, NJ (US); Markus Kristofer Dahlgren, Shelton, CT (US); Eric Therrien, Bronx, NY (US)

(73) Assignees: D. E. Shaw Research, LLC, New York, NY (US); Relay Therapeutics, Inc., Cambridge, MA (US)

( * ) Notice: Subject to any disclaimer, the term of this patent is extended or adjusted under 35 U.S.C. 154(b) by 0 days.

(21) Appl. No.: 16/616,361

(22) PCT Filed: May 25, 2018

(86) PCT No.: PCT/US2018/034614
§ 371 (c)(1),
(2) Date: Nov. 22, 2019

(87) PCT Pub. No.: WO2018/218133
PCT Pub. Date: Nov. 29, 2018

(65) Prior Publication Data
US 2020/0172546 A1 Jun. 4, 2020

Related U.S. Application Data

(60) Provisional application No. 62/511,583, filed on May 26, 2017, provisional application No. 62/646,091, filed on Mar. 21, 2018, provisional application No. 62/661,882, filed on Apr. 24, 2018.

(51) Int. Cl.
*A61K 31/4985* (2006.01)
*C07D 487/04* (2006.01)
*C07D 519/00* (2006.01)

(52) U.S. Cl.
CPC ......... *C07D 487/04* (2013.01); *C07D 519/00* (2013.01)

(58) Field of Classification Search
CPC .................. A61K 31/4985; C07D 487/04
USPC ........................... 514/249; 544/350
See application file for complete search history.

(56) References Cited

U.S. PATENT DOCUMENTS

| | | |
|---|---|---|
| 10,280,171 B2 | 5/2019 | Jones et al. |
| 10,934,302 B1 | 3/2021 | Taylor et al. |
| 2011/0130396 A1 | 6/2011 | Hoelzemann et al. |
| 2017/0001975 A1 | 1/2017 | Chen et al. |
| 2017/0015680 A1 | 1/2017 | Chen et al. |
| 2017/0204080 A1 | 7/2017 | Chen et al. |
| 2017/0342078 A1 | 11/2017 | Jones et al. |
| 2018/0186770 A1 | 7/2018 | Chen et al. |
| 2018/0251471 A1 | 9/2018 | Chen et al. |
| 2019/0077792 A1 | 3/2019 | Volkmann et al. |
| 2019/0127378 A1 | 5/2019 | Ma et al. |
| 2019/0185475 A1 | 6/2019 | Bagdanoff et al. |

(Continued)

FOREIGN PATENT DOCUMENTS

| | | |
|---|---|---|
| CN | 107286150 A | 10/2017 |
| CN | 110143949 A | 8/2019 |

(Continued)

OTHER PUBLICATIONS

Chloe, Copin et al. "Snar Versus Buchwald-Hartwig Amination/Amidation in the Imidazo[2,1-b] [1,3,4]thiadiazole Series," European Journal of Organic Chemistry, vol. 2015, No. 31, Sep. 29, 2015, pp. 6932-6942.

(Continued)

*Primary Examiner* — Douglas M Willis
(74) *Attorney, Agent, or Firm* — Alston & Bird LLP

(57) ABSTRACT

The present disclosure relates to compounds of formula (I) and pharmaceutical compositions thereof and methods for inhibiting the activity of SHP2 phosphatase with the compounds and compositions of the disclosure. The present disclosure further relates to, but is not limited to, methods for treating disorders associated with SHP2 deregulation with the compounds and compositions of the disclosure.

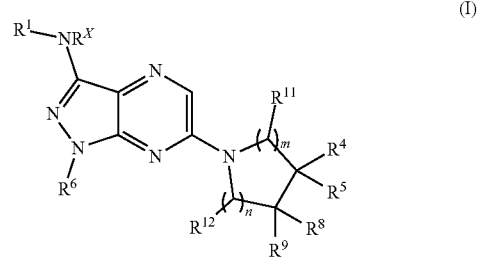

(I)

54 Claims, No Drawings

(56) References Cited

U.S. PATENT DOCUMENTS

| | | |
|---|---|---|
| 2019/0210977 A1 | 7/2019 | Jogalekar et al. |
| 2019/0270746 A1 | 9/2019 | Jones et al. |
| 2019/0290649 A1 | 9/2019 | Xie et al. |
| 2019/0307745 A1 | 10/2019 | Albrecht et al. |
| 2019/0389867 A1 | 12/2019 | Jones et al. |
| 2020/0002330 A1 | 1/2020 | Chen et al. |
| 2020/0017511 A1 | 1/2020 | Blank et al. |
| 2020/0017517 A1 | 1/2020 | Gill et al. |
| 2020/0048249 A1 | 2/2020 | Jones et al. |
| 2020/0062760 A1 | 2/2020 | Giordanetto et al. |
| 2020/0108071 A1 | 4/2020 | Chin et al. |
| 2020/0115389 A1 | 4/2020 | Fu et al. |
| 2020/0253969 A1 | 8/2020 | Taylor et al. |
| 2020/0392161 A1 | 12/2020 | Walters et al. |
| 2021/0069188 A1 | 3/2021 | Taylor et al. |
| 2021/0085677 A1 | 3/2021 | Taylor et al. |

FOREIGN PATENT DOCUMENTS

| | | |
|---|---|---|
| CN | 111153899 A | 5/2020 |
| TW | 201925186 A | 7/2019 |
| WO | WO-2004/111060 A1 | 12/2004 |
| WO | WO-2020076723 A1 | 1/2007 |
| WO | WO-2010/011666 A2 | 1/2010 |
| WO | WO-2010/097798 A1 | 9/2010 |
| WO | WO-2010/121212 A2 | 10/2010 |
| WO | WO-2011/130396 A1 | 10/2011 |
| WO | WO 2015/107493 A1 | 7/2015 |
| WO | WO-2015/107494 A1 | 7/2015 |
| WO | WO-2015/107495 A1 | 7/2015 |
| WO | WO-2016/203404 A1 | 12/2016 |
| WO | WO-2016/203406 A1 | 12/2016 |
| WO | WO-2017156397 A1 | 9/2017 |
| WO | WO-2017/210134 A1 | 12/2017 |
| WO | WO-2017/211303 A1 | 12/2017 |
| WO | WO-2018/013597 A1 | 1/2018 |
| WO | WO-2018/057884 A1 | 3/2018 |
| WO | WO-2018/081091 A1 | 5/2018 |
| WO | WO-2018/172984 A1 | 9/2018 |
| WO | WO-2018/218133 A1 | 11/2018 |
| WO | WO-2019051084 A1 | 3/2019 |
| WO | WO-2019/067843 A1 | 4/2019 |
| WO | WO-2019075265 A1 | 4/2019 |
| WO | WO-2019118909 A1 | 6/2019 |
| WO | WO-2019/165073 A1 | 8/2019 |
| WO | WO-2019158019 A1 | 8/2019 |
| WO | WO-2019/183364 A1 | 9/2019 |
| WO | WO-2019/183367 A1 | 9/2019 |
| WO | WO-2019167000 A1 | 9/2019 |
| WO | WO-2019199792 A1 | 10/2019 |
| WO | WO-2019233810 A1 | 12/2019 |
| WO | WO-2020022323 A1 | 1/2020 |
| WO | WO-2020063760 A1 | 4/2020 |
| WO | WO-2020065452 A1 | 4/2020 |
| WO | WO-2020065453 A1 | 4/2020 |
| WO | WO-2020073945 A1 | 4/2020 |
| WO | WO-2020073949 A1 | 4/2020 |
| WO | WO-2020081848 A1 | 4/2020 |
| WO | WO-2020094018 A1 | 5/2020 |
| WO | WO-2020094104 A1 | 5/2020 |

OTHER PUBLICATIONS

Larochelle, Jonathan et al. "Identification of An Allosteric Benzothiazolopyrimidone Inhibitor of the Oncogenic Protein Tyrosine Phosphatase SHP2," Bioorganic & Medicinal Chemistry, vol. 25, No. 24, Oct. 20, 2017, pp. 6479-6485.

Temple, Kayla et al. "Identification of the Minimum PAR4 Inhibitor Pharmacophore and Optimization of a Series of 2-Methoxy-6-Arylimidazo[2,1-b][1,3,4]Thiadiazoles," Bioorganic & Medicinal Chemistry Letters, Pergamon, Amsterdam, NL, vol. 26, No. 22, 11 Oct. 11, 2016, pp. 5481-5486.

Yokoi, Taiyo et al. "Quantitative Structure-Activity Relationship of Substituted Imidazothiadiazoles for Their Binding Against the Ecdysone Receptor of Sf-9 Cells," Bioorganic & Medicinal Chemistry Letters, vol. 27, No. 23, Oct. 13, 2017, pp. 5305-5309.

Saifidin, Safarov et al. "Preparation of 5-Bromo-6-phenylimidazo(2,1-b)(1,3,4)thiadiazol-2-ylamines," Journal of Heterocyclic Chemistry, Wiley-Blackwell Publishing, Inc, US, vol. 45, No. 1, Jan. 1, 2008, pp. 299-302.

Krasavin M et al. "Tert-Butyl Isocyanide Revisited as a Convertible Reagent in the Groebke-Blackburn Reaction," Tetrahedron Letters, Elsevier, Amsterdam, NL, vol. 49, No. 51, Dec. 15, 2008, pp. 7318-7321.

Shen, Jiayi et al. "3-Aminopyrazolopyrazine Derivatives as Spleen Tyrosine Kinase Inhibitors," Hemical Biology & Drug Design, vol. 88, No. 5, 2016, pp. 690-698.

Jorge, Fortanet et al. "Allosteric Inhibition of SHP2: Identification of a Potent, Selective, and Orally Efficacious Phosphatase Inhibitor," J. Med. Chem. 2016, 59, 17, pp. 7773-7782.

Bollu et al. Clin Cancer Res. May 1, 2017; 23(9): 2136-2142. (Year: 2017).

Lazo et al. SLAS Discovery 2017, vol. 22(9) 1071-1083 (Year: 2017).

Jones et al. U.S. Appl. No. 62/343,455, filed May 31, 2016. (Year: 2016).

International Search Report and Written Opinion for International Patent Application PCT/US2019/023389 dated May 10, 2019 (12 pages).

U.S. Appl. No. 16/651,733, dated Mar. 27, 2020.
U.S. Appl. No. 16/344,061, dated Mar. 22, 2019.
U.S. Appl. No. 16/971,435, dated Aug. 20, 2020.
U.S. Appl. No. 16/982,395, dated Sep. 18, 2020.
U.S. Appl. No. 16/982,401, dated Sep. 18, 2020.
U.S. Appl. No. 16/886,105, dated May 28, 2020.
U.S. Appl. No. 17/029,376, dated Sep. 23, 2020.

Hellmuth et al., "Specific inhibitors of the protein tyrosine phosphatase Shp2 identified by high-throughput docking," PNAS, 105(20), 7275-7280, (2008).

Horig et al., "From bench to clinic and back: Perspective on the 1st IQPC Translational Research Conference" Journal of Translational Medicine, 2, 44, (Dec. 2004).

Schafer et al., "Failure is an option: learning from unsuccessful proof-of-concept trials," Drug Discovery Today, 13, 913-916, (Nov. 2018).

U.S. Appl. No. 16/335,933, Non-Final Office Action dated Jan. 8, 2020.

U.S. Appl. No. 16/355,061, Non-Final Office Action dated Feb. 19, 2021.

U.S. Appl. No. 16/355,061, Requirement for Restriction/Eiection dated Jul. 31, 2020.

U.S. Appl. No. 16/886,105, Notice of Allowance dated Sep. 9, 2020.
U.S. Appl. No. 16/886,105, Notice of Allowance dated Nov. 4, 2020.

U.S. Appl. No. 16/335,933, Final Office Action dated Aug. 26, 2020.

WIPO Application No. PCT/US2017/052950, PCT International Preliminary Report on Patentability dated Mar. 26, 2019.

WIPO Application No. PCT/US2017/052950, PCT International Search Report and Written Opinion of the International Searching Authority dated Mar. 29, 2018.

WIPO Application No. PCT/US2017/058048, PCT International Preliminary Report on Patentability dated Apr. 30, 2019.

WIPO Application No. PCT/US2017/058048, PCT International Search Report and Written Opinion of the International Searching Authority dated May 3, 2018.

WIPO Application No. PCT/US2018/034614, PCT International Preliminary Report on Patentability dated Nov. 26, 2019.

WIPO Application No. PCT/US2018/034614, PCT International Search Report and Written Opinion of the International Searching Authority dated Nov. 29, 2018.

WIPO Application No. PCT/US2018/053322, PCT International Preliminary Report on Patentability dated Mar. 31, 2020.

WIPO Application No. PCT/US2018/053322, PCT International Search Report and Written Opinion of the International Searching Authority dated Apr. 4, 2019.

(56) References Cited

OTHER PUBLICATIONS

WIPO Application No. PCT/US2019/023389, PCT International Preliminary Report on Patentability dated Sep. 22, 2020.
WIPO Application No. PCT/US2020/052118 PCT International Search Report and Written Opinion of the International Searching Authority dated Dec. 14, 2020.
Aceto, N. et al., "Tyrosine phosphatase SHP2 promotes breast cancer progression and maintains tumor-initiating cells via activation of key transcription factors and a positive feedback signaling loop," Nature Medicine, 18(4):529-538, (2012).
Gould, P.L., "Salt selection for basic drugs," Int J. Pharmaceutics, 33:201-217, (1986).
Grossman, K.S. et al., "The tyrosine phosphatase Shp2 in development and cancer," Adv. Cancer Res., 106:53-89, (2010).
Bentires-Alj, M. et al., "Activating Mutations of the Noonan Syndrome-Associated SHP2/PTPN11 Gene in Human Solid Tumors and Adult Acute Myelogenous Leukemia," Cancer Res., 64:8816-8820, (2004).
Berge, et al., "Pharmaceutical Salts," J. Pharm. Sci., 66(1):1, (1977).
Cai, P. et al., "Expression and clinical significance of tyrosine phosphatase SHP-2 in colon cancer," Biomedicine & Pharmacotherapy, 68:285-290, (2014).
Chen, Y.-N.P. et al., "Allosteric inhibition of SHP2 phosphatase inhibits cancers driven by receptor tyrosine kinases," Nature, 535:158-152, (2016).
Furcht, C.M. et al., "Diminished functional role and altered localization of SHP2 in non-small cell lung cancer cells with EGFR-activating mutations," Oncogene, 32:2346-2355, (2013).
Schneeberger, V.E. et al., "Inhibition of Shp2 suppresses mutant EGFR-induced lung tumors in transgenic mouse model of lung adenocarcinoma," Oncotarget, 6:6191-6202, (2015).
Wang, J. et al., "Inhibition of SHP2 ameliorates the pathogenesis of systemic lupus erythematosus," The Journal of Clinical Invest. 126:2077-2092, (2016).

SUBSTITUTED PYRAZOLO[3,4-B]PYRAZINES AS SHP2 PHOSPHATASE INHIBITORS

CROSS REFERENCE TO RELATED APPLICATIONS

This application claims the benefit of, and priority to, U.S. provisional application Ser. No. 62/511,583, filed May 26, 2017; 62/646,091, filed Mar. 21, 2018; and 62/661,882, filed Apr. 24, 2018; the contents of each of which are hereby incorporated by reference in their entirety.

BACKGROUND

Src homology region 2 (SH2)-containing protein tyrosine phosphatase 2 (SHP2) is a protein tyrosine phosphatase encoded by the PTPN11 gene. SHP2 contains two Src homology 2 (SH2) $NH_2$-terminal domains and a C-terminal protein-tyrosine phosphatase domain. It is ubiquitously expressed in various tissues and cell types. SHP2 plays an important role in diverse signaling pathways to regulate cellular biological processes and is involved in the signaling pathways of a variety of growth factors and cytokines. Within a single signaling pathway, SHP2 can play both positive (signal enhancing) and negative (signal diminishing) roles in intracellular signaling processes. SHP2 is believed to function by dephosphorylating its associated signaling molecules, thereby attenuating the local signaling flow. However, the main effect of SHP2 action in most signaling pathways (e.g., growth factor, cytokine, and extracellular matrix receptors) is to enhance signal transduction. For example, SHP2 is a positive regulator of the ERK/MAPK signaling pathway, playing a key role in regulating cellular proliferation and survival. (For a review of SHP2 phosphatase, see, e.g, K. S. Grossman et al., *Adv. Cancer Res.* 2010, 106, 53-89; and references cited therein.)

In the basal state, SHP2 is normally auto-inhibited due to intramolecular interactions between its N-terminal SH2 (N-SH2) domain and its catalytic (PTP) domain, which blocks access to the catalytic site. Activating proteins that interact with the SH2 domains induce a conformational change that reverses this inhibition and allows substrate access to the catalytic site. Mutations in the PTPN11 gene that affect the N-SH2 or PTP domain residues involved in basal inhibition of SHP2 result in more readily activatable forms of SHP2 protein, which can lead to unregulated or increased SHP2 activity. Such activated mutants of SHP2 have been associated with developmental disorders such as Noonan syndrome, where nearly all mutated forms of SHP2 demonstrate increased PTP activity. Thus, there is a need for SHP2 phosphatase inhibitor compounds and methods for treating cancer and other disorders with these compounds.

SUMMARY

In an embodiment, the present disclosure provides a compound of Formula I, or a pharmaceutically acceptable salt or stereoisomer thereof, wherein Formula I is represented by:

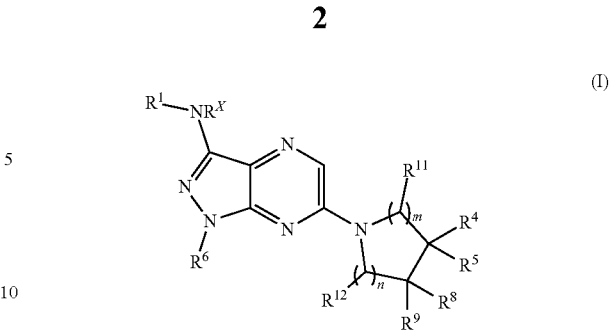

wherein:

$R^X$ together with $R^1$ and the nitrogen to which they are attached form a nitrogen-containing monocyclic, bicyclic or tricyclic ring system selected from the group consisting of a 8-14 membered bicyclic heteroaryl, a 11-15 membered tricyclic heteroaryl, a 5-7 membered monocyclic heteroaryl, and a 4-7 membered heterocyclyl, wherein the nitrogen-containing monocyclic, bicyclic or tricyclic ring system may optionally be substituted with one, two or more substituents each independently selected from the group consisting of $R^{10}$, —$OR^{10}$, —$S(O)_wR^{10}$ (wherein w is 0, 1 or 2), —$C_{1-6}$alkyl-$S(O)_w$—$C_{1-3}$alkyl, —$N(R^{10})_2$, —$N(CO)R^{10}$, —N—S$(O)_w$—$R^{10}$ (where w is 0, 1 or 2), —$OS(O)_w$—$R^{10}$ (wherein w is 0, 1, or 2), —$S(O)_w$—$N(R^{10})_2$ (wherein w is 0, 1 or 2), —$S(O)(NH)R^{10}$, —N(H)—$SO_2$—$C_{1-3}$alkyl, —$N(SO_2$—$C_{1-3}$alkyl$)_2$, $P(O)(R^{10})_2$, —$C(O)R^{10}$, —$C(O)OR^{10}$, —$C(O)N(R^{10})_2$, oxo, halogen, hydroxyl, cyano, nitro, —$C(\!=\!N$—$OR^a)$—$C_{1-3}$alkyl, —$C(\!=\!N$—$OR^a)$—H, —$S(O)(NR^a)C_{1-3}$alkyl,

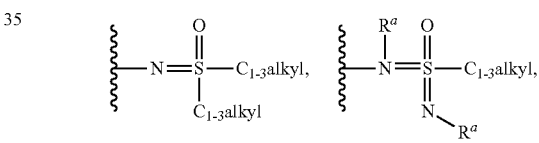

phenyl (optionally substituted with one, two or three halogen, —O-phenyl, $C_{1-3}$alkyl or $C_{1-3}$haloalkyl), $C_{1-3}$alkyl, $C_{2-6}$-alkynyl, $C_{1-3}$haloalkyl, $C_{3-6}$cycloalkyl, heterocyclyl (optionally substituted with one, two or three halogen, oxo, $C_{1-3}$alkyl or $C_{1-3}$haloalkyl), and heteroaryl (optionally substituted with one, two or three halogen, —$C(O)N(R^{10})_2$, $C_{1-3}$alkyl, $C_{1-3}$alkyl-O—$C_{1-3}$alkyl, $C_{1-3}$alkyl-OH, or $C_{1-3}$haloalkyl);

$R^{10}$ is independently selected from the group consisting of hydrogen, $C_{1-6}$alkyl, $C_{2-6}$ alkenyl, $C_{2-6}$alkynyl, $C_{3-6}$cycloalkyl, $C_{5-6}$cycloalkenyl, $C_{2-6}$heteroalkyl, heterocycloalkyl, aryl, heteroaryl, and $P(O)(R^{20})_2$; wherein $C_{1-6}$alkyl, $C_{2-6}$alkenyl, $C_{2-6}$-alkynyl, $C_{3-6}$cycloalkyl, $C_{5-6}$cycloalkenyl, $C_{2-6}$heteroalkyl, heterocycloalkyl, aryl, and heteroaryl may optionally be substituted by one, two, three or more substituents each independently selected from the group consisting of halogen, hydroxyl, cyano, —$NR^aC(O)$—$R^{20}$, —$C(O)$—$R^{20}$, —$C(NR^a)R^b$, —$NR^aR^b$, $C_{1-6}$alkyl, $C_{1-6}$haloalkyl and $C_{1-6}$alkoxy;

$R^{20}$ is selected from the group consisting of hydrogen, hydroxyl, halogen, —$NR^aR^b$, $C_{1-6}$alkyl and $C_{1-6}$alkoxy;

$R^4$ and $R^5$ are each independently, selected from the group consisting of H, —OH, —$(C_1$-$C_6)$alkyl, —$O(C_1$-$C_6)$alkyl, —$(C_1$-$C_6)$alkyl-O—$R^6$, —$C(O)N(R^6)_2$, —$N(R^6)_2$, halogen, —$(C_1$-$C_6)$alkyl-$N(R^6)_2$, or cyano, wherein said —$(C_1$-$C_6)$alkyl, —$O(C_1$-$C_6)$alkyl, —$(C_1$-$C_6)$alkyl-O—$R^6$, or —$(C_1$-

$C_6$)alkyl-N($R^6$)$_2$ is optionally substituted with one or more substituents selected from the group consisting of —OH, —NH$_2$, oxo, and halogen, or $R^4$ and $R^5$, taken together with the atoms to which they are attached, form a 3-7 membered carbocyclic or heterocyclic saturated or partially unsaturated ring, which ring is optionally substituted with one or more substituents selected from the group consisting of —OH, —($C_1$-$C_6$)alkyl, —O($C_1$-$C_6$)alkyl, —N($R^6$)$_2$, halogen, oxo, or cyano;

or $R^4$ and $R^8$, taken together with the atoms to which they are attached, form a 4-7 membered carbocyclic or heterocyclic ring, which ring is optionally substituted with —OH, —($C_1$-$C_6$)alkyl, —O($C_1$-$C_6$)alkyl, —N($R^6$)$_2$, halogen, oxo, or cyano;

or $R^4$ is absent, and $R^4$ and $R^8$, taken together with the atoms to which they are attached, form a 3-membered carbocyclic or heterocyclic ring, which ring is optionally substituted with —OH, —($C_1$-$C_6$)alkyl, —O($C_1$-$C_6$)alkyl, —N($R^6$)$_2$, halogen, oxo, or cyano;

$R^6$ is independently for each occurrence selected from the group consisting of H, —($C_1$-$C_6$)alkyl, —C(O)O$C_{1-4}$alkyl, and phenyl;

$R^{11}$ and $R^{12}$ are, each independently selected from the group consisting of, H, —OH, —($C_1$-$C_6$)alkyl, —O($C_1$-$C_6$)alkyl, —($C_1$-$C_6$)alkyl-O—$R^6$, aryl, arylalkylene, heteroaryl, heteroarylalkylene, —C(O)N($R^6$)$_2$, —N($R^6$)$_2$, halogen, —($C_1$-$C_6$)alkyl-N($R^6$)$_2$, —CO$_2$H, or cyano, wherein said —($C_1$-$C_6$)alkyl, —O($C_1$-$C_6$)alkyl, —($C_1$-$C_6$)alkyl-O—$R^6$, aryl, arylalkylene, heteroaryl, heteroarylalkylene, or —($C_1$-$C_6$)alkyl-N($R^6$)$_2$ is optionally substituted with one or more substituents selected from the group consisting of —OH, —N(H)$_2$, and halogen;

or $R^{11}$ and $R^{12}$, taken together with the atoms to which they are attached, form a 5-7 membered heterocyclic ring;

or $R^4$ and $R^{12}$, taken together with the atoms to which they are attached, form a 5-7 membered carbocyclic or heterocyclic ring;

or $R^8$ and $R^{11}$, taken together with the atoms to which they are attached, form a 5-7 membered carbocyclic or heterocyclic ring;

$R^8$ and $R^9$ are each independently selected from the group consisting of H, —($C_1$-$C_6$)alkyl, —($C_1$-$C_6$)alkyl-N($R^6$)$_2$, —O$R^6$, —($C_1$-$C_6$)alkyl-O—$R^6$, —C(O)NH$_2$, —N($R^6$)$_2$, halogen, or cyano;

$R^a$ and $R^b$ are independently selected, for each occurrence, from the group consisting of hydrogen and $C_{1-6}$alkyl; wherein $C_{1-6}$alkyl may optionally be substituted by one or more substituents selected from halogen, cyano, oxo and hydroxyl;

or $R^a$ and $R^b$, together with the nitrogen to which they are attached, may form a 4-6 membered monocyclic heterocyclic ring, which may have an additional heteroatom selected from the group consisting of O, S, and N; wherein the 4-6 membered heterocyclic ring may optionally be substituted by one or more substituents selected from the group consisting of halogen, cyano, oxo or hydroxyl;

and each of m and n is, independently, 0, 1, 2, or 3, with m+n being at least 2 and no more than 4.

The disclosure also provides pharmaceutical compositions containing the compounds described herein. Further, the disclosure provides a method of inhibiting SHP2 phosphatase activity in a subject by administering a therapeutically effective amount of a compound or composition described herein, to a subject, e.g., a human, in need. The method may include additionally administering a therapeutically effective amount of an antibody, an antibody-drug conjugate, an immunomodulator, or a histone deacetylase inhibitor.

The disclosure further provides a method of treating a disorder in a subject by administering a therapeutically effective amount of a compound or composition described herein, to a subject in need thereof. Examples of disorders include Noonan syndrome, neutropenia, diabetes, neuroblastoma, melanoma, acute myeloid leukemia, juvenile leukemia, juvenile myelomonocytic leukemia, breast cancer, lung cancer, and colorectal cancer. In addition to the compound or composition described herein, such method may include administration of a therapeutically effective amount of an antibody, an antibody-drug conjugate, an immunomodulator, or a histone deacetylase inhibitor.

The present disclosure is based, in part, on certain discoveries which are described more fully in the Examples section of the present application. For example, the present disclosure is based, in part, on the discovery of compounds disclosed herein, e.g., of Formula (I), Formula (II), Formula (III), Formula (IV), Formula (V), Formula (VI), Formula (VII), Formula (VIII), Formula (IX), Formula (X), Formula (XI), Formula (XII), Formula (XIII), or Formula (XIV) and the SHP2 phosphatase inhibition exhibited by such compounds.

These and other embodiments of the disclosure are further described in the following sections of the application, including the Detailed Description, Examples, and Claims. Still other objects and advantages of the disclosure will become apparent by those of skill in the art from the disclosure herein, which are simply illustrative and not restrictive. Thus, other embodiments will be recognized by the ordinarily skilled artisan without departing from the spirit and scope of the disclosure.

DETAILED DESCRIPTION

Activating SHP2 mutations have been detected in juvenile myelomonocytic leukemia (e.g., Q506P), chronic myelomonocytic leukemia (e.g., Y63C), neuroblastoma (e.g., T507K), melanoma (e.g., R138Q), acute myeloid leukemia (e.g., G503V), breast cancer, lung cancer (e.g., E76V), colorectal cancer (e.g., E76G). (M. Bentires-Alj et al., in Cancer Res. 2004, 64, 8816-8820; and references cited therein. SHP2 phosphatase inhibitors are disclosed, e.g., in WO 2015/107493; WO 2015/107494; WO 2015/107495; and J. G. Fortanet et al., in *J. Med. Chem.* 2016, DOI: 10.1021/acs.jmedchem.6b00680; and references cited therein. The effects of SHP2 phsophatase inhibition are described, e.g., Y.-N. P. Chen et al., in Nature, 2016, doi:10.1038/nature18621; J. Wang et al., in *J. Clin. Invest.* 2016, 126, 2077-2092; and references cited therein.

The compounds and/or compositions of the disclosure, alone or in combination with other treatments, may be effective in treating, reducing, and/or suppressing disorders related to SHP2 phosphatase activity such as, e.g., Noonan syndrome, Leopard Syndrome, diabetes, neuroblastoma, melanoma, juvenile leukemia, juvenile myelomonocytic leukemia (JMML), chronic myelomonocytic leukemia, acute myeloid leukemia, HER2-positive breast cancer, triple-negative breast cancer, ductal carcinoma of the breast, invasive ductal carcinoma of the breast, non-small cell lung cancer (including adenocarcinoma of the lung), colorectal cancer, esophageal cancer, gastric cancer, squamous-cell carcinoma of the head and neck (SCCHN), neutropenia (Kostmann's syndrome), and systemic lupus erythematosus. See, e.g, N. Aceto et al. *Nature Medicine*, 2012, 28, 529-538;

C. M. Furcht et al. *Oncogene*, 2013, 32, 2346-2355; V. E. Schneeberger et al. *Oncotarget*, 2015, 6, 6191-6202; P. Cai et al., Biomedicine & *Pharmacotherapy* 2014, 68, 285-290; and references cited therein.

Abbreviations and Definitions

The term "isomer" as used herein refers to a compound having the identical chemical formula but different structural or optical configurations. The term "stereoisomer" as used herein refers to and includes isomeric molecules that have the same molecular formula but differ in positioning of atoms and/or functional groups in the space. All stereoisomers of the present compounds (e.g., those which may exist due to asymmetric carbons on various substituents), including enantiomeric forms and diastereomeric forms, are contemplated within the scope of this disclosure.

The term "tautomer" as used herein refers to one of two or more structural isomers which exist in equilibrium and which are readily converted from one isomeric form to another. It is understood that tautomers encompass valence tautomers and proton tautomers (also known as prototropic tautomers). Valence tautomers include interconversions by reorganization of some of the bonding electrons. Proton tautomers include interconversions via migration of a proton, such as keto-enol and imine-enamine isomerizations.

The term "isotopic substitution" as used herein refers to the substitution of an atom with its isotope. The term "isotope" as used herein refers to an atom having the same atomic number as that of atoms dominant in nature but having a mass number (neutron number) different from the mass number of the atoms dominant in nature. It is understood that a compound with an isotopic substitution refers to a compound in which at least one atom contained therein is substituted with its isotope. Atoms that can be substituted with its isotope include, but are not limited to, hydrogen, carbon, and oxygen. Examples of the isotope of a hydrogen atom include $^2H$ (also represented as D) and $^3H$. Examples of the isotope of a carbon atom include $^{13}C$ and $^{14}C$. Examples of the isotope of an oxygen atom include $^{18}O$.

The term "alkyl", as used herein, unless otherwise indicated, refers to both branched and straight-chain saturated aliphatic hydrocarbon groups having the specified number of carbon atoms; for example, "$C_1$-$C_{10}$ alkyl" denotes alkyl having 1 to 10 carbon atoms, and straight or branched hydrocarbons of 1-6, 1-4, or 1-3 carbon atoms, referred to herein as $C_{1-6}$ alkyl, $C_{1-4}$ alkyl, and $C_{1-3}$ alkyl, respectively. Examples of alkyl include, but are not limited to, methyl, ethyl, n-propyl, i-propyl, n-butyl, i-butyl, sec-butyl, t-butyl, n-pentyl, n-hexyl, 2-methylbutyl, 2-methylpentyl, 2-ethylbutyl, 3-methylpentyl, and 4-methylpentyl.

The term "cycloalkyl," as used herein, refers to saturated cyclic alkyl moieties having 3 or more carbon atoms, for example, 3-10, 3-6, or 4-6 carbons, referred to herein as $C_{3-10}$ cycloalkyl, $C_{3-6}$ cycloalkyl or $C_{4-6}$ cycloalkyl, respectively for example. Unless otherwise stated, such saturated cyclic alkyl moieties can contain up to 18 carbon atoms and include monocycloalkyl, polycycloalkyl, and benzocycloalkyl structures. Monocycloalkyl refers to groups having a single ring group. Polycycloalkyl denotes hydrocarbon systems containing two or more ring systems with one or more ring carbon atoms in common; i.e., a spiro, fused, or bridged structure. Benzocycloalkyl signifies a monocyclic alkyl group fused to a benzene ring, referred to herein as $C_{8-12}$benzocycloalkyl, for example. Examples of monocycloalkyl groups include, but are not limited to, cyclopropyl, cyclobutyl, cyclopentyl, cyclohexyl, cycloheptyl, cyclooctyl, cyclononyl, cyclodecyl, cycloundecyl, cyclododecyl, cyclotridecyl, cyclotetradecyl, cyclopentadecyl, cyclohexadecyl, cycloheptadecyl, and cyclooctadecyl. Examples of polycycloalkyl groups include, but are not limited to, decahydronaphthalene, spiro[4.5]decyl, bicyclo[2.2.1]heptyl, bicyclo[3.2.1]octyl, pinanyl, norbornyl, adamantyl, and bicyclo[2.2.2]octyl. Examples of benzocycloalkyl groups include, but are not limited to, tetrahydronaphthyl, indanyl, and 1.2-benzocycloheptanyl.

The terms "heteroaryl" or "heteroaromatic group" as used herein refers to a monocyclic aromatic 5-7 membered ring system containing one or more heteroatoms, for example one to three heteroatoms, such as nitrogen, oxygen, and sulfur, or a 8-14 (e.g. 8-12) membered bicyclic or 11-15 membered tricyclic unsaturated or partially unsaturated ring system containing one or more heteroatoms, for example one to three heteroatoms, such as nitrogen, oxygen, and sulfur. Where possible, said heteroaryl ring may be linked to the adjacent radical though carbon or nitrogen. Examples of heteroaryl rings include but are not limited to furan, thiophene, pyrrole, thiazole, oxazole, isothiazole, isoxazole, imidazole, pyrazole, triazole, pyridine or pyrimidine, tetrahydroquinoline, 1,2,3,4-tetrahydroquinolin-1-yl, 1,2,3,4-tetrahydro-1,5-naphthyridin-1-yl, 1,2,3,4-tetrahydroquinolin-1-yl, 1,2,3,4-tetrahydroquinoxalin-1-yl, 1,2,3,4-tetrahydropyrido[2,3-b]pyrazin-1-yl, 1H-benzo[d]imidazol-1-yl, indolin-1-yl, 2,3-dihydro-1H-pyrrolo[3,2-b]pyridin-1-yl, 2,3-dihydro-1H-pyrrolo[3,2-c]pyridin-1-yl, isoindolin-2-yl, 2,3,4,5-tetrahydrobenzo[f][1,4]oxazepin-4-yl, 2-(3,4-dihydroisoquinolin-1(2H)-one), 2-(3,4-dihydroisoquinolin-1(2H)-one), 2,3-dihydro-1H-pyrido[2,3-b][1,4]oxazin-1-yl, piperidin-1-yl, 1-(1,2,3,4-tetrahydro-6H-pyrido[1,2-a]pyrimidin-6-one), 1,2,3,4-tetrahydro-1,8-naphthyridin-1-yl, 1-(3,4-dihydro-1,5-naphthyridin-2(1H)-one), 2,3,4,5-tetrahydro-1H-benzo[b]azepin-1-yl, 1-(2,3-dihydroquinolin-4 (1H)-one), 2,3-dihydro-1H-pyrido[2,3-b][1,4]oxazin-1-yl, 1,2,3,4-tetrahydro-1,6-naphthyridin-1-yl, 5,6,7,8-tetrahydro-4H-pyrazolo[1,5-a][1,3]diazepin-4-yl, 3,4-dihydroquinoxalin-1-yl-2(1H)-one, 2,3,4,6-tetrahydro-1,6-naphthyridin-1-yl-5(1H)-one, 1,2,3,4-tetrahydroisoquinolin-2-yl, 1,2,3,4-tetrahydro-2,7-naphthyridin-2-yl, 1,2,3,4-tetrahydro-2,6-naphthyridin-2-yl, 3,4-dihydro-2H-benzo[b][1,4] thiazin-4-yl 11-dioxide, 1,2,3,4-tetrahydropyrazino[2,3-d] pyridazin-1-yl, 1,4-dihydropyrido[3,4-b]pyrazin-1-yl-3 (2H)-one, 5,6,7,8-tetrahydro-1,6-naphthyridin-6-yl, 5,6,7,8-tetrahydro-1,7-naphthyridin-7-yl, 1,2,3,4-tetrahydropyrido [3,4-b]pyrazin-1-yl, 5,8-dihydropteridin-5-yl-7(6H)-one, 4,5,6,7-tetrahydrothieno[3,2-b]pyridin-4-yl, 5,6,7,8-tetrahydropyrazino[2,3-c]pyridazin-5-yl, and 1,2,6,7,8,9-hexahydro-3H-pyrrolo[3,4-f]quinolin-3-only, etc.

The terms "heterocyclyl", "heterocyclylalkyl" or "heterocyclic group" are art-recognized and refer to saturated 4-10 (e.g., 4-7) membered monocyclic and bicyclic ring structures, including bridged or fused rings, and whose ring structures include one to three heteroatoms, such as nitrogen, oxygen, and sulfur. Where possible, heterocyclyl rings may be linked to the adjacent radical through carbon or nitrogen.

The term "pharmaceutically acceptable salt" is intended to include salts derived from inorganic or organic acids including, e.g., hydrochloric, hydrobromic, sulfuric, nitric, perchloric, phosphoric, formic, acetic, lactic, maleic, fumaric, succinic, tartaric, glycolic, salicylic, citric, methanesulfonic, benzenesulfonic, benzoic, malonic, trifluoroacetic, trichloroacetic, naphthalene-2 sulfonic and other acids; and salts derived from inorganic or organic bases including, e.g., sodium, potassium, calcium, magnesium, zinc, ammonia, lysine, arginine, histidine, polyhydroxylated amines or tetrafluoroborate. Exemplary pharmaceutically acceptable salts are found, e.g., in Berge, et al. (*J. Pharm. Sci.* 1977, 66(1), 1; and Gould, P. L., *Int. J. Pharmaceutics* 1986, 33, 201-217, each hereby incorporated by reference in its entirety. Pharmaceutically acceptable salts are also intended to encompass hemi-salts, wherein the ratio of compound:acid is respectively 2:1. Exemplary hemi-salts are those salts derived from acids comprising two carboxylic acid groups, such as malic acid, fumaric acid, maleic acid, succinic acid, tartaric acid, glutaric acid, oxalic acid, adipic acid and citric acid. Other exemplary hemi-salts are those salts derived from diprotic mineral acids such as sulfuric acid. Exemplary preferred hemi-salts include, but are not limited to, hemimaleate, hemifumarate, and hemisuccinate.

As used herein the term "about" is used herein to mean approximately, roughly, around, or in the region of. When the term "about" is used in conjunction with a numerical range, it modifies that range by extending the boundaries above and below the numerical values set forth. In general, the term "about" is used herein to modify a numerical value above and below the stated value by a variance of 20 percent up or down (higher or lower).

An "effective amount", "sufficient amount" or "therapeutically effective amount" as used herein is an amount of a compound that is sufficient to effect beneficial or desired results, including clinical results. As such, the effective amount may be sufficient, e.g., to reduce or ameliorate the severity and/or duration of afflictions related to SHP2 phosphatase, or one or more symptoms thereof, prevent the advancement of conditions or symptoms related to afflictions related to SHP2 phosphatase, or enhance or otherwise improve the prophylactic or therapeutic effect(s) of another therapy. An effective amount also includes the amount of the compound that avoids or substantially attenuates undesirable side effects.

As used herein and as well understood in the art, "treatment" is an approach for obtaining beneficial or desired results, including clinical results. Beneficial or desired clinical results may include, but are not limited to, alleviation or amelioration of one or more symptoms or conditions, diminution of extent of disease or affliction, a stabilized (i.e., not worsening) state of disease or affliction, preventing spread of disease or affliction, delay or slowing of disease or affliction progression, amelioration or palliation of the disease or affliction state and remission (whether partial or total), whether detectable or undetectable. "Treatment" can also mean prolonging survival as compared to expected survival if not receiving treatment.

The phrase "in need thereof" refers to the need for symptomatic or asymptomatic relief from conditions related to SHP2 phosphatase activity or that may otherwise be relieved by the compounds and/or compositions of the disclosure.

The present disclosure provides, for example, a compound of Formula I, or a pharmaceutically acceptable salt or stereoisomer thereof, wherein Formula I is represented by:

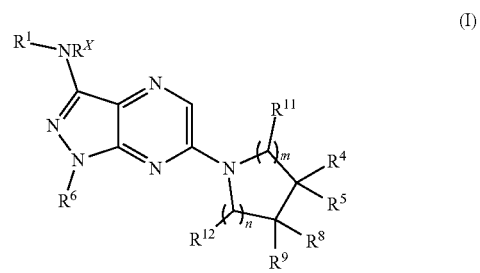

wherein:
$R^X$ together with $R^1$ and the nitrogen to which they are attached form a nitrogen-containing monocyclic, bicyclic or tricyclic ring system selected from the group consisting of a 8-14 membered bicyclic heteroaryl, a 11-15 membered tricyclic heteroaryl, a 5-7 membered monocyclic heteroaryl, and a 4-7 membered heterocyclyl, wherein the nitrogen-containing monocyclic, bicyclic or tricyclic ring system may optionally be substituted with one, two or more substituents each independently selected from the group consisting of $R^{10}$, —$OR^{10}$, —$S(O)_wR^{10}$ (wherein w is 0, 1 or 2), —$C_{1-6}$alkyl-$S(O)_w$—$C_{1-3}$alkyl, —$N(R^{10})_2$, —$N(CO)R^{10}$, —N—S$(O)_w$—$R^{10}$ (where w is 0, 1 or 2), —$OS(O)_w$—$R^{10}$ (wherein w is 0, 1, or 2), —$S(O)_w$—$N(R^{10})_2$ (wherein w is 0, 1 or 2), —$S(O)(NH)R^{10}$, —$N(H)$—$SO_2$—$C_{1-3}$alkyl, —$N(SO_2$—$C_{1-3}$alkyl$)_2$, $P(O)(R^{10})_2$, —$C(O)R^{10}$, —$C(O)OR^{10}$, —$C(O)N(R^{10})_2$, oxo, halogen, hydroxyl, cyano, nitro, —$C(=N$—$OR^a)$—$C_{1-3}$alkyl, —$C(=N$—$OR^a)$—H, —$S(O)(NR^a)$—$C_{1-3}$alkyl,

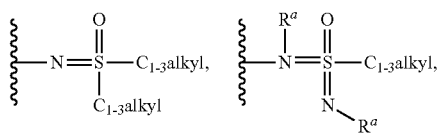

phenyl (optionally substituted with one, two or three halogen, —O-phenyl, $C_{1-3}$alkyl or $C_{1-3}$haloalkyl), $C_{1-3}$alkyl, $C_{2-6}$alkynyl, $C_{1-3}$haloalkyl, $C_{3-6}$cycloalkyl, heterocyclyl (optionally substituted with one, two or three halogen, oxo, $C_{1-3}$alkyl or $C_{1-3}$haloalkyl), and heteroaryl (optionally substituted with one, two or three halogen, —$C(O)N(R^{10})_2$, $C_{1-3}$alkyl, $C_{1-3}$alkyl-O—$C_{1-3}$alkyl, $C_{1-3}$ alkyl-OH, or $C_{1-3}$haloalkyl);

$R^{10}$ is independently selected from the group consisting of hydrogen, $C_{1-6}$alkyl, $C_{2-6}$ alkenyl, $C_{2-6}$alkynyl, $C_{3-6}$cycloalkyl, $C_{5-6}$cycloalkenyl, $C_{2-6}$heteroalkyl, heterocycloalkyl, aryl, heteroaryl, and $P(O)(R^{20})_2$; wherein $C_{1-6}$alkyl, $C_{2-6}$alkenyl, $C_{2-6}$alkynyl, $C_{3-6}$cycloalkyl, $C_{5-6}$cycloalkenyl, $C_{2-6}$heteroalkyl, heterocycloalkyl, aryl, and heteroaryl may optionally be substituted by one, two, three or more substituents each independently selected from the group consisting of halogen, hydroxyl, cyano, —$NR^aC(O)$—$R^{20}$, —$C(O)$—$R^{20}$, —$C(NR^a)$—$R^b$, —$NR^aR^b$, $C_{1-6}$alkyl, $C_{1-6}$haloalkyl and $C_{1-6}$alkoxy;

$R^{20}$ is selected from the group consisting of hydrogen, hydroxyl, halogen, —$NR^aR^b$, $C_{1-6}$alkyl and $C_{1-6}$alkoxy;

$R^4$ and $R^5$ are each independently, selected from the group consisting of H, —OH, —$(C_1$-$C_6)$alkyl, —$O(C_1$-$C_6)$alkyl, —$(C_1$-$C_6)$alkyl-O—$R^6$, —$C(O)N(R^6)_2$, —$N(R^6)_2$, halogen, —$(C_1$-$C_6)$alkyl-$N(R^6)_2$, or cyano, wherein said —$(C_1$-$C_6)$alkyl, —$O(C_1$-$C_6)$alkyl, —$(C_1$-$C_6)$alkyl-O—$R^6$, or —$(C_1$-

$C_6$)alkyl-N($R^6$)$_2$ is optionally substituted with one or more substituents selected from the group consisting of —OH, —NH$_2$, oxo, and halogen, or $R^4$ and $R^5$, taken together with the atoms to which they are attached, form a 3-7 membered carbocyclic or heterocyclic saturated or partially unsaturated ring, which ring is optionally substituted with one or more substituents selected from the group consisting of —OH, —($C_1$-$C_6$)alkyl, —O($C_1$-$C_6$)alkyl, —N($R^6$)$_2$, halogen, oxo, or cyano;

or $R^4$ and $R^8$, taken together with the atoms to which they are attached, form a 4-7 membered carbocyclic or heterocyclic ring, which ring is optionally substituted with —OH, —($C_1$-$C_6$)alkyl, —O($C_1$-$C_6$)alkyl, —N($R^6$)$_2$, halogen, oxo, or cyano;

or $R^4$ is absent, and $R^4$ and Re, taken together with the atoms to which they are attached, form a 3-membered carbocyclic or heterocyclic ring, which ring is optionally substituted with —OH, —($C_1$-$C_6$)alkyl, —O($C_1$-$C_6$)alkyl, —N($R^6$)$_2$, halogen, oxo, or cyano;

$R^6$ is independently for each occurrence selected from the group consisting of H, —($C_1$-$C_6$)alkyl, —C(O)O$C_{1-4}$alkyl, and phenyl;

$R^{11}$ and $R^{12}$ are, each independently selected from the group consisting of, H, —OH, —($C_1$-$C_6$)alkyl, —O($C_1$-$C_6$)alkyl, —($C_1$-$C_6$)alkyl-O—$R^6$, aryl, arylalkylene, heteroaryl, heteroarylalkylene, —C(O)N($R^6$)$_2$, —N($R^6$)$_2$, halogen, —($C_1$-$C_6$)alkyl-N($R^6$)2, —CO$_2$H, or cyano, wherein said —($C_1$-$C_6$)alkyl, —O($C_1$-$C_6$)alkyl, —($C_1$-$C_6$)alkyl-O—$R^6$, aryl, arylalkylene, heteroaryl, heteroarylalkylene, or —($C_1$-$C_6$)alkyl-N($R^6$)$_2$ is optionally substituted with one or more substituents selected from the group consisting of —OH, —N(H)$_2$, and halogen;

or $R^{11}$ and $R^{12}$, taken together with the atoms to which they are attached, form a 5-7 membered heterocyclic ring;

or $R^4$ and $R^{12}$, taken together with the atoms to which they are attached, form a 5-7 membered carbocyclic or heterocyclic ring;

or $R^8$ and $R^{11}$, taken together with the atoms to which they are attached, form a 5-7 membered carbocyclic or heterocyclic ring;

$R^8$ and $R^9$ are each independently selected from the group consisting of H, —($C_1$-$C_6$)alkyl, —($C_1$-$C_6$)alkyl-N($R^6$)$_2$, —O$R^6$, —($C_1$-$C_6$)alkyl-O—$R^6$, —C(O)NH$_2$, —N($R^6$)$_2$, halogen, or cyano;

$R^a$ and $R^b$ are independently selected, for each occurrence, from the group consisting of hydrogen and $C_{1-6}$alkyl; wherein $C_{1-6}$alkyl may optionally be substituted by one or more substituents selected from halogen, cyano, oxo and hydroxyl;

or $R^a$ and $R^b$, together with the nitrogen to which they are attached, may form a 4-6 membered monocyclic heterocyclic ring, which may have an additional heteroatom selected from the group consisting of O, S, and N; wherein the 4-6 membered heterocyclic ring may optionally be substituted by one or more substituents selected from the group consisting of halogen, cyano, oxo or hydroxyl;

and each of m and n is, independently, 0, 1, 2, or 3, with m+n being at least 2 and no more than 4.

In some embodiments, $R^X$ together with $R^1$ and the nitrogen to which they are attached form a ring moiety selected from the group consisting of 1,2,3,4-tetrahydroquinolin-1-yl, 1,2,3,4-tetrahydro-1,5-naphthyridin-1-yl, 1,2,3,4-tetrahydroquinolin-1-yl, 1,2,3,4-tetrahydroquinoxalin-1-yl, 1,2,3,4-tetrahydropyrido[2,3-b]pyrazin-1-yl, 1H-benzo[d]imidazol-1-yl, indolin-1-yl, 2,3-dihydro-1H-pyrrolo[3,2-b]pyridin-1-yl, 2,3-dihydro-1H-pyrrolo[3,2-c]pyridin-1-yl, isoindolin-2-yl, 2,3,4,5-tetrahydrobenzo[f][1,4]oxazepin-4-yl, 2-(3,4-dihydroisoquinolin-1(2H)-one), 2-(3,4-dihydroisoquinolin-1(2H)-one), 2,3-dihydro-1H-pyrido[2,3-b][1,4]oxazin-1-yl, piperidin-1-yl, 1-(1,2,3,4-tetrahydro-6H-pyrido[1,2-a]pyrimidin-6-one), 1,2,3,4-tetrahydro-1,8-naphthyridin-1-yl, 1-(3,4-dihydro-1,5-naphthyridin-2(1H)-one), 2,3,4,5-tetrahydro-1H-benzo[b]azepin-1-yl, 1-(2,3-dihydroquinolin-4(1H)-one), 2,3-dihydro-1H-pyrido[2,3-b][1,4]oxazin-1-yl, 1,2,3,4-tetrahydro-1,6-naphthyridin-1-yl, 5,6,7,8-tetrahydro-4H-pyrazolo[1,5-a][1,3]diazepin-4-yl, 3,4-dihydroquinoxalin-1-yl-2(1H)-one, 2,3,4,6-tetrahydro-1,6-naphthyridin-1-yl-5(1H)-one, 1,2,3,4-tetrahydroisoquinolin-2-yl, 1,2,3,4-tetrahydro-2,7-naphthyridin-2-yl, 1,2,3,4-tetrahydro-2,6-naphthyridin-2-yl, 3,4-dihydro-2H-benzo[b][1,4]thiazin-4-yl 11-dioxide, 1,2,3,4-tetrahydropyrazino[2,3-d]pyridazin-1-yl, 1,4-dihydropyrido[3,4-b]pyrazin-1-yl-3(2H)-one, 5,6,7,8-tetrahydro-1,6-naphthyridin-6-yl, 5,6,7,8-tetrahydro-1,7-naphthyridin-7-yl, 1,2,3,4-tetrahydropyrido[3,4-b]pyrazin-1-yl, 5,8-dihydropteridin-5-yl-7(6H)-one, 4,5,6,7-tetrahydrothieno[3,2-b]pyridin-4-yl, 5,6,7,8-tetrahydropyrazino[2,3-c]pyridazin-5-yl, and 1,2,6,7,8,9-hexahydro-3H-pyrrolo[3,4-f]quinolin-3-onyl; wherein the nitrogen ring moiety may be optionally substituted with one or two substituents each independently selected from the group consisting of Cl, F, —CN, $C_{1-4}$alkyl, —O$C_{1-4}$alkyl, $C_{2-6}$alkenyl, $C_{2-4}$alkynyl, $C_{3-6}$ cycloalkyl, $C_{5-6}$cycloalkenyl, —C(H)=N—OCH$_3$, —C(H)=N—OH, —C(CH$_3$)=N—OH, —(CH$_2$)$_{0-1}$C(O)NH$_2$, —(CH$_2$)$_{0-1}$C(O)NH$C_{1-4}$alkyl, —(CH$_2$)$_{0-1}$C(O)N($C_{1-4}$alkyl)$_2$, —(CH$_2$)$_{0-1}$C(O)O$C_{1-4}$alkyl, —(CH$_2$)$_{0-1}$C(O)OH, —S(O)$_2$$C_{1-4}$alkyl, —(CH$_2$)$_{0-1}$NH$_2$, —(CH$_2$)$_{0-1}$NH$C_{1-4}$alkyl, —(CH$_2$)$_{0-1}$($C_{1-4}$alkyl)$_2$, —(CH$_2$)$_{0-1}$NH(CO)$C_{1-4}$alkyl, phenyl, optionally substituted heteroaryl and optionally substituted heterocyclyl, wherein $C_{1-4}$alkyl or $C_{3-6}$cycloalkyl may be optionally substituted with cyano, one, two or three fluorine atoms, one or two hydroxyl groups, or one or two —O$C_{1-2}$alkyl groups.

In some embodiments, heteroaryl is selected from the group consisting of 2-pyridyl, 3-pyridyl, 4-pyridyl, 1,2,4-triazol-3-yl, thiazol-2-yl, pyrazol-1-yl, pyrazol-3-yl, pyrazol-4-yl, imidazol-2-yl, oxazol-2-yl, oxazol-5-yl, isoxazol-5-yl, thiazol-2-yl, thiazol-5-yl, 1,3,4-thiadiazol-2-yl, and 1,2,4-oxadiazol-3-yl, 1,3,4-oxadiazol-2-yl, 1,2,4-triazol-2-yl, and 1,3,4-triazol-2-yl; wherein heteroaryl may be optionally substituted with $C_{1-2}$alkyl (optionally substituted with one, two or three fluorine atoms, one or two 2 hydroxyl groups, or one or two —O$C_{1-2}$alkyl groups).

In some embodiments, heterocyclyl is selected from the group consisting of tetrahydrofuran-3-yl, tetrahydrofuran-2-yl, pyrrolidine-1-yl, piperazin-1-yl, piperidin-4-yl, piperidin-1-yl, 1,2,3,6-tetrahydropyridin-4-yl, 2,5-dihydrofuran-3-yl, piperazin-1-yl-3-one, morpholino, tetrahydropyran-2-yl, 1,2,4-oxadiazo-3-yl-5-one, and pyrrolidin-2-one-4-yl; wherein heterocyclyl may be optionally substituted with hydroxyl or $C_{1-2}$alkyl (optionally substituted with one, two or three fluorine atoms, one or two 2 hydroxyl groups, or one or two —O$C_{1-2}$alkyl groups).

In some embodiments, $R^X$ together with $R^1$ and the nitrogen to which they are attached form a 1,2,3,4-tetrahydroquinoline moiety optionally substituted with one, two or three halo, —C(O)N($R^{10}$)$_2$, $C_{1-3}$alkyl, $C_{1-3}$haloalkyl, and heteroaryl (optionally substituted with one, two or three halogen, —C(O)N($R^{10}$)$_2$$C_{1-3}$alkyl, $C_{1-3}$alkyl-O—$C_{1-3}$alkyl, $C_{1-3}$alkyl-OH, or $C_{1-3}$ haloalkyl).

In some embodiments, $R^X$ together with $R^1$ and the nitrogen to which they are attached form a 1,2,3,4-tetrahydro-1,5,napthyridine moiety optionally substituted with one, two or three halo, —C(O)N($R^{10}$)$_2$, $C_{1-3}$alkyl, $C_{1-3}$haloalkyl, and heteroaryl (optionally substituted with one, two or three halogen, —C(O)N($R^{10}$)$_2$C$_{1-3}$alkyl, C$_{1-3}$alkyl-O—C$_{1-3}$alkyl, C$_{1-3}$alkyl-OH, or C$_{1-3}$haloalkyl).

In some embodiments, m is an integer selected from 1 or 2; and n is 1.

In some embodiments, $R^4$ and $R^5$ are independently selected from the group consisting of H, —OH, —(C$_1$-C$_3$)alkyl, —(C$_1$-C$_3$)alkyl-COOH, —O(C$_1$-C$_3$)alkyl, —(C$_1$-C$_3$)alkyl-O—$R^6$, —C(O)NH$_2$, —N($R^6$)$_2$, halogen, —(C$_1$-C$_3$)alkyl-N($R^6$)$_2$, and cyano, wherein said —(C$_1$-C$_3$)alkyl, —O(C$_1$-C$_3$)alkyl, —(C$_1$-C$_3$)alkyl-O—$R^6$, or —(C$_1$-C$_3$)alkyl-N($R^6$)$_2$, is optionally substituted with one or more substituents selected from the group consisting of —OH, —N($R^6$)$_2$, and halogen;

or $R^4$ and $R^5$, taken together with the atoms to which they are attached, form a 3-7 membered carbocyclic or heterocyclic ring; which ring is optionally substituted with one or more substituents selected from the group consisting of —OH, —(C$_1$-C$_6$)alkyl, —O(C$_1$-C$_6$)alkyl, —N($R^6$)$_2$, halogen, oxo, or cyano;

or $R^4$ and $R^8$, taken together with the atoms to which they are attached, form a 4-7 membered carbocyclic or heterocyclic ring;

or $R^4$ is a bond, and $R^4$ and $R^8$, taken together with the atoms to which they are attached, form a 3-membered carbocyclic or heterocyclic ring; and each $R^6$ is independently H or —(C$_1$-C$_3$)alkyl.

In some embodiments, the moiety

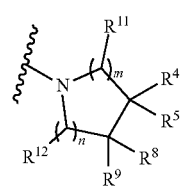

of Formula I is selected from the group consisting of:

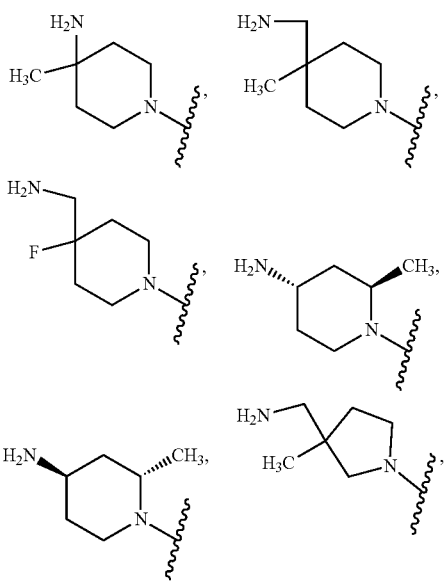

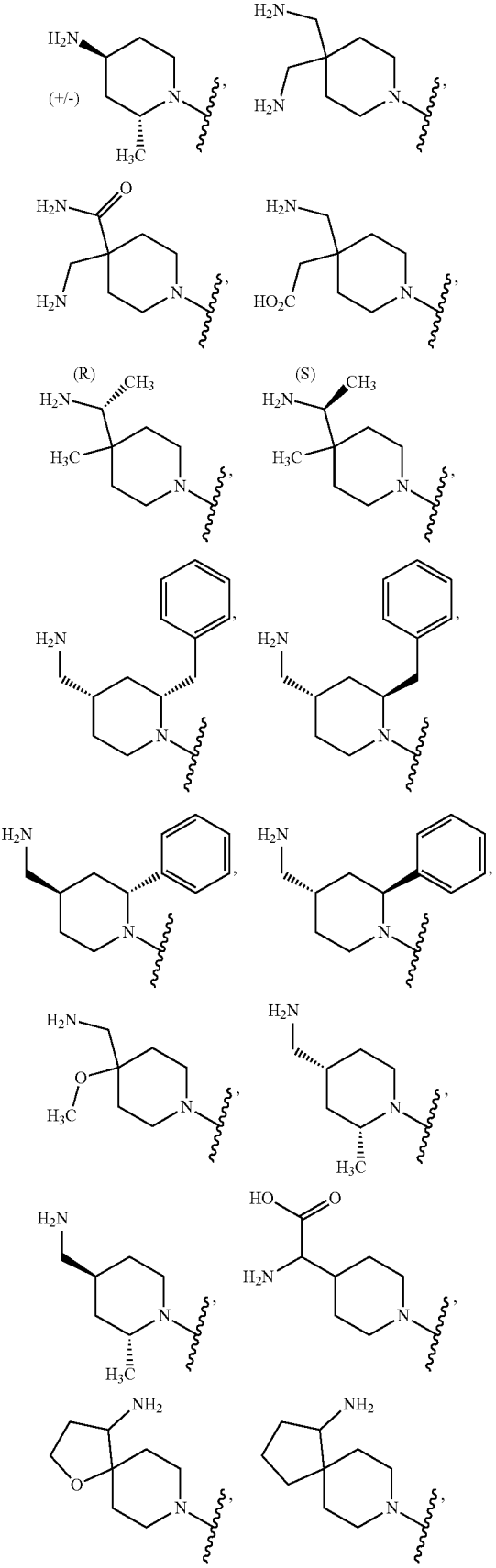

-continued
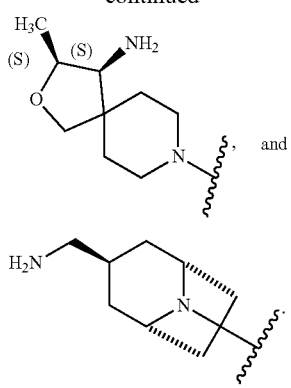
, and
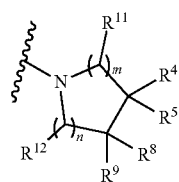
In some embodiments, the moiety
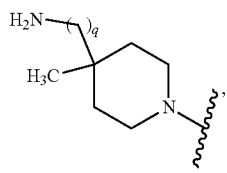
of Formula I is represented by:
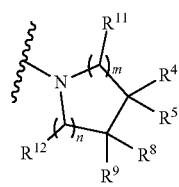
wherein q is 0 or 1.
In some embodiments, the moiety
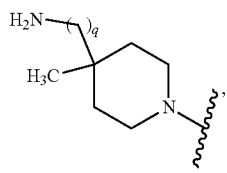
of Formula I is represented by:
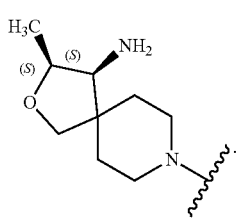
In some embodiments, the moiety
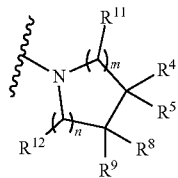
of Formula I is selected from the group consisting of:
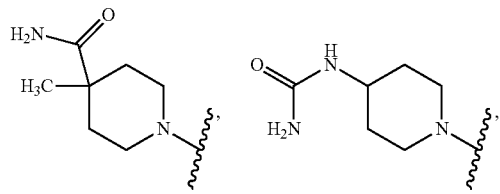
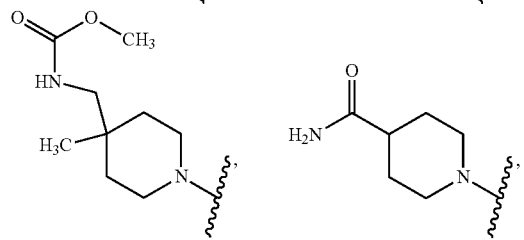
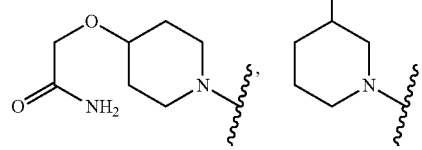
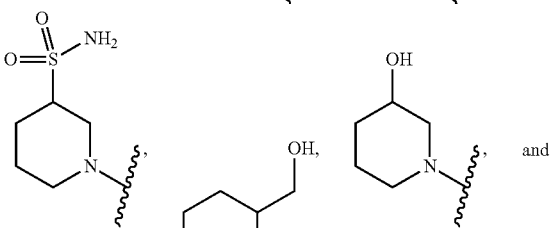
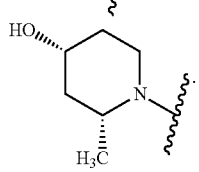
In some embodiments, the moiety
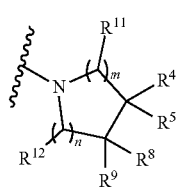

of Formula I is selected from the group consisting of:

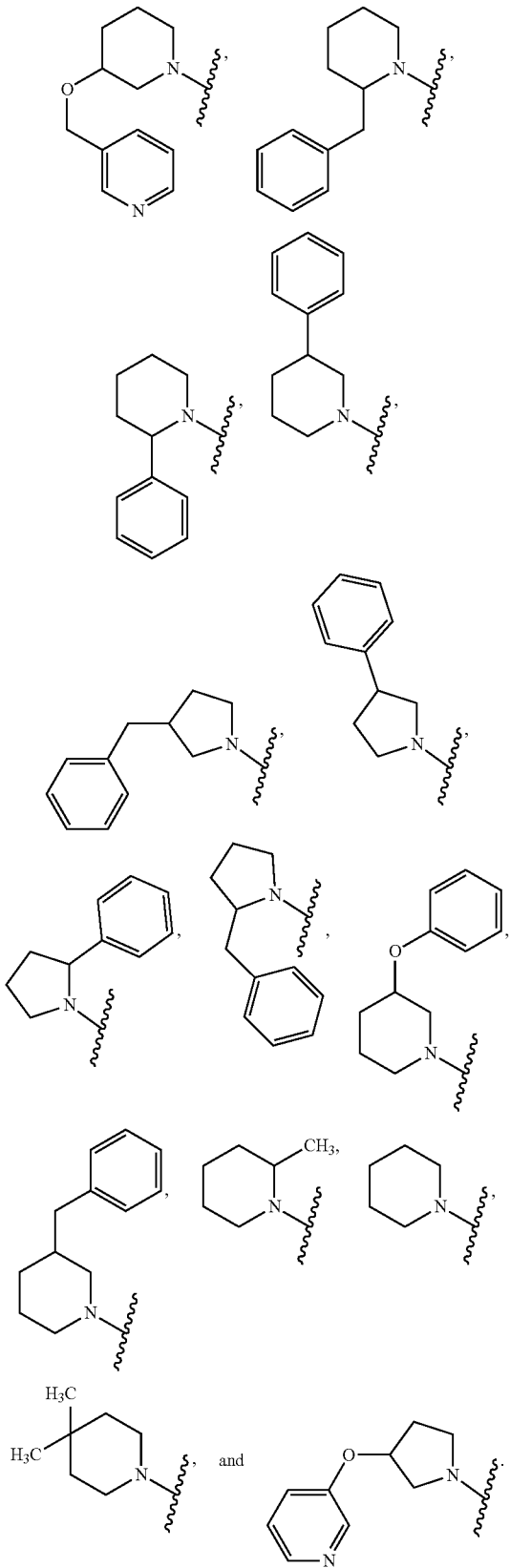

The present disclosure also provides, for example, a compound of Formula II, or a pharmaceutically acceptable salt or stereoisomer thereof, wherein Formula II is represented by:

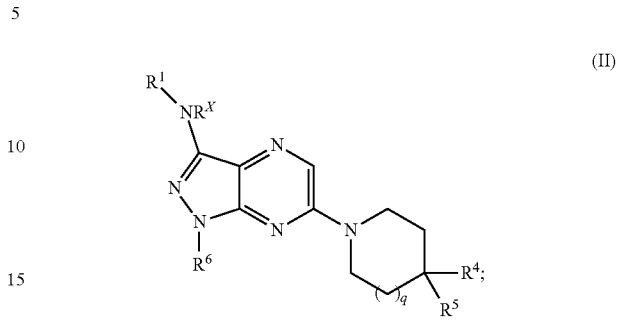

wherein:

$R^X$ together with $R^1$ and the nitrogen to which they are attached form a nitrogen-containing monocyclic, bicyclic or tricyclic ring system selected from the group consisting of a 8-14 membered bicyclic heteroaryl, a 8-14 membered tricyclic heteroaryl, a 5-7 membered monocyclic heteroaryl, and a 4-7 membered heterocyclyl, wherein the nitrogen-containing monocyclic, bicyclic or tricyclic ring system may optionally be substituted with one, two or more substituents each independently selected from the group consisting of $R^{10}$, —$OR^{10}$, —$S(O)_w R^{10}$ (wherein w is 0, 1 or 2), —$C_{1-6}$alkyl-$S(O)_w$—$C_{1-3}$alkyl, —$N(R^{10})_2$, —$N(CO)R^{10}$, —N—$S(O)_w$—$R^{10}$ (where w is 0, 1 or 2), —$OS(O)_w$—$R^{10}$ (wherein w is 0, 1, or 2), —$S(O)_w$—$N(R^{10})_2$ (wherein w is 0, 1 or 2), —$S(O)(NH)R^{10}$, —N(H)—$SO_2$—$C_{1-3}$alkyl, —$N(SO_2$—$C_{1-3}$alkyl$)_2$, $P(O)(R^{10})_2$, —$C(O)R^{10}$, —$C(O)OR^{10}$, —$C(O)N(R^{10})_2$, oxo, halogen, hydroxyl, cyano, nitro, —C(=N—$OR^a$)—$C_{1-3}$alkyl, —C(=N—$OR^a$)—H, —S(O)($NR^a$)—$C_{1-3}$alkyl, phenyl (optionally substituted with one, two or three halogen, —O-phenyl, $C_{1-3}$alkyl or $C_{1-3}$haloalkyl), $C_{1-3}$alkyl, $C_{2-6}$alkynyl, $C_{1-3}$haloalkyl, $C_{1-6}$cycloalkyl, heterocyclyl (optionally substituted with one, two or three halogen, oxo, $C_{1-3}$ alkyl or $C_{1-3}$haloalkyl), and heteroaryl (optionally substituted with one, two or three halogen, —$C(O)N(R^{10})_2$, $C_{1-3}$alkyl, $C_{1-3}$alkyl-O—$C_{1-3}$alkyl, $C_{1-3}$alkyl-OH, or $C_{1-3}$haloalkyl);

$R^{10}$ is independently selected from the group consisting of hydrogen, $C_{1-6}$alkyl, $C_{2-6}$ alkenyl, $C_{2-6}$alkynyl, $C_{3-6}$cycloalkyl, $C_{5-6}$cycloalkenyl, $C_{2-6}$heteroalkyl, heterocycloalkyl, aryl, heteroaryl, and $P(O)(R^{20})_2$; wherein $C_{1-6}$alkyl, $C_{2-6}$alkenyl, $C_{2-6}$alkynyl, $C_{3-6}$cycloalkyl, $C_{5-6}$cycloalkenyl, $C_{2-6}$heteroalkyl, heterocycloalkyl, aryl, and heteroaryl may optionally be substituted by one, two, three or more substituents each independently selected from the group consisting of halogen, hydroxyl, cyano, —$NR^aC(O)$—$R^{20}$, —$C(O)$—$R^{20}$, —$C(NR^a)R^b$, —$NR^aR^b$, $C_{1-6}$alkyl, $C_{1-6}$haloalkyl and $C_{1-6}$alkoxy;

$R^{20}$ is selected from the group consisting of hydrogen, hydroxyl, halogen, —$NR^aR^b$, $C_{1-6}$alkyl and $C_{1-6}$alkoxy;

$R^4$ and $R^5$ are each independently, selected from the group consisting of H, —OH, —$(C_1-C_6)$alkyl, —$O(C_1-C_6)$alkyl, —$(C_1-C_6)$alkyl-O—$R^6$, —$C(O)N(R^6)_2$, —$N(R)_2$, halogen, —$(C_1-C_6)$alkyl-$N(R^6)_2$, or cyano, wherein said —$(C_1-C_6)$alkyl, —$O(C_1-C_6)$alkyl, —$(C_1-C_6)$alkyl-O—$R^6$, or —$(C_1-C_6)$alkyl-$N(R^6)_2$ is optionally substituted with one or more substituents selected from the group consisting of —OH, —$NH_2$, oxo, and halogen, or $R^4$ and $R_5$, taken together with the atoms to which they are attached, form a 3-7 membered carbocyclic or heterocyclic saturated or partially unsaturated ring, which ring is optionally substituted with one or more substituents selected from the group consisting of —OH, —$(C_1-C_6)$alkyl, —$O(C_1-C_6)$alkyl, —$N(R^6)_2$, halogen, oxo, or cyano;

or $R^4$ and $R^8$, taken together with the atoms to which they are attached, form a 4-7 membered carbocyclic or heterocyclic ring, which ring is optionally substituted with —OH, —($C_1$-$C_6$)alkyl, —O($C_1$-$C_6$)alkyl, —N($R^6$)$_2$, halogen, oxo, or cyano;

or $R^4$ is absent, and $R^4$ and Re, taken together with the atoms to which they are attached, form a 3-membered carbocyclic or heterocyclic ring, which ring is optionally substituted with —OH, —($C_1$-$C_6$)alkyl, —O($C_1$-$C_6$)alkyl, —N($R^6$)$_2$, halogen, oxo, or cyano;

$R^6$ is independently for each occurrence selected from the group consisting of H, —($C_1$-$C_6$)alkyl, —C(O)O$C_{1-4}$alkyl, and phenyl;

$R^{11}$ and $R^{12}$ are, each independently selected from the group consisting of, H, —OH, —($C_1$-$C_6$)alkyl, —O($C_1$-$C_6$)alkyl, —($C_1$-$C_6$)alkyl-O—$R^6$, aryl, arylalkylene, heteroaryl, heteroarylalkylene, —C(O)N($R^6$)$_2$, —N($R^6$)$_2$, halogen, —($C_1$-$C_6$)alkyl-N($R^6$)$_2$, —CO$_2$H, or cyano, wherein said —($C_1$-$C_6$)alkyl, —O($C_1$-$C_6$)alkyl, —($C_1$-$C_6$)alkyl-O—$R^6$, aryl, arylalkylene, heteroaryl, heteroarylalkylene, or —($C_1$-$C_6$)alkyl-N($R^6$)$_2$ is optionally substituted with one or more substituents selected from the group consisting of —OH, —N(H)$_2$, and halogen;

or $R^{11}$ and $R^{12}$, taken together with the atoms to which they are attached, form a 5-7 membered heterocyclic ring;

or $R^4$ and $R^{12}$, taken together with the atoms to which they are attached, form a 5-7 membered carbocyclic or heterocyclic ring;

or $R^8$ and $R^{11}$, taken together with the atoms to which they are attached, form a 5-7 membered carbocyclic or heterocyclic ring;

$R^8$ and $R^9$ are each independently selected from the group consisting of H, —($C_1$-$C_6$)alkyl, —($C_1$-$C_6$)alkyl-N($R^6$)$_2$, —OR$^6$, —($C_1$-$C_6$)alkyl-O—$R^6$, —C(O)NH$_2$, —N($R^6$)$_2$, halogen, or cyano;

$R^a$ and $R^b$ are independently selected, for each occurrence, from the group consisting of hydrogen and $C_{1-6}$alkyl; wherein $C_{1-6}$alkyl may optionally be substituted by one or more substituents selected from halogen, cyano, oxo and hydroxyl;

or $R^a$ and $R^b$, together with the nitrogen to which they are attached, may form a 4-6 membered monocyclic heterocyclic ring, which may have an additional heteroatom selected from the group consisting of O, S, and N; wherein the 4-6 membered heterocyclic ring may optionally be substituted by one or more substituents selected from the group consisting of halogen, cyano, oxo or hydroxyl; and q is 0 or 1.

In some embodiments, $R^X$ together with $R^1$ and the nitrogen to which they are attached form a ring moiety selected from the group consisting of 1,2,3,4-tetrahydroquinolin-1-yl, 1,2,3,4-tetrahydro-1,5-naphthyridin-1-yl, 1,2,3,4-tetrahydroquinolin-1-yl, 1,2,3,4-tetrahydroquinoxalin-1-yl, 1,2,3,4-tetrahydropyrido[2,3-b]pyrazin-1-yl, 1H-benzo[d]imidazol-1-yl, indolin-1-yl, 2,3-dihydro-1H-pyrrolo[3,2-b]pyridin-1-yl, 2,3-dihydro-1H-pyrrolo[3,2-c]pyridin-1-yl, isoindolin-2-yl, 2,3,4,5-tetrahydrobenzo[f][1,4]oxazepin-4-yl, 2-(3,4-dihydroisoquinolin-1(2H)-one), 2-(3,4-dihydroisoquinolin-1(2H)-one), 2,3-dihydro-1H-pyrido[2,3-b][1,4]oxazin-1-yl, piperidin-1-yl, 1-(1,2,3,4-tetrahydro-6H-pyrido[1,2-a]pyrimidin-6-one), 1,2,3,4-tetrahydro-1,8-naphthyridin-1-yl, 1-(3,4-dihydro-1,5-naphthyridin-2(1H)-one), 2,3,4,5-tetrahydro-1H-benzo[b]azepin-1-yl, 1-(2,3-dihydroquinolin-4(1H)-one), 2,3-dihydro-1H-pyrido[2,3-b][1,4]oxazin-1-yl, 1,2,3,4-tetrahydro-1,6-naphthyridin-1-yl, 5,6,7,8-tetrahydro-4H-pyrazolo[1,5-a][1,3]diazepin-4-yl, 3,4-dihydroquinoxalin-1-yl-2(1H)-one, 2,3,4,6-tetrahydro-1,6-naphthyridin-1-yl-5(1H)-one, 1,2,3,4-tetrahydroisoquinolin-2-yl, 1,2,3,4-tetrahydro-2,7-naphthyridin-2-yl, 1,2,3,4-tetrahydro-2,6-naphthyridin-2-yl, 3,4-dihydro-2H-benzo[b][1,4]thiazin-4-yl 11-dioxide, 1,2,3,4-tetrahydropyrazino[2,3-d]pyridazin-1-yl, 1,4-dihydropyrido[3,4-b]pyrazin-1-yl-3(2H)-one, 5,6,7,8-tetrahydro-1,6-naphthyridin-6-yl, 5,6,7,8-tetrahydro-1,7-naphthyridin-7-yl, 1,2,3,4-tetrahydropyrido[3,4-b]pyrazin-1-yl, 5,8-dihydropteridin-5-yl-7(6H)-one, 4,5,6,7-tetrahydrothieno[3,2-b]pyridin-4-yl, 5,6,7,8-tetrahydropyrazino[2,3-c]pyridazin-5-yl, and 1,2,6,7,8,9-hexahydro-3H-pyrrolo[3,4-f]quinolin-3-only; wherein the nitrogen ring moiety may be optionally substituted with one or two substituents each independently selected from the group consisting of Cl, F, —CN, $C_{1-4}$alkyl, —O$C_{1-4}$alkyl, $C_{2-6}$alkenyl, $C_{2-4}$alkynyl, $C_{3-6}$ cycloalkyl, $C_{5-6}$cycloalkenyl, —C(H)=N—OCH$_3$, —C(H)=N—OH, —C(CH$_3$)=N—OH, —(CH$_2$)$_{0-1}$C(O)NH$_2$, —(CH$_2$)$_{0-1}$C(O)NHC$_{1-4}$alkyl, —(CH$_2$)$_{0-1}$C(O)N(C$_{1-4}$alkyl)$_2$, —(CH$_2$)$_{0-1}$C(O)OC$_{1-4}$alkyl, —(CH$_2$)$_{0-1}$C(O)OH, —S(O)$_2$C$_{1-4}$alkyl, —(CH$_2$)$_{0-1}$NH$_2$, —(CH$_2$)$_{0-1}$NHC$_{1-4}$alkyl, —(CH$_2$)$_{0-1}$(C$_{1-4}$alkyl)$_2$, —(CH$_2$)$_{0-1}$NH(CO)C$_{1-4}$alkyl, phenyl, optionally substituted heteroaryl and optionally substituted heterocyclyl, wherein $C_{1-4}$alkyl or $C_{3-6}$cycloalkyl may be optionally substituted with cyano, one, two or three fluorine atoms, one or two hydroxyl groups, or one or two —O$C_{1-2}$alkyl groups.

In some embodiments, heteroaryl is selected from the group consisting of 2-pyridyl, 3-pyridyl, 4-pyridyl, 1,2,4-triazol-3-yl, thiazol-2-yl, pyrazol-1-yl, pyrazol-3-yl, pyrazol-4-yl, imidazol-2-yl, oxazol-2-yl, oxazol-5-yl, isoxazol-5-yl, thiazol-2-yl, thiazol-5-yl, 1,3,4-thiadiazol-2-yl, and 1,2,4-oxadiazol-3-yl, 1,3,4-oxadiazol-2-yl, 1,2,4-triazol-2-yl, and 1,3,4-triazol-2-yl; wherein heteroaryl may be optionally substituted with $C_{1-2}$alkyl (optionally substituted with one to three fluorine atoms, up to 2 hydroxyl groups, or up to two —O$C_{1-2}$ alkyl groups).

In some embodiments, heterocyclyl heterocyclyl is selected from the group consisting of tetrahydrofuran-3-yl, tetrahydrofuran-2-yl, pyrrolidine-1-yl, piperazin-1-yl, piperidin-4-yl, piperidin-1-yl, 1,2,3,6-tetrahydropyridin-4-yl, 2,5-dihydrofuran-3-yl, piperazin-1-yl-3-one, morpholino, tetrahydropyran-2-yl, 1,2,4-oxadiazo-3-yl-5-one, and pyrrolidin-2-one-4-yl; wherein heterocyclyl may be optionally substituted with hydroxyl or $C_{1-2}$alkyl (optionally substituted with one, two or three fluorine atoms, one or two 2 hydroxyl groups, or one or two —O$C_{1-2}$alkyl groups).

In some embodiments, $R^X$ together with $R^1$ and the nitrogen to which they are attached form a 1,2,3,4-tetrahydroquinoline moiety optionally substituted with one, two or three halo, —C(O)N($R^{10}$)$_2$, $C_{1-3}$alkyl, $C_{1-3}$haloalkyl, and heteroaryl (optionally substituted with one, two or three halogen, —C(O)N($R^{10}$)$_2$C$_{1-3}$alkyl, $C_{1-3}$alkyl-O—$C_{1-3}$alkyl, $C_{1-3}$alkyl-OH, or $C_{1-3}$ haloalkyl).

In some embodiments, $R^X$ together with $R^1$ and the nitrogen to which they are attached form a 1,2,3,4-tetrahydro-1,5,napthyridine moiety optionally substituted with one, two or three halo, —C(O)N($R^{10}$)$_2$, $C_{1-3}$alkyl, $C_{1-3}$haloalkyl, and heteroaryl (optionally substituted with one, two or three halogen, —C(O)N($R^{10}$)$_2$C$_{1-3}$alkyl, $C_{1-3}$alkyl-O—$C_{1-3}$alkyl, $C_{1-3}$ alkyl-OH, or $C_{1-3}$haloalkyl).

In some embodiments, $R^4$ and $R^5$ are independently selected from the group consisting of hydrogen, halogen, hydroxyl, —($C_1$-$C_3$)alkyl, —($C_1$-$C_3$)alkoxy, and —N(R)$_2$, wherein said —($C_1$-$C_3$)alkyl is optionally substituted with one or more substituents selected from the group consisting of —OH, —N($R^6$)$_2$, and halogen.

In some embodiments, $R^4$ and $R^5$ are independently selected from the group consisting of fluorine, $-NH_2$, $-CH_3$, $-OCH_3$, $-CH_2OH$, $-CH_2NH_2$ and $-CH(NH)_2CH_3$.

In some embodiments, $R^4$ and $R^5$ taken together, are selected from the group consisting of:

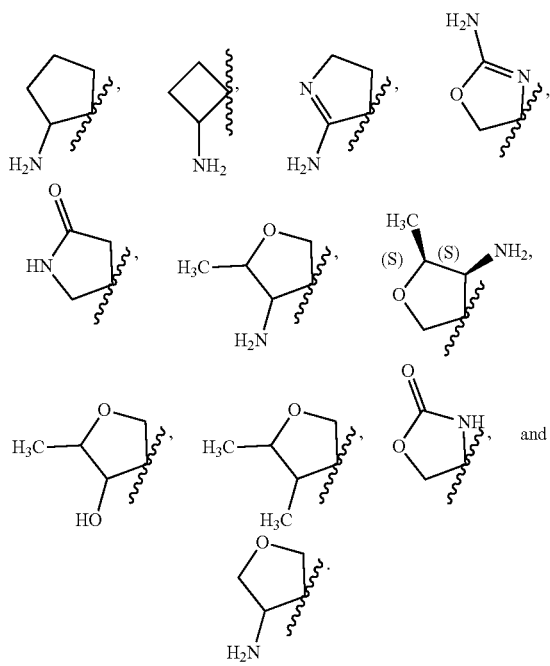

In some embodiments, q is 1.

Also disclosed herein, for example, is a compound of Formula III, or a pharmaceutically acceptable salt or stereoisomer thereof, wherein Formula III is represented by:

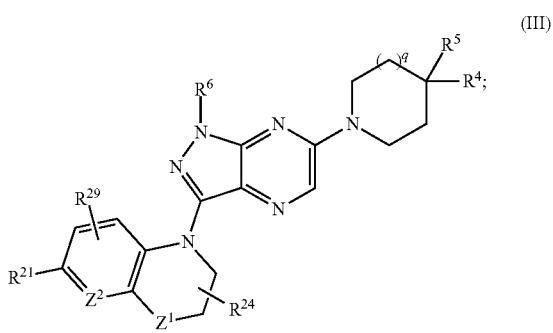

wherein:
$Z^2$ is selected from the group consisting of $CR^{22}$ and N;
$Z^1$ is selected from the group consisting of: $NR^{61}$, $C(R^{23})_2$; C(O), and O;
$R^{21}$ is selected from the group consisting of hydrogen, halogen, cyano, hydroxyl, $N(R^6)_2$, $C_1$-$C_6$alkyl, $C_3$-$C_6$cycloalkyl, $C_1$-$C_6$alkyoxy, $-C(O)N(R^6)_2$, heterocycloalkyl, phenyl, and heteroaryl, wherein $C_1$-$C_6$alkyl, $C_3$-$C_6$cycloalkyl, $C_1$-$C_6$alkyoxy, heterocycloalkyl, phenyl, and heteroaryl may each be substituted by one, two or three or more substituents each selected from the group consisting of halo, $-C(O)-OR^{26}$, $-C(O)R^{26}$, $-C(O)N(R^6)_2$, $-N(R^6)_2$, $C_{1-3}$ alkyl (optionally substituted by hydroxyl or methoxy), $C_1$-$C_3$alkyoxy, and $C_{1-3}$haloalkyl;

$R^{22}$ is independently selected from the group consisting of hydrogen, halogen, cyano, hydroxyl, $N(R^6)_2$, $C_1$-$C_6$alkyl, $C_3$-$C_6$cycloalkyl, $C_1$-$C_6$alkyoxy, $-C(O)N(R^6)_2$, heterocycloalkyl, phenyl, and heteroaryl, wherein $C_1$-$C_6$alkyl, $C_3$-$C_6$cycloalkyl, $C_1$-$C_6$alkyoxy, heterocycloalkyl, phenyl, and heteroaryl may each be substituted by one, two or three or more substituents each selected from the group consisting of halo, oxo, hydroxyl, cyano, $-C(O)-OR^{26}$, $-C(O)R^{26}$, $-C(O)N(R^6)_2$, $-N(R^6)_2$, $C_{1-3}$alkyl (optionally substituted by hydroxyl or methoxy), $C_1$-$C_3$alkyoxy, and $C_{1-3}$haloalkyl;

$R^{29}$ is selected from the group consisting of hydrogen, halogen, $N(R^6)_2$, $C_1$-$C_6$alkyl, $C_3$-$C_6$cycloalkyl, $C_1$-$C_6$alkyoxy, $-C(O)N(R^6)_2$, heterocycloalkyl, phenyl, and heteroaryl; wherein $C_1$-$C_6$alkyl, $C_3$-$C_6$cycloalkyl, $C_1$-$C_6$alkyoxy, heterocycloalkyl, phenyl, and heteroaryl may each be substituted by one, two or three or more substituents each selected from the group consisting of halo, $-C(O)R^{26}$, $-C(O)-OR^{26}$, $-C(O)N(R^6)_2$, $-N(R^6)_2$, $C_{1-3}$alkyl (optionally substituted by hydroxyl or methoxy) and $C_{1-3}$haloalkyl;

q is 0 or 1;
$R^{23}$ independently, for each occurrence, is selected from the group consisting of H, halogen, and $C_1$-$C_6$alkyl;
$R^{24}$ is selected from the group consisting of H, halogen, and $C_1$-$C_6$alkyl;
$R^{26}$ is selected from the group consisting of hydrogen and $C_{1-3}$alkyl;
$R^4$ and $R^5$ are each independently selected from the group consisting of hydrogen, $C_1$-$C_6$)alkyl, $-C(O)N(R^6)_2$, $-N(R^6)_2$, halogen, and cyano, wherein said $-(C_1$-$C_6)$alkyl is optionally substituted with one or more substituents selected from the group consisting of $-OH$, $-N(R^6)_2$, oxo, and halogen,
or $R^4$ and $R^5$, taken together with the carbon to which they are attached, form a 4-6 membered carbocyclic or heterocyclic ring, which ring is optionally substituted with one or two substituents each independently selected from the group consisting of $(C_1$-$C_6)$alkyl, $-O(C_1$-$C_6)$alkyl, $-N(R^6)_2$, $-C(O)N(R)_2$, halogen, oxo, and cyano;
$R^6$ is independently for each occurrence selected from the group consisting of H, $-(C_1$-$C_6)$alkyl, $-C(O)OC_{1-4}$alkyl, and phenyl; and
$R^{61}$ is selected from the group consisting of hydrogen, $-(C_1$-$C_6)$alkyl (optionally substituted with one or two halogens), $-C(O)-(C_1$-$C_6)$alkyl, $C_{3-6}$cycloalkyl (optionally substituted with one or two hydroxyl or $C_{1-2}$alkyl) and phenyl.

In some embodiments, $Z^2$ is N. In some embodiments, $Z^2$ is CH. In some embodiments, $Z^1$ is $C(R^{23})_2$.

In some embodiments, $R^{23}$ for each occurrence is hydrogen. In some embodiments, $R^{23}$ for each occurrence is methyl.

In some embodiments, $R^{22}$ and $R^{24}$, for each occurrence, is hydrogen.

In some embodiments, $R^{21}$ is selected from the group consisting of H, halogen, cyano, $CF_3$, $N(R^6)_2$, $C(O)N(R^6)_2$, heteroaryl, and phenyl. In some embodiments, $R^{21}$ is C(O)NHCH_3.

In some embodiments, $R^{21}$ is heteroaryl. In some embodiments, $R^{21}$ is selected from the group consisting of selected from the group consisting of:

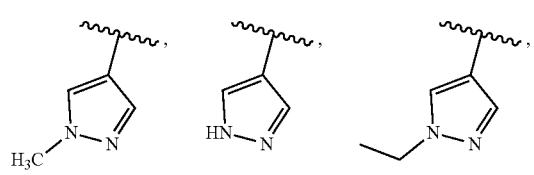

21
-continued

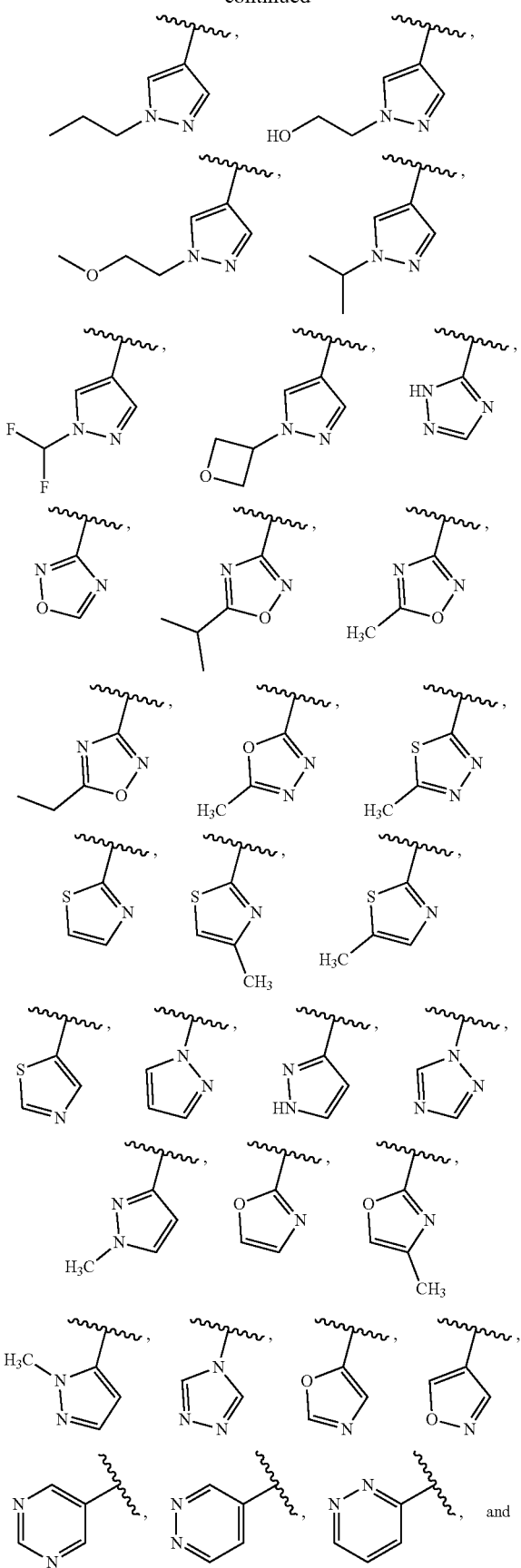

22
-continued

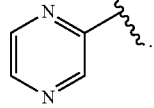

In some embodiments, $R^{21}$ is hydrogen.

In some embodiments, $R^4$ and $R^5$ are independently selected from the group consisting of hydrogen, halogen, hydroxyl, —$(C_1$-$C_3)$alkyl, —$(C_1$-$C_3)$alkoxy, and —$N(R)_2$, wherein said —$(C_1$-$C_3)$alkyl is optionally substituted with one or more substituents selected from the group consisting of —OH, —$N(R^6)_2$, and halogen.

In some embodiments, $R^4$ and $R^5$ are independently selected from the group consisting of fluorine, —$NH_2$, —$CH_3$, —$OCH_3$, —$CH_2OH$, —$CH_2NH_2$ and —CH$(NH_2)_2CH_3$.

In some embodiments, $R^4$ and $R^5$ taken together, are selected from the group consisting of:

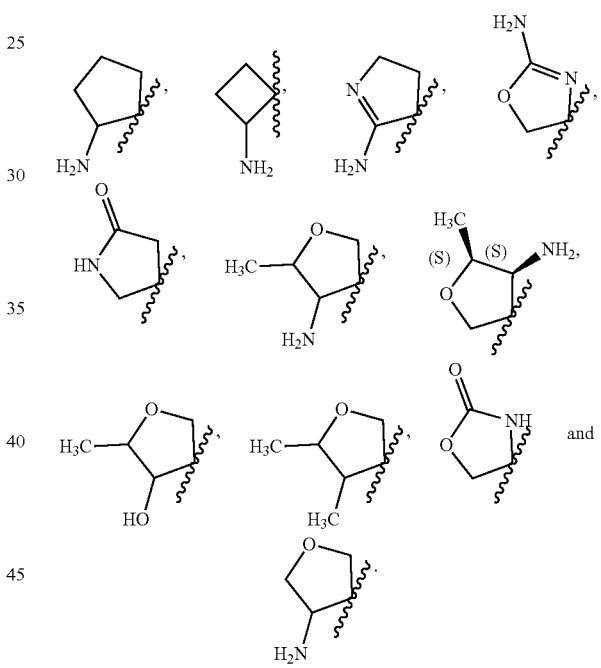

In some embodiments, q is 1.

Also disclosed herein, for example, is a compound of Formula IV, or a pharmaceutically acceptable salt or stereoisomer thereof, wherein Formula IV is represented by:

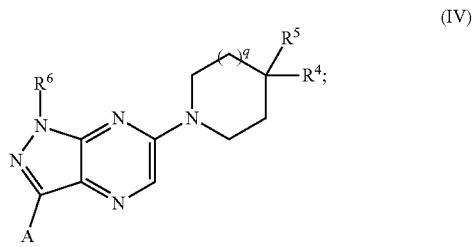

(IV)

wherein:

A is selected from the group consisting of:

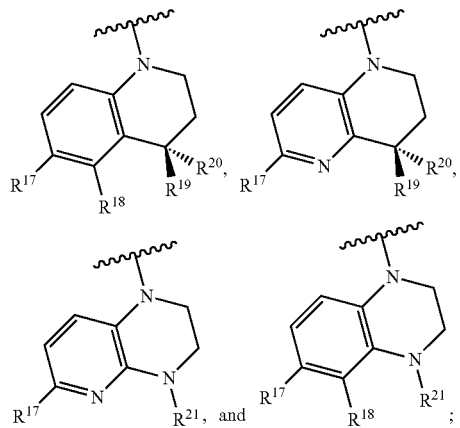

wherein:

$R^{17}$ is selected from the group consisting of H, Cl, F, $CHF_2$, $CF_3$, —CN, $C_{1-4}$alkyl, $C_{3-6}$ cycloalkyl, $C_{5-6}$cycloalkenyl, —$OC_{1-4}$alkyl, —O-heteroaryl, $C_{2-4}$alkenyl, $C_{2-4}$alkynyl, —C≡N—$OC_{1-4}$alkyl, —C≡N—OH, —$C(C_{1-4}$alkyl)=N—OH, —$(CH_2)_{0-1}C(O)NH_2$, —$(CH_2)_{0-1}C(O)NHC_{1-4}$alkyl, —$(CH_2)_{0-1}C(O)NHC_{1-4}$alkyl-heteroaryl, —$(CH_2)_{0-1}C(O)N(C_{1-4}$alkyl$)_2$, —$(CH_2)_{0-1}C(O)OC_{1-4}$alkyl, —$(CH_2)_{0-1}C(O)OH$, —$(CH_2)_{0-1}S(O)_2C_{1-4}$alkyl, —$(CH_2)_{0-1}NH_2$, —$(CH_2)_{0-1}NHC_{1-4}$alkyl, —$(CH_2)_{0-1}(C_{1-4}$alkyl$)_2$, —$(CH_2)_{0-1}NH(CO)C_{1-4}$alkyl, phenyl, heteroaryl, and heterocyclyl, wherein heteroaryl and O-heteroaryl may optionally be substituted with one or more $C_{1-2}$alkyl (optionally substituted with one, two or three fluorine atoms, one or two hydroxyl groups, or one or two —$OC_{1-2}$alkyl groups); and wherein heterocyclyl may optionally be substituted with one or more hydroxyl or $C_{1-2}$alkyl (optionally substituted with one, two or three fluorine atoms, one or two hydroxyl groups, or one or two —$OC_{1-2}$alkyl groups);

$R^{18}$ is selected from the group consisting of H, Cl, F, —CN, $NO_2$, $C_{1-4}$alkyl, $C_{3-4}$ cycloalkyl, $C_{2-4}$alkenyl, $C_{2-4}$alkynyl, —$OC_{1-4}$alkyl, —$(CH_2)_{0-1}C(O)NH_2$, —$(CH_2)_{0-1}C(O)NHC_{1-4}$alkyl, —$(CH_2)_{0-1}C(O)N(C_{1-4}$alkyl$)_2$, —$(CH_2)_{0-1}C(O)OC_{1-4}$alkyl, —$(CH_2)_{0-1}C(O)OH$, $NH_2$, —$NHC(O)C_{1-4}$alkyl, —$NHS(O)_2C_{1-4}$alkyl, —N(S(O)$_2C_{1-4}$alkyl$)_2$, —$N(C_{1-4}$alkyl$)S(O)_2C_{1-4}$alkyl, —N=S(O)($C_{1-4}$alkyl$)_2$, —$(CH_2)_{0-1}SC_{1-4}$alkyl, —$(CH_2)_{0-1}S(O)C_{1-4}$alkyl, —$(CH_2)_{0-1}S(O)_2C_{1-4}$alkyl, —$S(O)_2C_{3-4}$cycloalkyl, —$S(O)_2$heteroaryl, —S(O)(=NH)$C_{1-4}$alkyl, —S(O)(=$NC_{1-4}$alkyl)$C_{1-4}$alkyl, phenyl, heteroaryl, and heterocyclyl;

wherein phenyl, heteroaryl and heterocyclyl may optionally be substituted with one or more groups independently selected from the group consisting of F, $C_{1-2}$alkyl (optionally substituted with one, two or three fluorine atoms, one or two hydroxyl groups, or one or two —$OC_{1-2}$alkyl groups), cyclopropyl, —$C(O)NH_2$, —$C(O)NHC_{1-4}$alkyl, —$C(O)N(C_{1-4}$ alkyl$)_2$, —$C(O)OC_{1-4}$alkyl, and —C(O)OH;

each of $R^{19}$ and $R^{20}$ is independently selected from the group consisting of H and —$C_{1-4}$ alkyl; or $R^{19}$ and $R^{20}$ together with the carbon atom to which they are attached form a $C_{2-4}$ alkenyl moiety which may optionally be substituted with one or two fluorine atoms;

$R^{21}$ is selected from the group consisting of H, $C_{1-4}$alkyl, —$C_{3-4}$cycloalkyl, —$(CH_2)_{0-4}C(O)C_{1-4}$alkyl, —$(CH_2)_{0-4}C(O)OC_{1-4}$alkyl, —$(CH_2)_{0-4}C(O)NH_2$, —$(CH_2)_{0-4}C(O)NHC_{1-4}$alkyl, —$(CH_2)_{0-4}C(O)N(C_{1-4}$alkyl$)_2$, —$(CH_2)_{0-4}S(O)_2C_{1-4}$alkyl, and heterocyclyl;

wherein each $C_{1-4}$alkyl, $C_{2-4}$alkenyl, $C_{2-4}$alkynyl, $C_{3-4}$cycloalkyl, $C_{3-6}$cycloalkyl, or $C_{5-6}$cycloalkenyl of $R^7$, $R^{18}$, $R^{19}$, $R^{20}$, or $R^{21}$ may optionally be substituted with one, two or three fluorine atoms, one or two cyano groups, one or two hydroxyl groups, one or two —$C_{1-2}$ alkyl groups, or one or two —$OC_{1-2}$alkyl groups;

$R^4$ and $R^5$ are each independently selected from the group consisting of hydrogen, $C_1$-$C_6$)alkyl, —$C(O)N(R^6)_2$, —$N(R^6)_2$, halogen, and cyano, wherein said —($C_1$-$C_6$)alkyl is optionally substituted with one or more substituents selected from the group consisting of —OH, —$N(R^6)_2$, oxo, and halogen, or $R^4$ and $R^5$, taken together with the carbon to which they are attached, form a 4-6 membered carbocyclic or heterocyclic ring, which ring is optionally substituted with one or two substituents each independently selected from the group consisting of ($C_1$-$C_6$)alkyl, —O($C_1$-$C_6$)alkyl, —$N(R^6)_2$, —$C(O)N(R)_2$, halogen, oxo, and cyano; and $R^6$ is independently for each occurrence selected from the group consisting of H, —($C_1$-$C_6$)alkyl, —$C(O)OC_{1-4}$alkyl, and phenyl.

In some embodiments, $R^{17}$ is selected from the group consisting of 2-pyridyl, 3-pyridyl, 4-pyridyl, 1,2,4-triazol-3-yl, thiazol-2-yl, pyrazol-1-yl, pyrazol-3-yl, pyrazol-4-yl, imidazol-2-yl, oxazol-2-yl, oxazol-5-yl, isoxazol-5-yl, thiazol-2-yl, thiazol-5-yl, 1,3,4-thiadiazol-2-yl, 1,2,4-oxadiazol-3-yl, 1,3,4-oxadiazol-2-yl, 1,2,4-triazol-2-yl, and 1,3,4-triazol-2-yl; wherein $R^7$ may optionally be substituted with one, two or three fluorine atoms, one or two hydroxyl groups, or one or two —$OC_{1-2}$alkyl groups.

In some embodiments, $R^{17}$ is selected from the group consisting of tetrahydrofuran-3-yl, pyrrolidine-1-yl, piperazin-1-yl, piperidin-4-yl, piperidin-1-yl, 1,2,3,6-tetrahydropyridin-4-yl, 2,5-dihydrofuran-3-yl, piperazin-1-yl-3-one, morpholino, tetrahydropyran-2-yl, and 1,2,4-oxadiazo-3-yl-5-one; wherein $R^7$ may optionally be substituted with one or more hydroxyl or $C_{1-2}$alkyl (optionally substituted with one, two or three fluorine atoms, one or two hydroxyl groups, or one or two —$OC_{1-2}$alkyl groups).

In some embodiments, $R^{18}$ is selected from the group consisting of phenyl, 2-pyridyl, 3-pyridyl, 4-pyridyl, pyrazol-3-yl, pyrazol-4-yl, thiazol-2-yl, 1,2,4-oxadiazol-3-yl, and 1,3,4-oxadiazol-2-yl; wherein $R^{18}$ may optionally be substituted with one or more groups independently selected from the group consisting of F, $C_{1-2}$alkyl (optionally substituted with one, two or three fluorine atoms, one or two hydroxyl groups, or one or two —$OC_{1-2}$alkyl groups), cyclopropyl, —$C(O)NH_2$, —$C(O)NHC_{1-4}$alkyl, —$C(O)N(C_{1-4}$alkyl$)_2$, —$C(O)OC_{1-4}$alkyl, and —C(O)OH.

In some embodiments, $R^{18}$ is selected from the group consisting of —$(CH_2)_{0-1}$-morpholino, tetrahydropyranyl, tetrahydrofuranyl, oxiranyl, isothiazolidin-2-yl-1,1-dioxide, pyrrolidin-2-one-4-yl, and —$(CH_2)_{0-1}$-oxazolidin-3-yl-2-one; wherein $R^{18}$ may optionally be substituted with one or more groups independently selected from the group consisting of F, $C_{1-2}$alkyl (optionally substituted with one, two or three fluorine atoms, one or two hydroxyl groups, or one or two —$OC_{1-2}$alkyl groups), cyclopropyl, —$C(O)NH_2$, —$C(O)NHC_{1-4}$alkyl, —$C(O)N(C_{1-4}$alkyl$)_2$, —$C(O)OC_{1-4}$alkyl, and —C(O)OH.

In some embodiments, $R^{19}$ is —$CH_3$ or —$CHF_2$, $R^{20}$ is H, and the carbon to which $R^{19}$ and $R^{20}$ are attached has an (R)-configuration. In some embodiments, $R^{19}$ is H, $R^{20}$ is —CH$_3$ or —CHF$_2$, and the carbon to which R$^{19}$ and R$^{20}$ are attached has an (S)-configuration.

In some embodiments, R$^4$ and R$^5$ are independently selected from the group consisting of hydrogen, halogen, hydroxyl, —(C$_1$-C$_3$)alkyl, —(C$_1$-C$_3$)alkoxy, and —N(R$^6$)$_2$, wherein said —(C$_1$-C$_3$)alkyl is optionally substituted with one or more substituents selected from the group consisting of —OH, —N(R$^6$)$_2$, and halogen. In some embodiments, R$^4$ and R$^5$ are independently selected from the group consisting of fluorine, —NH$_2$, —CH$_3$, —OCH$_3$, —CH$_2$OH, —CH$_2$NH$_2$ and —CH(NH)$_2$CH$_3$.

In some embodiments, R$^4$ and R$^5$ taken together, are selected from the group consisting of:

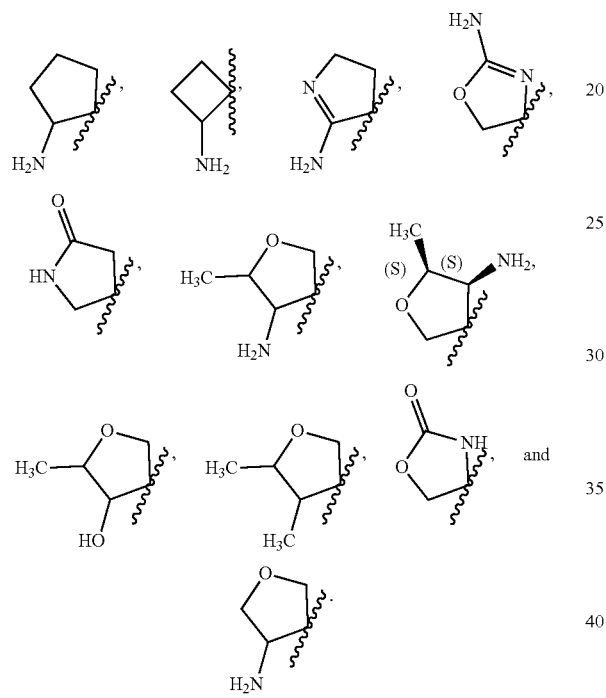

In some embodiments, q is 1.

In some embodiments, a disclosed compound is represented by any one of Formulas:

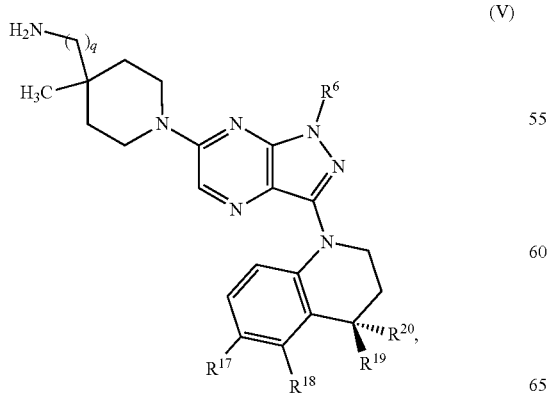
(V)

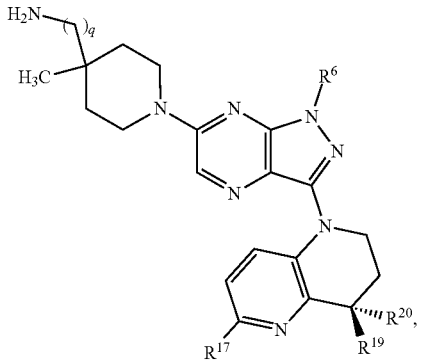
(VI)

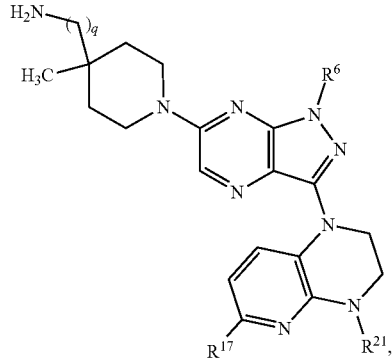
(VII)

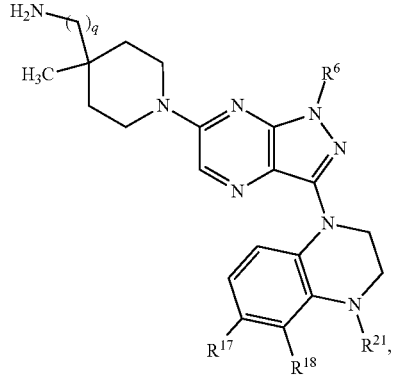
(VIII)

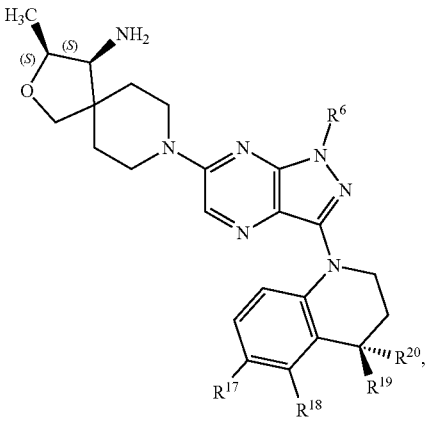
(IX)

-continued
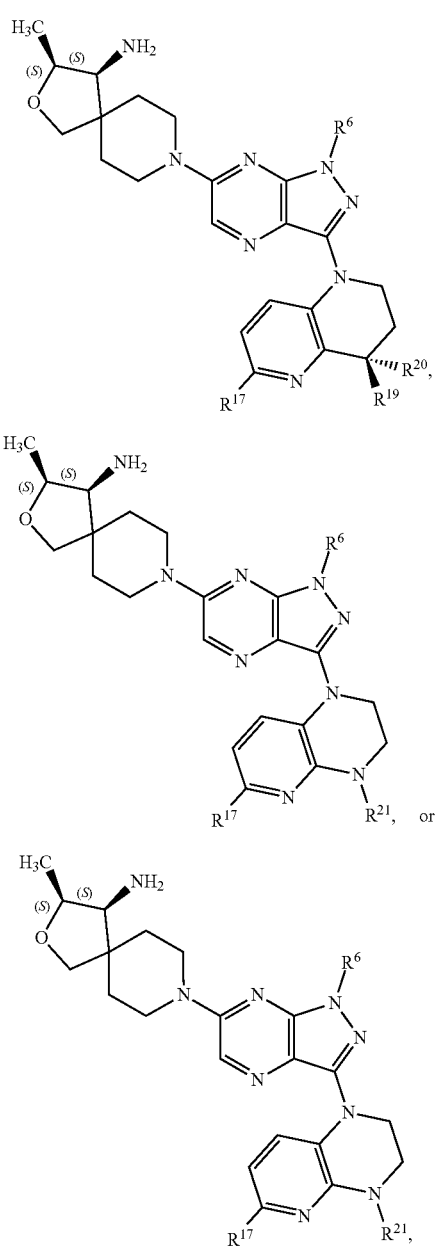
$R^6$ is H and each of q, $R^{17}$, $R^{18}$, $R^{19}$, $R^{20}$, and $R^{21}$ is as defined herein.
Examples of compounds of the present disclosure include those listed in Table 1, or a pharmaceutically acceptable salt or stereoisomer thereof.
In some embodiments, the moiety
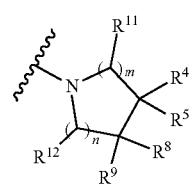
is selected from the group consisting of
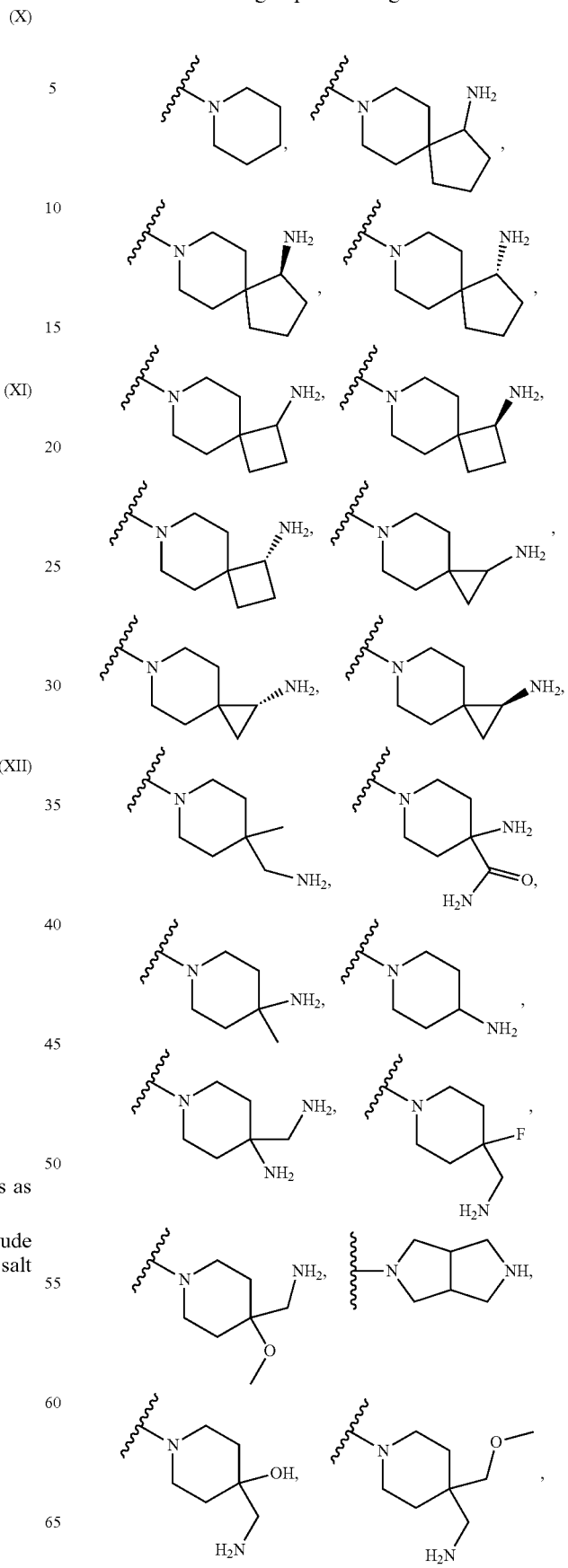

-continued

In some embodiments, the moiety is selected from the group consisting of

-continued

In some embodiments, the moiety shown below is referred to as $R^2$.

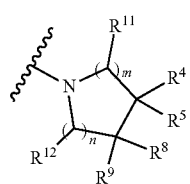

In some embodiments, $R^2$ is

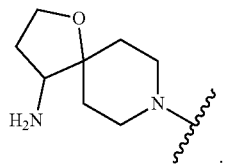 [SMILES: *N1CCC2(CC1)OCCC2N]

In some embodiments, $R^2$ is

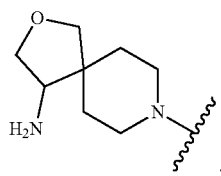 [SMILES: *N1CCC2(CC1)COCC2N]

In some embodiments, $R^2$ is

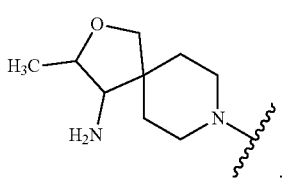 [SMILES: *N1CCC2(CC1)COC(C)C2N]

In some embodiments, $R^2$ is

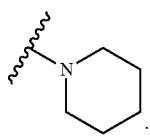

In some embodiments, $R^2$ is

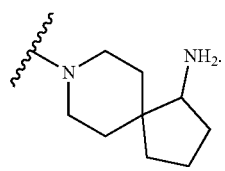 [SMILES: *N1CCC2(CCCC2N)CC1]

In some embodiments, $R^2$ is

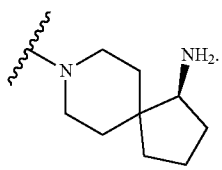 [SMILES: *N1CCC2(CCC[C@@H]2N)CC1]

In some embodiments, $R^2$ is

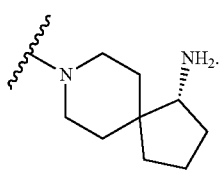 [SMILES: *N1CCC2(CCC[C@H]2N)CC1]

In some embodiments, $R^2$ is

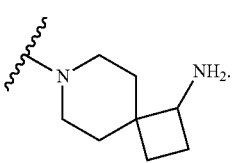 [SMILES: *N1CCC2(CCC2N)CC1]

In some embodiments, $R^2$ is

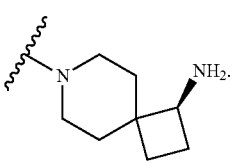 [SMILES: *N1CCC2(CC[C@@H]2N)CC1]

In some embodiments, $R^2$ is

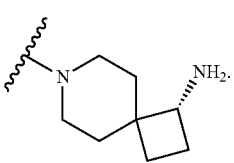 [SMILES: *N1CCC2(CC[C@H]2N)CC1]

In some embodiments, $R^2$ is

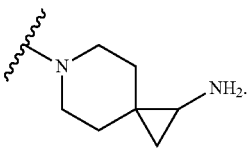 [SMILES: *N1CCC2(CC1)CC2N]

In some embodiments R² is
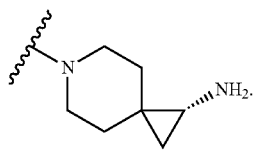 [SMILES: *N1CCC2(CC1)C[C@H]2N]
In some embodiments, R² is
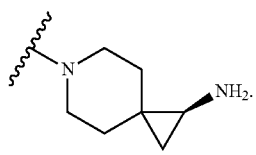 [SMILES: *N1CCC2(CC1)C[C@@H]2N]
In some embodiments, R² is
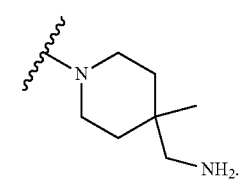 [SMILES: *N1CCC(C)(CN)CC1]
In some embodiments, R² is
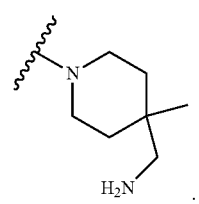
In some embodiments, R² is
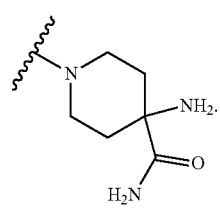 [SMILES: *N1CCC(N)(C(N)=O)CC1]
In some embodiments, R² is
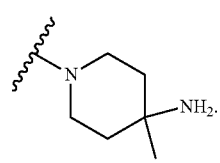 [SMILES: *N1CCC(C)(N)CC1]
In some embodiments, R² is
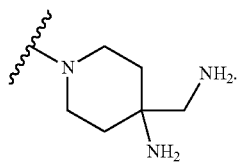 [SMILES: *N1CCC(N)(CN)CC1]
In some embodiments, R² is
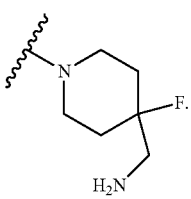
In some embodiments, R² is
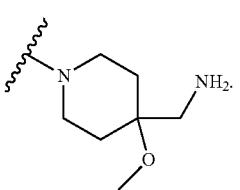 [SMILES: *N1CCC(CN)(OC)CC1]
In some embodiments, R² is
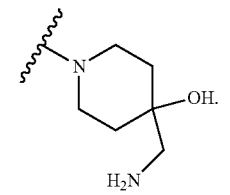 [SMILES: *N1CCC(O)(CN)CC1]
In some embodiments, R² is
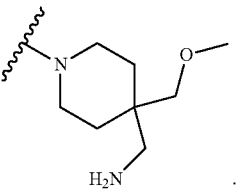
In some embodiments, R² is
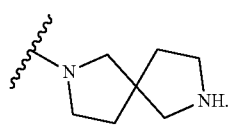 [SMILES: *N1CCC2(CCNC2)C1]

In some embodiments, R² is
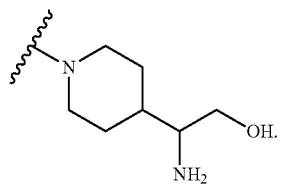
In some embodiments, R²
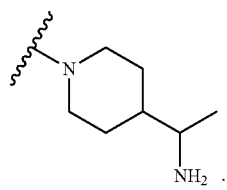 [SMILES: *N1CCC(C(C)N)CC1]
In some embodiments, R² is
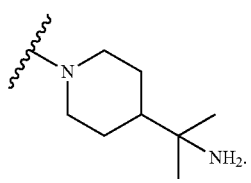 [SMILES: *N1CCC(C(C)(C)N)CC1]
In some embodiments, R² is
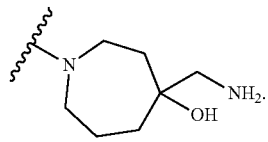 [SMILES: *N1CCCC(O)(CN)CC1]
In some embodiments, R² is
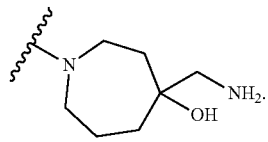 [SMILES: *N1CCCC(O)(CN)CC1]
In some embodiments, R2 is
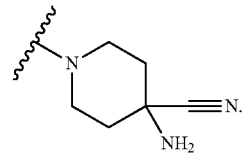
In some embodiments, R² is
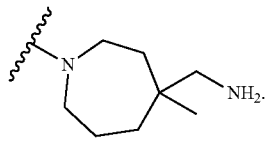 [SMILES: *N1CCCC(C)(CN)CC1]
In some embodiments, R² is
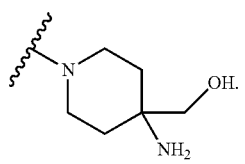
In some embodiments, R² is
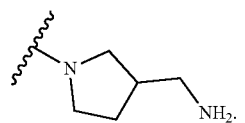 [SMILES: *N1CCC(CN)C1]
In some embodiments, R² is
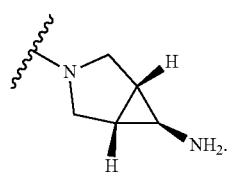 [SMILES: *N1C[C@@H]2[C@@H](N)[C@@H]2C1]
In some embodiments, R² is
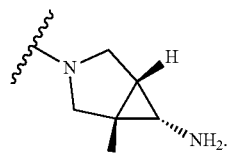
In some embodiments, R² is
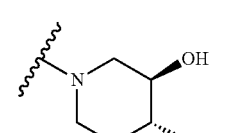

In some embodiments, R² is

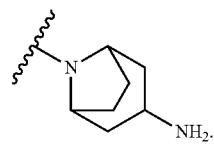 [SMILES: *N1C2CCC1CC(N)C2]

In some embodiments, R² is

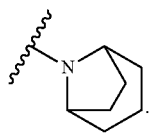

In some embodiments, R² is

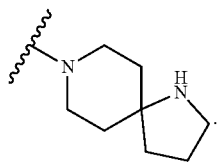 [SMILES: *N1CCC2(CCCN2)CC1]

In some embodiments, R² is

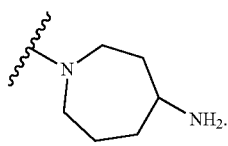 [SMILES: *N1CCCC(N)CC1]

In some embodiments, R² is

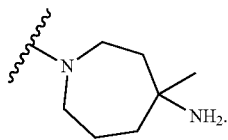 [SMILES: *N1CCCC(C)(N)CC1]

In some embodiments, R² is

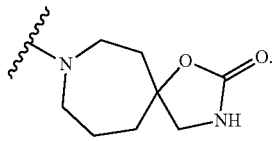 [SMILES: *N1CCCC2(CC1)CNC(=O)O2]

In some embodiments, R² is

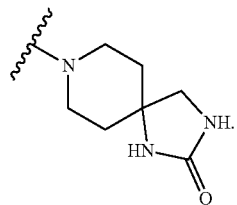 [SMILES: *N1CCC2(CC1)CNC(=O)N2]

In some embodiments, R² is

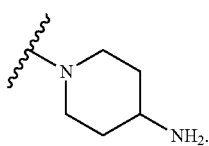

In some embodiments, R² is

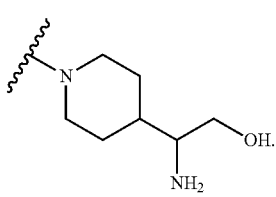

In some embodiments, R² is

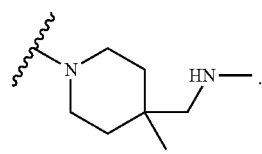 [SMILES: *N1CCC(C)(CNC)CC1]

In another embodiment, SHP2 phosphatase inhibitors described herein encompass compounds of Formula XIII, or a pharmaceutically acceptable salt or stereoisomer thereof, wherein Formula XIII is represented by:

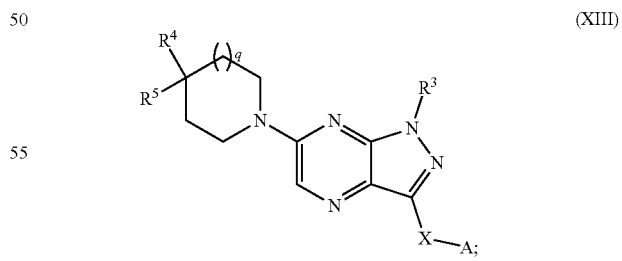

(XIII)

wherein:
X is selected from the group consisting of —NR^{X1}CH₂— and —S—CH₂—;
q is 0 or 1;
A is selected from the group consisting of phenyl and pyridyl, wherein A is optionally substituted with one, two or more substituents each independently selected from the group consisting of —R$^{10}$, —N(R)$_2$, —C(O)N(R)$_2$, oxo, halogen, and cyano;

or A is —C$_{1-6}$alkyl-NR$^a$R$^b$;

R$^{10}$ is independently selected for each occurrence from the group consisting of —(C$_1$-C$_6$)alkyl, —(C$_1$-C$_6$)haloalkyl, (C$_3$-C$_6$)cycloalkyl, heterocycloalkyl, phenyl, and heteroaryl, wherein R$^{10}$ may be substituted one, two or three or more substituents each selected from the group consisting of halo, C(O)R$^{20}$, C$_{1-6}$alkyl and C$_{1-6}$haloalkyl;

R$^{20}$ is selected from the group consisting of —OH, halo, or —(C$_1$-C$_6$)alkyl;

R$^{X1}$ is selected from the group consisting of hydrogen and C$_{1-6}$alkyl;

R$^3$ is selected from the group consisting of hydrogen and C$_{1-6}$alkyl;

R$^4$ and R$^5$ are each independently, selected from the group consisting of H, C$_1$-C$_6$)alkyl, —C(O)N(R$^6$)$_2$, —N(R$^6$)$_2$, halogen, and cyano; wherein —(C$_1$-C$_6$)alkyl is optionally substituted with one or more substituents selected from the group consisting of —OH, —N(R$^6$)$_2$, oxo, and halogen;

or R$^4$ and R$^5$, taken together with the carbon to which they are attached, form a 3-7 membered carbocyclic or heterocyclic ring, which ring is optionally substituted with one or two substituents each independently selected from the group consisting of (C$_1$-C$_6$)alkyl, —O(C$_1$-C$_6$)alkyl, —N(R$^6$)$_2$, —C(O)N(R$^6$)$_2$, halogen, oxo, and cyano; and R$^a$ and R$^b$ are independently selected, for each occurrence, from the group consisting of hydrogen and C$_{1-6}$ alkyl.

For example, the A moiety of Formula (XIII) may be phenyl; wherein phenyl may optionally be substituted by one, two, or three substituents each independently selected from the group consisting of —OR$^{10}$, halogen, and cyano; or A may be pyridyl; wherein pyridyl may optionally be substituted by one, two, or three substituents each independently selected from the group consisting of —OR$^{10}$, halogen, and cyano. In some embodiments, A may be selected from the group consisting of —CH$_2$—NH$_2$, —CH$_2$—N(H)CH— and —CH$_2$—N(CH$_3$)$_2$. In some embodiments, R$^3$ may be hydrogen.

In some embodiments, R$^4$ and R$^5$ of Formula (XIII) may be, for example, independently selected from the group consisting of —(C$_1$-C$_3$)alkyl and —N(R$^6$)$_2$, wherein —(C$_1$-C$_3$)alkyl is optionally substituted with one or more substituents each independently selected from the group consisting of hydroxyl, —N(R$^6$)$_2$, and halogen. For example, R$^4$ and R$^5$ may be independently selected from the group consisting of —NH$_2$, —CH$_3$, and —CH$_2$NH$_2$. In some embodiments, q is 1.

Additional SHP2 phosphatase inhibitors described herein encompass compounds of Formula (XIV), or a pharmaceutically acceptable salt or stereoisomer thereof, wherein Formula (XIV) is represented by:

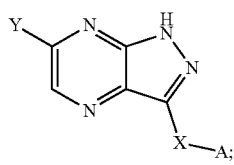

(XIV)

wherein:

X is selected from the group consisting of —NH—, —NCH$_3$—, —O— and —S—;

A is selected from the group consisting of phenyl, pyridyl, pyridonyl, piperidinyl, quinazolinyl, imidazo[1,2-a]pyridinyl, pyrazolo[1,5-a]pyridyl, indolyl, isoquinolinyl, and pyrrolo[2,3-b]pyridyl;

wherein A may optionally be substituted on one or more available carbons by a substituent each independently selected from R$^f$; and wherein pyridonyl, piperidinyl, indolyl, and pyrrolo[2,3-b]pyridyl may optionally be substituted on an available nitrogen by a substituent selected from R$_g$;

R$^f$ is independently selected for each occurrence from the group consisting of hydrogen, chloro, fluoro, —CH$_3$, —CF$_3$, —OCH$_3$, —NH$_2$, —N(H)CH$_3$, —C(O)—NH$_2$, —COOH, —C(NH)—O—C(O)—CF$_3$, —C$_{1-2}$alkyl-C(O)—O—C$_{1-2}$alkyl, and a 5-membered heteroaryl;

R$^g$ is selected from the group consisting of hydrogen, —CH$_3$, and —C(O)CH$_3$;

Y is represented by:

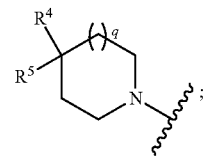

R4 is selected from the group consisting of fluoro and —CH$_3$;

R$^5$ is selected from the group consisting of —NH$_2$ and —CH$_2$—NH$_2$; or R$^4$ and R$^5$, taken together with the carbon to which they are attached, form a tetrahydrofuranyl or cyclopentyl ring; wherein tetrahydrofuranyl or cyclopentyl may optionally be substituted by one or two substituents each independently selected from the group consisting of —NH$_2$ and —CH$_3$; and is 0 or 1 e.g., q may be 0.

For example, Y may be:

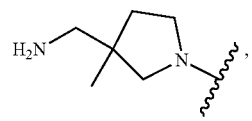

or for example, Y may be selected from the group consisting of

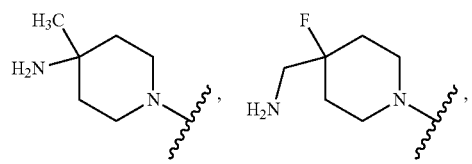

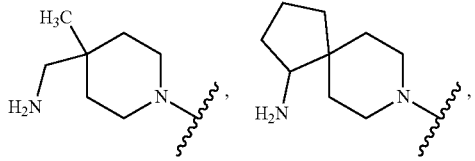

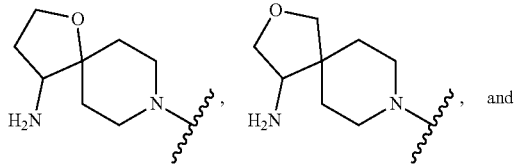

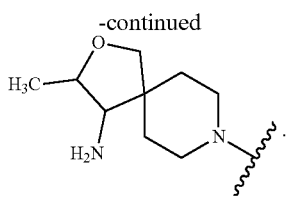

Compounds or compositions of the disclosure can be useful in applications that benefit from inhibition of SHP2 phosphatase enzymes. For example, inhibition of SHP2 phosphatase may offer a therapeutic approach for the treatment of cancer. (See, e.g., Y.-N. P. Chen et al., in Nature, 2016, doi:10.1038/nature18621; and references cited therein; each of which hereby incorporated by reference in its entirety.) Inhibition of SHP2 phosphatase also has been found to ameliorate the pathogensis of systemic lupus erythematosus. (See, e.g., J. Wang et al., in. *J. Clin. Invest.* 2016, 126, 2077-2092; and references cited therein; each of which hereby incorporated by reference in its entirety.)

In some embodiments, compounds or compositions of the disclosure can be useful in suppressing tumor cell growth. In some embodiments, compounds or compositions of the disclosure can be useful in ameliorating the pathogenesis of systemic lupus erythematosus. In some embodiments, compounds or compositions of the disclosure can be useful in the treatment of various other disorders, including Noonan syndrome (NS), diabetes, neuroblastoma, melanoma, juvenile leukemia, juvenile myelomonocytic leukemia (JMML), chronic myelomonocytic leukemia, acute myeloid leukemia, HER2-positive breast cancer, triple-negative breast cancer, ductal carcinoma of the breast, invasive ductal carcinoma of the breast, non-small cell lung cancer (including adenocarcinoma of the lung), colorectal cancer (SW480, SW620, CACO2, HCT116, HT29 colon cancer cell lines), esophageal cancer, gastric cancer, squamous-cell carcinoma of the head and neck (SCCHN), and neutropenia (Kostmann's syndrome).

In some embodiments, compounds or compositions of the disclosure can be used in combination with other treatments and/or cancer therapies. For example, compounds or compositions of the disclosure can be used in combination with, but are not limited to, antibodies, antibody-drug conjugates, kinase inhibitors, immunomodulators, and histone deacetylase inhibitors. The compounds or compositions of the disclosure can also be used in combination with other treatments and/or cancer therapies as disclosed in WO 2015/107495; and references cited therein; each of which is hereby incorporated by reference in its entirety. For example, the compounds disclosed herein (or pharmaceutical compositions containing them) can be used in the treatment of one or more of the diseases mentioned herein, alone or in combination with another therapeutic agent. For example, a compound disclosed herein can be used in combination with the following agents: BCR-ABL inhibitors: imatinib mesylate; inilotinib hydrochloride; nilotinib; dasatinib; bosutinib; ponatinib; bafetinib; danusertib; saracatinib; N-[2-[(1S,4R)-6-[[4-(Cyclobutylamino)-5-(trifluoromethyl)-2-pyrimidinyl]amino]-1,2,3,4-tetrahydronaphthalen-1,4-imin-9-yl]-2-oxoethyl]-acetamide. ALK inhibitors: crizotinib; 5-chloro-N4-(2-(isopropylsulfonyl)phenyl)-N2-(2-methoxy-4-(4-(4-methylpiperazin-1-yl)piperidin-1-yl)phenyl)pyrimidine-2,4-diamine, ceritinib, alectinib, brigatinib, entrecinib. BRAF inhibitors: vemurafenib and dabrafenib. FGFR inhibitors: infigratinib, dovitinib, erdafitinib, BLU-554, AZD4547, FLT3 inhibitors: sunitinib malate; midostaurin; tanutinib; sorafenib, lestaurtinib, quizartinib and crenolanib. MEK Inhibitors: trametinib, combimetinib, binimetinib, selumetinib. VEGF receptor inhibitors: bevacizumab, axitinib, aflibercept, (N-methyl-2-[[3-[(E)-2-pyridin-2-ylethenyl]-1H-indazol-6-yl]sulfanyl] benzamide, brivanib alaninate ((S)—(R)-1-(4-(4-Fluoro-2-methyl-1H-indol-5-yloxy)-5-methylpyrrolo[2,1-f][1,2,4]triazin-6-yloxy)propan-2-yl)2-aminopropanoate, motesanib (N-(2,3-dihydro-3,3-dimethyl-1H-indol-6-yl)-2-[(4-pyridinylmethyl)amino]-3-pyridinecarboxamide, pasireotide, sorafenib. Tyrosine kinase inhibitors: erlotinib hydrochloride, linifanib, sunitinib malate, pazopanib. Epidermal growth factor receptor (EGFR) inhibitors: gefitnib, osimertinib, cetuximab, panitumumab. HER2 receptor inhibitors: trastuzumab, neratinib, lapatinib or lapatinib ditosylate. MET inhibitors: crizotinib, cabozantinib. CD20 antibodies: rituximab, tositumomab, ofatumumab. DNA Synthesis inhibitors: capecitabine, gemcitabine hydrochloride, nelarabine, hydroxycarbamide. Antineoplastic agents: oxaliplatin. HER dimerization inhibitors: pertuzumab. Human Granulocyte colony-stimulating factor (G-CSF) modulators: filgrastim. Immunomodulators: Afutuzumab, lenalidomide, thalidomide. CD40 inhibitors: Dacetuzumab. Pro-apoptotic receptor agonists (PARAs): Dulanermin. Heat Shock Protein (HSP) inhibitors: Tanespimycin (17-allylamino-17-demethoxygeldanamycin). Hedgehog antagonists: 2-chloro-N-[4-chloro-3-(2-pyridinyl)phenyl]-4-(methylsulfonyl)-benzamide. Proteasome inhibitors: Bortezomib. PI3K inhibitors: 4-[2-(1H-Indazol-4-yl)-6-[[4-(methylsulfonyl)piperazin-1-yl]methyl]thieno[3,2-d]pyrimidin-4-yl]mocholine, 2-Methyl-2-[4-[3-methyl-2-oxo-8-(quinolin-3-yl)-2,3-dihydroimidazo[4,5-c]quinolin-1-yl]phenyl]propionitrile, buparlisib, taselisib, idelalisib, duvelisib, TGR 1202. Phospholipase A2 inhibitors: Anagrelide. BCL-2 inhibitors: 4-[4-[[2-(4-chlorophenyl)-5,5-dimethyl-1-cyclohexen-1-yl] methyl]-1-piperazinyl]-N-[[4-[[(1R)-3-(4-morpholinyl)-1-[(phenylthio)methyl]propyl] amino]-3-[(trifluoromethyl) sulfonyl]phenyl]sulfonyl]benzamide. Mitogen-activated protein kinase kinase (MEK) inhibitors: XL-518. Aromatase inhibitors: Exemestane, letrozole, anastrozole, faslodex, tamoxifen. Topoisomerase I inhibitors: Irinotecan, topotecan hydrochloride. Topoisomerase II inhibitors: etoposide, teniposide. mTOR inhibitors: Temsirolimus, ridaforolimus, everolimus. Osteoclastic bone resorption inhibitors: 1-Hydroxy-2-imidazol-1-yl-phosphonoethyl) phosphonic acid monohydrate. CD33 Antibody Drug Conjugates: Gemtuzumab ozogamicin. CD22 Antibody Drug Conjugates: Inotuzumab ozogamicin. CD20 Antibody Drug Conjugates: Ibritumomab tiuxetan. Somatostain analogs: octreotide. Synthetic Interleukin-11 (IL-11): oprelvekin. Synthetic erythropoietin: Darbepoetin alfa. Receptor Activator for Nuclear Factor κ B (RANK) inhibitors: Denosumab. Thrombopoietin mimetic peptides: Romiplostim. Cell growth stimulators: Palifermin. Anti-Insulin-like Growth Factor-1 receptor (IGF-1R) antibodies: Figitumumab. Anti-CS1 antibodies: Elotuzumab. CD52 antibodies: Alemtuzumab. CTLA-4 inhibitors: Tremelimumab, ipilimumab. PD1 inhibitors: Nivolumab; pembrolizumab; an immunoadhesin; Pidilizumab; and AMP-224. PDL1 inhibitors: MSB0010718C; YW243.55.S70, MPDL3280A; MEDI-4736, MSB-0010718C, or MDX-1105. LAG-3 inhibitors: BMS-986016. GITR agonists: GITR fusion proteins and anti-GITR antibodies. Histone deacetylase inhibitors (HDI): Voninostat. Anti-CTLA4 antibodies: Tremelimumab; and Ipilimumab. Alkylating agents: Temozolomide, dactinomycin, melphalan, altretamine carmustine, bendamustine, busulfan, carboplatin, lomustine, cisplatin, chlorambucil, cyclophosphamide, dacarbazine, altretamine, ifosfamide, procarbazine, mechlorethamine, mustine and mechloroethamine hydrochloride, streptozocin, thiotepa. Biologic response modifiers: *bacillus* calmette-guerin, denileukin diftitox. Anti-tumor antibiotics: doxorubicin, bleomycin, daunorubicin, daunorubicin liposomal, mitoxantrone, epirubicin, idarubicin, mitomycin C. Anti-microtubule agents: Estramustine. Cathepsin K inhibitors: Odanacatib. Epothilone B analogs: Ixabepilone. TpoR agonists: Eltrombopag. Anti-mitotic agents: Docetaxel. Adrenal steroid inhibitors: aminoglutethimide. Anti-androgens: Nilutamide, Androgen Receptor inhibitors: enzalutamide, abiraterone acetate, orteronel, galeterone, and seviteronel, bicalutamide, flutamide. Androgens: Fluoxymesterone. CDK1 inhibitors: Alvocidib, palbociclib, ribociclib, trilaciclib, abemaciclib. Gonadotropin-releasing hormone (GnRH) receptor agonists: Leuprolide or leuprolide acetate. Taxane anti-neoplastic agents: Cabazitaxel (1-hydroxy-10-dimethoxy-9-oxo-5,20-epoxytax-11-ene-2a,4,13a-triyl-4-acetate-2-benzoate-13-[(2R,3S)-3-{[(tert-butoxy)carbonyl] amino}-2-hydroxy-3-phenylpropanoate), larotaxel ((2α,3ξ, 4α,5β,7α,10β,13α)-4,10-bis(acetyloxy)-13-({(2R,3S)-3-[(tert-butoxycarbonyl) amino]-2-hydroxy-3-phenylpropanoyl}oxy)-1-hydroxy-9-oxo-5,20-epoxy-7,19-cyclotax-11-en-2-yl benzoate). 5HT1a receptor agonists: Xaliproden (also known as SR57746, 1-[2-(2-naphthyl) ethyl]-4-[3-(trifluoromethyl)phenyl]-1,2,3,6-tetrahydropyridine. HPC vaccines: Cervarix® sold by GlaxoSmithKline, Gardasil® sold by Merck; Iron Chelating agents: Deferasinox. Anti-metabolites: Claribine (2-chlorodeoxyadenosine), 5-fluorouracil, 6-thioguanine, pemetrexed, cytarabine, cytarabine liposomal, decitabine, hydroxyurea, fludarabine, floxuridine, cladribine, methotrexate, pentostatin. Bisphosphonates: Pamidronate. Demethylating agents: 5-azacitidine, decitabine. Plant Alkaloids: Paclitaxel protein-bound; vinblastine, vincristine, vinorelbine, paclitaxel. Retinoids: Alitretinoin (sold under the tradename Panretin®), tretinoin (all-trans retinoic acid, also known as ATRA, sold under the tradename Vesanoid®), Isotretinoin (13-cis-retinoic acid, sold under the tradenames Accutane®, Amnesteem®, Claravis®, Claras®, Decutan®, Isotane®, Izotech®, Oratane®, Isotret®, and Sotret®), bexarotene (sold under the tradename Targretin®). Glucocorticosteroids: Hydrocortisone (also known as cortisone, hydrocortisone sodium succinate, hydrocortisone sodium phosphate, and sold under the tradenames Ala-Cort®, Hydrocortisone Phosphate, Solu-Cortef®, Hydrocort Acetate® and Lanacort®), dexamethazone ((8S,9R,10S,11S,13S,14S,16R,17R)-9-fluoro-11,17-dihydroxy-17-(2-hydroxy acetyl)-10,13,16-trimethyl-6,7,8,9,10,11,12,13,14,15,16,17-dodecahydro-3H-cyclopenta[a] phenanthren-3-one), prednisolone (sold under the tradenames Delta-Cortel®, Orapred®, Pediapred® and Prelone®), prednisone (sold under the tradenames Deltasone®, Liquid Red®, Meticorten® and Orasone®), methylprednisolone (also known as 6-Methylprednisolone, Methylprednisolone Acetate, Methylprednisolone Sodium Succinate, sold under the tradenames Duralone®, Medralone®, Medrol®, M-Prednisol® and Solu-Medrol®). Cytokines: interleukin-2 (also known as aldesleukin and IL-2, sold under the tradename Proleukin®), interleukin-11 (also known as oprevelkin, sold under the tradename Neumega®), alpha interferon alfa (also known as IFN-alpha, sold under the tradenames Intron® A, and Roferon-A®). Estrogen receptor downregulators: Fulvestrant (sold under the tradename Faslodex®). Anti-estrogens: tamoxifen (sold under the tradename Novaldex®). Toremifene (sold under the tradename Fareston®). Selective estrogen receptor modulators (SERMs): Raloxifene (sold under the tradename Evista®). Leutinizing hormone releasing hormone (LHRH) agonists: Goserelin (sold under the tradename Zoladex®); Progesterones: megestrol (also known as megestrol acetate, sold under the tradename Megace®); Miscellaneous cytotoxic agents: Arsenic trioxide (sold under the tradename Trisenox®), asparaginase (also known as L-asparaginase, *Erwinia* L-asparaginase, sold under the tradenames Elspar® and Kidrolase®). Anti-nausea drugs: NK-1 receptor antagonists: Casopitant (sold under the tradenames Rezonic® and Zunrisa® by GlaxoSmithKline); and Cytoprotective agents: Amifostine (sold under the tradename Ethyol®), leucovorin (also known as calcium leucovorin, citrovorum factor and folinic acid). Immune checkpoint inhibitors: The term "immune checkpoints" refers to a group of molecules on the cell surface of CD4 and CD8 T cells. Immune checkpoint molecules include, but are not limited to, Programmed Death 1 (PD-1), Cytotoxic T-Lymphocyte Antigen 4 (CTLA-4), B7H1, B7H4, OX-40, CD 137, CD40, and LAG3. Immunotherapeutic agents which can act as immune checkpoint inhibitors useful in the methods of the present disclosure, include, but are not limited to, inhibitors of PD-L1, PD-L2, CTLA4, TIM3, LAG3, VISTA, BTLA, TIGIT, LAIR1, CD 160, 2B4 and/or TGFR beta.

The compounds described herein can function as allosteric inhibitors and block the activation of SHP2 by targeting the auto-inhibited conformation of SHP2.

The compounds described herein can also inhibit SHP2 function through incorporation into agents that catalyze the destruction of SHP2. For example, the compounds can be incorporated into proteolysis targeting chimeras (PROTACs). A PROTAC is a bifunctional molecule, with one portion capable of engaging an E3 ubiquitin ligase, and the other portion having the ability to bind to a target protein meant for degradation by the cellular protein quality control machinery. Recruitment of the target protein to the specific E3 ligase results in its tagging for destruction (i.e., ubiquitination) and subsequent degradation by the proteasome. Any E3 ligase can be used. The portion of the PROTAC that engages the E3 ligase is connected to the portion of the PROTAC that engages the target protein via a linker which consists of a variable chain of atoms. Recruitment of SHP2 to the E3 ligase will thus result in the destruction of the SHP2 protein. The variable chain of atoms can include, for example, rings, heteroatoms, and/or repeating polymeric units. It can be rigid or flexible. It can be attached to the two portions described above using standard techniques.

The compounds described herein can be linked to one end of a variable chain, while the other end of the variable chain can be bound to the E3 ligase. Recruitment of SHP2 to the ligase will thus result in the destruction of the SHP2 protein.

In some embodiments, compounds or compositions of the disclosure can be used in combination with an antibody. In some embodiments, compounds or compositions of the disclosure can be used in combination with an antibody-drug conjugate. In some embodiments, compounds or compositions of the disclosure can be used in combination with a kinase inhibitor. In some embodiments, compounds or compositions of the disclosure can be used in combination with an immunomodulator. In some embodiments, compounds or compositions of the disclosure can be used in combination with a histone deacetylase inhibitor.

In some embodiments, a compound disclosed herein can be administered to a subject in need of treatment at dosages ranging from about 0.0001 mg to about 100 mg/kg body weight of the subject to be treated per day, such as from about 1.0 to 10 mg/kg. However, additional variations are within the scope of the disclosure.

In some embodiments, a compound disclosed herein can be administered alone or in combination with pharmaceutically acceptable carriers, such as diluents, fillers, aqueous solution, and even organic solvents. The compound and/or compositions of the disclosure can be administered as a tablet, powder, lozenge, syrup, injectable solution, and the like. Additional ingredients, such as flavoring, binder, excipients, and the like are within the scope of the disclosure.

In some embodiments, pharmaceutically acceptable compositions can contain a compound disclosed herein and/or a pharmaceutically acceptable salt thereof at a concentration ranging from about 0.01 to about 2.0 wt %, such as 0.01 to about 1 wt % or about 0.05 to about 0.5 wt/o. The composition can be formulated as a solution, suspension, ointment, or a capsule, and the like. The pharmaceutical composition can be prepared as an aqueous solution and can contain additional components, such as preservatives, buffers, tonicity agents, antioxidants, stabilizers, viscosity-modifying ingredients and the like.

In some embodiments, the present disclosure provides for the use of pharmaceutical compositions and/or medicaments comprised of a compound disclosed herein or a pharmaceutically acceptable salt thereof, in a method of treating a disease state, and/or condition caused by or related to SHP2 phosphatase.

In some embodiments, the method of treatment comprises the steps of: i) identifying a subject in need of such treatment; (ii) providing a compound disclosed herein or a pharmaceutically acceptable salt thereof; and (iii) administering said disclosed compound in a therapeutically effective amount to treat, suppress and/or prevent the disease state or condition in a subject in need of such treatment.

In some embodiments, the method of treatment comprises the steps of: i) identifying a subject in need of such treatment; (ii) providing a composition comprising a compound disclosed herein or a pharmaceutically acceptable salt thereof; and (iii) administering said composition in a therapeutically effective amount to treat, suppress and/or prevent the disease state or condition in a subject in need of such treatment.

In some embodiments, the subject is an animal. Animals include all members of the animal kingdom, but are not limited to humans, mice, rats, cats, monkeys, dogs, horses, and swine. In some embodiments, the subject is a human. In some embodiments, the subject is a mouse, a rat, a cat, a monkey, a dog, a horse, or a pig.

In some embodiments, the compound or composition is administered orally. In some embodiments, the compound or composition is administered intravenously.

In some embodiments, the methods comprise administering to the subject an effective amount of a compound disclosed herein or a pharmaceutically acceptable salt thereof, or a composition comprising a compound disclosed herein or a pharmaceutically acceptable salt thereof, and a pharmaceutically acceptable carrier.

Pharmaceutically acceptable carriers are well-known to those skilled in the art, and include, e.g., adjuvants, diluents, excipients, fillers, lubricants and vehicles. In some embodiments, the carrier is a diluent, adjuvant, excipient, or vehicle. In some embodiments, the carrier is a diluent, adjuvant, or excipient. In some embodiments, the carrier is a diluent or adjuvant. In some embodiments, the carrier is an excipient. Often, the pharmaceutically acceptable carrier is chemically inert toward the active compounds and is non-toxic under the conditions of use. Examples of pharmaceutically acceptable carriers may include, e.g., water or saline solution, polymers such as polyethylene glycol, carbohydrates and derivatives thereof, oils, fatty acids, or alcohols. Non-limiting examples of oils as pharmaceutical carriers include oils of petroleum, animal, vegetable or synthetic origin, such as peanut oil, soybean oil, mineral oil, sesame oil and the like. The pharmaceutical carriers may also be saline, gum acacia, gelatin, starch paste, talc, keratin, colloidal silica, urea, and the like. In addition, auxiliary, stabilizing, thickening, lubricating and coloring agents may be used. Other examples of suitable pharmaceutical carriers are described in e.g., Remington's: The Science and Practice of Pharmacy, 22nd Ed. (Allen, Loyd V., Jr ed., Pharmaceutical Press (2012)); Modern Pharmaceutics, $5^{th}$ Ed. (Alexander T. Florence, Juergen Siepmann, CRC Press (2009)); Handbook of Pharmaceutical Excipients, $7^{th}$ Ed. (Rowe, Raymond C.; Sheskey, Paul J.; Cook, Walter G.; Fenton, Marian E. eds., Pharmaceutical Press (2012)) (each of which hereby incorporated by reference in its entirety).

In some embodiments, the method of treatment, prevention and/or suppression of a condition related to SHP2 phosphatase comprises the steps of: i) identifying a subject in need of such treatment; (ii) providing a compound disclosed herein or a pharmaceutically acceptable salt thereof; or a composition comprising a compound disclosed herein or a pharmaceutically acceptable salt thereof, and a pharmaceutically acceptable carrier; and (iii) administering said compound or composition in a therapeutically effective amount to treat, prevent and/or suppress the disease state or condition related to SHP2 phosphatase in a subject in need of such treatment.

In some embodiments, the compounds of the disclosure are formulated into pharmaceutical compositions for administration to subjects in a biologically compatible form suitable for administration in vivo. According to another aspect, the present disclosure provides a pharmaceutical composition comprising a compound disclosed herein in admixture with a pharmaceutically acceptable diluent and/or carrier. The pharmaceutically-acceptable carrier is "acceptable" in the sense of being compatible with the other ingredients of the composition and not deleterious to the recipient thereof. The pharmaceutically-acceptable carriers employed herein may be selected from various organic or inorganic materials that are used as materials for pharmaceutical formulations and which are incorporated as analgesic agents, buffers, binders, disintegrants, diluents, emulsifiers, excipients, extenders, glidants, solubilizers, stabilizers, suspending agents, tonicity agents, vehicles and viscosity-increasing agents. Pharmaceutical additives, such as antioxidants, aromatics, colorants, flavor-improving agents, preservatives, and sweeteners, may also be added. Examples of acceptable pharmaceutical carriers include carboxymethyl cellulose, crystalline cellulose, glycerin, gum arabic, lactose, magnesium stearate, methyl cellulose, powders, saline, sodium alginate, sucrose, starch, talc and water, among others. In some embodiments, the term "pharmaceutically acceptable" means approved by a regulatory agency of the Federal or a state government or listed in the U.S. Pharmacopeia or other generally recognized pharmacopeia for use in animals, and more particularly in humans.

Surfacta
nts such as, e.g., detergents, are also suitable for use in the formulations. Specific examples of surfactants include polyvinylpyrrolidone, polyvinyl alcohols, copolymers of vinyl acetate and of vinylpyrrolidone, polyethylene glycols, benzyl alcohol, mannitol, glycerol, sorbitol or polyoxyethylenated esters of sorbitan; lecithin or sodium carboxymethylcellulose; or acrylic derivatives, such as methacrylates and others, anionic surfactants, such as alkaline stearates, in particular sodium, potassium or ammonium stearate; calcium stearate or triethanolamine stearate; alkyl sulfates, in particular sodium lauryl sulfate and sodium cetyl sulfate; sodium dodecylbenzenesulphonate or sodium dioctyl sulphosuccinate; or fatty acids, in particular those derived from coconut oil, cationic surfactants, such as water-soluble quaternary ammonium salts of formula $N^+R'R''R'''R''''T$, in which the R radicals are identical or different optionally hydroxylated hydrocarbon radicals and Y is an anion of a strong acid, such as halide, sulfate and sulfonate anions; cetyltrimethylammonium bromide is one of the cationic surfactants which can be used, amine salts of formula $N^+R'R'R'''$, in which the R radicals are identical or different optionally hydroxylated hydrocarbon radicals; octadecylamine hydrochloride is one of the cationic surfactants which can be used, non-ionic surfactants, such as optionally polyoxyethylenated esters of sorbitan, in particular Polysorbate 80, or polyoxyethylenated alkyl ethers; polyethylene glycol stearate, polyoxyethylenated derivatives of castor oil, polyglycerol esters, polyoxyethylenated fatty alcohols, polyoxyethylenated fatty acids or copolymers of ethylene oxide and of propylene oxide, amphoteric surfactants, such as substituted lauryl compounds of betaine.

When administered to a subject, a compound disclosed herein and pharmaceutically acceptable carriers can be sterile. Suitable pharmaceutical carriers may also include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, polyethylene glycol 300, water, ethanol, polysorbate 20, and the like. The present compositions, if desired, may also contain minor amounts of wetting or emulsifying agents, or pH buffering agents.

The pharmaceutical formulations of the present disclosure are prepared by methods well-known in the pharmaceutical arts. Optionally, one or more accessory ingredients (e.g., buffers, flavoring agents, surface active agents, and the like) also are added. The choice of carrier is determined by the solubility and chemical nature of the compounds, chosen route of administration and standard pharmaceutical practice.

Additionally, the compounds and/or compositions of the present disclosure are administered to a human or animal subject by known procedures including oral administration, sublingual or buccal administration. In some embodiments, the compound and/or composition is administered orally.

For oral administration, a formulation of the compounds of the disclosure may be presented in dosage forms such as capsules, tablets, powders, granules, or as a suspension or solution. Capsule formulations may be gelatin, soft-gel or solid. Tablets and capsule formulations may further contain one or more adjuvants, binders, diluents, disintegrants, excipients, fillers, or lubricants, each of which are known in the art. Examples of such include carbohydrates such as lactose or sucrose, dibasic calcium phosphate anhydrous, corn starch, mannitol, xylitol, cellulose or derivatives thereof, microcrystalline cellulose, gelatin, stearates, silicon dioxide, talc, sodium starch glycolate, acacia, flavoring agents, preservatives, buffering agents, disintegrants, and colorants. Orally administered compositions may contain one or more optional agents such as, e.g., sweetening agents such as fructose, aspartame or saccharin; flavoring agents such as peppermint, oil of wintergreen, or cherry; coloring agents; and preservative agents, to provide a pharmaceutically palatable preparation.

In some embodiments, the composition is in unit dose form such as a tablet, capsule or single-dose vial. Suitable unit doses, i.e., therapeutically effective amounts, may be determined during clinical trials designed appropriately for each of the conditions for which administration of a chosen compound is indicated and will, of course, vary depending on the desired clinical endpoint.

In accordance with the methods of the present disclosure, the compounds of the disclosure are administered to the subject in a therapeutically effective amount, e.g., to reduce or ameliorate symptoms related to SHP2 phosphatase activity in the subject. This amount is readily determined by the skilled artisan, based upon known procedures, including analysis of titration curves established in vivo and methods and assays disclosed herein.

In some embodiments, the methods comprise administration of a therapeutically effective dosage of the compounds of the disclosure. In some embodiments, the therapeutically effective dosage is at least about 0.0001 mg/kg body weight, at least about 0.001 mg/kg body weight, at least about 0.01 mg/kg body weight, at least about 0.05 mg/kg body weight, at least about 0.1 mg/kg body weight, at least about 0.25 mg/kg body weight, at least about 0.3 mg/kg body weight, at least about 0.5 mg/kg body weight, at least about 0.75 mg/kg body weight, at least about 1 mg/kg body weight, at least about 2 mg/kg body weight, at least about 3 mg/kg body weight, at least about 4 mg/kg body weight, at least about 5 mg/kg body weight, at least about 6 mg/kg body weight, at least about 7 mg/kg body weight, at least about 8 mg/kg body weight, at least about 9 mg/kg body weight, at least about 10 mg/kg body weight, at least about 15 mg/kg body weight, at least about 20 mg/kg body weight, at least about 25 mg/kg body weight, at least about 30 mg/kg body weight, at least about 40 mg/kg body weight, at least about 50 mg/kg body weight, at least about 75 mg/kg body weight, at least about 100 mg/kg body weight, at least about 200 mg/kg body weight, at least about 250 mg/kg body weight, at least about 300 mg/kg body weight, at least about 350 mg/kg body weight, at least about 400 mg/kg body weight, at least about 450 mg/kg body weight, at least about 500 mg/kg body weight, at least about 550 mg/kg body weight, at least about 600 mg/kg body weight, at least about 650 mg/kg body weight, at least about 700 mg/kg body weight, at least about 750 mg/kg body weight, at least about 800 mg/kg body weight, at least about 900 mg/kg body weight, or at least about 1000 mg/kg body weight. It will be recognized that any of the dosages listed herein may constitute an upper or lower dosage range, and may be combined with any other dosage to constitute a dosage range comprising an upper and lower limit.

In some embodiments, the therapeutically effective dosage is in the range of about 0.1 mg to about 10 mg/kg body weight, about 0.1 mg to about 6 mg/kg body weight, about 0.1 mg to about 4 mg/kg body weight, or about 0.1 mg to about 2 mg/kg body weight.

In some embodiments the therapeutically effective dosage is in the range of about 1 to 500 mg, about 2 to 150 mg, about 2 to 120 mg, about 2 to 80 mg, about 2 to 40 mg, about 5 to 150 mg, about 5 to 120 mg, about 5 to 80 mg, about 10 to 150 mg, about 10 to 120 mg, about 10 to 80 mg, about 10 to 40 mg, about 20 to 150 mg, about 20 to 120 mg, about 20 to 80 mg, about 20 to 40 mg, about 40 to 150 mg, about 40 to 120 mg or about 40 to 80 mg.

In some embodiments, the methods comprise a single dosage or administration (e.g., as a single injection or deposition). Alternatively, the methods comprise administration once daily, twice daily, three times daily or four times daily to a subject in need thereof for a period of from about 2 to about 28 days, or from about 7 to about 10 days, or from about 7 to about 15 days, or longer. In some embodiments, the methods comprise chronic administration. In yet other embodiments, the methods comprise administration over the course of several weeks, months, years or decades. In still other embodiments, the methods comprise administration over the course of several weeks. In still other embodiments, the methods comprise administration over the course of several months. In still other embodiments, the methods comprise administration over the course of several years. In still other embodiments, the methods comprise administration over the course of several decades.

The dosage administered can vary depending upon known factors such as the pharmacodynamic characteristics of the active ingredient and its mode and route of administration; time of administration of active ingredient; age, sex, health and weight of the recipient; nature and extent of symptoms; kind of concurrent treatment, frequency of treatment and the effect desired; and rate of excretion. These are all readily determined and may be used by the skilled artisan to adjust or titrate dosages and/or dosing regimens.

The precise dose to be employed in the compositions will also depend on the route of administration, and should be decided according to the judgment of the practitioner and each subject's circumstances. In specific embodiments of the disclosure, suitable dose ranges for oral administration of the compounds of the disclosure are generally about 1 mg/day to about 1000 mg/day. In some embodiments, the oral dose is about 1 mg/day to about 800 mg/day. In some embodiments, the oral dose is about 1 mg/day to about 500 mg/day. In some embodiments, the oral dose is about 1 mg/day to about 250 mg/day. In some embodiments, the oral dose is about 1 mg/day to about 100 mg/day. In some embodiments, the oral dose is about 5 mg/day to about 50 mg/day. In some embodiments, the oral dose is about 5 mg/day. In some embodiments, the oral dose is about 10 mg/day. In some embodiments, the oral dose is about 20 mg/day. In some embodiments, the oral dose is about 30 mg/day. In some embodiments, the oral dose is about 40 mg/day. In some embodiments, the oral dose is about 50 mg/day. In some embodiments, the oral dose is about 60 mg/day. In some embodiments, the oral dose is about 70 mg/day. In some embodiments, the oral dose is about 100 mg/day. It will be recognized that any of the dosages listed herein may constitute an upper or lower dosage range, and may be combined with any other dosage to constitute a dosage range comprising an upper and lower limit.

Any of the compounds and/or compositions of the disclosure may be provided in a kit comprising the compounds and/or compositions. Thus, in some embodiments, the compound and/or composition of the disclosure is provided in a kit.

Those skilled in the art will recognize, or be able to ascertain using no more than routine experimentation, many equivalents to the specific embodiments of the disclosure described herein. Such equivalents are intended to be within the scope of the present disclosure.

The disclosure is further described by the following non-limiting Examples.

EXAMPLES

The compounds described herein can be prepared in a number of ways based on the teachings contained herein and synthetic procedures known in the art. In the description of the synthetic methods described below, it is to be understood that all proposed reaction conditions, including choice of solvent, reaction atmosphere, reaction temperature, duration of the experiment and workup procedures, can be chosen to be the conditions standard for that reaction, unless otherwise indicated. It is understood by one skilled in the art of organic synthesis that the functionality present on various portions of the molecule should be compatible with the reagents and reactions proposed. Substituents not compatible with the reaction conditions will be apparent to one skilled in the art, and alternate methods are therefore indicated. The starting materials for the examples are either commercially available or are readily prepared by standard methods from known materials.

At least some of the compounds identified as "Intermediates" herein are contemplated as compounds of the disclosure.

Examples are provided herein to facilitate a more complete understanding of the disclosure. The following examples serve to illustrate the exemplary modes of making and practicing the disclosure. However, the scope of the disclosure is not to be construed as limited to specific embodiments disclosed in these Examples, which are illustrative only. The compounds of Formula (I), for example, can generally be prepared according to exemplary Scheme 1:

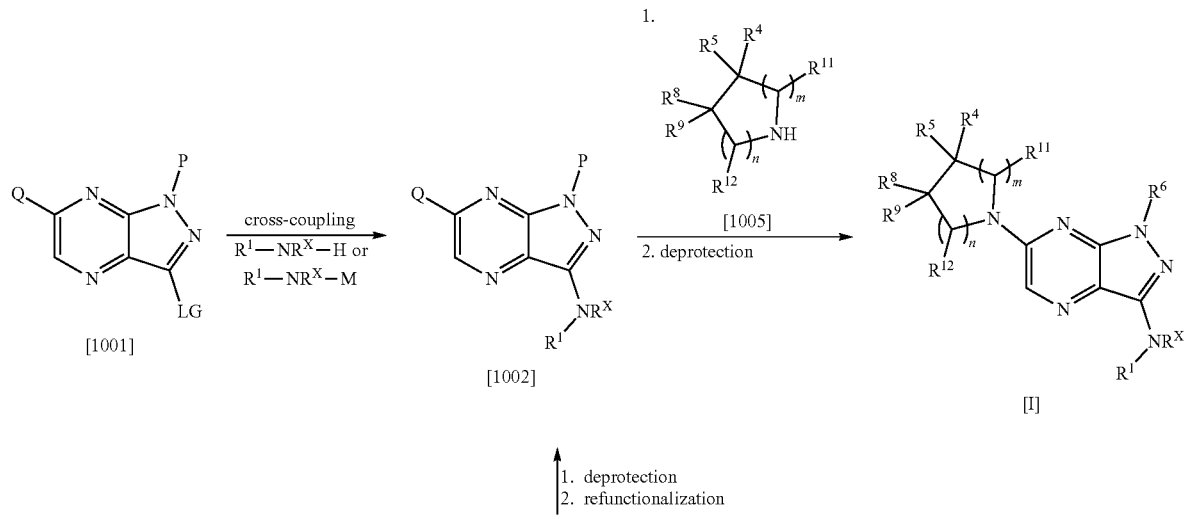

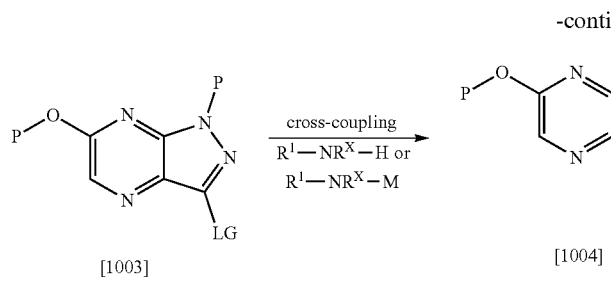

where $NR^X$, $R^1$, $R^4$, $R^5$, $R^6$, $R^8$, $R^9$, $R^{11}$, and $R^{12}$ are as defined as elsewhere herein, Q is independently a halogen, such as Cl, Br, i, and the like, or any other leaving group, such as $OSO_2Me$, OMs, OTs, OTf, and the like. LG is a leaving group, such as Cl, Br, I, OTs, OTf, and the like, and P is a protecting group, such as 4-methoxybenzyl and the like. Alternative protecting groups that can be used are described, e.g., in Greene el al., Protective Groups in Organic Synthesis (4$^{th}$ ed. 2006).

As shown in Scheme 1, an aryl compound such as a compound of Formula 1001 undergoes a cross-coupling reaction with a metalated or otherwise activated moiety to provide a compound of Formula 1002. The compound of Formula 1002 then undergoes a substitution reaction with an amine such as Compound 1005, followed by removal of the protecting group to provide a compound of Formula (I). In some embodiments, LG is I. In some embodiments, LG is Cl. In some embodiments, LG is OTf or OTs. Alternatively, a protected heteroaryl ether, such as a compound of Formula 1003, undergoes a cross-coupling reaction to provide a compound of Formula 1004. The ether protecting group is subsequently removed and the resulting hydroxyl group activated to form a Q group, such as $OSO_2Me$, OMs, OTs, OTf, and the like, to form a compound of Formula 1002, which can then be carried forward to prepare compounds having the Formula (I).

Alternatively, compounds of the invention can generally be prepared according to exemplary Scheme 2:

Scheme 2

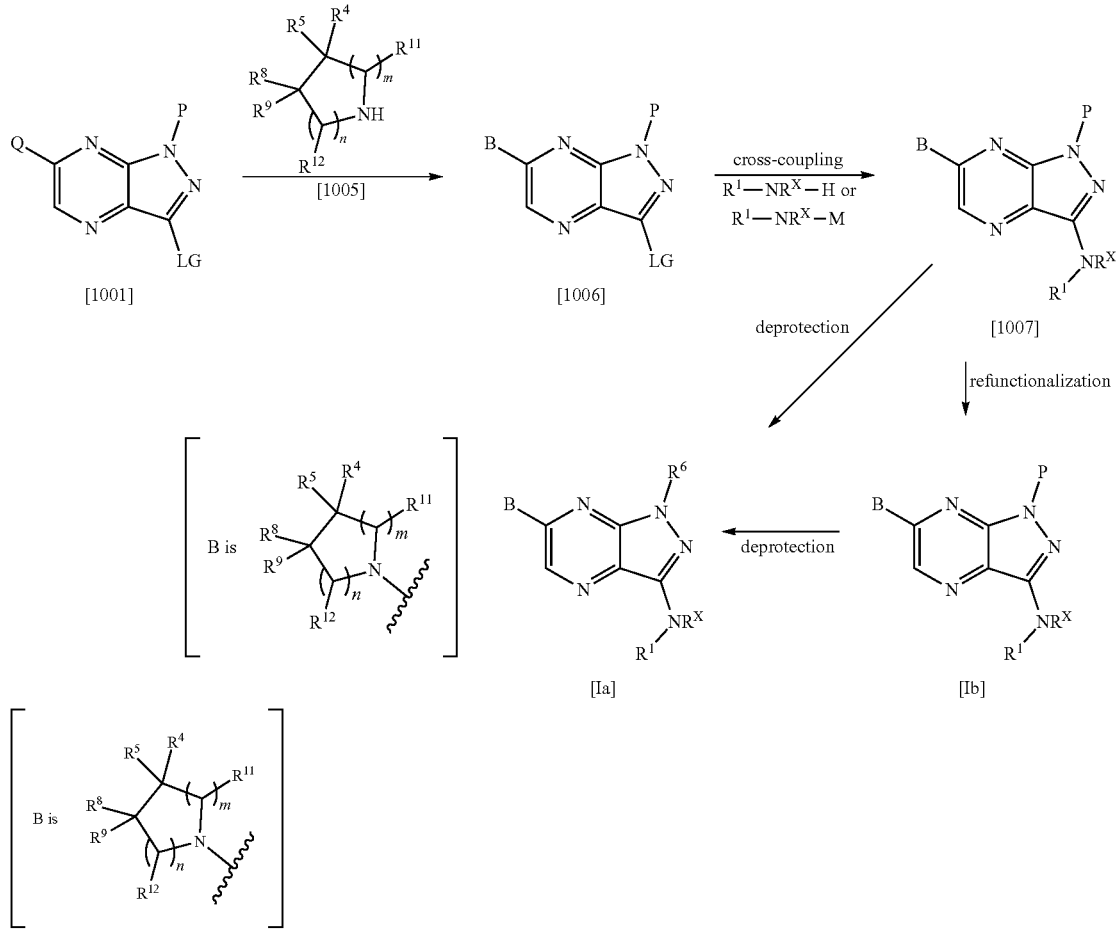

wherein $NR^X$, $R^1$, $R^4$, $R^5$, $R^6$, $R^8$, $R^9$, $R^{11}$, and $R^{12}$ are as defined as elsewhere herein, Q is independently a halogen, such as Cl, Br, I, and the like, or any other leaving group, such as $OSO_2Me$, OMs, OTs, OTf, and the like. LG is a leaving group, such as Cl, Br, I, OTs, OTf, and the like, and P is a protecting group, such as 4-methoxybenzyl and the like. Alternative protecting groups that can be used are described, e.g., in Greene et al., Protective Groups in Organic Synthesis (4$^{th}$ ed. 2006).

As shown in Scheme 2, an aryl compound such as a compound of Formula 1001 undergoes a undergoes a substitution reaction with an amine such as 1005 to provide a compound of Formula 1006. The compound of Formula 1006 then undergoes a cross-coupling reaction with a metalated or otherwise activated moiety to provide a compound of Formula 1007. In some embodiments, the compound of Formula 1007 can be deprotected to produce a compound of Formula (I). In other embodiments, the compound of Formula 1007 can be left protected and functional groups on the $R^1$ moiety refunctionalized by methods known to those of ordinary skill in the art.

In some embodiments, the cross-coupling reaction is a Buchwald-Hartwig reaction. In some embodiments, the cross-coupling reaction is a Chan-Lam coupling reaction. In some embodiments, the cross-coupling reaction is an Ullmann reaction. In some embodiments, the cross-coupling reaction is a Suzuki reaction. In some embodiments, the cross-coupling reaction is a Stille reaction. In some embodiments, the cross-coupling reaction is a Negishi reaction. In some embodiments, the cross-coupling reaction is a Hiyama reaction. Other cross-coupling reactions may be employed as would be apparent to one of ordinary skill in the art.

In some embodiments, the protecting group is removed under acidic conditions, such as HBr in AcOH, Conditions for removal of the protecting group will depend on the nature of the protecting group. Conditions for the removal of various protecting groups can be found, e.g., in Greene et al., Protective Groups in Organic Synthesis (4$^{th}$ ed 2006)

Reactions were monitored and final products were characterized using one of the following methods. LCMS standard conditions were: Waters HPLC system equipped with an Alliance 2695 main module, Waters 996 diode array detector and ZQ micromass ESI-MS detector. Mobile phase A: $H_2O$ (10.0 mM $NH_4HCO_2$), mobile phase B: $CH_3CN$. HPLC conditions were: XBridge C18 column, 4.6×30 mm, 3.5 μm, 0.0-0.2 min. isocratic (5% B), 0.2-2.0 min. gradient (5-100% B), 3.0-3.0 min. isocratic (100% B); flow rate: 3.0 mL/min; UV channel: 254 nm.

Purification of some racemic products was performed using semi preparative HPLC A, semi preparative HPLC B, or semi preparative SFC. Semi preparative HPLC A: Gilson 215 system equipped with a Waters 996 diode array detector and a Waters 2525 pump. Semi preparative HPLC B: Waters 2767 system equipped with a Waters 996 diode array detector, 2×Waters 515 pumps, a Waters 2525 pump and a ZQ micromass ESI-MS detector. Semi preparative SFC: Mettler Toledo Minigram SFC equipped with a Knauer K-2501 UV detector and an Alcott Model 1719 Autosampler.

Product homogeneity and enantiomeric excess determination were performed using Analytical HPLC A: Agilent 1100 HPLC system equipped with an Agilent G1315A diode array detector.

Nuclear Magnetic resonance: NMR spectra were recorded on Bruker Avance II Ultra shield spectrometer.

ABBREVIATIONS

Ac: acetyl
AcOH: acetic acid
ACN: acetonitrile
Ad: adamantyl
AIBN: 2,2'-azo bisisobutyronitrile
Anhyd: anhydrous
Aq: aqueous
$B_2Pin_2$: bis(pinacolato)diboron-4,4,4',4',5,5,5',5'-octamethyl-2,2'-bi(1,3,2-dioxaborolane)
BINAP: 2,2'-bis(diphenylphosphino)-1,1'-binaphthyl
$BH_3$: Borane
Bn: benzyl
Boc: tert-butoxycarbonyl
$Boc_2O$: di-tert-butyl dicarbonate
BPO: benzoyl peroxide
$^n$BuOH: n-butanol
CDI: carbonyldiimidazole
COD: cyclooctadiene
d: days
DABCO: 1,4-diazobicyclo[2.2.2]octane
DAST: diethylaminosulfur trifluoride
dba: dibenzylideneacetone
DBU: 1,8-diazobicyclo[5.4.0]undec-7-ene
DCE: 1,2-dichloroethane
DCM: dichloromethane
DEA: diethylamine
DHP: dihydropyran
DIBAL-H: diisobutylaluminum hydride
DIPA: diisopropylamine
DIPEA or DIEA: N,N-diisopropylethylamine
DMA: N,N-dimethylacetamide
DME: 1,2-dimethoxyethane
DMAP: 4-dimethylaminopyridine
DMF: N,N-dimethylformamide
DMP: Dess-Martin periodinane
DMSO-dimethyl sulfoxide
DPPA: diphenylphosphoryl azide
dppf: 1,1'-bis(diphenylphosphino)ferrocene
EDC or EDCI: 1-(3-dimethylaminopropyl)-3-ethylcarbodiimide hydrochloride
ee: enantiomeric excess
ESI: electrospray ionization
EA: ethyl acetate
EtOAc: ethyl acetate
EtOH: ethanol
FA: formic acid
h or hrs: hours
HATU: N,N,N',N'-tetramethyl-O-(7-azabenzotriazol-1-yl)uronium hexafluorophosphate
HCl: hydrochloric acid
HPLC: high performance liquid chromatography
HOAc: acetic acid
IBX: 2-iodoxybenzoic acid
IPA: isopropyl alcohol
KHMDS: potassium hexamethyldisilazide
$K_2CO_3$: potassium carbonate
LAH: lithium aluminum hydride
LDA: lithium diisopropylamide
m-CPBA: meta-chloroperbenzoic acid
M: molar
MeCN: acetonitrile
MeOH: methanol
$Me_2S$: dimethyl sulfide
MeONa: sodium methylate
MeI: iodomethane
min: minutes
mL: milliliters
mM: millimolar mmol: millimoles
MPa: mega pascal
MOMCL: methyl chloromethyl ether
MsCl: methanesulfonyl chloride
MTBE: methyl tert-butyl ether
nBuLi: n-butyllithium
NaNO$_2$: sodium nitrite
NaOH: sodium hydroxide
Na$_2$SO$_4$: sodium sulfate
NBS: N-bromosuccinimide
NCS: N-chlorosuccinimide
NFSI: N-Fluorobenzenesulfonimide
NMO: N-methylmorpholine N-oxide
NMP: N-methylpyrrolidine
NMR: Nuclear Magnetic Resonance
° C.: degrees Celsius
Pd/C: Palladium on Carbon
Pd(OAc)$_2$: Palladium Acetate
PBS: phosphate buffered saline
PE: petroleum ether
POCl$_3$: phosphorus oxychloride
PPh$_3$: triphenylphosphine
PyBOP: (Benzotriazol-1-yloxy)tripyrrolidinophosphonium hexafluorophosphate
Rel: relative
R.T, or rt: room temperature
RuPhos: 2-Dicyclohexylphosphino-2',6'-diisopropoxybiphenyl
sat: saturated
SEMCl: chloromethyl-2-trimethylsilylethyl ether
SFC: supercritical fluid chromatography
SOCl$_2$: sulfur dichloride
tBuOK: potassium tert-butoxide
TBAB: tetrabutylammonium bromide
TBAI: tetrabutylammonium iodide
TEA: triethylamine
Tf: trifluoromethanesulfonate
TfAA, TFMSA or Tf$_2$O: trifluoromethanesulfonic anhydride
TFA: trifluoracetic acid
TIPS: triisopropylsilyl
THF: tetrahydrofuran
THP: tetrahydropyran
TLC: thin layer chromatography
TMEDA: tetramethylethylenediamine
pTSA: para-toluenesulfonic acid
wt: weight
Xantphos: 4,5-bis(diphenylphosphino)-9,9-dimethylxanthene Syntheses of Intermediates Synthesis of tert-butyl ((1-(3-bromo-1-(4-methoxybenzyl)-1H-pyrazolo[3,4-b]pyrazin-6-yl-3-methylpyrrolidin-3-yl)methyl)carbamate, Used in the Preparation of Compound 26

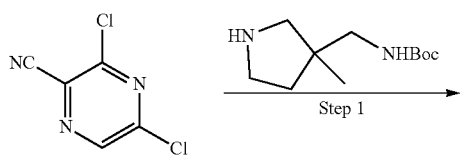

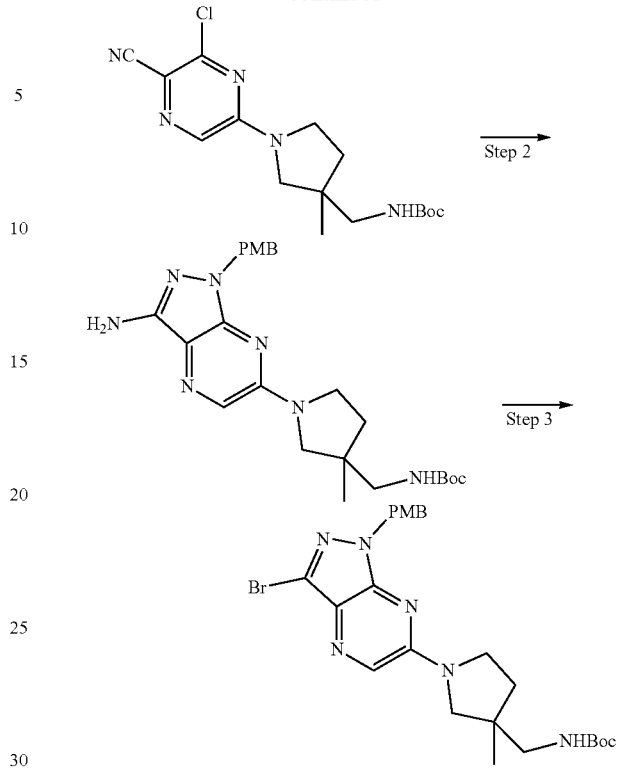

Step 1: A mixture of tert-butyl ((3-methylpyrrolidin-3-yl)methyl)carbamate (1.0 g, 4.7 mmol, CAS #125290-87-1), 3,5-dichloropyrazine-2-carbonitrile (810.0 mg, 4.7 mmol, CAS #313339-92-) and DIPEA (3.0 g, 23.3 mmol) in DMF (25.0 mL) was stirred at 70° C. for 2 hours. The reaction mixture was diluted with water (50 mL), and extracted with ethyl acetate (50 mL×2). The combined organic layers were washed with brine (30 mL), dried over anhydrous Na$_2$SO$_4$, filtered and concentrated under reduced pressure to give a residue, which was purified by column chromatography (Petroleum ether: Ethyl acetate=6:1~4:1) to afford tert-butyl ((1-(6-chloro-5-cyanopyrazin-2-yl)-3-methylpyrrolidin-3-yl)methyl)carbamate (1.4 g, 79.7% yield) as a yellow oil.

Step 2: To a mixture of (4-methoxybenzyl)hydrazine dihydrochloride (1.1 g, 4.8 mmol) and triethylamine (2.0 g, 19.9 mmol) in EtOH (30.0 mL) was added tert-butyl ((1-(6-chloro-5-cyanopyrazin-2-yl)-3-methylpyrrolidin-3-yl)methyl)carbamate (1.4 g, 4.0 mmol). The reaction mixture was stirred at 90° C. for 18 hours. On completion, the reaction mixture was concentrated in vacuo to give a residue, which was purified by column chromatography (Petroleum ether: Ethyl acetate=7:1 to 3:1) to afford the product of tert-butyl ((1-(3-amino-1-(4-methoxybenzyl)-1H-pyrazolo[3,4-b]pyrazin-6-yl)-3-methylpyrrolidin-3-yl)methyl)carbamate (1.4 g, 73.1% yield) as a yellow solid. LCMS m/z: 468.2 (M+H)$^+$ Step 3: To a mixture of tert-butyl ((1-(3-amino-1-(4-methoxybenzyl)-1H-pyrazolo[3,4-b]pyrazin-6-yl)-3-methylpyrrolidin-3-yl)methyl)carbamate (1.3 g, 2.8 mmol) and NaNO$_2$ (229.0 mg, 3.3 mmol) in MeCN (30.0 mL) at 0° C. was added HBr (4.8 g, 27.7 mmol, 47%), then the mixture was stirred at 0° C. for 1 hour. Next, CuBr (39.8 mg, 278.0 umol) was added at 0° C., and the reaction mixture was stirred for another 1 hour. The reaction was quenched with sat Na$_2$SO$_3$ (5.0 mL) and the reaction mixture was concentrated in vacuo to give a residue. The residue was dissolved in water (20.0 mL) and adjusted to pH=10 at 0° C. with NH₃.H₂O, which was then extracted with ethyl acetate (25.0 mL×2). The combined organic layers were washed with water (20.0 mL) and brine (20.0 mL), dried over anhydrous Na₂SO₄, filtered and concentrated in vacuo to give a residue, which was purified by column chromatography (petroleum ether: ethyl acetate=4:1~1:1) to afford the product of tert-butyl ((1-(3-bromo-1-(4-methoxybenzyl)-1H-pyrazolo[3,4-b]pyrazin-6-yl)-3-methylpyrrolidin-3-yl)methyl)carbamate (830.0 mg, 54.7% yield) as a yellow solid. LCMS m/z: 531.1/533.1 (M+H)⁺.

Synthesis of tert-butyl ((1-(3-iodo-1-(tetrahydro-2H-pyran-2-yl)-1H-pyrazolo[3,4-b]pyrazin-6-yl)-4-methylpiperidin-4-yl)methyl)carbamate, Used in the Preparation of Compound 33

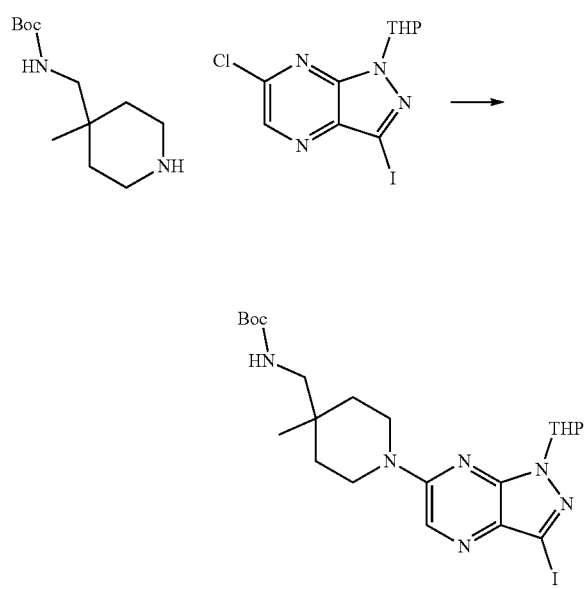

To a solution of 6-chloro-3-iodo-1-(tetrahydro-2H-pyran-2-yl)-1H-pyrazolo[3,4-b]pyrazine (CAS 2215028-64-9) (5 g, 13.7 mmol) and tert-butyl ((4-methylpiperidin-4-yl)methyl)carbamate (3.42 g, 15.0 mmol, CAS #1158759-03-5) in DMF (50 mL) was added N-ethyl-N-isopropylpropan-2-amine (7.12 mL, 41.0 mmol). The reaction mixture was stirred at room temperature for 12 h. On completion, EtOAc and water were added and the layers separated. The aqueous layer was extracted with EtOAc (3×). The combined organic layers were washed with brine, dried over Na₂SO₄, filtered and concentrated. The residue was purified by silica gel chromatography with 30% EtOAc in heptanes. Tert-butyl ((1-(3-iodo-1-(tetrahydro-2H-pyran-2-yl)-1H-pyrazolo[3,4-b]pyrazin-6-yl)-4-methylpiperidin-4-yl)methyl)carbamate (7.49 g, 13.4 mmol) was obtained as a light yellow powder. LCMS m/z: 557.3 (M+H)⁺.

Preparation of 5-(pyridin-2-yl)-1,2,3,4-tetrahydroquinoline, Used in the Synthesis of Compound 59

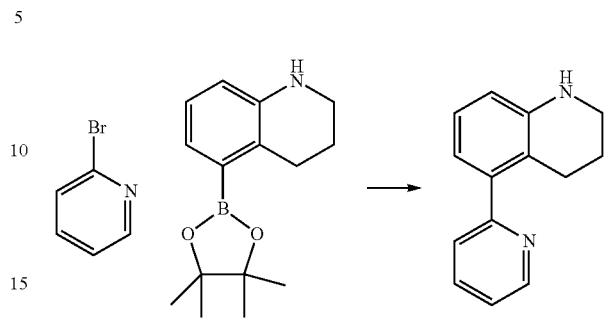

5-(Pyridin-2-yl)-1,2,3,4-tetrahydroquinoline was prepared from 2-bromopyridine in similar manner as described for (5-(4-methylpyridin-3-yl)-1,2,3,4-tetrahydroquinoline). LCMS: [M+H]⁺=211.

Preparation of 2-(1,2,3,4-tetrahydroquinolin-5-yl)thiazole, Used in the Synthesis of Compound 64

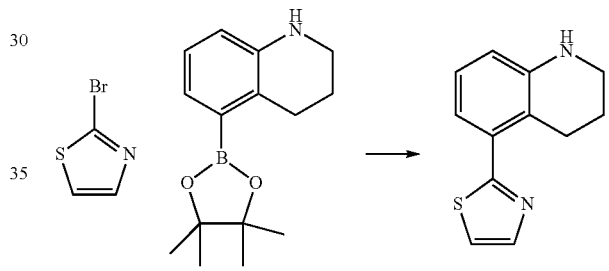

2-(1,2,3,4-Tetrahydroquinolin-5-yl)thiazole was prepared from 2-bromothiazole in similar manner as (5-(4-methylpyridin-3-yl)-1,2,3,4-tetrahydroquinoline). LCMS: [M+H]⁺=217.

Synthesis of 5-phenyl-1,2,3,4-tetrahydroquinoline, Used in the Preparation of Compound 65

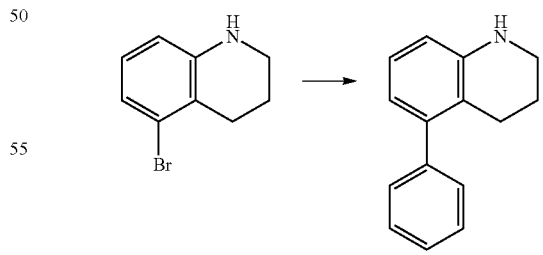

A mixture of 5-bromo-1,2,3,4-tetrahydroquinoline (300 mg, 1.4 mmol, 1.0 eq), phenylboronic acid (188 mg, 1.5 mmol, 1.1 eq), cesium carbonate (1.37 g, 4.2 mmol, 3.0 eq), and Pd(dppf)Cl₂ (103 mg, 141 µmol, 0.1 eq) in dioxane (10 mL) and water (1 mL) was evacuated and refilled with nitrogen three times. The the mixture was stirred at 100° C. for 15 h before being concentrated in vacuo. The residue was purified by silica gel chromatography (eluting with petroleum ether/ethyl acetate) to afford 5-phenyl-1,2,3,4-tetrahydroquinoline (270 mg, 91.5% yield) as a yellow oil.

Synthesis of 4-methyl-1-(3-(5-(pyridin-3-yl)-3,4-dihydroquinolin-1(2H)-yl)-1H-pyrazolo[3,4-b]pyrazin-6-yl)piperidin-4-amine, Used in the Preparation of Compound

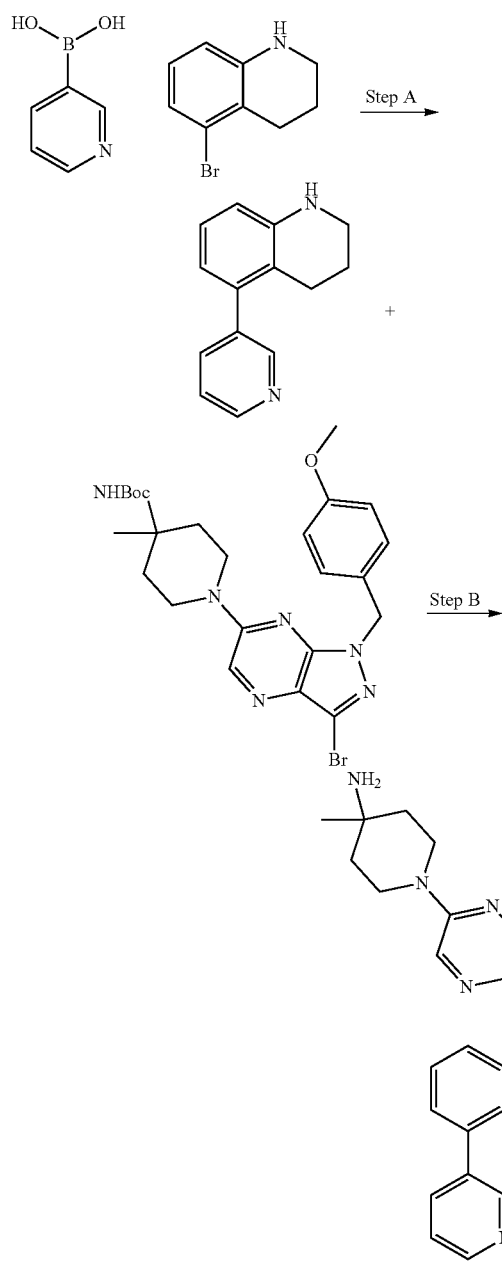

Step a: A solution of pyridin-3-ylboronic acid (115 mg, 0.943 mmol), 5-bromo-1,2,3,4-tetrahydroquinoline (100 mg, 0.4715 mmol), tetrakis(triphenylphosphine)palladium (54.4 mg, 0.04715 mmol), and potassium carbonate (259 mg, 1.88 mmol) in dioxane (4 mL) and water (1 mL) was stirred at 95° C. for 2 h. The reaction mixture was concentrated in vacuo. The residue was purified by normal phase using 0-65% ethyl acetate in heptanes. The product 5-(pyridin-3-yl)-1,2,3,4-tetrahydroquinoline (82.0 mg, 0.3899 mmol, 83% yield) was obtained as an off-white solid. LCMS: [M+H]$^+$=211.

Synthesis of 5-(pyridin-3-yl)-1,2,3,4-tetrahydroquinoline, used in the preparation of Compound 66

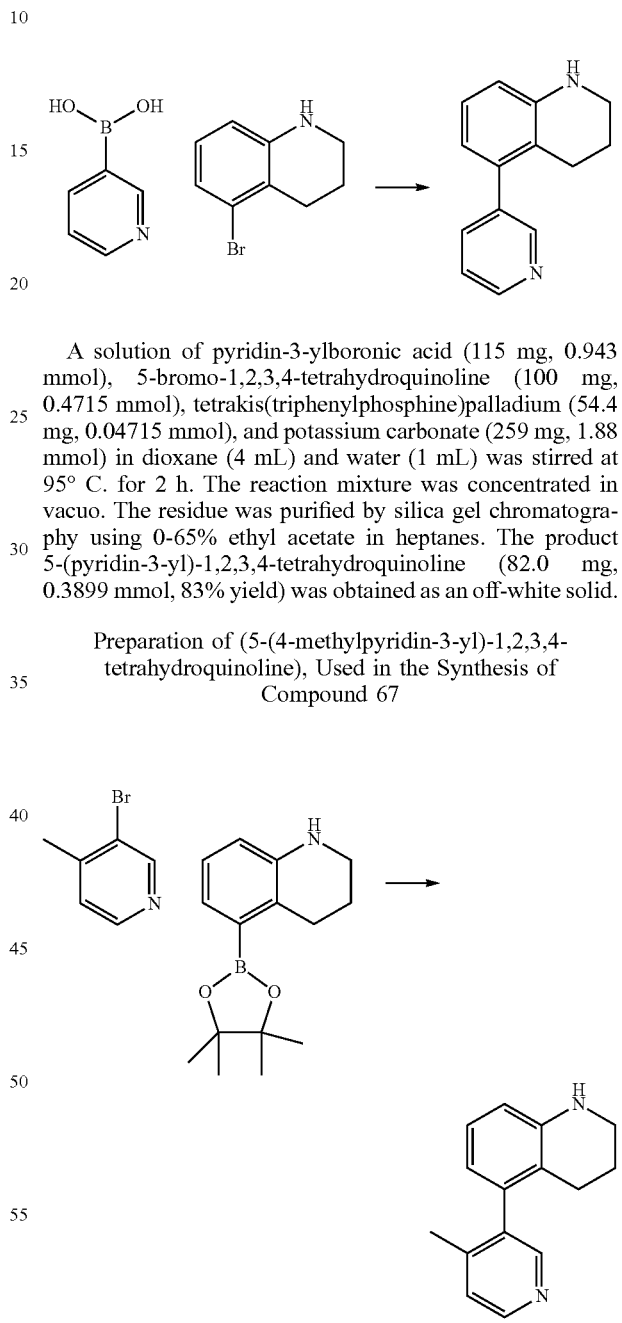

A solution of pyridin-3-ylboronic acid (115 mg, 0.943 mmol), 5-bromo-1,2,3,4-tetrahydroquinoline (100 mg, 0.4715 mmol), tetrakis(triphenylphosphine)palladium (54.4 mg, 0.04715 mmol), and potassium carbonate (259 mg, 1.88 mmol) in dioxane (4 mL) and water (1 mL) was stirred at 95° C. for 2 h. The reaction mixture was concentrated in vacuo. The residue was purified by silica gel chromatography using 0-65% ethyl acetate in heptanes. The product 5-(pyridin-3-yl)-1,2,3,4-tetrahydroquinoline (82.0 mg, 0.3899 mmol, 83% yield) was obtained as an off-white solid.

Preparation of (5-(4-methylpyridin-3-yl)-1,2,3,4-tetrahydroquinoline), Used in the Synthesis of Compound 67

A mixture of 3-bromo-4-methyl pyridine (40 mg, 0.232 mmol), 5-(4,4,5,5-tetramethyl-1,3,2-dioxaborolan-2-yl)-1,2,3,4-tetrahydroquinoline (90.6 mg, 0.301 mmol), potassium carbonate (96.1 mg, 0.696 mmol), and tetrakis(triphenylphosphine)palladium (26.8 mg, 0.023 mmol), in a sealed tube in 5 mL of a 4:1 mix of dioxane:water was degassed with nitrogen, capped, and stirred 3 hours at 95° C.

The mixture was then cooled to room temperature, concentrated down to near dryness, and loaded as a silica gel slurry onto a 12 gram silica gel column, which was eluted with a heptane to EA gradient over 30 minutes to yield 5-(4-methylpyridin-3-yl)-1,2,3,4-tetrahydroquinoline (47.0 mg, 90% yield) as a yellow oil which solidified upon standing. LCMS: [M+H]$^+$=225.

Synthesis of 4-(3-pyridyl)-2,3-dihydro-1H-quinoxaline, Used in the Preparation of Compound 68

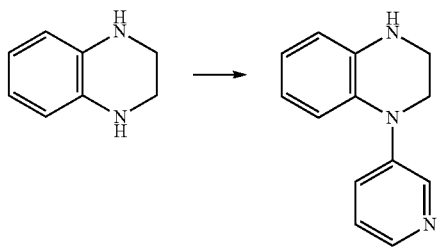 [SMILES: c1ccc2c(c1)NCCN2 ; c1cncc(N2CCNc3ccccc32)c1]

A round bottomed flask was charged with 1,2,3,4-tetrahydroquinoxaline (500.0 mg, 3.7 mmol, 1.0 eq), 3-iodopyridine (840.3 mg, 4.1 mmol, 1.1 eq), RuPhos (173.9 mg, 372.6 umol, 0.1 eq), RuPhos-Pd-G4 (313.8 mg, 372.6 umol, 0.1 eq), and tBuONa (1.1 g, 11.2 mmol, 3.0 eq). Dioxane (8 mL) was added, and the reaction mixture was evacuated and refilled 3 times with nitrogen before being stirred at 80° C. for 12 h The reaction mixture was concentrated in vacuo and purified by flash silica gel chromatography (eluting with dichloromethane and methanol) to afford 4-(3-pyridyl)-2,3-dihydro-1H-quinoxaline (0.5 g, 63.5% yield) as a black brown solid.

Synthesis of 5-(4-fluorophenyl)-1,2,3,4-tetrahydroquinoline, Used in the Preparation of Compound 69

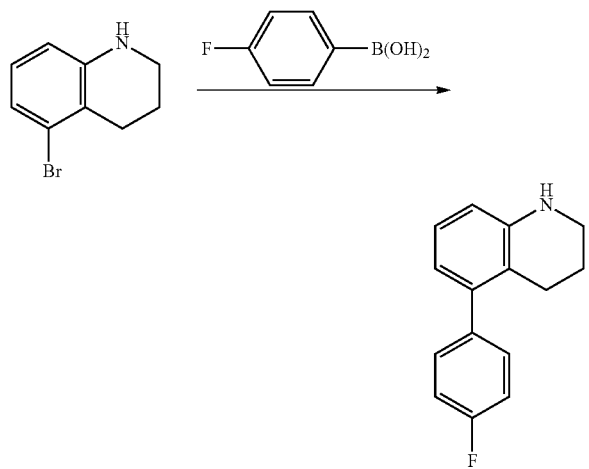

5-Bromo-1,2,3,4-tetrahydroquinoline (300.0 mg, 1.4 mmol, CAS #114744-50-2), (4-fluorophenyl)boronic acid (216.0 mg, 1.6 mmol), Pd(dppf)Cl$_2$ (103.0 mg, 141 µmol) and Cs$_2$CO$_3$ (919.0 mg, 2.8 mmol) were added in the mixture of dioxane (20.0 mL) and H$_2$O (2.0 mL). The reaction mixture was evacuated and refilled 3 times with N$_2$ and stirred at 100° C. for 12 hours. On completion, the reaction mixture was concentrated under reduced pressure to give a residue and purified by flash silica gel chromatography (Petroleum ether:EtOAc=100:0 to 100:10) to afford the product of 5-(4-fluorophenyl)-1,2,3,4-tetrahydroquinoline (300.0 mg, 93.7% yield) as a yellow solid.

Synthesis of 5-(3,4-difluorophenyl)-1,2,3,4-tetrahydroquinoline, Used in the Preparation of Compound 70

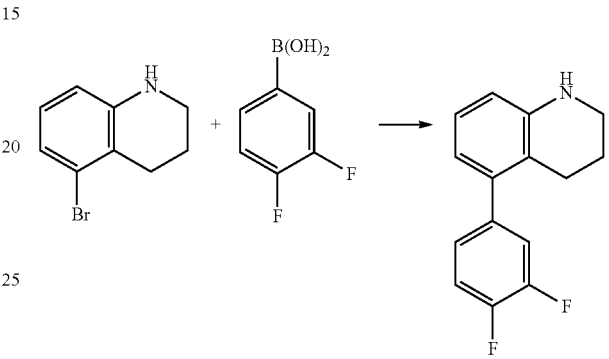

The mixture of 5-bromo-1,2,3,4-tetrahydroquinoline (300 mg, 1.4 mmol, 1.0 eq), (3,4-difluorophenyl)boronic acid (244 mg, 1.5 mmol, 1.1 eq), Cs$_2$CO$_3$ (1.37 g, 4.2 mmol, 3.0 eq) and Pd(dppf)Cl$_2$ (103 mg, 141 µmol, 0.1 eq) in dioxane (10 mL) and H$_2$O (1 mL) was evacuated and refilled for 3 times using N$_2$. Then the mixture was stirred at 100° C. for 15 hours under N$_2$ atmosphere. The mixture was concentrated under reduced pressure and the residue was purified by column chromatography (Petroleum ether/Ethyl acetate=100:0-100:20) to afford the desired product of 5-(3,4-difluorophenyl)-1,2,3,4-tetrahydroquinoline (340 mg, 98.5% yield) as a colorless oil. LCMS m/z: 245.8 (M)$^+$.

Preparation of ethyl 2-(1,2,3,4-tetrahydroquinolin-5-yl)thiazole-4-carboxylate, Used for the Preparation of Compound 71

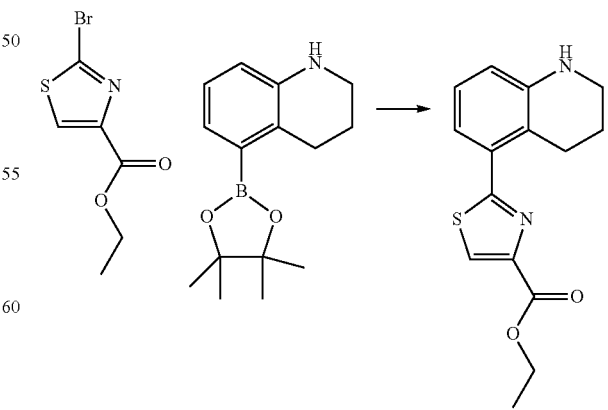

Ethyl 2-(1,2,3,4-tetrahydroquinolin-5-yl)thiazole-4-carboxylate was prepared from ethyl 2-bromothiazole-4-car-

Synthesis of 5-(3,4,5-trifluorophenyl)-1,2,3,4-tetrahydroquinoline, Used in the Preparation of Compound 72

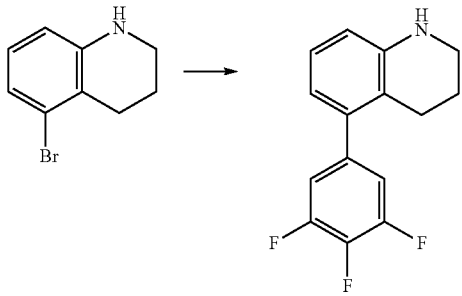 [SMILES: Brc1cccc2c1CCCN2 ; Fc1cc(-c2cccc3c2CCCN3)cc(F)c1F]

5-Bromo-1,2,3,4-tetrahydroquinoline (300.0 mg, 1.4 mmol), (3,4,5-trifluorophenyl)boronic acid (248.0 mg, 1.4 mmol), Pd(dppf)Cl2 (103.0 mg, 141 µmol), and cesium carbonate (919.0 mg, 2.8 mmol) were added to a mixture of dioxane (20.0 mL) and water (2.0 mL). The reaction mixture was evacuated and refilled with nitrogen three times before being stirred at 100° C. for 12 h. The reaction mixture was concentrated in vacuo to give a residue that was purified by silica gel chromatography (eluting with petroleum ether/ethyl acetate). Concentration in vacuo led to 5-(3,4,5-trifluorophenyl)-1,2,3,4-tetrahydroquinoline (200.0 mg, 53.9% yield) as a yellow solid.

Synthesis of 5-(3-methyl-[1,2,4]triazolo[4,3-a]pyridin-8-yl)-1,2,3,4-tetrahydroquinoline, Used in the Preparation of Compound 73

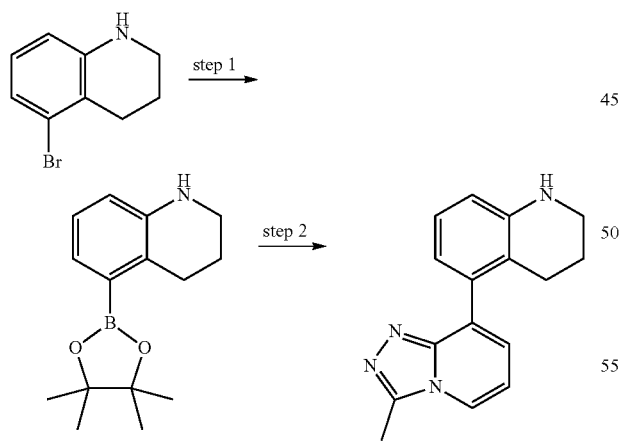

Step 1: 5-bromo-1,2,3,4-tetrahydroquinoline (500 mg, 2.35 mmol), Bis(pinacolato)diboron (774 mg, 3.05 mmol) Pddppf-dichloromethane adduct (97.1 mg, 0.1175 mmol) and potassium acetate (922 mg, 9.40 mmol) were dissolved in dioxane (10 mL) and stirred at 100° C. 18 h. The mixture was cooled to room temperature, diluted with ethyl acetate, and filtered through a pad of celite. The residue was purified by silica gel chromatography (eluting with 0-100% ethyl acetate in heptanes to give 5-(4,4,5,5-tetramethyl-1,3,2-dioxaborolan-2-yl)-1,2,3,4-tetrahydroquinoline (413 mg, 1.59 mmol, 67.8% yield).

Step 2: 5-(4,4,5,5-tetramethyl-1,3,2-dioxaborolan-2-yl)-1,2,3,4-tetrahydroquinoline (100 mg, 0.3858 mmol), 8-bromo-3-methyl-[1,2,4]triazolo[4,3-a]pyridine (63 mg, 0.2967 mmol, CAS #54230-90-9), tetrakis(triphenylphosphine)palladium (34 mg, 0.02967 mmol), and potassium carbonate (82 mg, 0.5935 mmol) were dissolved in dioxane (4 mL) and water (1 mL) and stirred at 95° C. for 3 h. The mixture was cooled to room temperature and partitioned between water and ethyl acetate. Following separation of the layers, the organic phase was dried over sodium sulfate, filtered, and concentrated in vacuo. The crude residue was purified by silica gel chromatography (eluting with 0-100% ethyl acetate in heptanes to give 5-(3-methyl-[1,2,4]triazolo[4,3-a]pyridin-8-yl)-1,2,3,4-tetrahydroquinoline (31.8 mg, 0.1203 mmol, 41% yield).

Synthesis of 5-(3-phenoxyphenyl)-1,2,3,4-tetrahydroquinoline, Used in the Preparation of Compound 75

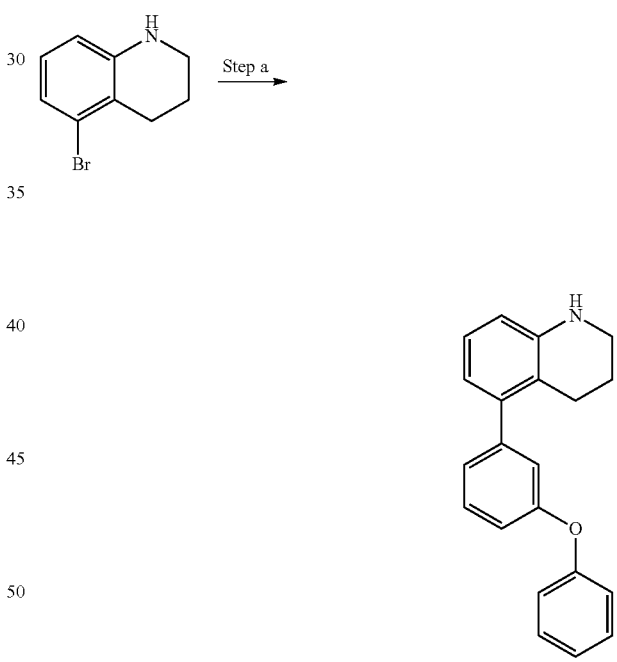

Step a: A solution of (3-phenoxyphenyl)boronic acid (500 mg, 2.34 mmol), 5-bromo-1,2,3,4-tetrahydroquinoline (250 mg, 1.17 mmol), tetrakis(triphenylphosphine)Palladium (135 mg, 0.117 mmol) and potassium carbonate (646 mg, 4.68 mmol) in dioxane/water (4:1, 5 mL) was stirred at 95 C for 1 h. Concentrated and purified on flash silica gel chromatography with 0-65% EtOAc in heptanes, followed by a second purification with 0-5% MeOH in DCM to give 5-(3-phenoxyphenyl)-1,2,3,4-tetrahydroquinoline (192 mg, 0.6380 mmol, 90% pure) as a light yellow oil. LCMS: [M+H]302.15.

Synthesis of 5-(difluoromethyl)-1,2,3,4-tetrahydroquinoline, Used in the Preparation of Compound 78

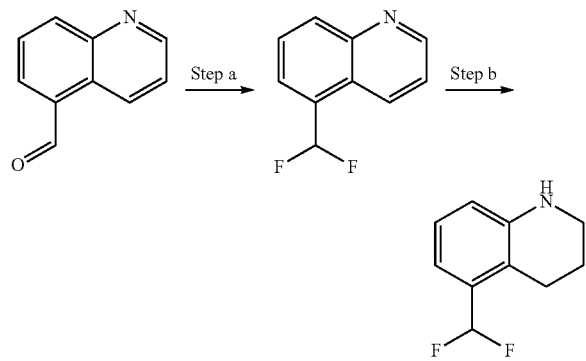

Step a: To a solution of triethylamine trihydrofluoride (517 μL, 3.18 mmol) in DCM (3 ml) was added (diethylamino)difluorosulfonium tetrafluoroborate (545 mg, 2.38 mmol) and stirred until dissolved. Added quinoline-5-carbaldehyde (0.250 g, 1.59 mmol). Stirred at room temperature overnight. Quenched with 5% aq. sodium bicarb solution and stirred at rt. Extracted twice using DCM. Combined organic layers, dried over $Na_2SO_4$, filtered and concentrated. Purified by flash silica gel chromatography with 0-100% EtOAc in heptanes to give 5-(difluoromethyl)quinoline (100 mg, 0.5581 mmol).

Step b: Cycled a solution of 5-(difluoromethyl)quinoline (100 mg, 0.5581 mmol) in MeOH (10 mL) through H-Cube (10% Pd/C cartridge, 70 C, 70 bar, 1 mL/min). Reaction was complete after 10 min. Purified by flash silica gel chromatography using 0-5% MeOH in DCM w/1% NH4OH to give 5-(difluoromethyl)-1,2,3,4-tetrahydroquinoline (35.0 mg, 0.1910 mmol). LCMS: [M+H] 184.06. 1H NMR (400 MHz, DMSO-d6) δ ppm 2.55 (br s, 1H) 2.71-2.79 (m, 2H) 2.91-2.98 (m, 2H) 3.31 (s, 1H) 6.95 (s, 1H) 7.09 (s, 1H) 7.14-7.25 (m, 2H) 7.33 (d, J=7.57 Hz, 1H).

Synthesis of Methyl 1,2,3,4-tetrahydroquinoline-5-carboxylate, Used in the Preparation of Compound 79

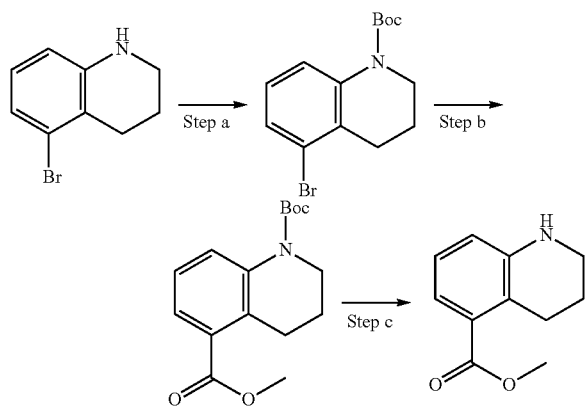

Step a: To a solution of 5-bromo-1,2,3,4-tetrahydroquinoline (1.0 g, 4.71 mmol) in THF (30.0 mL) was added NaHMDS (9.42 mL, 9.42 mmol, 1.0 M in THF) under $N_2$. The reaction was stirred at 25° C. for 2 h. $(Boc)_2O$ (2.05 g, 9.42 mmol) was added thereto, and the reaction mixture was stirred at 25° C. for 12 h. To the mixture was added $H_2O$ (30.0 mL), then the solution was extracted with EtOAc (30.0 mL×2). The combined organic layers were washed with saturated $NH_4Cl$ (20.0 mL), dried anhydrous $Na_2SO_4$, filtered and concentrated in vacuo to give crude product. The residue was purified by flash silica gel chromatography (Ethyl acetate in Petroleum ether from 0% to 5%) to give tert-butyl 5-bromo-3,4-dihydroquinoline-1(2H)-carboxylate (1.5 g, 102% yield) as orange oil.

Step b: A solution of tert-butyl 5-bromo-3,4-dihydroquinoline-1(2H)-carboxylate (1.5 g, 4.8 mmol), $Pd(dppf)Cl_2$ (702.0 mg, 960.0 umol) and $Et_3N$ (1.44 g, 14.3 mmol) in MeOH (30.0 mL) was degassed and purged with CO for three times. The reaction mixture was stirred at 80° C. for 12 h under CO (50 psi). On completion, the reaction mixture was concentrated in vacuo. The residue was purified by flash silica gel chromatography (Ethyl acetate in Petroleum ether from 0% to 5%) to give 1-tert-butyl 5-methyl 3,4-dihydroquinoline-1,5(2H)-dicarboxylate (400.0 mg, 28.7% yield) as yellow oil.

Step c: A solution of 1-tert-butyl 5-methyl 3,4-dihydroquinoline-1,5(2H)-dicarboxylate (400.0 mg, 1.37 mmol) in HCl/MeOH (3.42 mL, 4.0 M) was stirred at 25° C. for 12 h. On completion, the reaction mixture was concentrated in vacuum to give methyl 1,2,3,4-tetrahydroquinoline-5-carboxylate (350.0 mg, crude) as yellow solid. LCMS m/z 191.9(M)⁺.

Synthesis of 4-propyl-1,2,3,4-tetrahydroquinoline, Used in the Preparation of Compound 83

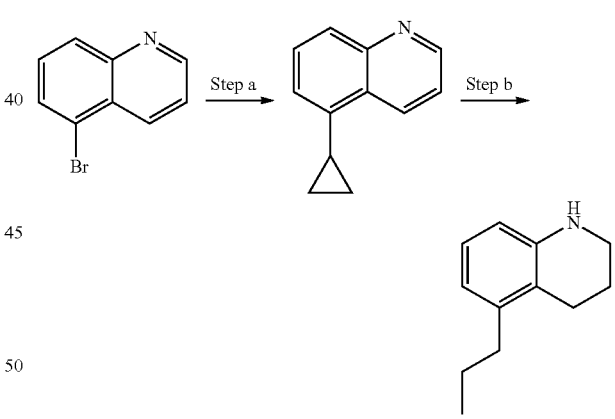

Step a: To a solution of 4-bromoquinoline (500 mg, 2.40 mmol) and potassium carbonate (663 mg, 4.80 mmol) in Dioxane (5 mL) was added Pd(Ph3)4 (277 mg, 0.2399 mmol) and 2-cyclopropyl-4,4,5,5-tetramethyl-1,3,2-dioxaborolane (403 mg, 2.40 mmol). Flushed with nitrogen. Heated to 100 C overnight. Partitioned between water and EtOAc. Separated layers, extracted aqueous layer with EtOAc (2×), combined organic layers, dried over $Na_2SO_4$, filtered and concentrated. Purified by flash silica gel chromatography using 0-10% MeOH in DCM to give 4-cyclopropylquinoline (124 mg, 0.7327 mmol).

Step b: Cycled solution of 4-cyclopropylquinoline (124 mg, 0.7327 mmol) in MeOH (10 mL) through H-cube (10% Pd/C, 70 C, 70 bar, 1 mL/min) for 30 min in a continuous loop. Concentrated to give crude 4-propyl-1,2,3,4-tetrahydroquinoline (114 mg), which was used in next step without purifying. 1H NMR (400 MHz, DMSO-d6) δ ppm 0.90 (t, J=7.08 Hz, 3H) 1.23-1.35 (m, 1H) 1.35-1.45 (m, 2H) 1.47-1.56 (m, 1H) 1.63-1.77 (m, 2H) 2.59-2.67 (m, 1H) 3.09-3.19 (m, 2H) 5.58-5.64 (m, 1H) 6.35-6.41 (m, 2H) 6.78-6.83 (m, 1H) 6.84 (d, J=7.57 Hz, 1H)

Synthesis of 4-ethyl-1,2,3,4-tetrahydroquinoline, Used in the Preparation of Compound

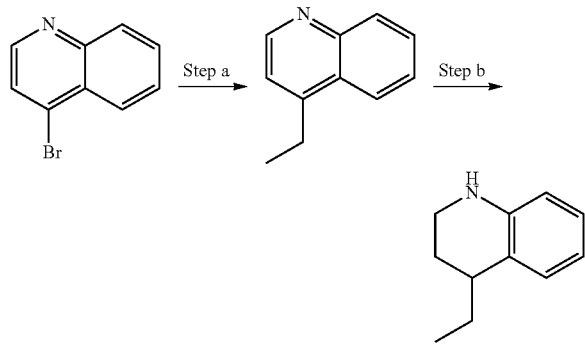

Step a: In a microwave vial, combined 4-bromoquinoline (500 mg, 2.40 mmol), potassium phosphate (1.01 g, 4.80 mmol), tetrakis(triphenylphosphane) palladium (277 mg, 0.240 mmol), and ethylboronic acid (354 mg, 4.80 mmol) and dissolved in DME (20 mL). Heated in uW at 120 C for 2 h. Partitioned between EtOAc and water. Separated layers, dried over Na$_2$SO$_4$, concentrated and purified by flash silica gel chromatography to give 4-ethylquinoline (234 mg, 1.48 mmol) as a yellow oil.

Step b: Cycled solution of 4-ethylquinoline (200 mg, 1.27 mmol) in MeOH (20 mL) through H-cube (10% Pd/C, 70 C, 70 bar, 1 mL/min) for 3 h in a continuous loop. Concentrated to give crude 4-ethyl-1,2,3,4-tetrahydroquinoline (165 mg, 1.02 mmol) which was used in the next step without purifying. LCMS: [M+H] 162.06.

Synthesis of 4-methyl-1,2,3,4-tetrahydro-1,5-naphthyridine and 8-methyl-1,2,3,4-tetrahydro-1,5-naphthyridine, Used in the Preparation of Compound 90

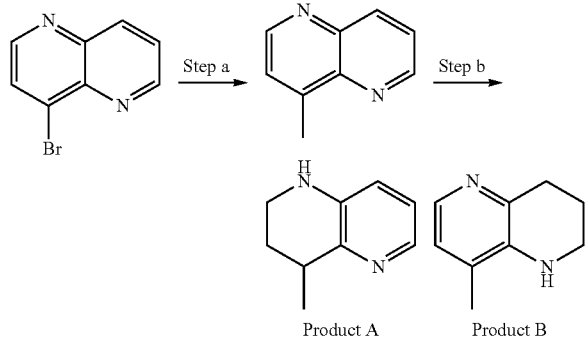

Step a: To a solution of 4-bromo-1,5-naphthyridine dihydrobromide (250 mg, 0.6740 mmol) and potassium carbonate (185 mg, 1.34 mmol) in dioxane (2.5 mL) was added Pd(Ph3)4 (77.8 mg, 0.0674 mmol) and 2,4,6-trimethyl-1,3,5,2,4,6-trioxatriborinane (375 μL, 2.69 mmol). Flushed with nitrogen. Stirred at rt for 2 h, then heated to 100 C overnight. Partitioned between water and EtOAc. Separated layers, extracted organic layer with EtOAc (2×). Combined organic layers, dried over Na$_2$SO$_4$, filtered and concentrated. Purified by flash silica gel chromatography using 0-10% MeOH in DCM to give 4-methyl-1,5-naphthyridine (50.0 mg, 0.3468 mmol).

Step b: Cycled a solution of 4-methyl-1,5-naphthyridine (141 mg, 0.9779 mmol) in MeOH (20 mL) through H-Cube (10% Pd/C, 70 C, 70 bar, 1 mL/min) for 90 min. Concentrated to give 142 mg crude material as a 5:1 mixture of Product A to Product B. Carried crude mixture onto next step without purifying further.

Synthesis of (2R,4R)-1-(3-iodo-1-(tetrahydro-2H-pyran-2-yl)-1H-pyrazolo[3,4-b]pyrazin-6-yl)-2-methylpiperidin-4-ol, Used in the Preparation of Compound 95

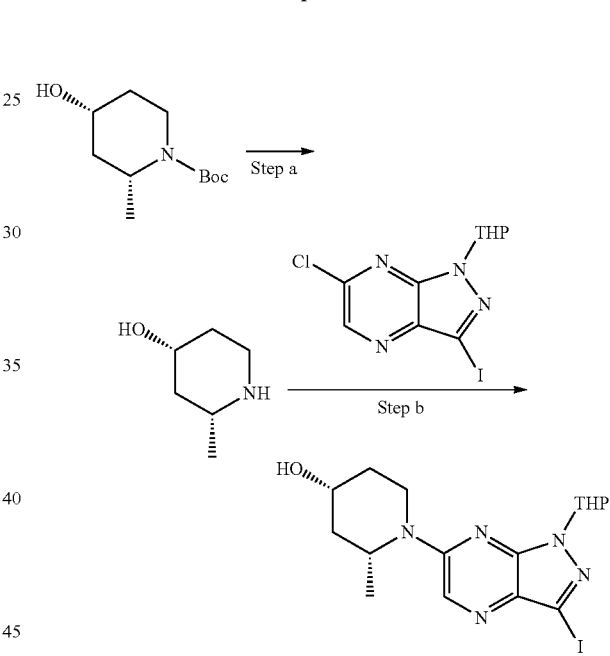

Step a: The compound of (2R,4R)-tert-butyl 4-hydroxy-2-methylpiperidine-1-carboxylate (400 mg, 1.8 mmol) was added in HCl/MeOH (10 mL, 2N). The reaction mixture was stirred at 25° C. for 12 hours. On completion, the mixture was adjusted to pH=7~8 with NaHCO$_3$ solid and filtered. The filtrate was concentrated to give the product of (2R, 4R)-2-methylpiperidin-4-ol (300 mg) as a white solid.

Step b: The compound of 6-chloro-3-iodo-1-(tetrahydro-2H-pyran-2-yl)-1H-pyrazolo[3,4-b]pyrazine (600 mg, 1.6 mmol), (2R,4R)-2-methylpiperidin-4-ol (207 mg, 1.80 mmol) and CsF (747 mg, 4.9 mmol) were placed into DMSO (10 mL). The reaction mixture was stirred at 70° C. for 20 hours. The reaction mixture was then diluted with EtOAc (100 mL) and H$_2$O (30 mL), the partitioned layers were separated. The organic phase was washed with H$_2$O (30 mL×3), brine (50 mL), dried over anhydrous Na$_2$SO$_4$, filtered and concentrated to give a residue. The residue was purified by flash silica gel chromatography (Ethyl acetate/Petroleum ether=0/100 to 70/100) to afford the product of (2R,4R)-1-(3-iodo-1-(tetrahydro-2H-pyran-2-yl)-1H-pyrazolo[3,4-b]pyrazin-6-yl)-2-methylpiperidin-4-ol (530 mg, 73% yield) as a white solid. LCMS m/z 443.9 (M)$^+$.

Synthesis of 4-phenyl-1,2,3,4-tetrahydroquinoline, Used in the Preparation of Compound 96

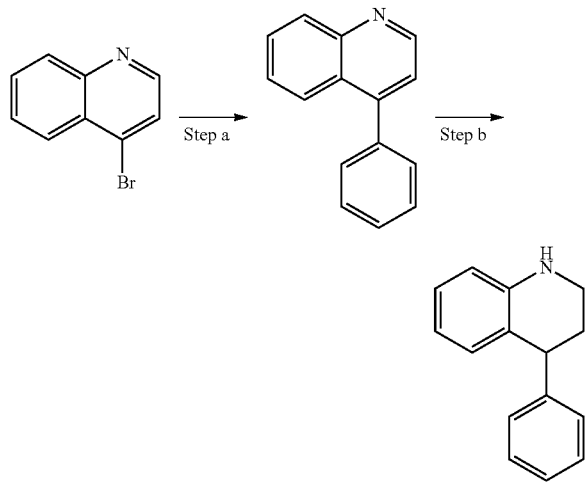

Step a: A solution of 4-bromoquinoline (200.0 mg, 961.0 μmol) and phenylboronic acid (140.0 mg, 1.2 mmol) in dioxane (10.0 mL) and H$_2$O (1.0 mL) was added Pd(dppf)Cl$_2$ (70.3 mg, 96.1 μmol) and Cs$_2$CO$_3$ (625.0 mg, 1.9 mmol). The reaction mixture was degassed and purged with N$_2$ gas 3 times and stirred at 100° C. for 12 hours under N$_2$ atmosphere. Then the reaction mixture was concentrated under reduced pressure. The residue was purified by column chromatography (Petroleum ether/Ethyl acetate=100:0 to 100:50). The product of 4-phenylquinoline (180.0 mg, 91% yield) was obtained as a light yellow oil.

Step b: A solution of 4-phenylquinoline (180.0 mg, 876.0 μmol), diphenyl hydrogen phosphate (43.7 mg, 175.0 μmol) and diethyl 2,6-dimethyl-1,4-dihydropyridine-3,5-dicarboxylate (663.0 mg, 2.6 mmol) in toluene (5.0 mL) was stirred at 80° C. for 12 hours under N$_2$ gas. The reaction mixture was concentrated under reduced pressure. The residue was purified by column chromatography (Petroleum ether/Ethyl acetate=100:0 to 100:10). The product of 4-phenyl-1,2,3,4-tetrahydroquinoline (180.0 mg, 98% yield) was obtained as light yellow oil. LCMS m/z: 210.0 (M+H)$^+$.

Synthesis of Methyl 1,2,3,4-tetrahydroquinoline-4-carboxylate, Used in the Preparation of Compound 99

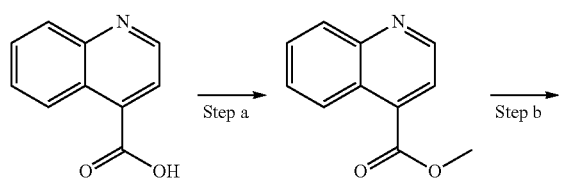

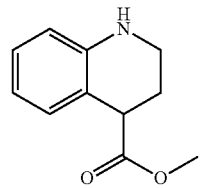

Step a: SOCl$_2$ (15.0 mL) was added drop-wise in MeOH (20.0 mL) at 0° C. Then quinoline-4-carboxylic acid (2.0 g, 11.5 mmol) in MeOH (10.0 mL) was added and stirred at 90° C. for 2 h. The solution was poured into H$_2$O (100.0 mL) and then extracted with EtOAc (50.0 mL×2). The combined organic layers were washed with saturated NaCl (50.0 mL), dried over anhydrous Na$_2$SO$_4$, filtered and concentrated in vacuo to give crude product as orange gum. The residue was purified by flash silica gel chromatography (20 g, Ethyl acetate in Petroleum ether from 0% to 25%) to give methyl quinoline-4-carboxylate (2.0 g, 93.0% yield) as yellow oil.

Step b: A solution of methyl quinoline-4-carboxylate (1.90 g, 10.1 mmol), diethyl 2,6-dimethyl-1,4-dihydropyridine-3,5-dicarboxylate (7.67 g, 30.3 mmol) and diphenyl phosphate (503.0 mg, 2.02 mmol) in toluene (50.0 mL) was stirred at 80° C. for 12 h under N$_2$. The solution was poured into H$_2$O (100.0 mL) and then extracted with EtOAc (50.0 mL×2). The combined organic layers were washed with saturated NaCl (50.0 mL), dried over anhydrous Na$_2$SO$_4$, filtered and concentrated in vacuo to give crude product as brown gum. The residue was purified by flash silica gel chromatography (40 g, Ethyl acetate in Petroleum ether from 0% to 10%) to give methyl 1,2,3,4-tetrahydroquinoline-4-carboxylate (1.1 g, 56.9% yield) as yellow oil.

Synthesis of 4-(trifluoromethyl)-1,2,3,4-tetrahydroquinoline, Used in the Preparation of Compound 106

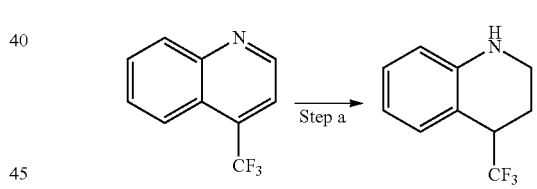

Step a: A solution of 4-(trifluoromethyl)quinoline (400 mg, 2.0 mmol), diphenyl hydrogen phosphate (101 mg, 0.4 mmol) and diethyl Hantzsch ester (1.5 g, 6.0 mmol) in PhMe (15 ml) was stirred at 80° C. for 12 hours under N$_2$. The mixture was concentrated and purified by flash silica gel chromatography (Petroleum ether:EtOAc=100:0 to 100:10) to afford the product of 4-(trifluoromethyl)-1,2,3,4-tetrahydroquinoline (300 mg, 74% yield) as a colorless oil. LCMS m/z: 201.9.

Synthesis of N-(1-(1-(3-iodo-1-(tetrahydro-2H-pyran-2-yl)-1H-pyrazolo[3,4-b]pyrazin-6-yl)4-methylpiperidin-4-yl)ethyl)-2-methylpropane-2-sulfinamide, Used in the Preparation of Compound 110

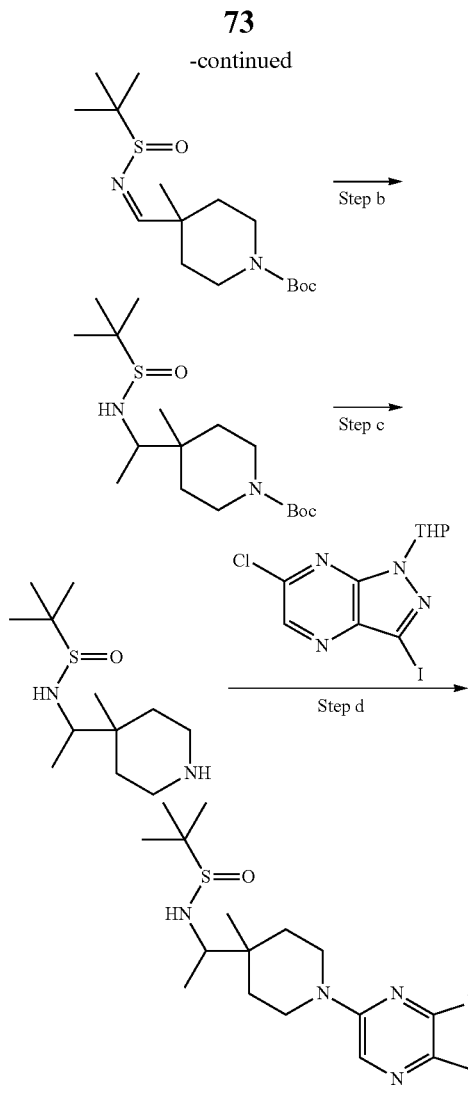

product of tert-butyl 4-(1-(1,1-dimethylethylsulfinamido)ethyl)-4-methylpiperidine-1-carboxylate (800 mg, 58.8% yield) as a yellow oil.

Step c: To a mixture of tert-butyl 4-(1-(1,1-dimethylethylsulfinamido)ethyl)-4-methylpiperidine-1-carboxylate (800 mg, 2.3 mmol) in DCM (15 mL) was added TFA (1.5 mL), and the resulting mixture was stirred at 20° C. for 2 hours. The reaction mixture was concentrated under reduced pressure to afford the product of 2-methyl-N-(1-(4-methylpiperidin-4-yl)ethyl)propane-2-sulfinamide (600 mg, crude) as a yellow oil.

Step d: To a mixture of 6-chloro-3-iodo-1-(tetrahydro-2H-pyran-2-yl)-1H-pyrazolo[3,4-b]pyrazine (500 mg, 1.4 mmol) and 2-methyl-N-(1-(4-methylpiperidin-4-yl)ethyl)propane-2-sulfinamide (505 mg, 2.1 mmol) in DMSO (15 mL) was added DIPEA (5 mL), and the resulting mixture was stirred at 70° C. for 12 hours. The reaction mixture was diluted with H₂O (20 mL) and extracted with EtOAc (25 mL×2). The organic phase was combined, washed with brine, dried over Na₂SO₄ and concentrated in vacuo to give a residue, which was purified by silica gel chromatography (Petroleum ether: Ethyl acetate=1:0 to 0:1) to afford the product of N-(1-(1-(3-iodo-1-(tetrahydro-2H-pyran-2-yl)-1H-pyrazolo[3,4-b]pyrazin-6-yl)-4-methylpiperidin-4-yl)ethyl)-2-methylpropane-2-sulfinamide (370 mg, 47% yield) as a yellow solid.

Synthesis of 1,2,3,4-tetrahydroquinoline-4-carbonitrile, Used in the Preparation of Compound 117

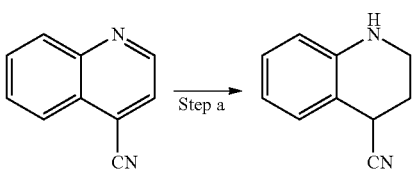 [SMILES: N#Cc1ccnc2ccccc12 ; N#CC1CCNc2ccccc21]

Step a: Quinoline-4-carbonitrile (300.0 mg, 1.9 mmol), diphenyl hydrogen phosphate (97.0 mg, 388.0 μmol) and diethyl 2,6-dimethyl-1,4-dihydropyridine-3,5-dicarboxylate (1.5 g, 5.8 mmol) were added in toluene (10.0 mL), the reaction mixture was stirred at 80° C. for 12 hours. The reaction mixture was concentrated under reduced pressure and purified by flash silica gel chromatography (EtOAc in Petroleum ether=0~30%) to afford 1,2,3,4-tetrahydroquinoline-4-carbonitrile (200.0 mg, 65.3% yield) as a off-white oil.

Synthesis of 5-methyl-1,2,3,4-tetrahydroquinoline-6-carbonitrile, Intermediate Used in the Preparation of Compound 120 and Compound 208

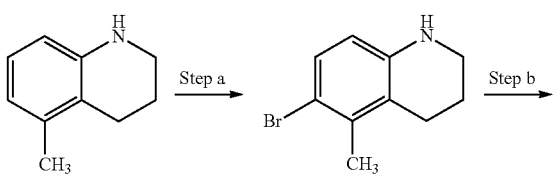

Step a: To a mixture of tert-butyl 4-formyl-4-methylpiperidine-1-carboxylate (1.0 g, 4.4 mmol) in anhydrous THF (15 mL) was added 2-methylpropane-2-sulfinamide (637 mg, 5.3 mmol) followed by Ti(OEt)₄ (2.0 g, 8.8 mmol). The resulting mixture was stirred at 20° C. for 12 hours. The reaction mixture was quenched with sat NH₄Cl and diluted with EtOAc (20 mL). The mixture was filtered and the filtrate was washed with H₂O (20 mL×2). The organic phase was dried over Na₂SO₄ and concentrated in vacuo to give a residue. The residue was purified by silica gel chromatography (Petroleum ether:Ethyl acetate=6:1 to 4:1) to afford the product of (Z)-tert-butyl 4-(((tert-butylsulfinyl)imino)methyl)-4-methylpiperidine-1-carboxylate (1.4 g, 94.0% yield) as a colorless oil.

Step b: To a mixture of (Z)-tert-butyl 4-(((tert-butylsulfinyl)imino)methyl)-4-methylpiperidine-1-carboxylate (1.3 g, 3.9 mmol) in anhydrous THF (20 mL) at −70° C. under N₂ atmosphere was added CH₃Li (1.6 M, 4.9 mL, 7.9 mmol), the resulting mixture was stirred at this temperature for 2 hours. The reaction mixture was quenched with sat.NH₄Cl, diluted with EtOAc (30 mL) and washed with H₂O (25 mL×2). The organic phase was separated, washed with brine, dried over Na₂SO₄ and concentrated in vacuo to give a residue, which was purified by silica gel chromatography (Petroleum ether: Ethyl acetate=1:1 to 1:5) to afford the

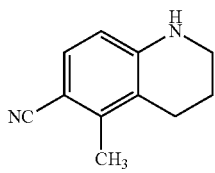

Step a: 5-methyl-1,2,3,4-tetrahydroquinoline (273 mg, 1.85 mmol) was dissolved in ACN (3.0 mL) in a round bottom flask and cooled to 0° C. before a solution of N-bromosuccinimide (493 mg, 2.78 mmol) in ACN (3.7 mL) was added. The reaction stirred at 0° C. for 5 min before adding sat. Na$_2$S$_2$O$_3$ at the same temperature. The reaction was warmed to ambient temperature and Et$_2$O was added. The organic layer was extracted with Et$_2$O (3×), and combined organic extracts were dried, concentrated and purified via silica gel chromatography (2-20% EtOAc in hexanes) to furnish 6-bromo-5-methyl-1,2,3,4-tetrahydroquinoline (208 mg, 0.920 mmol) in 50% yield, along with the dibrominated analog, which was not isolated. LCMS: [M+] 226.1 and 228.1.

Step b: A resealable vial was charged with 6-bromo-5-methyl-1,2,3,4-tetrahydroquinoline (208 mg, 0.920 mmol), [(2-Di-tert-butylphosphino-2',4',6'-triisopropyl-1,1'-biphenyl)-2-(2'-amino-1,1'-biphenyl)] palladium(II) methanesulfonate (73.0 mg, 0.11 mmol), and zinc dicyanide (129 mg, 1.10 mmol) before being evacuated and backfilled with nitrogen (3×). A mixture of H$_2$O (2.5 mL) and THF (0.5 mL) was then added and the reaction was heated to 40° C. for 16 h. After cooling, the reaction was partitioned between EtOAc and sat. sodium bicarbonate. The organic layer was extracted with EtOAc (3×), dried, concentrated and purified via silica gel chromatography (8-66% EtOAc in hexanes) to provide 5-methyl-1,2,3,4-tetrahydroquinoline-6-carbonitrile (110 mg, 0.639 mmol) as a white solid in 69% yield. LCMS: [M+H]+ 173.1.

Synthesis of 5-(1-methyl-1H-pyrazol-4-yl)-1,2,3,4-tetrahydroquinoline, Intermediate Used in the Preparation of Compound 121 and Compound 209

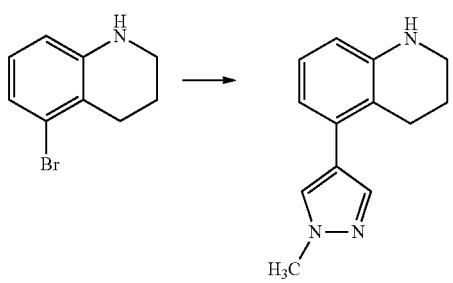 [SMILES: Brc1cccc2c1CCCN2 ; Cn1cc(-c2cccc3c2CCCN3)cn1]

A reaction vial containing 5-bromo-1,2,3,4-tetrahydroquinoline (230 mg, 1.08 mmol), 1-methyl-4-(4,4,5,5-tetramethyl-1,3,2-dioxaborolan-2-yl)-1H-pyrazole (360 mg, 1.73 mmol), palladium tetrakis (124 mg, 0.110 mmol) and K$_2$CO$_3$ (596 mg, 4.30 mmol) was charged with dioxane (2.90 mL) and H$_2$O (0.70 mL). The reaction was degassed for 5 min, before being heated to 95° C. for 16 h. Following cooling to ambient temperature, the reaction was partitioned between dichloromethane and water and the organic layer was extracted (3×), concentrated and purified via silica gel chromatography (10-100% EtOAc in hexanes) to furnish 5-(1-methyl-1H-pyrazol-4-yl)-1,2,3,4-tetrahydroquinoline (129 mg, 0.605 mmol) in 56% yield. LCMS: [M+H]+ 214.2

Step b: 5-cyclopropyl-1,2,3,4-tetrahydroquinoline (522 mg, 3.01 mmol) was dissolved in ACN (4.0 mL) in a round bottom flask and cooled to 0° C. before a solution of N-bromosuccinimide (533 mg, 3.0 mmol) in ACN (4.0 mL) was added. The reaction stirred at 0° C. for 5 min before adding sat. Na$_2$S$_2$O$_3$ at the same temperature. The reaction was warmed to ambient temperature and Et$_2$O was added. The organic layer was extracted with Et$_2$O (3×), and combined organic extracts were dried, concentrated and purified via silica gel chromatography (2-20% EtOAc in hexanes) to furnish 6-bromo-5-cyclopropyl-1,2,3,4-tetrahydroquinoline (300 mg, 1.19 mmol) in 40% yield, along with the dibrominated analog, which was not isolated. LCMS: [M+] 252.1 and 254.1.

Step c: A resealable vial was charged with 6-bromo-5-cyclopropyl-1,2,3,4-tetrahydroquinoline (300 mg, 1.19 mmol), [(2-Di-tert-butylphosphino-2',4',6'-triisopropyl-1,1'-biphenyl)-2-(2'-amino-1,1'-biphenyl)] palladium(II) methanesulfonate (94.0 mg, 0.12 mmol), and zinc dicyanide (167 mg, 1.43 mmol) before being evacuated and backfilled with nitrogen (3×). A mixture of H$_2$O (3.3 mL) and THF (0.66 mL) was then added and the reaction was heated to 40° C. for 16 h. After cooling, the reaction was partitioned between EtOAc and sat. sodium bicarbonate. The organic layer was extracted with EtOAc (3×), dried, concentrated and purified via silica gel chromatography (15-40% EtOAc in hexanes) to provide 5-cyclopropyl-1,2,3,4-tetrahydroquinoline-6-carbonitrile (102 mg, 0.514 mmol) as a white solid in 43% yield. LCMS: [M+H]+ 199.2.

Synthesis of 5-cyclopropyl-1,2,3,4-tetrahydroquinoline-6-carbonitrile, Intermediate Used in the Preparation of Compounds 122 and 207

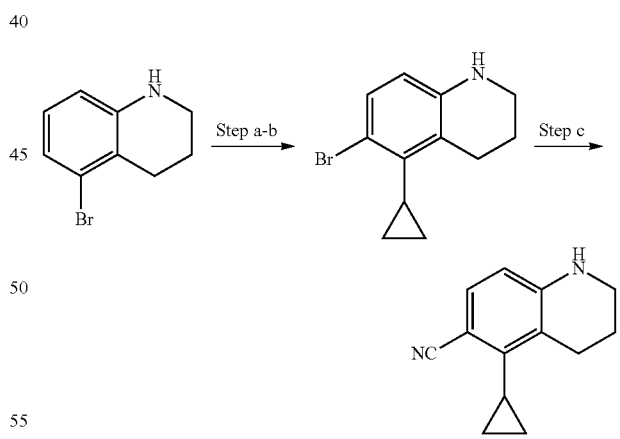

Step a: A reaction vial was charged with 5-bromo-1,2,3,4-tetrahydroquinoline (1000 mg, 4.70 mmol), cyclopropylboronic acid (2.60 g, 9.40 mmol), palladium tetrakis (530 mg, 0.460 mmol) and K$_2$CO$_3$ (2.60 g, 18.8 mmol) and dissolved in dioxane (12.4 mL) and H$_2$O (3.2 mL). The reaction was degassed for 5 min, before being heated to 100° C. for 16 h. Following cooling to ambient temperature, the reaction was partitioned between dichloromethane and water and the organic layer was extracted (3×), concentrated and purified via silica gel chromatography (0-10% EtOAc in hexanes) to provide 5-cyclopropyl-1,2,3,4-tetrahydroquinoline (522 mg, 3.01 mmol) in 64% yield.

Synthesis of 5,6,7,8-tetrahydro-1,5-naphthyridine-2-carbonitrile, Used in the Preparation of Compound 126

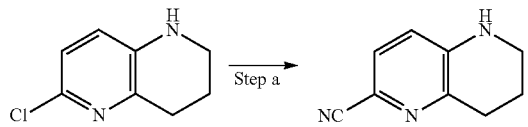 [SMILES: Clc1ccc2c(n1)CCCN2 ; N#Cc1ccc2c(n1)CCCN2]

Step a: The mixture of 6-chloro-1,2,3,4-tetrahydro-1,5-naphthyridine (300 mg, 1.77 mmol, 1.0 eq), Zn(CN)$_2$ (518 mg, 4.42 mmol, 2.5 eq), Zn (58 mg, 885 µmol, 0.5 eq), Pd$_2$(dba)$_3$ (324 mg, 354 µmol, 0.2 eq) and dppf (98 mg, 177 µmol, 0.1 eq) in DMF (5 mL) was evacuated and refilled 3 times using N$_2$, then stirred at 120° C. for 10 hours. The mixture was then concentrated under reduced pressure and the residue was purified by column chromatography (Petroleum ether/Ethyl acetate=1:0~1:1) to afford the desired product of 5,6,7,8-tetrahydro-1,5-naphthyridine-2-carbonitrile (100 mg, 36% yield) as a yellow solid. LCMS m/z: 160.1 (M+H)$^+$.

Synthesis of 5-(1-methyl-1H-pyrazol-4-yl)-1,2,3,4-tetrahydroquinoline-6-carbonitrile, Intermediate for Compound 131

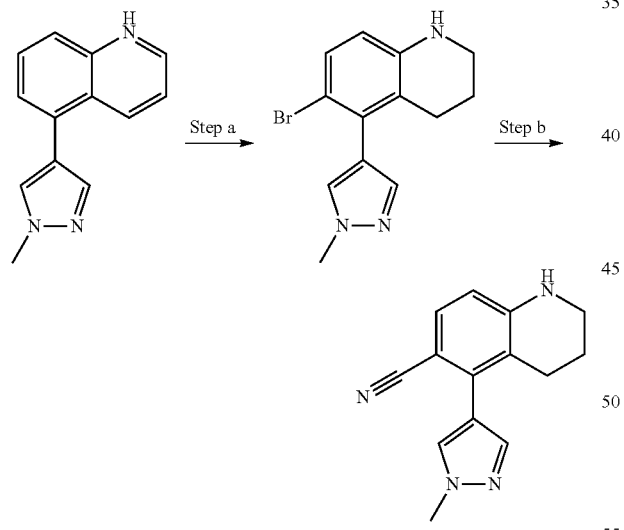

Step a: A round bottomed flask was charged with 5-(1-methyl-1H-pyrazol-4-yl)-1,2,3,4-tetrahydroquinoline (460 mg, 2.16 mmol, 1 equiv.) and a stirbar. Acetonitrile (3 mL) and dioxane (1 mL) was added, and the solution was cooled to 0 C for the addition of N-bromosuccinimide (384 mg, 2.16 mmol, 1 equiv.) in acetonitrile (3 mL). After 5 min, the reaction was quenched with a saturated solution of sodium bisulfite. The product was extracted three times from the aqueous layer with diethyl ether. The combined organic fractions were concentrated in vacuo, and the residue was purified by silica gel chromatography (eluting with ethyl acetate and heptanes) to yield 6-bromo-5-(1-methyl-1H-pyrazol-4-yl)-1,2,3,4-tetrahydroquinoline (228 mg).

Step b: A microwave vial was charged with 6-bromo-5-(1-methyl-1H-pyrazol-4-yl)-1,2,3,4-tetrahydroquinoline (228 mg, 0.78 mmol, 1 equiv.), dicyanozinc (110 mg, 0.94 mmol, 1.2 equiv), tBuXPhos G3 (62 mg, 0.087 mmol, 0.1 equiv), and a stirbar before being sealed and evacuated/backfilled with nitrogen three times. 1:5 THF:water (0.3 volumes) was added, and the mixture was stirred at 40 C overnight. The reaction mixture was diluted with ethyl acetate and extract three times. The combined organic layers were dried with sodium sulfate, and concentrated in vacuo. The residue was purified by silica gel chromatography (eluting with ethyl acetate and heptanes) to yield 5-(1-methyl-1H-pyrazol-4-yl)-1,2,3,4-tetrahydroquinoline-6-carbonitrile (65 mg).

Synthesis of 2-benzylpiperidin-4-yl)methanamine for Use in Compound 158 and Compound 159

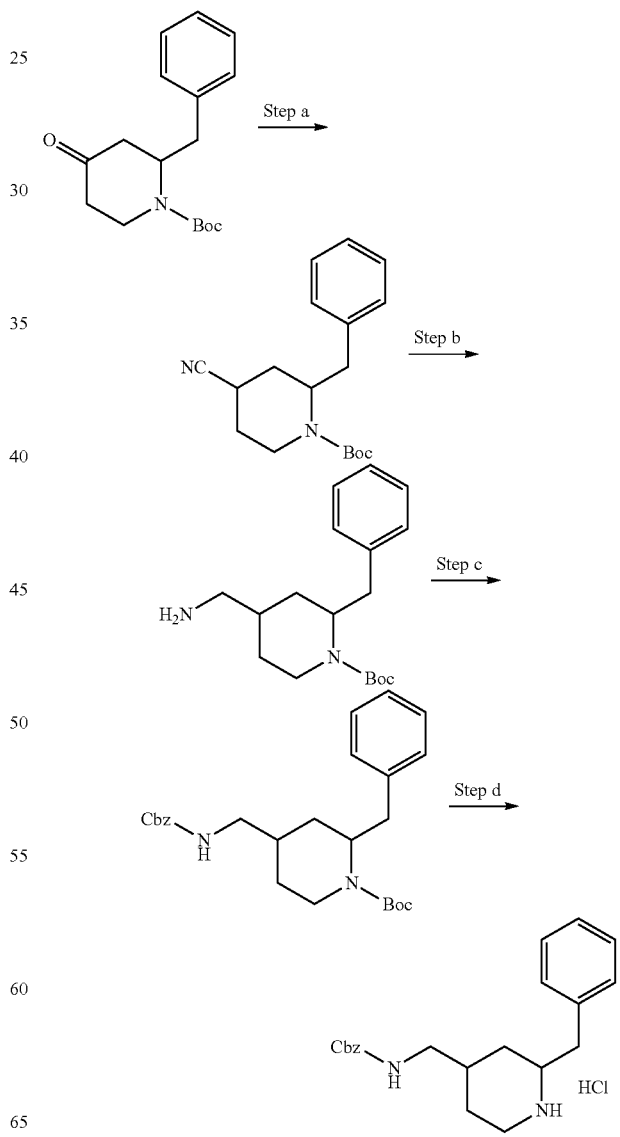

Step a: To a solution of tert-butyl 2-benzyl-4-oxopiperidine-1-carboxylate (2.10 g, 7.26 mmol, 1.0 eq) in DME (30 mL) was added TosMIC (2.13 g, 10.89 mmol, 1.5 eq) in DME (30 mL) and t-BuOK (2.44 g, 21.77 mmol, 3.0 eq) at −10° C. under N2. Then the mixture was stirred at −10° C. for 30 min, the mixture was stirred at 25° C. for 16 hr. TLC (petroleum ether/ethyl acetate=5/1) showed that compound 1 (Rf=0.28) was consumed and a new spot (Rf=0.3) was formed. The reaction mixture was poured into water (80 mL) and extracted with ethyl acetate (50 mL*3). Then combined organic layer was washed with brine (50 mL), dried over Na2SO4, filtered and concentrated. The residue was purified by column chromatography (SiO$_2$, petroleum ether/ethyl acetate=20/1-5/1, Rf=0.3) to give tert-butyl 2-benzyl-4-cyanopiperidine-1-carboxylate (1.3 g, crude) as a light yellow oil. 1H NMR (400 MHz CDCl3) δ: 7.34-7.16 (m, 5H), 4.56-4.45 (m, 1H), 4.21 (s, 1H), 3.30-2.71 (m, 4H), 1.98 (d, J=14.0 Hz, 1H), 1.83-1.73 (m, 3H), 1.41-1.30 (m, 9H).

Step b: To a solution of tert-butyl 2-benzyl-4-cyanopiperidine-1-carboxylate (1.22 g, 4.05 mmol, 1.00 eq) in methyl alcohol (20 mL) was added Raney-Ni (0.50 g, 5.84 mmol, 1.44 eq). Then the mixture was stirred under H2 (50 psi) at 25° C. for 32 hr. LCMS (EW7754-10-P1A) showed that the desired MS (Rt=0.693 min) was detected. The reaction mixture was filtered and the filtrate was concentrated under vacuum to give tert-butyl 4-(aminomethyl)-2-benzylpiperidine-1-carboxylate (1.1 g, crude) as a colorless oil.

Step c: To a solution of tert-butyl 4-(aminomethyl)-2-benzylpiperidine-1-carboxylate (1.1 g, 3.61 mmol, 1.00 eq) in dichloromethane (10 mL) was added DIPEA (607.10 mg, 4.70 mmol, 818.20 uL, 1.30 eq) and CbzCl (678.05 mg, 3.97 mmol, 565.05 uL, 1.10 eq). Then the mixture was stirred at 25° C. for 2 hr. LCMS (EW7754-12-P1A) showed that desired MS (Rt=1.009 min) was detected. The reaction mixture was poured into water (30 mL) and extracted with ethyl acetate (50 mL*3). Then combined organic layer was washed with brine (20 mL), dried over Na2SO4, filtered and concentrated. The residue was purified by column chromatography (SiO2, petroleum ether/ethyl acetate=10/1-5/1, Rf=0.5) to provide tert-butyl 2-benzyl-4-((((benzyloxy)carbonyl)amino)methyl)piperidine-1-carboxylate (1.4 g, 2.55 mmol, 70.5% yield, 79.8% purity) as a yellow oil.

Step d: To a solution of tert-butyl 2-benzyl-4-((((benzyloxy)carbonyl)amino)methyl)piperidine-1-carboxylate (0.9 g, 2.04 mmol, 1 eq) in HCl/ethyl acetate (10 mL) was stirred at 25° C. for 2 hr. TLC (petroleum ether/ethyl acetate=3/1) showed that compound 4 (Rf=0.5) was consumed and a new spot (Rf=0) was formed. The reaction mixture was concentrated to give benzyl ((2-benzylpiperidin-4-yl)methyl)carbamate hydrochloride (0.85933 g, crude, HCl) as a light yellow gum. 1H NMR (400 MHz DMSO-d6): δ 8.82-8.74 (m, 2H), 7.37-7.22 (m, 10H), 4.97 (dd, J=16.8 Hz, J=12.4 Hz, 2H), 3.57 (s, 1H), 3.26 (s, 1H), 3.08-2.87 (m, 5H), 2.52 (d, J=1.6 Hz, 2H), 1.98 (s, 5H), 1.75-1.23 (m, 4H).

Synthesis of 4-methyl-6-(4H-1,2,4-triazol-3-yl)-1,2,3,4-tetrahydroquinoline, Intermediate for Compound 165

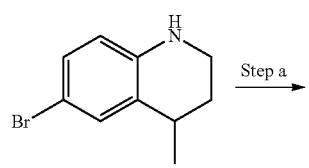

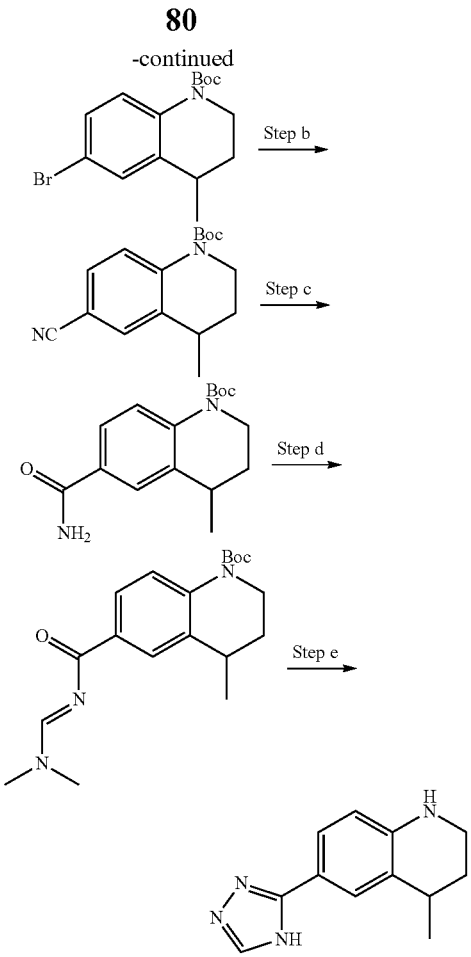

Step a: To a round bottomed flask containing a solution of 6-bromo-4-methyl-1,2,3,4-tetrahydroquinoline (1 g, 4.42 mmol) in THF (30 mL) was added sodium bis(trimethylsilyl)amide (8.84 mL, 8.84 mmol) under nitrogen. The reaction was stirred 2 h before the addition of di-tert-butyl dicarbonate (1.01 mL, 4.42 mmol). The suspension stirred at room temperature overnight before the addition of water. The product was extracted three times with ethyl acetate. The combined organic layers were washed with brine, dried over sodium sulfate, filtered and concentrated in vacuo. The crude residue was purified by silica gel chromatography (eluting with ethyl acetate and heptanes) to yield tert-butyl 6-bromo-4-methyl-3,4-dihydroquinoline-1(2H)-carboxylate (1.24 g, 3.80 mmol) as a yellow oil.

Step b: In a resealable vial, tert-butyl 6-bromo-4-methyl-3,4-dihydroquinoline-1(2H)-carboxylate (1.24 g, 3.80 mmol), dicyanozinc (446 mg, 3.80 mmol) and 2-(2-aminophenyl)benzen-1-ide di-tert-butyl({2-[2,4,6-tris(propan-2-yl)phenyl]phenyl})phosphane dipalladiumylium methanesulfonate (171 mg, 0.19 mmol) were combined. The flask was evacuated and backfilled with nitrogen three times before the addition of THF (2 mL) and water (10 mL), and the reaction was stirred at 40 C. After completion, the mixture was partitioned between sat. NaHCO$_3$ and EtOAc and stirred for 2 h. The organic layer was separated, and the aqueous layer was washed twice with EtOAc. The combined organic layers were dried over sodium sulfate, filtered, and concentration in vacuo. The residue was purified by silica gel chromatography (eluting with ethyl acetate and heptanes) to yield tert-butyl 6-cyano-4-methyl-3,4-dihydroquinoline-1(2H)-carboxylate (756 mg, 2.77 mmol) as an off-white solid.

Step c: In a round bottomed flask, tert-butyl 6-cyano-4-methyl-3,4-dihydroquinoline-1(2H)-carboxylate (500 mg, 1.83 mmol) was dissolved in DMSO (10 mL) and cooled to 0 C. 50% aq. hydrogen peroxide (1 mL, 1.83 mmol) was added, followed by potassium carbonate (75.8 mg, 0.549 mmol), and the mixture was stirred at room temperature. After 30 min, the mixture was heated to 60 C, and ethanol (2 mL) was added. After 2 h, the mixture was partitioned between EtOAc and water. The water layer was washed EtOAc. The organic layers were combined and concentrated in vacuo to yield tert-butyl 6-carbamoyl-4-methyl-3,4-dihydroquinoline-1(2H)-carboxylate (602 mg, 2.07 mmol) as a residue that was used in the next step without further purification.

Step d: In a round bottomed flask tert-butyl 6-carbamoyl-4-methyl-3,4-dihydroquinoline-1(2H)-carboxylate (600 mg, 2.06 mmol) was dissolved in toluene (10 mL). 1,1-dimethoxy-N,N-dimethylmethanamine (818 µL, 6.18 mmol) was added, and the mixture was heated to 100 C 45 min before the solvent was removed in vacuo. The residue was purified by silica gel chromatography (eluting with ethyl acetate and heptanes) to yield (E)-tert-butyl 6-(((dimethylamino)methylene)carbamoyl)-4-methyl-3,4-dihydroquinoline-1(2H)-carboxylate (688 mg, 1.99 mmol).

Step e: (E)-tert-butyl 6-(((dimethylamino)methylene)carbamoyl)-4-methyl-3,4-dihydroquinoline-1(2H)-carboxylate (300 mg, 0.8684 mmol) was dissolved in dioxane (3 mL) and added to a vial containing hydrazine hydrate (92.9 µL, 0.9552 mmol) and acetic acid (3 mL, 52.4 mmol). The solution was stirred at 90 C 30 min and overnight at room temperature. The mixture was concentrated in vacuo before being diluted with water and extracted twice with diethyl ether. The organic layers were dried over sodium sulfate and concentrated. The resulting residue was taken up in methanol (5 mL) for the addition of a few drops of conc. HCl. The solution was stirred at 60 C overnight before being concentrated in vacuo to yield 4-methyl-6-(1H-1,2,4-triazol-5-yl)-1,2,3,4-tetrahydroquinoline hydrochloride (169 mg, 0.6740 mmol).

Synthesis of rel-benzyl (((2S,4R)-2-phenylpiperidin-4-yl)methyl)carbamate hydrochloride and rel-benzyl (((2S,4S)-2-phenylpiperidin-4-yl)methyl)carbamate hydrochloride for Use in Compound 167 and Compound 168

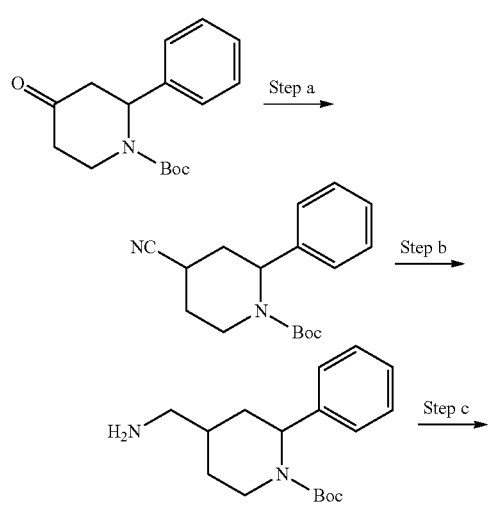

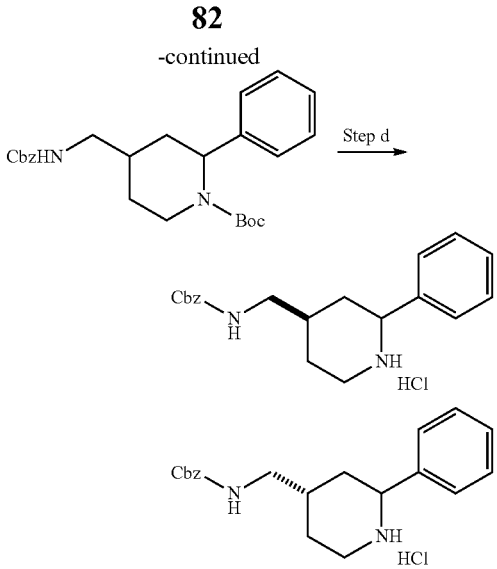

Step a: To a solution of tert-butyl 4-oxo-2-phenylpiperidine-1-carboxylate (2.3 g, 8.35 mmol, 1 eq) in DME (30 mL) was added TosMIC (2.45 g, 12.53 mmol, 1.5 eq) in DME (30 mL) and t-BuOK (2.81 g, 25.06 mmol, 3 eq) at −10° C. under N2. After stirring at −10° C. for 30 min, the mixture was stirred at 25° C. for 16 hr. TLC (petroleum ether/ethyl acetate=5/1) showed that compound 5 (Rf=0.28) was consumed and a new spot (Rf=0.25) was formed. The reaction mixture was poured into water (80 mL) and extracted with ethyl acetate (50 mL*3). Then combined organic layer was washed with brine (50 mL), dried over Na2SO4, filtered and concentrated. The residue was purified by column chromatography (SiO2, petroleum ether/ethyl acetate=20/1-5/1, Rf=0.25) to give tert-butyl 4-cyano-2-phenylpiperidine-1-carboxylate (1 g, crude) as a yellow oil. 1H NMR (400 MHz CDCl3): δ: 7.50-7.47 (m, 2H), 7.40-7.36 (m, 1H), 7.27-7.25 (d, J=8.0 Hz, 2H), 5.66 (s, 1H), 4.28-4.25 (m, 1H), 2.91-2.72 (m, 3H), 2.29-2.24 (m, 1H), 2.03-1.91 (m, 1H), 1.90-1.87 (m, 1H), 1.58 (s, 9H).

Step b: To a solution of tert-butyl 4-cyano-2-phenylpiperidine-1-carboxylate (1 g, 3.49 mmol, 1 eq) in methyl alcohol (20 mL) was added Raney-Ni (0.5 g, 5.84 mmol, 1.67 eq). Then the mixture was stirred under H2 (50 psi) at 25° C. for 32 hr. LCMS (EW7754-11-P1A) showed that the desired MS (Rt=0.658 min) was detected. The reaction mixture was filtered and the filtrate was concentrated under vacuum to give tert-butyl 4-(aminomethyl)-2-phenylpiperidine-1-carboxylate (0.8 g, crude) as a colorless oil.

Step c: To a solution of tert-butyl 4-(aminomethyl)-2-phenylpiperidine-1-carboxylate (0.8 g, 2.75 mmol, 1 eq) in dichloromethane (10 mL) was added DIPEA (462.85 mg, 3.58 mmol, 623.79 uL, 1.3 eq) and CbzCl (516.95 mg, 3.03 mmol, 430.79 uL, 1.1 eq). Then the mixture was stirred at 25° C. for 2 hr. LCMS (EW7754-13-PIA) showed that the desired Ms (Rt=0.996 min) was detected. The reaction mixture was poured into water (30 mL) and extracted with ethyl acetate (50 mL*2). Then combined organic layer was washed with brine (20 mL), dried over Na2SO4, filtered and concentrated. The residue was purified by column chromatography (SiO2, Petroleum ether/Ethyl acetate=10/1-5/1, Rf=0.5) to give tert-butyl 4-((((benzyloxy)carbonyl)amino)methyl)-2-phenylpiperidine-1-carboxylate (1.1 g, 2.14 mmol, 77.5% yield, 82.4% purity) as a colorless oil.

Step d: To a solution of tert-butyl 4-((((benzyloxy)carbonyl)amino)methyl)-2-phenylpiperidine-1-carboxylate (0.74 g, 1.73 mmol, 1 eq) in HCl/ethyl acetate (10 mL) was stirred at 25° C. for 2 hr. The reaction mixture was concentrated to give rel-benzyl (((2S,4R)-2-phenylpiperidin-4-yl)methyl) carbamate hydrochloride and rel-benzyl (((2S,4S)-2-phenylpiperidin-4-yl)methyl)carbamate hydrochloride (678.94 mg, crude, HCl) as a white solid. 1HNMR (400 MHz DMSO-d6): δ 9.13 (s, 2H), 7.55-7.31 (m, 10H), 5.07-4.99 (m, 2H), 4.43 (d, J=10.0 Hz, 1H), 3.26-3.13 (m, 3H), 2.52 (d, J=1.6 Hz, 2H), 2.05-1.96 (m, 3H), 1.80-1.65 (m, 2H).

Synthesis of 4-(1,3-thiazol-2-yl)-2,3-dihydro-1H-indole, A-Ring for Compound 173 and Compound 221

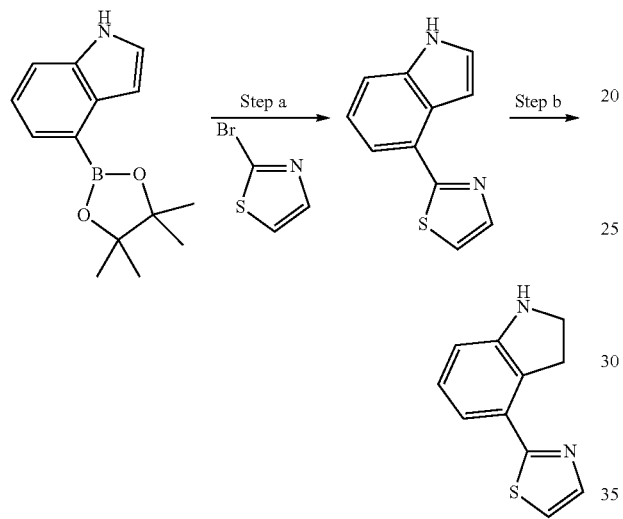

Step a: The mixture of 4-(4,4,5,5-tetramethyl-1,3,2-dioxaborolan-2-yl)-1H-indole (4 g, 16.4 mmol, 1.0 eq), 2-bromo-1,3-thiazole (4.0 g, 24.5 mmol, 1.5 eq), Pd(dppf)Cl₂ (1.2 g, 1.6 mmol, 0.1 eq) and K₂CO₃ (6.8 g, 49.1 mmol, 3.0 eq) in dioxane (50 mL) and H₂O (5 mL) was evacuated and refilled for 3 times using N₂ and stirred at 90° C. for 6 hours. LCMS indicated that the starting material was remained and one main new peak with desired MS was detected. The mixture was diluted with H₂O (50 mL), extracted with EtOAc (70 mL×2). The organic layer was washed with brine (50 mL), dried over anhydrous Na₂SO₄, filtered and concentrated under reduced pressure. The residue was purified by column chromatography (Petroleum ether/Ethyl acetate=20:1~8:1) to afford 4-(1,3-thiazol-2-yl)-1H-indole (1.7 g, 52% yield) as a yellow solid.

Step b: To a mixture of 4-(1,3-thiazol-2-yl)-1H-indole (2 g, 9.98 mmol, 1.0 eq) in AcOH (15 mL) was added NaBH₃CN (1.88 g, 29.9 mmol, 1.0 eq). The mixture was stirred at 30° C. for 4 hours. LCMS indicated that the starting material was consumed completely and one main new peak with desired MS was detected. The mixture was concentrated under reduced pressure. The residue was diluted with EtOAc (70 mL), adjusted with saturated NaHCO₃ to pH=8. The organic layer was washed with brine (30 mL), dried over anhydrous Na₂SO₄, filtered and concentrated under reduced pressure. The residue was purified by column chromatography (Petroleum ether/Ethyl acetate=20:1~5:1) to afford the desired product of 4-(1,3-thiazol-2-yl)-2,3-dihydro-1H-indole (1.05 g, 52% yield) as a yellow oil.

Synthesis of 4-methyl-1,2,3,4-tetrahydroquinoxaline-6-carbonitrile, Used in the Synthesis of Compound 184

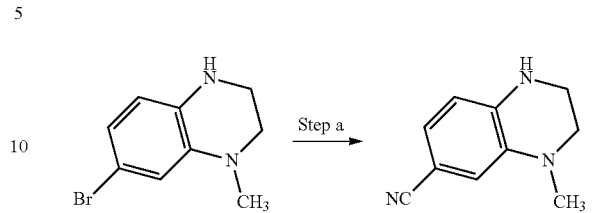

Step a: A resealable reaction vial was charged with 7-bromo-1-methyl-1,2,3,4-tetrahydroquinoxaline (250 mg, 1.10 mmol), zincdicarbonitrile (258 mg, 2.20 mmol), palladium(1+) 2'-amino-1,1'-biphenyl-2-yl di-tert-butyl[2',4',6'-tris(propan-2-yl)-[1,1'-biphenyl]-2-yl]phosphane methanesulfonate (87.3 mg, 0.1100 mmol), dioxane (6 mL) and water (1 mL). The mixture was bubbled with nitrogen for 10 min. The vial was sealed, and the mixture was stirred at 90° C. for 2 hrs. The reaction mixture was concentrated and the residue was purified by flash silica gel chromatography (eluting with ethyl acetate:heptanes=20:80 to 40:60) to afford 4-methyl-1,2,3,4-tetrahydroquinoxaline-6-carbonitrile (67 mg) as a yellow solid. LCMS: [M+H]⁺ 174.

Synthesis of 4-acetyl-1,2,3,4-tetrahydroquinoxaline-6-carbonitrile, Intermediate Used in the Preparation of Compound 187 and Compound 302

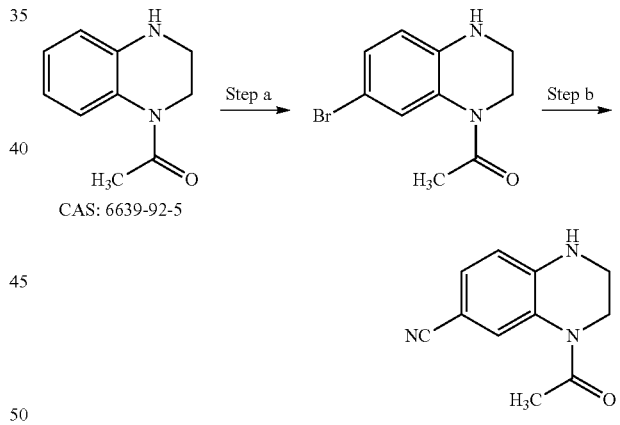

Step a: A round bottom flask containing 1-(3,4-dihydroquinoxalin-1(2H)-yl)ethan-1-one (192 mg, 1.09 mmol) (CAS: 6639-92-5) in ACN (1.5 mL) was cooled to 0° C. A solution of N-bromosuccinimide (192 mg, 1.09 mmol) in ACN (1.7 mL) was added and the reaction stirred at 0° C. for 5 min before adding sat. Na₂S₂O₃ at the same temperature. The reaction was warmed to ambient temperature and Et₂O was added. The organic layer was extracted with Et₂O (3×), and combined organic extracts were dried, concentrated and purified via silica gel chromatography (18-100% EtOAc in hexanes) to provide 1-(7-bromo-3,4-dihydroquinoxalin-1 (2H)-yl)ethan-1-one (194 mg, 0.760 mmol) in 70% yield, along with the dibrominated analog, which was not isolated. LCMS: [M+] 255.1 and 257.1.

Step b: A resealable vial was charged with 1-(7-bromo-3,4-dihydroquinoxalin-1(2H)-yl)ethan-1-one (122 mg, 0.0.480 mmol), [(2-Di-tert-butylphosphino-2',4',6'-triisopropyl-1,1'-biphenyl)-2-(2'-amino-1,1'-biphenyl)] palladium (II) methanesulfonate (38.0 mg, 0.048 mmol), and zinc dicyanide (67 mg, 0.57 mmol) before being evacuated and backfilled with nitrogen (3×). A mixture of H₂O (1.3 mL) and THF (0.25 mL) was then added and the reaction was heated to 40° C. for 16 h. The reaction was cooled to ambient temperature and partitioned between EtOAc and sat. sodium bicarbonate. The organic layer was extracted with EtOAc (3×), dried, concentrated and purified via silica gel chromatography (25-100% EtOAc in hexanes) to provide 4-acetyl-1,2,3,4-tetrahydroquinoxaline-6-carbonitrile (48.0 mg, 0.239 mmol) in 50% yield. LCMS: [M+]201.2.

Synthesis of 6-(1-methyl-1H-pyrazol-4-yl)-2,3-dihydro-1H-pyrido[2,3-b][1,4]oxazine, Intermediate Used in the Preparation of Compound 188 and Compound 324

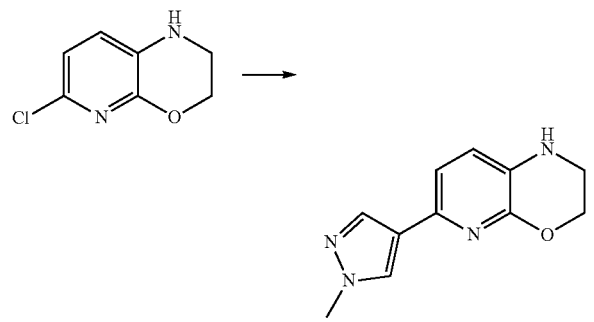

A resealable reaction vial was charged with 6-bromo-1H,2H,3H-pyrido[2,3-b][1,4]oxazine (555 mg, 2.58 mmol), (1-methyl-1H-pyrazol-4-yl)boronic acid (487 mg, 3.87 mmol), [2 (222 mg, 0.258 mmol), dipotassium carbonate (713 mg, 5.16 mmol), and a stirbar before being evacuated and purged with nitrogen three times. 10:1 dioxane:water (5.5 mL) was added, and the mixture was stirred at 90° C. 18 h. The mixture was diluted with ethyl acetate, filtered, and concentrated in vacuo with celite. The crude material was purified by silica gel chromatography (eluting with ethyl acetate, heptanes, and methanol). Product-containing fractions were concentrated in vacuo to yield 1-methyl-4-{1H,2H,3H-pyrido[2,3-b][1,4]oxazin-6-yl}-1H-pyrazole (540 mg, 2.49 mmol) as a orange oil. LCMS: [M+H]+ 217.

Synthesis of N-methyl-3,4-dibydroquinoxaline-1(2H)-carboxamide, Intermediate Used in the Preparation of Compound 342 and Compound 189

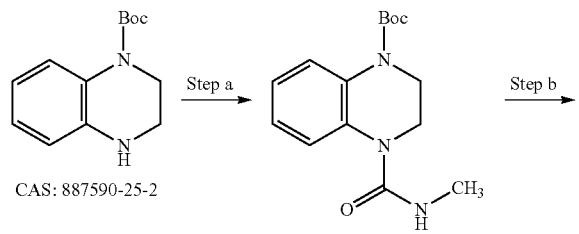

-continued

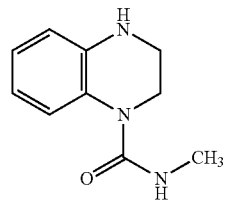

Step a: A round bottom flask was charged with tert-butyl 3,4-dihydroquinoxaline-1(2H)-carboxylate (150 mg, 0.640 mmol) (CAS: 887590-25-2) in DMF (6.40 mL) before the addition of N-methyl-1H-imidazole-1-carboxamide (800 mg, 6.40 mmol) and triethylamine (0.356 mL, 2.56 mmol) and the reaction was heated to 80° C. for 16 h. After cooling to ambient temperature, the residue was concentrated to dryness and purified via silica gel chromatography (10-100% EtOAc in hexanes) to furnish tert-butyl 4-(methylcarbamoyl)-3,4-dihydroquinoxaline-1(2H)-carboxylate (73.0 mg, 0.25 mmol) in 40% yield. LCMS: [M+Na]+314.

Step b: To a round bottom flask containing tert-butyl 4-(methylcarbamoyl)-3,4-dihydroquinoxaline-1(2H)-carboxylate (73.0 mg, 0.25 mmol) in dichloromethane (4.0 mL) was added trifluoroacetic acid (0.50 mL) and the reaction was stirred at room temperature for 1 h. Solvent was evaporated and the residue was purified via silica gel chromatography (10-100% EtOAc in hexanes) to provide N-methyl-3,4-dihydroquinoxaline-1(2H)-carboxamide (47.8 mg, 0.25 mmol) in quantitative yield.

Synthesis of 5-methanesulfinyl-1,2,3,4-tetrahydroquinoline, A-Ring for Compound 192

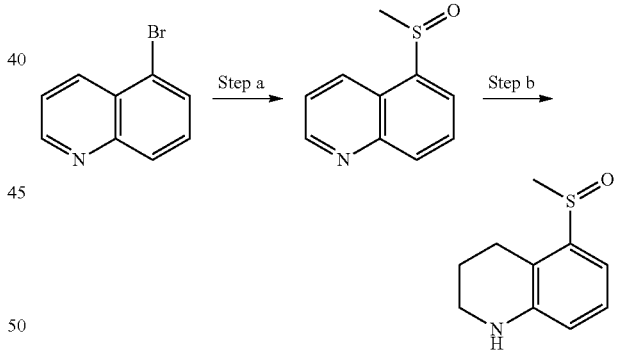

Step a: A mixture of 5-bromoquinoline (2 g, 9.6 mmol), NaSCH₃ (1 g, 14.4 mmol) and DMF (25 mL) was placed into autoclave. The mixture was stirred at 130° C. for 1.5 h. The mixture was then cold to 15° C. The aq. NaClO (27.0 mL, 40 mmol, 10%) was added. The mixture was stirred at 15° C. for 5 min. The reaction was quenched by saturated Na₂SO₃ (20 mL). The mixture was extracted with ethyl acetate (100 mL×3). The combined organic layers were washed with brine (100 mL), dried over anhydrous Na₂SO₄, filtered and concentrated to give a residue. The residue was purified by flash silica gel chromatography (Ethyl acetate: Petroleum ether=50:100 to 100:100 then EtOAc: MeOH=100:10) to give the product of 5-methanesulfinylquinoline (700 mg, 38% yield in 2 steps) as a yellow solid.

Step b: A solution of 5-methanesulfinylquinoline (500 mg, 2.6 mmol), diphenoxyphosphinic acid (130 mg, 0.5 mmol) and 2-[5-(ethoxycarbonyl)-2,6-dimethyl-1,4-dihydropyridine-3-carbonyloxy]ethylium (1.64 g, 6.5 mmol) in PhMe (25 ml) was stirred at 80° C. for 12 hours under $N_2$. The mixture was concentrated and purified by flash silica gel chromatography (Petroleum ether:EtOAc=100:50 to 100:100, then MeOH:EtOAc=10:100) to afford the product of 5-methanesulfinyl-1,2,3,4-tetrahydroquinoline (400 mg, 78% yield) as a yellow solid.

Synthesis of 6-chloro-4-methyl-1,2,3,4-tetrahydropyrido[2,3-b]pyrazine, Intermediate Used in the Preparation of Compound 195

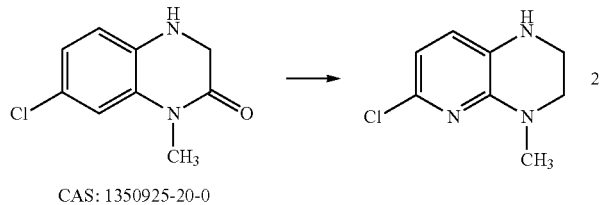

CAS: 1350925-20-0

A suspension of 6-chloro-4-methyl-1H,2H,3H,4H-pyrido[2,3-b]pyrazin-3-one (120 mg, 0.6072 mmol) in THF (1.2 mL) was added dropwise to lithium aluminum hydride (1.0M in THF, 3.03 mL, 3.03 mmol). Upon the cessation of gas evolution, the reaction vessel was sealed and heated to 65° C. for 16 h. The reaction was cooled and ice was added slowly until gas evolution was no longer observed. EtOAc was added to the reaction, and the organic layer was extracted with EtOAc (3×), concentrated and purified via silica gel chromatography (10-100% EtOAc in hexanes) to furnish 6-chloro-4-methyl-1,2,3,4-tetrahydropyrido[2,3-b]pyrazine (74.0 mg, 0.403 mmol) in 66% yield. LCMS: [M+H]+ 184.1.

Synthesis of tert-butyl ((3S,4S)-8-(3-iodo-1-(tetrahydro-2H-pyran-2-yl)-1H-pyrazolo[3,4-b]pyrazin-6-yl)-3-methyl-2-oxa-8-azaspiro[4.5]decan-4-yl)carbamate, Used in the Preparation of Compound 200

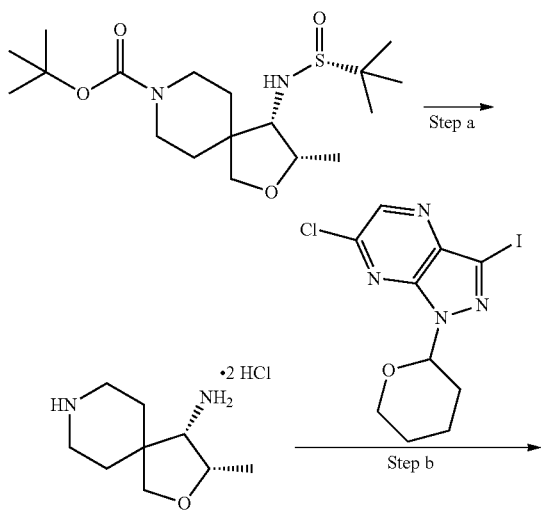

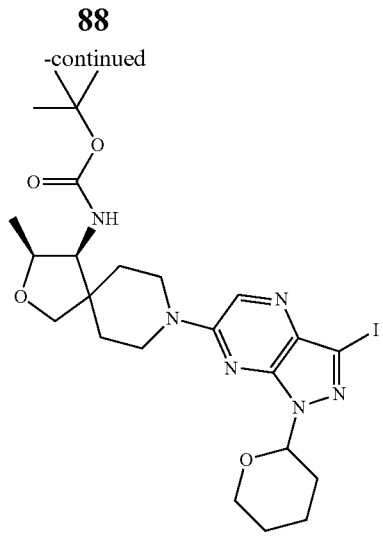

Step a: To a solution of tert-butyl (3S,4S)-4-(((R)-tert-butylsulfinyl)amino)-3-methyl-2-oxa-8-azaspiro[4.5]decane-8-carboxylate (40.0 g, 107 mmol, 1.00 eq) in MeOH (800 mL) was added HCl/MeOH (4 M, 267 mL, 10.0 eq). The mixture was stirred at 25° C. for 5 hrs, then the reaction mixture was concentrated. Next, methyl tert-butyl ether (500 mL) was added to the residue which was stirred for 15 min. Then the mixture was concentrated to give (3S,4S)-3-methyl-2-oxa-8-azaspiro[4.5]decan-4-amine (29.3 g, crude, 2HCl) as a white solid. $^1$H NMR: 400 MHz DMSO δ: 9.23-9.19 (m, 2H), 8.39 (s, 3H), 4.23-4.20 (m, 1H), 3.83-3.81 (d, J=9.2 Hz, 1H), 3.64-3.61 (d, J=8.8 Hz, 1H), 3.22 (m, 1H), 3.15 (m, 1H), 2.93-2.85 (m, 2H), 2.01-1.69 (m, 4H), 1.25-1.22 (d, J=11.2 Hz, 3H).

Step b: To a mixture of (3S,4S)-3-methyl-2-oxa-8-azaspiro[4.5]decan-4-amine (29.3 g, 120 mmol, 1.00 eq, 2HCl) in DMF (240 mL) was added DIPEA (62.3 g, 482 mmol, 84.0 mL, 4.00 eq) and 6-chloro-3-iodo-1-(tetrahydro-2H-pyran-2-yl)-1H-pyrazolo[3,4-b]pyrazine (46.1 g, 127 mmol, 1.05 eq) at 25° C. The mixture was heated to 50° C., and stirred at 50° C. for 4 hrs. To the mixture was added Boc$_2$O (31.6 g, 145 mmol, 33.2 mL, 1.20 eq) at 25° C. The mixture was stirred at 50° C. for 3 hrs. The mixture was diluted with methyl tert-butyl ether (1.50 L), washed with brine (500 mL*3), dried over Na$_2$SO$_4$ and concentrated under vacuum. The residue was purified by column chromatography (SiO$_2$, petroleum ether: ethyl acetate=1:0 to 0:1) to give tert-butyl ((3S,4S)-8-(3-iodo-1-(tetrahydro-2H-pyran-2-yl)-1H-pyrazolo[3,4-b]pyrazin-6-yl)-3-methyl-2-oxa-8-azaspiro[4.5]decan-4-yl)carbamate (50.5 g, 84.4 mmol) as a light yellow solid. LCMS m/z: 599.5 (M+1)$^+$, $^1$H NMR: 400 MHz CDCl$_3$ δ: 8.17 (s, 1H), 5.79-5.76 (d, J=12 Hz, 1H), 4.65-4.62 (d, J=10.4 Hz, 1H), 4.19-4.09 (m, 1H), 4.05-4.02 (m, 1H), 3.74-3.64 (m, 8H), 2.65-2.63 (m, 1H), 2.15-2.04 (m, 1H), 1.92-1.75 (m, 8H), 1.45 (s, 9H), 1.22-1.21 (m, J=6.4 Hz, 3H).

The building blocks for Compound 211 and Compound 213 were prepared according to reported procedures, starting from (S)-1-(4-methoxyphenyl)ethan-1-amine and 8-azaspiro[4.5]decan-1-one or 2-oxa-8-azaspiro[4.5]decan-4-one, and the resulting intermediates were used in a route analogous to that used for Compound 179.

Synthesis of Benzyl (8-(3-iodo-1-(tetrahydro-2H-pyran-2-yl)-1H-pyrazolo[3,4-b]pyrazin-6-yl)-8-azaspiro[4.5]decan-1-yl)carbamate, Used in the Preparation of Compound 211

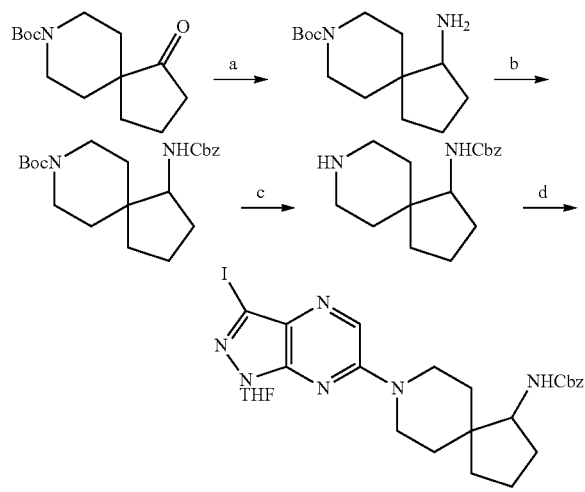

Step a: A mixture tert-butyl 1-oxo-8-azaspiro[4.5]decane-8-carboxylate (1000 mg, 3.94 mmol, CAS #191805-29-5) and ammonium acetate (3037 mg, 39.4 mmol) in ethanol (10 mL) was stirred at room temperature for 5 min. Sodium cyanoborohydride (297 mg, 4.73 mmol) was added in three parts. The mixture was heated under microwave for 99 min at 110° C. The residue was dissolved in water and ethyl acetate and stirred vigorously. The ethyl acetate phase was separated, dried over MgSO$_4$, filtered and concentrated to give crude product, which was taken to the next step without purification. MS (ES+) m/z 198.1 ((M-C4H9)+1)$^+$.

Step b: Triethylamine (713 mL, 5.11 mmol) and benzyl chloroformate (810 mg, 4.72 mmol) were added to a solution of spiroamine (1000 mg, 3.93 mmol) in dichloromethane (25 mL) at 0° C. The resulting mixture was stirred at room temperature for 15 h, treated with saturated sodium bicarbonate and extracted two times with dichloromethane. The combined organic extracts were washed with brine, dried over MgSO4, filtered and concentrated. The residue was purified by chromatography on silica gel (hexane/Et$_2$O, 5:1 to 1:1) to afford desired product tert-butyl 1-(((benzyloxy)carbonyl)amino)-8-azaspiro[4.5]decane-8-carboxylate (800 mg, 53% over two steps) as a clear oil. MS (ES+) m/z 333.1((M-C4H9)+1)$^+$.

Step c: Tert-butyl 1-(((benzyloxy)carbonyl)amino)-8-azaspiro[4.5]decane-8-carboxylate (200 mg, 0.51 mmol) was dissolved in DCM (2 mL) and HCl in dioxane (4M, 2 mL, 8.0 mmol) was added. The mixture was stirred 15 min at room temperature and then concentrated under vacuum. The solid was dissolved in DCM and washed with a saturated solution of NaHCO$_3$. The aqueous phase was extracted three further times with DCM. The organic phase was combined, dried over MgSO4, filtered and concentrated to give pure benzyl 8-azaspiro[4.5]decan-1-ylcarbamate (136 mg, 92%). $^1$H NMR (500 MHz, CDCl3) δ 7.40-7.21 (m, 5H), 5.01 (dd, J=37.9, 12.2 Hz, 2H), 4.58 (s, 1H), 2.87 (s, 2H), 2.63 (dt, J=21.3, 10.7 Hz, 2H), 2.05-1.84 (m, 1H), 1.80-1.61 (m, 3H), 1.56 (dd, J=11.0, 8.2 Hz, 2H), 1.45-1.28 (m, 3H), 1.28-1.10 (m, 3H). MS (ES+) m/z 288.4 (M+H)$^+$.

Step d: To a 10 mL seal tube, 6-chloro-3-iodo-1-(tetrahydro-2H-pyran-2-yl)-1H-pyrazolo[3,4-b]pyrazine (300 mg, 0.82 mmol), benzyl 8-azaspiro[4.5]decan-1-ylcarbamate (400 mg, 1.23 mmol), cesium fluoride (250 mg, 1.65 mmol) and potassium phosphate (350 mg, 1.65 mmol) were suspended in dimethylacetamide (4 mL). The resulting heterogeneous mixture was then heated at 85° C. for 5 h. The reaction mixture was then cooled to room temperature, poured into water (20 mL) and ethyl acetate (20 mL) was added. The layers were separated and the aqueous layer was extracted with ethyl acetate (2×20 mL). The organic layers were combined, washed with brine (300 mL), dried over anhydrous MgSO4, filtered and concentrated under reduced pressure. The crude residue was purified by flash chromatography using a gradient of ethyl acetate in hexanes (0 to 100%) to give benzyl (8-(3-iodo-1-(tetrahydro-2H-pyran-2-yl)-1H-pyrazolo[3,4-b]pyrazin-6-yl)-8-azaspiro[4.5]decan-1-yl)carbamate (370 mg, 73%) as a white solid after drying under high vacuum overnight. LCMS m/z 617.2 [M+H]$^+$; 1H NMR (500 MHz, CDCl3) δ 8.42 (d, J=9.5 Hz, 1H), 7.34-7.16 (m, 5H), 5.68 (dt, J=19.2, 9.6 Hz, 1H), 5.03-4.90 (m, 2H), 4.31-4.17 (m, 3H), 3.91 (d, J=10.9 Hz, 1H), 3.68-3.59 (m, 2H), 3.23 (dd, J=13.1, 6.8 Hz, 2H), 2.45-2.33 (m, 2H), 1.99 (t, J=6.8 Hz, 1H), 1.86 (ddd, J=15.4, 10.4, 3.3 Hz, 2H), 1.60-1.43 (m, 6H), 1.43-1.30 (m, 4H).

Synthesis of 8-(3-iodo-1-(tetrahydro-2H-pyran-2-yl)-1H-pyrazolo[3,4-b]pyrazin-6-yl)-N-(4-methoxybenzyl)-2-oxa-8-azaspiro[4.5]decan-4-amine, Used in the Preparation of Compound 213

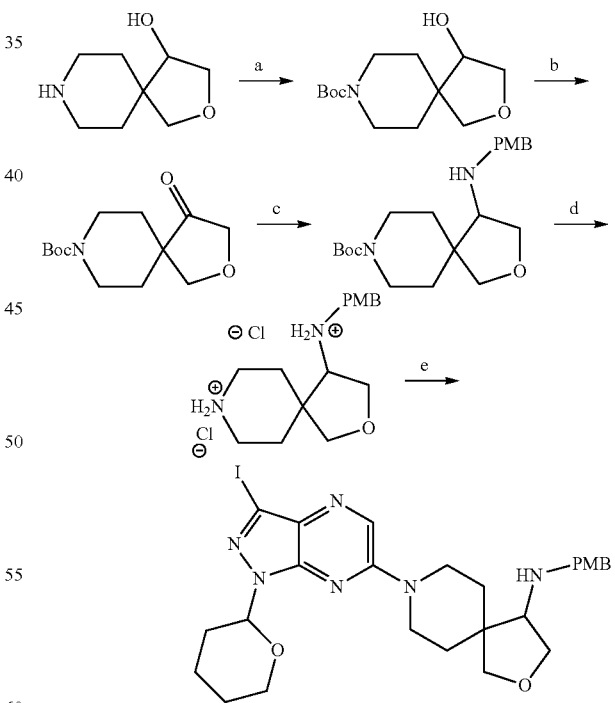

Step a: 2-oxa-8-azaspiro[4.5]decan-4-ol (500 mg, 3.18 mmol, CAS #777049-50-0) was suspended in DCM (30 mL). Di-tert-butyl dicarbonate (833 mg, 3.82 mmol) was added to the mixture and the reaction stirred at room temperature until TLC showed complete conversion to desired product. The mixture was then made slightly acidic with 1M hydrochloric acid (pH=5), and was extracted with ethyl acetate (2×). The combined organics were washed with brine and then dried over magnesium sulfate, filtered and concentrated in vacuo. Tert-butyl 4-hydroxy-2-oxa-8-azaspiro[4.5]decane-8-carboxylate was obtained as white solid (682 mg, 83% yield). $^1$H NMR: (400 MHz, CDCl$_3$) δ 4.10 (dd, J=10.2, 4.7 Hz, 1H), 4.01 (dt, J=4.7, 1.6 Hz, 1H), 3.74 (d, J=8.6 Hz, 1H), 3.73 (dd, J=10.7, 2.0 Hz, 1H), 3.67 (d, J=8.6 Hz, 1H), 3.65-3.61 (m, 2H), 3.27 (dt, J=13.7, 6.7 Hz, 1H), 3.14 (ddd, J=12.9, 9.0, 3.5 Hz, 1H) 1.84-1.79 (m, 1H), 1.76 (ddd, J=13.3, 9.0, 3.9 Hz, 1H), 1.56 (ddd, J=13.3, 6.3, 3.5 Hz, 1H) 1.50-1.49 (m, 2H), 1.47 (s, 9H).

Step b: tert-butyl 4-hydroxy-2-oxa-8-azaspro[4.5]decane-8-carboxylate (682 mg, 2.65 mmol) was dissolve in DCM (20 mL). Sodium bicarbonate (890 g, 10.60 mmol) and the Dess-Martin periodinane (2.25 g, 5.30 mmol) were added to the mixture. The reaction mixture was stirred at room temperature until TLC showed complete conversion to desired product. A 1:1:1 mixture of NaHCO$_3$ (sat.): Na$_2$S$_2$O$_3$ (sat.): DCM (10 mL in total) was added slowly (a few mL portions as gas was evolved). This mixture was stirred until two clear layer was observed (about h). The mixture was transferred to a separatory funnel and extracted with DCM (3×). The combined organics were washed with brine and then dried over magnesium sulfate, filtered and concentrated in vacuo. Ter-butyl 4-oxo-2-oxa-8-azaspiro[4.5]decane-8-carboxylate was obtained as white solid (609 mg g, 90% yield). LCMS m/z 256.2 [M+H$^+$].

Step c: tert-butyl 4-oxo-2-oxa-8-azaspiro[4.5]decane-8-carboxylate (609 mg, 2.39 mmol) was suspended in dichloroethane (15.0 mL). 4-methoxybenzylamine (0.34 mL, 2.62 mmol) and sodium cyanoborohydride (749 mg, 11.93 mmol) was added to the mixture and the reaction was stirred at room temperature overnight. The mixture was then quenched with sat. sodium bicarbonate solution and stirred for 1 h. The mixture was then extracted with ethyl acetate (3×), the combined organics were washed with brine and then dried over magnesium sulfate, filtered and concentrated in vacuo. The desired product was purified using flash chromatography with 10-100% EtOAc in hexanes. This gave tert-butyl 4-((4-methoxybenzyl)amino)-2-oxa-8-azaspiro[4.5]decane-8-carboxylate (489 mg, 54% yield) as a clear oil. LCMS m/z 377.3 [M+H$^+$].

Step d: tert-butyl 4-((4-methoxybenzyl)amino)-2-oxa-8-azaspiro[4.5]decane-8-carboxylate (489 mg, 1.29 mmol) was dissolved in a 4 M solution of HCl in dioxane (10 mL). The mixture was stirred for 1 hr at room temperature. The mixture was then concentrated in vacuo providing 4-((4-methoxybenzyl)ammonio)-2-oxa-8-azaspiro[4.5]decan-8-ium chloride (394 mg, 88% yield) as a white solid. LCMS m/z 277.2 [M+H$^+$].

Step e: 4-((4-methoxybenzyl)ammonio)-2-oxa-8-azaspiro[4.5]decan-8-ium chloride (394 mg, 1.13 mmol) was dissolved in NMP (5.0 mL). Potassium phosphate tribasic (426 mg, 2.0 mmol), cesium fluoride (305 mg, 2.00 mmol) and 6-chloro-3-iodo-1-(tetrahydro-2H-pyran-2-yl)-1H-pyrazolo[3,4-b]pyrazine (365 mg, 1.00 mmol) was added to the mixture. The reaction was stirred at 85° C. until LCMS showed complete conversion to desired product. The mixture was cooled to room temperature and the desired product was purified using 20-100% MeCN in 10 mM ammonium bicarbonate buffer on reverse phase chromatography to give 8-(3-iodo-1-(tetrahydro-2H-pyran-2-yl)-1H-pyrazolo[3,4-b]pyrazin-6-yl)-N-(4-methoxybenzyl)-2-oxa-8-azaspiro[4.5]decan-4-amine (311 mg, 46% yield) after lyophilization. LCMS m/z 605.3 [M+H$^+$], 521.2 [M-THP$^+$]. $^1$H NMR (400 MHz, CDCl$_3$) δ 8.17 (s, 1H), 7.25-7.20 (m, 2H), 6.88-6.82 (m, 2H), 5.77 (d, J=8.7 Hz, 1H), 4.08 (dd, J=24.7, 9.4 Hz, 3H), 3.82 (d, J=14.7 Hz, 1H), 3.78 (s, 3H), 3.77-3.59 (m, 4H), 3.37 (s, 1H), 3.00 (t, J=5.5 Hz, 1H), 2.70-2.56 (m, 1H), 2.14 (d, J=6.3 Hz, 1H), 1.92 (d, J=11.6 Hz, 1H), 1.76 (dd, J=19.8, 11.8 Hz, 2H), 1.64-1.49 (m, 8H).

Synthesis of 4-methyl-1,2,3,4-tetrahydroquinoline-6-carbonitrile, Intermediate Used in the Preparation of Compound 218

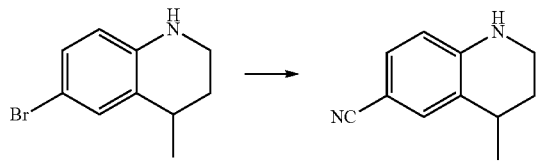

In a resealable vial, 6-bromo-4-methyl-1,2,3,4-tetrahydroquinoline (1 g, 4.42 mmol) (CAS 946837-99-6) was combined with dicyanozinc (518 mg, 4.42 mmol) and tBuXPhos G4 (199 mg, 0.2210 mmol). The vessel was evacuated and backfilled with nitrogen three times. THF (2 mL) and water (10 mL) were added, and the solution stirred at 40 C 3 d. The mixture was partitioned between sat. NaHCO$_3$ and EtOAc. The organic layer was washed twice with ethyl acetate, washed with brine, dried over sodium sulfate, filtered, and concentrated in vacuo. The resulting residue was purified by silica gel chromatography (eluting with ethyl acetate and heptanes) to yield 4-methyl-1,2,3,4-tetrahydroquinoline-6-carbonitrile (407 mg, 2.36 mmol) as an off-white solid.

Synthesis of rel-(R)-6-bromo-4-methyl-1,2,3,4-tetrahydroquinoline and rel-(S)-6-bromo-4-methyl-1,2,3,4-tetrahydroquinoline, Used in the Preparation of Compound 219 and 220

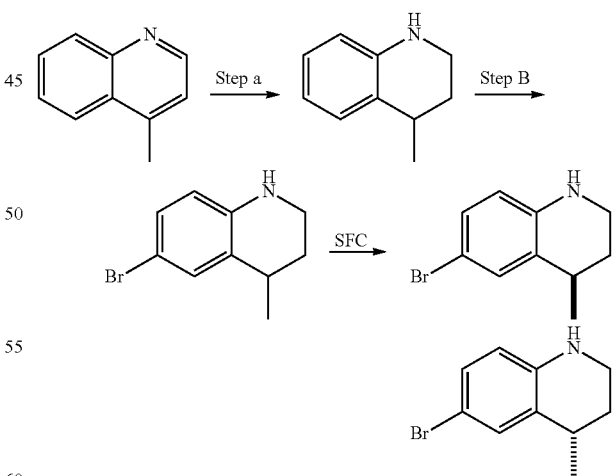

Step a: To a solution of 4-methylquinoline (400 g, 2.79 mol, 370 mL, 1.00 eq) in toluene (2.00 L) was added Pd/C (40.0 g, 10.0% purity). The suspension was degassed under vacuum and purged with H2 several times. The mixture was stirred under H2 (3 MPa) at 120° C. for 32 h. TLC (Petroleum ether/Ethyl acetate=5/1) showed compound 1

(Rf=0.3) was consumed and the desired spot (Rf=0.7) was detected. The mixture was filtered, and the filtrate was concentrated under vacuum. The crude product was purified by silica gel chromatography eluted with Petroleum ether (Rf=0.7). 4-methyl-1,2,3,4-tetrahydroquinoline (900 g, 5.16 mol, 92.3% yield, 84.4% purity) was obtained as a light yellow oil. 1H NMR: 400 MHz CDCl3 7.11-7.09 (d, J=8.0 Hz, 1H), 7.02-6.98 (ddd, J=1.2, 7.4, 8.0 Hz, 1H), 6.69-6.65 (dt, J=1.2, 7.4 Hz, 1H), 6.52-6.50 (dd, J=1.2, 8.0 Hz, 1H), 3.88 (s, 1H), 3.39-3.30 (m, 2H), 2.98-2.93 (m, 1H), 2.05-2.01 (m, 1H), 1.76-1.66 (m, 1H), 1.34-1.33 (d, J=4.0 Hz, 3H).

Step b: To a solution of 4-methyl-1,2,3,4-tetrahydroquinoline (400 g, 1.00 eq, 84.4% purity) in DMF (1.20 L) was added NBS (428 g, 2.41 mol, 1.05 eq) in DMF (800 mL) drop-wise slowly at −20° C. The mixture was stirred at −20-0° C. for 0.5 h under a nitrogen atmosphere. TLC (Petroleum ether/Ethyl acetate=10/1) showed compound 2 (Rf=0.45) was consumed and the desired spot (Rf=0.4) was detected. The mixture was poured into water (6.00 L) then extracted with ethyl acetate (3.00 L*3). The combined organic layers were dried over Na2SO4, concentrated under vacuum. 946837-99-6 (570 g, crude) was obtained as brown oil. 946837-99-6 (700 g) was dissolved with ethyl acetate (1.50 L) and concentrated under vacuum. The residue was purified by silica gel chromatography (Petroleum ether-Petroleum ether/ethyl acetate=20/1, Rf=0.4). 6-bromo-4-methyl-1,2,3,4-tetrahydroquinoline (230 g, 990 mmol, 97.4% purity) was obtained as an off-white solid. 1H NMR: 400 MHz CDCl3 7.15-7.14 (dd, J=0.8, 2.0 Hz, 1H), 7.05-7.02 (dd, J=2.0, 8.0 Hz, 1H), 6.36-6.34 (d, J=8.4 Hz, 1H), 3.87 (s, 1H), 3.35-3.25 (m, 2H), 2.93-2.85 (m, 1H), 1.97-1.93 (m, 1H), 1.68-1.64 (m, 1H), 1.29-1.27 (d, J=8.0 Hz, 3H).

SFC: 6-bromo-4-methyl-1,2,3,4-tetrahydroquinoline was separated into its individual enantiomers by preparative SFC: Instrument: Thar 200 preparative SFC (SFC-20); Column: Chiral Cel OJ, 300×50 mm I.D., 10 μm; Mobile phase: A for C02 and B for ETOH; Gradient: B 20%; Flow rate: 240 mL/min; Back pressure: 100 bar; Column temperature: 38° C.; Wavelength: 220 nm; Cycle time: 3.7 min; Sample preparation: Compound was dissolved in ~2300 mL; ETOH\DCM; Injection: 4 ml per injection; Ee values: faster eluting isomer: 99.7%; slower eluting isomer: 99.5%.

Synthesis of (R)-4-methyl-1,2,3,4-tetrahydroquinoline-6-carbonitrile, Intermediate Used in the Preparation of Compound 219

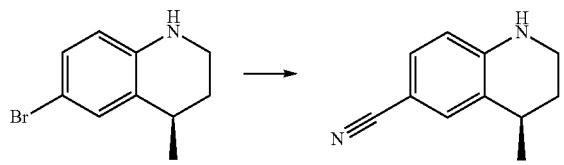

A resealable reaction vial was charged with (4R)-6-bromo-4-methyl-1,2,3,4-tetrahydroquinoline (400 mg, 1.76 mmol), zinc dicarbonitrile (206 mg, 1.76 mmol), Pd/tBuXPhos G3 (69.9 mg, 0.08800 mmol), dioxane (6 mL) and water (0.5 mL). Nitrogen was bubbled through the mixture for 10 min before the vial was sealed and the mixture was stirred at 90° C. After 2.5 h, the reaction mixture was charged with further zinc dicarbonitrile (206 mg, 1.76 mmol) and Pd/tBuXPhos G3 (69.9 mg, 0.08800 mmol). After 18 h, the reaction was diluted with ethyl acetate, filtered, and concentrated in vacuo with silica gel. Purification by silica gel chromatography (eluting with ethyl acetate and heptanes) yielded (R)-4-methyl-1,2,3,4-tetrahydroquinoline-6-carbonitrile (250 mg) as a white fluffy solid. LCMS: [M+H]+ 173.

Synthesis of (4S)-4-methyl-1,2,3,4-tetrahydroquinoline-6-carbonitrile, Intermediate for Compound 220

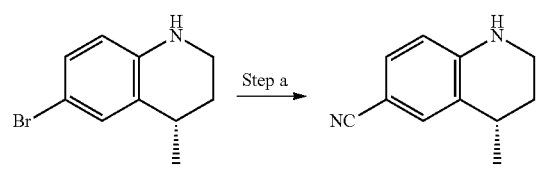

A solution of (4S)-6-bromo-4-methyl-1,2,3,4-tetrahydroquinoline (1.9 g, 8.4 mmol), Zn(CN)2 (2.0 g, 16.8 mmol), Pd2(dba)3 (614 mg, 0.67 mmol), dppf (743 mg, 1.3 mmol) and Zn (65 mg, 1.0 mmol) in DMF (100 mL) was stirred at 120° C. for 12 h under N2. The reaction mixture was concentrated and H2O (50 mL) was added, extracted with ethyl acetate (50 mL×3). The combined organic layers were washed with brine (50 mL), dried over anhydrous Na2SO4, filtered and concentrated to give a residue. The residue was purified by flash silica gel chromatography (Petroleum ether: Ethyl acetate=100:0 to 100:20) to afford the product of (4S)-4-methyl-1,2,3,4-tetrahydroquinoline-6-carbonitrile (1.3 g, 90.2% yield) as a yellow solid. LCMS [M+H]+ 214.1.

Synthesis of 7-fluoro-4-methyl-1,2,3,4-tetrahydroquinoline-6-carbonitrile, Intermediate for Compound 223

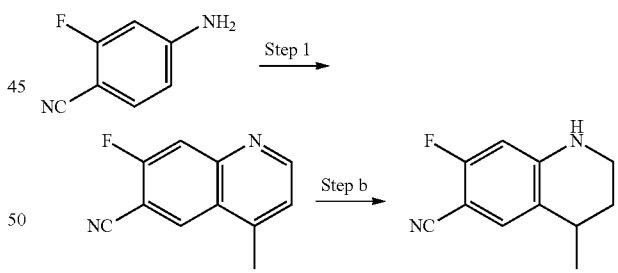

Step a: Adding ethanol (27.0 mL), 4-amino-2-fluorobenzonitrile (3.0 g, 22.0 mmol) and 2,3,5,6-tetrachloro-2,5-cyclohexadiene-1,4-dione (5.77 g, 23.5 mmol) to a 250 mL 3-neck-flask and stirred for 2-5 min under N2, then conc. HCl (5.5 mL, 66.0 mmol, 12 N) was added and stirred at 75° C. Diluted methyl vinyl ketone (2.31 g, 33.0 mmol) in EtOH (3.0 mL) was added slowly to reaction mixture over 30 min. The reaction mixture was stirred at 75° C. for 12 h. THF (33.0 mL) was added at 75° C., and stirred for 1 hour at 60° C. Cooled to room temperature and stirred for 1 additional hour. LCMS showed 40% desired product was detected. The reaction mixture was filtered, the filtered cake was washed with THF (100.0 mL) to give compound 3 (1.0 g) as a gray solid. Then the mixture was concentrated under reduced pressure. The residue was triturated by THF (50.0 mL). The filtered cake was wash with THF (50.0 mL) to give the compound 3a (2.0 g) as a gray solid.

Step b: A mixture of 7-fluoro-4-methylquinoline-6-carbonitrile (500.0 mg, 2.68 mmol), (R)-BINOL-phosphoric acid (46.6 mg, 134.0 μmol) and 3,5-diethyl 2,6-dimethyl-1,4-dihydropyridine-3,5-dicarboxylate (1.62 g, 6.43 mmol) was stirred at 100° C. for 12 h. TLC (Petroleum ether/EtOAc=4: 1) showed the starting material was consumed completely and one new spot with similar polarity was formed. The reaction mixture was concentrated under reduced pressure and purified by column chromatography (EtOAc in Petroleum ether=0~10%) to afford the racemic product of 7-fluoro-4-methyl-1,2,3,4-tetrahydroquinoline-6-carbonitrile (300 mg, 1.57 mmol) as a tan solid.

Synthesis of 3-(1,2,3,4-tetrahydro-1,6-naphthyridin-5-yl)oxazolidin-2-one, Used in the Preparation of Compound 225

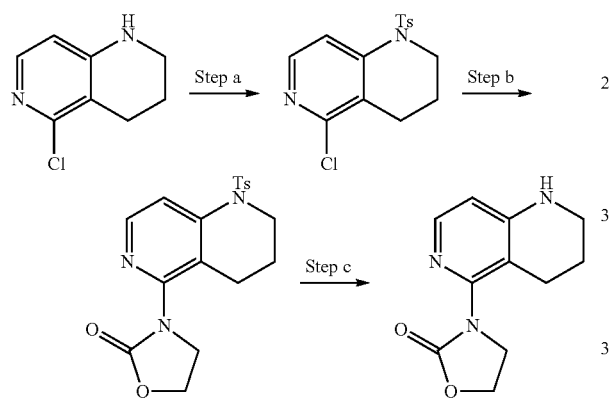

Step a: A resealable reaction vial was charged with 5-chloro-1,2,3,4-tetrahydro-1,6-naphthyridine (200 mg, 1.18 mmol),THF (5 mL) and NaHMDS (258 mg, 1.41 mmol). After a few seconds, ppte crashed out. After 15 min, the reaction was charged with TsCl (268 mg, 1.41 mmol) and stirred at room temperature 18 h. The mixture was diluted with ethyl acetate and brine, and the organic layer was separated and concentrated in vacuo. 5-chloro-1-tosyl-1,2, 3,4-tetrahydro-1,6-naphthyridine (165 mg) was isolated following purification by silica gel chromatography (eluting with ethyl acetate and heptanes). LCMS: [M+H]+ 323.

Step b: A resealable reaction vial was charged with 5-chloro-1-(4-methylbenzenesulfonyl)-1,2,3,4-tetrahydro-1, 6-naphthyridine (165 mg, 0.5111 mmol), 1,3-oxazolidin-2-one (66.7 mg, 0.7666 mmol), Cs2CO3 (332 mg, 1.02 mmol), Pd/XantPhos G4 (49.1 mg, 0.05111 mmol) and dioxane (6 mL). The mixture was bubbled with nitrogen for 10 minutes, the vial was sealed and heated at 90° C. 18 h. The mixture was diluted with EA, filtered and pre-absorbed onto silica gel for purification by silica gel chromatography (eluting with 60-100% EA/hep). The main peak fractions were pooled and concentrated to yield 3-(1-tosyl-1,2,3,4-tetrahydro-1,6-naphthyridin-5-yl)oxazolidin-2-one (167 mg) as a light yellow foam. LCMS: [M+H]+ 374.

Step c: 3-[1-(4-methylbenzenesulfonyl)-1,2,3,4-tetrahydro-1,6-naphthyridin-5-yl]-1,3-oxazolidin-2-one (168 mg, 0.4498 mmol) was dissolved in H2SO4 (3 mL) and stirred at rt for 45 min. The reaction was slowly added to sat. bicarb then solid bicarb was added until gas evolution stopped. The aq. layer was extracted with ethyl acetate, dried over sodium sulfate, and concentrated in vacuo to yield the title compound, which was used without purification.

Synthesis of 5-(1-methyl-1H-pyrazol-4-yl)-1,2,3,4-tetrahydro-1,6-naphthyridine, Intermediate Used in the Preparation of Compound 226

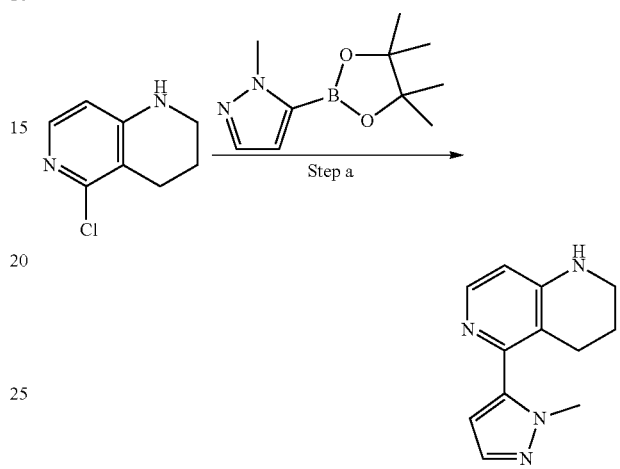

Step a: A mixture of 5-chloro-1,2,3,4-tetrahydro-1,6-naphthyridine (110 mg, 0.6 mmol, CAS #98490-61-0), 1-methyl-5-(4,4,5,5-tetramethyl-1,3,2-dioxaborolan-2-yl)-1H-pyrazole (162 mg, 0.8 mmol), Pd(dppf)Cl2.CH2Cl2 (106 mg, 0.1 mmol) and K2CO3 (224 mg, 1.6 mmol) in the solvent of dioxane (6 mL) and H2O (0.6 mL) was evacuated and refilled 3 times using N2. The mixture was stirred at 90° C. for 12 hours under N2. The reaction mixture was concentrated to give a residue, which was purified by flash silica gel chromatography (DCM:MeOH=100:0 to 100:10) to give the product of 5-(1-methyl-1H-pyrazol-5-yl)-1,2,3,4-tetrahydro-1,6-naphthyridine (100 mg, 71.9% yield) as a brown oil. LCMS m/z: 215.4 (M+H)+.

Synthesis of 1,2,3,4-tetrahydro-1,6-naphthyridine-5-carbonitrile, Intermediate Used in the Preparation of Compound 228

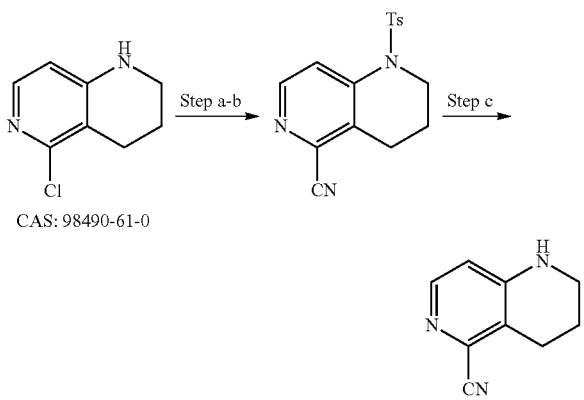

CAS: 98490-61-0

Step a: A round bottom flask was charged with 5-chloro-1,2,3,4-tetrahydro-1,6-naphthyridine (100 mg, 0.590 mmol)

(CAS:98490-61-0) in THF (2.0 mL) and placed under an atmosphere of nitrogen before the addition of NaHMDS (1.0 M in THF, 1.18 mL, 1.18 mmol). The reaction stirred at ambient temperature for 15 min before the addition of tosyl chloride (225 mg, 1.18 mmol). After 5 min, the reaction was quenched by the addition of EtOAc and water. The organic layer was extracted with EtOAc (3×), concentrated and purified via silica gel chromatography (10-100% EtOAc in hexanes) to furnish 5-chloro-1-tosyl-1,2,3,4-tetrahydro-1,6-naphthyridine (100 mg, 0.310 mmol) in 53% yield. [M+H]+ 323.2.

Step b: A resealable vial was charged with furnish 5-chloro-1-tosyl-1,2,3,4-tetrahydro-1,6-naphthyridine (100 mg, 0.310 mmol), [(2-Di-tert-butylphosphino-2',4',6'-triisopropyl-1,1'-biphenyl)-2-(2'-amino-1,1'-biphenyl)] palladium(II) methanesulfonate (25.0 mg, 0.031 mmol), and zinc dicyanide (44.0 mg, 0.372 mmol) before being evacuated and backfilled with nitrogen (3×). A mixture of H$_2$O (0.8 mL) and THF (0.2 mL) was then added and the reaction was heated to 40° C. for 16 h. The reaction was cooled to ambient temperature and partitioned between EtOAc and sat. sodium bicarbonate. The organic layer was extracted with EtOAc (3×), dried, concentrated and purified via silica gel chromatography 85-66% EtOAc in hexanes) to provide 1-tosyl-1,2,3,4-tetrahydro-1,6-naphthyridine-5-carbonitrile (61.0 mg, 0.195 mmol) in 63% yield. LCMS: [M+H]+ 314.2.

Step c: A round bottom flask containing 1-tosyl-1,2,3,4-tetrahydro-1,6-naphthyridine-5-carbonitrile (61.0 mg, 0.195 mmol) was charged with sulfuric acid (1.15 mL). The reaction stirred at ambient temperature for 5 min before being slowly added to an Erlenmeyer flask containing sat. sodium bicarbonate till gas evolution ceased. The reaction was then partitioned between EtOAc and sat. sodium bicarbonate, and the organic layer was extracted with EtOAc (3×). Combined organic extracts were dried to yield 1,2,3,4-tetrahydro-1,6-naphthyridine-5-carbonitrile (25.0 mg, 0.157 mmol) which was used in subsequent steps without further purification. LCMS: [M+H]+ 160.2.

Synthesis of 4-(difluoromethylidene)-1,2,3,4-tetrahydroquinoline, Used in the Preparation of Compound 231

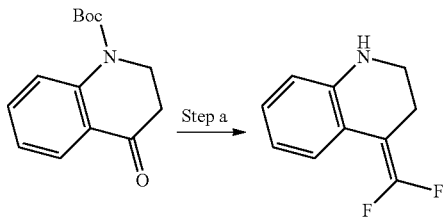 [SMILES: CC(C)(C)OC(=O)N1CCC(=O)c2ccccc21 ; FC(F)=C1CCNc2ccccc21]

Step a: A resealable reaction vial was charged with tert-butyl 4-oxo-1,2,3,4-tetrahydroquinoline-1-carboxylate (250 mg, 1.01 mmol), 2-difluoromethanesulfonylpyridine (162 mg, 0.8416 mmol) in DMF (10 mL). The solution was cooled to −50° C., and charged with (tert-butoxy)potassium (1.51 mL, 1.51 mmol) and stirred for 2 hrs at −40° C. The reaction was charged with sat. NH4Cl (2 mL) and 3N HCl (2 mL), warmed to rt and stirred for 0.5 hrs. The reaction was partitioned between ethyl acetate and brine. The org layer was dried, concentrated and the residue was purified by flash silica gel chromatography (eluting with ethyl acetate:heptanes=0:100 to 15:85) to afford a colorless oil. The residue was dissolved in DCM (2 mL) and charged with TFA (1 mL) and stirred for 30 min. The solvent was removed to afford 4-(difluoromethylidene)-1,2,3,4-tetrahydroquinoline (45 mg) as a colorless oil. LCMS: [M+H]+ 182.

Synthesis of 5-cyclopropyl-1,2,3,4-tetrahydro-1,6-naphthyridine, Intermediate Used in the Preparation of Compound 232

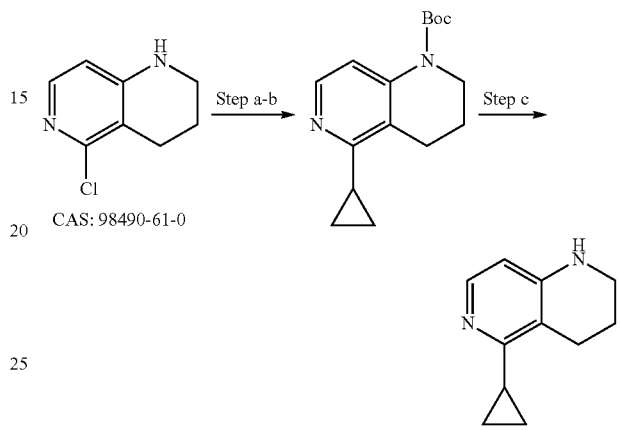

CAS: 98490-61-0

Step a: A round bottom flask containing 5-chloro-1,2,3,4-tetrahydro-1,6-naphthyridine (200 mg, 1.18 mmol) (CAS: 98490-61-0) in THF (7.0 mL) was placed under an atmosphere of nitrogen before the addition of NaHMDS (1.0 M in THF, 2.40 mL, 2.40 mmol) at ambient temperature. Following the addition of di-tert-butyl dicarbonate (458 mg, 2.40 mmol) the reaction stirred at ambient temperature for 16 h. After the addition of EtOAc and water, the organic layer was extracted with EtOAc (3×), concentrated and purified via silica gel chromatography (isocratic, 25% EtOAc in hexanes) to furnish tert-butyl 5-chloro-3,4-dihydro-1,6-naphthyridine-1(2H)-carboxylate (277 mg, 1.03 mmol) as a white solid.

Step b: A reaction vial was charged with tert-butyl 5-chloro-3,4-dihydro-1,6-naphthyridine-1(2H)-carboxylate (138 mg, 0.510 mmol), cyclopropylboronic acid (88.0 mg, 1.02 mmol), palladium tetrakis (59.0 mg, 0.051 mmol) and K$_2$CO$_3$ (281 mg, 2.04 mmol) and dissolved in dioxane (1.36 mL) and H$_2$O (0.34 mL). The reaction was degassed for 5 min, before being heated to 100° C. for 16 h. Only partial conversion was observed, so the reaction was cooled and additional cyclopropylboronic acid (88.0 mg, 1.02 mmol) and palladium tetrakis (59.0 mg, 0.051 mmol) were added, the reaction was again sparged for 5 min before heating again to 100° C. for 4 h. Following cooling to ambient temperature, the reaction was partitioned between dichloromethane and water and the organic layer was extracted (3×), concentrated and purified via silica gel chromatography (5-50% EtOAc in hexanes) to provide tert-butyl 5-cyclopropyl-3,4-dihydro-1,6-naphthyridine-1(2H)-carboxylate (63.0 mg, 0.230 mmol) in 45% yield.

Step c: To a round bottom flask tert-butyl 5-cyclopropyl-3,4-dihydro-1,6-naphthyridine-1(2H)-carboxylate (63.0 mg, 0.230 mmol) in dichloromethane (2.3 mL) was added trifluoroacetic acid (0.175 mL) and the reaction was stirred at room temperature for 16 h. Solvent was evaporated and the residue was purified via silica gel chromatography (0-20% MeOH in dichloromethane with 0.1% NH$_3$ H$_2$O) to 5-cyclopropyl-1,2,3,4-tetrahydro-1,6-naphthyridine (40 mg, 0.23 mmol) in quantitative yield. LCMS: [M+H]+ 175.2.

Synthesis of 5-(difuoromethyl)-1,2,3,4-tetrahydro-1,6-naphthyridine, Used in the Preparation of Compound 236

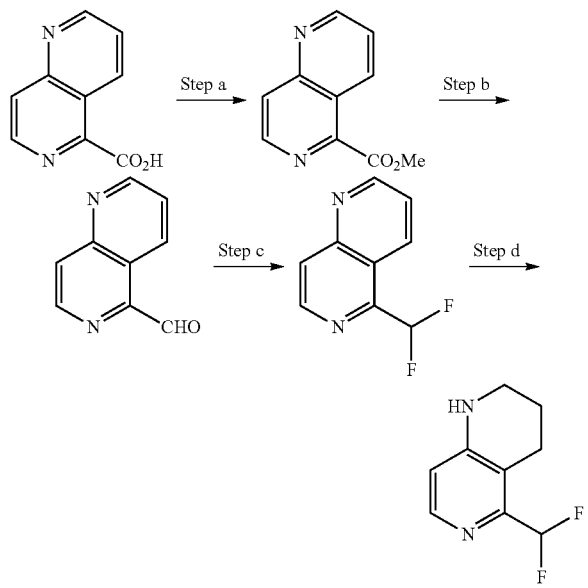

Step a: SOCl2 (8.0 mL) was added in MeOH (20.0 mL) dropwise at 0° C. To the mixture was added 1,6-naphthyridine-5-carboxylic acid (1.0 g, 5.74 mmol) and stirred at 90° C. for 12 h. Orange solution was observed. Desired product was observed from LCMS. The mixture was concentrated in vacuum. The residue was added in saturated $NaHCO_3$ (10.0 mL) and then extracted with EtOAc (10.0 mL×2). The combined organic layers were concentrated in vacuum to give methyl 1,6-naphthyridine-5-carboxylate (1.0 g, crude) as a yellow solid.

Step b: To a solution of methyl 1,6-naphthyridine-5-carboxylate (300.0 mg, 1.59 mmol) in THF (10.0 mL) at −78° C. under N2 was added DIBAL-H (2.38 mL, 2.38 mmol). The mixture was stirred at −78° C. for 1 h. TLC (petroleum ether:EtOAc=1:1) showed starting material consumed and new spot was formed. To the mixture was added 10% AcOH (15.0 mL) and extracted with EtOAc (20.0 mL×2). The combined organic layers were washed $NaHCO_3$ (20.0 mL), dried over anhydrous Na2SO4, filtered and concentrated in vacuum to give 1,6-naphthyridine-5-carbaldehyde (300.0 mg, crude) as a yellow solid. The solid was used in the next step without further purification.

Step c: To a solution of 1,6-naphthyridine-5-carbaldehyde (300.0 mg, 1.89 mmol) in DCM (10.0 mL) at 0° C. under N2 was added DAST (611.0 mg, 3.78 mmol). The mixture was stirred at 0° C. for 1 h. Orange solution was observed. To the mixture was added saturated $NaHCO_3$ (10.0 mL) and extracted with DCM (10.0 mL×2). The combined organic layers were washed with brine (20.0 mL), dried over anhydrous Na2SO4, filtered and concentrated in vacuum to give crude product as orange gum. The residue was purified by flash silica gel chromatography (Ethyl acetate in Petroleum ether from 0% to 20%) to give 5-(difuoromethyl)-1,6-naphthyridine (120.0 mg, 35.2% yield) as an orange oil.

Step d: A solution of 5-(difluoromethyl)-1,6-naphthyridine (120.0 mg, 666 μmol), 3,5-diethyl 2,6-dimethyl-1,4-dihydropyridine-3,5-dicarboxylate (402.0 mg, 1.59 mmol) and diphenoxyphosphinic acid (33.2 mg, 133.0 umol) in dioxane (5.0 mL) was stirred at 90° C. for 12 h under N2. Yellow solution was observed. TLC (petroleum ether:EtOAc=2:1) showed new spots were observed. The solution was concentrated in vacuum to remove solvent. The residue was purified by flash silica gel chromatography (Ethyl acetate in Petroleum ether from 0% to 30%) to give the product of 5-(difluoromethyl)-1,2,3,4-tetrahydro-1,6-naphthyridine (90.0 mg, 73.7% yield) as a yellow oil.

Synthesis of 6-(3,6-dihydro-2H-pyran-4-yl)-1,2,3,4-tetrahydro-1,5-naphthyridine, Used in the Preparation of Compound 237

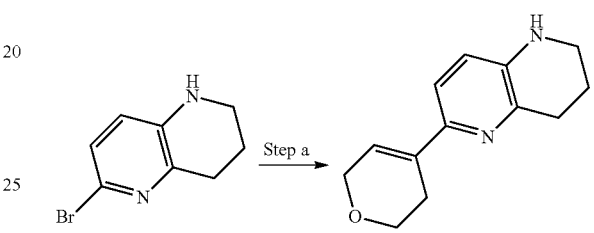

Step a: A resealable reaction vial was charged with 6-bromo-1,2,3,4-tetrahydro-1,5-naphthyridine (250 mg, 1.17 mmol), 2-(3,6-dihydro-2H-pyran-4-yl)-4,4,5,5-tetramethyl-1,3,2-dioxaborolane (367 mg, 1.75 mmol), tetrakis (triphenylphosphane) palladium (135 mg, 0.117 mmol), dipotassium carbonate (485 mg, 3.51 mmol), dioxane (9 mL) and water (1 mL). The mixture was bubbled with nitrogen for 5 min, the vial was sealed, and the mixture was stirred at 90° C. for 16 hrs. The reaction was poured in brine, extracted with ethyl acetate, dried and purified by flash silica gel chromatography (eluting with ethyl acetate:heptanes=20:80 to 80:20) to afford 6-(3,6-dihydro-2H-pyran-4-yl)-1,2,3,4-tetrahydro-1,5-naphthyridine (250 mg) as a brown oil. LCMS: [M+H]+ 217.

Synthesis of 6-(oxan-4-yl)-1,2,3,4-tetrahydro-1,5-naphthyridine, Used in the Preparation of Compound 239

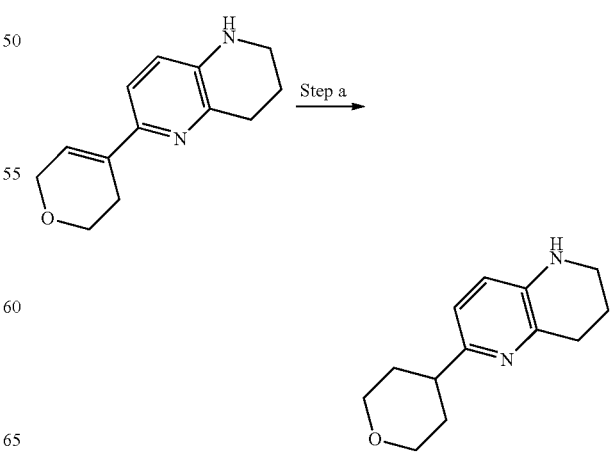

Step a: 6-(3,6-dihydro-2H-pyran-4-yl)-1,2,3,4-tetrahydro-1,5-naphthyridine (100 mg, 0.4623 mmol) was dissolved in MeOH and ethyl acetate (1/1, 10 mL). The solution was pumped through a 10% Pd/C cartridge at 1 mL/min under 5 bars of $H_2$ at RT for 60 min. The solvent was removed to afford 6-(oxan-4-yl)-1,2,3,4-tetrahydro-1,5-naphthyridine (95 mg) as a light yellow solid. LCMS: [M+H]$^+$ 219.

Synthesis of 6-methyl-1,2,3,4,5,6-hexahydro-1,6-naphthyridin-5-one, Used in the Preparation of Compound 240

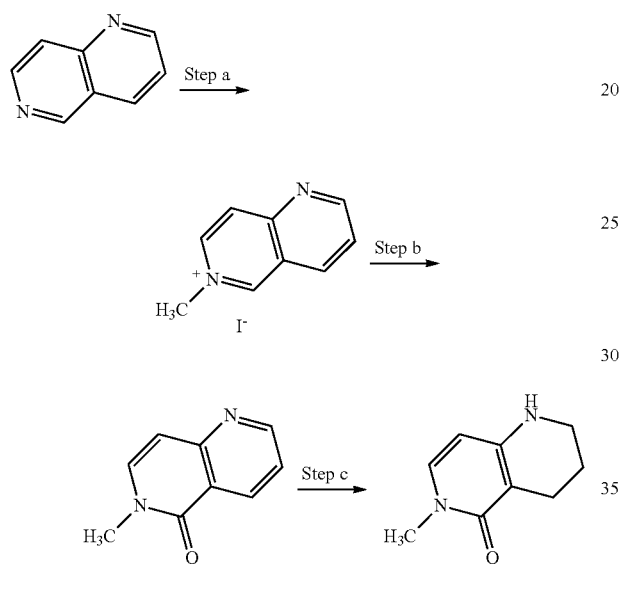

Step a: 1,6-naphthyridine (0.965 g, 7.41 mmol) was dissolved in MeOH (8.5 mL) and charged with iodomethane (921 µL, 14.8 mmol). The vial was sealed and heated to 65° C. and stirred for 16 hrs. The solvent was removed, the residue taken up in a small amount of MeOH (1-2 mL) and ethyla acetate was charged. The mixture was filtered, washed with EA and air dried to constant weight to afford 6-methyl-1,6-naphthyridin-6-ium iodide (1.56 g).

Step b: 6-methyl-1,6-naphthyridin-6-ium iodide (1.56 g, 5.73 mmol) was suspended in water (10 mL) and cooled to 0° C. The reaction was charged with NaOH (1.25 g, 31.5 mmol) in water (10 mL) and tripotassium hexakis(iminomethanide) iron (4.04 g, 12.3 mmol) in water (10 mL). The solution was stirred for 1 hr at 0° C. then overnight at rt. The mixture was extracted with $CHCl_3$, dried and concentrated. The residue was purified by flash silica gel chromatography (eluting with MeOH:DCM=0:100 to 10:90) to afford 6-methyl-5,6-dihydro-1,6-naphthyridin-5-one (540 mg) as a light yellow solid. LCMS: [M+H]$^+$ 161.

Step c: 6-methyl-5,6-dihydro-1,6-naphthyridin-5-one (109 mg, 0.6805 mmol) was dissolved in MeOH (10 mL). The solution was pumped a 10% Pd/C cartridge at 1 mL/min under 70 bars of $H_2$ at 70° C. for 90 min. Solvent was removed to afford 6-methyl-1,2,3,4,5,6-hexahydro-1,6-naphthyridin-5-one (90 mg) as a white solid. LCMS: [M+H]$^+$ 165.

Synthesis of 4-methyl-1,2,3,4-tetrahydropyrido[2,3-b]pyrazine, Intermediate Used in the Preparation of Compound 245

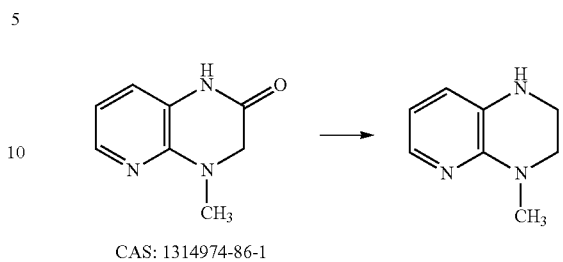

CAS: 1314974-86-1

Lithium aluminum hydride (1.0 M in THF, 2.46 mL, 2.46 mmol) was added to a microwave vial under an atmosphere of nitrogen before the slow addition of 4-methyl-3,4-dihydropyrido[2,3-b]pyrazin-2(1H)-one (200 mg, 1.23 mmol) (CAS: 1314974-86-1) in THF (2.0 mL). Following addition, the reaction was heated to 65° C. for 5 h until consumption of the starting material by TLC (EtOAc). Following slow addition of 1N NaOH, the reaction was filtered through celite, rinsing with dichloromethane to yield 4-methyl-1,2,3,4-tetrahydropyrido[2,3-b]pyrazine (174 mg) which was used without further purification. LCMS: [M+H]+ 150.2.

Synthesis 5,6,7,8-tetrahydro-1,5-naphthyridine-2-carbonitrile, Intermediate Used in the Preparation of Compound 248

5,6,7,8-tetrahydro-1,5-naphthyridine-2-carbonitrile is commercially available (CAS: 1219022-67-9).

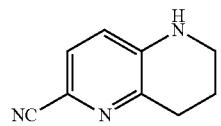

CAS: 1219022-67-9

Synthesis of 4-methyl-1H,2H,3H,4H-pyrido[3,4-b]pyrazin-3-one, Used in the Synthesis of Compound 249

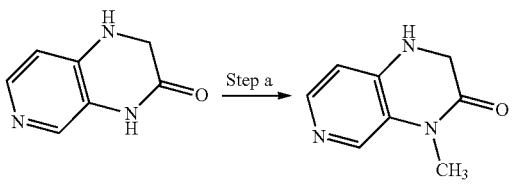

Step a: 1H,2H,3H,4H-pyrido[3,4-b]pyrazin-3-one (113 mg, 0.7576 mmol) was suspended in DMF (5 mL) and charged with sodium hydride (30.1 mg, 0.7576 mmol). The mixture was stirred for 30 min (came solution) and iodomethane (46.9 µL, 0.7576 mmol) was added and stirred at rt for 30 min. The reaction concentrated and the residue purified on Prep-HPLC (5-10% ACN/Water+0.1% $NH_4OH$) to afford 4-methyl-1H,2H,3H,4H-pyrido[3,4-b]pyrazin-3-one (18 mg) as a white solid. LCMS: [M+H]$^+$ 164.

Synthesis of 4-(difluoromethyl)-1,2,3,4-tetrahydroquinoline, Used in the Synthesis of Compound 250

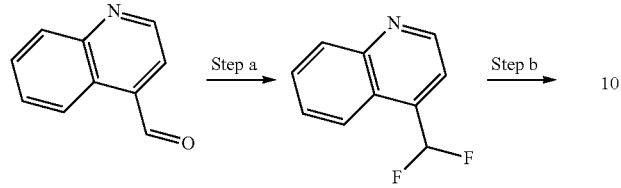

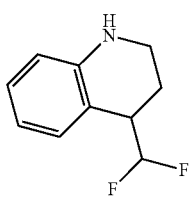

Step a: Quinoline-4-carbaldehyde (1 g, 6.36 mmol) in DCM (20 mL) was cooled to 0° C., and charged with DAST (2.56 g, 15.9 mmol). The mixture was stirred for 1 hr at 0° C. then let warm to rt and stirred for 20 hrs. The reaction mixture was cooled to −10° C. carefully quenched with sat. bicarb and extracted with DCM. The organic layer was concentrated and purified by flash silica gel chromatography (eluting with ethyl acetate:heptanes=25:75 to 50:50) to afford 4-(difluoromethyl)quinoline (890 mg) as a colorless oil that crystallized to a white solid upon standing. LCMS: [M+H]$^+$ 180.

Step b: A resealable reaction vial was charged with 4-(difluoromethyl)quinoline (435 mg, 2.42 mmol), 3,5-diethyl 2,6-dimethyl-1,4-dihydropyridine-3,5-dicarboxylate (1.53 g, 6.05 mmol), diphenoxyphosphinic acid (30.2 mg, 0.121 mmol), toluene (6 mL). The vial was sealed the mixture was stirred at 50° C. for 20 hrs. The reaction mixture was concentrated and purified by flash silica gel chromatography (eluting with ethyl acetate:heptanes=0:100 to 30:100) to afford 4-(difluoromethyl)-1,2,3,4-tetrahydroquinoline (375 mg) as a colorless oil. LCMS: [M+H]$^+$ 184.

Synthesis of 4-(oxan-4-yl)-1,2,3,4-tetrahydroquinoline, Used in the Preparation of Compound 251

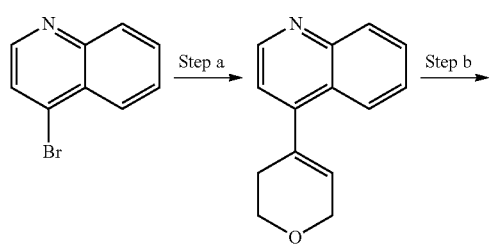

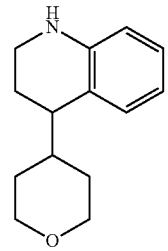

Step a: A resealable reaction vial was charged with 4-bromoquinoline (250 mg, 1.20 mmol), 2-(3,6-dihydro-2H-pyran-4-yl)-4,4,5,5-tetramethyl-1,3,2-dioxaborolane (504 mg, 2.40 mmol), tetrakis(triphenylphosphane) palladium (138 mg, 0.1199 mmol) and dipotassium carbonate (331 mg, 2.40 mmol). Evacuated and backfilled with N$_2$ (3×). Added dioxane (9 mL) and water (1 mL). Stirred at 90 C for 12 h. The reaction was poured in water/brine, extracted with EA, dried and purified by flash silica gel chromatography using 50-100% EtOAc in heptanes to give 4-(3,6-dihydro-2H-pyran-4-yl)quinoline (224 mg, 1.06 mmol) as a yellow oil.

Step b: Circulated a solution of 4-(3,6-dihydro-2H-pyran-4-yl)quinoline (224 mg, 1.06 mmol) in MeOH (10 mL) on H-Cube (10% Pd/C, 70 C, 70 bar, 1 mL/min) at 70 C/70 bar for 1 h. Concentrated and purified by flash silica gel chromatography w/0-100% EtOAc. Combined fractions and concentrated to give 4-(oxan-4-yl)-1,2,3,4-tetrahydroquinoline (155 mg, 0.7132 mmol) as a white solid.

Synthesis of Synthesis of 6-(1H-pyrazol-1-yl)-1,2,3,4-tetrahydro-1,5-naphthyridine, Used in the Preparation of Compound 252

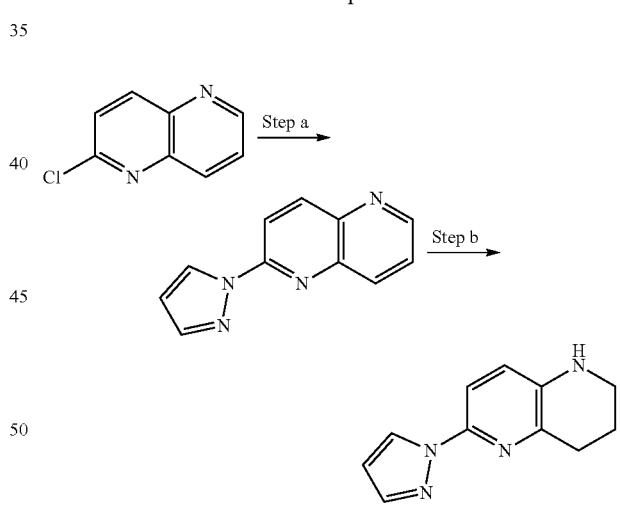

Step a: To a solution of 2-chloro-4a,8a-dihydro-1,5-naphthyridine (300 mg, 1.80 mmol) in toluene (30 ml) was added 1H-pyrazole (183 mg, 2.70 mmol), CuI (34.2 mg, 180 μmol), (1R,2R)—N1,N2-dimethylcyclohexane-1,2-diamine (128 mg, 900 umol) and K2CO3 (496 mg, 3.60 mmol), the mixture was stirred at 110° C. for 12 hours under N2. LCMS showed the product formed. The reaction was concentrated to dryness. The resulting crude material was purified by silica gel chromatography (eluent:Petroluem ether/Ethyl acetate=2:1) to give 2-(1H-pyrazol-1-yl)-4a,8a-dihydro-1,5-naphthyridine (310 mg, 1.56 mmol) as a white solid.

Step b: A solution of 2-(1H-pyrazol-1-yl)-1,5-naphthyridine (100 mg, 509 μmol), diphenoxyphosphinic acid (25.2 mg, 101 µmol) and 3,5-diethyl 2,6-dimethyl-1,4-dihydropyridine-3,5-dicarboxylate (385 mg, 1.52 mmol) in toluene (10 mL) was stirred at 80° C. for 12 hours under N2. TLC (Petroleum ether:EtOAc=1:1) showed the reaction was complete. The mixture was concentrated and purified by flash silica gel chromatography (Petroleum ether:EtOAc=5:1 to 2:1) to afford the product of 6-(1H-pyrazol-1-yl)-1,2,3,4-tetrahydro-1,5-naphthyridine (30.0 mg, 149 µmol, 29.7% yield) as a colorless oil.

Synthesis of Synthesis of 6-[1-(oxan-2-yl)-1H-pyrazol-4-yl]-1,2,3,4-tetrahydro-1,5-naphthyridine, Used in the Preparation of Used in the Preparation of Compound 259

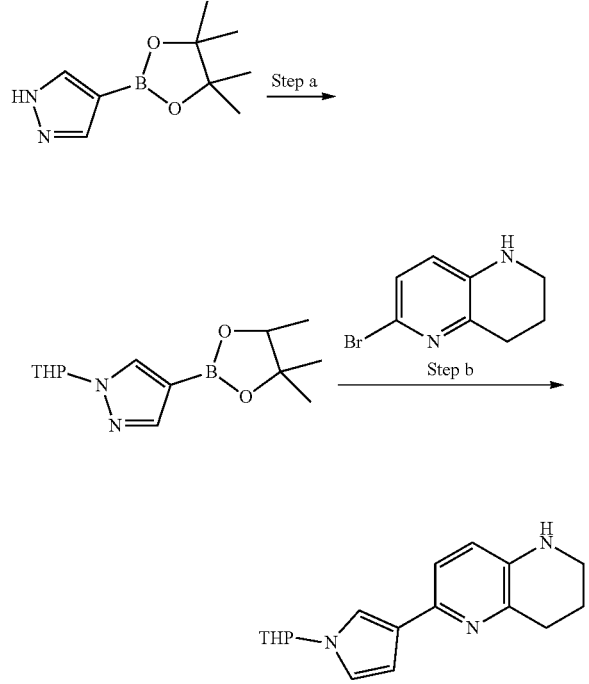

Step a: A mixture of 4-(4,4,5,5-tetramethyl-1,3,2-dioxaborolan-2-yl)-1H-pyrazole (500 mg, 2.6 mmol), DHP (280 mg, 3.3 mmol), TFA (58.6 mg, 514 µmol) in toluene (15 mL) was stirred at 90° C. for 2 hours. TLC (Petroleum ether: Ethyl acetate=2:1) showed the reaction was consumed completely. After cooling to room temperature, the reaction mixture was partitioned between ethyl acetate (40 mL) and sat. NaHCO₃ (20 mL) and separated, the aqueous layer was extracted with ethyl acetate (30 mL). The combined organic layers were washed with brine (20 mL), dried over anhydrous Na2SO4 and concentrated in vacuum to give a residue, which was purified by silica gel chromatography (Ethyl acetate in Petroleum: 15% to 30%) to afford the product of 1-(oxan-2-yl)-4-(4,4,5,5-tetramethyl-1,3,2-dioxaborolan-2-yl)-1H-pyrazole (490 mg, 68.6% yield) as a colorless oil.

Step b: A mixture of 6-bromo-1,2,3,4-tetrahydro-1,5-naphthyridine (250 mg, 1.2 mmol), 1-(oxan-2-yl)-4-(4,4,5,5-tetramethyl-1,3,2-dioxaborolan-2-yl)-1H-pyrazole (486 mg, 1.8 mmol), Pd(dppf)Cl2.CH2Cl2 (142 mg, 175 µmol) and K2CO3 (402 mg, 2.9 mmol) in dioxane (15 mL)/H2O (3 mL) was stirred at 90° C. for 12 hours under N2 atmosphere. The reaction mixture was concentrated in vacuum to give a residue, which was purified by silica gel chromatography (Ethyl acetate in Petroleum ether: 75% to 85%) to afford the product of 6-[1-(oxan-2-yl)-1H-pyrazol-4-yl]-1,2,3,4-tetrahydro-1,5-naphthyridine (280 mg, 84.3% yield) as a yellow oil.

Synthesis of 6-chloro-1,2,3,4-tetrahydro-1,5-naphthyridine, A-Ring for Compound 260

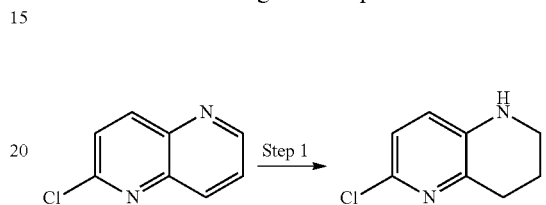

Step a: A solution of 2-chloro-1,5-naphthyridine (900 mg, 5.5 mmol), diphenoxyphosphinic acid (272 mg, 1.1 mmol) and 2-[5-(ethoxycarbonyl)-2,6-dimethyl-1,4-dihydropyridine-3-carbonyloxy]ethylium (4.1 g, 16.3 mmol) in toluene (50 ml). The reaction mixture was evacuated and refilled for 3 times using N₂. The mixture was stirred at 80° C. for 12 hours under N₂. The mixture was concentrated and purified by flash silica gel chromatography (Petroleum ether:EtOAc=100:0 to 100:20) to afford the product of 6-chloro-1,2,3,4-tetrahydro-1,5-naphthyridine (780 mg, 84% yield) as an off-white solid.

Synthesis of (4S)-4-methyl-5-(1-methyl-1H-pyrazol-4-yl)-1,2,3,4-tetrahydroquinoline and (4R)-4-methyl-5-(1-methyl-1H-pyrazol-4-yl)-1,2,3,4-tetrahydroquinoline, Used in the Preparation of Compound 277 and Compound 278

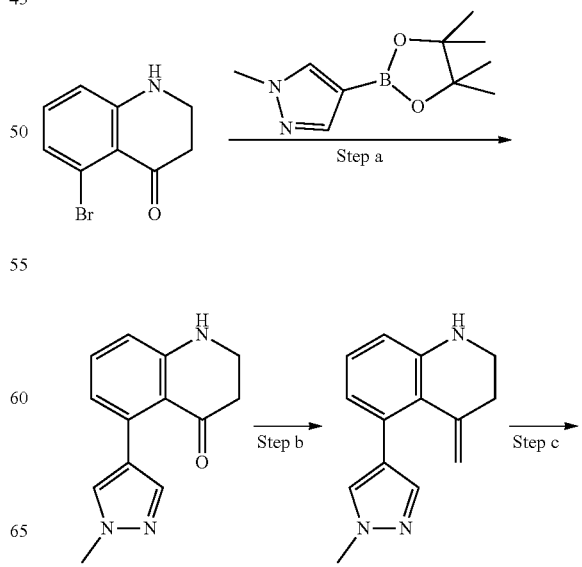

-continued

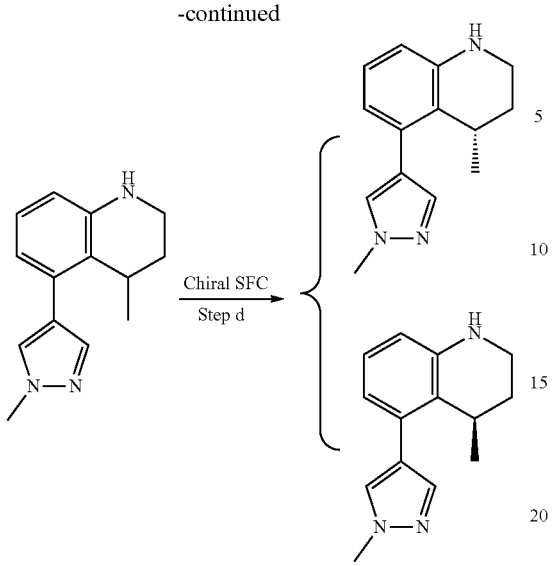

quinoline (45.0 mg, 47.5% yield) as a white solid and (4R)-4-methyl-5-(1-methyl-1H-pyrazol-4-yl)-1,2,3,4-tetra-hydroquinoline (45.0 mg, 47.5% yield) as a white solid. The absolute configuration was arbitrarily assigned.

Synthesis of 6-(1H-1,2,4-triazol-1-yl)-1,2,3,4-tetra-hydro-1,5-naphthyridine, Used in the Preparation of Compound 279

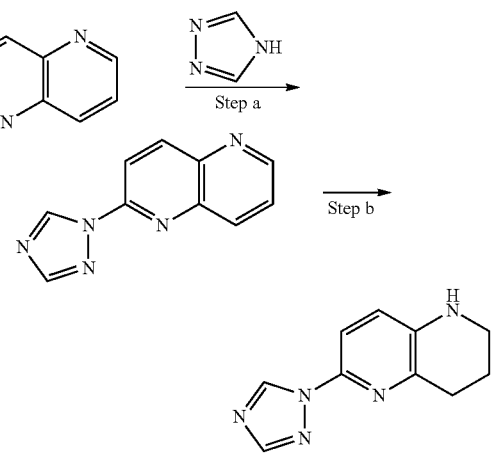

Step a: A mixture of 5-bromo-2,3-dihydroquinolin-4(1H)-one, CAS 1391268-61-3 (950.0 mg, 4.2 mmol), 1-methyl-4-(4,4,5,5-tetramethyl-1,3,2-dioxaborolan-2-yl)-1H-pyrazole (1.2 g, 5.9 mmol), Pd(dppf)Cl$_2$ (307.0 mg, 0.4 mmol) and K$_2$CO$_3$ (1.2 g, 8.4 mmol) in dioxane (12.0 mL)/H$_2$O (4.0 mL) was stirred at 90° C. for 12 hours under N$_2$ atmosphere. The reaction mixture was concentrated in vacuo to give a residue, which was purified by silica gel chromatography (Ethyl acetate in Petroleum: 100%) to afford the product of 5-(1-methyl-1H-pyrazol-4-yl)-2,3-dihydroquinolin-4(1H)-one (935.0 mg, 98.0% yield) as a yellow solid.

Step b: To a mixture of Ph$_3$PCH$_3$Br (1.6 g, 4.6 mmol) in THF (10.0 mL) at 0° C. was added t-BuOK (5.5 mL, 5.5 mmol, 1.0 M in THF), the resulting mixture was stirred at this temperature for 0.5 hour. 5-(1-Methyl-1H-pyrazol-4-yl)-2,3-dihydroquinolin-4(1H)-one (420.0 mg, 1.8 mmol) in THF (5.0 mL) was added drop-wise at 0° C. The reaction mixture was warmed to 25° C., and stirred for 2.5 hours. The reaction mixture was diluted with H$_2$O (25.0 mL), washed with ethyl acetate (30.0 mL×2). The organic phase was washed with brine (15.0 mL), dried over anhydrous Na$_2$SO$_4$, filtered and concentrated in vacuo to give a residue, which was purified by silica gel chromatography (Ethyl acetate in Petroleum: 60% to 75%). to afford the product of 5-(1-methyl-1H-pyrazol-4-yl)-4-methylene-1,2,3,4-tetrahydroquinoline (600.0 mg, combined batches) as a white solid.

Step c: To a mixture of 5-(1-methyl-1H-pyrazol-4-yl)-4-methylidene-1,2,3,4-tetrahydroquinoline (530.0 mg, 2.4 mmol) in EtOH (15.0 mL) was added Pd/C (83.1 mg, 10 wt % wet), and the resulting mixture was stirred at 25° C. for 12 hours under H$_2$ (15 psi.). The reaction mixture was concentrated in vacuo to give a residue, which was purified by silica gel chromatography (Ethyl acetate in Petroleum ether: 60% to 80%) to afford the product of 4-methyl-5-(1-methyl-1H-pyrazol-4-yl)-1,2,3,4-tetrahydroquinoline (380.0 mg, 71.1% yield) as a white solid.

Step d: 4-Methyl-5-(1-methyl-1H-pyrazol-4-yl)-1,2,3,4-tetrahydroquinoline (95.0 mg, 417.0 µmol) was separated by chiral SFC (Column: ChiralPak AY-3 150×4.6 mm I.D., 3 um Mobile phase: A: CO$_2$ B: Methanol (0.05% DEA) Gradient: from 5% to 40% of B in 5.5 min and hold 40% for 3 min, then 5% of B for 1.5 min Flow rate: 2.5 mL/min Column temperature: 40° C.) to afford the product of (4S)-4-methyl-5-(1-methyl-1H-pyrazol-4-yl)-1,2,3,4-tetrahydro- Step a: To the mixture of 4H-1,2,4-triazole (31.3 mg, 0.45 mmol) and 2-chloro-1,5-naphthyridine (50.0 mg, 0.3 mmol) in DMF (2.0 mL) was added Cs$_2$CO$_3$ (0.42 g, 1.30 mmol) under N$_2$. The mixture was stirred at 100° C. under N$_2$ for 12 hrs. The mixture was concentrated in vacuo and purified by flash silica gel chromatography (petroleum ether/ EtOAc=1/0 to 1/1) to give the product of 2-(1H-1,2,4-triazol-1-yl)-1,5-naphthyridine (50.0 mg, 83.7% yield) as a white solid.

Step b: To the mixture of 2-(1H-1,2,4-triazol-1-yl)-1,5-naphthyridine (50 mg, 0.25 mmol) and BINOL-phosphoric acid (8.81 mg, 25.3 µmol) in toluene (4.0 mL) was added diethyl 2,6-dimethyl-1,4-dihydropyridine-3,5-dicarboxylate (160 mg, 0.63 mmol). The mixture was stirred at 100° C. under N$_2$ for 12 hrs. The mixture was concentrated in vacuo and purified by flash silica gel chromatography (petroleum ether/EtOAc=1/0 to 1/1) to give the product of 6-(1H-1,2, 4-triazol-1-yl)-1,2,3,4-tetrahydro-1,5-naphthyridine (40.0 mg, 78.8% yield) as an off-white solid.

Synthesis of 6-(pyridazin-4-yl)-1,2,3,4-tetrahydro-1, 5-naphthyridine, Used in the Preparation of Compound 305

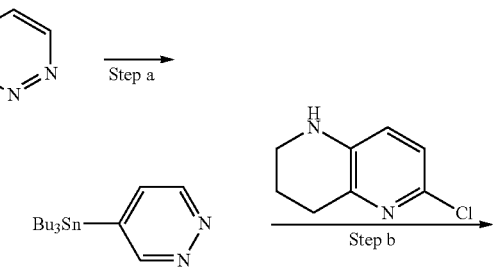

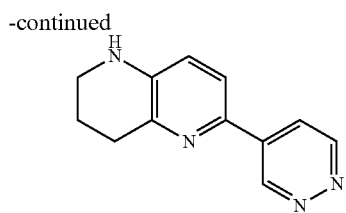

Step a: To a solution of pyridazine (1.10 g, 13.7 mmol) and tributyl(chloro)stannane (4.88 g, 15.0 mmol) in THF (10.0 mL) was added LDA (2.0 M in THF, 6.85 mL, 13.7 mmol) drop-wise at −70° C. under $N_2$. Then the mixture was stirred at −70° C. for 1 hour. The reaction was quenched with saturated $NH_4Cl$ (50.0 mL) and extracted with EtOAc (50.0 mL×3). The organic layers were dried over anhydrous $Na_2SO_4$, and concentrated under reduced pressure. The residue was purified by column chromatography (EtOAc in Petroleum ether=0~30%) to afford 4-(tributylstannyl)pyridazine (2.60 g, 7.04 mmol, 51.0% yield) as a light yellow oil.

Step b: A mixture of 6-chloro-1,2,3,4-tetrahydro-1,5-naphthyridine (100.0 mg, 593.0 μmol), 4-(tributylstannyl)pyridazine (262.0 mg, 711.0 μmol) and $Pd(PPh_3)_4$ (136.0 mg, 118.0 μmol) in toluene (5.0 mL) was stirred at 110° C. for 14 hours under $N_2$. LCMS showed the starting material was consumed completely and 60% of desired product was found. The mixture was poured into water (50.0 mL) and extracted with EtOAc (50.0 mL×3), the organic layers were dried over anhydrous $Na_2SO_4$, filtered and concentrated under reduced pressure. The residue was purified by column chromatography (EtOAc in Petroleum ether=0~100%) to afford 6-(pyridazin-4-yl)-1,2,3,4-tetrahydro-1,5-naphthyridine (55.0 mg, crude) as a yellow solid. LCMS m/z: 213.4 $(M+H)^+$.

Synthesis of 5-(morpholin-4-yl)-1,2,3,4-tetrahydro-1,6-naphthyridine, Used in the Preparation of Compound 307

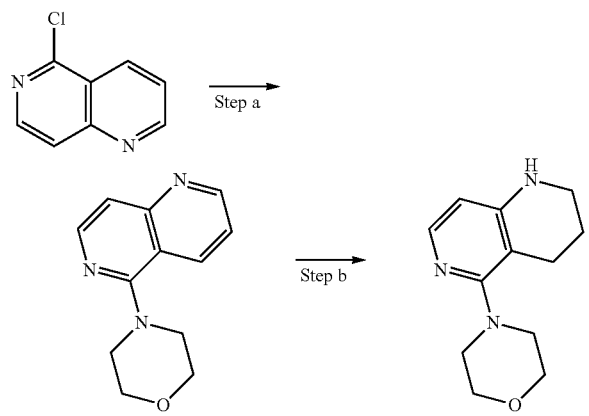

Step a: 5-Chloro-1,6-naphthyridine (200.0 mg, 1.2 mmol, CAS #23616-32-2) and morpholine (315.0 mg, 3.6 mmol) were added in dioxane (3.0 mL), the reaction mixture was stirred at 130° C. for 2 hours under microwave. The reaction mixture was concentrated under reduced pressure to give a residue and purified by flash silica gel chromatography (Petroleum ether:Ethyl acetate=100:0 to 100:70) to afford 5-(morpholin-4-yl)-1,6-naphthyridine (200.0 mg, 77% yield) as a yellow solid.

Step b: 5-(Morpholin-4-yl)-1,6-naphthyridine (200.0 mg, 929.0 μmol), 3,5-diethyl 2,6-dimethyl-1,4-dihydropyridine-3,5-dicarboxylate (516.0 mg, 2.0 mmol) and BINOL-phosphoric acid (64.4 mg, 185.0 μmol) were added in dioxane (10.0 mL). The reaction mixture was evacuated and refilled 3 times with $N_2$ and stirred at 90° C. for 12 hours. The reaction mixture was concentrated under reduced pressure to give a residue which was purified by flash silica gel chromatography (Petroleum ether:Ethyl acetate=100:0 to 0:100) to afford the 5-(morpholin-4-yl)-1,2,3,4-tetrahydro-1,6-naphthyridine (120.0 mg, 96% purity, 56.6% yield) as a yellow solid. LCMS m/z: 220.0 $(M+H)^+$.

Synthesis of 6-(4H-1,2,4-triazol-4-yl)-1,2,3,4-tetrahydro-1,5-naphthyridine, Used in the Preparation of Compound 308

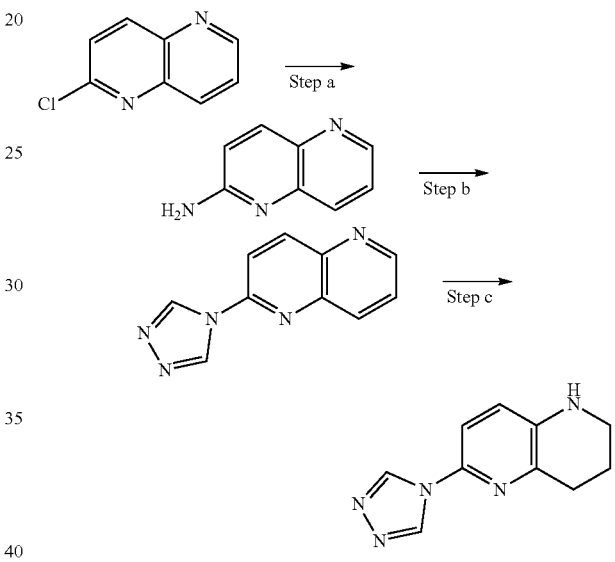

Step a: A solution of 2-chloro-1,5-naphthyridine (600.0 mg, 3.6 mmol), $Cu(OAc)_2$ (66.1 mg, 364.0 umol) and 28% aq. ammonia (4.53 g, 36.4 mmol) in NMP (2.0 mL) in sealed tube was heated to 150° C. for 12 hours. The reaction mixture was poured into water (30.0 mL). The precipitate was collected by filtration and dried in vacuo to give 1,5-naphthyridin-2-amine (420.0 mg, 79.5% yield) as a light blue solid.

Step b: A solution of (E)-N'—[(E)-N'—[(N,N-dimethylamino)methylidene]amino]-N,N-dimethylmethanimidamide dihydrochloride (589.0 mg, 2.7 mmol) and 1,5-naphthyridin-2-amine (200.0 mg, 1.4 mmol) in pyridine (10.0 mL) was stirred at 100° C. for 12 hours. The reaction mixture was evaporated in vacuo. The residue was purified by silica gel column (MeOH in EtOAc=0~10%) to give 2-(4H-1,2,4-triazol-4-yl)-1,5-naphthyridine (220.0 mg, 81.4% yield) as a white solid.

Step c: A mixture of 2-(4H-1,2,4-triazol-4-yl)-1,5-naphthyridine (200.0 mg, 1.0 mmol), 3,5-diethyl 2,6-dimethyl-1,4-dihydropyridine-3,5-dicarboxylate (536.0 mg, 2.1 mmol) and BINOL-phosphoric acid (35.1 mg, 101.0 umol) in dioxane (50.0 mL) was stirred at 110° C. for 6 hours. The reaction mixture was evaporated in vacuo. The residue was purified by silica gel column (MeOH in EtOAc=0~10%) to give 6-(4H-1,2,4-triazol-4-yl)-1,2,3,4-tetrahydro-1,5-naphthyridine (160.0 mg, 78.8% yield) as a yellow solid.

Synthesis of 5-[1-(oxan-2-yl)-1H-pyrazol-4-yl]-1,2,3,4-tetrahydro-1,6-naphthyridine, Used in the Preparation of Compound 289

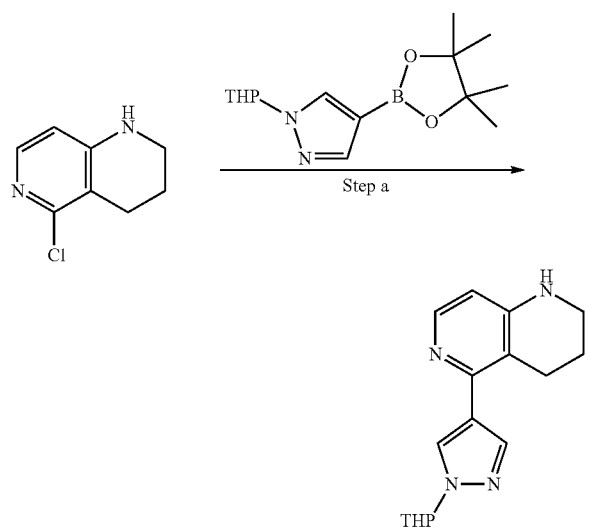

Step a: A mixture of 5-chloro-1,2,3,4-tetrahydro-1,6-naphthyridine (100 mg, 593 μmol, CAS #98490-61-0), 1-(oxan-2-yl)-4-(4,4,5,5-tetramethyl-1,3,2-dioxaborolan-2-yl)-1H-pyrazole (197 mg, 711 μmol), Pd(dppf)Cl$_2$·CH$_2$Cl$_2$ (96.3 mg, 118 μmol) and K$_2$CO$_3$ (162 mg, 1.2 mmol) in dioxane (12 mL)/H$_2$O (3 mL) was stirred at 90° C. for 12 hours under N$_2$ atmosphere. The reaction mixture was diluted with ethyl acetate (25 mL), and washed with H$_2$O (20 mL×2). The organic phase was washed with brine (15 mL), dried over anhydrous Na$_2$SO$_4$ and concentrated in vacuo to give a residue. The residue was purified by silica gel chromatography (Methanol in Dichloromethane: 10% to 20%, 0.5% NH$_3$·H$_2$O) to afford the product of 5-[1-(oxan-2-yl)-1H-pyrazol-4-yl]-1,2,3,4-tetrahydro-1,6-naphthyridine (115 mg, 68.4% yield) as a brown oil. LCMS m/z: 285.4 (M+H)$^+$.

Synthesis of 6-(difluoromethyl)-1,2,3,4-tetrahydro-1,5-naphthyridine, Used in the Preparation of Compound 297

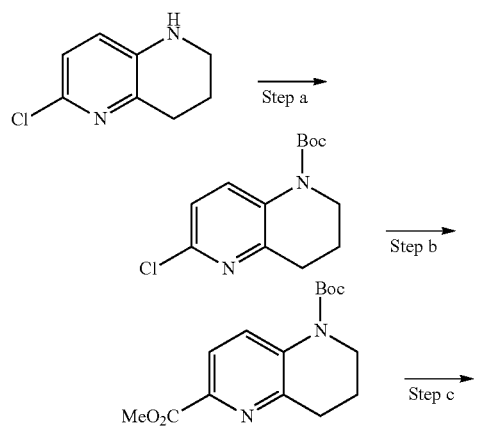

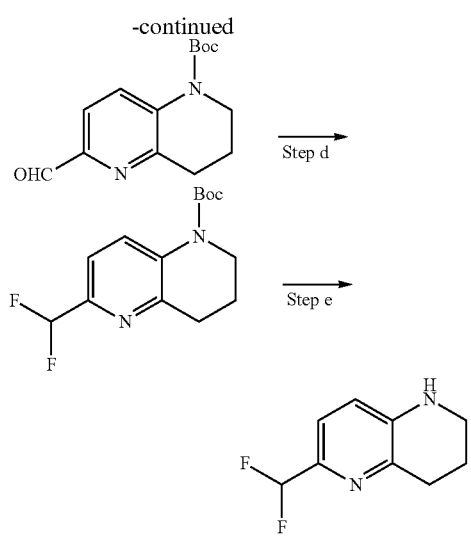

Step a: To a solution of 6-chloro-1,2,3,4-tetrahydro-1,5-naphthyridine (1 g, 5.9 mmol) in THF (20 mL) at 0° C. under N$_2$ was added NaHMDS (11.8 mL, 11.8 mmol, 1M in THF). The mixture was stirred at 0° C. for 1 h. Then to the mixture was added Boc$_2$O (1.9 g, 8.9 mmol). The mixture was stirred at 25° C. for 4 h. The reaction was quenched by addition of sat. NH$_4$Cl (20 mL) and the mixture was extracted with EtOAc (30 mL×3). The combined organic layers were washed with brine (50 mL), dried over anhydrous Na$_2$SO$_4$, filtered and concentrated to give a residue. The residue was purified by flash silica gel chromatography (Ethyl acetate/Petroleum ether=0/100 to 20/100) to give product of tert-butyl 6-chloro-1,2,3,4-tetrahydro-1,5-naphthyridine-1-carboxylate (500 mg, 31.4% yield) as a yellow solid.

Step b: A solution of tert-butyl 6-chloro-1,2,3,4-tetrahydro-1,5-naphthyridine-1-carboxylate (500 mg, 1.8 mmol), Pd(dppf)Cl$_2$ (340 mg, 0.5 mmol) and TEA (0.8 mL, 5.6 mmol) in MeOH (15 mL) was stirred at 80° C. for 48 h under CO (50 psi). The solution was concentrated to give a residue. The residue was purified by flash silica gel chromatography (Ethyl acetate/Petroleum ether=0/100 to 50/100) to give the product of 1-tert-butyl 6-methyl 1,2,3,4-tetrahydro-1,5-naphthyridine-1,6-dicarboxylate (340 mg, 62.6% yield) as an off-white solid.

Step c: To a solution of 1-tert-butyl 6-methyl 1,2,3,4-tetrahydro-1,5-naphthyridine-1,6-dicarboxylate (340 mg, 1.2 mmol) in THF (10 mL) was added DIBAL-H (1.7 mL, 1.7 mmol, 1M in toluene) at −78° C. under N$_2$. The solution was stirred for 2 hours at −78° C. The reaction was quenched by a solution of 10% aqueous AcOH (20 mL) at −78° C. and the mixture was extracted with EtOAc (30 mL×3). The combined organic layers were adjusted pH to 8-9 with sat.NaHCO$_3$ and separated. The organic layer was washed with brine (50 mL), dried over anhydrous Na$_2$SO$_4$, filtered and concentrated to give a residue. The residue was purified by flash silica gel chromatography (Ethyl acetate/Petroleum ether=0/100 to 100/100) to give the product of tert-butyl 6-formyl-1,2,3,4-tetrahydro-1,5-naphthyridine-1-carboxylate (220 mg, 72.3% yield) as a white solid.

Step d: The compound of tert-butyl 6-formyl-1,2,3,4-tetrahydro-1,5-naphthyridine-1-carboxylate (220 mg, 0.8 mmol) was placed in DCM (10 mL). DAST (0.3 mL, 2.1 mmol) was added at 0° C. The mixture was stirred at 0° C. for 1 hour. The mixture was concentrated to give the product tert-butyl 6-(difluoromethyl)-1,2,3,4-tetrahydro-1,5-naphthyridine-1-carboxylate (120 mg, crude product) as a yellow solid Step e: The compound of tert-butyl 6-(difluoromethyl)-1,2,3,4-tetrahydro-1,5-naphthyridine-1-carboxylate (120 mg, 0.4 mmol) was dissolved in HCl/MeOH (10 mL, 2N). The mixture was stirred at 25° C. for 12 h. The mixture was concentrated to give a residue. The residue was diluted with MeOH (5 mL) and DCM (5 mL). The pH was adjusted to 8-9 by addition of NaHCO₃ (s). The mixture was filtered and concentrated to give the product of 6-(difluoromethyl)-1,2,3,4-tetrahydro-1,5-naphthyridine (75.0 mg, crude product) as a yellow solid.

Synthesis of 6-(pyrimidin-5-yl)-1,2,3,4-tetrahydro-1,5-naphthyridine, Used in the Preparation of Compound 304

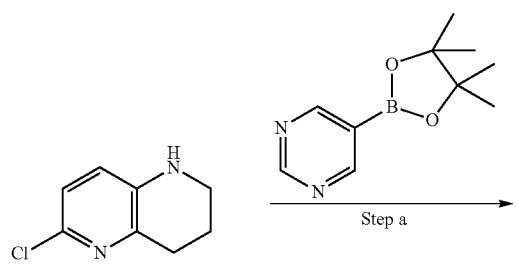

Step a: A solution of of 6-chloro-1,2,3,4-tetrahydro-1,5-naphthyridine CAS: 1196151-85-5 (150 mg, 0.9 mmol), 5-(4,4,5,5-tetramethyl-1,3,2-dioxaborolan-2-yl)pyrimidine (218 mg, 1.1 mmol), Pd(dppf)Cl₂·CH₂Cl₂ (144 mg, 0.2 mmol) and K₂CO₃ (306 mg, 2.2 mmol) in dioxane (6.0 mL) and H₂O (0.6 mL) was evacuated and refilled 3 times using N₂. The mixture was stirred at 90° C. for 12 hours under N₂. The reaction mixture was concentrated to give a residue which was diluted with EtOAc (20 mL) and H₂O (20 mL) and the partitioned layers were separated. The aqueous phase was extracted with ethyl acetate (20 mL×3). The combined organic layers were washed with brine (30 mL), dried over anhydrous Na₂SO₄, filtered and concentrated to give a residue which was purified by flash silica gel chromatography (Ethyl acetate/Petroleum ether=0/100 to 80/100) to give 6-(pyrimidin-5-yl)-1,2,3,4-tetrahydro-1,5-naphthyridine (180 mg, 96% yield) as a brown solid. LCMS m/z: 213.4 (M+H)⁺.

Synthesis of Synthesis of (4R)-4-(difluoromethyl)-1,2,3,4-tetrahydroquinoline-6-carbonitrile and (4S)-4-(difluoromethyl)-1,2,3,4-tetrahydroquinoline-6-carbonitrile, Used in the Preparation of Compound 326 and Compound 327

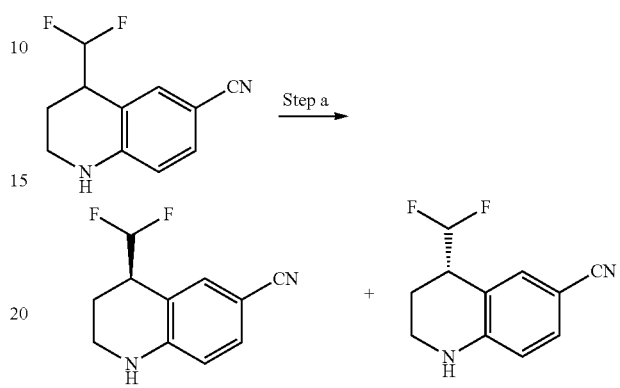

Step a: The compound of 4-(difluoromethyl)-1,2,3,4-tetrahydroquinoline-6-carbonitrile (100 mg, 0.5 mmol) was separated by chiral SFC (Column: ChiralCel OD-3 150×4.6 mm I.D., 3 um. Mobile phase: A: CO2 B: Methanol (0.05% DEA), Gradient: from 5% to 40% of B in 5.5 min and hold 40% for 3 min, then 5% of B for 1.5 min, Flow rate: 2.5 mL/min, Column temperature: 40° C.) to give the product of (4R)-4-(difluoromethyl)-1,2,3,4-tetrahydroquinoline-6-carbonitrile (34.6 mg, 34.6% yield) as a white solid and (4S)-4-(difluoromethyl)-1,2,3,4-tetrahydroquinoline-6-carbonitrile (28.5 mg, 28.5% yield) as a white solid. The absolute configuration was assigned randomly.

Synthesis of 5,6,7,8-tetrahydropteridin-7-one, for Use in the Preparation of Compound 322

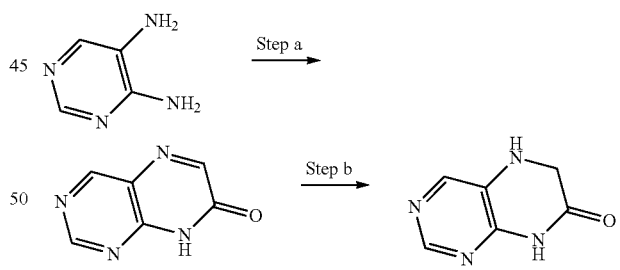

Step a: Pyrimidine-4,5-diamine (990 mg, 8.99 mmol) and sodium acetate (1.39 g, 17.0 mmol) was suspended in water (9 mL) and 5N aqueous AcOH (2.23 mL, 11.2 mmol). The mixture was charged with methyl 2-hydroxy-2-methoxyacetate (1.60 g, 13.4 mmol) and heated to 90° C. for 1 hr. The mixture was cooled, pH was adjusted to 2 with 5H H₂SO₄, filtered, washed with water and air dried to constant weight to afford 7,8-dihydropteridin-7-one (960 mg) a light orange solid. LCMS: [M+H]⁺ 149.

Step b: 7,8-dihydropteridin-7-one (60 mg, 0.4050 mmol) was dissolved in MeOH (10 mL) then pumped through a Raney-Ni cartridge at 1 mL/min, under 5 bar of H₂ at 50° C. for 90 min. Solvent was removed, chased with toluene to afford 5,6,7,8-tetrahydropteridin-7-one (60 mg) as a light yellow solid. LCMS: [M+H]+ 151.

Synthesis of 1-(7-(1-methyl-1H-pyrazol-4-yl)-3,4-dihydroquinoxalin-1(2H)-yl)ethan-1-one, Intermediate Used in the Preparation of Compound 323

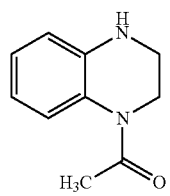

CAS: 6639-92-5

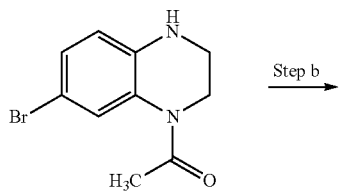

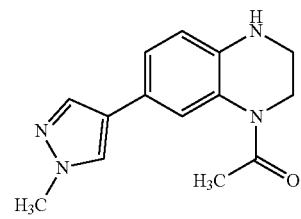

Step a: To a round bottom flask containing 1-(3,4-dihydroquinoxalin-1(2H)-yl)ethan-1-one (192 mg, 1.09 mmol) (CAS: 6639-92-5) was added ACN (1.5 mL) before it was cooled to 0° C. A solution of N-bromosuccinimide (192 mg, 1.09 mmol) in ACN (1.7 mL) was added and the reaction stirred at 0° C. for 5 min before adding sat. Na$_2$S$_2$O$_3$ at the same temperature. The reaction was warmed to ambient temperature and Et$_2$O was added. The organic layer was extracted with Et$_2$O (3×), and combined organic extracts were dried, concentrated and purified via silica gel chromatography (18-100% EtOAc in hexanes) to provide 1-(7-bromo-3,4-dihydroquinoxalin-1(2H)-yl)ethan-1-one (194 mg, 0.760 mmol) in 70% yield, along with the dibrominated analog, which was not isolated. LCMS: [M+] 255.1 and 257.1.

Step b: A reaction vial containing 1-(7-bromo-3,4-dihydroquinoxalin-1(2H)-yl)ethan-1-one (72 mg, 0.29 mmol), 1-methyl-4-(4,4,5,5-tetramethyl-1,3,2-dioxaborolan-2-yl)-1H-pyrazole (97.0 mg, 0.47 mmol), palladium tetrakis (33.5 mg, 0.0.29 mmol) and K$_2$CO$_3$ (120 mg, 0.87 mmol) was charged with dioxane (0.80 mL) and H$_2$O (0.20 mL). The reaction was degassed for 5 min, before being heated to 95° C. for 16 h. Following cooling to ambient temperature, the reaction was filtered through celite, rinsing with dichloromethane. The residue was concentrated and purified via silica gel chromatography (0-20% MeOH in dichloromethane with 0.1% NH$_3$ H$_2$O) to furnish 1-(7-(1-methyl-1H-pyrazol-4-yl)-3,4-dihydroquinoxalin-1(2H)-yl)ethan-1-one (28.0 mg, 0.110 mmol) in 38% yield. LCMS: [M+H]+ 257.2.

Synthesis of 5-methanesulfonyl-6-methyl-1,2,3,4-tetrahydroquinoline, for Use in the Preparation of Compound 345 and 5-methanesulfonyl-6-phenyl-1,2,3,4-tetrahydroquinoline, for Use in the Preparation of Compound 346

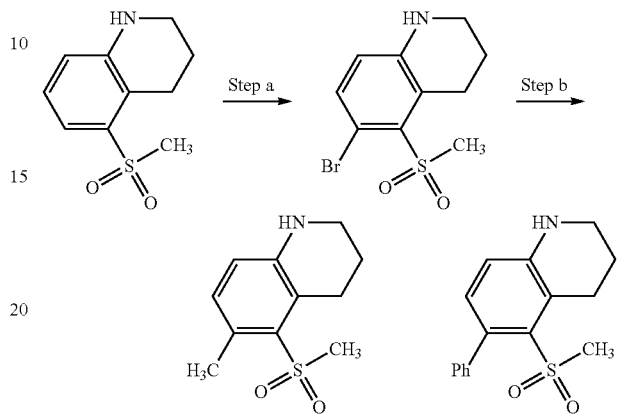

Step a: 5-methanesulfonyl-1,2,3,4-tetrahydroquinoline (505 mg, 2.39 mmol) in DMF (5 mL) was cooled to 0° C., and charged with 1-bromopyrrolidine-2,5-dione (425 mg, 2.39 mmol) in DMF (1 mL). The resulting solution was stirred at 0° C. for 1 h. The mixture was charged with water and extracted with ethyl acetate, dried and concentrated. The residue purified on C18 (20-50% ACN/water+0.1% FA) to afford 6-bromo-5-methanesulfonyl-1,2,3,4-tetrahydroquinoline (300 mg) as a yellow solid. LCMS: [M+H]+ 290.

Step b: A resealable reaction vial was charged with 6-bromo-5-methanesulfonyl-1,2,3,4-tetrahydroquinoline (125 mg, 0.4307 mmol), trimethyl-1,3,5,2,4,6-trioxatriborinane (81.0 mg, 0.6460 mmol), tetrakis(triphenylphosphane) palladium (49.7 mg, 0.04307 mmol), disodium carbonate (68.4 mg, 0.6460 mmol), and dioxane/water (5/1, 6 mL). The mixture was stirred at 90° C. for 16 hrs. The reaction mixture was concentrated and purified by flash silica gel chromatography (eluting with ethyl acetate:heptanes=20:80 to 50:50) to afford 2 product isolated separately: 5-methanesulfonyl-6-methyl-1,2,3,4-tetrahydroquinoline (25 mg) (LCMS: [M+H]+ 226) and 5-methanesulfonyl-6-phenyl-1,2,3,4-tetrahydroquinoline (25 mg) (LCMS: [M+H]+ 288) as colorless oils.

Synthesis of 1-(3,4-dihydroquinoxalin-1(2H)-yl)propan-1-one, Intermediate Used in the Preparation of Compound 360 and Compound 193

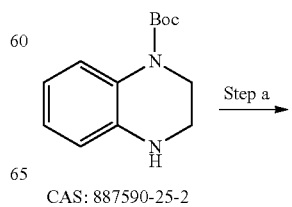

CAS: 887590-25-2

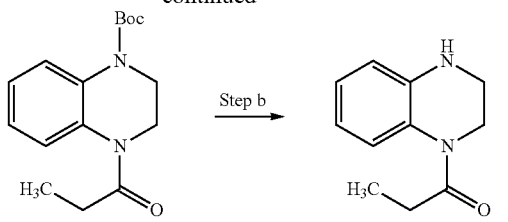

Step a: A reaction vial was charged with tert-butyl 1,2,3,4-tetrahydroquinoxaline-1-carboxylate (150 mg, 0.640 mmol) in DMF (6.4 mL) and TEA (0.356 mL) was added, followed by propanoyl chloride (0.070 mL, 0.768 mmol). The reaction was stirred at ambient temperature for 45 min before the addition of EtOAc and sat. sodium bicarbonate. The organic layer was extracted with EtOAc (3×), and the combined organic extracts were concentrated and purified via silica gel chromatography (10-100% EtOAc in hexanes) to yield tert-butyl 4-propionyl-3,4-dihydroquinoxaline-1(2H)-carboxylate, which was isolated contaminated with unreacted starting material, and was carried on to the subsequent step as this mixture.

Step b: To a vial containing tert-butyl 4-propionyl-3,4-dihydroquinoxaline-1(2H)-carboxylate in dichloromethane (4.0 mL) was added trifluoroacetic acid (0.5 mL). The reaction was stirred at ambient temperature for 45 min before being concentrated and purified via silica gel chromatography (10-100% EtOAc in hexanes) to yield 1-(3,4-dihydroquinoxalin-1(2H)-yl)propan-1-one (76.0 mg, 0.400 mmol) in 61% yield over two steps. LCMS: [M+H]+ 191.1.

Synthesis of 6-(4-methyl-1,3-thiazol-2-yl)-1,2,3,4-tetrahydro-1,5-naphthyridine, Used in the Preparation of Compound 361

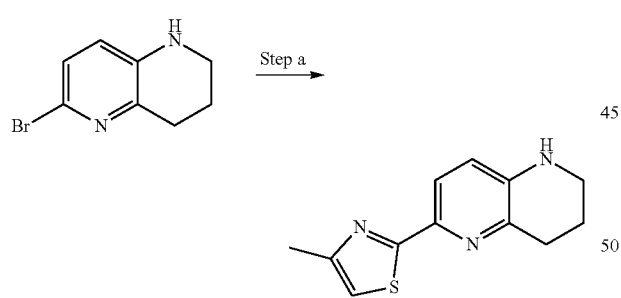

Step a: 6-bromo-1,2,3,4-tetrahydro-1,5-naphthyridine (200 mg, 0.9386 mmol), XPhos G4 (161 mg, 0.1877 mmol) and Pd2(dba)3 (171 mg, 0.1877 mmol) were added to a reaction vial. Vial was evacuated and backfilled with $N_2$ (3×). Added dioxane (3 mL) followed by 4-methyl-2-(tributylstannyl)-1,3-thiazole (364 mg, 0.9386 mmol). Stirred at 100 C for 4 h. Partitioned between EtOAc and water. Separated layers, washed with EtOAc (2×). Combined organic layers, dried over $Na_2SO_4$, filtered and concentrated. Purified by flash silica gel chromatography using 0-100% EtOAc in heptanes to give 6-(4-methyl-1,3-thiazol-2-yl)-1,2,3,4-tetrahydro-1,5-naphthyridine (89.0 mg, 0.3847 mmol) as a yellow powder. LCMS: [M+H] 232.28.

Synthesis of (R)-6-bromo-4-methyl-1,2,3,4-tetrahydro-1,5-naphthyridine and (S)-6-bromo-4-methyl-1,2,3,4-tetrahydro-1,5-naphthyridine, Used in the Preparation of Compound 362

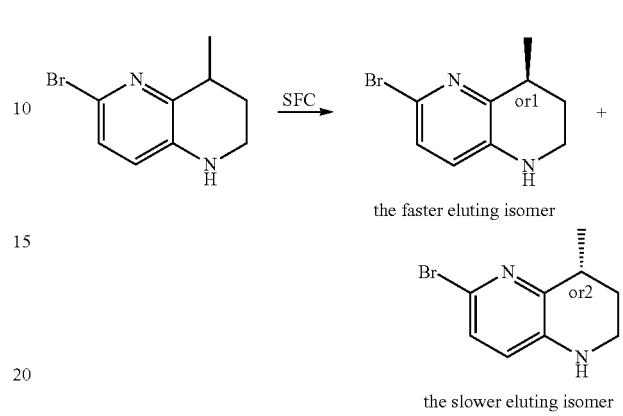

the faster eluting isomer the slower eluting isomer 6-bromo-4-methyl-1,2,3,4-tetrahydro-1,5-naphthyridine (24.00 g, 105.0 mmol) was separated by preparative SFC (column: DAICEL CHIRALPAK AD(250 mm×50 mm, 10 um), Mobile phase: 0.1% NH3.H2O, EtOH (Begin B: 25%, End B: 25%), Flow rate: 200 mL/min, Injections: 500) to afford the product of rel-(S)-6-bromo-4-methyl-1,2,3,4-tetrahydro-1,5-naphthyridine (11.30 g, 49.7 mmol, Rt=3.08 min, the faster eluting isomer) as a yellow solid and rel-(R)-6-bromo-4-methyl-1,2,3,4-tetrahydro-1,5-naphthyridine (11.0 g, 48.4 mmol, Rt=3.77 min, the slower eluting isomer) as a yellow solid. Stereochemical assignments were made arbitrarily. Based on the data from analogs made with each compound, it was determined that the later-eluting compound led to more active analogs. LCMS: [M+H]+ 228.7.

1-cyclopropyl-8-methyl-1,2,3,4-tetrahydroquinoxaline, Intermediate Used in the Preparation of Compound 379

1-Cyclopropyl-8-methyl-1,2,3,4-tetrahydroquinoxaline is commercially available (CAS: 1553271-94-5).

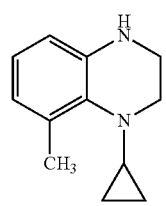

CAS: 1553271-94-5

Synthesis of 1-methyl-7-(1-methyl-1H-pyrazol-4-yl)-1,2,3,4-tetrahydroquinoxaline, for Compound 381

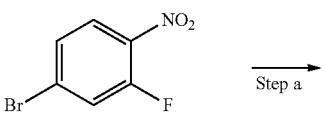

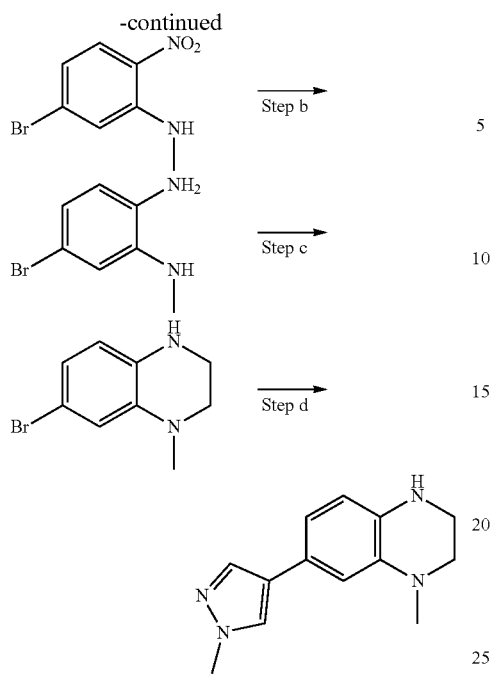

Step a: To the mixture of 4-bromo-2-fluoro-1-nitrobenzene (25.0 g, 113.0 mmol) in MeOH (100.0 mL) and THF (50.0 mL) was added MeNH2 (67.5 mL, 135.0 mmol, 2 M in THF) dropwise. The mixture was stirred at 10° C. for 12 hours. TLC (petroleum ether/EtOAc=10/1) showed a new spot formed and major of 1 remained. MeNH2 (60.0 mL, 2 M in THF) was added to the mixture and the mixture was stirred at 45° C. for 12 hours. The mixture was concentrated in vacuum to give residue. Water (200.0 mL) added to the mixture and the mixture was extracted with EtOAc (200.0 mL×2). The organic layers were washed with brine and dried over anhydrous Na2SO4, filtered and the filtrate was concentrated in vacuum to give the product of 5-bromo-N-methyl-2-nitroaniline (25.5 g, 97.7% yield) as a yellow solid.

Step b: To the mixture of 5-bromo-N-methyl-2-nitroaniline (10.0 g, 43.2 mmol) in MeOH (150.0 mL) was added sodium dithionite (67.5 g, 388.0 mmol) in H2O (60.0 mL) dropwise. The mixture was stirred at 60° C. for 12 hours. The mixture was filtered and the filtrate was concentrated in vacuum. The residue was extracted with EtOAc (200.0 mL×3), the organic layers were washed with H2O (100.0 mL) and brine (100.0 mL), dried over anhydrous Na2SO4. The mixture was filtered and the filtrate was concentrated in vacuum to give the product of 5-bromo-N1-methylbenzene-1,2-diamine (8.60 g, crude) as a brown oil.

Step c: A mixture of 5-bromo-N1-methylbenzene-1,2-diamine (1.0 g, 4.97 mmol), 1,2-dibromoethane (2.13 mL, 24.8 mmol) and TBAB (4.80 g, 14.9 mmol) was stirred at 60° C. for 12 hours. The mixture was concentrated in vacuum and purified by flash silica gel chromatography (petroleum ether/EtOAc=1/0 to 2/1) to give the product of 7-bromo-1-methyl-1,2,3,4-tetrahydroquinoxaline (233.0 mg, 20.8% yield) as a brown solid.

Step d: To the mixture of 7-bromo-1-methyl-1,2,3,4-tetrahydroquinoxaline (100.0 mg, 0.44 mmol) and 1-methyl-4-(4,4,5,5-tetramethyl-1,3,2-dioxaborolan-2-yl)-1H-pyrazole (137.0 mg, 0.66 mmol) in dioxane (5.0 mL) and H2O (1.0 mL) was added Pd(dppf)Cl2 (32.1 mg, 44 umol) and K3PO4 (205.0 mg, 0.97 mmol) under N2. The mixture was stirred at 100° C. under N2 for 12 hours. The mixture was concentrated in vacuum and purified by flash silica gel (petroleum ether/EtOAc=1/0 to 1/1) to give the product of 1-methyl-7-(1-methyl-1H-pyrazol-4-yl)-1,2,3,4-tetrahydroquinoxaline (35.9 mg, 35.9% yield) as a yellow oil. LCMS 229.1 [M+H]+

Synthesis of 6-(5-methyl-1,3-thiazol-2-yl)-1,2,3,4-tetrahydro-1,5-naphthyridine, Used in the Preparation of Compound 382

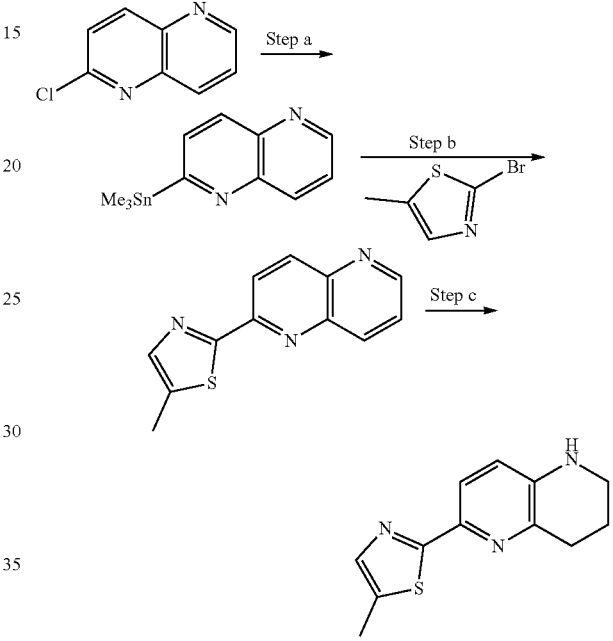

Step a: To a solution of 2-chloro-1,5-naphthyridine (1.0 g, 6.1 mmol, 1.0 eq) and Sn2Me6 (3.0 g, 9.1 mmol, 1.5 eq) in toluene (15 mL) was added Pd(PPh3)4 (2.1 g, 1.8 mmol, 0.3 eq). The mixture was stirred at 60° C. for 10 hours. LCMS indicated that the starting material was consumed completely and one main new peak with desired MS was detected. The reaction mixture will be used in the next step directly without further purification.

Step b: To a solution of 2-(trimethylstannyl)-1,5-naphthyridine (1.8 g, 6.0 mmol, 1.0 eq) and Pd(PPh3)4 (2.1 g, 1.8 mmol, 0.3 eq) in toluene (15 mL) was added 2-bromo-5-methyl-1,3-thiazole (1.1 g, 6.0 mmol, 1.0 eq). The mixture was stirred at 110° C. for 10 hours. LCMS indicated that the starting material was consumed completely and one main new peak with desired MS was detected. The mixture was quenched with saturated KF (50 mL), extracted with EtOAc (50 mL×2). The organic layer was washed with brine (50 mL), dried over anhydrous Na2SO4, filtered and concentrated under reduced pressure. The residue was purified by column chromatography (Petroleum ether/Ethyl acetate=1:0~3:1) to afford 2-(5-methyl-1,3-thiazol-2-yl)-1,5-naphthyridine (530 mg, 38.6% yield) as a yellow solid.

Step c: The mixture of 2-(5-methyl-1,3-thiazol-2-yl)-1,5-naphthyridine (300 mg, 1.3 mmol, 1.0 eq) and PtO2 (59.4 mg, 262 μmol, 0.2 eq) in MeOH (5 mL) was evacuated and refilled for 3 times using H2, stirred at 15° C. for 12 hours and 30° C. for 20 hours under H2 atmosphere (15 psi). LCMS indicated a small amount of the starting material was remained and one main new peak with desired MS was detected. The mixture was filtered and the filtrate was concentrated under reduced pressure. The residue was purified by column chromatography (Petroleum ether/Ethyl acetate=1:0-1:1) to afford the desired product of 6-(5-methyl-1,3-thiazol-2-yl)-1,2,3,4-tetrahydro-1,5-naphthyridine (90 mg, 60% purity, 17.8% yield) as a yellow solid.

Synthesis of 4-methyl-1H,2H,3H,4H-pyrido[2,3-b]pyrazine-6-carbonitrile, A-Ring for Compound 383

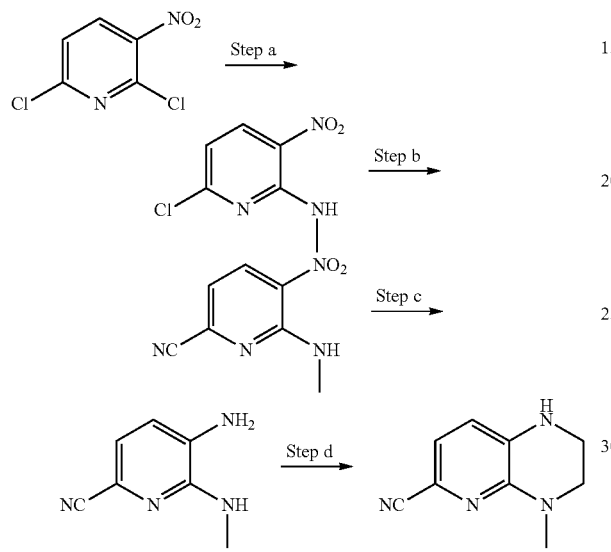

Step a: To a mixture of 2,6-dichloro-3-nitropyridine (10.0 g, 51.8 mmol) and Na₂CO, (13.6 g, 129 mmol) in EtOH (100 mL) at 0° C. was added MeNH₂/EtOH (30% wet., 8.5 g) dropwise. After addition, the reaction mixture was warmed to 15° C. slowly and stirred for 3 hours. The reaction mixture was concentrated in vacuum to give a residue, which was dissolved in ethyl acetate (80 mL), washed with H₂O (70 mL×2). The organic phase was washed with brine (60 mL), dried over anhydrous Na₂SO₄, filtered and concentrated in vacuum. The residue was crystallized with ethanol to afford the product of 6-chloro-N-methyl-3-nitropyridin-2-amine (8.2 g, 84.4% yield) as a light yellow solid.

Step b: A mixture of 6-chloro-N-methyl-3-nitropyridin-2-amine (2.0 g, 10.6 mmol), Zn(CN)₂ (1.8 g, 15.9 mmol), Pd₂(dba)₃ (961 mg, 1.1 mmol) and dppf (1.2 g, 2.1 mmol) in DMF (50 mL) was stirred at 120° C. for 12 hours under N₂ atmosphere. TLC (Petroleum ether: Ethyl acetate=5:1) showed the reaction was consumed completely. The reaction mixture was diluted with ethyl acetate (100 mL), washed with H₂O (90 mL×2). The organic phase was washed with brine (30 mL), dried over anhydrous Na₂SO₄, filtered and concentrated in vacuum to give a residue, which was purified by silica gel chromatography (Ethyl acetate in Petroleum ether: 20% to 35%) to afford the product of 6-(methylamino)-5-nitropyridine-2-carbonitrile (1.1 g, 58.5% yield) as a yellow solid.

Step c: A mixture of 6-(methylamino)-5-nitropyridine-2-carbonitrile (1.0 g, 5.6 mmol), NH₄Cl (890 mg, 16.8 mmol) and Fe (1.6 g, 28.0 mmol) in EtOH (10 mL)/2N HCl (2 mL) was stirred at 50° C. for 3 hours. TLC (Petroleum ether: Ethyl acetate=4:1) showed the reaction was consumed completely. The reaction mixture was filtered and the filtrate was concentrated in vacuum to afford the product of 5-amino-6-(methylamino)picolinonitrile (830 mg, crude) as a black solid.

Step d: A mixture of 5-amino-6-(methylamino)pyridine-2-carbonitrile (830 mg, 5.6 mmol, crude) and 1,2-dibromoethane (5.3 g, 28 mmol) in TBAB (5.4 g, 16.7 mmol) was stirred at 60° C. for 12 hours. The reaction mixture was diluted with H₂O (50 mL), extracted with ethyl acetate (60 mL×2). The organic phases were washed with brine (20 mL), dried over anhydrous Na₂SO₄, filtered and concentrated in vacuum to give a residue, which was purified by silica gel chromatography (Ethyl acetate in Petroleum ether: 35% to 45%) to afford the product of 4-methyl-1H,2H,3H,4H-pyrido[2,3-b]pyrazine-6-carbonitrile (240 mg) as a brown solid.

Synthesis of 4-(propan-2-yl)-1H,2H,3H,4H-pyrido[2,3-b]pyrazine, for Use in the Preparation of Compound 387

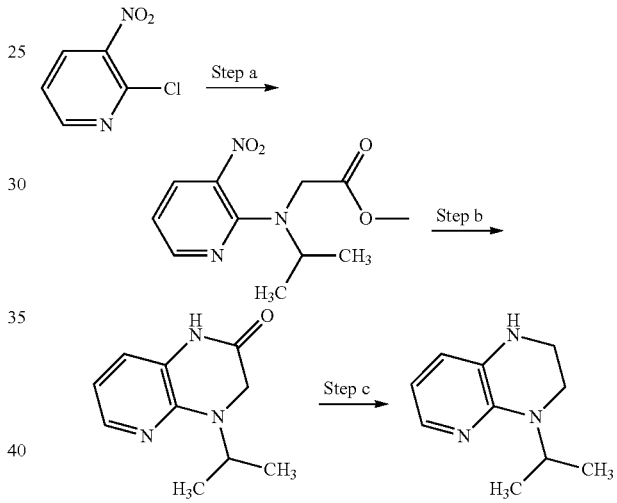

Step a: A resealable reaction vial was charged with 2-chloro-3-nitropyridine (500 mg, 3.15 mmol) in DMF (13 mL), ethylbis(propan-2-yl)amine (822 µL, 4.72 mmol), methyl 2-[(propan-2-yl)amino]acetate (432 mg, 3.30 mmol). The vial was sealed, and the mixture was stirred at 80° C. for 16 hrs. The cooled mixture was charged with water (10 mL) and extracted with ethyl acetate and concentrated. The residue was purified by flash silica gel chromatography (eluting with ethyl acetate:heptanes=0:100 to 40:60) to afford methyl 2-[(3-nitropyridin-2-yl)(propan-2-yl)amino]acetate (630 mg) as a yellow solid.

Step b: Methyl 2-[(3-nitropyridin-2-yl)(propan-2-yl)amino]acetate (630 mg, 2.48 mmol) was dissolved in AcOH (6 mL) and charged with iron (415 mg, 7.44 mmol). The mixture was heated 90° C. for 1 hr. The reaction was diluted with MeOH, filtered on celite and concentrated. The residue was taken up in DCM and washed with sat. bicarb. The aq. layer was back-extracted with CHCl₃/IPA (3/1). The org layers combined, dried, concentrated. The residue was purified by flash silica gel chromatography (eluting with ethyl acetate:heptanes=0:100 to 50:50) to afford 4-(propan-2-yl)-1H,2H,3H,4H-pyrido[2,3-b]pyrazin-2-one (260 mg) as a white crystalline solid. LCMS: [M+H]⁺ 192.

Step c: A resealable reaction vial was charged with 4-(propan-2-yl)-1H,2H,3H,4H-pyrido[2,3-b]pyrazin-2-one (100 mg, 0.5229 mmol) and THF (6 mL). The reaction was charged with lithioalumane (1.04 mL, 1.04 mmol) and the mixture was stirred at 25° C. for 1 hr. The reaction was cooled to 0° C., and quenched with 1N NaOH until gas evolution stopped (4 drops). The reaction was diluted with THF and DCM, charged with celite, filtered and concentrated to 4-(propan-2-yl)-1H,2H,3H,4H-pyrido[2,3-b]pyrazine (95 mg) as a colorless oil. LCMS: [M+H]+ 178.

Synthesis of 5-methanesulfonyl-1,2,3,4-tetrahydroquinoline-6-carbonitrile, for Use in the Preparation of Compound 388

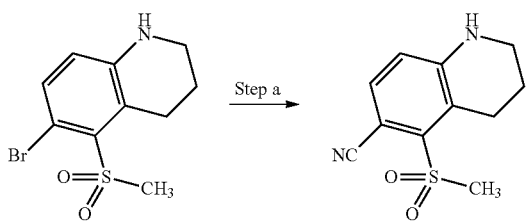 [SMILES: CS(=O)(=O)c1c(Br)ccc2c1CCCN2 ; CS(=O)(=O)c1c(C#N)ccc2c1CCCN2]

Step a: A resealable reaction vial was charged with 6-bromo-5-methanesulfonyl-1,2,3,4-tetrahydroquinoline (166 mg, 0.5720 mmol) (preparation described in Compound 346), zincdicarbonitrile (133 mg, 1.14 mmol), palladium(1+) 2'-amino-1,1'-biphenyl-2-yl di-tert-butyl[2',4',6'-tris(propan-2-yl)-[1,1'-biphenyl]-2-yl]phosphane methanesulfonate (45.4 mg, 0.05719 mmol), dioxane (6 mL) and water (0.5 mL). The mixture was bubbled with nitrogen for 5 min. The vial was sealed, and the mixture was stirred at 90° C. for 8 hrs. The reaction mixture was concentrated and purified by flash silica gel chromatography (eluting with ethyl acetate:heptanes=20:80 to 100:0) to afford 5-methanesulfonyl-1,2,3,4-tetrahydroquinoline-6-carbonitrile (140 mg) as a tan solid. LCMS: [M+H]+ 237.

Synthesis of 5-(5-methyl-1,3,4-oxadiazol-2-yl)-1,2,3,4-tetrahydroquinoline, A-Ring for Compound 389

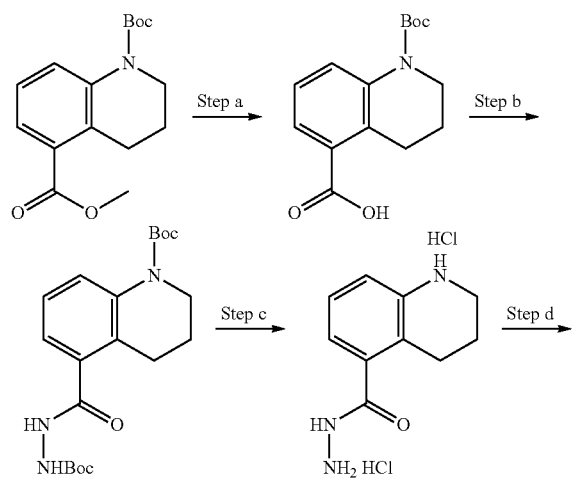

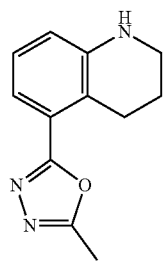

Step a: The mixture of 1-tert-butyl 5-methyl 1,2,3,4-tetrahydroquinoline-1,5-dicarboxylate (250 mg, 858 μmol, 1.0 eq) and LiOH (62 mg, 2.6 mmol, 3.0 eq) in MeOH (5 mL) and H2O (0.5 mL) was stirred at 50° C. for 10 hours. LCMS indicated that the starting material was consumed completely and one main new peak with desired MS was detected. The mixture was adjusted with 2N HCl to pH=7. The mixture was concentrated under reduced pressure to afford 1-[(tert-butoxy)carbonyl]-1,2,3,4-tetrahydroquinoline-5-carboxylic acid (350 mg, crude) as a white solid.

Step b: The mixture of 1-[(tert-butoxy)carbonyl]-1,2,3,4-tetrahydroquinoline-5-carboxylic acid (237 mg, 854 μmol, 1.0 eq), NH2NHBoc (168 mg, 1.3 mmol, 1.5 eq), HATU (972 mg, 2.6 mmol, 3.0 eq) and TEA (353 μL, 2.6 mmol, 3.0 eq) in DMF (5 mL) was stirred at 50° C. for 12 hours. TLC (Petroleum ether/Ethyl acetate=2:1) indicated that the starting material was consumed completely and one main new spot with lower polarity formed. The mixture was diluted with H2O (20 mL), extracted with EtOAc (20 mL×3). The organic layer was washed with brine (20 mL), dried over anhydrous Na2SO4, filtered and concentrated under reduced pressure. The residue was purified by column chromatography (Petroleum ether/Ethyl acetate=10:0-3:1) to afford the desired product of tert-butyl 5-{N-[(tert-butoxy)carbonyl]hydrazinecarbonyl}-1,2,3,4-tetrahydroquinoline-1-carboxylate (460 mg, crude) as a white solid.

Step c: The mixture of tert-butyl 5-{N-[(tert-butoxy)carbonyl]hydrazinecarbonyl}-1,2,3,4-tetrahydroquinoline-1-carboxylate (460 mg, 70% purity, 822 μmol, 1.0 eq) in HCl/MeOH (5 mL, 4M) was stirred at 15° C. for 1.5 hours. LCMS indicated that the starting material was consumed completely and one main new peak with desired MS was detected. The mixture was concentrated under reduced pressure to afford the desired product of 1,2,3,4-tetrahydroquinoline-5-carbohydrazide dihydrochloride (217 mg, 100% yield) as a white solid.

Step d: The mixture of 1,2,3,4-tetrahydroquinoline-5-carbohydrazide dihydrochloride (217 mg, 821 μmol, 1.0 eq) and MeC(OEt)3 (2.7 g, 16.4 mmol, 20 eq) in dioxane (5 mL) was stirred at 120° C. for 10 hours. LCMS indicated that the starting material was consumed completely and one main new peak with desired MS was detected. The mixture was concentrated under reduced pressure and the residue was purified by column chromatography (Petroleum ether/Ethyl acetate=1:0~3:1) to afford the desired product of 5-(5-methyl-1,3,4-oxadiazol-2-yl)-1,2,3,4-tetrahydroquinoline (123 mg, 69.8% yield) as a white solid.

Synthesis of 5-(methoxymethyl)-1,2,3,4-tetrahydroquinoline, Used in the Synthesis of Compound 390

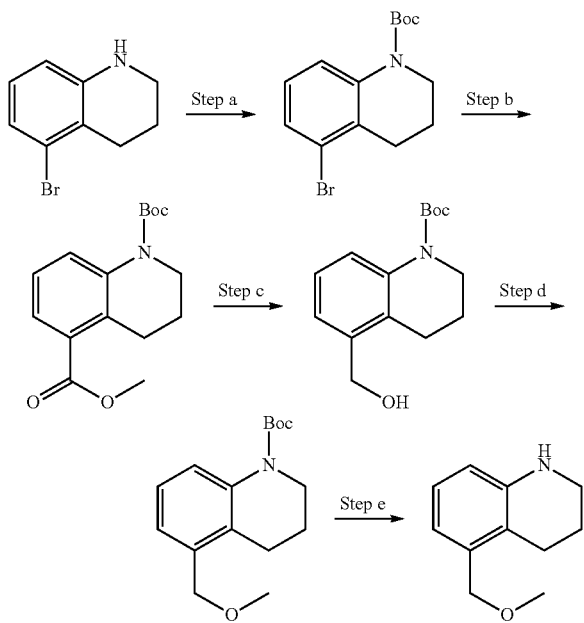

Step a: A solution of 5-bromo-1,2,3,4-tetrahydroquinoline (2.0 g, 9.42 mmol) in THF (40.0 mL) was added NaHMDS (28.2 mL, 28.2 mmol, 1M) under $N_2$ at 20° C. The reaction was stirred for 2 h. Brown solution was observed. $(Boc)_2O$ (4.30 mL, 18.8 mmol) in THF (30.0 mL) was added, the reaction mixture was stirred at 20° C. for 10 h under $N_2$. Yellow solution was observed. TLC (EtOAc/Petroleum ether=1/10) showed a small amount of starting material was remained and a new main spot with lower polarity was formed. The combined mixture was diluted with water (200.0 mL) and extracted with EtOAc (200.0 mL×3). The combined organic layers were washed with water (300.0 mL) and brine (300.0 mL), dried over anhydrous $Na_2SO_4$, filtered and concentrated under reduced pressure. The residue was purified by column chromatography (EtOAc in Petroleum ether=0~2%) to afford tert-butyl 5-bromo-1,2,3,4-tetrahydroquinoline-1-carboxylate (4.9 g, crude) which was confirmed by HNMR Step b: To a solution of tert-butyl 5-bromo-1,2,3,4-tetrahydroquinoline-1-carboxylate (1.5 g, 4.8 mmol) in MeOH (20 mL) were added $Pd(dppf)Cl_2$ (351 mg, 480 µmol) and TEA (1.4 g, 14.3 mmol). The mixture was evacuated and refilled for 3 times using CO, then stirred at 80° C. for 12 hours under CO (50 psi). LCMS showed the desired product formed. The reaction mixture was concentrated and was purified by silica gel chromatography (elution: Petroleum ether:ethyl acetate=5:1) to afford the product of 1-tert-butyl 5-methyl 1,2,3,4-tetrahydroquinoline-1,5-dicarboxylate (1.3 g, 90.0% yield) as a yellow solid.

Step c: To a solution of 1-tert-butyl 5-methyl 1,2,3,4-tetrahydroquinoline-1,5-dicarboxylate (750 mg, 2.6 mmol) in THF (5 mL) was added $LiBH_4$ (107 mg, 5.1 mmol) at 0° C., the mixture was stirred at 25° C. for 12 hours under $N_2$. LCMS showed the desired product formed. The reaction was quenched by sat.$NH_4Cl$ (40 mL), extracted with EtOAc (50 mL×3). The combined organic layers were dried over anhydrous $Na_2SO_4$, filtered and concentrated to dryness. The resulting crude material was purified by silica gel chromatography (eluent: Petroleum ether:Ethyl acetate=3:1) to give tert-butyl 5-(hydroxymethyl)-1,2,3,4-tetrahydroquinoline-1-carboxylate (680 mg, 100% yield) as a colorless oil.

Step d: To a solution of tert-butyl 5-(hydroxymethyl)-1,2,3,4-tetrahydroquinoline-1-carboxylate (250 mg, 949 µmol) in DMF (2 ml) was added NaH (75.5 mg, 1.9 mmol) at 0° C., the mixture was stirred at 25° C. for 1 hour. Then MeI (1.1 g, 7.6 mmol) was added at 0° C., the mixture was stirred at 25° C. for 6 hours, LCMS showed the desired product formed. The reaction mixture was quenched by brine (10 mL), extracted with EtOAc (20 mL×3), the combined organic layers dried over anhydrous $Na_2SO_4$, filtered and concentrated to dryness. The resulting crude material was purified by silica gel chromatography (eluent: Petroleum ether:Ethyl acetate=5:1) to give tert-butyl 5-(methoxymethyl)-1,2,3,4-tetrahydroquinoline-1-carboxylate (240 mg, 91.2% yield) as a colorless oil.

Step e: To a solution of tert-butyl 5-(methoxymethyl)-1,2,3,4-tetrahydroquinoline-1-carboxylate (180 mg, 648 µmol) in MeOH (1 mL) was added HCl/MeOH (3.2 mL, 4 M)) at 0° C., the mixture was stirred at 20° C. for 6 hours. LCMS showed the desired product formed. The reaction mixture was concentrated to dryness, MeOH (2 mL) and $K_2CO_3$ (100 mg) were added. The mixture was filtered and the filtrate was concentrated to dryness, which was purified by silica gel chromatography (eluent: Petroleum ether:Ethyl acetate=5:1) to give 5-(methoxymethyl)-1,2,3,4-tetrahydroquinoline (110 mg, 96.4% yield) as a white solid.

Synthesis of 2-(1,2,3,4-tetrahydroquinolin-5-yl)-1$\lambda^6$, 2-thiazolidine-1,1-dione, for Use in the Preparation of Compound 392

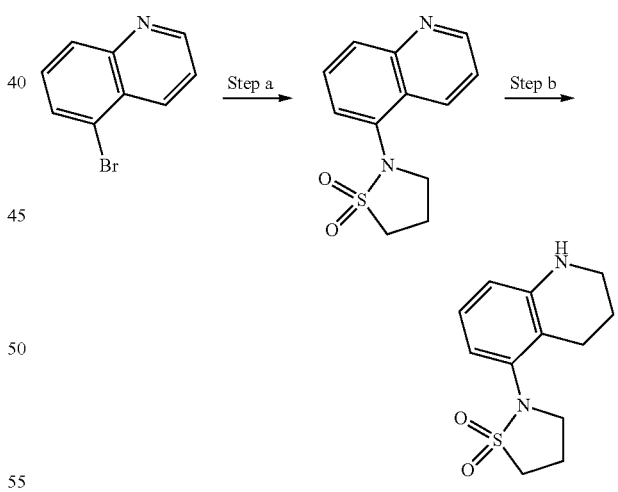

Step a: A resealable reaction vial was charged with 5-bromoquinoline (200 mg, 0.9612 mmol), 1$\lambda^6$,2-thiazolidine-1,1-dione (139 mg, 1.15 mmol), dipotassium carbonate (265 mg, 1.92 mmol), tBuXPhos/Pd G3 (76.2 mg, 0.09612 mmol), and 2-MeTHF (8 mL). The mixture was bubbled nitrogen for 5 min, the vial was sealed, and the mixture was stirred at 80° C. for 72 hrs. The reaction mixture and concentrated. The residue was purified by flash silica gel chromatography (eluting with ethyl acetate:heptanes=20:80 to 100:0) to afford 2-(quinolin-5-yl)-1$\lambda^6$,2-thiazolidine-1,1-dione (50 mg) as a white solid. LCMS: $[M+H]^+$ 249.

Step b: 13.15 2-(quinolin-5-yl)-1λ⁶,2-thiazolidine-1,1-dione (50 mg, 0.2053 mmol) was dissolved in MeOH (10 mL) and pumped through a 10% Pd/C at 2 mL/min under 30 bars of H₂ at 30° C. for 45 min. Solvent was removed to afford 2-(1,2,3,4-tetrahydroquinolin-5-yl)-1λ⁶,2-thiazolidine-1,1-dione (50 mg) as a colorless oil. LCMS: [M+H]⁺ 253.

Synthesis of 4-(oxan-4-yl)-1H,2H,3H,4H-pyrido[2,3-b]pyrazine, for Use in the Preparation of Compound 393

Synthesis of 1-methyl-7-(1,3-oxazol-2-yl)-1,2,3,4-tetrahydroquinoxaline, Used in the Preparation of Compound 395

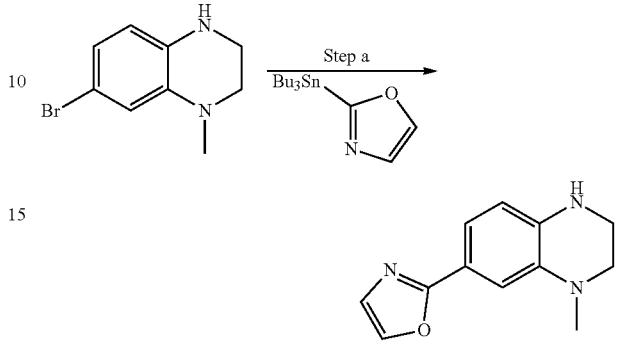

Step a: A mixture of 7-bromo-1-methyl-1,2,3,4-tetrahydroquinoxaline (200.0 mg, 0.88 mmol), 2-(tributylstannyl)-1,3-oxazole (315.0 mg, 0.88 mmol) and Pd(PPh₃)₄ (101.0 mg, 0.088 mmol) in toluene (15.0 mL) was stirred at 110° C. under N₂ for 12 hours. After concentration, the residue was purified by silica column (Ethyl acetate in Petroleum ether=0-100%) to give the desired 1-methyl-7-(1,3-oxazol-2-yl)-1,2,3,4-tetrahydroquinoxaline (75.0 mg, 39.6% yield) as a yellow oil.

Synthesis of tert-butyl N-[(3S,4S)-8-[3-iodo-1-(oxan-2-yl)-1H-pyrazolo[3,4-b]pyrazin-6-yl]-3-methyl-2-oxa-8-azaspiro[4.5]decan-4-yl]carbamate, A-Ring for Compound 398

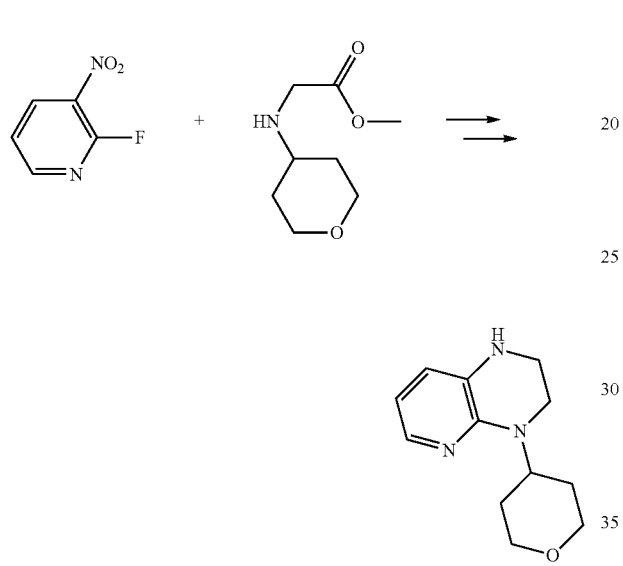

4-(oxan-4-yl)-1H,2H,3H,4H-pyrido[2,3-b]pyrazine (240 mg) (LCMS: [M+H]⁺ 220) was prepared using 2-fluoro-3-nitropyridine (400 mg, 2.81 mmol) and methyl 2-[(oxan-4-yl)amino]acetate (486 mg, 2.81 mmol) following the procedure used for the building block of Compound 387.

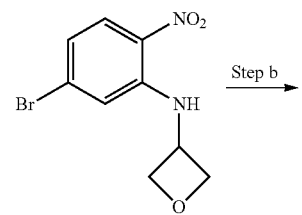

Synthesis of 4H,5H,6H,7H-thieno[3,2-b]pyridine, Used in the Preparation of Compound 394

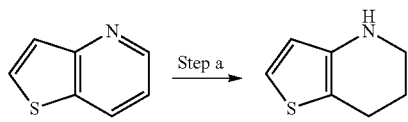 [SMILES: c1cnc2ccsc2c1 ; c1cc2c(s1)CCCN2]

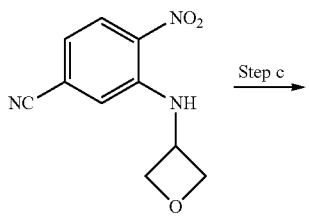

Step a: A mixture of thieno[3,2-b]pyridine (150.0 mg, 1.10 mmol), 3,5-diethyl 2,6-dimethyl-1,4-dihydropyridine-3,5-dicarboxylate (612.0 mg, 2.42 mmol) and diphenoxyphosphinic acid (27.5 mg, 110.0 μmol) in dioxane (5.0 mL) was stirred at 100° C. for 12 hours under N₂. LCMS showed the desired product formed. Concentrated in vacuum, the residue was purified by silica gel column (EtOAc in Petroleum ether=0~20%) to give 4H,5H,6H,7H-thieno[3,2-b]pyridine (160.0 mg, 65% purity, 67.9% yield) as a red oil.

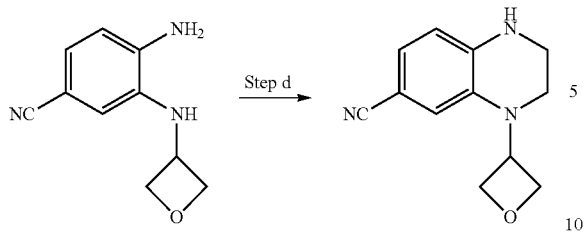

Step a: A solution of 4-bromo-2-fluoro-1-nitrobenzene (500.0 mg, 2.27 mmol), oxetan-3-amine (198.0 mg, 2.72 mmol) and TEA (687.0 mg, 6.81 mmol) in EtOH (10.0 mL) was stirred at 50° C. for 12 h. Yellow solution was observed. TLC (petroleum ether:EtOAc=10:1) showed the starting material consumed and a new spot was observed. The mixture was concentrated in vacuum to remove solvent. The residue was purified by flash silica gel chromatography (20 g, Ethyl acetate in Petroleum ether from 0% to 20%) to give N-(5-bromo-2-nitrophenyl)oxetan-3-amine (600.0 mg, 96.9% yield) as a yellow solid.

Step b: A solution of N-(5-bromo-2-nitrophenyl)oxetan-3-amine (600.0 mg, 2.19 mmol), $Zn(CN)_2$ (385.0 mg, 3.28 mmol), $Pd_2(dba)_3$ (500.0 mg, 547.0 umol) and dppf (72.7 mg, 131.0 umol) in DMF (50.0 mL) was stirred at 120° C. for 12 h under $N_2$. Brown solution was observed. TLC (petroleum ether:EtOAc=5:1) showed a new spot was observed and starting material consumed. The solution was added into $H_2O$ (200.0 mL) and then extracted with EtOAc (200.0 mL×2). The combined organic layers were washed with brine (200.0 mL), dried over anhydrous $Na_2SO_4$, filtered and concentrated in vacuum to give the crude product as a brown gum. The residue was purified by flash silica gel chromatography (12 g, Ethyl acetate in Petroleum ether from 0% to 35%) to give 4-nitro-3-[(oxetan-3-yl)amino]benzonitrile (480.0 mg, 100% yield) as an orange solid.

Step c: A solution of 4-nitro-3-[(oxetan-3-yl)amino]benzonitrile (300.0 mg, 1.36 mmol) and Pd/C (100.0 mg, 10%, wet) in THF (20.0 mL) was stirred at 20° C. for 2 h under $H_2$ (15 psi). Brown solution was observed. Desired mass ion was observed from LCMS. The mixture was filtered and filtrate was concentrated in vacuum to give 4-amino-3-[(oxetan-3-yl)amino]benzonitrile (240.0 mg, 93.3% yield) as a yellow gum. The gum was used in the next step without further purification.

Step d: A mixture of 4-amino-3-[(oxetan-3-yl)amino]benzonitrile (240.0 mg, 1.26 mmol), 1,2-dibromoethane (1.18 g, 6.30 mmol), TBAB (2.03 g, 6.30 mmol) and TEA (636.0 mg, 6.30 mmol) was stirred at 60° C. for 12 h. Orange solution was observed. Desired mass ion was observed from LCMS. The mixture was concentrated in vacuum to remove solvent. The mixture was added into $H_2O$ (100.0 mL) and then extracted with EtOAc (100.0 mL×2). The combined organic layers were washed with brine (100.0 mL), dried over anhydrous $Na_2SO_4$, filtered and concentrated in vacuum to give the crude product as an orange gum. The residue was purified by flash silica gel chromatography (4 g, Ethyl acetate in Petroleum ether from 0% to 35%) to give tert-butyl N-[(3S,4S)-8-[3-iodo-1-(oxan-2-yl)-1H-pyrazolo[3,4-b]pyrazin-6-yl]-3-methyl-2-oxa-8-azaspiro[4.5]decan-4-yl]carbamate (220.0 mg, 81.8% yield) as an orange oil.

Synthesis of 5-[(3R)-oxolan-3-yl]-1,2,3,4-tetrahydroquinoline, Used in the Preparation of Compound 400

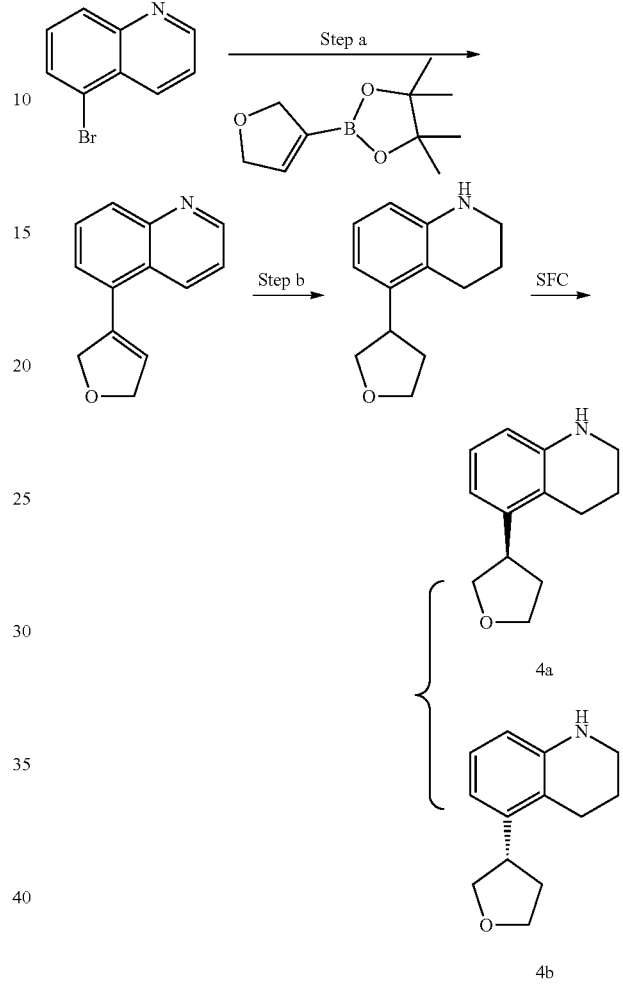

Step a: To a solution of 2-(2,5-dihydrofuran-3-yl)-4,4,5,5-tetramethyl-1,3,2-dioxaborolane (240.0 mg, 1.2 mmol) and 6-bromoquinoline (278.0 mg, 1.3 mmol) in dioxane (5.0 mL) and water (0.5 mL) was added $Pd(dppf)Cl_2$ (89.3 mg, 122 μmol) and $K_2CO_3$ (337.0 mg, 2.4 mmol). The reaction mixture was purged with $N_2$ for 3 min, and the reaction was stirred at 100° C. for 12 hours. LCMS showed the starting material was consumed completely and 37% desired product formed. The reaction mixture was concentrated under reduced pressure. The residue was purified by column chromatography (Petroleum ether/Ethyl acetate=100:0 to 100:20). The product of 5-(2,5-dihydrofuran-3-yl)quinoline (220.0 mg, 1.1 mmol, 91.6% yield) was obtained as a yellow oil.

Step b: A solution of 5-(2,5-dihydrofuran-3-yl)quinoline (210.0 mg, 1.1 mmol) and $PtO_2$ (48.1 mg) in MeOH (3.0 mL) was stirred at 10° C. for 12 hours under $H_2$ (15 psi). TLC (Petroleum ether/Ethyl acetate=2:1) showed the starting material was disappeared and a new spot with lower polarity was formed. $PtO_2$ was filtered off and the filtrate was concentrated under reduced pressure to give the product 5-(oxolan-3-yl)-1,2,3,4-tetrahydroquinoline (180.0 mg, 885.0 μmol, 83.7% yield) as a white solid.

SFC: The compound 4 (95.0 mg, 467.0 μmol) was separated by preparative SFC. Column: Phenomenex-Amylose-1 (250 mm×30 mm, 5 um). Condition: 0.1% NH$_3$.H$_2$O EtOH. Begin B 15%, end B 15%. Flow rate: 50 mL/min. The product of 5-[(3R)-oxolan-3-yl]-1,2,3,4-tetrahydroquinoline (4a, 45.0 mg, 221 μmol, 47.4% yield, the faster eluting isomer) was obtained as a white solid.

Synthesis of 5-[(3S)-oxolan-3-yl]-1,2,3,4-tetrahydroquinoline, Used in the Preparation of Compound 401

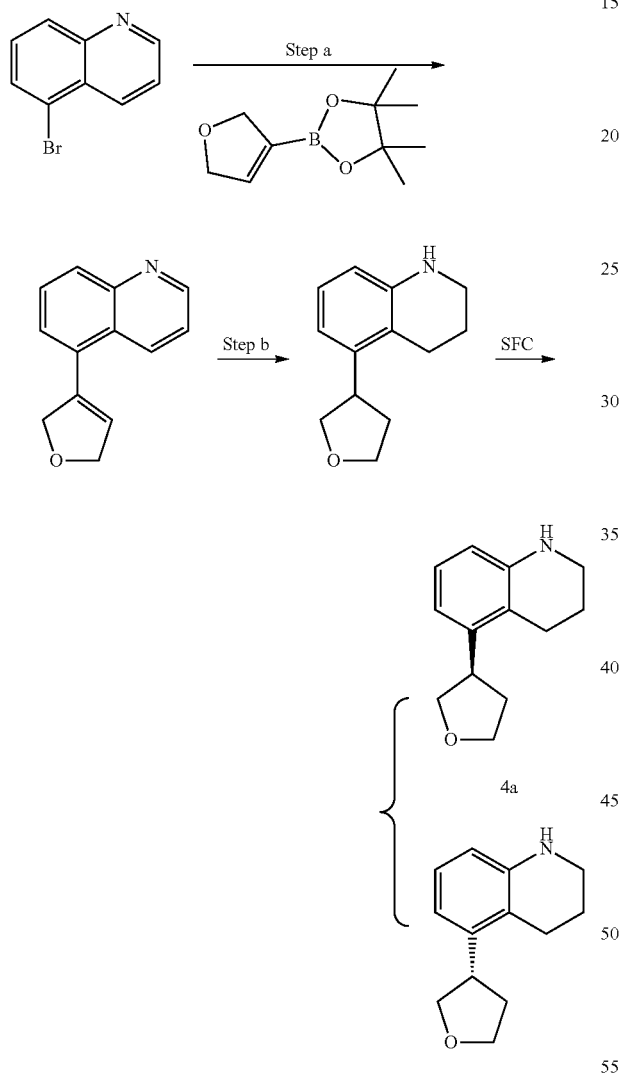

4a

4b

SFC: 5-(tetrahydrofuran-3-yl)-1,2,3,4-tetrahydroquinoline (95.0 mg, 467.0 μmol) was separated by preparative SFC. Column: Phenomenex-Amylose-1 (250 mm×30 mm, 5 um). Condition: 0.1% NH$_3$.H$_2$O EtOH. Begin B 15%, end B 15%. Flow rate: 50 mL/min. The product of 5-[(3S)-oxolan-3-yl]-1,2,3,4-tetrahydroquinoline (45.0 mg, 221 μmol, 47.4% yield, the faster eluting isomer) was obtained as a white solid.

Synthesis of rel-(4R)-4-(oxolan-3-yl)-1,2,3,4-tetrahydroquinoxaline-6-carbonitrile, Used in the Preparation of Compound 402

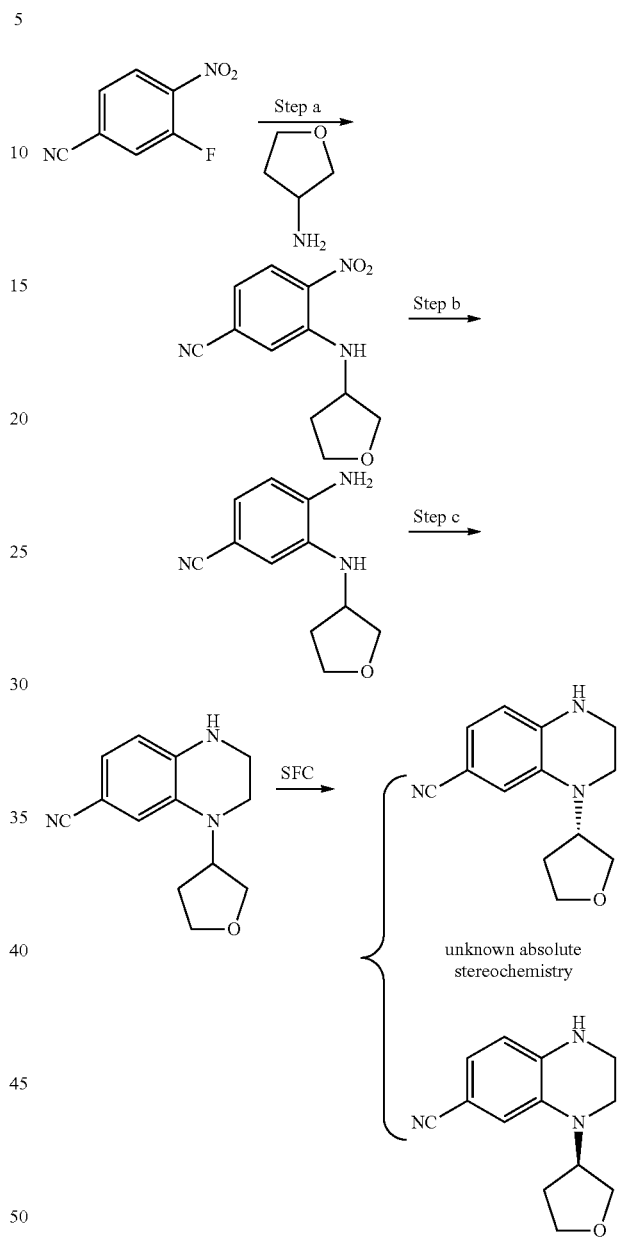

unknown absolute stereochemistry

Step a: The mixture of 3-fluoro-4-nitrobenzonitrile (1.0 g, 6.0 mmol, 1.0 eq), oxolan-3-amine (629 mg, 7.2 mmol, 1.2 eq) and TEA (2.4 mL, 18.0 mmol, 3.0 eq) in EtOH (15 mL) was stirred at 60° C. for 3 hours. TLC (Petroleum ether/Ethyl acetate=5:1) showed that the starting material was consumed completely and one main new spot with higher polarity was formed. The mixture was concentrated under reduced pressure and the residue was purified by column chromatography (Petroleum ether/Ethyl acetate=10:0-5:1) to afford 4-nitro-3-[(oxolan-3-yl)amino]benzonitrile (1.3 g, 92.8% yield) as a red solid.

Step b: The mixture of 4-nitro-3-[(oxolan-3-yl)amino]benzonitrile (700 mg, 3.0 mmol, 1.0 eq) and 10% Pd/C (100 mg, wet) in MeOH (10 mL) was evacuated and refilled for 3 times using H$_2$, stirred at 15° C. for 2 hours under H$_2$ (15 psi) atmosphere. TLC (Petroleum ether/Ethyl acetate=1:1) indicated that the starting material was consumed completely and one main new spot with higher polarity was formed. The mixture was filtered and the filtrate was concentrated under reduced pressure to afford the desired product of 4-amino-3-[(oxolan-3-yl)amino]benzonitrile (560 mg, 91.9% yield) as a white solid.

Step c: The mixture of 4-amino-3-[(oxolan-3-yl)amino]benzonitrile (300 mg, 1.5 mmol, 1.0 eq) and TBAB (4.7 g, 14.7 mmol, 10.0 eq) in 1,2-dibromoethane (2.8 g, 14.7 mmol, 10.0 eq) was stirred at 60° C. for 12 hours. LCMS indicated that the starting material was remained and one main new peak with desired MS was detected. TEA (609 uL, 4.4 mmol, 3.0 eq) was added into the mixture and the mixture was stirred at 60° C. for another 20 hours. LCMS indicated that a small amount of the starting material was remained and one main new peak with desired MS was detected. The mixture was diluted with H₂O (30 mL), extracted with EtOAc (30 mL×2). The organic layer was washed with brine (30 mL), dried over anhydrous Na₂SO₄, filtered and concentrated under reduced pressure. The residue was purified by column chromatography (Petroleum ether/Ethyl acetate=1:0-3:1) to afford the desired product of 4-(oxolan-3-yl)-1,2,3,4-tetrahydroquinoxaline-6-carbonitrile (210 mg, 62.3% yield) as a yellow oil.

SFC: 4-(oxolan-3-yl)-1,2,3,4-tetrahydroquinoxaline-6-carbonitrile (150 mg, 654 μmol, 1.0 eq) was separated by SFC (Column: DAICEL CHIRALPAK AD (250 mm*30 mm, 10 um). Condition: Ethanol (0.1% NH₃/H₂O). Begin B 45%, end B 45%. Flow rate: 70 mL/min.) to afford rel-(4R)-4-(oxolan-3-yl)-1,2,3,4-tetrahydroquinoxaline-6-carbonitrile (70.0 mg, 46.9% yield, a faster eluting isomer) as a white solid.

Synthesis of rel-(4S)-4-(oxolan-3-yl)-1,2,3,4-tetrahydroquinoxaline-6-carbonitrile, Used in the Preparation of Compound 403

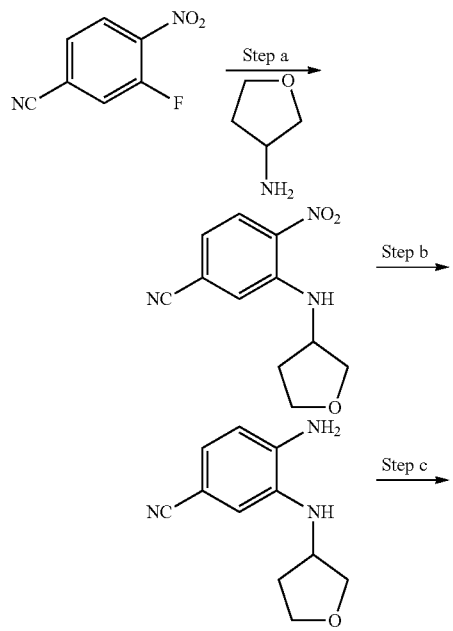

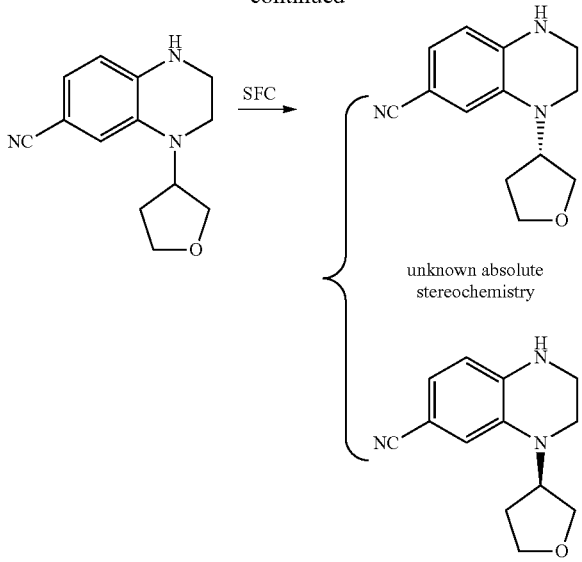

unknown absolute stereochemistry

SFC: 4-(oxolan-3-yl)-1,2,3,4-tetrahydroquinoxaline-6-carbonitrile (150 mg, 654 μmol, 1.0 eq) was separated by SFC (Column: DAICEL CHIRALPAK AD (250 mm*30 mm, 10 um). Condition: Ethanol (0.1% NH₃/H₂O). Begin B 45%, end B 45%. Flow rate: 70 mL/min.) to afford rel-(4S)-4-(oxolan-3-yl)-1,2,3,4-tetrahydroquinoxaline-6-carbonitrile (50.0 mg, 33.5% yield, a slower eluting isomer) was obtained as a white solid.

Synthesis of 4-ethyl-1,2,3,4-tetrahydroquinoxaline-6-carbonitrile, Used in the Preparation of Compound 405

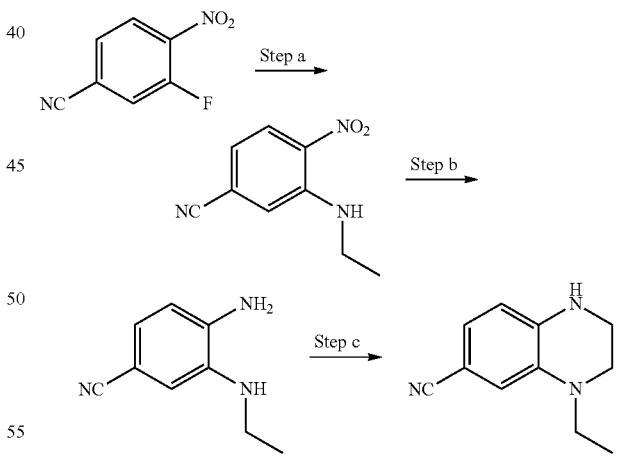

Step a: 3-Fluoro-4-nitrobenzonitrile (500.0 mg, 3.0 mmol), Et₃N (1.2 mL, 9.0 mmol) and EtNH₂ (271.0 mg, 6.0 mmol) were added in EtOH (15.0 mL), the reaction mixture was stirred at 50° C. for 12 hours. LCMS indicated 98% of desired product formed. The reaction mixture was concentrated under reduced pressure to afford the product of 3-(ethylamino)-4-nitrobenzonitrile (650.0 mg, crude) as a yellow solid.

Step b: 3-(Ethylamino)-4-nitrobenzonitrile (575.0 mg, crude) and 10% wet Pd/C (100.0 mg) were added in MeOH (16.0 mL), the reaction mixture was evacuated and refilled for 3 times with H$_2$ (15 psi) and stirred at 15° C. for 12 hours. LCMS indicated 83% of desired product formed. The reaction mixture was filtered and concentrated under reduced pressure to afford the product of 4-amino-3-(ethylamino) benzonitrile (550.0 mg, crude) as a yellow solid.

Step c: 4-Amino-3-(ethylamino) benzonitrile (300.0 mg, crude) and 1,2-dibromoethane (1.7 g, 9.3 mmol) were added in TBAB (286.0 mg, 1.9 mmol), the reaction mixture was stirred at 60° C. for 12 hours. LCMS indicated 33% of desired product formed. TLC (Petroleum ether:Ethyl acetate=2:1) indicated one main spot formed. The reaction mixture was concentrated under reduced pressure and purified by flash silica gel chromatography (Petroleum ether:Ethyl acetate=2:1) to afford the product of 4-ethyl-1,2,3,4-tetrahydroquinoxaline-6-carbonitrile (120.0 mg) as a yellow solid.

Synthesis of 4-(2-methoxyethyl)-1,2,3,4-tetrahydroquinoxaline-6-carbonitrile, Used in the Preparation of Compound 406

C. for 12 hours under H$_2$ (15 psi). LCMS indicated 69% of desired product formed. The reaction mixture was filtered and concentrated under reduced pressure to afford the product of 4-amino-3-[(2-methoxyethyl)amino]benzonitrile (600.0 mg, crude) as a yellow solid which was used in next step without further purification.

Step c: 4-Amino-3-[(2-methoxyethyl)amino]benzonitrile (300.0 mg, crude), 1,2-dibromoethane (1.5 g, 7.8 mmol) and TBAB (720.0 mg, 4.7 mmol) were added in the bottle, the reaction mixture was stirred at 60° C. for 12 hours. LCMS indicated 43% of desired product formed. TLC (Petroleum ether:Ethyl acetate=2:1) indicated one main spot formed. The reaction mixture was concentrated under reduced pressure, diluted with Ethyl acetate (30.0 mL), washed with H$_2$O (20.0 mL×3) and brine (20.0 mL), the organic phase was dried over anhydrous Na$_2$SO$_4$, concentrated under reduced pressure to give a residue and purified by flash silica gel chromatography (Petroleum ether:Ethyl acetate=100:0 to 100:50) to afford the product of 4-(2-methoxyethyl)-1,2,3,4-tetrahydroquinoxaline-6-carbonitrile (150.0 mg) as a yellow solid.

Synthesis of 6-(5-methyl-1,3,4-thiadiazol-2-yl)-1,2,3,4-tetrahydro-1,5-naphthyridine, Used in the Preparation of Compound 407

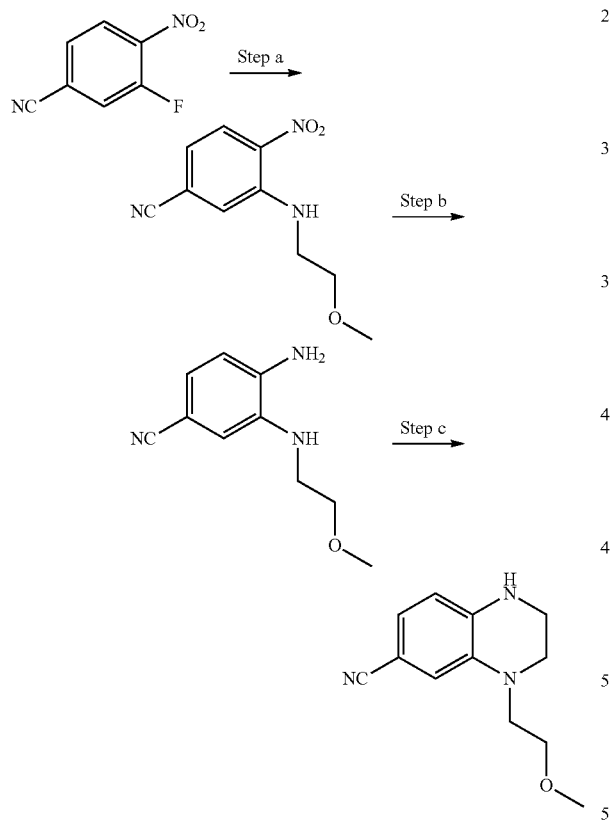

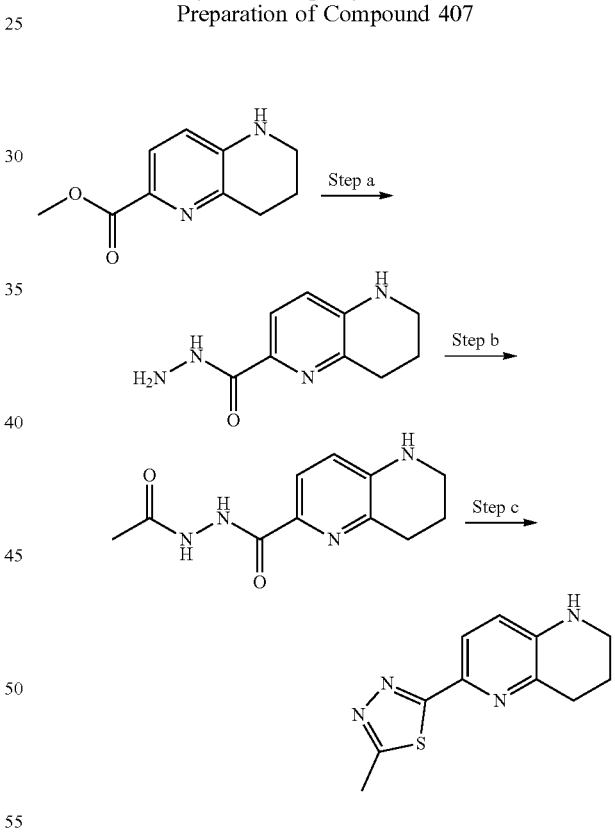

Step a: 3-Fluoro-4-nitrobenzonitrile (500.0 mg, 3.0 mmol), 2-methoxyethan-1-amine (226.0 mg, 3.0 mmol) and Et$_3$N (1.3 mL, 9.0 mmol) were added in EtOH (10.0 mL), the reaction mixture was stirred at 50° C. for 12 hours. LCMS indicated 99% of desired product formed. The reaction mixture was concentrated under reduced pressure to give the product of 3-[(2-methoxyethyl)amino]-4-nitrobenzonitrile (700.0 mg, crude) as a yellow solid.

Step b: 3-[(2-Methoxyethyl)amino]-4-nitrobenzonitrile (600.0 mg, crude) and 10% wet Pd/C (100.0 mg) were added in MeOH (15.0 mL), the reaction mixture was stirred at 25°

Step a: To a solution of methyl 5,6,7,8-tetrahydro-1,5-naphthyridine-2-carboxylate (500 mg, 2.60 mmol) in MeOH (5 mL) was added hydrazine (151 µL, 3.12 mmol). Heated to reflux for 48 h. Cooled to rt. Material precipitated. Filtered, washed with MeOH, Concentrated filtrate, redissolved in MeOH (5 mL). Transferred to a microwave vial and added an additional 2.4 equivalents of hydrazine (302 uL). Heated in microwave at 120 C for 60 min. Concentrated and combined with precipitate to give 5,6,7,8-tetrahydro-1,5-naphthyridine-2-carbohydrazide (400 mg, 2.08 mmol).

Step b: To a solution of 5,6,7,8-tetrahydro-1,5-naphthyridine-2-carbohydrazide (100 mg, 0.5202 mmol) in DCM (2 mL) was added ethylbis(propan-2-yl)amine (275 µL, 1.56 mmol) followed by 0.5 eq. acetic anhydride (25 uL). Stirred at rt for 2 h. Concentrated, dried under high vac. Carried on to next step without quantifying or further purification.

Step c: To a solution of N'-acetyl-5,6,7,8-tetrahydro-1,5-naphthyridine-2-c (121 mg, 0.5165 mmol) in toluene (3 mL) was added Lawesson's Reagent (416 mg, 1.03 mmol). Stirred at 80 C for 1 h. Partitioned between EtOAc and water. Extracted with EtOAc (3×). Combined org layers, washed with brine. Dried org over Na$_2$SO$_4$, filtered and concentrated. Purified by flash silica gel chromatography using 0-5% MeOH in DCM, followed by a second purification using 0-100% EtOAc in heptanes to give 6-(5-methyl-1,3,4-thiadiazol-2-yl)-1,2,3,4-tetrahydro-1,5-naphthyridine (47.0 mg, 0.2023 mmol). LCMS: [M+H] 233.24. 1H NMR (400 MHz, DMSO-d6) δ ppm 7.72 (br d, J=8.54 Hz, 1H) 7.51-7.65 (m, 1H) 6.85 (br d, J=8.30 Hz, 1H) 6.55-6.65 (m, 1H) 3.98-4.06 (m, 1H) 3.72-3.81 (m, 1H) 3.19-3.25 (m, 1H) 2.80 (br t, J=6.35 Hz, 1H) 2.62-2.71 (m, 2H) 2.26-2.36 (m, 1H) 1.98 (s, 1H) 1.83-1.92 (m, 2H) 1.11-1.21 (m, 2H).

Synthesis of 4-(2-methanesulfonylethyl)-1,2,3,4-tetrahydroquinoxaline-6-carbonitrile, Used in the Preparation of Compound 408

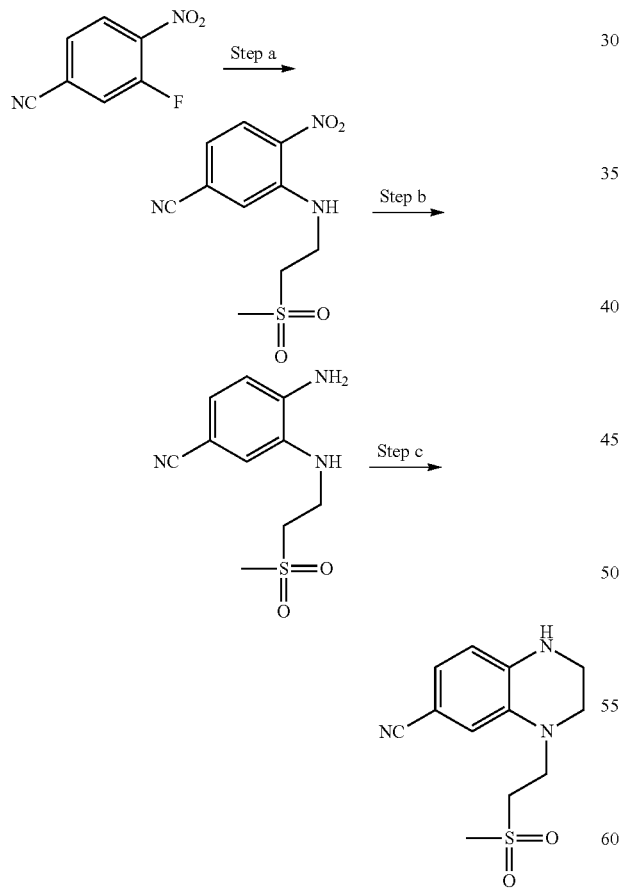

Step a: A mixture of 3-fluoro-4-nitrobenzonitrile (518.0 mg, 3.1 mmol), 2-methanesulfonylethan-1-amine hydrochloride (600.0 mg, 3.8 mmol) and TEA (1.3 mL, 9.4 mmol) in EtOH (10.0 mL) were stirred at 60° C. for 12 hours. An orange suspension was found. TLC (EtOAc) showed one main new peak formed. The mixture was concentrated under reduced pressure, diluted with H$_2$O (100.0 mL) and extracted with EtOAc (100.0 mL×3). The combined organic layers were washed with H$_2$O (100.0 mL) and brine (100.0 mL), dried over anhydrous Na$_2$SO$_4$, filtered and concentrated under reduced pressure to afford the product of 3-[(2-methanesulfonylethyl)amino]-4-nitrobenzonitrile (530.0 mg, crude) as a yellow solid.

Step b: A mixture of 3-[(2-methanesulfonylethyl)amino]-4-nitrobenzonitrile (530.0 mg, 1.9 mmol) and 10% wet Pd/C (200.0 mg) was stirred at 20° C. for 12 hours under H$_2$ (15 psi). LCMS showed one main peak with desired MS formed. The mixture was filtered and concentrated under reduced pressure to give the product of 4-amino-3-[(2-methanesulfonylethyl)amino]benzonitrile (185.0 mg, crude) as a white solid.

Step c: A mixture of 4-amino-3-[(2-methanesulfonylethyl)amino]benzonitrile (185.0 mg, 773.0 µmol), TBAB (936.0 mg, 3.8 mmol) and TEA (534.0 µL, 3.8 mmol) was stirred at 60° C. for 12 hours. LCMS showed one main peak with desired MS (254 nm) was found. The mixture was concentrated under reduced pressure to give a residue, the residue was diluted with H$_2$O (50.0 mL), extracted with EtOAc (50.0 mL×3). The organic layers were washed with brine (50.0 mL), dried over anhydrous Na$_2$SO$_4$, filtered and concentrated under reduced pressure to give a residue and purified by flash silica gel chromatography (Ethyl acetate in Petroleum ether=0%~70%) to afford 4-(2-methanesulfonylethyl)-1,2,3,4-tetrahydroquinoxaline-6-carbonitrile (90.0 mg, crude) as an off-white solid.

Synthesis of 4-(propan-2-yl)-1,2,3,4-tetrahydroquinoxaline-6-carbonitrile, Used in the Preparation of Compound 409

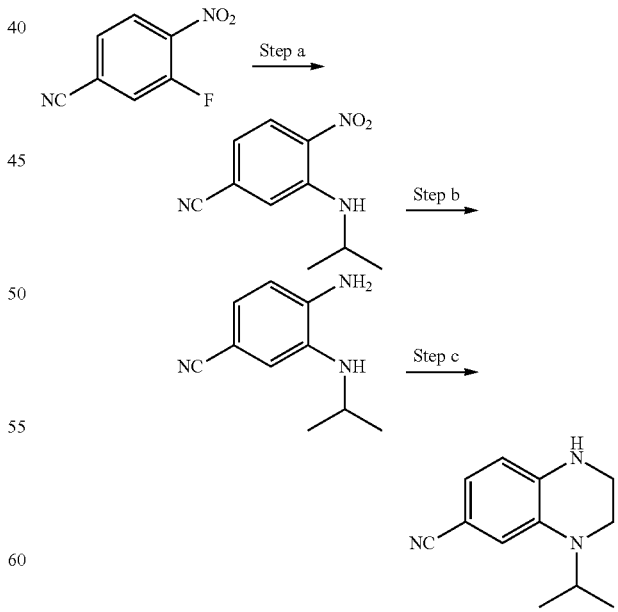

Step a: A mixture of 3-fluoro-4-nitrobenzonitrile (500.0 mg, 3.0 mmol), propan-2-amine (195.0 mg, 3.3 mmol) and TEA (1.3 mL, 9.0 mmol) in dioxane (10.0 mL) were stirred at 60° C. for 12 hours. A yellow solution was found. LCMS showed one main new peak formed. The reaction mixture was concentrated under reduced pressure to give 4-nitro-3-[(propan-2-yl)amino]benzonitrile (800.0 mg, crude) as a yellow solid which was used in next step without further purification.

Step b: To a solution of 4-nitro-3-[(propan-2-yl)amino]benzonitrile (700.0 mg, 3.4 mmol) in MeOH (10.0 mL) was added 10% wet Pd/C (100.0 mg), and the mixture was stirred at 15° C. for 12 hours under H$_2$ (15 psi). LCMS showed one main new peak with desired MS formed. The combined mixture was filtered and concentrated under reduced pressure to give the product of 4-amino-3-[(propan-2-yl)amino]benzonitrile (750.0 mg, crude) as a brown oil which was used in next step without further purification.

Step c: A mixture of 4-amino-3-[(propan-2-yl)amino]benzonitrile (300.0 mg, 1.7 mmol), tetrabutylammonium bromide (1.3 g, 5.2 mmol) and 1,2-dibromoethane (1.6 g, 8.6 mmol) was stirred at 60° C. for 12 hours. LCMS showed 32.9% of desired MS formed. The reaction mixture was concentrated under reduced pressure, diluted with EtOAc (50.0 mL), washed with H$_2$O (50.0 mL×2) and brine (50.0 mL). The organic layers were dried over anhydrous Na$_2$SO$_4$, filtered and concentrated under reduced pressure to give a residue and purified by column chromatography (EtOAc in Petroleum ether=0%~20%) to afford the product of 4-(propan-2-yl)-1,2,3,4-tetrahydroquinoxaline-6-carbonitrile (60.0 mg, 298.0 μmol) as a brown solid and 90.0 mg of starting material was recovered.

Synthesis of 6-[2-(trimethylsilyl)ethynyl]-1,2,3,4-tetrahydro-1,5-naphthyridine, Used in the Preparation of Compound 410

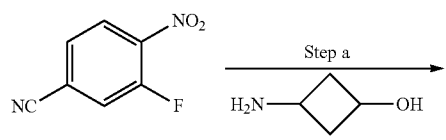

Step a: A resealable reaction vial was charged with 6-bromo-1,2,3,4-tetrahydro-1,5-naphthyridine (250 mg, 1.17 mmol), dicaesio carbonate (570 mg, 1.75 mmol), XPhos/Pd G4 (201 mg, 0.234 mmol) and ACN (6 mL). The mixture was bubbled with nitrogen and charged with ethynyltrimethylsilane (485 μL, 3.51 mmol). The mixture further bubbled for 10 min, the vial was sealed, and the mixture was stirred at 80° C. for 6 hrs. The reaction was concentrated and the residue was purified by flash silica gel chromatography (eluting with ethyl acetate:heptanes=0:100 to 70:30) to afford 6-[2-(trimethylsilyl)ethynyl]-1,2,3,4-tetrahydro-1,5-naphthyridine (105 mg) as a tan crystalline solid. LCMS: [M+H]$^+$ 231

Synthesis of 4-(3-[(tert-butyldimethylsilyl)oxy]cyclobutyl)-1,2,3,4-tetrahydroquinoxaline-6-carbonitrile, Used in the Preparation of Compound 411

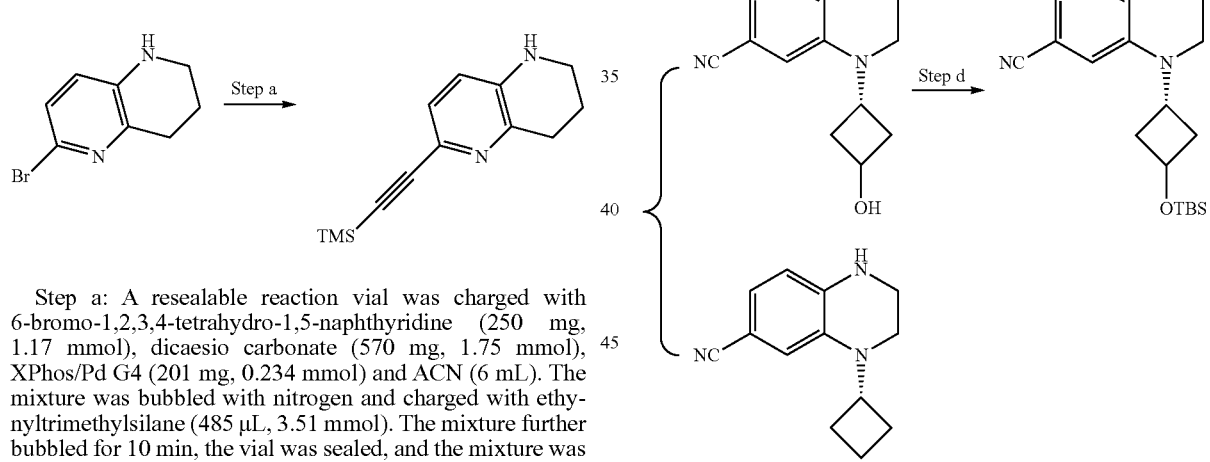

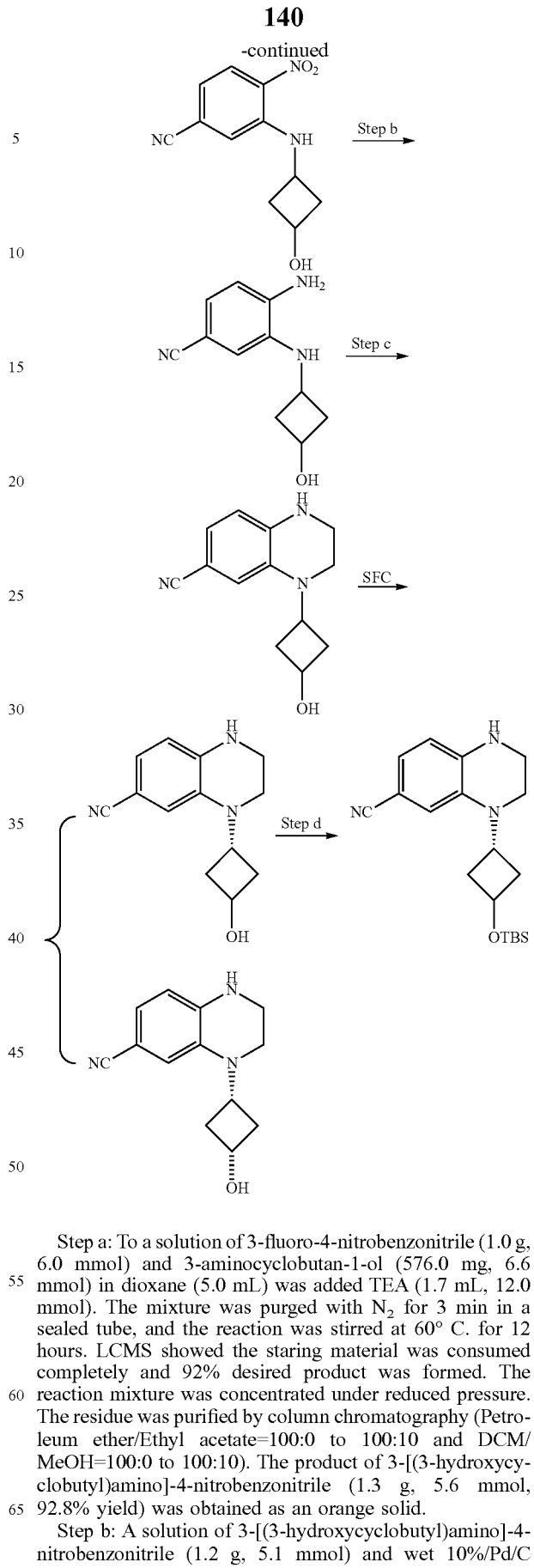

Step a: To a solution of 3-fluoro-4-nitrobenzonitrile (1.0 g, 6.0 mmol) and 3-aminocyclobutan-1-ol (576.0 mg, 6.6 mmol) in dioxane (5.0 mL) was added TEA (1.7 mL, 12.0 mmol). The mixture was purged with N$_2$ for 3 min in a sealed tube, and the reaction was stirred at 60° C. for 12 hours. LCMS showed the staring material was consumed completely and 92% desired product was formed. The reaction mixture was concentrated under reduced pressure. The residue was purified by column chromatography (Petroleum ether/Ethyl acetate=100:0 to 100:10 and DCM/MeOH=100:0 to 100:10). The product of 3-[(3-hydroxycyclobutyl)amino]-4-nitrobenzonitrile (1.3 g, 5.6 mmol, 92.8% yield) was obtained as an orange solid.

Step b: A solution of 3-[(3-hydroxycyclobutyl)amino]-4-nitrobenzonitrile (1.2 g, 5.1 mmol) and wet 10%/Pd/C (200.0 mg) in MeOH (10.0 mL) was stirred at 10° C. for 12 hours under H$_2$ (15 psi). LCMS showed the starting material was consumed completely and 100% desired product was formed. Pd/C was filtered and the filtrate was concentrated under reduced pressure. The residue (1.0 g, 96.1% yield) was used for the next step directly.

Step c: A mixture of 4-amino-3-[(3-hydroxycyclobutyl)amnion]benzonitrile (500.0 mg, 2.5 mmol), 1,2-dibromoethane (2.3 g, 12.3 mmol), TEA (744.0 mg, 7.4 mmol) and TBAB (1.6 g, 4.9 mmol) was stirred at 60° C. for 12 hours. LCMS showed 22% starting material was remained and 49% desired product was formed. The reaction mixture was concentrated under reduced pressure. The residue was diluted with water (50.0 mL) and extracted ethyl acetate (50.0 mL×2). The combined organic layers were washed with water (30.0 mL) and brine (30.0 mL), dried over anhydrous Na$_2$SO$_4$, filtered and concentrated under reduced pressure to give a residue. The residue was purified by column chromatography (Petroleum ether/Ethyl acetate=100:0 to 100:80). The product of 4-(3-hydroxycyclobutyl)-1,2,3,4-tetrahydroquinoxaline-6-carbonitrile (480.0 mg, 2.1 mmol, 85.1% yield) was obtained as a light yellow solid.

SFC: The compound 4-(3-hydroxycyclobutyl)-1,2,3,4-tetrahydroquinoxaline-6-carbonitrile (95.0 mg, 414.0 umol) was separated by SFC. Column: DAICEL CHIRALPAK AD-H(250 mm×30 mm, 5 um). Condition: 0.1% NH$_3$.H$_2$O EtOH. Begin B 40%, end B 40%. Flow rate: 50 mL/min. The trans-isoform (45.0 mg, 196 μmol, 47.4% yield, a faster eluting isomer) was obtained as a light yellow solid and trans-form.

Step d: To a solution of 4-(3-hydroxycyclobutyl)-1,2,3,4-tetrahydroquinoxaline-6-carbonitrile (40.0 mg, 174.0 μmol) in DCM (5.0 mL) was added TBSCl (52.4 mg, 348.0 μmol) and imidazole (23.6 mg, 348.0 μmol). The reaction mixture was stirred at 40° C. for 1 hour. LCMS showed the starting material was consumed completely and 97% desired product was formed. The reaction mixture was concentrated under reduced pressure. The residue was purified by column chromatography (Petroleum ether/Ethyl acetate=100:0 to 100:30). The product 4-{3-[(tert-butyldimethylsilyl)oxy]cyclobutyl}-1,2,3,4-tetrahydroquinoxaline-6-carbonitrile (55.0 mg, 160 μmol, 92.1% yield) was obtained as a light yellow solid.

Synthesis of 4-{3-[(tert-butyldimethylsilyl)oxy]cyclobutyl}-1,2,3,4-tetrahydroquinoxaline-6-carbonitrile, Used in the Preparation of Compound 412

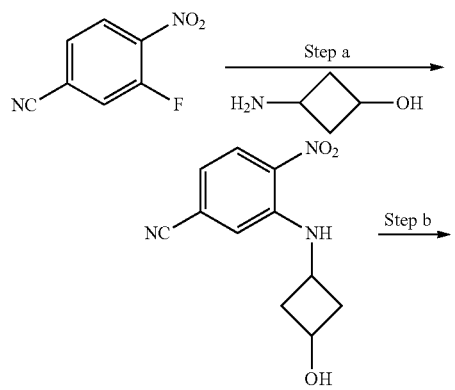

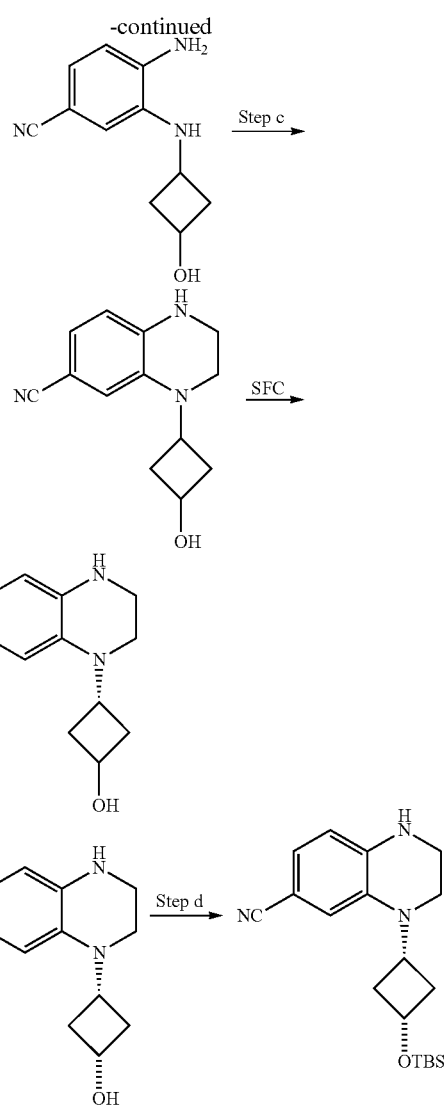

The synthetic procedure for 4-(3-hydroxycyclobutyl)-1,2,3,4-tetrahydroquinoxaline-6-carbonitrile was described in Compound 411.

SFC: The compound 4-(3-hydroxycyclobutyl)-1,2,3,4-tetrahydroquinoxaline-6-carbonitrile (95.0 mg, 414.0 umol) was separated by SFC. Column: DAICEL CHIRALPAK AD-H(250 mm×30 mm, 5 um). Condition: 0.1% NH$_3$.H$_2$O EtOH. Begin B 40%, end B 40%. Flow rate: 50 mL/min. The cis-isoform (45.0 mg, 196 μmol, 47.4% yield, a slower eluting isomer) was obtained as a light yellow solid and cis-form.

Step d: To a solution of 4-(3-hydroxycyclobutyl)-1,2,3,4-tetrahydroquinoxaline-6-carbonitrile (40.0 mg, 174.0 μmol) in DCM (5.0 mL) was added TBSCl (52.4 mg, 348.0 μmol) and imidazole (23.6 mg, 348.0 μmol). The reaction mixture was stirred at 40° C. for 1 hour. LCMS showed the starting material was consumed completely and 96% desired product was formed. The reaction mixture was concentrated under reduced pressure. The residue was purified by column chromatography (Petroleum ether/Ethyl acetate=100:0 to 100:30). The product 4-{3-[(tert-butyldimethylsilyl)oxy]cyclobutyl}-1,2,3,4-tetrahydroquinoxaline-6-carbonitrile (55.0 mg, 160.0 μmol, 92.1% yield) was obtained as a light yellow solid.

Synthesis of 8-methyl-5H,6H,7H,8H-pyridazino[3,4-b]pyrazine, Used in the Preparation of Compound 413

Synthesis of of 1-methyl-1H,2H,3H,4H-pyridazino[4,5-b]pyrazine, Used in the Preparation of Compound 414

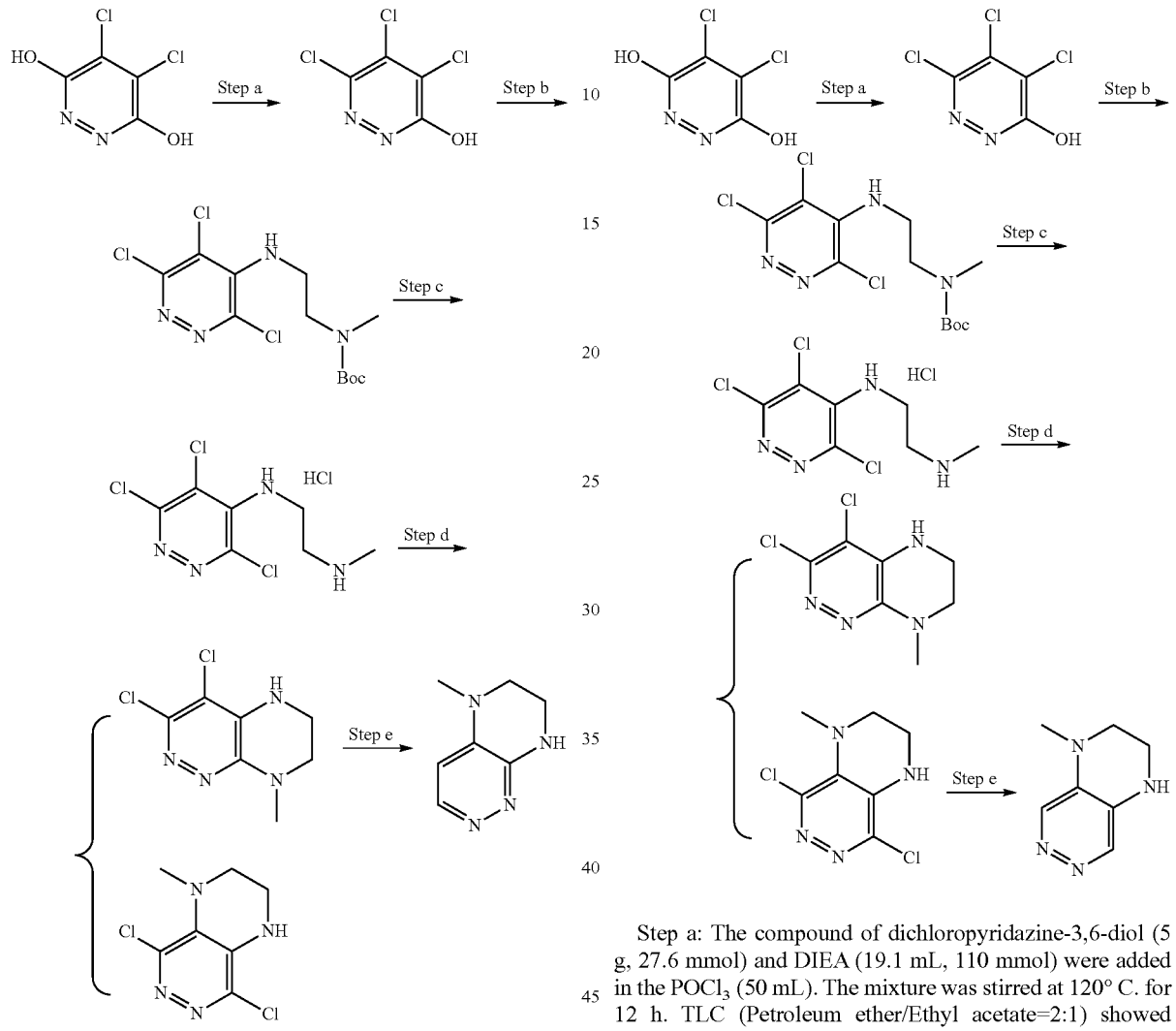

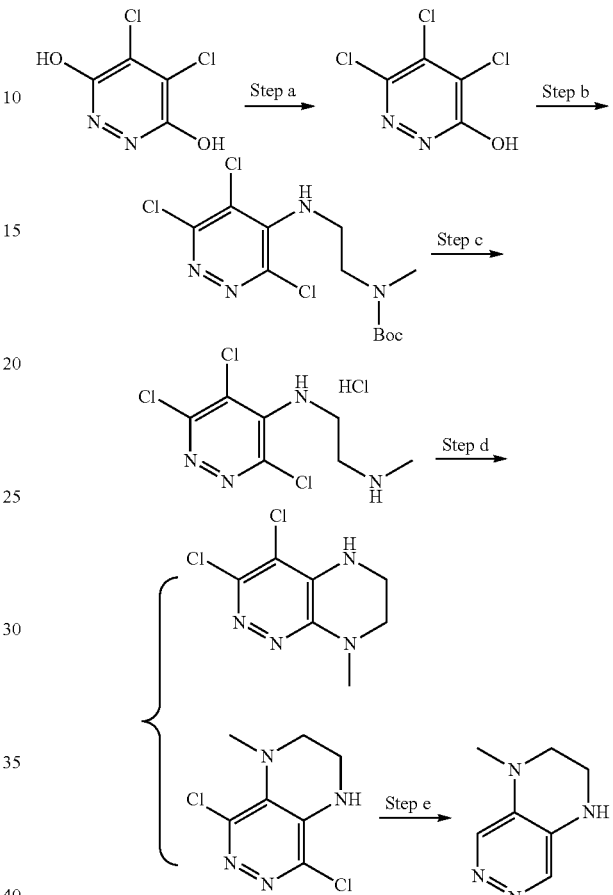

The synthetic procedure for 3,4-dichloro-8-methyl-5H,6H,7H,8H-pyridazino[3,4-b]pyrazine was described in preparation of the intermediate used for Compound 414.

Step e: The compound of 3,4-dichloro-8-methyl-5H,6H,7H,8H-pyridazino[3,4-b]pyrazine (2.2 g, 10.0 mmol) was dissolved in EtOH (30 mL) and THF (20 mL). 10% Pd/C (220 mg, wet) and TEA (4.1 mL, 30.0 mmol) was added. The reaction mixture was evacuated and refilled for 3 times using $H_2$. The reaction mixture was stirred at 25° C. for 12 hours under $H_2$ (15 psi). The reaction mixture was filtered through a pad of celite and washed with MeOH (50 mL). The filtrate was concentrated to give a residue. The residue was dissolved in sat.NaHCO$_3$ (50 mL). The mixture was lyophilized to give a white solid which was triturated with MeOH (100 mL). The mixture was filtered and the filtrate was concentrated to give a residue. The residue was purified by flash silica gel chromatography (EtOAc:MeOH=100:0 to 100:40) to afford the product of 8-methyl-5H,6H,7H,8H-pyridazino[3,4-b]pyrazine (1.93 g, crude) as a white solid.

Step a: The compound of dichloropyridazine-3,6-diol (5 g, 27.6 mmol) and DIEA (19.1 mL, 110 mmol) were added in the POCl$_3$ (50 mL). The mixture was stirred at 120° C. for 12 h. TLC (Petroleum ether/Ethyl acetate=2:1) showed compound 1 was consumed completely and a new spot formed. (Monitor reaction: diluted with EtOAc and quenched the reaction mixture with saturated NaHCO$_3$ (0° C.) before TLC check). The reaction mixture was concentrated to give a residue which was diluted with EtOAc (100 mL). The mixture was added slowly into ice cooled sat. NaHCO$_3$ (100 mL). The partitioned layers were separated. The aqueous phase was extracted with ethyl acetate (100 mL×3). The combined organic layers were washed with brine (150 mL), dried over anhydrous Na$_2$SO$_4$, filtered and concentrated to give the product of tetrachloropyridazine (6.3 g, crude product) as a brown solid.

Step b: The compound of tetrachloropyridazine (5.5 g, 25.2 mmol), tert-butyl N-(2-aminoethyl)-N-methylcarbamate (4.8 g, 27.7 mmol) and TEA (13.8 mL, 100 mmol) were placed in DMF (80 mL). The mixture was stirred at 25° C. for 12 h. The reaction mixture was concentrated and H$_2$O (100 mL) was added, extracted with ethyl acetate (100 mL×3). The combined organic layers were washed with brine (150 mL), dried over anhydrous Na$_2$SO4, filtered and concentrated to give a residue. The residue was purified by flash silica gel chromatography (Petroleum ether:Ethyl acetate=100:10 to 100:40) to afford the product of tert-butyl N-methyl-N-{2-[(3,5,6-trichloropyridazin-4-yl)amino]ethyl}carbamate (6.60 g, 73.6% yield) as an off-white solid.

Step c: The compound of tert-butyl N-methyl-N-{2-[(3,5,6-trichloropyridazin-4-yl)amino]ethyl}carbamate (6.6 g, 18.5 mmol) was added into HCl/MeOH (100 mL, 2M). The mixture was stirred at 25° C. for 12 h. The mixture was concentrated to give the product of 3,5,6-trichloro-N-[2-(methylamino)ethyl]pyridazin-4-amine hydrochloride (5.4 g, crude product) as a white solid which was used in next step without further purification.

Step d: The compound of 3,5,6-trichloro-N-[2-(methylamino)ethyl]pyridazin-4-amine hydrochloride (5.4 g, 18.4 mmol) and TEA (12.7 mL, 92.0 mmol) were placed in DMF (100 mL). The mixture was stirred at 25° C. for 12 h. The reaction mixture was concentrated to give a residue. The residue was triturated with H₂O (100 mL). A lot of precipitate formed, the solid was collected by filtration. The filter cake was dried to give the product of 3,4-dichloro-8-methyl-5H,6H,7H,8H-pyridazino[3,4-b]pyrazine (5) (2.5 g, 62% yield) as a white solid. The aqueous phase was extracted with EtOAc (100 mL×3). The combined organic layers were washed with brine (100 mL), dried over anhydrous Na₂SO₄, filtered and concentrated to give a residue which was purified by flash silica gel chromatography (Ethyl acetate/Petroleum ether=50/100 to 80/100) to give the product of 5,8-dichloro-1-methyl-1H,2H,3H,4H-pyridazino[4,5-b]pyrazine (5a) (500 mg, 12.4% yield) as a white solid.

Step e: The compound of 5,8-dichloro-1-methyl-1H,2H,3H,4H-pyridazino[4,5-b]pyrazine (400 mg, 1.8 mmol) was dissolved in EtOH (20 mL). 10% Pd/C (50 mg, wet) and TEA (0.7 mL, 5.5 mmol) was added. The reaction mixture was evacuated and refilled for 3 times using H₂. The reaction mixture was stirred at 25° C. for 12 hours under H₂ (15 psi). The reaction mixture was filtered through a pad of celite and washed with MeOH (20 mL). The filtrate was concentrated in vacuum to give a residue. The residue was dissolved in sat.NaHCO₃ (20 mL). The mixture was lyophilized to give a residue. The residue was purified by flash silica gel chromatography (EtOAc:MeOH=100:0 to 100:40) to afford the product of 1-methyl-1H,2H,3H,4H-pyridazino[4,5-b]pyrazine (205 mg, 1.36 mmol) as a white solid.

Synthesis of 1-methyl-7-(1,3-thiazol-2-yl)-1,2,3,4-tetrahydroquinoxaline, Used in the Preparation of Compound 415

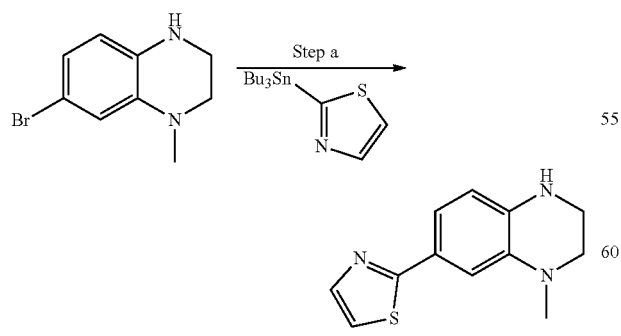

Step a: To the mixture of 7-bromo-1-methyl-1,2,3,4-tetrahydroquinoxaline (0.2 g, 0.9 mmol) and 2-(tributylstannyl)-1,3-thiazole (0.3 mL, 1.0 mmol) in toluene (10.0 mL) was added Pd(PPh₃)₄ (0.1 g, 88.0 μmol) under N₂. The mixture was stirred at 110° C. under N₂ for 12 hours. The mixture was concentrated in vacuum to give a residue and purified by flash silica gel chromatography (petroleum ether/EtOAc=1/0 to 0/1) to give the product 1-methyl-7-(1,3-thiazol-2-yl)-1,2,3,4-tetrahydroquinoxaline (43.9 mg, 21.6% yield) as an off-white solid.

Synthesis of 5-methanesulfonyl-1,2,3,4-tetrahydro-1,6-naphthyridine, Used in the Preparation of Compound 416

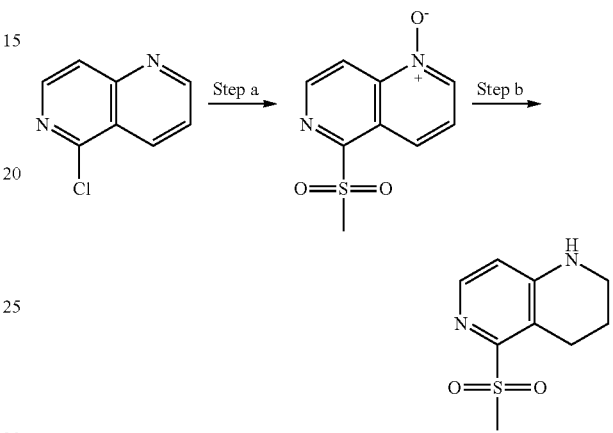

Step a: To the mixture of 5-chloro-1,6-naphthyridine (0.2 g, 1.2 mmol) in DMF (2.0 mL) was added NaSMe (500.0 mg, 7.1 mmol). The mixture was stirred at 80° C. for 12 hours. LCMS showed 2 mass was found. 10% aqueous NaClO (2.0 mL) was added to the mixture and the mixture was stirred at 10° C. for 12 hours. The mixture was poured into water (10.0 mL) and extracted with EtOAc (15.0 mL×2). The organic layers were washed with Sat. Na₂S₂O₃ solution and brine, dried over anhydrous Na₂SO₄. The mixture was filtered and the filtrate was concentrated in vacuum to give the product 5-(methylsulfonyl)-1,6-naphthyridine 1-oxide (150.0 mg, 55.1% yield) as an off-white solid.

Step b: To the mixture of 5-(methylsulfonyl)-1,6-naphthyridine 1-oxide (115.0 mg, 0.5 mmol) in MeOH (5.0 mL) and THF (2.0 mL) was added PtO₂ (50.0 mg, 0.2 mmol). The mixture was stirred at 10° C. under H₂ (15 psi) for 12 hours. LCMS showed no 2 remained and ¹HNMR showed a incomplete reduced intermediate formed. The mixture was filtered and PtO₂ was added to the filtrate. The mixture was stirred at 10° C. under H₂ (15 psi) for another 12 hours. The mixture was filtered and filtrate was concentrated in vacuum to give the product 5-methanesulfonyl-1,2,3,4-tetrahydro-1,6-naphthyridine(80.0 mg, 74.0% yield) as a colorless oil.

Synthesis of 1-methyl-7-(5-methyl-1,3,4-oxadiazol-2-yl)-1,2,3,4-tetrahydroquinoxaline, Used in the Preparation of Compound 417

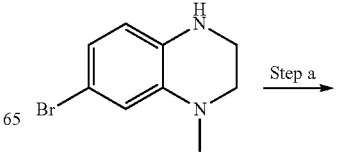

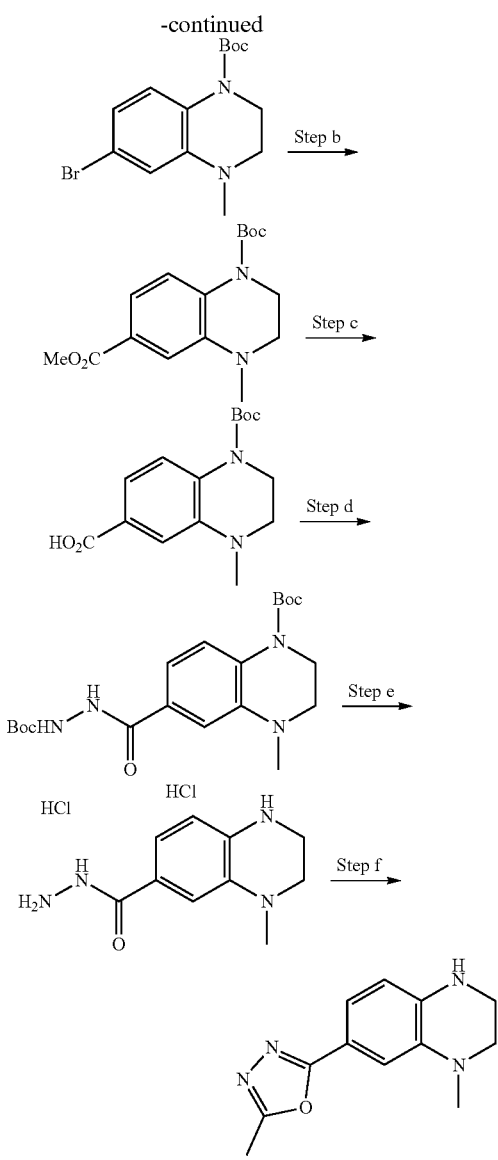

Step a: To the mixture of 7-bromo-1-methyl-1,2,3,4-tetrahydroquinoxaline (0.5 g, 2.2 mmol) in THF (15.0 mL) was added NaHMDS (6.60 mL, 6.60 mmol, 1M in THF) under $N_2$ at 0° C. The mixture was stirred at 0° C. for 30 min. $Boc_2O$ (1.0 mL, 4.4 mmol) was added to the mixture and the mixture was stirred at 10° C. for 2 hours. LCMS showed 87.8% product formed. Sat. $NH_4Cl$ (5.0 mL) was added to the mixture and the mixture was poured into water (20.0 mL). The mixture was extracted with EtOAc (30.0 mL×3). The organic layers were washed with water (20.0 mL×2) and brine (30.0 mL), dried over anhydrous $Na_2SO_4$. The mixture was filtered and the filtrate was concentrated in vacuum to give the product of tert-butyl 6-bromo-4-methyl-1,2,3,4-tetrahydroquinoxaline-1-carboxylate (0.57 g, 79.1% yield) as a colorless oil.

Step b: To the mixture of tert-butyl 6-bromo-4-methyl-1,2,3,4-tetrahydroquinoxaline-1-carboxylate (0.5 g, 1.6 mmol) and TEA (6.5 mL, 4.7 mmol) in MeOH (20.0 mL) was added $Pd(dppf)Cl_2$ (115.0 mg, 158.0 μmol). The mixture was stirred at 70° C. under CO (40 psi) for 18 hours. The mixture was filtered and the filtrate was concentrated in vacuum to give residue. The residue was purified by flash silica gel chromatography (petroleum ether/EtOAc=1/0 to 5/1 to 4/1) to give 2 (300.0 mg) and 1-tert-butyl 6-methyl 4-methyl-1,2,3,4-tetrahydroquinoxaline-1,6-dicarboxylate (221.0 mg, 45.6% yield) as an off-white solid.

Step c: To the mixture of 1-tert-butyl 6-methyl 4-methyl-1,2,3,4-tetrahydroquinoxaline-1,6-dicarboxylate (0.2 mg, 0.7 mmol) in MeOH (5.0 mL) and $H_2O$ (1.0 mL) was added NaOH (85.9 mg, 2.2 mmol). The mixture was stirred at 40° C. for 12 hours. The mixture was concentrated in vacuum to remove MeOH. A solution of HCl (2 N) was added to the mixture until pH=7 and a lot of white solid precipitated out. The mixture was filtered and the filter cake was dried in vacuum to give the product of 1-[(tert-butoxy)carbonyl]-4-methyl-1,2,3,4-tetrahydroquinoxaline-6-carboxylic acid (175.0 mg, 83.7% yield) as a white solid.

Step d: To the mixture of 1-[(tert-butoxy)carbonyl]-4-methyl-1,2,3,4-tetrahydroquinoxaline-6-carboxylic acid (150.0 mg, 0.5 mmol) and (tert-butoxy)carbohydrazide (0.1 g, 0.8 mmol) in DMF (5.0 mL) were added HATU (233.0 mg, 615.0 mol) and DIEA (252.0 μL, 1.5 mmol). The mixture was stirred at 10° C. for 2 hours. The mixture was poured into water (30.0 mL) and extracted with EtOAc (25.0 mL×3). The organic layers was washed with $H_2O$ (30.0 mL×2) and brine (30.0 mL), dried over anhydrous $Na_2SO_4$. The mixture was filtered and the filtrate was concentrated in vacuum to give residue. The residue was purified by flash silica gel chromatography (petroleum ether/EtOAc=1/0 to 2/3) to give the product of tert-butyl 6-{N-[(tert-butoxy)carbonyl]hydrazinecarbonyl}-4-methyl-1,2,3,4-tetrahydroquinoxaline-1-carboxylate (210.0 mg, 100% yield) an off white solid.

Step e: A mixture of tert-butyl 6-{N-[(tert-butoxy)carbonyl]hydrazinecarbonyl}-4-methyl-1,2,3,4-tetrahydroquinoxaline-1-carboxylate (210.0 mg, 506.0 μmol) in 4 N HCl/MeOH (5.0 mL) was stirred at 40° C. for 2 hours. The mixture was concentrated in vacuum to give the product of 4-methyl-1,2,3,4-tetrahydroquinoxaline-6-carbohydrazide dihydrochloride (130.0 mg, 465.0 μmol, 92.8% yield) as a yellow solid.

Step f: To the mixture of 4-methyl-1,2,3,4-tetrahydroquinoxaline-6-carbohydrazide dihydrochloride (130.0 mg, 465.0 μmol) in dioxane (5.0 mL) was added $MeC(OEt)_3$ (425.0 μL, 2.3 mmol). The mixture was stirred at 110° C. under $N_2$ for 12 hours. The mixture was concentrated in vacuum and purified by flash silica gel chromatography (petroleum ether/EtOAc=1/0 to 2/3) to give the product 1-methyl-7-(5-methyl-1,3,4-oxadiazol-2-yl)-1,2,3,4-tetrahydroquinoxaline (73.5 mg, 68.6% yield) as an off-white solid.

Synthesis of dimethyl[(1,2,3,4-tetrahydroquinolin-5-yl)imino]-$\lambda^6$-sulfanone, A-Ring for Compound 418

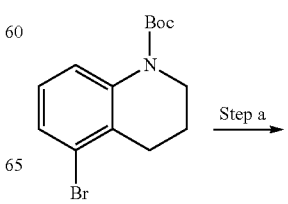

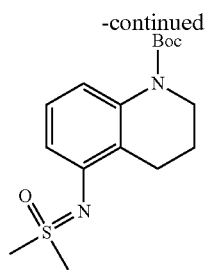

Step b →

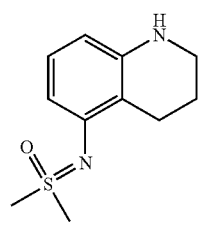

Step a: A mixture of tert-butyl 5-bromo-1,2,3,4-tetrahydroquinoline-1-carboxylate (300.0 mg, 960.0 μmol), iminodimethyl-λ⁶-sulfanone (107.0 mg, 1.15 mmol), Cs₂CO₃ (622.0 mg, 1.91 mmol), and XantPhos-Pd-G4 (92.3 mg, 96.0 μmol) in toluene (20.0 mL) was stirred at 100° C. for 2 hours under N₂. TLC (EtOAc/Petroleum ether=10/1) showed the starting material was consumed completely and one new spot with larger polarity was found. Concentrated in vacuum, the residue was purified by silica gel chromatography (EtOAc in Petroleum ether=0~100%) to afford tert-butyl 5-{[dimethyl(oxo)-λ⁶-sulfanylidene]amino}-1,2,3,4-tetrahydroquinoline-1-carboxylate (250.0 mg, 80.3% yield) as a yellow solid.

Step b: A solution of tert-butyl 5-{[dimethyl(oxo)-λ⁶-sulfanylidene]amino}-1,2,3,4-tetrahydroquinoline-1-carboxylate (240.0 mg, 739.0 μmol) in 4 M HCl/MeOH (20.0 mL) was stirred at 20° C. for 4 hours. A lot of white precipitate formed. HNMR showed the desired product formed. Concentrated in vacuum, the residue was dissolved in DCM/MeOH (50.0 mL, 10:1) and basified with solid K₂CO₃. The mixture was filtered and the filtrate was evaporated to give dimethyl[(1,2,3,4-tetrahydroquinolin-5-yl)imino]-λ⁶-sulfanone (140.0 mg, 84.8% yield) as a light yellow solid.

Synthesis of methyl[(R)-methyl(oxo)(1,2,3,4-tetrahydroquinolin-5-yl)-λ⁶-sulfanylidene]amine, Used in the Preparation of Compound 419

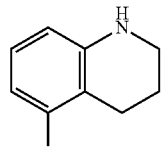

Step a →

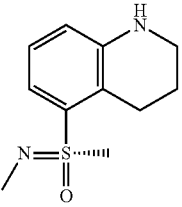

Step b →

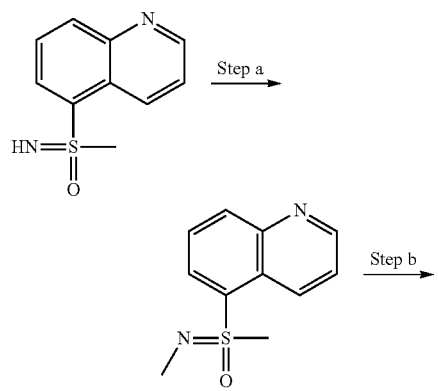

unknown absolute stereochemistry

Step a: A mixture of imino(methyl)(quinolin-5-yl)-λ⁶-sulfanone (200.0 mg, 0.97 mmol), HCHO (4.0 mL, 54.2 mmol) in HCOOH (15.0 mL) was stirred at 100° C. for 12 hours. LCMS showed starting material was still remained and the desired product formed. After concentration, the residue was purified by silica column (Methanol in Dichloromethane=0~40%) to give the desired product of methyl [methyl(oxo)(quinolin-5-yl)-λ⁶-sulfanylidene]amine (200.0 mg, 93.8% yield) as a yellow oil.

Step b: A mixture of methyl[methyl(oxo)(quinolin-5-yl)-λ⁶-sulfanylidene]amine (200.0 mg, 0.91 mmol), 3,5-diethyl 2,6-dimethyl-1,4-dihydropyridine-3,5-dicarboxylate (549.0 mg, 2.17 mmol) and (PhO)₂P(O)OH (45.2 mg, 0.18 mmol) in toluene (15.0 mL) was stirred at 80° C. under N₂ for 12 hours. LCMS showed starting material was consumed completely and 11% of desired product formed. After concentration, the residue was purified by silica column (Methanol in Dichloromethane=0~50%) to give the desired methyl [methyl (oxo)(1,2,3,4-tetrahydroquinolin-5-yl)-λ⁶-sulfanylidene]amine (120.0 mg, 59.1% yield) as a yellow oil.

SFC: The compound of methyl[methyl(oxo)(1,2,3,4-tetrahydroquinolin-5-yl)-λ⁶-sulfanylidene]amine (120.0 mg, 534 μmol) was separated by preparative SFC (Column: DAICEL CHIRALCEL OJ-H (250 mm*30 mm, 5 μm), Mobile phase: A: CO₂, B: Ethanol (0.1% NH₃.H₂O), Gradient: from 20% to 20% of B, Flow rate: 50 mL/min, Column temp: 35° C.) to give the desired methyl[(R)-methyl (oxo)(1,2,3,4-tetrahydroquinolin-5-yl)-λ⁶-sulfanylidene] amine (the slower eluting isomer: 50.0 mg, 42.0% yield) as a yellow solid.

SFC-E, Column: Chiralcel OJ-3 150×4.6 mm I.D., 3 μm Mobile phase: A: CO₂ B: ethanol (0.05% DEA) Gradient: from 5% to 40% of B in 5 min and hold 40% for 2.5 min, then 5% of B for 2.5 min, Flow rate: 2.5 mL/min Column temp.: 35° C., Wavelength: 220 nm Rt=2.875 min, e.e=98.4%.

151

Synthesis of methyl[methyl(oxo)(1,2,3,4-tetrahydro-quinolin-5-yl)-λ⁶-sulfanylidene]amine, Used in the Preparation of Compound 420

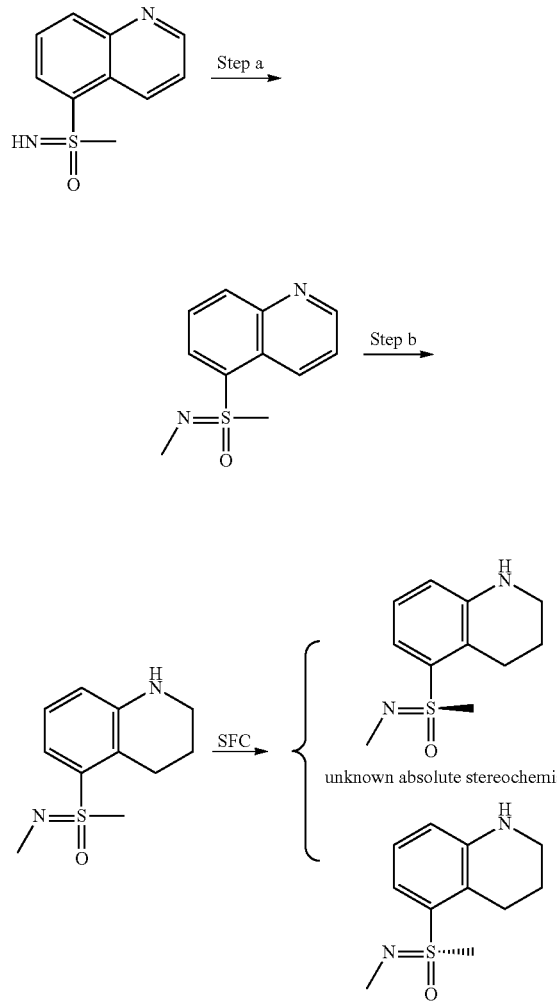

152

Synthesis of tert-butyl N—[(S)-methyl(oxo)(1,2,3,4-tetrahydroquinolin-5-yl)-6-sulfanylidene]carbamate, Used in the Preparation of Compound 421

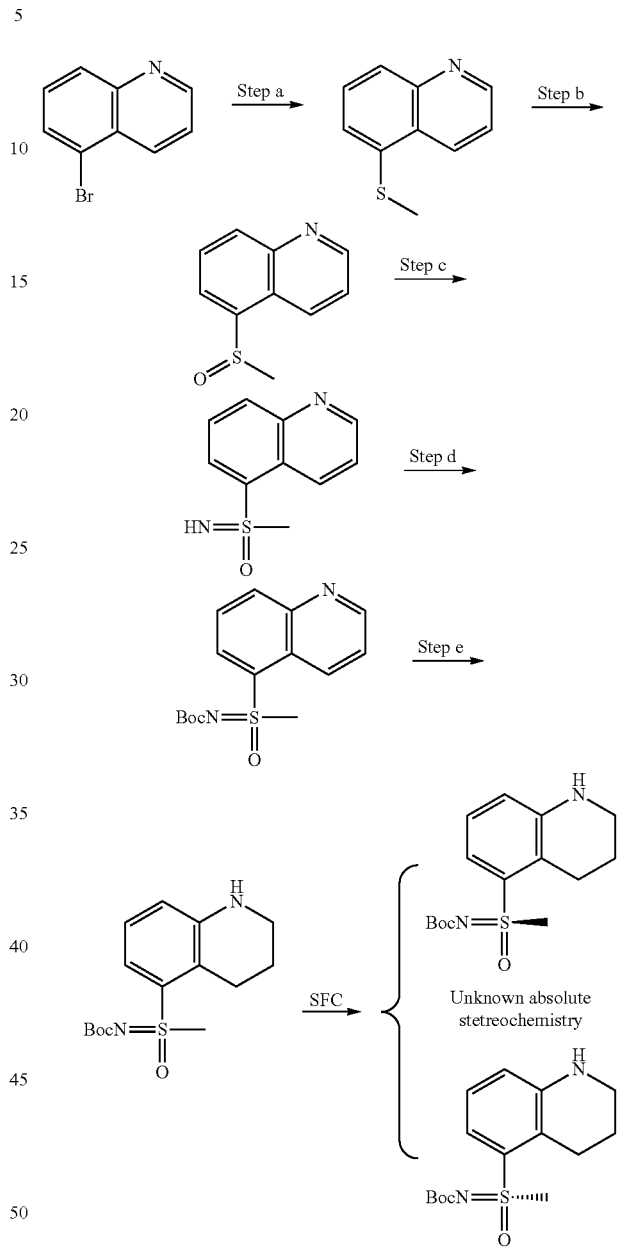

The synthetic procedure for methyl [methyl (oxo)(1,2,3,4-tetrahydroquinolin-5-yl)-λ⁶-sulfanylidene]amine is described in synthesis of the intermediate used for Compound 419.

SFC: The compound of methyl[methyl(oxo)(1,2,3,4-tetrahydroquinolin-5-yl)-λ⁶-sulfanylidene]amine (120.0 mg, 534 µmol) was separated by preparative SFC (Column: DAICEL CHIRALCEL OJ-H (250 mm*30 mm, 5 µm), Mobile phase: A: CO$_2$, B: Ethanol (0.1% NH$_3$.H$_2$O), Gradient: from 20% to 20% of B, Flow rate: 50 mL/min, Column temp: 35° C.) to give the desired methyl[(S)-methyl (oxo)(1,2,3,4-tetrahydroquinolin-5-yl)-λ⁶-sulfanylidene] amine (the faster eluting isomer, 3A: 50.0 mg, 42.0% yield). SFC-E, Column: Chiralcel OJ-3 150×4.6 mm I.D., 3 µm Mobile phase: A: CO$_2$ B: ethanol (0.05% DEA) Gradient: from 5% to 40% of B in 5 min and hold 40% for 2.5 min, then 5% of B for 2.5 min, Flow rate: 2.5 mL/min Column temp.: 35° C., Wavelength: 220 nm, Rt=2.633 min, e.e=99.2%.

Step a: A mixture of 5-bromoquinoline (5.0 g, 24.0 mmol), MeSNa (1.97 g, 28.1 mmol) and DMF (40.0 mL) was stirred at 130° C. for 1.5 h under N$_2$. TLC (Petroleum ether/Ethyl acetate=5:1) showed starting material was consumed completely and a new spot formed. LCMS showed starting material was consumed completely and the desired product formed. The mixture (4.2 g, crude) was used in next step without further workup.

Step b: To a mixture of 5-(methylsulfanyl) quinoline (4.20 g, crude) in DMF (40.0 mL) was added 10% aqueous NaClO (52.9 g, 71.6 mmol). After stirred for 10 min at 15° C., LCMS showed starting material was consumed completely and the desired product formed. The mixture was quenched with sat. Na$_2$SO$_3$ (60.0 mL) and extracted with ethyl acetate (60.0 mL×3). The combined organic layers were concentrated in vacuum. The residue was purified by silica column (Ethyl acetate in Petroleum ether=0~100%) to give the desired 5-methanesulfinylquinoline (3.60 g) as a yellow solid.

Step c: To a mixture of 5-(methylsulfinyl) quinoline (1.00 g, 5.23 mmol) and $NH_2CO_2NH_4$ (1.63 g, 20.9 mmol) in MeOH (30.0 mL) was added PhT(OAc)$_2$ (5.02 g, 15.6 mmol). The mixture was stirred 0.5 hour at 20° C. LCMS showed starting material was still remained and the desired product formed. After concentration, the residue was purified by silica column (Methanol in Dichloromethane=0~50%) to give the desired 5-(S-methylsulfonimidoyl) quinoline (0.79 g, 73.1% yield) as yellow oil.

Step d: To a solution of imino (methyl) (quinolin-5-yl)-$\lambda^6$-sulfanone (200.0 mg, 0.97 mmol) in THF (5.0 mL) was added 1.0 M t-BuOK (1.16 mL, 1.16 mmol) at 0° C. After 10 min, Boc$_2$O (420.0 mg, 1.93 mmol) was added. The mixture was stirred for 1 hour at 15° C. LCMS showed starting material was consumed completely and 88% the desired product formed. The mixture was diluted with $H_2O$ (20.0 mL) and extracted with ethyl acetate (20.0 mL×3). The combined organic layers were washed with brine (10.0 mL), dried over anhydrous $Na_2SO_4$, filtered and concentrated in vacuum. The residue was purified by silica column (Methanol in Dichloromethane=0~30%) to give tert-butyl N-[methyl (oxo) (quinolin-5-yl)-$\lambda^6$-sulfanylidene] carbamate (210.0 mg, 70.9% yield) as a yellow solid.

Step e: A mixture of 2-methylpropan-1-ylium-2-yl N-[methyl(oxo)(quinolin-5-yl)-$\lambda^6$-sulfanylidene]carbamate (210.0 mg, 0.69 mmol), 3,5-diethyl 2,6-dimethyl-1,4-dihydropyridine-3,5-dicarboxylate (415.0 mg, 1.64 mmol) and (PhO)$_2$P(O)OH (34.2 mg, 0.14 mmol) in Tol (15.0 mL) was stirred at 80° C. under $N_2$ for 12 hours. LCMS showed starting material was consumed completely and the desired product formed. After concentration, the residue was purified by silica column (Ethyl acetate in petroleum ether=0~100%) to give the desired tert-butyl N-[methyl (oxo) (1,2,3,4-tetrahydroquinolin-5-yl)-$\lambda^6$-sulfanylidene] carbamate (170.0 mg, 80.1% yield) as a yellow oil.

SFC: The compound of tert-butyl N-[methyl(oxo)(1,2,3,4-tetrahydroquinolin-5-yl)-$\lambda^6$-sulfanylidene]carbamate (170.0 mg, 547.0 µmol) was separated by preparative SFC ((Column: DAICEL CHIRALCEL OJ-H (250 mm*30 mm, 5 µm), Mobile phase: A: $CO_2$, B: Ethanol (0.1% $NH_3.H_2O$), Gradient: from 40% to 40% of B, Flow rate: 70 mL/min, Column temp: 35° C.) to give the desired tert-butyl N—[(S)-methyl(oxo(1,2,3,4-tetrahydroquinolin-5-yl)-$\lambda^6$-sulfanylidene]carbamate (the faster eluting isomer, 74.0 mg, 43.7% yield) as a yellow solid.

SFC-E, Column: Chiralpak AD-3 150×4.6 mm I.D., 3 um Mobile phase: A: $CO_2$ B:ethanol (0.05% DEA) Gradient: from 5% to 40% of B in 5 min and hold 40% for 2.5 min, then 5% of B for 2.5 min Flow rate: 2.5 mL/min Column temp.: 35° C., Wavelength: 220 nm, $R_t$=3.134 min, e.e.=99.8%.

Synthesis of tert-butyl N—[(R)-methyl(oxo)(1,2,3,4-tetrahydroquinolin-5-yl)-$\lambda^6$-sulfanylidene]carbamate, Used in the Preparation of Compound 422

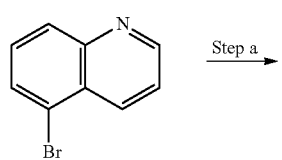

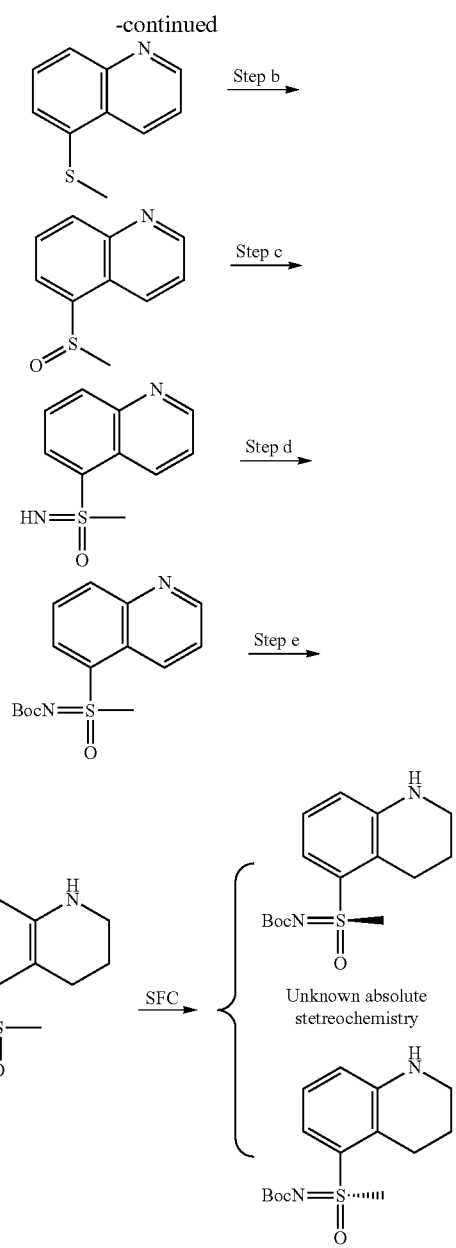

The synthetic procedure for tert-butyl N-[methyl(oxo)(1,2,3,4-tetrahydroquinolin-5-yl)-$\lambda^6$-sulfanylidene]carbamate is described in synthesis of the intermediate for Compound 421.

SFC: The compound of tert-butyl N-[methyl(oxo)(1,2,3,4-tetrahydroquinolin-5-yl)-$\lambda^6$-sulfanylidene]carbamate (170.0 mg, 547.0 µmol) was separated by preparative SFC ((Column: DAICEL CHIRALCEL OJ-H (250 mm*30 mm, 5 µm), Mobile phase: A: $CO_2$, B: Ethanol (0.1% $NH_3.H_2O$), Gradient: from 40% to 40% of B, Flow rate: 70 mL/min, Column temp: 35° C.) to give the desired tert-butyl N—[(R)-methyl(oxo)(1,2,3,4-tetrahydroquinolin-5-yl)-$\lambda^6$-sulfanylidene]carbamate (the slower eluting isomer, 84.0 mg, 49.7% yield) as a yellow solid.

SFC-E, Column: Chiralpak AD-3 150×4.6 mm I.D., 3 um Mobile phase: A: $CO_2$ B:ethanol (0.05% DEA) Gradient: from 5% to 40% of B in 5 min and hold 40% for 2.5 min, then 5% of B for 2.5 min Flow rate: 2.5 mL/min Column temp.: 35° C., Wavelength: 220 nm, $R_t$=4.012 min, e.e.=94.8%.

Synthesis of 2-(1,2,3,4-tetrahydro-1,6-naphthyridin-5-yl)thiazole, Used in the Preparation of Compound 424

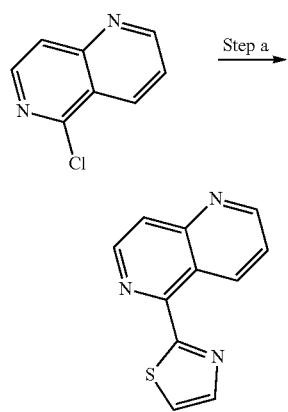

Step a: A mixture of 5-chloro-1,6-naphthyridine (400.0 mg, 2.43 mmol), 2-(tributylstannyl)-1,3-thiazole (909.0 mg, 2.43 mmol) and Pd(PPh$_3$)$_4$ (280.0 mg, 0.024 mmol) in toluene (15.0 mL) was stirred at 110° C. under N$_2$ for 12 hours. After concentration, the residue was purified by silica column (Ethyl acetate in Petroleum ether=0-100%) to give the desired 5-(1,3-thiazol-2-yl)-1,6-naphthyridine (400.0 mg, 77.2%) as a yellow solid.

Step b: A mixture of 5-(1,3-thiazol-2-yl)-1,6-naphthyridine (360.0 mg, 1.68 mmol) and PtO$_2$ (38.1 mg, 0.17 mmol) in MeOH (15.0 mL) was stirred at 25° C. under H$_2$ (15 psi) for 12 hours. The mixture was filtered and the filtrate was concentrated in vacuum to give the desired 2-(1,2,3,4-tetrahydro-1,6-naphthyridin-5-yl)thiazole (280.0 mg, crude) as a yellow oil.

Synthesis of (4R)-4-methyl-6-[1-(oxan-2-yl)-1H-pyrazol-5-yl]-1,2,3,4-tetrahydro-1,5-naphthyridine, Used in the Preparation of Compound 432

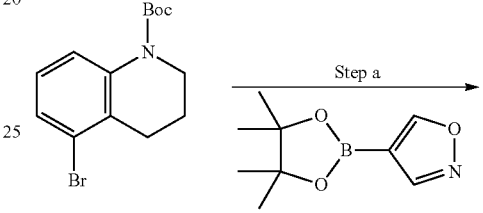

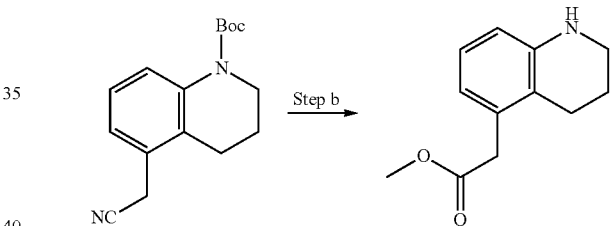

Step a: To a solution of (4R)-6-bromo-4-methyl-1,2,3,4-tetrahydro-1,5-naphthyridine (100 mg, 440 µmol) in dioxane (10 mL) and H$_2$O (1 mL) were added Cs$_2$CO$_3$ (286 mg, 880 µmol), 1-(oxan-2-yl)-5-(4,4,5,5-tetramethyl-1,3,2-dioxaborolan-2-yl)-1H-pyrazole (122 mg, 440 umol and Pd(dppf)Cl$_2$ (41.0 mg, 44.0 umol), the mixture was stirred at 100° C. for 12 hours under N$_2$ atmosphere. LCMS showed the desired product formed. The reaction mixture was concentrated in vacuum and purified by silica gel column (elution: Petroleum ether:Ethyl acetate=1:5 to 1:1) to give (4R)-4-methyl-6-[1-(oxan-2-yl)-1H-pyrazol-5-yl]-1,2,3,4-tetrahydro-1,5-naphthyridine (88.0 mg, 67.1% yield) as a yellow solid.

Synthesis of methyl 2-(1,2,3,4-tetrahydroquinolin-5-yl)acetate, Used in the Preparation of Compound 435

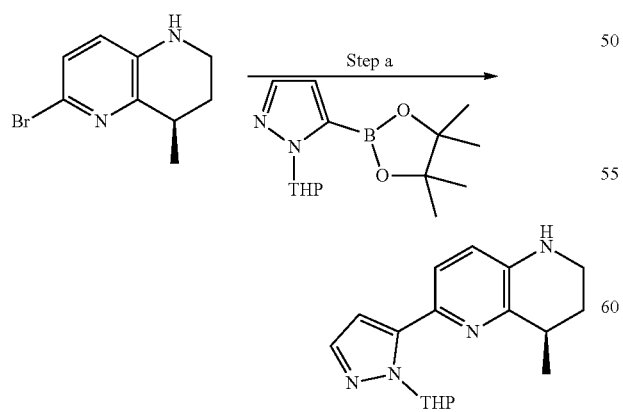

Step a: A mixture of tert-butyl 5-bromo-1,2,3,4-tetrahydroquinoline-1-carboxylate (500.0 mg, 1.60 mmol), 4-(4,4,5,5-tetranethyl-1,3,2-dioxaborolan-2-yl)-1,2-oxazole (374.0 mg, 1.92 mmol), Pd(dppf)Cl$_2$ (117.0 mg, 160.0 µmol) and KF (464.0 mg, 8.00 mmol) in DMSO/H$_2$O (10.0 mL/2.0 mL) was stirred at 130° C. for 12 hours under N$_2$. TLC (Petroleum ether/EtOAc=10/1) showed the starting material was consumed completely and one new spot with larger polarity was found. The reaction mixture was poured into EtOAc (100.0 mL) and washed with (30.0 mL×3). The organic layer was concentrated and purified by (EtOAc in Petroleum ether=0~30%) to give tert-butyl 5-(cyanomethyl)-1,2,3,4-tetrahydroquinoline-1-carboxylate (270.0 mg, 62.0% yield) as a yellow solid.

Step b: A solution of tert-butyl 5-(cyanomethyl)-1,2,3,4-tetrahydroquinoline-1-carboxylate (270.0 mg, 991.0 µmol) in 4 M HCl/MeOH (2.0 mL) was stirred at 50° C. for 14 hours. LCMS showed the desired product formed. The reaction mixture was evaporated in vacuum. The residue was poured into saturated NaHCO$_3$ (30.0 mL) and extracted with EtOAc (30.0 mL×2). The organic layers were concentrated and purified by silica gel column (EtOAc in Petroleum ether=0~20%) to give methyl 2-(1,2,3,4-tetrahydroquinolin-5-yl)acetate (110.0 mg, 54.1% yield) as a yellow oil.

Synthesis of 4-{2-[(tert-butyldimethylsilyl)oxy]ethyl}-1,2,3,4-tetrahydroquinoxaline-6-carbonitrile, Used in the Preparation of Compound 439

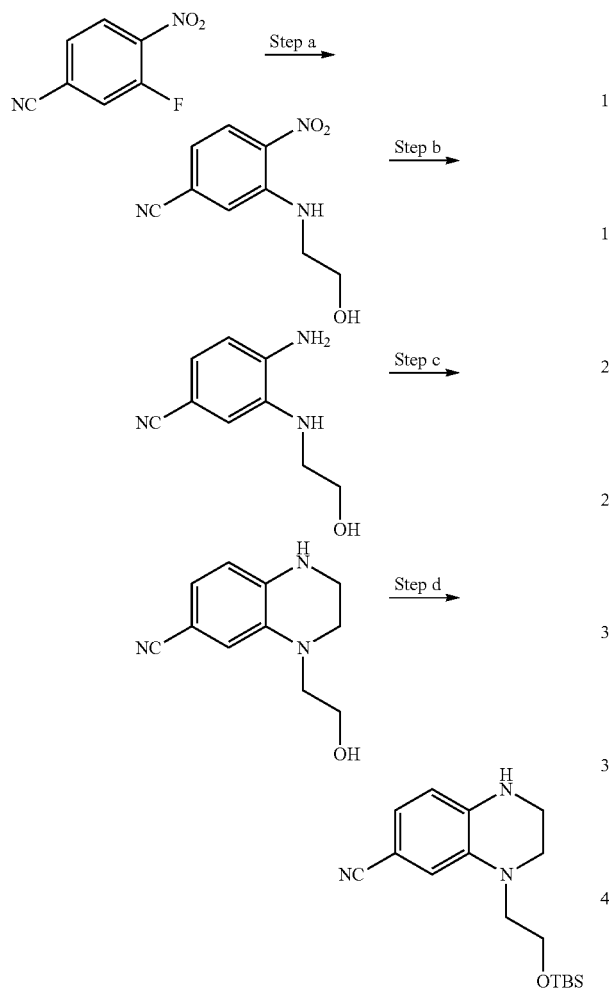

Step a: 3-Fluoro-4-nitrobenzonitrile (500.0 mg, 3.0 mmol), $NH_2CH_2CH_2OH$ (275.0 mg, 4.5 mmol) and $Et_3N$ (1.3 mL, 9.0 mmol) were added in EtOH (20.0 mL), the reaction mixture was stirred at 50° C. for 12 hours. LCMS indicated 100% of desired product formed. The reaction mixture was concentrated under reduced pressure to afford the product of 3-[(2-hydroxyethyl)amino]-4-nitrobenzonitrile (700.0 mg, crude) as a yellow solid.

Step b: 3-[(2-Hydroxyethyl)amino]-4-nitrobenzonitrile (623.0 mg, crude) and 10% wet Pd/C (200.0 mg) were added in MeOH (10.0 mL), the reaction mixture was stirred at 15° C. for 12 hours under $H_2$ (15 psi). LCMS indicated 99% of desired product formed. The reaction mixture was filtered and concentrated under reduced pressure to afford the product of 4-amino-3-[(2-hydroxyethyl)amino]benzonitrile (600.0 mg, crude) as a yellow solid which was used in next step without further purification.

Step c: Crude 4-Amino-3-[(2-hydroxyethyl)amino]benzonitrile (300.0 mg), 1,2-dibromoethane (1.6 g, 8.5 mmol) and TBAB (1.6 g, 5.1 mmol) were added in bottle, the reaction mixture was stirred at 60° C. for 12 hours. LCMS indicated 43% of desired product formed. TLC (Petroleum ether:Ethyl acetate=10:1) indicated one new spot formed. The reaction mixture was concentrated under reduced pressure to give a residue and purified by flash silica gel chromatography (Petroleum ether:Ethyl acetate=100:0 to 100:10) to afford the product of 4-(2-hydroxyethyl)-1,2,3,4-tetrahydroquinoxaline-6-carbonitrile (130.0 mg) as a colorless oil.

Step d: 4-(2-hydroxyethyl)-1,2,3,4-tetrahydroquinoxaline-6-carbonitrile (100.0 mg, 492.0 μmol), TBSCl (148.0 mg, 983.0 μmol) and Imidazole (100.0 mg, 1.5 mmol) were added in DCM (5.0 mL), the reaction mixture was stirred at 40° C. for 1 hour. LCMS indicated 95% of desired product formed. The reaction mixture was concentrated under reduced pressure and purified by flash silica gel chromatography (Petroleum ether:Ethyl acetate=100:0 to 100:10) to afford the product of 4-{2-[(tert-butyldimethylsilyl)oxy]ethyl}-1,2,3,4-tetrahydroquinoxaline-6-carbonitrile (100.0 mg, 64.5% yield) as a colorless oil.

Synthesis of 1-methyl-8-(1-methyl-1H-pyrazol-4-yl)-1,2,3,4-tetrahydroquinoxaline, Used in the Preparation of Compound 440

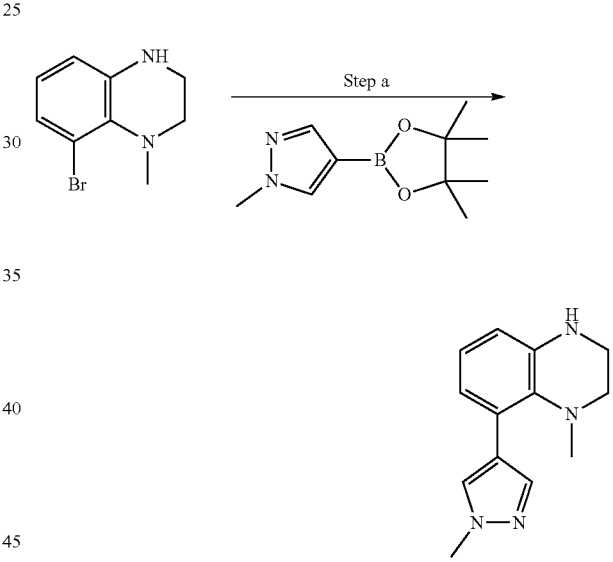

Step a: A mixture of 8-bromo-1-methyl-1,2,3,4-tetrahydroquinoxaline (300.0 mg, 1.32 mmol), 1-methyl-4-(4,4,5,5-tetramethyl-1,3,2-dioxaborolan-2-yl)-1H-pyrazole (301.0 mg, 1.45 mmol), Pd(dppf)Cl₂ (96.6 mg, 132.0 umol) and $Cs_2CO_3$ (858.0 mg, 2.64 mmol) in dioxane (10.0 mL) and $H_2O$ (1.0 mL) was stirred at 100° C. for 16 hours under $N_2$. Brown solution was observed. Desired mass ion was observed from LCMS. The solution was added into $H_2O$ (50.0 mL) and then extracted with EtOAc (50.0 mL×2). The combined organic layers were washed with brine (50.0 mL), dried over anhydrous $Na_2SO_4$, filtered and concentrated in vacuum to give the crude product as a brown gum. The residue was purified by flash silica gel chromatography (12.0 g, Ethyl acetate in Petroleum ether from 0% to 50%) to give 1-methyl-8-(1-methyl-1H-pyrazol-4-yl)-1,2,3,4-tetrahydroquinoxaline (130.0 mg, 43.1% yield) as an orange oil.

Synthesis of 2-(1,2,3,4-tetrahydroquinolin-5-yl)acetonitrile, Used in the Preparation of Compound 441

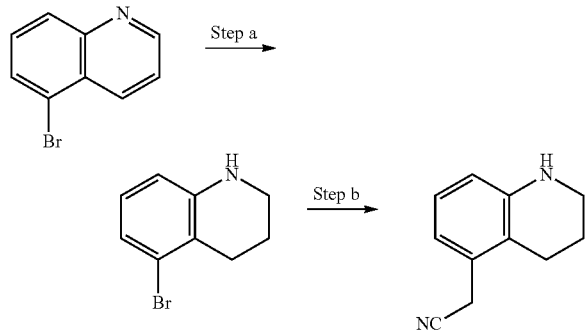

Step a: 5-Bromoquinoline (5.0 g, 24.0 mmol) was added in CH$_3$COOH (50.0 mL), NaBH$_3$CN (5.2 g, 84.0 mmol) was added in one portion, the reaction mixture was stirred at 5° C. for 2 hours. TLC (Petroleum ether:Ethyl acetate=10:1) indicated one main spot formed. The reaction mixture was diluted with EtOAc(500.0 mL), adjusted pH=8 by adding saturated NaHCO$_3$, the organic phase was concentrated under reduced pressure and purified by flash silica gel chromatography (Petroleum ether:EtOAc=10:1) to afford the product of 5-bromo-1,2,3,4-tetrahydroquinoline (4.5 g, 88.4% yield) as a yellow oil.

Step b: 5-bromo-1,2,3,4-tetrahydroquinoline (4.5 g, 21.2 mmol), 4-(4,4,5,5-tetramethyl-1,3,2-dioxaborolan-2-yl)-1,2-oxazole (4.1 g, 21.2 mmol), Pd(dppf)Cl$_2$ (1.5 g, 2.1 mmol) and KF (4.9 g, 84.8 mmol) were added in the mixture of DMSO (100.0 mL) and H$_2$O (20.0 mL), the reaction mixture was evacuated and refilled for 3 times with N$_2$ and stirred at 100° C. for 2 hours and stirred at 130° C. for 12 hours. TLC (Petroleum ether:Ethyl acetate=2:1) indicated one new spot formed. The reaction mixture was diluted with EtOAc (1000.0 mL), washed with H$_2$O (500.0 mL×3) and brine, dried over anhydrous Na$_2$SO$_4$, the organic phase was concentrated under reduced pressure and purified by flash silica gel chromatography (Petroleum ether:EtOAc=2:1) to afford the product of 2-(1,2,3,4-tetrahydroquinolin-5-yl)acetonitrile (1.3 g, 35.6% yield) as a yellow solid.

Synthesis of (R)-8-methyl-5,6,7,8-tetrahydro-1,5-naphthyridine-2-carbonitrile and (S)-8-methyl-5,6,7,8-tetrahydro-1,5-naphthyridine-2-carbonitrile, Used in the Preparation of Compound 452

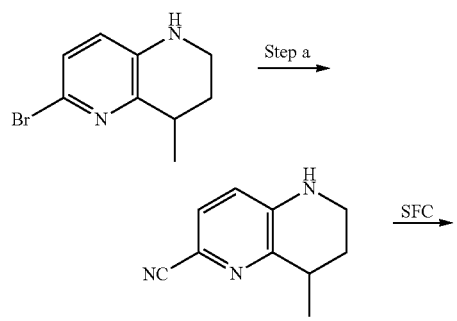

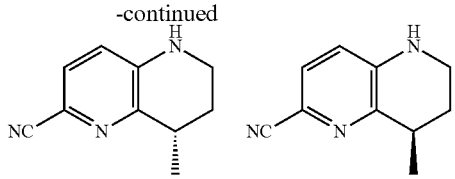

Step a: A solution of 6-bromo-4-methyl-1,2,3,4-tetrahydro-1,5-naphthyridine (1 g, 4.40 mmol), zincdicarbonitrile (774 mg, 6.60 mmol), Pd2(dba)3 (80.5 mg, 88.0 umol), dppf (97.6 mg, 176 umol) and Zn (34.3 mg, 528 umol) in DMF (20 mL) was stirred at 120° C. for 12 h under N2. The solution was added into H2O (50 mL) and then extracted with EtOAc (50 mL×2). The combined organic layers were washed with saturated NaCl (20 mL), dried over anhydrous Na2SO4, filtered and concentrated in vacuum to give crude product as brown gum. The residue was purified by flash silica gel chromatography (40 g, Ethyl acetate in Petroleum ether from 0% to 45%) to give product (760 mg, 99.7% yield) as orange gum. LCMS: [M+H]+ 174.

SFC: 8-methyl-5,6,7,8-tetrahydro-1,5-naphthyridine-2-carbonitrile (120 mg, 692 μmol) was purified by SFC (Column: ChiralPak IC-3 150×4.6 mm I.D., 3 um, Mobile phase: A: CO2 B:IPA (0.05% DEA), Gradient: from 5% to 40% of B in 5.5 min and hold 40% for 3 min, then 5% of B for 1.5 min, Flow rate: 2.5 mL/min Column temperature: 40° C.). (8R)-8-methyl-5,6,7,8-tetrahydro-1,5-naphthyridine-2-carbonitrile (60.0 mg, 346 μmol) and (8S)-8-methyl-5,6,7,8-tetrahydro-1,5-naphthyridine-2-carbonitrile (60.0 mg, 346 μmol) were obtained as white solid.

Synthesis of 5-(isopropylsulfonyl)-1,2,3,4-tetrahydroquinoline, Used in the Preparation of Compound 456

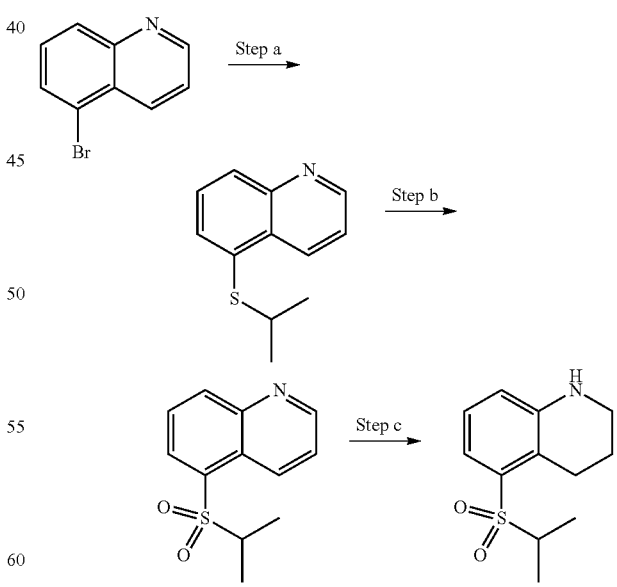

Step a: A solution of 5-bromoquinoline (1.00 g, 4.81 mmol, 1 eq), propane-2-thiol (549.50 mg, 7.22 mmol, 673.41 uL, 1.5 eq), Xantphos (556.63 mg, 962.00 umol, 0.2 eq), Pd2(dba)3 (440.46 mg, 481.00 umol, 0.1 eq) and DIEA (1.86 g, 14.43 mmol, 2.51 mL, 3 eq) in dioxane (10 mL) was stirred at 100° C. under N2 for 12 hrs at sealed tuble. TLC (Petroleum ether/Ethyl acetate=8/1) showed that compound 1 (Rf=0.35) was consumed and a major spot (Rf=0.3) was given. The reaction mixture was cooled to 25° C., and filtered through a pad of celite. The filtrate was concentrated under vacuum. The residue was purified by column chromatography (SiO2, Petroleum ether/Ethyl acetate=1/0~10/1, Rf=0.3 to give 5-(isopropylthio)quinoline (860 mg, 4.12 mmol, 85.5% yield, 97.3% purity) as a yellow oil. LCMS: m/z=204.2 (M+H)+.

Step b: To a solution of 5-(isopropylthio)quinoline (200 mg, 957.19 umol, 1 eq) in DCM (2 mL) was added m-CPBA (412.95 mg, 1.91 mmol, 80% purity, 2 eq) 0° C. Then the mixture was stirred at 25° C. for 2 hrs. LCMS (EW10678-1-P1A1) showed that the desired Ms (Rt=0.663 min) was detected. The reaction mixture was poured into saturated Na2SO3 solution (20 mL) and extracted with DCM (20 mL*2). The organic layer was washed with saturated Na2CO3 solution (20 mL*1), dried over Na2SO4, filtered and concentrated to give 5-(isopropylsulfonyl)quinoline (200 mg, crude) as a yellow oil. LCMS: m/z=236.0 (M+1)+.

Step c: To a solution of 5-(isopropylsulfonyl)quinoline (200 mg, 849.97 umol, 1 eq) in MeOH (10 mL) was added PtO2 (0.1 g, 440.38 umol, 5.18e-1 eq) at 20° C. under N2. Then the mixture was stirred under H2 (50 psi) at 25° C. for 16 hrs. LCMS (EW10678-2-P1A2) showed that the desired Ms (Rt=0.721 min) was detected. The reaction mixture was filtered. The filtrate was concentrated. The residue was purified by column: Phenomenex Synergi C18 150*25*10 um; mobile phase: [water (0.05% HCl)-ACN]; B %: 20%-40%, 11 min. Then the residue was lyophilized to give 5-(isopropylsulfonyl)-1,2,3,4-tetrahydroquinoline (79.0 mg, 280.72 umol, 33.0% yield, 98.0% purity, HCl) as a yellow solid. LCMS: m/z=240.2 (M+1)+.

Synthesis of 5-(cyclopropylsulfonyl)-1,2,3,4-tetrahydroquinoline, Used in the Preparation of Compound 457

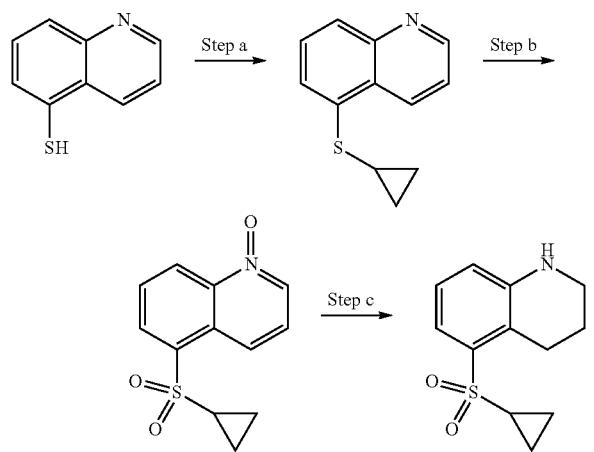

Step a: A solution of quinoline-5-thiol (500 mg, 3.10 mmol, 1 eq), bromocyclopropane (750.36 mg, 6.20 mmol, 496.93 uL, 2 eq) and Cs2CO3 (2.02 g, 6.20 mmol, 2 eq) in DMF (5 mL) was stirred at 100° C. for 16 hrs. LCMS (EW10678-9-P1A1) showed that the desired Ms (Rt=0.715 min) was detected. The reaction mixture was cooled to 25° C., and poured into H2O (50 mL), extracted with ethyl acetate (50 mL*3). The organic layer was dried over Na2SO4, filtered and concentrated. The residue was purified by column chromatography SiO2, Petroleum ether/Ethyl acetate=1/0-10/1, (Rf=0.45, Petroleum ether/Ethyl acetate=1/1) to give 5-(cyclopropylthio)quinoline (300 mg, 1.35 mmol, 43.4% yield, 90.4% purity) as a yellow oil. LCMS: m/z=201.9 (M+H)+.

Step b: To a solution of 5-(cyclopropylthio)quinoline (300 mg, 1.35 mmol, 1 eq) in DCM (6 mL) was added m-CPBA (581.26 mg, 2.69 mmol, 80% purity, 2 eq). Then the mixture was stirred at 25° C. for 16 hrs. LCMS (EW10678-11-P1A) showed that the desired Ms (Rt=0.297 min) was detected. The reaction mixture was poured into saturated Na2SO3 solution (40 mL) and extracted with DCM (40 mL*2). The organic layer was dried over Na2SO4, filtered and concentrated to give 5-(cyclopropylsulfonyl)quinoline 1-oxide (300 mg, 1.20 mmol, 89.3% yield) as a yellow solid. LCMS: m/z=250.0 (M+H)+.

Step c: To a solution of 5-(cyclopropylsulfonyl)quinoline 1-oxide (0.3 g, 1.20 mmol, 1 eq) in MeOH (12 mL) was added PtO2 (0.15 g, 660.56 umol, 5.49e-1 eq) under N2. Then the mixture was stirred under H2 (50 psi) at 25° C. for 16 hrs. LCMS (EW10678-16-P1A2) showed that the desired Ms (Rt=0.503 min) was detected. The reaction mixture was filtered through a pad of celite. The filtrate was concentrated. The residue was purified by column: Phenomenex Synergi C18 150*25*10 um; mobile phase: [water (0.05% HCl)-ACN]; B %: 20%-50%, 10 min. Then the mixture was lyophilized to give 5-(cyclopropylsulfonyl)-1,2,3,4-tetrahydroquinoline (99.23 mg, 355.20 umol, 29.5% yield, 98.0% purity, HCl) as a yellow solid. LCMS: m/z=238.2 (M+1)+.

Synthesis of 5-((2-methoxyethyl)sulfonyl)-1,2,3,4-tetrahydroquinoline, Used in the Preparation of Compound 460

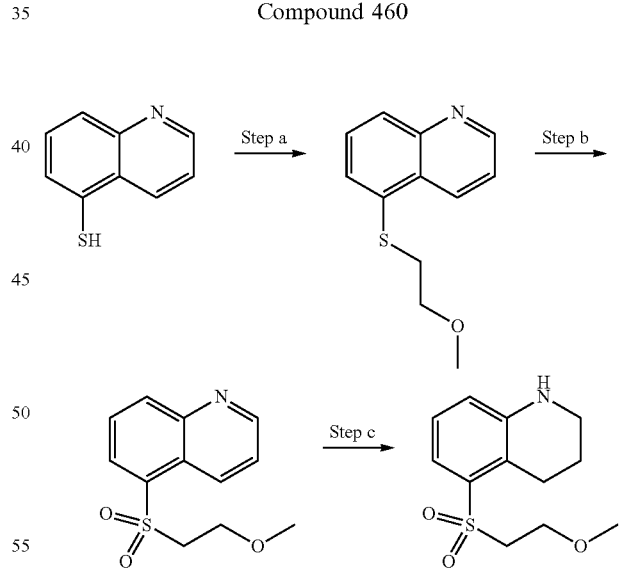

Step a: A solution of quinoline-5-thiol (500 mg, 3.10 mmol, 1 eq), 2-methoxyethyl 4-methylbenzenesulfonate (857.00 mg, 3.72 mmol, 1.2 eq), Cs2CO3 (1.21 g, 3.72 mmol, 1.2 eq) in DMF (5 mL) was stirred at 85° C. for 12 h. TLC (Petroleum ether/Ethyl acetate=3/1) showed that the compound 3 (Rf=0) was consumed and a major spot (Rf=0.24) was given. The reaction mixture was filtered and the filtrate was poured into water (30 mL), extracted with ethyl acetate (20 mL*2). The organic layer was concentrated under vacuum. The residue was purified by column chromatography (SiO$_2$, Petroleum ether/Ethyl acetate=3/1, Rf=0.24) to give 5-((2-methoxyethyl)thio)quinoline (480 mg, 1.99 mmol, 64.01% yield, 90.7% purity) as a red oil. LCMS: m/z=220.0 (M+1)+.

Step b: To the solution of 5-((2-methoxyethyl)thio)quinoline (480 mg, 1.99 mmol, 1 eq) in DCM (5 mL) was added m-CPBA (856.47 mg, 3.97 mmol, 80% purity, 2 eq). Then the reaction mixture was stirred at 20° C. for 30 min. LCMS (EW10591-15-P1A1) showed the desired Ms (Rt=0.569 min) was given. The reaction mixture was poured into 10% saturated Na2SO3 solution (30 mL) and stirred for 30 min. The mixture was extracted with DCM (10 mL*2). The combined organic layer was concentrated under vacuum to give 5-((2-methoxyethyl)sulfonyl)quinoline (500 mg, crude) as yellow oil. LCMS: m/z=252.1 (M+1)+.

Step c: A suspension of 5-((2-methoxyethyl)sulfonyl)quinoline (0.5 g, 1.99 mmol, 1 eq), PtO2 (0.3 g, 1.32 mmol, 6.64e-1 eq) in MeOH (20 mL) was stirred at 25° C. under H2 (50 psi) for 3 h. LCMS (EW10591-18-P1B) showed that the desired Ms (Rt=0.671 min) was given. The mixture was filtered through a pad of celite and the filtrate was concentrated under vacuum. The residue was purified by Pre-HPLC (column: Phenomenex Synergi C18 150*25*10 um; mobile phase: [water (0.05% HCl)-ACN]; B %: 16%-36%, 11 min). The mixture was concentrated to remove MeCN and adjusted to pH=8 with saturated NaHCO$_3$ solution. The mixture was extracted with ethyl acetate (30 mL*2). The combined organic layer was concentrated under vacuum to give 5-((2-methoxyethyl)sulfonyl)-1,2,3,4-tetrahydroquinoline (126.6 mg, 486.90 umol, 24.47% yield, 98.2% purity) as a yellow oil. LCMS: m/z=256.2 (M+H)+.

Synthesis of 1-methyl-7-(1-methyl-1H-pyrazol-4-yl)-1,2,3,4-tetrahydroquinoxaline, Used in the Synthesis of Compound 463

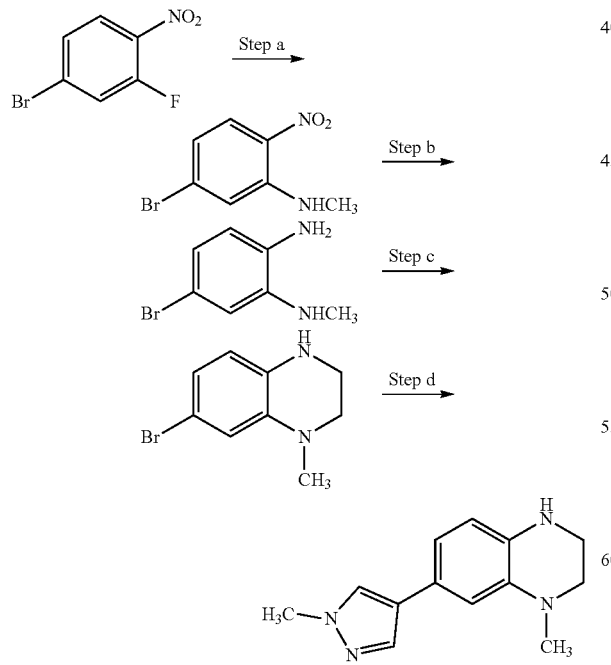

Step a: To 4-bromo-2-fluoro-1-nitrobenzene (25.0 g, 113 mmol) in MeOH (100 mL) and THF (50 mL) was added 2M MeNH$_2$ (67.5 mL, 135 mmol) dropwise. The mixture was stirred at 10° C. for 12 hours. When TLC analysis (10/6 EtOAc/petroleum ether) indicated that the reaction was incomplete, additional 2M MeNH$_2$ in THF (60 mL) was added to the mixture and stirring continued at 45° C. for another 12 hours. The mixture was concentrated under reduced pressure and water (200 mL) added to the concentrated, followed by extraction with EtOAc (200 mL×2). The combined organics were washed with brine, dried over anhydrous Na$_2$SO$_4$, filtered, and concentrated under reduced pressure to give 5-bromo-N-methyl-2-nitroaniline (25.5 g, 97.7% yield) as a yellow solid.

Step b: To 5-bromo-N-methyl-2-nitroaniline (10.0 g, 43.2 mmol) in MeOH (150 mL) was added sodium dithionite (67.5 g, 388 mmol) in H$_2$O (60 mL) dropwise. The mixture was stirred at 60° C. for 12 hours, filtered, and the filtrate was concentrated under reduced pressure. The concentrate was extracted with EtOAc (200 mL×3) and the combined organics washed with H$_2$O (100 mL), brine (100 mL), and dried over anhydrous Na$_2$SO$_4$. The mixture was filtered and the filtrate was concentrated under reduced pressure to give 5-bromo-N$^1$-methylbenzene-1,2-diamine (8.60 g, crude) as a brown oil.

Step c: A mixture of 5-bromo-N$^1$-methylbenzene-1,2-diamine (1.0 g, 4.97 mmol), 1,2-dibromoethane (2.13 mL, 24.8 mmol), and TBAB (4.80 g, 14.9 mmol) was stirred at 60° C. for 12 hours. The mixture was concentrated under reduced pressure and purified by flash silica gel chromatography (0-30% EtOAc/petroleum ether) to give 7-bromo-1-methyl-1,2,3,4-tetrahydroquinoxaline (233 mg, 20.8% yield) as a brown solid.

Step d: To the mixture of 7-bromo-1-methyl-1,2,3,4-tetrahydroquinoxaline (100 mg, 0.44 mmol) and 1-methyl-4-(4,4,5,5-tetramethyl-1,3,2-dioxaborolan-2-yl)-1H-pyrazole (137 mg, 0.66 mmol) in dioxane (5 mL) and H$_2$O (1 mL) was added Pd(dppf)Cl$_2$ (32.1 mg, 44 umol) and K$_3$PO$_4$ (205 mg, 0.97 mmol) under N$_2$. The mixture was stirred at 100° C. under N$_2$ for 12 hours, cooled, concentrated under reduced pressure, and purified by flash silica gel (0-50% EtOAc/petroleum ether) to give 1-methyl-7-(1-methyl-1H-pyrazol-4-yl)-1,2,3,4-tetrahydroquinoxaline (35.9 mg, 35.9% yield) as a yellow oil.

Synthesis of 5-(oxetan-3-ylsulfonyl)-1,2,3,4-tetrahydroquinoline, Used in the Preparation of Compound 464

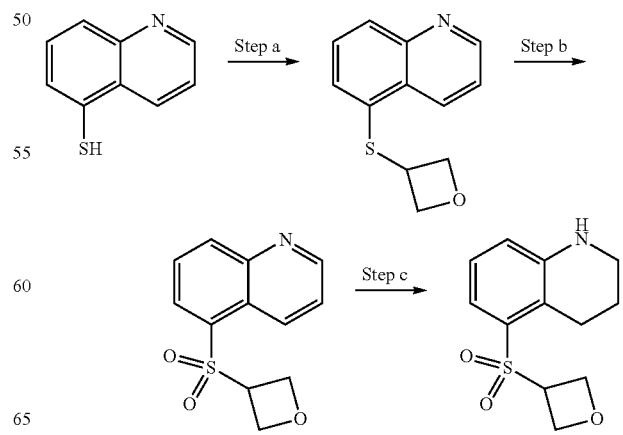

Step a: A suspension of quinoline-5-thiol (500 mg, 3.10 mmol, 1 eq), oxetan-3-yl 4-methylbenzenesulfonate (849.15 mg, 3.72 mmol, 1.2 eq) and Cs2CO3 (1.21 g, 3.72 mmol, 1.2 eq) in DMF (5 mL) was stirred at 80° C. for 12 h. LCMS (EW10591-12-P1A1) showed the desired Ms (Rt=0.719 min) was given. The reaction mixture was poured into water (20 mL) and extracted with ethyl acetate (30 mL*2). The combined organic layer was concentrated under vacuum. The residue was purified by column chromatography (SiO2, Petroleum ether/Ethyl acetate=1/1, Rf=0.2) to give 5-(oxetan-3-ylthio)quinoline (580 mg, crude) as a yellow oil. LCMS: m/z=218.2 (M+H)+.

Step b: To the solution of 5-(oxetan-3-ylthio)quinoline (580 mg, 2.67 mmol, 1 eq) in DCM (5 mL) was added m-CPBA (1.15 g, 5.34 mmol, 80% purity, 2 eq). Then the mixture was stirred at 20° C. for 30 min. LCMS (EW10591-14-P1A1) showed that the desired Ms (Rt=0.558 min) was given. The reaction mixture was poured into 10% saturated Na2SO3 solution (30 mL) and stirred for 30 min. The mixture was extracted with DCM (10 mL*2). The combined organic layer was concentrated under vacuum to give 5-(oxetan-3-ylsulfonyl)quinoline (600 mg, 2.41 mmol, 90.17% yield) as yellow oil. LCMS: m/z=250.1 (M+H)+.

Step c: A suspension of 5-(oxetan-3-ylsulfonyl)quinoline (0.6 g, 2.41 mmol, 1 eq), PtO2 (546.55 mg, 2.41 mmol, 1 eq) in MeOH (20 mL) was stirred at 25° C. under H2 (50 psi) for 3 h. LCMS (EW10591-17-P1B) showed the desired MS (Rt=0.666 min) was given. The reaction mixture was filtered through a pad of celite and the filtrate was concentrated under vacuum. The residue was purified by Pre-HPLC (column: Phenomenex luna C18 150*25 10u; mobile phase: [water (0.1% TFA)-ACN]; B %: 30/6-48%, 10 min) to give 5-(oxetan-3-ylsulfonyl)-1,2,3,4-tetrahydroquinoline (41.05 mg, 152.81 umol, 6.35% yield, 94.3% purity) as a yellow solid. LCMS: m/z=254.2 (M+H)+.

Synthesis of 5-((1-methyl-1H-pyrazol-4-yl)sulfonyl)-1,2,3,4-tetrahydroquinoline, Used in the Preparation of Compound 465

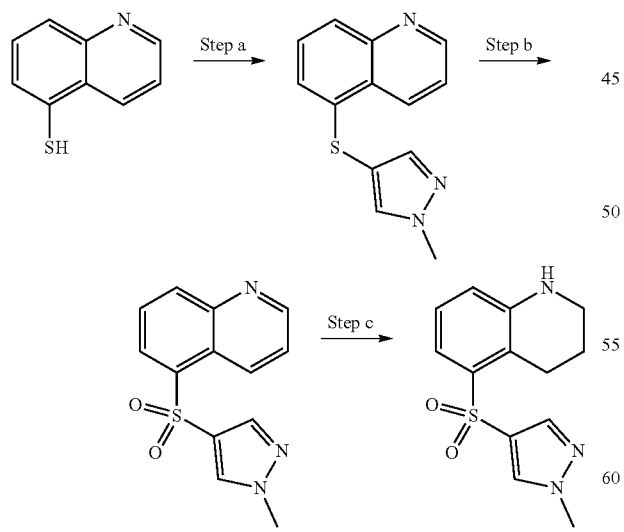

Step a: A solution of quinoline-5-thiol (800 mg, 4.96 mmol, 1 eq), 4-iodo-1-methyl-pyrazole (1.24 g, 5.95 mmol, 1.2 eq), CuI (94.50 mg, 496.21 umol, 0.1 eq), K2CO3 (1.03 g, 7.44 mmol, 1.5 eq) and 1,10-phenanthroline (178.84 mg, 992.41 umol, 0.2 eq) in DMF (8 mL) was stirred under N2 at 120° C. for 16 hrs. LCMS (EW10678-12-P1A) showed that the desired Ms (Rt=0.663 min) was detected. The reaction mixture was cooled to 20° C. and filtered. The filter cake was washed with ethyl acetate (30 mL*4). The filtrate was washed with brine (60 mL*1). The organic layer was dried over Na2SO4, filtered and concentrated. The residue was purified by column chromatography (SiO2, Petroleum ether/Ethyl acetate=1/0-10/1-0/1, Rf=0.1) to give 5-((1-methyl-1H-pyrazol-4-yl)thio)quinoline (700 mg, 1.94 mmol, 39.1% yield, 66.9% purity) as a yellow solid. LCMS: m/z=242.0 (M+1)+.

Step b: To a solution of 5-((1-methyl-1H-pyrazol-4-yl)thio)quinoline_1 (400 mg, 1.11 mmol, 1 eq) in DCM (8 mL) was added m-CPBA (478.41 mg, 2.22 mmol, 80% purity, 2 eq). Then the mixture was stirred at 25° C. for 30 min. LCMS (EW10678-14-P1A) showed that the desired Ms (Rt=0.603 min) was detected. The reaction mixture was poured into saturated Na2SO3 solution (100 mL) and extracted with DCM (100 mL*2). The organic layer was dried over Na2SO4, filtered and concentrated to give 5-((1-methyl-1H-pyrazol-4-yl)sulfonyl)quinoline (400 mg, crude) as yellow oil. LCMS: m/z=274.1 (M+1)+.

Step c: To a solution of 5-((1-methyl-1H-pyrazol-4-yl)sulfonyl)quinoline (400 mg, 1.46 mmol, 1 eq) in MeOH (16 mL) was added PtO2 (0.2 g, 880.76 umol, 6.02e-1 eq) under N2. Then the mixture was stirred under H2 (50 psi) at 25° C. for 16 hrs. LCMS (EW10678-15-P1A3) showed that the desired Ms (Rt=0.514 min) was detected. The reaction mixture was filtered through a pad of celite. The filtrate was concentrated. The residue was purified by column: Phenomenex Synergi C18 150*25*10 um; mobile phase: [water (0.05% HCl)-ACN]; B %: 20%-44%, 8 min. Then the residue was lyophilized to give 5-((1-methyl-1H-pyrazol-4-yl)sulfonyl)-1,2,3,4-tetrahydroquinoline (182.88 mg, 578.12 umol, 39.5% yield, 99.2% purity, HCl) as a light yellow solid. LCMS: m/z=278.2 (M+1)+.

Synthesis of cis-4-(3-methoxycyclobutyl)-1,2,3,4-tetrahydroquinoxaline-6-carbonitrile, Used in the Preparation of Compound 469

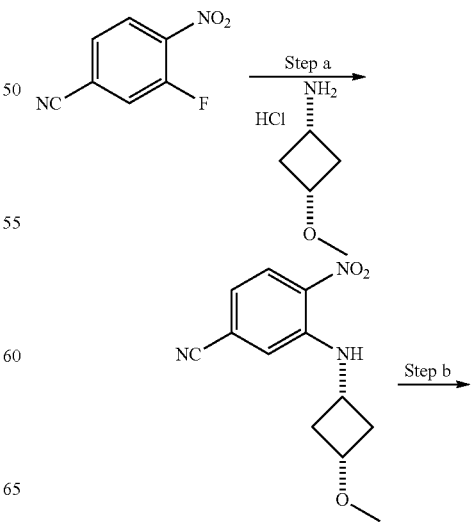

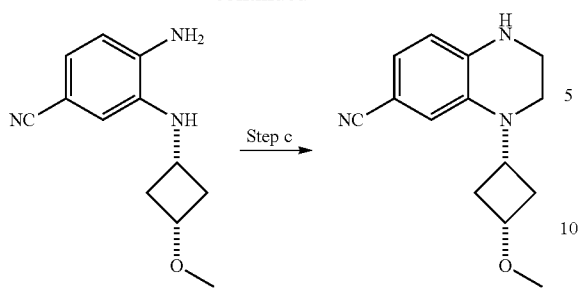

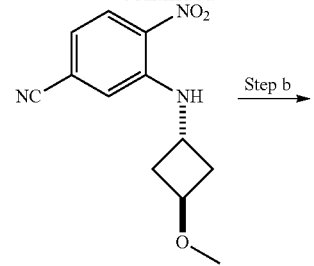

Step a: A mixture of cis-3-methoxycyclobutan-1-amine hydrochloride (1.00 g, 7.26 mmol), 3-fluoro-4-nitrobenzonitrile (1.20 g, 7.26 mmol) and Et₃N (2.19 g, 21.7 mmol) in EtOH (50.0 mL) was stirred at 80° C. for 2 hours. TLC (Petroleum ether/EtOAc=2/1) showed the starting material was consumed completely. The reaction was concentrated, dissolved in EtOAc (100.0 mL), washed with water (50.0 mL×2), dried over anhydrous Na₂SO₄, filtered and concentrated. The residue was purified by silica gel column (EtOAc in Petroleum ether=0~30%) to give cis-3-[(3-methoxycyclobutyl)amino]-4-nitrobenzonitrile (1.70 g, 94.9% yield) as a yellow solid.

Step b: A mixture of cis-3-[(3-methoxycyclobutyl)amino]-4-nitrobenzonitrile (1.70 g, 6.87 mmol) and Pd/C (0.2 g, 10% wet) in THF (20.0 mL) was stirred at 20° C. under H₂ (15 psi.) for 6 hours. LCMS showed the starting material was consumed completely. The reaction mixture was filtered and concentrated to give cis-4-amino-3-[(3-methoxycyclobutyl)amino]benzonitrile (1.30 g, 87.2% yield) as a light red solid.

Step c: A mixture of cis-4-amino-3-[(3-methoxycyclobutyl)amino]benzonitrile (1.30 g, 5.98 mmol), 1,2-dibromoethane (4.48 g, 23.9 mmol), TBAB (7.70 g, 23.9 mmol) and Et₃N (3.29 ml, 23.9 mmol) was stirred at 60° C. under N₂ for 12 hours. LCMS showed 13% of the starting material remained and about 60% of desired product formed. TLC (Petroleum ether/EtOAc=1/1) showed a little amount of the starting material remained and one major new spot with lower polarity was found. The reaction mixture was poured into water (100.0 mL) and extracted with DCM (50.0 mL×3). The organic layers were dried over anhydrous Na₂SO₄, filtered and concentrated. The residue was purified by silica gel column (EtOAc in Petroleum ether=0~30%) to give cis-4-(3-methoxycyclobutyl)-1,2,3,4-tetrahydroquinoxaline-6-carbonitrile (1.15 g, 79.3% yield) as a light red oil.

Synthesis of 4-[trans-3-methoxycyclobutyl]-1,2,3,4-tetrahydroquinoxaline-6-carbonitrile, Used in the Preparation of Compound 470

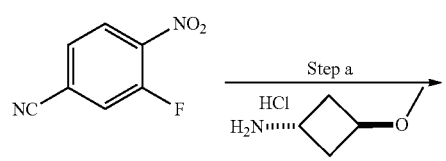

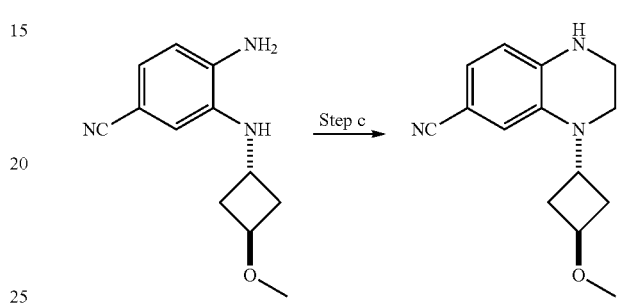

Step a: To the mixture of 3-fluoro-4-nitrobenzonitrile (1.2 g, 7.3 mmol) and trans-3-methoxycyclobutan-1-amine hydrochloride (1.0 g, 7.3 mmol) in EtOH (30.0 mL) was added TEA (4.0 mL, 29.0 mmol). The mixture was stirred at 60° C. for 12 hours. TLC (Petroleum ether/EtOAc=10/1) showed a new spot formed. The mixture was concentrated in vacuum and washed with Petroleum ether/EtOAc (5/2, 40.0 mL×3). The solid was dried in vacuum to give the product of 3-[(3-methoxycyclobutyl)amino]-4-nitrobenzonitrile (2.0 g, crude) as a yellow solid.

Step b: To the mixture of 3-[(3-methoxycyclobutyl)amino]-4-nitrobenzonitrile (2.0 g, 8.1 mmol) in THF (40.0 mL) was added 10% Pd/C (400 mg, wet). The mixture was stirred at 10° C. under H₂ (15 psi) for 2 hours. LCMS showed 100% desired product formed. The mixture was filtered and the filtrate was concentrated in vacuum to give the product of 4-amino-3-[(3-methoxycyclobutyl)amino]benzonitrile (1.8 g, crude) as a brown oil.

Step c: A mixture of 4-amino-3-[(3-methoxycyclobutyl)amino]benzonitrile (1.8 g, 8.3 mmol), TBAB (5.3 g, 16.5 mmol), TEA (4.6 mL, 33.1 mmol) and 1,2-dibromoethane (1.0 mL) was stirred at 60° C. for 12 hours. LCMS showed 47.3% start material left. 1,2-dibromoethane (3.0 mL) was added to the mixture and the mixture was stirred at 60° C. for another 4 hours. LCMS showed 77.1% desired product was formed and 16.0% start material left. The mixture was poured into water (50.0 mL) and extracted with DCM (50.0 mL×3). The organic layers washed with brine and dried over anhydrous Na₂SO₄. The mixture was filtered and the filtrate was concentrated in vacuum to give residue. The residue was purified by flash silica gel chromatography (Petroleum ether/EtOAc=1/0 to 1/1) to give the product of 4-[trans-3-methoxycyclobutyl]-1,2,3,4-tetrahydroquinoxaline-6-carbonitrile (440.0 mg, 21.8% yield) as an off-white solid. Another batch a mixture of start material and desired product (700.0 mg) was remained.

Synthesis of 4-(1-acetylazetidin-3-yl)-1,2,3,4-tetra-hydroquinoxaline-6-carbonitrile, Used in the Preparation of Compound 471

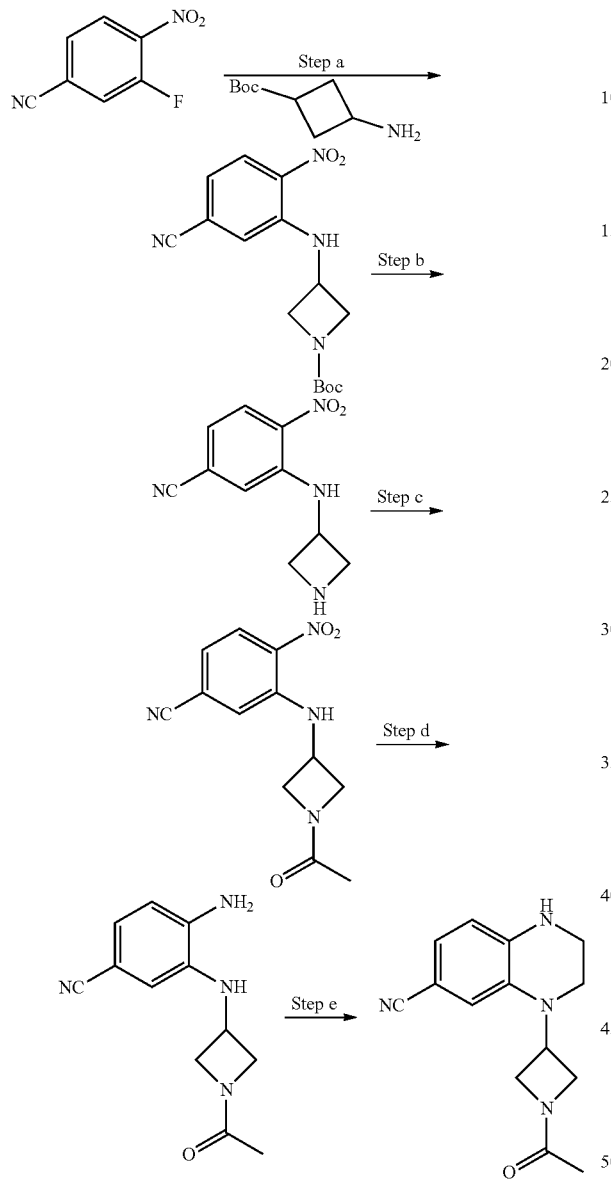

Step a: To a solution of 3-fluoro-4-nitrobenzonitrile (1.9 g, 11.6 mmol) in EtOH (20 mL) was added tert-butyl 3-aminoazetidine-1-carboxylate (2.0 g, 11.6 mmol) and Et₃N (2.3 g, 23.2 mmol). The mixture stirred at 40° C. for 12 hours. LCMS showed ~90% the desired product formed. The reaction mixture was concentrated to dryness, which was purified by silica gel chromatography (eluent: Petroleum ether:Ethyl acetate=5:1) to give tert-butyl 3-[(5-cyano-2-nitrophenyl)amino]azetidine-1-carboxylate (2.2 g, 59.6% yield) as a yellow solid.

Step b: To a solution of tert-butyl 3-[(5-cyano-2-nitrophenyl)amino]azetidine-1-carboxylate (2.0 g, 6.3 mmol) in DCM (50 mL) was added TFA (10 mL), the mixture stirred at 25° C. for 2 hours, LCMS showed the desired product formed. The reaction mixture was concentrated to dryness, MeOH (20 mL), DCM (200 mL) and K₂CO₃ (1 g) were added. The mixture was filtered and the filtrate was concentrated to dryness to give the product 3-[(azetidin-3-yl)amino]-4-nitrobenzonitrile (2.1 g, crude product) as a yellow solid.

Step c: A mixture of 3-[(azetidin-3-yl)amino]-4-nitrobenzonitrile (2 g, 9.2 mmol) in DCM (20 mL) was added TEA (1.9 g, 18.3 mmol) and AcCl (1.1 g, 13.7 mmol) at 0° C. The mixture stirred at 25° C. for 12 hours. LCMS showed the desired product was formed. The mixture washed with brine (10 mL) and concentrated. The residue was purified by column chromatography (Petroleum ether:Ethyl acetate=1:0 to 1:1) to give 3-[(1-acetylazetidin-3-yl)amino]-4-nitrobenzonitrile (1.2 g, 50.4% yield) as a yellow solid.

Step d: A solution of 3-[(1-acetylazetidin-3-yl)amino]-4-nitrobenzonitrile (1.1 g, 4.2 mmol) and wet 10% Pd/C (100 mg) in THF(10 mL) was stirred at 10° C. for 12 hours under H₂ (15 psi). LCMS showed the reaction was consumed completely. The reaction mixture was filtered and the filtrate was concentrated under reduced pressure to afford the product of 3-[(1-acetylazetidin-3-yl)amino]-4-aminobenzonitrile (780 mg, 71.5% yield), which was used in the next step without further purification.

Step e: TEA (1.1 g, 10.4 mmol), 1,2-dibromoethane (2.0 g, 10.4 mmol) and TBAB (837 mg, 2.6 mmol) was stirred at 60° C. for 12 hours. LCMS showed the reaction was consumed completely. The mixture was diluted with H₂O (20 mL) and extracted DCM (20 mL×3). The combined organic layers were washed with brine (30 mL), dried over anhydrous Na₂SO₄, filtered and concentrated under reduced pressure to give a residue. The residue was purified by column chromatography (DCM:MeOH=10:0 to 10:1) to afford the product of 4-(1-acetylazetidin-3-yl)-1,2,3,4-tetrahydroquinoxaline-6-carbonitrile (490 mg, 73.5% yield) as a light yellow solid.

Synthesis of tert-butyl (1-(3-mercapto-1-(tetra-hydro-2H-pyran-2-yl)-1H-pyrazolo[3,4-b]pyrazin-6-yl)-4-methylpiperidin-4-yl)carbamate, Used in the Preparation of Compound 477

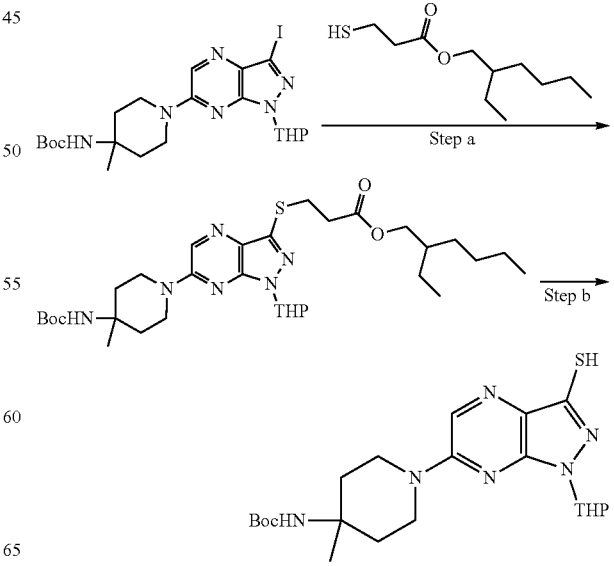

Step a: A microwave vial was charged with tert-butyl (1-(3-iodo-1-(tetrahydro-2H-pyran-2-yl)-1H-pyrazolo[3,4-b]pyrazin-6-yl)-4-methylpiperidin-4-yl)carbamate (390 mg, 719 μmol), (69.1 mg, 71.9 μmol), dioxane (4 mL), N-ethyl-N-isopropylpropan-2-amine (373 μL, 2.15 mmol) and 2-ethylhexyl 3-mercaptopropanoate (242 μL, 1.07 mmol). The vial was sealed, and the mixture was stirred in the microwave at 110° C. for 1 hr. The reaction was partitioned between EA/water, the organic layer was separated, washed with brine, dried and pre-adsorbed on SiO₂. The residue was purified on ISCO Si-12g (10-50% EA/heptanes) to give 2-ethylhexyl 3-((6-(4-((tert-butoxycarbonyl)amino)-4-methylpiperidin-1-yl)-1-(tetrahydro-2H-pyran-2-yl)-1H-pyrazolo[3,4-b]pyrazin-3-yl)thio)propanoate. LCMS m/z: 633.4 (M+H)⁺.

Step b: A resealable reaction vial was charged with 2-ethylhexyl 3-((6-(4-((tert-butoxycarbonyl)amino)-4-methylpiperidin-1-yl)-1-(tetrahydro-2H-pyran-2-yl)-1H-pyrazolo[3,4-b]pyrazin-3-yl)thio)propanoate (450 mg, 711 μmol) and THF (5 mL) then cooled to −78° C. 1M tBuOK in THF (239 mg, 2.13 mmol) was added which made the reaction mixture became a gel-like solid. The reaction was warmed up to 25° C., and diluted with THF (10 mL). After 2 hrs, the reaction mixture was partitioned between sat. NH₄Cl and ethyl acetate. The organic layer was separated, dried and concentrated to yield tert-butyl (1-(3-mercapto-1-(tetrahydro-2H-pyran-2-yl)-1H-pyrazolo[3,4-b]pyrazin-6-yl)-4-methylpiperidin-4-yl)carbamate as an orange foam. LCMS m/z: 471.2 (M+Na)+.

Synthesis of (1-acetyl-3-piperidyl) 4-methylbenzenesulfonate, Used in the Preparation of Compound 488

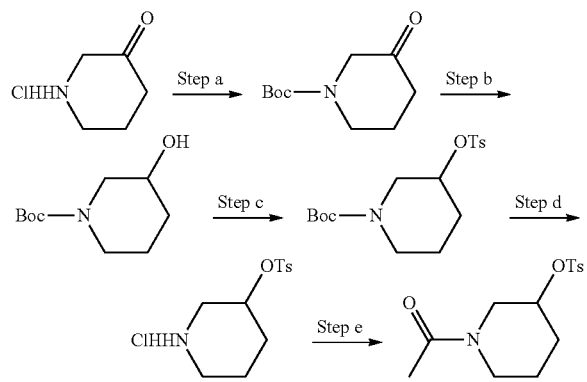

Step a: To a mixture of piperidin-3-one hydrochloride (5.0 g, 36.9 mmol) and TEA (11.2 g, 110.6 mmol) in DCM (50.0 mL) was added (Boc)₂O (12.1 g, 55.3 mmol). The reaction mixture was stirred at 10° C. for 12 hours. The reaction mixture was concentrated under reduced pressure to give a residue, which was purified by column chromatography (petroleum ether:ethyl acetate=20:1 to 10:1) to afford the product of tert-butyl 3-oxopiperidine-1-carboxylate (4.2 g, 54% yield) as a yellow oil.

Step b: To a mixture of tert-butyl 3-oxopiperidine-1-carboxylate (4.1 g, 20.6 mmol) in anhydrous MeOH (40.0 mL) at 0° C. was added NaBH4 (1.6 g, 41.2 mmol). Then the reaction mixture was stirred at 20° C. for 1 hour. The reaction mixture was concentrated under reduced pressure to give a residue, which was purified by column chromatography (petroleum ether:ethyl acetate=4:1 to 1:1) to afford the product of tert-butyl 3-hydroxypiperidine-1-carboxylate (2.1 g, 48% yield) as a colorless oil.

Step c: To a mixture of NaH (1.3 g, 31.3 mmol, 60% in mineral oil) in anhydrous THF (20.0 mL) at 0° C. was added tert-butyl 3-hydroxypiperidine-1-carboxylate (2.1 g, 10.4 mmol). After stirred for 30 min at this temperature, TsCl (3.0 g, 15.6 mmol) in THF (5.0 mL) was added. The reaction mixture was warmed to 20° C., and stirred for 1 hour. The reaction mixture was quenched by addition of sat NH₄Cl (5.0 mL) at 0° C., and then diluted with H₂O (20.0 mL), and extracted with ethyl acetate (25.0 mL×2). The combined organic layers were washed with brine (20.0 mL), dried over anhydrous Na2SO4, filtered and concentrated under reduced pressure to give a residue, which was purified by column chromatography (petroleum ether: ethyl acetate=10:1 to 6:1) to afford the product of tert-butyl 3-(p-tolylsulfonyloxy) piperidine-1-carboxylate (2.0 g, 52% yield) as a colorless oil.

Step d: A mixture of tert-butyl 3-(p-tolylsulfonyloxy) piperidine-1-carboxylate (1.0 g, 2.8 mmol) in 4 M HCl/MeOH (10.0 mL) was stirred at 15° C. for 1 hour. The reaction mixture was concentrated in vacuo to afford the product of piperidin-3-yl 4-methylbenzenesulfonate hydrochloride (810.0 mg, crude product) as colorless oil, which was used in the next step without further purification.

Step e: To a mixture of piperidin-3-yl 4-methylbenzenesulfonate hydrochloride (800.0 mg, 2.7 mmol) and TEA (1.4 g, 13.7 mmol) in anhydrous DCM (15.0 mL) at 0° C. was added a solution of AcCl (537.7 mg, 6.9 mmol) in anhydrous DCM (5.0 mL) slowly. The reaction mixture was warmed to 20° C. stirred for 2 hours. The reaction mixture was concentrated in vacuo. The residue was diluted with H₂O (30.0 mL) and extracted with ethyl acetate (35.0 mL×2). The combined organic layers were washed with brine (20.0 mL), dried over anhydrous Na₂SO₄, filtered and concentrated under reduced pressure to afford the product of (1-acetyl-3-piperidyl) 4-methylbenzenesulfonate (690.0 mg, crude product) as a yellow oil.

Synthesis of tert-butyl (1-(3-mercapto-1-(4-methoxybenzyl)-1H-pyrazolo[3,4-b]pyrazin-6-yl)-4-methylpiperidin-4-yl)carbamate, Used in the Preparation of 489

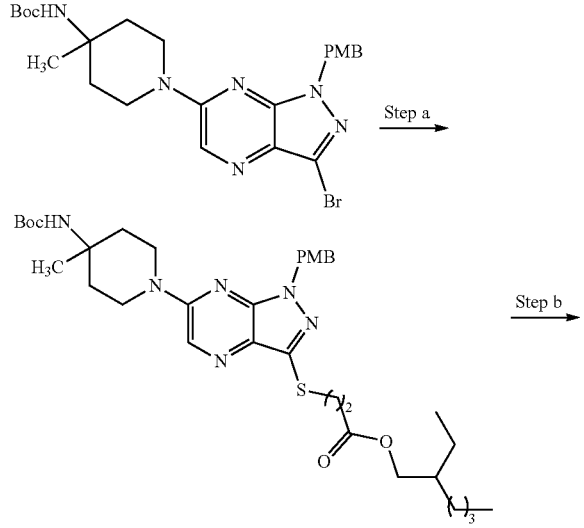

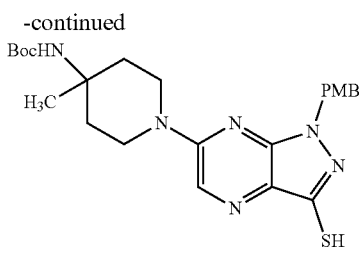

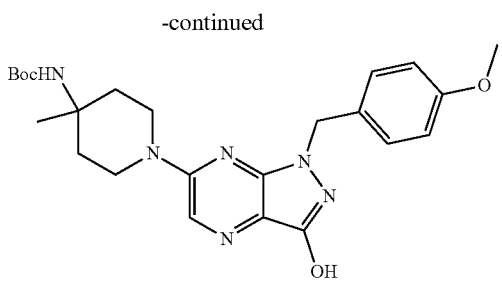

Step a: A resealable reaction vial was charged with tert-butyl (1-(3-bromo-1-(4-methoxybenzyl)-1H-pyrazolo[3,4-b]pyrazin-6-yl)-4-methylpiperidin-4-yl)carbamate (1.00 g, 1.88 mmol), 2-ethylhexyl 3-mercaptopropanoate (615 mg, 2.82 mmol), BrettPhos (100 mg, 188 μmol), BrettPhos-Pd G4 (173 mg, 188 μmol), DiEA (983 μL, 5.64 mmol) and a stirbar before being evacuated and purged with nitrogen three times. dioxane (25 mL) was added, and the mixture was stirred at 120° C. for 12 h. The reaction mixture was concentrated to give a residue, which was purified by by flash silica gel chromatography (Ethyl acetate/Petroleum ether=0/100 to 20/100) to afford the product 2-ethylhexyl 3-((6-(4-(((tert-butoxycarbonyl)amino)-4-methylpiperidin-1-yl)-1-(4-methoxybenzyl)-1H-pyrazolo[3,4-b]pyrazin-3-yl)thio)propanoate (1.00 g, 1.49 mmol) as a yellow oil. LCMS: [M+H]+ 669.3.

Step b: The compound 2-ethylhexyl 3-((6-(4-(((tert-butoxycarbonyl)amino)-4-methylpiperidin-1-yl)-1-(4-methoxybenzyl)-1H-pyrazolo[3,4-b]pyrazin-3-yl)thio)propanoate (700 mg, 1.04 mmol) was dissolved in THF (5 mL). The reaction mixture was cooled to −78° C., and t-BuOK (1 M, 3.12 mL, in THF) was added drop wise in 10 min under N2. The reaction mixture was stirred at −78° C. for 20 min, then diluted with DCM (30 mL) and acidified with HCl/MeOH (2 N) to pH=6 at −78° C. The mixture was washed with H2O (20 mL) and brine (20 ml). The organic layers were dried over anhydrous Na2SO4, filtered and concentrated to give the product tert-butyl (1-(3-mercapto-1-(4-methoxybenzyl)-1H-pyrazolo[3,4-b]pyrazin-6-yl)-4-methylpiperidin-4-yl)carbamate (500 mg, 1.03 mmol), which was carried on without further purification.

Synthesis of tert-butyl (1-(3-hydroxy-1-(4-methoxybenzyl)-1H-pyrazolo[3,4-b]pyrazin-6-yl)-4-methylpiperidin-4-yl)carbamate, Used in the Preparation of Compound 510

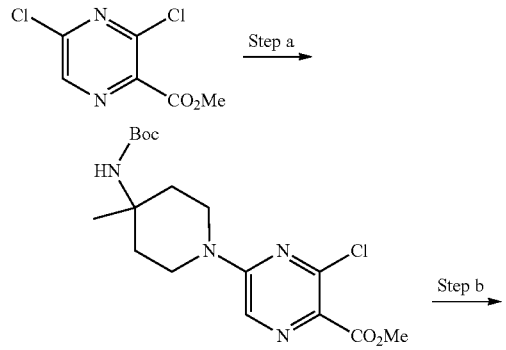

Step a: A resealable reaction vial was charged with methyl 3,5-dichloropyrazine-2-carboxylate (3.12 g, 15.0 mmol) and DMF (30 mL) then cooled to 0-5° C. The reaction was charged with tert-butyl (4-methylpiperidin-4-yl)carbamate (3.36 g, 15.7 mmol) and N-ethyl-N-isopropylpropan-2-amine (3.87 g, 30.0 mmol), and the mixture was stirred at 0-5° C. for 1 h. The reaction was partitioned between ethyl acetate/brine/water, the organic layer was dried over sodium sulfate and pre-adsorbed on SiO₂ (11g) before being purified by silica gel chromatography (eluting with ethyl acetate and heptane). The product containing fractions were pooled and concentrated in vacuo to yield methyl 5-(4-(((tert-butoxycarbonyl)amino)-4-methylpiperidin-1-yl)-3-chloropyrazine-2-carboxylate (5.14 g) as a light yellow foam. LCMS: [M+H]+ 407.3.

Step b: A round bottomed flask was charged with methyl 5-(4-(((tert-butoxycarbonyl)amino)-4-methylpiperidin-1-yl)-3-chloropyrazine-2-carboxylate (4.75 g, 12.3 mmol) (note: SM is foam/gum, was not thoroughly dried so amount is over-estimated), EtOH (45 mL), (4-methoxybenzyl)hydrazine hydrochloride (2.77 g, 14.7 mmol) and triethylamine (5.13 mL, 36.9 mmol). The solution was stirred at 75° C. 18 h. The mixture was cooled to rt, filtered, the cake washed with EtOH and air dried to constant weight to give tert-butyl (1-(3-hydroxy-1-(4-methoxybenzyl)-1H-pyrazolo[3,4-b]pyrazin-6-yl)-4-methylpiperidin-4-yl)carbamate (2.76 g) as a white solid. LCMS: [M+H]+ 469.5.

Synthesis of (rel)-5-[(3S)-1-methyl-5-oxopyrrolidin-3-yl]-1,2,3,4-tetrahydroquinoline-6-carbonitrile, Used in the Preparation of Compound 519

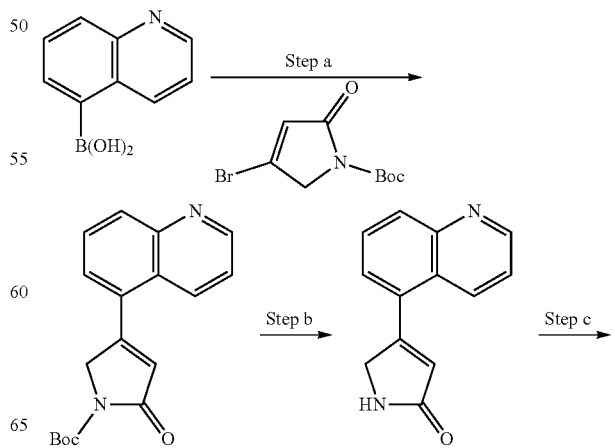

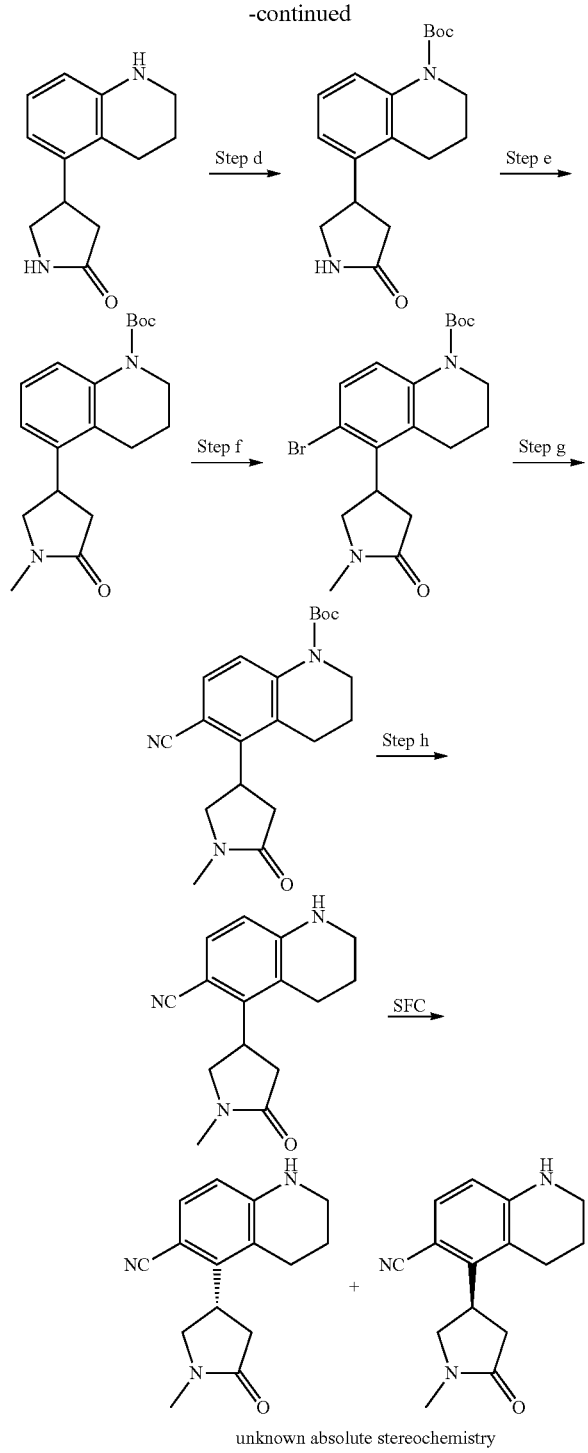

unknown absolute stereochemistry

Step a: A mixture of tert-butyl 4-bromo-2-oxo-2,5-dihydro-1H-pyrrole-1-carboxylate (4.4 g, 16.5 mmol), (quinolin-5-yl)boronic acid (3.4 g, 19.8 mmol), Pd(dppf)Cl$_2$ (603 mg, 825 μmol) and K$_2$CO$_3$ (4.6 g, 33.0 mmol) in dioxane (70 mL)/H$_2$O (10 mL) was stirred at 100° C. for 3 hours under N$_2$ atmosphere. LCMS showed the reaction was consumed completely. The reaction mixture was concentrated in vacuum to give a residue, which was dissolved in ethyl acetate (100 mL), washed with H$_2$O (80 mL×2). The organic phases were washed with brine (30 mL), dried over anhydrous Na$_2$SO$_4$, filtered and concentrated in vacuum to give a residue, which was purified by silica gel chromatography (Ethyl acetate in Petroleum ether=80% to 95%) to afford the product of tert-butyl 2-oxo-4-(quinolin-5-yl)-2,5-dihydro-1H-pyrrole-1-carboxylate (3.4 g, 67.3% yield) as a yellow solid.

Step b: A mixture of tert-butyl 2-oxo-4-(quinolin-5-yl)-2,5-dihydro-1H-pyrrole-1-carboxylate (3.4 g, 10.9 mmol) in HCl/MeOH (4 M, 50 mL) was stirred at 15° C. for 12 hours. LCMS showed the reaction was consumed completely. The reaction mixture was concentrated in vacuum to afford the product of 4-(quinolin-5-yl)-1H-pyrrol-2(5H)-one (2.1 g, 91.7% yield) as a yellow solid.

Step c: A mixture of 4-(quinolin-5-yl)-2,5-dihydro-1H-pyrrol-2-one (2.0 g, 9.5 mmol) and PtO$_2$ (215 mg, 951 μmol) in MeOH (40 mL) was stirred at 25° C. for 12 hours under H$_2$ atmosphere (15 psi). LCMS showed the reaction was consumed completely. The reaction mixture was filtered and concentrated in vacuum to afford the product of 4-(1,2,3,4-tetrahydroquinolin-5-yl)pyrrolidin-2-one (2.0 g, crude product) as a yellow solid.

Step d: A mixture of 4-(1,2,3,4-tetrahydroquinolin-5-yl)pyrrolidin-2-one (1.9 g, 8.8 mmol) and (Boc)$_2$O (1.9 g, 8.8 mmol) in dioxane (50 mL) was stirred at 80° C. for 12 hours. LCMS showed the reaction was consumed completely. The reaction mixture was concentrated in vacuum to give a residue, which was purified by silica gel chromatography (Methanol in Dichloromethane=0% to 8%) to afford the product of tert-butyl 5-(5-oxopyrrolidin-3-yl)-1,2,3,4-tetrahydroquinoline-1-carboxylate (1.5 g, 54.1% yield) as a yellow oil.

Step e: To a mixture of NaH (60% in mineral oil, 365 mg) in anhydrous THF (30 mL) at 0° C. was added the solution of tert-butyl 5-(5-oxopyrrolidin-3-yl)-1,2,3,4-tetrahydroquinoline-1-carboxylate (1.5 g, 4.6 mmol) in THF (10 mL), the resulting mixture was stirred for 30 min. MeI (3.3 g, 22.9 mmol) in THF (10 mL) was added, the reaction mixture was warmed to 20° C., and stirred for 11.5 hours. LCMS showed the reaction was consumed completely. The reaction mixture was quenched with sat.NH4Cl, diluted with H$_2$O (50 mL) and extracted with ethyl acetate (55 mL×2). The organic phases were washed with brine (30 mL), dried over anhydrous Na$_2$SO$_4$, filtered and concentrated in vacuum to give the crude product, which was purified by silica gel chromatography (Ethyl acetate as eluent) to afford the product of tert-butyl 5-(1-methyl-5-oxopyrrolidin-3-yl)-1,2,3,4-tetrahydroquinoline-1-carboxylate (1.2 g, 82.7% yield) as a yellow oil.

Step f: To a mixture of tert-butyl 5-(1-methyl-5-oxopyrrolidin-3-yl)-1,2,3,4-tetrahydroquinoline-1-carboxylate (650 mg, 2.0 mmol) in DMF (30 mL) at 0° C. was added NBS (380 mg, 2.2 mmol), the reaction mixture was warmed to 15° C., and stirred for 12 hours. LCMS showed the reaction was consumed completely. The reaction mixture was diluted with ethyl acetate (60 mL), extracted with H$_2$O (50 mL×2). The organic phase was washed with brine (20 mL), dried over anhydrous Na$_2$SO$_4$, filtered and concentrated in vacuum to give a residue, which was purified by silica gel chromatography (Ethyl acetate as eluent) to afford the product of tert-butyl 6-bromo-5-(1-methyl-5-oxopyrrolidin-3-yl)-1,2,3,4-tetrahydroquinoline-1-carboxylate (580 mg, 72.3% yield) as a colorless oil.

Step g: A mixture of tert-butyl 6-bromo-5-(1-methyl-5-oxopyrrolidin-3-yl)-1,2,3,4-tetrahydroquinoline-1-carboxylate (540 mg, 1.3 mmol), [(t-Bu$_3$P)$_2$]Pd (66.9 mg, 131 μmol) and Zn(CN)$_2$ (303 mg, 2.6 mmol) in DMF (25 mL) was stirred at 130° C. for 12 hours under N$_2$ atmosphere. LCMS showed the reaction was consumed completely. The reaction mixture was diluted with ethyl acetate (70 mL), washed with H₂O (50 mL×2). The organic phase was washed with brine (20 mL), dried over anhydrous Na₂SO₄, filtered and concentrated in vacuum to give a residue, which was purified by silica gel chromatography (Methanol in Dichloromethane=0% to 7%) to afford the product of tert-butyl 6-cyano-5-(1-methyl-5-oxopyrrolidin-3-yl)-1,2,3,4-tetrahydroquinoline-1-carboxylate (450 mg, 96.7% yield) as a colorless oil.

Step h: A mixture of tert-butyl 6-cyano-5-(1-methyl-5-oxopyrrolidin-3-yl)-1,2,3,4-tetrahydroquinoline-1-carboxylate (440 mg, 1.2 mmol) in HCl/MeOH (4M, 10 mL) was stirred at 25° C. for 2 hours. LCMS showed the reaction was consumed completely. The reaction mixture was diluted with MeOH (10 mL) and adjusted pH=8 with solid NaHCO₃. The mixture was filtered and concentrated in vacuum to give a residue, which was purified by prep-HPLC (NH₃.H₂O) to afford the product of 5-(1-methyl-5-oxopyrrolidin-3-yl)-1,2,3,4-tetrahydroquinoline-6-carbonitrile (140 mg, 44.5% yield) as a white solid.

SFC: The compound is separable in developing SFC (Column: ChiralPak AD-3 150×4.6 mm I.D., 3 um Gradient: 40% of EtOH (0.05% DEA) in CO₂ Flow rate: 2.5 mL/min Column temperature: 35° C.). The compound of rac-5-(1-methyl-5-oxopyrrolidin-3-yl)-1,2,3,4-tetrahydroquinoline-6-carbonitrile (140 mg, 548 μmol) was separated by preparative Chiral-SFC (Column: Phenomenex-Amylose-1 (250 mm*30 mm, 5 um). condition: 0.1% NH₃.H₂O EtOH, begin B: 30%, end B: 30%, Flow Rate: 50 ml/min) to afford the desired product of (rel)-5-[(3S)-1-methyl-5-oxopyrrolidin-3-yl]-1,2,3,4-tetrahydroquinoline-6-carbonitrile (57 mg, 41% yield) as a white solid, which was confirmed by HPLC, SFC (e.e.=99.8%, the faster eluting isomer) and (rel)-5-[(3R)-1-methyl-5-oxopyrrolidin-3-yl]-1,2,3,4-tetrahydroquinoline-6-carbonitrile (57 mg, 41% yield) as a white solid, which was confirmed by HPLC, SFC (R$_f$=4.863 min, e.e.=98.7%, the slower eluting isomer). The faster eluting isomer (R$_f$=4.607 min) is the peak 1 in developing SFC. The slower eluting isomer (R, =4.863 min) is the peak 2 in developing SFC.

Synthesis of 2-methyl-6,7,8,9-tetrahydro-1H-pyrrolo[3,4-J]quinolin-3-one, Used in the Preparation of Compound 520

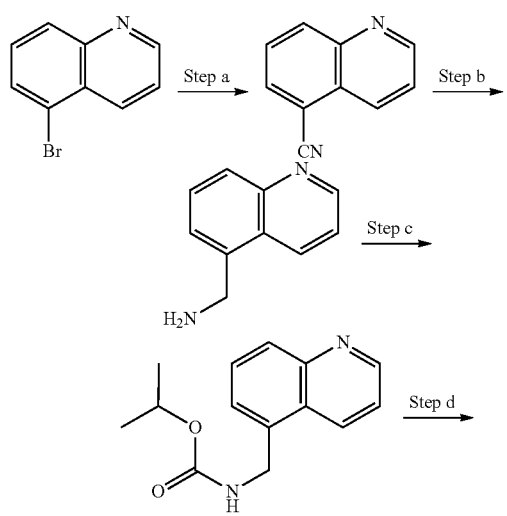

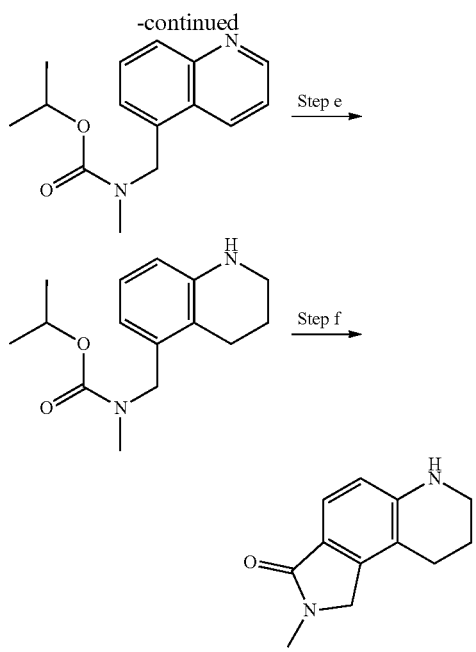

Step a: The mixture of 5-bromoquinoline (2.0 g, 9.61 mmol, 1.0 eq), Zn(CN)₂ (2.26 g, 19.23 mmol, 2.0 eq) and XantPhos-Pd-G4 (924.8 mg, 961.3 umol, 0.1 eq) in dioxane (20.0 mL) and H₂O (2.0 mL) was stirred at 80° C. for 16 hours under N₂. LCMS showed the starting material was consumed completely and the desired MS was detected. The reaction mixture was concentrated under reduced pressure. The residue was purified by silica gel column chromatography (Petroleum ether/Ethyl acetate=1:1) to afford the product of quinoline-5-carbonitrile (1.28 g, 84.6% yield) as a white solid.

Step b: To a solution of quinoline-5-carbonitrile (780.0 mg, 5.06 mmol, 1.0 eq) in MeOH (10.0 mL) were added Raney-Ni (300.0 mg, 5.11 mmol, 1.0 eq) and NH₃.H₂O (1.91 g, 2.10 mL, 28% purity). The reaction mixture was degassed and refilled with H₂ for three times. The reaction mixture was stirred at 15° C. for 16 hours under H₂ (15 psi). LCMS showed the starting material was consumed completely and the desired MS was detected. The reaction mixture was filtered through a pad of celite and washed with MeOH (5.0 mL×4). The filtrate was concentrated under reduced pressure to give a green residue. The residue was purified by silica gel column chromatography (DCM: MeOH=10:1) to afford the product of 5-quinolylmethanamine (550.0 mg, crude) as a green oil.

Step c: To a solution of 5-quinolylmethanamine (550.0 mg, 3.48 mmol, 1.0 eq) in DCM (7.0 mL) were added isopropyl carbonochloridate (852.1 mg, 6.95 mmol, 965.0 uL, 2.0 eq) and TEA (1.06 g, 10.43 mmol, 1.45 mL, 3.0 eq). The reaction mixture was stirred at 15° C. for 16 hours under N₂. LCMS showed the starting material was consumed completely and the desired MS was detected. The reaction mixture was concentrated under reduced pressure to give a yellow residue. The residue was purified by silica gel column chromatography (Petroleum ether/Ethyl acetate=0:1) to afford the product of isopropyl N-(5-quinolylmethyl)carbamate (670.0 mg, 78.5% yield) as a white solid.

Step d: To a solution of isopropyl-N-(5-quinolylmethyl)carbamate (830.0 mg, 3.40 mmol, 1.0 eq) and Cs₂CO₃ (3.32 g, 10.19 mmol, 3.0 eq) in DMF (10.0 mL) was added a solution of MeI (578.7 mg, 4.08 mmol, 253.8 uL, 1.2 eq) in DMF (2.0 mL). The reaction mixture was stirred at 15° C. for 16 hours under $N_2$. LCMS showed 40% of the starting material was remained and 42% of the desired product formed. The reaction mixture was concentrated under reduced pressure. The residue was washed with water (70.0 mL) and extracted with EtOAc (50.0 mL×3). The combined organic layer was concentrated under reduced pressure to give a red residue. The residue was purified by silica gel column chromatography (DCM:MeOH=10:1) to afford the product of isopropyl-N-methyl-N-(5-quinolylmethyl)carbamate (610.0 mg, crude) as a red oil. The crude product was purified again by silica gel column chromatography (Petroleum ether/Ethyl acetate=0:1) to afford the product of isopropyl-N-methyl-N-(5-quinolylmethyl)carbamate (210.0 mg, 96.4% yield) as a yellow oil.

Step e: To a solution of isopropyl-N-methyl-N-(5-quinolylmethyl)carbamate (130.0 mg, 503.3 umol, 1.0 eq) in MeOH (3.0 mL) was added $PtO_2$ (20.0 mg, 88.08 umol, 1.75 eq). The reaction mixture was degassed and refilled with $H_2$ for three times. The reaction mixture was stirred at 30° C. for 16 hours under $H_2$ (15 psi). LCMS showed the starting material was consumed completely and the desired MS was detected. The reaction mixture was filtered through a pad of celite and washed with MeOH (5.0 mL×3). The filtrate was concentrated under reduced pressure to give the product of isopropyl N-methyl-N-(1,2,3,4-tetrahydroquinolin-5-ylmethyl)carbamate (115.0 mg, 87.1% yield, crude) as a green oil.

Step f: To a solution of isopropyl N-methyl-N-(1,2,3,4-tetrahydroquinolin-5-ylmethyl)carbamate (60.0 mg, 228.7 umol, 1.0 eq) in DCM (3.8 mL) was added $P_2O_5$ (324.6 mg, 2.29 mmol, 10.0 eq). The reaction mixture was stirred at 40° C. for 16 hours under $N_2$. LCMS showed 10% of the starting material was remained and 60% of the desired product formed. The reaction mixture was adjusted to pH=8 by adding saturated $NaHCO_3$ aqueous solution and extracted with DCM (30.0 mL×2). The combined organic layer was dried over anhydrous $Na_2SO_4$ and concentrated under reduced pressure to give a yellow residue. The crude product on page ES9196-29 was combined with ES9196-30 for further purification. The combined crude product was purified by prep-HPLC ($NH_4HCO_3$) (column: Waters Xbridge 150×25 5 u; mobile phase: [water (10 mM $NH_4HCO_3$)-ACN]; B %: 15%-45%, 7 min) to afford the product of 2-methyl-6,7,8,9-tetrahydro-1H-pyrrolo[3,4-]quinolin-3-one (20.0 mg, 43.2% yield) as a white solid.

Synthesis of 5-[(2S)-oxolan-2-yl]-1,2,3,4-tetrahydroquinoline-6-carbonitrile, Used in the Preparation of Compound 522

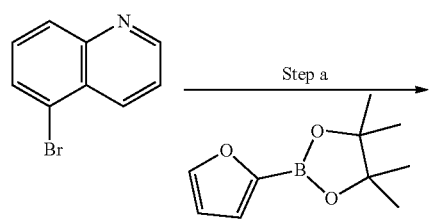

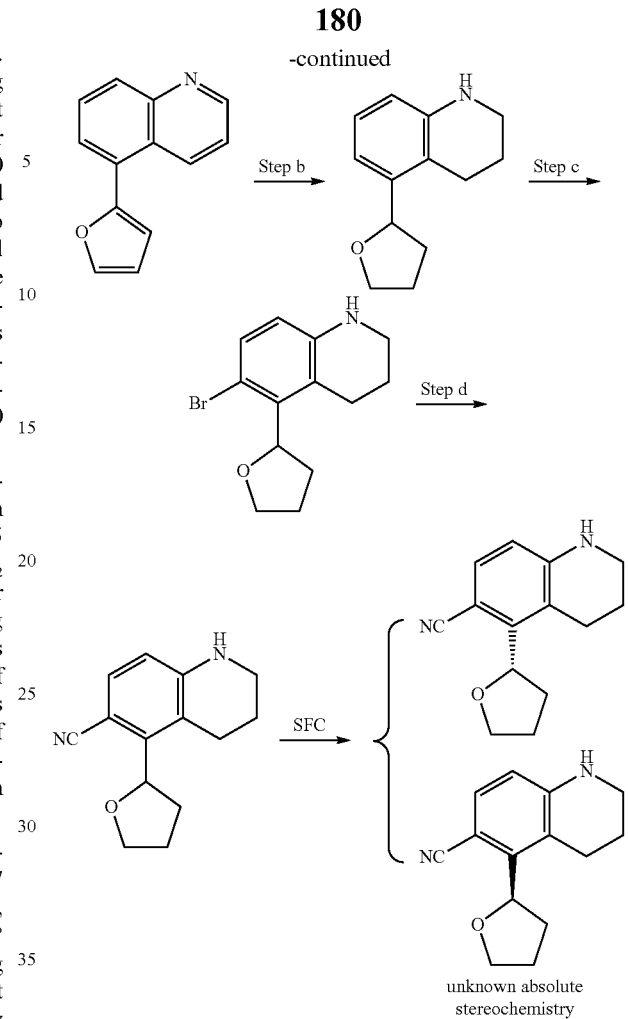

unknown absolute stereochemistry

Step a: A mixture of 5-bromoquinoline (3.9 g, 18.7 mmol), 2-(furan-2-yl)-4,4,5,5-tetramethyl-1,3,2-dioxaborolane (3.6 g, 18.7 mmol), Pd(dppf)$Cl_2$ (1.3 g, 1.8 mmol) and $K_2CO_3$ (7.7 g, 56.1 mmol) in dioxane/$H_2O$(40 mL/4 mL) was stirred at 90° C. under $N_2$ for 12 hours. After concentration, the residue was purified by silica column (Ethyl acetate in Petroleum ether 0-30%) to give the desired product of 5-(furan-2-yl) quinoline (3.6 g, 98.6% yield) as a yellow oil.

Step b: A mixture of 5-(furan-2-yl)quinoline (3.6 g, 18.4 mmol) and 10% Pd/C (0.4 g, wet) in MeOH (40 mL) was stirred at 30° C. for 1 day under $H_2$ (15 psi). LCMS showed 60% of starting material 2 was still remained. The mixture was filtered and the filtrate was concentrated to give a residue (3.7 g) which was dissolved in MeOH (40 mL). 10% Pd/C (0.8 g, wet) was added. The mixture was stirred at 30° C. for 1 day under $H_2$ (15 psi). LCMS showed 34.7% of starting material 2 was still remained. The mixture was filtered and the filtrate was concentrated in vacuum to give a residue (3.9 g) as a yellow oil. The residue was dissolved in MeOH (40 mL). 10% Pd/C (1 g, wet) was added. The mixture was stirred at 30° C. for 1 day under $H_2$ (15 psi). LCMS showed the no starting material 2 was remained and the 59% product formed. The mixture was filtered and the filtrate was concentrated in vacuum. The residue was purified by silica column (ethyl acetate in petroleum ether=0~50%) to give the desired product of 5-(oxolan-2-yl)-1,2,3,4-tetrahydroquinoline (1.6 g, crude) as a yellow oil.

Step c: To a solution of 5-(oxolan-2-yl)-1,2,3,4-tetrahydroquinoline (1.54 g, 7.57 mmol) in DMF (15.0 mL) was added NBS (1.34 g, 7.57 mmol) at 15° C. under $N_2$. The mixture was stirred at 15° C. for 0.5 h. The mixture was diluted with EtOAc (50 mL), washed with $H_2O$ (10 mL×3), brine (10 mL) and concentrated in vacuum. The residue was purified by silica column (ethyl acetate in petroleum ether=0~30%) to give the desired product of 6-bromo-5-(oxolan-2-yl)-1,2,3,4-tetrahydroquinoline (1.92 g, 90.1% yield) as a yellow oil.

Step d: A mixture of 6-bromo-5-(oxolan-2-yl)-1,2,3,4-tetrahydroquinoline (500 mg, 1.77 mmol), $Zn(CN)_2$ (415 mg, 3.54 mmol), $Pd(t-Bu_3P)_2$ (90.4 mg, 177 μmol) in DMF (2.0 mL) was stirred at 130° C. for 12 hours under $N_2$. After concentration, the residue was purified by silica column (ethyl acetate in petroleum ether=0~50%) to give the desired SFC: The compound of rac-5-(oxolan-2-yl)-1,2,3,4-tetrahydroquinoline-6-carbonitrile (150 mg, 657 μmol) was separated by preparative chiral SFC (Column: DAICEL CHIRALCEL OJ-H(250 mm*30 mm, 5 um). Mobile phase: 30% of ethanol (0.1% $NH_3$—$H_2O$) in $CO_2$. Flow rate: 65 mL/min.) to afford the desired product of 5-[(2S)-oxolan-2-yl]-1,2,3,4-tetrahydroquinoline-6-carbonitrile (74.0 mg, 49.6% yield, $R_t$=2.864 min, e.e.=100%, the faster eluting isomer) as a yellow solid and the enantiomer 5-[(2R)-oxolan-2-yl]-1,2,3,4-tetrahydroquinoline-6-carbonitrile (75.0 mg, 50.3% yield, $R_t$=3.246 min, e.e.=100%, the slower eluting isomer) as a yellow solid.

Synthesis of (4S)-1-methyl-4-(1,2,3,4-tetrahydroquinolin-5-yl)pyrrolidin-2-one, Used in the Preparation of Compound 521 and Compound 523

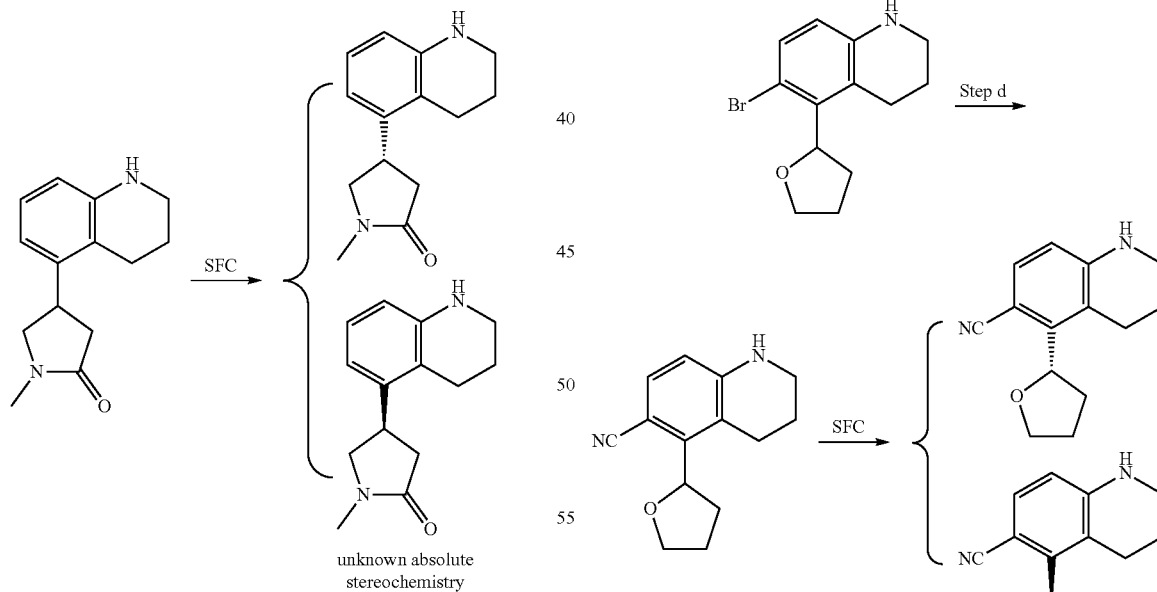

unknown absolute stereochemistry

The enantiomers of 1-methyl-4-(1,2,3,4-tetrahydroquinolin-5-yl)pyrrolidin-2-one were separable in developing SFC: (Column: Chiralpak AS-3 150×4.6 mm I.D., 3 um. Mobile phase: A: CO2; B: ethanol (0.05% DEA). Gradient: from 5% to 40% of B in 5 min and hold 40% for 2.5 min, then 5% of B for 2.5 min. Flow rate: 2.5 mL/min. Column temp: 35° C. ABPR: 1500 psi). The compound of 1-methyl-4-(1,2,3,4-tetrahydroquinolin-5-yl)pyrrolidin-2-one (230.0 mg, 998.68 umol, 1.0 eq) was separated by preparative SFC column: (DATCEL CHIR ALPAK A S-H (250 mm×30 mm, 5 um). Mobile phase: 0.1% $NH_3$—$H_2O$, EtOH. Begin B: 45%, End B: 45%. Flow rate: 50 mL/min) to afford the product of (4S)-1-methyl-4-(1,2,3,4-tetrahydroquinolin-5-yl)pyrrolidin-2-one (the faster eluting isomer, 105.0 mg, 455.9 umol, 45.7% yield): e.e.=99.4%, $R_t$=3.734 min, as a yellow oil and the enantiomer (4R)-1-methyl-4-(1,2,3,4-tetrahydroquinolin-5-yl)pyrrolidin-2-one (1b, the slower eluting isomer, 105.0 mg, 455.9 umol, 45.7% yield): e.e.=99.9%, $R_t$=4.728 min, as a yellow oil.

Synthesis of 5-[(2R)-oxolan-2-yl]-1,2,3,4-tetrahydroquinoline-6-carbonitrile, Used in the Preparation of Compound 524

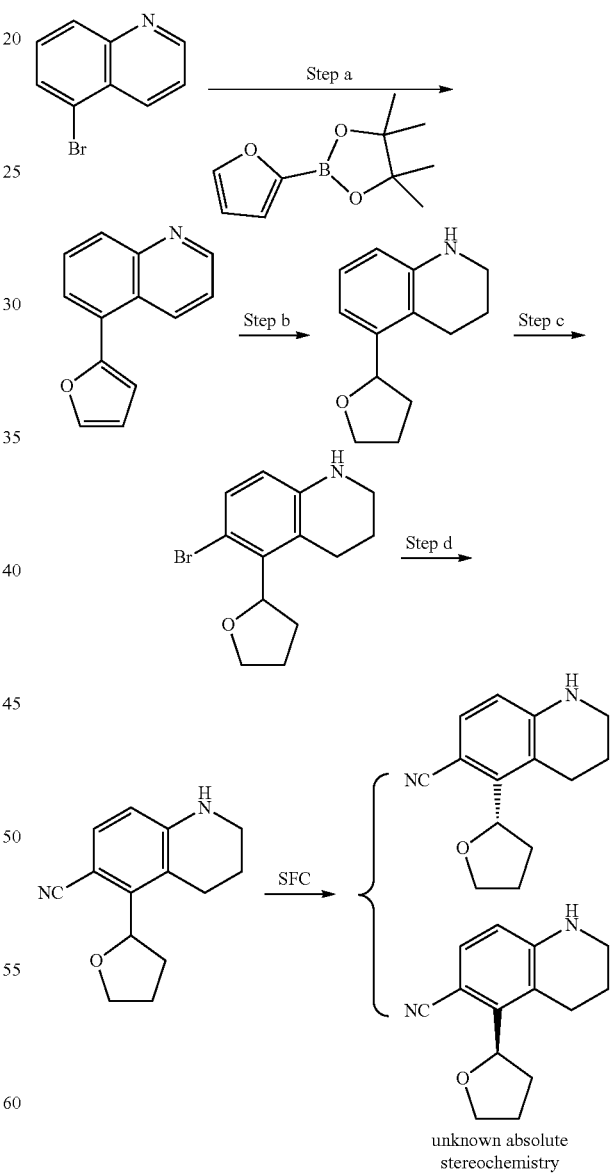

unknown absolute stereochemistry

Step a: A mixture of 5-bromoquinoline (3.9 g, 18.7 mmol), 2-(furan-2-yl)-4,4,5,5-tetramethyl-1,3,2-dioxaborolane (3.6 g, 18.7 mmol), $Pd(dppf)Cl_2$ (1.3 g, 1.8 mmol) and K₂CO₃ (7.7 g, 56.1 mmol) in dioxane/H₂O(40 mL/4 mL) was stirred at 90° C. under N₂ for 12 hours. After concentration, the residue was purified by silica column (Ethyl acetate in Petroleum ether 0-30%) to give the desired product of 5-(furan-2-yl) quinoline (3.6 g, 98.6% yield) as a yellow oil.

Step b: A mixture of 5-(furan-2-yl)quinoline (3.6 g, 18.4 mmol) and 10% Pd/C (0.4 g, wet) in MeOH (40 mL) was stirred at 30° C. for 1 day under H₂ (15 psi). LCMS showed 60% of starting material 2 was still remained. The mixture was filtered and the filtrate was concentrated to give a residue (3.7 g) which was dissolved in MeOH (40 mL). 10% Pd/C (0.8 g, wet) was added. The mixture was stirred at 30° C. for 1 day under H₂ (15 psi). LCMS showed 34.7% of starting material 2 was still remained. The mixture was filtered and the filtrate was concentrated in vacuum to give a residue (3.9 g) as a yellow oil. The residue was dissolved in MeOH (40 mL). 10% Pd/C (1 g, wet) was added. The mixture was stirred at 30° C. for 1 day under H₂ (15 psi). LCMS showed the no starting material 2 was remained and the 59% product formed. The mixture was filtered and the filtrate was concentrated in vacuum. The residue was purified by silica column (ethyl acetate in petroleum ether=0~50%) to give the desired product of 5-(oxolan-2-yl)-1,2,3,4-tetrahydroquinoline (1.6 g, crude) as a yellow oil.

Step c: To a solution of 5-(oxolan-2-yl)-1,2,3,4-tetrahydroquinoline (1.54 g, 7.57 mmol) in DMF (15.0 mL) was added NBS (1.34 g, 7.57 mmol) at 15° C. under N₂. The mixture was stirred at 15° C. for 0.5 h. The mixture was diluted with EtOAc (50 mL), washed with H₂O (10 mL×3), brine (10 mL) and concentrated in vacuum. The residue was purified by silica column (ethyl acetate in petroleum ether=0~30%) to give the desired product of 6-bromo-5-(oxolan-2-yl)-1,2,3,4-tetrahydroquinoline (1.92 g, 90.1% yield) as a yellow oil.

Step d: A mixture of 6-bromo-5-(oxolan-2-yl)-1,2,3,4-tetrahydroquinoline (500 mg, 1.77 mmol), Zn(CN)₂ (415 mg, 3.54 mmol), Pd(t-Bu₃P)₂ (90.4 mg, 177 µmol) in DMF (2.0 mL) was stirred at 130° C. for 12 hours under N₂. After concentration, the residue was purified by silica column (ethyl acetate in petroleum ether=0~50%) to give the desired SFC: The compound of rac-5-(oxolan-2-yl)-1,2,3,4-tetrahydroquinoline-6-carbonitrile (150 mg, 657 µmol) was separated by preparative chiral SFC (Column: DAICEL CHIRALCEL OJ-H(250 mm*30 mm, 5 um). Mobile phase: 30% of ethanol (0.1% NH₃.H₂O) in CO₂. Flow rate: 65 ml/min.) to afford the desired product 5-[(2R)-oxolan-2-yl]-1,2,3,4-tetrahydroquinoline-6-carbonitrile (75.0 mg, 50.3% yield, R_f=3.246 min, e.e.=100%, the slower eluting isomer) as a yellow solid and the enantiomer 5-[(2S)-oxolan-2-yl]-1,2,3,4-tetrahydroquinoline-6-carbonitrile (74.0 mg, 49.6% yield, R_f=2.864 min, e.e.=100%, the faster eluting isomer) as a yellow solid.

Synthesis of (rel)-5-[(3R)-1-methyl-5-oxopyrrolidin-3-yl]-1,2,3,4-tetrahydroquinoline-6-carbonitrile, Used in the Preparation of Compound 525

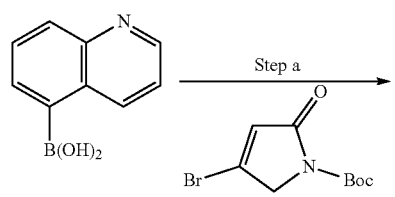

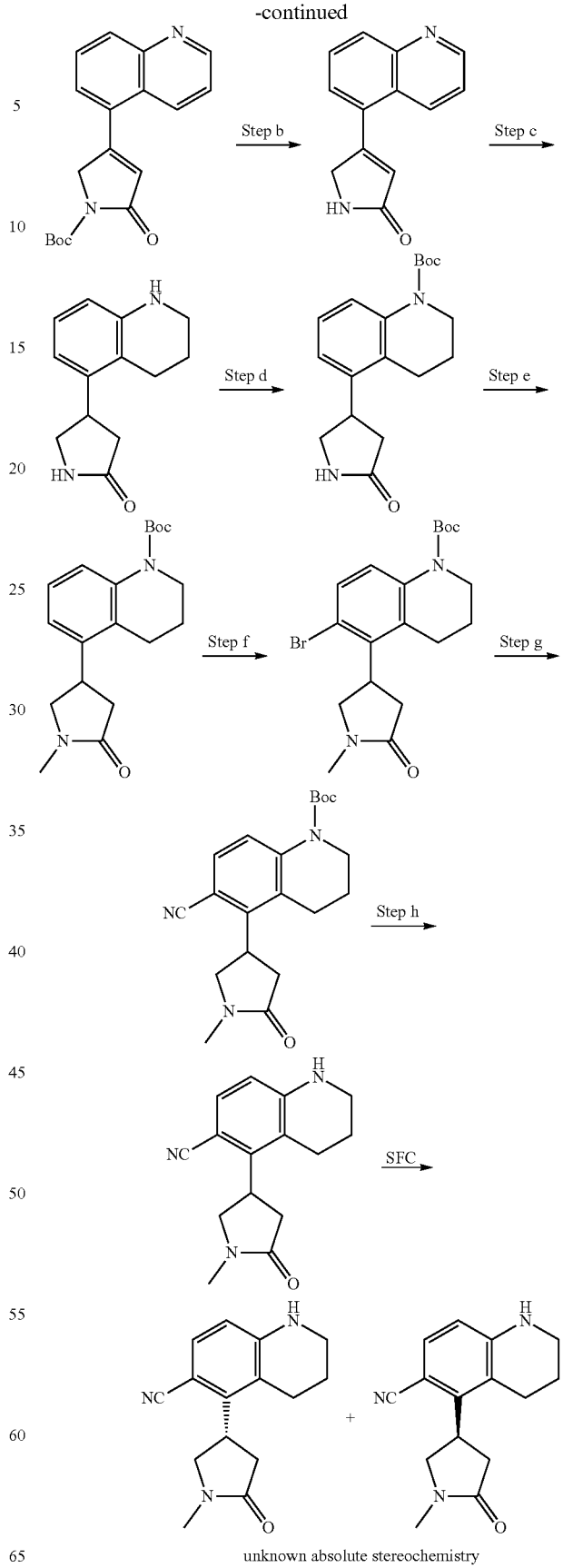

unknown absolute stereochemistry

Step a: A mixture of tert-butyl 4-bromo-2-oxo-2,5-dihydro-1H-pyrrole-1-carboxylate (4.4 g, 16.5 mmol), (quinolin-5-yl)boronic acid (3.4 g, 19.8 mmol), Pd(dppf)Cl$_2$ (603 mg, 825 µmol) and K$_2$CO$_3$ (4.6 g, 33.0 mmol) in dioxane (70 mL)/H$_2$O (10 mL) was stirred at 100° C. for 3 hours under N$_2$ atmosphere. LCMS showed the reaction was consumed completely. The reaction mixture was concentrated in vacuum to give a residue, which was dissolved in ethyl acetate (100 mL), washed with H$_2$O (80 mL×2). The organic phases were washed with brine (30 mL), dried over anhydrous Na$_2$SO$_4$, filtered and concentrated in vacuum to give a residue, which was purified by silica gel chromatography (Ethyl acetate in Petroleum ether=80% to 95%) to afford the product of tert-butyl 2-oxo-4-(quinolin-5-yl)-2,5-dihydro-1H-pyrrole-1-carboxylate (3.4 g, 67.3% yield) as a yellow solid, Step b: A mixture of tert-butyl 2-oxo-4-(quinolin-5-yl)-2,5-dihydro-1H-pyrrole-1-carboxylate (3.4 g, 10.9 mmol) in HCl/MeOH (4 M, 50 mL) was stirred at 15° C. for 12 hours. LCMS showed the reaction was consumed completely. The reaction mixture was concentrated in vacuum to afford the product of 4-(quinolin-5-yl)-1H-pyrrol-2(5H)-one (2.1 g, 91.7% yield) as a yellow solid.

Step c: A mixture of 4-(quinolin-5-yl)-2,5-dihydro-1H-pyrrol-2-one (2.0 g, 9.5 mmol) and PtO$_2$ (215 mg, 951 µmol) in MeOH (40 mL) was stirred at 25° C. for 12 hours under H$_2$ atmosphere (15 psi). LCMS showed the reaction was consumed completely. The reaction mixture was filtered and concentrated in vacuum to afford the product of 4-(1,2,3,4-tetrahydroquinolin-5-yl)pyrrolidin-2-one (2.0 g, crude product) as a yellow solid.

Step d: A mixture of 4-(1,2,3,4-tetrahydroquinolin-5-yl)pyrrolidin-2-one (1.9 g, 8.8 mmol) and (Boc)$_2$O (1.9 g, 8.8 mmol) in dioxane (50 mL) was stirred at 80° C. for 12 hours. LCMS showed the reaction was consumed completely. The reaction mixture was concentrated in vacuum to give a residue, which was purified by silica gel chromatography (Methanol in Dichloromethane=0% to 8%) to afford the product of tert-butyl 5-(5-oxopyrrolidin-3-yl)-1,2,3,4-tetrahydroquinoline-1-carboxylate (1.5 g, 54.1% yield) as a yellow oil.

Step e: To a mixture of NaH (60% in mineral oil, 365 mg) in anhydrous THF (30 mL) at 0° C. was added the solution of tert-butyl 5-(5-oxopyrrolidin-3-yl)-1,2,3,4-tetrahydroquinoline-1-carboxylate (1.5 g, 4.6 mmol) in THF (10 mL), the resulting mixture was stirred for 30 min. MeI (3.3 g, 22.9 mmol) in THF (10 mL) was added, the reaction mixture was warmed to 20° C., and stirred for 11.5 hours. LCMS showed the reaction was consumed completely. The reaction mixture was quenched with sat.NH$_4$Cl, diluted with H$_2$O (50 mL) and extracted with ethyl acetate (55 mL×2). The organic phases were washed with brine (30 mL), dried over anhydrous Na$_2$SO$_4$, filtered and concentrated in vacuum to give the crude product, which was purified by silica gel chromatography (Ethyl acetate as eluent) to afford the product of tert-butyl 5-(1-methyl-5-oxopyrrolidin-3-yl)-1,2,3,4-tetrahydroquinoline-1-carboxylate (1.2 g, 82.7% yield) as a yellow oil.

Step f: To a mixture of tert-butyl 5-(1-methyl-5-oxopyrrolidin-3-yl)-1,2,3,4-tetrahydroquinoline-1-carboxylate (650 mg, 2.0 mmol) in DMF (30 mL) at 0° C. was added NBS (380 mg, 2.2 mmol), the reaction mixture was warmed to 15° C., and stirred for 12 hours. LCMS showed the reaction was consumed completely. The reaction mixture was diluted with ethyl acetate (60 mL), extracted with H$_2$O (50 mL×2). The organic phase was washed with brine (20 mL), dried over anhydrous Na$_2$SO$_4$, filtered and concentrated in vacuum to give a residue, which was purified by silica gel chromatography (Ethyl acetate as eluent) to afford the product of tert-butyl 6-bromo-5-(1-methyl-5-oxopyrrolidin-3-yl)-1,2,3,4-tetrahydroquinoline-1-carboxylate (580 mg, 72.3% yield) as a colorless oil.

Step g: A mixture of tert-butyl 6-bromo-5-(1-methyl-5-oxopyrrolidin-3-yl)-1,2,3,4-tetrahydroquinoline-1-carboxylate (540 mg, 1.3 mmol), [(t-Bu$_3$P)$_2$]Pd (66.9 mg, 131 µmol) and Zn(CN)$_2$ (303 mg, 2.6 mmol) in DMF (25 mL) was stirred at 130° C. for 12 hours under N$_2$ atmosphere. LCMS showed the reaction was consumed completely. The reaction mixture was diluted with ethyl acetate (70 mL), washed with H$_2$O (50 mL×2). The organic phase was washed with brine (20 mL), dried over anhydrous Na$_2$SO$_4$, filtered and concentrated in vacuum to give a residue, which was purified by silica gel chromatography (Methanol in Dichloromethane=0% to 7%) to afford the product of tert-butyl 6-cyano-5-(1-methyl-5-oxopyrrolidin-3-yl)-1,2,3,4-tetrahydroquinoline-1-carboxylate (450 mg, 96.7% yield) as a colorless oil.

Step h: A mixture of tert-butyl 6-cyano-5-(1-methyl-5-oxopyrrolidin-3-yl)-1,2,3,4-tetrahydroquinoline-1-carboxylate (440 mg, 1.2 mmol) in HCl/MeOH (4M, 10 mL) was stirred at 25° C. for 2 hours. LCMS showed the reaction was consumed completely. The reaction mixture was diluted with MeOH (10 mL) and adjusted pH=8 with solid NaHCO$_3$. The mixture was filtered and concentrated in vacuum to give a residue, which was purified by prep-HPLC (NH$_3$.H$_2$O) to afford the product of 5-(1-methyl-5-oxopyrrolidin-3-yl)-1,2,3,4-tetrahydroquinoline-6-carbonitrile (140 mg, 44.5% yield) as a white solid.

SFC: The compound is separable in developing SFC (Column: ChiralPak AD-3 150×4.6 mm I.D., 3 um Gradient: 40% of EtOH (0.05% DEA) in CO$_2$ Flow rate: 2.5 mL/min Column temperature: 35° C.). The compound of rac-5-(1-methyl-5-oxopyrrolidin-3-yl)-1,2,3,4-tetrahydroquinoline-6-carbonitrile (140 mg, 548 µmol) was separated by preparative Chiral-SFC (Column: Phenomenex-Amylose-1 (250 mm*30 mm, 5 um). condition: 0.1% NH$_3$.H$_2$O EtOH, begin B: 30%, end B: 30%, Flow Rate: 50 ml/min) to afford the desired product of (rel)-5-[(3S)-1-methyl-5-oxopyrrolidin-3-yl]-1,2,3,4-tetrahydroquinoline-6-carbonitrile (57 mg, 41% yield) as a white solid, which was confirmed by HPLC, SFC (R$_t$=4.607 min, e.e.=99.8%, the faster eluting isomer) and (rel)-5-[(3R)-1-methyl-5-oxopyrrolidin-3-yl]-1,2,3,4-tetrahydroquinoline-6-carbonitrile (57 mg, 41% yield) as a white solid, which was confirmed by HPLC, SFC (R$_t$=4.863 min, e.e.=98.7%, the slower eluting isomer). The faster eluting isomer (R$_t$=4.607 min) is the peak 1 in developing SFC. The slower eluting isomer (R$_t$=4.863 min) is the peak 2 in developing SFC.

Synthesis of cis-4-{3-[(tert-butyldimethylsilyl)oxy]-3-methylcyclobutyl}-1,2,3,4-tetrahydroquinoxaline-6-carbonitrile, Used in the Preparation of Compound 526

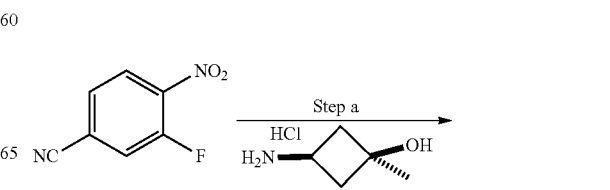

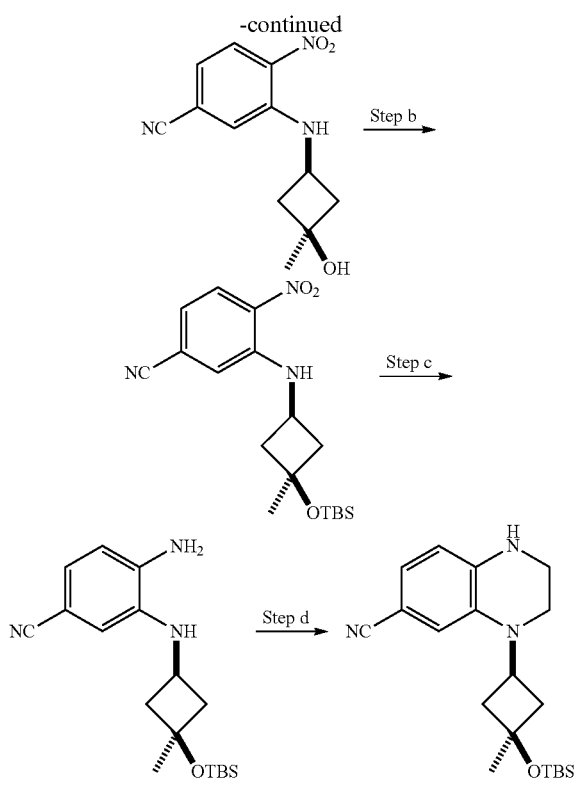

Step a: A solution of cis-3-amino-1-methylcyclobutan-1-ol hydrochloride (900.0 mg, 6.5 mmol) and TEA (1.8 mL, 13.0 mmol) in EtOH (10.0 mL) was stirred at 60° C. for 10 min. To a solution was added 3-fluoro-4-nitrobenzonitrile (1.20 g, 7.2 mmol). The reaction mixture was stirred at 60° C. for 1 hour. TLC (Petroleum ether:Ethyl acetate=2:1) showed starting material was remained and one new spot with larger polarity was found. The reaction mixture was concentrated under reduced pressure. The residue was purified by column chromatography (Petroleum ether:Ethyl acetate=100:0 to 100:10 and $CH_2Cl_2$:MeOH=100:0 to 100:10). The product of cis-3-[(3-hydroxy-3-methylcyclobutyl)amino]-4-nitrobenzonitrile (1.50 g, 6.1 mmol, 93.1% yield) was obtained as a yellow solid.

Step b: A solution of cis-3-[(3-hydroxy-3-methylcyclobutyl)amino]-4-nitrobenzonitrile (1.50 g, 6.1 mmol), imidazole (1.20 g, 18.1 mmol), TEA (839.0 uL, 6.1 mmol) and TBSCl (2.70 g, 18.1 mmol) in DCM (20.0 mL) was stirred at 40° C. for 12 hours. TLC (Petroleum ether: Ethyl acetate=2:1) showed starting material was disappeared and one new spot with lower polarity. The reaction mixture was concentrated under reduced pressure. The residue was purified by column chromatography (Petroleum ether: Ethyl acetate=100:0 to 100:30). The product of cis-3-({3-[(tert-butyldimethylsilyl)oxy]-3-methylcyclobutyl}amino)-4-nitrobenzonitrile (2.00 g, 5.5 mmol, 91.3% yield) was obtained as a yellow solid.

Step c: A solution of cis-3-({3-[(tert-butyldimethylsilyl)oxy]-3-methylcyclobutyl}amino)-4-nitrobenzonitrile (2.00 g, 5.53 mmol) and wet Pd/C (500.0 mg, 10%) in MeOH (15.0 mL) was stirred at 10° C. for 12 hours under $H_2$ (15 psi). TLC (Petroleum ether:Ethyl acetate=1:1) showed the starting material was disappeared and one spot with polarity was formed. Pd/C was filtered off and the filtrate was concentrated under reduced pressure. The residue (1.80 g, 98.3% yield) was used in the next step directly.

Step d: A mixture of cis-4-amino-3-({3-[(tert-butyldimethylsilyl)oxy]-3-methylcyclobutyl}amino)benzonitrile (1.80 g, 5.42 mmol), TBAB (5.20 g, 16.2 mmol), TEA (2.2 mL, 16.2 mmol) and 1,2-dibromoethane (5.0 mL) was stirred at 60° C. for 12 hours. LCMS showed the starting material was consumed completely and 53% desired product formed. The reaction mixture was concentrated under reduced pressure. The residue was diluted with water (100.0 mL) and extracted Ethyl acetate (100.0 mL×2). The combined organic layers were washed with water (100.0 mL) and brine (50.0 mL), dried over anhydrous $Na_2SO_4$, filtered and concentrated under reduced pressure to give a residue. The residue was purified by column chromatography (Petroleum ether: Ethyl acetate=100:0 to 100:10). The product cis-4-{3-[(tert-butyldimethylsilyl)oxy]-3-methylcyclobutyl}-1,2,3,4-tetrahydroquinoxaline-6-carbonitrile (1.10 g, 56.9% yield) was obtained as an off-white solid.

Synthesis of 4-{3-[(tert-butyldimethylsilyl)oxy]-3-methylcyclobutyl}-1,2,3,4-tetrahydroquinoxaline-6-carbonitrile, Used in the Preparation of Compound 527

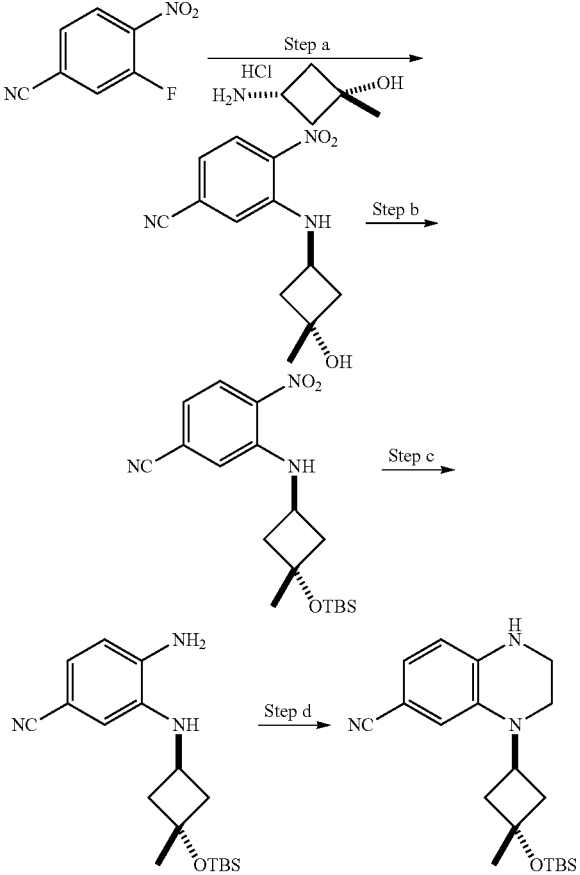

Step a: A solution of trans-3-amino-1-methylcyclobutan-1-ol hydrochloride (1.0 g, 7.3 mmol) and TEA (2.0 mL, 14.4 mmol) in EtOH (10.0 mL) was stirred at 60° C. for 10 min. To the solution was added 3-fluoro-4-nitrobenzonitrile (1.3 g, 7.9 mmol). The reaction mixture was stirred at 60° C. for 3 hours. TLC (Petroleum ether: Ethyl acetate=2:1) showed a little amount of 1 was remained and one new spot with larger polarity found. The reaction mixture was concentrated under reduced pressure. The residue was purified by column chromatography (Petroleum ether: Ethyl acetate=100:0 to 100:10 and DCM/MeOH=100:0 to 100:10). The product 3-[(3-hydroxy-3-methylcyclobutyl)amino]-4-nitrobenzonitrile (1.7 g, 6.8 mmol, 95.5% yield) was obtained as a yellow solid.

Step b: A solution of 3-[(3-hydroxy-3-methylcyclobutyl)amino]-4-nitrobenzonitrile (1.7 g, 6.9 mmol), TBSCl (2.8 g, 18.5 mmol), TEA (0.95 mL, 6.9 mmol) and imidazole (1.4 g, 20.6 mmol) in DCM (20.0 mL) was stirred at 40° C. for 12 hours. TLC (Petroleum ether: Ethyl acetate=2:1) showed starting material was disappeared and one new spot with lower polarity. The reaction mixture was concentrated under reduced pressure. The residue was purified by column chromatography (Petroleum ether: Ethyl acetate=100:0 to 100:30). The product 3-({3-[(tert-butyldimethylsilyl)oxy]-3-methylcyclobutyl}amino)-4-nitrobenzonitrile (2.2 g, 6.08 mmol, 88.7% yield) was obtained as a yellow solid.

Step c: A solution of 3-({3-[(tert-butyldimethylsilyl)oxy]-3-methylcyclobutyl}amino)-4-nitrobenzonitrile (2.2 g, 6.1 mmol) and wet Pd/C (500.0 mg, 10%) in MeOH (15.0 mL) was stirred at 10° C. for 12 hours under $H_2$ (15 psi). TLC ((Petroleum ether: Ethyl acetate=1:1) showed the starting material was disappeared and one spot with larger polarity was formed. Pd/C was filtered off and the filtrate was concentrated under reduced pressure. The residue (2.0 g, 99.5% yield) was used for the next step directly.

Step d: A mixture of 4-amino-3-({3-[(tert-butyldimethylsilyl)oxy]-3-methylcyclobutyl}amino)benzonitrile (2.0 g, 6.03 mmol), TBAB (5.8 g, 18.0 mmol), TEA (1.8 g, 18.0 mmol) and 1,2-dibromoethane (5.0 mL) was stirred at 60° C. for 12 hours. LCMS showed the starting material was consumed completely and 52% desired product formed. The reaction mixture was concentrated under reduced pressure. The residue was diluted with water (100.0 mL) and extracted ethyl acetate (100.0 mL×2). The combined organic layers were washed with water (100.0 mL) and brine (50.0 mL), dried over anhydrous $Na_2SO_4$, filtered and concentrated under reduced pressure to give a residue. The residue was purified by column chromatography (Petroleum ether: Ethyl acetate=100:0 to 100:10). The product 4-{3-[(tert-butyldimethylsilyl)oxy]-3-methylcyclobutyl}-1,2,3,4-tetrahydroquinoxaline-6-carbonitrile (1.08 g, 3.02 mmol, 50.2% yield) was obtained as an off-white solid.

Synthesis of 5-(cyanomethyl)-1,2,3,4-tetrahydroquinoline-6-carbonitrile, Used in the Preparation of Compound 528

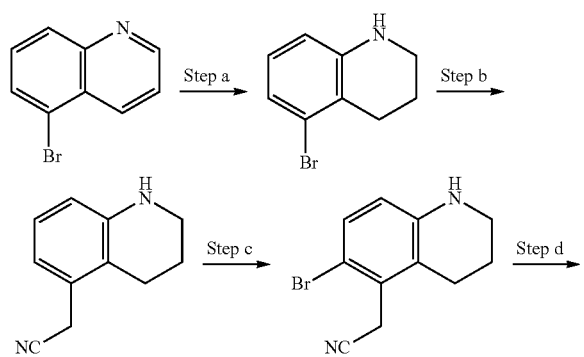

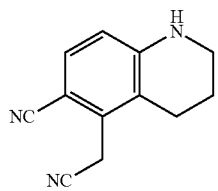

Step a: 5-Bromoquinoline (5.0 g, 24.0 mmol) was added in $CH_3COOH$ (50.0 mL), $NaBH_3CN$ (5.2 g, 84.0 mmol) was added in one portion, the reaction mixture was stirred at 5° C. for 2 hours. TLC (Petroleum ether:Ethyl acetate=10:1) indicated one main spot formed. The reaction mixture was diluted with EtOAc(500.0 mL), adjusted pH=8 by adding saturated $NaHCO_3$, the organic phase was concentrated under reduced pressure and purified by flash silica gel chromatography (Petroleum ether:EtOAc=10:1) to afford the product of 5-bromo-1,2,3,4-tetrahydroquinoline (4.5 g, 88.4% yield) as a yellow oil.

Step b: 5-bromo-1,2,3,4-tetrahydroquinoline (4.5 g, 21.2 mmol), 4-(4,4,5,5-tetramethyl-1,3,2-dioxaborolan-2-yl)-1,2-oxazole (4.1 g, 21.2 mmol), $Pd(dppf)Cl_2$ (1.5 g, 2.1 mmol) and KF (4.9 g, 84.8 mmol) were added in the mixture of DMSO (100.0 mL) and $H_2O$ (20.0 mL), the reaction mixture was evacuated and refilled for 3 times with $N_2$ and stirred at 100° C. for 2 hours and stirred at 130° C. for 12 hours. TLC (Petroleum ether:Ethyl acetate=2:1) indicated one new spot formed. The reaction mixture was diluted with EtOAc (1000.0 mL), washed with $H_2O$ (500.0 mL×3) and brine, dried over anhydrous $Na_2SO_4$, the organic phase was concentrated under reduced pressure and purified by flash silica gel chromatography (Petroleum ether:EtOAc=2:1) to afford the product of 2-(1,2,3,4-tetrahydroquinolin-5-yl)acetonitrile (1.3 g, 35.6% yield) as a yellow solid.

Step c: 2-(1,2,3,4-Tetrahydroquinolin-5-yl)acetonitrile (450.0 mg, 2.6 mmol) was dissolved in DMF (10.0 mL), NBS (464.0 mg, 2.6 mmol) dissolved in DMF (10.0 mL) was added in the reaction mixture, the reaction mixture was stirred at 15° C. for 2 hours. LCMS indicated 91% of desired product formed. The reaction mixture was diluted with EtOAc (300.0 mL), washed with $H_2O$ (100.0 mL×3), brine, dried over anhydrous $Na_2SO_4$, concentrated under reduced pressure and purified by flash silica gel chromatography (Petroleum ether:Ethyl acetate=100:0 to 100:30) to afford the product of 2-(6-bromo-1,2,3,4-tetrahydroquinolin-5-yl)acetonitrile (600.0 mg, 91.6% yield) as a white solid.

Step d: 2-(6-Bromo-1,2,3,4-tetrahydroquinolin-5-yl)acetonitrile (600.0 mg, 2.4 mmol), $Zn(CN)_2$ (416.0 mg, 3.6 mmol) and $Pd(t-Bu_3P)_2$ (243.0 mg, 476.0 μmol) were added in DMF (30.0 mL), the reaction mixture was evacuated and refilled for 3 times with $N_2$ and stirred at 100° C. for 12 hours. LCMS indicated 98% of desired product formed. The reaction mixture was concentrated under reduced pressure and purified by flash silica gel chromatography (Petroleum ether:Ethyl acetate=100:0 to 100:20) to afford the product of 5-(cyanomethyl)-1,2,3,4-tetrahydroquinoline-6-carbonitrile (356.7 mg, 75.9% yield) as a white solid.

Synthesis of 4-(2-fluoroethyl)-1,2,3,4-tetrahydroquinoxaline-6-carbonitrile, Used in the Preparation of Compound 529

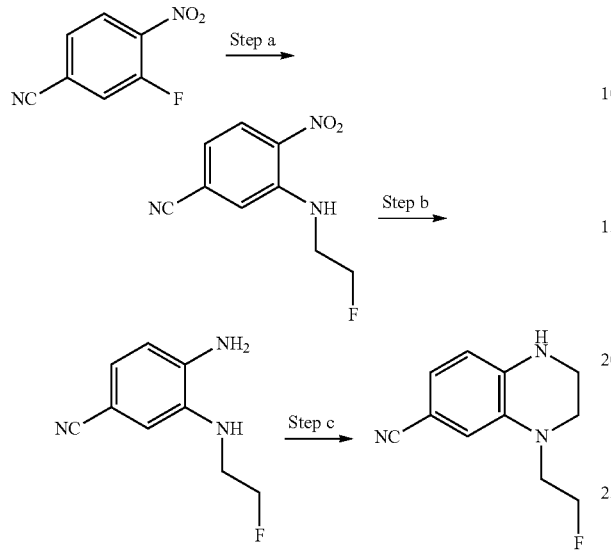

Step a: A solution of 2-fluoroethan-1-amine hydrochloride (1.0 g, 10.0 mmol) and Et₃N (4.2 mL, 30.0 mmol) in EtOH (10.0 mL) was stirred at 40° C. for 15 min. To a reaction mixture was added 3-fluoro-4-nitrobenzonitrile (1.7 g, 10.0 mmol). The reaction was stirred at 40° C. for 12 hours. TLC (Petroleum ether: Ethyl acetate=2:1) showed the starting material was disappeared and one spot with lower polarity was formed. The reaction mixture was concentrated under reduced pressure to give the residue (2.0 g, 9.56 mmol, 95.6% yield).

Step b: A solution of 3-[(2-fluoroethyl)amino]-4-nitrobenzonitrile (2.0 g, 9.56 mmol) and wet Pd/C (500 mg, 10%) in MeOH (20.0 mL) was stirred at 10° C. for 12 hours under H₂ (15 psi). TLC (Petroleum ether: Ethyl acetate=1:1) showed the starting material was disappeared and one main spot with larger polarity formed. Pd/C was filtered off and the filtrate was concentrated under reduced pressure. The residue (1.6 g, 93.5% yield) was used in the next step directly.

Step c: A mixture of 4-amino-3-[(2-fluoroethyl)amino] benzonitrile (1.4 g, 7.8 mmol), TBAB (7.5 g, 23.4 mmol), TEA (2.2 mL, 15.6 mmol) and 1,2-dibromoethane (5.0 mL) was stirred at 60° C. for 10 hours. TLC (Petroleum ether: Ethyl acetate=2:1) showed a little amount of starting material was remained and main spot with lower polarity was formed. The reaction mixture was concentrated under reduced pressure. The residue was diluted with water (100.0 mL) and extracted ethyl acetate (100.0 mL×2). The combined organic layers were washed with water (50.0 mL) and brine (50.0 mL), dried over anhydrous Na₂SO₄, filtered and concentrated under reduced pressure to give a residue. The residue was purified by column chromatography (Petroleum ether: Ethyl acetate=100:0 to 100:20). The product 4-(2-fluoroethyl)-1,2,3,4-tetrahydroquinoxaline-6-carbonitrile (950.0 mg, 4.6 mmol, 59.3% yield) was obtained as a light yellow solid.

Synthesis of 4-(3,3-difluorocyclobutyl)-1,2,3,4-tetrahydroquinoxaline-6-carbonitrile, Used in the Preparation of Compound 530

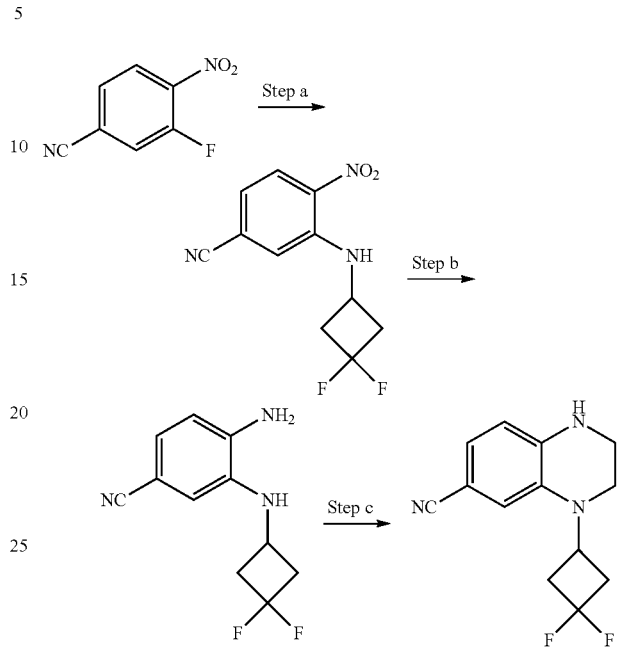

Step a: A solution of 3,3-difluorocyclobutan-1-amine hydrochloride (950.0 mg, 6.6 mmol) and TEA (2.7 mL, 19.8 mmol) in EtOH (15.0 mL) was stirred at 60° C. for 10 min. To a mixture solution was added 3-fluoro-4-nitrobenzonitrile (1.1 g, 6.6 mmol). The reaction was stirred at 60° C. for 12 hours. LCMS showed a little amount of starting material was remained and 93% desired product formed. TLC (Petroleum ether: Ethyl acetate=4:1) showed the starting material and product overlapped completely. The reaction mixture was concentrated under reduced pressure. The residue was purified by column chromatography (Petroleum ether: Ethyl acetate=100:0 to 100:20). The product 3-[(3,3-difluorocyclobutyl)amino]-4-nitrobenzonitrile (1.6 g, 6.3 mmol, 95.8% yield) was obtained as a yellow solid.

Step b: A solution of 3-[(3,3-difluorocyclobutyl)amino]-4-nitrobenzonitrile (1.6 g, 6.3 mmol) and 10% Pd/C (200 mg, wet) in MeOH (15.0 mL) was purged with H2 for 3 min and stirred at 10° C. for 12 hours under H2 (15 psi). TLC (Petroleum ether:Ethyl acetate=2:1) showed the starting material was disappeared and a main spot with larger polarity was formed. Pd/C was filtered off and the filtrate was concentrated under reduced pressure. The residue was purified by column chromatography (Petroleum ether: Ethyl acetate=100:0 to 100:40). The product 4-amino-3-[(3,3-difluorocyclobutyl)amino]benzonitrile (850.0 mg, 3.8 mmol, 60.7% yield) was obtained as a light yellow solid.

Step c: A solution of 4-amino-3-[(3,3-difluorocyclobutyl)amino]benzonitrile (810.0 mg, 3.6 mmol), TBAB (3.5 g, 10.8 mmol), TEA (2.0 mL, 14.4 mmol) and 1,2-dibromoethane (5.0 mL) was stirred at 60° C. for 5 hours. LCMS showed 63% desired product formed at 254 nm. The reaction mixture was diluted with water (100.0 mL) and extracted ethyl acetate (100.0 mL×2). The combined organic layers were washed with water (80.0 mL) and brine (80.0 mL), dried over anhydrous Na2SO4, filtered and concentrated under reduced pressure to give a residue. The residue was purified by column chromatography (Petroleum ether:

Ethyl acetate=100:0 to 100:20). The residue was diluted with MeOH (10.0 mL). The residue was purified by prep-HPLC (HCl). The starting material (300 mg) was recovered. The product 4-(3,3-difluorocyclobutyl)-1,2,3,4-tetrahydroquinoxaline-6-carbonitrile hydrochloride (430 mg, 1.5 mmol, 41.7% yield) was obtained as an off-white solid. LCMS: [M+H]+ 250.1.

Synthesis of 4,5,6,7-tetrahydrothiazolo[5,4-b]pyridine, Used in the Preparation of Compound 531

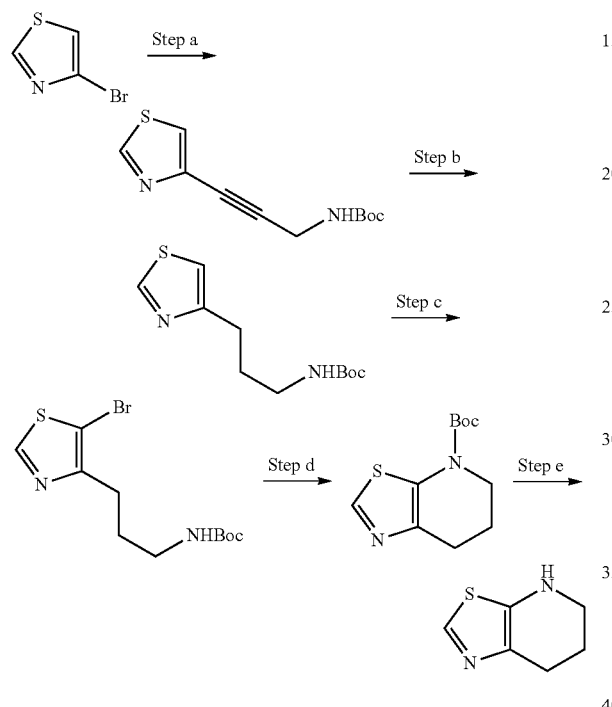

Step a: A mixture of 4-bromo-1,3-thiazole (1.00 g, 6.09 mmol), tert-butyl N-(prop-2-yn-1-yl)carbamate (1.13 g, 7.30 mmol), CuI (115.0 mg, 609.0 umol), Pd(PPh3)4 (703.0 mg, 609 umol) and Et3N (1.22 g, 12.10 mmol) in THF (20 mL) was stirred at 70° C. under N2 for 4 hours. LCMS showed the desired product formed. Concentrated under reduced pressure, the residue was purified by silica gel column (EtOAc in Petroleum ether=0~50%) to give the product of tert-butyl N-[3-(1,3-thiazol-4-yl)prop-2-yn-1-yl]carbamate (600.0 mg, 41.3% yield) as a yellow solid.

Step b: A mixture of tert-butyl N-[3-(1,3-thiazol-4-yl)prop-2-yn-1-yl]carbamate (600.0 mg, 2.5 mmol) and Raney Ni (0.2 g) in THF (2 mL) and MeOH (10 mL) was stirred at 20° C. under H2 (15 psi.) for 12 hours. LCMS showed the one main peak with desired MS formed. The reaction mixture was filtered and concentrated in vacuum to give the product of tert-butyl N-[3-(1,3-thiazol-4-yl)propyl]carbamate (600.0 mg, 98.6% yield) as a yellow oil.

Step c: A mixture of tert-butyl N-[3-(1,3-thiazol-4-yl)propyl]carbamate (500.0 mg, 2.1 mmol) and NBS (546.0 mg, 3.1 mmol) in DMF (10 mL) was stirred at 40° C. for 1 hour. TLC (Petroleum ether/EtOAc=3/1) showed the one new spot with lower polarity formed. The reaction mixture was poured into EtOAc (50 mL) and washed with water (20 mL×2). The organic layer was concentrated in vacuum and purified by silica gel column (Petroleum ether/EtOAc=3/1) to give the product of tert-butyl N-[3-(5-bromo-1,3-thiazol-4-yl)propyl]carbamate (600.0 mg, 90.7% yield) as a colorless oil.

Step d: A mixture of tert-butyl N-[3-(5-bromo-1,3-thiazol-4-yl)propyl]carbamate (600.0 mg, 1.86 mmol), Pd2(dba)3 (170.0 mg, 186.0 µmol), BINAP (115.0 mg, 186.0 µmol) and Cs2CO3 (1.21 g, 3.72 mmol) in PhMe (20 mL) was stirred at 100° C. under N2 for 12 hours. TLC (Petroleum ether/EtOAc=2/1) showed one new spot with a little higher polarity formed, and a small amount of the starting material remained. The reaction mixture was concentrated and purified by silica gel column (Petroleum ether/EtOAc=5/1) to give the product of tert-butyl 4H,5H,6H,7H-[1,3]thiazolo[5,4-b]pyridine-4-carboxylate (400.0 mg, crude) as a yellow oil.

Step e: A solution of tert-butyl 4H,5H,6H,7H-[1,3]thiazolo[5,4-b]pyridine-4-carboxylate (200.0 mg, 832.0 µmol) in 4 M HCl/MeOH (10 mL) was stirred at 20° C. under 2 hours. LCMS showed the desired product formed. This combined mixture was concentrated under reduced pressure. The residue was purified by silica gel column (MeOH in DCM=0~10%, 0.5% NH3.H2O) to give 4H,5H,6H,7H-[1,3]thiazolo[5,4-b]pyridine (100.0 mg) as a red oil.

Synthesis of 4-(3-fluorobicyclo[1.1.1]pentan-1-yl)-1,2,3,4-tetrahydroquinoxaline-6-carbonitrile, Used in the Preparation of Compound 532

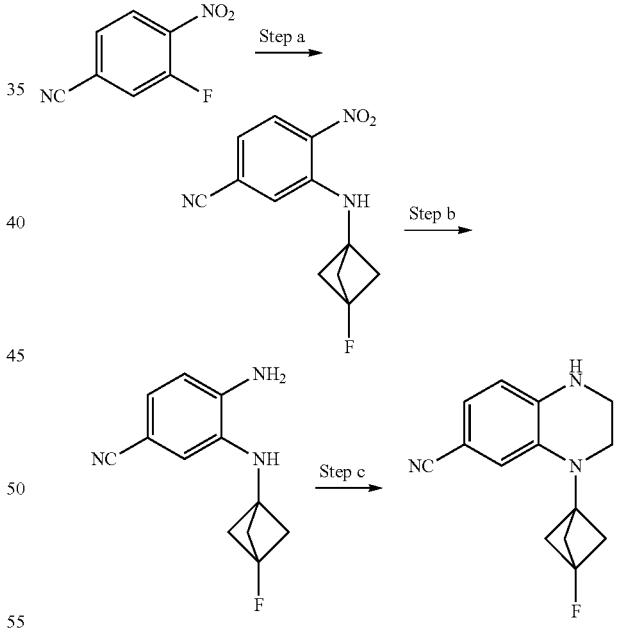

Step a: A solution of 3-fluoro-4-nitrobenzonitrile (651.0 mg, 3.92 mmol) and 3-fluorobicyclo[1.1.1]pentan-1-amine hydrochloride (450.0 mg, 3.3 mmol) in TEA (1.0 mL) was stirred at 100° C. for 12 hours. TLC (Petroleum ether:Ethyl acetate=2:1) showed the starting material was remained and a new yellow spot with larger polarity formed. The reaction mixture was concentrated under reduced pressure. The residue was purified by column chromatography (Petroleum ether:Ethyl acetate=100:0 to 100:30) to give the crude product which was further purified by TLC (Petroleum ether: Ethyl acetate=4:1) to afford the product of 3-((3- fluorobicyclo[1.1.1]pentan-1-yl)amino)-4-nitrobenzonitrile (320.0 mg, 39.6% yield) as a yellow solid.

Step b: A mixture of 3-({3-fluorobicyclo[1.1.1]pentan-1-yl}amino)-4-nitrobenzonitrile (300.0 mg) and 10% Pd/C (100.0 mg, wet) in MeOH (2.0 mL) was purged with H2 for 3 min and stirred at 10° C. for 12 hours under H2 (15 psi). Pd/C was filtered off and the filtrate was added HCl/MeOH (5.0 mL, 4M) and concentrated under reduced pressure to give the crude product of 4-amino-3-({3-fluorobicyclo[1.1.1]pentan-1-yl}amino)benzonitrile (200.0 mg, 1HCl salt).

Step c: A mixture of 4-amino-3-({3-fluorobicyclo[1.1.1]pentan-1-yl}amino)benzonitrile hydrochloride (200.0 mg) 1,2-dibromoethane (3.0 mL, 788.0 μmol), TBAB (760.0 mg, 2.4 mmol) and TEA (435.0 μL, 3.2 mmol) was stirred at 60° C. for 24 hours under N2. TLC (Petroleum ether: Ethyl acetate=4:1) showed the starting material disappeared and a main spot with lower polarity found. The residue was diluted with water (50.0 mL) and extracted ethyl acetate (50.0 mL×2). The combined organic layers were washed with water (20.0 mL) and brine (20.0 mL), dried over anhydrous Na2SO4, filtered and concentrated under reduced pressure to give a residue. The residue was purified by column chromatography (Petroleum ether: Ethyl acetate=100:0 to 100:30). The product of 4-{3-fluorobicyclo[1.1.1]pentan-1-yl}-1,2,3,4-tetrahydroquinoxaline-6-carbonitrile (200.0 mg) was obtained as a black solid. LCMS: [M+H]+ 243.9.

Synthesis of 1-(3-bromo-1-(4-methoxybenzyl)-1H-pyrazolo[3,4-b]pyrazin-6-yl)-4-methylpiperidin-4-amine, Used in the Preparation of Compound 6

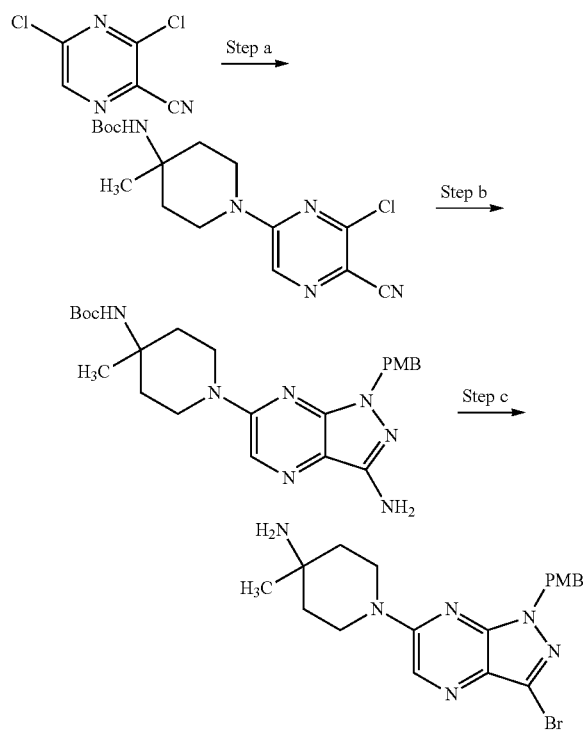

Step a: A round bottomed flask was charged with 3,5-dichloropyrazine-2-carbonitrile (0.3 g, 1.7 mmol, 1.0 eq, CAS #313339-92-3), tert-butyl N-(4-methyl-4-piperidyl)carbamate (0.37 g, 1.7 mmol, 1.0 eq, CAS #163271-08-7), and CsF (0.78 g, 5.2 mmol, 3.0 eq). Dimethylsulfoxide (5.7 mL) was added and the reaction mixture was stirred at 70° C. for 2.5 hours. The reaction mixture was diluted with EtOAc (100 mL), washed with saturated NaHCO3 (30 mL), H2O (30 mL×2), and brine (30 mL). The organic layer was dried over anhydrous Na2SO4, filtered, and concentrated under reduced pressure to give a yellow solid. The residue was purified by column chromatography (25-50% EtOAc/petroleum ether) to afford the product of tert-butyl N-[1-(6-chloro-5-cyano-pyrazin-2-yl)-4-methyl-4-piperidyl]carbamate (0.5 g, 83% yield) as a yellow solid: LCMS [M-tBu]+=295.

Step b: tert-Butyl N-[1-(6-chloro-5-cyano-pyrazin-2-yl)-4-methyl-4-piperidyl]carbamate (4.0 g, 11.4 mmol, 1.0 eq), Et3N (5.7 g, 56.8 mmol, 7.9 mL, 5.0 eq) and (4-methoxyphenyl)methylhydrazine, 2HCl (3.1 g, 13.6 mmol, 1.2 eq) were taken up in EtOH (50 mL). The mixture was stirred at 90° C. for 16 hours. A parallel reaction was run with the same ratio of materials, starting from 1 g of tert-butyl N-[1-(6-chloro-5-cyano-pyrazin-2-yl)-4-methyl-4-piperidyl]carbamate. Both reaction mixtures were combined and concentrated under reduced pressure to give a residue, which was triturated with H2O (50 mL) and extracted with ethyl acetate (100 mL×2). The combined organics were washed with brine (50 mL), dried over anhydrous sodium sulfate, filtered, and concentrated under reduced pressure to give a residue. The residue was purified by flash silica gel chromatography (25-60% EtOAc/petroleum ether) to afford tert-butyl-N-[1-[3-amino-1-[(4-methoxyphenyl)methyl]pyrazolo[3,4-b]pyrazin-6-yl]-4-methyl-4-piperidyl]carbamate (4.8 g) as a yellow solid: LCMS [M+H]+=468.

Step c: A round bottomed flask was charged with tert-butyl N-[1-[3-amino-1-[(4-methoxyphenyl)methyl]pyrazolo[3,4-b] pyrazin-6-yl]-4-methyl-4-piperidyl]carbamate (8.2 g, 17.5 mmol, 1.0 eq) and NaNO2 (1.4 g, 21.0 mmol, 1.2 eq). Acetonitrile (150 mL) was added, followed by HBr (30.0 mL, 47% solution) and the mixture stirred at 0° C. for 1 hr. CuBr (251 mg, 1.7 mmol, 0.10 eq) was added at 0° C., and the reaction mixture allowed to warm to 25° C. for 1 h. The pH was adjusted to 10 with ammonium hydroxide and extracted with ethyl acetate (150 mL×3). The combined organics were washed with H2O (100 mL), brine (100 mL), dried over anhydrous sodium sulfate, filtered, and concentrated under reduced pressure to give a residue. The residue was purified by flash silica gel chromatography (eluting with methylene chloride and methanol) to afford 1-[3-bromo-1-[(4-methoxyphenyl)methyl]pyrazolo[3,4-b]pyrazin-6-yl]-4-methyl-piperidin-4-amine (6.6 g, 76.7% yield) as a red solid. LCMS: [M+H]+=431/433.

Synthesis of 6-(2,5-dihydrofuran-3-yl)-1,2,3,4-tetrahydro-1,5-naphthyridine, Used in Preparation of Compound 309 and Compound 336

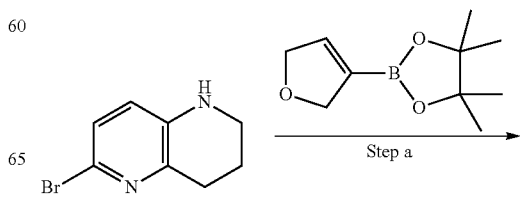

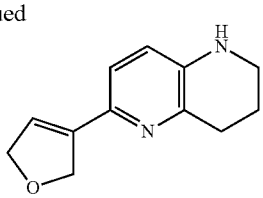

Step a: A mixture of 6-bromo-1,2,3,4-tetrahydro-1,5-naphthyridine (145 mg, 680 μmol), 2-(2,5-dihydrofuran-3-yl)-4,4,5,5-tetramethyl-1,3,2-dioxaborolane (198 mg, 1.0 mmol), Pd(dppf)Cl₂ (99.5 mg, 136 μmol) and K₂CO₃ (186 mg, 1.4 mmol) in dioxane (9 mL)/H₂O (3 mL) was stirred at 90° C. for 12 hours under N₂ atmosphere. The reaction mixture was diluted with ethyl acetate (20 mL), and washed with H₂O (15 mL×2). The organic phase was washed with brine (15 mL), dried over anhydrous Na₂SO₄, filtered and concentrated in vacuo to give a residue, which was purified by silica gel chromatography (Ethyl acetate in Petroleum ether: 30% to 50%) to afford the product of 6-(2,5-dihydrofuran-3-yl)-1,2,3,4-tetrahydro-1,5-naphthyridine (55 mg, 40.1% yield) as a white solid. LCMS m/z: 203.4 (M+H)+.

Synthesis of 6-[(1-methyl-1H-pyrazol-4-yl) oxy]-1, 2, 3, 4-tetrahydro-1,5-naphthyridine, Used in Preparation of Compound 314

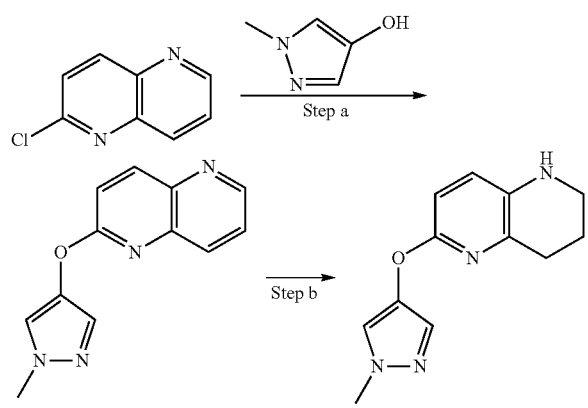

Step a: To a solution of 1-methyl-1H-pyrazol-4-ol (183 mg, 1.87 mmol) and 2-chloro-1,5-naphthyridine (306 mg, 1.87 μmol) in DMF (10.0 mL) was added Cs₂CO₃ (911 mg, 2.80 mmol)). The mixture was heated to 100° C. for 2 h. The mixture was diluted with H₂O (20 mL) and extracted with ethyl acetate (15 mL×3). The combined organic layers were washed with brine (10 mL), dried over anhydrous Na₂SO₄, filtered and concentrated. The residue was purified by silica column (Ethyl acetate in Petroleum ether 0-100%) to give the desired product of 2-[(1-methyl-1H-pyrazol-4-yl) oxy]-1,5-naphthyridine (415 mg, 98.5% yield) as a white solid.

Step b: To a solution of 2-[(1-methyl-1H-pyrazol-4-yl) oxy]-1,5-naphthyridine (410 mg, 1.8 mmol) and 3,5-diethyl 2,6-dimethyl-1,4-dihydropyridine-3,5-dicarboxylate (1.10 g, 4.35 mmol) in PhMe (10 mL) was added diphenoxyphosphinic acid (90.5 mg, 0.36 mmol). The solution was stirred at 80° C. for 12 h. The mixture was directly concentrated in vacuo. The residue was purified by silica column (Ethyl acetate in Petroleum ether 0-100%) to give the desired product of 6-[(1-methyl-1H-pyrazol-4-yl) oxy]-1, 2, 3, 4-tetrahydro-1,5-naphthyridine (300 mg, 71.9% yield) as a yellow oil. LCMS m/z: 231.1 (M+H)+.

Synthesis of 6-methoxy-1, 2, 3, 4-tetrahydro-1,5-naphthyridine, Used in Preparation of Compound 315

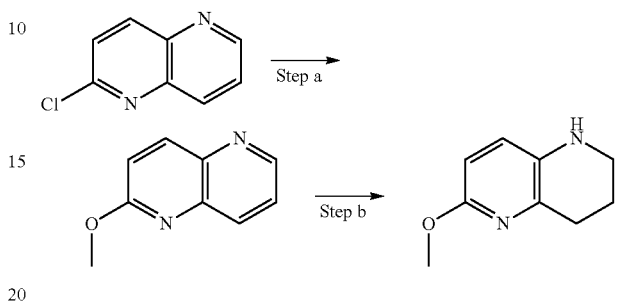

Step a: To a solution of 2-chloro-1,5-naphthyridine (300 mg, 1.82 mmol) in MeOH (10 mL) was added MeONa (492 mg, 9.11 mmol) and the solution was stirred at 70° C. for 2 h. The solution was then concentrated in vacuo. The residue was diluted with H₂O (20 mL) and extracted with ethyl acetate (15 mL×3). The combined organic layers were washed with brine (10 mL), dried over anhydrous Na₂SO₄, filtered and concentrated to give the desired product of 2-methoxy-1,5-naphthyridine (320 mg, crude) as a yellow oil.

Step b: To a solution of 2-methoxy-1,5-naphthyridine (320 mg, 1.99 mmol) and 3,5-diethyl 2,6-dimethyl-1,4-dihydropyridine-3,5-dicarboxylate (1.20 g, 4.77 mmol) in PhMe (10 mL) was added diphenoxyphosphinic acid (99.5 mg, 0.40 mmol). The solution was stirred at 80° C. for 12 h. After concentration, the residue was purified by silica column chromatography (Ethyl acetate in Petroleum ether 0-50%) to give impure product, which was re-purified by prep. HPLC (NH₃) to give the desired product of 6-methoxy-1, 2, 3, 4-tetrahydro-1,5-naphthyridine (130 mg, 39.8% yield) as a yellow oil. LCMS m/z: 165.1 (M+H)+.

Synthesis of 6-[1-(difluoromethyl)-1H-pyrazol-4-yl]-1,2,3,4-tetrahydro-1,5-naphthyridine, Used in Preparation of Compound 317

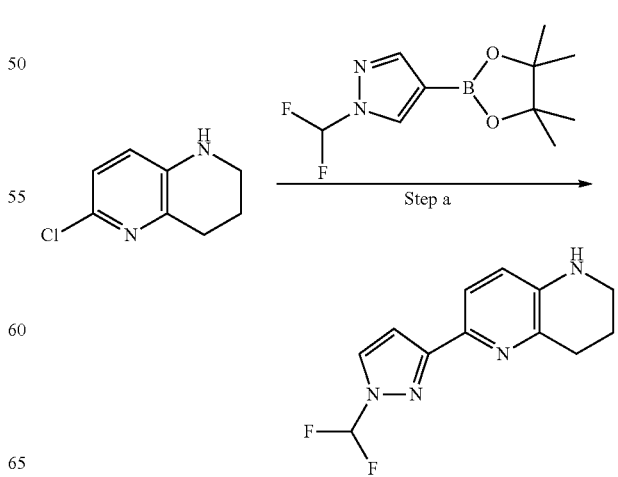

Step a: 1-(Difluoromethyl)-4-(4,4,5,5-tetramethyl-1,3,2-dioxaborolan-2-yl)-1H-pyrazole (200.0 mg, 819.0 μmol, CAS #1206640-82-5), 6-chloro-1,2,3,4-tetrahydro-1,5-naphthyridine (138.0 mg, 819.0 μmol), Pd(dppf)Cl$_2$ (119.0 mg, 163.0 μmol), and K$_2$CO$_3$ (338.0 mg, 2.5 mmol) were added in the mixture of dioxane (10.0 mL) and H2O (1.0 mL). The reaction mixture was evacuated and refilled 3 times with N$_2$ and stirred at 100° C. for 12 hours. The reaction mixture was concentrated under reduced pressure to give a residue which was purified by flash silica gel chromatography (Petroleum ether:Ethyl acetate=100:0 to 100:30) to afford 6-[1-(difluoromethyl)-1H-pyrazol-4-yl]-1,2,3,4-tetrahydro-1,5-naphthyridine (120.0 mg, 81% purity, 47.6% yield) as a yellow solid. LCMS m/z: 251.0 (M+H)$^+$.

Synthesis of 6-(1,3-oxazol-5-yl)-1,2,3,4-tetrahydro-1,5-naphthyridine, Used in Preparation of Compound 318

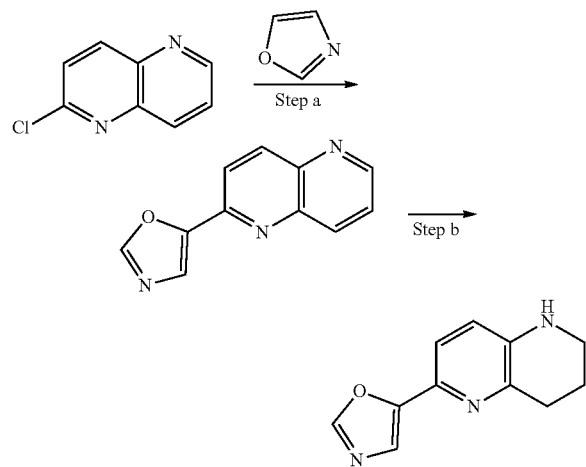

Step a: To a solution of 2-chloro-1,5-naphthyridine (500.0 mg, 3.00 mmol) and 1,3-oxazole (418.0 mg, 6.10 mmol) in DMA (10.0 mL) was added di-1-adamantylphosphine (108.0 mg, 303.0 μmol), pivalic acid (123.0 mg, 1.20 mmol), K$_2$CO$_3$ (1.30 g, 9.10 mmol) and Pd(OAc)$_2$ (68.0 mg, 303.0 μmol). The mixture was evacuated and refilled 3 times using N$_2$, then the reaction mixture was stirred at 110° C. for 12 hours. The reaction mixture was concentrated under reduced pressure. The residue was purified by column chromatography (Petroleum ether/Ethyl acetate=100:0 to 100:100) to obtain 2-(1,3-oxazol-5-yl)-1,5-naphthyridine (300.0 mg) as a light yellow solid.

Step b: A solution of 2-(1,3-oxazol-5-yl)-1,5-naphthyridine (300.0 mg, 1.52 mmol), BINOL-phosphoric acid (105.0 mg, 304.0 μmol) and diethyl 2,6-dimethyl-1,4-dihydropyridine-3,5-dicarboxylate (1.20 g, 4.60 mmol) in dioxane (5.0 mL) was stirred at 80° C. for 12 hours under N$_2$. The reaction mixture was concentrated under reduced pressure. The residue was purified by column chromatography (Petroleum ether/Ethyl acetate=100:0 to 100:80). The impure product was re-purified by prep-TLC (Petroleum ether/Ethyl acetate=1:4) to obtain 6-(1,3-oxazol-5-yl)-1,2,3,4-tetrahydro-1,5-naphthyridine (160.0 mg, 795.0 μmol, 52.4% yield) as a light yellow solid. LCMS m/z: 201.9 (M)+.

Synthesis of 6-(4-methyl-1,3-oxazol-2-yl)-1,2,3,4-tetrahydro-1,5-naphthyridine, Used in Preparation of Compound 328

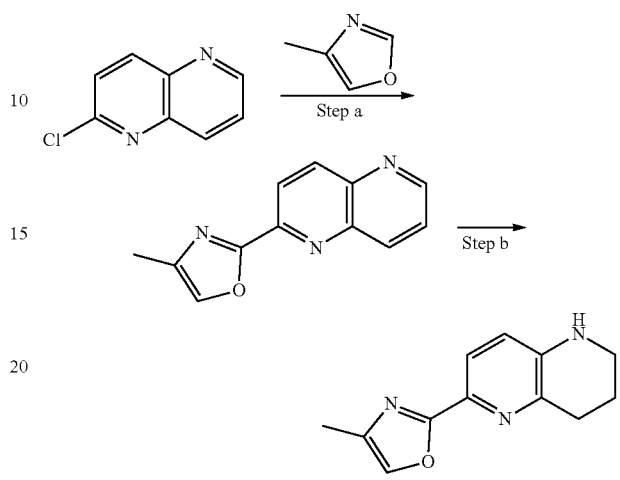

Step a: To the mixture of 2-chloro-1,5-naphthyridine (350 mg, 2.12 mmol) and 4-methyl-1,3-oxazole (264 mg, 3.18 mmol) in toluene (10.0 mL) were added Pd(OAc)$_2$ (96.0 mg, 424 μmol), t-BuOK (713 mg, 6.36 mmol) and RuPhos (296 mg, 636 μmol) under N$_2$. The mixture was stirred at 110° C. under N$_2$ for 12 hrs. The mixture was concentrated in vacuo and purified by flash silica gel chromatography (DCM/MeOH=1/0 to 9/1) to give 2-(4-methyl-1,3-oxazol-2-yl)-1,5-naphthyridine (130 mg) as a yellow solid.

Step b: To the mixture of 2-(4-methyl-1,3-oxazol-2-yl)-1,5-naphthyridine (160 mg, 615 μmol) and diethyl 2,6-dimethyl-1,4-dihydropyridine-3,5-dicarboxylate (387 mg, 1.53 mmol) in toluene (10.0 mL) was added 4-hydroxydinaphtho[2,1-d:1',2'-f][1,3,2]dioxaphosphepine 4-oxide (21.4 mg, 61.5 μmol) under N$_2$. The mixture was stirred at 100° C. under N$_2$ for 12 hrs. The mixture was concentrated in vacuo and purified by flash silica gel chromatography (DCM/MeOH=1/0 to 10/1) followed by prep-TLC (DCM/MeOH=20/1) to give 6-(4-methyl-1,3-oxazol-2-yl)-1,2,3,4-tetrahydro-1,5-naphthyridine (56.6 mg, 42.8% yield) as a brown solid. LCMS m/z: 215.9 (M)+.

Synthesis of tert-butyl 7-(pyridazin-4-yl)-1,2,3,4-tetrahydroquinoxaline-1-carboxylate, Used in Preparation of Compound 332

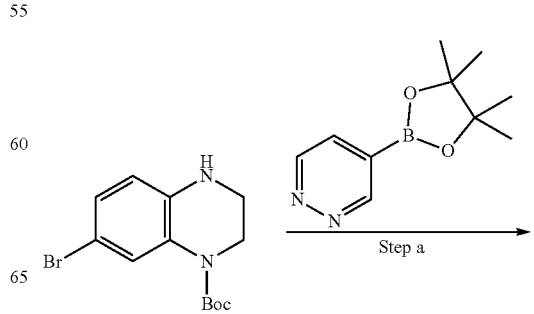

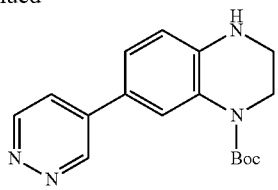

Step a: A solution of tert-butyl 7-bromo-1,2,3,4-tetrahydroquinoxaline-1-carboxylate (700 mg, 2.23 mmol), 4-(4,4,5,5-tetramethyl-1,3,2-dioxaborolan-2-yl)pyridazine (459 mg, 2.23 mmol), Pd(dppf)Cl$_2$ (1.63 g, 2.23 mmol) and K$_2$CO$_3$ (615 mg, 4.46 mmol) in Dioxane/H$_2$O=10:1 (50 mL) was stirred at 100° C. for 12 hours under N$_2$. The mixture was concentrated and purified by flash silica gel chromatography (eluent: Petroleum ether/Ethyl acetate=5:1 to 1:1) to afford tert-butyl 7-(pyridazin-4-yl)-1,2,3,4-tetrahydroquinoxaline-1-carboxylate (260 mg, 832 μmol, 37% yield) as a yellow oil.

Synthesis of
5-chloro-1,2,3,4-tetrahydro-1,6-naphthyridine, Used
in Preparation of Compound 333

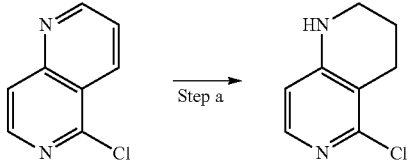 [SMILES: Clc1nccc2ncccc12 ; Clc1nccc2c1CCCN2]

A solution of 5-chloro-1,6-naphthyridine (4.00 g, 24.3 mmol, CAS #23616-32-2), 3,5-diethyl 2,6-dimethyl-1,4-dihydropyridine-3,5-dicarboxylate (14.70 g, 58.3 mmol) and diphenoxyphosphinic acid (1.21 g, 4.86 mmol) in toluene (200.0 mL) was stirred at 80° C. for 12 h under N$_2$. The solution was concentrated in vacuum to remove solvent. The residue was purified by flash silica gel chromatography (40 g, Ethyl acetate in Petroleum ether from 0% to 30%) to give 5-chloro-1,2,3,4-tetrahydro-1,6-naphthyridine (1.9 g, 46% yield) as an orange solid.

Synthesis of 6-(pyridazin-3-yl)-1,2,3,4-tetrahydro-1,
5-naphthyridine, Used in Preparation of Compound
348

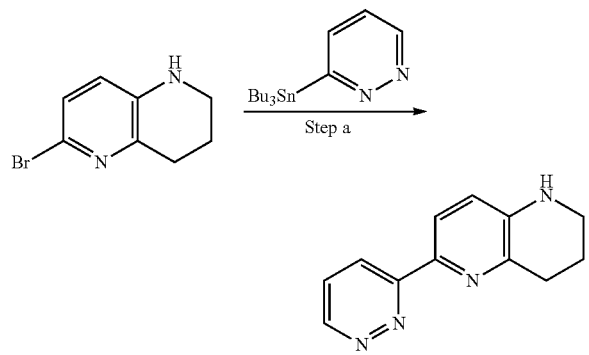

Step a: To a mixture of 6-bromo-1,2,3,4-tetrahydro-1,5-naphthyridine (100.0 mg, 469.0 μmol) and 3-(tributylstannyl)pyridazine (173.0 mg, 469.0 μmol) in toluene (10.0 mL) was added Pd(PPh$_3$)$_4$ (270.0 mg, 234.0 μmol), then the mixture was stirred at 110° C. for 24 h under N$_2$. The mixture was diluted with water (50.0 mL) and extracted with EtOAc (50.0 mL×3). The organic layers were washed with brine (50.0 mL), dried over anhydrous Na$_2$SO$_4$ and concentrated under reduced pressure. The residue was purified by column chromatography (MeOH in EtOAc=0~10%) to afford 6-(pyridazin-3-yl)-1,2,3,4-tetrahydro-1,5-naphthyridine (45 mg, 212 μmol, 45% yield) as a yellow solid. LCMS m/z 213.1 (M+H)$^+$.

Synthesis of 6-(pyrazin-2-yl)-1, 2, 3,
4-tetrahydro-1,5-naphthyridine, Used in Preparation
of Compound 350

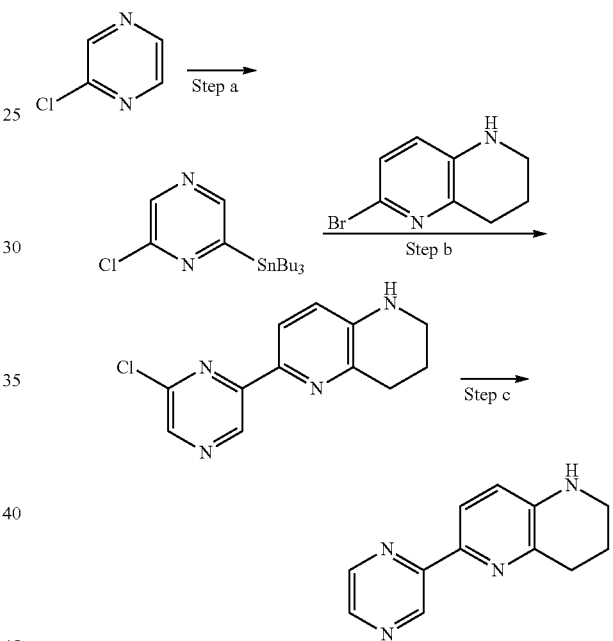

Step a: To a solution of HTMP (1.96 g, 13.9 mmol) in THF (20 mL) was added n-BuLi (5.56 mL, 13.9 mmol) at −50° C. under N$_2$. The solution was warmed to 0° C., and stirred for 20 min. 2-chloropyrazine (500 mg, 4.36 mmol) and Bu$_3$SnCl (1.41 g, 4.36 mmol) in THF (20 mL) was then added to the solution at −78° C. The solution was warmed to −40° C. for 3 h. The mixture was quenched with conc.HCl/EtOH/THF (1:4:5, 20 mL) at −40° C. and the mixture was warmed to 20° C. The mixture was neutralized with sat. NaHCO$_3$ and the volatiles were removed. The residue was diluted with H$_2$O (20 mL) and extracted with ethyl acetate (20 mL×3). The combined organic layers were washed with brine (15 mL), dried over anhydrous Na$_2$SO$_4$, filtered and concentrated in vacuo. The residue was purified by silica column (Ethyl acetate in Petroleum ether 0-10%) to give the desired product of 2-chloro-6-(tributylstannyl) pyrazine (1.16 g, 66.2% yield) as a yellow oil.

Step b: A mixture of 6-bromo-1,2,3,4-tetrahydro-1,5-naphthyridine (300 mg, 1.40 mmol), 2-chloro-6-(tributylstannyl)pyrazine (565 mg, 1.40 mmol) and Pd(PPh$_3$)$_4$ (323 mg, 280 μmol) in PhMe (15 mL) was stirred at 120° C. for 12 h under N₂ After concentration, the residue was purified by silica column (Ethyl acetate in Petroleum ether 0-40%) to give the desired product of 6-(6-chloropyrazin-2-yl)-1, 2, 3, 4-tetrahydro-1,5-naphthyridine (200 mg, 57.9%) as a yellow solid.

Step c: To a solution of 6-(6-chloropyrazin-2-yl)-1, 2, 3, 4-tetrahydro-1,5-naphthyridine (180 mg, 729 μmol) in MeOH (10 mL) was added K₂CO₃ (300 mg, 2.18 mmol) and Pd/C (10 wt % wet, 180 mg). The mixture was stirred at 15° C. for 12 h under H2 (15 psi). The reaction mixture was then filtered and the filtrate was concentrated in vacuo. The residue was purified by prep HPLC (NH₃) to give the desired product of 6-(pyrazin-2-yl)-1, 2, 3, 4-tetrahydro-1,5-naphthyridine (120 mg, 77% yield) as a yellow solid. LCMS m/z: 213.0 (M+H)+.

Synthesis of 2-(5,6,7,8-tetrahydro-1,5-naphthyridin-2-yl)acetonitrile, Used in Preparation of Compound 352

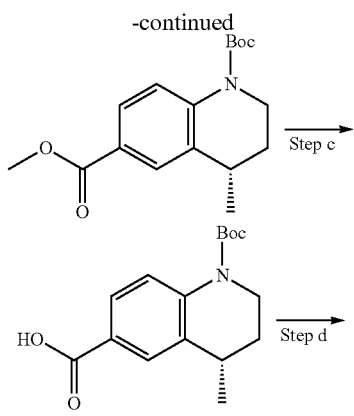

Step a: A solution of 6-bromo-1,2,3,4-tetrahydro-1,5-naphthyridine (300 mg, 1.40 mmol), 4-(4,4,5,5-tetramethyl-1,3,2-dioxaborolan-2-yl)-1,2-oxazole (273 mg, 1.40 mmol), Pd(dppf)Cl₂ (102 mg, 140 umol) and K₂CO₃ (386 mg, 2.80 umol) in dioxane:H₂O=10:1 (10 mL) was stirred at 110° C. for 12 hours. TLC (PE:EA=1:1) showed the desired product was formed. The mixture concentrated and the resulting crude material was purified by silica gel chromatography (eluent: Petroleum ether/Ethyl acetate=1:1) to give 2-(5,6,7,8-tetrahydro-1,5-naphthyridin-2-yl)acetonitrile (120 mg, 692 μmol, 49.5% yield) as a yellow oil.

Synthesis of (4S)-4-methyl-6-(5-methyl-1,3,4-oxadiazol-2-yl)-1,2,3,4-tetrahydroquinoline, Used in Preparation of Compound 353

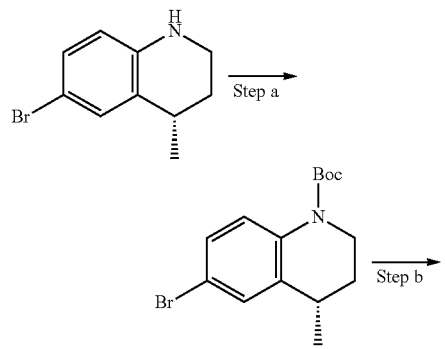

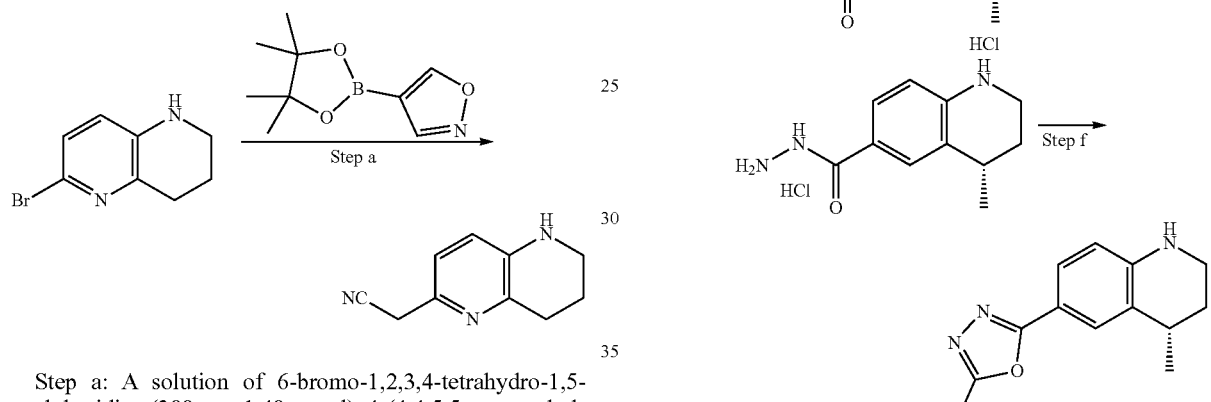

Step a: To a solution of (4S)-6-bromo-4-methyl-1,2,3,4-tetrahydroquinoline (1.0 g, 4.4 mmol, 1.0 eq) in THF (20 mL) was added NaHMDS (8.8 mL, 8.8 mmol, 1M in THF, 2.0 eq) dropwise under N₂ atmosphere. The mixture was stirred at 15° C. for 30 min. Then Boc₂O (1.3 g, 5.7 mmol, 1.3 eq) was added and the mixture was stirred at 15° C. for 10 hours. The mixture was quenched with saturated NH₄Cl and concentrated under reduced pressure. The residue was purified by column chromatography (Petroleum ether/Ethyl acetate=10:0-10:1) to afford the desired product of tert-butyl (4S)-6-bromo-4-methyl-1,2,3,4-tetrahydroquinoline-1-carboxylate (1.3 g, 90.2% yield) as a yellow oil.

Step b: The mixture of tert-butyl (4S)-6-bromo-4-methyl-1,2,3,4-tetrahydroquinoline-1-carboxylate (1.3 g, 4.0 mmol, 1.0 eq), Pd(dppf)Cl₂ (291 mg, 398 μmol, 0.1 eq) and TEA (1.2 g, 11.9 mmol, 3.0 eq) in MeOH (20 mL) was evacuated and refilled 3 times using CO. Then the reaction mixture was stirred at 80° C. for 72 hours under CO (50 psi) atmosphere. The mixture was concentrated under reduced pressure and the residue was purified by column chromatography (Petroleum ether/Ethyl acetate=1:0-10:1) to afford the desired product of 1-tert-butyl 6-methyl (4S)-4-methyl-1,2,3,4-tetrahydroquinoline-1,6-dicarboxylate (754 mg, 62.3% yield) as a yellow oil.

Step c: The mixture of 1-tert-butyl 6-methyl (4S)-4-methyl-1,2,3,4-tetrahydroquinoline-1,6-dicarboxylate (750 mg, 2.5 mmol, 1.0 eq) and LiOH (176 mg, 7.4 mmol, 3.0 eq) in MeOH (5 mL) and H₂O (0.5 mL) was stirred at 50° C. for 10 hours. The mixture was adjusted with 2N HCl to pH=7. The mixture was concentrated under reduced pressure to afford the product of (4S)-1-[(tert-butoxy)carbonyl]-4-methyl-1,2,3,4-tetrahydroquinoline-6-carboxylic acid (900 mg, crude) as a white solid.

Step d: The mixture of (4S)-1-[(tert-butoxy)carbonyl]-4-methyl-1,2,3,4-tetrahydroquinoline-6-carboxylic acid (450 mg, 80% purity, 1.2 mmol, 1.0 eq), NH$_2$NHBoc (242 mg, 1.8 mmol, 1.5 eq), HATU (1.4 g, 3.7 mmol, 3.0 eq) and TEA (371 mg, 3.7 mmol, 3.0 eq) in DMF (5 mL) was stirred at 50° C. for 12 hours. The mixture was diluted with H$_2$O (20 mL) and extracted with EtOAc (20 mL×3). The organic layer was washed with brine (20 mL), dried over anhydrous Na$_2$SO$_4$, filtered and concentrated under reduced pressure. The residue was purified by column chromatography (Petroleum ether/Ethyl acetate=10:0~4:1) to afford the desired product of tert-butyl (4S)-6-{N-[(tert-butoxy)carbonyl]hydrazinecarbonyl}-4-methyl-1,2,3,4-tetrahydroquinoline-1-carboxylate (377 mg, 75.7% yield) as a white solid.

Step e: The mixture of tert-butyl (4S)-6-{N'-[(tert-butoxy)carbonyl]hydrazinecarbonyl}-4-methyl-1,2,3,4-tetrahydroquinoline-1-carboxylate (377 mg, 929 μmol, 1.0 eq) in HCl/MeOH (5 mL, 4M) was stirred at 15° C. for 2 hours. The mixture was concentrated under reduced pressure and the residue was used in the next step directly without further purification.

Step f: To a solution of (4S)-4-methyl-1,2,3,4-tetrahydroquinoline-6-carbohydrazide dihydrochloride (250 mg, 898 μmol, 1.0 eq) in dioxane (5 mL) was added MeC(OEt)$_3$ (2.9 g, 17.9 mmol, 20 eq). The mixture was stirred at 120° C. for 10 hours. The mixture was concentrated under reduced pressure. The residue was purified by column chromatography (Petroleum ether/Ethyl acetate=10:0~3:1) to afford the desired product of (4S)-4-methyl-6-(5-methyl-1,3,4-oxadiazol-2-yl)-1,2,3,4-tetrahydroquinoline (155 mg, 75.6% yield) as a yellow solid. LCMS m/z: 230.4 (M+H)$^+$.

Synthesis of 6-(1,3-thiazol-5-yl)-1,2,3,4-tetrahydro-1,5-naphthyridine, Used in Preparation of Compound 356

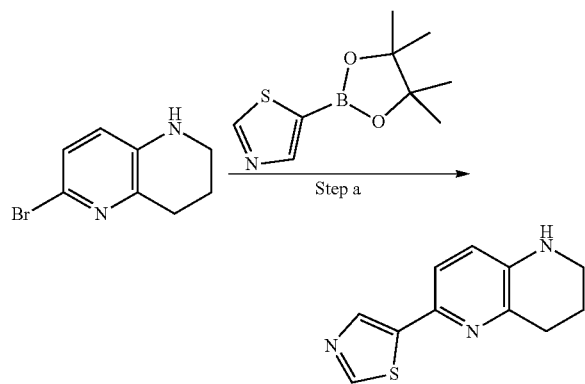

Step a: A solution of 6-bromo-1,2,3,4-tetrahydro-1,5-naphthyridine (300.0 mg, 1.40 mmol), 5-(4,4,5,5-tetramethyl-1,3,2-dioxaborolan-2-yl)-1,3-thiazole (295.0 mg, 1.40 mmol, CAS #1086111-09-2), Pd(dppf)Cl$_2$ (204.0 mg, 280.0 umol) and K$_3$PO$_4$ (888.0 mg, 4.19 mmol) in dioxane/H$_2$O (10.0 mL/1.0 mL) was stirred at 100° C. for 12 hours. The solution was added into H$_2$O (50.0 mL) and extracted with EtOAc (50.0 mL×2). The combined organic layers were washed with brine (50.0 mL), dried over anhydrous Na$_2$SO$_4$, filtered and concentrated in vacuo to give crude product as a brown gum. The residue was purified by flash silica gel chromatography (12 g, Ethyl acetate in Petroleum ether from 0% to 60%) to give 6-(1,3-thiazol-5-yl)-1,2,3,4-tetrahydro-1,5-naphthyridine (55.0 mg, 18.0% yield) as an orange oil. LCMS m/z: 217.9 (M)$^+$.

Synthesis of methyl (8S)-8-methyl-5,6,7,8-tetrahydro-1,5-naphthyridine-2-carboxylate, Used in Preparation of Compound 362

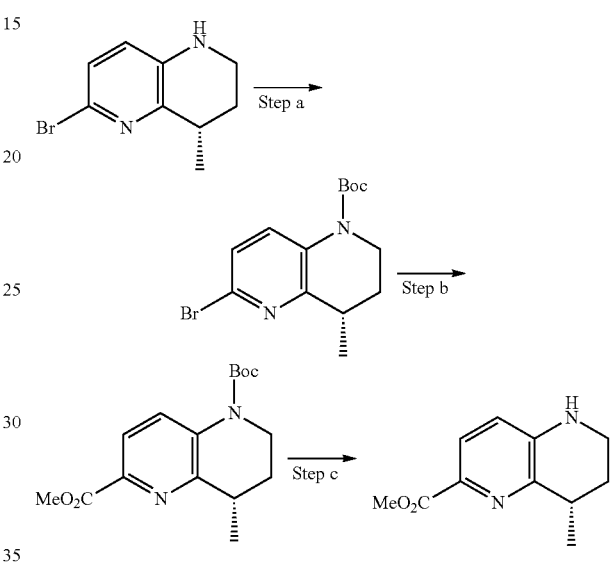

Step a: A solution of (4S)-6-bromo-4-methyl-1,2,3,4-tetrahydro-1,5-naphthyridine (5.0 g, 22.0 mmol) in THF (50.0 mL) was added 1 M NaHMDS (66.0 mL, 66.0 mmol) under N$_2$ at 20° C. The reaction was stirred for 2 hours. Next, (Boc)$_2$O (10.0 mL, 44.0 mmol) in THF(50.0 mL) was added, and the reaction mixture was stirred at 20° C. for 12 hours under N$_2$. The mixture was diluted with H$_2$O (500.0 mL), extracted with EtOAc (500.0 mL×2) and washed with brine (500.0 mL). The organic phase was dried over anhydrous Na$_2$SO$_4$, filtered and concentrated under reduced pressure and purified by flash silica gel chromatography (Ethyl acetate in Petroleum ether=0%~2%) to afford tert-butyl (4S)-6-bromo-4-methyl-1,2,3,4-tetrahydro-1,5-naphthyridine-1-carboxylate(6.65 g, 92.4% yield) as a light yellow solid.

Step b: To a solution of tert-butyl (4S)-6-bromo-4-methyl-1,2,3,4-tetrahydro-1,5-naphthyridine-1-carboxylate (6.65 g, 20.3 mmol) in MeOH (100.0 mL) was added Pd(dppf)Cl$_2$ (1.5 g, 2.0 mmol) and TEA (8.4 mL, 60.9 mmol). The mixture was evacuated and refilled 3 times with CO and stirred at 80° C. for 24 hours under CO (2 Mpa). The mixture was filtered and concentrated under reduced pressure to give a residue. The residue was diluted with EtOAc (250.0 mL) and the organic layer was separated. The organic layer was washed with H$_2$O (250.0 mL×2) and brine (250.0 mL), dried over anhydrous Na$_2$SO$_4$, filtered and concentrated under reduced pressure. The residue was purified by flash silica gel chromatography (Ethyl acetate in Petroleum ether=0~10%) to afford 1-tert-butyl 6-methyl (4S)-4-methyl-1,2,3,4-tetrahydro-1,5-naphthyridine-1,6-dicarboxylate (4.55 g, 73.2% yield) as an off-white solid.

Step c: A mixture of 1-tert-butyl 6-methyl (4S)-4-methyl-1,2,3,4-tetrahydro-1,5-naphthyridine-1,6-dicarboxylate (4.5 g, 14.6 mmol) in HCl/EtOAc (45.0 mL, 4N) was stirred at 20° C. for 4 hours. The mixture was diluted with H$_2$O (150.0 mL), washed with EtOAc (100.0 mL×2). The aqueous phase was adjusted to pH=8 with saturated NaHCO$_3$ and a lot of precipitate formed. The solid was collected by filtration and lyophilized. The filtrate was extracted with EtOAc (100.0 mL×2). The organic phase was dried over anhydrous Na$_2$SO$_4$, filtered and concentrated under reduced pressure to afford the product of methyl (8S)-8-methyl-5,6,7,8-tetrahydro-1,5-naphthyridine-2-carboxylate (2.4 g obtained in total, 81% yield) as a white solid. LCMS m/z: 207.1 (M+H)+.

Synthesis of methyl (8R)-8-methyl-5,6,7,8-tetrahydro-1,5-naphthyridine-2-carboxylate, Used in Preparation of Compound 363

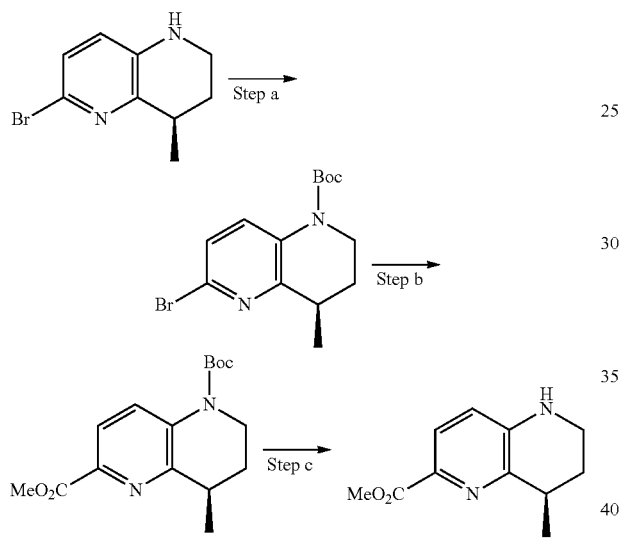

Methyl (8R)-8-methyl-5,6,7,8-tetrahydro-1,5-naphthyridine-2-carboxylate was synthesized as described above for the S enantiomer starting from (4R)-6-bromo-4-methyl-1,2,3,4-tetrahydro-1,5-naphthyridine.

Synthesis of (8R)-8-methyl-5,6,7,8-tetrahydro-1,5-naphthyridine-2-carbonitrile and (8S)-8-methyl-5,6,7,8-tetrahydro-1,5-naphthyridine-2-carbonitrile, Used in Preparation of Compound 370

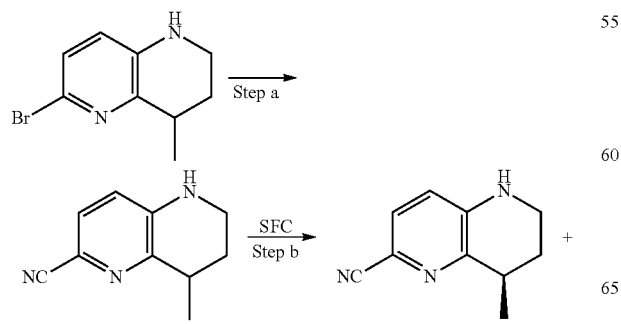

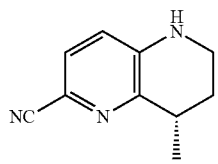

Step a: A solution of 6-bromo-4-methyl-1,2,3,4-tetrahydro-1,5-naphthyridine (1.00 g, 4.40 mmol), Zn(CN)$_2$ (774.0 mg, 6.60 mmol), Pd$_2$(dba)$_3$ (805.0 mg, 880.0 μmol), dppf (97.6 mg, 176.0 μmol) and Zn (34.3 mg, 528.0 μmol) in DMF (20.0 mL) was stirred at 120° C. for 12 hours under N$_2$. The solution was then poured into H$_2$O (50.0 mL) and extracted with EtOAc (50.0 mL×2). The combined organic layers were washed with brine (20.0 mL), dried over anhydrous Na$_2$SO$_4$, filtered and concentrated in vacuo to give crude product as a brown solid. The residue was purified by flash silica gel chromatography (40 g, EtOAc in petroleum ether from 0% to 45%) to give 8-methyl-5,6,7,8-tetrahydro-1,5-naphthyridine-2-carbonitrile (760.0 mg, 99.7% yield) as an orange solid.

Step b: 8-Methyl-5,6,7,8-tetrahydro-1,5-naphthyridine-2-carbonitrile (120.0 mg, 692.0 μmol) was purified by SFC (Column: ChiralPak IC-3 150×4.6 mm I.D., 3 um, Mobile phase: A: CO$_2$ B: IPA (0.05% DEA), Gradient: from 5% to 40% of B in 5.5 min and hold 40% for 3 min, then 5% of B for 1.5 min, Flow rate: 2.5 mL/min Column temperature: 40° C.). (8R)-8-methyl-5,6,7,8-tetrahydro-1,5-naphthyridine-2-carbonitrile (60.0 mg, 346.0 μmol) and (8S)-8-methyl-5,6,7,8-tetrahydro-1,5-naphthyridine-2-carbonitrile (60.0 mg, 346.0 μmol) were obtained as white solids. The absolute configuration was assigned randomly.

Synthesis of 6-(1-methyl-1H-pyrazol-4-yl)-1,2,3,4-tetrahydroquinoline, Used in Preparation of Compound 365

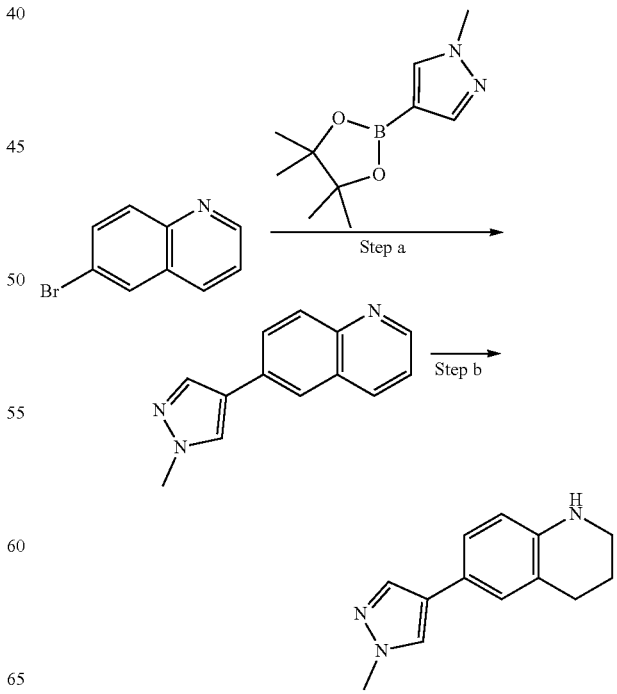

Step a: A mixture of 6-bromoquinoline (400.0 mg, 1.92 mmol), 1-methyl-4-(4,4,5,5-tetramethyl-1,3,2-dioxaborolan-2-yl)-1H-pyrazole (478.0 mg, 2.30 mmol) K₂CO₃ (662.0 mg, 4.80 mmol), and Pd(dppf)Cl₂ (70.0 mg, 0.09 mmol) in dioxane (20.0 mL)/H₂O (2.0 mL) was evacuated and refilled 3 times using N₂. The reaction mixture was then stirred at 100° C. for 12 hours under N₂ atmosphere. The mixture was then concentrated to give a residue which was purified by flash silica gel chromatography (Petroleum ether/Ethyl acetate=100:0 to 50:100) to give the product of 6-(1-methyl-1H-pyrazol-4-yl)quinoline (380.0 mg, 94.7% yield) as a white solid.

Step b: A solution of 6-(1-methyl-1H-pyrazol-4-yl)quinoline (380.0 mg, 1.81 mmol), 3,5-diethyl 2,6-dimethyl-1,4-dihydropyridine-3,5-dicarboxylate (1.37 g, 5.43 mmol) and diphenoxyphosphinic acid (90.5 mg, 0.36 mmol) in PhMe (15.0 mL) was stirred at 80° C. for 12 hours under N₂. The mixture was concentrated and purified by flash silica gel chromatography (Ethyl acetate:MeOH=100:0 to 100:10) to afford the product of 6-(1-methyl-1H-pyrazol-4-yl)-1,2,3,4-tetrahydroquinoline (250.0 mg, 64.7% yield) as a white solid. LCMS m/z: 214.1 (M+H)+.

Synthesis of 8-methanesulfonyl-1-methyl-1,2,3,4-tetrahydroquinoxaline, Used in Preparation of Compound 367

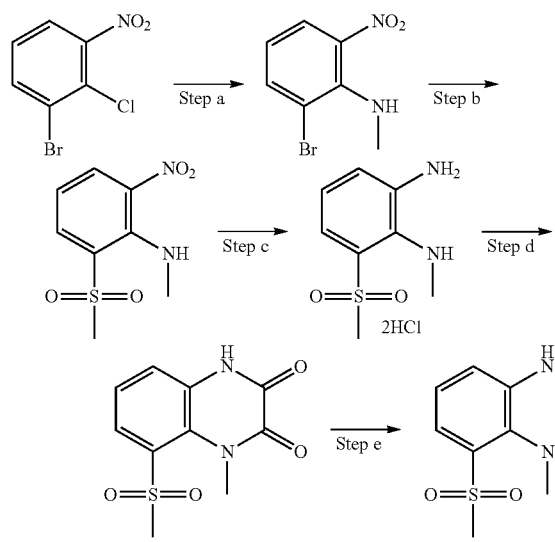

Step a: To a solution of 1-bromo-2-chloro-3-nitrobenzene (2.00 g, 8.45 mmol) in dioxane (5.0 mL) was added 40% aq. methanamine (1.96 g) and the reaction mixture was stirred at 100° C. under N₂ for 2 hours. The mixture was poured into EtOAc (100.0 mL) and washed with water (50.0 mL×2). The organic layer was dried over anhydrous Na₂SO₄, filtered and evaporated in vacuo to give 2-bromo-N-methyl-6-nitroaniline (1.94 g, 8.39 mmol, 99.4% yield) as red oil.

Step b: 2-Bromo-N-methyl-6-nitroaniline (600.0 mg, 2.59 mmol), sodium methanesulfinate (792.0 mg, 7.76 mmol) and CuI (1.96 g, 10.30 mmol) in NMP (10.0 mL) was degassed under N₂ and stirred at 140° C. for 2 hours. The reaction was quenched by the addition of EtOAc (100.0 mL), filtered through a pad of celite, eluting with EtOAc (50.0 mL). The organic solution was washed with water (50.0 mL×3), concentrated and purified by silica gel column (EtOAc in Petroleum ether=0~30%) to give 2-methanesulfonyl-N-methyl-6-nitroaniline (420.0 mg, 1.82 mmol, 70.4% yield) as a yellow solid.

Step c: A mixture of 2-methanesulfonyl-N-methyl-6-nitroaniline (420.0 mg, 1.82 mmol) and Pd/C (0.2 g, 10 wt % wet) in 2 N HCl (5.0 mL) and MeOH (20.0 mL) was hydrogenated under H₂ (15 psi) at 50° C. for 12 hours. The Pd/C was filtered off, and the filtrate was concentrated in vacuo to give 6-methanesulfonyl-N¹-methylbenzene-1,2-diamine dihydrochloride (450.0 mg, 1.64 mmol, 90.5% yield) as a red solid.

Step d: To a mixture of 6-methanesulfonyl-N-methylbenzene-1,2-diamine dihydrochloride (450.0 mg, 1.64 mmol) and pyridine (639.0 mg, 8.20 mmol) in DCM (20.0 mL) at 0° C. was added (COCl)₂ (416.0 mg, 3.28 mmol) drop-wise. The reaction was allowed to stir at 0-20° C. for 12 hours. The reaction mixture was poured into 1 N HCl (50.0 mL) and extracted with DCM (50.0 mL×3). The organic layers were concentrated in vacuo to give 8-methanesulfonyl-1-methyl-1,2,3,4-tetrahydroquinoxaline-2,3-dione (350.0 mg, crude) as a yellow solid.

Step e: To a solution of 8-methanesulfonyl-1-methyl-1,2,3,4-tetrahydroquinoxaline-2,3-dione (350.0 mg, 1.37 mmol) in THF (10.0 mL) was added 1.0 M BH₃-THF (13.7 mL, 13.7 mmol) and the reaction was stirred at 60° C. for 12 hours. The reaction was quenched with MeOH (5.0 mL) and concentrated in vacuo. The residue was purified by silica column (EtOAc in Petroleum ether=20~80%) to give 8-methanesulfonyl-1-methyl-1,2,3,4-tetrahydroquinoxaline (50.0 mg, 220.0 μmol, 16.1% yield) as a white solid. LCMS m/z: 227.0 (M+H)+.

Synthesis of 5-(ethanesulfonyl)-1, 2, 3, 4-tetrahydroquinoline, Used in Preparation of Compound 368

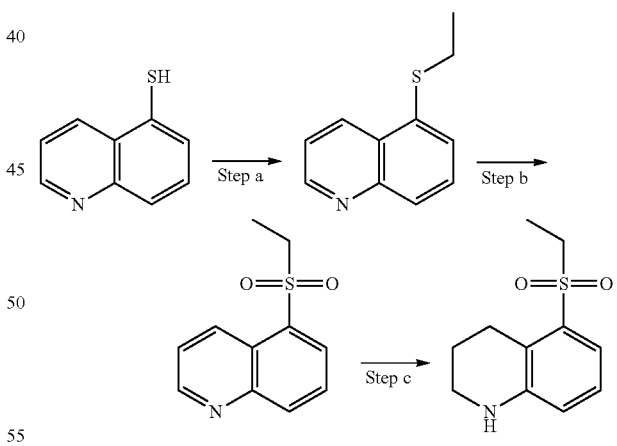

Step a: To a mixture of quinoline-5-thiol (CAS 3056-03-9) (600 mg, 3.72 mmol) and KOH (208 mg, 3.72 mmol) in EtOH (10 mL) was added EtI (580 mg, 3.72 mmol). The mixture was stirred for 12 h at 15° C. After concentration, the residue was diluted with ethyl acetate (50 mL), washed with H₂O (10 mL×3) and brine (10 mL). The organic layer was then dried over anhydrous Na₂SO₄, filtered and concentrated in vacuo to give 5-(ethylsulfanyl)quinoline (570 mg, 80.9% yield) as a yellow oil.

Step b: A mixture of 5-(ethylsulfanyl) quinoline (518 mg, 2.74 mmol) in DMF (1 mL) and NaClO (10% w/w, 10 mL)

was stirred at 50° C. for 12 h. The reaction mixture was then diluted with H₂O (30 mL) and extracted with ethyl acetate (30 mL×3). The combined organic layers were washed with brine (15 mL), dried over anhydrous Na₂SO₄, filtered and concentrated in vacuo. The residue was purified by silica column (Ethyl acetate in petroleum ether 0-50%) to give the desired product of 5-(ethanesulfonyl)quinoline (230 mg, 38% yield) as a yellow oil.

Step c: A mixture of 5-(ethanesulfonyl)quinoline (230 mg, 1.03 mmol), 3,5-diethyl 2,6-dimethyl-1,4-dihydropyridine-3,5-dicarboxylate (625 mg, 2.47 mmol) and diphenoxyphosphinic acid (51.5 mg, 206 µmol) in toluene (10 mL) was stirred at 80° C. for 12 h under N₂. After concentration, the residue was purified by silica column (ethyl acetate in oetroleum ether 0-50%) to give the desired product of 5-(ethanesulfonyl)-1, 2, 3, 4-tetrahydroquinoline (200 mg, 86% yield) as a yellow oil. LCMS m/z: 226.1.

Synthesis of 5-(dimethylphosphoryl)-1,2,3,4-tetrahydroquinoline, Used in Preparation of Compound 369

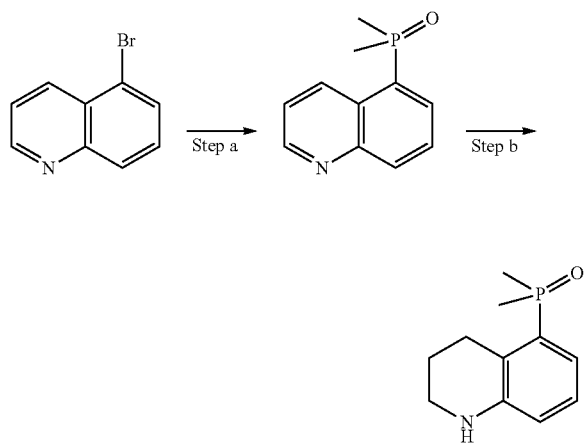

Step a: To the compound of 5-bromoquinoline (500 mg, 2.40 mmol), Pd(OAc)₂ (107 mg, 0.48 mmol), XantPhos (277 mg, 0.48 mmol), K₃PO₄ (560 mg, 2.64 mmol) and dimethylphosphinous acid (206 mg, 2.64 mmol) was added DMF (7.5 mL). The mixture was stirred at 130° C. for 12 h. To the mixture was then added H₂O (10 mL) and the mixture was extracted with ethyl acetate (30 mL×2). The combined organic layers were washed with brine (50 mL), dried over anhydrous Na₂SO₄, filtered and concentrated to give a residue which was purified by flash silica gel chromatography (Ethyl acetate:MeOH=100:0 to 100:10) to give 5-(dimethylphosphoryl)quinoline (380 mg, 77% yield) as a yellow oil.

Step b: A solution of 5-(dimethylphosphoryl)quinoline (380 mg, 1.85 mmol), 3,5-diethyl 2,6-dimethyl-1,4-dihydropyridine-3,5-dicarboxylate (1.40 g, 5.55 mmol) and diphenoxyphosphinic acid (92.5 mg, 0.37 mmol) in PhMe (15 mL) was stirred at 80° C. for 12 hours under N₂. The mixture was concentrated and purified by flash silica gel chromatography (EtOAc:MeOH=100:0 to 100:10) to afford the product of 5-(dimethylphosphoryl)-1,2,3,4-tetrahydroquinoline (540 mg) as a yellow oil.

Synthesis of 1-(5,6,7,8-tetrahydro-1,5-naphthyridin-2-yl)ethan-1-one, Used in Preparation of Compound 397

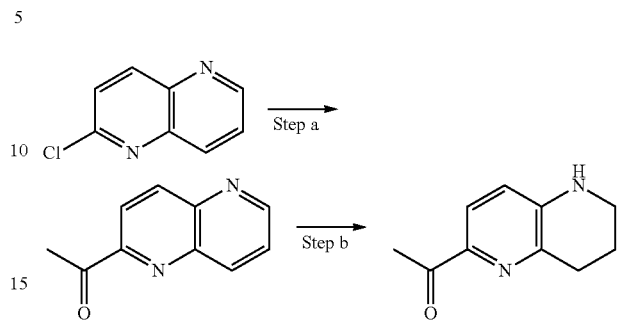

Step a: A mixture of 2-chloro-1,5-naphthyridine (2.00 g, 12.1 mmol), tributyl(1-ethoxyethenyl)stannane (5.23 g, 14.5 mmol), Pd₂(dba)₃ (600.0 mg, 0.66 mmol) and PPh₃ (317.0 mg, 1.21 mmol) in PhMe (50.0 mL) was stirred at 100° C. for 12 hours under N₂. Then to the reaction mixture was added 2 N HCl (50.0 mL) and the reaction mixture was stirred at 60° C. for 2 hours. The reaction mixture was then extracted with petroleum ether (50.0 mL×2). The aqueous was basified with saturated Na₂CO₃ until the pH=9.0 and extracted with EtOAc (50.0 mL×2). The combined organic layers were concentrated in vacuo and purified by silica gel column (Petroleum ether/EtOAc=100:0 to 100:50) to give the product of 1-(1,5-naphthyridin-2-yl)ethan-1-one (1.30 g, 62.5% yield) as a light red solid.

Step b: A solution of 1-(1,5-naphthyridin-2-yl)ethan-1-one (600.0 mg, 3.48 mmol), 3,5-diethyl 2,6-dimethyl-1,4-dihydropyridine-3,5-dicarboxylate (2.63 g, 10.4 mmol) and diphenoxyphosphinic acid (174.0 mg, 0.70 mmol) in toluene (12.0 mL) was stirred at 80° C. for 12 hours under N₂. The mixture was concentrated and purified by flash silica gel chromatography (petroleum ether:EtOAc=100:0 to 100:20) to afford 1-(5,6,7,8-tetrahydro-1,5-naphthyridin-2-yl)ethan-1-one (195.0 mg, 31.8% yield) as a yellow solid.

Synthesis of methyl 2-(7-cyano-1,2,3,4-tetrahydroquinoxalin-1-yl)acetate, Used in Preparation of Compound 399

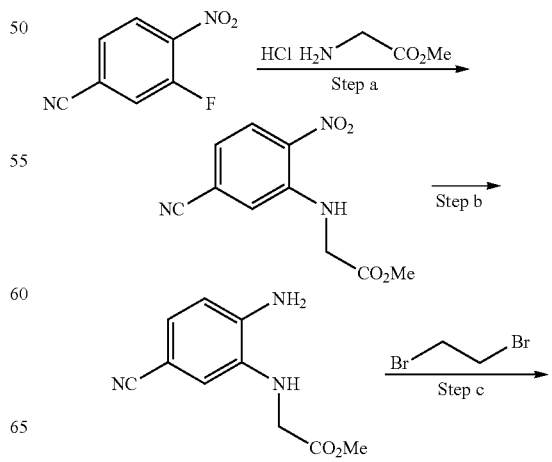

-continued

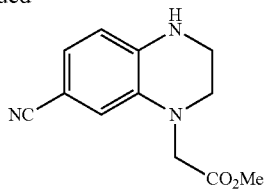

Step a: To a solution of methyl 2-aminoacetate hydrochloride (1.35 g, 10.8 mmol) and TEA (3.73 mL, 27.0 mmol) in MeOH (100.0 mL) was added 3-fluoro-4-nitrobenzonitrile (1.5 g, 9.03 mmol) at 50° C. The mixture was stirred at 50° C. for 0.5 h. The mixture was concentrated in vacuo and the residue was purified by flash silica gel chromatography (40 g, Ethyl acetate in Petroleum ether from 0% to 13%) to give methyl 2-[(5-cyano-2-nitrophenyl)amino]acetate (1.0 g, 47.1% yield) as a yellow solid.

Step b: A solution of methyl 2-[(5-cyano-2-nitrophenyl)amino]acetate (1.0 g, 4.25 mmol) and wet Pd/C (200.0 mg, 10 wt %) in THF (50.0 mL) was stirred at 20° C. for 0.5 h under $H_2$ (15 psi). The mixture was filtered and filtrate was concentrated in vacuo to give methyl 2-[(2-amino-5-cyanophenyl)amino]acetate (800.0 mg, 91.7% yield) as a yellow solid.

Step c: A mixture of methyl 2-[(2-amino-5-cyanophenyl)amino]acetate (500.0 mg, 2.43 mmol), 1,2-dibromoethane (1.82 g, 9.72 mmol), TBAB (3.13 g, 9.72 mmol) and TEA (1.34 mL. 9.72 mmol) was stirred at 60° C. for 12 h. The mixture was concentrated in vacuo to remove solvent. The mixture was then added into $H_2O$ (100.0 mL) and then extracted with EtOAc (100.0 mL×2). The combined organic layers were washed with brine (100.0 mL), dried over anhydrous $Na_2SO_4$, filtered and concentrated in vacuo to give crude product as a brown gum. The residue was purified by flash silica gel chromatography (12 g, Ethyl acetate in Petroleum ether from 0% to 30%) to give methyl 2-(7-cyano-1,2,3,4-tetrahydroquinoxalin-1-yl)acetate (300.0 mg, 53.4% yield) as an orange oil. LCMS m/z: 232.0 $(M+H)^+$.

Synthesis of Examples

Preparation of 1-(3-((2-chlorophenyl)thio)-1H-pyrazolo[3,4-b]pyrazin-6-yl)-4-methylpiperidin-4-amine, Compound 6

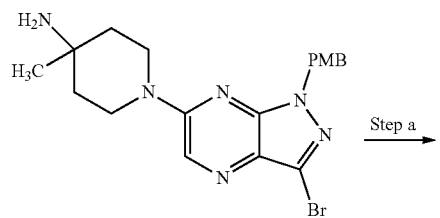

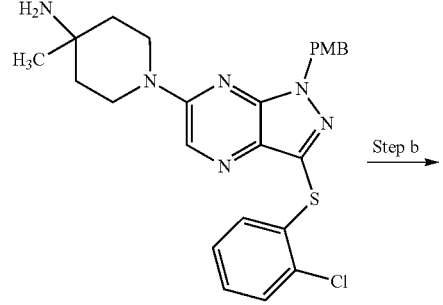

-continued

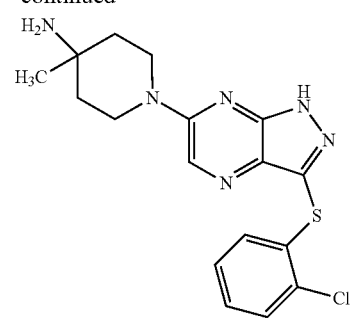

Step a: To a 5 mL vial were added 1-(3-bromo-1-(4-methoxybenzyl)-1H-pyrazolo[3,4-b]pyrazin-6-yl)-4-methylpiperidin-4-amine (50 mg, 0.12 mmol), $Pd_2dba_3$ (5 mg, 5 mol %), XantPhos (7 mg, 10 mol %), 2-chloro-thiophenol (16 μL, 0.14 mmol), and N,N-diisopropylethylamine (41 μL, 0.23 mmol), followed by dioxane (0.2 mL). The resulting mixture was sealed, degassed with nitrogen, and heated under microwave irradiation at 130° C. for 1.5 h. After full conversion, the volatiles were evaporated under reduced pressure. The resulting residue was purified by reversed phase chromatography (eluting with acetonitrile and water with 0.1% ammonium formate) to give 1-(3-((2-chlorophenyl)thio)-1-(4-methoxybenzyl)-1H-pyrazolo[3,4-b]pyrazin-6-yl)-4-methylpiperidin-4-amine (55 mg, 96%) as an off-white solid after lyophilization: LCMS [M+H]+=496.2.

Step b: In a 25-mL round bottomed flask, 1-(3-((2-chlorophenyl)thio)-1-(4-methoxybenzyl)-1H-pyrazolo[3,4-b]pyrazin-6-yl)-4-methylpiperidin-4-amine (57 mg, 0.115 mmol) was slowly dissolved in 33% hydrobromic acid in acetic acid (1 mL) at room temperature. The resulting yellow-orange mixture was placed in a preheated oil bath at 70° C. and stirred at this temperature for 45 min. After this time, the mixture cooled to room temperature and slowly dropped into diethyl ether (20 mL). The resulting yellow/orange precipitate was filtered through a piece of cotton. The gummy residue obtained was redissolved in water (3-4 mL) and neutralized with a solution of saturated sodium bicarbonate until the pH was neutral. The resulting aqueous solution was loaded onto a reversed phase chromatography column and purified using a gradient of acetonitrile in 0.1% formic acid in water (10 to 50%) to give 1-(3-((2-chlorophenyl)thio)-1H-pyrazolo[3,4-b]pyrazin-6-yl)-4-methylpiperidin-4-amine (24.2 mg, 56%) as an off-white solid.

Preparation of (4-methyl-1-(3-(phenylthio)-1H-pyrazolo[3,4-b]pyrazin-6-yl)piperidin-4-yl)methanamine, Compound 7

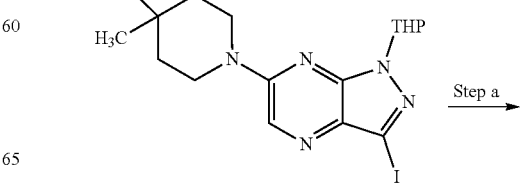

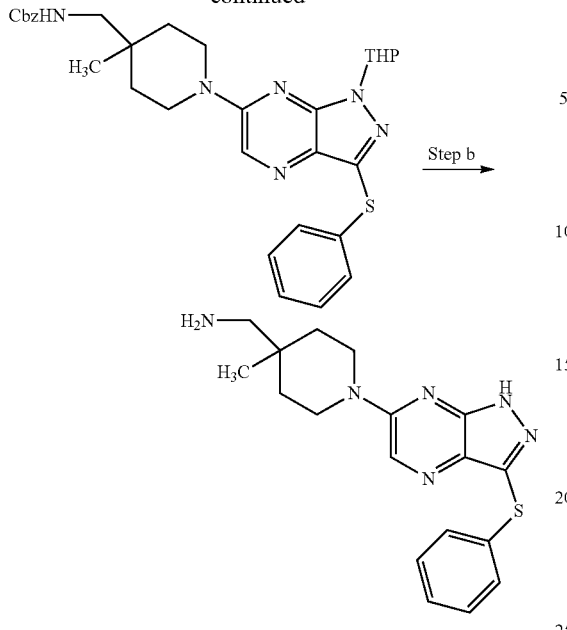

Step a: Benzyl ((1-(3-iodo-1-(tetrahydro-2H-pyran-2-yl)-1H-pyrazolo[3,4-b]pyrazin-6-yl)-4-methylpiperidin-4-yl)methyl)carbamate (50 mg, 0.085 mmol) was dissolved in i-PrOH (0.9 mL) in a 5 mL vial. Copper iodide (16 mg, 0.085 mmol), potassium carbonate (24 mg, 0.170 mmol), ethylene glycol (10 μL, 0.17 mmol), and thiophenol (19 μL. 0.102 mmol) were successively added and the vial was flushed with N₂, sealed, and placed in a preheated oil bath at 100° C. The resulting yellow heterogeneous mixture was stirred at this temperature for 5 hrs. After this time, additional copper iodide (16 mg) and thiophenol (19 μL) were added and the resulting mixture heated overnight at 100° C. After full conversion, the mixture was cooled to room temperature, filtered through a piece of cotton, and the vial and cotton rinsed with ethyl acetate. The filtrate was washed with aqueous ammonia (2×10 mL), brine (2×10 mL), and the organics dried over anhydrous Na₂SO₄, filtered, and concentrated under reduced pressure. The crude material was purified by flash chromatography using a gradient of ethyl acetate in hexanes (0 to 70%), affording benzyl ((4-methyl-1-(3-(phenylthio)-1-(tetrahydro-2H-pyran-2-yl)-1H-pyrazolo[3,4-b]pyrazin-6-yl)piperidin-4-yl)methyl)carbamate (45 mg, 93%) as a pale yellow oil: LCMS [M+H]⁺=573.1.

Step b: Benzyl ((4-methyl-1-(3-(phenylthio)-1-(tetrahydro-2H-pyran-2-yl)-1H-pyrazolo[3,4-b]pyrazin-6-yl)piperidin-4-yl)methyl)carbamate (45 mg, 0.079 mmol) was slowly dissolved in 33% hydrobromic acid in acetic acid (1 mL) at 0-4° C. The resulting yellow-orange mixture was stirred at this temperature for 5 min and allowed to progressively reach room temperature. The reaction mixture was stirred an additional 40 min at room temperature. The mixture was slowly dropped into diethyl ether (20 mL). A gummy yellow precipitate formed which was redissolved in water (10 mL). The layers were separated and the aqueous layer basified with sat. aq. Na₂CO₃ solution (30 mL), followed by the addition of dichloromethane (20 mL). The layer was further extracted with dichloromethane (3×10 mL) and the combined organics were dried over anhydrous Na₂SO₄, filtered, and concentrated under reduced pressure to provide (4-methyl-1-(3-(phenylthio)-1H-pyrazolo[3,4-b]pyrazin-6-yl)piperidin-4-yl)methanamine (17.7 mg, 64%) as an off-white solid after lyophilization.

Preparation of 4-methyl-1-(3-((2-(trifluoromethyl)pyridin-3-yl)thio)-1H-pyrazolo[3,4-b]pyrazin-6-yl)piperidin-4-amine, Compound 8

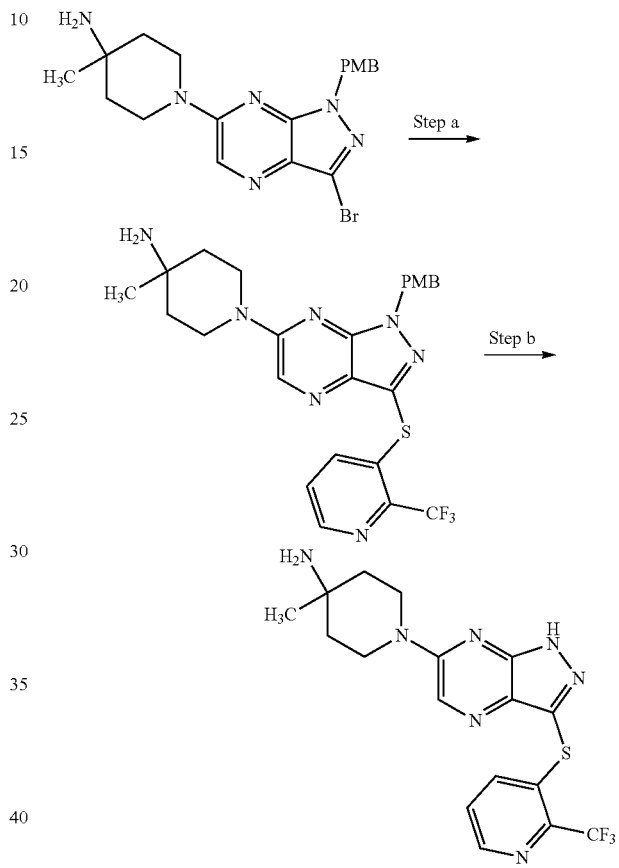

Step a: 1-(3-Bromo-1-(4-methoxybenzyl)-1H-pyrazolo[3,4-b]pyrazin-6-yl)-4-methylpiperidin-4-amine (50 mg, 0.12 mmol), Pd₂dba₃ (53 mg, 0.06 mmol), XantPhos (69 mg, 0.12 mmol), 2-(trifluoromethyl)pyridine-3-thiol (42 mg, 0.23 mmol, 1801693-48-0), and N,N-diisopropylethylamine (41 μL, 0.23 mmol) were successively added in a 5 mL vial, followed by the addition of dioxane (0.3 mL). The resulting mixture was sealed, degassed with N₂, and heated under microwave irradiation at 130° C. for 1.5 hrs. The volatiles were removed under reduced pressure and the resulting residue purified by reversed phase chromatography (25 to 65% gradient of acetonitrile/10 mM aqueous ammonium formate) to give 1-(1-(4-methoxybenzyl)-3-((2-(trifluoromethyl)pyridin-3-yl)thio)-1H-pyrazolo[3,4-b]pyrazin-6-yl)-4-methylpiperidin-4-amine (32 mg, 52%) as an off-white solid after lyophilization: LCMS [M+H]⁺=530.5.

Step b: 1-(1-(4-Methoxybenzyl)-3-((2-(trifluoromethyl)pyridin-3-yl)thio)-1H-pyrazolo[3,4-b]pyrazin-6-yl)-4-methylpiperidin-4-amine (32 mg, 0.06 mmol) was slowly dissolved in 33% hydrobromic acid in acetic acid (1 mL) at room temperature. The resulting yellow-orange mixture was placed in a preheated oil bath at 70° C., and stirred at this temperature for 1 hr. After this time, the mixture was allowed to cool to room temperature, then slowly dropped into diethyl ether (20 mL). The resulting yellow/orange precipitate was filtered through a piece of cotton. The gummy residue was redissolved in water (3-4 mL), loaded on a reversed phase chromatography column, and purified using a gradient of acetonitrile/0.1% formic acid in water (0 to 50%) to give 4-methyl-1-(3-((2-(trifluoromethyl)pyridin-3-yl)thio)-1H-pyrazolo[3,4-b]pyrazin-6-yl)piperidin-4-amine (16 mg, 65%) as an off-white solid.

Preparation of (1-(3-((2-chlorophenyl)thio)-1H-pyrazolo[3,4-b]pyrazin-6-yl)-4-methylpiperidin-4-yl)methanamine, Compound 9

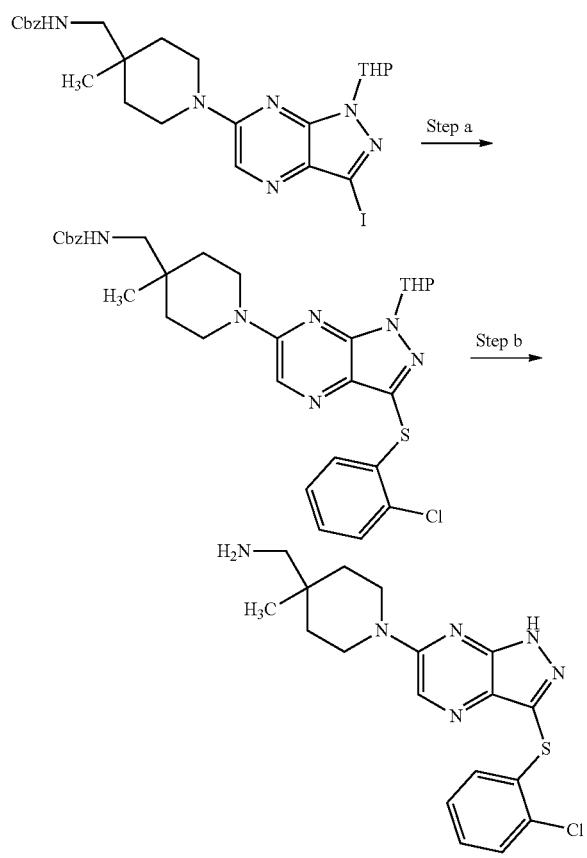

Step a: Benzyl ((1-(3-iodo-1-(tetrahydro-2H-pyran-2-yl)-1H-pyrazolo[3,4-b]pyrazin-6-yl)-4-methylpiperidin-4-yl)methyl)carbamate (50 mg, 0.085 mmol) was dissolved in i-PrOH (0.9 mL) in a 5 mL vial. Copper iodide (32 mg, 0.17 mmol), potassium carbonate (24 mg, 0.170 mmol), ethylene glycol (10 μL, 0.17 mmol), and 2-chloro-thiophenol (20 μL, 0.17 mmol) were successively added and the vial flushed with $N_2$, sealed, and placed in a preheated oil bath at 100° C. The resulting yellow heterogeneous mixture was stirred at this temperature for 5 hr. Additional copper iodide (16 mg) and 2-chloro-thiophenol (19 μL) were added and the resulting mixture heated overnight at 100° C. The mixture was cooled to room temperature, filtered through a piece of cotton, and the vial and cotton rinsed with ethyl acetate. The filtrate was washed with aqueous ammonia (2×10 mL), brine (2×10 mL), and the organic layer dried over anhydrous $Na_2SO_4$, filtered, and concentrated under reduced pressure. The crude material was purified by flash chromatography using a gradient of ethyl acetate in hexanes (0 to 70%), affording benzyl ((1-(3-((2-chlorophenyl)thio)-1-(tetrahydro-2H-pyran-2-yl)-1H-pyrazolo[3,4-b]pyrazin-6-yl)-4-methylpiperidin-4-yl)methyl)carbamate (40 mg, 60% purity by LCMS): LCMS [M+H]$^+$=607.4.

Step b: Benzyl ((1-(3-((2-chlorophenyl)thio)-1-(tetrahydro-2H-pyran-2-yl)-1H-pyrazolo[3,4-b]pyrazin-6-yl)-4-methylpiperidin-4-yl)methyl)carbamate (20 mg, 0.033 mmol) was slowly dissolved in 33% hydrobromic acid in acetic acid (1 mL) at 0-4° C. The resulting yellow-orange mixture was stirred at this temperature for 5 min and allowed to progressively reach room temperature. The reaction was stirred an additional 40 min at room temperature then slowly dropped into diethyl ether (20 mL). The gummy yellow precipitate formed was redissolved in water (10 mL) and the aqueous layer basified with sat. aq. $Na_2CO_3$ solution (30 mL), followed by the addition of dichloromethane (20 mL). The layers were separated and the aqueous layer back-extracted with dichloromethane (3×10 mL). The combined organics were dried over anhydrous $Na_2SO_4$, filtered, and concentrated under reduced pressure. The crude residue was purified by reversed phase chromatography (15 to 70% gradient of acetonitrile/10 mM aqueous ammonium formate) to give (1-(3-((2-chlorophenyl)thio)-1H-pyrazolo[3,4-b]pyrazin-6-yl)-4-methylpiperidin-4-yl)methanamine (4.1 mg, 32%) as a pale yellow solid after lyophilization.

Synthesis of 2-((6-(4-amino-4-methylpiperidin-1-yl)-1H-pyrazolo[3,4-b]pyrazin-3-yl)thio)benzonitrile, Compound 10

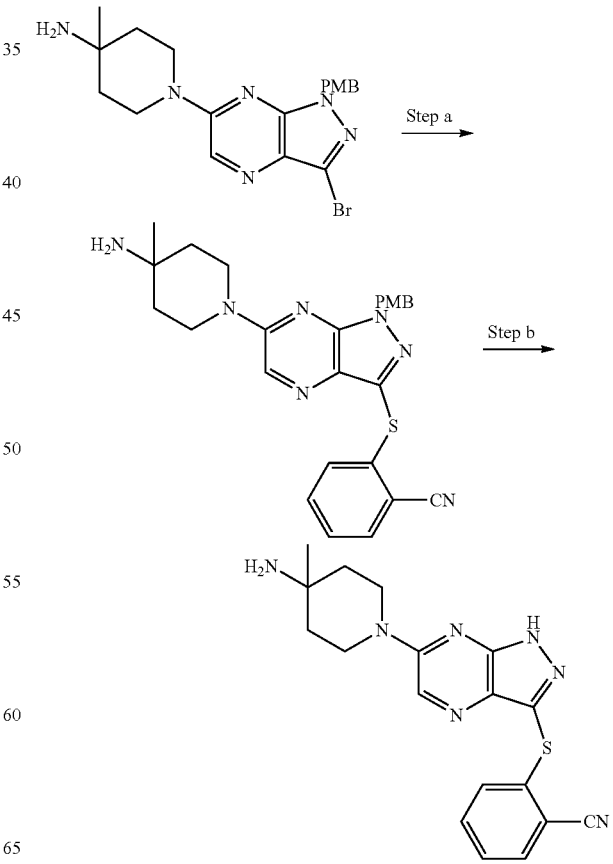

Step a: To a flame-dried Biotage microwave vial equipped with a conic magnetic stirbar and a septum was added the 1-(3-bromo-1-(4-methoxybenzyl)-1H-pyrazolo[3,4-b]pyrazin-6-yl)-4-methylpiperidin-4-amine (43 mg, 0.100 mmol, 1.0 equiv). Anhydrous 1,4-Dioxane (0.500 mL, 0.20 M) and DIPEA (25.8 mg, 0.034 mL, 2.0 equiv) were added. The solution was degassed by passing a flow of nitrogen through the solution with a balloon of nitrogen for 5 minutes. Pd2(dba)3 (9.2 mg, 0.01 mmol, 0.10 equiv), XantPhos (11.6 mg, 0.0200 mmol, 0.2 equiv), and 2-cyanothiophenol (20.3 mg, 0.150 mmol, 1.5 equiv) were added to the solution. The septum was taken off the vial and a blue microwave cap was rapidly crimped on the vial. The solution was heated to 130° C. using an oil bath and heated for 16 hours. After 3 hours, additional of Pd2(dba)3 (36 mg, 0.04 mmol, 40 mol %), XantPhos (46.4 mg, 0.08 mmol, 80 mol %), and 2-cyanothiophenol (20.3 mg, 0.150 mmol, 1.5 equiv) were added to the vial which was crimped with a new seal cap. The reaction was further heated at 130° C. for overnight. The vial was opened to air and transferred to a 60 mL extraction funnel using DCM. The solution was quenched with a sat. aq. sol. NaHCO3 (approx. 10 mL). The biphasic mixture was extracted and the layers were separated. The aqueous layer was further extracted with DCM (3×10 mL) and the organic layers were combined. The organic layers were then washed with brine (3×10 mL), dried over Na2SO4, filtered and evaporated to dryness. It resulted in a yellow film which was purified by silica gel chromatography (eluting with ethyl acetate, hexanes, and methanol). Concentration of the product-containing fractions in vacuo yielded 2-((6-(4-amino-4-methylpiperidin-1-yl)-1-(4-methoxybenzyl)-1H-pyrazolo[3,4-b]pyrazin-3-yl)thio)benzonitrile (26 mg, 53% yield) as a yellow oil.

Step b: To a 20 mL scintillation vial equipped with a magnetic stirbar was added 2-((6-(4-amino-4-methylpiperidin-1-yl)-1-(4-methoxybenzyl)-1H-pyrazolo[3,4-b]pyrazin-3-yl)thio)benzonitrile (26 mg, 0.062 mmol, 1.00 equiv). Excess 33% HBr in AcOH (1.0 mL) was added, and the reaction was stirred at 80° C. 1 h. The reaction was cooled to room temperature and quenched by addition of water (10 mL), followed by ethyl acetate (10 mL). The aqueous layer was further extracted with EtOAc (2×20 mL). The aqueous layer was basified by the addition of Na2CO3 sat. aq, and diluted with more DCM (15 mL). The aqueous layer was back-extracted and layers were separated. The aqueous layer was extracted with more DCM (3×20 mL). Organic layer was then dried over Na2SO4, filtered, concentrated in vacuo, and lyophilized to yield the title compound (12 mg, 61%) as a yellow powder.

Preparation of 6-(4-(aminomethyl)-4-methylpiperidin-1-yl)-N-(2-chlorophenyl)-1H-pyrazolo[3,4-b]pyrazin-3-amine, Compound 11

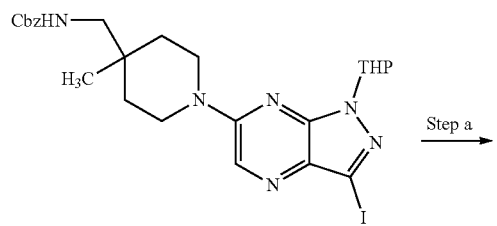

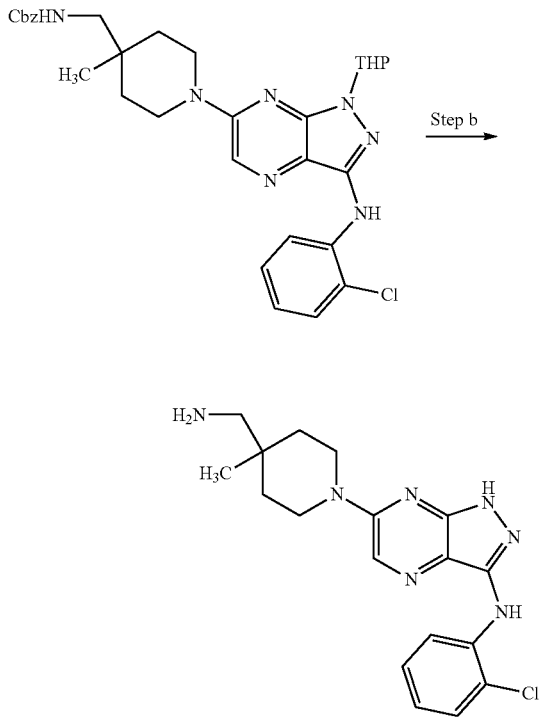

Step a: Benzyl ((1-(3-iodo-1-(tetrahydro-2H-pyran-2-yl)-1H-pyrazolo[3,4-b]pyrazin-6-yl)-4-methylpiperidin-4-yl)methyl)carbamate (70 mg, 0.119 mmol), SPhos Pd G1 (4.6 mg, 5 mol %), 2-chloroaniline (45 mg, 0.136 mmol), and potassium phosphate (50 mg, 0.237 mmol) were successively added to a 5 mL vial, followed by the addition of degassed dioxane (0.6 mL) and degassed water (0.2 mL). The resulting mixture was sealed, degassed with N2 and heated at 100° C. overnight. After full conversion, the volatiles were evaporated under reduced pressure. The crude residue was purified by flash chromatography (0 to 100% gradient of ethyl acetate/hexanes) to give benzyl ((1-(3-((2-chlorophenyl)amino)-1-(tetrahydro-2H-pyran-2-yl)-1H-pyrazolo[3,4-b]pyrazin-6-yl)-4-methylpiperidin-4-yl)methyl)carbamate (10 mg, 14%) as a yellow solid. MS m/z 590.2 [M+H]+.

Step b: Benzyl ((1-(3-((2-chlorophenyl)amino)-1-(tetrahydro-2H-pyran-2-yl)-1H-pyrazolo[3,4-b]pyrazin-6-yl)-4-methylpiperidin-4-yl)methyl)carbamate (10 mg, 0.0169 mmol) was slowly dissolved in 33% hydrobromic acid in acetic acid (1 mL), at 0-4° C. The resulting yellow-orange mixture was stirred at this temperature for 5 min and allowed to progressively reach room temperature. The reaction was stirred an additional 70 min at room temperature, followed by the addition of diethyl ether (2.5 mL). The liquid was removed and the precipitate remaining triturated with diethyl ether (2 mL). The crude residue was purified by reversed phase chromatography (0 to 50% gradient of acetonitrile/10 mM aqueous ammonium formate) to provide 6-(4-(aminomethyl)-4-methylpiperidin-1-yl)-N-(2-chlorophenyl)-1H-pyrazolo[3,4-b]pyrazin-3-amine (2.5 mg, 33%) as an off white solid after lyophilization.

221

Preparation of 6-(4-amino-4-methylpiperidin-1-yl)-N-(2-chloropyridin-3-yl)-1H-pyrazolo[3,4-b]pyrazin-3-amine, Compound 12

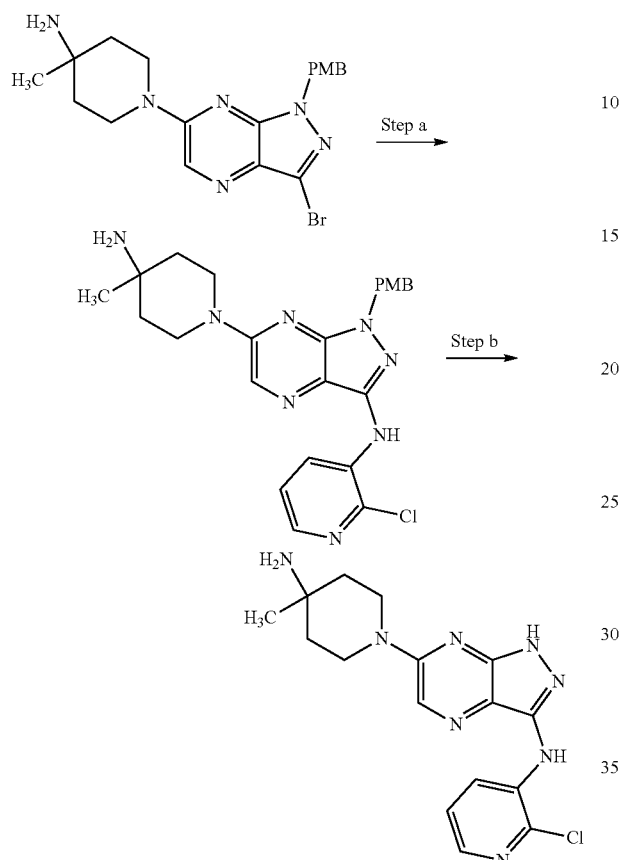

Step a: 1-(3-Bromo-1-(4-methoxybenzyl)-1H-pyrazolo[3,4-b]pyrazin-6-yl)-4-methylpiperidin-4-amine (70 mg, 0.162 mmol), tBuXPhos Pd G1 (11.2 mg, 10 mol %), 2-chloropyridin-3-amine (63 mg, 0.487 mmol), and sodium tert-butoxide (31 mg, 0.3246 mmol) were successively added to a 5 mL vial, followed by the addition of degassed toluene (0.8 mL). The resulting mixture was sealed, degassed with $N_2$, and heated at 100° C. overnight. The volatiles were evaporated under reduced pressure and the residue purified by flash chromatography (0 to 100% gradient of methanol/dichloromethane) to give 6-(4-amino-4-methylpiperidin-1-yl)-N-(2-chloropyridin-3-yl)-1-(4-methoxybenzyl)-1H-pyrazolo[3,4-b]pyrazin-3-amine (5 mg, 06%) as a yellow solid: LCMS [M+H]$^+$=479.2.

Step b: 6-(4-Amino-4-methylpiperidin-1-yl)-N-(2-chloropyridin-3-yl)-1-(4-methoxybenzyl)-1H-pyrazolo[3,4-b]pyrazin-3-amine (5 mg, 0.013 mmol) was slowly dissolved in 33% hydrobromic acid in acetic acid (1 mL) at 0-4° C. The resulting yellow-orange mixture was stirred at this temperature for 5 min and heated to 80° C. for 4 hours. After cooling, diethyl ether (2.5 mL) was added to the mixture. The liquid was removed from the resulting precipitate which was triturated with diethyl ether (2 mL). The crude residue was purified by reversed phase chromatography (0 to 50% gradient of acetonitrile/10 mM aqueous ammonium formate) to provide 6-(4-amino-4-methylpiperidin-1-yl)-N-(2-

222 chloropyridin-3-yl)-1H-pyrazolo[3,4-b]pyrazin-3-amine (1.3 mg, 33%) as a brownish solid after lyophilization.

Preparation of 1-(3-((2,3-dichlorophenyl)thio)-1H-pyrazolo[3,4-b]pyrazin-6-yl)-4-methylpiperidin-4-amine, Compound 13

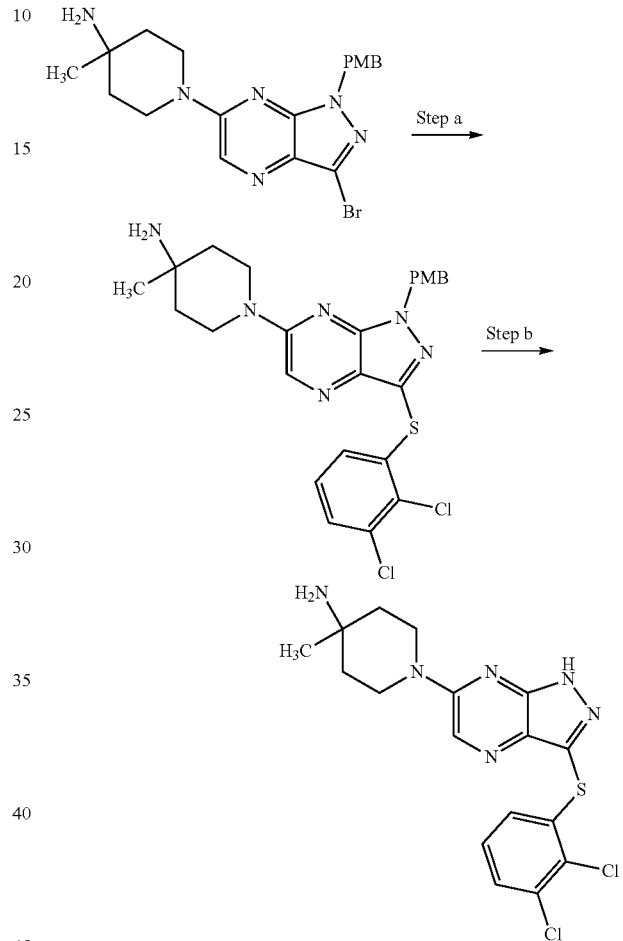

Step a: 1-(3-Bromo-1-(4-methoxybenzyl)-1H-pyrazolo[3,4-b]pyrazin-6-yl)-4-methylpiperidin-4-amine (70 mg, 0.16 mmol), Pd$_2$dba$_3$ (15 mg, 0.02 mmol), XantPhos (19 mg, 0.03 mmol), 2,3-dichlorothiophenol (35 mg, 0.20 mmol) and N,N-diisopropylethylamine (57 µL, 0.33 mmol) were successively added to a 5 mL vial, followed by the addition of dioxane (0.3 mL). The resulting mixture was sealed, degassed with $N_2$, and heated under microwave irradiation at 130° C. for 1.5 hours. After cooling, the mixture was filtered through a pad of celite, the cake washed with EtOAc (20 mL), and the filtrate concentrated under reduced pressure. The resulting residue was purified by reversed phase chromatography (35 to 75% gradient of acetonitrile/10 mM aqueous ammonium formate) to give 1-(3-((2,3-dichlorophenyl)thio)-1-(4-methoxybenzyl)-1H-pyrazolo[3,4-b]pyrazin-6-yl)-4-methylpiperidin-4-amine (45 mg, 52%) as a pale orange solid after lyophilization: LCMS [M+H]$^+$=529.4.

Step b: 1-(3-((2,3-Dichlorophenyl)thio)-1-(4-methoxybenzyl)-1-pyrazolo[3,4-b]pyrazin-6-yl)-4-methylpiperidin-4-amine (45 mg, 0.08 mmol) was slowly dissolved in 33% hydrobromic acid in acetic acid (2 mL) at room temperature. The resulting yellow-orange mixture was then placed in a preheated oil bath at 70° C., and stirred at this temperature for 1 hr. The mixture was allowed to cool then slowly dropped into diethyl ether (20 mL). The resulting yellow/orange precipitate was filtered through a piece of cotton and the gummy residue redissolved in water (3-4 mL), loaded on a reversed phase chromatography column, and purified using a gradient of acetonitrile/0.1% formic acid in water (0 to 55%) to give 1-(3-((2,3-dichlorophenyl)thio)-1H-pyrazolo[3,4-b]pyrazin-6-yl)-4-methylpiperidin-4-amine (27 mg, 77%) as a pale yellow solid.

Preparation of 4-methyl-1-(3-((1-methyl-1H-imidazol-2-yl)thio)-1H-pyrazolo[3,4-b]pyrazin-6-yl)piperidin-4-amine, Compound 14

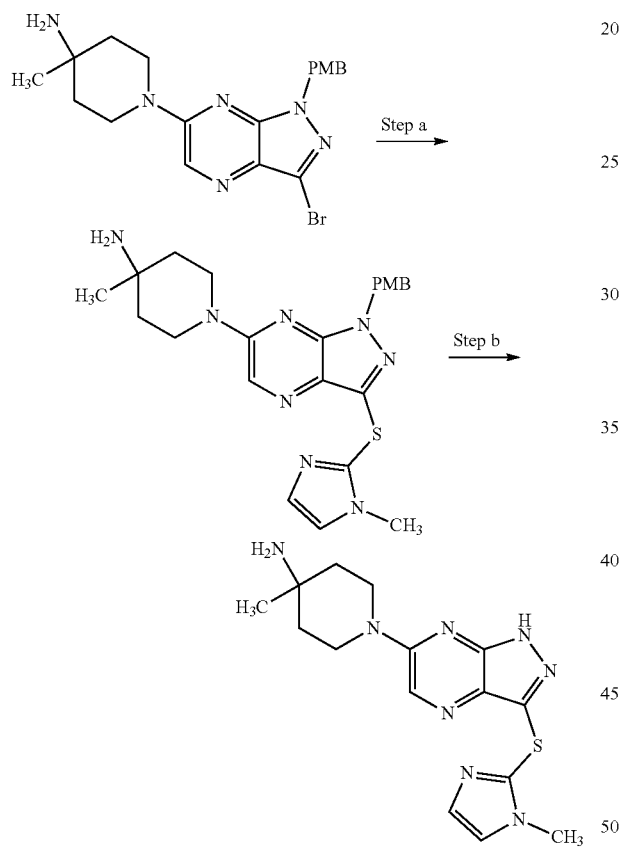

Step a: 1-(3-Bromo-1-(4-methoxybenzyl)-1H-pyrazolo[3,4-b]pyrazin-6-yl)-4-methylpiperidin-4-amine (50 mg, 0.12 mmol), 1-methyl-1H-imidazole-2-thiol (40 mg, 0.35 mmol), Pd$_2$(dba)$_3$ (33 mg, 0.06 mmol), and XantPhos (67 mg, 0.12 mmol) were all added to a nitrogen flushed microwave vial. A previously degassed (by sparging) mixture of dioxane (1 mL) and DIPEA (0.04 mL, 0.23 mmol) was added to the flushed microwave vial. The entire mixture was then heated to 110° C. for 1 hour in the microwave. After cooling, the reaction was filtered through a pad of celite, which was washed with MeOH. The filtrate was concentrated under vacuum and the product purified by reverse phased flash chromatography using a 0-60% gradient of MeCN in 10 mM ammonium formate to provide 1-(1-(4-methoxybenzyl)-3-((1-methyl-1H-imidazol-2-yl)thio)-1H-pyrazolo[3,4-b]pyrazin-6-yl)-4-methylpiperidin-4-amine as a white solid (31.6 mg, 57% yield) after lyophilization: LCMS [M+H]$^+$ =465.4.

Step b: 4-Methyl-1-(3-((1-methyl-1H-imidazol-2-yl)thio)-1H-pyrazolo[3,4-b]pyrazin-6-yl)piperidin-4-amine (31.6 mg, 0.07 mmol) was slowly dissolved in 33% hydrobromic acid in acetic acid (2 mL). The resulting mixture was heated at 80° C. for 4 hours. After cooling, diethyl ether (4 mL) was added to the mixture to form a yellow precipitate. After removal of the liquid, the precipitate was triturated with diethyl ether (4 mL), and the resulting solid purified by reversed phase flash chromatography using a 0-60% gradient of MeCN in 10 mM ammonium bicarbonate to provide 4-methyl-1-(3-((1-methyl-1H-imidazol-2-yl)thio)-1H-pyrazolo[3,4-b]pyrazin-6-yl)piperidin-4-amine as a white solid (12 mg, 52% yield) after lyophilization.

Preparation of (1-(3-benzyl-1H-pyrazolo[3,4-b]pyrazin-6-yl)-4-methylpiperidin-4-yl)methanamine, Compound 15

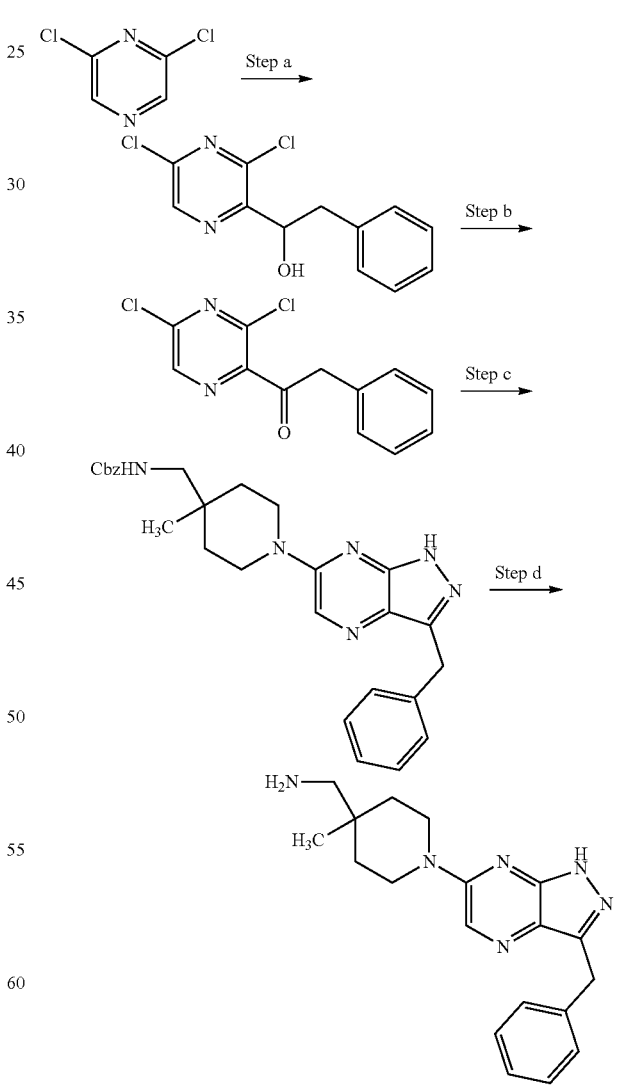

Step a: To a cold (−78° C.) solution of 2,2,6,6-tetramethylpiperidine (1.46 mL, 8.7 mmol) in THF (67 mL) was added n-BuLi (2.5 M, 3.2 mL, 8.1 mmol). After addition, the mixture was warmed up to 0° C., and stirred for 30 min. After cooling again to −78° C., 2,6-dichloropyrimidine (1.0 g, 6.7 mmo) in THF (3 mL) was added dropwise. After stirring at −78° C. for 30 min., 2-phenylacetaldehyde (1.2 mL, 10.1 mmol) was added to the mixture and the reaction stirred at −78° C. for 3 hrs followed by warming to room temperature. The mixture was diluted with saturated aqueous ammonium chloride solution then extracted with dichloromethane. The organics were dried over magnesium sulfate, filtered, and concentrated under reduced pressure. The residue was purified by column chromatography on silica gel (AcOEt/hexane gradient) to give 1-(3,5-dichloropyrazin-2-yl)-2-phenylethanol (595 mg, 33%) as an orange oil: LCMS [M—H$_2$O]+=251.1.

Step b: (1-(3,5-Dichloropyrazin-2-yl)-2-phenylethanol (160 mg, 0.60 mmol) was dissolved in dichloromethane (3 mL). Dess-Martin periodinane (322 mg, 0.82 mmol) was added and the mixture stirred for 2 hours. An aqueous solution of NaHCO$_3$ and Na$_2$S$_2$O$_3$ was added and the mixture stirred until the white solid went into the aqueous phase. The aqueous layer was extracted with DCM (2×) and the combined organics dried over magnesium sulfate, filtered, and concentrated under reduced pressure to afford 1-(3,5-dichloropyrazin-2-yl)-2-phenylethanone (89 mg, 56%) as a yellow solid: LCMS [M+H]$^+$=267.0.

Step c: To a solution of (1-(3,5-dichloropyrazin-2-yl)-2-phenylethanone (89 mg, 0.33 mmol) in DMAc (1.5 mL) at 0-5° C. was slowly added benzyl ((4-methylpiperidin-4-yl)methyl)carbamate (87 mg, 0.33 mmol, CAS #236406-24-9), followed by the addition of cesium fluoride (152 mg, 1.0 mmol). The mixture was stirred at 75° C. for 3 hr then hydrazine monohydrate (470 µL, 1.0 mmol) was slowly added at 0-5° C. (exothermic). After the addition was complete, the reaction mixture was heated at 90° C. for 1-5 hrs. After cooling to 0° C., water (10 mL) and EtOAc (10 mL) were added and the aqueous layer was extracted with EtOAc (10 mL). The combined organics were washed with water (10 mL), brine (10 mL), dried over magnesium sulfate, and concentrated under reduced pressure. The residue was purified by chromatography on silica gel (hexane/EtOAc=1:1, 1:3) to afford benzyl ((1-(3-benzyl-1H-pyrazolo[3,4-b]pyrazin-6-yl)-4-methylpiperidin-4-yl)methyl)carbamate (53 mg, 32%) as a yellow foam: LCMS [M+H]$^+$=471.2; $^1$H-NMR (500 MHz, DMSO-d$_6$) δ 12.75 (s, 1H), 8.32 (s, 1H), 7.37-7.27 (m, 7H), 7.27-7.22 (m, 2H), 7.18-7.13 (m, 1H), 5.02 (s, 2H), 4.15 (s, 2H), 3.95-3.84 (m, 2H), 3.52-3.41 (m, 2H), 2.96 (d, J=6.4 Hz, 2H), 1.50-1.41 (m, 2H), 1.34-1.25 (m, 2H), 0.93 (s, 3H).

Step d: HBr in acid acetic (33% wt %, 1.0 mL) was added dropwise to benzyl ((1-(3-benzyl-1H-pyrazolo[3,4-b]pyrazin-6-yl)-4-methylpiperidin-4-yl)methyl)carbamate (50 mg, 0.11 mmol). The mixture was stirred for 1 hr at room temperature, then diluted with DMF and water, and concentrated under reduced pressure to afford a yellow oil. The residue was dissolved in a minimum of DMF and purified by reversed phase chromatography (C18, 0 to 80% gradient of MeCN/(10 mM NH$_4$HCO$_3$ in water, pH 10) to give (1-(3-benzyl-1H-pyrazolo[3,4-b]pyrazin-6-yl)-4-methylpiperidin-4-yl)methanamine (28 mg, 78%) as a white solid.

Preparation of (4-methyl-1-(3-(1-phenylvinyl)-1H-pyrazolo[3,4-b]pyrazin-6-yl)piperidin-4-yl)methanamine, Compound 16

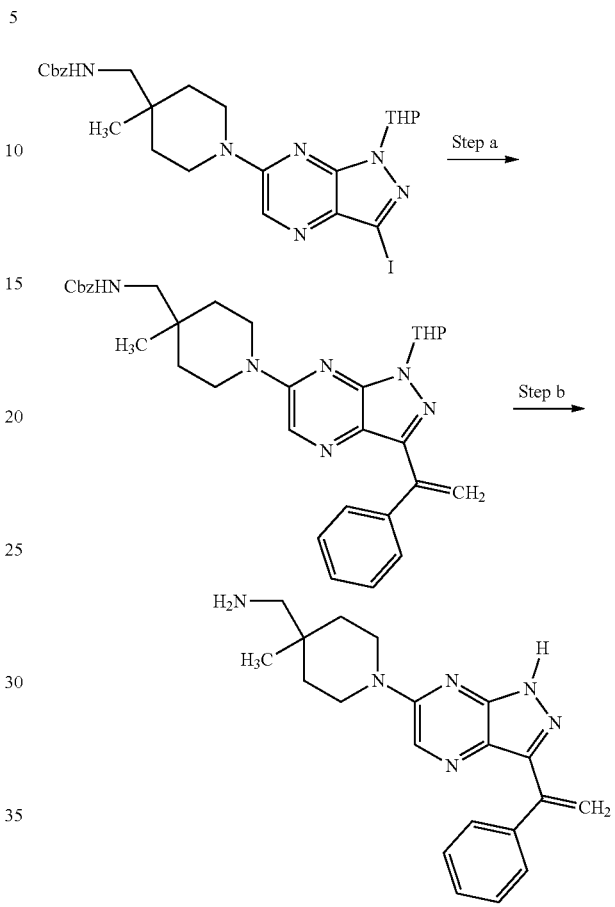

Step a: Benzyl ((1-(3-iodo-1-(tetrahydro-2H-pyran-2-yl)-1H-pyrazolo[3,4-b]pyrazin-6-yl)-4-methylpiperidin-4-yl)methyl)carbamate (100 mg, 0.17 mmol) was dissolved in acetonitrile (1.7 mL) and the mixture degassed with N$_2$ for 10 min. After this time, (1-phenylvinyl)boronic acid (0.038 g, 0.25 mmol), Pd(dppf)Cl$_2$—CH$_2$Cl$_2$ (7.7 mg, 8.47 µmol), and potassium carbonate (70 mg, 0.508 mmol) were added. The reaction vial was sealed and the resulting mixture was heated at 120° C. under microwave irradiation for 45 min. The mixture was concentrated under reduced pressure with silica to give a crude material dry pack which was subsequently purified by flash chromatography using a gradient of ethyl acetate in hexanes (0 to 100%) to afford benzyl ((4-methyl-1-(3-(1-phenylvinyl)-1-(tetrahydro-2H-pyran-2-yl)-1H-pyrazolo[3,4-b]pyrazin-6-yl)piperidin-4-yl)methyl)carbamate (89 mg, 93%) as a yellow oil: LCMS [M+H]$^+$=567.5.

Step b: To a mixture of benzyl ((4-methyl-1-(3-(1-phenylvinyl)-1-(tetrahydro-2H-pyran-2-yl)-1H-pyrazolo[3,4-b]pyrazin-6-yl)piperidin-4-yl)methyl)carbamate (40 mg, 0.071 mmol) in acetic acid (2.7 ml) was added very slowly 33% w/w hydrogen bromide in acetic acid (0.8 mL). The resulting mixture was stirred at room temperature for 2 h. After this time, diethyl ether was added to form a precipitate that was isolated by filtration. The crude product was purified by reversed phase chromatography using a gradient of acetonitrile in 0.1% formic acid in water (0 to 100%) to give (4-methyl-1-(3-(1-phenylvinyl)-1H-pyrazolo[3,4-b]pyrazin-6-yl)piperidin-4-yl)methanamine (16 mg, 57%) as yellow formate salt after lyophilization.

Preparation of (4-methyl-1-(3-(1-phenylethyl)-1H-pyrazolo[3,4-b]pyrazin-6-yl)piperidin-4-yl)methanamine, Compound 17

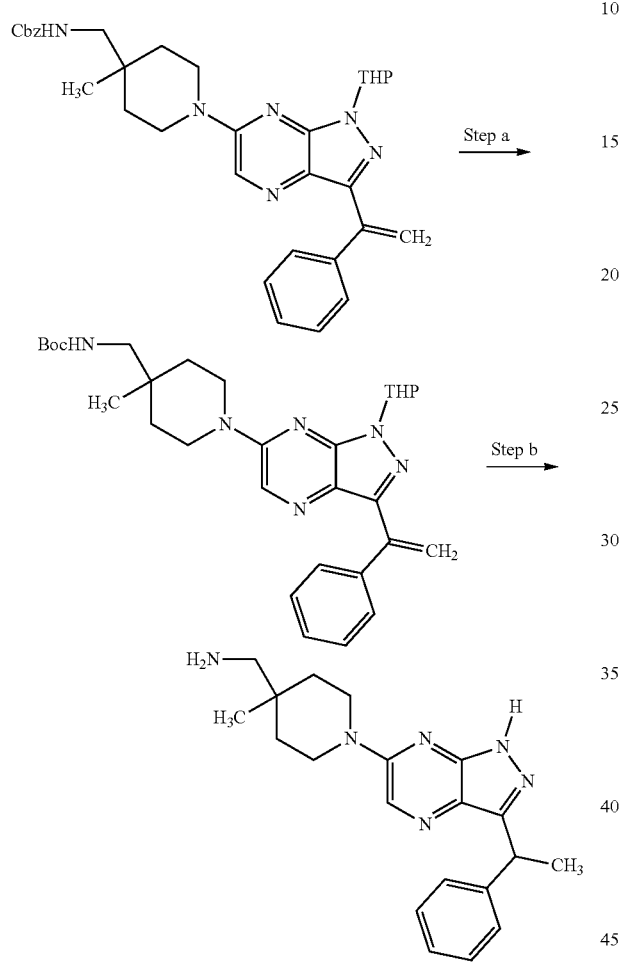

Step a: To a mixture of benzyl ((4-methyl-1-(3-(1-phenylvinyl)-1-(tetrahydro-2H-pyran-2-yl)-1H-pyrazolo[3,4-b]pyrazin-6-yl)piperidin-4-yl)methyl)carbamate (40 mg, 0.071 mmol) in methanol/ethyl acetate (0.7 mL, 1:1 ratio) was added palladium on carbon (7.5 mg, 7.06 μmol) and di-tert-butyl dicarbonate (31 mg, 0.141 mmol). The reaction mixture was hydrogenated under 45 psi of $H_2$ for 18 hrs at room temperature. After this time, the mixture was filtered through a pad of celite, which was washed with ethyl acetate. The filtrate was concentrated under reduced pressure to afford tert-butyl ((4-methyl-1-(3-(1-phenylethyl)-1-(tetrahydro-2H-pyran-2-yl)-1H-pyrazolo[3,4-b]pyrazin-6-yl)piperidin-4-yl)methyl)carbamate (36 mg, 95%) as a crude intermediate. LCMS [M+H]+=535.5.

Step b: To a mixture of tert-butyl ((4-methyl-1-(3-(1-phenylethyl)-1-(tetrahydro-2H-pyran-2-yl)-1H-pyrazolo[3,4-b]pyrazin-6-yl)piperidin-4-yl)methyl)carbamate (0.040 g, 0.075 mmol) in dioxane (0.37 mL) was added hydrogen chloride (4M in dioxane) (0.94 mL). After stirring for 3 h at room temperature, the volatiles were removed under reduced pressure and the residue purified by reversed phase chromatography using a gradient of acetonitrile in 0.1% formic acid in water (0 to 100%) to give (4-methyl-1-(3-(1-phenylethyl)-1H-pyrazolo[3,4-b]pyrazin-6-yl)piperidin-4-yl)methanamine (11 mg, 37%) as a yellow formate salt after lyophilization.

Preparation of (6-(4-(aminomethyl)-4-methylpiperidin-1-yl)-1H-pyrazolo[3,4-b]pyrazin-3-yl)(phenyl)methanone, Compound 18

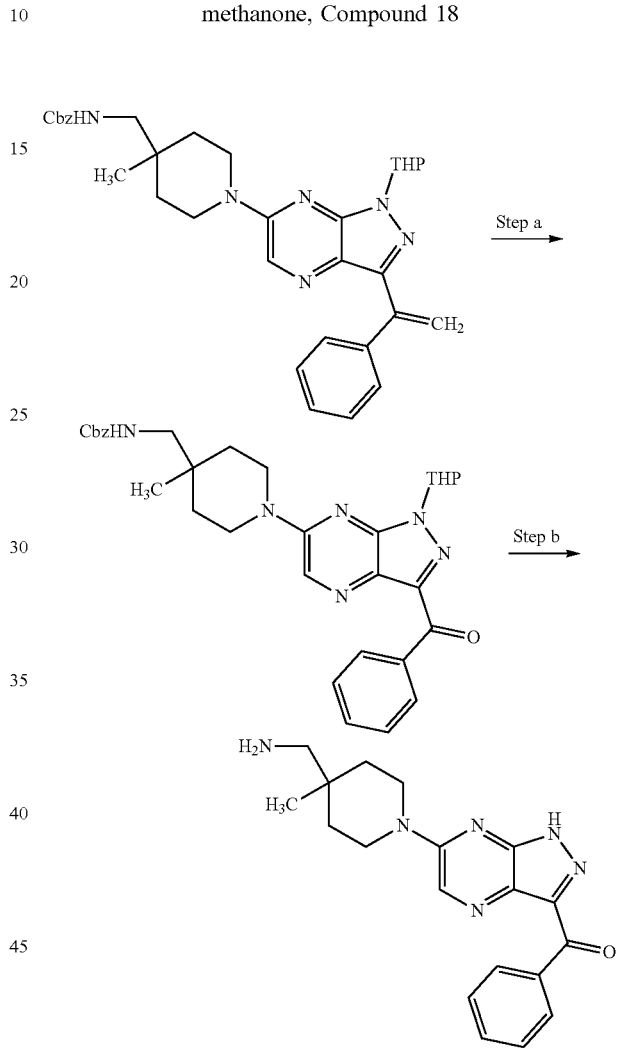

Step a: To a mixture of benzyl ((4-methyl-1-(3-(1-phenylvinyl)-1-(tetrahydro-2H-pyran-2-yl)-1H-pyrazolo[3,4-b]pyrazin-6-yl)piperidin-4-yl)methyl)carbamate (160 mg, 0.282 mmol) in acetonitrile (2.8 mL) was added sodium periodate (302 mg, 1.412 mmol) and osmium(VIII) oxide (90 μL, 0.014 mmol). The resulting mixture was stirred for 15 hrs at 60° C. The mixture was cooled to room temperature and concentrated under reduced pressure with silica to give a crude material dry pack. This crude material was purified by flash chromatography using a gradient of ethyl acetate in hexanes (0 to 100%) to give benzyl ((1-(3-benzoyl-1-(tetrahydro-2H-pyran-2-yl)-1H-pyrazolo[3,4-b]pyrazin-6-yl)-4-methylpiperidin-4-yl) methyl)carbamate (118 mg, 73%) as a yellow oil: LCMS [M+H]+=569.5.

Step b: To a mixture of benzyl ((1-(3-benzoyl-1-(tetrahydro-2H-pyran-2-yl)-1H-pyrazolo[3,4-b]pyrazin-6-yl)-4-methylpiperidin-4-yl)methyl)carbamate (30 mg, 0.053 mmol) in acetic acid (0.53 mL) was added 33% w/w hydrogen bromide in acetic acid (0.60 mL). The resulting mixture was stirred at room temperature for 3 hrs. After this time, the reaction mixture was concentrated under reduced pressure and the residue purified by reversed phase chromatography using a gradient of acetonitrile in 0.1% formic acid in water (0 to 100%) to give (6-(4-(aminomethyl)-4-methylpiperidin-1-yl)-1H-pyrazolo[3,4-b]pyrazin-3-yl)(phenyl)methanone (18 mg, 86%) as a yellow formate salt after lyophilization.

Preparation of 1-(6-(4-(aminomethyl)-4-methylpiperidin-1-yl)-1H-pyrazolo[3,4-b]pyrazin-3-yl)-1-phenylethanol, Compound 19

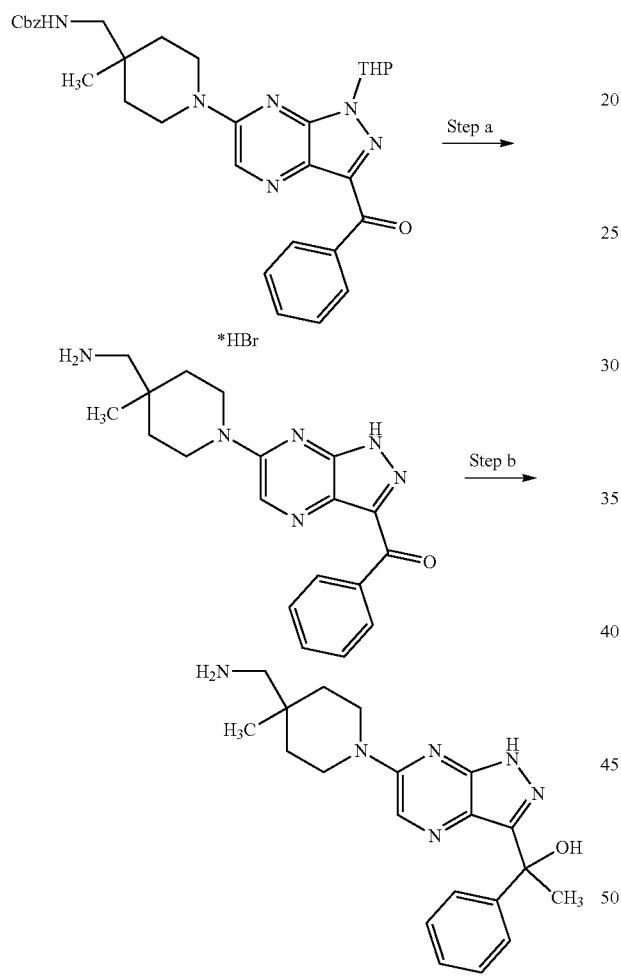

Step a: To a mixture of benzyl ((1-(3-benzoyl-1-(tetrahydro-2H-pyran-2-yl)-1H-pyrazolo[3,4-b]pyrazin-6-yl)-4-methylpiperidin-4-yl)methyl)carbamate (30 mg, 0.053 mmol) in acetic acid (0.53 mL) was added 33% w/w hydrogen bromide in acetic acid (0.60 mL). The resulting mixture is stirred at room temperature for 3 hrs. After this time, diethyl ether was added to form a precipitate that was isolated by filtration to give (6-(4-(aminomethyl)-4-methylpiperidin-1-yl)-1H-pyrazolo[3,4-b]pyrazin-3-yl)(phenyl)methanone hydrobromide as a yellow powder: LCMS [M+H]+=351.2.

Step b: To a mixture of (6-(4-(aminomethyl)-4-methylpiperidin-1-yl)-1H-pyrazolo[3,4-b]pyrazin-3-yl)(phenyl)methanone hydrobromide (18 mg, 0.042 mmol) in anhydrous tetrahydrofuran (2 mL) was added methylmagnesium bromide (3M in diethyl ether) (70 μL, 0.209 mmol). The resulting mixture was stirred for 5 hrs at room temperature then quenched with a sat. aq. NaHCO₃ solution (1 mL) and diluted in DMF (1 mL). The mixture was concentrated under reduced pressure and the residue purified by reversed phase chromatography using a gradient of acetonitrile in 0.1% formic acid in water (0 to 100%) to give 1-(6-(4-(aminomethyl)-4-methylpiperidin-1-yl)-1H-pyrazolo[3,4-b]pyrazin-3-yl)-1-phenylethanol (10 mg, 58%) as a yellow powder after lyophilization.

Synthesis of 1-(3-(1H-benzo[d]imidazol-1-yl)-1H-pyrazolo[3,4-b]pyrazin-6-yl)-4-methylpiperidin-4-amine, Compound 20

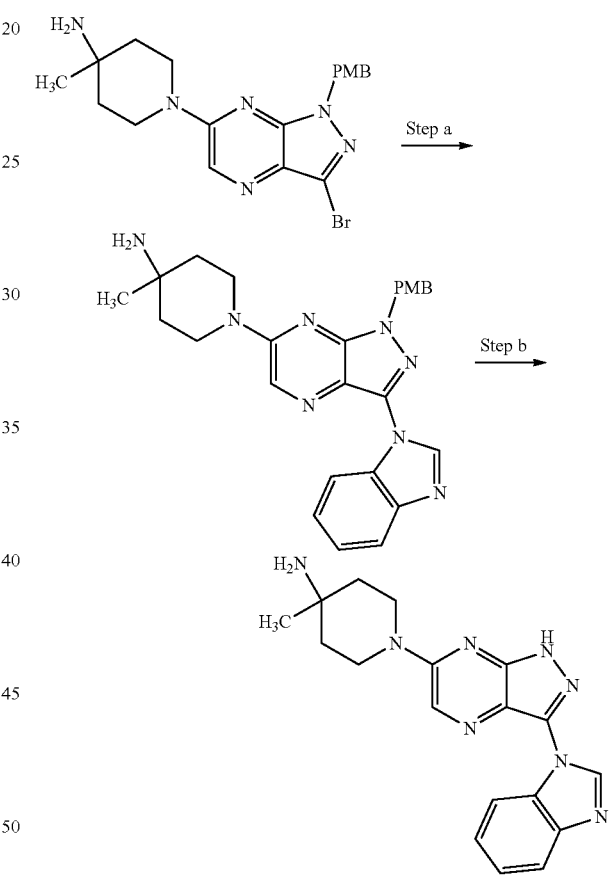

Step a: To a flame-dried, nitrogen-flushed Biotage 0.5-2.0 mL vial equipped with a conic magnetic stirbar and a 14/20 white septa was added 1-(3-bromo-1-(4-methoxybenzyl)-1H-pyrazolo[3,4-b]pyrazin-6-yl)-4-methylpiperidin-4-amine (43 mg, 0.10 mmol, 1.0 equiv) and anhydrous dimethylsulfoxide (0.50 mL, 0.20 M). The solution was degassed by flowing nitrogen from a balloon through the solution for 5 min. The following reactants/catalysts were successively added to the vial: copper(II)oxide (2.86 mg, 0.010 mmol, 0.20 equiv), 4,7-di-methoxy-1,10-phenanthroline (9.6 mg, 0.04 mmol, 0.4 equiv), benzimidazole (17.8 mg, 0.150 mmol, 1.5 equiv), PEG-4000 (20 mg), and cesium carbonate (65 mg, 0.20 mmol, 2.0 equiv). The septum was removed from the vial, and a blue microwave cap was rapidly crimped on the vial. The solution was warmed to 130° C. using an oil bath and heated at this temperature for 16 hours. The reaction mixture was cooled and transferred to a 60 mL extraction funnel using dichloromethane, where the reaction was quenched with a saturated aqueous solution of sodium bicarbonate (approx. 10 mL). The aqueous layer was further extracted with dichloromethane (3×10 mL) and the combined organics were combined, washed with brine (3×10 mL), dried over sodium sulfate, filtered, and concentrated under reduced pressure. The resulting 1-(3-(1H-benzo[d]imidazol-1-yl)-1-(4-methoxybenzyl)-1H-pyrazolo[3,4-b]pyrazin-6-yl)-4-methylpiperidin-4-amine (LCMS [M+H]⁺=469) was taken directly to next step.

Step b: 1-(3-(1H-Benzo[d]imidazol-1-yl)-1-(4-methoxybenzyl)-1H-pyrazolo[3,4-b]pyrazin-6-yl)-4-methylpiperidin-4-amine (46 mg, 0.100 mmol, 1.0 equiv) was dissolved in anhydrous dichloroethane (1.0 mL, 0.10 M) in a 20 mL scintillation vial. Hydrobromic acid (33% in acetic acid, 1.0 mL) was added and the vial capped firmly with a Teflon cap. The reaction mixture was heated at 80° C. for 16 hours. After cooling, the reaction was quenched by the addition of diethyl ether (10 mL). The resulting suspension was stirred for 10 min and the ether supernatant was disposed of. This trituration step was repeated three times before the evaporation of residual ether was affected with a stream of nitrogen. The resulting solid was dissolved in a minimum of dimethylformamide and aqueous sodium carbonate and purified by reversed C18 chromatography using a SNAP Biotage 12 g column (eluting with acetonitrile/water/0.1% ammonium carbonate) to yield 1-(3-(1H-benzo[d]imidazol-1-yl)-1H-pyrazolo[3,4-b]pyrazin-6-yl)-4-methylpiperidin-4-amine as an off-white solid (12 mg, 34%).

Synthesis of 1-(3-(3,4-dihydroquinolin-1(2H)-yl)-1H-pyrazolo[3,4-b]pyrazin-6-yl)-4-methylpiperidin-4-amine hydrochloride, Compound 23

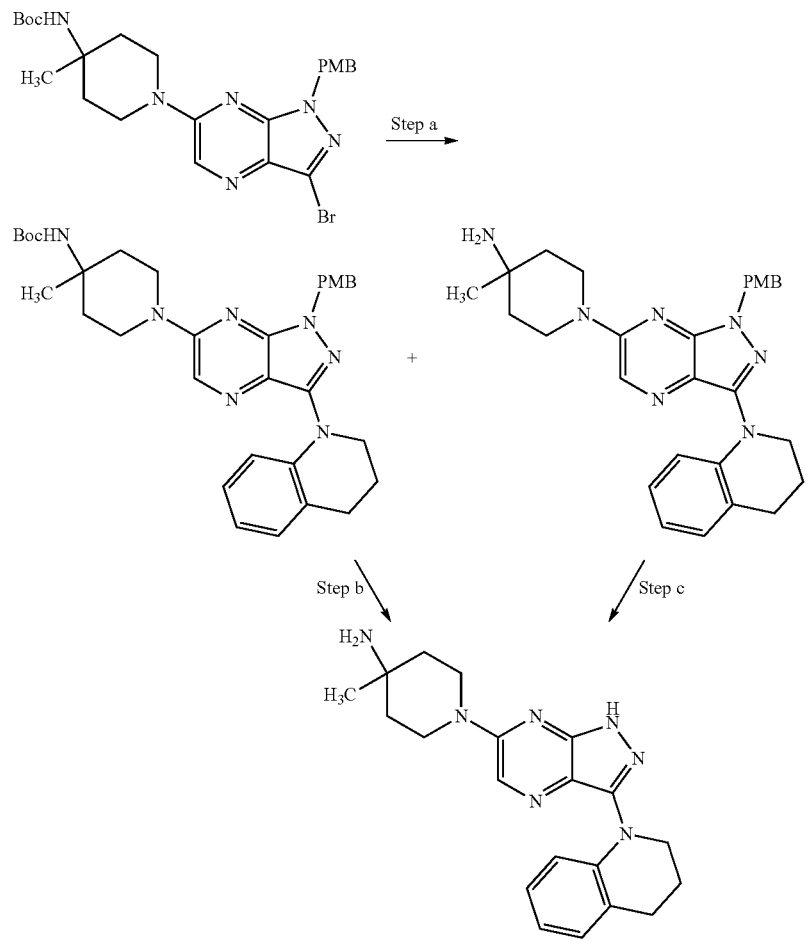

Step a: tert-Butyl (1-(3-bromo-1-(4-methoxybenzyl)-1H-pyrazolo[3,4-b]pyrazin-6-yl)-4-methylpiperidin-4-yl)carbamate (prepared by the route used for Compound 33) (300 mg, 0.56 mmol, 1.0 eq), 1,2,3,4-tetrahydroquinoline (83 mg, 0.62 mmol, 1.1 eq), RuPhos (26 mg, 56 umol, 0.1 eq), Ruphos Pd G4 (48 mg, 56 umol, 0.1 eq), and t-BuONa (163 mg, 1.7 mmol, 3.0 eq) were taken up in dioxane (10 mL). The mixture was evacuated and backfilled with nitrogen three times before being stirred at 120° C. for 10 hrs. The mixture was concentrated under reduced pressure, diluted with ethyl acetate (70 mL), washed with saturated sodium bicarbonate (30 mL×2), water (30 mL), and brine (30 mL×2). The organics were dried over anhydrous sodium sulfate, filtered, and concentrated under reduced pressure to give a yellow oil, which was purified by silica gel chromatography to afford tert-butyl N-[1-[3-(3,4-dihydro-2H-quinolin-1-yl)-1-[(4-methoxyphenyl)methyl]pyrazolo[3,4-b]pyrazin-6-yl]-4-methyl-4-piperidyl]carbamate (0.2 g) as a yellow oil and 1-[3-(3,4-dihydro-2H-quinolin-1-yl)-1-[(4-methoxyphenyl)methyl]pyrazolo[3,4-b]pyrazin-6-yl]-4-methyl-piperidin-4-amine (0.1 g) as a yellow oil.

Step b: tert-Butyl N-[1-[3-(3,4-dihydro-2H-quinolin-1-yl)-1-[(4-methoxyphenyl)methyl]pyrazolo[3,4-b]pyrazin-6-yl]-4-methyl-4-piperidyl]carbamate (200 mg, 0.34 mmol, 1.0 eq) was dissolved in trifluoroacetic acid (5 mL) and trifluoromethyl sulfonic acid (0.5 mL). The reaction mixture was stirred at 100° C. for 1 hr. before being combined with the product from Step c for purification.

Step c: 1-[3-(3,4-Dihydro-2H-quinolin-1-yl)-1-[(4-methoxyphenyl)methyl]pyrazolo[3,4-b]pyrazin-6-yl]-4-methyl-piperidin-4-amine (100 mg, 0.2 mmol, 1.0 eq) was dissolved in trifluoroacetic acid (5 mL) and trifluoromethyl sulfonic acid (0.5 mL) and the mixture stirred at 100° C. for 1 hr. The reaction mixture was combined with the reaction mixture from Step b. The solvent was removed under reduced pressure, the residue was diluted with ethyl acetate (70 mL), and the organics washed with saturated sodium bicarbonate (30 mL×2), water (30 mL), and brine (30 mL×2), dried over anhydrous sodium sulfate, filtered, and concentrated under reduced pressure to give a yellow oil, which was purified by reversed phase prep-HPLC (eluting with acetonitrile/water/0.1% HCl) to afford 1-(3-(3,4-dihydroquinolin-1(2H)-yl)-1H-pyrazolo[3,4-b]pyrazin-6-yl)-4-methylpiperidin-4-amine hydrochloride (16 mg) as a brown solid.

The following compounds were synthesized via the same route as Compound 23, using building blocks that were either commercially available or that are described here. The pyrazolo-pyrazine ring was protected with either PMB (as shown above) or a THP group. The product of Step a could lead to mixture of protected and deprotected amines as seen for Compound 23, or as the fully protected intermediate, in which case Step c was not necessary. Compounds synthesized via Compound 23 method included Compound 21, Compound 22, Compound 27, Compound 28, Compound 29, Compound 30, Compound 31, Compound 32, Compound 34, Compound 35, Compound 36, Compound 37, Compound 38, Compound 43, Compound 47, Compound 56, Compound 59, Compound 60, Compound 61, Compound 62, Compound 64, Compound 67.

Syntheses of rel-(2R,4S)-1-(3-(3,4-Dihydro-1,5-naphthyridin-1(2H)-yl)-1H-pyrazolo[3,4-b]pyrazin-6-yl)-2-methylpiperidin-4-amine and rel-(2R,4S)-1-(3-(3,4-dihydro-1,5-naphthyridin-1(2H)-yl)-1H-pyrazolo[3,4-b]pyrazin-6-yl)-2-methylpiperidin-4-amine, Compound 24 and Compound 25

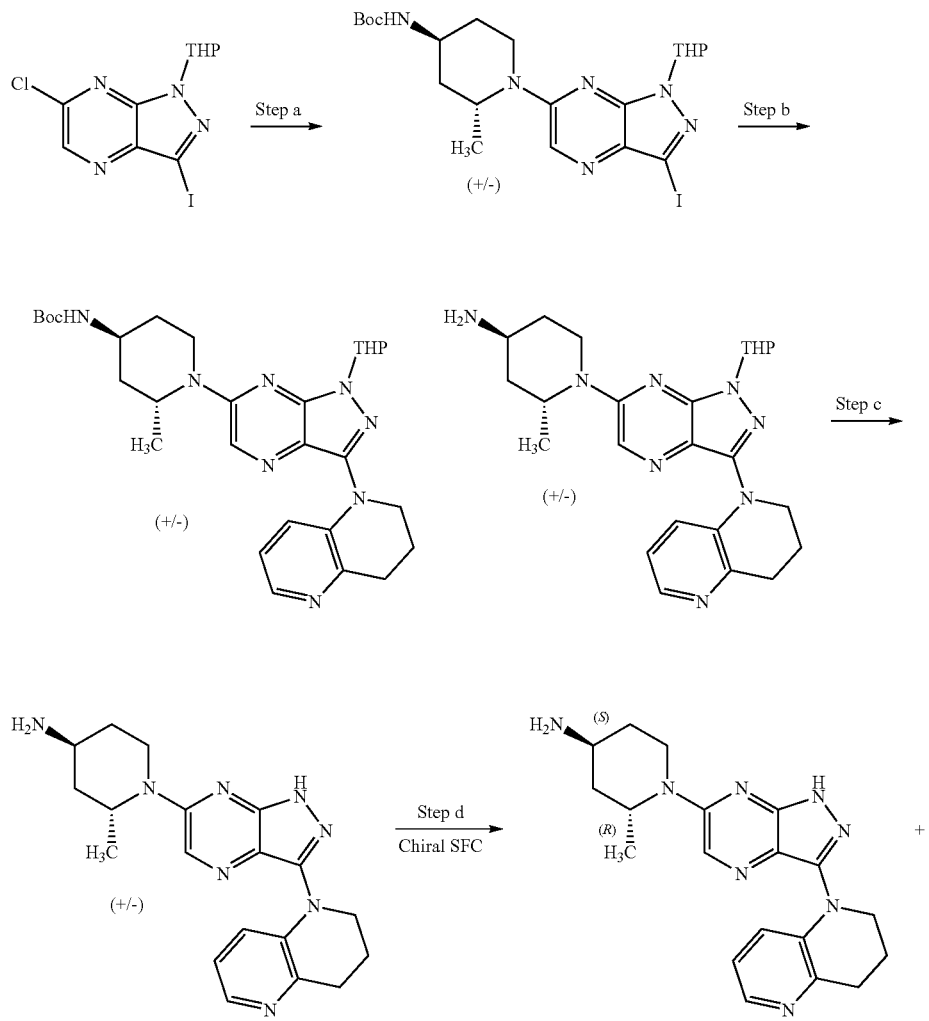

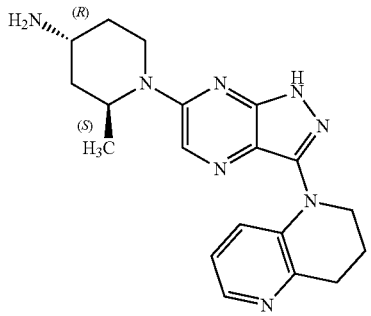

Step a: A mixture of 6-chloro-3-iodo-1-(tetrahydro-2H-pyran-2-yl)-1H-pyrazolo[3,4-b]pyrazine (300.0 mg, 822 µmol), tert-butyl (2-methylpiperidin-4-yl)carbamate (176.0 mg, 822 µmol, CAS #1281674-64-3), and diisopropylethylamine (428.0 µL, 2.46 mmol) in dimethylsulfoxide (15.0 mL) was stirred at 80° C. for 3 hrs. The reaction mixture was cooled, diluted with ethyl acetate (100.0 mL), washed with water (50.0 mL×3), brine (30.0 mL), and dried over anhydrous sodium sulfate. The mixture was filtered, and concentrated under reduced pressure to give a residue that was purified by flash silica gel chromatography (eluting with petroleum ether/ethyl acetate) to afford tert-butyl (1-(3-iodo-1-(tetrahydro-2H-pyran-2-yl)-1H-pyrazolo[3,4-b]pyrazin-6-yl)-2-methylpiperidin-4-yl)carbamate (700.0 mg, combined product) as a yellow solid.

Step b: A mixture of tert-butyl (1-(3-iodo-1-(tetrahydro-2H-pyran-2-yl)-1H-pyrazolo[3,4-b]pyrazin-6-yl)-2-methylpiperidin-4-yl)carbamate (360.0 mg, 663 µmol), 1,2,3,4-tetrahydro-1,5-naphthyridine (88.9 mg, 663 µmol), RuPhos-Pd-G4 (57.0 mg, 66.3 µmol), RuPhos (30.8 mg, 66.3 µmol), and t-BuONa (190.0 mg, 2.0 mmol) in dioxane (20.0 mL) was evacuated and backfilled with nitrogen three times before being stirred at 80° C. for 12 hrs. The reaction mixture was concentrated under reduced pressure and purified by flash silica gel chromatography (eluting with petroleum ether/ethyl acetate, then dichloromethane/methanol) to afford tert-butyl (1-(3-(3,4-dihydro-1,5-naphthyridin-1(2H)-yl)-1-(tetrahydro-2H-pyran-2-yl)-1H-pyrazolo[3,4-b]pyrazin-6-yl)-2-methylpiperidin-4-yl)carbamate (400.0 mg, combined product) as a yellow solid and 1-(3-(3,4-dihydro-1,5-naphthyridin-1(2H)-yl)-1-(tetrahydro-2H-pyran-2-yl)-1H-pyrazolo[3,4-b]pyrazin-6-yl)-2-methylpiperidin-4-amine (300.0 mg, combined product) as a yellow solid.

Step c: tert-Butyl ((2R,4S)-1-(3-(3,4-dihydro-1,5-naphthyridin-1(2H)-yl)-1H-pyrazolo[3,4-b]pyrazin-6-yl)-2-methylpiperidin-4-yl)carbamate (400.0 mg, 861 µmol) was added to 4N HCl/methanol (10.0 mL) and the reaction mixture was stirred at 25° C. for 12 hours. The mixture was concentrated under reduced pressure and purified by reversed phase prep-HPLC (eluting with acetonitrile/water/0.1% ammonium hydroxide) to afford rac-(2R,4S)-1-(3-(3,4-dihydro-1,5-naphthyridin-1(2H)-yl)-1H-pyrazolo[3,4-b]pyrazin-6-yl)-2-methylpiperidin-4-amine (150.0 mg, combined product) as a yellow solid: LCMS [M+H]⁺=365.3; ¹H-NMR (400 MHz, DMSO-d₆): δ 8.26 (s, 1H), 7.91-7.89 (m, 1H), 7.49-7.46 (m, 1H), 6.98-6.94 (m, 1H), 4.86-4.83 (m, 1H), 4.35-4.30 (m, 1H), 3.96-3.93 (m, 2H), 3.04-2.93 (m, 4H), 2.10-2.04 (m, 2H), 1.88-1.73 (m, 2H), 1.40-1.35 (m, 1H), 1.19-1.16 (m, 4H).

Step d: rac-(2R,4S)-1-(3-(3,4-dihydro-1,5-naphthyridin-1(2H)-yl)-1H-pyrazolo[3,4-b]pyrazin-6-yl)-2-methylpiperidin-4-amine (120.0 mg, 329 µmol) was purified by chiral SFC: column—Chiralpak AD-3 100×4.6 mm I.D, 3 µm; mobile phase A—CO₂ mobile phase B—ethanol (0.1% ethanolamine); gradient: from 5% to 40% of B in 4.5 min and hold 40% for 2.5 min, then 5% of B for 1 min; flow rate: 2.8 mL/min; and column temperature–40° C. rel-(2R,4S)-1-(3-(3,4-Dihydro-1,5-naphthyridin-1(2H)-yl)-1H-pyrazolo[3,4-b]pyrazin-6-yl)-2-methylpiperidin-4-amine (40.9 mg, 112 µmol, e.e.=100%) was obtained as a yellow solid: LCMS [M+H]⁺=365.3; ¹H-NMR (400 MHz, DMSO-d4): δ 8.26 (s, 1H), 7.91-7.88 (m, 1H), 7.49-7.47 (m, 1H), 6.98-6.94 (m, 1H), 4.86-4.82 (m, 1H), 4.34-4.30 (m, 1H), 3.96-3.92 (m, 2H), 3.07-2.92 (m, 4H), 2.10-2.05 (m, 2H), 1.88-1.73 (m, 2H), 1.39-1.37 (m, 1H), 1.22-1.13 (m, 4H). rel-(2S,4R)-1-(3-(3,4-dihydro-1,5-naphthyridin-1(2H)-yl)-1H-pyrazolo[3,4-b]pyrazin-6-yl)-2-methylpiperidin-4-amine (38.4 mg, 105 µmol, e.e.=91.7%) was obtained as a yellow solid: LCMS [M+H]⁺=365.3; ¹H-NMR (400 MHz, DMSO-d₆): δ 8.31 (s, 1H), 7.96-7.94 (m, 1H), 7.55-7.52 (m, 1H), 7.03-6.99 (m, 1H), 4.96-4.88 (m, 1H), 4.40-4.36 (m, 1H), 4.02-3.98 (m, 2H), 3.12-2.97 (m, 4H), 2.15-2.08 (m, 2H), 1.94-1.79 (m, 2H), 1.46-1.43 (m, 1H), 1.28-1.21 (m, 4H).

Synthesis of (1-(3-(3,4-dihydro-1,5-naphthyridin-1 (2H)-yl)-1H-pyrazolo[3,4-b]pyrazin-6-yl)-3-methylpyrrolidin-3-yl)methanamine dihydrochloride, Compound 26

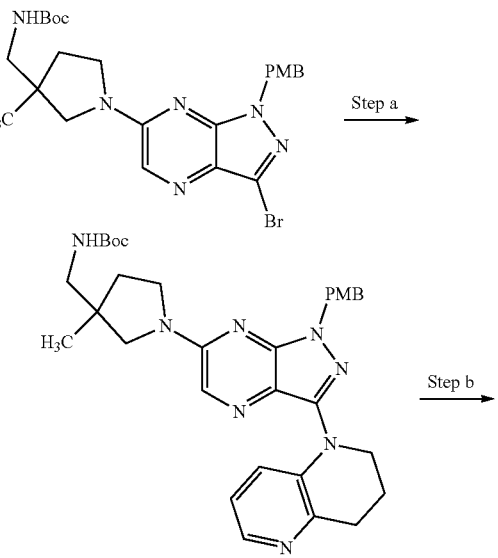

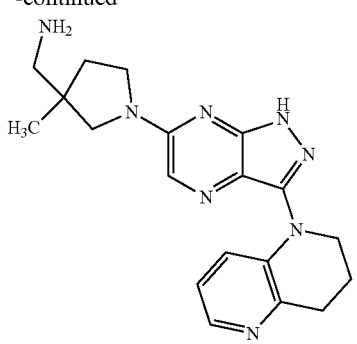

Step a: tert-Butyl-((1-(3-bromo-1-(4-methoxybenzyl)-1H-pyrazolo[3,4-b]pyrazin-6-yl)-3-methylpyrrolidin-3-yl)methyl)carbamate (prepared via the route used for Compound 33) (200 mg, 376 µmol), 1,2,3,4-tetrahydro-1,5-naphthyridine (55.4 mg, 413 µmol), RuPhos (17.5 mg, 37.6 µmol), RuPhos-Pd-G4 (31.9 mg, 37.6 µmol), and t-BuONa (107 mg, 1.12 mmol) were combined in dioxane (10 mL), and the mixture stirred at 120° C. for 10 hrs. The reaction mixture was concentrated under reduced pressure to give a yellow solid, which was purified by silica gel chromatography (eluting with petroleum ether:ethyl acetate=100:0 to 100:50) to provide tert-butyl-((1-(3-(3,4-dihydro-1,5-naphthyridin-1(2H)-yl)-1-(4-methoxybenzyl)-1H-pyrazolo[3,4-b]pyrazin-6-yl)-3-methylpyrrolidin-3-yl))methyl)carbamate (150 mg, 256 µmol) as a yellow solid.

Step b: tert-Butyl ((1-(3-(3,4-dihydro-1,5-naphthyridin-1(2H)-yl)-1-(4-methoxybenzyl)-1H-pyrazolo[3,4-b]pyrazin-6-yl)-3-methylpyrrolidin-3-yl)methyl)carbamate (150 mg, 308 µmol) was taken up in trifluoroacetic acid (5 mL) and trifluoromethylsulfonic acid (0.4 mL) and the mixture was stirred at 85° C. for 30 min. After cooling, the reaction mixture was concentrated under reduced pressure to give a yellow solid which was purified by prep-HPLC (eluting with acetonitrile/water/0.1% hydrochloric acid) to afford (1-(3-(3,4-dihydro-1,5-naphthyridin-1(2H)-yl)-1H-pyrazolo[3,4-b]pyrazin-6-yl)-3-methylpyrrolidin-3-yl)methanamine dihydrochloride (33.5 mg, 25.0% yield, HCl salt) as a yellow solid after lyophilization.

Synthesis of (1-(3-(3,4-dihydroquinolin-1(2H)-yl)-1H-pyrazolo[3,4-b]pyrazin-6-yl)-4-methylpiperidin-4-yl)methanamine, Compound 33

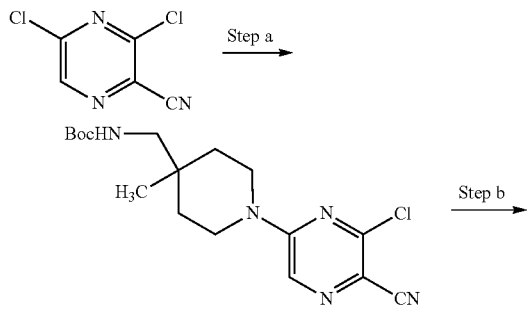

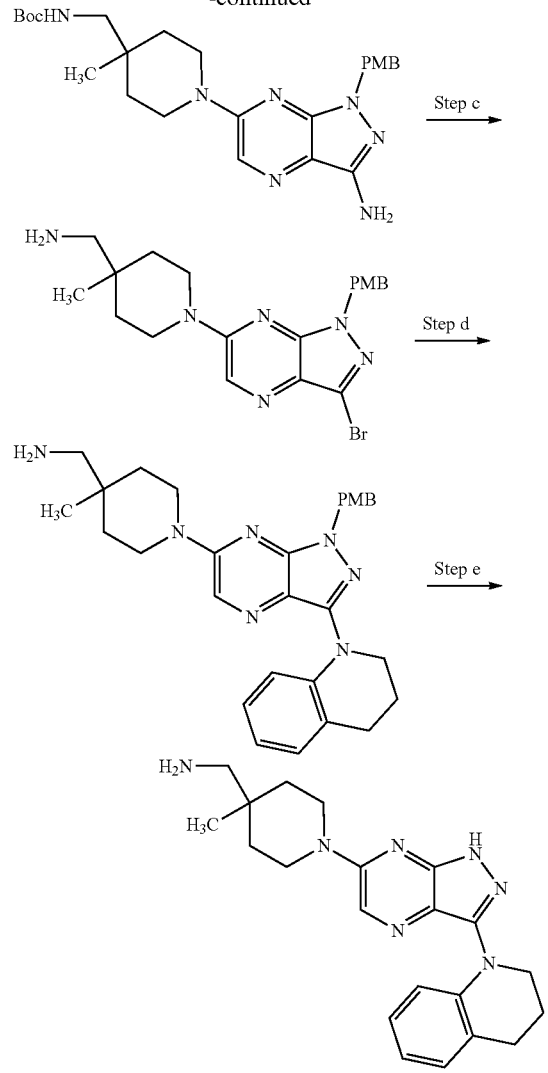

Step a: 3,5-Dichloropyrazine-2-carbonitrile (500 mg, 2.9 mmol), tert-butyl ((4-methylpiperidin-4-yl)methyl)carbamate hydrochloride (655 mg, 2.9 mmol, CAS #1158759-03-5), and diisopropylethylamine (1.5 mL, 287 µmol) were taken up in dimethyl sulfoxide (10 mL) and stirred at 70° C. for 1 hr. After cooling, the reaction mixture was diluted with ethyl acetate (100 mL), washed with water (50 mL×4), brine (30 mL), dried over anhydrous sodium sulfate, and filtered. The combined organics were concentrated under reduced pressure, and purified by flash silica gel chromatography (eluting with ethyl acetate:petroleum ether=0:100 to 50:100) to afford tert-butyl ((1-(6-chloro-5-cyanopyrazin-2-yl)-4-methylpiperidin-4-yl)methyl)carbamate (900 mg, 86% yield) as a yellow solid.

Step b: tert-Butyl ((1-(6-chloro-5-cyanopyrazin-2-yl)-4-methylpiperidin-4-yl)methyl)carbamate (900 mg, 2.5 mmol), (4-methoxybenzyl)hydrazine (447.0 mg, 2.9 mmol), and triethylamine (1.7 mL, 12.2 mmol) were taken up in ethanol (10 mL) and stirred at 90° C. for 12 hrs. After cooling, the mixture was concentrated under reduced pressure and purified by silica gel chromatography (petroleum ether:ethyl acetate=100:0 to 100:80) to afford tert-butyl ((1-(3-amino-1-(4-methoxybenzyl)-1H-pyrazolo[3,4-b]pyrazin-6-yl)-4-methylpiperidin-4-yl)methyl)carbamate (900 mg, 77% yield) as a yellow solid.

Step c: tert-Butyl ((1-(3-amino-1-(4-methoxybenzyl)-1H-pyrazolo[3,4-b]pyrazin-6-yl)-4-methylpiperidin-4-yl)methyl)carbamate (900 mg, 1.2 mmol), sodium nitrite (153 mg, 2.2 mmol), and hydrogen bromide (5.4 mL, 48% aq, 46.5 mmol) were taken up in acetonitrile (10.0 mL) and the reaction was stirred at 0° C. for 1 hr. Copper(I) bromide (53.3 mg, 0.37 mmol) was added at 0° C., and then warmed to 25° C. before and stirred for another 1 hr. The reaction mixture was concentrated under reduced pressure and purified by flash column chromatography (petroleum ether:ethyl acetate=100:0 to 100:20) to afford tert-butyl ((1-(3-bromo-1-(4-methoxybenzyl)-1H-pyrazolo[3,4-b]pyrazin-6-yl)-4-methylpiperidin-4-yl)methyl)carbamate (500 mg, 50% yield) as a yellow solid.

Step d: (1-(3-Bromo-1-(4-methoxybenzyl)-1H-pyrazolo[3,4-b]pyrazin-6-yl)-4-methylpiperidin-4-yl)methanamine (300 mg, 0.67 mmol), 1,2,3,4-tetrahydroquinoline (99 mg, 0.74 mmol), RuPhos (31 mg, 67 µmol), RuPhos-Pd-G4 (58 mg, 67 µmol), and t-BuONa (193 mg, 2.0 mmol) were taken up in dioxane (5 mL) and the mixture evacuated and refilled three times with nitrogen before being stirred at 120° C. for 12 hrs. After cooling, the reaction mixture was concentrated under reduced pressure and purified by silica gel chromatography (petroleum ether:EtOAc=100:0 to 100:30) to afford (1-(3-(3,4-dihydroquinolin-1(2H)-yl)-1-(4-methoxybenzyl)-1H-pyrazolo[3,4-b]pyrazin-6-yl)-4-methylpiperidin-4-yl)methanamine (60 mg, 13% yield) as a yellow solid.

Step e: (1-(3-(3,4-Dihydroquinolin-1(2H)-yl)-1-(4-methoxybenzyl)-1H-pyrazolo[3,4-b]pyrazin-6-yl)-4-methylpiperidin-4-yl)methanamine (60 mg, 0.12 mmol) was added to the mixture of trifluoromethylsulfonic acid (0.2 mL) and trifluoroacetic acid (2.0 mL) and the reaction mixture stirred at 90° C. for 0.5 hrs. After cooling, the reaction mixture was concentrated under reduced pressure, diluted with methanol (5 mL), and the pH adjusted to 9 by adding ammonium hydroxide (aq.). The mixture was purified by prep-HPLC (eluting with acetonitrile and water, both with 0.1% ammonium hydroxide) to afford (1-(3-(3,4-dihydroquinolin-1(2H)-yl)-1H-pyrazolo[3,4-b]pyrazin-6-yl)-4-methylpiperidin-4-yl)methanamine (4.0 mg, 8.8% yield) as a yellow solid: LCMS [M+H]$^+$=378.1.

The following compounds were synthesized via the same route as Compound 33, using the relevant appropriate building blocks (which were either commercially available or prepared as described in the intermediates section). The pyrazolo-pyrazine ring was protected with either PMB (as shown above) or a THP group. In some cases, other intermediates were prepared using the relevant substituted piperidine or pyrrolidine building blocks. Standard cross coupling conditions apply for Step d, which also included using Pd$_2$(dba)$_3$, Xantphos, and t-BuONa for the coupling. Compounds synthesized via the method described for Compound 33 include: Compound 40, Compound 41, Compound 44, Compound 45, Compound 46, Compound 48, Compound 49, Compound 50, Compound 52, Compound 57, Compound 59, Compound 61, Compound 63, Compound 65, Compound 66, Compound 67, Compound 68, Compound 69, Compound 70, Compound 72, Compound 73, Compound 75, Compound 77, Compound 78, Compound 81, Compound 83, Compound 84, Compound 85, Compound 86, Compound 87, Compound 88, Compound 89, Compound 90, Compound 91, Compound 92, Compound 93, Compound 94, Compound 96, Compound 106, Compound 117, Compound 118, Compound 120, Compound 121, Compound 122, Compound 123, Compound 124, Compound 125, Compound 126, Compound 127, Compound 130, Compound 131, Compound 132, Compound 133, Compound 134, Compound 135, Compound 136, Compound 163, Compound 164, Compound 165, Compound 169, Compound 170, Compound 173, Compound 182, Compound 184, Compound 185, Compound 186, Compound 187, Compound 188, Compound 189, Compound 190, Compound 191, Compound 192, Compound 193, Compound 195.

Synthesis of 1-(6-(4-amino-4-methylpiperidin-1-yl)-1H-pyrazolo[3,4-b]pyrazin-3-yl)-3,4-dihydro-1,5-naphthyridin-2(1H)-one, Compound 39

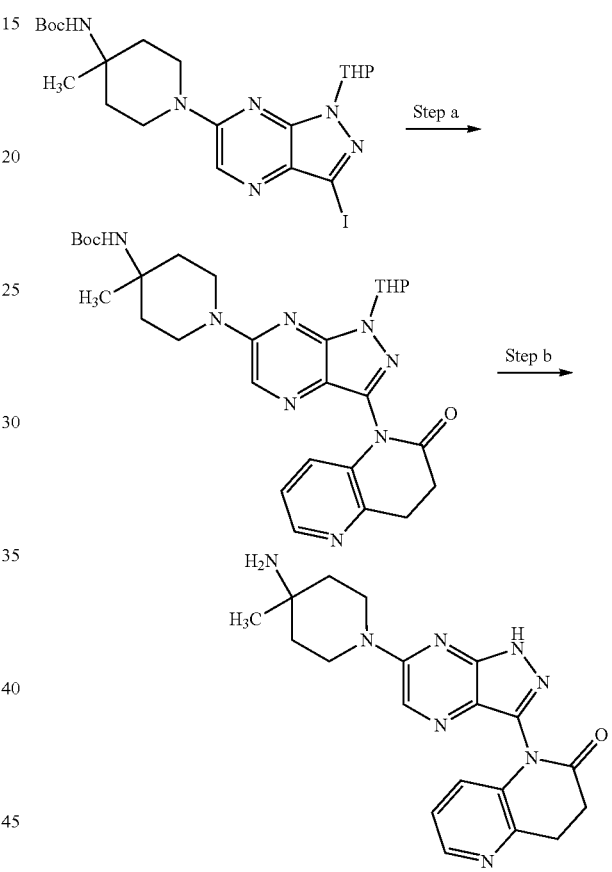

Step a: tert-Butyl (1-(3-iodo-1-(tetrahydro-2H-pyran-2-yl)-1H-pyrazolo[3,4-b]pyrazin-6-yl)-4-methylpiperidin-4-yl)carbamate (200.0 mg, 368.0 µmol, synthesized via Step a of Compound 486), 3,4-dihydro-1,5-naphthyridin-2(1H)-one (162.0 mg, 1.1 mmol), CuI (7.0 mg, 36.8 µmol), potassium carbonate (152.0 mg, 1.1 mmol), and (1S,2S)—N$^1$,N$^2$-dimethylcyclohexane-1,2-diamine (5.2 mg, 36.8 µmol) were taken up in toluene (5 mL). The reaction flask was evacuated and refilled 3 times with nitrogen and the mixture was stirred at 110° C. for 12 hrs. After cooling, the mixture was concentrated under reduced pressure to give a residue that was purified by silica gel chromatography (eluting with petroleum ether:ethyl acetate=10:0 to 10:3) to afford tert-butyl (4-methyl-1-(3-(2-oxo-3,4-dihydro-1,5-naphthyridin-1(2H)-yl)-1-(tetrahydro-2H-pyran-2-yl)-1H-pyrazolo[3,4-b]pyrazin-6-yl)piperidin-4-yl)carbamate (100.0 mg, 48.3% yield) as a yellow solid.

Step b: A flask was charged with tert-butyl N-[4-methyl-1-[3-(2-oxo-3,4-dihydro-1,5-naphthyridin-1-yl)-1-tetrahydropyran-2-yl-pyrazolo[3,4-b]pyrazin-6-yl]-4-piperidyl]carbamate (180.0 mg, 319.9 umol) followed by trifluoroacetic acid (2.0 mL). The reaction mixture was stirred at 50° C. for 12 hrs, cooled, and concentrated under reduced pressure. The residue was purified by prep-HPLC (eluting with acetonitrile/water/0.1% hydrochloric acid) to afford 1-[6-(4-amino-4-methyl-1-piperidyl)-1H-pyrazolo[3,4-b]pyrazin-3-yl]-3,4-dihydro-1,5-naphthyridin-2-one (22.0 mg, 15.9/6 yield, HCl salt) as a yellow solid.

Synthesis of 1-(6-(4-amino-4-methylpiperidin-1-yl)-1H-pyrazolo[3,4-b]pyrazin-3-yl)-1,2,3,4-tetrahydro-1,6-naphthyridin-5-amine Compound 42

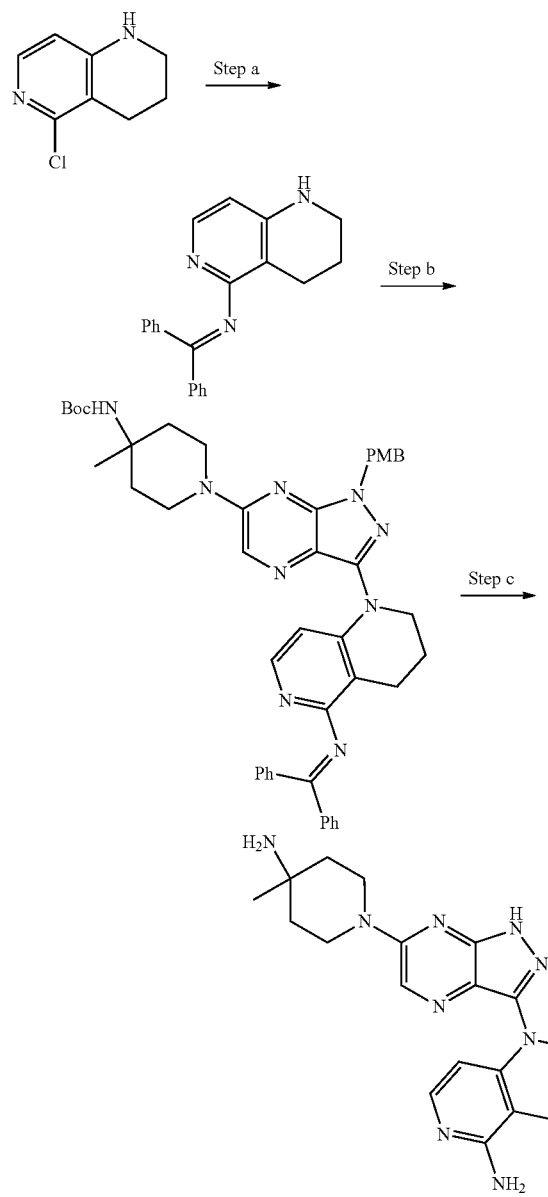

Step a: To a solution of 5-chloro-1,2,3,4-tetrahydro-1,6-naphthyridine (150 mg, 889 µmol, CAS #98490-61-0) and diphenylmethanimine (177 mg, 977 µmol) in toluene (5 mL) was added t-BuONa (170 mg, 1.77 mmol), Pd₂(dba)₃ (81.3 mg, 177 µmol), and 2,2'-bis(diphenylphosphino)-1,1'-bi-naphthyl (110 mg, 177 µmol). The mixture was degassed and purged with nitrogen three times, then stirred at 110° C. for 12 hrs under a nitrogen atmosphere. After cooling, the reaction mixture was concentrated under reduced pressure and the residue purified by silica gel chromatography (eluting with petroleum ether/ethyl acetate=100:0 to 100:100) to afford N-(diphenylmethylene)-1,2,3,4-tetrahydro-1,6-naphthyridin-5-amine (180 mg, 574 µmol, 64.7% yield) as a light yellow solid.

Step b: To a solution of tert-butyl (1-(3-bromo-1-(4-methoxybenzyl)-1H-pyrazolo[3,4-b]pyrazin-6-yl)-4-methylpiperidin-4-yl)carbamate (200 mg, 376 µmol) and N-(diphenylmethylene)-1,2,3,4-tetrahydro-1,6-naphthyridin-5-amine (117 mg, 376 µmol) in dioxane (5 mL) was added RuPhos-Pd-G4 (91.3 mg, 112 µmol), t-BuONa (72.2 mg, 752 µmol), and RuPhos (52.2 mg, 112 µmol). The reaction mixture was purged with nitrogen for 3 min, then stirred at 120° C. for 12 hrs under a nitrogen atmosphere. After cooling, the reaction mixture was concentrated under reduced pressure and purified by silica gel chromatography (eluting with petroleum ether/ethyl acetate=100:0 to 100:80) to afford tert-butyl (1-(3-(5-((diphenylmethylene)amino)-3,4-dihydro-1,6-naphthyridin-1(2H)-yl)-1-(4-methoxybenzyl)-1H-pyrazolo[3,4-b]pyrazin-6-yl)-4-methylpiperidin-4-yl)carbamate (200 mg, 261 µmol, 69.6% yield) as a yellow gum.

Step c: A solution of tert-butyl (1-(3-(5-((diphenylmethylene)amino)-3,4-dihydro-1,6-naphthyridin-1(2H)-yl)-1-(4-methoxybenzyl)-1H-pyrazolo[3,4-b]pyrazin-6-yl)-4-methylpiperidin-4-yl)carbamate (180 mg, 235 µmol) in trifluoroacetic acid (5 mL) was stirred at 80° C. for 50 h and then 100° C. for 22 hrs. After cooling, the reaction mixture was concentrated under reduced pressure, the residue diluted with methanol and the pH adjusted to 10 with ammonium hydroxide (aq.). The mixture was then purified by prep-HPLC (eluting with acetonitrile/water/0.1% ammonium hydroxide) to afford 1-(6-(4-amino-4-methylpiperidin-1-yl)-1H-pyrazolo[3,4-b]pyrazin-3-yl)-1,2,3,4-tetrahydro-1,6-naphthyridin-5-amine (35.0 mg, 92.2 µmol, 39.2% yield) as an off-white solid.

Separation of (R)-(4-methyl-1-(3-(4-methyl-3,4-dihydroquinolin-1(2H)-yl)-1H-pyrazolo[3,4-b]pyrazin-6-yl)piperidin-4-yl)methanamine, Compound 49 and (S)-(4-methyl-1-(3-(4-methyl-3,4-dihydroquinolin-1(2H)-yl)-1H-pyrazolo[3,4-b]pyrazin-6-yl)piperidin-4-yl)methanamine, Compound 50

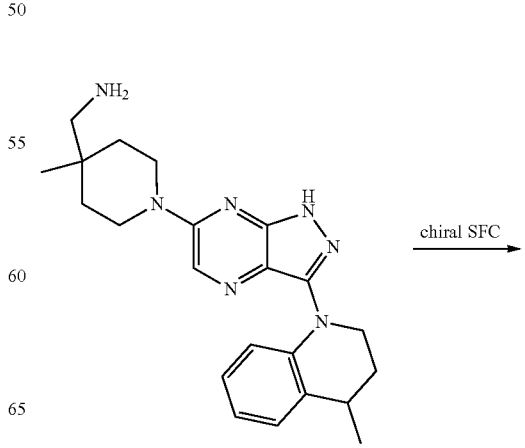

243

-continued

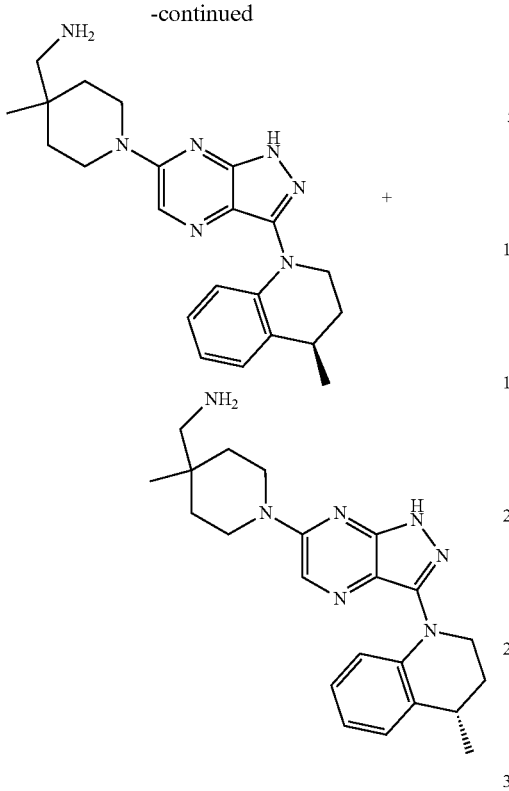

(4-methyl-1-(3-(4-methyl-3,4-dihydroquinolin-1(2H)-yl)-1H-pyrazolo[3,4-b]pyrazin-6-yl)piperidin-4-yl)methanamine (70 mg, 178 μmol) was synthesized as described above for Compound 33, using as 4-methyl-1,2,3,4-tetrahydroquinoline amine in Step d. This compound was then separated by Chiral-SFC (Column: Chiralcel OJ-3 50×4.6 mm I.D., 3 um Mobile phase: A: $CO_2$ B:ethanol (0.05% DEA) Gradient: hold 5% for 0.2 min, then from 5% to 40% of B in 1.4 min and hold 40% for 1.05 min, then 5% of B for 0.35 min. Flow rate: 4 mL/min Column temp:40° C.). The absolute configuration of both enantiomers were assigned randomly. (R)-(4-methyl-1-(3-(4-methyl-3,4-dihydroquinolin-1(2H)-yl)-1H-pyrazolo[3,4-b]pyrazin-6-yl)piperidin-4-yl)methanamine (18.0 mg, 45.9 μmol, e.e.=100%) was obtained as a yellow solid. LCMS: calc. for $C22H_{29}N_7$: 391.2, found: [M+H]+ 392.1. (S)-(4-methyl-1-(3-(4-methyl-3,4-dihydroquinolin-1(2H)-yl)-1H-pyrazolo[3,4-b]pyrazin-6-yl)piperidin-4-yl)methanamine (20.0 mg, 51.0 μmol, e.e.=96.7%) was obtained as a yellow solid. LCMS: calc. for $C_{22}H_{29}N_7$: 391.2, found: [M+H]+ 392.1.

Synthesis of 5-(6-(4-(aminomethyl)-4-methylpiperidin-1-yl)-1H-pyrazolo[3,4-b]pyrazin-3-yl)-5,6,7,8-tetrahydro-1,5-naphthyridin-2-amine, Compound 51

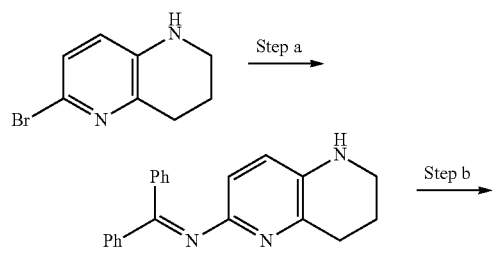

244

-continued

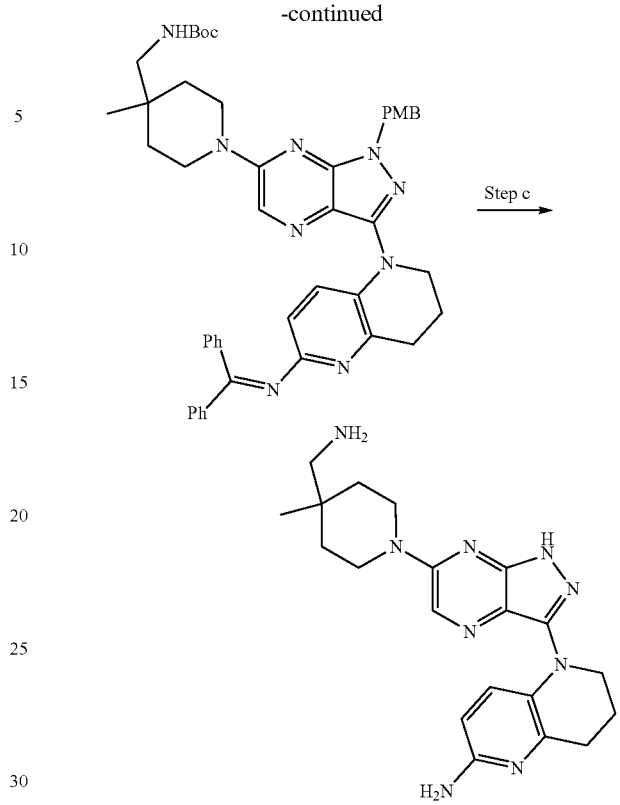

Step a: To a solution of 6-bromo-1,2,3,4-tetrahydro-1,5-naphthyridine (30 mg, 140 μmol) and diphenylmethanimine (27.9 mg, 154 μmol) in toluene (5 mL) was added $Pd_2(dba)$; (12.8 mg, 14.0 μmol), BINAP (8.71 mg, 14.0 μmol), and sodium tert-butoxide (26.8 mg, 280 μmol). The mixture was degassed and purged with nitrogen three times before being stirred at 110° C. for 12 hrs under a nitrogen atmosphere. After cooling, the reaction mixture was concentrated under reduced pressure and the product purified by silica gel chromatography (eluting with petroleum ether/ethyl acetate) to afford N-(diphenylmethylene)-5,6,7,8-tetrahydro-1,5-naphthyridin-2-amine (230 mg, 733 μmol, 71.4% yield) as a brown solid.

Step b: To a solution of tert-butyl ((1-(3-bromo-1-(4-methoxybenzyl)-1H-pyrazolo[3,4-b]pyrazin-6-yl)-4-methylpiperidin-4-yl)methyl)carbamate (360 mg, 659 μmol) and N-(diphenylmethylene)-5,6,7,8-tetrahydro-1,5-naphthyridin-2-amine (226 mg, 724 μmol) in dioxane (10 mL) were added RuPhos (65.9 μmol, 30.7 mg), RuPhos-Pd-G4 (65.9 μmol, 56.0 mg), and sodium tert-butoxide (1.31 mmol, 125 mg). The reaction mixture was evacuated and backfilled with nitrogen three times, followed by stirring at 100° C. for 12 hrs. After cooling, the reaction mixture was concentrated under reduced pressure and the residue purified by column chromatography (eluting with dichloromethane and methanol) to afford tert-butyl ((1-(3-(6-((diphenylmethylene)amino)-3,4-dihydro-1,5-naphthyridin-1(2H)-yl)-1-(4-methoxybenzyl)-1H-pyrazolo[3,4-b]pyrazin-6-yl)-4-methylpiperidin-4-yl)methyl)carbamate (500 mg, 449 μmol, 97.6% yield) as a yellow solid.

Step c: A solution of tert-butyl ((1-(3-(6-((diphenylmethylene)amino)-3,4-dihydro-1,5-naphthyridin-1(2H)-yl)-1-(4-methoxybenzyl)-1H-pyrazolo[3,4-b]pyrazin-6-yl)-4-methylpiperidin-4-yl)methyl)carbamate (480 mg, 617 μmol) in trifluoroacetic acid (10 mL) and trifluoromethylsulfonic acid (2.0 mL) was stirred at 20° C. for 6 hrs. After cooling, the reaction mixture was concentrated under reduced pressure, diluted with methanol (5.0 mL) and dimethylformamide (5.0 mL) and the pH adjusted to 7-10 with ammonium hydroxide. The reaction mixture was purified by prep-HPLC (eluting with acetonitrile/water/0.1% formic acid) to afford 5-(6-(4-(aminomethyl)-4-methylpiperidin-1-yl)-1H-pyrazolo[3,4-b]pyrazin-3-yl)-5,6,7,8-tetrahydro-1,5-naphthyridin-2-amine (100 mg, 254 μmol, 41.3% yield) as a yellow solid.

Synthesis of 8-(3-(3,4-dihydro-1,5-naphthyridin-1(2H)-yl)-1H-pyrazolo[3,4-b]pyrazin-6-yl)-8-azaspiro[4.5]decan-1-amine, Compound 53

Synthesis of 1-(6-(4-amino-4-methylpiperidin-1-yl)-1H-pyrazolo[3,4-b]pyrazin-3-yl)-1,2,3,4-tetrahydroquinoline-6-carboxamide, Compound 54

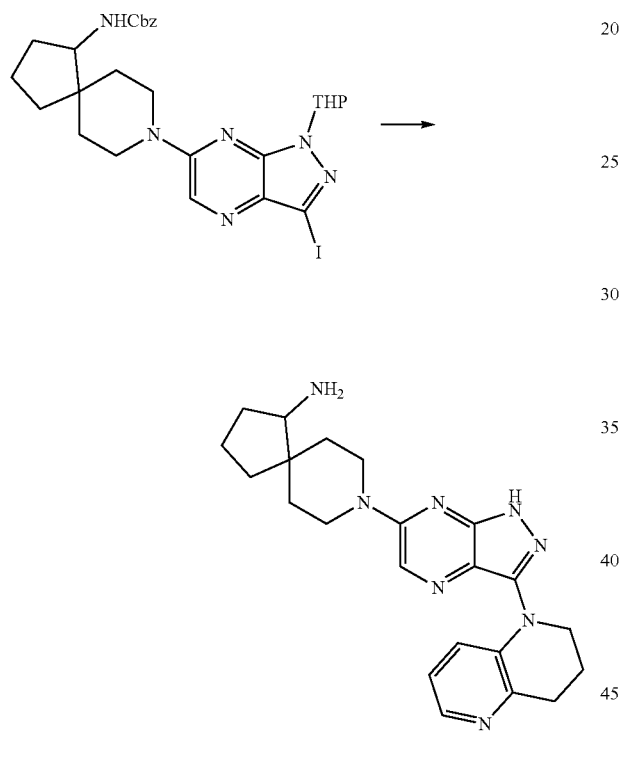
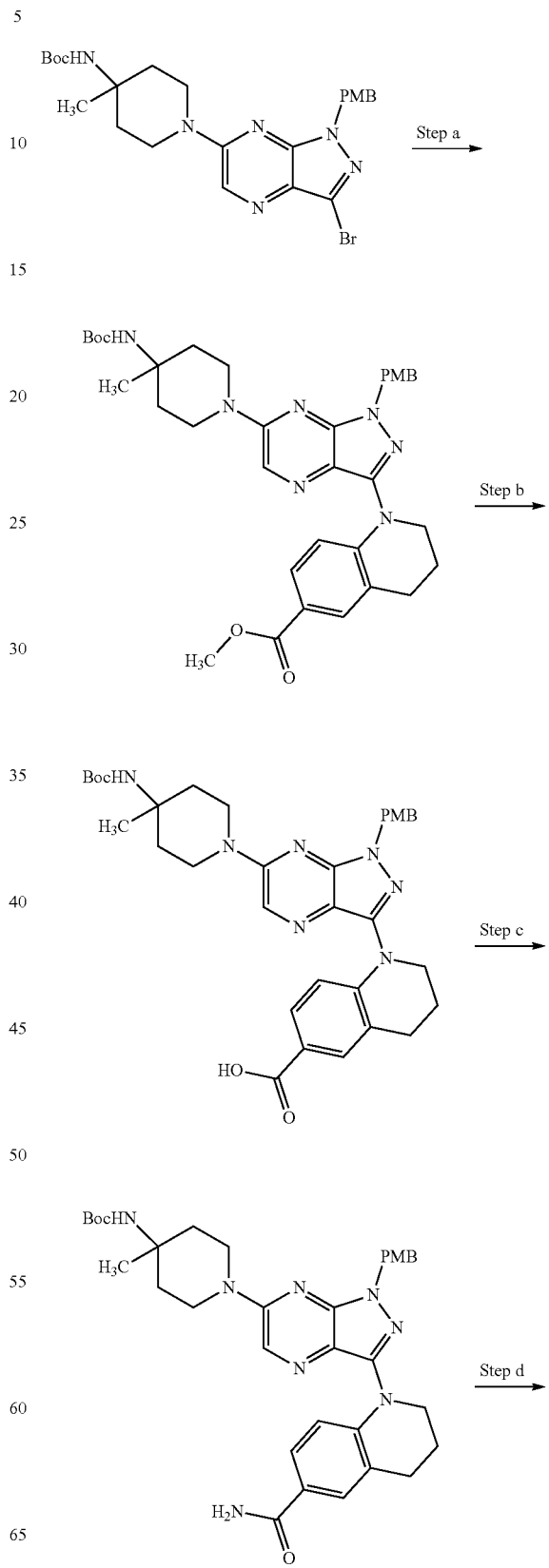

A resealable reaction vial was charged with benzyl (8-(3-iodo-1-(tetrahydro-2H-pyran-2-yl)-1H-pyrazolo[3,4-b]pyrazin-6-yl)-8-azaspiro[4.5]decan-1-yl)carbamate (131 mg, 0.2124 mmol), 1,2,3,4-tetrahydro-1,5-naphthyridine (31.3 mg, 0.2336 mmol), sodium 2-methylpropan-2-olate (40.8 mg, 0.4248 mmol), RuPhos/Pd G4 (18.0 mg, 0.02124 mmol), and dioxane (5 mL). Nitrogen gas was bubbled through the mixture for 10 min, the vial sealed, and the mixture stirred at 90° C. for 5 hrs. After cooling, the reaction mixture was diluted with ethyl acetate and brine. The organics were dried over sodium sulfate, filtered, and concentrated under reduced pressure. The residue was purified by reversed phase HPLC (eluting with acetonitrile/water/0.1% ammonium formate) to afford 8-(3-(3,4-dihydro-1,5-naphthyridin-1(2H)-yl)-1H-pyrazolo[3,4-b]pyrazin-6-yl)-8-azaspiro[4.5]decan-1-amine (2 mg) as an amorphous off-white solid after lyophilization.

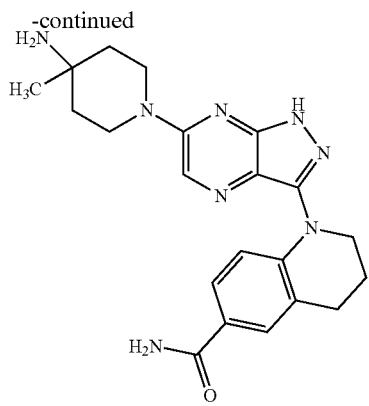

Step a: tert-Butyl (1-(3-bromo-1-(4-methoxybenzyl)-1H-pyrazolo[3,4-b]pyrazin-6-yl)-4-methylpiperidin-4-yl)carbamate (0.2 g, 376.0 μmol), methyl 1,2,3,4-tetrahydroquinoline-6-carboxylate (71.9 mg, 375.0 μmol, CAS #177478-49-8), RuPhos (17.5 mg, 37.6 μmol), RuPhos-Pd-G4 (31.9 mg, 37.6 μmol), and t-BuONa (107.0 mg, 1.1 mmol) were taken up in dioxane (10 mL). The reaction mixture was evacuated and backfilled three times with nitrogen before being stirred at 120° C. for 12 hrs. After cooling, the reaction mixture was concentrated under reduced pressure and the residue purified by silica gel chromatography (eluting with ethyl acetate/petroleum ether=0:100 to 30:100) to afford methyl 1-(6-(4-((tert-butoxycarbonyl)amino)-4-methylpiperidin-1-yl)-1-(4-methoxybenzyl)-1H-pyrazolo[3,4-b]pyrazin-3-yl)-1,2,3,4-tetrahydroquinoline-6-carboxylate (180.0 mg, 74.6% yield) as a yellow solid.

Step b: To methyl 1-(6-(4-((tert-butoxycarbonyl)amino)-4-methylpiperidin-1-yl)-1-(4-methoxybenzyl)-1H-pyrazolo[3,4-b]pyrazin-3-yl)-1,2,3,4-tetrahydroquinoline-6-carboxylate (160.0 mg, 249 μmol) dissolved in methanol (3.0 mL) was added sodium hydroxide (19.9 mg, 498.0 μmol) in water (1.0 mL). The reaction mixture was stirred at 70° C. for 12 hrs. After cooling, the reaction mixture was concentrated under reduced pressure and diluted with water (20 mL), the pH adjusted to 5 by the addition of 2N hydrochloric acid, and extracted with dichloromethane (30 mL×2). The organics were washed with brine, dried over anhydrous sodium sulfate, filtered, and concentrated under reduced pressure to give 1-(6-(4-((tert-butoxycarbonyl)amino)-4-methylpiperidin-1-yl)-1-(4-methoxybenzyl)-1H-pyrazolo[3,4-b]pyrazin-3-yl)-1,2,3,4-tetrahydroquinoline-6-carboxylic acid (160.0 mg, 96.1% yield) as a yellow solid.

Step c: To a solution of 1-(6-(4-((tert-butoxycarbonyl)amino)-4-methylpiperidin-1-yl)-1-(4-methoxybenzyl)-1H-pyrazolo[3,4-b]pyrazin-3-yl)-1,2,3,4-tetrahydroquinoline-6-carboxylic acid (150.0 mg, 238.0 μmol) in tetrahydrofuran (12 mL) and dichloromethane (6 mL), and triethylamine (96.3 mg, 952.0 μmol) was added HATU (180.0 mg, 476.0 μmol) in one portion and the reaction mixture stirred for 15 min. Ammonium carbonate (91.3 mg, 952.0 μmol) was added and the mixture was stirred for another 2 hrs. The reaction mixture was diluted with ethyl acetate (30 mL), washed with brine (20 mL×2), and concentrated under reduced pressure to afford tert-butyl (1-(3-(6-carbamoyl-3,4-dihydroquinolin-1(2H)-yl)-1-(4-methoxybenzyl)-1H-pyrazolo[3,4-b]pyrazin-6-yl)-4-methylpiperidin-4-yl)carbamate (150.0 mg, crude) as a yellow solid.

Step d: tert-Butyl (1-(3-(6-carbamoyl-3,4-dihydroquinolin-1(2H)-yl)-1-(4-methoxybenzyl)-1H-pyrazolo[3,4-b]pyrazin-6-yl)-4-methylpiperidin-4-yl) carbamate (150.0 mg, 239 μmol) and trifluoromethylsulfonic acid (0.2 mL) were combined in trifluoroacetic acid (2.0 mL) and the reaction mixture stirred at 90° C. for 30 min. After cooling, the mixture was concentrated under reduced pressure, diluted with methanol (5.0 mL), and the pH adjusted to 9 by adding ammonium hydroxide. Purification by prep-HPLC (eluting with acetonitrile/water/0.1% hydrochloric acid) afforded 1-(6-(4-amino-4-methylpiperidin-1-yl)-1H-pyrazolo[3,4-b]pyrazin-3-yl)-1,2,3,4-tetrahydroquinoline-6-carboxamide (43.2 mg, 44.4% yield) as a yellow solid.

Synthesis of 8-(3-(3,4-dihydro-1,5-naphthyridin-1(2H)-yl)-1H-pyrazolo[3,4-b]pyrazin-6-yl)-1-oxa-8-azaspiro[4.5]decan-4-amine, Compound 55

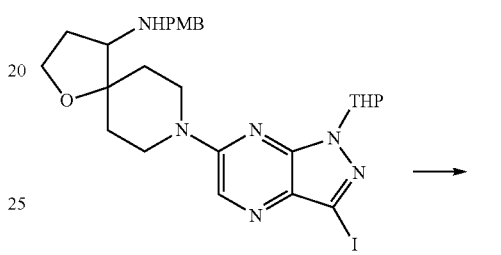

A resealable reaction vial was charged with 8-(3-iodo-1-(tetrahydro-2H-pyran-2-yl)-1H-pyrazolo[3,4-b]pyrazin-6-yl)-N-(4-methoxybenzyl)-1-oxa-8-azaspiro[4.5]decan-4-amine (125 mg, 0.2067 mmol), 1,2,3,4-tetrahydro-1,5-naphthyridine (30.4 mg, 0.2273 mmol), sodium 2-methylpropan-2-olate (39.7 mg, 0.4134 mmol), RuPhos/Pd G4 (17.5 mg, 0.02067 mmol), and dioxane (5 mL). Nitrogen was bubbled through the mixture for 10 min, the vial was sealed, and the mixture was stirred at 90° C. 3 hrs. The mixture was cooled to room temperature and concentrated under reduced pressure. The residue was then dissolved in trifluoroacetic acid (3 mL) and heated to 100° C. under microwave irradiation for 1 hr, then at 130° C. for 1 hr. The reaction mixture was diluted with methanol, concentrated under reduced pressure, stripped with methanol, and dissolved in dimethysulfoxide (with 0.2 mL aqueous ammonium hydroxide). The mixture was then purified by reversed phase HPLC (eluting with acetonitrile/water/0.1% ammonium formate) to provide 8-(3-(3,4-dihydro-1,5-naphthyridin-1(2H)-yl)-1H-pyrazolo[3,4-b]pyrazin-6-yl)-1-oxa-8-azaspiro[4.5]decan-4-amine (22 mg) as a yellow solid after lyophilization.

249

Synthesis of 1-(6-(4-(aminomethyl)-4-methylpiperidin-1-yl)-1H-pyrazolo[3,4-b]pyrazin-3-yl)-1,2,3,4-tetrahydroquinoline-6-carboxamide, Compound 58

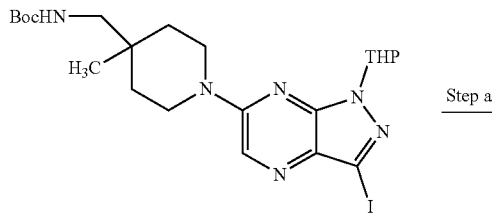

Step a →

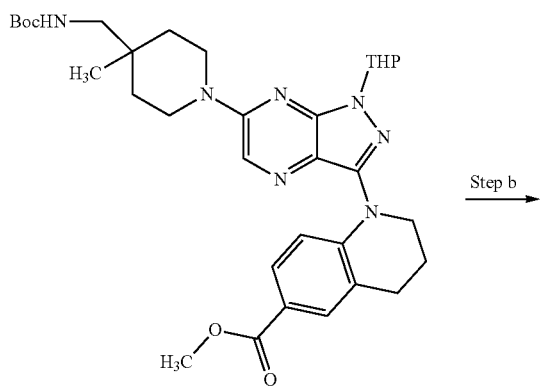

Step b →

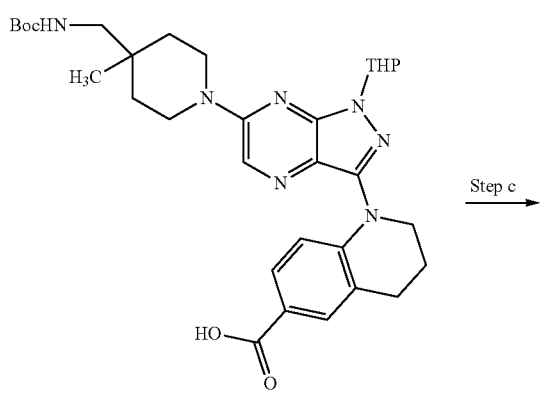

Step c →

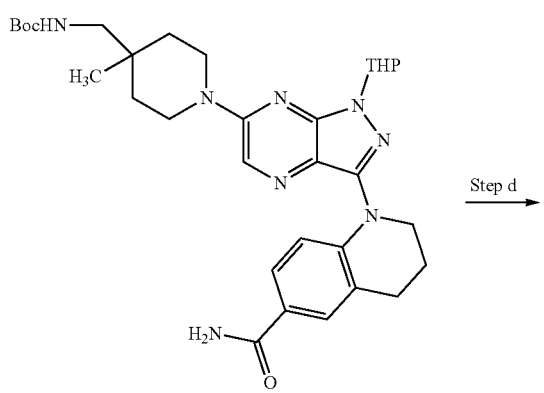

Step d →

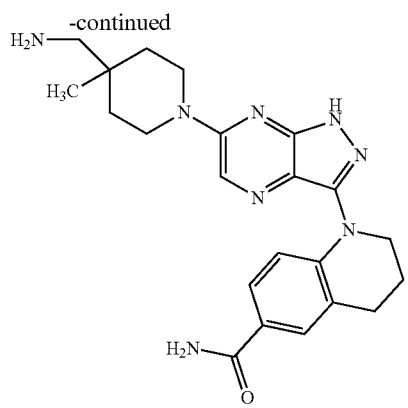

Step a: tert-Butyl ((1-(3-iodo-1-(tetrahydro-2H-pyran-2-yl)-1H-pyrazolo[3,4-b]pyrazin-6-yl)-4-methylpiperidin-4-yl)methyl)carbamate (200.0 mg, 359 µmol), methyl 1,2,3,4-tetrahydroquinoline-6-carboxylate (68.6 mg, 359 µmol), RuPhos (33.4 mg, 71.8 µmol), RuPhos-Pd-G4 (61.7 mg, 71.8 µmol), and t-BuONa (68.9 mg, 718 µmol) were combined in dioxane (15.0 mL) and the reaction mixture evacuated and backfilled with nitrogen three times before being stirred at 70° C. for 12 hrs. After cooling, the reaction mixture was concentrated under reduced pressure and purified by flash silica gel chromatography (eluting with petroleum ether/ethyl acetate) to afford methyl 1-(6-(4-(((tert-butoxycarbonyl)amino)methyl)-4-methylpiperidin-1-yl)-1-(tetrahydro-2H-pyran-2-yl)-1H-pyrazolo[3,4-b]pyrazin-3-yl)-1,2,3,4-tetrahydroquinoline-6-carboxylate (160.0 mg, 72.0% yield) as a yellow solid.

Step b: Methyl 1-(6-(4-(((tert-butoxycarbonyl)amino)methyl)-4-methylpiperidin-1-yl)-1-(tetrahydro-2H-pyran-2-yl)-1H-pyrazolo[3,4-b]pyrazin-3-yl)-1,2,3,4-tetrahydroquinoline-6-carboxylate (160 mg, 258 µmol) was dissolved in methanol (10 mL). Sodium hydroxide (30.9 mg, 774 µmol) and water (2.0 mL) was added and the reaction mixture was stirred at 70° C. for 12 hrs. After cooling, the reaction mixture was concentrated under reduced pressure, diluted with water (20 mL), the pH adjusted to 5 via the addition of 2N hydrochloric acid, and extracted with dichloromethane (30 mL×2). The combined organics were washed with saturated brine (30 mL), dried over anhydrous sodium sulfate, filtered, and concentrated under reduced pressure to give 1-(6-(4-(((tert-butoxycarbonyl)amino)methyl)-4-methylpiperidin-1-yl)-1-(tetrahydro-2H-pyran-2-yl)-1H-pyrazolo[3,4-b]pyrazin-3-yl)-1,2,3,4-tetrahydroquinoline-6-carboxylic acid (130.0 mg, crude) as a yellow solid.

Step c: 1-(6-(4-(((tert-butoxycarbonyl)amino)methyl)-4-methylpiperidin-1-yl)-1-(tetrahydro-2H-pyran-2-yl)-1H-pyrazolo[3,4-b]pyrazin-3-yl)-1,2,3,4-tetrahydroquinoline-6-carboxylic acid (130.0 mg, 214 µmol) was dissolved in tetrahydrofuran (10 mL). Ethyl chloroformate (81.1 µL, 642 µmol) was added at 0° C., and the reaction mixture stirred for 15 min. Then triethylamine (88.9 µL, 642 µmol) was added in one portion, and the reaction mixture was warmed to 25° C., and stirred for 12 hrs. After this time, the mixture was concentrated under reduced pressure and purified by flash silica gel chromatography (eluting with dichloromethane and methanol) to afford tert-butyl ((1-(3-(6-carbamoyl-3,4-dihydroquinolin-1(2H)-yl)-1-(tetrahydro-2H-pyran-2-yl)-1H-pyrazolo[3,4-b]pyrazin-6-yl)-4-methylpiperidin-4-yl)methyl)carbamate (50.0 mg, 36.4% yield) as a yellow solid.

Step d: tert-Butyl ((1-(3-(6-carbamoyl-3,4-dihydroquinolin-1(2H)-yl)-1-(tetrahydro-2H-pyran-2-yl)-1H-pyrazolo[3,4-b]pyrazin-6-yl)-4-methylpiperidin-4-yl)methyl)carbamate (50.0 mg, 99.2 µmol) was added to 4N HCl/methanol (5 mL), and the reaction mixture stirred at 25° C. for 2 hrs. After this time, the mixture was concentrated under reduced pressure and purified by prep-HPLC (eluting with acetonitrile/water/0.1% hydrochloric acid) to afford 1-(6-(4-(aminomethyl)-4-methylpiperidin-1-yl)-1H-pyrazolo[3,4-b]pyrazin-3-yl)-1,2,3,4-tetrahydroquinoline-6-carboxamide (18.0 mg, 52% yield, HCl salt) as a yellow solid.

Synthesis of 2-(1-(6-(4-amino-4-methylpiperidin-1-yl)-1H-pyrazolo[3,4-b]pyrazin-3-yl)-1,2,3,4-tetrahydroquinolin-5-yl)thiazole-4-carboxylic acid, Compound 71

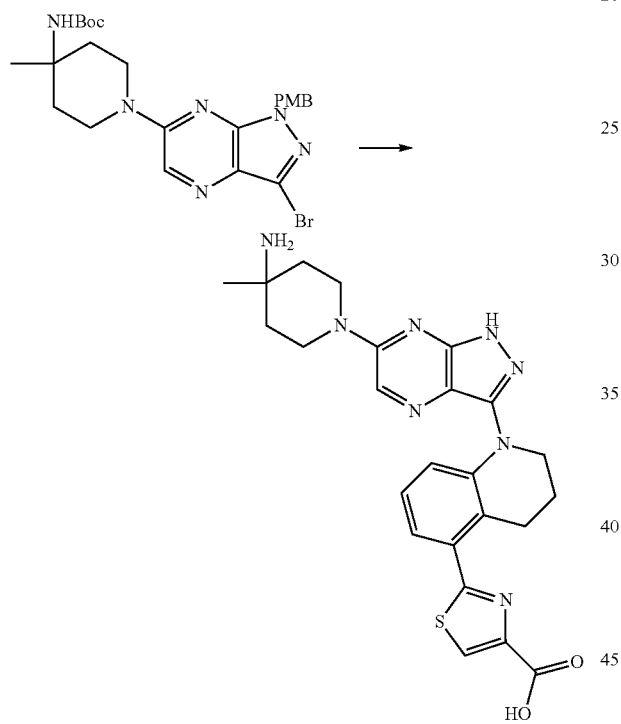

A mixture of tert-butyl (1-(3-bromo-1-(4-methoxybenzyl)-1H-pyrazolo[3,4-b]pyrazin-6-yl)-4-methylpiperidin-4-yl)carbamate (100 mg, 0.188 mmol), ethyl 2-(1,2,3,4-tetrahydroquinolin-5-yl)thiazole-4-carboxylate (54.2 mg, 0.188 mmol), sodium tert-butoxide (36.1 mg, 0.376 mmol), and RuPhos Pd G4 (15.9 mg, 0.019 mmol) in dioxane (5 mL) was degassed with nitrogen in a sealed tube, which was then sealed and stirred at 100° C. for 23 hours. The mixture was concentrated down after filtering through a celite plug with 10% MeOH/DCM (5×5 mL) and then dried before taking up in~1.5 mL TFA and heating in a microwave at 110° C. for 1 hour. Excess TFA was removed under reduced pressure. The crude mixture was purified by silica gel chromatography (eluting with DCM/MeOH). Product-containing fractions were pooled and concentrated in vacuo to yield 2-(1-(6-(4-amino-4-methylpiperidin-1-yl)-1H-pyrazolo[3,4-b]pyrazin-3-yl)-1,2,3,4-tetrahydroquinolin-5-yl)thiazole-4-carboxylic acid (5.6 mg) as a yellow solid.

rac-(2R,4S)-1-(3-(3,4-dihydro-1,5-naphthyridin-1(2H)-yl)-1H-pyrazolo[3,4-b]pyrazin-6-yl)-2-methylpiperidin-4-amine, Compound 74

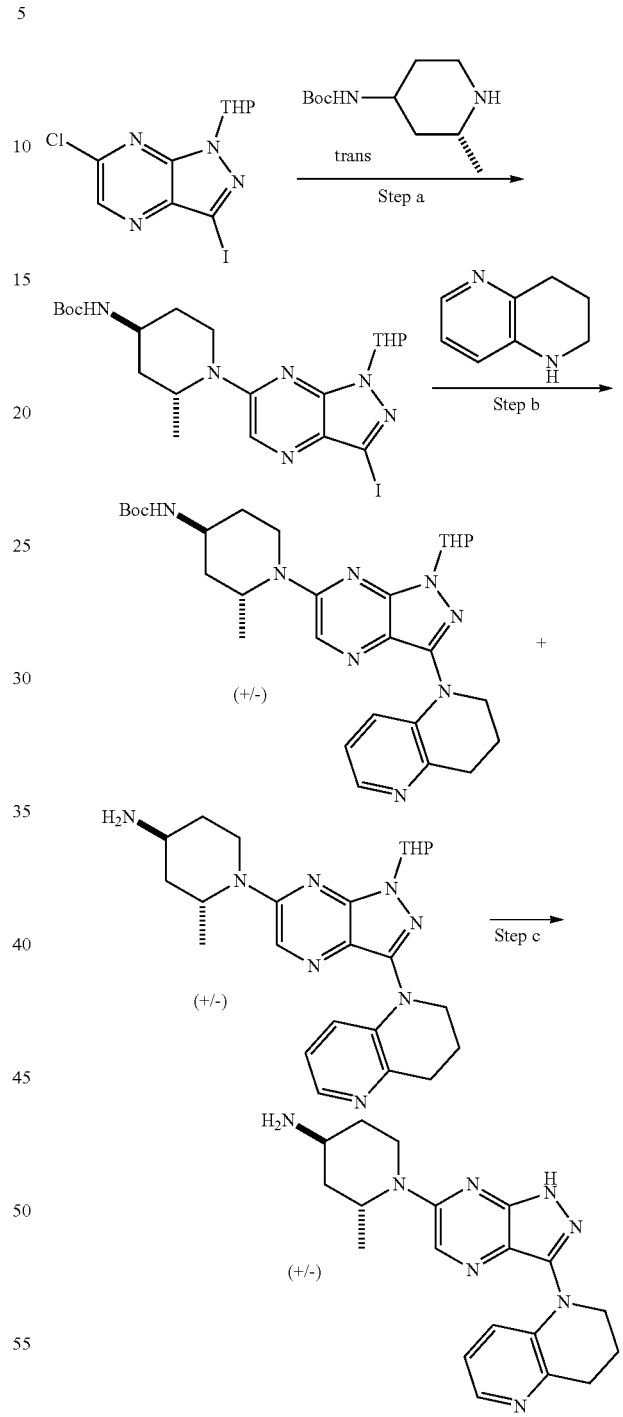

Step a: A mixture of 6-chloro-3-iodo-1-(tetrahydro-2H-pyran-2-yl)-1H-pyrazolo[3,4-b]pyrazine (300.0 mg, 822 µmol), tert-butyl (2-methylpiperidin-4-yl)carbamate (176.0 mg, 822 µmol) and DIPEA (428.0 µL, 2.46 mmol) in DMSO (15.0 mL) was stirred at 80° C. for 3 hours. The reaction mixture was diluted with EtOAc (100.0 mL), and the organic layer was separated, washed with H₂O (50.0 mL×3), brine (30.0 mL), dried over anhydrous Na₂SO₄, filtered and concentrated under reduced pressure to give a residue. The residue was purified by flash silica gel chromatography (Petroleum ether:Ethyl acetate=100:0 to 100:10) to afford the product of tert-butyl (1-(3-iodo-1-(tetrahydro-2H-pyran-2-yl)-1H-pyrazolo[3,4-b]pyrazin-6-yl)-2-methylpiperidin-4-yl)carbamate (700.0 mg, combined product) as a yellow solid.

Step b: A mixture of tert-butyl (1-(3-iodo-1-(tetrahydro-2H-pyran-2-yl)-1H-pyrazolo[3,4-b]pyrazin-6-yl)-2-methylpiperidin-4-yl)carbamate (360.0 mg, 663 μmol), 1,2,3,4-tetrahydro-1,5-naphthyridine (88.9 mg, 663 μmol), RuPhos-Pd-G4 (57.0 mg, 66.3 μmol), RuPhos (30.8 mg, 66.3 μmol) and t-BuONa (190.0 mg, 2.0 mmol) in dioxane (20.0 mL) was evacuated and refilled for 3 times with N$_2$ and stirred at 80° C. for 12 hours. The reaction mixture was concentrated under reduced pressure and purified by flash silica gel chromatography (Petroleum ether:Ethyl acetate=100:0 to 0:100, DCM:MeOH=100:20) to afford the product of tert-butyl (1-(3-(3,4-dihydro-1,5-naphthyridin-1(2H)-yl)-1-(tetrahydro-2H-pyran-2-yl)-1H-pyrazolo[3,4-b]pyrazin-6-yl)-2-methylpiperidin-4-yl)carbamate (400.0 mg) as a yellow solid and 1-(3-(3,4-dihydro-1,5-naphthyridin-1(2H)-yl)-1-(tetrahydro-2H-pyran-2-yl)-1H-pyrazolo[3,4-b]pyrazin-6-yl)-2-methylpiperidin-4-amine (300.0 mg) as a yellow solid. LCMS m/z: 448.9 (M+H)+ and 549.2 (M+H)+.

Step c: rac-Tert-butyl ((2R,4S)-1-(3-(3,4-dihydro-1,5-naphthyridin-1(2H)-yl)-1H-pyrazolo[3,4-b]pyrazin-6-yl)-2-methylpiperidin-4-yl)carbamate (400.0 mg, 861 μmol) was added in 4N HCl/MeOH (10.0 mL), and the reaction mixture was stirred at 25° C. for 12 hours. The reaction mixture was concentrated under reduced pressure and purified by prep-HPLC (NH$_3$.H$_2$O) to afford rac-(2R,4S)-1-(3-(3,4-dihydro-1,5-naphthyridin-1(2H)-yl)-1H-pyrazolo[3,4-b]pyrazin-6-yl)-2-methylpiperidin-4-amine (150.0 mg) as a yellow solid.

Synthesis of 1-(6-(4-(Aminomethyl)-4-methylpiperidin-1-yl)-1H-pyrazolo[3,4-b]pyrazin-3-yl)-N-methyl-1,2,3,4-tetrahydroquinoline-5-carboxamide, Compound 79

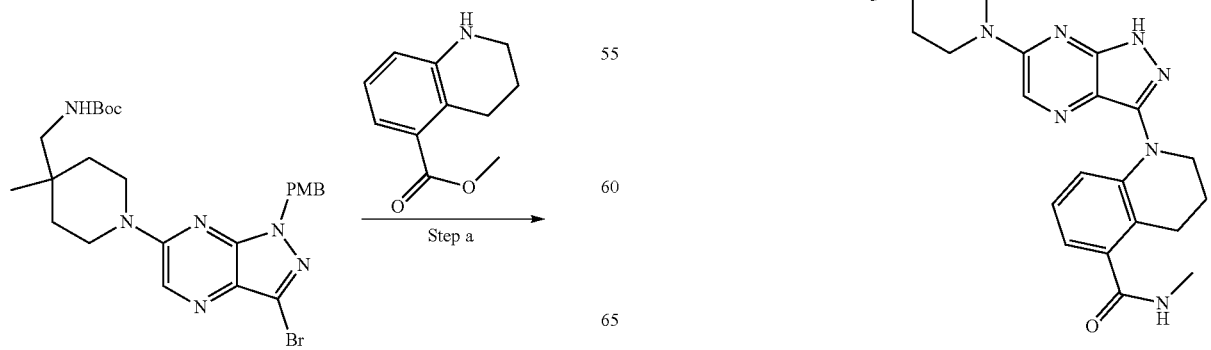

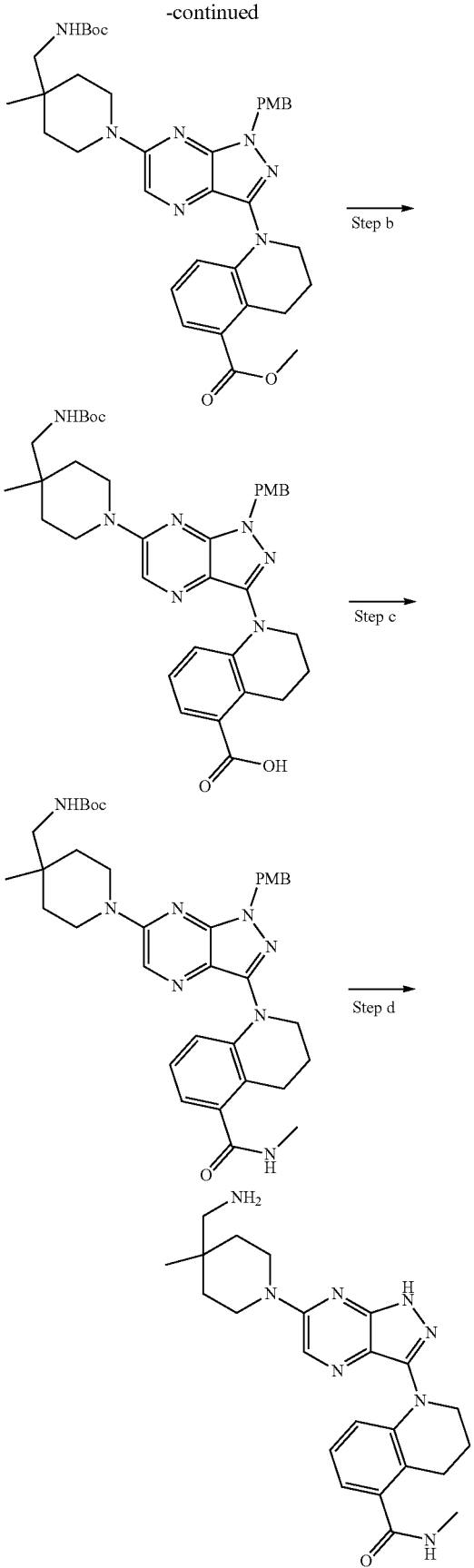

Step a: A solution of tert-butyl ((1-(3-bromo-1-(4-methoxybenzyl)-1H-pyrazolo[3,4-b]pyrazin-6-yl)-4-methylpiperidin-4-yl)methyl)carbamate (150.0 mg, 274.0 μmol), methyl 1,2,3,4-tetrahydroquinoline-5-carboxylate (52.3 mg, 274.0 μmol), RuPhos (25.5 mg, 54.8 umol), RuPhos-Pd-G4 (44.3 mg, 54.8 umol) and t-BuONa (52.6 mg, 548.0 umol) in dioxane (5.0 mL) under $N_2$ was stirred at 70° C. for 12 h. The reaction mixture was concentrated in vacuo to give crude product. The residue was purified by prep-TLC (petroleum ether:EtOAc=1:1) to give methyl 1-(6-(4-(((tert-butoxycarbonyl)amino)methyl)-4-methylpiperidin-1-yl)-1-(4-methoxybenzyl)-1H-pyrazolo[3,4-b]pyrazin-3-yl)-1,2,3,4-tetrahydroquinoline-5-carboxylate (150.0 mg, 83.7% yield) as yellow gum. LCMS m/z 656.2 (M+H)+.

Step b: To a solution of methyl 1-(6-(4-(((tert-butoxycarbonyl)amino)methyl)-4-methylpiperidin-1-yl)-1-(4-methoxybenzyl)-1H-pyrazolo[3,4-b]pyrazin-3-yl)-1,2,3,4-tetrahydroquinoline-5-carboxylate (150.0 mg, 228.0 μmol) in MeOH/$H_2O$ (3.0 mL/1.0 mL) was added KOH (38.3 mg, 684.0 umol) and stirred at 25° C. for 12 h. The reaction mixture was stirred at 50° C. for another 2 h. The reaction mixture was concentrated in vacuo to give 1-(6-(4-(((tert-butoxycarbonyl)amino)methyl)-4-methylpiperidin-1-yl)-1-(4-methoxybenzyl)-1H-pyrazolo[3,4-b]pyrazin-3-yl)-1,2,3,4-tetrahydroquinoline-5-carboxylic acid (180.0 mg, crude) as yellow gum. LCMS m/z 642.3 $(M+H)^+$.

Step c: A solution of 1-(6-(4-(((tert-butoxycarbonyl)amino)methyl)-4-methylpiperidin-1-yl)-1-(4-methoxybenzyl)-1H-pyrazolo[3,4-b]pyrazin-3-yl)-1,2,3,4-tetrahydroquinoline-5-carboxylic acid (180.0 mg, 280.0 μmol), methanamine hydrochloride (28.3 mg, 420.0 μmol), HATU (212.0 mg, 560.0 umol) and DIPEA (108.0 mg, 840.0 umol) in DMF (5.0 mL) was stirred at 40° C. for 12 h. On completion, the solution was added into $H_2O$ (10.0 mL) and then extracted with EtOAc (10.0 mL×2). The combined organic layers were washed with saturated $NH_4Cl$ (10.0 mL), dried over anhydrous $Na_2SO_4$, filtered and concentrated in vacuo to give tert-butyl ((1-(1-(4-methoxybenzyl)-3-(5-(methylcarbamoyl)-3,4-dihydroquinolin-1(2H)-yl)-1H-pyrazolo[3,4-b]pyrazin-6-yl)-4-methylpiperidin-4-yl)methyl)carbamate (200.0 mg, crude) as yellow gum. LCMS m/z 622.3 $(M+H)^+$.

Step d: A solution of tert-butyl ((1-(1-(4-methoxybenzyl)-3-(5-(methylcarbamoyl)-3,4-dihydroquinolin-1(2H)-yl)-1H-pyrazolo[3,4-b]pyrazin-6-yl)-4-methylpiperidin-4-yl)methyl)carbamate (200.0 mg, 305.0 μmol) in TFA/TfOH (3.0 mL/0.3 mL) was stirred at 25° C. for 12 h. On completion, the reaction mixture was concentrated in vacuo. The residue was diluted with MeOH (5.0 mL), and adjusted to pH=7 with $NH_3.H_2O$. The mixture was purified by prep-HPLC (HCl) to give 1-(6-(4-(Aminomethyl)-4-methylpiperidin-1-yl)-1H-pyrazolo[3,4-b]pyrazin-3-yl)-N-methyl-1,2,3,4-tetrahydroquinoline-5-carboxamide hydrochloride (24.2 mg, 16.9% yield) as orange solid. LCMS: calc. for $C_{23}H_{30}N_8O$: 434.3, found: $[M+H]^+$ 435.1. $^1$HNMR (400 MHz, MeOD $d_4$): δ 8.35 (s, 1H), 7.36 (s, J=8.0 Hz, 1H), 7.20-7.26 (m, 1H), 7.12 (d, J=8.0 Hz, 1H), 4.15-4.26 (m, 2H), 4.10-4.15 (m, 2H), 3.60-3.68 (m, 2H), 2.95 (s, 4H), 2.93 (s, 3H), 2.15-2.00 (m, 2H), 1.60-1.72 (m, 4H), 1.24 (s, 3H).

Synthesis of 1-(6-(4-(Aminomethyl)-4-methylpiperidin-1-yl)-1H-pyrazolo[3,4-b]pyrazin-3-yl)-N,N-dimethyl-1,2,3,4-tetrahydroquinoline-5-carboxamide, Compound 80

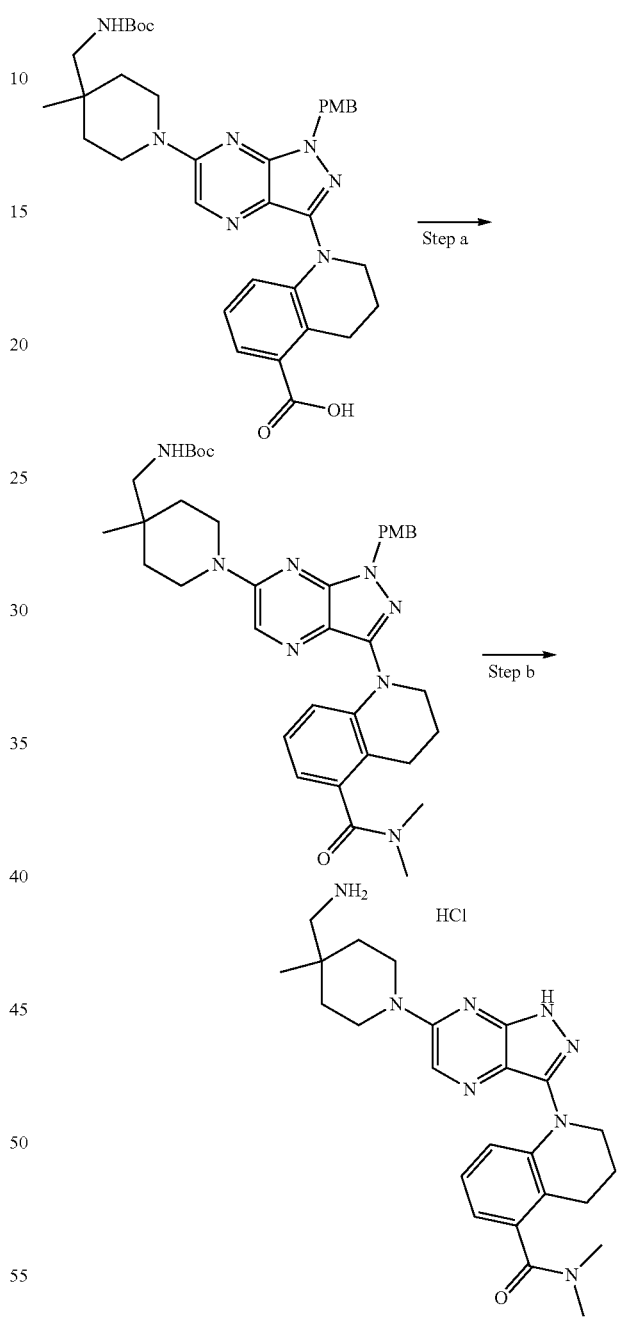

Step a: A solution of 1-(6-(4-(((tert-butoxycarbonyl)amino)methyl)-4-methylpiperidin-1-yl)-1-(4-methoxybenzyl)-1H-pyrazolo[3,4-b]pyrazin-3-yl)-1,2,3,4-tetrahydroquinoline-5-carboxylic acid (150.0 mg, 233.0 μmol, synthesized via Steps a-b of Compound 79), dimethylamine hydrochloride (28.4 mg, 349.0 μmol), HATU (177.0 mg, 466.0 umol) and DIPEA (90.1 mg, 699.0 umol) in DMF (5.0 mL) was stirred at 50° C. for 3 h. On completion, the reaction mixture was concentrated in vacuo to remove solvent. The residue was washed with water (5.0 mL), filtered and dried to give tert-butyl ((1-(3-(5-(dimethylcarbamoyl)-3,4-dihydroquinolin-1(2H)-yl)-1-(4-methoxybenzyl)-1H-pyrazolo[3,4-b]pyrazin-6-yl)-4-methylpiperidin-4-yl)methyl)carbamate (150.0 mg) as yellow solid. LCMS m/z 669.3 (M+H)⁺.

Step b: A solution of tert-butyl ((1-(3-(5-(dimethylcarbamoyl)-3,4-dihydroquinolin-1(2H)-yl)-1-(4-methoxybenzyl)-1H-pyrazolo[3,4-b]pyrazin-6-yl)-4-methylpiperidin-4-yl)methyl)carbamate (150.0 mg, 224.0 µmol) in TFA/TfOH (3.0 mL/0.3 mL) was stirred at 25° C. for 12 h. On completion, the reaction mixture was concentrated in vacuo. The residue was diluted with MeOH (5.0 mL), adjusted pH=7 with NH₃.H₂O and purified by prep-HPLC (HCl) to give 1-(6-(4-(Aminomethyl)-4-methylpiperidin-1-yl)-1H-pyrazolo[3,4-b]pyrazin-3-yl)-N,N-dimethyl-1,2,3,4-tetrahydroquinoline-5-carboxamide hydrochloride (20.7 mg, 19.1% yield) as orange solid. LCMS: calc. for $C_{24}H_{32}N_8O$: 448.3, found: [M+H]⁺ 449.2. ¹HNMR (400 MHz, Methanol_d₄): δ 8.39 (s, 1H), 7.35 (d, 1=8.0 Hz, 1H), 7.25-7.29 (m, 1H), 7.00 (d, J=8.0 Hz, 1H), 4.18-4.26 (m, 4H), 3.63-3.90 (m, 2H), 3.16 (s, 3H), 2.95 (s, 5H), 2.60-2.90 (m, 2H), 2.00-2.16 (m, 2H), 1.60-1.71 (m, 4H), 1.24 (s, 3H).

Synthesis of (4-(aminomethyl)-1-(3-(3,4-dihydro-1, 5-naphthyridin-1(2H)-yl)-1H-pyrazolo[3,4-b] pyrazin-6-yl)piperidin-4-yl)methanol dihydrochloride, Compound 82

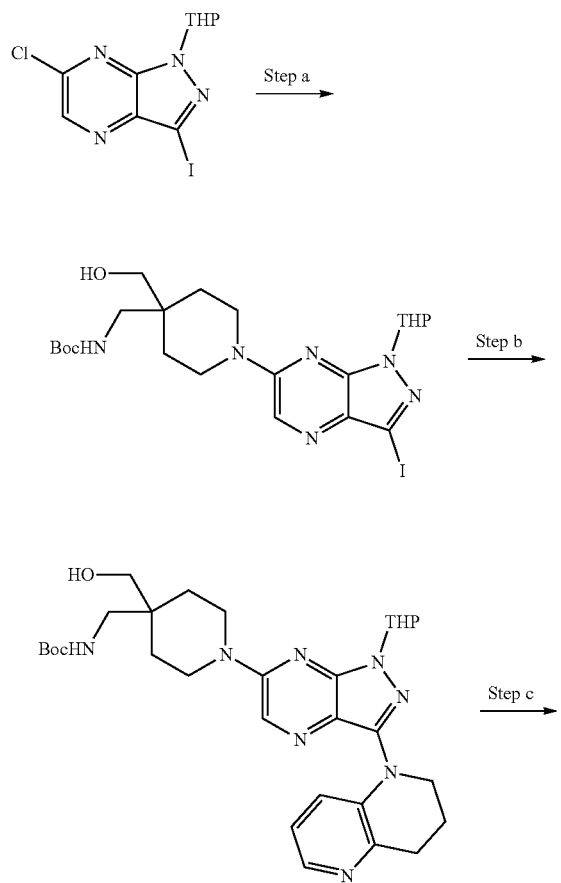

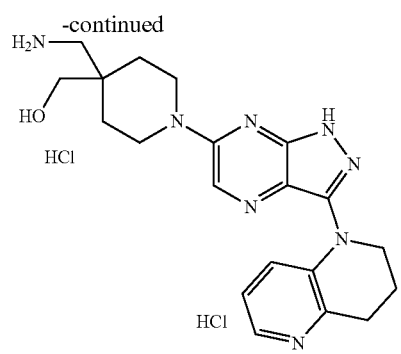

Step a: A mixture of 6-chloro-3-iodo-1-(tetrahydro-2H-pyran-2-yl)-1H-pyrazolo[3,4-b]pyrazine (300 mg, 822 µmol) and tert-butyl ((4-(hydroxymethyl)piperidin-4-yl) methyl)carbamate (220 mg, 904 µmol) in DIEA (10 mL) was stirred at 130° C. for 12 hours. The reaction mixture was concentrated under reduced pressure to give a residue, which was purified by column chromatography (Petroleum ether: Ethyl acetate=1:1~0:1) to afford the product of tert-butyl ((4-(hydroxymethyl)-1-(3-iodo-1-(tetrahydro-2H-pyran-2-yl)-1H-pyrazolo[3,4-b]pyrazin-6-yl)piperidin-4-yl)methyl) carbamate (340 mg, 70.6% yield) as a yellow solid.

Step b: A mixture of tert-butyl ((4-(hydroxymethyl)-1-(3-iodo-1-(tetrahydro-2H-pyran-2-yl)-1H-pyrazolo[3,4-b] pyrazin-6-yl)piperidin-4-yl)methyl)carbamate (290 mg, 506 µmol), 1,2,3,4-tetrahydro-1,5-naphthyridine (74.6 mg, 556 µmol), RuPhos (47 mg, 101 µmol), RuPhos-Pd-G4 (82.4 mg, 101 µmol) and Cs2CO3 (492 mg, 1.5 mmol) in dioxane (15 mL) was stirred at 70° C. for 12 hours under N2 atmosphere. The reaction mixture was concentrated under reduced pressure to give a residue, which was purified by column chromatography (Ethyl acetate: Methyl alcohol=10: 1-20:1) to afford the product of tert-butyl ((1-(3-(3,4-dihydro-1,5-naphthyridin-1(2H)-yl)-1-(tetrahydro-2H-pyran-2-yl)-1H-pyrazolo[3,4-b]pyrazin-6-yl)-4-(hydroxymethyl) piperidin-4-yl)methyl)carbamate (150 mg, crude) as a yellow solid.

Step c: A mixture of tert-butyl ((1-(3-(3,4-dihydro-1,5-naphthyridin-1(2H)-yl)-1-(tetrahydro-2H-pyran-2-yl)-1H-pyrazolo[3,4-b]pyrazin-6-yl)-4-(hydroxymethyl)piperidin-4-yl)methyl)carbamate (150 mg, 155 µmol) in 4M HCl/ MeOH (5 mL) was stirred at 20° C. for 2 hours. The reaction mixture was concentrated under reduced pressure to give a residue, which was purified by prep-HPLC (HCl) to afford the product of (4-(aminomethyl)-1-(3-(3,4-dihydro-1,5-naphthyridin-1(2H)-yl)-1H-pyrazolo[3,4-b]pyrazin-6-yl)piperidin-4-yl)methanol dihydrochloride (9.8 mg, 13.5% yield) as a orange solid.

Synthesis of (2R,4R)-1-(3-(3,4-dihydro-1,5-naphthyridin-1(2H)-yl)-1H-pyrazolo[3,4-b]pyrazin-6-yl)-2-methylpiperidin-4-ol, Compound 95

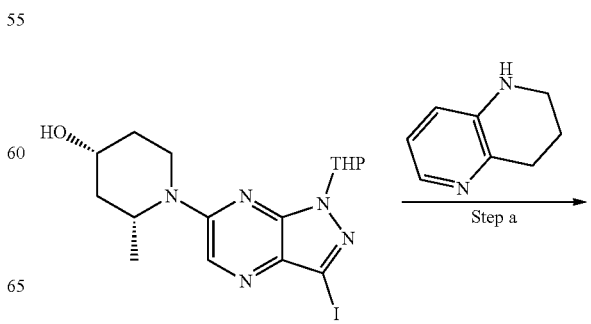

259
-continued

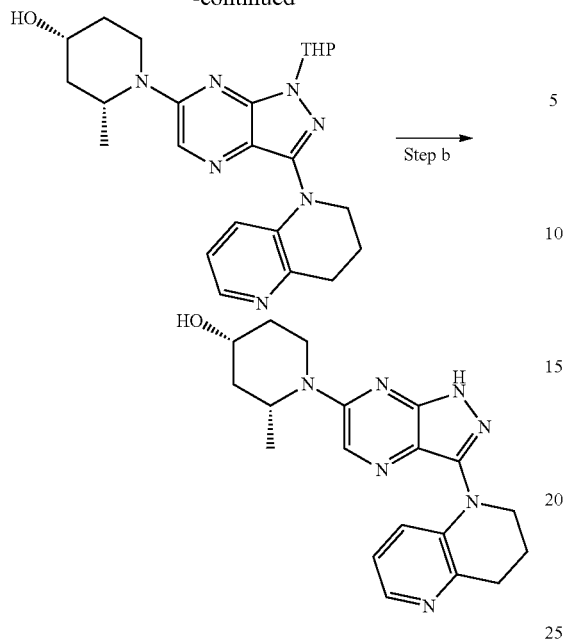

Step a: The compound (2R,4R)-1-(3-iodo-1-(tetrahydro-2H-pyran-2-yl)-1H-pyrazolo[3,4-b]pyrazin-6-yl)-2-methylpiperidin-4-ol (100 mg, 0.2 mmol), 1,2,3,4-tetrahydro-1,5-naphthyridine (36 mg, 0.3 mmol), RuPhos (10 mg, 0.02 mmol), RuPhos-Pd-G4 (19 mg, 0.02 mmol) and t-BuONa (64 mg, 0.6 mmol) were added in dioxane (10 mL). The mixture was evacuated and refilled 3 times using $N_2$ gas. The reaction mixture was stirred at 80° C. for 12 hours. The reaction was concentrated to give a residue which was purified by prep-TLC (Ethyl acetate) to afford the product of (2R,4R)-1-(3-(3,4-dihydro-1,5-naphthyridin-1(2H)-yl)-1-(tetrahydro-2H-pyran-2-yl)-1H-pyrazolo[3,4-b]pyrazin-6-yl)-2-methylpiperidin-4-ol (100 mg, 99% yield) as a yellow oil.

Step b: The compound (2R,4R)-1-(3-(3,4-dihydro-1,5-naphthyridin-1(2H)-yl)-1-(tetrahydro-2H-pyran-2-yl)-1H-pyrazolo[3,4-b]pyrazin-6-yl)-2-methylpiperidin-4-ol (50 mg, 0.1 mmol) was added to HCl/MeOH (5 mL, 2N). The reaction mixture was stirred at 25° C. for 12 hours. The mixture was then filtered and purified by prep-HPLC (HCl) to give the product of (2R,4R)-1-(3-(3,4-dihydro-1,5-naphthyridin-1(2H)-yl)-1H-pyrazolo[3,4-b]pyrazin-6-yl)-2-methylpiperidin-4-ol (6.3 mg, 15% yield) as a yellow solid.

Synthesis of (1-(3-(3,4-dihydro-1,5-naphthyridin-1(2H)-yl)-1H-pyrazolo[3,4-b]pyrazin-6-yl)-4-propylpiperidin-4-yl)methanamine dihydrochloride, Compound 97

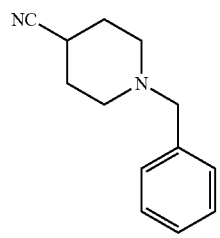

260
-continued

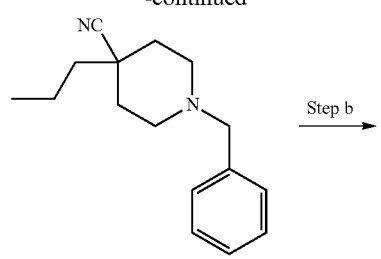

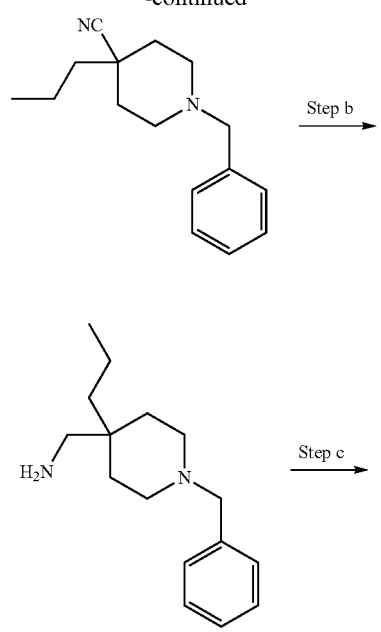

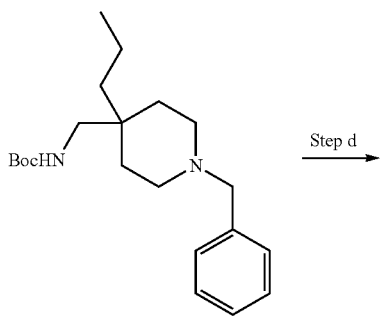

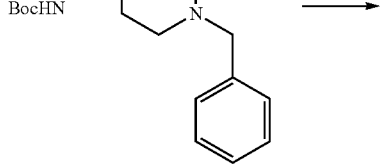

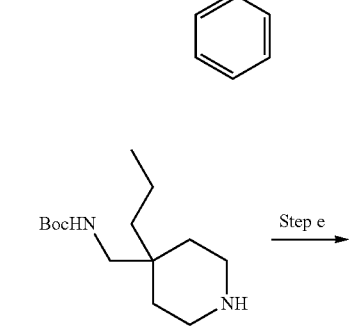

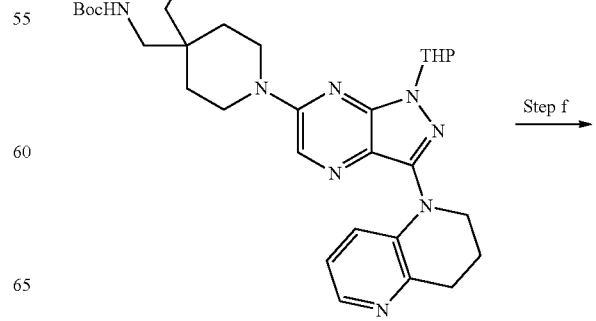

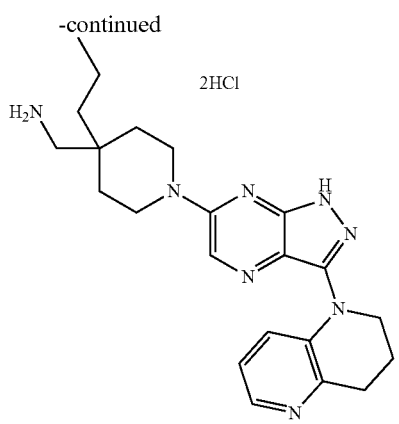

Step a: To a solution of 1-benzylpiperidine-4-carbonitrile (2 g, 10.0 mmol) in THF (20 ml) was added NaHMDS (1 M, 19.9 mmol, 19.9 mL) at −40° C., the mixture was stirred at −40° C. for 20 minutes. After n-PrI (2.48 g, 14.9 mmol) was added slowly at −40° C., the reaction was stirred at 20° C. for 2 hours. LCMS showed the product's MS was found. The reaction was quenched by sat. NH4Cl (40 mL), washed with brine (40 mL), extracted with EtOAc (50 mL×3). The combined organic layers were dried over anhydrous Na2SO4, filtered and concentrated to dryness. The resulting crude material was purified by silica gel chromatography (Petroleum ether/ethyl acetate=20:1) to give 1-benzyl-4-propylpiperidine-4-carbonitrile (2.10 g, 8.66 mmol, 87.1% yield) as a white oil.

Step b: To a solution of 1-benzyl-4-propylpiperidine-4-carbonitrile (1 g, 4.1 mmol) in THF (10.0 mL) was added LiAlH4 (312 mg, 8.2 mmol) and the reaction was stirred at 30° C. for 2 h. TLC (DCM/CH3OH=10/1) showed one new spot with higher polarity was found. The reaction was quenched with NaOH (2 N, 20 mL), filtered through a pad of celite and washed with EtOAc (50 mL). The filtrate was separated and the aqueous was extracted with EtOAc (50 mL×2). The organic layers were dried over anhydrous Na2SO4, filtered and concentrated in vacuum to give (1-benzyl-4-propylpiperidin-4-yl) methanamine (0.7 g, 69.2% yield) as a white solid.

Step c: A mixture of (1-benzyl-4-propylpiperidin-4-yl) methanamine (0.7 g, 2.8 mmol) in DCM (10.0 mL) added TEA (857 mg, 8.49 mmol) and tert-butyl ((4-methylpiperidin-4-yl)methyl)carbamate (925 mg, 4.24 mmol) stirred at 25° C. for 2 h. LCMS showed ~50% desired product formed. The reaction mixture was diluted with DCM (20 mL) and washed with water (10 mL×2). The organic layer was concentrated and purified by (Petroleum ether/ethyl acetate=10:1) to afford tert-butyl (((1-benzyl-4-propylpiperidin-4-yl) methyl) carbamate (760 mg, 2.19 mmol, 77.5% yield) as a yellow solid.

Step d: To solution of tert-butyl ((1-benzyl-4-ethylpiperidin-4-yl) methyl) carbamate (0.6 g, 1.8 mmol) in MeOH (10 mL) was added 10% Pd/C (10 mg) and stirred at 30° C. for 12 hours under H2 (15 psi). TLC (DCM/CH3OH=10/1) showed the starting material was consumed completely. Pd/C was removed off by filtration and the filtrate was concentrated under reduced pressure to give tert-butyl ((4-ethylpiperidin-4-yl) methyl) carbamate (349 mg, 1.44 mmol, 80.0% yield) as a white oil.

Step e: To a solution of 1-(6-chloro-1-(tetrahydro-2H-pyran-2-yl)-1H-pyrazolo[3,4-b]pyrazin-3-yl)-1,2,3,4-tetrahydro-1,5-naphthyridine (200 mg, 539 μmol) in DMSO (5 ml) was added DIEA (65.7 mg, 539 umol) and tert-butyl ((4-propylpiperidin-4-yl)methyl)carbamate (207 mg, 808 μmol), the mixture was stirred at 70° C. for 6 hours. TLC (Petroleum ether:EtOAc=1:3) showed most of the product formed. The reaction mixture was quenched by satd. NaCl (40 mL), extracted with EtOAc (50 mL×3). The combined organic layers were dried over anhydrous Na2SO4, filtered and concentrated to dryness. The resulting crude material was purified by silica gel chromatography (elution: Petroleum ether/ethyl acetate=1:1) to give tert-butyl ((1-(3-(3,4-dihydro-1,5-naphthyridin-1(2H)-yl)-1-(tetrahydro-2H-pyran-2-yl)-1H-pyrazolo[3,4-b]pyrazin-6-yl)-4-propylpiperidin-4-yl)methyl)carbamate (105 mg, 177 μmol, 33.0% yield) as a yellow oil.

Step f: To a solution of tert-butyl ((1-(3-(3,4-dihydro-1,5-naphthyridin-1(2H)-yl)-1-(tetrahydro-2H-pyran-2-yl)-1H-pyrazolo[3,4-b]pyrazin-6-yl)-4-propylpiperidin-4-yl)methyl)carbamate (100 mg, 169 μmol) in MeOH (5 ml) was added HCl/MeOH (2 mL, 4N)) at 0° C., the mixture was stirred at 30° C. for 6 hours. LCMS showed ~80% desired product formed. The reaction mixture was concentrated and the residue was purified by prep-HPLC (HCl) to afford the product of (1-(3-(3,4-dihydro-1,5-naphthyridin-1(2H)-yl)-1H-pyrazolo[3,4-b]pyrazin-6-yl)-4-propylpiperidin-4-yl) methanamine dihydrochloride (25.4 mg, 52.9 μmol, 2HCl salt, 31.3% yield) as a yellow solid.

Synthesis of (1-(3-(3,4-dihydro-1,5-naphthyridin-1(2H)-yl)-1H-pyrazolo[3,4-b]pyrazin-6-yl)-4-ethylpiperidin-4-yl)methanamine dihydrochloride, Compound 98

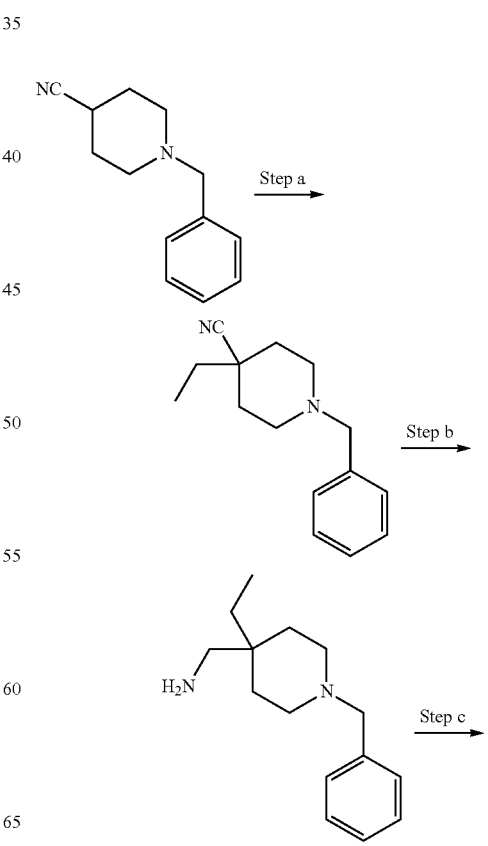

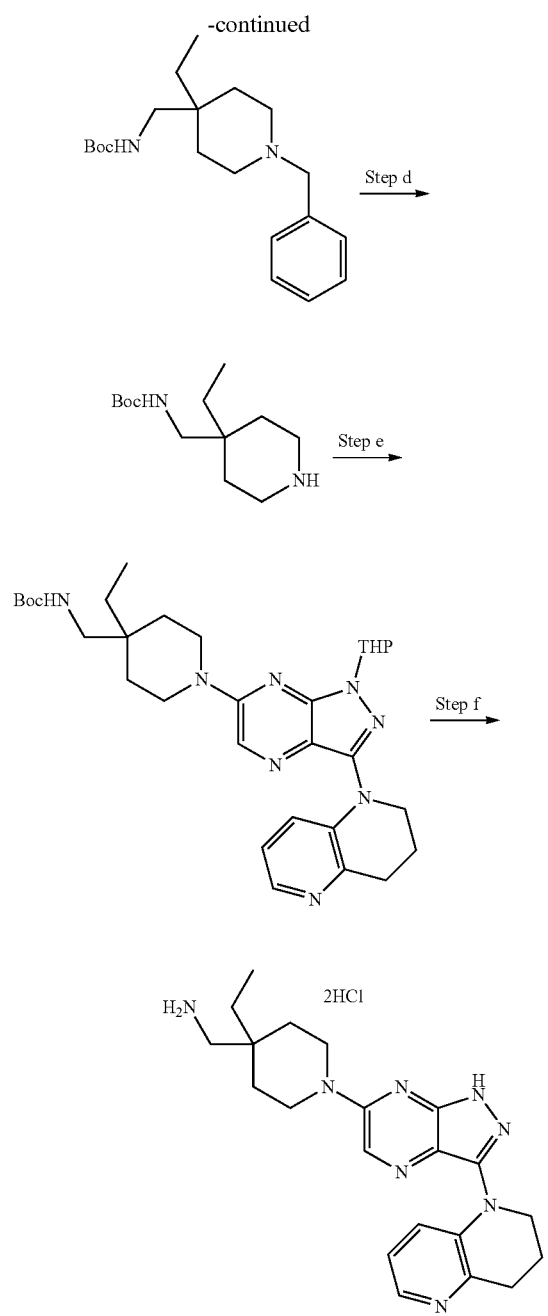

Step a: To a solution of 1-benzylpiperidine-4-carbonitrile (2.0 g, 9.98 mmol) in THF (20 ml) was added NaHMDS (1 M, 19.9 mmol, 19.9 mL) at −40° C., the mixture was stirred at −40° C. for 20 min. EtI (2.32 g, 14.9 mmol) was added slowly at −40° C., the reaction mixture was stirred at 20° C. for 2 hours. LCMS showed the product's MS was found. The reaction mixture was quenched by sat. NH4Cl (40 mL), washed with brine (40 mL), extracted with EtOAc (50 mL×3). The combined organic layers were dried over anhydrous Na2SO4, filtered and concentrated to dryness. The resulting crude material was purified by silica gel chromatography (Petroleum ether/ethyl acetate=20:1) to give 1-benzyl-4-ethylpiperidine-4-carbonitrile (2.10 g, 9.19 mmol, 92.5% yield) as a white oil.

Step b: To a solution of 1-benzyl-4-ethylpiperidine-4-carbonitrile (1 g, 4.37 mmol) in THF (10.0 mL) was added LiAlH4 (664 mg, 17.5 mmol) and the reaction was stirred at 30° C. for 2 h. TLC (DCM/CH3OH=10/1) showed one new spot with higher polarity was found. The reaction was quenched with NaOH (2 N, 40 mL), filtered through a pad of celite and washed with EtOAc (50 mL). The filtrate was separated and the aqueous was extracted with EtOAc (50 mL×2). The organic layers were dried over anhydrous Na2SO4, filtered and concentrated in vacuum to give (1-benzyl-4-ethylpiperidin-4-yl) methanamine (0.8 g, 3.44 mmol, 79.2% yield) as a white solid.

Step c: A mixture of (1-benzyl-4-ethylpiperidin-4-yl) methanamine (0.9 g, 3.87 mmol), tert-butyl ((4-methylpiperidin-4-yl)methyl)carbamate (1.26 g, 5.80 mmol) and TEA (783 mg, 7.74 mmol) in DCM (10.0 mL) was stirred at 26° C. for 2 h. LCMS showed 90% desired product formed. The reaction mixture was diluted with DCM (20 mL) and washed with water (10 mL×2). The organic layer was concentrated and purified by (Petroleum ether/ethyl acetate=10:1) to afford tert-butyl ((1-benzyl-4-ethylpiperidin-4-yl)methyl)carbamate (1.26 g, 3.78 mmol, 92.5% yield) as a yellow solid.

Step d: To solution of tert-butyl ((1-benzyl-4-ethylpiperidin-4-yl) methyl) carbamate (1.0 g, 3.00 mmol) in MeOH (10 mL) was added 10% Pd/C (10 mg) and stirred at 30° C. for 12 hours under H2 (15 psi). TLC (DCM/CH3OH=10/1) showed the starting material was consumed completely. Pd/C was removed and the reaction mixture was concentrated under reduced pressure to give tert-butyl ((4-ethylpiperidin-4-yl) methyl) carbamate (0.6 g, 2.47 mmol, 82.5% yield).

Step e: To a solution of tert-butyl ((4-ethylpiperidin-4-yl) methyl)carbamate (150 mg, 618 μmol) in DMSO (5 ml) was added DIEA (150 mg, 1.23 mmol) and 1-(6-chloro-1-(tetrahydro-2H-pyran-2-yl)-1H-pyrazolo[3,4-b]pyrazin-3-yl)-1,2,3,4-tetrahydro-1,5-naphthyridine (206 mg, 556 μmol), the mixture was stirred at 70° C. for 2 hours. LCMS showed 59% product formed. The reaction mixture was quenched by sat. NaCl (40 mL), extracted with EtOAc (50 mL×3). The combined organic layers were dried over anhydrous Na2SO4, filtered and concentrated to dryness. The resulting crude material was purified by silica gel chromatography (elution: Petroleum ether/ethyl acetate=1:1) to give tert-butyl((1-(3-(3,4-dihydro-1,5-naphthyridin-1(2H)-yl)-1-(tetrahydro-2H-pyran-2-yl)-1H-pyrazolo[3,4-b]pyrazin-6-yl)-4-ethylpiperidin-4-yl)methyl)carbamate (110 mg, 190 μmol, 30.8% yield) as a yellow oil.

Step f: To a solution of tert-butyl ((1-(3-(3,4-dihydro-1,5-naphthyridin-1(2H)-yl)-1-(tetrahydro-2H-pyran-2-yl)-1H-pyrazolo[3,4-b]pyrazin-6-yl)-4-ethylpiperidin-4-yl) methyl)carbamate (110 mg, 190 μmol) in MeOH (5 ml) was added HCl/MeOH (2.0 mL, 4N)) at 0° C., the mixture was stirred at 30° C. for 6 hours. LCMS showed ~90% the desired product formed. The reaction mixture was concentrated and the residue was purified by prep-HPLC (HCl) to afford the product of (1-(3-(3,4-dihydro-1,5-naphthyridin-1 (2H)-yl)-1H-pyrazolo[3,4-b]pyrazin-6-yl)-4-ethylpiperidin-4-yl)methanamine dihydrochloride (30.8 mg, 66.1 μmol, 2 HCl salt, 34.8% yield) as a yellow solid.

Synthesis of (1-(6-(4-(Aminomethyl)-4-methylpiperidin-1-yl)-1H-pyrazolo[3,4-b]pyrazin-3-yl)-1,2,3,4-tetrahydroquinolin-4-yl)methanol, Compound 99

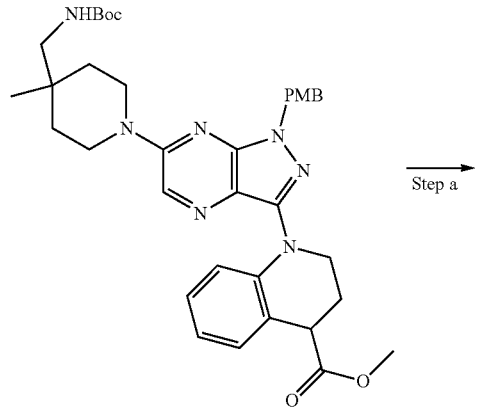

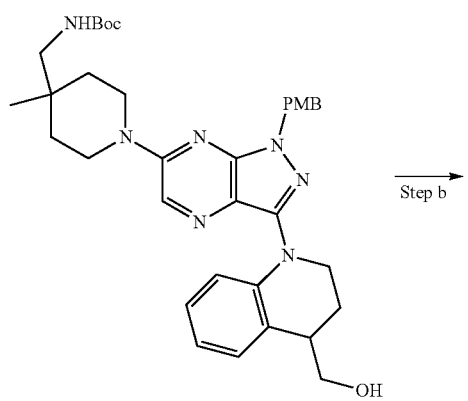

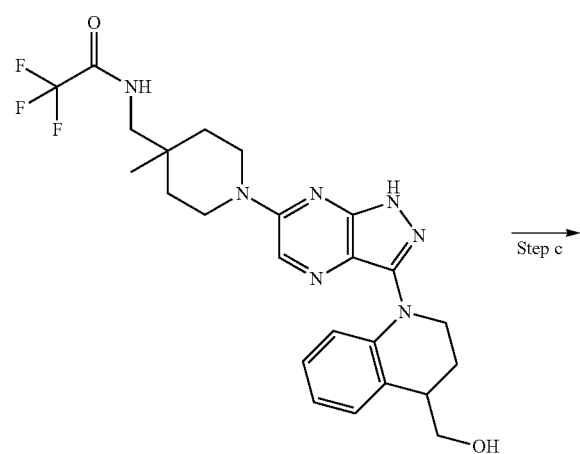

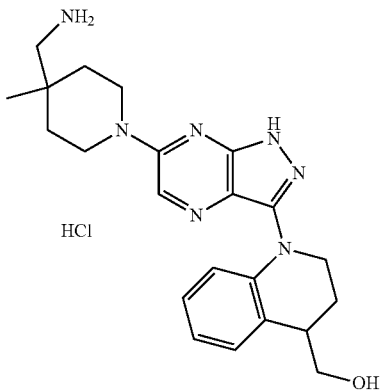

Step a: To a solution of methyl 1-(6-(4-(((tert-butoxycarbonyl)amino)methyl)-4-methylpiperidin-1-yl)-1-(4-methoxybenzyl)-1H-pyrazolo[3,4-b]pyrazin-3-yl)-1,2,3,4-tetrahydroquinoline-4-carboxylate (150.0 mg, 228.0 μmol, synthesized as described for Compound 33) in THF (5.0 mL) at 0° C. was added LAH (26.6 mg, 684.0 umol). The reaction mixture was stirred at 0° C. for 1 h. On completion, the reaction mixture was poured into $H_2O$ (10.0 mL) and then extracted with EtOAc (10.0 mL×2). The combined organic layers were washed with saturated NaCl (20.0 mL), dried over anhydrous $Na_2SO_4$, filtered and concentrated in vacuo to give crude product as yellow gum. The residue was purified by flash silica gel chromatography (4 g, Ethyl acetate in Petroleum ether from 0% to 40%) to give tert-butyl ((1-(3-(4-(hydroxymethyl)-3,4-dihydroquinolin-1(2H)-yl)-1-(4-methoxybenzyl)-1H-pyrazolo[3,4-b]pyrazin-6-yl)-4-methylpiperidin-4-yl)methyl)carbamate (70.0 mg, 48.9% yield) as orange oil.

Step b: A solution of tert-butyl ((1-(3-(4-(hydroxymethyl)-3,4-dihydroquinolin-1(2H)-yl)-1-(4-methoxybenzyl)-1H-pyrazolo[3,4-b]pyrazin-6-yl)-4-methylpiperidin-4-yl)methyl)carbamate (70.0 mg, 111.0 μmol) in TFA/TfOH (2.0 mL/0.2 mL) was stirred at 25° C. for 1 h. On completion, the reaction mixture was concentrated in vacuo to give 2,2,2-trifluoro-N-((1-(3-(4-(hydroxymethyl)-3,4-dihydroquinolin-1(2H)-yl)-1H-pyrazolo[3,4-b]pyrazin-6-yl)-4-methylpiperidin-4-yl)methyl)acetamide (100.0 mg) as brown gum.

Step c: A solution of 2,2,2-trifluoro-N-((1-(3-(4-(hydroxymethyl)-3,4-dihydroquinolin-1(2H)-yl)-1H-pyrazolo[3,4-b]pyrazin-6-yl)-4-methylpiperidin-4-yl)methyl)acetamide (100.0 mg, 198.0 μmol) and NaOH (15.8 mg, 396.0 umol) in MeOH (3.0 mL) was stirred at 25° C. for 12 h. The reaction mixture was purified by prep-HPLC (HCl) to give (1-(6-(4-(Aminomethyl)-4-methylpiperidin-1-yl)-1H-pyrazolo[3,4-b]pyrazin-3-yl)-1,2,3,4-tetrahydroquinolin-4-yl)methanol hydrochloride (41.5 mg, 47.2% yield) as orange solid.

Synthesis of 1-(6-(4-(Aminomethyl)-4-methylpiperidin-1-yl)-1H-pyrazolo[3,4-b]pyrazin-3-yl)-N-methyl-1,2,3,4-tetrahydroquinoline-4-carboxamide, Compound 100

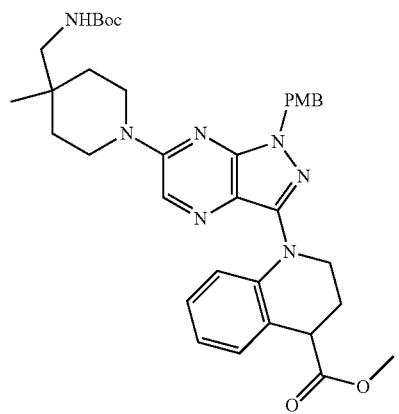

Step a →

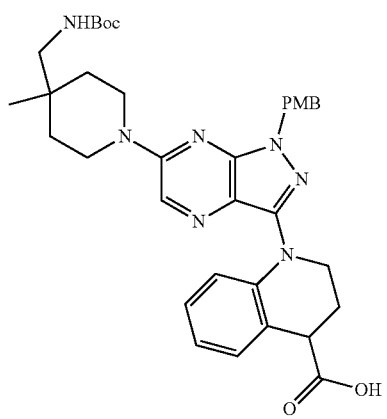

Step b →

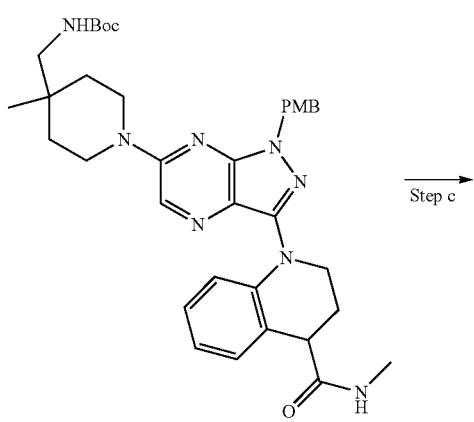

Step c →

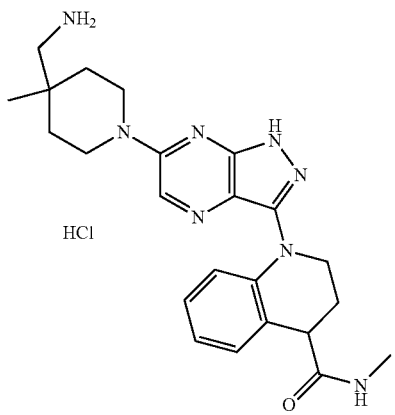

Step a: A solution of methyl 1-(6-(4-(((tert-butoxycarbonyl)amino)methyl)-4-methylpiperidin-1-yl)-1-(4-methoxybenzyl)-1H-pyrazolo[3,4-b]pyrazin-3-yl)-1,2,3,4-tetrahydroquinoline-4-carboxylate (180.0 mg, 274.0 μmol, synthesized using the method described for Compound 33, using methyl 1,2,3,4-tetrahydroquinoline-4-carboxylate in Step d) and KOH (46.1 mg, 822.0 umol) in MeOH/H₂O (3.0 mL/5 mL) was stirred at 40° C. for 12 h. The reaction mixture was concentrated in vacuum to give crude product. The residue was purified by flash silica gel chromatography (4 g, MeOH in DCM from 0% to 5%) to give 1-(6-(4-(((tert-butoxycarbonyl)amino)methyl)-4-methylpiperidin-1-yl)-1-(4-methoxybenzyl)-1H-pyrazolo[3,4-b]pyrazin-3-yl)-1,2,3,4-tetrahydroquinoline-4-carboxylic acid (150.0 mg, 85.7% yield) as yellow oil.

Step b: A solution of 1-(6-(4-(((tert-butoxycarbonyl)amino)methyl)-4-methylpiperidin-1-yl)-1-(4-methoxybenzyl)-1H-pyrazolo[3,4-b]pyrazin-3-yl)-1,2,3,4-tetrahydroquinoline-4-carboxylic acid (150.0 mg, 233.0 μmol), methanamine in THF (233.0 uL, 466.0 μmol, 2.0 M), HATU (177.0 mg, 466.0 umol) and DIEA (90.1 mg, 699.0 umol) in DMF (5.0 mL) was stirred at 40° C. for 2 h. The solution was added into H₂O (10.0 mL) and then extracted with EtOAc (10.0 mL×2). The combined organic layers were washed with saturated NaCl (20.0 mL), dried over anhydrous Na₂SO₄, filtered and concentrated in vacuo to give tert-butyl ((1-(1-(4-methoxybenzyl)-3-(4-(methylcarbamoyl)-3,4-dihydroquinolin-1(2H)-yl)-1H-pyrazolo[3,4-b]pyrazin-6-yl)-4-methylpiperidin-4-yl)methyl)carbamate (200.0 mg, crude) as orange gum.

Step c: A solution of tert-butyl ((1-(1-(4-methoxybenzyl)-3-(4-(methylcarbamoyl)-3,4-dihydroquinolin-1(2H)-yl)-1H-pyrazolo[3,4-b]pyrazin-6-yl)-4-methylpiperidin-4-yl)methyl)carbamate (200.0 mg, 305.0 μmol) in TFA/TfOH (3.0 mL/0.3 mL) was stirred at 25° C. for 1 h. The reaction mixture was concentrated in vacuo. The residue was diluted with MeOH (5.0 mL), adjusted to pH=9 with NH₃.H₂O, and purified by prep-HPLC (HCl). 1-(6-(4-(Aminomethyl)-4-methylpiperidin-1-yl)-1H-pyrazolo[3,4-b]pyrazin-3-yl)-N-methyl-1,2,3,4-tetrahydroquinoline-4-carboxamide hydrochloride (46.5 mg, 32.5% yield) was obtained as orange solid.

Synthesis of (1-(3-(3,4-dihydro-1,5-naphthyridin-1 (2H)-yl)-1H-pyrazolo[3,4-b]pyrazin-6-yl)-4-methoxypiperidin-4-yl)methanamine, Compound 101

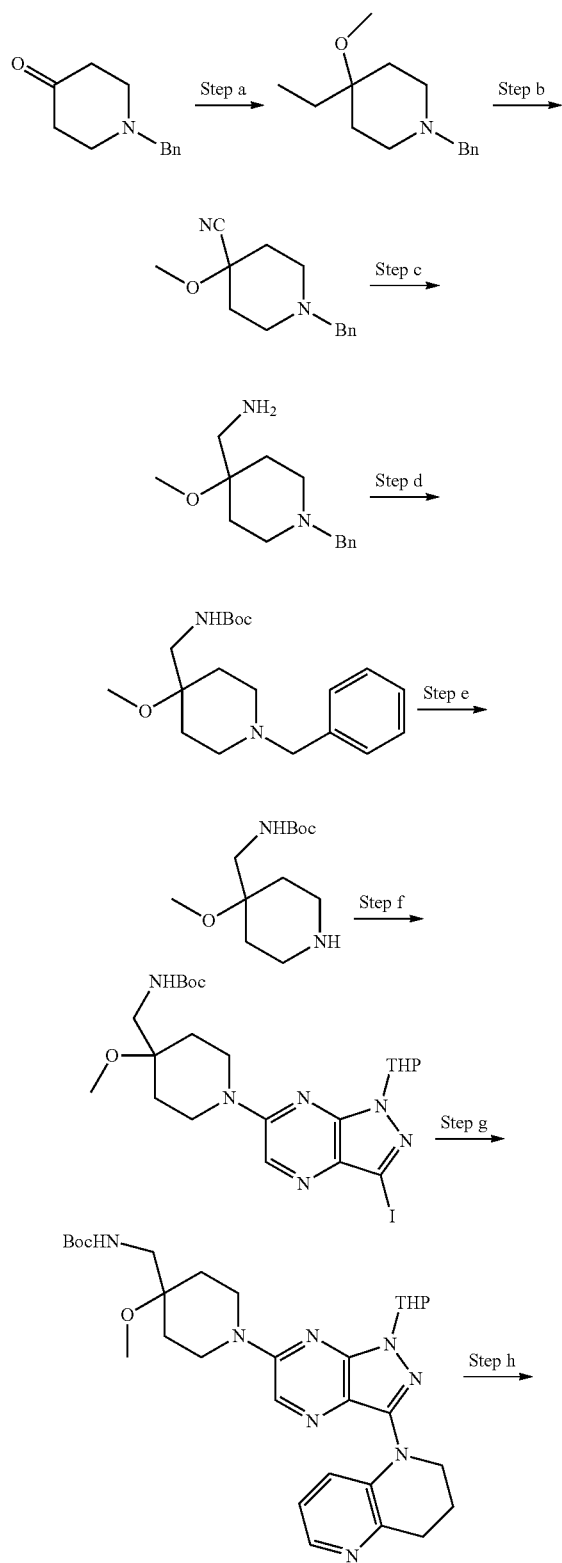

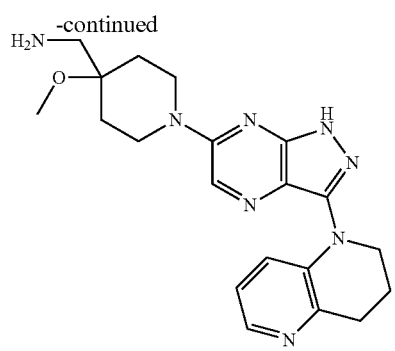

Step a: To a solution of 1-benzylpiperidin-4-one (10.0 g, 52.8 mmol) in MeOH (100.0 mL) at 0° C. was added AcCl (6.2 g, 79.1 mmol) slowly and the reaction was stirred at 0° C. for 2 h. LCMS showed one main peak with desired MS was found. The reaction was diluted with EtOAc (200.0 mL), washed with saturated NaHCO3 (100.0 mL×2) and brine (100.0 mL). The organic layer was dried over anhydrous Na2SO4, filtered and concentrated in vacuum. The residue was purified by silica gel chromatography (Petroleum ether/EtOAc=2/1) to give 1-benzyl-4,4-dimethoxypiperidine (10.8 g, 87.0% yield) as a colorless oil.

Step b: To a solution of 1-benzyl-4,4-dimethoxypiperidine (5.00 g, 21.2 mmol) and TMSCN (3.15 g, 31.8 mmol) in DCM (50.0 mL) was added ZnI2 (0.66 g, 2.2 mmol) at 0° C., and the reaction was stirred at 25° C. for 12 h. LCMS showed main the starting material remained. Another batch of ZnI2 (9.44 g, 29.6 mmol) was added into reaction and the reaction was stirred at 25° C. for 12 h. TLC showed the starting material was consumed completely. The solid was filtered off and the cake was washed with DCM (100.0 mL). The filtrate was washed with saturated NaHCO$_3$ (50.0 mL×2). The organic layer was dried over anhydrous Na2SO4, filtered and evaporated in vacuum to give 1-benzyl-4-methoxypiperidine-4-carbonitrile (4.30 g, 88.1% yield) as a golden oil.

Step c: To a solution of 1-benzyl-4-methoxypiperidine-4-carbonitrile (1.00 g, 4.34 mmol) in THF (20.0 mL) was added LAH (247.0 mg, 6.51 mmol) and the reaction was stirred at 30° C. for 2 h. LCMS showed the desired product formed. The reaction was quenched with NaOH (10 N, 4.0 mL), filtered through celite and washed with EtOAc (50.0 mL). The filtrate was concentrated in vacuum to give (1-benzyl-4-methoxypiperidin-4-yl)methanamine (1.05 g, crude) as a golden oil.

Step d: To a solution of (1-benzyl-4-methoxypiperidin-4-yl)methanamine (1.05 g, 4.48 mmol) in DCM (20.0 mL) was added Boc2O (1.95 g, 8.96 mmol) and the reaction was stirred at 20° C. for 2 h. LCMS showed the desired product formed. The reaction mixture was concentrated in vacuum. The residue was purified by silica gel chromatography (Petroleum ether/EtOAc=1/1) to give tert-butyl ((1-benzyl-4-methoxypiperidin-4-yl)methyl)carbamate (1.25 g, 83.8% yield) as a golden oil.

Step e: A mixture of tert-butyl ((1-benzyl-4-methoxypiperidin-4-yl)methyl)carbamate (1.2 g, 3.58 mmol) and Pd/C (300.0 mg, 10%) in MeOH (20.0 mL) was hydrogenated under H2 (15 psi) at 20° C. for 12 h. TLC (Petroleum ether/EtOAc=1:1) showed one new spot with larger polarity was found. The reaction mixture was filtered through celite and washed with MeOH (20.0 mL). The filtrate was concentrated in vacuum to afford tert-butyl ((4-methoxypiperidin-4-yl)methyl)carbamate (800.0 mg, 91.5% yield) as a colorless oil.

Step f: A mixture of tert-butyl ((4-methoxypiperidin-4-yl)methyl)carbamate (200.0 mg, 822.0 μmol), 6-chloro-3-iodo- 1-(tetrahydro-2H-pyran-2-yl)-1H-pyrazolo[3,4-b]pyrazine (250.0 mg, 685.0 μmol) and TEA (137.0 mg, 1.36 mmol) in NMP (10.0 mL) was stirred at 110° C. for 2 hours. TLC (Petroleum ether/EtOAc=2/1, Rf=0.7) showed the reaction worked completely and one new spot with larger polarity was found. The reaction mixture was diluted with EtOAc (50.0 mL), washed with water (50.0 mL×3). The organic layer was dried over anhydrous Na2SO4, filtered and concentrated in vacuum. The residue was purified by silica gel chromatography (Petroleum ether/EtOAc=2/1) to afford tert-butyl ((1-(3-iodo-1-(tetrahydro-2H-pyran-2-yl)-1H-pyrazolo[3,4-b]pyrazin-6-yl)-4-methoxypiperidin-4-yl)methyl)carbamate (380.0 mg, 96.9% yield) as a light yellow solid.

Step g: A mixture of tert-butyl ((1-(3-iodo-1-(tetrahydro-2H-pyran-2-yl)-1H-pyrazolo[3,4-b]pyrazin-6-yl)-4-methoxypiperidin-4-yl)methyl)carbamate (150.0 mg, 262.0 μmol), 1,2,3,4-tetrahydro-1,5-naphthyridine (52.7 mg, 393.0 μmol), t-BuONa (50.3 mg, 524.0 umol), RuPhos (24.4 mg, 52.4 umol) and RuPhos-Pd-G4 (22.2 mg, 26.2 umol) in dioxane (5.0 mL) was stirred at 90° C. for 14 h under N2. LCMS showed 57% of peak with the desired MS was found. This reaction was poured into water (50.0 mL) and extracted with EtOAc (50.0 mL×3). The combined organic layers were dried over anhydrous Na2SO4, filtered and concentrated in vacuum. The residue was purified by silica gel chromatography (Petroleum ether/EtOAc=1/1 to 1/3) to afford tert-butyl ((1-(3-(3,4-dihydro-1,5-naphthyridin-1(2H)-yl)-1-(tetrahydro-2H-pyran-2-yl)-1H-pyrazolo[3,4-b]pyrazin-6-yl)-4-methoxypiperidin-4-yl)methyl)carbamate (120.0 mg, 79.4% yield) as a yellow solid.

Step h: A solution of tert-butyl ((1-(3-(3,4-dihydro-1,5-naphthyridin-1(2H)-yl)-1-(tetrahydro-2H-pyran-2-yl)-1H-pyrazolo[3,4-b]pyrazin-6-yl)-4-methoxypiperidin-4-yl)methyl)carbamate (120.0 mg, 207.0 μmol) in TFA (5.0 mL) was stirred at 20° C. for 12 h. LCMS showed main peak with the desired MS was found. The reaction mixture was evaporated in vacuum. The residue was diluted with MeOH (5.0 mL), basified with NH3.H2O to pH=9 and purified by prep-HPLC (NH3.H2O) to afford (1-(3-(3,4-dihydro-1,5-naphthyridin-1(2H)-yl)-1H-pyrazolo[3,4-b]pyrazin-6-yl)-4-methoxypiperidin-4-yl)methanamine (41.5 mg, 50.8% yield) as a yellow solid.

Synthesis of (S)-tert-butyl ((1-(3-(4-ethyl-3,4-dihydroquinolin-1(2H)-yl)-1H-pyrazolo[3,4-b]pyrazin-6-yl)-4-methylpiperidin-4-yl)methyl)carbamate, Compound 102, and (R)-tert-butyl ((1-(3-(4-ethyl-3,4-dihydroquinolin-1(2H)-yl)-1H-pyrazolo[3,4-b]pyrazin-6-yl)-4-methylpiperidin-4-yl)methyl)carbamate, Compound 103

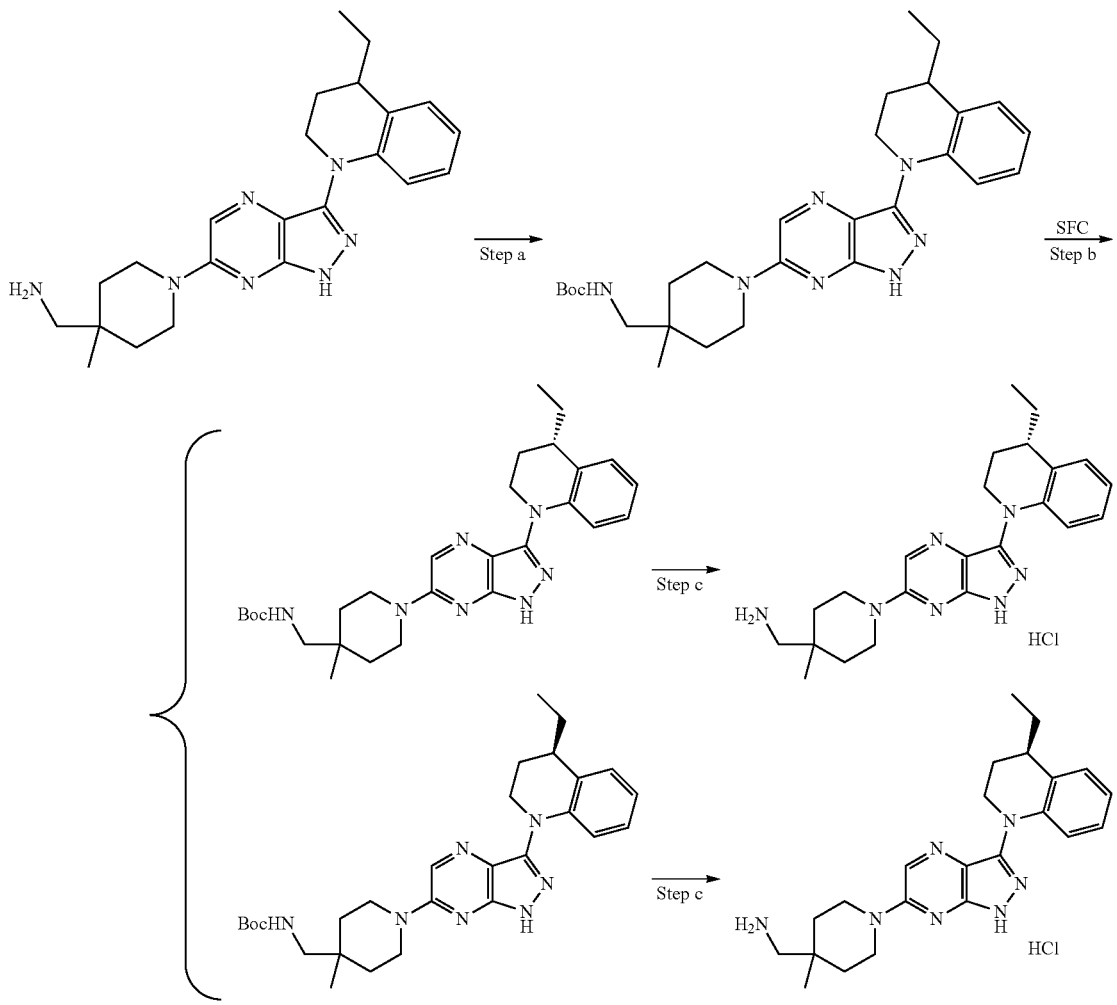

Step a: To a solution of (1-(3-(4-ethyl-3,4-dihydroquinolin-1(2H)-yl)-1H-pyrazolo[3,4-b]pyrazin-6-yl)-4-methylpiperidin-4-yl)methanamine (80.0 mg, 197.0 μmol, synthesized as described for Compound 33) and (Boc)$_2$O (51.5 mg, 236.0 umol) in DCM (10.0 mL) was added TEA (39.8 mg, 394.0 umol) and the reaction mixture was stirred at 25° C. for 12 hours. The reaction mixture was concentrated under reduced pressure. The residue was purified by column chromatography (Petroleum ether/Ethyl acetate=100:0 to 100:50). The product tert-butyl ((1-(3-(4-ethyl-3,4-dihydroquinolin-1(2H)-yl)-1H-pyrazolo[3,4-b]pyrazin-6-yl)-4-methylpiperidin-4-yl)methyl)carbamate (90.0 mg, 90.3% yield) was obtained as a yellow solid.

Step b: Tert-butyl ((1-(3-(4-ethyl-3,4-dihydroquinolin-1(2H)-yl)-1H-pyrazolo[3,4-b]pyrazin-6-yl)-4-methylpiperidin-4-yl)methyl)carbamate (90.0 mg, 177.0 μmol) was separated by chiral SFC (Column: Chiralcel OJ-250×30 mm i.D., 5 um Mobile phase: A: CO$_2$ B: ethanol (0.1% NH$_3$—H$_2$O) Gradient: 30% B, Flow rate: 50 mL/min Column temp: 40° C.). The product of (S)-tert-butyl ((1-(3-(4-ethyl-3,4-dihydroquinolin-1(2H)-yl)-1H-pyrazolo[3,4-b]pyrazin-6-yl)-4-methylpiperidin-4-yl)methyl)carbamate (45.0 mg) was obtained as a yellow solid. The product of (R)-tert-butyl ((1-(3-(4-ethyl-3,4-dihydroquinolin-1(2H)-yl)-1H-pyrazolo[3,4-b]pyrazin-6-yl)-4-methylpiperidin-4-yl)methyl)carbamate (55.0 mg) was obtained as a yellow solid. The absolute configuration was arbitrarily assigned.

Step c: A solution of (S)-tert-butyl ((1-(3-(4-ethyl-3,4-dihydroquinolin-1(2H)-yl)-1H-pyrazolo[3,4-b]pyrazin-6-yl)-4-methylpiperidin-4-yl)methyl)carbamate (45.0 mg, 88.9 μmol) in HCl (2.0 mL, 4.0 N) was stirred at 25° C. for 1 hour. The reaction mixture was concentrated under reduced pressure to give rel-(S)-(1-(3-(4-ethyl-3,4-dihydroquinolin-1(2H)-yl)-1H-pyrazolo[3,4-b]pyrazin-6-yl)-4-methylpiperidin-4-yl)methanamine hydrochloride (35.0 mg, 89.2% yield) was obtained as a yellow solid. LCMS: calc. for C$_{23}$H$_{31}$N$_7$: 405.3, found: [M+H]+ 406.0. ee: 100%. $^1$HNMR (400 MHz, Methanol_d$_4$): δ 8.25 (s, 1H), 7.18-7.21 (m, 1H), 6.95-7.03 (m, 2H), 6.86-6.90 (m, 1H), 4.16-4.21 (m, 2H), 3.93-4.06 (m, 2H), 3.54-3.62 (m, 2H), 2.93 (s, 2H), 2.78-2.83 (m, 1H), 2.11-2.23 (m, 1H), 1.97-2.06 (m, 2H), 1.83-1.90 (m, 1H), 1.63-1.67 (m, 4H), 1.23 (s, 3H), 1.05 (t, J=7.2 Hz, 3H).

Step c was repeated for (R)-tert-butyl ((1-(3-(4-ethyl-3,4-dihydroquinolin-1(2H)-yl)-1H-pyrazolo[3,4-b]pyrazin-6-yl)-4-methylpiperidin-4-yl)methyl)carbamate to give rel-(R)-(1-(3-(4-ethyl-3,4-dihydroquinolin-1(2H)-yl)-1H-pyrazolo[3,4-b]pyrazin-6-yl)-4-methylpiperidin-4-yl)methanamine hydrochloride (46.0 mg, 96.4% yield) was obtained as a yellow solid. LCMS: calc. for C23H31N7: 405.3, found: [M+H]+ 406.0. ee: 93%. $^1$HNMR (400 MHz, Methanol_d$_4$): δ 8.23 (s, 1H), 7.16-7.19 (m, 1H), 6.96-7.00 (m, 1H), 6.90-6.93 (m, 1H), 6.82-6.86 (m, 1H), 4.16-4.20 (m, 2H), 3.92-4.00 (m, 2H), 3.53-3.61 (m, 2H), 2.93 (s, 2H), 2.78-2.82 (m, 1H), 2.12-2.20 (m, 1H), 1.96-2.06 (m, 2H), 1.83-1.90 (m, 1H), 1.63-1.67 (m, 4H), 1.23 (s, 3H), 1.05 (t, J=7.2 Hz, 3H).

Synthesis of ((2R,4S)-1-(3-(3,4-dihydro-1,5-naphthyridin-1(2H)-yl)-1H-pyrazolo[3,4-b]pyrazin-6-yl)-2-methylpiperidin-4-yl)methanamine and ((2R,4R)-1-(3-(3,4-dihydro-1,5-naphthyridin-1(2H)-yl)-1H-pyrazolo[3,4-b]pyrazin-6-yl)-2-methylpiperidin-4-yl)methanamine, Compound 104 and Compound 109

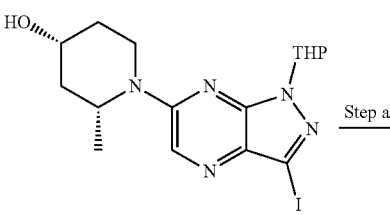

Step a

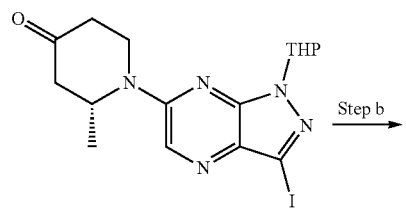

Step b

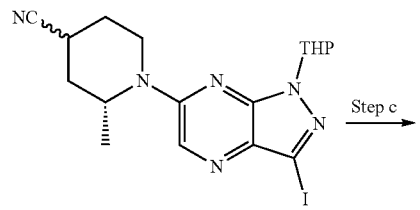

Step c

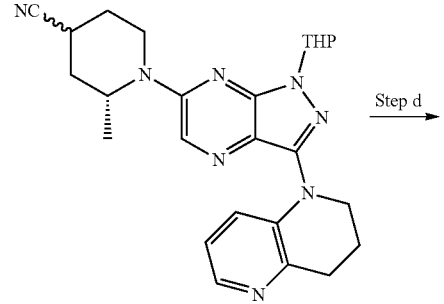

Step d

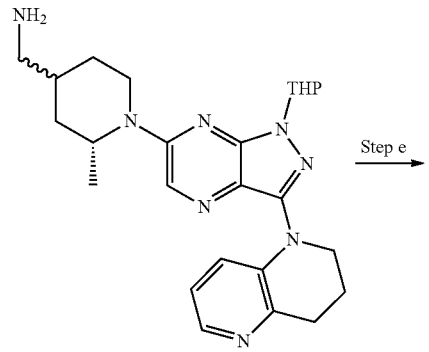

Step e

-continued

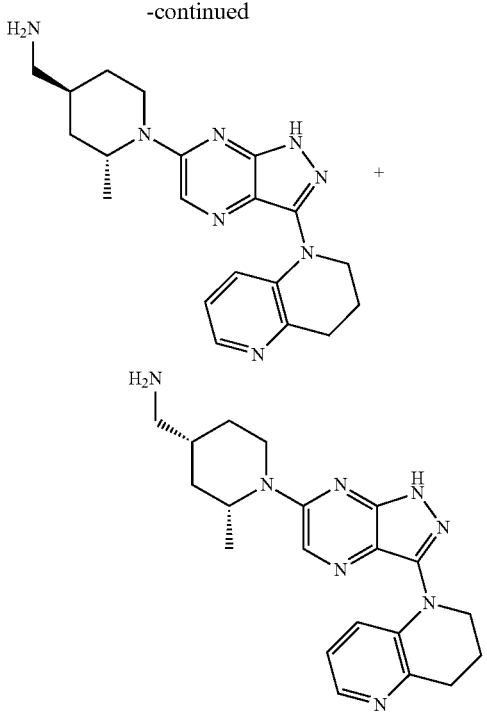

Step a: (2R,4R)-1-(3-iodo-1-(tetrahydro-2H-pyran-2-yl)-1H-pyrazolo[3,4-b]pyrazin-6-yl)-2-methylpiperidin-4-ol (600 mg, 1.3 mmol) (formed from the reaction of (2R,4R)-2-methylpiperidin-4-ol and 6-chloro-3-iodo-1-(tetrahydro-2H-pyran-2-yl)-1H-pyrazolo[3,4-b]pyrazine in DMSO, similar to conditions used for compound 33) was dissolved in DCM (25 mL). Dess-Martin periodinane (687 mg, 1.6 mmol) was added at 0° C. The reaction mixture was stirred at 25° C. for 2 hours. The reaction was quenched with sat, Na2SO3 (10 mL). The sat. NaHCO₃ (20 mL) was added. The partitioned layers were separated. The aqueous phase was extracted with DCM (20 mL×2). The combined organic layers were washed with brine (50 mL×2), dried over anhydrous Na2SO4, filtered and concentrated to give a residue which was purified by flash silica gel chromatography (Ethyl acetate/Petroleum ether=0/100 to 50/100) to afford the product of (2R)-1-(3-iodo-1-(tetrahydro-2H-pyran-2-yl)-1H-pyrazolo[3,4-b]pyrazin-6-yl)-2-methylpiperidin-4-one (500 mg, 84% yield) as a white solid.

Step b: The compound of TosMIC (263 mg, 1.3 mmol) in THF (2 mL) was added in the solution of t-BuOK (2.3 mL, 2.3 mmol, 1M, in THF) in THF (2 mL) at −78° C., and the mixture was stirred for 15 min. (2R)-1-(3-iodo-1-(tetrahydro-2H-pyran-2-yl)-1H-pyrazolo[3,4-b]pyrazin-6-yl)-2-methylpiperidin-4-one (0.4 g, 0.9 mmol) in THF (5 mL) was added dropwise at −78° C., and the reaction mixture was stirred at −78° C. for 2 hours. MeOH (5 mL) was added at −78° C. The mixture was heated at 70° C. for 2 h. The reaction mixture was concentrated to give a residue which was diluted with EtOAc (20 mL) and H2O (20 mL), the partitioned layers were separated. The aqueous phase was extracted with EtOAc (20 mL×3). The combined organic layers were washed with brine (50 mL), dried over anhydrous Na2SO4, filtered and concentrated to give a residue. The residue was purified by flash silica gel chromatography (Ethyl acetate/Petroleum ether=0/100 to 50/100) to afford the product of (2R)-1-(3-iodo-1-(tetrahydro-2H-pyran-2-yl)-1H-pyrazolo[3,4-b]pyrazin-6-yl)-2-methylpiperidine-4-carbonitrile (300 mg, 73% yield) as a white solid.

Step c: The compound of (2R)-1-(3-iodo-1-(tetrahydro-2H-pyran-2-yl)-1H-pyrazolo[3,4-b]pyrazin-6-yl)-2-methylpiperidine-4-carbonitrile (250 mg, 0.5 mmol), 1,2,3,4-tetrahydro-1,5-naphthyridine (89 mg, 0.6 mmol), Xantphos (32 mg, 0.05 mmol), Pd2(dba)3 (47 mg, 0.05 mmol) and t-BuONa (105 mg, 1.1 mmol) were added in PhMe (20 mL). The mixture was evacuated and refilled for 3 times using N2. The reaction mixture was stirred at 120° C. for 12 hour. The reaction was concentrated to give a residue which was purified by flash silica gel chromatography (DCM:MeOH=100:0 to 100:10) to afford the product of (2R)-1-(3-(3,4-dihydro-1,5-naphthyridin-1(2H)-yl)-1-(tetrahydro-2H-pyran-2-yl)-1H-pyrazolo[3,4-b]pyrazin-6-yl)-2-methylpiperidine-4-carbonitrile (140 mg, 55% yield) as a yellow oil.

Step d: The compound of (2R)-1-(3-(3,4-dihydro-1,5-naphthyridin-1(2H)-yl)-1-(tetrahydro-2H-pyran-2-yl)-1H-pyrazolo[3,4-b]pyrazin-6-yl)-2-methylpiperidine-4-carbonitrile (120 mg, 0.2 mmol) was dissolved in THF (10 mL). LiAlH4 (30 mg, 0.8 mmol) was added at 0° C. The reaction mixture was stirred at 25° C. for 2 hours. The reaction was quenched with 10% aq. NaOH (10 mL). The mixture was diluted with H2O (10 mL) and EtOAc (40 mL), the partitioned layers were separated. The aqueous phase was extracted with EtOAc (20 mL×2). The combined organic layers were washed with brine (50 mL), dried over anhydrous Na2SO4, filtered and concentrated to give the product of ((2R)-1-(3-(3,4-dihydro-1,5-naphthyridin-1(2H)-yl)-1-(tetrahydro-2H-pyran-2-yl)-1H-pyrazolo[3,4-b]pyrazin-6-yl)-2-methylpiperidin-4-yl)methanamine (120 mg, crude product) as a yellow solid.

Step e: The compound of ((2R)-1-(3-(3,4-dihydro-1,5-naphthyridin-1(2H)-yl)-1-(tetrahydro-2H-pyran-2-yl)-1H-pyrazolo[3,4-b]pyrazin-6-yl)-2-methylpiperidin-4-yl)methanamine (110 mg, 237 µmol) was added in HCl/MeOH (2 mL, 2N). The reaction mixture was stirred at 25° C. for 4 hours. The reaction mixture was concentrated and purified by prep-HPLC (HCOOH) to afford the product of ((2R,4S)-1-(3-(3,4-dihydro-1,5-naphthyridin-1(2H)-yl)-1H-pyrazolo[3,4-b]pyrazin-6-yl)-2-methylpiperidin-4-yl)methanamine (10.0 mg, HCOOH salt, 11% yield, e.e.=100%) as a yellow solid.

Step f: The mixture was purified by prep-HPLC (HCl) to give the product of ((2R,4R)-1-(3-(3,4-dihydro-1,5-naphthyridin-1(2H)-yl)-1H-pyrazolo[3,4-b]pyrazin-6-yl)-2-methylpiperidin-4-yl)methanamine (7.00 mg, 18.4 µmol, HCl salt, 8% yield, e.e.=100%) as a yellow solid.

Synthesis of 1-(6-(4-(aminomethyl)-4-methylpiperidin-1-yl)-1H-pyrazolo[3,4-b]pyrazin-3-yl)-N-methylindoline-4-carboxamide, Compound 107

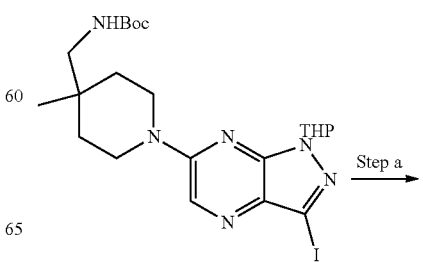

277

-continued

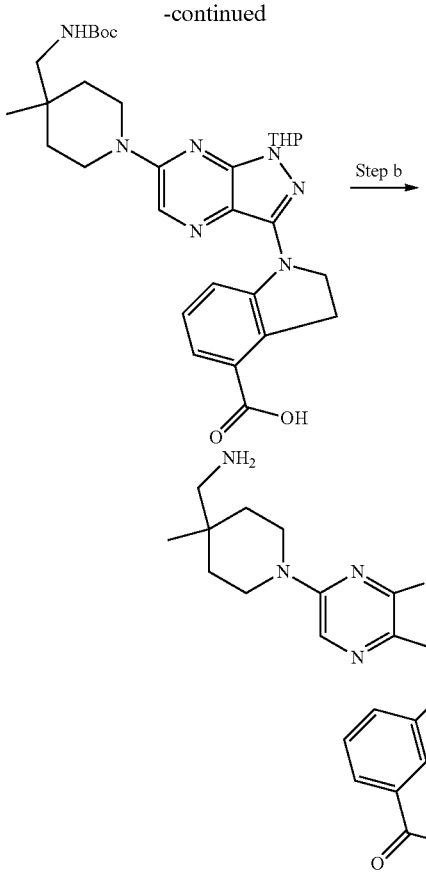

Step b

Step a: tert-butyl (((1-(3-iodo-1-(tetrahydro-2H-pyran-2-yl)-1H-pyrazolo[3,4-b]pyrazin-6-yl)-4-methylpiperidin-4-yl)methyl)carbamate (200 mg, 0.3594 mmol), methyl indoline-4-carboxylate (95.5 mg, 0.5391 mmol), RuPhos G3 (30.0 mg, 0.03594 mmol), and sodium 2-methylpropan-2-olate (69.0 mg, 0.7188 mmol) were taken up in dioxane (5 mL) and the mixture was stirred at 90° C. for 24 hrs. Aqueous NaOH (1 N, 2 mL) added and stirred at 90° C. for 20 hrs. The reaction mixture was cooled, filtered, concentrated, taken up in EtOAc water and charged with ~2 mL of 1N HCl. The layers were separated and the aqueous layer back extracted with EtOAc. The combined organic layer was dried with Na2SO4, filtered, concentrated and lyophilized from dioxane to give 1-(6-(4-(((tert-butoxycarbonyl)amino)methyl)-4-methylpiperidin-1-yl)-1-(tetrahydro-2H-pyran-2-yl)-1H-pyrazolo[3,4-b]pyrazin-3-yl)indoline-4-carboxylic acid (254 mg) as a yellow amorphous solid Step b: 1-(6-(4-(((tert-butoxycarbonyl)amino)methyl)-4-methylpiperidin-1-yl)-1-(tetrahydro-2H-pyran-2-yl)-1H-pyrazolo[3,4-b]pyrazin-3-yl)indoline-4-carboxylic acid (100 mg, 0.1690 mmol), HATU (96.3 mg, 0.2535 mmol) were taken up in DMF (3 mL) and N-ethyl-N-isopropylpropan-2-amine (58.7 µL, 0.338 mmol). The solution was stirred at rt for 1 hr then 2M NHMe (845 µL, 1.69 mmol) was added. After 16 hrs the reaction was partitioned between water and DCM and brine. The org layer was dried and concentrated. The residue dissolved in MeOH (4 mL), charged with c. HCl (1 mL) and heated to 60° C. After 2 hr the solution was concentrated, dissolved in DMSO and charged with NH4OH until solution remained cloudy. The residue was purified on prep-HPLC (5-40% ACN/water+0.1% FA). The product containing fractions were pooled and

278 concentrated and lyophilized from ACN/water to afford 1-(6-(4-(aminomethyl)-4-methylpiperidin-1-yl)-1H-pyrazolo[3,4-b]pyrazin-3-yl)-N-methylindoline-4-carboxamide (47 mg) as a yellow solid. LCMS: [M+H]+ 421.

Synthesis of 1-(6-(4-(aminomethyl)-4-methylpiperidin-1-yl)-1H-pyrazolo[3,4-b]pyrazin-3-yl)indoline-4-carboxamide, Compound 108

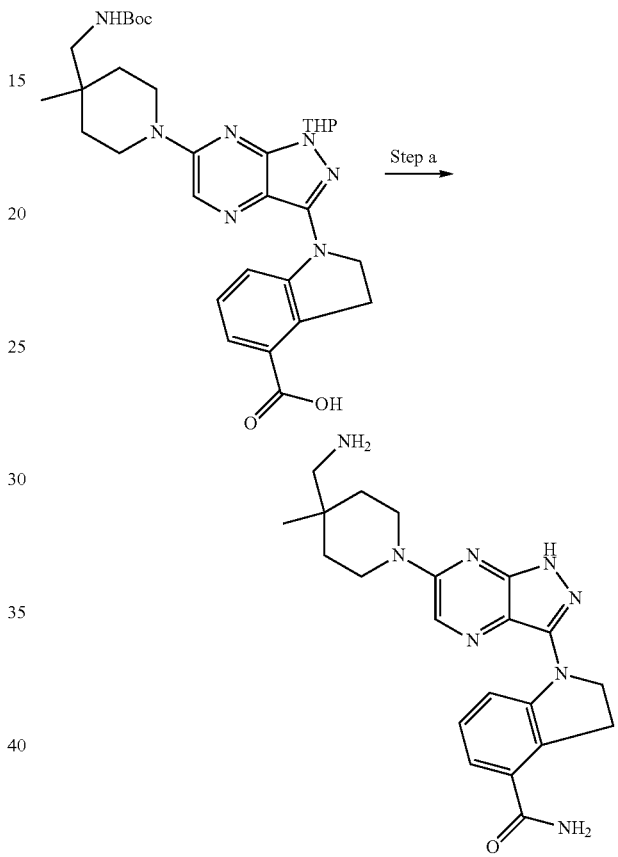

Step a

Step a: A resealable reaction vial was charged with 1-(6-(4-(((tert-butoxycarbonyl)amino)methyl)-4-methylpiperidin-1-yl)-1-(tetrahydro-2H-pyran-2-yl)-1H-pyrazolo[3,4-b]pyrazin-3-yl)indoline-4-carboxylic acid (100 mg, 0.1690 mmol) (prepared as described for compound 107), HATU (96.3 mg, 0.2535 mmol), DMF (3 mL) and N-ethyl-N-isopropylpropan-2-amine (58.7 µL, 0.338 mmol). The solution was stirred at rt for 1 hr then 7N ammonia in MeOH (241 µL, 1.69 mmol) was added and stirred for 16 hrs. After 16 hrs the reaction was partitioned between water and DCM and brine. The org layer was dried and concentrated. The residue dissolved in MeOH (4 mL), charged with c. HCl (1 mL) and heated to 60° C. After 2 hr the solution was concentrated, dissolved in DMSO and charged with NH4OH until solution remained cloudy. The residue was purified on prep-HPLC (5-40% ACN/water+0.1% FA). The product containing fractions were pooled and concentrated and lyophilized from ACN/water to afford 1-(6-(4-(aminomethyl)-4-methylpiperidin-1-yl)-1H-pyrazolo[3,4-b]pyrazin-3-yl)indoline-4-carboxamide (44 mg) a yellow solid. LCMS: [M+H]+ 407.

Synthesis of Rel-(R)-1-(1-(3-(3,4-dihydro-1,5-naphthyridin-1(2H)-yl)-1H-pyrazolo[3,4-b]pyrazin-6-yl)-4-methylpiperidin-4-yl)ethanamine, Compound 110 and Rel-(S)-1-(1-(3-(3,4-dihydro-1,5-naphthyridin-1(2H)-yl)-1H-pyrazolo[3,4-b]pyrazin-6-yl)-4-methylpiperidin-4-yl)ethanamine, Compound 111

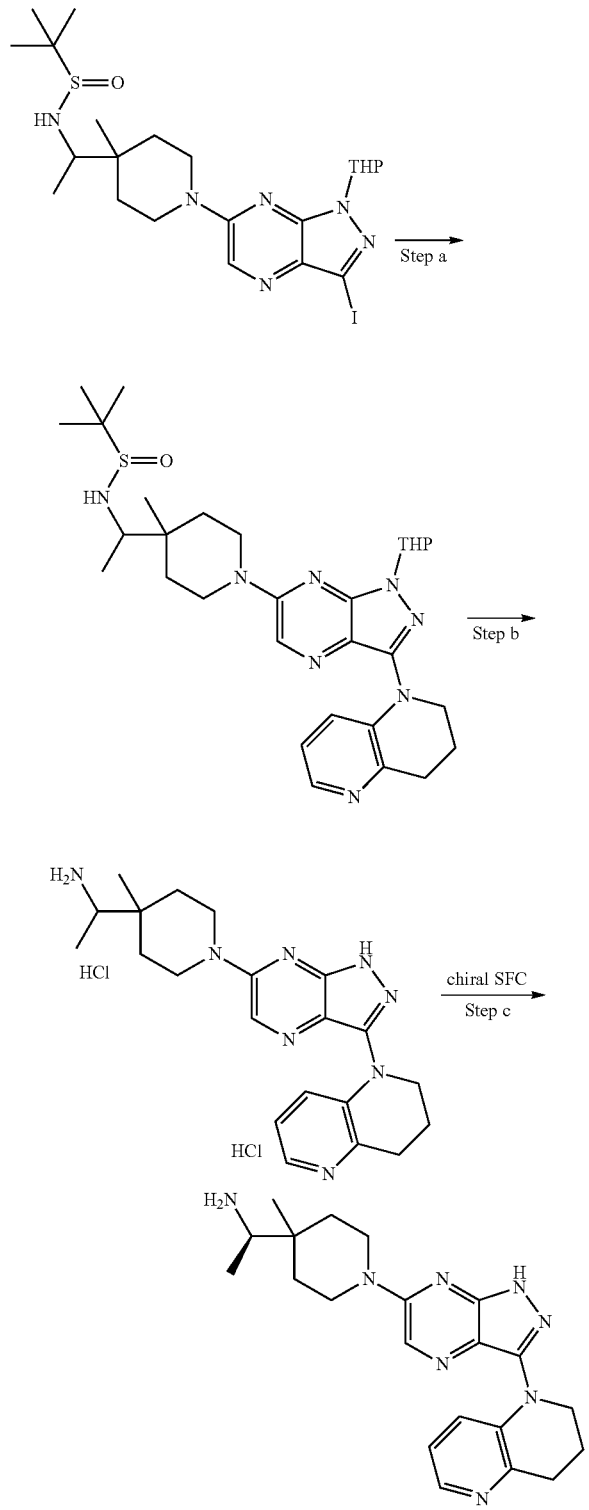

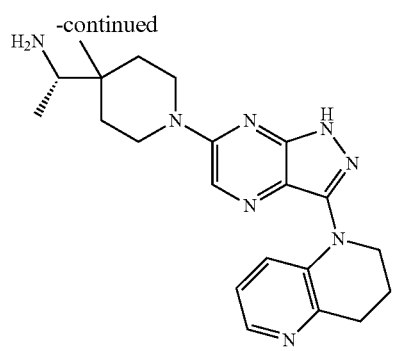

-continued

Step a: A mixture of N-(1-(1-(3-iodo-1-(tetrahydro-2H-pyran-2-yl)-1H-pyrazolo[3,4-b]pyrazin-6-yl)-4-methylpiperidin-4-yl)ethyl)-2-methylpropane-2-sulfinamide (370 mg, 644 µmol), 1,2,3,4-tetrahydro-1,5-naphthyridine (95.0 mg, 708 µmol), Pd$_2$(dba)$_3$ (58.8 mg, 64.3 µmol), XantPhos (74.0 mg, 128 µmol) and Cs$_2$CO$_3$ (417 mg, 1.3 mmol) in dioxane (10 mL) was stirred at 80° C. for 12 hours under N$_2$ atmosphere. The reaction mixture was concentrated under reduced pressure to give a residue, which was purified by column chromatography (Dichloromethane:Methanol=10:1) to afford the product of N-(1-(1-(3-(3,4-dihydro-1,5-naphthyridin-1(2H)-yl)-1-(tetrahydro-2H-pyran-2-yl)-1H-pyrazolo[3,4-b]pyrazin-6-yl)-4-methylpiperidin-4-yl)ethyl)-2-methylpropane-2-sulfinamide (450 mg, crude) as a brown oil.

Step b: A mixture of N-(1-(1-(3-(3,4-dihydro-1,5-naphthyridin-1(2H)-yl)-1-(tetrahydro-2H-pyran-2-yl)-1H-pyrazolo[3,4-b]pyrazin-6-yl)-4-methylpiperidin-4-yl)ethyl)-2-methylpropane-2-sulfinamide (450 mg, 774 µmol) in 4M HCl/MeOH (10 mL) was stirred at 20° C. for 2 hours. The reaction mixture was concentrated under reduced pressure to give a residue, which was purified by prep-HPLC (HCl) to afford the product of 1-(1-(3-(3,4-dihydro-1,5-naphthyridin-1(2H)-yl)-1H-pyrazolo[3,4-b]pyrazin-6-yl)-4-methylpiperidin-4-yl)ethanamine dihydrochloride (110 mg, 30% yield) as a yellow solid. LCMS: calc. for C$_{21}$H$_{30}$Cl$_2$N$_8$: 392.2, found: [M+H]$_+$ 393.1. $^1$HNMR (400 MHz, Methanol-d$_4$): δ 8.34 (s, 1H), 8.07-8.04 (m, 2H), 7.60-7.56 (m, 1H), 4.42-4.33 (m, 2H), 4.11-4.08 (m, 2H), 3.45-3.37 (m, 2H), 3.29 (t, J=6.8 Hz, 2H), 3.25-3.20 (m, 1H), 2.35-2.29 (m, 2H), 1.72-1.61 (m, 4H), 1.32 (d, J=6.8 Hz, 3H), 1.18 (s, 3H).

Step c: 1-(1-(3-(3,4-dihydro-1,5-naphthyridin-1(2H)-yl)-1H-pyrazolo[3,4-b]pyrazin-6-yl)-4-methylpiperidin-4-yl)ethanamine dihydrochloride (98.0 mg, 210 µmol) was purified by chiral SFC. (Column: Chiralcel OJ-3 100×4.6 mm I.D., 3 µm Mobile phase: A: CO$_2$ B: ethanol (0.1% ethanolamine) Gradient: from 5% to 40% of B in 4.5 min and hold 40% for 2.5 min, then 5% of B for 1 min. Flow rate: 2.8 mL/min Column temperature: 40° C.). Rel-(R)-1-(1-(3-(3,4-dihydro-1,5-naphthyridin-1(2H)-yl)-1H-pyrazolo[3,4-b]pyrazin-6-yl)-4-methylpiperidin-4-yl)ethanamine (23.9 mg, 60.8 µmol, e.e.=98.0%) was obtained as a yellow solid. LCMS: calc. for C$_{21}$H$_{28}$N$_8$: 392.2, found: [M+H]+ 393.0. ee: 100%. $^1$HNMR (400 MHz, Methanol_d$_4$): δ 8.21 (s, 1H), 7.88 (d, J=4.4 Hz, 1H), 7.32 (d, J=8.8 Hz, 1H), 7.03-6.99 (m, 1H), 4.32-4.27 (m, 2H), 3.95 (t, J=5.2 Hz, 2H), 3.39-3.35 (m, 2H), 3.06 (t, J=6.0 Hz, 2H), 2.73 (q, J=6.8 Hz, 1H), 2.23-2.20 (m, 2H), 1.63-1.54 (m, 4H), 1.32 (d, J=6.8 Hz, 3H), 1.06 (s, 3H). Rel-(S)-1-(1-(3-(3,4-dihydro-1,5-naphthyridin-1(2H)-yl)-1H-pyrazolo[3,4-b]pyrazin-6-yl)-4-methylpiperidin-4-yl)ethanamine (30.4 mg, 77.4 µmol, e.e. =92.1%) was obtained as a yellow solid. LCMS: calc.

for $C_{21}H_{2}$&Ne: 392.2, found: [M+H]⁺ 393.0. ee: 92%.
¹HNMR (400 MHz, Methanol_d₄): δ 8.27 (s, 1H), 7.95 (br, 1H), 7.60 (d, J=8.4 Hz, 1H), 7.24-7.21 (m, 1H), 4.40-4.31 (m, 2H), 4.00 (t, J=5.2 Hz, 2H), 3.42-3.33 (m, 2H), 3.22 (q, J=6.8 Hz, 1H), 3.14 (t, J=6.8 Hz, 2H), 2.28-2.22 (m, 2H), 1.69-1.62 (m, 4H), 1.32 (d, J=6.4 Hz, 3H), 1.18 (s, 3H).

Synthesis of 1-(6-(4-(aminomethyl)-4-methylpiperidin-1-yl)-1H-pyrazolo[3,4-b]pyrazin-3-yl)-4-methyl-1,2,3,4-tetrahydroquinoline-6-carboxamide formate, Compound 112

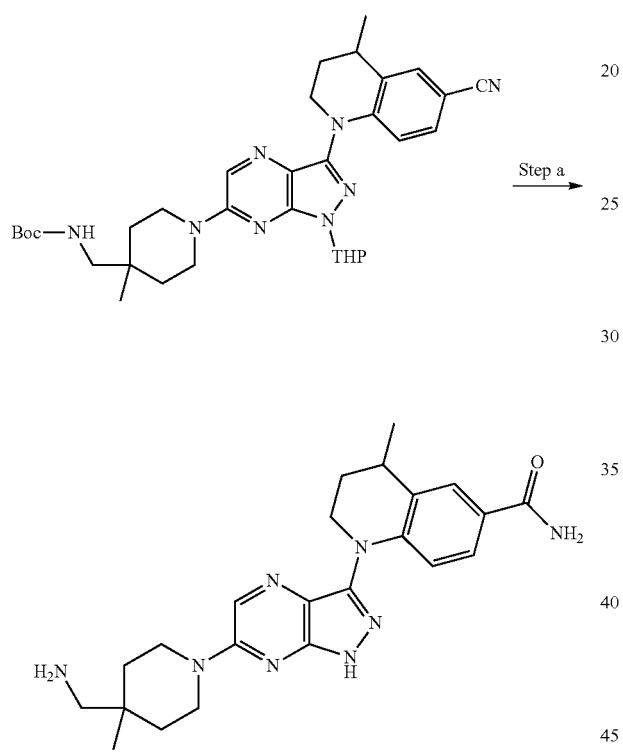

Step a: To a solution tert-butyl ((1-(3-(6-cyano-4-methyl-3,4-dihydroquinolin-1(2H)-yl)-1-(tetrahydro-2H-pyran-2-yl)-1H-pyrazolo[3,4-b]pyrazin-6-yl)-4-methylpiperidin-4-yl)methyl)carbamate (prepared via a route analogous to that used for Compound 33 50 mg, 0.08322 mmol) in DMSO (1 mL) at 0 C was added 50% aq. hydrogen peroxide (1 mL, 0.08322 mmol) and potassium carbonate (3.44 mg, 0.02496 mmol). Stirred at ambient temp for 3 h. Partitioned between EtOAc and water. Extracted water with EtOAc (1x). Combined organic layers and concentrated. Resuspended in MeOH (1 mL). Added conc. HCl (0.25 uL). Stirred at rt overnight. Concentrated, chased with toluene (3×). Purified by HPLC using 5-30% acetonitrile in water w/0.1% formic acid to give 1-(6-(4-(aminomethyl)-4-methylpiperidin-1-yl)-1H-pyrazolo[3,4-b]pyrazin-3-yl)-4-methyl-1,2,3,4-tetrahydroquinoline-6-carboxamide formate (3.00 mg, 0.006242 mmol).

Synthesis of 1-(6-(4-(aminomethyl)-4-methylpiperidin-1-yl)-1H-pyrazolo[3,4-b]pyrazin-3-yl)-N-methylindoline-5-carboxamide, Compound 113

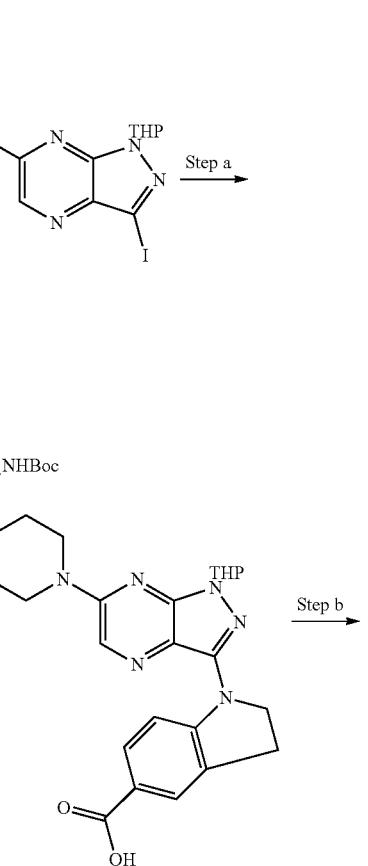

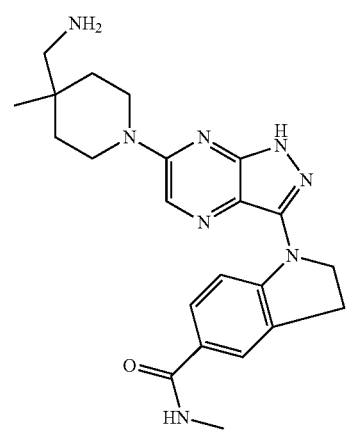

Step a: A resealable reaction vial was charged with tert-butyl ((1-(3-iodo-1-(tetrahydro-2H-pyran-2-yl)-1H-pyrazolo[3,4-b]pyrazin-6-yl)-4-methylpiperidin-4-yl)methyl)carbamate (200 mg, 0.3594 mmol), methyl indoline-5-carboxylate (95.5 mg, 0.5391 mmol), RuPhos Pd G4 (30.5 mg, 0.03594 mmol), sodium 2-methylpropan-2-olate (69.0 mg, 0.7188 mmol) and Dioxane (5 mL). The mixture was bubbled with N2 for 10 min then stirred at 90° C. for 20 hrs. Aqueous NaOH (1 N, 2 mL) was added and stirred at 90° C. for 4 hrs. The mixture was cooled, filtered, concentrated and taken up in water. The pH was adjusted to 4 by addition of 1 N HCl (~500 uL). The gel-like suspension was extracted 3× with EtOAc. The combined organic was dried with Na₂SO₄, filtered, concentrated then chased with MTBE to afford 1-(6-(4-(((tert-butoxycarbonyl)amino)methyl)-4-methylpiperidin-1-yl)-1-(tetrahydro-2H-pyran-2-yl)-1H-pyrazolo[3,4-b]pyrazin-3-yl)indoline-5-carboxylic acid (225 mg) as a yellow solid. LCMS: [M+H]⁺ 592.

Step b: A resealable reaction vial was charged with 1-(6-(4-(((tert-butoxycarbonyl)amino)methyl)-4-methylpiperidin-1-yl)-1-(tetrahydro-2H-pyran-2-yl)-1H-pyrazolo[3,4-b]pyrazin-3-yl)indoline-5-carboxylic acid (105 mg, 0.1774 mmol), HATU (101 mg, 0.2661 mmol), DMF (3 mL) and N-ethyl-N-isopropylpropan-2-amine (61.7 µL, 0.3548 mmol). The solution was stirred at rt for 1 hr then 2M NH₂Me (885 µL, 1.77 mmol) was added. After 16 hrs, the reaction was partitioned between water and DCM and brine. The org layer was dried and concentrated. The residue dissolved in MeOH (4 mL), charged with c. HCl (1 mL) and heated to 60° C. After 1 hr, the mixture was filtered to afford 1-(6-(4-(aminomethyl)-4-methylpiperidin-1-yl)-1H-pyrazolo[3,4-b]pyrazin-3-yl)-N-methylindoline-5-carboxamide (50 mg) as a yellow solid. LCMS: [M+H]+ 421.

Synthesis of 1-(6-(4-(aminomethyl)-4-methylpiperidin-1-yl)-1H-pyrazolo[3,4-b]pyrazin-3-yl)indoline-5-carboxamide, Compound 114

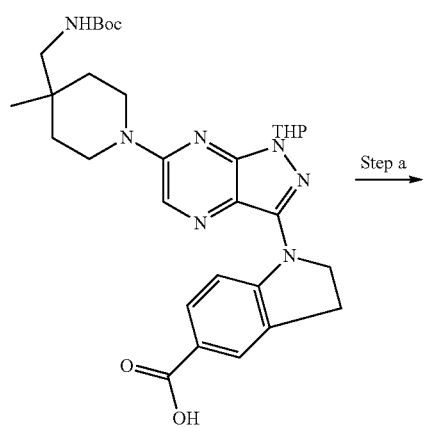

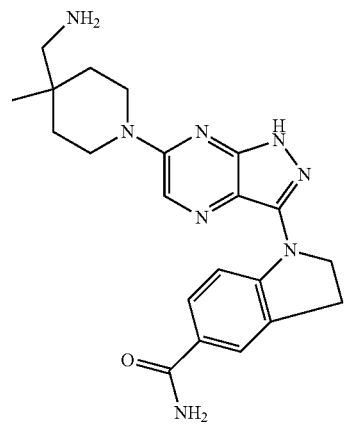

Step a: A resealable reaction vial was charged with 1-(6-(4-(((tert-butoxycarbonyl)amino)methyl)-4-methylpiperidin-1l-yl)-1-(tetrahydro-2H-pyran-2-yl)-1H-pyrazolo[3,4-b]pyrazin-3-yl)indoline-4-carboxylic acid (100 mg, 0.1690 mmol) (prepared as described for compound 113), HATU (96.3 mg, 0.2535 mmol), DMF (3 mL) and N-ethyl-N-isopropylpropan-2-amine (58.7 µL, 0.338 mmol). The solution was stirred at rt for 1 hr then 7N ammonia in MeOH (252 µL, 1.77 mmol) was added and stirred for 16 hrs. After 16 hrs the reaction was partitioned between water and DCM and brine. The org layer was dried and concentrated. The residue dissolved in MeOH (4 mL), charged with c. HCl (1 mL) and heated to 60° C. After 2 hr the solution was concentrated, dissolved in DMSO and charged with NH₄OH until solution remained cloudy. The residue was purified on prep-HPLC (5-40% ACN/water+0.1% FA). The product containing fractions were pooled and concentrated and lyophilized from ACN/water to afford 1-(6-(4-(aminomethyl)-4-methylpiperidin-1-yl)-1H-pyrazolo[3,4-b]pyrazin-3-yl)indoline-5-carboxamide (28 mg) a yellow solid. LCMS: [M+H]⁺ 407.

Synthesis of Rel-(S)-1-(6-(4-(aminomethyl)-4-methylpiperidin-1-yl)-1H-pyrazolo[3,4-b]pyrazin-3-yl)-4-methyl-1,2,3,4-tetrahydroquinoline-6-carbonitrile, Compound 115 and Rel-(R)-1-(6-(4-(aminomethyl)-4-methylpiperidin-1-yl)-1H-pyrazolo[3,4-b]pyrazin-3-yl)-4-methyl-1,2,3,4-tetrahydroquinoline-6-carbonitrile, Compound 116 droquinoline-6-carbonitrile (15.2 mg, 38% yield, ee: 93.7%) was obtained as a orange solid. LCMS: calc. for $C_{23}H_{28}N_8$: 416.2, found: [M+H]+ 417.1. ee: 94%. $^1$HNMR (400 MHz, CD$_3$OD): δ 8.25 (s, 1H), 7.49 (s, 1H), 7.21 (d, J=8.8 Hz, 1H), 6.75 (d, J=8.8 Hz, 1H), 4.14-4.08 (m, 2H), 4.05-3.85 (m, 2H), 3.60-3.54 (m, 2H), 3.10-3.07 (m, 1H), 2.69 (s, 2H), 2.20-2.15 (m, 1H), 1.90-1.80 (m, 1H), 1.65-1.54 (m, 4H), 1.42 (d, J=6.8 Hz, 3H), 1.14 (s, 3H).

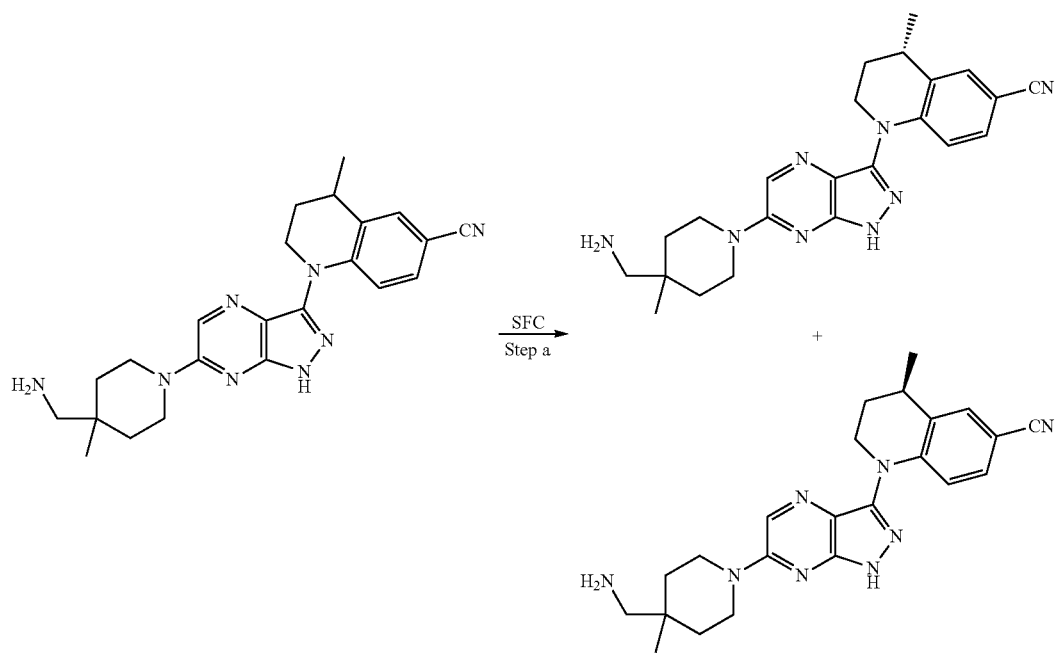 [SMILES: CC1CCN(c2n[nH]c3nc(N4CCC(C)(CN)CC4)cnc23)c2ccc(C#N)cc21 ; "SFC" ; C[C@@H]1CCN(c2n[nH]c3nc(N4CCC(C)(CN)CC4)cnc23)c2ccc(C#N)cc21 ; C[C@H]1CCN(c2n[nH]c3nc(N4CCC(C)(CN)CC4)cnc23)c2ccc(C#N)cc21]

1-(6-(4-(Aminomethyl)-4-methylpiperidin-1-yl)-1H-pyrazolo[3,4-b]pyrazin-3-yl)-4-methyl-1,2,3,4-tetrahydroquinoline-6-carbonitrile (40.0 mg, 96.0 μmol, synthesized as described for Compound 33) was separated by chiral-SFC (Column: Chiralcel OJ-3 100×4.6 mm I.D., 3 μm Mobile phase: A: CO$_2$ B: ethanol (0.1% ethanolamine) Gradient: from 5% to 40% of B in 4.5 min and hold 40% for 2.5 min, then 5% of B for 1 min Flow rate: 2.8 mL/min Column temperature:40° C.). The absolute configuration was arbitrarily assigned. Rel-(S)-1-(6-(4-(aminomethyl)-4-methylpiperidin-1-yl)-1H-pyrazolo[3,4-b]pyrazin-3-yl)-4-methyl-1,2,3,4-tetrahydroquinoline-6-carbonitrile (14.3 mg, 35.8% yield, ee: 99.1%) was obtained as a orange solid. LCMS: calc. for $C_{23}H_{28}N_8$: 416.2, found: [M+H]$^+$ 417.0. ee: 99%. $^1$HNMR (400 MHz, CD$_3$OD): δ 8.24 (s, 1H), 7.49 (s, 1H), 7.21 (d, J=8.8 Hz, 1H), 6.75 (d, J=8.8 Hz, 1H), 4.11-4.06 (m, 2H), 3.98-3.86 (m, 2H), 3.60-3.52 (m, 2H), 3.10-3.06 (m, 1H), 2.60 (s, 2H), 2.25-2.15 (m, 1H), 1.92-1.85 (m, 1H), 1.63-1.49 (m, 4H), 1.42 (d, J=7.2 Hz, 3H), 1.10 (s, 3H). Rel-(R)-1-(6-(4-(aminomethyl)-4-methylpiperidin-1-yl)-1H-pyrazolo[3,4-b]pyrazin-3-yl)-1H-pyrazolo[3,4-b]pyrazin-3-yl)-4-methyl-1,2,3,4-tetrahy- Synthesis of 1-(6-(4-(aminomethyl)-4-methylpiperidin-1-yl)-1H-pyrazolo[3,4-b]pyrazin-3-yl)-1,2,3,4-tetrahydroquinolin-4-ol, Compound 119

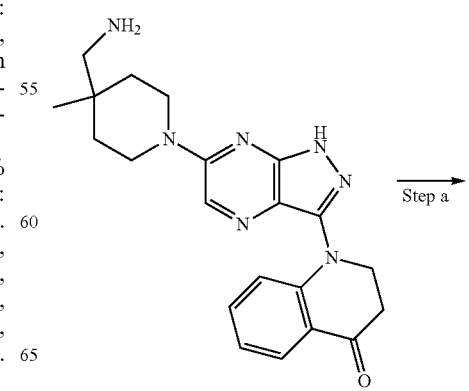

287

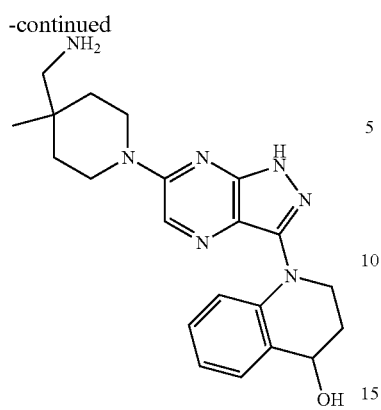

Step a: 1-(6-(4-(Aminomethyl)-4-methylpiperidin-1-yl)-1H-pyrazolo[3,4-b]pyrazin-3-yl)-2,3-dihydroquinolin-4

288

(1H)-one (30.0 mg, 76.6 μmol, synthesized as described for Compound 33) and NaBH$_4$ (9.18 mg, 306 μmol) were added in THF (2.0 mL), the reaction mixture was stirred at 25° C. for 1 hour. The reaction mixture was purified by prep-HPLC (NH$_3$.H$_2$O) to afford the product of 1-(6-(4-(aminomethyl)-4-methylpiperidin-1-yl)-1H-pyrazolo[3,4-b]pyrazin-3-yl)-1,2,3,4-tetrahydroquinolin-4-ol (8.8 mg, 29.2% yield) as a yellow solid.

Synthesis of Rel-(S)-(4-methyl-1-(3-(4-methyl-3,4-dihydro-1,5-naphthyridin-1(2H)-yl)-1H-pyrazolo[3,4-b]pyrazin-6-yl)piperidin-4-yl)methanamine, Compound 128 and Rel-(R)-(4-methyl-1-(3-(4-methyl-3,4-dihydro-1,5-naphthyridin-1(2H)-yl)-1H-pyrazolo[3,4-b]pyrazin-6-yl)piperidin-4-yl)methanamine, Compound 129

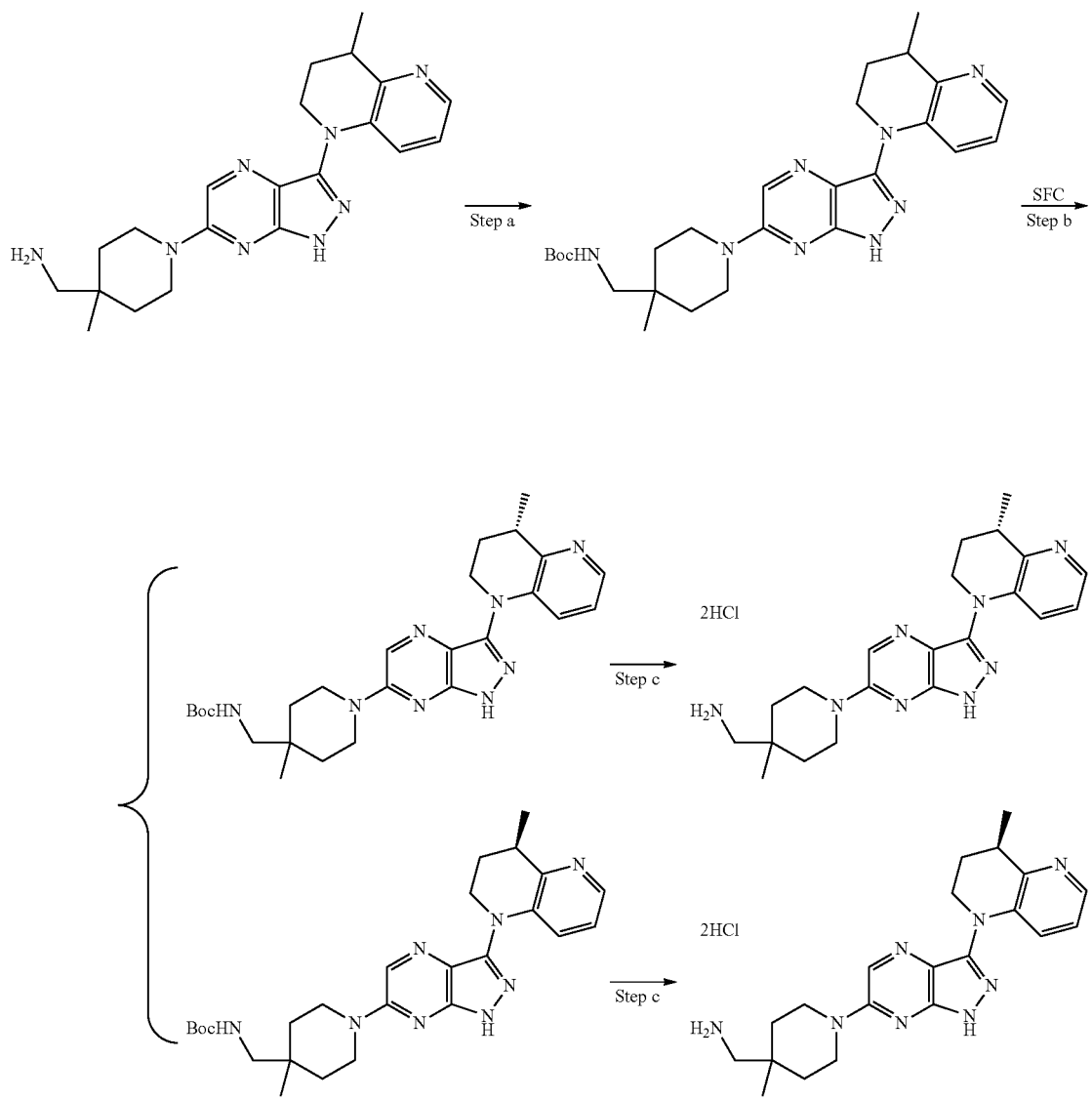

Step a: To a solution of (4-methyl-1-(3-(4-methyl-3,4-dihydro-1,5-naphthyridin-1(2H)-yl)-1H-pyrazolo[3,4-b]pyrazin-6-yl)piperidin-4-yl)methanamine (50.0 mg, 127.0 mol, synthesized via the method described for Compound 33) in THF (5.0 mL) was added TEA (25.7 mg, 254.0 µmol) and Boc₂O (33.1 mg, 152.0 µmol). The reaction mixture was stirred at 25° C. for 30 min. The reaction mixture was concentrated under reduced pressure. The residue was purified by prep-TLC (DCM/MeOH=10:1). The product of tert-butyl ((4-methyl-1-(3-(4-methyl-3,4-dihydro-1,5-naphthyridin-1(2H)-yl)-1H-pyrazolo[3,4-b]pyrazin-6-yl)piperidin-4-yl)methyl)carbamate (40.0 mg, 64.0% yield) was obtained as a yellow solid.

Step b: Tert-butyl ((4-methyl-1-(3-(4-methyl-3,4-dihydro-1,5-naphthyridin-1(2H)-yl)-1H-pyrazolo[3,4-b]pyrazin-6-yl)piperidin-4-yl)methyl)carbamate (40.0 mg) was separated by SFC (Column: ChiralPak IC-3 150×4.6 mm I.D., 3 um Mobile phase: A: CO₂ B: Ethanol (0.05% DEA), Gradient: from 5% to 40% of B in 5.5 min and hold 40% for 3 min, then 5% of B for 1.5 min, Flow rate: 2.5 mL/min Column temperature: 40° C.). (S)-tert-butyl ((4-methyl-1-(3-(4-methyl-3,4-dihydro-1,5-naphthyridin-1(2H)-yl)-1H-pyrazolo[3,4-b]pyrazin-6-yl)piperidin-4-yl)methyl)carbamate (5.0 mg, 37.5% yield) was obtained as a yellow solid and (R)-tert-butyl ((4-methyl-1-(3-(4-methyl-3,4-dihydro-1,5-naphthyridin-1(2H)-yl)-1H-pyrazolo[3,4-b]pyrazin-6-yl)piperidin-4-yl)methyl)carbamate (20.0 mg, 50.1% yield) was obtained as a yellow solid. The absolute configuration was arbitrarily assigned.

Step c: A solution of rel-(S)-tert-butyl ((4-methyl-1-(3-(4-methyl-3,4-dihydro-1,5-naphthyridin-1(2H)-yl)-1H-pyrazolo[3,4-b]pyrazin-6-yl)piperidin-4-yl)methyl)carbamate (15.0 mg, 30.4 µmol) in HCl/MeOH (5.0 mL, 4.0 N) was stirred at 30° C. for 2 hours. The reaction mixture was concentrated under reduced pressure. The residue was purified by prep-HPLC (HCl). Rel-(S)-(4-methyl-1-(3-(4-methyl-3,4-dihydro-1,5-naphthyridin-1(2H)-yl)-1H-pyrazolo[3,4-b]pyrazin-6-yl)piperidin-4-yl)methanamine dihydrochloride (10.0 mg, 70.9% yield) was obtained as a yellow solid. LCMS: calc. for C₂₁H₂₈N₈: 392.2, found: [M+H]⁺393.3. SFC: e.e.=100.0%, Column: ChiralCel OJ-H 150×4.6 mm I.D., 5 um Mobile phase: A: CO₂ B: Methanol (0.05% DEA) Gradient: from 5% to 40% of B in 5.5 min and hold 40% for 3 min, then 5% of B for 1.5 min Flow rate: 2.5 mL/min Column temperature: 40° C. ¹HNMR (400 MHz, CD₃OD): δ 8.33 (s, 1H), 8.03-8.08 (m, 2H), 7.56-7.61 (m, 1H), 4.03-4.20 (m, 4H), 3.55-3.63 (m, 2H), 3.47-3.52 (m, 1H), 2.95 (s, 2H), 2.32-2.42 (m, 1H), 2.09-2.15 (m, 1H), 1.64-1.71 (m, 4H), 1.57-1.60 (m, 3H), 1.24 (s, 3H).

Step c was also replicated for rel-(R)-tert-butyl ((4-methyl-1-(3-(4-methyl-3,4-dihydro-1,5-naphthyridin-1(2H)-yl)-1H-pyrazolo[3,4-b]pyrazin-6-yl)piperidin-4-yl)methyl)carbamate to obtain Rel-(R)-(4-methyl-1-(3-(4-methyl-3,4-dihydro-1,5-naphthyridin-1(2H)-yl)-1H-pyrazolo[3,4-h]pyrazin-6-yl)piperidin-4-yl)methanamine dihydrochloride (7.00 mg, 37.2% yield) was obtained as a yellow solid. LCMS: calc. for C₂₁H₂₈N₈: 392.2, found: [M+H]⁺ 393.3. SFC: e.e.=96.7%, Column: ChiralCel OJ-H 150×4.6 mm I.D., 5 um Mobile phase: A: CO₂ B: Methanol (0.05% DEA) Gradient: from 5% to 40% of B in 5.5 min and hold 40% for 3 min, then 5% of B for 1.5 min Flow rate: 2.5 mL/min Column temperature: 40° C. ¹HNMR (400 MHz, CD₃OD): δ 8.32 (s, 1H), 8.03-8.08 (m, 2H), 7.56-7.61 (m, 1H), 4.03-4.20 (m, 4H), 3.55-3.63 (m, 2H), 3.47-3.52 (m, 1H), 2.95 (s, 2H), 2.32-2.42 (m, 1H), 2.09-2.15 (m, 1H), 1.64-1.71 (m, 4H), 1.57-1.60 (m, 3H), 1.24 (s, 3H).

Synthesis of disulfanediylbis(ethane-2,1-diyl) bis(((1-(3-(3,4-dihydro-1,5-naphthyridin-1(2H)-yl)-1H-pyrazolo[3,4-b]pyrazin-6-yl)-4-methylpiperidin-4-yl)methyl)carbamate), Compound 166

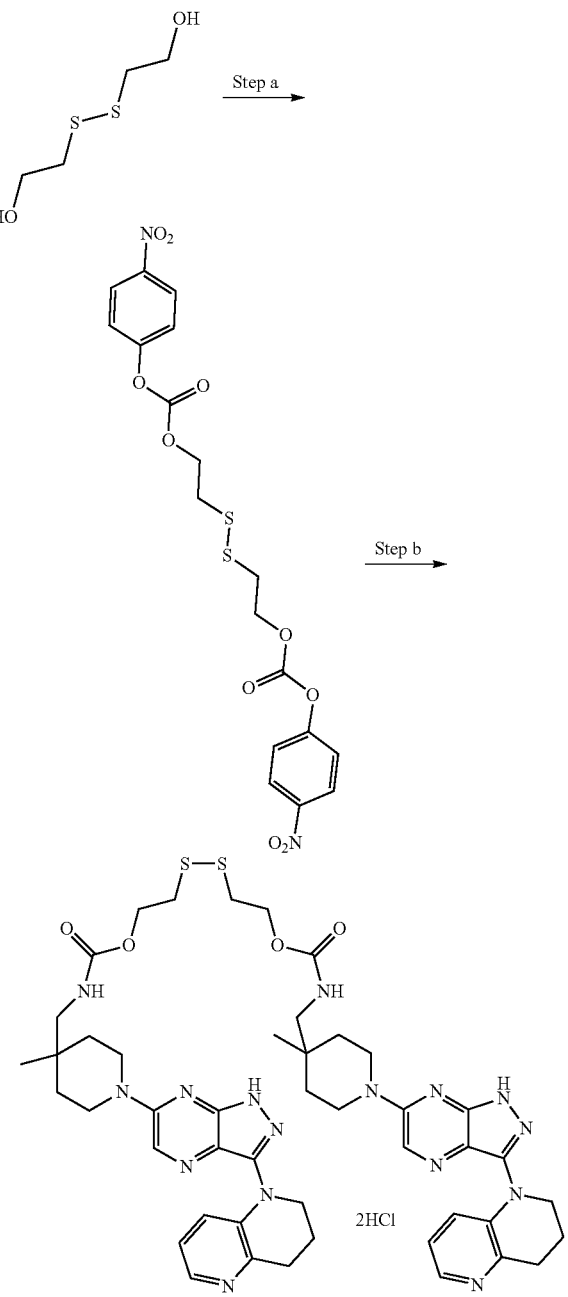

Step a: To a solution of 2-[(2-hydroxyethyl)disulfanyl]ethan-1-ol (400.0 mg, 2.59 mmol) in DCM (15.0 mL) was added 4-nitrophenyl chloroformate (1.30 g, 6.47 mmol) and pyridine (1.02 g, 12.90 mmol) at 0° C., and the reaction mixture was allowed to warm to 30° C., and stirred for 4 hours. TLC (Petroleum ether/Ethyl acetate=4/1) showed the starting material disappeared and two new spots formed. The mixture was diluted with DCM (50.0 mL), and washed sequentially with sat. NaHCO₃ (30.0 mL×3), water (30.0 mL), 10% citric acid (30.0 mL×2), water (30.0 mL), and brine (30.0 mL). The organic layer was dried over anhydrous Na2SO4, filtered and concentrated. The residue was purified by column chromatography (Petroleum ether/Ethyl acetate=100:0 to 100:50). The product of 2-[(2-{[(4-nitrophenoxy)carbonyl]oxy}ethyl)disulfanyl]ethyl 4-nitrophenyl carbonate (300.0 mg, 24.0% yield) was obtained as a light yellow oil.

Step b: To a solution of 1-{4-methyl-1-[3-(1,2,3,4-tetrahydro-1,5-naphthyridin-1-yl)-1H-pyrazolo[3,4-b]pyrazin-6-yl]piperidin-4-yl}methanamine (46.5 mg, 123.0 μmol) in DMF (5.0 mL) was added 2-[(2-{[(4-nitrophenoxy)carbonyl]oxy}ethyl)disulfanyl]ethyl 4-nitrophenyl carbonate (120.0 mg, 247.0 μmol) and DIEA (95.6 mg, 740.0 μmol). The reaction mixture was stirred at 30° C. for 12 hours. TLC (DCM/MeOH=10:1) showed the starting material disappeared and new spot with lower polarity formed. The reaction mixture was concentrated under reduced pressure. The residue was diluted with water (10.0 mL) and extracted with DCM (10.0 mL×2). The combined organic layers were washed with water (10.0 mL×2), dried over anhydrous Na2SO4, filtered and concentrated under reduced pressure. The reaction mixture was concentrated under reduced pressure. The residue was diluted with MeOH (5.0 mL). The residue was purified by prep-HPLC (HCl). disulfanediylbis(ethane-2,1-diyl) bis(((1-(3-(3,4-dihydro-1,5-naphthyridin-1(2H)-yl)-1H-pyrazolo[3,4-b]pyrazin-6-yl)-4-methylpiperidin-4-yl)methyl)carbamate) (40.0 mg, 15.6% yield) was obtained as a yellow solid.

Synthesis of (1-(3-(6-(1,2,4-oxadiazol-3-yl)-3,4-dihydroquinolin-1(2H)-yl)-1H-pyrazolo[3,4-b]pyrazin-6-yl)-4-methylpiperidin-4-yl)methanamine, Compound 172

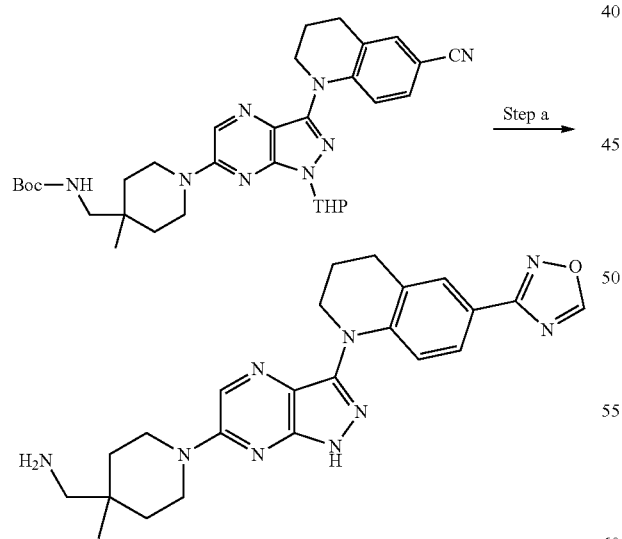

Step a: To a solution of tert-butyl N-({1-[3-(6-cyano-1,2,3,4-tetrahydroquinolin-1-yl)-1-(oxan-2-yl)-1H-pyrazolo[3,4-b]pyrazin-6-yl]-4-methylpiperidin-4-yl}methyl)carbamate (prepared as described for Compound 33 with the appropriate building blocks, 104 mg, 0.1772 mmol) in EtOH (1 mL) was added hydroxylamine (43.4 μL, 0.7088 mmol). Heated at 50 C overnight. Concentrated, then redissolved material in triethoxymethane (736 μL, 4.43 mmol). Added 3 drops of TFA. Stirred at 60 C for 90 min. Concentrated. Partitioned between EtOAc and water. Washed water layer 2× with EtOAc. Combined organic layers and washed with brine. Dried over Na₂SO₄, filtered and concentrated. Dissolved in MeOH (2 mL). Added conc. HC (0.5 mL) and stirred at it for 15 min. Concentrated, triturated with toluene (3×). Purified by HPLC using 10-40% acetonitrile in water w/0.1% formic acid to give (1-(3-(6-(1,2,4-oxadiazol-3-yl)-3,4-dihydroquinolin-1(2H)-yl)-1H-pyrazolo[3,4-b]pyrazin-6-yl)-4-methylpiperidin-4-yl)methanamine (30 mg, 0.061 mmol).

Synthesis of methyl ((1-(3-(6-cyano-3,4-dihydroquinolin-1(2H)-yl)-1H-pyrazolo[3,4-b]pyrazin-6-yl)-4-methylpiperidin-4-yl)methyl)carbamate, Compound 174

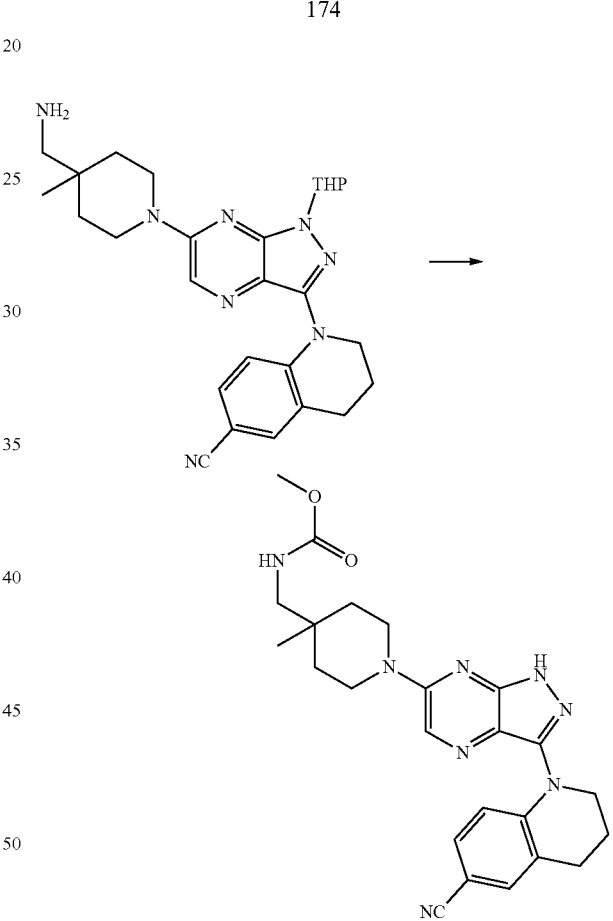

Step a: To a solution of 1-{6-[4-(aminomethyl)-4-methylpiperidin-1-yl]-1-(oxan-2-yl)-1H-pyrazolo[3,4-b]pyrazin-3-yl}-1,2,3,4-tetrahydroquinoline-6-carbonitrile (50 mg, 0.1027 mmol) in DCM (1 mL). Added ethylbis(propan-2-yl)amine (17.7 μL, 0.1027 mmol) and methyl carbonochloridate (7.95 μL, 0.1027 mmol). Stirred at rt overnight. Concentrated. Redissolved in 2 mL MeOH. Added 0.5 mL conc. HCl and stirred at for 2 h. Concentrated. Purified on by flash silica gel chromatography using 0-100% EtOAc in Heptanes to give methyl N-((1-[3-(6-cyano-1,2,3,4-tetrahydroquinolin-1-yl)-1H-pyrazolo[3,4-b]pyrazin-6-yl]-4-methylpiperidin-4-yl)methyl)carbamate (25.2 mg, 0.05471 mmol) Synthesis of 5-(6-(4-(aminomethyl)-4-methylpiperidin-1-yl)-1H-pyrazolo[3,4-b]pyrazin-3-yl)-5,6,7,8-tetrahydro-1,5-naphthyridine-2-carboxamide, Compound 175

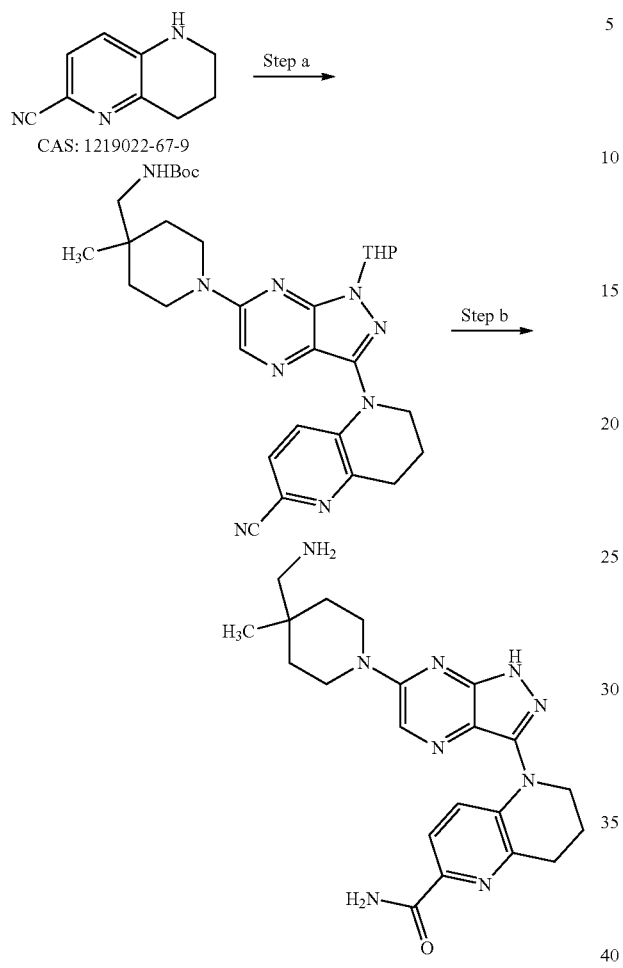

Step a: Tert-butyl ((1-(3-(6-cyano-3,4-dihydro-1,5-naphthyridin-1(2H)-yl)-1-(tetrahydro-2H-pyran-2-yl)-1H-pyrazolo[3,4-b]pyrazin-6-yl)-4-methylpiperidin-4-yl)methyl)carbamate (86.0 mg, 0.15 mmol) was prepared following the procedure detailed for compound 33 beginning from commercially available 5,6,7,8-tetrahydro-1,5-naphthyridine-2-carbonitrile (CAS: 1219022-67-9).

Step b: To a microwave vial containing tert-butyl ((1-(3-(6-cyano-3,4-dihydro-1,5-naphthyridin-1(2H)-yl)-1-(tetrahydro-2H-pyran-2-yl)-1H-pyrazolo[3,4-b]pyrazin-6-yl)-4-methylpiperidin-4-yl)methyl)carbamate (86.0 mg, 0.15 mmol) in a mixture of DMSO (0.80 mL), EtOH (0.20 mL) and H$_2$O$_2$ (0.10 mL) was added K$_2$CO$_3$ (6.0 mg, 0.043 mmol). The reaction vessel was sealed and heated to 60° C. for 16 h. Following cooling to ambient temperature and partitioning between EtOAc and brine, the organic residue was extracted (3×) and concentrated to dryness. The residue was dissolved in EtOH (1.0 mL) and HCl (4.0 M in dioxane, 0.5 mL) was added and the reaction aged at ambient temperature for 16 h. The residue was concentrated to dryness and purified by silica gel chromatography (5-20% MeOH in dichloromethane with 0.1% NH$_3$ H$_2$O) to furnish 5-(6-(4-(aminomethyl)-4-methylpiperidin-1-yl)-1H-pyrazolo[3,4-b]pyrazin-3-yl)-5,6,7,8-tetrahydro-1,5-naphthyridine-2-carboxamide (32.9 mg 0.078 mmol) in 52% yield over two steps. LCMS: [M+H]+ 422.5 Synthesis of 1-[4-(aminomethyl)-1-[3-(1,2,3,4-tetrahydro-1,5-naphthyridin-1-yl)-1H-pyrazolo[3,4-b]pyrazin-6-yl]piperidin-4-yl]methanamine dihydrochloride, Compound 177

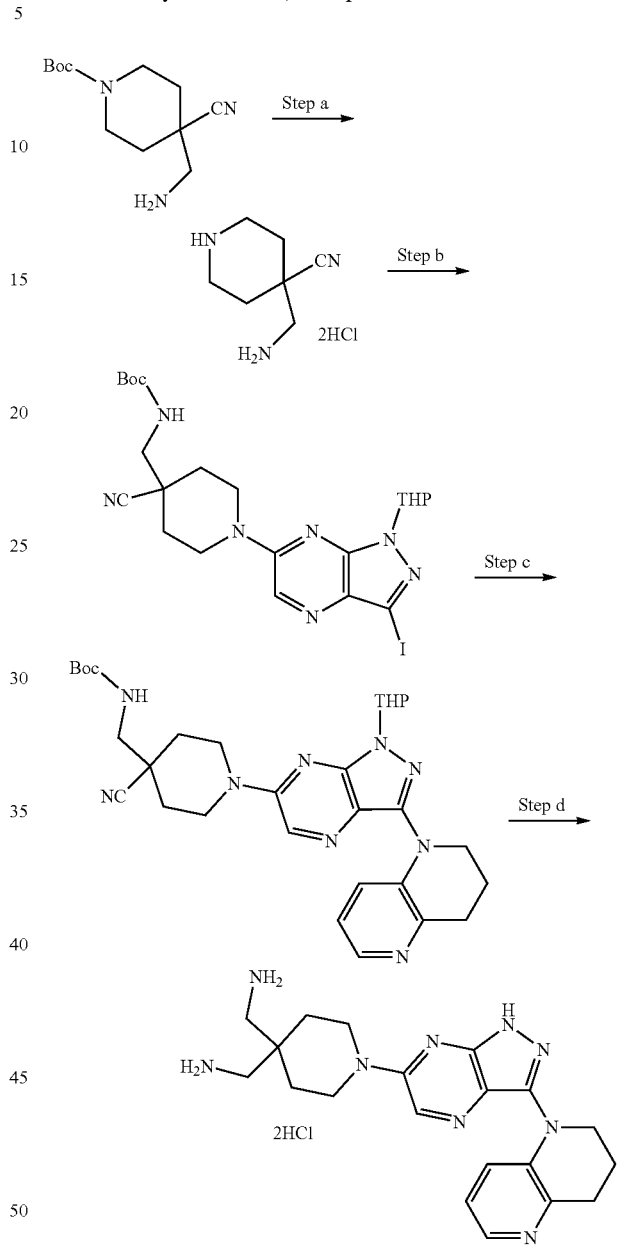

Step a: To tert-butyl 4-(aminomethyl)-4-cyanopiperidine-1-carboxylate (237 mg, 0.9903 mmol, CAS #1207178-51-5) in MeOH (5 mL) was added hydrogen chloride (2.47 mL, 9.90 mmol). The mixture was stirred at rt for 1 h. Removed half of solvent, added MBTE and filtered off solid. Washed precipitate with MBTE. Recovered 4-(aminomethyl)piperidine-4-carbonitrile dihydrochloride (204 mg, 0.9617 mmol)

Step b: To a solution of and 4-(aminomethyl)piperidine-4-carbonitrile dihydrochloride (0.204 g, 0.9570 mmol) and 6-chloro-3-iodo-1-(oxan-2-yl)-1H-pyrazolo[3,4-b]pyrazine (348 mg, 0.957 mmol) in DMF (5 mL) was added diethyl(propan-2-yl)amine (595 uL, 3.82 mmol). Stirred at 50 C for 12 h. Cooled to rt and added di-tert-butyl dicarbonate (437 μL, 1.91 mmol) and stirred at rt for 1 h. Partitioned between EtOAc and water. Washed water layer with EtOAc (2×). Combined organic layers, washed with brine, and dried over Na₂SO₄. Filtered and concentrated to give a yellow oil. Purified by flash silica gel chromatography (0-50% EtOAc in heptanes) to give tert-butyl N-({4-cyano-1-[3-iodo-1-(oxan-2-yl)-1H-pyrazolo[3,4-b]pyrazin-6-yl]piperidin-4-yl}methyl)carbamate (325 mg, 0.5727 mmol).

Step c: Methyl 4-(([(tert-butoxy)carbonyl]amino)methyl)-1-[3-iodo-1-(oxan-2-yl)-1H-pyrazolo[3,4-b]pyrazin-6-yl]piperidine-4-carboxylate (325 mg, 0.5412 mmol), 1,2,3,4-tetrahydro-1,5-naphthyridine (79.8 mg, 0.5953 mmol), Xantphos G4 (104 mg, 0.1082 mmol), and sodium 2-methylpropan-2-olate (108 mg, 1.13 mmol) were weighed into a reaction vial. Evacuated and backfilled with N₂ (3×). Added toluene (5 mL). Heated to 80 C for 4 h. Filtered through a pad of celite and concentrated. Purified by flash silica gel chromatography (0-10% MeOH in EtOAc) to give tert-butyl N-((4-cyano-1-[1-(oxan-2-yl)-3-(1,2,3,4-tetrahydro-1,5-naphthyridin-1-yl)-1H-pyrazolo[3,4-b]pyrazin-6-yl]piperidin-4-yl)methyl)carbamate (217 mg, 0.3782 mmol).

Step d: A solution of tert-butyl N-((4-cyano-1-[1-(oxan-2-yl)-3-(1,2,3,4-tetrahydro-1,5-naphthyridin-1-yl)-1H-pyrazolo[3,4-b]pyrazin-6-yl]piperidin-4-yl)methyl)carbamate (60 mg, 0.1045 mmol) in methanol (1.5 mL) and ammonia in methanol (7N, 0.5 mL) was cycled through H-Cube (10% Pd/C cartridge, 10 bar, 50 C, 1 mL/min) for 3 h. Concentrated and purified by flash silica gel chromatography using methanol in DCM (0-10%, with 1% NH₄OH). Recovered tert-butyl N-([4-(aminomethyl)-1-[1-(oxan-2-yl)-3-(1,2,3,4-tetrahydro-1,5-naphthyridin-1-yl)-1H-pyrazolo[3,4-b]pyrazin-6-yl]piperidin-4-yl]methyl)carbamate (28.0 mg, 0.04846 mmol). Dissolved material in methanol (1 mL). Added conc. HCl (200 uL) and stirred at rt for 2 h. Concentrated, chased with toluene (3×) to give a residue. Added ethyl acetate and sonicated. Collected precipitate by filtration to give 1-[4-(aminomethyl)-1-[3-(1,2,3,4-tetrahydro-1,5-naphthyridin-1-yl)-1H-pyrazolo[3,4-b]pyrazin-6-yl]piperidin-4-yl]methanamine dihydrochloride (18.0 mg, 0.03859 mmol).

Synthesis of 2-amino-2-{1-[3-(1,2,3,4-tetrahydro-1,5-naphthyridin-1-yl)-1H-pyrazolo[3,4-b]pyrazin-6-yl]piperidin-4-yl}acetic acid dihydrochloride, Compound 178

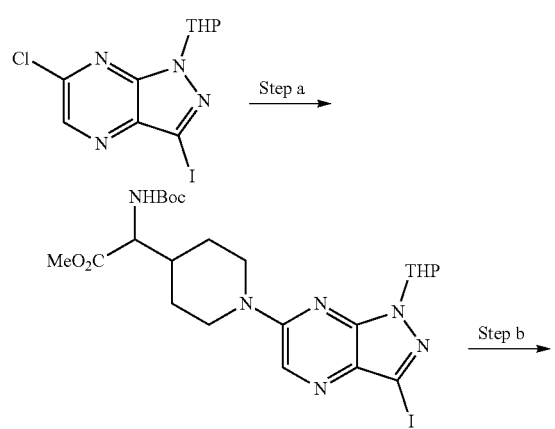

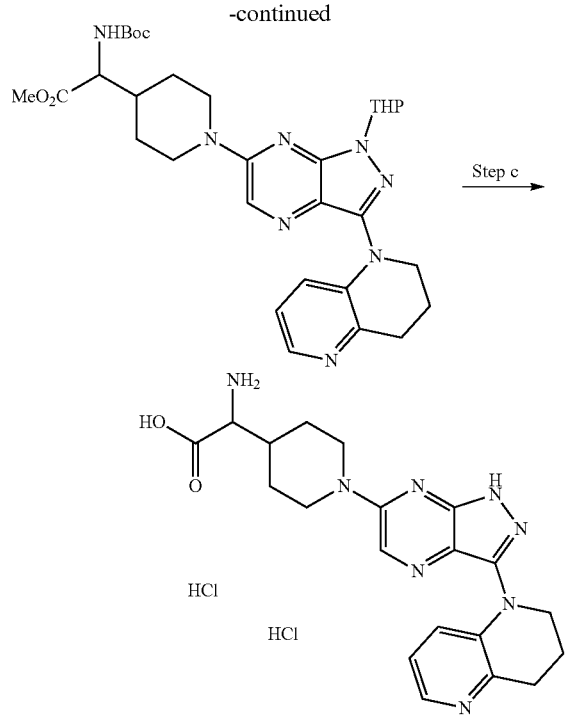

Step a: To a solution of 6-chloro-3-iodo-1-(oxan-2-yl)-1H-pyrazolo[3,4-b]pyrazine (500 mg, 1.37 mmol) and methyl 2-{[(tert-butoxy)carbonyl]amino}-2-(piperidin-4-yl)acetate (373 mg, 1.37 mmol) in DMF (5 mL) was added CsF (624 mg, 4.11 mmol). The mixture was heated to 80° C. for 12 hours. LCMS indicated the main peak with desired MS. The mixture was diluted with ethyl acetate (50 mL), washed with H2O (10 mL×3) and brine (20 mL), dried over anhydrous Na2SO4, filtered and concentrated. The residue was purified by silica column (Ethyl acetate in Petroleum 0~50%) to give the desired product of methyl 2-{[(tert-butoxy)carbonyl]amino}-2-{1-[3-iodo-1-(oxan-2-yl)-1H-pyrazolo[3,4-b]pyrazin-6-yl]piperidin-4-yl}acetate (660 mg, 80% yield) as a yellow solid.

Step b: To a mixture of methyl 2-{[(tert-butoxy)carbonyl]amino}-2-{1-[3-iodo-1-(oxan-2-yl)-1H-pyrazolo[3,4-b]pyrazin-6-yl]piperidin-4-yl}acetate (200 mg, 0.33 mmol), 1,2,3,4-tetrahydro-1,5-naphthyridine (53.6 mg, 0.40 mmol), RuPhos (31 mg, 0.067 mmol) and Cs2CO3 (327 mg, 1.0 mmol) in PhMe (5 mL) was added RuPhos-Pd-G4 (28.4 mg, 0.033 mmol). The mixture was heated to 100° C., and stirred for 12 hours. LCMS showed 3 was consumed completely and the desired product formed. The mixture was concentrated in vacuum. The residue was purified by silica column (Ethyl acetate in Petroleum 0~100%) to give the desired product of methyl 2-{[(tert-butoxy)carbonyl]amino}-2-{1-[1-(oxan-2-yl)-3-(1,2,3,4-tetrahydro-1,5-naphthyridin-1-yl)-1H-pyrazolo[3,4-b]pyrazin-6-yl]piperidin-4-yl}acetate (150 mg, 74.2% yield) as a yellow solid.

Step c: To a solution methyl 2-{[(tert-butoxy)carbonyl]amino}-2-{1-[1-(oxan-2-yl)-3-(1,2,3,4-tetrahydro-1,5-naphthyridin-1-yl)-1H-pyrazolo[3,4-b]pyrazin-6-yl]piperidin-4-yl) acetate (140 mg, 0.23 mmol) in MeOH (2 mL)/H2O (0.5 mL) was added LiOH.H2O (19.3 mg, 0.46 mmol). The solution was stirred for 2 h at 25° C. LCMS indicated 5 was hydrolyzed completely. The mixture was concentrated in vacuum. 4 M HCl/dioxane (15 mL) was added, the reaction mixture was stirred at 25° C. for 1 hour. LCMS showed the desired product peak formed. The solution was concentrated in vacuum. The residue was purified by prep. HPLC (HCl) to give 2-amino-2-{1-[3-(1,2,3,4-tetrahydro-1,5-naphthyridin-1-yl)-1H-pyrazolo[3,4-b]pyrazin-6-yl]piperidin-4-yl}acetic acid dihydrochloride (52.1 mg, yield 46.9%) as a yellow solid.

Synthesis of 1-(6-(4-ethyl-4-methylpiperidin-1-yl)-1H-pyrazolo[3,4-b]pyrazin-3-yl)-1,2,3,4-tetrahydro-1,5-naphthyridine, Compound 179

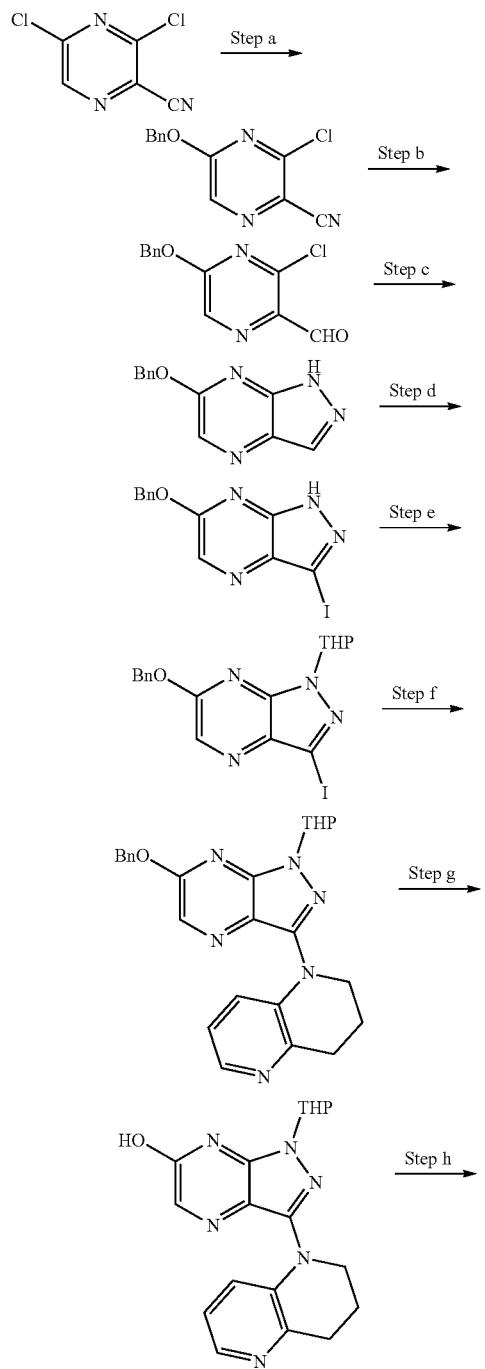

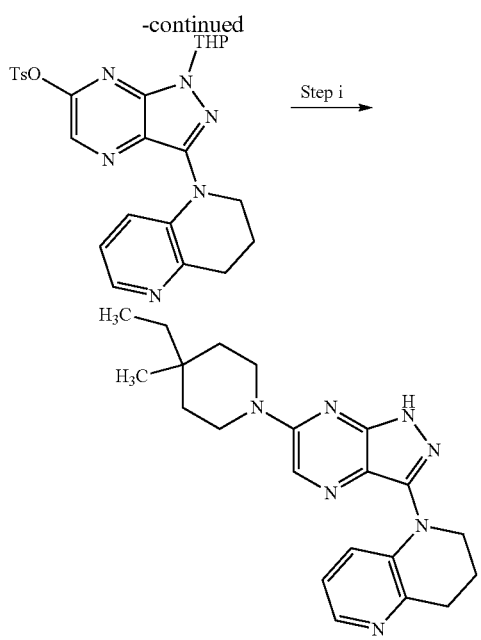

Step a: A solution of benzyl alcohol (30.8 g, 0.285 mol, 29.6 mL) in dry THF (450 mL) was cooled to 0° C. NaH (12.4 g, 0.311 mol, 60% purity, 1.2 eq.) was added slowly to the mixture at 0° C. After addition, the mixture was stirred at 25 C for 1 hour. The resultant solution was then added to a solution of 3,5-dichloropymazine-2-carbonitrile (45.0 g, 258 mmol, 1.0 eq.) in dry THF (450 mL) at −78° C. The mixture was stirred at −78° C. for 30 minutes. After this time, the reaction mixture was poured into water (1.0 L) and extracted with EtOAc (1.0 L×3). The combined organics were washed with brine (500 mL), dried over $Na_2SO_4$, filtered, and concentrated under reduced pressure. The residue was triturated with 10:1 petroleum ether/EtOAc (1.50 L) at 25° C. for 30 minutes. The resulting suspension was filtered and the filter cake washed with petroleum ether (200 mL). The filter cake was dried under reduced pressure to give 5-(benzyloxy)-3-chloropyrazine-2-carbonitrile (79.3 g, 300 mmol, 57.9% yield, 93% purity) as a white solid: ESMS $(M+H)^+$=245.9; $^1$H-NMR (400 MHz, $CDCl_3$) δ 8.23 (s, 1H), 7.5-7.39 (m, 5H), 5.48 (s, 2H).

Step b: To a solution of 5-(benzyloxy)-3-chloropyrazine-2-carbonitrile (20.0 g, 75.6 mmol, 1.0 eq) in dry THF (200 mL) at −78° C. was added DIBAL-H (1.0 M, 227 mL, 3.0 eq) under an atmosphere of nitrogen. The mixture was stirred at −78° C. for 1 hour. The reaction was quenched by the addition of a solution of 10% aqueous HOAc (2.0 L) at −78° C. and the mixture extracted with EtOAc (1.50 L×3). Saturated $NaHCO_3$ (aq) was added to the organics with agitation until a pH of 8-9 was obtained. The organic layer was washed with brine (1.0 L), dried over $Na_2SO_4$, filtered, and concentrated under reduced pressure. The residue was triturated with a mixture of EtOAc (300 mL) and petroleum ether (6.0 L). The resulting precipitate was collected by filtration to give 5-(benzyloxy)-3-chloropyrazine-2-carbaldehyde (11.3 g, crude) as a brown oil: ESMS $(2M+H)^+$=497.9; $^1$H-NMR (400 MHz, $CDCl_3$) δ 10.27 (s, 1H), 8.33 (s, 1H), 7.50-7.40 (m, 5H), 5.51 (s, 2H).

Step c: A mixture of 5-(benzyloxy)-3-chloropyrazine-2-carbaldehyde (11.3 g, 45.4 mmol, 1.0 eq) and hydrazine hydrate (6.96 g, 137 mmol, 6.76 mL, 3.0 eq) in EtOH (113 mL) was stirred at 25° C. Triethylamine (23.0 g, 228 mmol, 31.6 mL, 5.0 eq) was added and the reaction mixture heated to 80° C., and stirred at this temperature for 16 hours. The reaction mixture was cooled and concentrated under reduced pressure to give a residue. The residue was dissolved with EtOAc (500 mL) and washed with sat. aq. NH$_4$Cl (500 mL). The organics were dried over Na$_2$SO$_4$, filtered, and concentrated to give 6-(benzyloxy)-1H-pyrazolo[3,4-b]pyrazine (9.5 g) as a brown solid: ESMS (M+H)$^+$=227.0; $^1$H-NMR (400 MHz, CDCl$_3$) δ 11.07 (br s, 1H), 8.29 (s, 1H), 8.25 (s, 1H), 7.50-7.47 (m, 2H), 7.44-7.36 (m, 3H), 5.46 (s, 2H).

Step d: To a solution of 6-(benzyloxy)-1H-pyrazolo[3,4-b]pyrazine (9.50 g, 35.4 mmol, 1.0 eq) in DMF (190 mL) was added N-iodosuccinimide (10.4 g, 46 mmol, 1.3 eq) at 25° C. The mixture was then heated to 80° C., and stirred for 1 hour. The reaction was cooled to 25° C., and then poured into ice-water (2.0 L). The mixture was extracted with EtOAc (2.0 L). The organic layer was washed with 10% aq. Na$_2$SO$_3$ (500 mL×2) and brine (500 mL), dried over Na$_2$SO$_4$, filtered, and concentrated under reduced pressure to give 6-(benzyloxy)-3-iodo-1H-pyrazolo[3,4-b]pyrazine (24.7 g, 68.5 mmol, 96.8% yield) as a yellow solid: ESMS (M+H)$^+$=352.8; $^1$H-NMR (400 MHz, CDCl$_3$) δ 10.73 (br s, 1H), 8.27 (s, 1H), 8.03 (s, 1H), 7.50-7.47 (m, 2H), 7.44-7.38 (m, 3H), 5.46 (s, 2H).

Step e: To a solution of 6-(benzyloxy)-3-iodo-1H-pyrazolo[3,4-b]pyrazine (12.1 g, 34.3 mmol, 1.0 eq) in DCM (20 mL) was added dihydropyran (8.65 g, 103 mmol, 9.40 mL, 3.0 eq) and TsOH.H$_2$O (1.96 g, 10.3 mmol, 0.3 eq). The mixture was stirred at 25° C. for 30 minutes. Three reaction batches in parallel were combined for work-up. The mixture was poured into saturated NaHCO$_3$ solution (250 mL) and then extracted with EtOAc (250 mL×2). The combined organics were washed with brine (500 mL), dried over Na$_2$SO$_4$, filtered, and concentrated under reduced pressure. The residue was purified by silica gel chromatography (30:1 petroleum ether/EtOAc) to give 6-(benzyloxy)-3-iodo-1-(tetrahydro-2H-pyran-2-yl)-1H-pyrazolo[3,4-b]pyrazine (34.0 g, 73.4 mmol, 71.5% yield) as a yellow solid: ESMS (M+H)$^+$=436.8; $^1$H-NMR (400 MHz, CDCl$_3$) δ 8.24 (s, 1H), 7.51 (br d, J=6.8 Hz, 2H), 7.45-7.37 (m, 3H), 5.87 (dd, J=2.6, 10.2 Hz, 1H), 5.50 (d, J=1.6 Hz, 2H), 4.19-4.11 (m, 1H), 3.84-3.75 (m, 1H), 2.74-2.61 (m, 1H), 2.23-2.14 (m, 1H), 1.99 (br dd, J=2.4, 12.8 Hz, 1H), 1.86-1.75 (m, 2H), 1.69-1.63 (m, 1H).

Step f: To a mixture of 6-(benzyloxy)-3-iodo-1-(tetrahydro-2H-pyran-2-yl)-1H-pyrazolo[3,4-b]pyrazine (12.9 g, 27.9 mmol, 1.0 eq) and 1,2,3,4-tetrahydro-1,5-naphthyridine (3.74 g, 27.9 mmol, 1.0 eq) in toluene (130 mL) was added RuPhos (2.60 g, 5.57 mmol, 0.2 eq), Pd$_2$(dba)$_3$ (766 mg, 836 µmol, 0.03 eq) and Cs$_2$CO$_3$ (27.3 g, 83.6 mmol, 3.0 eq) at 25° C. under an atmosphere of nitrogen. The mixture was stirred at 100° C. for 20 hours. The mixture was filtered and the filtrate was added to water (500 mL) and extracted with EtOAc (500 mL). The combined organics were washed with 0.5 M aq HCl (200 mL). The aqueous layer was further extracted with DCM (200 mL×2). The combined organics were washed with sat. NaHCO$_3$ (200 mL), brine (200 mL), dried over Na$_2$SO$_4$, filtered, and concentrated under reduced pressure. The residue was purified by flash silica gel chromatography (ISCO®; 330 g SepaFlash® Silica Flash Column, 10-30% EtOAc/petroleum Ether® 120 mL/min) to give 1-(6-(benzyloxy)-1-(tetrahydro-2H-pyran-2-yl)-1H-pyrazolo[3,4-b]pyrazin-3-yl)-1,2,3,4-tetrahydro-1,5-naphthyridine (17.6 g, 35.8 mmol, 64.3% yield) as a yellow solid: ESMS (M+H)+=443.1; $^1$H-NMR (400 MHz, CDCl$_3$) δ 8.12 (s, 1H), 8.05 (dd, J=1.2, 4.6 Hz, 1H), 7.70 (dd, J=1.2, 8.4 Hz, 1H), 7.52 (br d, J=6.8 Hz, 2H), 7.45-7.35 (m, 3H), 6.97 (dd, J=4.6, 8.4 Hz, 1H), 5.86 (dd, J=2.4, 10.2 Hz, 1H), 5.50 (d, J=2.2 Hz, 2H), 4.19-4.12 (m, 2H), 3.86-3.76 (m, 1H), 3.07 (t, J=6.6 Hz, 2H), 2.73-2.58 (m, 1H), 2.25-2.13 (m, 3H), 1.98 (br d, J=12.8 Hz, 1H), 1.80 (br t, J=9.7 Hz, 2H), 1.74-1.63 (m, 2H).

Step g: To a solution of 1-(6-(benzyloxy)-1-(tetrahydro-2H-pyran-2-yl)-1H-pyrazolo[3,4-b]pyrazin-3-yl)-1,2,3,4-tetrahydro-1,5-naphthyridine (9.0 g, 20.4 mmol, 1.0 eq) in MeOH (950 mL) was added Pd(OH)$_2$/C (1.14 g, 4.07 mmol, 50% wt, 0.20 eq) under an atmosphere of nitrogen. The suspension was degassed under vacuum and purged with hydrogen gas several times. The mixture was stirred under an atmosphere of hydrogen (50 psi) at 25° C. for 30 hours. Two reaction batches in parallel were combined for work-up. The mixture was filtered and the filter cake was dried under reduced pressure to give 3-(3,4-dihydro-1,5-naphthyridin-1(2H)-yl)-1-(tetrahydro-2H-pyran-2-yl)-1H-pyrazolo[3,4-b]pyrazin-6-ol (13.7 g, crude) contained in Pd(OH)$_2$/C as a blackish solid: $^1$H-NMR (400 MHz, DMSO-d$_6$) δ 12.60 (br s, 1H), 8.05-7.91 (m, 2H), 7.64 (br d, J=8.4 Hz, 1H), 7.02 (dd, J=4.4, 8.2 Hz, 1H), 5.68 (br d, J=8.7 Hz, 1H), 4.02 (br s, 2H), 3.94 (br d, J=11.2 Hz, 1H), 3.67-3.58 (m, 1H), 2.94 (br t, J=6.4 Hz, 2H), 2.40-2.30 (m, 1H), 2.11-1.98 (m, 3H), 1.89 (br d, J=10.8 Hz, 1H), 1.71 (br s, 1H), 1.55 (br s, 2H).

Step h: To a mixture of 3-(3,4-dihydro-1,5-naphthyridin-1(2H)-yl)-1-(tetrahydro-2H-pyran-2-yl)-1H-pyrazolo[3,4-b]pyrazin-6-ol (7.0 g, 19.9 mmol, 1.0 eq) in dry DCM (70 mL) was added diisopropylethylamine (2.82 g, 21.9 mmol, 3.81 mL, 1.1 eq) at 25° C. The mixture was cooled to 0° C., and added to a solution of p-TsCl (4.54 g, 23.9 mmol, 1.20 eq) in dry DCM (70 mL) at 0° C. The mixture was stirred at 0-10° C. for 1 hour. Two reaction batches run in parallel were combined for work-up. The reaction mixture was poured into ice-water (250 mL) and extracted with EtOAc (250 mL×3). The combined organics were washed with brine (200 mL), dried over Na$_2$SO$_4$, filtered, and concentrated under reduced pressure. The residue was purified by silica gel chromatography (20-50% petroleum ether/EtOAc) to give 3-(3,4-dihydro-1,5-naphthyridin-1(2H)-yl)-1-(tetrahydro-2H-pyran-2-yl)-1H-pyrazolo[3,4-b]pyrazin-6-yl 4-methylbenzenesulfonate (16.4 g, 30.1 mmol, 75.6% yield) as a red foam: ESMS (M+H)+=507.1; $^1$H-NMR (400 MHz, CDCl$_3$) δ: 8.23 (s, 1H), 8.10 (dd, J=1.4, 4.6 Hz, 1H), 8.00 (d, J=8.4 Hz, 2H), 7.76 (dd, J=1.4, 8.4 Hz, 1H), 7.41 (d, J=8.2 Hz, 2H), 7.00 (dd, J=4.6, 8.4 Hz, 1H), 5.68 (dd, J=2.4, 10.5 Hz, 1H), 4.19-4.13 (m, 2H), 4.10 (br s, 1H), 3.72 (dt, J=2.4, 11.2 Hz, 1H), 3.06 (t, J=6.6 Hz, 2H), 2.59-2.51 (m, 1H), 2.49 (s, 3H), 2.22-2.11 (m, 3H), 1.91 (br dd, J=2.2, 12.9 Hz, 1H), 1.79-1.71 (m, 2H), 1.64 (br d, J=6.8 Hz, 1H), 6.8 Hz, 1H).

Step i: To a solution of 3-(3,4-dihydro-1,5-naphthyridin-1(2H)-yl)-1-(tetrahydro-2H-pyran-2-yl)-1H-pyrazolo[3,4-b]pyrazin-6-yl 4-methylbenzenesulfonate (50 mg, 0.1 mmol) and 4-ethyl-4-methylpiperidine (16 mg, 0.13 mmol, CAS #4045-31-2) in dioxane (1 mL) was added diisopropylethylamine (50 µL, 0.3 mmol). The mixture was stirred for 16 hours at 120° C., cooled, then concentrated under reduced pressure. The residue was diluted into MeOH (1 mL) and HCl in dioxane (200 µL, 50 mmol) was added and the mixture was stirred for 16 hours at room temperature. The solution was concentrated under reduced pressure and the residue was purified by reversed phase chromatography using a gradient of 35-55% MeCN in 10 mM AmForm to afford 1-(6-(4-ethyl-4-methylpiperidin-1-yl)-1H-pyrazolo[3,4-b]pyrazin-3-yl)-1,2,3,4-tetrahydro-1,5-naphthyridine as a yellow solid (16.7 mg, 45%) after lyophilization: $^1$H-NMR (500 MHz, DMSO-d$_6$) δ 12.56 (s, 1H), 8.28 (s, 1H), 7.89 (dd, J=4.6, 1.4 Hz, 1H), 7.48 (dd, J=8.4, 1.4 Hz, 1H), 6.96 (dd, J=8.4, 4.6 Hz, 1H), 3.97-3.92 (m, 2H), 3.90-3.83 (m, 2H), 3.54-3.47 (m, 2H), 2.93 (t, J=6.5 Hz, 2H), 2.09-2.03 (m, 2H), 1.45-1.35 (m, 4H), 1.32 (q, J=7.5 Hz, 2H), 0.94 (s, 3H), 0.82 (t, J=7.5 Hz, 3H).

The following compounds were made via the same route used for Compound 179, using commercially available starting materials or intermediates prepared as described above: Compound 76, Compound 137, Compound 138, Compound 139, Compound 140, Compound 141, Compound 142, Compound 143, Compound 144, Compound 145, Compound 146, Compound 147, Compound 148, Compound 149, Compound 150, Compound 151, Compound 152, Compound 153, Compound 154, Compound 155, Compound 156, Compound 157, Compound 158, Compound 159, Compound 160, Compound 161, Compound 162, Compound 167, Compound 168, Compound 176, Compound 211, Compound 212, Compound 213, Compound 214, and Compound 215.

Synthesis of 4-(aminomethyl)-1-(3-(3,4-dihydro-1,5-naphthyridin-1(2H)-yl)-1H-pyrazolo[3,4-b]pyrazin-6-yl)piperidine-4-carboxamide, Compound 180

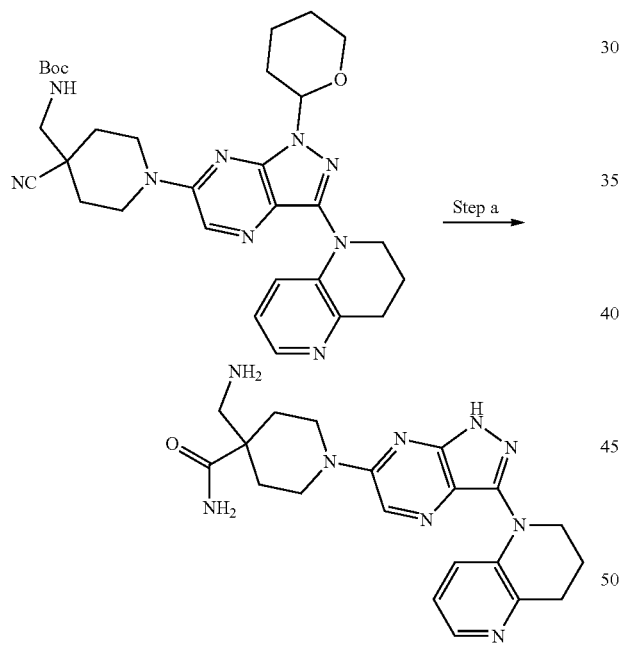

Step a: To a solution of tert-butyl N-((4-cyano-1-[1-(oxan-2-yl)-3-(1,2,3,4-tetrahydro-1,5-naphthyridin-1-yl)-1H-pyrazolo[3,4-b]pyrazin-6-yl]piperidin-4-yl)methyl)carbamate (Compound 177, Step c, 92 mg, 0.1603 mmol) in DMSO (10 mL) at 0 C was added 50% aq. hydrogen peroxide (500 uL, 0.1603 mmol) (1 mL) and dipotassium carbonate (44.3 mg, 0.3206 mmol). Heated at 60 C for 1 h. Purified by HPLC using 10-40% acetonitrile in water w/0.1% formic acid. Combined fractions, concentrated, and redissolved reside in MeOH (2 mL). Added conc. HCl (200 uL). Stirred at rt overnight. Concentrated, then purified by HPLC using 10-40% acetonitrile in water w/0.1% NH4OH to give 4-(aminomethyl)-1-[3-(1,2,3,4-tetrahydro-1,5-naphthyridin-1-yl)-1H-pyrazolo[3,4-b]pyrazin-6-yl]piperidine-4-carboxamide (10.0 mg, 0.02454 mmol).

Synthesis of 1-{6-[4-(aminomethyl)-4-methylpiperidin-1-yl]-1H-pyrazolo[3,4-b]pyrazin-3-yl}-4-(difluoromethyl)-1,2,3,4-tetrahydroquinoline-6-carbonitrile, Compound 181

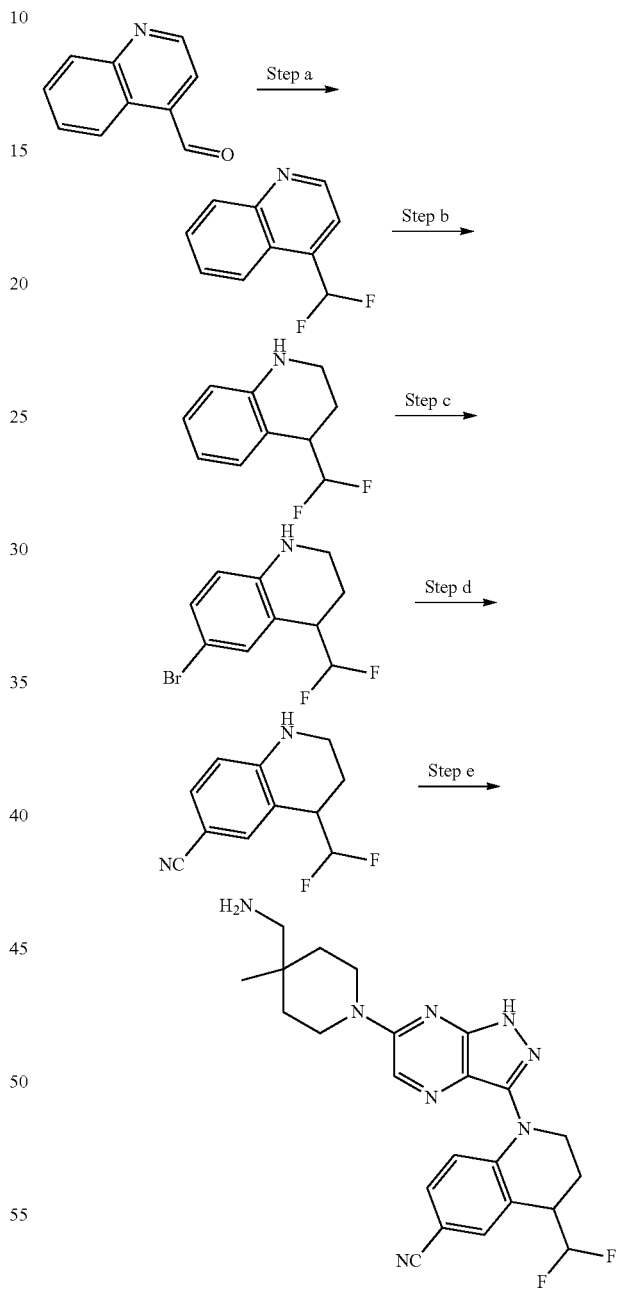

Step a: Quinoline-4-carbaldehyde (1 g, 6.36 mmol) in DCM (20 mL) was cooled to 0° C., and charged with DAST (2.56 g, 15.9 mmol). The mixture was stirred for 1 hr at 0° C. then let warm to rt and stirred for 20 hrs. The reaction mixture was cooled to −10° C. carefully quenched with sat. bicarb and extracted with DCM. The organic layer was concentrated and purified by flash silica gel chromatography (eluting with ethyl acetate:heptanes=25:75 to 50:50) to afford 4-(difluoromethyl)quinoline (890 mg) as a colorless oil that crystallized to a white solid upon standing. LCMS: [M+H]⁺ 180.

Step b: A resealable reaction vial was charged with 4-(difluoromethyl)quinoline (435 mg, 2.42 mmol), 3,5-diethyl 2,6-dimethyl-1,4-dihydropyridine-3,5-dicarboxylate (1.53 g, 6.05 mmol), diphenoxyphosphinic acid (30.2 mg, 0.121 mmol), toluene (6 mL). The vial was sealed the mixture was stirred at 50° C. for 20 hrs. The reaction mixture was concentrated and purified by flash silica gel chromatography (eluting with ethyl acetate:heptanes=0:100 to 30:100) to afford 4-(difluoromethyl)-1,2,3,4-tetrahydroquinoline (375 mg) as a colorless oil. LCMS: [M+H]⁺ 184.

Step c: 4-(difluoromethyl)-1,2,3,4-tetrahydroquinoline (325 mg, 1.77 mmol) in DMF (5 mL) was cooled to 0° C., and charged with 1-bromopyrrolidine-2,5-dione (315 mg, 1.77 mmol) in DMF (1 mL). The resulting solution was stirred at 0° C. for 30 min. The mixture was charged with water and extracted with ethyl acetate, dried and concentrated and purified by flash silica gel chromatography (eluting with ethyl acetate:heptanes=0:100 to 100:0) to afford 6-bromo-4-(difluoromethyl)-1,2,3,4-tetrahydroquinoline (450 mg) as yellow solid. LCMS: [M+H]⁺ 261/263.

Step d: A resealable reaction vial was charged with 6-bromo-4-(difluoromethyl)-1,2,3,4-tetrahydroquinoline (230 mg, 0.8775 mmol), zincdicarbonitrile (205 mg, 1.75 mmol), tBuBrettPhos/Pd G3 (69.7 mg, 0.08775 mmol), dioxane (6 mL) and water (1 mL). The mixture was bubbled with nitrogen for 10 min. The vial was sealed, and the mixture was stirred at 90° C. for 2 hrs. The reaction mixture concentrated and purified by flash silica gel chromatography (eluting with ethyl acetate:heptanes=0:100 to 40:60) to afford 4-(difluoromethyl)-1,2,3,4-tetrahydroquinoline-6-carbonitrile (140 mg) as a yellow solid. LCMS: [M+H]⁺ 209.

Step e: 1-{6-[4-(aminomethyl)-4-methylpiperidin-1-yl]-1H-pyrazolo[3,4-b]pyrazin-3-yl}-4-(difluoromethyl)-1,2,3,4-tetrahydroquinoline-6-carbonitrile (36 mg) (LCMS: [M+H]⁺ 453) was prepared using tert-butyl N-[(3S,4S)-8-[3-iodo-1-(oxan-2-yl)-1H-pyrazolo[3,4-b]pyrazin-6-yl]-3-methyl-2-oxa-8-azaspiro[4.5]decan-4-yl]carbamate (63 mg, 0.113 mmol), and 4-(difluoromethyl)-1,2,3,4-tetrahydroquinoline-6-carbonitrile (25 mg, 0.118 mmol) using conditions described for the preparation of Compound 33.

Synthesis of 1-(4-methyl-1-{3-[(4S)-4-methyl-6-(1,2,4-oxadiazol-3-yl)-1,2,3,4-tetrahydroquinolin-1-yl]-1H-pyrazolo[3,4-b]pyrazin-6-yl}piperidin-4-yl)methanamine, Compound 183

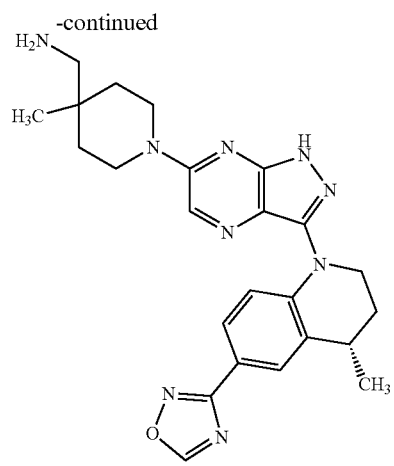

Step a: tert-butyl N-[(1-{3-[(4S)-6-cyano-4-methyl-1,2,3,4-tetrahydroquinolin-1-yl]-1-(oxan-2-yl)-1H-pyrazolo[3,4-b]pyrazin-6-yl}-4-methylpiperidin-4-yl)methyl]carbamate (238 mg, 0.3961 mmol) in EtOH (5 mL) was charged with hydroxylamine (192 µL, 3.16 mmol). The vial was sealed, and the mixture heated to 55° C. for 6 hrs. The mixture was concentrated and chased with EtOH. The residue was dissolved in (diethoxymethoxy)ethane (1.63 mL, 9.90 mmol), TFA (3 drops) and heated to 60° C. for 4 hrs. The reaction was partitioned between ethyl acetate and water, dried and purified by flash silica gel chromatography (eluting with ethyl acetate:heptanes=20:80 to 75:25) to afford tert-butyl N-[(4-methyl-1-{3-[(4S)-4-methyl-6-(1,2,4-oxadiazol-3-yl)-1,2,3,4-tetrahydroquinolin-1-yl]-1-(oxan-2-yl)-1H-pyrazolo[3,4-b]pyrazin-6-yl}piperidin-4-yl)methyl]carbamate (190 mg). The residue was dissolved in MeOH (5 mL) and 4N HCl (1 mL) and heated to 60° C. for 2 hrs. The solvent was removed, chased with MeOH and purified on prep-HPLC (10-40% ACN/water+0.1% FA) to afford 1-(4-methyl-1-{3-[(4S)-4-methyl-6-(1,2,4-oxadiazol-3-yl)-1,2,3,4-tetrahydroquinolin-1-yl]-1H-pyrazolo[3,4-b]pyrazin-6-yl}piperidin-4-yl)methanamine (117 mg) as a yellow solid. LCMS: [M+H]+ 460.

Synthesis of 1-(4-(6-(4-(aminomethyl)-4-methylpiperidin-1-yl)-1H-pyrazolo[3,4-b]pyrazin-3-yl)-3,4-dihydroquinoxalin-1(2H)-yl)-2-hydroxyethan-1-one, Compound 194

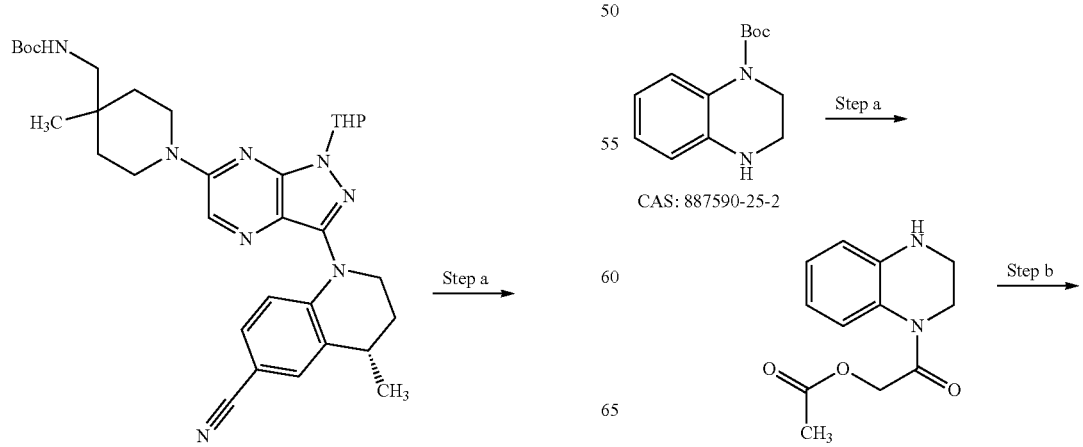

-continued

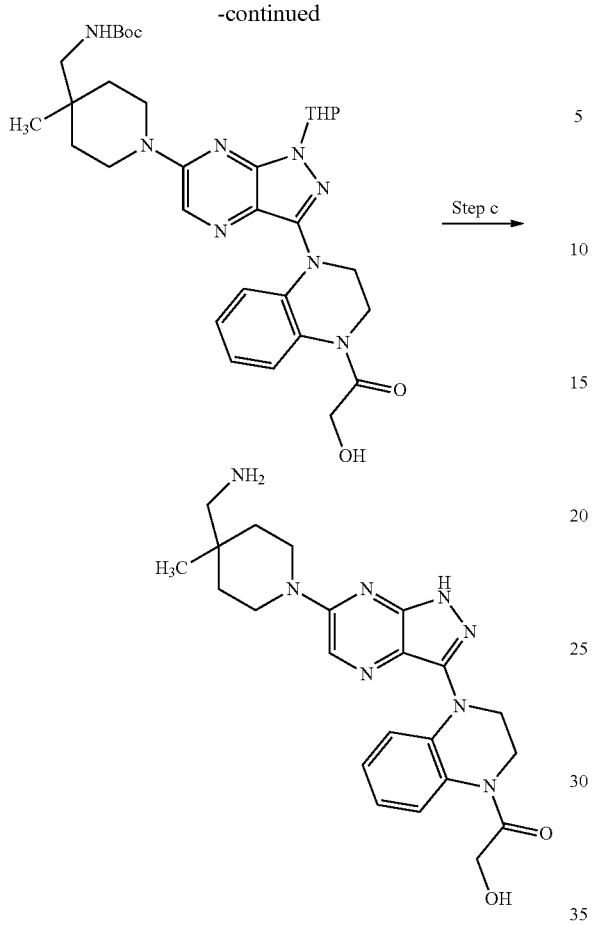

Step a: A reaction vial was charged with tert-butyl 1,2,3,4-tetrahydroquinoxaline-1-carboxylate (150 mg, 0.640 mmol) (CAS:887590-25-2) in DMF (1.28 mL) and TEA (0.356 mL) was added, followed by 2-chloro-2-oxoethyl acetate (0.082 mL, 0.768 mmol). The reaction was stirred at ambient temperature for 45 min before the addition of EtOAc and sat. sodium bicarbonate. The organic layer was extracted with EtOAc (3×), and the combined organic extracts were concentrated and purified via silica gel chromatography (10-100% EtOAc in hexanes) to yield tert-butyl 4-(2-acetoxyacetyl)-3,4-dihydroquinoxaline-1(2H)-carboxylate. This material was dissolved in dichloromethane (4.0 mL) and trifluoroacetic acid (0.5 mL) was added and the reaction stirred for 45 min. Solvent was then evaporated and the residue was purified via silica gel chromatography (10-100% EtOAc in hexanes) to furnish 2-(3,4-dihydroquinoxalin-1(2H)-yl)-2-oxoethyl acetate (96.0 mg, 0.410 mmol) in 64% yield over two steps. LCMS: [M+H]+ 235.2.

Step b: A resealable reaction vial was charged with tert-butyl ((1-(3-iodo-1-(tetrahydro-2H-pyran-2-yl)-1H-pyrazolo[3,4-b]pyrazin-6-yl)-4-methylpiperidin-4-yl)methyl)carbamate (80.0 mg, 0.144 mmol), 2-(3,4-dihydroquinoxalin-1(2H)-yl)-2-oxoethyl acetate (37.0 mg, 0.158 mmol), methanesulfonato[4,5-bis(diphenylphosphino)-9,9-dimethylxanthene](2'-methylamino-1,1'-biphenyl-2-yl)palladium(II) (13.8 mg, 0.0144 mmol) and sodium tert-butoxide (20.7 mg, 0.216 mmol) before the vessel was evacuated and backfilled with nitrogen (3×). Following the addition of toluene (2.0 mL) the reaction was heated to 80° C. for 16 h. The reaction was cooled, and the organic layer was partitioned between EtOAc and water. Following extraction of the organic layer with EtOAc (3×), the residue was concentrated and purified via silica gel chromatography (0-20% MeOH in dichloromethane with 0.1% $NH_3$ $H_2O$) to furnish tert-butyl (((1-(3-(4-(2-hydroxyacetyl)-3,4-dihydroquinoxalin-1(2H)-yl)-1-(tetrahydro-2H-pyran-2-yl)-1H-pyrazolo[3,4-b]pyrazin-6-yl)-4-methylpiperidin-4-yl)methyl)carbamate (13.0 mg, 0.021 mmol). LCMS: [M+H]+ 621.6.

Step c: To a round bottom flask containing tert-butyl (((1-(3-(4-(2-hydroxyacetyl)-3,4-dihydroquinoxalin-1(2H)-yl)-1-(tetrahydro-2H-pyran-2-yl)-1H-pyrazolo[3,4-b]pyrazin-6-yl)-4-methylpiperidin-4-yl)methyl)carbamate (13.0 mg, 0.021 mmol) in methanol (2.0 mL) was added HCl (4.0M in dioxane, 0.5 mL). After stirring at ambient temperature for 15 min, the solvent was evaporated and the residue was purified via prep HPLC (5-30% ACN in $H_2O$ with 0.1% $CH_2OH$) to furnish 1-(4-(6-(4-(aminomethyl)-4-methylpiperidin-1-yl)-1H-pyrazolo[3,4-b]pyrazin-3-yl)-3,4-dihydroquinoxalin-1(2H)-yl)-2-hydroxyethan-1-one (0.60 mg, 0.0014 mmol) in 7% yield. LCMS: [M+H]+ 437.5.

Synthesis of 1-(4-methyl-1-{3-[(4S)-4-methyl-6-(1,3-thiazol-2-yl)-1,2,3,4-tetrahydro-1,5-naphthyridin-1-yl]-1H-pyrazolo[3,4-b]pyrazin-6-yl}piperidin-4-yl)methanamine hydrochloride and 1-(4-methyl-1-{3-[(4R)-4-methyl-6-(1,3-thiazol-2-yl)-1,2,3,4-tetrahydro-1,5-naphthyridin-1-yl]-1H-pyrazolo[3,4-b]pyrazin-6-yl}piperidin-4-yl)methanamine hydrochloride, Compound 196 and Compound 197

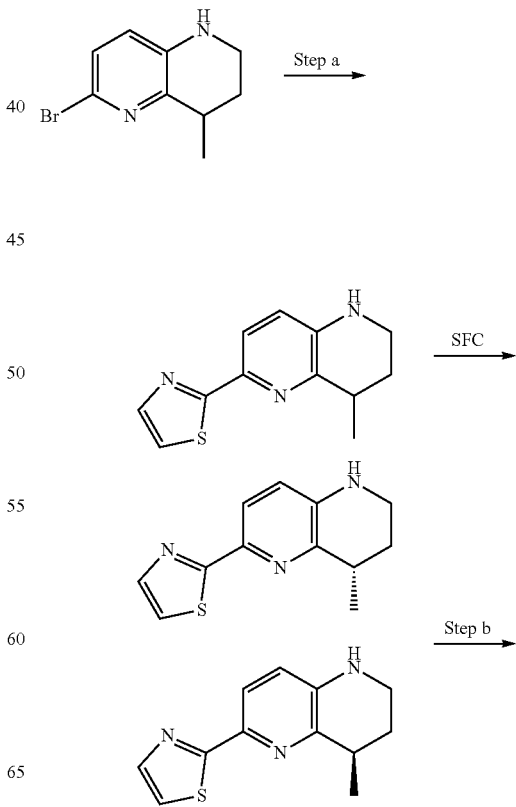

-continued

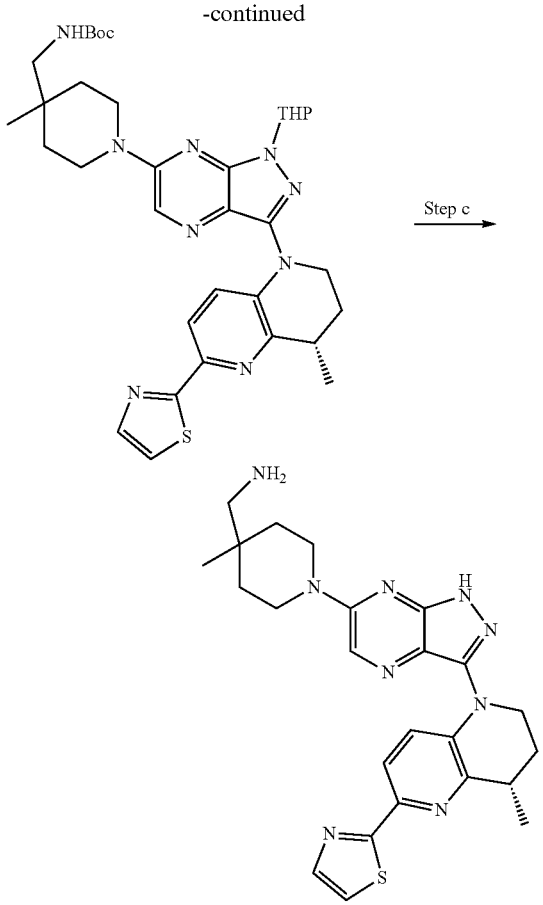

Step a: To a solution of 6-bromo-4-methyl-1,2,3,4-tetrahydro-1,5-naphthyridine (500.0 mg, 2.2 mmol) and 2-(tributylstannyl)-1,3-thiazole (905.0 mg, 2.4 mmol) in toluene (10.0 mL) was added Pd(PPh3)4 (254.0 mg, 220.0 umol). The reaction mixture was purged with N2 for 3 min, and the reaction was stirred at 110° C. for 12 hours under N2. LCMS showed the starting material was consumed completely and 26% desired product was formed. The reaction mixture was concentrated under reduced pressure. The residue was purified by column chromatography (Petroleum ether/Ethyl acetate=100:0 to 100:100). The product of 4-methyl-6-(1,3-thiazol-2-yl)-1,2,3,4-tetrahydro-1,5-naphthyridine (480.0 mg, 2.1 mmol, 94.4% yield) was obtained as a yellow solid. A portion of that solid (95.0 mg, 410.0 µmol) was used for SFC. Column: Phenomenex-Cellulose-2 (250×30 mm, 5 um). Condition: 0.1% NH3.H2O MeOH. Begin B 45%, end B 45%. Flow rate: 60 mL/min. The product of (4S)-4-methyl-6-(1,3-thiazol-2-yl)-1,2,3,4-tetrahydro-1,5-naphthyridine (40.0 mg, 172.0 µmol, 42.1% yield, a faster eluting isomer) was obtained as a yellow solid and (4R)-4-methyl-6-(1,3-thiazol-2-yl)-1,2,3,4-tetrahydro-1,5-naphthyridine (50.0 mg, 216.0 µmol, 52.7% yield, a slower eluting isomer) was obtained as a yellow solid. Stereochemistry was defined arbitrarily.

Step b: To a solution of tert-butyl N-((1-[3-iodo-1-(oxan-2-yl)-1H-pyrazolo[3,4-b]pyrazin-6-yl]-4-methylpiperidin-4-yl)methyl)carbamate (95.7 mg, 172.0 µmol) and (4S)-4-methyl-6-(1,3-thiazol-2-yl)-1,2,3,4-tetrahydro-1,5-naphthyridine (40.0 mg, 172.0 µmol) in toluene (5.0 mL) was added RuPhos-Pd-G4 (14.6 mg, 17.2 µmol), RuPhos (8.0 mg, 17.2 µmol) and Cs2CO3 (112.0 mg, 344.0 umol).

The reaction mixture was purged with N2 for 3 min, and the reaction was stirred at 100° C. for 12 hours under N2. LCMS showed the starting material was consumed completely and 61% desired product was formed. The reaction mixture was concentrated under reduced pressure. The residue was purified by column chromatography (Petroleum ether/Ethyl acetate=100:0 to 100:40). The product of tert-butyl N-[(4-methyl-1-{3-[(4S)-4-methyl-6-(1,3-thiazol-2-yl)-1,2,3,4-tetrahydro-1,5-naphthyridin-1-yl]-1-(oxan-2-yl)-1H-pyrazolo[3,4-b]pyrazin-6-yl)piperidin-4-yl)methyl]carbamate (110 mg, 166 µmol, 97.3% yield) was obtained as a yellow solid.

Step c: A solution of tert-butyl N-[(4-methyl-1-(3-[(4S)-4-methyl-6-(1,3-thiazol-2-yl)-1,2,3,4-tetrahydro-1,5-naphthyridin-1-yl]-1-(oxan-2-yl)-1H-pyrazolo[3,4-b]pyrazin-6-yl}piperidin-4-yl)methyl]carbamate (110.0 mg, 166.0 µmol) in HCl/MeOH (5.0 mL, 4M) was stirred at 10° C. for 1.5 hours. LCMS showed the starting material was consumed completely and 100% desired product was formed. The reaction mixture was concentrated under reduced pressure. The residue was diluted with MeOH (5.0 mL). The residue was purified by prep-HPLC (HCl). The product 1-(4-methyl-1-{3-[(4S)-4-methyl-6-(1,3-thiazol-2-yl)-1,2,3,4-tetrahydro-1,5-naphthyridin-1-yl]-1H-pyrazolo[3,4-b]pyrazin-6-yl}piperidin-4-yl)methanamine hydrochloride (81.0 mg, 158.0 µmol, 95.2% yield) was obtained as a yellow solid.

1-(4-methyl-1-{3-[(4R)-4-methyl-6-(1,3-thiazol-2-yl)-1,2,3,4-tetrahydro-1,5-naphthyridin-1-yl]-1H-pyrazolo[3,4-b]pyrazin-6-yl}piperidin-4-yl)methanamine hydrochloride was prepared by the same route, using (4R)-4-methyl-6-(1,3-thiazol-2-yl)-1,2,3,4-tetrahydro-1,5-naphthyridine.

Synthesis of 1-(4-methyl-1-{3-[(4S)-4-methyl-6-(4H-1,2,4-triazol-3-yl)-1,2,3,4-tetrahydro-1,5-naphthyridin-1-yl]-1H-pyrazolo[3,4-b]pyrazin-6-yl}piperidin-4-yl)methanamine and 1-(4-methyl-1-{3-[(4R)-4-methyl-6-(4H-1,2,4-triazol-3-yl)-1,2,3,4-tetrahydro-1,5-naphthyridin-1-yl]-1H-pyrazolo[3,4-b]pyrazin-6-yl}piperidin-4-yl)methanamine, Compound 198 and Compound 199

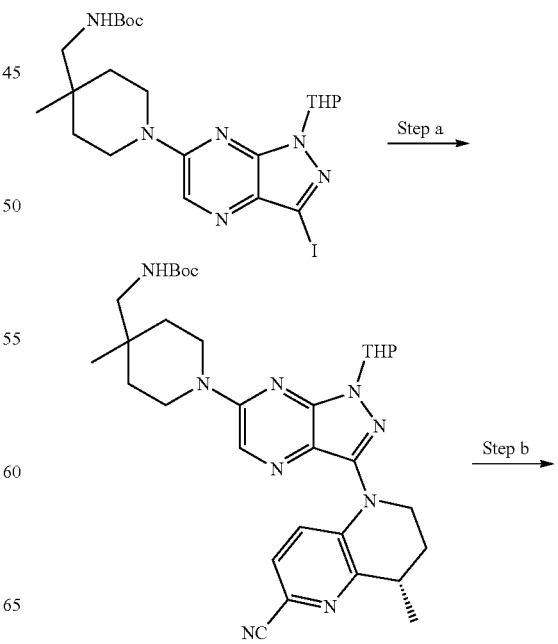

309

-continued

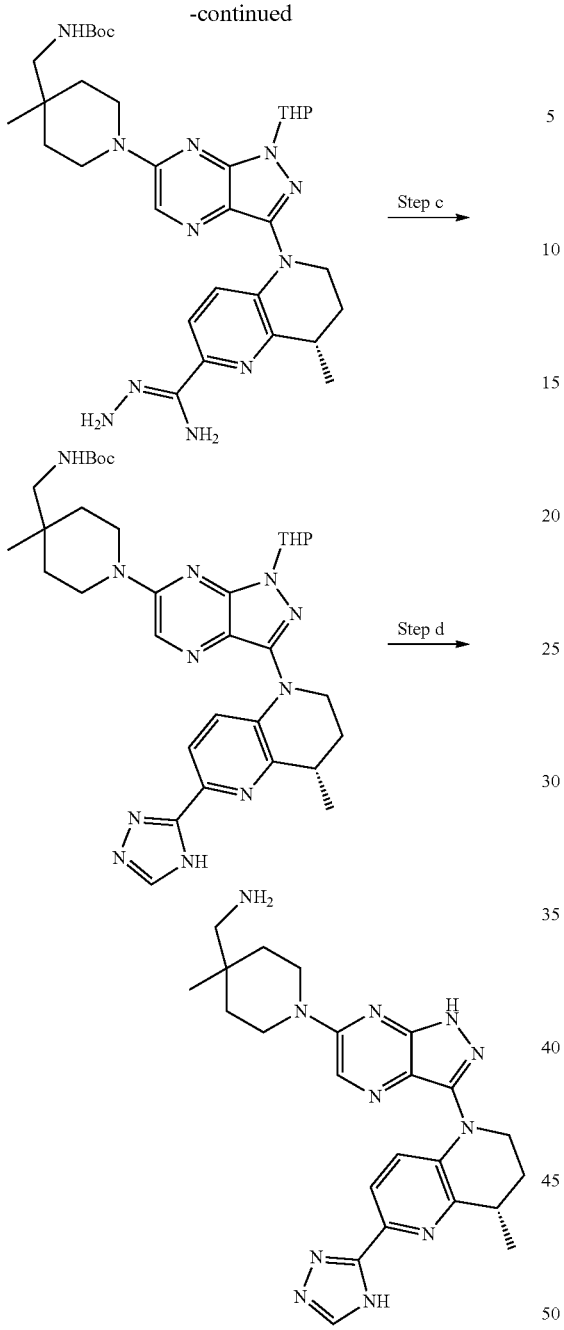

Step a: The compound of tert-butyl N-((1-[3-iodo-1-(oxan-2-yl)-1H-pyrazolo[3,4-b]pyrazin-6-yl]-4-methylpiperidin-4-yl)methyl)carbamate (150 mg, 0.3 mmol), (8S)-8-methyl-5,6,7,8-tetrahydro-1,5-naphthyridine-2-carbonitrile (51 mg, 0.3 mmol) (prepared using the same route as used for Compound 33, using the appropriate building blocks), XantPhos-Pd-G4 (12.8 mg, 0.01 mmol) and $Cs_2CO_3$ (175 mg, 0.6 mmol) were placed in PhMe (20 mL). The mixture was evacuated and refilled for 3 times using N2. The reaction mixture was stirred at 100° C. for 12 hours. The mixture was filtered and the filtrate was concentrated to give a residue. The residue was purified by silica gel column (Petroleum ether:Ethyl acetate=100:20 to 100:50) to give the product of tert-butyl N-[(1-{3-[(4S)-6-cyano-4-methyl-1,2,3,4-tetrahydro-1,5-naphthyridin-1-yl]-1-(oxan-2-yl)-

310

1H-pyrazolo[3,4-b]pyrazin-6-yl}-4-methylpiperidin-4-yl)methyl]carbamate (134 mg, 83.2% yield) as a colorless oil.

Step b: The mixture of rel-tert-butyl N-[(1-(3-[(4R)-6-cyano-4-methyl-1,2,3,4-tetrahydro-1,5-naphthyridin-1-yl]-1-(oxan-2-yl)-1H-pyrazolo[3,4-b]pyrazin-6-yl)-4-methylpiperidin-4-yl)methyl]carbamate (130 mg, 0.2 mmol) and $NH_2NH_2.H_2O$ (1.1 mL, 98%) in EtOH (10 mL) was stirred at 80° C. for 30 hours. The mixture was concentrated to give the product of rel-tert-butyl N-[(1-{3-[(4R)-6-[(Z)—N'-aminocarbamimidoyl]-4-methyl-1,2,3,4-tetrahydro-1,5-naphthyridin-1-yl]-1-(oxan-2-yl)-1H-pyrazolo[3,4-b]pyrazin-6-yl}-4-methylpiperidin-4-yl)methyl]carbamate (150 mg, crude) which will be used in the next step directly without further purification.

Step c: The mixture of tert-butyl N-[(1-{3-[(4S)-6-[(Z)—N'-aminocarbamimidoyl]-4-methyl-1,2,3,4-tetrahydro-1,5-naphthyridin-1-yl]-1-(oxan-2-yl)-1H-pyrazolo[3,4-b]pyrazin-6-yl}-4-methylpiperidin-4-yl)methyl]carbamate (130 mg, 0.2 mmol), TFA (1 drop) were added in HC(OEt)3 (6.8 mL). The mixture was stirred at 150° C. for 3 h. The mixture was concentrated to give a residue. The residue was dissolved in EtOH (20 mL), $K_2CO_3$ (1.0 g) was added. The mixture was stirred at 90° C. for 2 h. The mixture was concentrated to give the product 4 (150 mg, crude) which was used in next step without further purification.

Step d: The compound of tert-butyl N-[(4-methyl-1-{3-[(4S)-4-methyl-6-(4H-1,2,4-triazol-3-yl)-1,2,3,4-tetrahydro-1,5-naphthyridin-1-yl]-1-(oxan-2-yl)-1H-pyrazolo[3,4-b]pyrazin-6-yl}piperidin-4-yl)methyl]carbamate (100 mg, 0.1 mmol) was added into HCl/MeOH (4 mL, 2M). The mixture was stirred at 25° C. for 12 h. The mixture was concentrated and was purified by prep-HPLC ($NH_3.H_2O$) to afford the product of 1-(4-methyl-1-(3-[(4S)-4-methyl-6-(4H-1,2,4-triazol-3-yl)-1,2,3,4-tetrahydro-1,5-naphthyridin-1-yl]-1H-pyrazolo[3,4-b]pyrazin-6-yl)piperidin-4-yl)methanamine (7.20 mg, 10.1% yield) as a yellow solid.

Compound 199 was prepared via the same route, starting from (8R)-8-methyl-5,6,7,8-tetrahydro-1,5-naphthyridine-2-carbonitrile, and was isolated as an orange solid.

Synthesis of (3S)-8-(3-(3,4-dihydro-1,5-naphthyridin-1(2H)-yl)-1H-pyrazolo[3,4-b]pyrazin-6-yl)-3-methyl-2-oxa-8-azaspiro[4.5]decan-4-ol, Compound 201

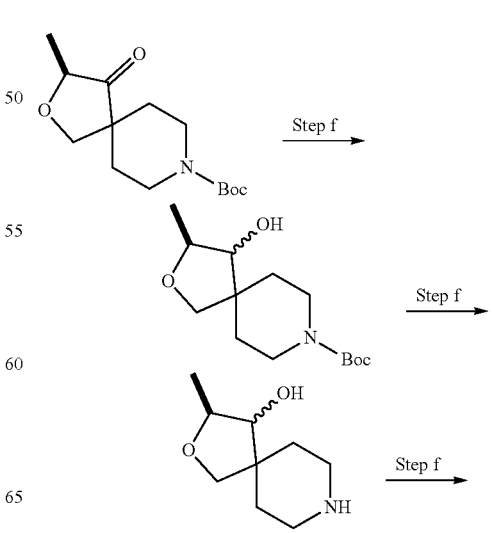

-continued

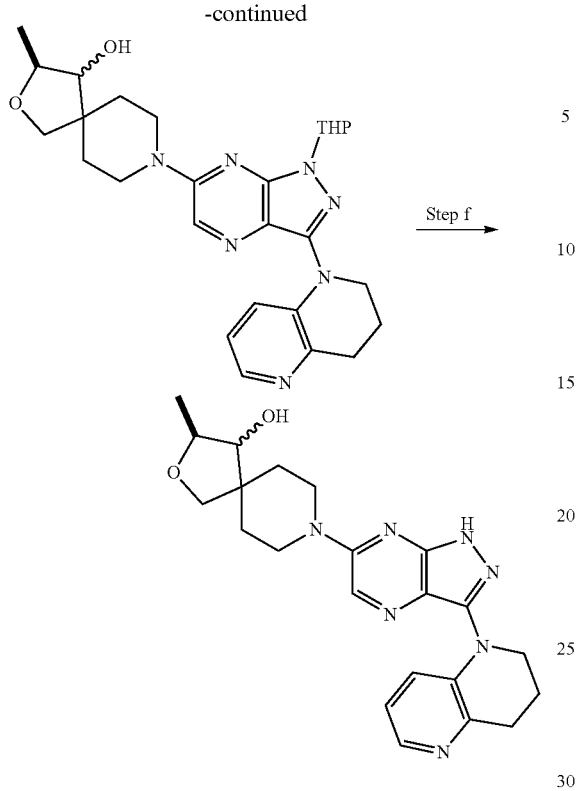

Step a: To a mixture of (S)-tert-butyl 3-methyl-4-oxo-2-oxa-8-azaspiro[4.5]decane-8-carboxylate (200 mg, 742 μmol) in anhydrous MeOH (5 mL) was added NaBH4 (28.1 mg, 742 μmol) at 0° C. The reaction mixture was stirred at 0° C. for 0.5 hour. TLC (Petroleum ether: Ethyl acetate=2:1) showed the reaction was consumed completely. The reaction mixture was quenched by sat. NH4Cl (2 mL) and concentrated in vacuum to give the product of (3S)-tert-butyl 4-hydroxy-3-methyl-2-oxa-8-azaspiro[4.5]decane-8-carboxylate (200 mg, crude), which was used directly in the next step without further purification.

Step b: To a mixture of (3S)-tert-butyl 4-hydroxy-3-methyl-2-oxa-8-azaspiro[4.5]decane-8-carboxylate (200 mg, 737 μmol) in DCM (3 mL) was added TFA (1 mL), the resulting mixture was stirred at 20° C. for 2 hours. TLC (Dichloromethane:Methanol=10:1) showed the reaction was consumed completely. The reaction mixture was concentrated in vacuum to give the product of (3S)-3-methyl-2-oxa-8-azaspiro[4.5]decan-4-ol (100 mg, crude), which was used directly in the next step without further purification.

Step c: A mixture of 1-(6-chloro-1-(tetrahydro-2H-pyran-2-yl)-1H-pyrazolo[3,4-b]pyrazin-3-yl)-1,2,3,4-tetrahydro-1,5-naphthyridine (166 mg, 448 μmol) and (3S)-3-methyl-2-oxa-8-azaspiro[4.5]decan-4-ol (100 mg, 583 μmol) in DIEA (5 mL) was stirred at 130° C. for 12 hours. The reaction mixture was concentrated under reduced pressure to give a residue, which was purified by column chromatography (Dichloromethane:Methanol=10:1) to afford the desired product of (3S)-8-(3-(3,4-dihydro-1,5-naphthyridin-1(2H)-yl)-1-(tetrahydro-2H-pyran-2-yl)-1H-pyrazolo[3,4-b]pyrazin-6-yl)-3-methyl-2-oxa-8-azaspiro[4.5]decan-4-ol (100 mg, crude) as a yellow oil.

Step d: A mixture of (3S)-8-(3-(3,4-dihydro-1,5-naphthyridin-1(2H)-yl)-1-(tetrahydro-2H-pyran-2-yl)-1H-pyrazolo[3,4-b]pyrazin-6-yl)-3-methyl-2-oxa-8-azaspiro[4.5]decan-4-ol (100 mg, crude) in HCl/MeOH (1 M, 5 mL) was stirred at 25° C. for 1 hours. The reaction mixture was concentrated under reduced pressure to give a residue, which was purified by prep-HPLC (NH3-H2O) to afford the product of (3S)-8-(3-(3,4-dihydro-1,5-naphthyridin-1(2H)-yl)-1H-pyrazolo[3,4-b]pyrazin-6-yl)-3-methyl-2-oxa-8-azaspiro[4.5]decan-4-ol (4.7 mg, 5.7% yield) as a yellow solid, SFC showed the d.r. is 78:22.

Synthesis of 8-(3-(3,4-dihydro-1,5-naphthyridin-1(2H)-yl)-1H-pyrazolo[3,4-b]pyrazin-6-yl)-2,8-diazaspiro[4.5]dec-1-en-1-amine dihydrochloride, Compound 202

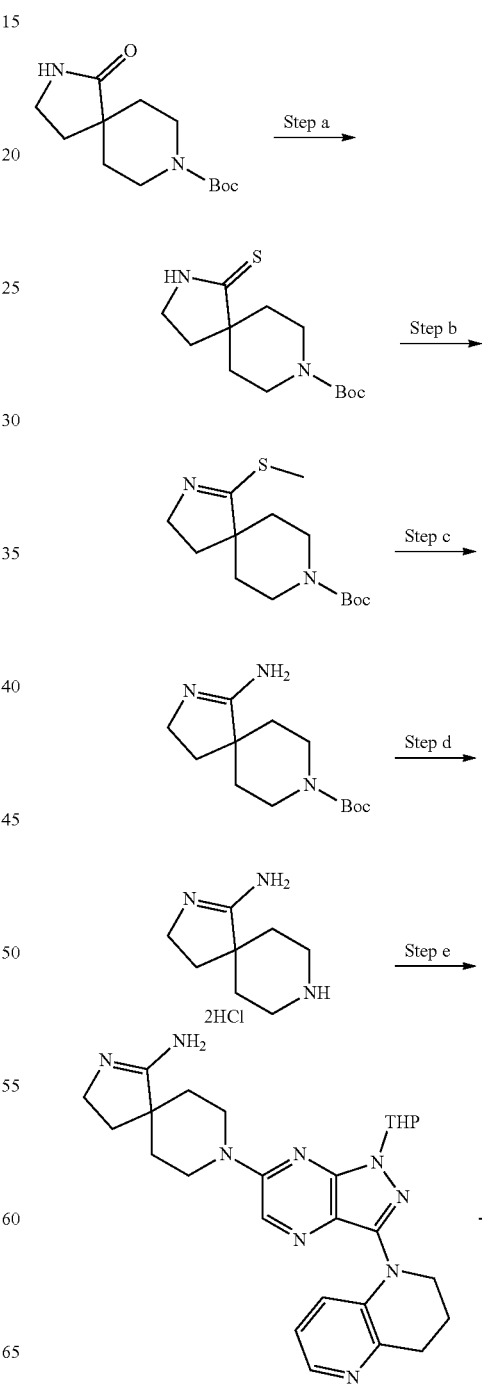

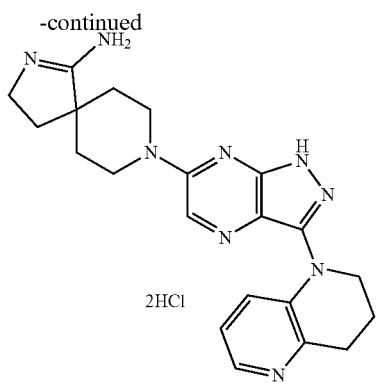

Step a: To a solution of tert-butyl 1-oxo-2,8-diazaspiro[4.5]decane-8-carboxylate (1.4 g, 5.5 mmol) in dichloromethane (30 mL) was added P2S5 (1.2 g, 5.5 mmol) followed by TMS2O (8.9 g, 54.9 mmol). The reaction was stirred at 30° C. for 12 hours. TLC (Petroleum ether/ethyl acetate=1/1) showed the starting material was consumed completely, then diluted with EtOAc and filtered through a pad of celite. The filtrate was concentrated under reduced pressure. The resulting crude material was purified by silica gel chromatography (Petroleum ether/ethyl acetate; 2:1) to give tert-butyl 1-thioxo-2,8-diazaspiro[4.5]decane-8-carboxylate (699 mg, 2.6 mmol, 47.2% yield) as a white solid.

Step b: To a solution of tert-butyl 1-thioxo-2,8-diazaspiro[4.5]decane-8-carboxylate (0.6 g, 2.2 mmol) in THF (5 ml) was added MeI (3.1 g, 22.1 mmol) at 0° C., the mixture was stirred at 30° C. for 16 hours. TLC (Petroleum ether/ethyl acetate=1/1) showed the starting material was consumed completely, then the mixture concentrated and the crude material was purified by silica gel chromatography (Petroleum ether/ethyl acetate=2:1) to give tert-butyl 1-(methylthio)-2,8-diazaspiro[4.5]dec-1-ene-8-carboxylate (480 mg, 1.7 mmol, 76.4% yield) as a yellow solid.

Step c: The reaction of tert-butyl 1-(methylthio)-2,8-diazaspiro[4.5]dec-1-ene-8-carboxylate (0.6 g, 2.1 mmol) in MeOH (10 mL) was added 7M NH3/MeOH (6 mL) and heated to 100° C. for 8 h. LCMS showed 80% product formed. The mixture was concentrated and purified by (DCM/MeOH=10/1) to afford tert-butyl 1-amino-2,8-diazaspiro[4.5]dec-1-ene-8-carboxylate (400 mg, 1.6 mmol, 75.1% yield) as a yellow solid.

Step d: To a solution of tert-butyl 1-amino-2,8-diazaspiro[4.5]dec-1-ene-8-carboxylate (0.4 g, 1.6 mmol) in MeOH (5 mL) was added HCl/MeOH (2 mL, 4N)) at 0° C., the mixture was stirred at 30° C. for 2 hours. LCMS showed ~80% of the desired product formed. The reaction mixture was concentrated to afford the product of 2,8-diazaspiro[4.5]dec-1-en-1-amine dihydrochloride (300 mg, 1.3 mmol, 2HCl salt, 84.5% yield) as a yellow solid.

Step e: To a solution of 2,8-diazaspiro[4.5]dec-1-en-1-amine (0.1 g, 652 μmol) in DMSO (2 mL) was added DIEA (158 mg, 1.30 mmol) and 1-(6-chloro-1-(tetrahydro-2H-pyran-2-yl)-1H-pyrazolo[3,4-b]pyrazin-3-yl)-1,2,3,4-tetrahydro-1,5-naphthyridine (362 mg, 978 μmol), the mixture was stirred at 35° C. for 2 hours. LCMS showed the product formed as a major peak. The reaction was quenched by sat. NH4Cl (10 mL), extracted with EtOAc (30 mL×3). The reaction mixture was concentrated and was purified by prep-HPLC (NH4OH) to afford the product of 8-(3-(3,4-dihydro-1,5-naphthyridin-1(2H)-yl)-1-(tetrahydro-2H-pyran-2-yl)-1H-pyrazolo[3,4-b]pyrazin-6-yl)-2,8-diazaspiro[4.5]dec-1-en-1-amine (70.0 mg, 143 μmol, 22.0% yield) as a yellow solid.

Step f: To a solution of 8-(3-(3,4-dihydro-1,5-naphthyridin-1(2H)-yl)-1-(tetrahydro-2H-pyran-2-yl)-1H-pyrazolo[3,4-b]pyrazin-6-yl)-2,8-diazaspiro[4.5]dec-1-en-1-amine (0.09 g, 184 μmol) in MeOH (5 mL) was added HCl/MeOH (2 mL, 4N) at 0° C., the mixture was stirred at 30° C. for 2 hours. LCMS showed ~80% of the desired product formed. The reaction mixture was concentrated and was purified by prep-HPLC (HCl) to afford the product of 8-(3-(3,4-dihydro-1,5-naphthyridin-1(2H)-yl)-1H-pyrazolo[3,4-b]pyrazin-6-yl)-2,8-diazaspiro[4.5]dec-1-en-1-amine dihydrochloride (58.3 mg, 122 μmol, 2HCl salt, 66.5% yield) as a yellow solid.

Synthesis of 2-(3-(3,4-dihydro-1,5-naphthyridin-1(2H)-yl)-1H-pyrazolo[3,4-b]pyrazin-6-yl)-2-azaspiro[4.4]nonan-6-amine, rel-(5R,6R)-2-(3-(3,4-dihydro-1,5-naphthyridin-1(2H)-yl)-1H-pyrazolo[3,4-b]pyrazin-6-yl)-2-azaspiro[4.4]nonan-6-amine, rel-(5S,6S)-2-(3-(3,4-dihydro-1,5-naphthyridin-1(2H)-yl)-1H-pyrazolo[3,4-b]pyrazin-6-yl)-2-azaspiro[4.4]nonan-6-amine, and rel-(5S,6R)-2-(3-(3,4-dihydro-1,5-naphthyridin-1(2H)-yl)-1H-pyrazolo[3,4-b]pyrazin-6-yl)-2-azaspiro[4.4]nonan-6-amine, Compounds 203, 204, 205, and 206

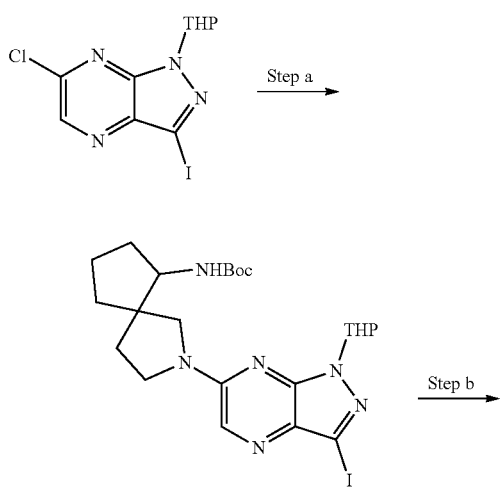

-continued
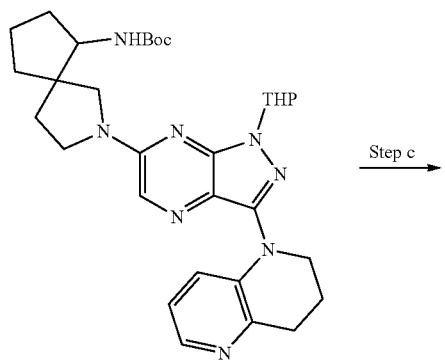
Step c
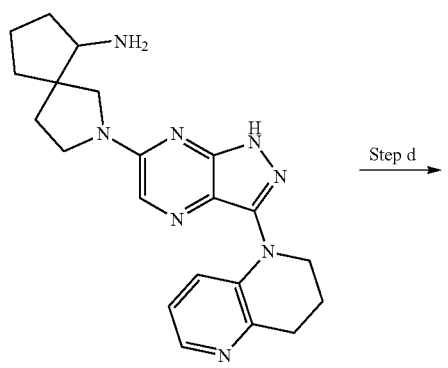
Step d
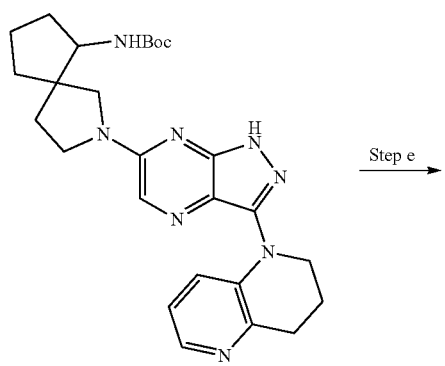
Step e
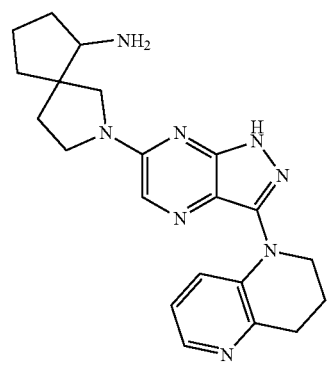

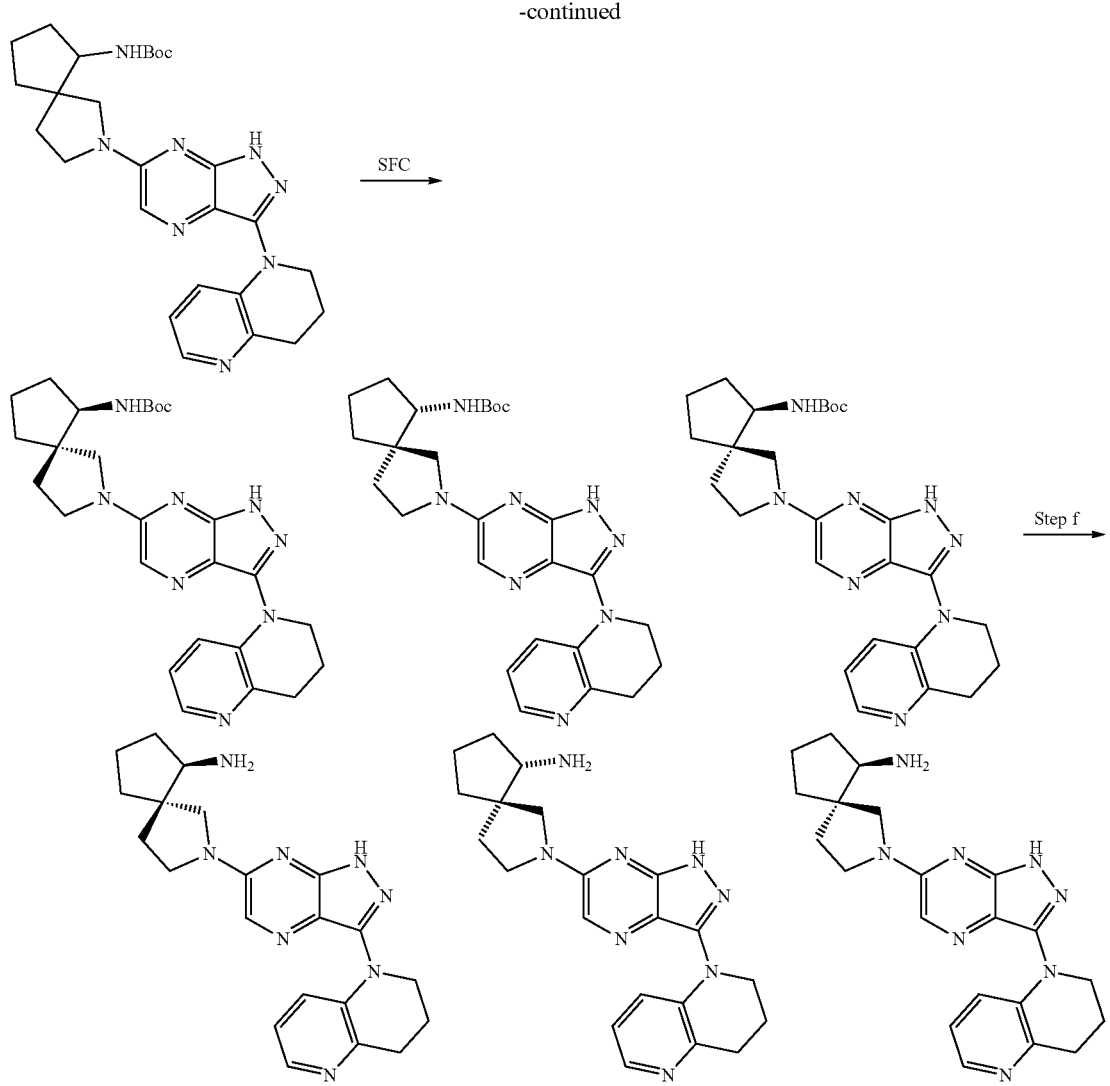

Step a: A mixture of tert-butyl 2-azaspiro[4.4]nonan-6-ylcarbamate (250.0 mg, 1.04 mmol) (CAS 186203-05-4), 6-chloro-3-iodo-1-(tetrahydro-2H-pyran-2-yl)-1H-pyrazolo[3,4-b]pyrazine (415.0 mg, 1.14 mmol) and TEA (210.0 mg, 2.08 mmol) in NMP (1.0 mL) was stirred at 120° C. for 2 hours. LCMS showed ~94% of the peak with desired MS was found. The combined reaction mixture was poured into water (40.0 mL). The precipitate was collected by filtration and purified by silica gel chromatography (Petroleum ether/EtOAc=2/1) to afford tert-butyl (2-(3-iodo-1-(tetrahydro-2H-pyran-2-yl)-1H-pyrazolo[3,4-b]pyrazin-6-yl)-2-azaspiro[4.4]nonan-6-yl)carbamate (1.10 g, combined product) as a yellow solid.

Step b: A mixture of tert-butyl (2-(3-iodo-1-(tetrahydro-2H-pyran-2-yl)-1H-pyrazolo[3,4-b]pyrazin-6-yl)-2-azaspiro[4.4]nonan-6-yl)carbamate (600.0 mg, 1.05 mmol), 1,2,3,4-tetrahydro-1,5-naphthyridine (281.0 mg, 2.10 mmol), t-BuONa (201.0 mg, 2.1 mmol), RuPhos (97.9 mg, 210.0 umol) and RuPhos-Pd-G4 (89.2 mg, 105.0 umol) in dioxane (10.0 mL) was stirred at 110° C. for 4 hours under N2. LCMS showed ~50% of the desired product formed. This reaction was concentrated in vacuum. The residue was purified by silica gel chromatography (DCM/MeOH=10/1) to afford the product of 2-(3-(3,4-dihydro-1,5-naphthyridin-1(2H)-yl)-1-(tetrahydro-2H-pyran-2-yl)-1H-pyrazolo[3,4-b]pyrazin-6-yl)-2-azaspiro[4.4]nonan-6-amine (600.0 mg, crude) as yellow solid.

Step c: A solution of 2-(3-(3,4-dihydro-1,5-naphthyridin-1(2H)-yl)-1-(tetrahydro-2H-pyran-2-yl)-1H-pyrazolo[3,4-b]pyrazin-6-yl)-2-azaspiro[4.4]nonan-6-amine (580.0 mg, 1.22 mmol) in TFA/DCM (5.0/10.0 mL) was stirred at 20° C. for 2 hours. LCMS showed the desired product formed. The solvent was removed under reduced pressure to afford the product of 2-(3-(3,4-dihydro-1,5-naphthyridin-1(2H)-yl)-1H-pyrazolo[3,4-b]pyrazin-6-yl)-2-azaspiro[4.4]nonan-6-amine (340.0 mg, TFA salt, crude) as yellow gum.

Step d: To a mixture of 2-(3-(3,4-dihydro-1,5-naphthyridin-1(2H)-yl)-1H-pyrazolo[3,4-b]pyrazin-6-yl)-2-azaspiro[4.4]nonan-6-amine (202.0 mg, 518.0 umol) in DCM (5.0 mL) was added TEA (104.0 mg, 1.03 mmol) and Boc2O (224.0 mg, 1.03 mmol) and stirred at 20° C. for 1 hour. TLC (MeOH/DCM=1/10, Rf=0.6) showed the starting material was consumed completely. The combined reaction mixture was concentrated in vacuum. The residue was purified by silica gel chromatography (MeOH/DCM=1/20) to give tert-butyl (2-(3-(3,4-dihydro-1,5-naphthyridin-1(2H)-yl)-1H- pyrazolo[3,4-b]pyrazin-6-yl)-2-azaspiro[4.4]nonan-6-yl) carbamate (360.0 mg, combined product) as yellow solid.

Step e: A solution of tert-butyl (2-(3-(3,4-dihydro-1,5-naphthyridin-1(2H)-yl)-1H-pyrazolo[3,4-b]pyrazin-6-yl)-2-azaspiro[4.4]nonan-6-yl)carbamate (40.0 mg, 81.5 µmol) in TFA (0.5 mL) and DCM (0.5 mL) was stirred at 20° C. for 12 hours. HPLC showed the reaction worked completely. Removal of all solvent in vacuum, the residue was dissolved in MeOH (2.0 mL), adjusted pH=9.0 with NH3.H2O and purified by prep-HPLC (NH3.H2O) to give 2-(3-(3,4-dihydro-1,5-naphthyridin-1(2H)-yl)-1H-pyrazolo[3,4-b]pyrazin-6-yl)-2-azaspiro[4.4]nonan-6-amine (18.0 mg, 46.0 µmol) as yellow solid. LCMS: [M+H]+ 391.3.

SFC separation: Tert-butyl (2-(3-(3,4-dihydro-1,5-naphthyridin-1(2H)-yl)-1H-pyrazolo[3,4-b]pyrazin-6-yl)-2-azaspiro[4.4]nonan-6-yl)carbamate (280.0 mg, 570.0 µmol) was separated by SFC (column: Chiralpak AD-3) to afford peak 1 (120.0 mg, two peaks in SFC, column: Chiralpak AS-3) as yellow solid and peak 2 (100.0 mg, e.e.=97.3%, single peak in SFC, P2) as a yellow solid. The peak 1 (120.0 mg) was separated by SFC (column: Chiralpak AS-3) to afford peak 11 (30.0 mg, e.e.=90.4%, single peak in SFC, P11) as a yellow solid and P12 (70 mg, e.e.=96.1%, single peak in SFC, P12) as a yellow solid. Note: Peak 12 and peak 2 are a pair of enantiomers, confirmed by HNMR.

Step f-1: A solution of tert-butyl ((5R,6R)-2-(3-(3,4-dihydro-1,5-naphthyridin-1(2H)-yl)-1H-pyrazolo[3,4-b]pyrazin-6-yl)-2-azaspiro[4.4]nonan-6-yl)carbamate (70.0 mg, 142.0 µmol) in TFA (5.0 mL) was stirred at 20° C. for 12 hours. LCMS showed the reaction worked completely. Removal off all solvent in vacuum, the residue was dissolved in MeOH (2.0 mL), adjusted pH=9.0 with NH3.H2O and purified by prep-HPLC (NH3.H2O) to give rel-(5R,6R)-2-(3-(3,4-dihydro-1,5-naphthyridin-1(2H)-yl)-1H-pyrazolo[3,4-b]pyrazin-6-yl)-2-azaspiro[4.4]nonan-6-amine (31.6 mg, 57.0% yield) as yellow solid.

Step f-2: A solution of tert-butyl ((5S,6S)-2-(3-(3,4-dihydro-1,5-naphthyridin-1(2H)-yl)-1H-pyrazolo[3,4-b]pyrazin-6-yl)-2-azaspiro[4.4]nonan-6-yl)carbamate (100.0 mg, 203.0 µmol) in TFA (5.0 mL) was stirred at 20° C. for 12 hours. LCMS showed the reaction worked completely. Removal off all solvent in vacuum, the residue was dissolved in MeOH (3.0 mL), adjusted pH=9.0 with NH3.H2O and purified by prep-HPLC (NH3.H2O) to give rel-(5S,6S)-2-(3-(3,4-dihydro-1,5-naphthyridin-1(2H)-yl)-1H-pyrazolo[3,4-b]pyrazin-6-yl)-2-azaspiro[4.4]nonan-6-amine (41.5 mg, 52.3% yield) as yellow solid.

Step f-3: A solution of tert-butyl ((5S,6R)-2-(3-(3,4-dihydro-1,5-naphthyridin-1(2H)-yl)-1H-pyrazolo[3,4-b]pyrazin-6-yl)-2-azaspiro[4.4]nonan-6-yl)carbamate (30.0 mg, 61.1 µmol) in TFA (5.0 mL) was stirred at 20° C. for 12 hours. LCMS showed the reaction worked completely. Removal off all solvent in vacuum, the residue was dissolved in MeOH (2.0 mL), adjusted pH=9.0 with NH3.H2O and purified by prep-HPLC (NH3.H2O) to give rel-(5S,6R)-2-(3-(3,4-dihydro-1,5-naphthyridin-1(2H)-yl)-1H-pyrazolo[3,4-b]pyrazin-6-yl)-2-azaspiro[4.4]nonan-6-amine (12.3 mg, 51.6% yield) as yellow solid.

Synthesis of 8-(3-(3,4-dihydro-1,5-naphthyridin-1(2H)-yl)-1H-pyrazolo[3,4-b]pyrazin-6-yl)-3-oxa-1,8-diazaspiro[4.5]dec-1-en-2-amine hydrochloride, Compound 216

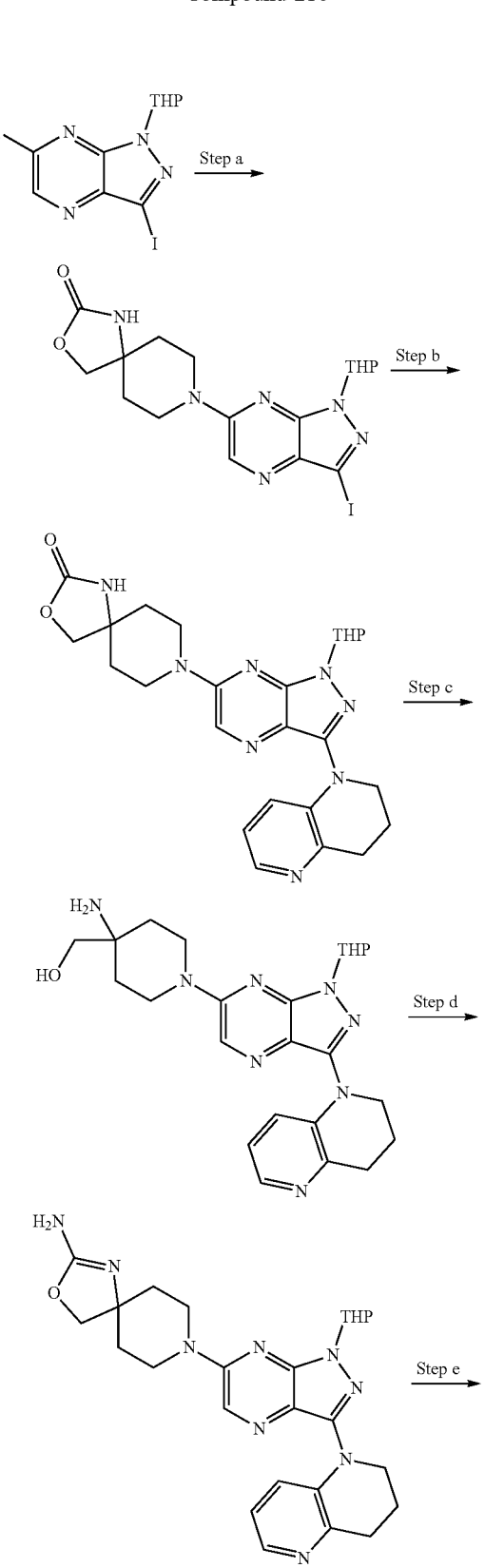

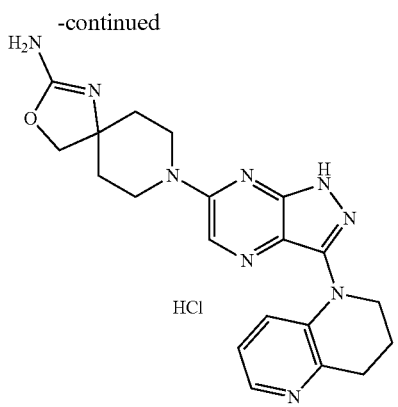

HCl

Step a: A mixture of 6-chloro-3-iodo-1-(tetrahydro-2H-pyran-2-yl)-1H-pyrazolo[3,4-b]pyrazine (371 mg, 1.0 mmol), 3-oxa-1,8-diazaspiro[4.5]decan-2-one (170 mg, 1.1 mmol) and CsF (467 mg, 3.1 mmol) in DMSO (10 mL) was stirred at 70° C. for 2 hours. TLC (Petroleum ether: Ethyl acetate=10:1) showed the reaction was consumed completely. The reaction mixture was diluted with H2O (20 mL), extracted with ethyl acetate (25 mL×2). The organic phase was washed with brine (15 mL), dried over anhydrous Na2SO4 and concentrated in vacuum to give a residue, which was purified by silica gel chromatography (Dichloromethane:Methanol=20:1 to 10:1) to afford the product of 8-(3-iodo-1-(tetrahydro-2H-pyran-2-yl)-1H-pyrazolo[3,4-b]pyrazin-6-yl)-3-oxa-1,8-diazaspiro[4.5]decan-2-one (440 mg, 89.2% yield) as a white solid.

Step b: A mixture of 8-[3-iodo-1-(oxan-2-yl)-1H-pyrazolo[3,4-b]pyrazin-6-yl]-3-oxa-1,8-diazaspiro[4.5]decan-2-one (390 mg, 805 μmol), 1,2,3,4-tetrahydro-1,5-naphthyridine (118 mg, 885 μmol), Pd2(dba)3 (74 mg, 81 μmol), Xantphos (93 mg, 161 μmol) and t-BuONa (231 mg, 2.4 mmol) in toluene (10 mL) was stirred at 80° C. for 12 hours under N2 atmosphere. The reaction mixture was concentrated in vacuum to give a residue, which was purified by silica gel chromatography (Dichloromethane:Methanol=30:1 to 20:1) to afford the product of 8-(3-(3,4-dihydro-1,5-naphthyridin-1(2H)-yl)-1-(tetrahydro-2H-pyran-2-yl)-1H-pyrazolo[3,4-b]pyrazin-6-yl)-3-oxa-1,8-diazaspiro[4.5]decan-2-one (280 mg, 71% yield) as a yellow solid.

Step c: A mixture of 8-(3-(3,4-dihydro-1,5-naphthyridin-1(2H)-yl)-1-(tetrahydro-2H-pyran-2-yl)-1H-pyrazolo[3,4-b]pyrazin-6-yl)-3-oxa-1,8-diazaspiro[4.5]decan-2-one (280 mg, 570 μmol) and LiOH (82 mg, 3.4 mmol) in MeOH (5 mL)/H2O (5 mL) was stirred at 80° C. for 24 hours. The reaction mixture was concentrated in vacuum to give the crude product, which was purified by silica gel chromatography (Dichloromethane:Methanol=10:1 to 5:1) to afford the product of (4-amino-1-(3-(3,4-dihydro-1,5-naphthyridin-1(2H)-yl)-1-(tetrahydro-2H-pyran-2-yl)-1H-pyrazolo[3,4-b]pyrazin-6-yl)piperidin-4-yl)methanol (200 mg, 75.7% yield) as a yellow solid.

Step d: To a mixture of (4-amino-1-[1-(oxan-2-yl)-3-(1,2,3,4-tetrahydro-1,5-naphthyridin-1-yl)-1H-pyrazolo[3,4-b]pyrazin-6-yl]piperidin-4-yl)methanol (150 mg, 322 μmol) in THF (10 mL) at 0° C. was added K2CO3 (133 mg, 965 μmol) and BrCN (102 mg, 965 μmol), then the mixture was stirred at 25° C. for 12 hours. The reaction mixture was concentrated in vacuum to give a residue, which was purified by silica gel chromatography (Dichloromethanol=30:1 to 10:1) to afford the product of 8-(3-(3,4-dihydro-1,5-naphthyridin-1(2H)-yl)-1-(tetrahydro-2H-pyran-2-yl)-1H-pyrazolo[3,4-b]pyrazin-6-yl)-3-oxa-1,8-diazaspiro[4.5]dec-1-en-2-amine (80 mg, 50.9% yield) as a yellow solid.

Step e: A mixture of 8-(3-(3,4-dihydro-1,5-naphthyridin-1(2H)-yl)-1-(tetrahydro-2H-pyran-2-yl)-1H-pyrazolo[3,4-b]pyrazin-6-yl)-3-oxa-1,8-diazaspiro[4.5]dec-1-en-2-amine (80 mg, 163 μmol) in HCl/MeOH (4M, 5 mL) was stirred at 30° C. for 2 hours. The reaction mixture was concentrated under reduced pressure to give a residue, which was purified by prep-HPLC (HCl) to afford the product of 8-(3-(3,4-dihydro-1,5-naphthyridin-1(2H)-yl)-1H-pyrazolo[3,4-b]pyrazin-6-yl)-3-oxa-1,8-diazaspiro[4.5]dec-1-en-2-amine hydrochloride (37.4 mg, 51.9% yield) as a yellow solid.

Synthesis of 8-[3-(4-methyl-1,2,3,4-tetrahydro-1,5-naphthyridin-1-yl)-1H-pyrazolo[3,4-b]pyrazin-6-yl]-2,8-diazaspiro[4.5]decan-3-one and 2-[4-(aminomethyl)-1-[3-(4-methyl-1,2,3,4-tetrahydro-1,5-naphthyridin-1-yl)-1H-pyrazolo[3,4-b]pyrazin-6-yl]piperidin-4-yl]acetic acid, Compound 222 and Compound 171

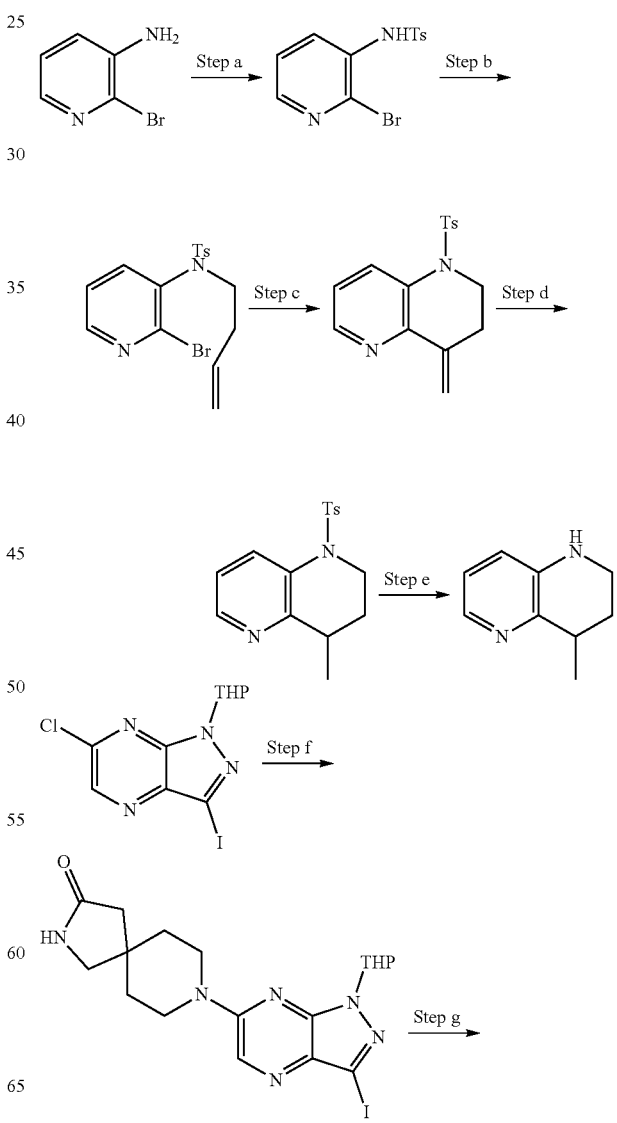

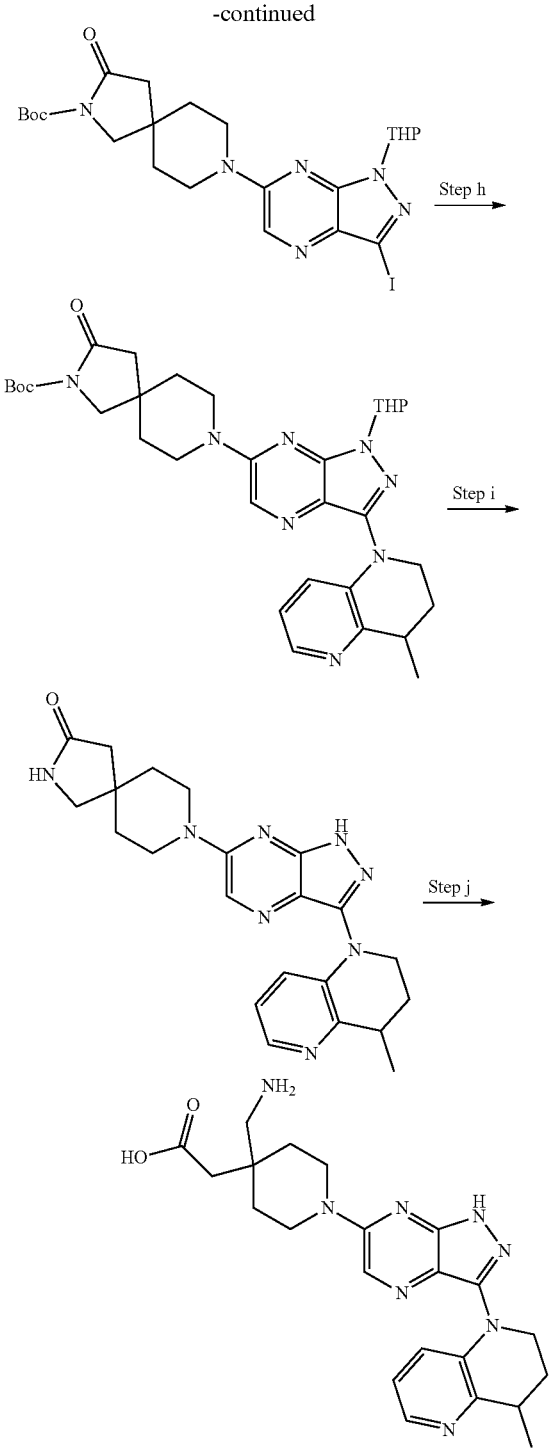

Step a: To a mixture of 2-bromopyridin-3-amine (5.0 g, 28.8 mmol) and pyridine (13.8 mL, 172.0 mmol) in DCM (50.0 mL) was added TsCl (6.0 g, 31.6 mmol). The mixture was stirred at 20° C. for 12 h. LCMS showed 89.7% desired product formed. The mixture was washed with 2 N HCl (50.0 mL×2) and H2O (50.0 mL). The organic layer was dried over anhydrous Na2SO4. The mixture was filtered and the filtrate was concentrated in vacuo to give N-(2-bromopyridin-3-yl)-4-methylbenzenesulfonamide (8.77 g, 93.0% yield) as a yellow solid.

Step b: To a mixture of N-(2-bromopyridin-3-yl)-4-methylbenzenesulfonamide (8.00 g, 24.4 mmol) and PPh3 (12.70 g, 48.8 mmol) in THF (100.0 mL) was added but-3-en-1-ol (3.1 mL, 36.5 mmol) and DIAD (7.37 g, 36.5 mmol). The mixture was stirred at 0-15° C. for 4 h under N2. LCMS showed 36.6% desired product formed and TLC (Petroleum ether/EtOAc=10/1) showed a new spot was found. The mixture was concentrated in vacuum and purified by flash silica gel chromatography (Petroleum ether/EtOAc=1/0 to 5/2) to give N-(2-bromopyridin-3-yl)-N-(but-3-en-1-yl)-4-methylbenzenesulfonamide (9.30 g, crude) as a yellow solid.

Step c: To a mixture of N-(2-bromopyridin-3-yl)-N-(but-3-en-1-yl)-4-methylbenzene-1-sulfonamide (9.00 g, 23.6 mmol) and Et3N (9.79 mL, 70.8 mmol) in DMA (100.0 mL) were added (o-tol)3P (2.15 g, 7.08 mmol) and Pd(OAc)2 (635.0 mg, 2.8 mmol). The mixture was stirred at 130° C. under N2 for 12 h. LCMS showed 40.4% desired product formed and TLC (Petroleum ether/EtOAc=5/1, Rf=0.3) showed a new spot was found. The mixture was poured into water (150.0 mL) and extracted with EtOAc (100.0 mL×3). The organic layers were washed with brine (50.0 mL×3) and dried over anhydrous Na2SO4, filtered and concentrated to give residue. The residue was purified by flash silica gel column chromatography (Petroleum ether/EtOAc=1/0 to 5/1) to give 4-methylene-1-tosyl-1,2,3,4-tetrahydro-1,5-naphthyridine (4.70 g, crude) as a yellow solid.

Step d: A mixture of 1-(4-methylbenzenesulfonyl)-4-methylidene-1,2,3,4-tetrahydro-1,5-naphthyridine (500.0 mg, 1.7 mmol) and Pd/C (100.0 mg) in THF (20.0 mL) was hydrogenated under H2 (15 psi) at 30° C. for 4 hours. LCMS showed one main peak with desired MS was found. The reaction mixture was filtered through a pad of celite and washed with THF (20.0 mL). The filtrate was concentrated in vacuum to give 4-methyl-1-(4-methylbenzenesulfonyl)-1,2,3,4-tetrahydro-1,5-naphthyridine (400.0 mg, 79.8% yield) as a colorless oil.

Step e: A mixture of 4-methyl-1-(4-methylbenzenesulfonyl)-1,2,3,4-tetrahydro-1,5-naphthyridine (400.0 mg, 1.3 mmol) and Mg (173.0 mg, 6.6 mmol) in MeOH (20.0 mL) was stirred at 60° C. for 12 h. TLC (Petroleum ether/EtOAc=2/1, Rf=0.35) showed one new spot with larger polarity was found. The reaction mixture was filtered through a pad of celite and washed with EtOAc (50.0 mL). The filtrate was concentrated in vacuum and purified by silica gel chromatography (Petroleum ether/EtOAc=1/1) to give 4-methyl-1,2,3,4-tetrahydro-1,5-naphthyridine (144.0 mg, 73.8% yield) as a yellow solid.

Step f: A mixture of 6-chloro-3-iodo-1-(oxan-2-yl)-1H-pyrazolo[3,4-b]pyrazine (300.0 mg, 822.0 μmol), 2,8-diazaspiro[4.5]decan-3-one (139.0 mg, 904.0 μmol) and TEA (124.0 mg, 1.23 mmol) in NMP (2.5 mL) was stirred at 120° C. for 2 hours. LCMS showed one main peak with desired MS was found. The reaction mixture was poured into water (30.0 mL). The precipitate was collected by filtration, washed with TBME (5.0 mL) and dried to give 8-[3-iodo-1-(oxan-2-yl)-1H-pyrazolo[3,4-b]pyrazin-6-yl]-2,8-diazaspiro[4.5]decan-3-one (280.0 mg, 70.7% yield) as a yellow solid.

Step g: To a mixture of 8-[3-iodo-1-(oxan-2-yl)-1H-pyrazolo[3,4-b]pyrazin-6-yl]-2,8-diazaspiro[4.5]decan-3-one (280.0 mg, 580.0 μmol), TEA (58.6 mg, 580.0 umol) and DMAP (14.1 mg, 116.0 umol) in DCM (20.0 mL) was added Boc2O (379.0 mg, 1.74 mmol) and stirred at 30° C. for 4 hours. LCMS showed one main peak with desired MS was found. The reaction mixture was washed with water (20.0 mL×2), dried over anhydrous Na2SO4, filtered and concentrated in vacuum. The residue was purified by silica gel chromatography (Petroleum ether/EtOAc=1/1, Rf=0.3) to give tert-butyl 8-[3-iodo-1-(oxan-2-yl)-1H-pyrazolo[3,4-b]pyrazin-6-yl]-3-oxo-2,8-diazaspiro[4.5]decane-2-carboxylate (330.0 mg, 97.9% yield) as white solid.

Step h: A mixture of tert-butyl 8-[3-iodo-1-(oxan-2-yl)-1H-pyrazolo[3,4-b]pyrazin-6-yl]-3-oxo-2,8-diazaspiro[4.5]decane-2-carboxylate (110.0 mg, 188.0 μmol), 4-methyl-1,2,3,4-tetrahydro-1,5-naphthyridine (36.1 mg, 244.0 μmol), Cs2CO3 (184.0 mg, 564.0 umol), RuPhos (17.5 mg, 37.6 umol) and RuPhos-Pd-G4 (15.9 mg, 18.8 umol) in toluene (10.0 mL) was stirred at 100° C. for 14 h under N2. LCMS showed the starting material was consumed and the desired product formed. The reaction mixture was poured into water (20.0 mL) and extracted with EtOAc (20.0 mL×2). The combined organic layers were dried over anhydrous Na2SO4, filtered and evaporated in vacuum. The residue was purified by silica gel chromatography (EtOAc in Petroleum ether=50~100%) to afford tert-butyl 8-[3-(4-methyl-1,2,3,4-tetrahydro-1,5-naphthyridin-1-yl)-1-(oxan-2-yl)-1H-pyrazolo[3,4-b]pyrazin-6-yl]-3-oxo-2,8-diazaspiro[4.5]decane-2-carboxylate (95.0 mg, 84.0% yield) as a yellow solid.

Step i: A solution of tert-butyl 8-[3-(4-methyl-1,2,3,4-tetrahydro-1,5-naphthyridin-1-yl)-1-(oxan-2-yl)-1H-pyrazolo[3,4-b]pyrazin-6-yl]-3-oxo-2,8-diazaspiro[4.5]decane-2-carboxylate (95.0 mg, 157.0 μmol) in TFA (2.0 mL) was stirred at 25° C. for 2 h. LCMS showed the desired product formed. The solvent was removed in vacuum. The residue was diluted with MeOH (5.0 mL), basified with NaOH (1 N) to pH=7.0 and purified by prep-HPLC (aqueous ammonia) to give 8-[3-(4-methyl-1,2,3,4-tetrahydro-1,5-naphthyridin-1-yl)-1H-pyrazolo[3,4-b]pyrazin-6-yl]-2,8-diazaspiro[4.5]decan-3-one (35.0 mg, 53.2% yield) as yellow solid.

Step j: A solution of 2-[4-(aminomethyl)-1-[3-(4-methyl-1,2,3,4-tetrahydro-1,5-naphthyridin-1-yl)-1H-pyrazolo[3,4-b]pyrazin-6-yl]piperidin-4-yl]acetic acid (75.0 mg, 179.0 umol) in NaOH (10 N, 1.0 mL) and EtOH (2.0 mL) in sealed tube was heated by microwave at 110° C. for 2 h. LCMS showed 74% of desired product was found. The reaction mixture was acidified with HCl (2 N) to pH=5.0, and purified by prep-HPLC (ammonia) to afford 2-[4-(aminomethyl)-1-[3-(4-methyl-1,2,3,4-tetrahydro-1,5-naphthyridin-1-yl)-1H-pyrazolo[3,4-b]pyrazin-6-yl]piperidin-4-yl]acetic acid (23.0 mg, 29.4% yield) as a yellow solid.

Synthesis of (3S,4S)-3-methyl-8-(3-(6-(1-methyl-1H-pyrazol-4-yl)-3,4-dihydro-1,5-naphthyridin-1(2H)-yl)-1H-pyrazolo[3,4-b]pyrazin-6-yl)-2-oxa-8-azaspiro[4.5]decan-4-amine, Compound 224

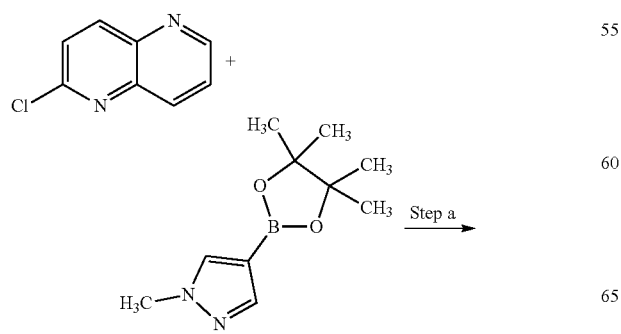

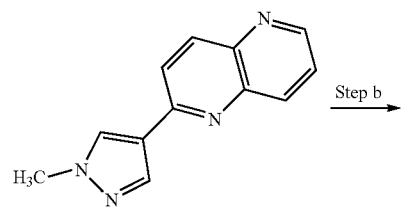

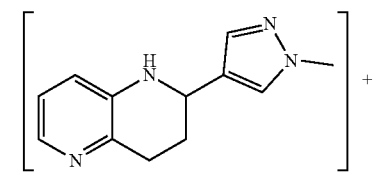

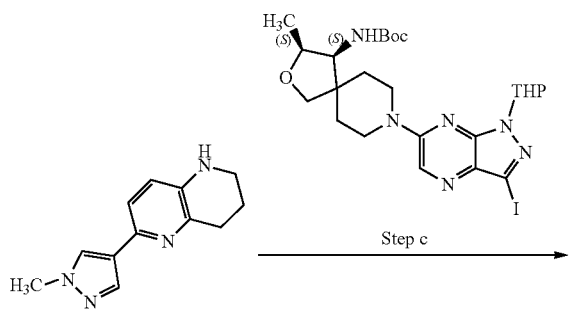

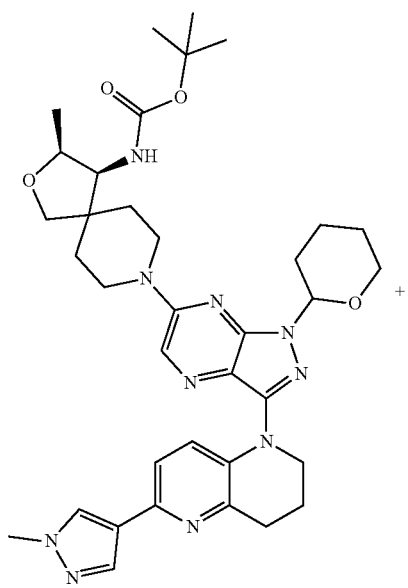

-continued

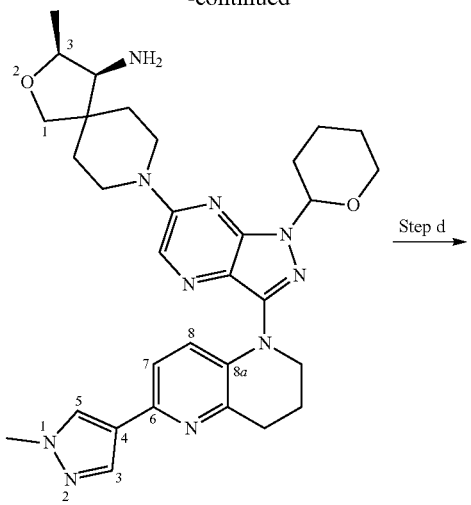

Step d →

Step a: To the mixture of 2-chloro-1,5-naphthyridine (500 mg, 3.03 mmol) and 1-methyl-4-(4,4,5,5-tetramethyl-1,3,2-dioxaborolan-2-yl)-1H-pyrazole (692 mg, 3.33 mmol, CAS #761446-44-0) in dioxane (10 mL) and H₂O (2 mL) were added Pd(dppf)Cl₂ (443 mg, 606 μmol) and K₃PO₄·3H₂O (1.98 g, 9.08 mmol). The mixture was stirred at 100° C. under N₂ for 12 hours. The mixture was concentrated under reduced pressure and purified by flash silica gel chromatography (0-100% EtOAc/petroleum ether) to give 2-(1-methyl-1H-pyrazol-4-yl)-1,5-naphthyridine (489 mg, 76.7% yield) as an off-white solid.

Step b: To a mixture of 2-(1-methyl-1H-pyrazol-4-yl)-1,5-naphthyridine (400 mg, 1.90 mmol) and 3,5-diethyl 2,6-dimethyl-1,4-dihydropyridine-3,5-dicarboxylate (1.15 g, 4.56 mmol) in toluene (10 mL) was added diphenoxyphosphinic acid (48 mg, 0.19 mmol). The mixture was stirred at 100° C. under N₂ for 12 hrs. The mixture was concentrated under reduced pressure and purified by flash silica gel chromatography (0-10% MeOH/MeOH) to give 6-(1-methyl-1H-pyrazol-4-yl)-1,2,3,4-tetrahydro-1,5-naphthyridine (80 mg, combined product) and 2-(1-methyl-1H-pyrazol-4-yl)-1,2,3,4-tetrahydro-1,5-naphthyridine (300 mg, combined product).

Step c: To the mixture of tert-butyl N-[(3S,4S)-8-[3-iodo-1-(oxan-2-yl)-1H-pyrazolo[3,4-b]pyrazin-6-yl]-3-methyl-2-oxa-8-azaspiro[4.5]decan-4-yl]carbamate (140 mg, 233 μmol) and 6-(1-methyl-1H-pyrazol-4-yl)-1,2,3,4-tetrahydro-1,5-naphthyridine (59.7 mg, 279 μmol) in toluene (15 mL) was added Pd₂(dba)₃ (48.8 mg, 53.3 μmol), XantPhos (70 mg, 121 μmol) and t-BuONa (89.5 mg, 932 μmol). The mixture was stirred at 100° C. under N₂ for 3 hrs. The mixture was concentrated in vacuo and purified by flash silica gel chromatography (1-5% MeOH/DCM) to give tert-butyl N-[(3S,4S)-3-methyl-8-{3-[6-(1-methyl-1H-pyrazol-4-yl)-1,2,3,4-tetrahydro-1,5-naphthyridin-1-yl]-1-(oxan-2-yl)-1H-pyrazolo[3,4-b]pyrazin-6-yl}-2-oxa-8-azaspiro[4.5]decan-4-yl]carbamate (80 mg, crude product) as a yellow solid and (3S,4S)-3-methyl-8-{3-[6-(1-methyl-1H-pyrazol-4-yl)-1,2,3,4-tetrahydro-1,5-naphthyridin-1-yl]-1-(oxan-2-yl)-1H-pyrazolo[3,4-b]pyrazin-6-yl}-2-oxa-8-azaspiro[4.5]decan-4-amine (60 mg, combined product) as a yellow solid.

Step d: A mixture of (3S,4S)-3-methyl-8-(3-[6-(1-methyl-1H-pyrazol-4-yl)-1,2,3,4-tetrahydro-1,5-naphthyridin-1-yl]-1-(oxan-2-yl)-1H-pyrazolo[3,4-b]pyrazin-6-yl)-2-oxa-8-azaspiro[4.5]decan-4-amine (60 mg, 0.10 mol) in HCl/MeOH (4N, 5.0 mL) was stirred at 20° C. for 12 hrs. The mixture was concentrated in vacuum, followed by the addition of THF (2 mL) and a drop MeOH. The mixture was adjusted with Na₂CO₃ solid to a pH of 8. The mixture was concentrated in vacuum and purified by flash silica gel chromatography (0-5% MeOH/DCM) to afford (3S,4S)-3-methyl-8-{3-[6-(1-methyl-1H-pyrazol-4-yl)-1,2,3,4-tetrahydro-1,5-naphthyridin-1-yl]-1H-pyrazolo[3,4-b]pyrazin-6-yl}-2-oxa-8-azaspiro[4.5]decan-4-amine (31.5 mg, 61.3% yield): ESMS [M+H]⁺=501.1; ¹H-NMR (400 MHz, CD₃OD) δ 8.22 (s, 1H), 8.02 (s, 1H), 7.91 (s, 1H), 7.37 (d, J=8.8 Hz, 1H), 7.25 (d, J=8.8 Hz, 1H), 4.26-4.17 (m, 2H), 3.99-3.89 (m, 6H), 3.75 (d, J=8.8 Hz, 1H), 3.51-3.35 (m, 2H), 3.09-3.03 (m, 3H), 2.23-2.20 (m, 2H), 1.88-1.72 (m, 4H), 1.24 (d, J=6.4 Hz, 1H).

Synthesis of (3S,4S)-3-methyl-8-(3-((S)-4-methyl-6-(1,2,4-oxadiazol-3-yl)-3,4-dihydroquinolin-1(2H)-yl)-1H-pyrazolo[3,4-b]pyrazin-6-yl)-2-oxa-8-azaspiro[4.5]decan-4-amine, Compound 227

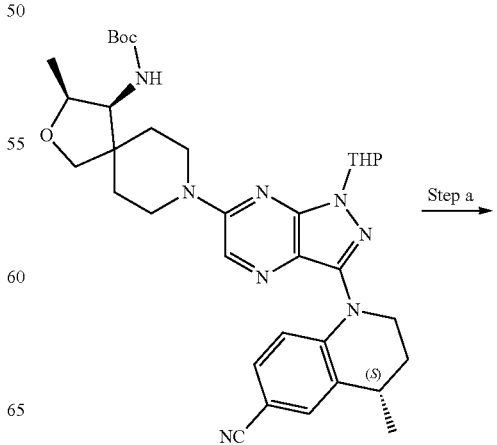

Step a →

329
-continued

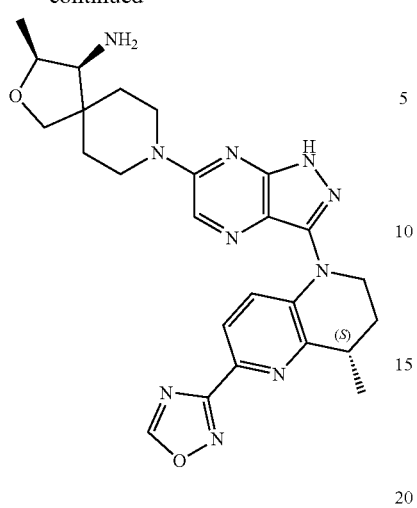

Step a: Compound was prepared using conditions as described in the synthesis of Compound 172.

Synthesis of (4R)-1-{6-[(3S,4S)-4-amino-3-methyl-2-oxa-8-azaspiro[4.5]decan-8-yl]-1H-pyrazolo[3,4-b]pyrazin-3-yl}-5-fluoro-4-methyl-1,2,3,4-tetrahydroquinoline-6-carbonitrile and (4S)-1-{6-[(3S,4S)-4-amino-3-methyl-2-oxa-8-azaspiro[4.5]decan-8-yl]-1H-pyrazolo[3,4-b]pyrazin-3-yl}-5-fluoro-4-methyl-1,2,3,4-tetrahydroquinoline-6-carbonitrile, Compound 229 and Compound 23

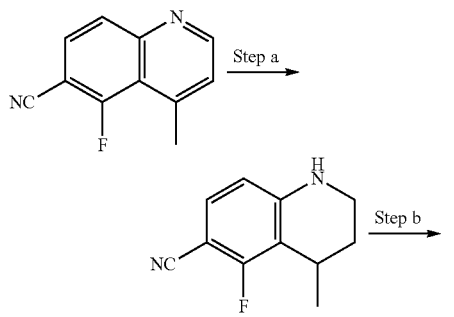

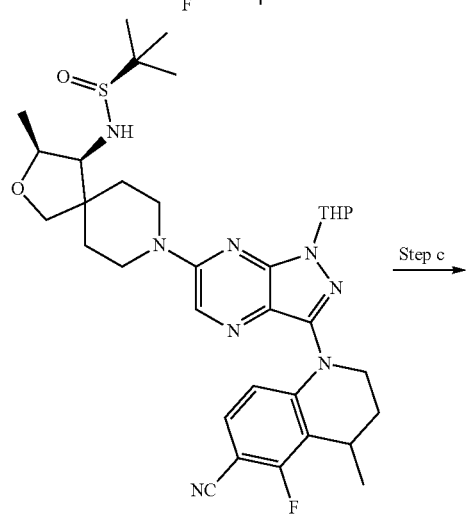

330
-continued

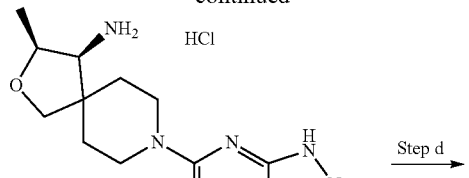

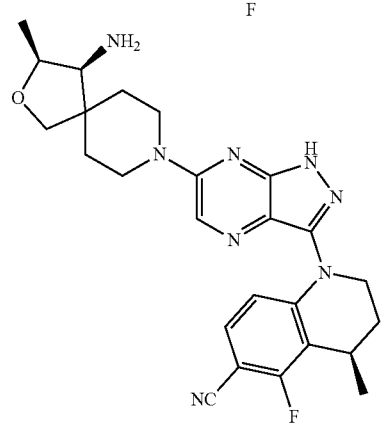

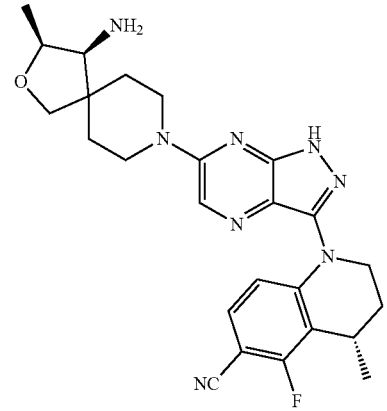 [SMILES: C[C@@H]1OCC2(CCN(c3cnc4c(N5CC[C@H](C)c6c5ccc(C#N)c6F)n[nH]c4n3)CC2)[C@@H]1N]

Step a: A mixture of 5-fluoro-4-methylquinoline-6-carbonitrile (500.0 mg, 2.68 mmol) (prepared as described for compound 223), (R)-BINOL-phosphoric acid (46.6 mg, 134.0 µmol) and 3,5-diethyl 2,6-dimethyl-1,4-dihydropyridine-3,5-dicarboxylate (1.62 g, 6.43 mmol) in toluene (8.0 mL) was stirred at 50° C. for 12 h under N2. TLC (Petroleum ether/EtOAc=4/1) showed the starting material was consumed completely and one spot with similar polarity was formed. The reaction mixture was concentrated under reduced pressure and purified by column chromatography (EtOAc in Petroleum ether=0~10%) to afford 5-fluoro-4-methyl-1,2,3,4-tetrahydroquinoline-6-carbonitrile (260.0 mg, 51.0% yield) as a off-white solid.

Step b: To a solution of (S)—N-[(3S,4S)-8-[3-iodo-1-(oxan-2-yl)-1H-pyrazolo[3,4-b]pyrazin-6-yl]-3-methyl-2-oxa-8-azaspiro[4.5]decan-4-yl]-2-methylpropane-2-sulfinamide (120.0 mg, 199.0 µmol) and 5-fluoro-4-methyl-1,2,3,4-tetrahydroquinoline-6-carbonitrile (75.7 mg, 398.0 µmol)

in toluene (5.0 mL) was added Pd2(dba)3 (36.4 mg, 39.8 µmol), XantPhos (46.0 mg, 79.6 µmol) and t-BuONa (57.3 mg, 597.0 µmol). The mixture was evacuated and refilled for 3 times using N2. The reaction mixture was stirred at 100° C. for 12 hours under N2. LCMS showed 38% peak with desired MS was detected. The reaction mixture was extracted with EtOAc (60.0 mL) and water (100.0 mL×2) and washed with brine (100.0 mL). The organic layers were dried over anhydrous Na2SO4. Then the residue was concentrated under reduced and purified by column chromatography (EtOAc in Petroleum ether=0~100%) to afford (S)—N-[(3S,4S)-8-{3-[6-cyano-5-fluoro-4-methyl-1,2,3,4-tetrahydroquinolin-1-yl]-1-(oxan-2-yl)-1H-pyrazolo[3,4-b]pyrazin-6-yl}-3-methyl-2-oxa-8-azaspiro[4.5]decan-4-yl]-2-methylpropane-2-sulfinamide (110.0 mg, 83.3% yield) as a yellow oil.

Step c: To a solution of (S)—N-[(3S,4S)-8-{3-[6-cyano-5-fluoro-4-methyl-1,2,3,4-tetrahydroquinolin-1-yl]-1-(oxan-2-yl)-1H-pyrazolo[3,4-b]pyrazin-6-yl}-3-methyl-2-oxa-8-azaspiro[4.5]decan-4-yl]-2-methylpropane-2-sulfinamide (110.0 mg, 165.0 µmol) in dioxane (8.0 mL) was added 4 N HCl/dioxane (2.0 mL), then the mixture was stirred at 25° C. for 10 h. The mixture was concentrated under reduced pressure to give a residue, then to the residue in DCM (8.0 mL) was added TFA (1.0 mL) and stirred at 25° C. for another 12 h. LCMS showed the starting material was consumed completely and 56% peak with desired MS was detected. The reaction mixture was concentrated under reduced pressure and the residue was purified by prep-HPLC (HCl) to afford 1-{6-[(3S,4S)-4-amino-3-methyl-2-oxa-8-azaspiro[4.5]decan-8-yl]-1H-pyrazolo[3,4-b]pyrazin-3-yl}-5-fluoro-4-methyl-1,2,3,4-tetrahydroquinoline-6-carbonitrile hydrochloride (40.0 mg, 50.8% yield) as a yellow solid.

Step d: 1-{6-[(3S,4S)-4-amino-3-methyl-2-oxa-8-azaspiro[4.5]decan-8-yl]-1H-pyrazolo[3,4-b]pyrazin-3-yl}-5-fluoro-4-methyl-1,2,3,4-tetrahydroquinoline-6-carbonitrile hydrochloride (40.0 mg, 83.9 µmol) was purified by chiral SFC (Column: Chiralpak OJ 250 mm×30 mm, 5 um Mobile phase: 30% of methanol (0.1% NH3.H2O methanol) in CO2. Flow rate: 60 mL/min Column temperature: 40° C.) to afford the product of (4R*)-1-{6-[(3S,4S)-4-amino-3-methyl-2-oxa-8-azaspiro[4.5]decan-8-yl]-1H-pyrazolo[3,4-b]pyrazin-3-yl}-5-fluoro-4-methyl-1,2,3,4-tetrahydroquinoline-6-carbonitrile (18.1 mg, 45.3% yield) as yellow solid and (4S*)-1-{6-[(3S,4S)-4-amino-3-methyl-2-oxa-8-azaspiro[4.5]decan-8-yl]-1H-pyrazolo[3,4-b]pyrazin-3-yl}-5-fluoro-4-methyl-1,2,3,4-tetrahydroquinoline-6-carbonitrile (19.2 mg, 48.1% yield) as yellow solid. Stereochemistry at the 4 position was assigned arbitrarily.

Synthesis of 5-(6-((3S,4S)-4-amino-3-methyl-2-oxa-8-azaspiro[4.5]decan-8-yl)-1H-pyrazolo[3,4-b]pyrazin-3-yl)-5,6,7,8-tetrahydro-1,5-naphthyridine-2-carboxamide, Compound 243

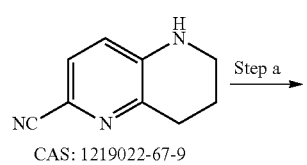
CAS: 1219022-67-9

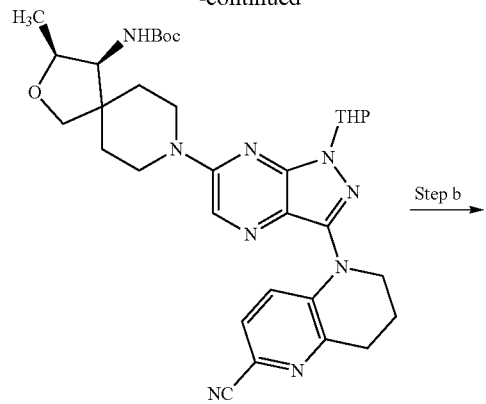

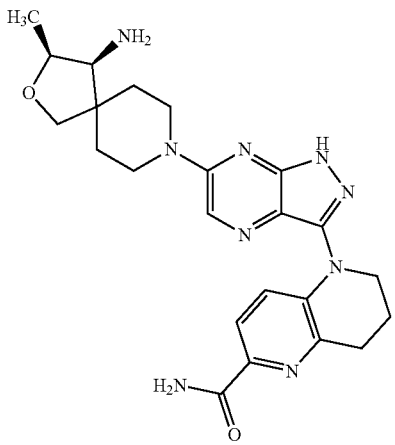

Step a: Tert-butyl ((3S,4S)-8-(3-(6-cyano-3,4-dihydro-1,5-naphthyridin-1(2H)-yl)-1-(tetrahydro-2H-pyran-2-yl)-1H-pyrazolo[3,4-b]pyrazin-6-yl)-3-methyl-2-oxa-8-azaspiro[4.5]decan-4-yl)carbamate (80.0 mg, 0.13 mmol) was prepared following the procedure detailed for Compound 33 beginning from commercially available 5,6,7,8-tetrahydro-1,5-naphthyridine-2-carbonitrile (CAS: 1219022-67-9).

Step b: To a microwave vial Tert-butyl ((3S,4S)-8-(3-(6-cyano-3,4-dihydro-1,5-naphthyridin-1(2H)-yl)-1-(tetrahydro-2H-pyran-2-yl)-1H-pyrazolo[3,4-b]pyrazin-6-yl)-3-methyl-2-oxa-8-azaspiro[4.5]decan-4-yl)carbamate (80.0 mg, 0.13 mmol) in a mixture of DMSO (0.70 mL), EtOH (0.14 mL) and H2O2 (0.07 mL) was added K2CO3 (5.3 mg, 0.038 mmol). The reaction vessel was sealed and heated to 60° C. for 16 h. Following cooling to ambient temperature and partitioning between EtOAc and brine, the organic residue was extracted (3×) and concentrated to dryness. The residue was dissolved in EtOH (0.7 mL) and HCl (4.0 M in dioxane, 0.7 mL) was added and the reaction aged at ambient temperature for 16 h. The residue was concentrated to dryness and purified by silica gel chromatography (0-20% MeOH in dichloromethane with 0.1% NH3 H2O) to furnish 5-(6-((3S,4S)-4-amino-3-methyl-2-oxa-8-azaspiro[4.5]decan-8-yl)-1H-pyrazolo[3,4-b]pyrazin-3-yl)-5,6,7,8-tetrahydro-1,5-naphthyridine-2-carboxamide (42.0 mg, 0.09 mmol) in 70% yield over two steps. LCMS: [M+H]+ 464.5.

Synthesis 1-(6-((3S,4S)-4-amino-3-methyl-2-oxa-8-azaspiro[4.5]decan-8-yl)-1H-pyrazolo[3,4-b]pyrazin-3-yl)-1,2,3,4-tetrahydroquinoline-5-carboxylic Acid, Compound 244

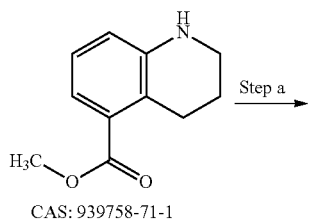

CAS: 939758-71-1

Step a →

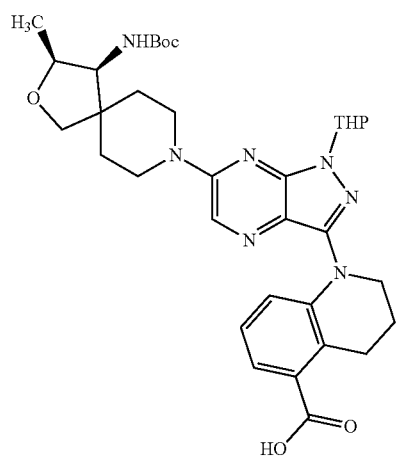

Step b →

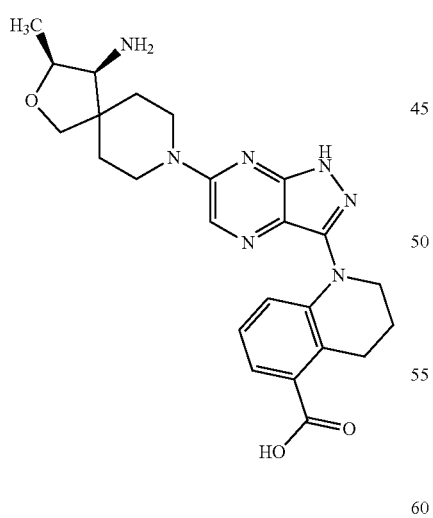

Step a: 1-(6-((3S,4S)-4-((tert-butoxycarbonyl)amino)-3-methyl-2-oxa-8-azaspiro[4.5]decan-8-yl)-1-(tetrahydro-2H-pyran-2-yl)-1H-pyrazolo[3,4-b]pyrazin-3-yl)-1,2,3,4-tetrahydroquinoline-5-carboxylic acid (25.5 mg, 0.040 mmol) resulted from the coupling procedure detailed for Compound 33, beginning with commercially available methyl 1,2,3,4-tetrahydroquinoline-5-carboxylate (CAS: 939758-71-1).

Step b: To 1-(6-((3S,4S)-4-((tert-butoxycarbonyl)amino)-3-methyl-2-oxa-8-azaspiro[4.5]decan-8-yl)-1-(tetrahydro-2H-pyran-2-yl)-1H-pyrazolo[3,4-b]pyrazin-3-yl)-1,2,3,4-tetrahydroquinoline-5-carboxylic acid (25.5 mg, 0.040 mmol) in THF (0.60 mL) was added HCl (4.0M in dioxane, 0.20 mL) and the reaction stirred at room temperature for 16 h. After evaporation of solvent, the crude residue was purified via prep HPLC (5-50% ACN in H$_2$O with 0.1% CH$_2$OH) to furnish 1-(6-((3S,4S)-4-amino-3-methyl-2-oxa-8-azaspiro[4.5]decan-8-yl)-1H-pyrazolo[3,4-b]pyrazin-3-yl)-1,2,3,4-tetrahydroquinoline-5-carboxylic acid (1.3 mg, 0.003 mmol). LCMS: [M+H]+ 464.5.

Synthesis of (3S,4S)-8-(3-(6-(1,2,4-oxadiazol-3-yl)-3,4-dihydro-1,5-naphthyridin-1(2H)-yl)-1H-pyrazolo[3,4-b]pyrazin-6-yl)-3-methyl-2-oxa-8-azaspiro[4.5]decan-4-amine, Compound 246

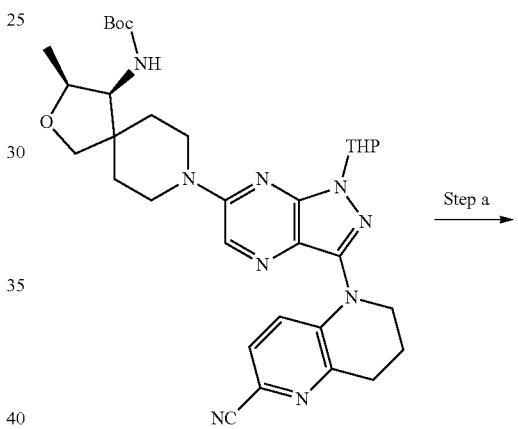

Step a →

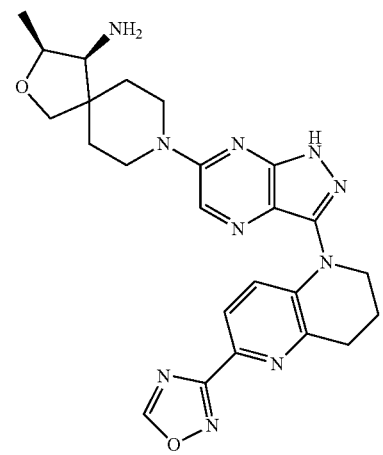

Step a: Compound was prepared using conditions described in the syntheses of Compound 172.

Synthesis of methyl 6-[(3S,4S)amino-3-methyl-2-oxa-8-azaspiro[4.5]decan-8-yl]-3-(1,2,3,4-tetrahydro-1,5-naphthyridin-1-yl)-1H-pyrazolo[3,4-b]pyrazine-1-carboxylate hydrochloride, Compound 253

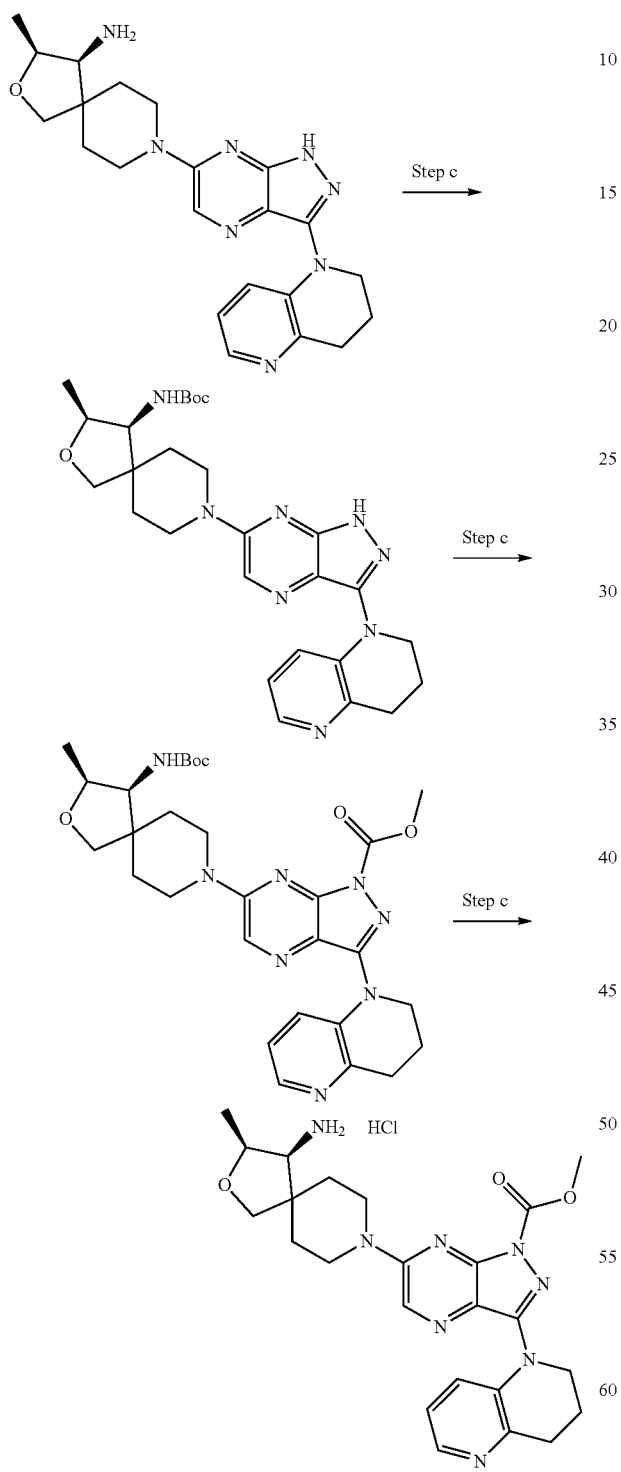

0.2 mmol) and Boc2O (43 mg. 0.2 mmol) were added into in THF (3 mL) and H2O (10 mL), then saturated NaHCO3 (8 mL) was added. The mixture was stirred at 25° C. for 12 h. The mixture was concentrated to give a residue and purified by prep-TLC (DCM:Methanol=100:10) to give the product of tert-butyl N-[(3S,4S)-3-methyl-8-[3-(1,2,3,4-tetrahydro-1,5-naphthyridin-1-yl)-1H-pyrazolo[3,4-b]pyrazin-6-yl]-2-oxa-8-azaspiro[4.5]decan-4-yl]carbamate (50.0 mg, 57.8% yield) as a yellow oil.

Step b: The solution of t-BuOK (0.2 mL, 0.2 mmol, 1M in THF) was added in the mixture of tert-butyl N-[(3S,4S)-3-methyl-8-[3-(1,2,3,4-tetrahydro-1,5-naphthyridin-1-yl)-1H-pyrazolo[3,4-b]pyrazin-6-yl]-2-oxa-8-azaspiro[4.5]decan-4-yl]carbamate (70 mg, 0.1 mmol) in THF (1 mL) at 0° C. The mixture was stirred at 25° C. for 0.5 h, then methyl chloroformate (20 μL, 0.2 mmol) was added at 0° C., and the mixture was stirred at 25° C. for 1 h. The reaction mixture was diluted with EtOAc (20 mL) and H2O (20 mL). The partitioned layers were separated. The aqueous phase was extracted with ethyl acetate (20 mL×3). The combined organic layers were washed with brine (20 mL), dried over anhydrous Na2SO4, filtered and concentrated to give the product of methyl 6-[(3S,4S)-4-{[(tert-butoxy)carbonyl]amino}-3-methyl-2-oxa-8-azaspiro[4.5]decan-8-yl]-3-(1,2,3,4-tetrahydro-1,5-naphthyridin-1-yl)-1H-pyrazolo[3,4-b]pyrazine-1-carboxylate (70.0 mg, 90.3% yield) as a yellow oil.

Step c: The compound of methyl 6-[(3S,4S)-4-{[(tert-butoxy)carbonyl]amino}-3-methyl-2-oxa-8-azaspiro[4.5]decan-8-yl]-3-(1,2,3,4-tetrahydro-1,5-naphthyridin-1-yl)-1H-pyrazolo[3,4-b]pyrazine-1-carboxylate (70 mg, 0.1 mmol) was added in 2 N HCl/MeOH (2 mL). The mixture was stirred at 25° C. for 12 h. The reaction mixture was concentrated and purified by prep-HPLC (HCl) to afford the product of methyl 6-[(3S,4S)-4-amino-3-methyl-2-oxa-8-azaspiro[4.5]decan-8-yl]-3-(1,2,3,4-tetrahydro-1,5-naphthyridin-1-yl)-1H-pyrazolo[3,4-b]pyrazine-1-carboxylate hydrochloride (22.6 mg, 36.5% yield) as a yellow solid.

Synthesis of (3S,4S)-8-(3-(6-(1H-pyrazol-3-yl)-3,4-dihydro-1,5-naphthyridin-1(2H)-yl)-1H-pyrazolo[3,4-b]pyrazin-6-yl)-3-methyl-2-oxa-8-azaspiro[4.5]decan-4-amine, Compound 254

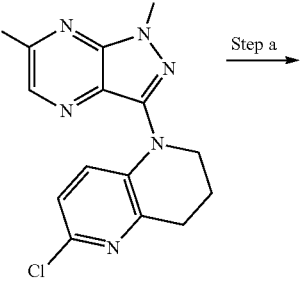

Step a: The compound of (3S,4S)-3-methyl-8-[3-(1,2,3,4-tetrahydro-1,5-naphthyridin-1-yl)-1H-pyrazolo[3,4-b]pyrazin-6-yl]-2-oxa-8-azaspiro[4.5]decan-4-amine (70 mg, -continued

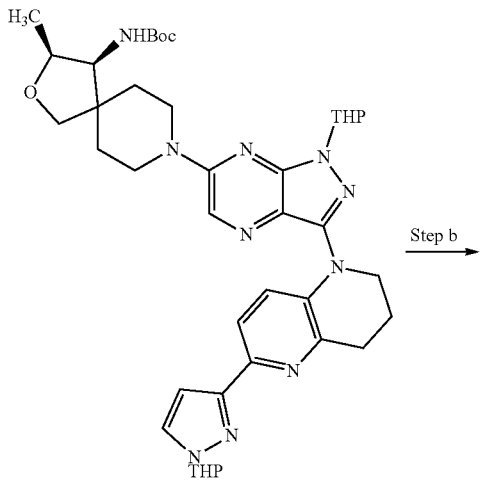

Step b

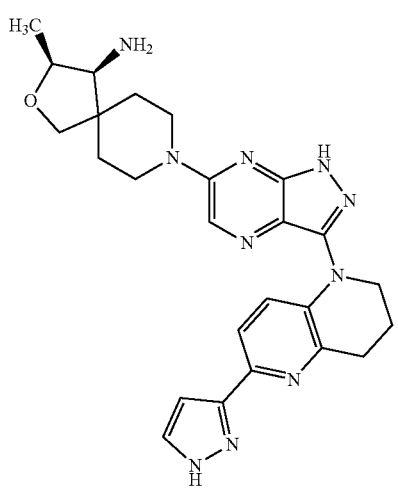

Step a: A mixture of tert-butyl N-[(3S,4S)-8-[3-(6-chloro-1,2,3,4-tetrahydro-1,5-naphthyridin-1-yl)-1-(oxan-2-yl)-1H-pyrazolo[3,4-b]pyrazin-6-yl]-3-methyl-2-oxa-8-azaspiro[4.5]decan-4-yl]carbamate (110 mg, 172 μmol, synthesized as described for Compound 33, with 6-chloro-1,2,3,4-tetrahydro-1,5-naphthyridine as the coupling partner), 1-(oxan-2-yl)-5-(4,4,5,5-tetramethyl-1,3,2-dioxaborolan-2-yl)-1H-pyrazole (71.7 mg, 258 μmol, CAS #903550-26-5), Pd(dppf)Cl₂·CH₂Cl₂ (31.5 mg, 34.4 μmol), and K₂CO₃ (59.2 mg, 429 μmol) in dioxane (10 mL)/H₂O (2 mL) was stirred at 90° C. for 12 hours under N₂ atmosphere. The reaction mixture was concentrated in vacuo to give a residue, which was purified by silica gel chromatography (85-95% EtOAc/petroleum ether) to afford tert-butyl ((3S,4S)-3-methyl-8-(1-(tetrahydro-2H-pyran-2-yl)-3-(6-(1-(tetrahydro-2H-pyran-2-yl)-1H-pyrazol-5-yl)-3,4-dihydro-1,5-naphthyridin-1(2H)-yl)-1H-pyrazolo[3,4-b]pyrazin-6-yl)-2-oxa-8-azaspiro[4.5]decan-4-yl)carbamate (45 mg, 34.8% yield) as a yellow oil.

Step b: A mixture of tert-butyl ((3S,4S)-3-methyl-8-(1-(tetrahydro-2H-pyran-2-yl)-3-(6-(1-(tetrahydro-2H-pyran-2-yl)-1H-pyrazol-5-yl)-3,4-dihydro-1,5-naphthyridin-1(2H)-yl)-1H-pyrazolo[3,4-b]pyrazin-6-yl)-2-oxa-8-azaspiro[4.5]decan-4-yl)carbamate (45 mg, 59.6 μmol) in 4M HCl/MeOH (5 mL) was stirred at 20° C. for 0.5 hour. The mixture was concentrated under reduced pressure to give a residue, which was purified by prep-HPLC (ACN/aq. HCl) to afford (3S,4S)-8-(3-(6-(1H-pyrazol-3-yl)-3,4-dihydro-1,5-naphthyridin-1(2H)-yl)-1H-pyrazolo[3,4-b]pyrazin-6-yl)-3-methyl-2-oxa-8-azaspiro[4.5]decan-4-amine dihydrochloride (9.5 mg, 29% yield) as a yellow solid: ESMS [M+H]⁺ =487.2; ¹H-NMR (400 MHz, methanol-d₄): δ 8.36 (s, 1H), 8.13 (d, J=8.8 Hz, 1H), 7.95 (d, J=9.2 Hz, 1H), 7.89 (d, J=2.4 Hz, 1H), 7.02 (d, J=2.4 Hz, 1H), 4.52-4.31 (m, 3H), 4.14-4.11 (m, 2H), 4.03 (d, J=9.2 Hz, 1H), 3.92 (d, J=9.2 Hz, 1H), 3.48 (d, J=4.0 Hz, 1H), 3.39-3.34 (m, 3H), 3.27-3.24 (m, 1H), 2.36-2.28 (m, 2H), 1.94-1.88 (m, 3H), 1.79-1.76 (m, 1H), 1.35 (d, J=6.4 Hz, 3H).

Synthesis of (3S,4S)-3-methyl-8-{3-[6-(1-methyl-1H-pyrazol-5-yl)-1,2,3,4-tetrahydro-1,5-naphthyridin-1-yl]-1H-pyrazolo[3,4-b]pyrazin-6-yl}-2-oxa-8-azaspiro[4.5]decan-4-amine hydrochloride, Compound 255

Synthesis of (3S,4S)-3-methyl-8-{3-[6-(1-methyl-1H-pyrazol-5-yl)-1,2,3,4-tetrahydro-1,5-naphthyridin-1-yl]-1H-pyrazolo[3,4-b]pyrazin-6-yl}-2-oxa-8-azaspiro[4.5]decan-4-amine hydrochloride was prepared as schematically illustrated below.

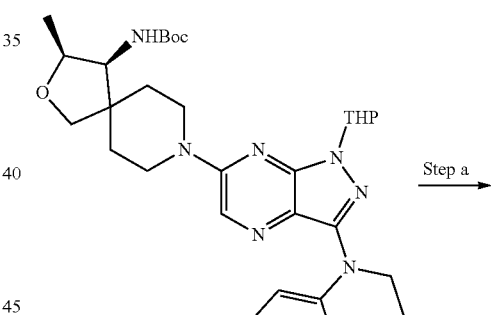

Step a

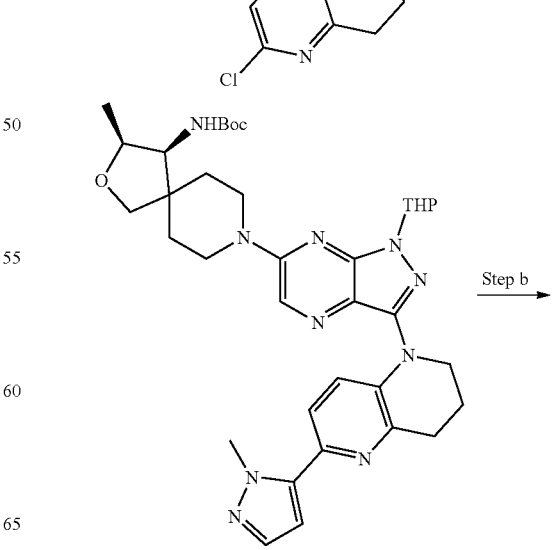

Step b

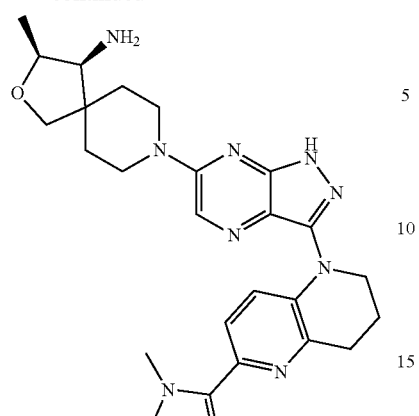

Step a: A mixture of tert-butyl N-[(3S,4S)-8-[3-(6-chloro-1,2,3,4-tetrahydro-1,5-naphthyridin-1-yl)-1-(oxan-2-yl)-1H-pyrazolo[3,4-b]pyrazin-6-yl]-3-methyl-2-oxa-8-azaspiro[4.5]decan-4-yl]carbamate (100 mg, 0.1 mmol), 1-methyl-5-(4,4,5,5-tetramethyl-1,3,2-dioxaborolan-2-yl)-1H-pyrazole (39 mg, 0.2 mmol), Pd(dppf)Cl2.DCM (25 mg, 0.03 mmol) and K2CO3 (54 mg, 0.4 mmol) in dioxane (5 mL)/H2O (0.5 mL) was evacuated and refilled for 3 times using N2 and stirred at 90° C. for 12 hours under N2 atmosphere. The reaction mixture was concentrated to give a residue, which was purified by flash silica gel chromatography (Ethyl acetate/Petroleum ether=0/100 to 80/100) to give the product of tert-butyl N-[(3S,4S)-3-methyl-8-{3-[6-(1-methyl-1H-pyrazol-5-yl)-1,2,3,4-tetrahydro-1,5-naphthyridin-1-yl]-1-(oxan-2-yl)-1H-pyrazolo[3,4-b]pyrazin-6-yl}-2-oxa-8-azaspiro[4.5]decan-4-yl]carbamate (80.0 mg, 75.4% yield) as a yellow oil.

Step b: The compound of tert-butyl N-[(3S,4S)-3-methyl-8-{3-[6-(1-methyl-1H-pyrazol-5-yl)-1,2,3,4-tetrahydro-1,5-naphthyridin-1-yl]-1-(oxan-2-yl)-1H-pyrazolo[3,4-b]pyrazin-6-yl}-2-oxa-8-azaspiro[4.5]decan-4-yl]carbamate (80 mg, 116 µmol) was added in 2 N HCl/MeOH (2 mL). The mixture was stirred at 25° C. for 12 hrs. The reaction mixture was concentrated and purified by prep-HPLC (HCl) to afford the product of(3S,4S)-3-methyl-8-{3-[6-(1-methyl-1H-pyrazol-5-yl)-1,2,3,4-tetrahydro-1,5-naphthyridin-1-yl]-1H-pyrazolo[3,4-b]pyrazin-6-yl}-2-oxa-8-azaspiro[4.5]decan-4-amine hydrochloride (41.5 mg, 66.6% yield) as a yellow solid.

Synthesis of (3S,4S)-3-methyl-8-{3-[6-(piperazin-1-yl)-1,2,3,4-tetrahydro-1,5-naphthyridin-1-yl]-1H-pyrazolo[3,4-b]pyrazin-6-yl}-2-oxa-8-azaspiro[4.5]decan-4-amine dihydrochloride, Compound 256

Synthesis of (3S,4S)-3-methyl-8-{3-[6-(piperazin-1-yl)-1,2,3,4-tetrahydro-1,5-naphthyridin-1-yl]-1H-pyrazolo[3,4-b]pyrazin-6-yl}-2-oxa-8-azaspiro[4.5]decan-4-amine dihydrochloride was prepared as schematically illustrated below.

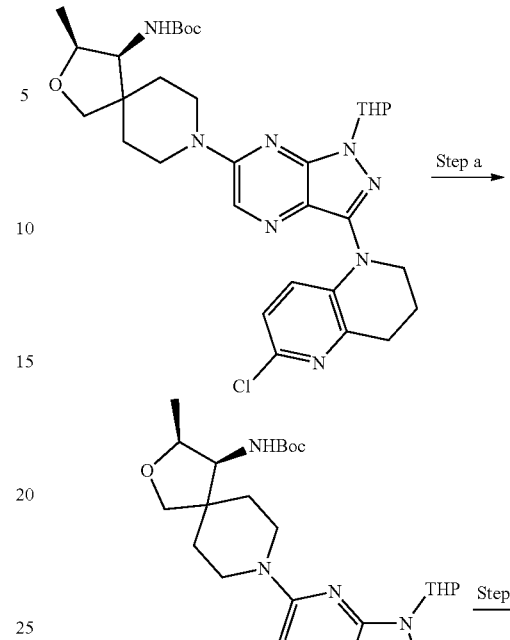

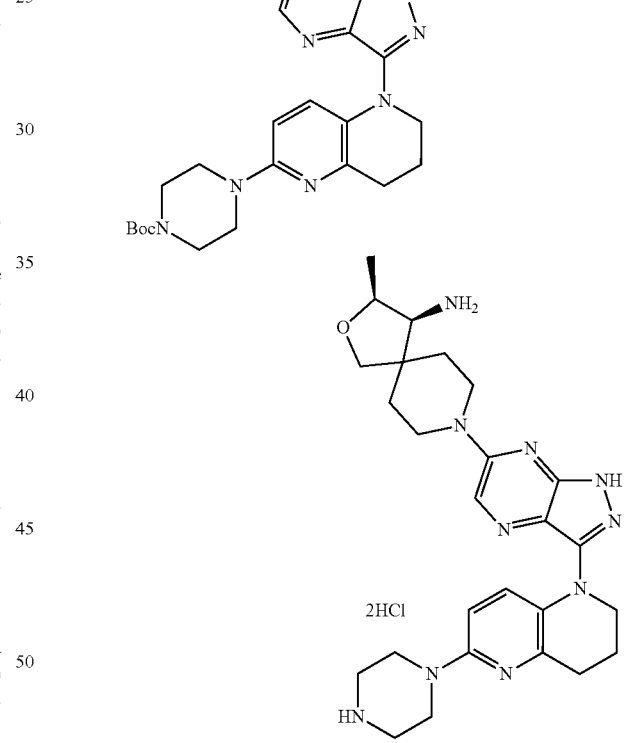

Step a: The mixture of tert-butyl N-[(3S,4S)-8-[3-(6-chloro-1,2,3,4-tetrahydro-1,5-naphthyridin-1-yl)-1-(oxan-2-yl)-1H-pyrazolo[3,4-b]pyrazin-6-yl]-3-methyl-2-oxa-8-azaspiro[4.5]decan-4-yl]carbamate (150 mg, 234 µmol, 1.0 eq), tert-butyl piperazine-1-carboxylate (57 mg, 304 µmol, 1.3 eq), XPhos (22 mg, 47 µmol, 0.3 eq), Pd2(bda)3 (43 mg, 47 µmol, 0.3 eq) and t-BuONa (67 mg, 702 µmol, 3.0 eq) in dioxane (10 mL) was evacuated and refilled for 3 times using N2, stirred at 100° C. for 5 hours. LCMS indicated that the starting material was consumed completely and one main new peak with desired MS was detected. The combined mixture was concentrated under reduced pressure. The residue was purified by column chromatography (Petroleum ether/Ethyl acetate=10:1-1:1) to afford the desired product of tert-butyl 4-(5-{6-[(3S,4S)-4-{[(tert-butoxy)carbonyl] amino}-3-methyl-2-oxa-8-azaspiro[4.5]decan-8-yl]-1-(oxan-2-yl)-1H-pyrazolo[3,4-b]pyrazin-3-yl}-5,6,7,8-tetrahydro-1,5-naphthyridin-2-yl)piperazine-1-carboxylate (135 mg, combined product) as a yellow solid.

Step b: The mixture of tert-butyl 4-(5-{6-[(3S,4S)-4-{[(tert-butoxy)carbonyl]amino}-3-methyl-2-oxa-8-azaspiro[4.5]decan-8-yl]-1-(oxan-2-yl)-1H-pyrazolo[3,4-b]pyrazin-3-yl}-5,6,7,8-tetrahydro-1,5-naphthyridin-2-yl)piperazine-1-carboxylate (135 mg, 171 μmol, 1.0 eq) in HCl/MeOH (5 mL, 4M) was stirred at 15° C. for 20 hours. LCMS indicated that the starting material was consumed completely and one main new peak with desired MS was detected. The mixture was concentrated under reduced pressure and the residue was purified by prep-HPLC (HCl) to afford (3S,4S)-3-methyl-8-{3-[6-(piperazin-1-yl)-1,2,3,4-tetrahydro-1,5-naphthyridin-1-yl]-1H-pyrazolo[3,4-b]pyrazin-6-yl}-2-oxa-8-azaspiro[4.5]decan-4-amine dihydrochloride (63.0 mg, 63.8% yield) as a yellow solid Synthesis of 1-{6-[(3S,4S)-4-amino-3-methyl-2-oxa-8-azaspiro[4.5]decan-8-yl]-1H-pyrazolo[3,4-b]pyrazin-3-yl}-1H,2H,3H,4H-pyrido[2,3-b]pyrazine-4-carboxamide hydrochloride, Compound 258

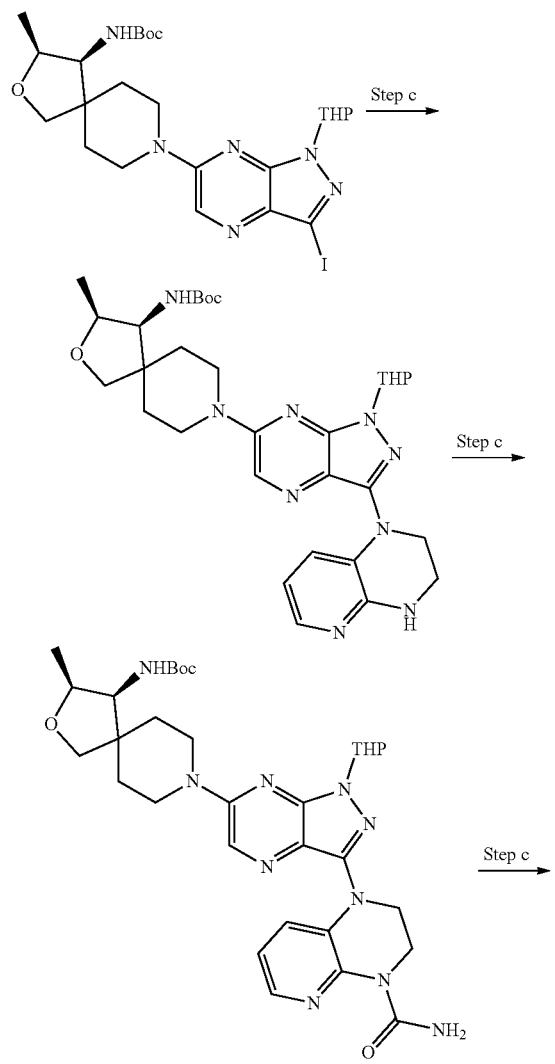

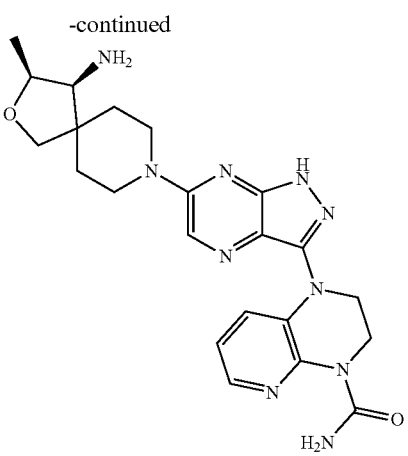

Step a: To a solution of tert-butyl N-[(3S,4S)-8-[3-iodo-1-(oxan-2-yl)-1H-pyrazolo[3,4-b]pyrazin-6-yl]-3-methyl-2-oxa-8-azaspiro[4.5]decan-4-yl]carbamate (200.0 mg, 334.0 μmol) and 1H,2H,3H,4H-pyrido[2,3-b]pyrazine (54.0 mg, 400.0 μmol) in PhMe (5.0 mL) were added Pd2(dba)3 (30.5 mg, 33.4 μmol), XantPhos (19.3 mg, 33.4 μmol) and t-BuONa (64.1 mg, 668.0 μmol). The mixture was evacuated and refilled for 3 times using N2. The reaction mixture was stirred at 100° C. for 12 hours. LCMS showed the starting material was consumed completely and 49% desired product formed. The reaction mixture was concentrated under reduced pressure. The residue was purified by column chromatography (Petroleum ether/Ethyl acetate=100:0 to 100:100 and DCM/MeOH=100:0 to 100:10). The product of tert-butyl N-[(3S,4S)-3-methyl-8-[1-(oxan-2-yl)-3-{1H,2H,3H,4H-pyrido[2,3-b]pyrazin-1-yl}-1H-pyrazolo[3,4-b]pyrazin-6-yl]-2-oxa-8-azaspiro[4.5]decan-4-yl]carbamate (150.0 mg, 74.2% yield) was obtained as a yellow solid.

Step b: To a cooled (0° C.) solution of tert-butyl N-[(3S,4S)-3-methyl-8-[1-(oxan-2-yl)-3-{1H,2H,3H,4H-pyrido[2,3-b]pyrazin-1-yl}-1H-pyrazolo[3,4-b]pyrazin-6-yl]-2-oxa-8-azaspiro[4.5]decan-4-yl]carbamate (130.0 mg, 214.0 μmol) in DCM (5.0 mL) was added trichloroethanecarbonyl isocyanate (60.4 mg, 321.0 μmol). After being stirred for 1 hour at 0° C., a solution of KOH in MeOH (1M, 107.0 uL) was added. The reaction mixture was warmed to 20° C., and stirred 16 hours under N2. LCMS showed the starting material was consumed completely and 64% desired product was detected at 254 nm. The reaction mixture was concentrated under reduced pressure to give the residue (200.0 mg, crude), which was used for next step directly without further purification.

Step c: A solution of tert-butyl N-[(3S,4S)-8-(3-{4-carbamoyl-1H,2H,3H,4H-pyrido[2,3-b]pyrazin-1-yl}-1-(oxan-2-yl)-1H-pyrazolo[3,4-b]pyrazin-6-yl)-3-methyl-2-oxa-8-azaspiro[4.5]decan-4-yl]carbamate (200.0 mg, 308.0 μmol) in HCl/MeOH (3.0 mL, 4 N) was stirred at 20° C. for 4 hours. LCMS showed the starting material was consumed completely and 37% desired product formed. The reaction mixture was concentrated under reduced pressure. The residue was diluted with MeOH (5.0 mL). The residue was purified by prep-HPLC (HCl). The product of 1-{6-[(3S,4S)-4-amino-3-methyl-2-oxa-8-azaspiro[4.5]decan-8-yl]-1H-pyrazolo[3,4-b]pyrazin-3-yl}-1H,2H,3H,4H-pyrido[2,3-b]pyrazine-4-carboxamide hydrochloride (15.0 mg, 9.7% yield) was obtained as an orange solid.

Synthesis of (3S)-1-(5-{6-[(3S,4S)-4-amino-3-methyl-2-oxa-8-azaspiro[4.5]decan-8-yl]-1H-pyrazolo[3,4-b]pyrazin-3-yl}-5,6,7,8-tetrahydro-1,5-naphthyridin-2-yl)pyrrolidin-3-ol, Compound 261

Synthesis of (3S)-1-(5-{6-[(3S,4S)-4-amino-3-methyl-2-oxa-8-azaspiro[4.5]decan-8-yl]-1H-pyrazolo[3,4-b]pyrazin-3-yl}-5,6,7,8-tetrahydro-1,5-naphthyridin-2-yl)pyrrolidin-3-ol was prepared as schematically illustrated below.

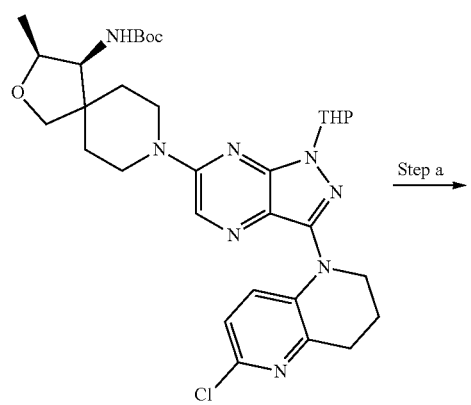

Step a →

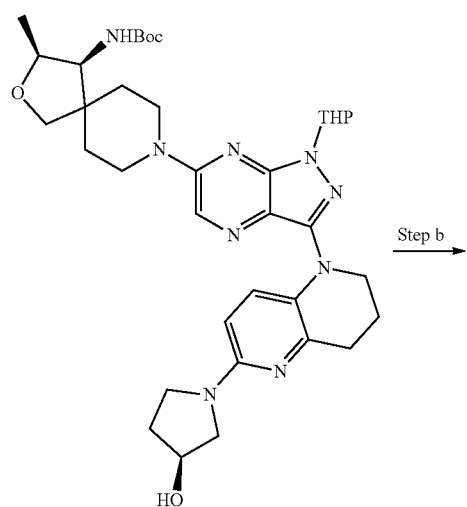

Step b →

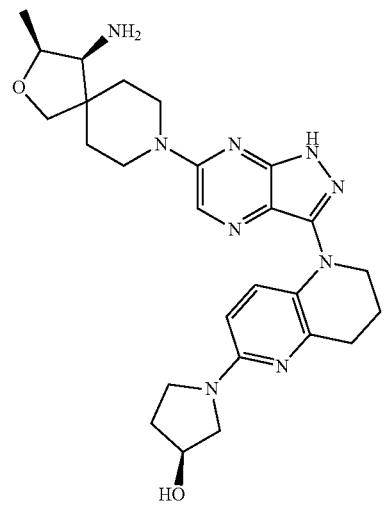

Step a: Tert-butyl N-[(3S,4S)-8-[3-(6-chloro-1,2,3,4-tetrahydro-1,5-naphthyridin-1-yl)-1-(oxan-2-yl)-1H-pyrazolo[3,4-b]pyrazin-6-yl]-3-methyl-2-oxa-8-azaspiro[4.5]decan-4-yl]carbamate (formed via a route similar to that used for Compound 33, using 6-chloro-tetrahydronaphthyridine, 130.0 mg, 203.0 µmol), (3S)-pyrrolidin-3-ol (26.4 mg, 304.0 µmol), Pd2(dba)3 (92.4 mg, 101.0 µmol), XPhos (48.0 mg, 101.0 µmol) and t-BuONa (58.5 mg, 609.0 µmol) were added in dioxane (10.0 mL), the reaction mixture was stirred at 90° C. for 12 hours. LCMS indicated 18% of desired product formed. The reaction was concentrated under reduced pressure to give a residue and purified by flash silica gel chromatography (Petroleum ether:Ethyl acetate=2:1, DCM:MeOH=10:1) to afford the product of tert-butyl N-[(3S,4S)-8-(3-{6-[(3S)-3-hydroxypyrrolidin-1-yl]-1,2,3,4-tetrahydro-1,5-naphthyridin-1-yl}-1-(oxan-2-yl)-1H-pyrazolo[3,4-b]pyrazin-6-yl)-3-methyl-2-oxa-8-azaspiro[4.5]decan-4-yl]carbamate (160.0 mg, 76% purity, 86.4% yield) as a yellow solid.

Step b: Tert-butyl N-[(3S,4S)-8-(3-{6-[(3S)-3-hydroxypyrrolidin-1-yl]-1,2,3,4-tetrahydro-1,5-naphthyridin-1-yl}-1-(oxan-2-yl)-1H-pyrazolo[3,4-b]pyrazin-6-yl)-3-methyl-2-oxa-8-azaspiro[4.5]decan-4-yl]carbamate (160.0 mg, 175.0 µmol, 76% purity) was added in 4N HCl/MeOH (6.0 mL), the reaction mixture was stirred at 25° C. for 12 hours. LCMS indicated 63% of desired product formed. The reaction mixture was concentrated under reduced pressure to give a residue and purified by prep. HPLC (HCl) to afford the product of (3S)-1-(5-{6-[(3S,4S)-4-amino-3-methyl-2-oxa-8-azaspiro[4.5]decan-8-yl]-1H-pyrazolo[3,4-b]pyrazin-3-yl}-5,6,7,8-tetrahydro-1,5-naphthyridin-2-yl)pyrrolidin-3-ol hydrochloride (66.7 mg, 70.3% yield) as a yellow solid.

Synthesis of (3S,4S)-8-{3-[(4R)-7-fluoro-4-methyl-1,2,3,4-tetrahydro-1,5-naphthyridin-1-yl]-1H-pyrazolo[3,4-b]pyrazin-6-yl}-3-methyl-2-oxa-8-azaspiro[4.5]decan-4-amine hydrochloride and (3S,4S)-8-{3-[(4S)-7-fluoro-4-methyl-1,2,3,4-tetrahydro-1,5-naphthyridin-1-yl]-1H-pyrazolo[3,4-b]pyrazin-6-yl}-3-methyl-2-oxa-8-azaspiro[4.5]decan-4-amine hydrochloride, Compound 262 and Compound 263

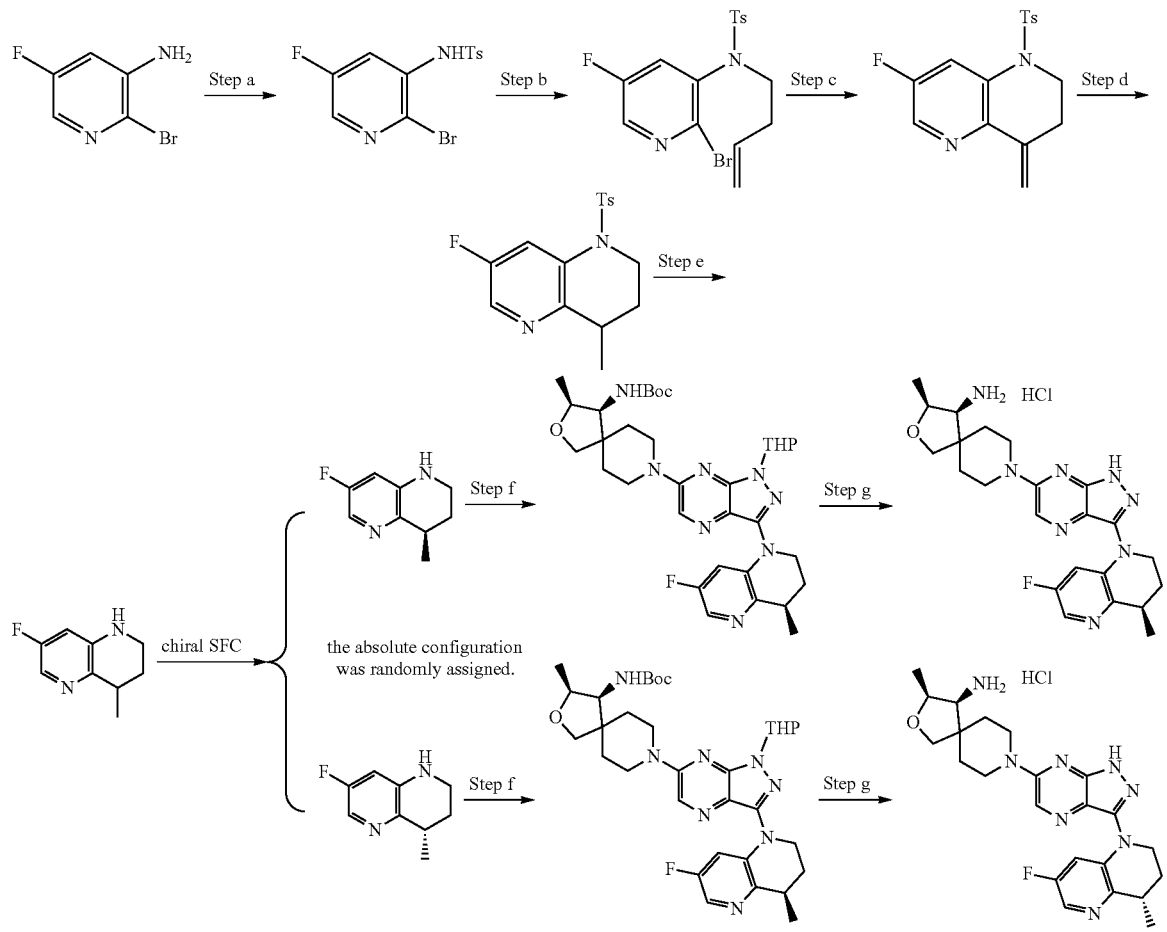

Step a: TsCl (10.9 g, 57.5 mmol) in DCM(50 mL) was added in the mixture of 2-bromo-5-fluoropyridin-3-amine (10 g, 52.3 mmol) in DCM (50 mL), pyridine (25.2 mL, 313 mmol) was added. The reaction was stirred at 25° C. for 12 h. The mixture was washed with 2 N HCl solution (100 mL×2) and H2O (100 mL). The organic layer was dried over anhydrous Na2SO4, filtered and concentrated to give a residue. The residue was triturated with Ethyl acetate/Petroleum ether=1:1 (100 mL). A lot of precipitate formed, the solid was collected by filtration to give the product of N-(2-bromo-5-fluoropyridin-3-yl)-4-methylbenzene-1-sulfonamide (10.0 g, 55.5% yield) as a white solid.

Step b: The compound of but-3-en-1-ol (3.7 mL, 43.3 mmol) and DIAD (8.5 mL, 43.3 mmol) was added in the mixture of N-(2-bromo-5-fluoropyridin-3-yl)-4-methylbenzenesulfonamide (10 g, 28.9 mmol) and PPh3 (15.1 g, 57.8 mmol) in THF (100 mL) at 25° C. for 12 h. The mixture was concentrated to give a residue which was purified by flash column chromatography (Ethyl acetate:Petroleum ether=0:1 to 1:5) to give the product of N-(2-bromo-5-fluoropyridin-3-yl)-N-(but-3-en-1-yl)-4-methylbenzenesulfonamide (12.8 g, crude) as a white solid.

Step c: The compound of Pd(OAc)2 (1.2 g, 5.2 mmol), XPhos (2.5 g, 5.2 mmol) and TEA (15 mL, 107 mmol) were added in the mixture of N-(2-bromo-5-fluoropyridin-3-yl)-N-(but-3-en-1-yl)-4-methylbenzene-1-sulfonamide (10.5 g, 26.2 mmol) in DMA (150 mL). The reaction mixture was evacuated and refilled for 3 times using N2. The mixture was stirred at 130° C. for 12 h under N2. The mixture was diluted with H2O (50 mL) and EtOAc (500 mL), the partitioned layers were separated. The organic layer were washed with brine (100 mL×3) and dried over anhydrous Na2SO4, filtered and concentrated to give a residue which was purified by flash silica gel column chromatography (Petroleum ether:EtOAc=1:0 to 5:1) to give a product of 7-fluoro-1-(4-methylbenzenesulfonyl)-4-methylidene-1,2,3,4-tetrahydro-1,5-naphthyridine (5.85 g, combined product) as a yellow solid.

Step d: The compound of Pd/C (10% wet, 200 mg) was added in the mixture of 7-fluoro-1-(4-methylbenzenesulfonyl)-4-methylidene-1,2,3,4-tetrahydro-1,5-naphthyridine (2 g, 6.3 mmol) in MeOH (20 mL). The reaction mixture was evacuated and refilled for 3 times using H2. The mixture was stirred at 25° C. for 12 h under H2 (15 psi). The mixture was filtered through a pad of celite. The filtrate was concentrated to give the product of 7-fluoro-4-methyl-1-(4-methylbenzenesulfonyl)-1,2,3,4-tetrahydro-1,5-naphthyridine (1.40 g, 69.7% yield) as a yellow solid.

Step e: The compound of 7-fluoro-4-methyl-1-(4-methylbenzenesulfonyl)-1,2,3,4-tetrahydro-1,5-naphthyridine (0.7 g, 2.18 mmol) was placed in a round-bottom flask. Conc. H2SO4 (5 mL) was added and the mixture was stirred at 25° C. for 0.5 h. The combined mixture was adjusted to pH=9-10 with saturated NaHCO₃ at 0° C., and extracted with ethyl acetate (20 mL×3). The combined organic layers were washed with brine (20 mL), dried over anhydrous Na2SO4, filtered and concentrated to give a residue which was purified by flash silica gel chromatography (Petroleum ether:Ethyl acetate=100:20) to give the product of 7-fluoro-4-methyl-1,2,3,4-tetrahydro-1,5-naphthyridine (120 mg, combined product) as a white solid. The residue was separated by chiral SFC ("Column: Chiralpak IC-3 150×4.6 mm I.D., 3 um Mobile phase: A: CO2 B:IPA (0.05% DEA), Gradient: from 5% to 40% of B in 5.5 min and hold 40% for 3 min, then 5% of B for 1.5 min. Flow rate: 2.5 mL/min, Column temperature: 40° C.) to give the product of (4R)-7-fluoro-4-methyl-1,2,3,4-tetrahydro-1,5-naphthyridine (55.5 mg, 92.5% yield) as a white solid and (4S)-7-fluoro-4-methyl-1,2,3,4-tetrahydro-1,5-naphthyridine(55.5 mg, 92.5%) as a white solid. The absolute configuration was assigned randomly.

Step f: The compound of tert-butyl N-[(3S,4S)-8-[3-iodo-1-(oxan-2-yl)-1H-pyrazolo[3,4-b]pyrazin-6-yl]-3-methyl-2-oxa-8-azaspiro[4.5]decan-4-yl]carbamate (200 mg, 334 µmol), (4R)-7-fluoro-4-methyl-1,2,3,4-tetrahydro-1,5-naphthyridine (55.5 mg, 334 µmol), XantPhos (57.8 mg, 100 µmol), Pd2(dba)3 (85.0 mg, 100 µmol) and t-BuONa (64.1 mg, 668 µmol) were added in PhMe (15 mL). The mixture was evacuated and refilled for 3 times using N2. The reaction mixture was stirred at 120° C. for 12 hours. The reaction was concentrated to give a residue which was purified by flash silica gel chromatography (Petroleum ether: Ethyl acetate=100:0 to 0:100) to afford the product of tert-butyl N-[(3S,4S)-8-(3-[(4R)-7-fluoro-4-methyl-1,2,3,4-tetrahydro-1,5-naphthyridin-1-yl]-1-(oxan-2-yl)-1H-pyrazolo[3,4-b]pyrazin-6-yl)-3-methyl-2-oxa-8-azaspiro[4.5]decan-4-yl]carbamate (65.0 mg, 30.6% yield) as a yellow oil.

Step g: The compound of tert-butyl N-[(3S,4S)-8-(3-[(4R)-7-fluoro-4-methyl-1,2,3,4-tetrahydro-1,5-naphthyridin-1-yl]-1-(oxan-2-yl)-1H-pyrazolo[3,4-b]pyrazin-6-yl)-3-methyl-2-oxa-8-azaspiro[4.5]decan-4-yl]carbamate (60 mg, 0.1 mmol) was added HCl/MeOH (2 mL, 2 N) was added. The mixture was stirred at 25° C. for 12 h. The reaction mixture was concentrated and purified by prep-HPLC (HCl) to afford the product of (3S,4S)-8-{3-[(4R)-7-fluoro-4-methyl-1,2,3,4-tetrahydro-1,5-naphthyridin-1-yl]-1H-pyrazolo[3,4-b]pyrazin-6-yl}-3-methyl-2-oxa-8-azaspiro[4.5]decan-4-amine hydrochloride (16.7 mg, 34.1 µmol) as a yellow solid.

(3S,4S)-8-{3-[(4S)-7-fluoro-4-methyl-1,2,3,4-tetrahydro-1,5-naphthyridin-1-yl]-1H-pyrazolo[3,4-b]pyrazin-6-yl}-3-methyl-2-oxa-8-azaspiro[4.5]decan-4-amine hydrochloride (66.1 mg, 135 µmol) was isolated as a yellow solid via the same route, using the opposite enantiomer obtained following the separation in step e. Absolute stereochemistry at the 4-position was arbitrarily assigned.

Synthesis of (8R)-5-(6-[(3S,4S)-4-amino-3-methyl-2-oxa-8-azaspiro[4.5]decan-8-yl]-1H-pyrazolo[3,4-b]pyrazin-3-yl)-8-methyl-5,6,7,8-tetrahydro-1,5-naphthyridine-2-carboxamide and (8S)-5-(6-[(3S,4S)-4-amino-3-methyl-2-oxa-8-azaspiro[4.5]decan-8-yl]-1H-pyrazolo[3,4-b]pyrazin-3-yl)-8-methyl-5,6,7,8-tetrahydro-1,5-naphthyridine-2-carboxamide, Compound 265 and Compound 264

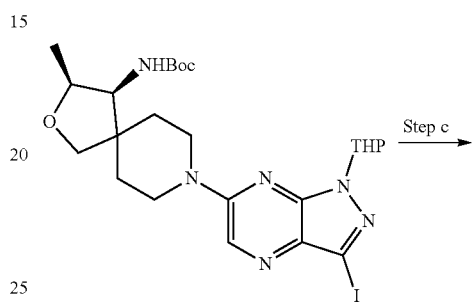

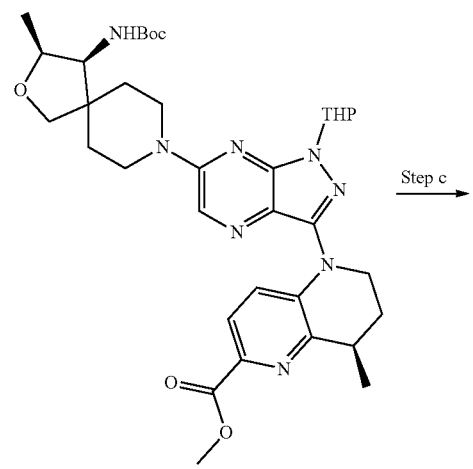

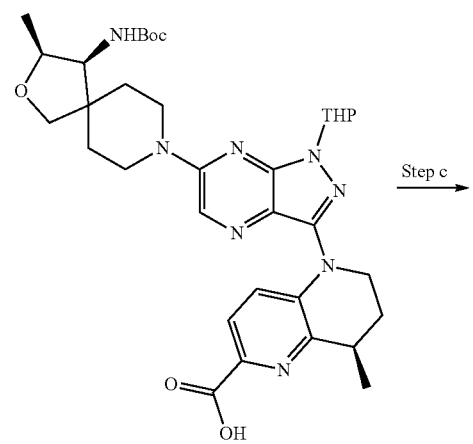

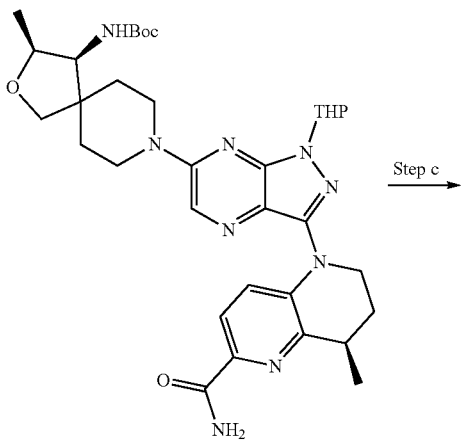

Step c →

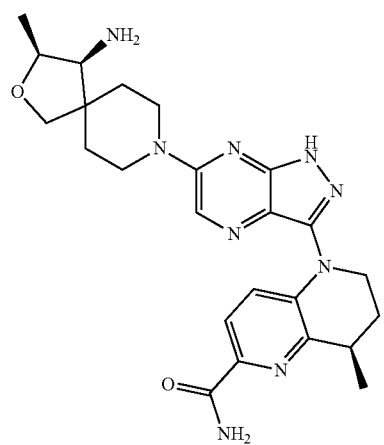 [SMILES: C[C@@H]1CCN(c2n[nH]c3nc(N4CCC5(CC4)CO[C@@H](C)[C@H]5N)cnc23)c2ccc(C(N)=O)nc21]

Step a: A mixture of methyl (8R)-8-methyl-5,6,7,8-tetrahydro-1,5-naphthyridine-2-carboxylate (50.0 mg, 242.0 µmol), tert-butyl N-[(3S,4S)-8-[3-iodo-1-(oxan-2-yl)-1H-pyrazolo[3,4-b]pyrazin-6-yl]-3-methyl-2-oxa-8-azaspiro[4.5]decan-4-yl]carbamate (173.0 mg, 290.0 µmol), Cs2CO3 (236.0 mg, 726.0 µmol), RuPhos (33.8 mg, 72.6 µmol) and RuPhos-Pd-G4 (30.8 mg, 36.3 µmol) in toluene (5.0 mL) was stirred at 100° C. for 14 hours under N2. LCMS showed the starting material was consumed completely and 28% peak with desired MS was detected. The reaction mixture was poured into EtOAc (150.0 mL), washed with water (50.0 mL) and brine (50.0 mL). The organic layer was dried over anhydrous Na2SO4, filtered and concentrated in vacuum. The residue was purified by column chromatography (EtOAc in Petroleum ether=0~90%) to afford methyl (8R)-5-{6-[(3S,4S)-4-{[(tert-butoxy)carbonyl]amino}-3-methyl-2-oxa-8-azaspiro[4.5]decan-8-yl]-1-(oxan-2-yl)-1H-pyrazolo[3,4-b]pyrazin-3-yl}-8-methyl-5,6,7,8-tetrahydro-1,5-naphthyridine-2-carboxylate (120.0 mg, crude) as a yellow solid.

Step b: To a solution of methyl (8R)-5-{6-[(3S,4S)-4-{[(tert-butoxy)carbonyl]amino}-3-methyl-2-oxa-8-azaspiro[4.5]decan-8-yl]-1-(oxan-2-yl)-1H-pyrazolo[3,4-b]pyrazin-3-yl}-8-methyl-5,6,7,8-tetrahydro-1,5-naphthyridine-2-carboxylate (120.0 mg, 177.0 µmol) in MeOH (5.0 mL) was added NaOH (3.0 mL, 9.0 mmol, 3.0 M). The mixture was stirred at 50° C. for 3 hours. LCMS showed the starting material was consumed completely and one main peak with desired MS formed. The mixture was concentrated to about 3 mL and extracted with EtOAc (10.0 mL, discarded). The aqueous was adjusted pH=6 with 1N HCl and extracted with EtOAc (10.0 mL×3). The combined organic layers were dried over anhydrous Na2SO4, filtered and concentrated under reduced pressure to get (8R)-5-{6-[(3S,4S)-4-{[(tert-butoxy)carbonyl]amino}-3-methyl-2-oxa-8-azaspiro[4.5]decan-8-yl]-1-(oxan-2-yl)-1H-pyrazolo[3,4-b]pyrazin-3-yl}-8-methyl-5,6,7,8-tetrahydro-1,5-naphthyridine-2-carboxylic acid (90.0 mg, 135 µmol, 77.0% yield) as a yellow solid.

Step c: A solution of (8R)-5-{6-[(3S,4S)-4-{[(tert-butoxy)carbonyl]amino}-3-methyl-2-oxa-8-azaspiro[4.5]decan-8-yl]-1-(oxan-2-yl)-1H-pyrazolo[3,4-b]pyrazin-3-yl}-8-methyl-5,6,7,8-tetrahydro-1,5-naphthyridine-2-carboxylic acid (90.0 mg, 135.0 µmol), (NH4)2CO3 (64.8 mg, 675.0 µmol), HATU (153.0 mg, 405.0 µmol) and DIEA (87.0 mg, 675.0 µmol) in DMF (5.0 mL) was stirred at 45° C. for 1 hour. Orange solution was observed. LCMS showed the starting material was consumed completely and one main peak with desired MS formed. The mixture was concentrated under reduced pressure. The residue was dissolved in EtOAc (150.0 mL), washed with water (50.0 mL) and brine (50.0 mL), dried over anhydrous Na2SO4, filtered and concentrated under reduced pressure. The residue was purified by silica column (EtOAc in Petroleum ether=0~100%) to afford tert-butyl N-[(3S,4S)-8-{3-[(4R)-6-carbamoyl-4-methyl-1,2,3,4-tetrahydro-1,5-naphthyridin-1-yl]-1-(oxan-2-yl)-1H-pyrazolo[3,4-b]pyrazin-6-yl}-3-methyl-2-oxa-8-azaspiro[4.5]decan-4-yl]carbamate (75.0 mg, 113 µmol, 83.9% yield) as a yellow solid.

Step d: Tert-butyl N-[(3S,4S)-8-{3-[(4R)-6-carbamoyl-4-methyl-1,2,3,4-tetrahydro-1,5-naphthyridin-1-yl]-1-(oxan-2-yl)-1H-pyrazolo[3,4-b]pyrazin-6-yl}-3-methyl-2-oxa-8-azaspiro[4.5]decan-4-yl]carbamate (75.0 mg, 113.0 µmol) was added in 4 M HCl/dioxane (5.0 mL) and stirred at 25° C. for 12 hours. Yellow suspension was observed. LCMS showed the starting material was consumed completely and one main new peak with desired MS formed. The mixture was concentrated under reduced pressure to give a residue. The residue was dissolved in MeOH (8.0 mL), adjusted pH=8-9 with K2CO3, filtrated and concentrated under reduced pressure. The residue was purified by silica column (MeOH in DCM=0~8%) to afford (8R)-5-{6-[(3S,4S)-4-amino-3-methyl-2-oxa-8-azaspiro[4.5]decan-8-yl]-1H-pyrazolo[3,4-b]pyrazin-3-yl}-8-methyl-5,6,7,8-tetrahydro-1,5-naphthyridine-2-carboxamide (32.8 mg, 68.6 µmol, 60.8% yield) as a yellow solid.

(8S)-5-{6-[(3S,4S)-4-amino-3-methyl-2-oxa-8-azaspiro[4.5]decan-8-yl]-1H-pyrazolo[3,4-b]pyrazin-3-yl}-8-methyl-5,6,7,8-tetrahydro-1,5-naphthyridine-2-carboxamide was made by the same route, starting from methyl (8S)-8-methyl-5,6,7,8-tetrahydro-1,5-naphthyridine-2-carboxylate.

Synthesis of (3S,4S)-3-methyl-8-(3-((R)-4-methyl-6-(1-methyl-1H-pyrazol-4-yl)-3,4-dihydro-1,5-naphthyridin-1(2H)-yl)-1H-pyrazolo[3,4-b]pyrazin-6-yl)-2-oxa-8-azaspiro[4.5]decan-4-amine and (3S,4S)-3-methyl-8-(3-((S)-4-methyl-6-(1-methyl-1H-pyrazol-4-yl)-3,4-dihydro-1,5-naphthyridin-1(2H)-yl)-1H-pyrazolo[3,4-b]pyrazin-6-yl)-2-oxa-8-azaspiro[4.5]decan-4-amine, Compound 266 and Compound 284
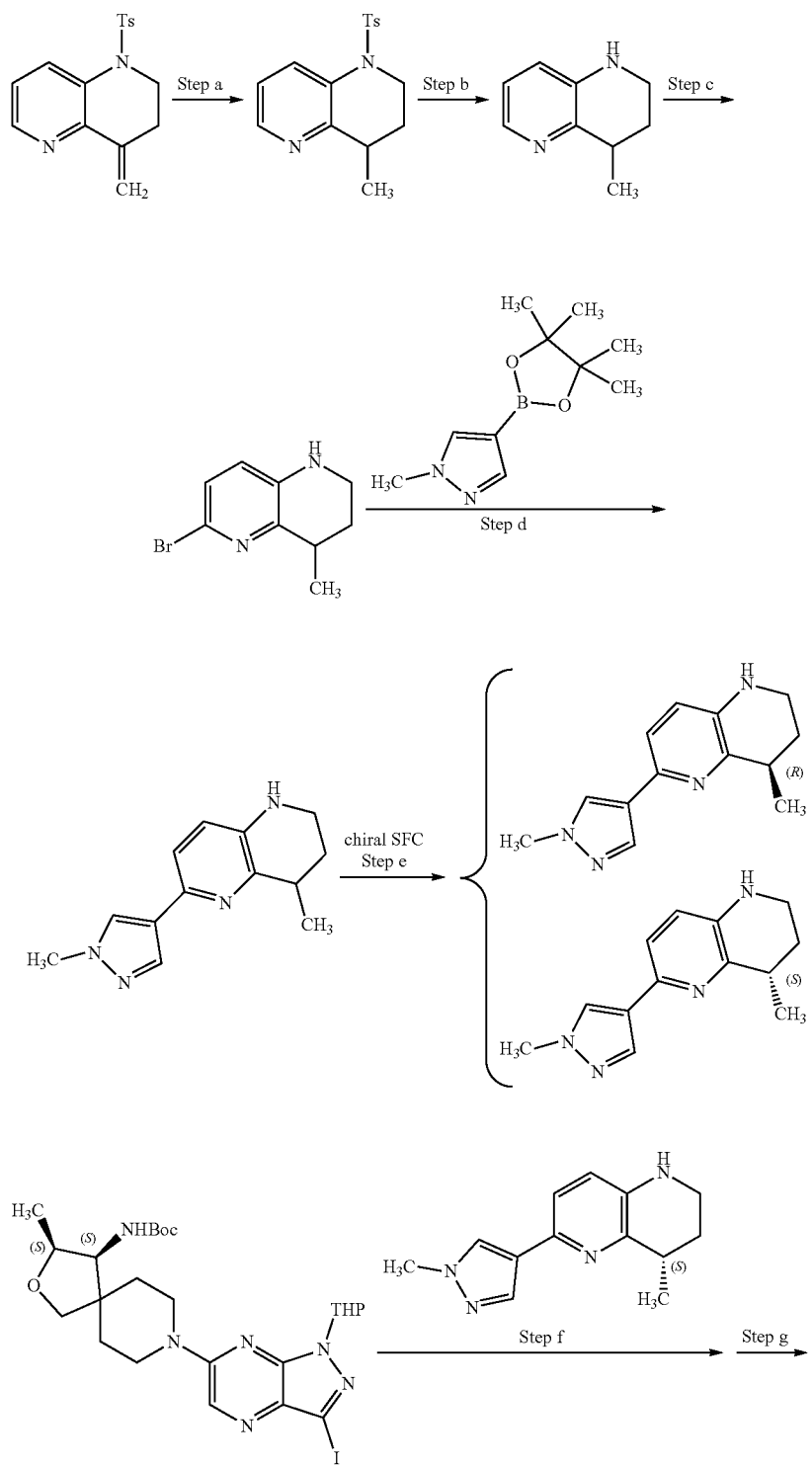

-continued

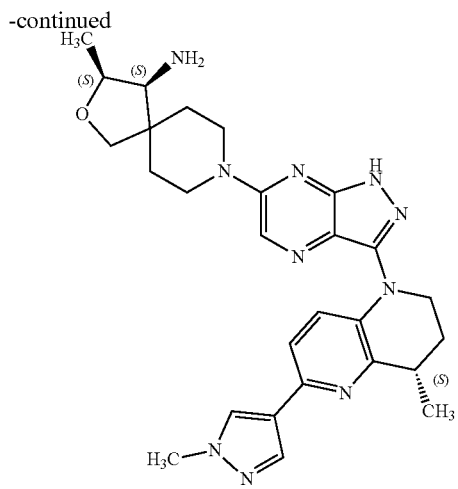

Step a: A mixture of 1-(4-methylbenzenesulfonyl)-4-methylidene-1,2,3,4-tetrahydro-1,5-naphthyridine (7.0 g, 23.3 mmol, 1.0 eq) and Pd/C (1.5 g, 10% wet) in MeOH (150 mL) was evacuated and refilled 3 times with hydrogen gas. The reaction mixture was stirred at 30° C. for 10 hours under an atmosphere of hydrogen (15 psi). The mixture was filtered and the filtrate concentrated under reduced pressure to afford 4-methyl-1-(4-methylbenzenesulfonyl)-1,2,3,4-tetrahydro-1,5-naphthyridine (17.3 g) as a white solid.

Step b: A mixture of 4-methyl-1-(4-methylbenzenesulfonyl)-1,2,3,4-tetrahydro-1,5-naphthyridine (15.0 g, 49.6 mmol, 1.0 eq) in $H_2SO_4$ (15 mL, 98%) was stirred at 30° C. for 2 hours. The mixture was adjusted with 2 N NaOH to a pH of 8 and filtered. The filtrate was extracted with EtOAc (100 mL×2) and the combined organics washed with brine (100 mL), dried over anhydrous $Na_2SO_4$, filtered, and concentrated under reduced pressure. The residue was purified by column chromatography (0-33% EtOAc/petroleum ether) to afford 4-methyl-1,2,3,4-tetrahydro-1,5-naphthyridine (7.3 g, 99.3% yield) as a white solid.

Step c: To 4-methyl-1,2,3,4-tetrahydro-1,5-naphthyridine (4.7 g, 31.7 mmol, 1.0 eq) in DMF (40 mL) at 0° C. was added dropwise NBS (5.9 g, 33.2 mmol, 1.05 eq) in DMF (20 mL). The mixture was stirred at 0° C. for 0.5 hour, then diluted with $H_2O$ (150 mL) and extracted with EtOAc (150 mL×2). The combined organics were washed with brine (40 mL), dried over anhydrous $Na_2SO_4$, filtered, and concentrated under reduced pressure. The residue was purified by column chromatography (5-25% EtOAc/petroleum ether) to afford 6-bromo-4-methyl-1,2,3,4-tetrahydro-1,5-naphthyridine (6.94 g, 96.5% yield) as a white solid.

Step d: A mixture of 6-bromo-4-methyl-1,2,3,4-tetrahydro-1,5-naphthyridine (300 mg, 1.32 mmol, 1.0 eq), 1-methyl-4-(4,4,5,5-tetramethyl-1,3,2-dioxaborolan-2-yl)-1H-pyrazole (328 mg, 1.58 mmol, 1.2 eq), Pd(dppf)$Cl_2$ (97 mg, 132 umol, 0.1 eq) and $K_2CO_3$ (547 mg, 3.96 mmol, 3.0 eq) in dioxane (10 mL) and $H_2O$ (1 mL) was evacuated and refilled 3 times with nitrogen gas and stirred at 90° C. for 6 hours. The mixture was concentrated under reduced pressure and the residue was purified by column chromatography (5-50% EtOAc/petroleum ether) to afford 4-methyl-6-(1-methyl-1H-pyrazol-4-yl)-1,2,3,4-tetrahydro-1,5-naphthyridine (240 mg, 79.7% yield) as a yellow oil.

Step e: rac-4-Methyl-6-(1-methyl-1H-pyrazol-4-yl)-1,2,3,4-tetrahydro-1,5-naphthyridine (150 mg, 657 μmol, 1.0 eq.) was separated by Chiral-SFC (Column: Chiralpak AD-3 150×4.6 mm I.D., 3 um Mobile phase: A: $CO_2$ B: ethanol (0.05% DEA) Gradient: from 5% to 40% of B in 5 min and hold 40% for 2.5 min, then 5% of B for 2.5 min. Flow rate: 2.5 ml-min Column temp.: 35° C.) to afford (4R)-4-methyl-6-(1-methyl-1H-pyrazol-4-yl)-1,2,3,4-tetrahydro-1,5-naphthyridine (70 mg, 46.9% yield) as a yellow solid and (4S)-4-methyl-6-(1-methyl-1H-pyrazol-4-yl)-1,2,3,4-tetrahydro-1,5-naphthyridine (70 mg, 46.9% yield) as a yellow solid.

Step f: A mixture of tert-butyl N-[(3S,4S)-8-[3-iodo-1-(oxan-2-yl)-1H-pyrazolo[3,4-b]pyrazin-6-yl]-3-methyl-2-oxa-8-azaspiro[4.5]decan-4-yl]carbamate (150 mg, 250 μmol, 1.0 eq), 4(S)-4-methyl-6-(1-methyl-1H-pyrazol-4-yl)-1,2,3,4-tetrahydro-1,5-naphthyridine (46 mg, 200 μmol, 0.8 eq), Pd$_2$(bda)$_3$ (69 mg, 75 μmol, 0.3 eq), XantPhos (43 mg, 75 μmol, 0.3 eq) and $Cs_2CO_3$ (244 mg, 750 μmol, 3.0 eq) in PhMe (10 mL) was evacuated and refilled 3 times with nitrogen gas and the reaction mixture stirred at 120° C. for 12 hours. The mixture was concentrated under reduced pressure and the residue purified by column chromatography (10-100% EtOAc/petroleum ether) to afford tert-butyl N-[(3S,4S)-3-methyl-8-{3-[(4S)-4-methyl-6-(1-methyl-1H-pyrazol-4-yl)-1,2,3,4-tetrahydro-1,5-naphthyridin-1-yl]-1-(oxan-2-yl)-1H-pyrazolo[3,4-b]pyrazin-6-yl}-2-oxa-8-azaspiro[4.5]decan-4-yl]carbamate (90 mg, 25.8% yield) as a yellow solid.

Step g: A mixture of tert-butyl N-[(3S,4S)-3-methyl-8-{3-[(4S)-4-methyl-6-(1-methyl-1H-pyrazol-4-yl)-1,2,3,4-tetrahydro-1,5-naphthyridin-1-yl]-1-(oxan-2-yl)-1H-pyrazolo[3,4-b]pyrazin-6-yl}-2-oxa-8-azaspiro[4.5]decan-4-yl]carbamate (90 mg, 64 μmol, 1.0 eq) in HCl/MeOH (5 mL, 4M) was stirred at 15° C. for 10 hours. The mixture was concentrated under reduced pressure and the residue was diluted with $H_2O$ (10 mL) and extracted with EtOAc (10 mL×2). The aqueous phase was adjusted with saturated $NaHCO_3$ to pH=7 and extracted with EtOAc (10 ml×2). The combined organics were concentrated under reduced pressure. The residue was dried in vacuum to afford (3S,4S)-3-methyl-8-{3-[(4S)-4-methyl-6-(1-methyl-1H-pyrazol-4-yl)-1,2,3,4-tetrahydro-1,5-naphthyridin-1-yl]-1H-pyrazolo[3,4-b]pyrazin-6-yl}-2-oxa-8-azaspiro[4.5]decan-4-amine (60 mg, 70% purity) as a yellow solid. Purification by prep-HPLC (acetonitrile/aq. HCl) to afford (3S,4S)-3-methyl-8-(3-[(4S)-4-methyl-6-(1-methyl-1H-pyrazol-4-yl)-1,2,3,4-tetrahydro-1,5-naphthyridin-1-yl]-1H-pyrazolo[3,4-b]pyrazin-6-yl)-2-oxa-8-azaspiro[4.5]decan-4-amine dihydrochloride (Compound 284, 8.8 mg, 23.3% yield) as a yellow solid: ESMS [M+H]⁺=515.1; ¹H-NMR (400 MHz, methanol-d₄): δ 8.37 (s, 1H), 8.35 (s, 1H), 8.13 (s, 1H), 8.10-8.07 (d, J=9.2 Hz, 1H), 7.76-7.73 (d, J=9.2 Hz, 1H), 4.51-4.32 (m, 4H), 4.19 (m, 2H), 4.05-4.00 (s, 3H), 3.93-3.91 (m, 1H), 3.60 (m, 1H), 3.45 (m, 1H), 3.30-3.26 (m, 2H), 2.36 (m, 1H), 2.16 (m, 1H), 1.96-1.93 (m, 3H), 1.79 (m, 1H), 1.60-1.57 (d, J=7.2 Hz, 3H), 1.36-1.34 (d, J=6.4 Hz, 3H).

Step f and Step g were similarly performed on 4(R)-4-methyl-6-(1-methyl-1H-pyrazol-4-yl)-1,2,3,4-tetrahydro-1,5-naphthyridine to afford (3S,4S)-3-methyl-8-{3-[(4R)-4-methyl-6-(1-methyl-1H-pyrazol-4-yl)-1,2,3,4-tetrahydro-1,5-naphthyridin-1-yl]-1H-pyrazolo[3,4-b]pyrazin-6-yl}-2-oxa-8-azaspiro[4.5]decan-4-amine dihydrochloride (Compound 266, 8.8 mg, 23.3% yield) as a yellow solid: ESMS [M+H]⁺=515.2; ¹H-NMR (400 MHz, methanol-d₄): δ ¹H-NMR (400 MHz, CDCl₃) δ 8.05 (s, 1H), 7.78 (s, 1H), 7.77 (s, 1H), 7.60-7.57 (d, J=8.8 Hz, 1H), 7.08-7.05 (d, J=8.4 Hz, 1H), 4.13-3.92 (m, 4H), 3.86 (s, 3H), 3.77-3.74 (m, 1H), 3.65-3.62 (m, 1H), 3.33 (m, 2H), 3.08-3.06 (m, 1H), 2.94-2.92 (m, 1H), 2.20-2.10 (m, 1H), 1.86-1.42 (m, 6H), 1.43-1.40 (d, J=7.2 Hz, 1H), 1.19-1.16 (d, J=7.2 Hz, 1H).

Synthesis of 1-{6-[(3S,4S)-4-amino-3-methyl-2-oxa-8-azaspiro[4.5]decan-8-yl]-1H-pyrazolo[3,4-b]pyrazin-3-yl}-4-methyl-3-oxo-1,2,3,4-tetrahydroquinoxaline-6-carbonitrile, Compound 275

Step a: tert-butyl N-[(3S,4S)-8-[3-(6-bromo-4-methyl-3-oxo-1,2,3,4-tetrahydroquinoxalin-1-yl)-1-(oxan-2-yl)-1H-pyrazolo[3,4-b]pyrazin-6-yl]-3-methyl-2-oxa-8-azaspiro[4.5]decan-4-yl]carbamate (570 mg) (LCMS: [M+H]⁺ 711) was prepared using tert-butyl N-[(3S,4S)-8-[3-iodo-1-(oxan-2-yl)-1H-pyrazolo[3,4-b]pyrazin-6-yl]-3-methyl-2-oxa-8-azaspiro[4.5]decan-4-yl]carbamate (625 mg, 1.04 mmol), and 7-bromo-1-methyl-1,2,3,4-tetrahydroquinoxalin-2-one (274 mg, 1.14 mmol, CAS: 1783487-69-3) using conditions described for the preparation of Compound 33.

Step b: A resealable reaction vial was charged with tert-butyl N-[(3S,4S)-8-[3-(6-bromo-4-methyl-3-oxo-1,2,3,4-tetrahydroquinoxalin-1-yl)-1-(oxan-2-yl)-1H-pyrazolo[3,4-b]pyrazin-6-yl]-3-methyl-2-oxa-8-azaspiro[4.5]decan-4-yl]carbamate (129 mg, 0.1812 mmol), zincdicarbonitrile (42.5 mg, 0.3624 mmol), Pd/tBuXPhos G3 (14.3 mg, 0.01812 mmol), dioxane (6 mL) and water (1 mL). The mixture was bubbled with nitrogen for 10 min. The vial was sealed, and the mixture was stirred at 90° C. for 16 hrs. The reaction was charged with EA and water, the organic layer was washed with water, dried and concentrated.

The residue was dissolved in DCM (5 mL) was charged with TFA (1 mL) and stirred at RT for 16 hrs. The mixture was concentrated and chased with ACN (3×). The residue was purified on prep-HPLC (10-40% ACN/water+0.1% FA) to afford 1-{6-[(3S,4S)-4-amino-3-methyl-2-oxa-8-azaspiro[4.5]decan-8-yl]-1H-pyrazolo[3,4-b]pyrazin-3-yl}-4-methyl-3-oxo-1,2,3,4-tetrahydroquinoxaline-6-carbonitrile (53 mg) as a yellow solid. LCMS: [M+H]⁺ 472.

Synthesis of (3S,4S)-3-methyl-8-{3-[6-(1-methyl-1H-pyrazol-3-yl)-1,2,3,4-tetrahydro-1,5-naphthyridin-1-yl]-1H-pyrazolo[3,4-b]pyrazin-6-yl}-2-oxa-8-azaspiro[4.5]decan-4-amine, Compound 280

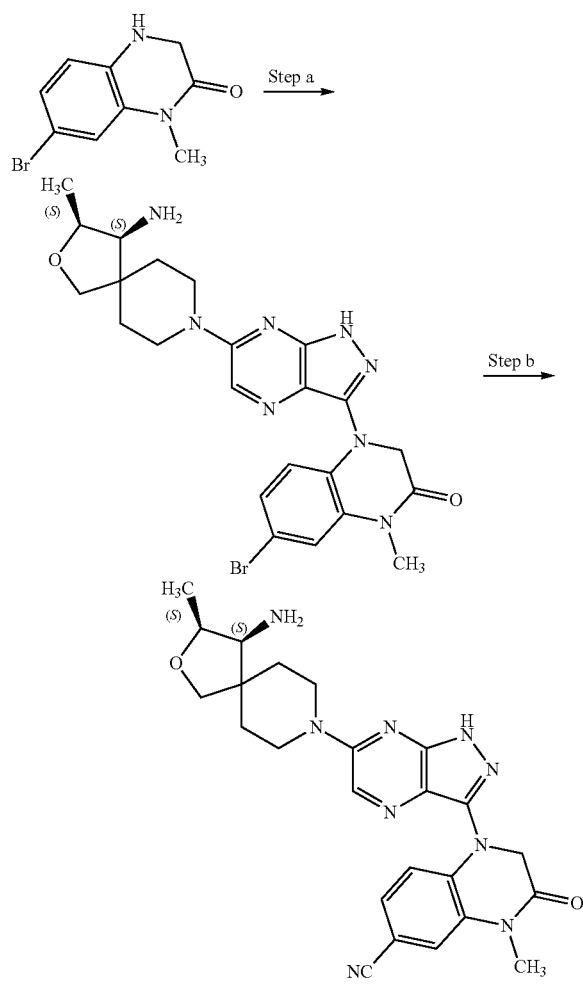

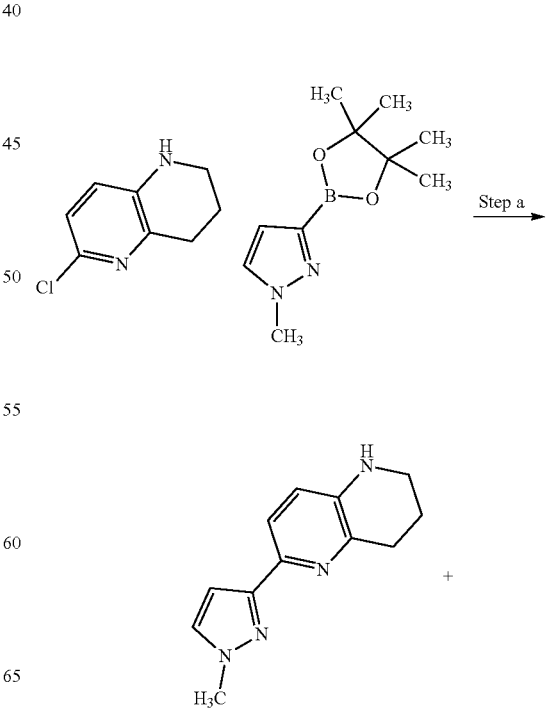

357

-continued

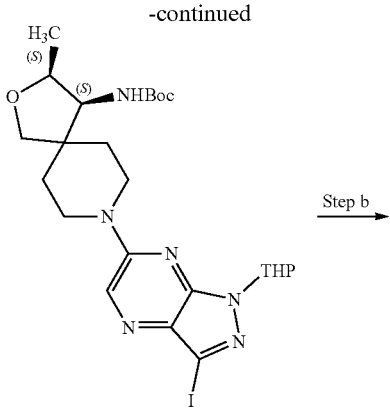

Step b →

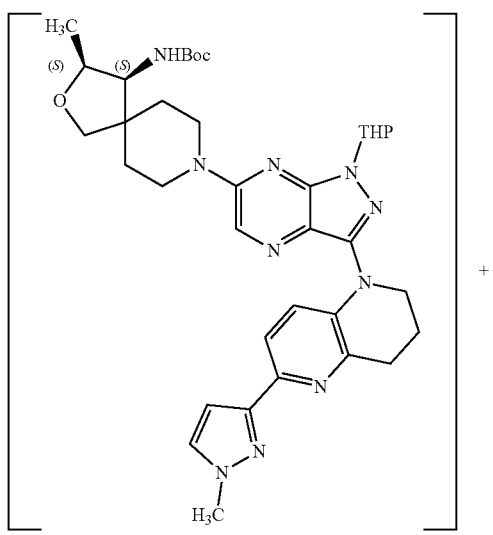

+

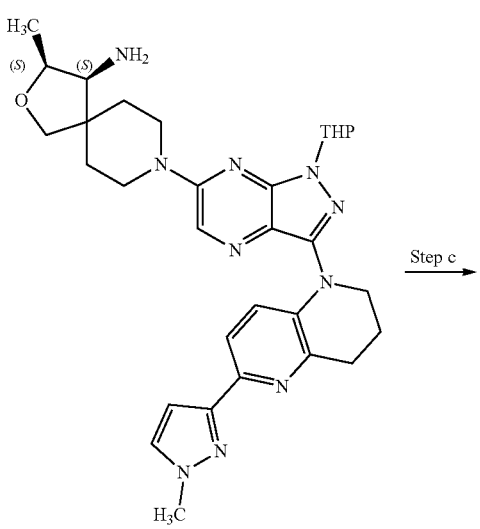

Step c →

358

-continued

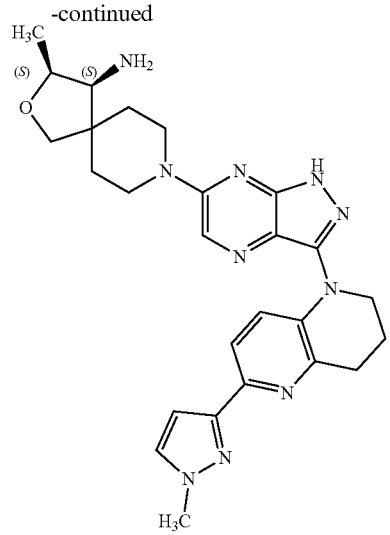

Step a: A mixture of 6-chloro-1,2,3,4-tetrahydro-1,5-naphthyridine (202 mg, 1.2 mmol), 1-methyl-3-(4,4,5,5-tetramethyl-1,3,2-dioxaborolan-2-yl)-1H-pyrazole (300 mg, 1.4 mmol, CAS #1020174-04-2), Pd(dppf)Cl$_2$ DCM (195 mg, 0.2 mmol) and K2CO$_3$ (414 mg, 3.0 mmol) in dioxane (8 mL)/H$_2$O (0.8 mL) was evacuated and refilled 3 times using N$_2$ gas. The mixture was stirred at 90° C. for 12 hours under N$_2$ atmosphere. The reaction mixture was concentrated to give a residue, which was purified by flash silica gel chromatography (0-10% MeOH/DCM) to give 6-(1-methyl-1H-pyrazol-3-yl)-1,2,3,4-tetrahydro-1,5-naphthyridine (180 mg, 70% yield) as a gray solid.

Step b: tert-Butyl N-[(3S,4S)-8-[3-iodo-1-(oxan-2-yl)-1H-pyrazolo[3,4-b]pyrazin-6-yl]-3-methyl-2-oxa-8-azaspiro[4.5]decan-4-yl]carbamate (150 mg, 0.2 mmol), 6-(1-methyl-1H-pyrazol-3-yl)-1,2,3,4-tetrahydro-1,5-naphthyridine (80 mg, 0.4 mmol), XantPhos (14 mg, 0.03 mmol), Pd$_2$(dba)$_3$ (21 mg, 0.03 mmol), and t-BuONa (48 mg, 0.5 mmol) were added in PhMe (3 mL). The mixture was evacuated and refilled 3 times with N$_2$ gas then stirred at 120° C. for 12 hours. The mixture was concentrated to give a residue which was purified by flash silica gel chromatography (0-100% EtOAc/petroleum ether then 0-10% MeOH/DCM) to afford tert-butyl N-[(3S,4S)-3-methyl-8-{3-[6-(1-methyl-1H-pyrazol-3-yl)-1,2,3,4-tetrahydro-1,5-naphthyridin-1-yl]-1-(oxan-2-yl)-1H-pyrazolo[3,4-b]pyrazin-6-yl}-2-oxa-8-azaspiro[4.5]decan-4-yl]carbamate (60 mg, 35% yield) as a yellow solid and (3S,4S)-3-methyl-8-{3-[6-(1-methyl-1H-pyrazol-3-yl)-1,2,3,4-tetrahydro-1,5-naphthyridin-1-yl]-1-(oxan-2-yl)-1H-pyrazolo[3,4-b]pyrazin-6-yl}-2-oxa-8-azaspiro[4.5]decan-4-amine (40 mg, 27.3% yield) as a yellow oil.

Step c: (3S,4S)-3-Methyl-8-{3-[6-(1-methyl-1H-pyrazol-3-yl)-1,2,3,4-tetrahydro-1,5-naphthyridin-1-yl]-1-(oxan-2-yl)-1H-pyrazolo[3,4-b]pyrazin-6-yl}-2-oxa-8-azaspiro[4.5]decan-4-amine (40 mg, 0.07 mmol) was added in 2 N HCl/MeOH (2 mL). The mixture was stirred at 25° C. for 12 hrs. On completion, the reaction mixture was concentrated under reduced pressure, and purified by prep-HPLC (acetonitrile/aq. HCl) to afford (3S,4S)-3-methyl-8-{3-[6-(1-methyl-1H-pyrazol-3-yl)-1,2,3,4-tetrahydro-1,5-naphthyridin-1-yl]-1H-pyrazolo[3,4-b]pyrazin-6-yl}-2-oxa-8-azaspiro[4.5]decan-4-amine hydrochloride (35.6 mg) as an orange solid: ESMS [M+H]$^+$=501.6; $^1$H-NMR (400 MHz, DMSO-d$_6$): δ 13.01-13.02 (s, 1H), 8.42 (s, 1H), 8.32 (s, 3H), 8.19-8.22 (m, 1H), 7.95-7.98 (m, 2H), 7.27-7.28 (m, 1H), 4.23-4.44 (m, 3H), 4.06-4.21 (m, 2H), 4.04-4.06 (m, 3H), 3.96-4.04 (m, 1H), 3.67-3.70 (m, 1H), 3.35-3.39 (m, 3H), 3.15-3.23 (m, 2H), 3.13-3.17 (m, 2H), 1.79-1.89 (m, 3H), 1.61-1.73 (m, 2H), 1.24-1.26 (m, 3H).

Synthesis of (3S,4S)-8-[3-(5-methanesulfonyl-1,2,3,4-tetrahydroquinolin-1-yl)-1H-pyrazolo[3,4-b]pyrazin-6-yl]-3-methyl-2-oxa-8-azaspiro[4.5]decan-4-amine, Compound 281

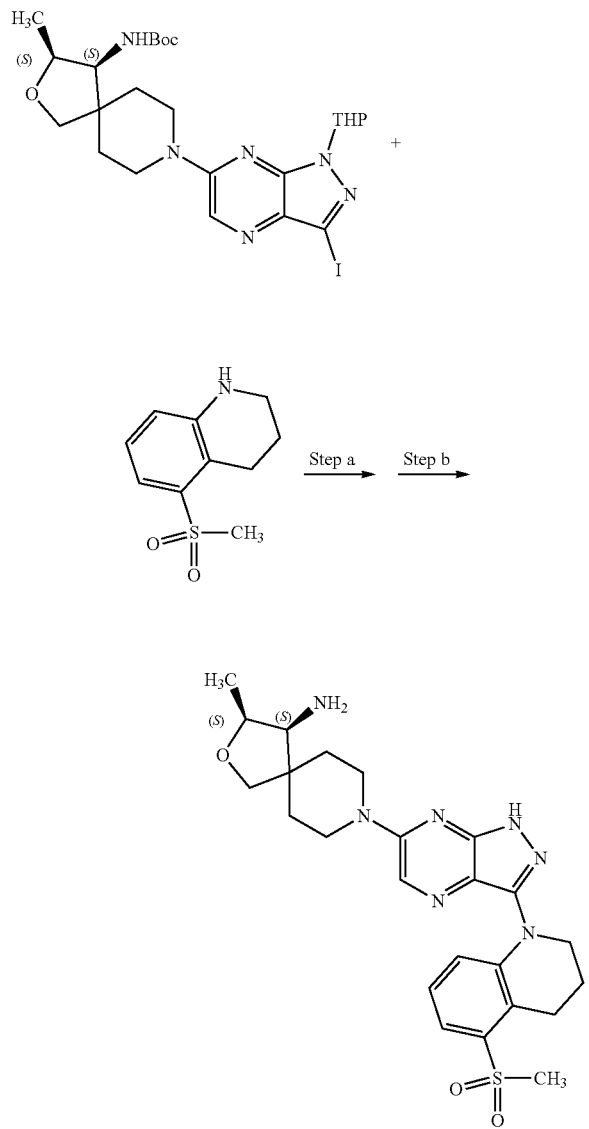

Step a: A mixture of 5-methanesulfonyl-1,2,3,4-tetrahydroquinoline (50 mg, 236 μmol, CAS #343944-90-1), tert-butyl N-[(3S,4S)-8-[3-iodo-1-(oxan-2-yl)-1H-pyrazolo[3,4-b]pyrazin-6-yl]-3-methyl-2-oxa-8-azaspiro[4.5]decan-4-yl]carbamate (155 mg, 259 μmol), $Cs_2CO_3$ (230 mg, 708 μmol), RuPhos (33 mg, 70.8 μmol), and RuPhos-Pd-G4 (30.1 mg, 35.4 μmol) in toluene (5 mL) was stirred at 100° C. for 14 hours under $N_2$. The mixture was cooled, concentrated under reduced pressure, poured into water (50 mL), and extracted with EtOAc (50 mL×3). The combined organics were washed with water (50 mL), brine (50 mL), dried over anhydrous $Na_2SO_4$, filtered, and concentrated under reduced pressure. The residue was purified by silica gel chromatography (0-100% EtOAc/petroleum ether) to afford tert-butyl N-[(3S,4S)-8-[3-(5-methanesulfonyl-1,2,3,4-tetrahydroquinolin-1-yl)-1-(oxan-2-yl)-1H-pyrazolo[3,4-b]pyrazin-6-yl]-3-methyl-2-oxa-8-azaspiro[4.5]decan-4-yl]carbamate (150 mg, 219 μmol, 93% yield) as a yellow solid.

Step b: tert-Butyl N-[(3S,4S)-8-[3-(5-methanesulfonyl-1,2,3,4-tetrahydroquinolin-1-yl)-1-(oxan-2-yl)-1H-pyrazolo[3,4-b]pyrazin-6-yl]-3-methyl-2-oxa-8-azaspiro[4.5]decan-4-yl]carbamate (145 mg, 212 μmol) was dissolved in 4N HCl/MeOH (5 mL) and stirred at 25° C. for 12 hours. The mixture was concentrated under reduced pressure and the residue dissolved in MeOH (10 mL), treated with $K_2CO_3$ (solid) to adjust the pH to 9, concentrated under reduced pressure, and purified by silica gel chromatography (0-8% MeOH/DCM) to afford (3S,4S)-8-[3-(5-methanesulfonyl-1,2,3,4-tetrahydroquinolin-1-yl)-1H-pyrazolo[3,4-b]pyrazin-6-yl]-3-methyl-2-oxa-8-azaspiro[4.5]decan-4-amine (73.7 mg, 148 μmol, 70.1% yield) as a yellow solid: ESMS [M+H]+=498.5; $^1$H-NMR (400 MHz, DMSO-$d_6$) δ 12.65 (br, 1H), 8.28 (s, 1H), 7.35 (d, J=7.2 Hz, 1H), 7.10-7.21 (m, 2H), 4.01-4.11 (m, 1H), 3.89-3.99 (m, 2H), 3.83-3.88 (m, 2H), 3.68 (d, J=8.4 Hz, 1H), 3.45-3.55 (m, 3H), 3.24 (s, 3H), 3.19-3.23 (m, 2H), 2.90 (d, J=5.2 Hz, 1H), 1.96-2.08 (m, 2H), 1.71-1.82 (m, 1H), 1.60-1.70 (m, 1H), 1.44-1.59 (m, 2H), 2.90 (d, J=6.8 Hz, 3H).

The following compounds were synthesized via the same route as Compound 281 using the appropriate building blocks. The pyrazolo-pyrazine ring was protected with either PMB or a THP (as shown above) group. Step a cross coupling could be performed under standard conditions, including using $Pd_2(dba)_3$, XantPhos and t-BuONa or Xant-Phos-Pd-G4 and $Cs_2CO_3$ as well as what is described above. Deprotection could also be achieved using TFA under standard conditions. Compounds synthesized via the method described for Compound 281 include: Compound 225, Compound 277, Compound 278, Compound 279, Compound 289, Compound 297, Compound 300, Compound 303, Compound 304, Compound 305, Compound 307, Compound 308, Compound 314, Compound 315, Compound 317, Compound 318, Compound 328, Compound 332, Compound 336, Compound 348, Compound 350, Compound 352, Compound 353, Compound 356, Compound 365, Compound 367, Compound 368, Compound 369, Compound 200, Compound 207, Compound 208, Compound 209, Compound 210, Compound 217, Compound 218, Compound 219, Compound 220, Compound 221, Compound 223, Compound 226, Compound 228, Compound 231, Compound 232, Compound 233, Compound 234, Compound 235, Compound 236, Compound 237, Compound 238, Compound 239, Compound 240, Compound 241, Compound 242, Compound 245, Compound 247, Compound 248, Compound 249, Compound 250, Compound 251, Compound 252, Compound 257, Compound 259, Compound 260, Compound 267, Compound 268, Compound 269, Compound 270, Compound 271, Compound 272, Compound 273, Compound 274, Compound 276, Compound 277, Compound 278, Compound 279, Compound 283, Compound 286, Compound 289, Compound 290, Compound 291, Compound 292, Compound 297, Compound 300, Compound 301, Compound 302, Compound 303, Compound 304, Compound 305, Compound 307, Compound 308, Compound 322, Compound 323, Compound 324, Compound 325, Compound 326, Compound 327, Compound 330, Compound 337, Compound 338, Compound 342, Compound 345, Compound 346, Compound 349, Compound 354, Compound 355, Compound 357, Compound 358, Compound 359, Compound 360, Compound 361, Compound 365, Compound 373, Compound 377, Compound 378, Compound 379, Compound 381, Compound 382, Compound 383, Compound 384, Compound 385, Compound 386, Compound 387, Compound 388, Compound 390, Compound 391, Compound 392, Compound 393, Compound 394, Compound 395, Compound 398, Compound 400, Compound 401 Compound 402, Compound 403, Compound 405, Compound 406, Compound 407, Compound 408, Compound 409, Compound 410, Compound 411, Compound 412, Compound 413, Compound 414, Compound 415, Compound 416, Compound 417, Compound 418, Compound 419, Compound 420, Compound 421, Compound 422, Compound 424, Compound 428, Compound 432, Compound 435, Compound 439, Compound 440, Compound 441, Compound 455, Compound 456, Compound 457, Compound 458, Compound 459, Compound 460, Compound 461, Compound 462, Compound 463, Compound 464, Compound 465, Compound 466, Compound 469, Compound 470, Compound 471, Compound 519, Compound 520, Compound 521, Compound 522, Compound 523, Compound 524, Compound 525, Compound 526, Compound 527, Compound 528, Compound 529, Compound 530, Compound 531, Compound 532.

Synthesis of 5-(6-((3S,4S)-4-amino-3-methyl-2-oxa-8-azaspiro[4.5]decan-8-yl)-1H-pyrazolo[3,4-b]pyrazin-3-yl)-N-methyl-5,6,7,8-tetrahydro-1,5-naphthyridine-2-carboxamide, Compound 282

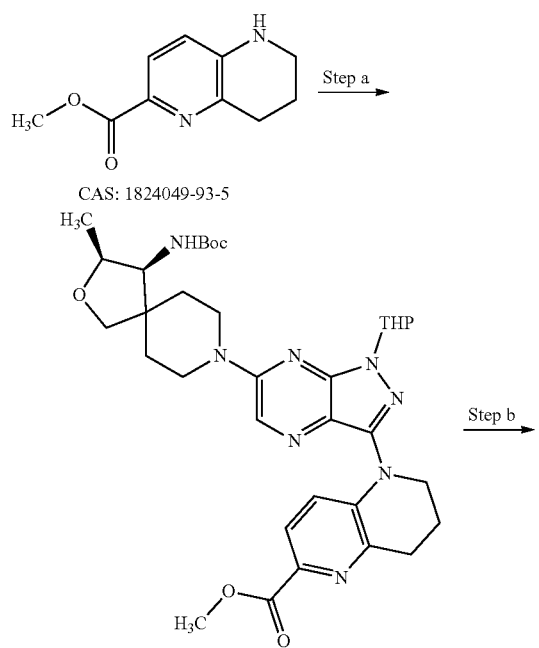

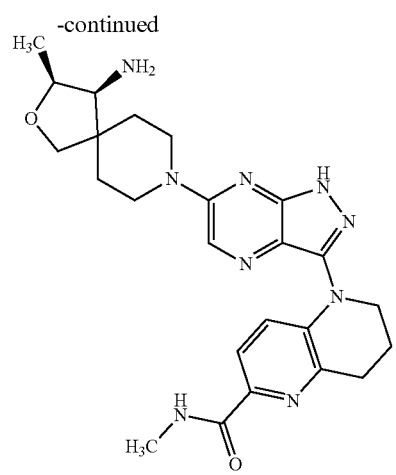

Step a: Methyl 5-(6-((3S,4S)-4-((tert-butoxycarbonyl)amino)-3-methyl-2-oxa-8-azaspiro[4.5]decan-8-yl)-1-(tetrahydro-2H-pyran-2-yl)-1H-pyrazolo[3,4-b]pyrazin-3-yl)-5,6,7,8-tetrahydro-1,5-naphthyridine-2-carboxylate (68.0 mg, 0.10 mmol) was prepared following the procedure detailed for Compound 33 beginning from commercially available Methyl 5,6,7,8-tetrahydro-1,5-naphthyridine-2-carboxylate (CAS: 1824049-93-5).

Step b: To a round bottom flask containing Methyl 5-(6-((3S,4S)-4-((tert-butoxycarbonyl)amino)-3-methyl-2-oxa-8-azaspiro[4.5]decan-8-yl)-1-(tetrahydro-2H-pyran-2-yl)-1H-pyrazolo[3,4-b]pyrazin-3-yl)-5,6,7,8-tetrahydro-1,5-naphthyridine-2-carboxylate (68.0 mg, 0.10 mmol) in a mixture of EtOH (0.50 mL) and H₂O (0.50 mL) was added NaOH (12.0 mg, 0.30 mmol). The reaction was stirred at ambient temperature for 16 h before the addition of 1N HCl. The organic layer was extracted with EtOAc (3×) before being concentrated to dryness and to yield 5-(6-((3S,4S)-4-((tert-butoxycarbonyl)amino)-3-methyl-2-oxa-8-azaspiro[4.5]decan-8-yl)-1-(tetrahydro-2H-pyran-2-yl)-1H-pyrazolo[3,4-b]pyrazin-3-yl)-5,6,7,8-tetrahydro-1,5-naphthyridine-2-carboxylic acid, which was used without further purification.

To the crude carboxylic acid, 5-(6-((3S,4S)-4-((tert-butoxycarbonyl)amino)-3-methyl-2-oxa-8-azaspiro[4.5]decan-8-yl)-1-(tetrahydro-2H-pyran-2-yl)-1H-pyrazolo[3,4-b]pyrazin-3-yl)-5,6,7,8-tetrahydro-1,5-naphthyridine-2-carboxylic acid, in DMF (1.60 mL) was added HATU (57.0 mg, 0.15 mmol) followed by methylamine (23.0 uL, 0.50 mmol) and Hunig's base (35 uL, 0.20 mmol). The reaction was stirred at ambient temperature for 16 h before additional HATU (24.0 mg, 0.06 mmol), methylamine (33 uL, 0.70 mmol) and Hunig's base (17 uL, 0.10 mmol) were added and the reaction stirred for an additional 16 h. Following partitioning between EtOAc and brine, the organic residue was extracted (3×), concentrated to dryness to furnish tert-butyl ((3S,4S)-3-methyl-8-(3-(6-(methylcarbamoyl)-3,4-dihydro-1,5-naphthyridin-1(2H)-yl)-1-(tetrahydro-2H-pyran-2-yl)-1H-pyrazolo[3,4-b]pyrazin-6-yl)-2-oxa-8-azaspiro[4.5]decan-4-yl)carbamate, which was used without further purification in the subsequent step.

The above isolated tert-butyl ((3S,4S)-3-methyl-8-(3-(6-(methylcarbamoyl)-3,4-dihydro-1,5-naphthyridin-1(2H)-yl)-1-(tetrahydro-2H-pyran-2-yl)-1H-pyrazolo[3,4-b]pyrazin-6-yl)-2-oxa-8-azaspiro[4.5]decan-4-yl)carbamate was dissolved in EtOH (0.60 mL) and HCl (4.0M in dioxanes, 0.30 mL) was added. The reaction stirred at ambient temperature for 16 h before being concentrated to dryness and purified prep HPLC (5-40% ACN in H₂O with 0.1% CH₂OH) to yield 5-(6-((3S,4S)-4-amino-3-methyl-2-oxa-8-azaspiro[4.5]decan-8-yl)-1H-pyrazolo[3,4-b]pyrazin-3-yl)-N-methyl-5,6,7,8-tetrahydro-1,5-naphthyridine-2-carboxamide (3.10 mg, 0.0065 mmol) as a yellow solid. LCMS: [M+H]+ 478.

Synthesis of (8S)-5-{6-[(3S,4S)-4-amino-3-methyl-2-oxa-8-azaspiro[4.5]decan-8-yl]-1H-pyrazolo[3,4-b]pyrazin-3-yl}-N,8-dimethyl-5,6,7,8-tetrahydro-1,5-naphthyridine-2-carboxamide, Compound 285

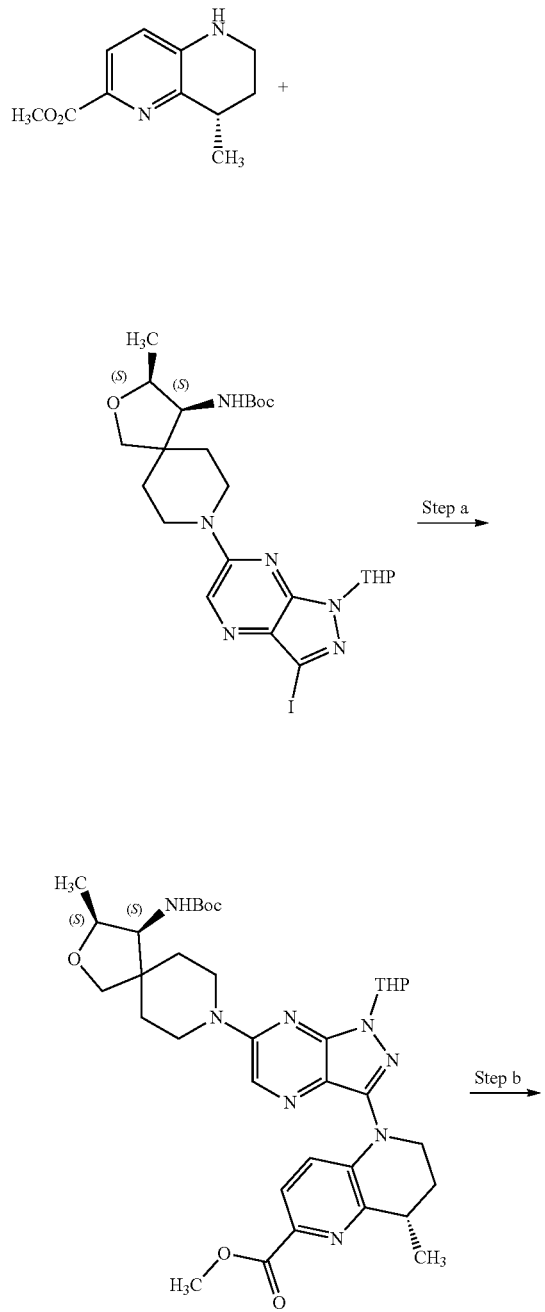

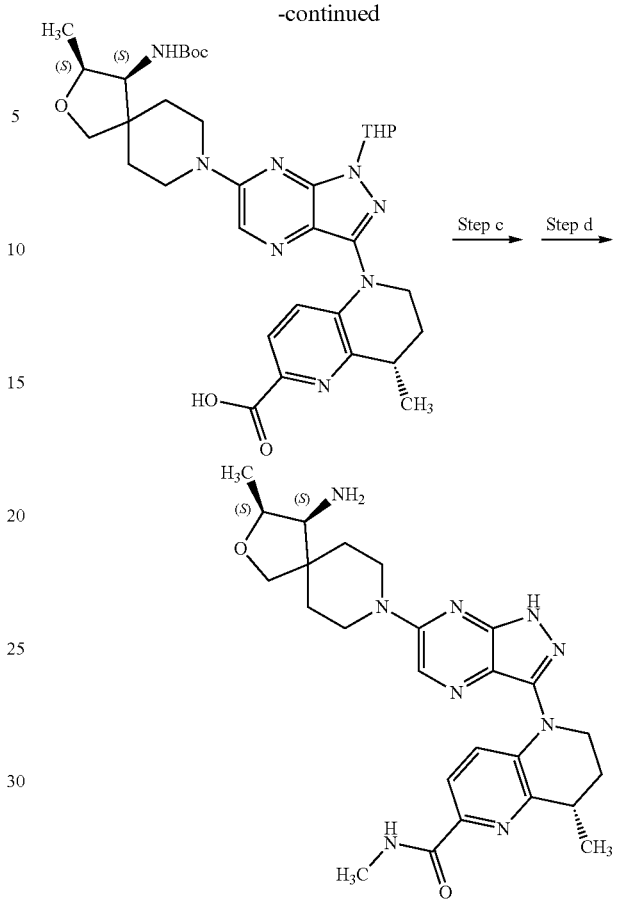

Step a: A mixture of methyl (8S)-8-methyl-5,6,7,8-tetrahydro-1,5-naphthyridine-2-carboxylate (210 mg, 1.0 mmol), tert-butyl N-[(3S,4S)-8-[3-iodo-1-(oxan-2-yl)-1H-pyrazolo[3,4-b]pyrazin-6-yl]-3-methyl-2-oxa-8-azaspiro[4.5]decan-4-yl]carbamate (634 mg, 1.1 mmol), XantPhos-Pd-G4 (97.2 mg, 0.1 mmol) and Cs₂CO₃ (821 mg, 2.5 mmol) in toluene (20 mL) was stirred at 100° C. for 12 hours under N₂. The mixture was diluted with EtOAc (200 mL), washed with water (200 mL) and brine (200 mL). The organics were dried over anhydrous Na₂SO₄, filtered, and concentrated under reduced pressure. The residue was purified by flash silica gel chromatography (0-80% EtOAc/petroleum ether) to afford methyl (8S)-5-{6-[(3S,4S)-4-{[(tert-butoxy)carbonyl]amino}-3-methyl-2-oxa-8-azaspiro[4.5]decan-8-yl]-1-(oxan-2-yl)-1H-pyrazolo[3,4-b]pyrazin-3-yl}-8-methyl-5,6,7,8-tetrahydro-1,5-naphthyridine-2-carboxylate (1.26 g) as a yellow solid.

Step b: To a solution of methyl (8S)-5-{6-[(3S,4S)-4-{[(tert-butoxy)carbonyl]amino}-3-methyl-2-oxa-8-azaspiro[4.5]decan-8-yl]-1-(oxan-2-yl)-1H-pyrazolo[3,4-b]pyrazin-3-yl}-8-methyl-5,6,7,8-tetrahydro-1,5-naphthyridine-2-carboxylate (900 mg, 1.3 mmol) in MeOH (10 mL) and H₂O (2.5 mL) was added LiOH (157 mg, 6.6 mmol). The mixture was stirred at 45° C. for 12 hours then concentrated under reduced pressure to about 5 mL and diluted with H₂O (200 mL). The pH was adjusted to 5-6 with 1N HCl and the solution extracted with EtOAc (100 mL×3). The combined organics were dried over anhydrous Na₂SO₄, filtered, and concentrated under reduced pressure to afford (8S)-5-{6-[(3S,4S)-4-{[(tert-butoxy)carbonyl]amino}-3-methyl-2-oxa-8-azaspiro[4.5]decan-8-yl]-1-(oxan-2-yl)-1H-pyrazolo

[3,4-b]pyrazin-3-yl}-8-methyl-5,6,7,8-tetrahydro-1,5-naphthyridine-2-carboxylic acid (1.75 g, crude) as a yellow solid.

Step c: A mixture of (8S)-5-{6-[(3S,4S)-4-{[(tert-butoxy)carbonyl]amino}-3-methyl-2-oxa-8-azaspiro[4.5]decan-8-yl]-1-(oxan-2-yl)-1H-pyrazolo[3,4-b]pyrazin-3-yl}-8-methyl-5,6,7,8-tetrahydro-1,5-naphthyridine-2-carboxylic acid (800 mg, 1.1 mmol), HATU (859 mg, 2.3 mmol), and TEA (780 μL, 5.6 mmol) in DCM (10 mL) was stirred at 15° C. for 10 min. MeNH$_2$.HCl (152 mg, 2.3 mmol) was added and the reaction mixture stirred at 15° C. for 12 hours. The mixture was concentrated under reduced pressure to give a residue which was taken up in H$_2$O (150 mL) and extracted with EtOAc (100 mL×3). The combined organics were washed with brine (100 mL), dried over anhydrous Na$_2$SO$_4$, filtered, and concentrated under reduced pressure to give tert-butyl N-[(3S,4S)-3-methyl-8-{3-[(4S)-4-methyl-6-(methylcarbamoyl)-1,2,3,4-tetrahydro-1,5-naphthyridin-1-yl]-1-(oxan-2-yl)-1H-pyrazolo[3,4-b]pyrazin-6-yl}-2-oxa-8-azaspiro[4.5]decan-4-yl]carbamate (1.9 g, crude) as a yellow solid.

Step d: To a solution of tert-butyl N-[(3S,4S)-3-methyl-8-{3-[(4S)-4-methyl-6-(methylcarbamoyl)-1,2,3,4-tetrahydro-1,5-naphthyridin-1-yl]-1-(oxan-2-yl)-1H-pyrazolo[3,4-b]pyrazin-6-yl}-2-oxa-8-azaspiro[4.5]decan-4-yl]carbamate (1.9 g, 2.8 mmol) in MeOH (10 mL) was added 4N HCl/MeOH (10 mL). The mixture was stirred at 25° C. for 1 hour then concentrated under reduced pressure, diluted with MeOH (15 mL), and the pH adjusted to 8-9 with solid K$_2$CO$_3$. The mixture was filtered and concentrated under reduced pressure and the residue purified by flash silica gel chromatography (0-8% MeOH/DCM) to give a impure product. This product was treated with 2N HCl (30 mL), extracted with DCM (20 mL×2). The aqueous layer was lyophilized to afford (8S)-5-{6-[(3S,4S)-4-amino-3-methyl-2-oxa-8-azaspiro[4.5]decan-8-yl]-1H-pyrazolo[3,4-b]pyrazin-3-yl}-N,8-dimethyl-5,6,7,8-tetrahydro-1,5-naphthyridine-2-carboxamide hydrochloride (837.4 mg, 56.5% yield) as a yellow solid: ESMS [M+H]+=492.3; $^1$H-NMR (400 MHz, methanol-d$_4$): 8.36 (s, 1H), 7.99 (s, 2H), 4.27-4.53 (m, 3H), 4.14-4.22 (m, 1H), 3.99-4.12 (m, 2H), 3.90 (d, J=9.2 Hz, 1H), 3.64-3.75 (m, 1H), 3.48 (d, J=4.0 Hz, 1H), 3.32-3.39 (m, 1H), 3.20-3.2 (m, 1H), 2.98 (s, 3H), 2.29-2.41 (m, 1H), 2.10-2.19 (m, 1H), 1.85-1.98 (m, 3H), 1.71-1.80 (m, 1H), 1.55 (d, J=6.8 Hz, 3H), 1.33 (d, J=6.4 Hz, 3H).

Synthesis of 4-(5-{6-[(3S,4S)-4-amino-3-methyl-2-oxa-8-azaspiro[4.5]decan-8-yl]-1H-pyrazolo[3,4-b]pyrazin-3-yl}-5,6,7,8-tetrahydro-1,5-naphthyridin-2-yl)-1-methylpiperazin-2-one, Compound 287

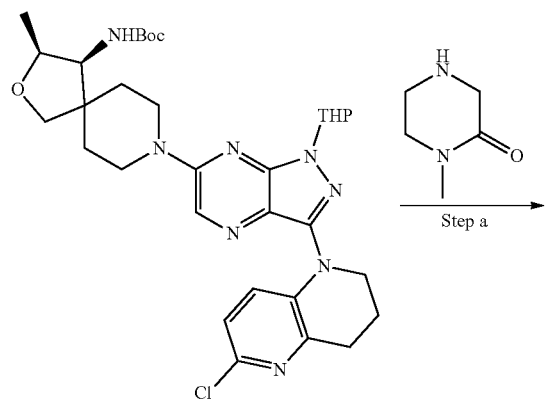

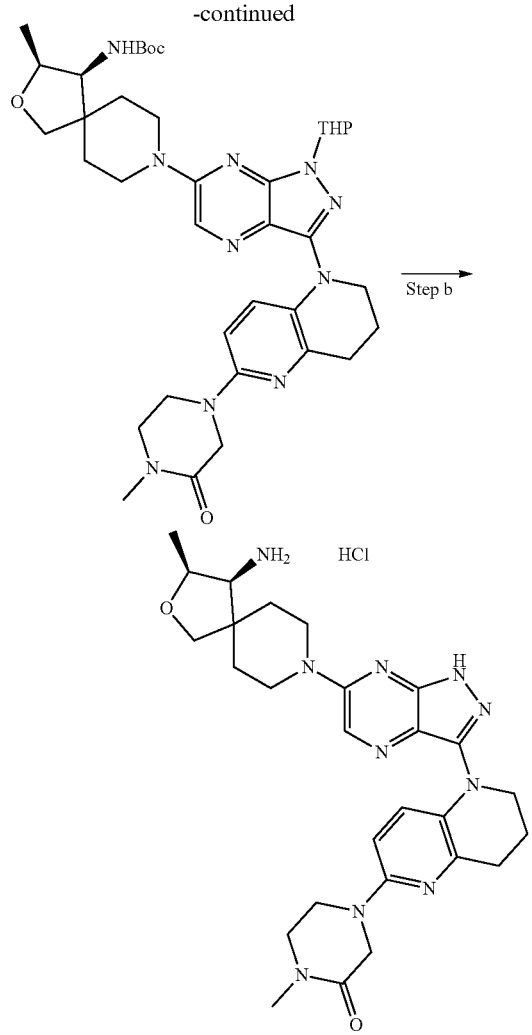

Step a: The mixture of tert-butyl N-[(3S,4S)-8-[3-(6-chloro-1,2,3,4-tetrahydro-1,5-naphthyridin-1-yl)-1-(oxan-2-yl)-1H-pyrazolo[3,4-b]pyrazin-6-yl]-3-methyl-2-oxa-8-azaspiro[4.5]decan-4-yl]carbamate (100 mg, 156 μmol, synthesized as described for Compound 33, with 6-chloro-1,2,3,4-tetrahydro-1,5-naphthyridine as the coupling partner), 1-methylpiperazin-2-one (19.5 mg, 171 μmol), XPhos (14.8 mg, 31.2 μmol), Pd$_2$(dba)$_3$ (28.5 mg, 31.2 μmol) and t-BuONa (44.9 mg, 468 μmol) in dioxane (10 mL) was evacuated and refilled 3 times using N$_2$. The mixture was stirred at 90° C. for 12 hours. The mixture was concentrated to give a residue, which was purified by flash silica gel chromatography (DCM MeOH=100:0 to 100:30) to give the product of tert-butyl N-[(3S,4S)-3-methyl-8-{3-[6-(4-methyl-3-oxopiperazin-1-yl)-1,2,3,4-tetrahydro-1,5-naphthyridin-1-yl]-1-(oxan-2-yl)-1H-pyrazolo[3,4-b]pyrazin-6-yl}-2-oxa-8-azaspiro[4.5]decan-4-yl]carbamate (90.0 mg, 81% yield) as a yellow oil.

Step b: The compound of tert-butyl N-[(3S,4S)-3-methyl-8-{3-[6-(4-methyl-3-oxopiperazin-1-yl)-1,2,3,4-tetrahydro-1,5-naphthyridin-1-yl]-1-(oxan-2-yl)-1H-pyrazolo[3,4-b]pyrazin-6-yl}-2-oxa-8-azaspiro[4.5]decan-4-yl]carbamate (90 mg, 125 μmol) was added in 2 M HCl/MeOH (2 mL). The mixture was stirred at 25° C. for 12 h. The mixture was concentrated and purified by prep-HPLC (HCl) to afford the product of 4-(5-{6-[(3S,4S)-4-amino-3-methyl-2-oxa-8- azaspiro[4.5]decan-8-yl]-1H-pyrazolo[3,4-b]pyrazin-3-yl}-5,6,7,8-tetrahydro-1,5-naphthyridin-2-yl)-1-methylpiperazin-2-one hydrochloride (12.0 mg, 16.8% yield) as an orange solid.

Synthesis of (4S)-1-{6-[(3S,4S)-4-amino-3-methyl-2-oxa-8-azaspiro[4.5]decan-8-yl]-1H-pyrazolo[3,4-b]pyrazin-3-yl}-N,4-dimethyl-1,2,3,4-tetrahydroquinoline-6-carboxamide, Compound 288

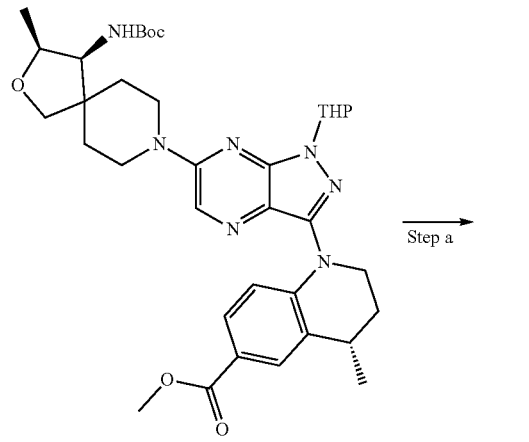

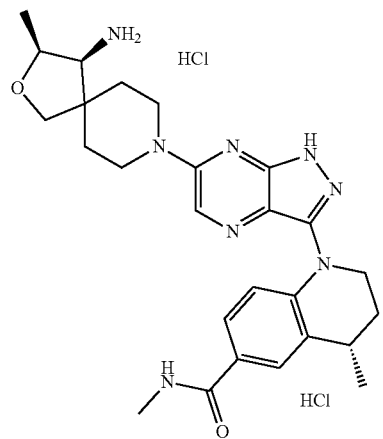

Step a: The mixture of methyl (4S)-1-{6-[(3S,4S)-4-{[(tert-butoxy)carbonyl]amino}-3-methyl-2-oxa-8-azaspiro[4.5]decan-8-yl]-1-(oxan-2-yl)-1H-pyrazolo[3,4-b]pyrazin-3-yl}-4-methyl-1,2,3,4-tetrahydroquinoline-6-carboxylate (30 mg, 44 µmol, 1.0 eq, synthesized via the method described for Compound 33) and LiOH (5.3 mg, 221 µmol, 5.0 eq) in MeOH (5 mL) and $H_2O$ (0.5 mL) was stirred at 40° C. for 20 hours. The mixture was adjusted with 2N HCl to pH=7. The mixture was concentrated under reduced pressure and the residue (37 mg, crude) was used in the next step directly without further purification.

Step b: The mixture of (4S)-1-{6-[(3S,4S)-4-{[(tert-butoxy)carbonyl]amino}-3-methyl-2-oxa-8-azaspiro[4.5]decan-8-yl]-1-(oxan-2-yl)-1H-pyrazolo[3,4-b]pyrazin-3-yl}-4-methyl-1,2,3,4-tetrahydroquinoline-6-carboxylic acid (25 mg, 38 µmol, 1.0 eq), HATU (43 mg, 113 µmol, 3.0 eq) and DIPEA (15 mg, 113 µmol, 3.0 eq) in DMF (2 mL) was stirred at 15° C. for 10 mins. Then $MeNH_2$/THF (0.56 mL, 2M in THF, 30.0 eq) was added and stirred at 15° C. for 3 hours. The mixture was diluted with saturated $NH_4Cl$ (10 mL), extracted with EtOAc (10 mL×2). The organic layer was washed with brine (20 mL), dried over anhydrous $Na_2SO_4$, filtered and concentrated under reduced pressure. The residue was purified by prep-TLC (DCM/MeOH=10:1) to afford the desired product of tert-butyl N-[(3S,4S)-3-methyl-8-{3-[(4S)-4-methyl-6-(methylcarbamoyl)-1,2,3,4-tetrahydroquinolin-1-yl]-1-(oxan-2-yl)-1H-pyrazolo[3,4-b]pyrazin-6-yl}-2-oxa-8-azaspiro[4.5]decan-4-yl]carbamate (20 mg, 79% yield) as a yellow solid.

Step c: The mixture of tert-butyl N-[(3S,4S)-3-methyl-8-{3-[(4S)-4-methyl-6-(methylcarbamoyl)-1,2,3,4-tetrahydroquinolin-1-yl]-1-(oxan-2-yl)-1H-pyrazolo[3,4-b]pyrazin-6-yl}-2-oxa-8-azaspiro[4.5]decan-4-yl]carbamate (20 mg, 30 µmol, 1.0 eq) in HCl/MeOH (3 mL, 4M) was stirred at 15° C. for 10 hours. The mixture was concentrated under reduced pressure and the residue was purified by prep-HPLC (HCl) to afford (4S)-1-{6-[(3S,4S)-4-amino-3-methyl-2-oxa-8-azaspiro[4.5]decan-8-yl]-1H-pyrazolo[3,4-b]pyrazin-3-yl}-N,4-dimethyl-1,2,3,4-tetrahydroquinoline-6-carboxamide dihydrochloride (6.5 mg, 39.1% yield) as a yellow solid.

369

Synthesis of (3S,4S)-3-methyl-8-{3-[6-(1,3-thiazol-2-yl)-1,2,3,4-tetrahydro-1,5-naphthyridin-1-yl]-1H-pyrazolo[3,4-b]pyrazin-6-yl}-2-oxa-8-azaspiro[4.5]decan-4-amine, Compound 293

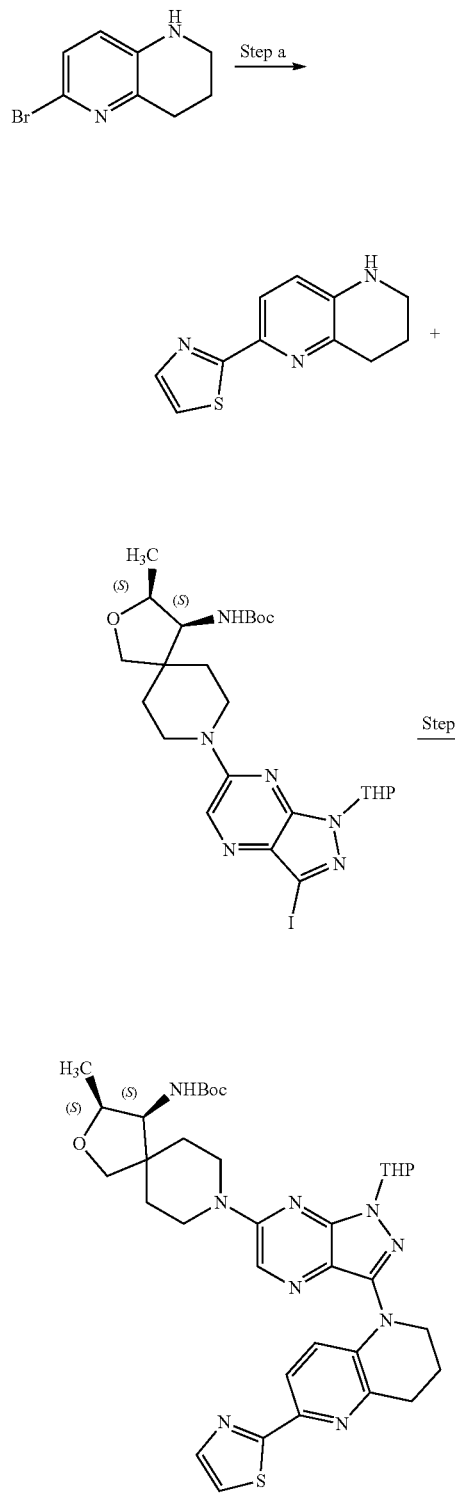

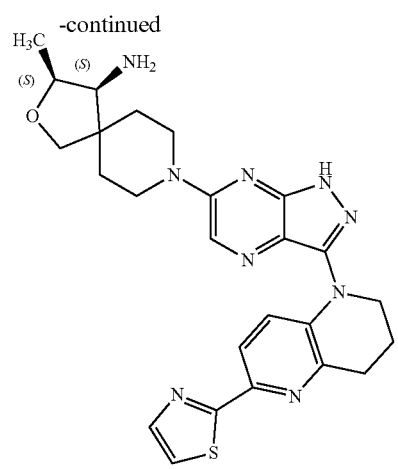

Step a: A mixture of 6-bromo-1,2,3,4-tetrahydro-1,5-naphthyridine (200 mg, 938 μmol), 2-(tributylstannyl)-1,3-thiazole (875 mg, 2.30 mmol), Pd$_2$(dba)$_3$ (257 mg, 281 μmol), and XPhos (223 mg, 469 μmol) in dioxane (10 mL) was stirred at 100° C. for 12 hours under N$_2$. The reaction mixture was quenched with KF (875 mg, solid) and concentrated under reduced pressure to give a residue. The residue was dissolved in EtOAc (100 mL) and washed with H$_2$O (30 mL×2). The organics were concentrated under reduced pressure to give a residue, which was purified by flash silica gel chromatography (0-70% EtOAc/petroleum ether) to afford 6-(1,3-thiazol-2-yl)-1,2,3,4-tetrahydro-1,5-naphthyridine (200 mg, 67% yield) as a yellow solid.

Step b: tert-Butyl N-[(3S,4S)-8-[3-iodo-1-(oxan-2-yl)-1H-pyrazolo[3,4-b]pyrazin-6-yl]-3-methyl-2-oxa-8-azaspiro[4.5]decan-4-yl]carbamate (150 mg, 250 μmol), 6-(1,3-thiazol-2-yl)-1,2,3,4-tetrahydro-1,5-naphthyridine (81.4 mg, 255.1 μmol), RuPhos-Pd-G4 (63.7 mg, 75 μmol), RuPhos (34.9 mg, 75 μmol), and Cs$_2$CO$_3$ (244 mg, 750 μmol) were taken up in PhMe (10 mL). The reaction mixture was evacuated and refilled 3 times with N$_2$ and stirred at 100° C. for 12 hours. The reaction mixture was concentrated under reduced pressure and purified by purified by flash silica gel chromatography (0-70% EtOAc/petroleum ether) to afford tert-butyl N-[(3S,4S)-3-methyl-8-[1-(oxan-2-yl)-3-[6-(1,3-thiazol-2-yl)-1,2,3,4-tetrahydro-1,5-naphthyridin-1-yl]-1H-pyrazolo[3,4-b]pyrazin-6-yl]-2-oxa-8-azaspiro[4.5]decan-4-yl]carbamate (230 mg, 94% yield) as a yellow solid.

Step c: tert-Butyl N-[(3S,4S)-3-methyl-8-[1-(oxan-2-yl)-3-[6-(1,3-thiazol-2-yl)-1,2,3,4-tetrahydro-1,5-naphthyridin-1-yl]-1H-pyrazolo[3,4-b]pyrazin-6-yl]-2-oxa-8-azaspiro[4.5]decan-4-yl]carbamate (200 mg, 203 μmol) and 4 M HCl/MeOH (5 mL) were taken up in MeOH (5 mL) and the reaction mixture stirred at 25° C. for 2 hours. The reaction mixture was concentrated under reduced pressure and purified by prep-HPLC (acetonitrile/aq. HCl) to afford (3S,4S)-3-methyl-8-{3-[6-(1,3-thiazol-2-yl)-1,2,3,4-tetrahydro-1,5-naphthyridin-1-yl]-1H-pyrazolo[3,4-b]pyrazin-6-yl}-2-oxa-8-azaspiro[4.5]decan-4-amine hydrochloride (93.6 mg, 85.8% yield) as a yellow solid: LCMS [M+H]$^+$=504.1; $^1$H-NMR (400 MHz, DMSO-d$_6$): δ 8.39 (s, 1H), 8.15 (br, 3H), 7.86 (d, J=3.2 Hz, 1H), 7.76 (d, J=8.8 Hz, 1H), 7.70 (d, J=3.2 Hz, 1H), 7.60 (d, J=8.8 Hz 1H), 4.32-4.26 (m, 2H), 4.24-4.20 (m, 2H), 4.04-4.00 (m, 2H), 3.96-3.93 (m, 1H), 3.40-3.38 (m, 1H), 3.21-3.18 (m, 2H), 3.05-3.01 (m, 2H), 2.17-2.12 (m, 2H), 1.85-1.72 (m, 2H), 1.63-1.59 (m, 2H), 1.24 (d, J=6.4 Hz, 3H).

Synthesis of (8S)-5-{6-[(3S,4S)-4-amino-3-methyl-2-oxa-8-azaspiro[4.5]decan-8-yl]-1H-pyrazolo[3,4-b]pyrazin-3-yl}-N,N,8-trimethyl-5,6,7,8-tetrahydro-1,5-naphthyridine-2-carboxamide, Compound 294

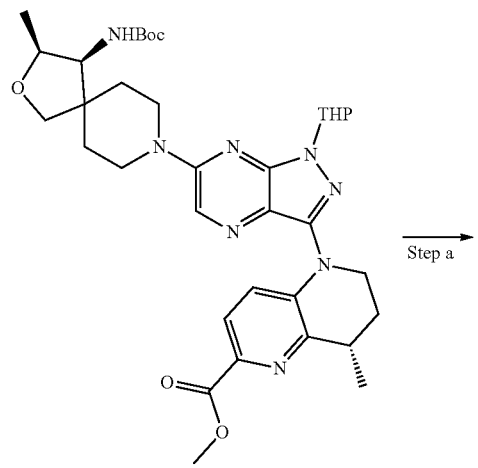

Step a

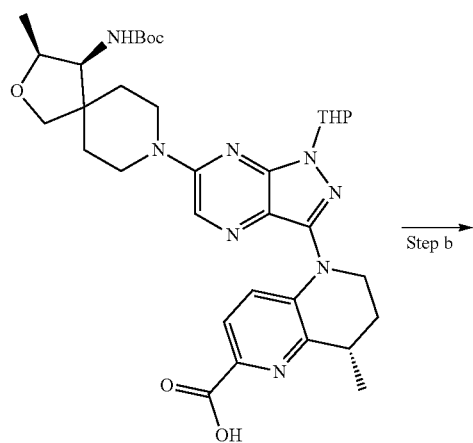

Step b

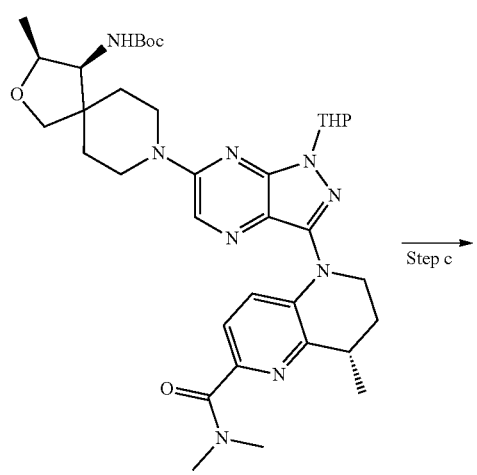

Step c

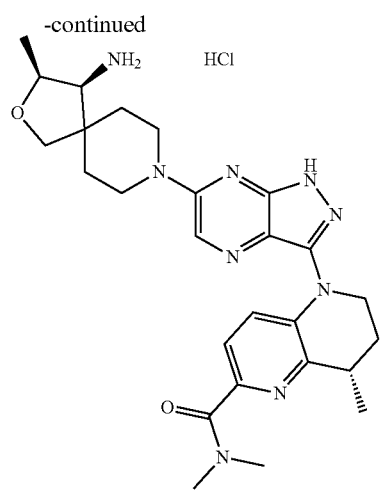

-continued

Step a: To a solution of methyl (8S)-5-{6-[(3S,4S)-4-{[(tert-butoxy)carbonyl]amino}-3-methyl-2-oxa-8-azaspiro[4.5]decan-8-yl]-1-(oxan-2-yl)-1H-pyrazolo[3,4-b]pyrazin-3-yl}-8-methyl-5,6,7,8-tetrahydro-1,5-naphthyridine-2-carboxylate (172.0 mg, 254.0 µmol, synthesized as described for Compound 33, Step a) in MeOH (10.0 mL) was added 3 N NaOH (5.0 mL, 15.0 mmol). The mixture was stirred at 50° C. for 3 hours. The mixture was concentrated to about 5 mL and diluted with water (50.0 mL), then extracted with EtOAc/petroleum ether (2/3, 50.0 mL). The organic layer was washed with water (30.0 mL). The organic layer was discarded and the combined water layers were adjusted pH=5-6 with 1 N HCl, and next extracted with EtOAc (50.0 mL×2). The combined organic layers were dried over anhydrous $Na_2SO_4$, filtered and concentrated under reduced pressure to afford (8S)-5-{6-[(3S,4S)-4-{[(tert-butoxy)carbonyl]amino}-3-methyl-2-oxa-8-azaspiro[4.5]decan-8-yl]-1-(oxan-2-yl)-1H-pyrazolo[3,4-h]pyrazin-3-yl}-8-methyl-5,6,7,8-tetrahydro-1,5-naphthyridine-2-carboxylic acid (140.0 mg, 211.0 µmol, 83.3% yield) as a yellow solid.

Step b: The mixture of (8S)-5-{6-[(3S,4S)-4-{[(tert-butoxy)carbonyl]amino}-3-methyl-2-oxa-8-azaspiro[4.5]decan-8-yl]-1-(oxan-2-yl)-1H-pyrazolo[3,4-b]pyrazin-3-yl}-8-methyl-5,6,7,8-tetrahydro-1,5-naphthyridine-2-carboxylic acid (85.0 mg, 128.0 µmol), HATU (97.3 mg, 256.0 µmol) and TEA (88.6 µL, 640.0 µmol) in DMF (2.0 mL) was stirred at 15° C. for 10 min. Then $Me_2NH \cdot HCl$ (12.2 mg, 150.0 µmol) was added and stirred at 15° C. for 1 hour. The mixture was poured into saturated $NH_4Cl$ (50.0 mL) and extracted with EtOAc (50.0 mL×3). The combined organic layers were washed with brine (50.0 mL), dried over anhydrous $Na_2SO_4$ and concentrated under reduced pressure. The residue was purified by column chromatography (MeOH in EtOAc=0~10%) to afford tert-butyl N-[(3S,4S)-8-{3-[(4S)-6-(dimethylcarbamoyl)-4-methyl-1,2,3,4-tetrahydro-1,5-naphthyridin-1-yl]-1-(oxan-2-yl)-1H-pyrazolo[3,4-b]pyrazin-6-yl}-3-methyl-2-oxa-8-azaspiro[4.5]decan-4-yl]carbamate (75.0 mg, 108.0 µmol, 84.9% yield) as a yellow solid.

Step c: To a solution of tert-butyl N-[(3S,4S)-8-{3-[(4S)-6-(dimethylcarbamoyl)-4-methyl-1,2,3,4-tetrahydro-1,5-naphthyridin-1-yl]-1-(oxan-2-yl)-1H-pyrazolo[3,4-b]pyrazin-6-yl}-3-methyl-2-oxa-8-azaspiro[4.5]decan-4-yl]carbamate (75.0 mg, 108.0 µmol) in DCM (2.0 mL) was added HCl/dioxane (5.0 mL, 4 M) and the yellow solution was stirred at 15° C. for 12 hours. The mixture was concentrated under reduced pressure and the residue was purified by prep-HPLC (HCl) to afford (8S)-5-{6-[(3S,4S)-4-amino-3-methyl-2-oxa-8-azaspiro[4.5]decan-8-yl]-1H-pyrazolo[3,4-b]pyrazin-3-yl}-N,N,8-trimethyl-5,6,7,8-tetrahydro-1,5-naphthyridine-2-carboxamide hydrochloride (24.2 mg, 44.6 μmol, 41.3% yield) as a yellow solid.

Synthesis of (3S,4S)-3-methyl-8-(3-(6-(oxazol-2-yl)-3,4-dihydro-1,5-naphthyridin-1(2H)-yl)-1H-pyrazolo[3,4-b]pyrazin-6-yl)-2-oxa-8-azaspiro[4.5]decan-4-amine, Compound 295

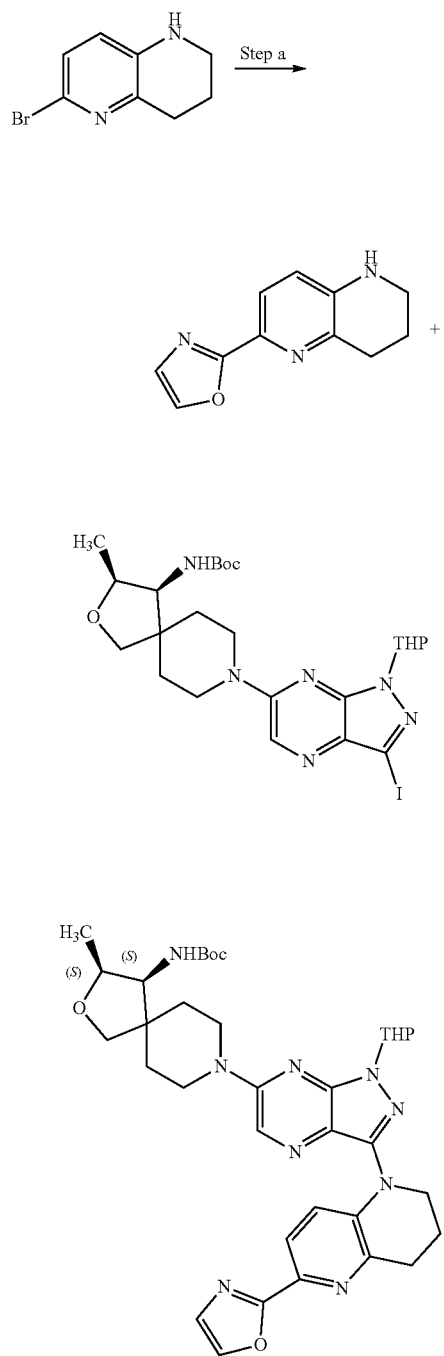

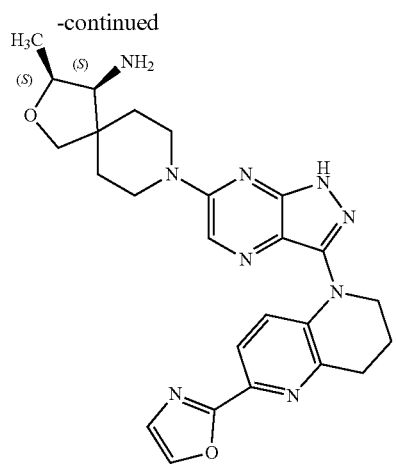

Step a: A mixture of 6-bromo-1,2,3,4-tetrahydro-1,5-naphthyridine (200 mg, 938 μmol, CAS #1219022-46-4), 2-(tributylstannyl)-1,3-oxazole (669 mg, 1.9 mmol), Pd₂(dba)₃ (171 mg, 187 μmol) and XPhos (133 mg, 281 μmol) in dioxane (10 mL) was stirred at 100° C. for 12 hours under N₂ atmosphere. After cooling to room temperature, KF (700 mg) was added and the reaction mixture stirred for 0.5 hour. The reaction mixture was diluted with ethyl acetate (25 mL), washed with H₂O (20 mL×2), and the combined organics washed with brine (15 mL), dried over anhydrous Na₂SO₄, and concentrated in vacuum to give a residue. Purification by silica gel chromatography (ethyl acetate as eluent) afforded 6-(1,3-oxazol-2-yl)-1,2,3,4-tetrahydro-1,5-naphthyridine (85 mg, 45.2% yield) as a brown oil.

Step b: A mixture of tert-butyl N-[(3S,4S)-8-[3-iodo-1-(oxan-2-yl)-1H-pyrazolo[3,4-b]pyrazin-6-yl]-3-methyl-2-oxa-8-azaspiro[4.5]decan-4-yl]carbamate (200 mg, 334 μmol), 6-(1,3-oxazol-2-yl)-1,2,3,4-tetrahydro-1,5-naphthyridine (80.4 mg, 400 μmol), Pd₂(dba)₃ (61.1 mg, 66.8 μmol), XantPhos (38.6 mg, 66.8 μmol) and i-BuONa (64.1 mg, 668 μmol) in toluene (10 mL) was stirred at 120° C. for 12 hours under N₂ atmosphere. The reaction mixture was cooled and concentrated in vacuo to give a residue, which was purified by silica gel chromatography (0-5% MeOH/DCM) to afford tert-butyl N-[(3S,4S)-3-methyl-8-[1-(oxan-2-yl)-3-[6-(1,3-oxazol-2-yl)-1,2,3,4-tetrahydro-1,5-naphthyridin-1-yl]-1H-pyrazolo[3,4-b]pyrazin-6-yl]-2-oxa-8-azaspiro[4.5]decan-4-yl]carbamate (100 mg, 44.6% yield) as a yellow solid.

Step c: A mixture of tert-butyl N-[(3S,4S)-3-methyl-8-[1-(oxan-2-yl)-3-[6-(1,3-oxazol-2-yl)-1,2,3,4-tetrahydro-1,5-naphthyridin-1-yl]-1H-pyrazolo[3,4-b]pyrazin-6-yl]-2-oxa-8-azaspiro[4.5]decan-4-yl]carbamate (100 mg, 148 μmol) in 4M HCl/MeOH (5 mL) was stirred at 20° C. for 0.5 hour. The reaction mixture was concentrated under reduced pressure to give a residue, which was purified by prep-HPLC (acetonitrile/aq. HCl) to afford (3S,4S)-3-methyl-8-(3-(6-(oxazol-2-yl)-3,4-dihydro-1,5-naphthyridin-1(2H)-yl)-1H-pyrazolo[3,4-b]pyrazin-6-yl)-2-oxa-8-azaspiro[4.5]decan-4-amine hydrochloride (8.4 mg, 11.6% yield) as a yellow solid: ESMS [M+H]⁺=488.1; ¹H-NMR (400 MHz, DMSO-d₆): δ 8.34 (s, 1H), 8.15 (s, 1H), 7.69 (d, J=8.4 Hz, 1H), 7.56 (d, J=8.8 Hz, 1H), 7.33 (s, 1H), 4.10-4.04 (m, 1H), 4.01-3.95 (m, 4H), 3.69 (d, J=8.4 Hz, 1H), 3.55-3.45 (m, 1H), 3.03 (t, J=6.4 Hz, 2H), 2.90 (d, J=5.2 Hz, 1H), 2.16-2.10 (m, 2H), 2.03-1.98 (m, 1H), 1.80-1.75 (m, 1H), 1.70-1.63 (m, 1H), 1.57-1.49 (m, 1H), 1.08 (d, J=6.4 Hz, 3H).

Synthesis of (3S,4S)-3-methyl-8-(3-(6-(1-methyl-1H-pyrazol-4-yl)-3,4-dihydropyrido[2,3-b]pyrazin-1(2H)-yl)-1H-pyrazolo[3,4-b]pyrazin-6-yl)-2-oxa-8-azaspiro[4.5]decan-4-amine, Compound 296

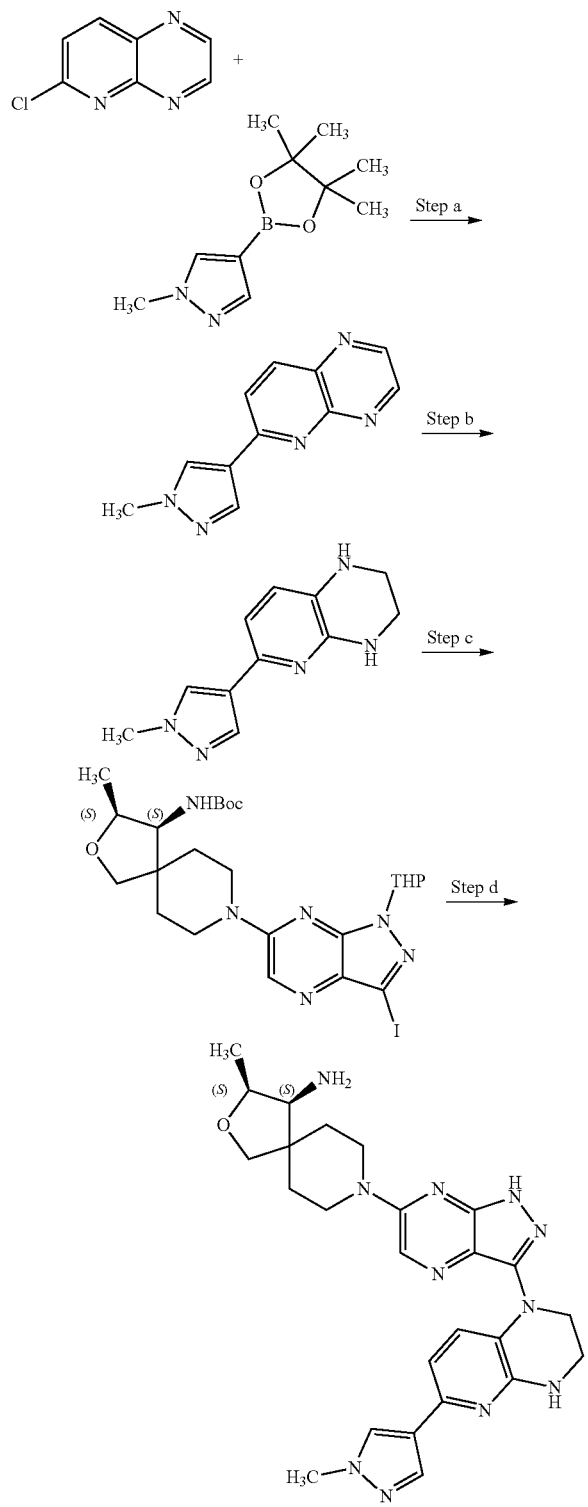

Step a: A mixture of 6-chloropyrido[2,3-b]pyrazine (200 mg, 1.2 mmol, CAS #68236-03-3), 1-methyl-4-(4,4,5,5-tetramethyl-1,3,2-dioxaborolan-2-yl)-1H-pyrazole (299 mg, 1.4 mmol), Pd(dppf)Cl$_2$ CH$_2$Cl$_2$ (97.9 mg, 120 µmol) and K$_2$CO$_3$ (412 mg, 3.0 mmol) in dioxane (10 mL)/H$_2$O (3 mL) was stirred at 90° C. for 12 hours under N$_2$ atmosphere. The reaction mixture was concentrated under reduced pressure to give a residue, which was purified by silica gel chromatography (5% to 10% MeOH/DCM) to afford 1-methyl-4-{pyrido[2,3-b]pyrazin-6-yl}-1H-pyrazole (200 mg, 79% yield) as a brown solid.

Step b: To a mixture of 1-methyl-4-{pyrido[2,3-b]pyrazin-6-yl}-1H-pyrazole (150 mg, 710 µmol) in MeOH (10 mL) was added PtO$_2$ (80.6 mg, 355 µmol), and the resulting mixture was stirred at 20° C. for 12 hours under H$_2$ (15 psi) atmosphere. The reaction mixture was filtered and the filtrate was concentrated in vacuo to give a residue, which was purified by prep-HPLC (acetonitrile/aq. NH$_3$) to afford 1-methyl-4-{1H,2H,3H,4H-pyrido[2,3-b]pyrazin-6-yl}-1H-pyrazole (140 mg, 92.1% yield) as a brown solid.

Step c: A mixture of tert-butyl N-[(3S,4S)-8-[3-iodo-1-(oxan-2-yl)-1H-pyrazolo[3,4-b]pyrazin-6-yl]-3-methyl-2-oxa-8-azaspiro[4.5]decan-4-yl]carbamate (300 mg, 501 µmol), 1-methyl-4-{1H,2H,3H,4H-pyrido[2,3-b]pyrazin-6-yl}-1H-pyrazole (129 mg, 601 µmol), Pd$_2$(dba)$_3$ (91.5 mg, 100 µmol), XantPhos (57.8 mg, 100 µmol), and t-BuONa (96.0 mg, 1.0 mmol) in toluene (15 mL) was stirred at 120° C. for 12 hours under N$_2$ atmosphere. The reaction mixture was concentrated in vacuo to give a residue, which was purified by silica gel chromatography (0% to 5% MeOH/DCM) to afford tert-butyl ((3S,4S)-3-methyl-8-(3-(6-(1-methyl-1H-pyrazol-4-yl)-3,4-dihydropyrido[2,3-b]pyrazin-1(2H)-yl)-1-(tetrahydro-2H-pyran-2-yl)-1H-pyrazolo[3,4-b]pyrazin-6-yl)-2-oxa-8-azaspiro[4.5]decan-4-yl)carbamate (250 mg, 73% yield) as a brown solid.

Step d: A mixture of tert-butyl ((3S,4S)-3-methyl-8-(3-(6-(1-methyl-1H-pyrazol-4-yl)-3,4-dihydropyrido[2,3-b]pyrazin-1(2H)-yl)-1-(tetrahydro-2H-pyran-2-yl)-1H-pyrazolo[3,4-b]pyrazin-6-yl)-2-oxa-8-azaspiro[4.5]decan-4-yl)carbamate (200 mg, 291 µmol) in HCl/MeOH (4 M, 5 mL) was stirred at 20° C. for 0.5 hour. The reaction mixture was concentrated under reduced pressure to give a residue, which was purified by prep-HPLC (acetonrile/aq. HCl) to afford (3S,4S)-3-methyl-8-(3-(6-(1-methyl-1H-pyrazol-4-yl)-3,4-dihydropyrido[2,3-b]pyrazin-1(2H)-yl)-1H-pyrazolo[3,4-b]pyrazin-6-yl)-2-oxa-8-azaspiro[4.5]decan-4-amine hydrochloride (51.5 mg, 33% yield) as a yellow solid: ESMS [M+H]$^+$=502.2; $^1$H-NMR (400 MHz, DMSO-d$_6$): δ 14.68 (s, 1H), 12.80 (s, 1H), 8.86 (s, 1H), 8.55 (s, 1H), 8.37 (s, 1H), 8.34 (s, 2H), 8.25 (s, 1H), 7.87 (d, J=8.4 Hz, 1H), 7.02 (d, J=8.4 Hz, 1H), 4.35-4.19 (m, 3H), 4.15-4.13 (m, 2H), 3.96 (d, J=9.2 Hz, 1H), 3.91 (s, 3H), 3.78-3.73 (m, 2H), 3.68 (d, J=9.2 Hz, 1H), 3.38-3.35 (m, 1H), 3.21-3.13 (m, 2H), 1.87-1.78 (m, 2H), 1.72-1.62 (m, 2H), 1.25 (d, J=6.8 Hz, 3H).

Synthesis of (R)-8-(3-(6-(1-methyl-1H-pyrazol-4-yl)-3,4-dihydro-1,5-naphthyridin-1(2H)-yl)-1H-pyrazolo[3,4-b]pyrazin-6-yl)8-azaspiro[4.5]decan-1-amine, Compound 298

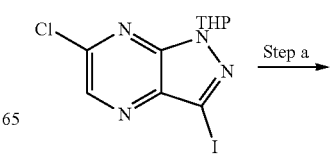

-continued

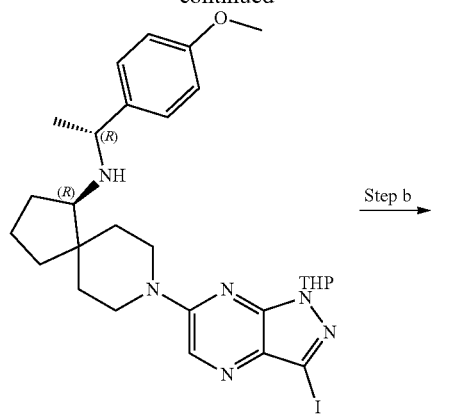

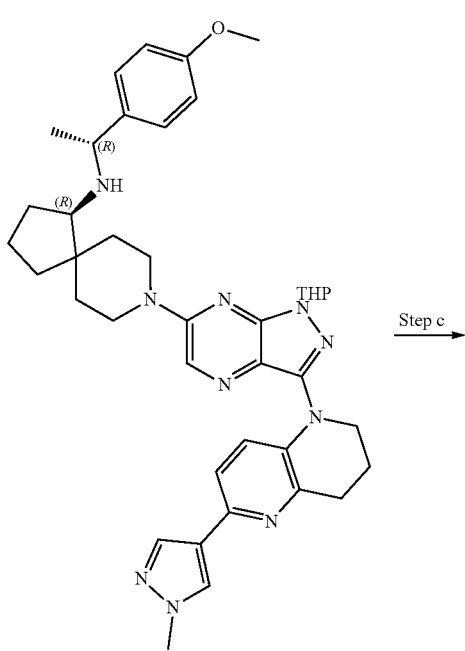

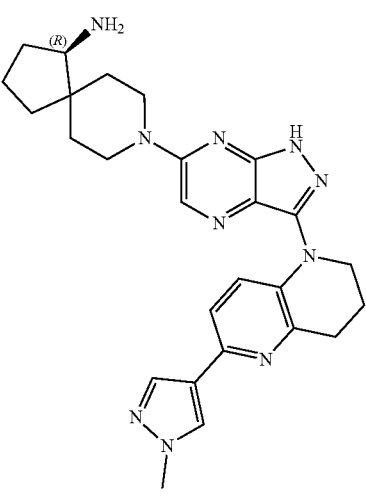

Step a: A resealable vial was charged with (1R)—N-[(1R)-1-(4-methoxyphenyl)ethyl]-8-azaspiro[4.5]decan-1-amine (299 mg, 1.04 mmol) (CAS 1801765-82-1), DMF (10 mL), and ethylbis(propan-2-yl)amine (905 µL, 5.20 mmol). The solution was charged with 6-chloro-3-iodo-1-(oxan-2-yl)-1H-pyrazolo[3,4-b]pyrazine (379 mg, 1.04 mmol) and heated to 60° C. 4 h. The reaction was cooled to room temperature and diluted with ethyl acetate and brine. The aqueous layer was extracted with ethyl acetate three times. The organic layers were combined, dried over sodium sulfate, pooled, and concentrated in vacuo. The residue was purified by silica gel chromatography (eluting with methylene chloride and methanol). The product containing fractions were pooled and concentrated in vacuo to yield (1R)-8-(3-iodo-1-(tetrahydro-2H-pyran-2-yl)-1H-pyrazolo[3,4-b]pyrazin-6-yl)-N—((R)-1-(4-methoxyphenyl)ethyl)-8-azaspiro[4.5]decan-1-amine (106 mg) as a white solid. LCMS: [M+H]+ 617.

Step b: A resealable reaction vial was charged with (1R)-8-[3-iodo-1-(oxan-2-yl)-1H-pyrazolo[3,4-b]pyrazin-6-yl]-N-[(1R)-1-(4-methoxyphenyl)ethyl]-8-azaspiro[4.5]decan-1-amine (51 mg, 0.08271 mmol), 6-(1-methyl-1H-pyrazol-4-yl)-1,2,3,4-tetrahydro-1,5-naphthyridine (17.7 mg, 0.08271 mmol), 9-{[5-(diphenylphosphanyl)-9,9-dimethyl-9H-xanthen-4-yl]diphenyl-$\lambda^4$-phosphanyl}-O-methanesulfonyl-8-methyl-8$\lambda^4$-aza-9-palladatricyclo[8.4.0.0$^{2,7}$]tetradeca-1(14),2,4,6,10,12-hexaene-9,9-bis(ylium)-10-uid-9-olate (7.95 mg, 0.008271 mmol), (tert-butoxy)sodium (11.9 mg, 0.1240 mmol), and toluene (5 mL). The mixture was bubbled with nitrogen for 5 min before the vial was sealed and stirred at 80° C. After 7 h, the mixture was diluted with ethyl acetate, charged with celite, filtered, and concentrated in vacuo. The residue was dissolved in trifluoroacetic acid (3 mL) and heated to 100° C. for 1 h in the microwave.

The solvent was removed in vacuo and dissolved in DMSO/water (3/1, 4 mL). The residue was purified by HPLC (eluting with 5-30% ACN/water). The product containing fractions were pooled, concentrated in vacuo, and lyophilized from acetonitrile/water to yield (R)-8-(3-(6-(1-methyl-1H-pyrazol-4-yl)-3,4-dihydro-1,5-naphthyridin-1(2H)-yl)-1H-pyrazolo[3,4-b]pyrazin-6-yl)-8-azaspiro[4.5]decan-1-amine (23 mg) as a yellow solid.

Synthesis of (4S)-8-{3-[(4S)-4-methyl-6-(1,2,4-oxadiazol-3-yl)-1,2,3,4-tetrahydroquinolin-1-yl]-1H-pyrazolo[3,4-b]pyrazin-6-yl}-2-oxa-8-azaspiro[4.5]decan-4-amine, Compound 299

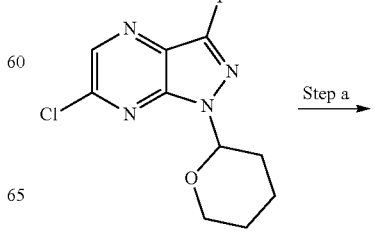

379
-continued

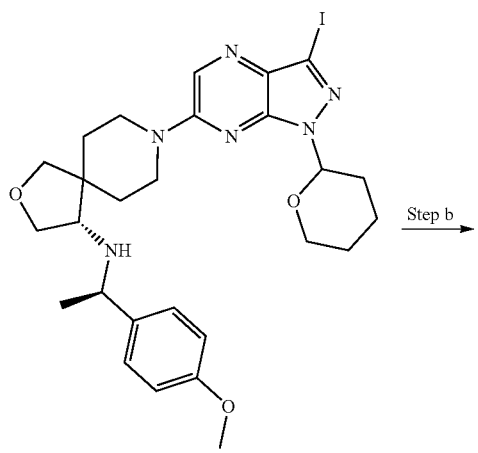

Step b

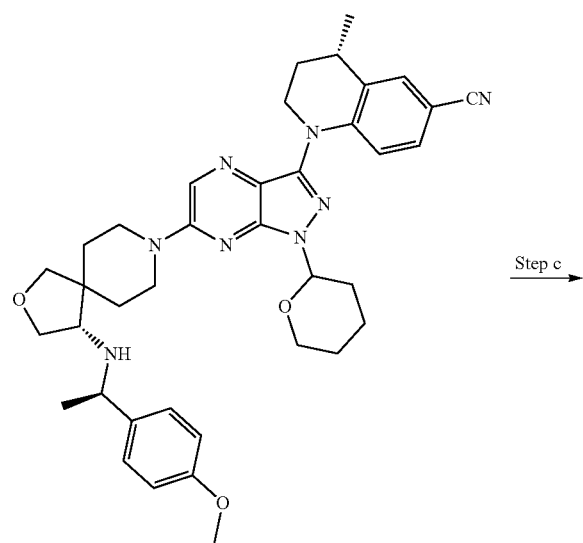

Step c

380
-continued

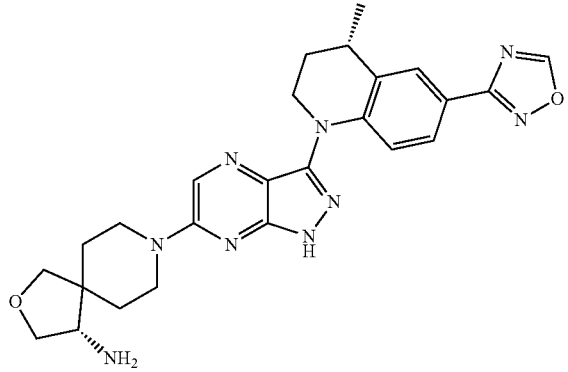 [SMILES: C[C@H]1CCN(c2n[nH]c3nc(N4CCC5(CC4)COC[C@H]5N)cnc23)c2ccc(-c3ncon3)cc21]

Step a: A resealable vial was charged with (4S)—N-[(1R)-1-(4-methoxyphenyl)ethyl]-2-oxa-8-azaspiro[4.5]decan-4-amine (461 mg, 1.59 mmol), DMF (10 mL) and ethylbis(propan-2-yl)amine (1.37 mL, 7.95 mmol). The solution was charged with 6-chloro-3-iodo-1-(oxan-2-yl)-1H-pyrazolo[3,4-b]pyrazine (579 mg, 1.59 mmol) and the solution heated at 60° C. for 5 hrs. After cooling, the reaction mixture was diluted with ethyl acetate, washed with water, brine, dried over anhydrous sodium sulfate, and filtered. The combined organics were concentrated under reduced pressure, and purified by flash silica gel chromatography (eluting with ethyl acetate:heptanes=25:75 to 75:25) to afford (4S)-8-[3-iodo-1-(oxan-2-yl)-1H-pyrazolo[3,4-b]pyrazin-6-yl]-N-[(1R)-1-(4-methoxyphenyl)ethyl]-2-oxa-8-azaspiro[4.5]decan-4-amine (240 mg) as a light yellow oil/foam. LCMS: [M+H]+ 619.

Step b: A resealable reaction vial was charged with (4S)-8-[3-iodo-1-(oxan-2-yl)-1H-pyrazolo[3,4-b]pyrazin-6-yl]-N-[(1R)-1-(4-methoxyphenyl)ethyl]-2-oxa-8-azaspiro[4.5]decan-4-amine (240 mg, 0.3880 mmol), (4S)-4-methyl-1,2,3,4-tetrahydroquinoline-6-carbonitrile (66.8 mg, 0.388 mmol), 9-{[5-(diphenylphosphanyl)-9,9-dimethyl-9H-xanthen-4-yl]diphenyl-)-λ4-phosphanyl}-O-methanesulfonyl-8-methyl-8λ4-aza-9-palladatricyclo[8.4.0.0²,⁷]tetradeca-1(14),2,4,6,10,12-hexaene-9,9-bis(ylium)-10-uid-9-olate (37.3 mg, 0.0388 mmol), (tert-butoxy)sodium (74.5 mg, 0.776 mmol) toluene (6 mL) and bubbled with nitrogen for 5 min, the vial was sealed the mixture was stirred at 80° C. for 1 hr. The reaction was diluted with ethyl acetate, charged with celite, filtered, pre-absorbed on SiO₂ (3 g) and purified by flash silica gel chromatography (eluting with MeOH:DCM=0:100 to 10:90) to afford (4S)-1-{6-[(4S)-4-{[(1R)-1-(4-methoxyphenyl)ethyl]amino}-2-oxa-8-azaspiro[4.5]decan-8-yl]-1-(oxan-2-yl)-1H-pyrazolo[3,4-b]pyrazin-3-yl}-4-methyl-1,2,3,4-tetrahydroquinoline-6-carbonitrile (245 mg) as a brown oil.

Step c: (4S)-1-{6-[(4S)-4-{[(1R)-1-(4-methoxyphenyl)ethyl]amino}-2-oxa-8-azaspiro[4.5]decan-8-yl]-1-(oxan-2-yl)-1H-pyrazolo[3,4-b]pyrazin-3-yl}-4-methyl-1,2,3,4-tetrahydroquinoline-6-carbonitrile (245 mg, 0.3696 mmol) in EtOH was charged with hydroxylamine (179 µL, 2.95 mmol) and heated to 60° C. for 8 hrs. The solvent removed and the residue was taken up in (diethoxymethoxy)ethane (1.36 g, 9.24 mmol), TFA (3 drops) and heated to 60° C. for 30 min. After cooling, the reaction mixture was diluted with ethyl acetate, washed with water, brine, dried over anhydrous sodium sulfate, and filtered. The combined organics were concentrated under reduced pressure, and purified by flash silica gel chromatography (eluting with ethyl acetate:heptanes=30:70 to 80:20) to afford (4S)—N-[(1R)-1-(4-

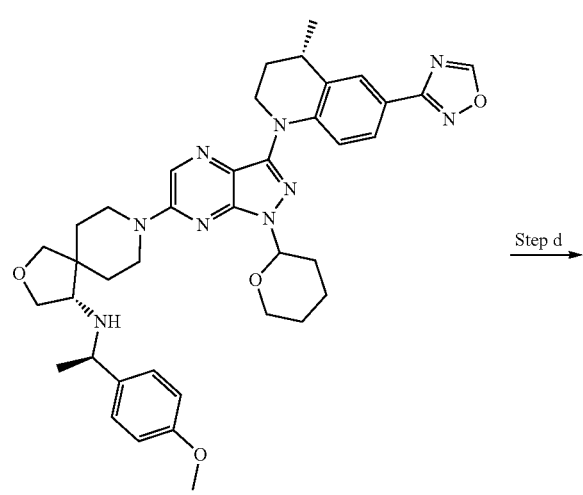

Step d methoxyphenyl)ethyl]-8-{3-[(4S)-4-methyl-6-(1,2,4-oxadi-azol-3-yl)-1,2,3,4-tetrahydroquinolin-1-yl]-1-(oxan-2-yl)-1H-pyrazolo[3,4-b]pyrazin-6-yl}-2-oxa-8-azaspiro[4.5]decan-4-amine (116 mg).

Step d: (4S)—N-[(1R)-1-(4-methoxyphenyl)ethyl]-8-{3-[(4S)-4-methyl-6-(1,2,4-oxadiazol-3-yl)-1,2,3,4-tetrahydroquinolin-1-yl]-1-(oxan-2-yl)-1H-pyrazolo[3,4-b]pyrazin-6-yl}-2-oxa-8-azaspiro[4.5]decan-4-amine (116 mg, 0.164 mmol) was dissolved in TFA (4 mL) and heated to 100° C. for 1 hr in the MW. The solvent was removed, the residue chased with MeOH, taken up in DMSO/water (3/1, 4 mL) and purified on prep-HPLC (5-10% ACN/water+0.1% FA) to afford (4S)-8-13-[(4S)-4-methyl-6-(1,2,4-oxadiazol-3-yl)-1,2,3,4-tetrahydroquinolin-1-yl]-1H-pyrazolo[3,4-b]pyrazin-6-yl)-2-oxa-8-azaspiro[4.5]decan-4-amine (52 mg). LCMS: [M+H]+ 488.

Synthesis of N-[(5-{6-[(3S,4S)-4-amino-3-methyl-2-oxa-8-azaspiro[4.5]decan-8-yl]-1H-pyrazolo[3,4-b]pyrazin-3-yl}-5,6,7,8-tetrahydro-1,5-naphthyridin-2-yl)methyl]acetamide dihydrochloride, Compound 306

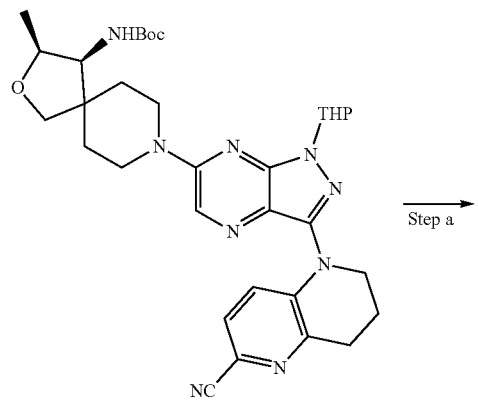

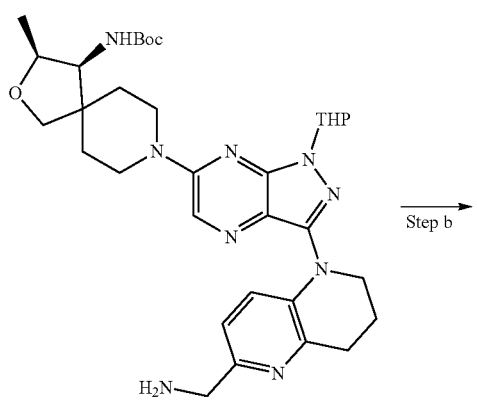

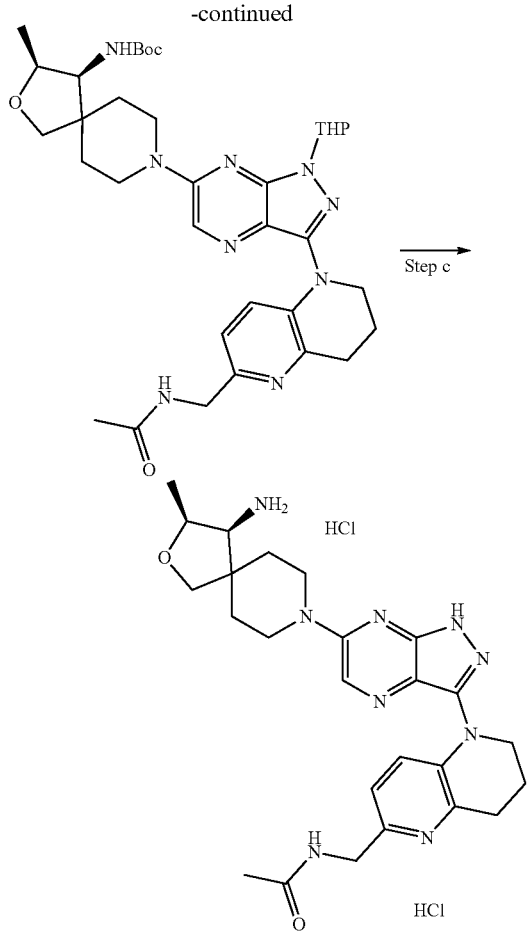

Step a: The mixture of tert-butyl N-[(3S,4S)-8-[3-(6-cyano-1,2,3,4-tetrahydro-1,5-naphthyridin-1-yl)-1-(oxan-2-yl)-1H-pyrazolo[3,4-b]pyrazin-6-yl]-3-methyl-2-oxa-8-azaspiro[4.5]decan-4-yl]carbamate (230 mg, 365 μmol, 1.0 eq, synthesized via Step a of Compound 33 using 5,6,7,8-tetrahydro-1,5-naphthyridine-2-carbonitrile as the coupling partner) and Raney Ni (200 mg) in MeOH (10 mL) was evacuated and refilled 3 times using H₂, then stirred at 15° C. for 10 hours under H₂ (15 psi) atmosphere. The mixture was warmed to 40° C. and stirred for 5 hours. The mixture was further warmed to 55° C. and stirred for 10 hours. On completion, the mixture was filtered and concentrated under reduced pressure. The residue was purified by column chromatography (Ethyl acetate:MeOH=10:0~1:1) to afford the desired product of tert-butyl N-[(3S,4S)-8-{3-[6-(aminomethyl)-1,2,3,4-tetrahydro-1,5-naphthyridin-1-yl]-1-(oxan-2-yl)-1H-pyrazolo[3,4-b]pyrazin-6-yl}-3-methyl-2-oxa-8-azaspiro[4.5]decan-4-yl]carbamate (130 mg, 56% yield) as a yellow solid.

Step b: The mixture of tert-butyl N-[(3S,4S)-8-{3-[6-(aminomethyl)-1,2,3,4-tetrahydro-1,5-naphthyridin-1-yl]-1-(oxan-2-yl)-1H-pyrazolo[3,4-b]pyrazin-6-yl}-3-methyl-2-oxa-8-azaspiro[4.5]decan-4-yl]carbamate (130 mg, 205 μmol, 1.0 eq), Ac₂O (42 mg, 410 μmol, 2.0 eq) and TEA (62 mg, 615 μmol, 3.0 eq) in DCM (10 mL) was stirred at 15° C. for 1 hour. On completion, the mixture was concentrated under reduced pressure and the residue was used in the next step directly without further purification.

Step c: The mixture of tert-butyl N-[(3S,4S)-8-(3-[6-(acetamidomethyl)-1,2,3,4-tetrahydro-1,5-naphthyridin-1- yl]-1-(oxan-2-yl)-1H-pyrazolo[3,4-b]pyrazin-6-yl)-3-methyl-2-oxa-8-azaspiro[4.5]decan-4-yl]carbamate (130 mg, 192 µmol, 1.0 eq) in HCl/MeOH (5 mL, 4M) was stirred at 15° C. for 10 hours. The mixture was concentrated under reduced pressure and the residue was purified by prep-HPLC (HCl) to afford the desired product of N-[(5-{6-[(3S,4S)-4-amino-3-methyl-2-oxa-8-azaspiro[4.5]decan-8-yl]-1H-pyrazolo[3,4-b]pyrazin-3-yl}-5,6,7,8-tetrahydro-1,5-naphthyridin-2-yl)methyl]acetamide dihydrochloride (33.1 mg, 30.6% yield) as a yellow solid.

Synthesis of (3S,4S)-3-methyl-8-(3-(6-(tetrahydrofuran-3-yl)-3,4-dihydro-1,5-naphthyridin-1(2H)-yl)-1H-pyrazolo[3,4-b]pyrazin-6-yl)-2-oxa-8-azaspiro[4.5]decan-4-amine, Compound 309

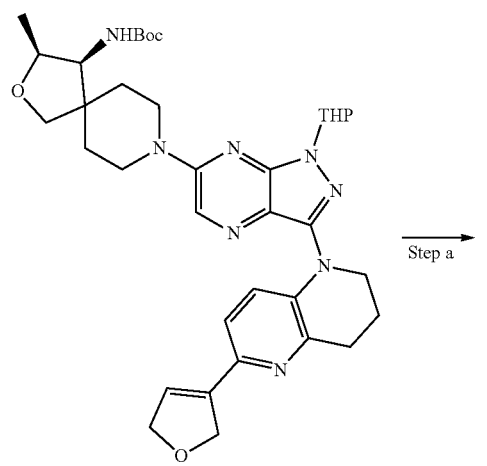

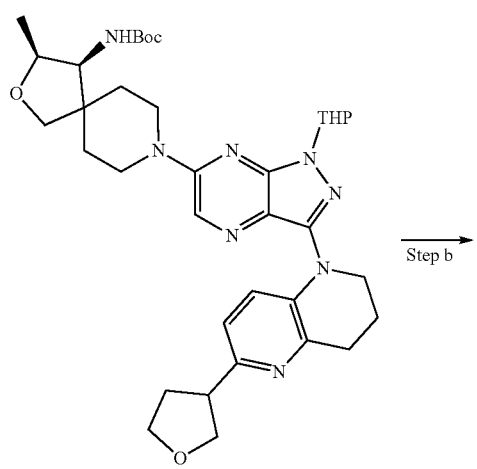

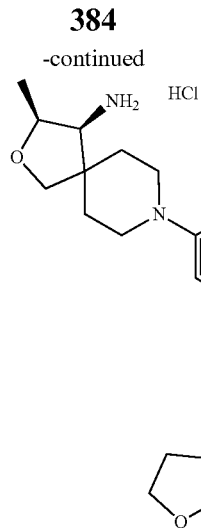

Step a: To a mixture of tert-butyl N-[(3S,4S)-8-{3-[6-(2,5-dihydrofuran-3-yl)-1,2,3,4-tetrahydro-1,5-naphthyridin-1-yl]-1-(oxan-2-yl)-1H-pyrazolo[3,4-b]pyrazin-6-yl}-3-methyl-2-oxa-8-azaspiro[4.5]decan-4-yl]carbamate (100 mg, 148 µmol, synthesized as described for Compound 281 with 6-(2,5-dihydrofuran-3-yl)-1,2,3,4-tetrahydro-1,5-naphthyridine as the coupling partner in Step a) in MeOH (5 mL) was added Pd/C (10 wt %, wet, 17.4 mg). The resulting mixture was stirred at 30° C. for 12 hours under $H_2$ (15 psi) atmosphere. The reaction mixture was filtered and the filtrate was concentrated in vacuo to give a residue, which was purified by silica gel chromatography (Ethyl acetate as eluent) to afford the product of tert-butyl N-[(3S,4S)-3-methyl-8-[1-(oxan-2-yl)-3-[6-(oxolan-3-yl)-1,2,3,4-tetrahydro-1,5-naphthyridin-1-yl]-1H-pyrazolo[3,4-b]pyrazin-6-yl]-2-oxa-8-azaspiro[4.5]decan-4-yl]carbamate (60 mg, 60.1% yield) as a yellow solid.

Step b: A mixture of tert-butyl N-[(3S,4S)-3-methyl-8-[1-(oxan-2-yl)-3-[6-(oxolan-3-yl)-1,2,3,4-tetrahydro-1,5-naphthyridin-1-yl]-1H-pyrazolo[3,4-b]pyrazin-6-yl]-2-oxa-8-azaspiro[4.5]decan-4-yl]carbamate (60 mg, 88.9 µmol) in HCl/MeOH (4M, 5 mL) was stirred at 15° C. for 0.5 hour. The reaction mixture was concentrated under reduced pressure to give a residue, which was purified by prep-HPLC (HCl) to afford the product of (3S,4S)-3-methyl-8-(3-(6-(tetrahydrofuran-3-yl)-3,4-dihydro-1,5-naphthyridin-1(2H)-yl)-1H-pyrazolo[3,4-b]pyrazin-6-yl)-2-oxa-8-azaspiro[4.5]decan-4-amine hydrochloride (6.7 mg, 14.3% yield) as a yellow solid.

Synthesis of (3S,4S)-3-methyl-8-(3-(4-methyl-6-(1-methyl-1H-pyrazol-4-yl)-3,4-dihydropyrido[2,3-b]pyrazin-1(2H)-yl)-1H-pyrazolo[3,4-b]pyrazin-6-yl)-2-oxa-8-azaspiro[4.5]decan-4-amine, Compound 310

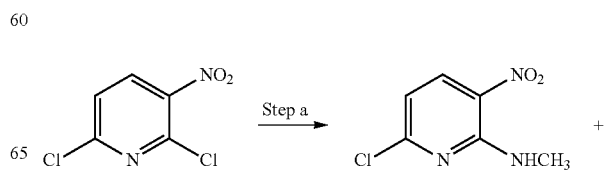

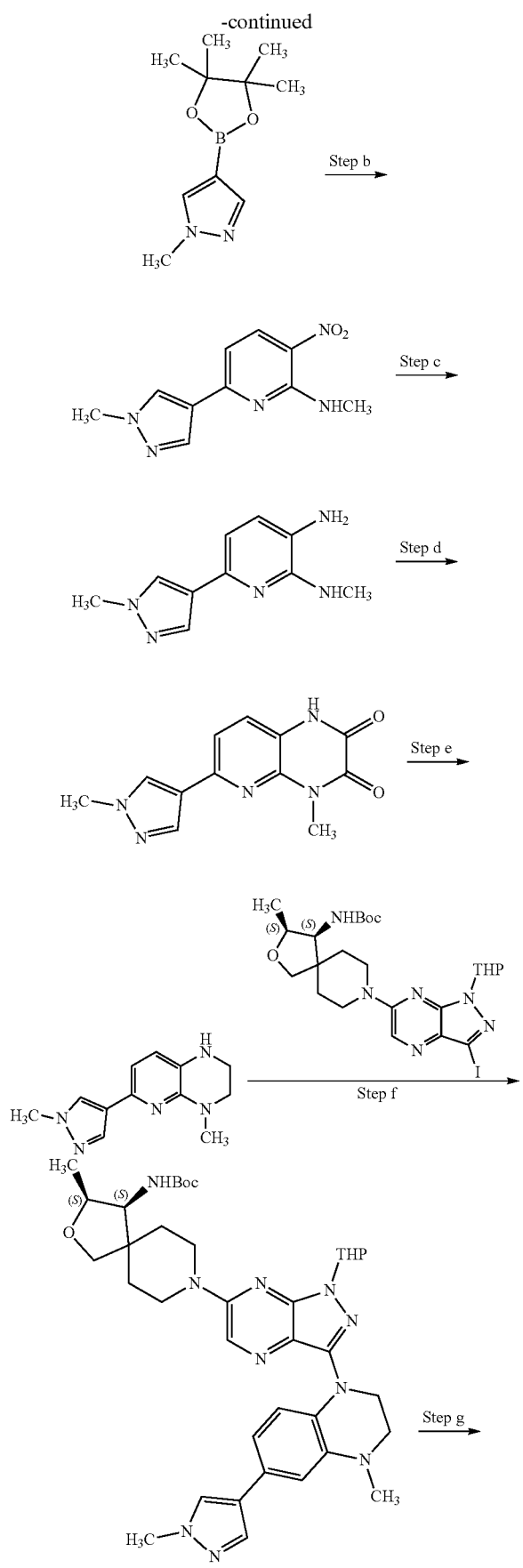

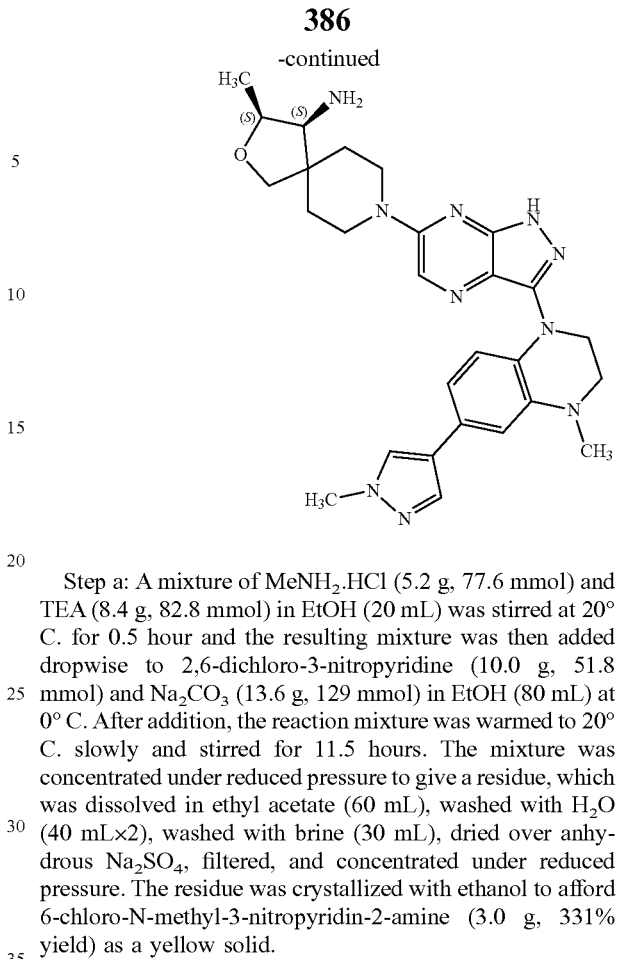

Step a: A mixture of MeNH₂.HCl (5.2 g, 77.6 mmol) and TEA (8.4 g, 82.8 mmol) in EtOH (20 mL) was stirred at 20° C. for 0.5 hour and the resulting mixture was then added dropwise to 2,6-dichloro-3-nitropyridine (10.0 g, 51.8 mmol) and Na₂CO₃ (13.6 g, 129 mmol) in EtOH (80 mL) at 0° C. After addition, the reaction mixture was warmed to 20° C. slowly and stirred for 11.5 hours. The mixture was concentrated under reduced pressure to give a residue, which was dissolved in ethyl acetate (60 mL), washed with H₂O (40 mL×2), washed with brine (30 mL), dried over anhydrous Na₂SO₄, filtered, and concentrated under reduced pressure. The residue was crystallized with ethanol to afford 6-chloro-N-methyl-3-nitropyridin-2-amine (3.0 g, 331% yield) as a yellow solid.

Step b: 6-Chloro-N-methyl-3-nitropyridin-2-amine (2.5 g, 13.3 mmol), 1-methyl-4-(4,4,5,5-tetramethyl-1,3,2-dioxaborolan-2-yl)-1H-pyrazole (3.3 g, 15.9 mmol), Pd(dppf)Cl₂ (973 mg, 1.3 mmol), and K₂CO₃ (3.7 g, 26.6 mmol) in dioxane (30 mL)/H₂O (5 mL) was stirred at 90° C. for 12 hours under N₂ atmosphere. The reaction mixture was diluted with ethyl acetate (50 mL), washed with H₂O (30 mL×2), washed with brine (20 mL), dried over anhydrous Na₂SO₄, filtered and concentrated under reduced pressure to give a residue. The residue then was purified by silica gel chromatography (50-60% EtOAc/petroleum ether) to afford N-methyl-6-(1-methyl-1H-pyrazol-4-yl)-3-nitropyridin-2-amine (1.8 g, 58% yield) as a yellow solid.

Step c: N-Methyl-6-(1-methyl-1H-pyrazol-4-yl)-3-nitropyridin-2-amine (500 mg, 2.1 mmol) and Pd/C (10 wt % wet, 126 mg) in EtOAc (20 mL) were stirred at 15° C. for 2 hours under H₂ (15 psi) atmosphere. The atmosphere was replaced with nitrogen and the mixture filtered and concentrated under reduced pressure to afford N²-methyl-6-(1-methyl-1H-pyrazol-4-yl)pyridine-2,3-diamine (420 mg, 97% yield) as a white solid.

Step d: To oxalic dichloride (313 mg, 2.5 mmol) in DCM (10 mL) at 0° C. under N₂ atmosphere was added N²-methyl-6-(1-methyl-1H-pyrazol-4-yl)pyridine-2,3-diamine (420 mg, 2.1 mmol) in DCM (10 mL), followed by the dropwise addition of pyridine (813 mg, 10.3 mmol). After addition was complete, the reaction mixture was warmed to 25° C., and stirred for 12 hours. The mixture was filtered and the filter cake dried under reduce pressure to afford 4-methyl-6-(1-methyl-1H-pyrazol-4-yl)pyrido[2,3-b]pyrazine-2,3(1H,4H)-dione (300 mg, crude product) as a brown solid.

Step e: To 4-methyl-6-(1-methyl-1H-pyrazol-4-yl)pyrido[2,3-b]pyrazine-2,3(1H,4H)-dione (300 mg, 1.2 mmol) in THF (20 mL) at 15° C. was added LAH (220 mg, 5.8 mmol). After addition, the reaction mixture was stirred at this temperature for 2 hours. The mixture was quenched with 15% NaOH (0.22 mL) and a resulting white precipitate formed which was removed by filtration. The filter cake was washed with THF and the filtrate concentrated under reduced pressure to afford 4-methyl-6-(1-methyl-1H-pyrazol-4-yl)-1,2,3,4-tetrahydropyrido[2,3-b]pyrazine (220 mg, crude product) as a green solid.

Step f: tert-Butyl N-[(3S,4S)-8-[3-iodo-1-(oxan-2-yl)-1H-pyrazolo[3,4-b]pyrazin-6-yl]-3-methyl-2-oxa-8-azaspiro[4.5]decan-4-yl]carbamate (180 mg, 300 μmol), 4-methyl-6-(1-methyl-1H-pyrazol-4-yl)-1,2,3,4-tetrahydropyrido[2,3-b]pyrazine (103 mg, 450 μmol), Pd$_2$(dba)$_3$ (54.9 mg, 60 μmol), XantPhos (52 mg, 90 μmol), and t-BuONa (57.6 mg, 600 μmol) in toluene (10 mL) were stirred at 120° C. for 12 hours under N$_2$ atmosphere. The reaction mixture was concentrated under reduced pressure to give a residue, which was purified by silica gel chromatography (0-15% MeOH/DCM) to afford tert-butyl N-[(3S,4S)-3-methyl-8-{3-[4-methyl-6-(1-methyl-1H-pyrazol-4-yl)-1H,2H,3H,4H-pyrido[2,3-b]pyrazin-1-yl]-1-(oxan-2-yl)-1H-pyrazolo[3,4-b]pyrazin-6-yl}-2-oxa-8-azaspiro[4.5]decan-4-yl]carbamate (120 mg, 57% yield) as a brown solid.

Step g: tert-Butyl N-[(3S,4S)-3-methyl-8-{3-[4-methyl-6-(1-methyl-1H-pyrazol-4-yl)-1H,2H,3H,4H-pyrido[2,3-b]pyrazin-1-yl]-1-(oxan-2-yl)-1H-pyrazolo[3,4-b]pyrazin-6-yl}-2-oxa-8-azaspiro[4.5]decan-4-yl]carbamate (120 mg, 171 μmol) in 4M HCl/MeOH (5 mL) was stirred at 15° C. for 0.5 hour. The reaction mixture was concentrated under reduced pressure to give a residue, which was purified by prep-HPLC (acetonitrile/aq. HCl) to afford (3S,4S)-3-methyl-8-(3-(4-methyl-6-(1-methyl-1H-pyrazol-4-yl)-3,4-dihydropyrido[2,3-b]pyrazin-1(2H)-yl)-1H-pyrazolo[3,4-b]pyrazin-6-yl)-2-oxa-8-azaspiro[4.5]decan-4-amine hydrochloride (45.2 mg, 47.8% yield) as a brown solid: ESMS [M+H]+=516.1; $^1$H-NMR (500 MHz, DMSO-d$_6$) δ 12.79 (br, 1H), 8.36-8.31 (m, 5H), 7.96 (s, 1H), 7.62 (d, J=8.0 Hz, 1H), 6.87 (d, J=8.4 Hz, 1H), 4.26-4.12 (m, 6H), 3.95 (d, J=9.2 Hz, 1H), 3.91 (s, 3H), 3.76 (br, 2H), 3.68 (d, J=9.2 Hz, 1H), 3.38 (s, 3H), 1.85-1.62 (m, 4H), 1.25 (d, J=6.8 Hz, 3H).

Synthesis of (3S,4S)-3-methyl-8-{3-[6-(1-propyl-1H-pyrazol-4-yl)-1,2,3,4-tetrahydro-1,5-naphthyridin-1-yl]-1H-pyrazolo[3,4-b] pyrazin-6-yl}-2-oxa-8-azaspiro[4.5]decan-4-amine, Compound 311

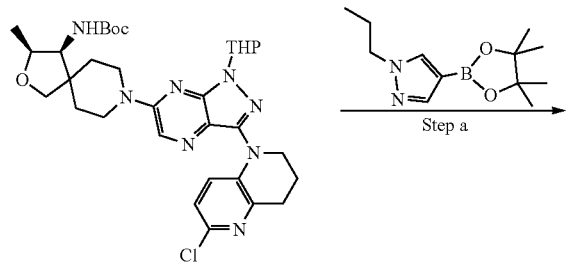

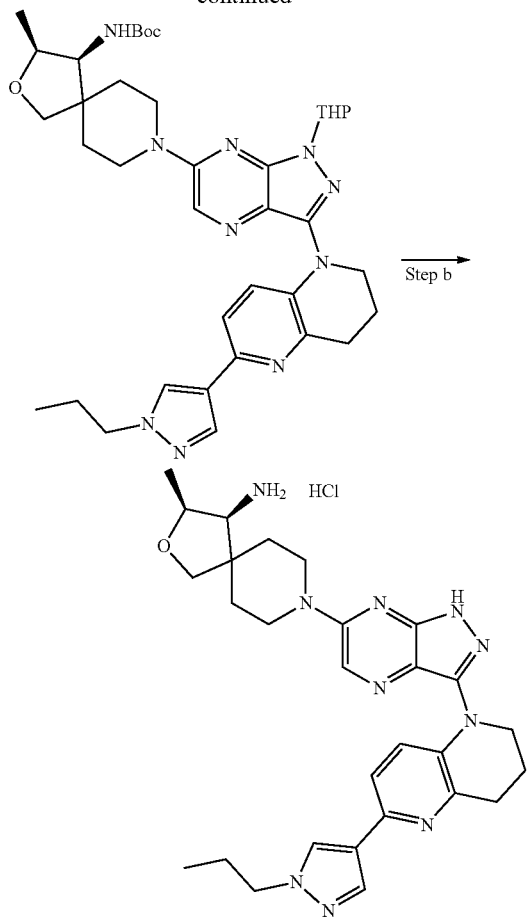

Step a: A mixture of tert-butyl N-[(3S,4S)-8-[3-(6-chloro-1,2,3,4-tetrahydro-1,5-naphthyridin-11-yl)-1-(oxan-2-yl)-1H-pyrazolo[3,4-b]pyrazin-6-yl]-3-methyl-2-oxa-8-azaspiro[4.5]decan-4-yl]carbamate (100 mg, 0.16 mmol, synthesized as described for Compound 281 using 6-chloro-1,2,3,4-tetrahydro-1,5-naphthyridine as the coupling partner in Step a). 1-propyl-4-(4,4,5,5-tetramethyl-1,3,2-dioxaborolan-2-yl)-1H-pyrazole (44.1 mg, 0.19 mmol, CAS #934586-51-3), Pd(dppf)Cl$_2$.CH$_2$Cl$_2$ (25.4 mg, 0.3 mmol) and K$_2$CO$_3$ (53.8 mg, 0.39 mmol) in dioxane (8 mL)/H$_2$O (0.8 mL) was evacuated and refilled 3 times using N$_2$. The mixture was stirred at 90° C. for 12 hours under N$_2$ atmosphere. The reaction mixture was concentrated to give a residue which was purified by flash silica gel chromatography (DCM:MeOH=100:0 to 100:10) to give tert-butyl N-[(3S,4S)-3-methyl-8-[1-(oxan-2-yl)-3-[6-(1-propyl-1H-pyrazol-4-yl)-1,2,3,4-tetrahydro-1,5-naphthyridin-1-yl]-1H-pyrazolo[3,4-b]pyrazin-6-yl]-2-oxa-8-azaspiro[4.5]decan-4-yl]carbamate (90.0 mg, 81% yield) as a yellow solid.

Step b: The compound of tert-butyl N-[(3S,4S)-3-methyl-8-[1-(oxan-2-yl)-3-[6-(1-propyl-1H-pyrazol-4-yl)-1,2,3,4-tetrahydro-1,5-naphthyridin-1-yl]-1H-pyrazolo[3,4-b]pyrazin-6-yl]-2-oxa-8-azaspiro[4.5]decan-4-yl]carbamate (90 mg, 0.13 mmol) was added in HCl/MeOH (2 mL, 2 N). The mixture was stirred at 25° C. for 12 h. The mixture was concentrated and purified by prep-HPLC (HCl) to afford the product of (3S,4S)-3-methyl-8-{3-[6-(1-propyl-1H-pyrazol-4-yl)-1,2,3,4-tetrahydro-1,5-naphthyridin-1-yl]-1H-pyrazolo[3,4-b]pyrazin-6-yl}-2-oxa-8-azaspiro[4.5]decan-4-amine hydrochloride (41.7 mg, 58.5% yield) as an orange solid.

Synthesis of (3S,4S)-8-(3-(6-(1-isopropyl-1H-pyrazol-4-yl)-3,4-dihydro-1,5-naphthyridin-1(2H)-yl)-1H-pyrazolo[3,4-b]pyrazin-6-yl)-3-methyl-2-oxa-8-azaspiro[4.5]decan-4-amine, Compound 312

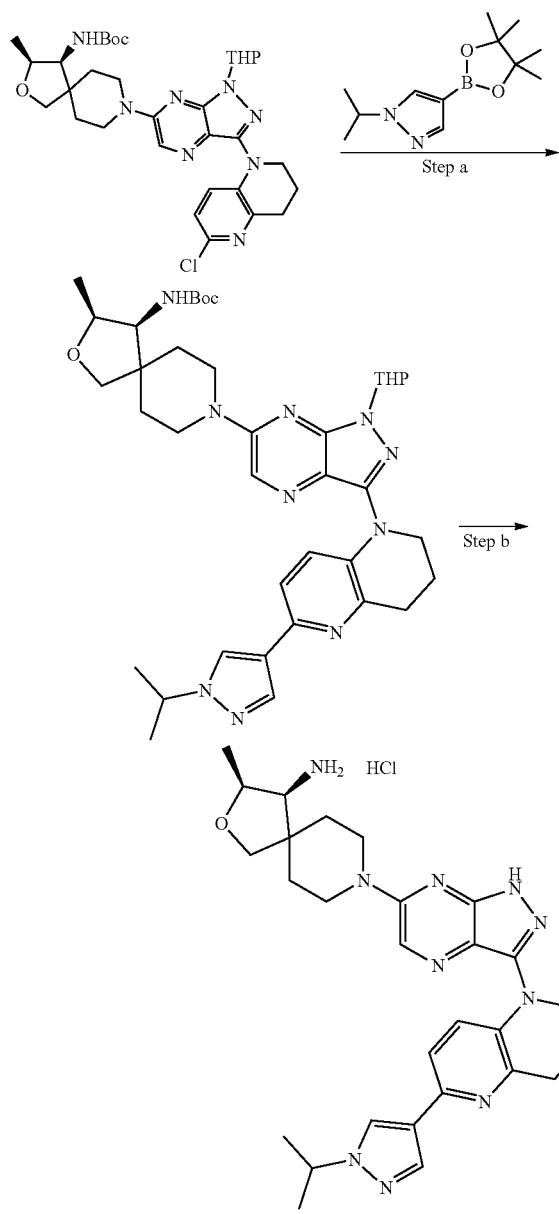

Step a: A mixture of tert-butyl N-[(3S,4S)-8-[3-(6-chloro-1,2,3,4-tetrahydro-1,5-naphthyridin-1-yl)-1-(oxan-2-yl)-1H-pyrazolo[3,4-b]pyrazin-6-yl]-3-methyl-2-oxa-8-azaspiro[4.5]decan-4-yl]carbamate (100 mg, 0.16 mmol, synthesized as described for Compound 231 using 6-chloro-1,2,3,4-tetrahydro-1,5-naphthyridine as the coupling partner in Step a), Pd(dppf)Cl$_2$—CH$_2$Cl$_2$ (25.4 mg, 0.03 mmol), K$_2$CO$_3$ (53.8 mg, 0.39 mmol) and 1-(propan-2-yl)-4-(4,4,5,5-tetramethyl-1,3,2-dioxaborolan-2-yl)-1H-pyrazole (44.1 mg, 0.19 mmol) in dioxane (5 mL)/H$_2$O (0.5 mL) was evacuated and refilled 3 times using N$_2$. The mixture was stirred at 90° C. for 12 hours under N$_2$ atmosphere. The reaction mixture was concentrated to give a residue which was purified by flash silica gel chromatography (Ethyl acetate/Petroleum ether=50/100 to 80/100) to give the product of tert-butyl N-[(3S,4S)-3-methyl-8-[1-(oxan-2-yl)-3-{6-[1-(propan-2-yl)-1H-pyrazol-4-yl]-1,2,3,4-tetrahydro-1,5-naphthyridin-1-yl}-1H-pyrazolo[3,4-b]pyrazin-6-yl]-2-oxa-8-azaspiro[4.5] decan-4-yl]carbamate (80.0 mg, 72% yield) as a yellow oil.

Step b: The compound of tert-butyl N-[(3S,4S)-3-methyl-8-[1-(oxan-2-yl)-3-(6-[1-(propan-2-yl)-1H-pyrazol-4-yl]-1,2,3,4-tetrahydro-1,5-naphthyridin-1-yl)-1H-pyrazolo[3,4-b]pyrazin-6-yl]-2-oxa-8-azaspiro[4.5]decan-4-yl]carbamate (80 mg, 112 µmol) was added in 2 N HCl/MeOH (2 mL) and the mixture was stirred at 25° C. for 12 h. The mixture was concentrated and purified by prep-HPLC (HCl) to afford the product of (3S,4S)-8-(3-(6-(1-isopropyl-1H-pyrazol-4-yl)-3,4-dihydro-1,5-naphthyridin-1(2H)-yl)-1H-pyrazolo[3,4-b]pyrazin-6-yl)-3-methyl-2-oxa-8-azaspiro[4.5]decan-4-amine hydrochloride (40.4 mg, 64% yield) as an orange solid.

Synthesis of 4-{6-[(3S,4S)-4-amino-3-methyl-2-oxa-8-azaspiro[4.5]decan-8-yl]-1H-pyrazolo[3,4-b]pyrazin-3-yl}-N-methyl-1H,2H,3H,4H-pyrido[2,3-b]pyrazine-1-carboxamide, Compound 313 and 1-{6-[(3S,4S)-4-amino-3-methyl-2-oxa-s-azaspiro[4.5]decan-8-yl]-1H-pyrazolo[3,4-b]pyrazin-3-yl}-N-methyl-1H,2H,3H,4H-pyrido[2,3-b]pyrazine-4-carboxamide, Compound 331

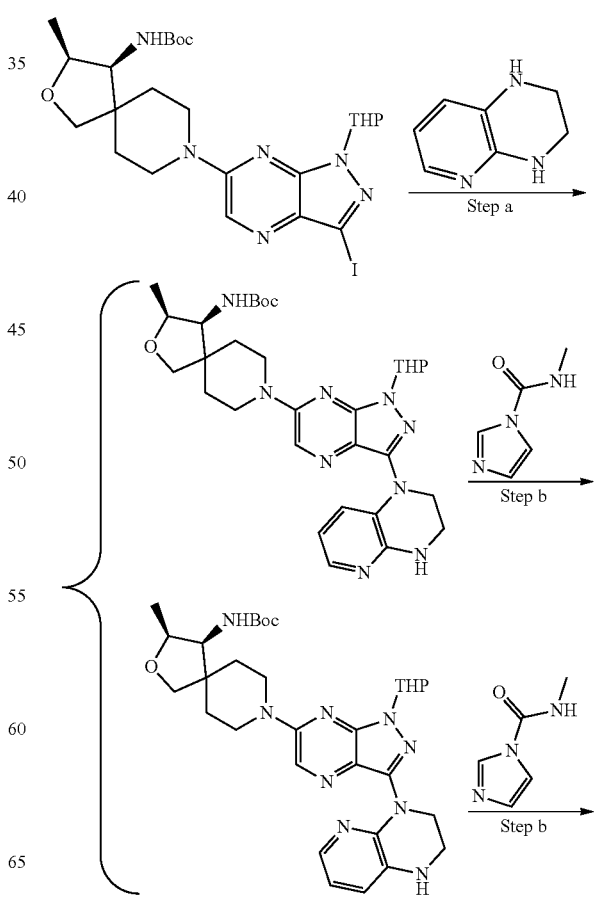

-continued

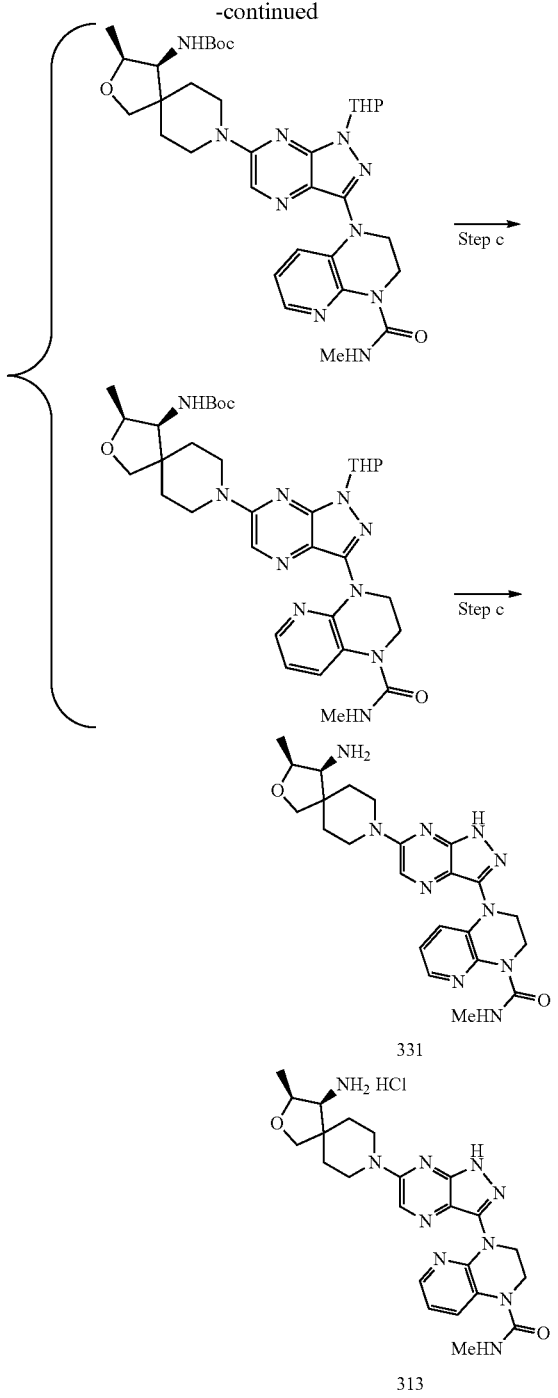

Step a: To a solution of tert-butyl N-[(3S,4S)-8-[3-iodo-1-(oxan-2-yl)-1H-pyrazolo[3,4-b]pyrazin-6-yl]-3-methyl-2-oxa-8-azaspiro[4.5]decan-4-yl]carbamate (500 mg, 835 µmol) and 1H,2H,3H,4H-pyrido[2,3-b]pyrazin-7-ylium (134 mg, 1.00 mmol) in PhMe (20 mL) was added Pd₂(dba)₃ (76.4 mg, 83.5 µmol), XantPhos (48.3 mg, 83.5 µmol) and t-BuONa (159 mg, 1.66 mmol). The mixture was evacuated and refilled 3 times using N₂ and the reaction mixture was stirred at 100° C. for 12 hours. The reaction mixture was concentrated under reduced pressure. The residue was purified by column chromatography (eluent:Petroluem ether/Ethyl acetate=100:0 to 100:100 and DCM/MeOH=100:0 to 100:10) to give the crude product. The crude product was purified by prep-HPLC (NH₄OH) to afford the tert-butyl N-[(3S,4S)-3-methyl-8-[1-(oxan-2-yl)-3-{1H,2H,3H,4H-pyrido[2,3-b]pyrazin-1-yl}-1H-pyrazolo[3,4-b]pyrazin-6-yl]-2-oxa-8-azaspiro[4.5]decan-4-yl]carbamate (150 mg, 247 µmol, 29.7% yield) as a yellow solid and tert-butyl N-[(3S,4S)-3-methyl-8-[1-(oxan-2-yl)-3-{1H,2H,3H,4H-pyrido[2,3-b]pyrazin-4-yl}-1H-pyrazolo[3,4-b]pyrazin-6-yl]-2-oxa-8-azaspiro[4.5]decan-4-yl]carbamate (80.0 mg, 132 µmol, 15.8 yield) as a yellow solid.

Step b: To a solution of tert-butyl N-[(3S,4S)-3-methyl-8-[1-(oxan-2-yl)-3-(1H,2H,3H,4H-pyrido[2,3-b]pyrazin-4-yl)-1H-pyrazolo[3,4-b]pyrazin-6-yl]-2-oxa-8-azaspiro[4.5]decan-4-yl]carbamate (60 mg, 99.0 µmol) in DMF (5 mL) was added Et₃N (39.9 mg, 396 umol) and N-methyl-1H-imidazole-1-carboxamide (247 mg, 1.98 mmol) at 25° C., and the mixture was stirred at 80° C. for 6 hours. The reaction mixture was evaporated in vacuo. The residue was purified by silica gel chromatography (eluent:CH₃OH/Ethyl acetate=0~10%) to give tert-butyl N-[(3S,4S)-3-methyl-8-{3-[1-(methylcarbamoyl)-1H,2H,3H,4H-pyrido[2,3-b]pyrazin-4-yl]-1-(oxan-2-yl)-1H-pyrazolo[3,4-b]pyrazin-6-yl}-2-oxa-8-azaspiro[4.5]decan-4-yl]carbamate (20.0 mg, 30.1 µmol, 30.4% yield) as a yellow solid.

Step c: To a solution of tert-butyl N-[(3S,4S)-3-methyl-8-{3-[1-(methylcarbamoyl)-1H,2H,3H,4H-pyrido[2,3-b]pyrazin-4-yl]-1-(oxan-2-yl)-1H-pyrazolo[3,4-b]pyrazin-6-yl}-2-oxa-8-azaspiro[4.5]decan-4-yl]carbamate (20 mg, 30.1 µmol) in MeOH (5 ml) was added HCl/MeOH (2 mL, 4 N) at 0° C., and the mixture was stirred at 30° C. for 6 hours. The reaction mixture was concentrated and purified by prep-HPLC (HCl) to afford the product of 4-{6-[(3S,4S)-4-amino-3-methyl-2-oxa-8-azaspiro[4.5]decan-8-yl]-1H-pyrazolo[3,4-b]pyrazin-3-yl}-N-methyl-1H,2H,3H,4H-pyrido[2,3-b]pyrazine-1-carboxamide hydrochloride (2.80 mg, 5.43 µmol, HCl salt, 18.0% yield) as a green solid. Steps b and c were also repeated with tert-butyl N-[(3S,4S)-3-methyl-8-[1-(oxan-2-yl)-3-{1H,2H,3H,4H-pyrido[2,3-b]pyrazin-1-yl}-1H-pyrazolo[3,4-b]pyrazin-6-yl]-2-oxa-8-azaspiro[4.5]decan-4-yl]carbamate to give 1-{6-[(3S,4S)-4-amino-3-methyl-2-oxa-8-azaspiro[4.5]decan-8-yl]-1H-pyrazolo[3,4-b]pyrazin-3-yl}-N-methyl-1H,2H,3H,4H-pyrido[2,3-b]pyrazine-4-carboxamide as a yellow solid for the final product.

Synthesis of (3S,4S)-3-methyl-8-{3-[6-(1-methyl-1H-pyrazol-4-yl)-1,2,3,4-tetrahydroquinoxalin-1-yl]-1H-pyrazolo[3,4-b]pyrazin-6-yl}-2-oxa-8-azaspiro[4.5]decan-4-amine, Compound 316

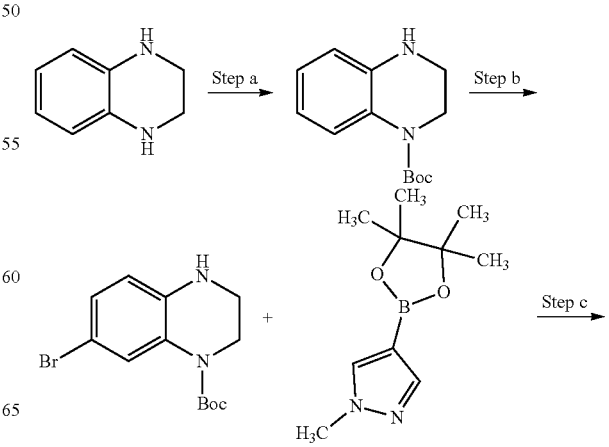

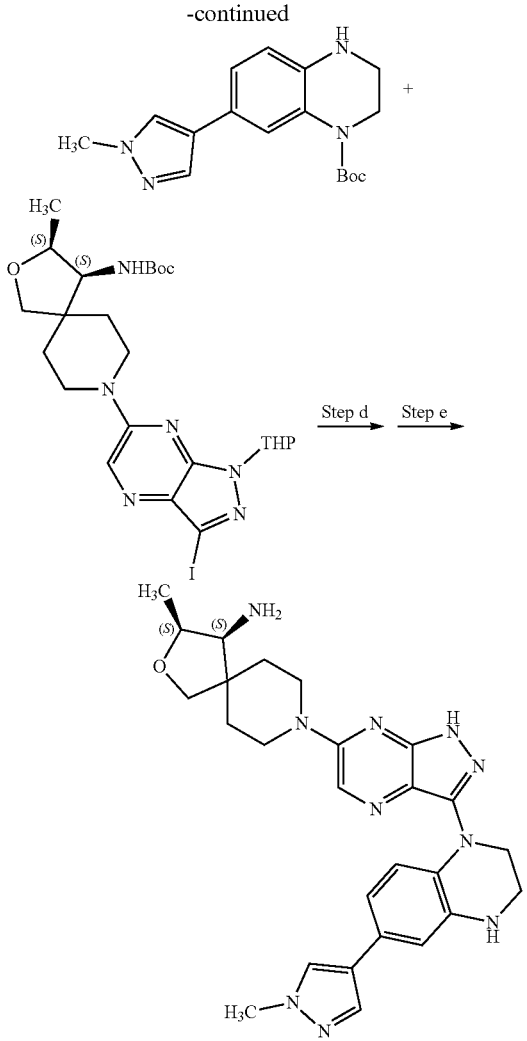

Step a: To the mixture of 1,2,3,4-tetrahydroquinoxaline (500 mg, 3.72 mmol) in THF (8 mL) and H₂O (2 mL) was added NaOH (0.3 g, 7.44 mmol) and Boc₂O (770 mg, 3.53 mmol). The mixture was stirred at 20° C. for 12 hrs then concentrated under reduced pressure, diluted with H₂O (30 mL), and extracted with EtOAc (30 mL×3). The combined organics were washed with brine, dried over anhydrous Na₂SO₄, filtered, and concentrated under reduced pressure. Purification of the residue by flash silica gel chromatography (0-20% EtOAc/petroleum ether) gave tert-butyl 1,2,3,4-tetrahydroquinoxaline-1-carboxylate (500 mg, 2.13 mmol, 57% yield) as a yellow oil.

Step b: To tert-butyl 1,2,3,4-tetrahydroquinoxaline-1-carboxylate (450 mg, 1.92 mmol) in MCCN (15 mL) was added NBS (306 mg, 1.72 mmol) slowly under N₂ at 0° C. The mixture was stirred at 0° C. for 1 hr. Water (50 mL) was added and the mixture concentrated under reduced pressure. The concentrate was extracted with EtOAc (50 mL×3) and the combined organics dried over anhydrous Na₂SO₄, filtered, and concentrated under reduced pressure. The residue was purified by flash silica gel chromatography (0-50% EtOAc/petroleum ether) to give tert-butyl 7-bromo-1,2,3,4-tetrahydroquinoxaline-1-carboxylate (850 mg).

Step c: tert-Butyl 7-bromo-1,2,3,4-tetrahydroquinoxaline-1-carboxylate (750 mg, 2.39 mmol) and 1-methyl-4-(4,4,5,5-tetramethyl-1,3,2-dioxaborolan-2-yl)-1H-pyrazole (497 mg, 2.39 mmol) were taken up in dioxane (15 mL) and H₂O (3 mL). K₃PO₄ (1.52 g, 7.17 mmol) and Pd(dppf)Cl₂ (0.35 g, 478 µmol) were added under N₂ and the mixture was stirred at 100° C. under N₂ for 12 hrs. The mixture was concentrated under reduced pressure and purified by flash silica gel chromatography (0-10% MeOH/DCM) to give tert-butyl 7-(1-methyl-1H-pyrazol-4-yl)-1,2,3,4-tetrahydroquinoxaline-1-carboxylate (540 mg, 68% yield) as an off-white solid.

Step d: To a mixture of tert-butyl N-[(3S,4S)-8-[3-iodo-1-(oxan-2-yl)-1H-pyrazolo[3,4-b]pyrazin-6-yl]-3-methyl-2-oxa-8-azaspiro[4.5]decan-4-yl]carbamate (200 mg, 334 µmol) and tert-butyl 7-(1-methyl-1H-pyrazol-4-yl)-1,2,3,4-tetrahydroquinoxaline-1-carboxylate (125 mg, 400 µmol) in toluene (10 mL) was added Pd₂(dba)₃ (30.5 mg, 33.4 µmol), XantPhos (38.6 mg, 66.8 µmol), and t-BuONa (96.1 mg, 1.00 mmol) under N₂. The mixture was stirred at 100° C. under N₂ for 12 hrs. After cooling, the mixture was concentrated under reduced pressure and purified by flash silica gel chromatography (0-10% MeOH/DCM) to give tert-butyl 4-{6-[(3S,4S)-4-{[(tert-butoxy)carbonyl]amino}-3-methyl-2-oxa-8-azaspiro[4.5]decan-8-yl]-1-(oxan-2-yl)-1H-pyrazolo[3,4-h]pyrazin-3-yl}-7-(1-methyl-1H-pyrazol-4-yl)-1,2,3,4-tetrahydroquinoxaline-1-carboxylate (200 mg, 76% yield) as a yellow solid.

Step e: To tert-butyl 4-{6-[(3S,4S)-4-amino-3-methyl-2-oxa-8-azaspiro[4.5]decan-8-yl]-1-(oxan-2-yl)-1H-pyrazolo[3,4-b]pyrazin-3-yl}-7-(1-methyl-1H-pyrazol-4-yl)-1,2,3,4-tetrahydroquinoxaline-1-carboxylate (200 mg, 292 µmol) in MeOH (5 mL) was added 4N HCl/MeOH (5 mL). The mixture was stirred at 20° C. for 12 hrs, concentrated under reduced pressure, and purified by prep-HPLC (acetonitrile/aq. HCl) to give (3S,4S)-3-methyl-8-{3-[6-(1-methyl-1H-pyrazol-4-yl)-1,2,3,4-tetrahydroquinoxalin-1-yl]-1H-pyrazolo[3,4-b]pyrazin-6-yl}-2-oxa-8-azaspiro[4.5]decan-4-amine dihydrochloride (75 mg, 45% yield) as a tan solid: ESMS [M+H]+=501.1; ¹H-NMR (400 MHz, CD₃OD) δ 8.35 (s, 1H), 8.10 (s, 1H), 7.98 (s, 1H), 7.48-7.42 (m, 2H), 7.27 (d, J=8.8 Hz, 1H), 4.51-4.27 (m, 5H), 4.05-3.91 (m, 5H), 3.84-3.82 (m, 2H), 3.48 (d, J=4.4 Hz, 1H), 3.27-3.27 (m, 2H), 1.94-1.76 (m, 4H), 1.35 (d, J=6.4 Hz, 3H).

Synthesis of (3S,4S)-3-methyl-8-{3-[6-(5-methyl-1,2,4-oxadiazol-3-yl)-1,2,3,4-tetrahydro-1,5-naphthyridin-1-yl]-1H-pyrazolo[3,4-b]pyrazin-6-yl}-2-oxa-8-azaspiro[4.5]decan-4-amine; Formic Acid, Compound 319

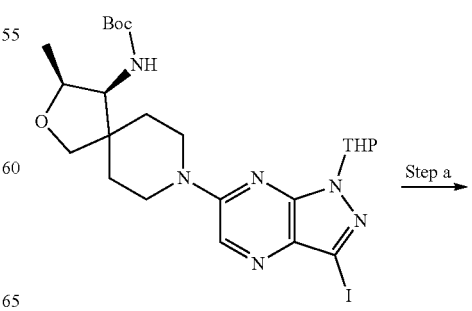

-continued

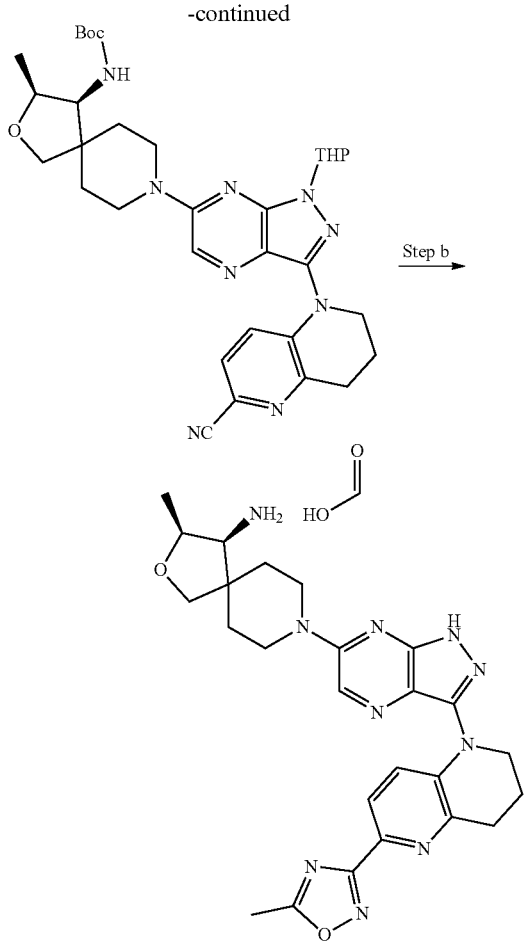

Step a: Methyl 1,2,3,4-tetrahydroquinoline-6-carboxylate (79.8 mg, 0.4177 mmol), tert-butyl N-[(3S,4S)-8-[3-iodo-1-(oxan-2-yl)-1H-pyrazolo[3,4-b]pyrazin-6-yl]-3-methyl-2-oxa-8-azaspiro[4.5]decan-4-yl]carbamate (250 mg, 0.4177 mmol), tris((1E,4E)-1,5-diphenylpenta-1,4-dien-3-one)dipalladium (38.2 mg, 0.04177 mmol), [5-(diphenylphosphanyl)-9,9-dimethyl-9H-xanthen-4-yl]diphenylphosphane (24.1 mg, 0.04177 mmol) and sodium 2-methylpropan-2-olate (60.2 mg, 0.6265 mmol) were combined in a vial and dissolved in toluene (5 mL). Evacuated and backfilled with $N_2$ (3×). Heated at 80 C for 3 h. Cooled, partitioned between EtOAc and water. Separated layers, washed aqueous layer with EtOAc (2×). Combined org layers, washed with brine, dried over $Na_2SO_4$, filtered and concentrated. Purified by flash silica gel chromatography using ethyl acetate in heptanes (0-100%) to give tert-butyl N-[(3S,4S)-8-[3-(6-cyano-1,2,3,4-tetrahydro-1,5-naphthyridin-1-yl)-1-(oxan-2-yl)-1H-pyrazolo[3,4-b]pyrazin-6-yl]-3-methyl-2-oxa-8-azaspiro[4.5]decan-4-yl]carbamate (177 mg, 0.2810 mmol) as a brown solid.

Step b: To a solution of tert-butyl N-[(3S,4S)-8-[3-(6-cyano-1,2,3,4-tetrahydro-1,5-naphthyridin-1-yl)-1-(oxan-2-yl)-1H-pyrazolo[3,4-b]pyrazin-6-yl]-3-methyl-2-oxa-8-azaspiro[4.5]decan-4-yl]carbamate (115 mg, 0.1826 mmol) in EtOH (2 mL) was added hydroxylamine (44.7 µL, 0.7304 mmol). Heated at 50 C for 30 min. Concentrated. Dissolved residue in 1,1,1-triethoxyethane (835 µL, 4.56 mmol). Added 3 drops of TFA. Stirred at 60 C for 90 min. Concentrated. Purified by flash silica gel chromatography using EtOAc in heptanes (0-100%). Combined fractions, concentrated, and redissolved in MeOH (2 mL). Added conc. HCl (200 uL). Stirred at 50 C for 1 h. Concentrated, chased with toluene (2×). Purified by HPLC using 5-30% acetonitrile in water w/0.1% formic acid to give (3S,4S)-3-methyl-8-(3-[6-(5-methyl-1,2,4-oxadiazol-3-yl)-1,2,3,4-tetrahydro-1,5-naphthyridin-1-yl]-1H-pyrazolo[3,4-b]pyrazin-6-yl)-2-oxa-8-azaspiro[4.5]decan-4-amine; formic acid (35.0 mg, 0.06379 mmol) Synthesis of (3S,4S)-8-(3-[6-(5-ethyl-1,2,4-oxadiazol-3-yl)-1,2,3,4-tetrahydro-1,5-naphthyridin-1-yl]-1H-pyrazolo[3,4-b]pyrazin-6-yl)-3-methyl-2-oxa-8-azaspiro[4.5]decan-4-amine; formic acid, Compound 320

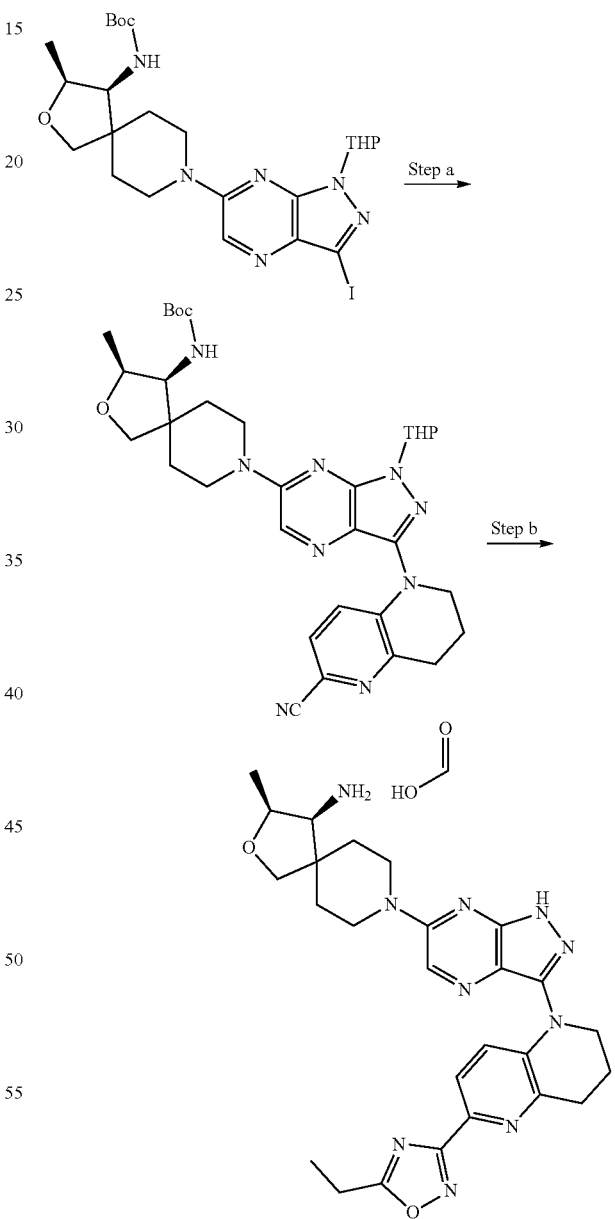

Step a: Prepared as described for Compound 319.
Step b: To a solution of tert-butyl N-[(3S,4S)-8-[3-(6-cyano-1,2,3,4-tetrahydro-1,5-naphthyridin-1-yl)-1-(oxan-2-yl)-1H-pyrazolo[3,4-b]pyrazin-6-yl]-3-methyl-2-oxa-8-azaspiro[4.5]decan-4-yl]carbamate (88 mg, 0.1397 mmol) in EtOH (2 mL) was added hydroxylamine (34.1 µL, 0.5588 mmol). Heated at 50 C for 30 min. Concentrated and dissolved residue in 1,1,1-trimethoxypropane (528 µL, 3.49 mmol) and EtOH (1 mL). Added 3 drops of TFA. Stirred at 60 C for 3 h. Concentrated. Purified by flash silica gel chromatography using EtOAc in heptanes (0-100%). Combined fractions, concentrated, and dissolved in MeOH (2 mL). Added conc. HCl (200 uL). Stirred at 50 C for 1 h. Concentrated, chased with toluene (2×), and purified by HPLC using 5-30% acetonitrile in water w/0.1% formic acid to give (3S,4S)-8-{3-[6-(5-ethyl-1,2,4-oxadiazol-3-yl)-1,2,3,4-tetrahydro-1,5-naphthyridin-1-yl]-1H-pyrazolo[3,4-b]pyrazin-6-yl}-3-methyl-2-oxa-8-azaspiro[4.5]decan-4-amine; formic acid (23.0 mg, 0.04087 mmol)

Synthesis of (3S,4S)-3-methyl-8-(3-{6-[5-(propan-2-yl)-1,2,4-oxadiazol-3-yl]-1,2,3,4-tetrahydro-1,5-naphthyridin-1-yl}-1H-pyrazolo[3,4-b]pyrazin-6-yl)-2-oxa-8-azaspiro[4.5]decan-4-amine; formic acid, Compound 321

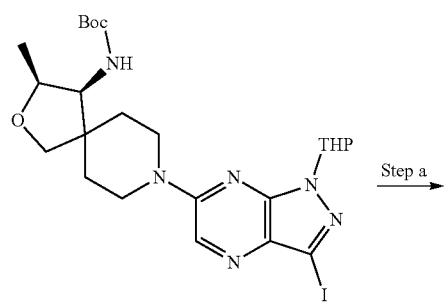

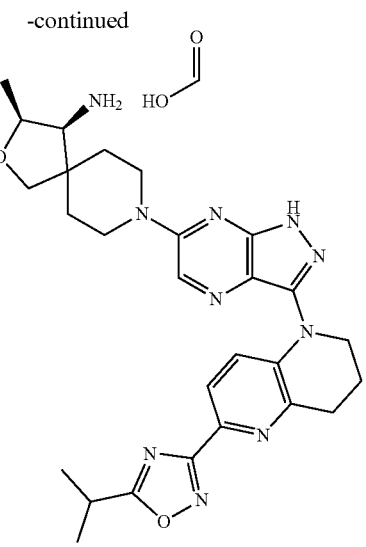

Step a: Prepared as described for Compound 319.

Step b: To a solution of tert-butyl N-[(3S,4S)-8-[3-(6-cyano-1,2,3,4-tetrahydro-1,5-naphthyridin-1-yl)-1-(oxan-2-yl)-1H-pyrazolo[3,4-b]pyrazin-6-yl]-3-methyl-2-oxa-8-azaspiro[4.5]decan-4-yl]carbamate (115 mg, 0.1826 mmol) in EtOH (2 mL) was hydroxylamine (44.7 µL, 0.7304 mmol). Heated at 50 C for 2 h. Meanwhile, to a solution of 2-methylpropanoic acid (168 µL, 1.82 mmol) in THF (5 mL) was added 1-(1H-imidazole-1-carbonyl)-1H-imidazole (88.8 mg, 0.5478 mmol). Stirred at rt for 2 h. Combined this material with concentrated amide oxime. Added additional 2-methylpropionic acid (1 mL) and heated reaction mixture at 130 C overnight. Concentrated, purified by flash silica gel chromatography using EtOAc in heptanes (0-100%), combined fractions and concentrated. Redissolved in MeOH (3 mL). Added conc. HCl (300 uL). Stirred at 50 C for 2 h. Concentrated, chased with toluene (3×), and purified by HPLC using 10-40% acetonitrile in water w/0.1% formic acid to give (3S,4S)-3-methyl-8-(3-{6-[5-(propan-2-yl)-1,2,4-oxadiazol-3-yl]-1,2,3,4-tetrahydro-1,5-naphthyridin-1-yl}-1H-pyrazolo[3,4-b]pyrazin-6-yl)-2-oxa-8-azaspiro[4.5]decan-4-amine; formic acid (30.0 mg, 0.05202 mmol)

Synthesis of 1-{6-[(3S,4S)-4-amino-3-methyl-2-oxa-8-azaspiro[4.5]decan-8-yl]-1H-pyrazolo[3,4-b]pyrazin-3-yl}-N-methyl-1,2,3,4-tetrahydroquinoxaline-6-carboxamide, Compound 329

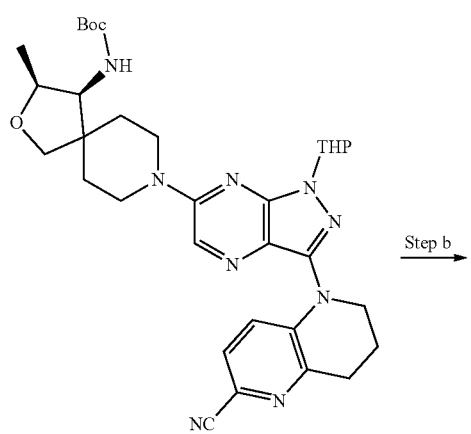

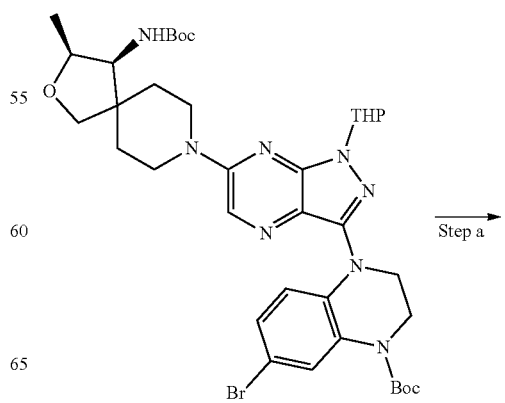

399

-continued

400

-continued

Step a: To a solution of tert-butyl 7-bromo-4-{6-[(3S,4S)-4-{[(tert-butoxy)carbonyl]amino}-3-methyl-2-oxa-8-azaspiro[4.5]decan-8-yl]-1-(oxan-2-yl)-1H-pyrazolo[3,4-b]pyrazin-3-yl}-1,2,3,4-tetrahydroquinoxaline-1-carboxylate (250.0 mg, 318.0 µmol, synthesized as described in Step a of Compound 281 with tert-butyl 7-bromo-1,2,3,4-tetrahydroquinoxaline-1-carboxylate as the coupling partner) in MeOH (10.0 mL) was added TEA (64.2 mg, 636.0 µmol) and Pd(dppf)Cl$_2$ (46.4 mg, 63.6 µmol). The mixture was evacuated and refilled 3 times using CO and then was stirred under CO (50 psi.) for 5 days. The reaction mixture was concentrated under reduced pressure. The residue was purified by column chromatography (Petroleum ether/Ethyl acetate=100:0 to 100:100 and DCM/MeOH=100:0 to 100:10) to give 1-tert-butyl 7-methyl 4-{6-[(3S,4S)-4-{[(tert-butoxy)carbonyl]amino}-3-methyl-2-oxa-8-azaspiro[4.5]decan-8-yl]-1-(oxan-2-yl)-1H-pyrazolo[3,4-b]pyrazin-3-yl}-1,2,3,4-tetrahydroquinoxaline-1,7-dicarboxylate (150.0 mg, 196.0 µmol, 61.9% yield) as a yellow solid.

Step b: A solution of 1-tert-butyl 7-methyl 4-{6-[(3S,4S)-4-{[(tert-butoxy)carbonyl]amino}-3-methyl-2-oxa-8-azaspiro[4.5]decan-8-yl]-1-(oxan-2-yl)-1H-pyrazolo[3,4-b]pyrazin-3-yl}-1,2,3,4-tetrahydroquinoxaline-1,7-dicarboxylate (150.0 mg, 196.0 µmol) and NaOH (46.8 mg, 1.17 mmol) in MeOH (5.0 mL) was stirred at 10° C. for 12 hours, then stirred at 50° C. for another 12 hours. The reaction mixture was then adjusted to pH=6-7 with AcOH and concentrated under reduced pressure to give the residue. The residue was diluted with water (10.0 mL) and extracted with EtOAc (10.0 mL×2). The combined organic layers were dried over anhydrous Na$_2$SO$_4$, filtered and concentrated under reduced pressure to give 4-[(tert-butoxy)carbonyl]-1-{6-[(3S,4S)-4-{[(tert-butoxy)carbonyl]amino}-3-methyl-2-oxa-8-azaspiro[4.5]decan-8-yl]-1-(oxan-2-yl)-1H-pyrazolo[3,4-b]pyrazin-3-yl}-1,2,3,4-tetrahydroquinoxaline-6-carboxylic acid (150.0 mg, crude), which was used for the next step directly.

Step c: To a solution of 4-[(tert-butoxy)carbonyl]-1-{6-[(3S,4S)-4-{[(tert-butoxy)carbonyl]amino}-3-methyl-2-oxa-8-azaspiro[4.5]decan-8-yl]-1-(oxan-2-yl)-1H-pyrazolo[3,4-b]pyrazin-3-yl}-1,2,3,4-tetrahydroquinoxaline-6-carboxylic acid (150.0 mg, 200.0 µmol), HATU (152.0 mg, 400.0 µmol) and TEA (55.3 µL, 400.0 µmol) in DMF (5.0 mL) was added MeNH$_2$.HCl (20.2 mg, 300.0 µmol). The reaction mixture was stirred at 10° C. for 1 hour. The reaction mixture was concentrated under reduced pressure to remove solvent. The residue was purified by column chromatography (Petroleum ether/Ethyl acetate=100:0 to 100:80) to give tert-butyl 4-{6-[(3S,4S)-4-{[(tert-butoxy)carbonyl]amino}-3-methyl-2-oxa-8-azaspiro[4.5]decan-8-yl]-1-(oxan-2-yl)-1H-pyrazolo[3,4-b]pyrazin-3-yl}-7-(methylcarbamoyl)-1,2,3,4-tetrahydroquinoxaline-1-carboxylate (200.0 mg) as a yellow solid.

Step d: A solution of tert-butyl 4-{6-[(3S,4S)-4-{[(tert-butoxy)carbonyl]amino}-3-methyl-2-oxa-8-azaspiro[4.5]decan-8-yl]-1-(oxan-2-yl)-1H-pyrazolo[3,4-b]pyrazin-3-yl}-7-(methylcarbamoyl)-1,2,3,4-tetrahydroquinoxaline-1-carboxylate (200.0 mg, 262.0 μmol) in HCl/MeOH (5.0 mL, 4 M) was stirred at 10° C. for 1 hour. The reaction mixture was concentrated under reduced pressure. Then the residue was diluted with MeOH (5.0 mL) and was purified by prep-HPLC (HCl). The product 1-{6-[(3S,4S)-4-amino-3-methyl-2-oxa-8-azaspiro[4.5]decan-8-yl]-1H-pyrazolo[3,4-b]pyrazin-3-yl}-N-methyl-1,2,3,4-tetrahydroquinoxaline-6-carboxamide hydrochloride (55.0 mg, 106.0 μmol, 41.0% yield) was obtained as a yellow solid.

Synthesis of (3S,4S)-8-(3-{6-[1-(2-methoxyethyl)-1H-pyrazol-4-yl]-1,2,3,4-tetrahydro-1,5-naphthyridin-1-yl}-1H-pyrazolo[3,4-b]pyrazin-6-yl)-3-methyl-2-oxa-8-azaspiro[4.5]decan-4-amine, Compound 333

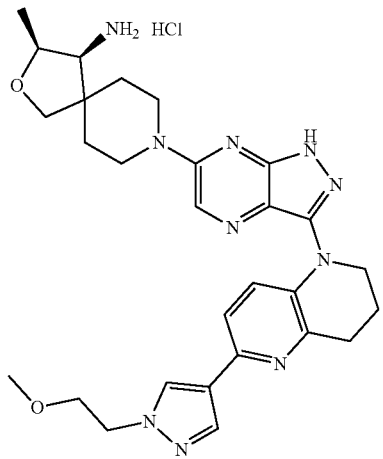

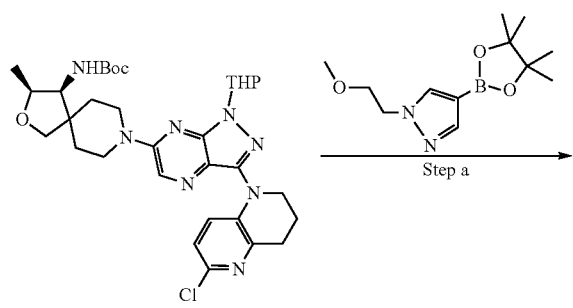

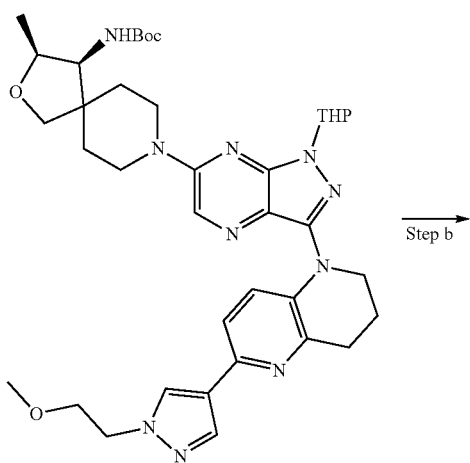

Step a: A mixture of tert-butyl N-[(3S,4S)-8-[3-(6-chloro-1,2,3,4-tetrahydro-1,5-naphthyridin-1-yl)-1-(oxan-2-yl)-1H-pyrazolo[3,4-b]pyrazin-6-yl]-3-methyl-2-oxa-8-azaspiro[4.5]decan-4-yl]carbamate (100 mg, 0.16 mmol, synthesized as described for Compound 281 using 6-chloro-1,2,3,4-tetrahydro-1,5-naphthyridine as the coupling partner in Step a), Pd(dppf)Cl$_2$ (22.8 mg, 0.03 mmol), K$_2$CO$_3$ (53.8 mg, 0.39 mmol) and 1-(2-methoxyethyl)-4-(4,4,5,5-tetramethyl-1,3,2-dioxaborolan-2-yl)-1H-pyrazole (58.9 mg, 0.23 mmol, CAS #847818-71-7) in dioxane (5 mL) and H$_2$O (0.5 mL) was evacuated and refilled 3 times using N$_2$ and stirred at 90° C. for 12 hours under N$_2$ atmosphere. The reaction mixture was concentrated to give a residue which was purified by flash silica gel chromatography (DCM:MeOH=100:0 to 100:10) to give tert-butyl N-[(3S,4S)-8-(3-{6-[1-(2-methoxyethyl)-1H-pyrazol-4-yl]-1,2,3,4-tetrahydro-1,5-naphthyridin-1-yl}-1-(oxan-2-yl)-1H-pyrazolo[3,4-b]pyrazin-6-yl)-3-methyl-2-oxa-8-azaspiro[4.5]decan-4-yl]carbamate (100 mg, 88% yield) as a yellow oil.

Step b: To the compound of tert-butyl N-[(3S,4S)-8-(3-{6-[1-(2-methoxyethyl)-1H-pyrazol-4-yl]-1,2,3,4-tetrahydro-1,5-naphthyridin-1-yl}-1-(oxan-2-yl)-1H-pyrazolo[3,4-b]pyrazin-6-yl)-3-methyl-2-oxa-8-azaspiro[4.5]decan-4-yl]carbamate (100 mg, 0.14 mmol) was added 2 N HCl/MeOH (4 mL). The mixture was stirred at 25° C. for 12 h. The reaction mixture was concentrated and purified by prep-HPLC (HCl) to afford the product of (3S,4S)-8-(3-{6-[1-(2-methoxyethyl)-1H-pyrazol-4-yl]-1,2,3,4-tetrahydro-1,5-naphthyridin-1-yl}-1H-pyrazolo[3,4-b]pyrazin-6-yl)-3-methyl-2-oxa-8-azaspiro[4.5]decan-4-amine hydrochloride (49.1 mg, 61.6% yield) as an orange solid.

Synthesis of (3S,4S)-8-{3-[6-(1-ethyl-1H-pyrazol-4-yl)-1,2,3,4-tetrahydro-1,5-naphthyridin-1-yl]-1H-pyrazolo[3,4-b]pyrazin-6-yl}-3-methyl-2-oxa-8-azaspiro[4.5]decan-4-amine, Compound 334

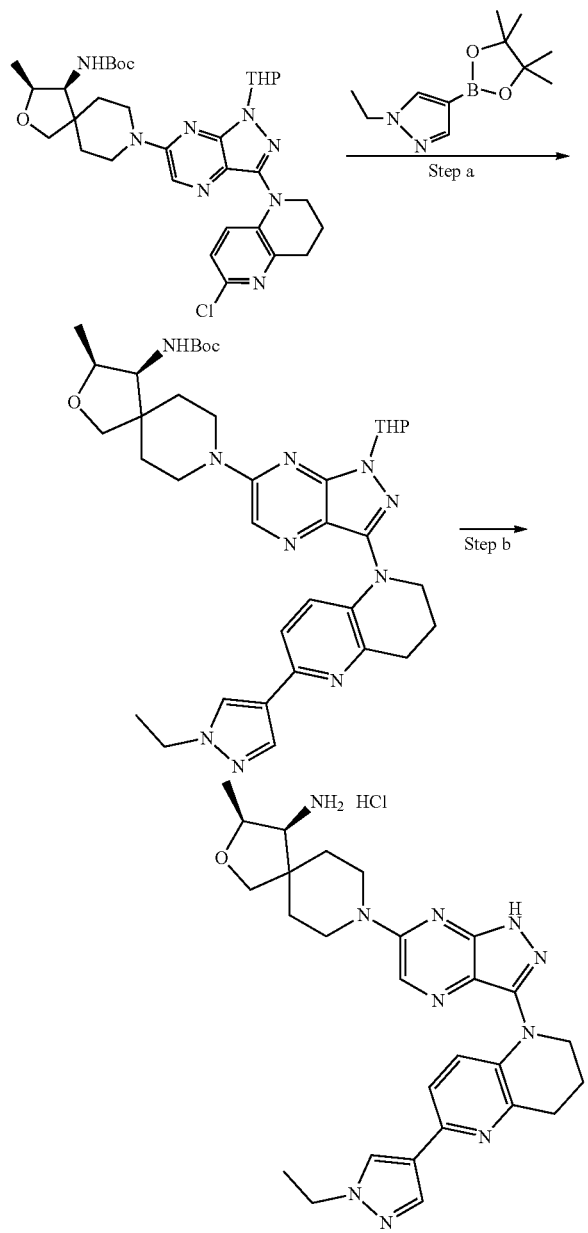

Step a: A mixture of tert-butyl N-[(3S,4S)-8-[3-(6-chloro-1,2,3,4-tetrahydro-1,5-naphthyridin-1-yl)-1-(oxan-2-yl)-1H-pyrazolo[3,4-b]pyrazin-6-yl]-3-methyl-2-oxa-8-azaspiro[4.5]decan-4-yl]carbamate (100 mg, 0.16 mmol, synthesized as described for Compound 281 using 6-chloro-1,2,3,4-tetrahydro-1,5-naphthyridine as the coupling partner in Step a), K₂CO₃ (54 mg, 0.39 mmol), Pd(dppf)Cl₂ (23 mg, 0.03 mmol) and 1-ethyl-4-(4,4,5,5-tetramethyl-1,3,2-dioxaborolan-2-yl)-1H-pyrazole (52 mg, 0.23 mmol, CAS #847818-70-6) in dioxane (5 mL) and H₂O (0.5 mL) was evacuated and refilled 3 times using N₂, then stirred at 90° C. for 12 hours under N₂ atmosphere. The reaction mixture was concentrated to give a residue which was purified by flash silica gel chromatography (DCM: MeOH=100:0 to 100:10) to give tert-butyl N-[(3S,4S)-8-{3-[6-(1-ethyl-1H-pyrazol-4-yl)-1,2,3,4-tetrahydro-1,5-naphthyridin-1-yl]-1-(oxan-2-yl)-1H-pyrazolo[3,4-b]pyrazin-6-yl}-3-methyl-2-oxa-8-azaspiro[4.5]decan-4-yl]carbamate (70.0 mg, 64.2% yield) as a yellow oil Step b: The compound of tert-butyl N-[(3S,4S)-8-{3-[6-(1-ethyl-1H-pyrazol-4-yl)-1,2,3,4-tetrahydro-1,5-naphthyridin-1-yl]-1-(oxan-2-yl)-1H-pyrazolo[3,4-b]pyrazin-6-yl}-3-methyl-2-oxa-8-azaspiro[4.5]decan-4-yl]carbamate (70 mg, 0.1 mmol) was added in 2 N HCl/MeOH (4 mL). The mixture was stirred at 25° C. for 12 h. The mixture was concentrated to give a residue which was purified by prep-HPLC(HCl) to give (3S,4S)-8-{3-[6-(1-ethyl-1H-pyrazol-4-yl)-1,2,3,4-tetrahydro-1,5-naphthyridin-1-yl]-1H-pyrazolo[3,4-b]pyrazin-6-yl}-3-methyl-2-oxa-8-azaspiro[4.5]decan-4-amine hydrochloride (49.7 mg, HCl salt, 90.1% yield) as an orange solid.

Synthesis of 1-{6-[(3S,4S)-4-amino-3-methyl-2-oxa-8-azaspiro[4.5]decan-8-yl]-1H-pyrazolo[3,4-b]pyrazin-3-yl)-1,2,3,4-tetrahydro-1,6-naphthyridine-5-carboxamide, Compound 335

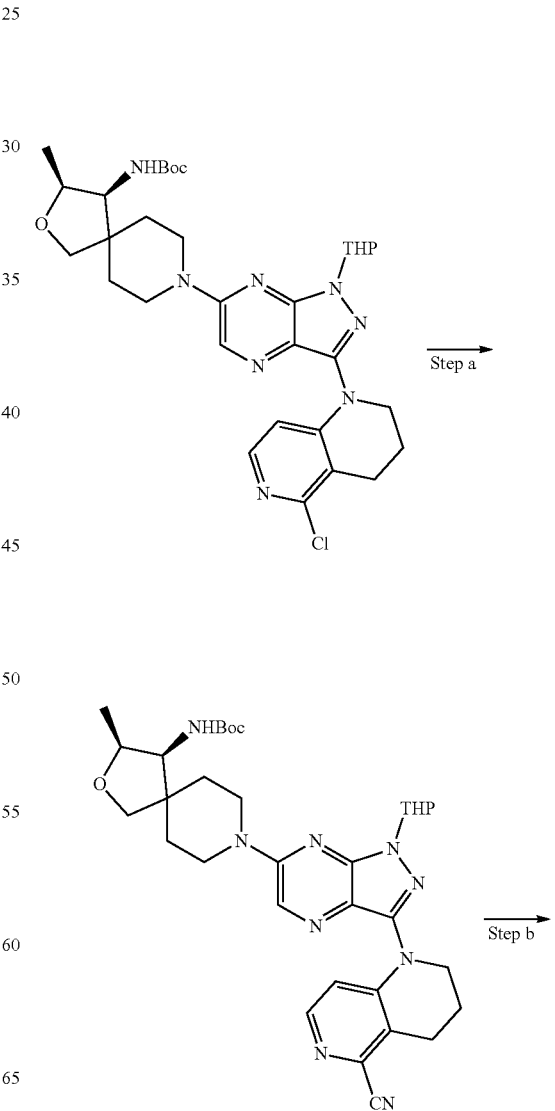

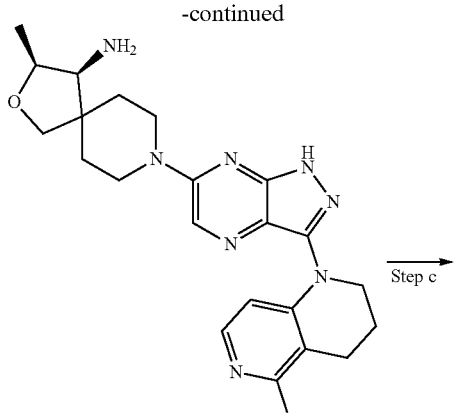

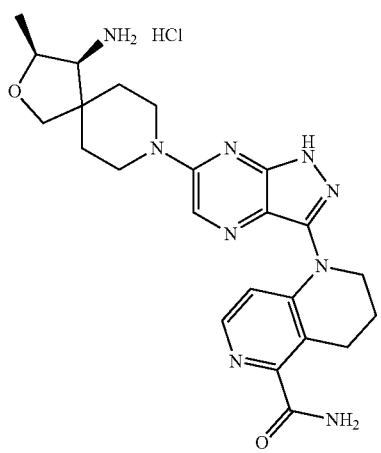

Step a: A solution of tert-butyl N-[(3S,4S)-8-[3-(5-chloro-1,2,3,4-tetrahydro-1,6-naphthyridin-1l-yl)-1-(oxan-2-yl)-1H-pyrazolo[3,4-b]pyrazin-6-yl]-3-methyl-2-oxa-8-azaspiro[4.5]decan-4-yl]carbamate (160.0 mg, 250.0 μmol, synthesized as described for Step a of Compound 281 with 5-chloro-1,2,3,4-tetrahydro-1,6-naphthyridine as the coupling partner), Zn(CN)$_2$ (73.3 mg, 625.0 μmol), Pd$_2$(dba)$_3$ (68.6 mg, 75.0 umol), dppf (8.32 mg, 15.0 umol) and Zn (3.90 mg, 60.0 umol) in DMF (5.0 mL) was stirred at 120° C. for 12 h under N$_2$. The solution was added into H$_2$O (20.0 mL) and then extracted with EtOAc (20.0 mL×2). The combined organic layers were washed with saturated NaCl (20.0 mL), dried over anhydrous Na$_2$SO$_4$, filtered and concentrated in vacuo to give crude product as brown gum. The residue was purified by flash silica gel chromatography (12 g, Ethyl acetate in Petroleum ether from 0% to 80%) to give tert-butyl N-[(3S,4S)-8-[3-(5-cyano-1,2,3,4-tetrahydro-1,6-naphthyridin-1-yl)-1-(oxan-2-yl)-1H-pyrazolo[3,4-b]pyrazin-6-yl]-3-methyl-2-oxa-8-azaspiro[4.5]decan-4-yl]carbamate (140.0 mg, 89.1% yield) as an orange oil.

Step b: A solution of tert-butyl N-[(3S,4S)-8-[3-(5-cyano-1,2,3,4-tetrahydro-1,6-naphthyridin-1-yl)-1-(oxan-2-yl)-1H-pyrazolo[3,4-b]pyrazin-6-yl]-3-methyl-2-oxa-8-azaspiro[4.5]decan-4-yl]carbamate (120.0 mg, 190.0 μmol) in 50% H$_2$SO$_4$ (10.0 mL) was stirred at 80° C. for 12 h. 1-(6-((3S,4S)-4-amino-3-methyl-2-oxa-8-azaspiro[4.5]decan-8-yl)-1H-pyrazolo[3,4-b]pyrazin-3-yl)-1,2,3,4-tetrahydro-1,6-naphthyridine-5-carbonitrile was isolated and brought on crude to the next step.

Step c: A solution of 1-(6-[(3S,4S)-4-amino-3-methyl-2-oxa-8-azaspiro[4.5]decan-8-yl]-1H-pyrazolo[3,4-b]pyrazin-3-yl)-1,2,3,4-tetrahydro-1,6-naphthyridine-5-carbonitrile (35.0 mg, 78.5 μmol) in conc. H$_2$SO$_4$ (5.0 mL) was stirred at 100° C. for 1 h. The mixture was added into ice-water (80.0 mL) dropwise. Then the mixture was adjusted to pH=9 with NaOH solid and extracted with EtOAc (100.0 mL×2). The combined organic layers were concentrated in vacuo to give crude product. The residue was purified by prep-HPLC (HCl) to give 1-{6-[(3S,4S)-4-amino-3-methyl-2-oxa-8-azaspiro[4.5]decan-8-yl]-1H-pyrazolo[3,4-b]pyrazin-3-yl}-1,2,3,4-tetrahydro-1,6-naphthyridine-5-carboxamide hydrochloride (2.30 mg, 4.60 μmol) as orange solid.

Synthesis of (1R)-7-[3-(1,2,3,4-tetrahydro-1,5-naphthyridin-1-yl)-1H-pyrazolo[3,4-b]pyrazin-6-yl]-7-azaspiro[3.5]nonan-1-amine, Compound 339

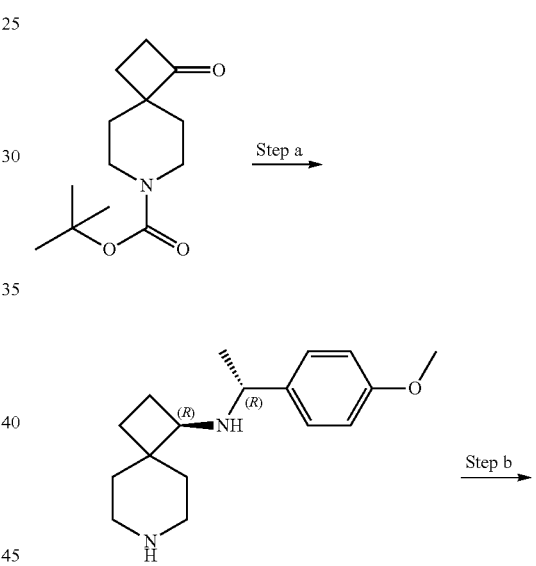

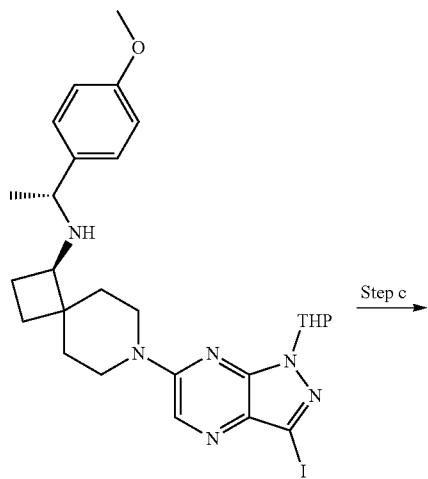

407
-continued

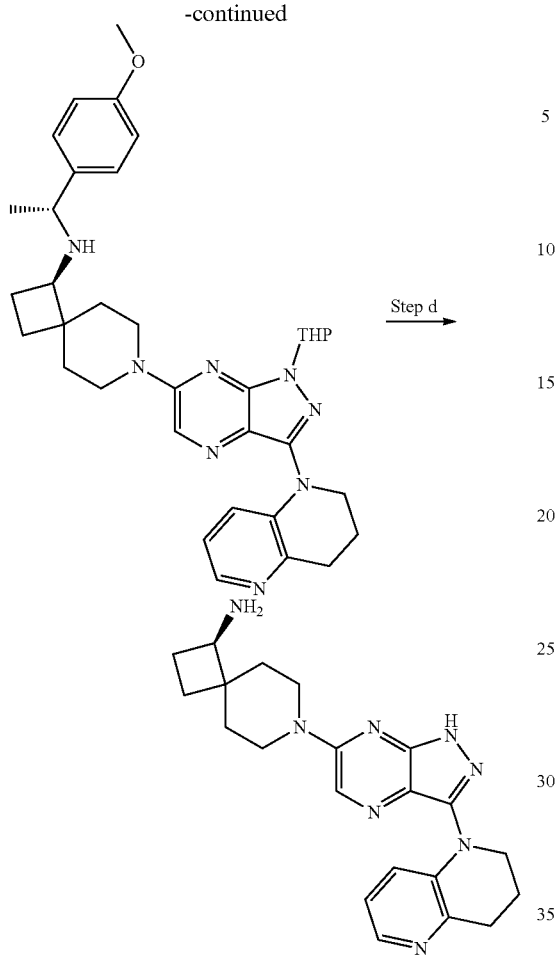

Step d

408

Step c and Step d: Conducted as described for Compound 33

Synthesis of (1S)-7-[3-(1,2,3,4-tetrahydro-1,5-naphthyridin-1-yl)-1H-pyrazolo[3,4-b]pyrazin-6-yl]-7-azaspiro[3.5]nonan-1-amine, Compound 340

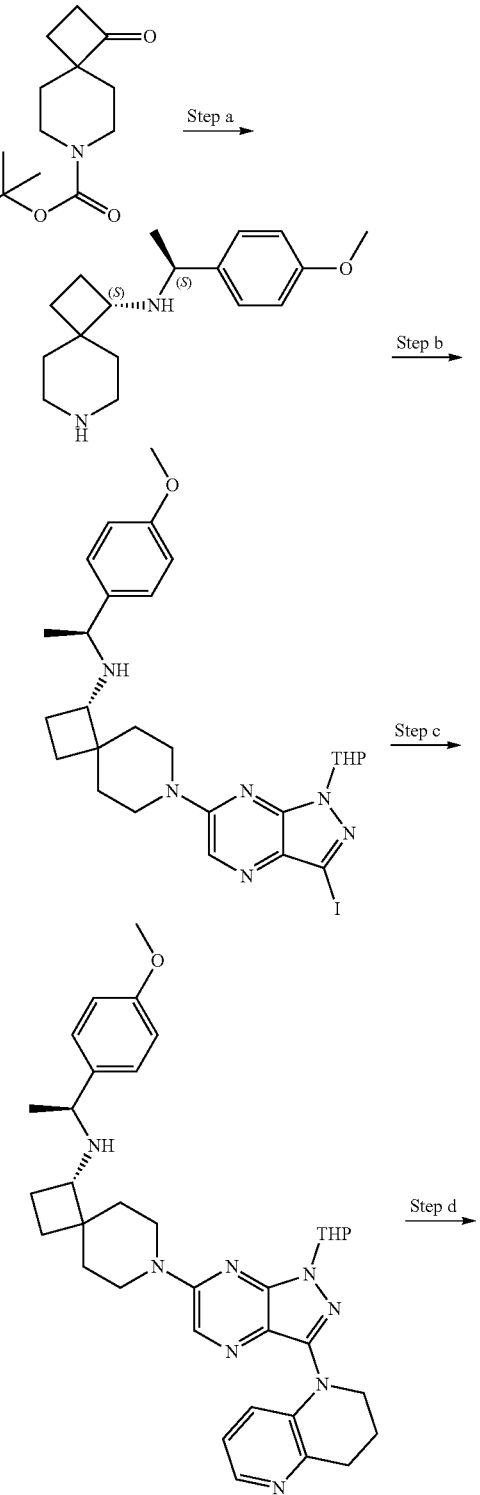

Step a: To a solution of tert-butyl 1-oxo-7-azaspiro[3.5]nonane-7-carboxylate (250 mg, 1.04 mmol, CAS #849203-60-7) and (1R)-1-(4-methoxyphenyl)ethan-1-amine (235 mg, 1.56 mmol) in DCE (10 mL) was added acetic acid (5.94 µL, 0.1040 mmol). After 1 h, added sodium cyanoborohydride (98.0 mg, 1.56 mmol). Stirred at rt for 1 h. Diluted with saturated aqueous sodium bicarbonate solution (5 mL) and extracted with EtOAc (3×10 mL). The combined organic phases were washed with brine and concentrated. Purified by flash silica gel chromatography using EtOAc/heptanes (0-50%) to give tert-butyl (1R)-1-{[(1R)-1-(4-methoxyphenyl)ethyl]amino}-7-azaspiro[3.5]nonane-7-carboxylate (227 mg, 0.6061 mmol). Redissolved material in DCM (5 mL). Added TFA (1 mL). Concentrated, chased with toluene (2×). Carried on to next step without further purification.

Step b: To a solution of 6-chloro-3-iodo-1-(oxan-2-yl)-1H-pyrazolo[3,4-b]pyrazine (168 mg, 0.4608 mmol) in DMF (5 mL) was added ethylbis(propan-2-yl)amine (802 µL, 4.60 mmol) followed by (1R)—N-[(1R)-1-(4-methoxyphenyl)ethyl]-7-azaspiro[3.5]nonan-1-amine (165 mg, 0.6012 mmol). Stirred at rt overnight. Partitioned between EtOAc and water. Extracted with EtOAc (3×). Combined organic layers, dried over Na$_2$SO$_4$, filtered and concentrated. Purified by flash silica gel chromatography using EtOAc in heptanes (0-100%) to give (1R)-7-[3-iodo-1-(oxan-2-yl)-1H-pyrazolo[3,4-b]pyrazin-6-yl]-N-[(1R)-1-(4-methoxyphenyl)ethyl]-7-azaspiro[3.5]nonan-1-amine (161 mg, 0.2672 mmol)

409

-continued

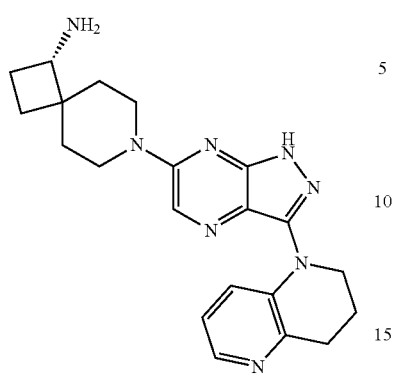

Step a: To a solution of tert-butyl 1-oxo-7-azaspiro[3.5]nonane-7-carboxylate (250 mg, 1.04 mmol, CAS #849203-60-7) and (1S)-1-(4-methoxyphenyl)ethan-1-amine (235 mg, 1.56 mmol) in DCE (5 mL) was added acetic acid (5.94 μL, 0.1040 mmol). Stirred at rt for 1 h. Diluted with saturated aqueous sodium bicarbonate solution (5 mL) and extracted with EtOAc (3×10 mL). The combined organic phases were washed with brine and concentrated. Purified by flash silica gel chromatography using EtOAc/heptanes (0-50 to give tert-butyl (1S)-1-{[(1S)-1-(4-methoxyphenyl)ethyl]amino}-7-azaspiro[3.5]nonane-7-carboxylate (177 mg, 0.4725 mmol).

Step b and step c: Conducted as described for Compound 33

Synthesis of N-(1-{6-[(3S,4S)-4-amino-3-methyl-2-oxa-8-azaspiro[4.5]decan-8-yl]-1H-pyrazolo[3,4-b]pyrazin-3-yl}-1,2,3,4-tetrahydroquinolin-5-yl)methanesulfonamide, Compound 343 and N-(1-{6-[(3S,4S)-4-amino-3-methyl-2-oxa-8-azaspiro[4.5]decan-8-yl]-1H-pyrazolo[3,4-b]pyrazin-3-yl}-1,2,3,4-tetrahydroquinolin-5-yl)-N-methanesulfonylmethanesulfonamide, Compound 344

410

-continued

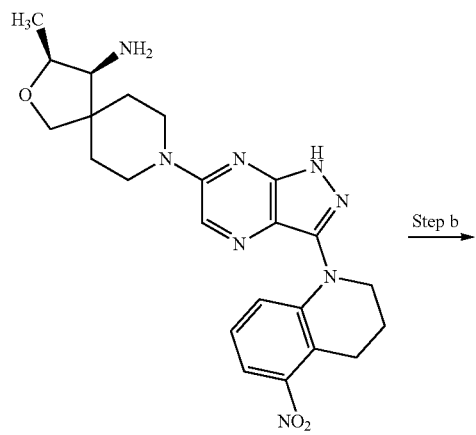

Step b

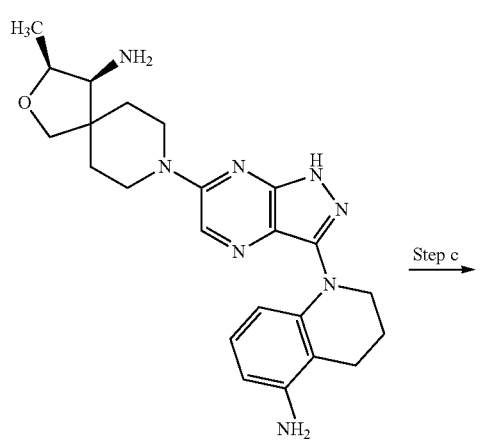

Step c

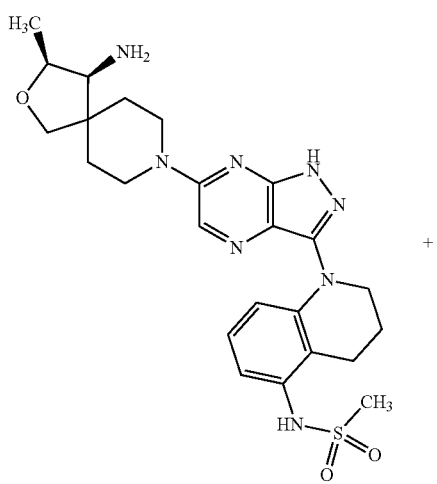

+

-continued

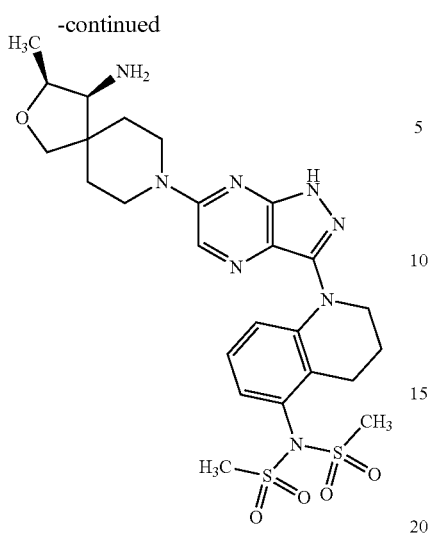

Synthesis of (8R)-5-{6-[(3S,4S)-4-amino-3-methyl-2-oxa-8-azaspiro[4.5]decan-8-yl]-1H-pyrazolo[3,4-b]pyrazin-3-yl}-N,N,8-trimethyl-5,6,7,8-tetrahydro-1,5-naphthyridine-2-carboxamide, Compound 347

Step a: tert-butyl N-[(3S,4S)-3-methyl-8-[3-(5-nitro-1,2,3,4-tetrahydroquinolin-1-yl)-1-(oxan-2-yl)-1H-pyrazolo[3,4-b]pyrazin-6-yl]-2-oxa-8-azaspiro[4.5]decan-4-yl]carbamate (74 mg) was prepared using tert-butyl N-[(3S,4S)-8-[3-iodo-1-(oxan-2-yl)-1H-pyrazolo[3,4-b]pyrazin-6-yl]-3-methyl-2-oxa-8-azaspiro[4.5]decan-4-yl]carbamate (200 mg, 0.3341 mmol), and 5-nitro-1,2,3,4-tetrahydroquinoline (59.5 mg, 0.3341 mmol) using conditions described for the preparation of Compound 33.

Step b: tert-butyl N-[(3S,4S)-3-methyl-8-[3-(5-nitro-1,2,3,4-tetrahydroquinolin-1-yl)-1-(oxan-2-yl)-1H-pyrazolo[3,4-b]pyrazin-6-yl]-2-oxa-8-azaspiro[4.5]decan-4-yl]carbamate (70 mg, 0.1078 mmol) was dissolved in EA and cycled through a 10% Pd/C cartridge at 1 mL/min, under 5 bars of hydrogen, at 30° C. for 1 hrs. The solution was concentrated and chased with DCM to afford tert-butyl N-[(3S,4S)-8-[3-(5-amino-1,2,3,4-tetrahydroquinolin-1-yl)-1-(oxan-2-yl)-1H-pyrazolo[3,4-b]pyrazin-6-yl]-3-methyl-2-oxa-8-azaspiro[4.5]decan-4-yl]carbamate (61 mg) as a yellow foam. LCMS: [M+H]$^+$ 619.7.

Step c: A resealable reaction vial was charged with tert-butyl N-[(3S,4S)-8-[3-(5-amino-1,2,3,4-tetrahydroquinolin-1-yl)-1-(oxan-2-yl)-1H-pyrazolo[3,4-b]pyrazin-6-yl]-3-methyl-2-oxa-8-azaspiro[4.5]decan-4-yl]carbamate (61 mg, 0.09858 mmol), DCM (5 mL), triethylamine (20.5 µL, 0.1478 mmol) and methanesulfonyl chloride (9.12 µL, 0.1182 mmol). The vial was sealed and the mixture was stirred at 25° C. for 1 hr. The mixture was charged with MeOH and quickly concentrated. The residue was taken up in MeOH (4 mL) and 4N HCl (1 mL) and heated to 60° C. for 15 min. Solvent was removed, the residue taken up in water (3 mL) and purified on preparative HPLC (5-30% ACN/water+0.1% FA) (2 inj). Two product were isolated separately to afford N-(1-{6-[(3S,4S)-4-amino-3-methyl-2-oxa-8-azaspiro[4.5]decan-8-yl]-1H-pyrazolo[3,4-b]pyrazin-3-yl}-1,2,3,4-tetrahydroquinolin-5-yl)methanesulfonamide (24 mg) as a yellow solid (LCMS: [M+H]$^+$ 513) and N-(1-{6-[(3S,4S)-4-amino-3-methyl-2-oxa-8-azaspiro[4.5]decan-8-yl]-1H-pyrazolo[3,4-b]pyrazin-3-yl}-1,2,3,4-tetrahydroquinolin-5-yl)-N-methanesulfonylmethanesulfonamide (15 mg) as a yellow solid (LCMS: [M+H]$^+$ 591).

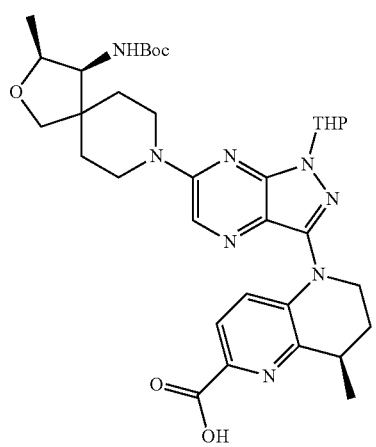

Step a

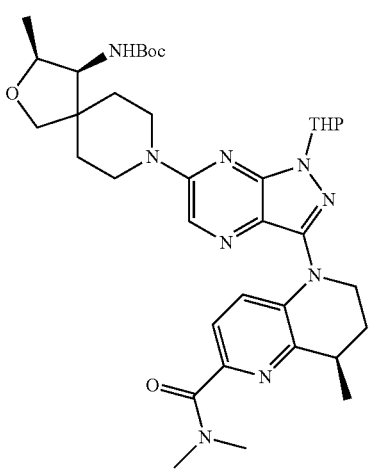 [SMILES: C[C@@H]1CCN(c2n[nH]c3nc(N4CCC5(CC4)CO[C@@H](C)[C@H]5N)cnc23)c2ccc(C(=O)N(C)C)nc21 ; Cl]

Step b

Step c

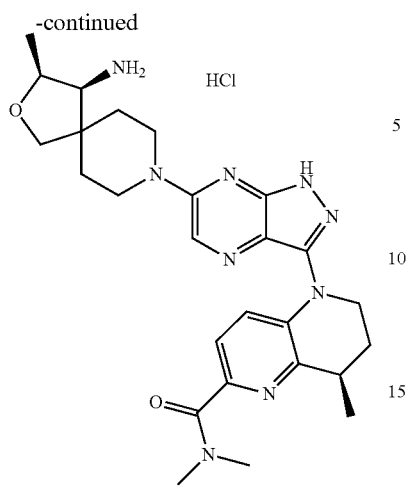

Step a: To a solution of methyl (8R)-5-{6-[(3S,4S)-4-{[(tert-butoxy)carbonyl]amino}-3-methyl-2-oxa-8-azaspiro[4.5]decan-8-yl]-1-(oxan-2-yl)-1H-pyrazolo[3,4-b]pyrazin-3-yl}-8-methyl-5,6,7,8-tetrahydro-1,5-naphthyridine-2-carboxylate (214.0 mg, 316.0 μmol, synthesized as described in Step a of Compound 281 with methyl (8R)-8-methyl-5,6,7,8-tetrahydro-1,5-naphthyridine-2-carboxylate, absolute stereochemistry arbitrarily assigned, as the coupling partner) in MeOH (10.0 mL) was added 3.0 N NaOH (5.0 mL, 15.0 mmol). The mixture was stirred at 50° C. for 3 hours. The mixture was concentrated to about 5 mL and diluted with water (50.0 mL), then extracted with EtOAc/Petroleum ether (2/3, 50.0 mL). The organic layer was washed with water (30.0 mL). The organic layer was discarded and the combined water layers were adjusted to pH=5-6 with 1 N HCl, then the aqueous was extracted with EtOAc (50.0 mL×2). The organic layers were dried over anhydrous Na₂SO₄, filtered and concentrated under reduced pressure to afford (8R)-5-{6-[(3S,4S)-4-{[(tert-butoxy)carbonyl]amino}-3-methyl-2-oxa-8-azaspiro[4.5]decan-8-yl]-1-(oxan-2-yl)-1H-pyrazolo[3,4-b]pyrazin-3-yl}-8-methyl-5,6,7,8-tetrahydro-1,5-naphthyridine-2-carboxylic acid (190.0 mg, 286.0 μmol, 90.9% yield) as a yellow solid.

Step b: The mixture of (8R)-5-{6-[(3S,4S)-4-{[(tert-butoxy)carbonyl]amino}-3-methyl-2-oxa-8-azaspiro[4.5]decan-8-yl]-1-(oxan-2-yl)-1H-pyrazolo[3,4-b]pyrazin-3-yl}-8-methyl-5,6,7,8-tetrahydro-1,5-naphthyridine-2-carboxylic acid (50.0 mg, 75.4 μmol), HATU (57.0 mg, 150.0 μmol) and TEA (52.1 μL, 377.0 μmol) in DMF (2.0 mL) was stirred at 15° C. for 10 mins. Then dimethylamine hydrochloride (12.2 mg, 150.0 μmol) was added and the mixture was stirred at 15° C. for 1 hour. The combined mixture was poured into saturated NH4Cl (50.0 mL) and extracted with EtOAc (50.0 mL×3). The combined organic layers were washed with brine (50.0 mL), dried over anhydrous Na₂SO₄ and concentrated under reduced pressure. The residue was purified by column chromatography (MeOH in EtOAc=0~10%) to afford tert-butyl N-[(3S,4S)-8-{3-[(4R)-6-(dimethylcarbamoyl)-4-methyl-1,2,3,4-tetrahydro-1,5-naphthyridin-1-yl]-1-(oxan-2-yl)-1H-pyrazolo[3,4-b]pyrazin-6-yl}-3-methyl-2-oxa-8-azaspiro[4.5]decan-4-yl]carbamate (90.0 mg, 130.0 μmol, combined batches) as a yellow solid.

Step c: To a solution of tert-butyl N-[(3S,4S)-8-{3-[(4R)-6-(dimethylcarbamoyl)-4-methyl-1,2,3,4-tetrahydro-1,5-naphthyridin-1-yl]-1-(oxan-2-yl)-1H-pyrazolo[3,4-b]pyrazin-6-yl}-3-methyl-2-oxa-8-azaspiro[4.5]decan-4-yl]carbamate (90.0 mg, 130.0 μmol) in DCM (3.0 mL) was added HCl/MeOH (2.0 mL, 4 M) and the mixture was stirred at 15° C. for 12 hours. The mixture was concentrated under reduced pressure and the residue was purified by prep-HPLC (HCl) to afford (8R)-5-{6-[(3S,4S)-4-amino-3-methyl-2-oxa-8-azaspiro[4.5]decan-8-yl]-1H-pyrazolo[3,4-h]pyrazin-3-yl}-N,N,8-trimethyl-5,6,7,8-tetrahydro-1,5-naphthyridine-2-carboxamide hydrochloride (28.5 mg, 52.5 μmol, 40.4% yield) as a yellow solid.

Synthesis of 2-[4-(5-{6-[(3S,4S)-4-amino-3-methyl-2-oxa-8-azaspiro[4.5]decan-8-yl]-1H-pyrazolo[3,4-b]pyrazin-3-yl}-5,6,7,8-tetrahydro-1,5-naphthyridin-2-yl)-1H-pyrazol-1-yl]ethan-1-ol, Compound 351

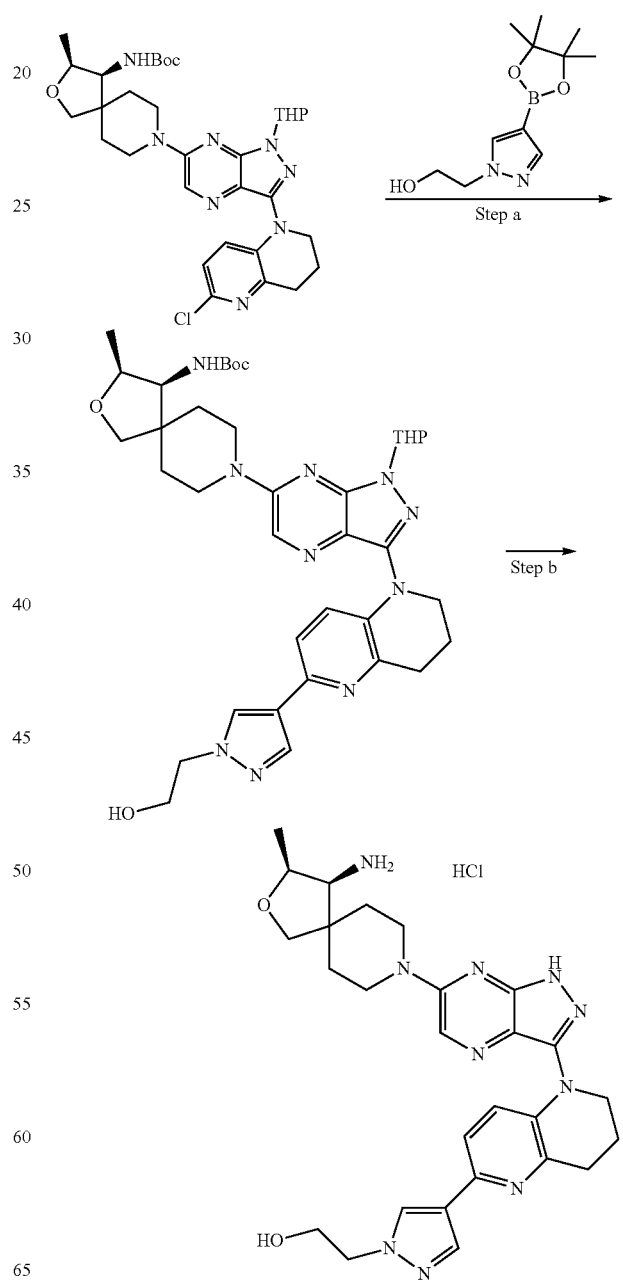

415

Step a: Tert-butyl N-[(3S,4S)-8-[3-(6-chloro-1,2,3,4-tetrahydro-1,5-naphthyridin-1-yl)-1-(oxan-2-yl)-1H-pyrazolo[3,4-b]pyrazin-6-yl]-3-methyl-2-oxa-8-azaspiro[4.5]decan-4-yl]carbamate (100.0 mg, 156.0 μmol, synthesized as described for Compound 281 using 6-chloro-1,2,3,4-tetrahydro-1,5-naphthyridine as the coupling partner in Step a), 2-[4-(4,4,5,5-tetramethyl-1,3,2-dioxaborolan-2-yl)-1H-pyrazol-1-yl]ethan-1-ol (37.1 mg, 156.0 μmol, CAS #1040377-08-9), Pd(dppf)Cl₂ (34.2 mg, 46.8 μmol) and K₂CO₃ (64.5 mg, 468.0 μmol) were added into the mixture of dioxane (10.0 mL) and H₂O (1.0 mL). The reaction mixture was evacuated and refilled 3 times with N₂ and stirred at 100° C. for 12 hours. The reaction mixture was concentrated under reduced pressure to give a residue and purified by flash silica gel chromatography (Petroleum ether: Ethyl acetate=100:30 to 0:100, DCM:MeOH=20:1) to afford tert-butyl N-[(3S,4S)-8-(3-{6-[1-(2-hydroxyethyl)-1H-pyrazol-4-yl]-1,2,3,4-tetrahydro-1,5-naphthyridin-1-yl}-1-(oxan-2-yl)-1H-pyrazolo[3,4-b]pyrazin-6-yl)-3-methyl-2-oxa-8-azaspiro[4.5]decan-4-yl]carbamate (110.0 mg, 86% purity, 85% yield) as a yellow solid.

Step b: Tert-butyl N-[(3S,4S)-8-(3-{6-[1-(2-hydroxyethyl)-1H-pyrazol-4-yl]-1,2,3,4-tetrahydro-1,5-naphthyridin-1-yl}-1-(oxan-2-yl)-1H-pyrazolo[3,4-b]pyrazin-6-yl)-3-methyl-2-oxa-8-azaspiro[4.5]decan-4-yl]carbamate (110.0 mg, 86.0% purity, 132.0 μmol) was added in 4.0 M HCl/MeOH (6.0 mL), the reaction mixture was stirred at 15° C. for 2 hours. The reaction mixture was concentrated under reduced pressure and purified by prep-HPLC (HCl) to afford 2-[4-(5-(6-[(3S,4S)-4-amino-3-methyl-2-oxa-8-azaspiro[4.5]decan-8-yl]-1H-pyrazolo[3,4-b]pyrazin-3-yl)-5,6,7,8-tetrahydro-1,5-naphthyridin-2-yl)-1H-pyrazol-1-yl]ethan-1-ol hydrochloride (20.2 mg, 27.0% yield) as a yellow solid.

Synthesis of (8S)-5-{6-[(3S,4S)-4-amino-3-methyl-2-oxa-8-azaspiro[4.5]decan-8-yl]-1H-pyrazolo[3,4-b]pyrazin-3-yl}-N,8-dimethyl-5,6,7,8-tetrahydro-1,5-naphthyridine-2-carboxamide, Compound 362, and (8R)-5-{6-[(3S,4S)-4-amino-3-methyl-2-oxa-8-azaspiro[4.5]decan-8-yl]-1H-pyrazolo[3,4-b]pyrazin-3-yl}-N,8-dimethyl-5,6,7,8-tetrahydro-1,5-naphthyridine-2-carboxamide, Compound 363

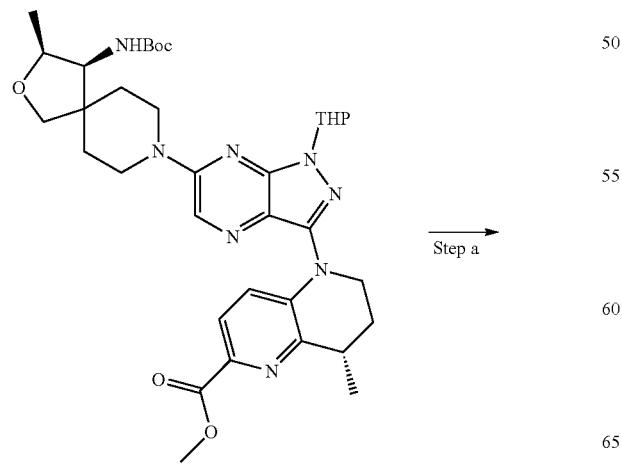

Step a →

416

-continued

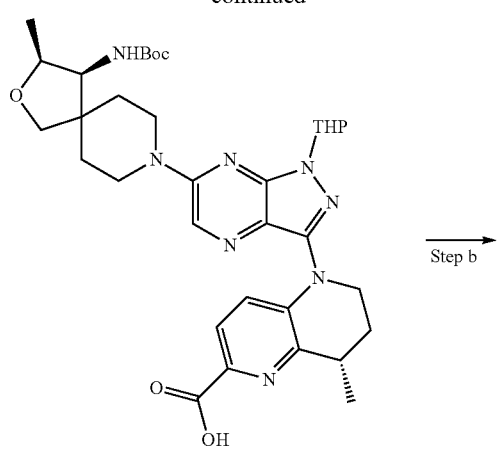

Step b →

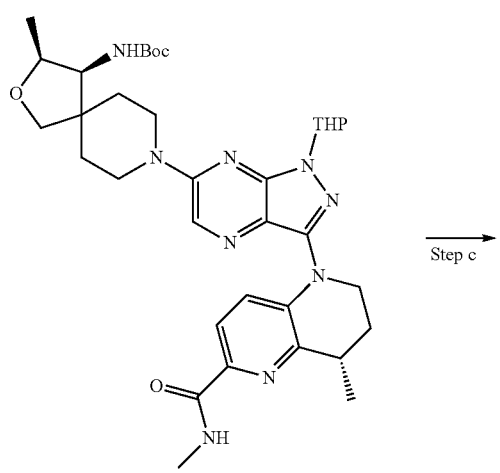

Step c →

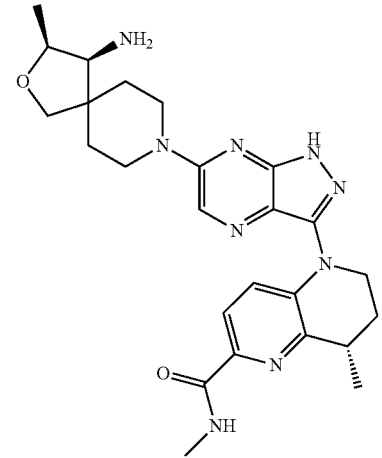

-continued

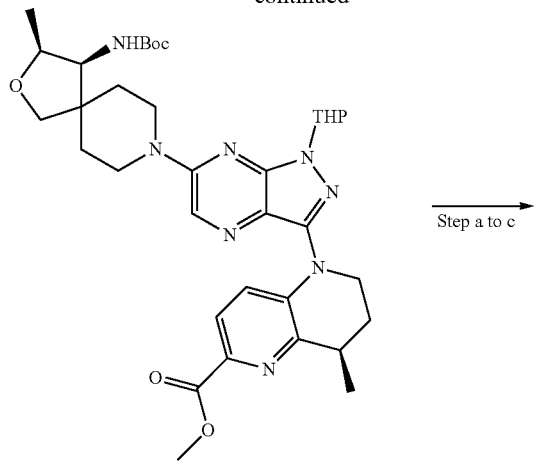

Step a to c →

Step a: To a solution of methyl (8S)-5-(6-[(3S,4S)-4-([(tert-butoxy)carbonyl]amino)-3-methyl-2-oxa-8-azaspiro[4.5]decan-8-yl]-1-(oxan-2-yl)-1H-pyrazolo[3,4-b]pyrazin-3-yl)-8-methyl-5,6,7,8-tetrahydro-1,5-naphthyridine-2-carboxylate (1.37 g, 2.02 mmol, synthesized as descrived for Step a of Compound 281 with methyl (8S)-8-methyl-5,6,7,8-tetrahydro-1,5-naphthyridine-2-carboxylate as the coupling partner) in MeOH (15.0 mL) and H₂O (4.0 mL) was added LiOH (241.0 mg, 10.1 mmol). Then the mixture was stirred at 45° C. for 12 hours. The reaction mixture was concentrated to about 8 mL and diluted in water (200.0 mL). The water layer was adjusted to pH=5-6 with 1N HCl then extracted with EtOAc (100.0 mL×3). The organic layers were dried over anhydrous Na₂SO₄, filtered and concentrated under reduced pressure to afford (8S)-5-{6-[(3S,4S)-4-{[(tert-butoxy)carbonyl]amino}-3-methyl-2-oxa-8-azaspiro[4.5]decan-8-yl]-1-(oxan-2-yl)-1H-pyrazolo[3,4-b]pyrazin-3-yl}-8-methyl-5,6,7,8-tetrahydro-1,5-naphthyridine-2-carboxylic acid (2.7 g, 91% purity) as a yellow solid.

Step b: The mixture of (8S)-5-{6-[(3S,4S)-4-{[(tert-butoxy)carbonyl]amino}-3-methyl-2-oxa-8-azaspiro[4.5]decan-8-yl]-1-(oxan-2-yl)-1H-pyrazolo[3,4-b]pyrazin-3-yl}-8-methyl-5,6,7,8-tetrahydro-1,5-naphthyridine-2-carboxylic acid (1.35 g, 1.84 mmol), HATU (1.04 g, 2.76 mmol) and TEA (1.01 mL, 7.36 mmol) in DCM (20.0 mL) was stirred at 15° C. for 10 min. Then MeNH₂.HCl (248.0 mg, 3.7 mmol) was added and the reaction was stirred at 15° C. for 12 hours. The reaction mixture was diluted with DCM (100.0 mL), and washed with H₂O (100.0 mL×3). The organic layer was dried over anhydrous Na₂SO₄, filtered and concentrated under reduced pressure to give a product of tert-butyl N-[(3S,4S)-3-methyl-8-{3-[(4S)-4-methyl-6-(methylcarbamoyl)-1,2,3,4-tetrahydro-1,5-naphthyridin-1-yl]-1-(oxan-2-yl)-1H-pyrazolo[3,4-b]pyrazin-6-yl}-2-oxa-8-azaspiro[4.5]decan-4-yl]carbamate (3.2 g, crude) as a yellow solid.

Step c: To a solution of tert-butyl N-[(3S,4S)-3-methyl-8-{3-[(4S)-4-methyl-6-(methylcarbamoyl)-1,2,3,4-tetrahydro-1,5-naphthyridin-1-yl]-1-(oxan-2-yl)-1H-pyrazolo[3,4-b]pyrazin-6-yl}-2-oxa-8-azaspiro[4.5]decan-4-yl]carbamate (1.5 g) in MeOH (5.0 mL) was added HCl/MeOH (10.0 mL, 4N) and the reaction mixture was stirred at 20° C. for 12 hours. The reaction mixture was concentrated under reduced pressure, diluted with MeOH (15.0 mL) and adjusted to pH=8-9 by solid K₂CO₃. The mixture was filtered, concentrated under reduced pressure and purified by flash silica gel chromatography (MeOH in DCM=0~6%) to give the product of (8S)-5-{6-[(3S,4S)-4-amino-3-methyl-2-oxa-8-azaspiro[4.5]decan-8-yl]-1H-pyrazolo[3,4-b]pyrazin-3-yl}-N,8-dimethyl-5,6,7,8-tetrahydro-1,5-naphthyridine-2-carboxamide (1.16 g) as a yellow solid. SFC: e.e.=83%.

Steps a through c were also repeated for methyl (8R)-5-{6-[(3S,4S)-4-{[(tert-butoxy)carbonyl]amino}-3-methyl-2-oxa-8-azaspiro[4.5]decan-8-yl]-1-(oxan-2-yl)-1H-pyrazolo[3,4-b]pyrazin-3-yl}-8-methyl-5,6,7,8-tetrahydro-1,5-naphthyridine-2-carboxylate to give (8R)-5-{6-[(3S,4S)-4-amino-3-methyl-2-oxa-8-azaspiro[4.5]decan-8-yl]-1H-pyrazolo[3,4-b]pyrazin-3-yl}-N,8-dimethyl-5,6,7,8-tetrahydro-1,5-naphthyridine-2-carboxamide hydrochloride as a yellow solid. SFC e.e.=98. Absolute stereochemistry of both isomers was arbitrarily assigned.

Synthesis of (8S)-5-{6-[(3S,4S)-4-amino-3-methyl-2-oxa-8-azaspiro[4.5]decan-8-yl]-1H-pyrazolo[3,4-b]pyrazin-3-yl}-N,N,8-trimethyl-5,6,7,8-tetrahydro-1,5-naphthyridine-2-carboxamide, Compound 364

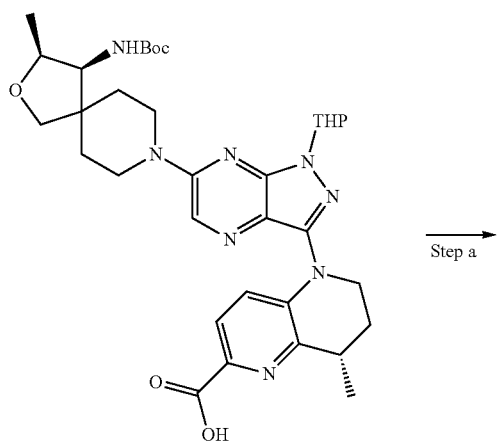

Step a →

419
-continued

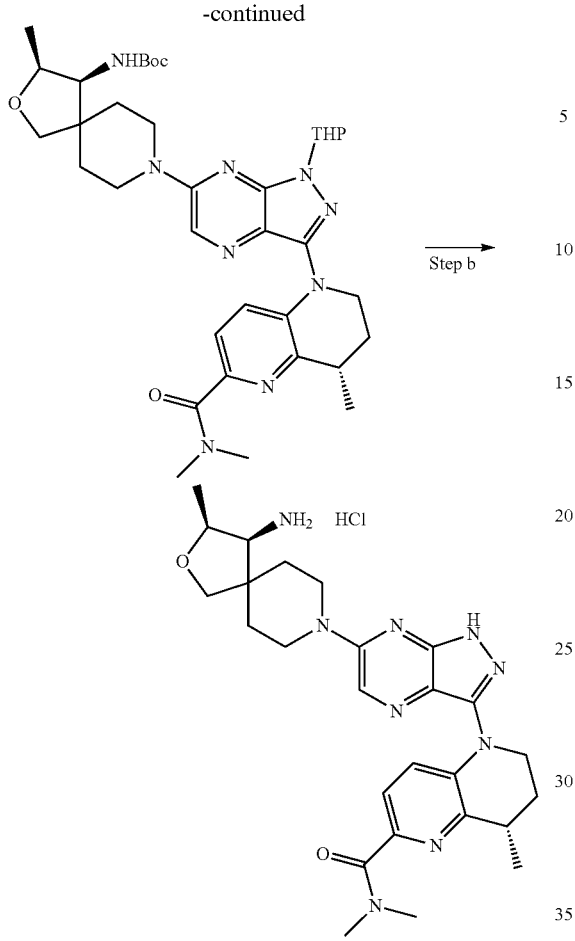

Step a: The mixture of (8S)-5-{6-[(3S,4S)-4-{[(tert-butoxy)carbonyl]amino}-3-methyl-2-oxa-8-azaspiro[4.5]decan-8-yl]-1-(oxan-2-yl)-1H-pyrazolo[3,4-b]pyrazin-3-yl}-8-methyl-5,6,7,8-tetrahydro-1,5-naphthyridine-2-carboxylic acid (85.0 mg, 128.0 μmol, synthesized via Step a of Compound 362), HATU (97.3 mg, 256.0 μmol) and TEA (88.6 μL, 640.0 μmol) in DMF (2.0 mL) was stirred at 15° C. for 10 min. Then Me$_2$NH HCl (12.2 mg, 150.0 μmol) was added and the reaction was stirred at 15° C. for 1 hour. The reaction mixture was poured into saturated NH$_4$Cl (50.0 mL) and extracted with EtOAc (50.0 mL×3). The combined organic layers were washed with brine (50.0 mL), dried over anhydrous Na$_2$SO$_4$ and concentrated under reduced pressure. The residue was purified by column chromatography (MeOH in EtOAc=0~10%) to afford tert-butyl N-[(3S,4S)-8-{3-[(4S)-6-(dimethylcarbamoyl)-4-methyl-1,2,3,4-tetrahydro-1,5-naphthyridin-1-yl]-1-(oxan-2-yl)-1H-pyrazolo[3,4-b]pyrazin-6-yl}-3-methyl-2-oxa-8-azaspiro[4.5]decan-4-yl]carbamate (75.0 mg, 108.0 μmol, 85% yield) as a yellow solid.

Step b: To a solution of tert-butyl N-[(3S,4S)-8-{3-[(4S)-6-(dimethylcarbamoyl)-4-methyl-1,2,3,4-tetrahydro-1,5-naphthyridin-1-yl]-1-(oxan-2-yl)-1H-pyrazolo[3,4-b]pyrazin-6-yl}-3-methyl-2-oxa-8-azaspiro[4.5]decan-4-yl]carbamate (75.0 mg, 108.0 μmol) in DCM (2.0 mL) was added HCl/dioxane (5.0 mL, 4 M) and the yellow solution was stirred at 15° C. for 12 hours. The mixture was concentrated under reduced pressure and the residue was purified by prep-HPLC (HCl) to afford (8S)-5-{6-[(3S,4S)-4-amino-3-methyl-2-oxa-8-azaspiro[4.5]decan-8-yl]-1H-

420 pyrazolo[3,4-b]pyrazin-3-yl}-N,N,8-trimethyl-5,6,7,8-tetrahydro-1,5-naphthyridine-2-carboxamide hydrochloride (24.2 mg, 44.6 μmol, 41.3% yield) as a yellow solid. SFC ee: 100%.

Synthesis of 1-{6-[(3S,4S)-4-amino-3-methyl-2-oxa-8-azaspiro[4.5]decan-8-yl]-1H-pyrazolo[3,4-b]pyrazin-3-yl}-N,4-dimethyl-1,2,3,4-tetrahydroquinoxaline-6-carboxamide. Compound 366

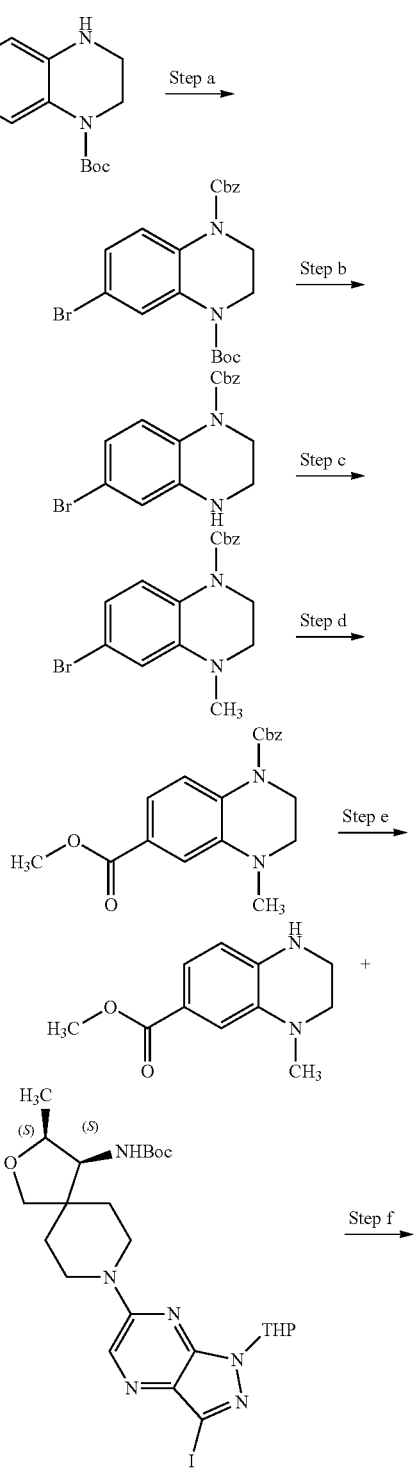

-continued

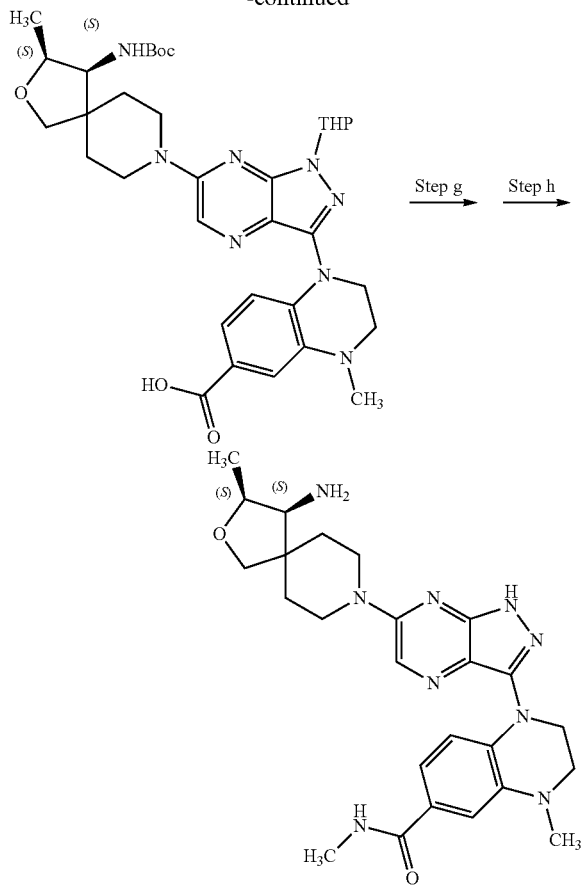

Step a: To a solution of tert-butyl 7-bromo-1,2,3,4-tetrahydroquinoxaline-1-carboxylate (1.20 g, 3.8 mmol) in THF (10 mL) was added 1 M NaHMDS (7.7 mL, 7.7 mmol) and CbzCl (979 mg, 5.7 mmol). The reaction mixture was stirred at 0° C. for 12 hours. The reaction mixture was concentrated under reduced pressure and purified by silica gel column chromatography (0-30% EtOAc/petroleum ether) to afford 1-benzyl 4-tert-butyl 6-bromo-1,2,3,4-tetrahydroquinoxaline-1,4-dicarboxylate (1.0 g, 2.2 mmol, 58% yield.) as a yellow oil.

Step b: A solution of 1-benzyl 4-tert-butyl 6-bromo-1,2,3,4-tetrahydroquinoxaline-1,4-dicarboxylate (1.0 g, 2.2 mmol) in HCl/MeOH (10 mL, 4 M) and DCM (5 mL) was stirred at 10° C. for 12 hours. The reaction mixture was concentrated under reduced pressure, the residue diluted with MeOH (5 mL) and the pH adjusted to 7-9 with $NH_3 \cdot H_2O$. Purification by silica gel column chromatography (0-30% EtOAc/petroleum ether) afforded benzyl 6-bromo-1,2,3,4-tetrahydroquinoxaline-1-carboxylate (800 mg, crude) as a white solid.

Step c: To a solution of benzyl 6-bromo-1,2,3,4-tetrahydroquinoxaline-1-carboxylate (800 mg, 2.3 mmol) in MeOH (10 mL) was added 25% HCHO (1.3 mL) dropwise followed by stirring at 25° C. for 30 min. To the mixture was added $NaBH_3CN$ (722 mg, 11.5 mmol) and stirring was continued at 25° C. for 12 hours. The reaction mixture was concentrated under reduced pressure and the residue purified by silica gel column chromatography (0-10% EtOAc/petroleum ether) to afford benzyl 6-bromo-4-methyl-1,2,3,4-tetrahydroquinoxaline-1-carboxylate (300 mg, 830 μmol, 36% yield) as a white solid.

Step d: To a solution of benzyl 6-bromo-4-methyl-1,2,3,4-tetrahydroquinoxaline-1-carboxylate (300 mg, 830 μmol) in MeOH (10 mL) was added TEA (167 mg, 1.7 mmol) and $Pd(dppf)Cl_2$ (121 mg, 166 μmol). The mixture was evacuated and refilled 3 times with carbon monoxide and then was stirred under CO (50 psi) at 80° C. for 2 days. The reaction mixture was concentrated under reduced pressure and the residue was purified by silica gel column chromatography (0-10% EtOAc/petroleum ether) to afford 1-benzyl 6-methyl 4-methyl-1,2,3,4-tetrahydroquinoxaline-1,6-dicarboxylate (240 mg, 705 μmol, 85% yield) as a light yellow solid.

Step e: To a solution of 1-benzyl 6-methyl 4-methyl-1,2,3,4-tetrahydroquinoxaline-1,6-dicarboxylate (240 mg, 705 μmol) in MeOH (10 mL) was added Pd/C (100 mg, 10 wt % wet). The reaction mixture was purged with $H_2$ for 3 min and stirred at 20° C. for 12 hours under and atmosphere of $H_2$ (15 psi). The atmosphere was replaced with nitrogen and Pd/C was filtered off. The filtrate was concentrated under reduced pressure to give methyl 4-methyl-1,2,3,4-tetrahydroquinoxaline-6-carboxylate (170 mg, crude) as a white solid, which was used directly in Step f.

Step f: To a solution of tert-butyl N-[(3S,4S)-8-[3-iodo-1-(oxan-2-yl)-1H-pyrazolo[3,4-b]pyrazin-6-yl]-3-methyl-2-oxa-8-azaspiro[4.5]decan-4-yl]carbamate (200 mg, 334 μmol) and methyl 4-methyl-1,2,3,4-tetrahydroquinoxaline-6-carboxylate (75.6 mg, 367 μmol) in dioxane (10 mL) was added $Pd_2(dba)_3$ (61.1 mg, 66.8 μmol), XantPhos (38.6 mg, 66.8 μmol), and t-BuONa (96.1 mg, 1.0 mmol). The reaction mixture was purged with $N_2$ for 3 min, and the reaction was stirred at 100° C. for 12 hours. The pH of the reaction mixture was adjusted to 6-7 by saturated NH4Cl and the mixture was concentrated under reduced pressure. The residue was diluted with water (30 mL) and extracted with EtOAc (30 mL×2). The combined organics were washed with water (30 mL×2), dried over anhydrous $Na_2SO_4$, filtered, and concentrated under reduced pressure. The residue was purified by silica gel column chromatography (0-100% EtOAc/petroleum ether then 0-10% MeOH/DCM) to afford 1-{6-[(3S,4S)-4-{[(tert-butoxy)carbonyl]amino}-3-methyl-2-oxa-8-azaspiro[4.5]decan-8-yl]-1-(oxan-2-yl)-1H-pyrazolo[3,4-b]pyrazin-3-yl}-4-methyl-1,2,3,4-tetrahydroquinoxaline-6-carboxylic acid (50 mg, 75.4 μmol, 23% yield) as a yellow solid.

Step g: To a solution of 1-{6-[(3S,4S)-4-{[(tert-butoxy)carbonyl]amino}-3-methyl-2-oxa-8-azaspiro[4.5]decan-8-yl]-1-(oxan-2-yl)-1H-pyrazolo[3,4-b]pyrazin-3-yl}-4-methyl-1,2,3,4-tetrahydroquinoxaline-6-carboxylic acid (70 mg, 105 μmol), HATU (40 mg, 105 μmol), and TEA (21.2 mg, 210 μmol) in DMF (3 mL) was added $MeNH_2 \cdot HCl$ (35.1 mg, 525 μmol). The reaction mixture was stirred at 10° C. for 12 hours then concentrated under reduced pressure. The residue was purified by silica gel column chromatography (0-100% EtOAc/petroleum ether) to afford tert-butyl N-[(3S,4S)-3-methyl-8-{3-[4-methyl-6-(methylcarbamoyl)-1,2,3,4-tetrahydroquinoxalin-1-yl]-1-(oxan-2-yl)-1H-pyrazolo[3,4-b]pyrazin-6-yl}-2-oxa-8-azaspiro[4.5]decan-4-yl]carbamate (70 mg, crude) as a yellow solid.

Step h: A solution of tert-butyl N-[(3S,4S)-3-methyl-8-{3-[4-methyl-6-(methylcarbamoyl)-1,2,3,4-tetrahydroquinoxalin-1-yl]-1-(oxan-2-yl)-1H-pyrazolo[3,4-b]pyrazin-6-yl}-2-oxa-8-azaspiro[4.5]decan-4-yl]carbamate (70 mg, 103 μmol) in 4M HCl/MeOH (3 mL) was stirred at 10° C. for 1 hour. The reaction mixture was concentrated under reduced pressure and the residue dissolved in MeOH (5 mL) and purified by prep-HPLC (acetonitrile/aq. HCl) to afford 1-{6-[(3S,4S)-4-amino-3-methyl-2-oxa-8-azaspiro[4.5]decan-8-yl]-1H-pyrazolo[3,4-b]pyrazin-3-yl}-N,4-dimethyl-1,2,3,4-

423 tetrahydroquinoxaline-6-carboxamide dihydrochloride (8.0 mg, 14.1 μmol, 13.7% yield) as a yellow solid: ESMS [M+H]+=491.8; ¹H-NMR (400 MHz, DMSO-d$_6$): δ 12.63 (br, 1H), 8.33 (s, 1H), 8.03-8.13 (m, 4H), 7.13 (s, 1H), 7.02 (s, 2H), 4.20-4.33 (m, 3H), 4.04-4.07 (m, 2H), 3.91-3.94 (m, 1H), 3.69-3.71 (m, 1H), 3.14-3.22 (m, 2H), 2.95 (s, 3H), 2.74-2.75 (m, 3H), 1.98-2.03 (m, 2H), 1.69-1.80 (m, 4H), 1.57-1.61 (m, 1H), 1.25 (d, J=6.4 Hz, 3H).

Synthesis of (3S,4S)-3-methyl-8-(3-[(4R)-4-methyl-6-(1,2,4-oxadiazol-3-yl)-1,2,3,4-tetrahydro-1,5-naphthyridin-1-yl]-1H-pyrazolo[3,4-b]pyrazin-6-yl)-2-oxa-8-azaspiro[4.5]decan-4-amine, Compound 371 and (3S,4S)-3-methyl-8-(3-[(4S)-4-methyl-6-(1,2,4-oxadiazol-3-yl)-1,2,3,4-tetrahydro-1,5-naphthyridin-1-yl]-1H-pyrazolo[3,4-b]pyrazin-6-yl)-2-oxa-8-azaspiro[4.5]decan-4-amine, Compound 370

424
-continued

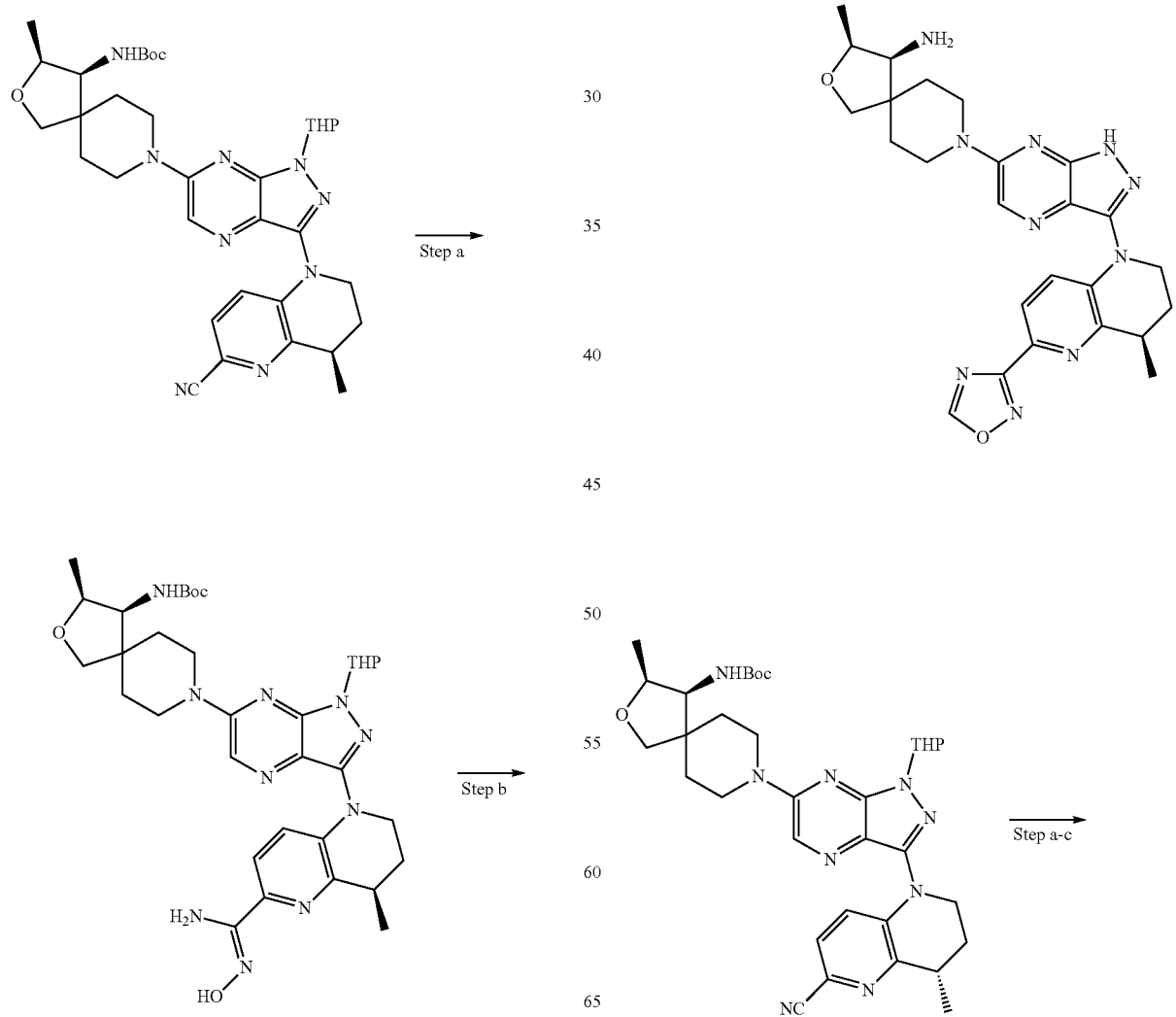

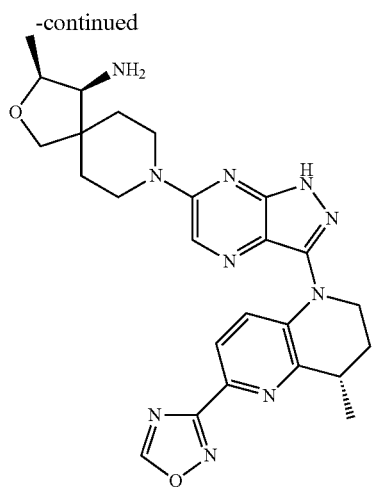

Step a: A solution of tert-butyl N-[(3S,4S)-8-{3-[(4R)-6-cyano-4-methyl-1,2,3,4-tetrahydro-1,5-naphthyridin-1-yl]-1-(oxan-2-yl)-1H-pyrazolo[3,4-b]pyrazin-6-yl}-3-methyl-2-oxa-8-azaspiro[4.5]decan-4-yl]carbamate (180.0 mg, 279.0 μmol, synthesized via Step a as described for Compound 281 using (8R)-8-methyl-5,6,7,8-tetrahydro-1,5-naphthyridine-2-carbonitrile as the coupling partner), hydroxylamine hydrochloride (25.1 mg, 362.0 μmol) and TEA (36.5 mg, 362.0 μmol) in EtOH (8.0 mL) was stirred at 50° C. for 2 hours. The mixture was concentrated in vacuo to give tert-butyl N-[(3S,4S)-8-{3-[(4R)-6-[(Z)—N-hydroxycarbamimidoyl]-4-methyl-1,2,3,4-tetrahydro-1,5-naphthyridin-1-yl]-1-(oxan-2-yl)-1H-pyrazolo[3,4-b]pyrazin-6-yl}-3-methyl-2-oxa-8-azaspiro[4.5]decan-4-yl]carbamate (230.0 mg, crude) as a yellow solid.

Step b: A solution of tert-butyl N-[(3S,4S)-8-{3-[(4R)-6-[(Z)—N-hydroxycarbamimidoyl]-4-methyl-1,2,3,4-tetrahydro-1,5-naphthyridin-1-yl]-1-(oxan-2-yl)-1H-pyrazolo[3,4-b]pyrazin-6-yl}-3-methyl-2-oxa-8-azaspiro[4.5]decan-4-yl]carbamate (230.0 mg) and $HC(OCH_3)_3$ (718.0 mg, 6.77 mmol) in dioxane (3.0 mL) was stirred at 120° C. for 10 hours. The solution was concentrated in vacuo to remove solvent. The residue was purified by flash silica gel chromatography (12 g, EtOAc in Petroleum ether from 0% to 70%) to give tert-butyl N-[(3S,4S)-3-methyl-8-{3-[(4R)-4-methyl-6-(1,2,4-oxadiazol-3-yl)-1,2,3,4-tetrahydro-1,5-naphthyridin-1-yl]-1-(oxan-2-yl)-1H-pyrazolo[3,4-b]pyrazin-6-yl}-2-oxa-8-azaspiro[4.5]decan-4-yl]carbamate (100.0 mg, 43.1% yield) as an orange oil.

Step c: A solution of tert-butyl N-[(3S,4S)-3-methyl-8-{3-[(4R)-4-methyl-6-(1,2,4-oxadiazol-3-yl)-1,2,3,4-tetrahydro-1,5-naphthyridin-1-yl]-1-(oxan-2-yl)-1H-pyrazolo[3,4-b]pyrazin-6-yl}-2-oxa-8-azaspiro[4.5]decan-4-yl]carbamate (100.0 mg, 145.0 μmol) in TFA/DCM (1.0 mL/10.0 mL) was stirred at 20° C. for 12 hours. The reaction mixture was concentrated in vacuo. The residue was diluted with MeOH (10.0 mL), and the pH adjusted to 9 with solid $K_2CO_3$, then the mixture was filtered. The solution was purified by prep-HPLC ($NH_3.H_2O$) to give (3S,4S)-3-methyl-8-{3-[(4R)-4-methyl-6-(1,2,4-oxadiazol-3-yl)-1,2,3,4-tetrahydro-1,5-naphthyridin-1-yl]-1H-pyrazolo[3,4-h]pyrazin-6-yl}-2-oxa-8-azaspiro[4.5]decan-4-amine (18.7 mg, 25.6% yield) as a yellow solid. SFC ee: 92%. Absolute configuration was arbitrarily assigned.

Steps a through c were repeated using (8S)-8-methyl-5,6,7,8-tetrahydro-1,5-naphthyridine-2-carbonitrile in the coupling step to form (3S,4S)-3-methyl-8-(3-[(4S)-4-methyl-6-(1,2,4-oxadiazol-3-yl)-1,2,3,4-tetrahydro-1,5-naphthyridin-1-yl]-1H-pyrazolo[3,4-b]pyrazin-6-yl)-2-oxa-8-azaspiro[4.5]decan-4-amine as the final compound. SFC ee: 91%. Absolute configuration was arbitrarily assigned.

Synthesis of (3S,4S)-3-methyl-8-(3-{6-[1-(oxetan-3-yl)-1H-pyrazol-4-yl]-1,2,3,4-tetrahydro-1,5-naphthyridin-1-yl}-1H-pyrazolo[3,4-b]pyrazin-6-yl)-2-oxa-8-azaspiro[4.5]decan-4-amine, Compound 372

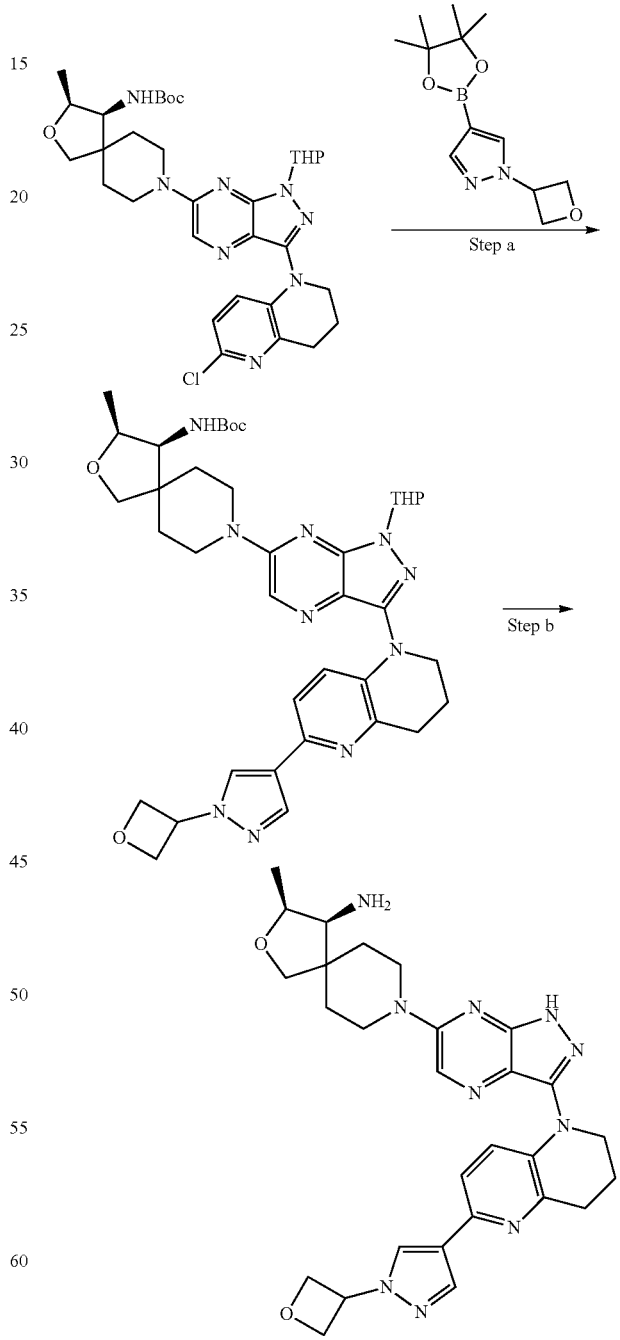

Step a: Teri-butyl N-[(3S,4S)-8-[3-(6-chloro-1,2,3,4-tetrahydro-1,5-naphthyridin-1-yl)-1-(oxan-2-yl)-1H-pyrazolo[3,4-b]pyrazin-6-yl]-3-methyl-2-oxa-8-azaspiro[4.5]decan- 4-yl]carbamate (100.0 mg, 156.0 μmol, synthesized as described for Compound 281 using 6-chloro-1,2,3,4-tetrahydro-1,5-naphthyridine as the coupling partner in Step a), 1-(oxetan-3-yl)-4-(4,4,5,5-tetramethyl-1,3,2-dioxaborolan-2-yl)-1H-pyrazole (58.5 mg, 234 μmol, CAS #1339890-99-1), K₂CO₃ (73.9 mg, 468 μmol) and Pd(dppf)Cl₂ (34.2 mg, 46.8 μmol) were added in the mixture of dioxane (10.0 mL) and H₂O (1 mL). The reaction mixture was evacuated and refilled 3 times with N₂ and stirred at 100° C. for 4 hours. The reaction mixture was concentrated under reduced pressure to give a residue and purified by flash silica gel chromatography (DCM:MeOH=20:1) to afford the product of tert-butyl N-[(3S,4,S)-3-methyl-8-[1-(oxan-2-yl)-3-{6-[1-(oxetan-3-yl)-1H-pyrazol-4-yl]-1,2,3,4-tetrahydro-1,5-naphthyridin-1-yl}-1H-pyrazolo[3,4-b]pyrazin-6-yl]-2-oxa-8-azaspiro[4.5]decan-4-yl]carbamate (100.0 mg, 88.4% yield) as a yellow solid.

Step b: Tert-butyl N-[(3S,4S)-3-methyl-8-[1-(oxan-2-yl)-3-{6-[1-(oxetan-3-yl)-1H-pyrazol-4-yl]-1,2,3,4-tetrahydro-1,5-naphthyridin-1-yl}-1H-pyrazolo[3,4-b]pyrazin-6-yl]-2-oxa-8-azaspiro[4.5]decan-4-yl]carbamate (100.0 mg, 137.0 μmol) was added to a mixture of TFA (3.0 mL) and DCM (3.0 mL), and the reaction mixture was stirred at 15° C. for 3 hours. The reaction mixture was concentrated under reduced pressure, diluted with MeOH (5.0 mL), and the pH was adjusted to 7 with K₂CO₃ (solid). The mixture was purified by prep-HPLC (NH₃.H₂O) to afford the product of (3S,4S)-3-methyl-8-(3-(6-[1-(oxetan-3-yl)-1H-pyrazol-4-yl]-1,2,3,4-tetrahydro-1,5-naphthyridin-1-yl)-1H-pyrazolo[3,4-b]pyrazin-6-yl)-2-oxa-8-azaspiro[4.5]decan-4-amine (12.6 mg, 16.9% yield) as a yellow solid.

Synthesis of N-(1-{6-[(3S,4S)-4-amino-3-methyl-2-oxa-8-azaspiro[4.5]decan-8-yl]-1H-pyrazolo[3,4-b]pyrazin-3-yl}-1,2,3,4-tetrahydroquinolin-5-yl)-N-methylmethanesulfonamide, Compound 37

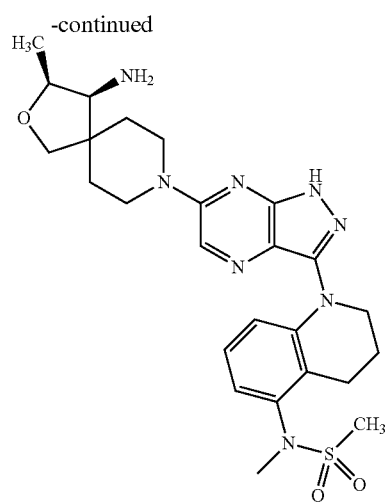

Step a: A resealable reaction vial was charged with tert-butyl N-[(3S,4S)-8-[3-(5-methanesulfonamido-1,2,3,4-tetrahydroquinolin-1-yl)-1-(oxan-2-yl)-1H-pyrazolo[3,4-b]pyrazin-6-yl]-3-methyl-2-oxa-8-azaspiro[4.5]decan-4-yl]carbamate (65 mg, 0.09327 mmol) (prepared as described for compound 343), dipotassium carbonate (25.7 mg, 0.1865 mmol) in DMF (5 mL) was charged with iodomethane (13.2 mg, 0.09327 mmol). The vial was sealed, and the mixture was stirred at 25° C. for 2 hrs. After cooling, the reaction mixture was diluted with ethyl acetate, washed with water, brine, dried over anhydrous sodium sulfate, and filtered. Residue was taken up in MeOH (4 mL) and 4N HCl (1 mL) and heated to 60° C. for 30 min. Solvent was removed and the residue purified on preparative HPLC (10-40% ACN/water+0.1% FA) to afford N-(1-{6-[(3S,4S)-4-amino-3-methyl-2-oxa-8-azaspiro[4.5]decan-8-yl]-1H-pyrazolo[3,4-b]pyrazin-3-yl}-1,2,3,4-tetrahydroquinolin-5-yl)-N-methylmethanesulfonamide (38 mg) as a yellow solid. LCMS: [M+H]+ 527.

Synthesis of (3S,4S)-8-[3-(5-amino-1,2,3,4-tetrahydroquinolin-1-yl)-1H-pyrazolo[3,4-b]pyrazin-6-yl]-3-methyl-2-oxa-8-azaspiro[4.5]decan-4-amine, Compound 375 and N-(1-{6-[(3S,4S)-4-amino-3-methyl-2-oxa-8-azaspiro[4.5]decan-8-yl]-1H-pyrazolo[3,4-b]pyrazin-3-yl}-1,2,3,4-tetrahydroquinolin-5-yl)acetamide, Compound 376

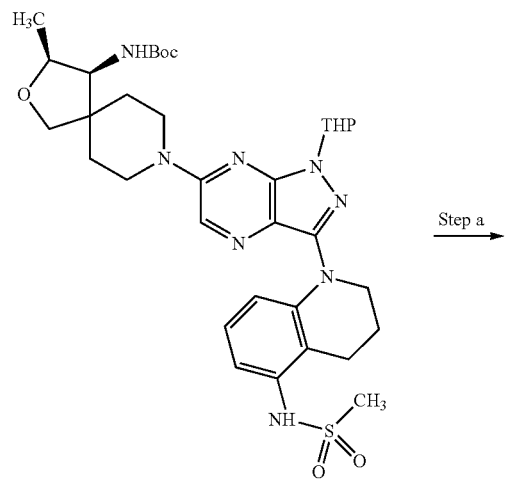

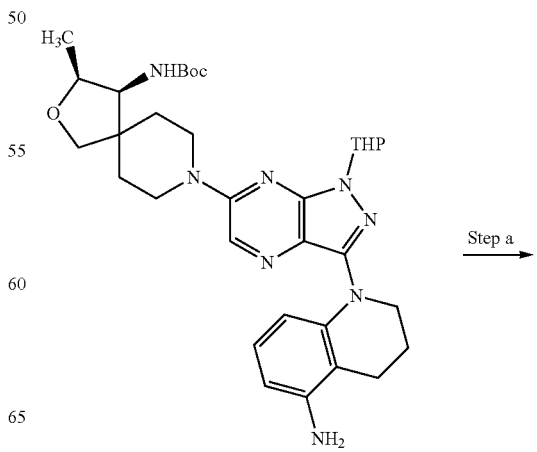

429
-continued

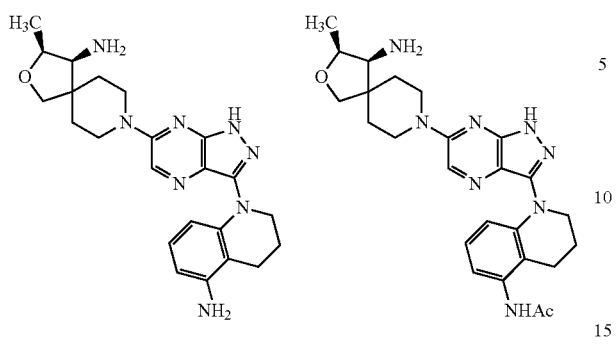

430
-continued

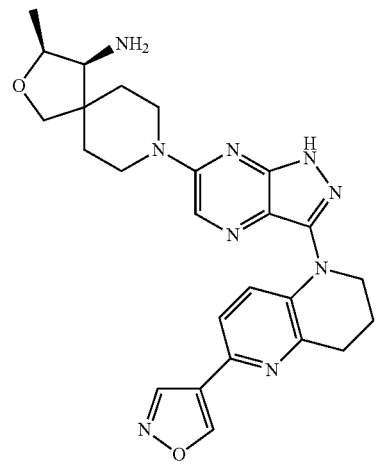

Step a: A resealable reaction vial was charged with tert-butyl N-[(3S,4S)-8-[3-(5-amino-1,2,3,4-tetrahydroquinolin-1-yl)-1-(oxan-2-yl)-1H-pyrazolo[3,4-b]pyrazin-6-yl]-3-methyl-2-oxa-8-azaspiro[4.5]decan-4-yl]carbamate (115 mg, 0.1858 mmol) (prepared as described for compound 343), DCM (5 mL), triethylamine (38.8 µL, 0.2787 mmol) and acetyl chloride (12.5 µL, 0.1765 mmol). The vial was sealed, and the mixture was stirred at 25° C. for 1 hr. The solvent was removed, and the residue was taken up in MeOH (4 mL) and 1N HCl (1 mL) and heated to 60° C. for 30 min. The solvent removed and purified on prep-HPLC (5-30% ACN/water+0.1% FA). Two product were isolated separately to afford (3S,4S)-8-[3-(5-amino-1,2,3,4-tetrahydroquinolin-1-yl)-1H-pyrazolo[3,4-b]pyrazin-6-yl]-3-methyl-2-oxa-8-azaspiro[4.5]decan-4-amine (15 mg) as a yellow solid (LCMS: [M+H]+ 435) and N-(1-{6-[(3S,4S)-4-amino-3-methyl-2-oxa-8-azaspiro[4.5]decan-8-yl]-1H-pyrazolo[3,4-b]pyrazin-3-yl}-1,2,3,4-tetrahydroquinolin-5-yl)acetamide (27 mg) as a yellow solid (LCMS: [M+H]+ 477)

Synthesis of (3S,4S)-3-methyl-8-{3-[6-(1,2-oxazol-4-yl)-1,2,3,4-tetrahydro-1,5-naphthyridin-1-yl]-1H-pyrazolo[3,4-b]pyrazin-6-yl}-2-oxa-8-azaspiro[4.5]decan-4-amine, Compound 380

Step a: The mixture of (3S,4S)-8-[3-(6-bromo-1,2,3,4-tetrahydro-1,5-naphthyridin-1-yl)-1H-pyrazolo[3,4-b]pyrazin-6-yl]-3-methyl-2-oxa-8-azaspiro[4.5]decan-4-amine (30 mg, 60 µmol, 1.0 eq, synthesized as described in Step a-b of Compound 281 with 6-bromo-1,2,3,4-tetrahydro-1,5-naphthyridine as the coupling partner in Step a), 4-(4,4,5,5-tetramethyl-1,3,2-dioxaborolan-2-yl)-1,2-oxazole (23 mg, 120 µmol, 2.0 eq, CAS #928664-98-6), CsF (27 mg, 180 µmol, 3.0 eq) and Pd-118 (CAS 95408-45-0) (12 mg, 18 µmol, 0.3 eq) in DME (3 mL) and H2O (0.3 mL) was evacuated and refilled 3 times using N2. The reaction mixture was stirred at 40° C. for 10 mins under microwave. The mixture was concentrated under reduced pressure and the residue was purified by column chromatography (DCM/MeOH=10:0~10:1) to afford impure product (37 mg, crude). The product was re-purified by prep-TLC (DCM/MeOH=10:1) to afford (3S,4S)-3-methyl-8-(3-[6-(1,2-oxazol-4-yl)-1,2,3,4-tetrahydro-1,5-naphthyridin-1-yl]-1H-pyrazolo[3,4-b]pyrazin-6-yl)-2-oxa-8-azaspiro[4.5]decan-4-amine (2.4 mg, 8.2% yield) as a yellow solid.

Synthesis of (3S,4S)-8-{3-[6-(cyclohex-1-en-1-yl)-1,2,3,4-tetrahydro-1,5-naphthyridin-1-yl]-1H-pyrazolo[3,4-b]pyrazin-6-yl}-3-methyl-2-oxa-8-azaspiro[4.5]decan-4-amine hydrochloride, Compound 396

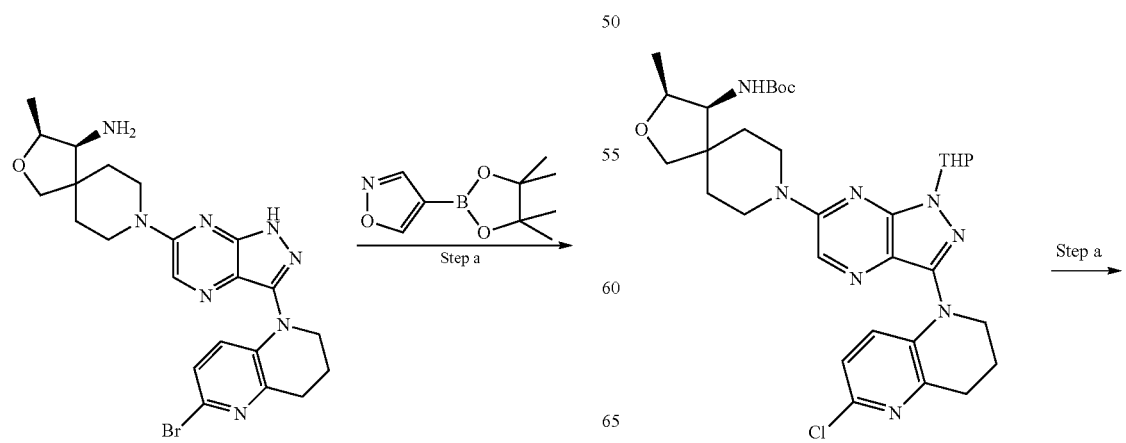

431

-continued

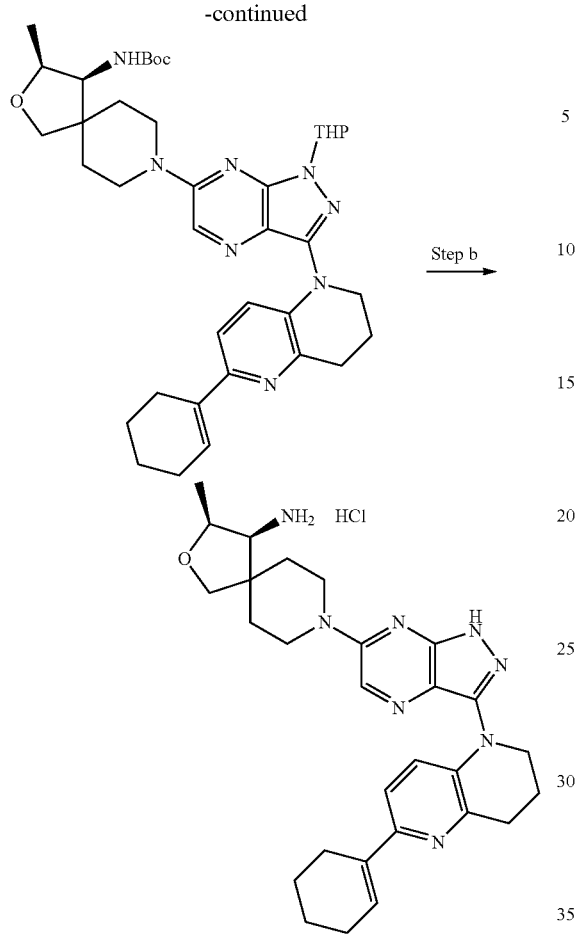

Step a: A mixture of tert-butyl N-[(3S,4S)-8-[3-(6-chloro-1,2,3,4-tetrahydro-1,5-naphthyridin-1-yl)-1-(oxan-2-yl)-1H-pyrazolo[3,4-b]pyrazin-6-yl]-3-methyl-2-oxa-8-azaspiro[4.5]decan-4-yl]carbamate (110.0 mg, 0.17 mmol) (prepared as described above), K2CO3 (59.2 mg, 0.43 mmol), Pd(dppf)Cl2 (12.5 mg, 17.2 μmol) and 2-(cyclohex-1-en-1-yl)-4,4,5,5-tetramethyl-1,3,2-dioxaborolane (39.3 mg, 0.19 mmol) in dioxane (5.0 mL)/H2O (0.5 mL) was evacuated and refilled for 3 times using N2 and stirred at 90° C. for 12 hours under N2 atmosphere. The reaction mixture was concentrated to give a residue which was purified by flash silica gel chromatography (Ethyl acetate/Petroleum ether=0/100 to 50/100) to give the product of tert-butyl N-[(3S,4S)-8-{3-[6-(cyclohex-1-en-1-yl)-1,2,3,4-tetrahydro-1,5-naphthyridin-1-yl]-1-(oxan-2-yl)-1H-pyrazolo[3,4-b]pyrazin-6-yl}-3-methyl-2-oxa-8-azaspiro[4.5]decan-4-yl]carbamate (45.0 mg, 38.4% yield) as a yellow oil.

Step b: The compound of tert-butyl N-[(3S,4S)-8-(3-[6-(cyclohex-1-en-1-yl)-1,2,3,4-tetrahydro-1,5-naphthyridin-1-yl]-1-(oxan-2-yl)-1H-pyrazolo[3,4-b]pyrazin-6-yl)-3-methyl-2-oxa-8-azaspiro[4.5]decan-4-yl]carbamate (45.0 mg, 0.66 mmol) was added in 2 N HCl/MeOH (4.0 mL). The mixture was stirred at 25° C. for 12 hours. The reaction mixture was concentrated to give a residue which was dissolved in MeOH (5.0 mL) and purified by prep-HPLC (HCl) to give (3S,4S)-8-{3-[6-(cyclohex-1-en-1-yl)-1,2,3,4-tetrahydro-1,5-naphthyridin-1-yl]-1H-pyrazolo[3,4-b]pyrazin-6-yl}-3-methyl-2-oxa-8-azaspiro[4.5]decan-4-amine hydrochloride (19.6 mg, 55.6% yield) as an orange solid.

432

Synthesis of (3,4S)-8-(3-{6-[(1Z)-1-(hydroxyimino)ethyl]-1,2,3,4-tetrahydro-1,5-naphthyridin-1-yl}-1H-pyrazolo[3,4-b]pyrazin-6-yl)-3-methyl-2-oxa-8-azaspiro[4.5]decan-4-amine, Compound 397

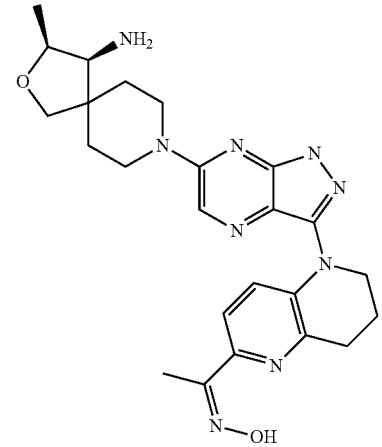

Step a: A solution of 1-(5-{6-[(3S,4S)-4-amino-3-methyl-2-oxa-8-azaspiro[4.5]decan-8-yl]-1H-pyrazolo[3,4-b]pyrazin-3-yl}-5,6,7,8-tetrahydro-1,5-naphthyridin-2-yl)ethan-1-one hydrochloride (60.0 mg, 0.12 mmol, synthesized as describe in Steps a-b for Compound 281, with 1-(5,6,7,8-tetrahydro-1,5-naphthyridin-2-yl)ethan-1-one as the coupling partner in Step a), NH2OH.HCl (10.8 mg, 0.16 mmol) and TEA (21.3 μL, 0.16 mmol) in EtOH (5.0 mL) was stirred at 50° C. for 2 hours. The mixture was concentrated and purified by prep-HPLC (NH3.H2O) to afford (3S,4S)-8-(3-(6-[(1Z)-1-(hydroxyimino)ethyl]-1,2,3,4-tetrahydro-1,5-naphthyridin-1-yl)-1H-pyrazolo[3,4-b]pyrazin-6-yl)-3-methyl-2-oxa-8-azaspiro[4.5]decan-4-amine (25.5 mg, 44.5% yield) as a yellow solid.

Synthesis of 2-(4-{6-[(3S,4S)-4-amino-3-methyl-2-oxa-8-azaspiro[4.5]decan-8-yl]-1H-pyrazolo[3,4-b]pyrazin-3-yl}-7-cyano-1,2,3,4-tetrahydroquinoxalin-1-yl)-N-methylacetamide, Compound 39

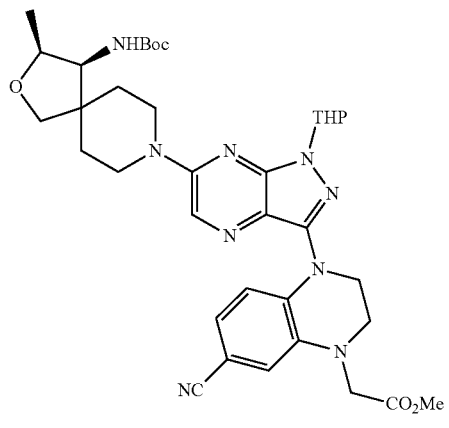

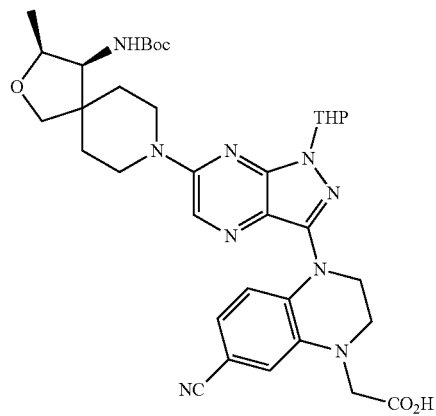

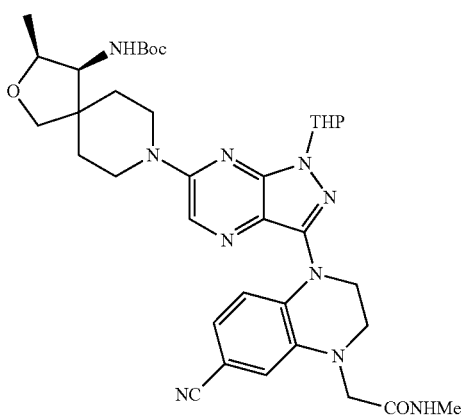

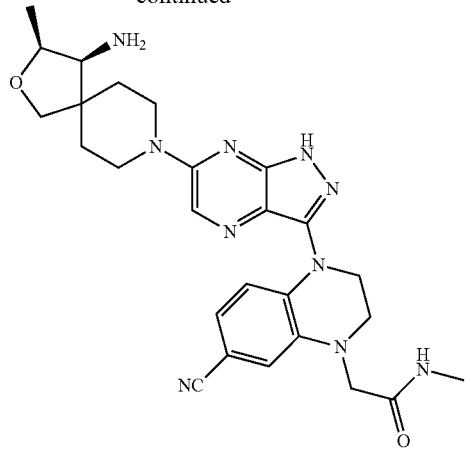

Step a: A solution of methyl 2-(4-{6-[(3S,4S)-4-{[(tert-butoxy)carbonyl]amino}-3-methyl-2-oxa-8-azaspiro[4.5]decan-8-yl]-1-(oxan-2-yl)-1H-pyrazolo[3,4-b]pyrazin-3-yl}-7-cyano-1,2,3,4-tetrahydroquinoxalin-1-yl)acetate (300.0 mg, 427.0 μmol, synthesized as described in Step a of Compound 281 using methyl 2-(7-cyano-1,2,3,4-tetrahydroquinoxalin-1-yl)acetate as the coupling partner) and $K_2CO_3$ (234.0 mg, 1.70 mmol) in MeOH (20.0 mL) was stirred at 60° C. for 12 h. The reaction mixture was concentrated in vacuo to give 2-(4-{6-[(3S,4S)-4-{[(tert-butoxy)carbonyl]amino}-3-methyl-2-oxa-8-azaspiro[4.5]decan-8-yl]-1-(oxan-2-yl)-1H-pyrazolo[3,4-b]pyrazin-3-yl}-7-cyano-1,2,3,4-tetrahydroquinoxalin-1-yl)acetic acid (350.0 mg, crude) as a yellow gum.

Step b: A solution of 2-(4-{6-[(3S,4S)-4-{[(tert-butoxy)carbonyl]amino}-3-methyl-2-oxa-8-azaspiro[4.5]decan-8-yl]-1-(oxan-2-yl)-1H-pyrazolo[3,4-b]pyrazin-3-yl}-7-cyano-1,2,3,4-tetrahydroquinoxalin-1-yl)acetic acid (150.0 mg, 218.0 μmol), $MeNH_2$—HCl (29.2 mg, 436.0 umol), HATU (248.0 mg, 654.0 umol) and DIPEA (117.0 uL, 654.0 umol) in DMF (5.0 mL) was stirred at 50° C. for 2 h. The solution was added into $H_2O$ (20.0 mL) and then extracted with EtOAc (20.0 mL×2). The combined organic layers were washed with brine (20.0 mL), dried over anhydrous $Na_2SO_4$, filtered and concentrated in vacuo to give the crude product as orange gum. The residue was purified by flash silica gel chromatography (12 g, MeOH in $CH_2Cl_2$ from 0% to 3%) to give tert-butyl N-[(3S,4S)-8-(3-{6-cyano-4-[(methylcarbamoyl)methyl]-1,2,3,4-tetrahydroquinoxalin-1-yl}-1-(oxan-2-yl)-1H-pyrazolo[3,4-b]pyrazin-6-yl)-3-methyl-2-oxa-8-azaspiro[4.5]decan-4-yl]carbamate (200.0 mg, crude, purity 60%) as a yellow oil.

Step c: A solution of tert-butyl N-[(3S,4S)-8-(3-{6-cyano-4-[(methylcarbamoyl)methyl]-1,2,3,4-tetrahydroquinoxalin-1-yl}-1-(oxan-2-yl)-1H-pyrazolo[3,4-b]pyrazin-6-yl)-3-methyl-2-oxa-8-azaspiro[4.5]decan-4-yl]carbamate (180.0 mg, 256.0 μmol) in TFA/DCM (3.0 mL/15.0 mL) was stirred at 25° C. for 1 h. The reaction mixture was concentrated in vacuo. The residue was diluted with THF (5.0 mL), adjusted to pH=8 with $Na_2CO_3$ solid and purified by prep-HPLC ($NH_3.H_2O$). 2-(4-{6-[(3S,4S)-4-amino-3-methyl-2-oxa-8-azaspiro[4.5]decan-8-yl]-1H-pyrazolo[3,4-b]pyrazin-3-yl}-7-cyano-1,2,3,4-tetrahydroquinoxalin-1-yl)-N-methylacetamide (13.2 mg, 25.5 μmol, 10% yield) was obtained as a yellow solid.

Synthesis of 1-{6-[(3S,4S)-4-amino-3-methyl-2-oxa-8-azaspiro[4.5]decan-8-yl]-1H-pyrazolo[3,4-b]pyrazin-3-yl}-N-methyl-1,2,3,4-tetrahydro-1,6-naphthyridine-5-carboxamide, Compound 404

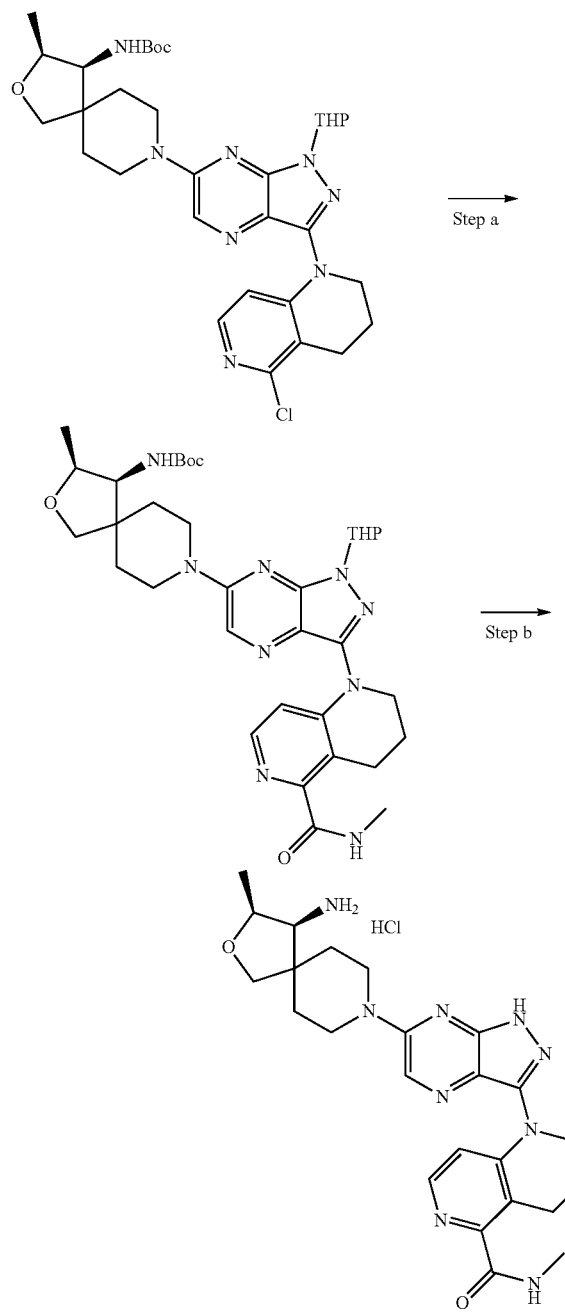

Step a: Tert-butyl N-[(3S,4S)-8-[3-(5-chloro-1,2,3,4-tetrahydro-1,6-naphthyridin-1-yl)-1-(oxan-2-yl)-1H-pyrazolo[3,4-b]pyrazin-6-yl]-3-methyl-2-oxa-8-azaspiro[4.5]decan-4-yl]carbamate (150.0 mg, 234.0 μmol, synthesized as described in Step a for Compound 281 using 5-chloro-1,2,3,4-tetrahydro-1,6-naphthyridine as the coupling partner), Pd(dppf)Cl$_2$ (34.2 mg, 46.8 μmol), MeNH$_2$.HCl (187.0 mg, 2.8 mmol) and Et$_3$N (323.0 μL, 2.3 mmol) were added to NMP (10.0 mL). The reaction mixture was stirred at 110° C. for 48 hours under CO (1.5 Mpa). The reaction mixture was then diluted with ethyl acetate (50.0 mL) and the organic layer was separated. The organic layers was washed with H$_2$O (30.0 mL×2), brine (30.0 mL), dried over anhydrous Na$_2$SO$_4$, filtered and concentrated under reduced pressure to give a residue. The residue was purified by flash silica gel chromatography (petroleum ether:ethyl acetate=100:0 to 100:70) to afford tert-butyl N-[(3S,4S)-3-methyl-8-{3-[5-(methylcarbamoyl)-1,2,3,4-tetrahydro-1,6-naphthyridin-1-yl]-1-(oxan-2-yl)-1H-pyrazolo[3,4-b]pyrazin-6-yl}-2-oxa-8-azaspiro[4.5]decan-4-yl]carbamate (80.0 mg, 51.9% yield) as a yellow solid.

Step b: Tert-butyl N-[(3S,4S)-3-methyl-8-{3-[5-(methylcarbamoyl)-1,2,3,4-tetrahydro-1,6-naphthyridin-1-yl]-1-(oxan-2-yl)-1H-pyrazolo[3,4-b]pyrazin-6-yl}-2-oxa-8-azaspiro[4.5]decan-4-yl]carbamate (60.0 mg, 90.6 μmol) was added to 4N HCl/MeOH (6.0 mL), and the reaction mixture was stirred at 25° C. for 2 hours. The reaction mixture was concentrated under reduced pressure and purified by prep-HPLC (HCl) to afford 1-{6-[(3S,4S)-4-amino-3-methyl-2-oxa-8-azaspiro[4.5]decan-8-yl]-1H-pyrazolo[3,4-b]pyrazin-3-yl}-N-methyl-1,2,3,4-tetrahydro-1,6-naphthyridine-5-carboxamide hydrochloride (31.8 mg, 68.3% yield, HCl salt) as a yellow solid.

Synthesis of 2-(4-{6-[(3S,4S)-4-amino-3-methyl-2-oxa-8-azaspiro[4.5]decan-8-yl]-1H-pyrazolo[3,4-b]pyrazin-3-yl}-7-cyano-1,2,3,4-tetrahydroquinoxalin-1-yl)acetic acid, Compound 423

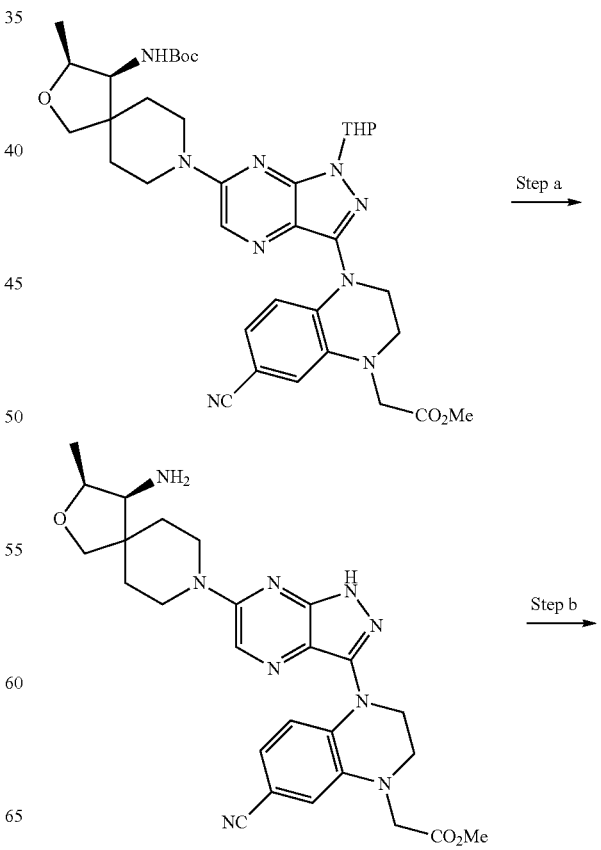

437

-continued

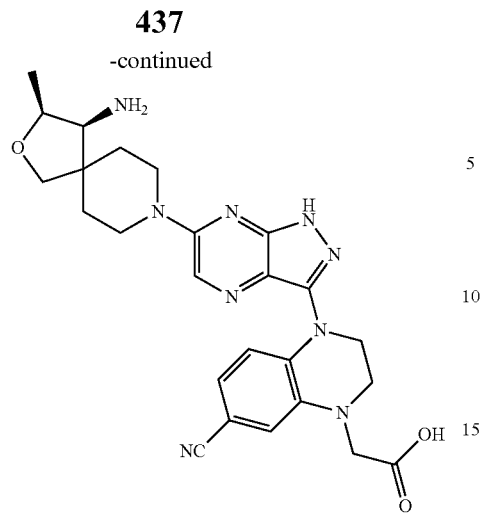

Step a: A solution of methyl 2-(4-{6-[(3S,4S)-4-{[(tert-butoxy)carbonyl]amino}-3-methyl-2-oxa-8-azaspiro[4.5]decan-8-yl]-1-(oxan-2-yl)-1H-pyrazolo[3,4-b]pyrazin-3-yl}-7-cyano-1,2,3,4-tetrahydroquinoxalin-1-yl)acetate (100.0 mg, 0.14 mmol) (formed by a coupling analogous to that described for compound 33, using methyl 2-(7-cyano-3,4-dihydroquinoxalin-1(2H)-yl)acetate, CAS 1892763-41-5) in TFA/DCM (2.0 mL/10.0 mL) was stirred at 25° C. for 1 hour. The reaction mixture was concentrated to give the residue. The residue was diluted with THF (5.0 mL), adjusted to pH=8 with Na2CO3 solid. The mixture was filtered and filtrated was concentrated in vacuum to give methyl 2-(4-{6-[(3S,4S)-4-amino-3-methyl-2-oxa-8-azaspiro[4.5]decan-8-yl]-1H-pyrazolo[3,4-b]pyrazin-3-yl}-7-cyano-1,2,3,4-tetrahydroquinoxalin-1-yl)acetate (120.0 mg, crude) as an orange gum. The gum was used in the next step without further purification.

Step b: A solution of methyl 2-(4-{6-[(3S,4S)-4-amino-3-methyl-2-oxa-8-azaspiro[4.5]decan-8-yl]-1H-pyrazolo[3,4-b]pyrazin-3-yl}-7-cyano-1,2,3,4-tetrahydroquinoxalin-1-yl)acetate (120.0 mg, 0.23 mmol) and K2CO3 (96.3 mg, 0.69 mmol) in MeOH (5.0 mL) was stirred at 60° C. for 12 hours. Orange suspension was observed. Desired mass ion was observed from LCMS. The mixture was filtered and filtrate was concentrated to give the residue. The residue was diluted with MeOH (5.0 mL) and purified by prep-HPLC (NH3.H2O). 2-(4-{6-[(3S,4S)-4-amino-3-methyl-2-oxa-8-azaspiro[4.5]decan-8-yl]-1H-pyrazolo[3,4-b]pyrazin-3-yl}-7-cyano-1,2,3,4-tetrahydroquinoxalin-1-yl)acetic acid (23.9 mg, 20.6% yield) was obtained as a yellow solid. LCMS: [M+H]+ 504.3

Synthesis of 2-(5-{6-[(3S,4S)-4-amino-3-methyl-2-oxa-8-azaspiro[4.5]decan-8-yl]-1H-pyrazolo[3,4-b]pyrazin-3-yl}-5,6,7,8-tetrahydro-1,5-naphthyridin-2-yl)-N-methylacetamide, Compound 425

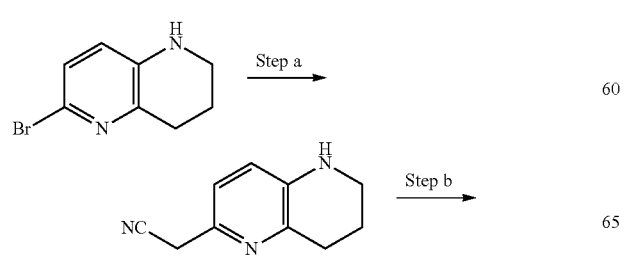

438

-continued

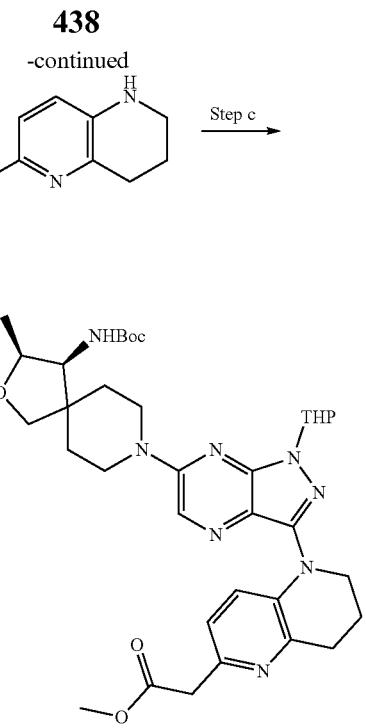

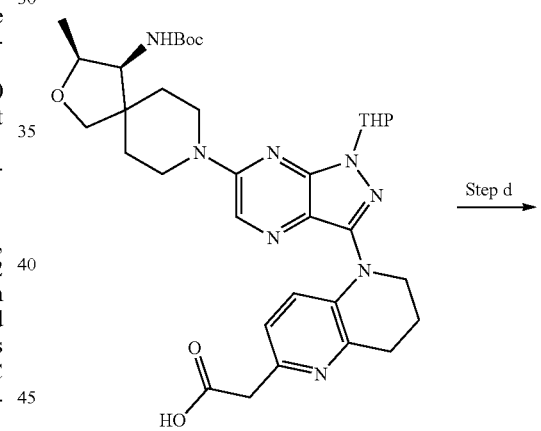

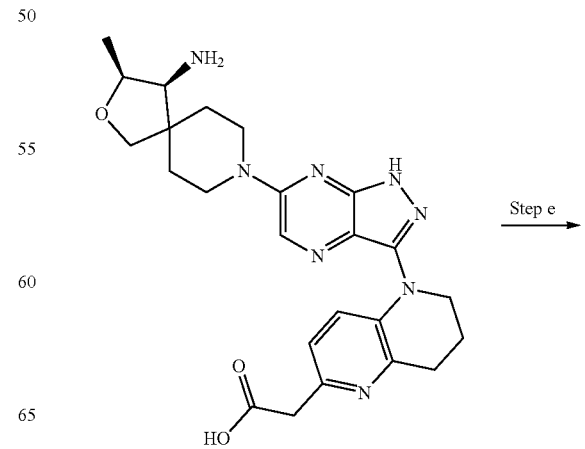

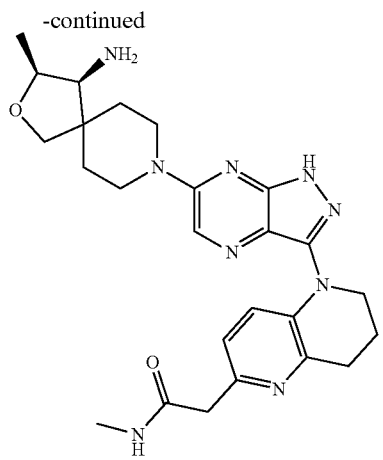

Step a: To a solution of 6-bromo-1,2,3,4-tetrahydro-1,5-naphthyridine (1 g, 4.7 mmol) in DMSO (20 mL) and H2O (5 mL) was added Pd(dppf)Cl2 (343 mg, 469 μmol), KF (812 mg, 14.0 mmol) and 4-(4,4,5,5-tetramethyl-1,3,2-dioxaborolan-2-yl)-1,2-oxazole (1.1 g, 5.6 mmol), the mixture was stirred at 130° C. for 12 hours under N2. Brine (25 mL) was added to the dark solution and extracted by EtOAc (3×25 mL). The combined organic phases were dried by anhydrous Na2SO4 and concentrated under reduced pressure. The resulting crude material was purified by silica gel chromatography (elution: Petroleum ether:ethyl acetate=2:1) to give 2-(5,6,7,8-tetrahydro-1,5-naphthyridin-2-yl)acetonitrile (520 mg, 64.0% yield) as a white solid.

Step b: To a solution of 2-(5,6,7,8-tetrahydro-1,5-naphthyridin-2-yl)acetonitrile (150 mg, 865 μmol) in MeOH (10 mL) was added Na (69.4 mg, 3.02 mmol) at 0° C., the mixture was stirred at 20° C. for 6 hours. LCMS showed the desired product formed. The reaction mixture was concentrated and the crude product (210 mg) as a yellow solid was directly used in the next step.

Step c: A solution of methyl 2-(5,6,7,8-tetrahydro-1,5-naphthyridin-2-yl)acetate (60 mg, 290 μmol), tert-butyl N-[(3S,4S)-8-[3-iodo-1-(oxan-2-yl)-1H-pyrazolo[3,4-b]pyrazin-6-yl]-3-methyl-2-oxa-8-azaspiro[4.5]decan-4-yl]carbamate (173 mg, 290 μmol), XantPhos-Pd-G4 (27.8 mg, 29.0 μmol) and Cs2CO3 (189 mg, 580 μmol) in toluene (5.0 mL) was stirred at 80° C. for 12 hours under N2. LCMS showed the desired product formed. The mixture was concentrated in vacuum. The residue was purified by flash silica gel chromatography (eluent:Petroleum ether:Ethyl acetate=1:1 to 0:1) to give methyl 2-(5-{6-[(3S,4S)-4-{[(tert-butoxy)carbonyl]amino}-3-methyl-2-oxa-8-azaspiro[4.5]decan-8-yl]-1-(oxan-2-yl)-1H-pyrazolo[3,4-b]pyrazin-3-yl}-5,6,7,8-tetrahydro-1,5-naphthyridin-2-yl)acetate (98.0 mg, 50.0% yield) as an orange oil.

Step d: To a solution of methyl 2-(5-{6-[(3S,4S)-4-{[(tert-butoxy)carbonyl]amino}-3-methyl-2-oxa-8-azaspiro[4.5]decan-8-yl]-1-(oxan-2-yl)-1H-pyrazolo[3,4-b]pyrazin-3-yl}-5,6,7,8-tetrahydro-1,5-naphthyridin-2-yl)acetate (90 mg, 132 μmol) in MeOH (5 mL) and H2O (1 mL) was added LiOH.H2O (55.0 mg, 1.31 mmol), the mixture was stirred at 50° C. for 2 hours. LCMS showed the desired product formed. The reaction mixture was added 1M HCl to pH=3 slowly, extracted with EtOAc (20 mL×3), the combined organic layers washed with brine (20 mL) and dried over anhydrous Na2SO4, filtered and concentrated to dryness. The crude product 2-(5-{6-[(3S,4S)-4-{[(tert-butoxy)carbonyl]amino}-3-methyl-2-oxa-8-azaspiro[4.5]decan-8-yl]-1-(oxan-2-yl)-1H-pyrazolo[3,4-b]pyrazin-3-yl}-5,6,7,8-tetrahydro-1,5-naphthyridin-2-yl)acetic acid (80 mg) was used directly in the next step.

Step e: To a solution of 2-(5-{6-[(3S,4S)-4-{[(tert-butoxy)carbonyl]amino}-3-methyl-2-oxa-8-azaspiro[4.5]decan-8-yl]-1-(oxan-2-yl)-1H-pyrazolo[3,4-b]pyrazin-3-yl}-5,6,7,8-tetrahydro-1,5-naphthyridin-2-yl)acetic acid (90 mg, 135 μmol) in MeOH (2 mL) was added 4 M MeOH/HCl (0.34 mL) at 0° C., the mixture was stirred at 25° C. for 2 hours. LCMS showed the desired product formed. The reaction mixture was concentrated to give 2-(5-{6-[(3S,4S)-4-amino-3-methyl-2-oxa-8-azaspiro[4.5]decan-8-yl]-1H-pyrazolo[3,4-b]pyrazin-3-yl}-5,6,7,8-tetrahydro-1,5-naphthyridin-2-yl)acetic acid hydrochloride (65.0 mg, 93.5% yield) as a white solid.

Step f: A mixture of 2-(5-{6-[(3S,4S)-4-amino-3-methyl-2-oxa-8-azaspiro[4.5]decan-8-yl]-1H-pyrazolo[3,4-b]pyrazin-3-yl}-5,6,7,8-tetrahydro-1,5-naphthyridin-2-yl)acetic acid hydrochloride (50 mg, 97.0 μmol), DIPEA (118 mg, 970 μmol), HATU (44.0 mg, 116 μmol) and MeNH2.HCl (6.4 mg, 97.0 μmol) in DMF (2 mL) was stirred at 25° C. for 12 hours under N2. LCMS showed the desired product formed, the mixture purified by prep-HPLC (NH3.H2O) to afford the 2-(5-{6-[(3S,4S)-4-amino-3-methyl-2-oxa-8-azaspiro[4.5]decan-8-yl]-1H-pyrazolo[3,4-b]pyrazin-3-yl}-5,6,7,8-tetrahydro-1,5-naphthyridin-2-yl)-N-methylacetamide (16.2 mg, 34.0% yield) as a yellow solid.

Synthesis of (3S,4S)-8-{3-[(4S)-6-[(1E)-(methoxyimino)methyl]-4-methyl-1,2,3,4-tetrahydroquinolin-1-yl]-1H-pyrazolo[3,4-b]pyrazin-6-yl}-3-methyl-2-oxa-8-azaspiro[4.5]decan-4-amine, Compound 426

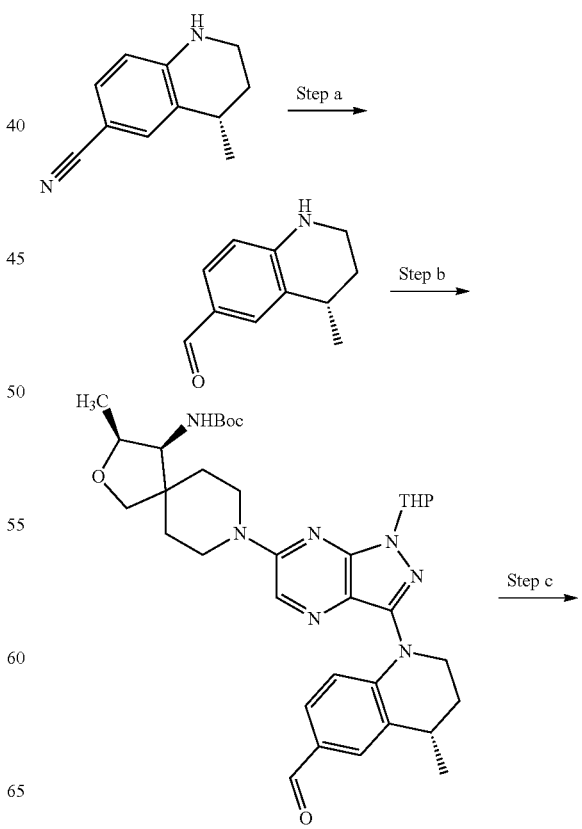

441

-continued

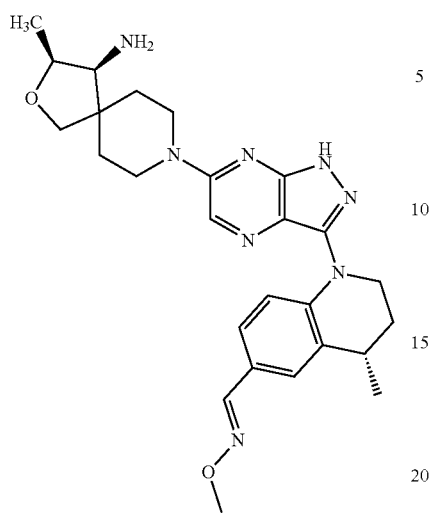

Step a: (4S)-4-methyl-1,2,3,4-tetrahydroquinoline-6-carbonitrile (100 mg, 0.5806 mmol) in THF (4 mL) was charged with 1M LAH(1.74 mL, 1.74 mmol) at rt and stirred for 15 min. The reaction was cooled to −10° C., charged with a few drops of methanol (until gas evolution ceased) and 1N HCl (2 mL) then the mixture was let warm to rt and stirred for 1 hr. The reaction mixture was partitioned between ethyl acetate and brine. The org layer was dried and concentrated to afford (4S)-4-methyl-1,2,3,4-tetrahydroquinoline-6-carbaldehyde (90 mg) as a yellow oil that crystallized upon standing. LCMS: [M+H]$^+$ 176.

Step b: tert-butyl N-[(3S,4S)-8-{3-[(4S)-6-formyl-4-methyl-1,2,3,4-tetrahydroquinolin-1-yl]-1-(oxan-2-yl)-1H-pyrazolo[3,4-b]pyrazin-6-yl}-3-methyl-2-oxa-8-azaspiro[4.5]decan-4-yl]carbamate (240 mg) was prepared using tert-butyl N-[(3S,4S)-8-[3-iodo-1-(oxan-2-yl)-1H-pyrazolo[3,4-b]pyrazin-6-yl]-3-methyl-2-oxa-8-azaspiro[4.5]decan-4-yl]carbamate (300 mg, 0.501 mmol), and (4S)-4-methyl-1,2,3,4-tetrahydroquinoline-6-carbaldehyde (87 mg, 0.501 mmol) using conditions described for the preparation of Compound 33.

Step c: tert-butyl N-[(3S,4S)-8-{3-[(4S)-6-formyl-4-methyl-1,2,3,4-tetrahydroquinolin-1-yl]-1-(oxan-2-yl)-1H-pyrazolo[3,4-b]pyrazin-6-yl}-3-methyl-2-oxa-8-azaspiro[4.5]decan-4-yl]carbamate (100 mg, 0.1548 mmol) in EtOH (4 mL) was charged with triethylamine (64.6 μL, 0.4644 mmol) and O-methylhydroxylamine hydrochloride (19.3 mg, 0.2322 mmol). The vial was sealed and stirred at 60° C. for 24 hrs. The cooled reaction mixture was charged with 4N hydrogen chloride (502 μL, 2.01 mmol) and stirred at rt for 2 hrs. Solvent was removed and purified on preparative HPLC to afford (3S,4S)-8-(3-[(4S)-6-[(1E)-(methoxyimino)methyl]-4-methyl-1,2,3,4-tetrahydroquinolin-1-yl]-1H-pyrazolo[3,4-b]pyrazin-6-yl)-3-methyl-2-oxa-8-azaspiro[4.5]decan-4-amine (36 mg, 20/1 E/Z ratio) of yellow solid. LCMS: [M+H]$^+$ 176.

442

Synthesis of (3S,4S)-3-methyl-8-{3-[6-(1,2,3,6-tetrahydropyridin-4-yl)-1,2,3,4-tetrahydro-1,5-naphthyridin-1-yl]-1H-pyrazolo[3,4-b]pyrazin-6-yl}-2-oxa-8-azaspiro[4.5]decan-4-amine hydrochloride, Compound 427

Step a: The mixture of tert-butyl N-[(3S,4S)-8-[3-(6-chloro-1,2,3,4-tetrahydro-1,5-naphthyridin-1-yl)-1-(oxan-2-yl)-1H-pyrazolo[3,4-b]pyrazin-6-yl]-3-methyl-2-oxa-8-azaspiro[4.5]decan-4-yl]carbamate (80.0 mg, 125.0 umol), Pd(dppf)Cl$_2$ (9.2 mg, 12.5 μmol), Cs$_2$CO$_3$ (122.0 mg, 375.0 umol) and tert-butyl 4-(4,4,5,5-tetramethyl-1,3,2-dioxaborolan-2-yl)-1,2,3,6-tetrahydropyridine-1-carboxylate (50.0 mg, 162 umol) in dioxane/H₂O (5.0 mL/0.5 mL) was stirred at 100° C. for 12 hours. The reaction mixture was concentrated and purified by flash silica gel chromatography (Ethyl acetate/Petroleum ether=0/100 to 50/100) to afford the product of tert-butyl 4-(5-{6-[(3S,4S)-4-{[(tert-butoxy) carbonyl]amino}-3-methyl-2-oxa-8-azaspiro[4.5]decan-8-yl]-1-(oxan-2-yl)-1H-pyrazolo[3,4-b]pyrazin-3-yl}-5,6,7,8-tetrahydro-1,5-naphthyridin-2-yl)-1,2,3,6-tetrahydropyridine-1-carboxylate (70.0 mg, 71.2% yield) as a yellow oil.

Step b: The compound of tert-butyl 4-(5-{6-[(3S,4S)-4-{[(tert-butoxy)carbonyl]amino}-3-methyl-2-oxa-8-azaspiro[4.5]decan-8-yl]-1-(oxan-2-yl)-1H-pyrazolo[3,4-b]pyrazin-3-yl}-5,6,7,8-tetrahydro-1,5-naphthyridin-2-yl)-1,2,3,6-tetrahydropyridine-1-carboxylate (70.0 mg, 89.0 umol) in 2 N HCl/MeOH (4.0 mL) was stirred at 25° C. for 12 hours. The reaction mixture was concentrated and was purified by prep-HPLC (HCl) to afford (3S,4S)-3-methyl-8-(3-[6-(1,2,3,6-tetrahydropyridin-4-yl)-1,2,3,4-tetrahydro-1,5-naphthyridin-1-yl]-1H-pyrazolo[3,4-b]pyrazin-6-yl)-2-oxa-8-azaspiro[4.5]decan-4-amine hydrochloride (29.6 mg, 61.9% yield) as a yellow solid.

Synthesis of (3S,4S)-8-{3-[6-chloro-5-(5-methyl-1,3,4-oxadiazol-2-yl)-1,2,3,4-tetrahydroquinolin-1-yl]-1H-pyrazolo[3,4-b]pyrazin-6-yl}-3-methyl-2-oxa-8-azaspiro[4.5]decan-4-amine, Compound 429

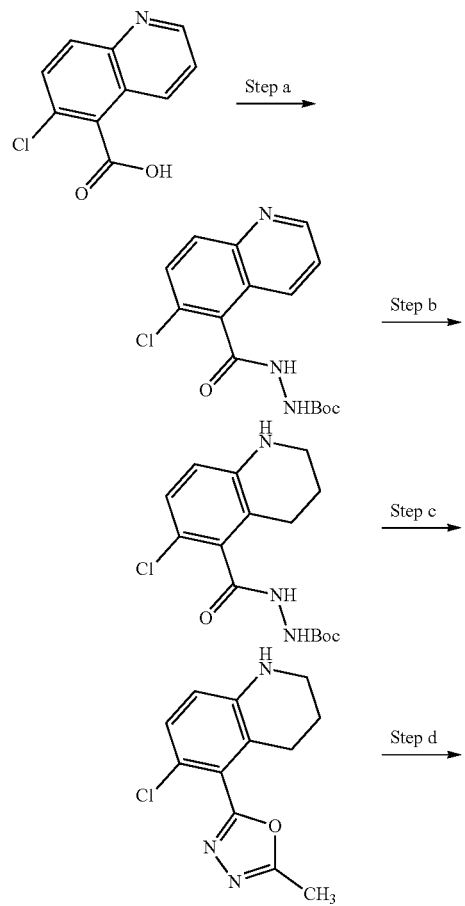

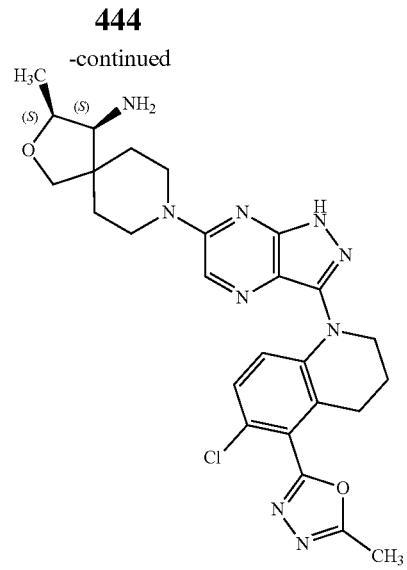

Step a: A resealable reaction vial was charged with 6-chloroquinoline-5-carboxylic acid (500 mg, 2.40 mmol), HATU (1.09 g, 2.88 mmol), DMF (12 mL) and triethylamine (668 μL, 4.80 mmol). The mixture was stirred for 10 min and charged with (tert-butoxy)carbohydrazide (380 mg, 2.88 mmol). The vial was sealed, and the mixture was stirred at 25° C. for 45 min. the reaction mixture was diluted with ethyl acetate, washed with water, brine, dried over anhydrous sodium sulfate, and filtered. The combined organics were concentrated under reduced pressure, and purified by flash silica gel chromatography (eluting with ethyl acetate: heptanes=25:75 to 75:25) to afford N'-[(tert-butoxy)carbonyl]-6-chloroquinoline-5-carbohydrazide (500 mg) as a yellow oil.

Step b: N'-[(tert-butoxy)carbonyl]-6-chloroquinoline-5-carbohydrazide (875 mg, 2.71 mmol), diphenoxyphosphinic acid (135 mg, 0.542 mmol) and 2-[5-(ethoxycarbonyl)-2,6-dimethyl-1,4-dihydropyridine-3-carbonyloxy]ethylium (2.05 g, 8.13 mmol) were dissolved in toluene (20 ml) and THF (10 mL). The vial was sealed, and the mixture stirred at 80° C. for 6 hrs. Solvent was removed and purified by flash silica gel chromatography (eluting with ethyl acetate: heptanes=0:100 to 50:50) to afford N'-[(tert-butoxy)carbonyl]-6-chloro-1,2,3,4-tetrahydroquinoline-5-carbohydrazide (351 mg) as a white solid. LCMS: [M+H]⁺ 326.

Step c: N'-[(tert-butoxy)carbonyl]-6-chloro-1,2,3,4-tetrahydroquinoline-5-carbohydrazide (350 mg, 1.07 mmol) in MeOH (4 mL) was charged with 4N HCl in dioxane (1 mL) and stirred at 60° C. for 6 hrs. Reaction mixture was concentrated to dryness, chased with dioxane to afford a peach solid. The solid was suspended in 1,1,1-triethoxyethane (3.92 mL, 21.4 mmol) and added a few drops of EtOH then heated to 200° C. in MW for 1 hr. The solvent was removed on rotavap, taken up in ethyl acetate and purified by flash silica gel chromatography (eluting with ethyl acetate:heptanes=20:80 to 60:40) to afford 6-chloro-5-(5-methyl-1,3,4-oxadiazol-2-yl)-1,2,3,4-tetrahydroquinoline (130 mg) as a white solid. LCMS: [M+H]⁺ 250.

Step d: (3S,4S)-8-{3-[6-chloro-5-(5-methyl-1,3,4-oxadiazol-2-yl)-1,2,3,4-tetrahydroquinolin-1-yl]-1H-pyrazolo[3,4-b]pyrazin-6-yl}-3-methyl-2-oxa-8-azaspiro[4.5]decan-4-amine (5 mg) (LCMS: [M+H]⁺ 536) was prepared using tert-butyl N-[(3S,4S)-8-[3-iodo-1-(oxan-2-yl)-1H-pyrazolo[3,4-b]pyrazin-6-yl]-3-methyl-2-oxa-8-azaspiro[4.5]decan-4-yl]carbamate (150 mg, 0.250 mmol), and 6-chloro-5-(5- methyl-1,3,4-oxadiazol-2-yl)-1,2,3,4-tetrahydroquinoline (63 mg, 0.250 mmol) using conditions described for the preparation of Compound 33.

Synthesis of (3S,4S)-3-methyl-8-{3-[(4S)-4-methyl-6-(1H-pyrazol-5-yl)-1,2,3,4-tetrahydro-1,5-naphthyridin-1-yl]-1H-pyrazolo[3,4-b]pyrazin-6-yl}-2-oxa-8-azaspiro[4.5]decan-4-amine, Compound 430

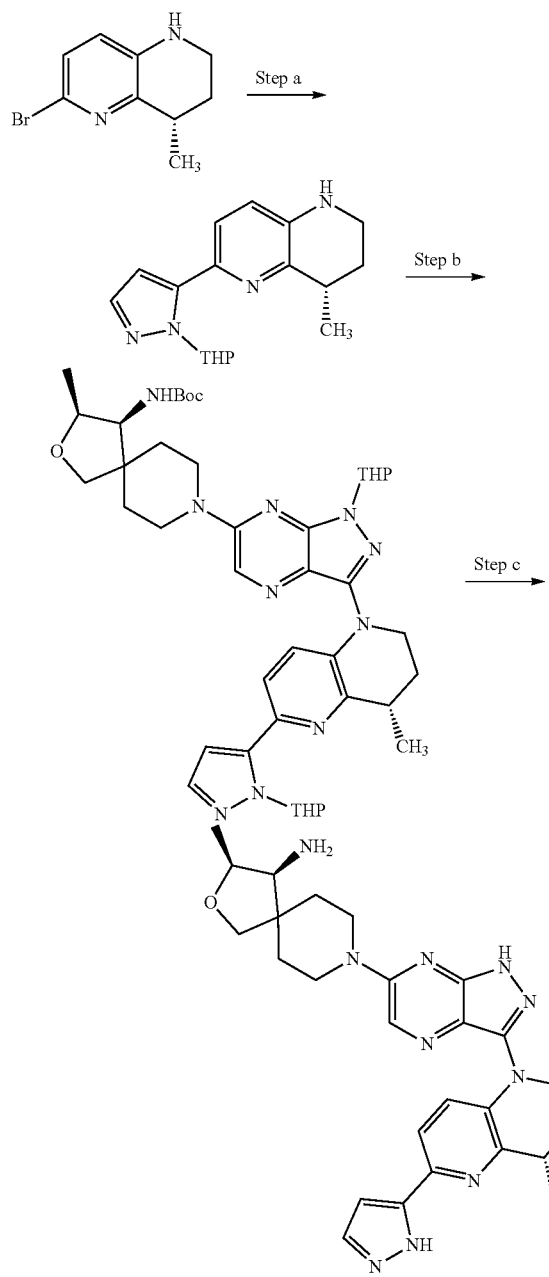

Step a: To a solution of (4S)-6-bromo-4-methyl-1,2,3,4-tetrahydro-1,5-naphthyridine (100 mg, 440 µmol) in dioxane (10 mL) and H₂O (1 mL) were added Cs₂CO₃ (286 mg, 880 µmol), 1-(oxan-2-yl)-5-(4,4,5,5-tetramethyl-1,3,2-dioxaborolan-2-yl)-1H-pyrazole (122 mg, 440 umol), and Pd(dppf)Cl₂ (42.3 mg, 44 umol). The reaction mixture was stirred at 100° C for 12 hours, concentrated under reduced pressure, and purified by silica gel column chromatography (50-70% EtOAc/petroleum ether) to give (4S)-4-methyl-6-[1-(oxan-2-yl)-1H-pyrazol-5-yl]-1,2,3,4-tetrahydro-1,5-naphthyridine (80 mg, 61% yield) as a yellow solid.

Step b: A mixture of (4R)-4-methyl-6-[1-(oxan-2-yl)-1H-pyrazol-5-yl]-1,2,3,4-tetrahydro-1,5-naphthyridine (60 mg, 201 µmol), Cs₂CO₃ (131 mg, 402 µmol), XantPhos-Pd-G4 (19.3 mg, 20.1 µmol) and tert-butyl N-[(3S,4S)-8-[3-iodo-1-(oxan-2-yl)-1H-pyrazolo[3,4-b]pyrazin-6-yl]-3-methyl-2-oxa-8-azaspiro[4.5]decan-4-yl]carbamate (120 mg, 201 µmol) in toluene (10 mL) was stirred at 100° C. for 2 hours under N₂. The reaction mixture was concentrated under reduced pressure and purified by silica gel chromatography (0-50% EtOAc/petroleum ether) to give tert-butyl N-[(3S,4S)-3-methyl-8-{3-[(4R)-4-methyl-6-[1-(oxan-2-yl)-1H-pyrazol-5-yl]-1,2,3,4-tetrahydro-1,5-naphthyridin-1-yl]-1-(oxan-2-yl)-1H-pyrazolo[3,4-b]pyrazin-6-yl}-2-oxa-8-azaspiro[4.5]decan-4-yl]carbamate (96 mg, 62% yield) as a yellow solid.

Step c: To a solution of tert-butyl N-[(3S,4S)-3-methyl-8-{3-[(4S)-4-methyl-6-[1-(oxan-2-yl)-1H-pyrazol-5-yl]-1,2,3,4-tetrahydro-1,5-naphthyridin-1-yl]-1-(oxan-2-yl)-1H-pyrazolo[3,4-b]pyrazin-6-yl}-2-oxa-8-azaspiro[4.5]decan-4-yl]carbamate (70 mg, 91 µmol) in MeOH (2 mL) was added 4M HCl/MeOH (680 uL), and the mixture was stirred at 30° C. for 4 hours. The reaction mixture was concentrated and purified by prep-HPLC (acetonitrile/aq. HCl) to afford (3S,4S)-3-methyl-8-{3-[(4S)-4-methyl-6-(1H-pyrazol-5-yl)-1,2,3,4-tetrahydro-1,5-naphthyridin-1-yl]-1H-pyrazolo[3,4-b]pyrazin-6-yl}-2-oxa-8-azaspiro[4.5]decan-4-amine hydrochloride (45 mg, 92% yield) as a yellow solid: ESMS: [M+H]+=501.1; ¹H-NMR (400 MHz, CD₃OD): δ 8.44 (s, 1H), 8.13-8.11 (m, 1H), 7.98-7.96 (m, 1H), 7.91-7.90 (m, 1H), 7.06 (s, 1H), 4.51-4.40 (m, 3H), 4.25-4.20 (m, 1H), 4.12-4.10 (m, 2H), 3.92-3.88 (m, 1H), 3.75-3.72 (m, 1H), 3.52-3.48 (m, 1H), 3.42-3.40 (m, 1H), 3.28-3.22 (m, 1H), 2.41-2.26 (m, 1H), 2.21-2.19 (m, 1H), 1.98-1.92 (m, 3H), 1.81-1.78 (m, 1H), 1.59 (d, J=5.2 Hz, 3H), 1.36 (d, J=6.4 Hz, 3H).

Synthesis of (1-{6-[(3S,4S)-4-amino-3-methyl-2-oxa-8-azaspiro[4.5]decan-8-yl]-1H-pyrazolo[3,4-b]pyrazin-3-yl}-1,2,3,4-tetrahydroquinolin-5-yl)methanol, Compound 431

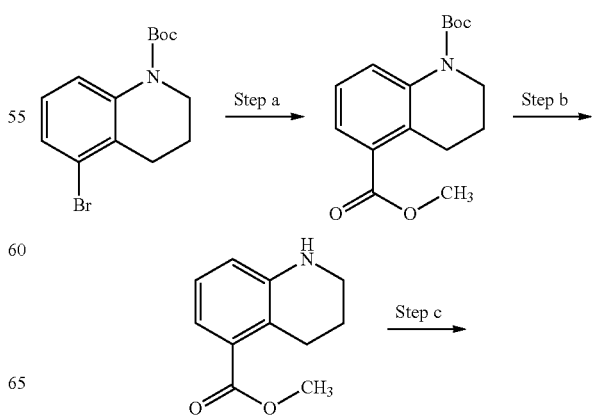

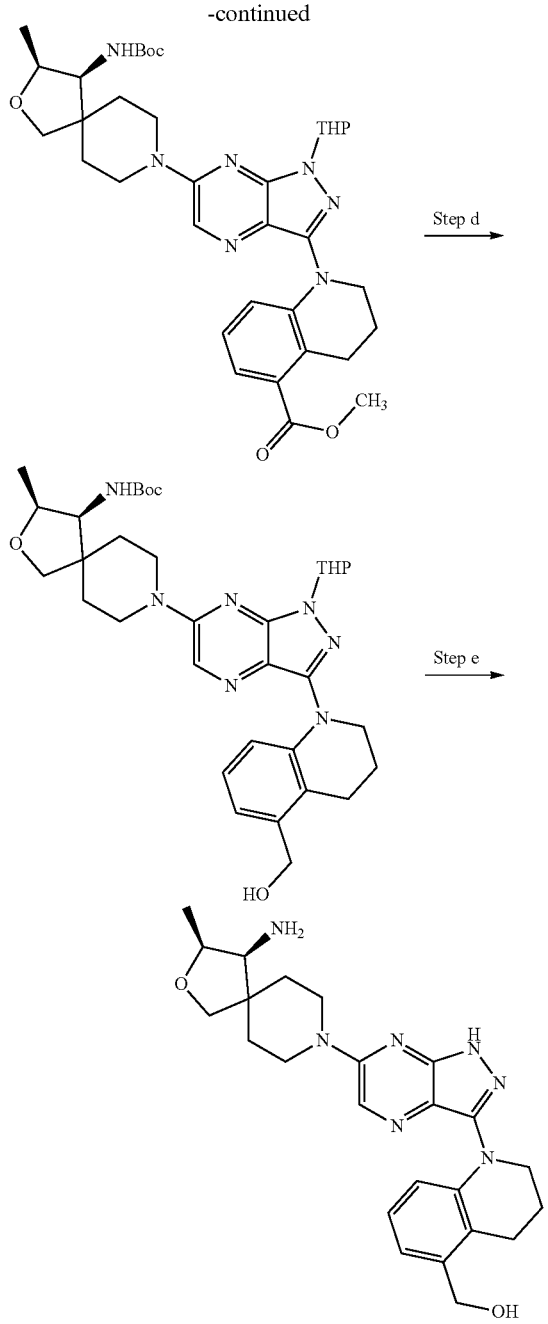

was concentrated under reduced pressure and MeOH (2 mL) and K$_2$CO$_3$ (100 mg) were added. The mixture was filtered and the filtrate concentrated under reduced pressure give methyl 1,2,3,4-tetrahydroquinoline-5-carboxylate (80 mg, 94% yield) as a colorless oil.

Step c: A mixture of methyl 1,2,3,4-tetrahydroquinoline-5-carboxylate (40 mg, 209 μmol), tert-butyl N-[(3S,4S)-8-[3-iodo-1-(oxan-2-yl)-1H-pyrazolo[3,4-b]pyrazin-6-yl]-3-methyl-2-oxa-8-azaspiro[4.5]decan-4-yl]carbamate (125 mg, 209 μmol), Cs$_2$CO$_3$ (136 mg, 418 μmol), XantPhos-Pd-G4 (19.4 mg, 20.9 μmol) in toluene (5 mL) was stirred at 100° C. for 12 hours under N$_2$. The reaction mixture concentrated under reduced pressure and purified by silica gel column chromatography (50% EtOAc/petroleum ether) to give methyl 1-{6-[(3S,4S)-4-{[(tert-butoxy)carbonyl]amino}-3-methyl-2-oxa-8-azaspiro[4.5]decan-8-yl]-1-(oxan-2-yl)-1H-pyrazolo[3,4-b]pyrazin-3-yl}-1,2,3,4-tetrahydroquinoline-5-carboxylate (80 mg, 58% yield) as a yellow solid.

Step d: To a mixture of methyl 1-(6-[(3S,4S)-4-{[(tert-butoxy)carbonyl]amino}-3-methyl-2-oxa-8-azaspiro[4.5]decan-8-yl]-1-(oxan-2-yl)-1H-pyrazolo[3,4-b]pyrazin-3-yl)-1,2,3,4-tetrahydroquinoline-5-carboxylate (74 mg, 111 μmol) in THF (10 mL) was added LiBH$_4$ (13.9 mg, 666 μmol) at 0° C., and the reaction mixture stirred at 25° C. for 2 hours. Sat, NH$_4$Cl (aq.) was then added slowly and the mixture extracted by EtOAc (20 mL×3). The combined organics were concentrated to give tert-butyl N-[(3S,4S)-8-{3-[5-(hydroxymethyl)-1,2,3,4-tetrahydroquinolin-1-yl]-1-(oxan-2-yl)-1H-pyrazolo[3,4-b]pyrazin-6-yl}-3-methyl-2-oxa-8-azaspiro[4.5]decan-4-yl]carbamate (70 mg, 99% yield) as a yellow solid.

Step e: A mixture of tert-butyl N-[(3S,4S)-8-{3-[5-(hydroxymethyl)-1,2,3,4-tetrahydroquinolin-1-yl]-1-(oxan-2-yl)-1H-pyrazolo[3,4-b]pyrazin-6-yl}-3-methyl-2-oxa-8-azaspiro[4.5]decan-4-yl]carbamate (50 mg, 78.8 μmol) in DCM (5 mL) and TFA (1 mL) was stirred at 40° C. for 6 hours under N$_2$. The reaction mixture was concentrated under reduced pressure and MeOH (2 mL) and K$_2$CO$_3$ (100 mg) were added. The mixture was filtered and the filtrate was concentrated under reduced pressure. Purification by prep-HPLC (acetonitrile/aq. NH$_3$—H$_2$O) afforded (1-{6-[(3S,4S)-4-amino-3-methyl-2-oxa-8-azaspiro[4.5]decan-8-yl]-1H-pyrazolo[3,4-b]pyrazin-3-yl}-1,2,3,4-tetrahydroquinolin-5-yl)methanol (26 mg, 73% yield) as a yellow solid: ESMS [M+H]+=450.2; $^1$H-NMR (400 MHz, CD$_3$OD): δ 8.16 (s, 1H), 6.98-6.78 (m, 2H), 6.77-6.76 (m, 1H), 4.66 (s, 2H), 4.26-2.23 (m, 3H), 3.92-3.86 (m, 3H), 3.76-3.74 (m, 1H), 3.49-3.40 (m, 2H), 3.12-3.10 (m, 1H), 2.92-2.88 (m, 2H), 2.20-2.02 (m, 2H), 1.88-1.62 (m, 4H), 1.25-1.23 (m, 3H).

Synthesis of (3S,4S)-3-methyl-8-{3-[5-(1,2,4-oxadiazol-3-yl)-1,2,3,4-tetrahydroquinolin-1-yl]-1H-pyrazolo[3,4-b]pyrazin-6-yl}-2-oxa-8-azaspiro[4.5]decan-4-amine, Compound 433

Step a: To a solution of tert-butyl 5-bromo-3,4-dihydroquinoline-1(2H)-carboxylate (1.5 g, 4.8 mmol) in MeOH (20 mL) was added Pd(dppf)Cl$_2$ (351 mg, 480 μmol) and TEA (1.4 g, 14.3 mmol) at 20° C. The mixture was evacuated and refilled 3 times with carbon monoxide, then stirred at 80° C. for 12 hours under and atmosphere of CO (50 psi). The reaction mixture was cooled and concentrated under reduced pressure, followed by silica gel chromatography purification (9-20% EtOAc/petroleum ether) to afford 1-tert-butyl 5-methyl 1,2,3,4-tetrahydroquinoline-1,5-dicarboxylate (1.3 g, 90% yield) as a yellow solid.

Step b: To a solution of 1-tert-butyl 5-methyl 1,2,3,4-tetrahydroquinoline-1,5-dicarboxylate (130 mg, 446 μmol) in MeOH (2 mL) was added 4M HCl/MeOH (2 mL) and the mixture stirred at 20° C. for 2 hours. The reaction mixture

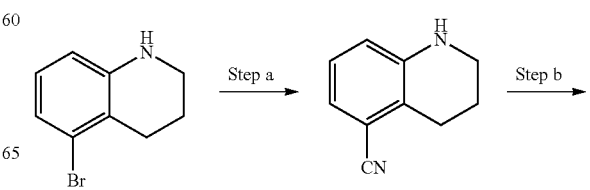

449
-continued

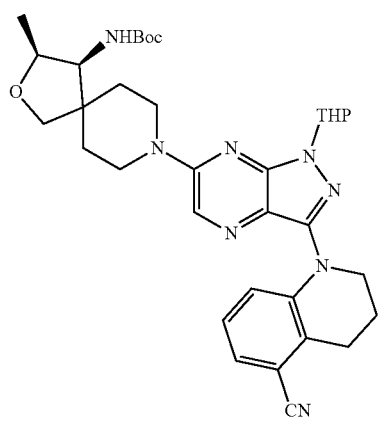

Step c →

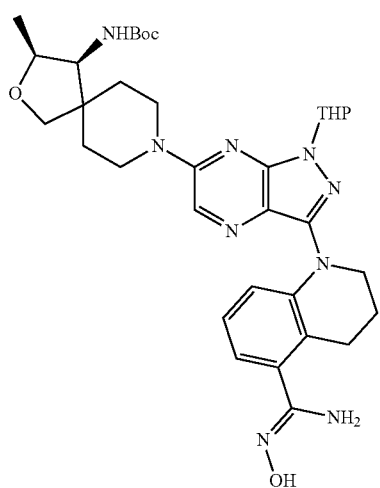

Step d →

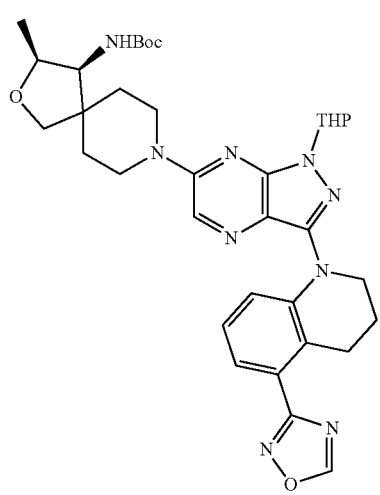

Step e →

450
-continued

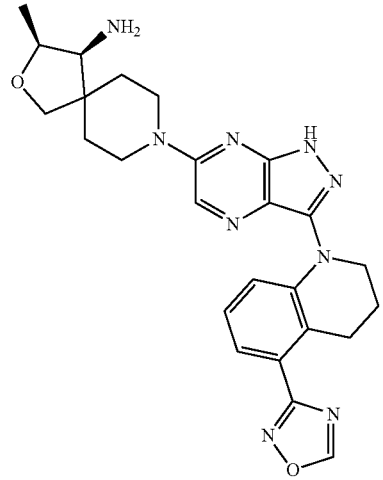 [SMILES: C[C@@H]1OCC2(CCN(c3cnc4c(N5CCCc6c(-c7ncon7)cccc65)n[nH]c4n3)CC2)[C@@H]1N]

Step a: A solution of 5-bromo-1,2,3,4-tetrahydroquinoline (500.0 mg, 2.35 mmol), Zn(CN)$_2$ (689.0 mg, 5.87 mmol), Pd2(dba)$_3$ (537.0 mg, 587.0 umol), dppf (64.9 mg, 120.0 umol) and Zn (18.3 mg, 280.0 umol) in DMF (15.0 mL) was stirred at 120° C. for 12 hours under N2. Brown solution was observed. Desired mass ion was observed from LCMS. The solution was added into H$_2$O (100.0 mL) and then extracted with EtOAc (100.0 mL×2). The combined organic layers were washed with brine (100.0 mL), dried over anhydrous Na2SO4, filtered and concentrated in vacuum to give crude product as a brown gum. The residue was purified by flash silica gel chromatography (12 g, Ethyl acetate in Petroleum ether from 0% to 15%) to give 1,2,3,4-tetrahydroquinoline-5-carbonitrile (370.0 mg, 99.7% yield) as an orange oil.

Step b: A solution of tert-butyl N-[(3S,4S)-8-[3-iodo-1-(oxan-2-yl)-1H-pyrazolo[3,4-b]pyrazin-6-yl]-3-methyl-2-oxa-8-azaspiro[4.5]decan-4-yl]carbamate (300.0 mg, 500.0 umol), 1,2,3,4-tetrahydroquinoline-5-carbonitrile (87.1 mg, 550.0 umol), XantPhos-Pd-G4 (48.1 mg, 50.0 umol) and Cs2CO3 (325.0 mg, 1.00 mmol) in PhMe (20.0 mL) was stirred at 80° C. for 12 hours under N2. Brown solution was observed. Desired mass ion was observed from LCMS. The reaction mixture was concentrated to give a residue. The residue was purified by flash silica gel chromatography (20 g, Ethyl acetate in Petroleum ether from 0% to 45%) to give tert-butyl N-[(3S,4S)-8-[3-(5-cyano-1,2,3,4-tetrahydroquinolin-1-yl)-1-(oxan-2-yl)-1H-pyrazolo[3,4-b]pyrazin-6-yl]-3-methyl-2-oxa-8-azaspiro[4.5]decan-4-yl]carbamate (270.0 mg, 85.9% yield) as a yellow oil.

Step c: A solution of tert-butyl N-[(3S,4S)-8-[3-(5-cyano-1,2,3,4-tetrahydroquinolin-1-yl)-1-(oxan-2-yl)-1H-pyrazolo[3,4-b]pyrazin-6-yl]-3-methyl-2-oxa-8-azaspiro[4.5]decan-4-yl]carbamate (270.0 mg, 430.0 umol), NH$_2$OH HCl (297.0 mg, 4.28 mmol) and TEA (432.0 mg, 4.28 mmol) in EtOH (10.0 mL) was stirred at 70° C. for 12 hours. Yellow suspension was observed. Desired mass ion was observed from LCMS. The reaction mixture was concentrated to give a residue. The solution was added into H$_2$O (30.0 mL) and then extracted with EtOAc (30.0 mL×2). The combined organic layers were washed with brine (30.0 mL), dried over anhydrous Na2SO4, filtered and concentrated in vacuum to give tert-butyl N-[(3S,4S)-8-{3-(5-[(Z)—N'-hydroxycarbamimidoyl]-1,2,3,4-tetrahydroquinolin-1-yl}-1-(oxan-2-yl)-1H-pyrazolo[3,4-b]pyrazin-6-yl)-3-methyl-2-oxa-8-azaspiro[4.5]decan-4-yl]carbamate (300.0 mg, crude) as a yellow gum. The gum was used in the next step without further purification.

Step d: A solution of tert-butyl N-[(3S,4S)-8-(3-{5-[(Z)—N'-hydroxycarbamimidoyl]-1,2,3,4-tetrahydroquinolin-1-yl}-1-(oxan-2-yl)-1H-pyrazolo[3,4-b]pyrazin-6-yl)-3-methyl-2-oxa-8-azaspiro[4.5]decan-4-yl]carbamate (300.0 mg, 450.0 umol), HC(OEt)3 (1.34 g, 9.06 mmol) and TsOH (23.2 mg, 140.0 umol) in dioxane (5.0 mL) was stirred at 120° C. for 12 hours. Orange solution was observed. Desired mass ion was observed from LCMS. The mixture was concentrated to give a residue. The residue was purified by flash silica gel chromatography (12 g, Ethyl acetate in Petroleum ether from 0% to 50%) to give tert-butyl N-[(3S,4S)-3-methyl-8-{3-[5-(1,2,4-oxadiazol-3-yl)-1,2,3,4-tetrahydroquinolin-1-yl]-1-(oxan-2-yl)-1H-pyrazolo[3,4-b]pyrazin-6-yl}-2-oxa-8-azaspiro[4.5]decan-4-yl]carbamate (130.0 mg, 42.7% yield) as a yellow oil.

Step e: A solution of tert-butyl N-[(3S,4S)-3-methyl-8-(3-[5-(1,2,4-oxadiazol-3-yl)-1,2,3,4-tetrahydroquinolin-1-yl]-1-(oxan-2-yl)-1H-pyrazolo[3,4-b]pyrazin-6-yl)-2-oxa-8-azaspiro[4.5]decan-4-yl]carbamate (120.0 mg, 180.0 umol) in TFA/DCM (2.0 mL/10.0 mL) was stirred at 25° C. for 1 hour. Orange solution was observed. Desired mass ion was observed from LCMS. The reaction mixture was concentrated in vacuum. The residue was diluted with THF (5.0 mL), adjusted to pH=8 with Na2CO3 solid and purified by prep-HPLC (NH3.H2O). (3S,4S)-3-methyl-8-{3-[5-(1,2,4-oxadiazol-3-yl)-1,2,3,4-tetrahydroquinolin-1-yl]-1H-pyrazolo[3,4-b]pyrazin-6-yl}-2-oxa-8-azaspiro[4.5]decan-4-amine (20.0 mg, 23.0% yield) was obtained as a yellow solid. HNMR showed the purity was not enough for delivery.

Step f: (3S,4S)-3-methyl-8-{3-[5-(1,2,4-oxadiazol-3-yl)-1,2,3,4-tetrahydroquinolin-1-yl]-1H-pyrazolo[3,4-b]pyrazin-6-yl}-2-oxa-8-azaspiro[4.5]decan-4-amine (18.0 mg, 36.9 umol) was purified by SFC (preparative Column: DAICEL CHIRALPAK AS-H(250 mm×30 mm, 5um), Mobile phase: 0.1% NH3.H2O EtOH (Begin B: 45%, End B: 45%), Flow rate: 50 mL/min, Injection: 120). (3S,4S)-3-methyl-8-{3-[5-(1,2,4-oxadiazol-3-yl)-1,2,3,4-tetrahydroquinolin-1-yl]-1H-pyrazolo[3,4-b]pyrazin-6-yl}-2-oxa-8-azaspiro[4.5]decan-4-amine (2.9 mg, 16.2% yield) was obtained as a yellow solid.

Synthesis of 2-(1-{6-[(3S,4S)-4-amino-3-methyl-2-oxa-8-azaspiro[4.5]decan-8-yl]-1H-pyrazolo[3,4-b]pyrazin-3-yl}-1,2,3,4-tetrahydroquinolin-5-yl)-N-methylacetamide hydrochloride, Compound 434

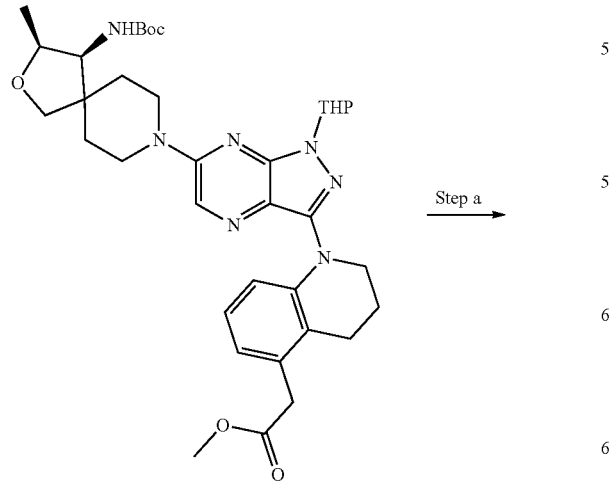

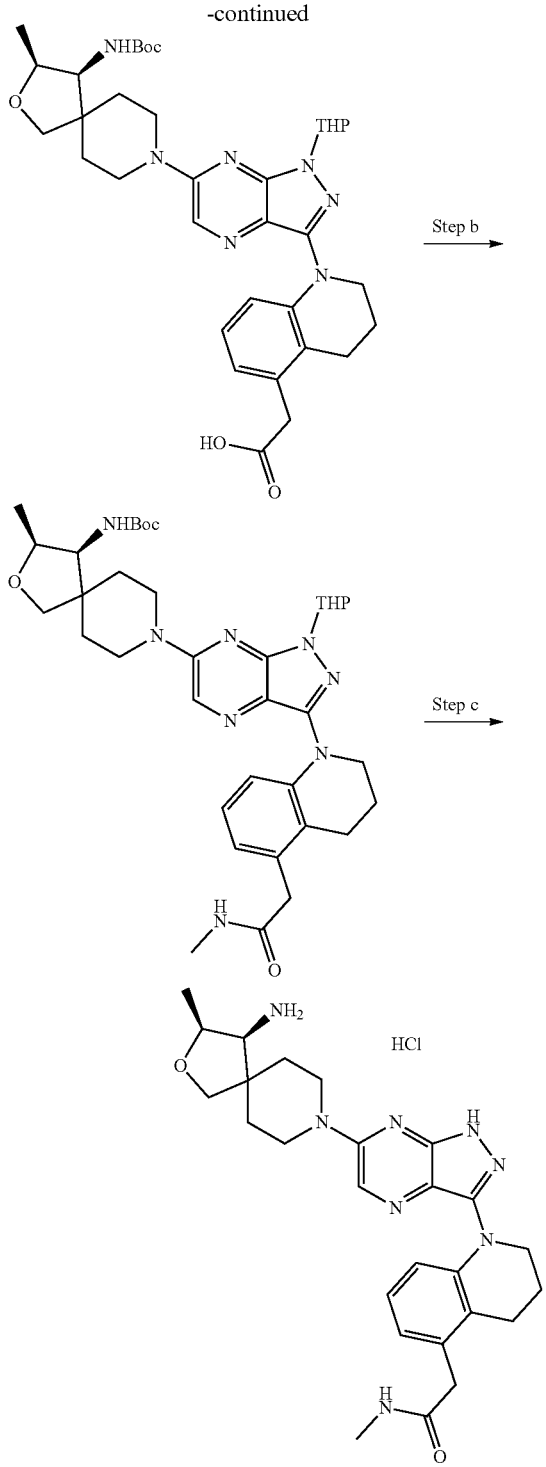

Step a: A solution of methyl 2-(1-{6-[(3S,4S)-4-{[(tert-butoxy)carbonyl]amino}-3-methyl-2-oxa-8-azaspiro[4.5]decan-8-yl]-1-(oxan-2-yl)-1H-pyrazolo[3,4-b]pyrazin-3-yl}-1,2,3,4-tetrahydroquinolin-5-yl)acetate (60.0 mg, 88.7 μmol) (formed from a coupling analogous to that for compound 33, using methyl 2-(1,2,3,4-tetrahydroquinolin-5-yl) acetate) and LiOH (10.6 mg, 443.0 μmol) in MeOH/H₂O (10.0 mL/2.0 mL) was stirred at 50° C. for 1 hour. LCMS showed the desired product formed. The reaction mixture was poured into water (20.0 mL), acidified with 2 N HCl to pH=3.0 and extracted with EtOAc (20.0 mL×2). The organic layers were dried over anhydrous Na2SO4, filtered and concentrated to give 2-(1-{6-[(3S,4S)-4-{[(tert-butoxy)carbonyl]amino}-3-methyl-2-oxa-8-azaspiro[4.5]decan-8-yl]-1-(oxan-2-yl)-1H-pyrazolo[3,4-b]pyrazin-3-yl}-1,2,3,4-tetrahydroquinolin-5-yl)acetic acid (55.0 mg, 93.6% yield) as a yellow solid.

Step b: A mixture of MeNH2 HCl (11.2 mg, 166.0 μmol), 2-(1-{6-[(3S,4S)-4-{[(tert-butoxy)carbonyl]amino}-3-methyl-2-oxa-8-azaspiro[4.5]decan-8-yl]-1-(oxan-2-yl)-1H-pyrazolo[3,4-b]pyrazin-3-yl}-1,2,3,4-tetrahydroquinolin-5-yl)acetic acid (55.0 mg, 83.1 μmol), HATU (47.1 mg, 124.0 μmol) and TEA (25.1 mg, 249.0 μmol) in DCM (10.0 mL) was stirred at 20° C. for 12 hours. LCMS showed the desired product formed. The reaction mixture was poured into water (30.0 mL) and extracted with DCM (20.0 mL×2). The organic layers were dried over anhydrous Na2SO4, filtered and concentrated to give tert-butyl N-[(3S,4S)-3-methyl-8-(3-{5-[(methylcarbamoyl)methyl]-1,2,3,4-tetrahydroquinolin-1-yl}-1-(oxan-2-yl)-1H-pyrazolo[3,4-b]pyrazin-6-yl)-2-oxa-8-azaspiro[4.5]decan-4-yl]carbamate (55.0 mg, crude) as a yellow solid.

Step c: A solution of tert-butyl N-[(3S,4S)-3-methyl-8-(3-{5-[(methylcarbamoyl)methyl]-1,2,3,4-tetrahydroquinolin-1-yl}-1-(oxan-2-yl)-1H-pyrazolo[3,4-b]pyrazin-6-yl)-2-oxa-8-azaspiro[4.5]decan-4-yl]carbamate (55.0 mg, 81.4 μmol) in 4 M HCl/MeOH (10.0 mL) was stirred at 40° C. for 2 hours under N2. LCMS showed the desired product formed. The reaction mixture was concentrated in vacuum, the residue was purified by prep-HPLC (HCl) to give 2-(1-{6-[(3S,4S)-4-amino-3-methyl-2-oxa-8-azaspiro[4.5]decan-8-yl]-1H-pyrazolo[3,4-b]pyrazin-3-yl}-1,2,3,4-tetrahydroquinolin-5-yl)-N-methylacetamide hydrochloride (35.0 mg, 81.5% yield) as a red solid.

Synthesis of (3S,4S)-8-(3-{6-[(1Z)-(hydroxyimino)methyl]-1,2,3,4-tetrahydro-1,5-naphthyridin-1-yl}-1H-pyrazolo[3,4-b]pyrazin-6-yl)-3-methyl-2-oxa-8-azaspiro[4.5]decan-4-amine hydrochloride, Compound 436

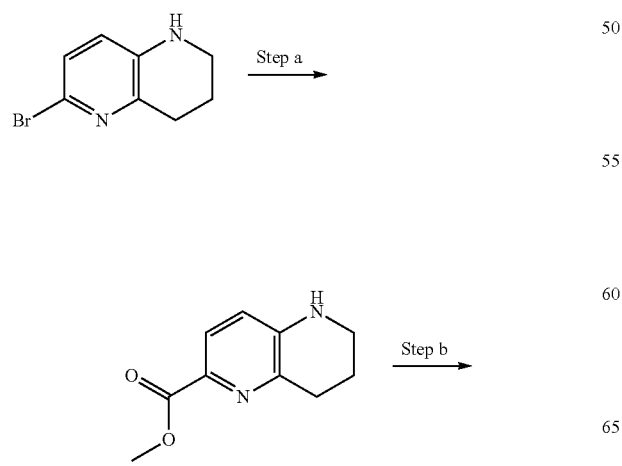

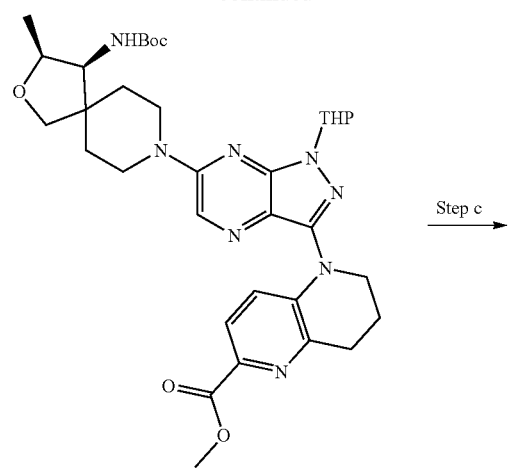

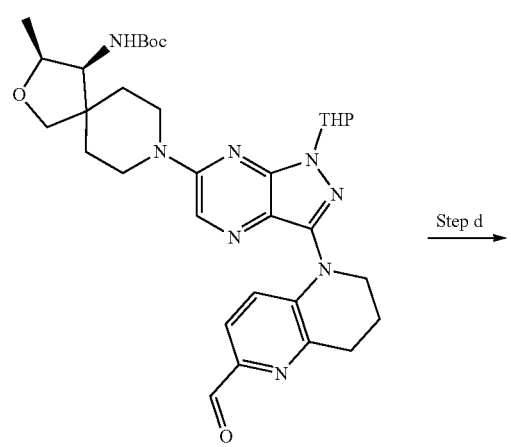

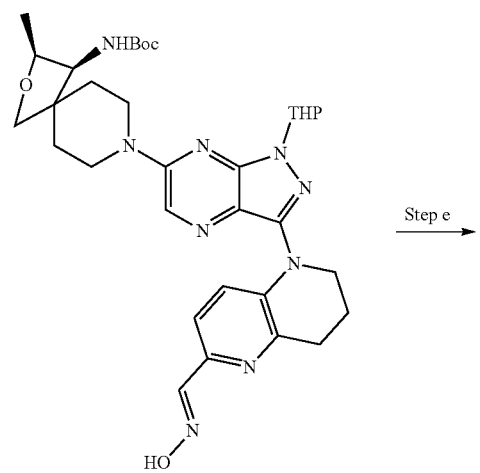

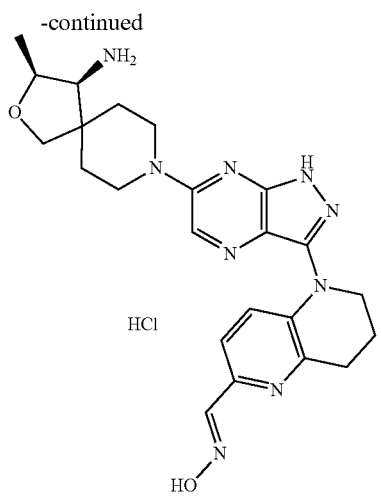

Step a: 6-Bromo-1,2,3,4-tetrahydro-1,5-naphthyridine (900.0 mg, 4.2 mmol), Pd(dppf)Cl2 (308.0 mg, 422.0 μmol) and TEA (1.7 mL, 12.6 mmol) were added in MeOH (20.0 mL), the reaction mixture was stirred at 80° C. for 48 hours under CO (50 psi). LCMS indicated 49% of desired product formed. The reaction mixture was concentrated under reduced pressure, the residue was purified by flash silica gel chromatography (Petroleum ether:Ethyl acetate=100:0 to 100:40) to afford the product of methyl 5,6,7,8-tetrahydro-1,5-naphthyridine-2-carboxylate (500.0 mg, 61.6% yield) as a yellow solid.

Step b: Methyl 5,6,7,8-tetrahydro-1,5-naphthyridine-2-carboxylate (48.0 mg, 250.0 μmol), tert-butyl N-[(3S,4S)-8-[3-iodo-1-(oxan-2-yl)-1H-pyrazolo[3,4-b]pyrazin-6-yl]-3-methyl-2-oxa-8-azaspiro[4.5]decan-4-yl]carbamate (150.0 mg, 250.0 μmol), XantPhos-Pd-G4 (24.0 mg, 25.0 μmol) and Cs2CO3 (163.0 mg, 500.0 μmol) were added in PhMe (15.0 mL), the reaction mixture was stirred at 100° C. for 12 hours under N2. LCMS indicated 18% of desired product formed. The reaction mixture was concentrated under reduced pressure. The residue was purified by flash silica gel chromatography (Petroleum ether:Ethyl acetate=100:0 to 100:50) to afford the product of methyl 5-(6-[(3S,4S)-4-{[(tert-butoxy)carbonyl]amino}-3-methyl-2-oxa-8-azaspiro[4.5]decan-8-yl]-1-(oxan-2-yl)-1H-pyrazolo[3,4-b]pyrazin-3-yl)-5,6,7,8-tetrahydro-1,5-naphthyridine-2-(160.0 mg, 43% purity, 41.6% yield) as a yellow solid.

Step c: Methyl 5-{6-[(3S,4S)-4-{[(tert-butoxy)carbonyl]amino}-3-methyl-2-oxa-8-azaspiro[4.5]decan-8-yl]-1-(oxan-2-yl)-1H-pyrazolo[3,4-b]pyrazin-3-yl}-5,6,7,8-tetrahydro-1,5-naphthyridine-2-carboxylate (160.0 mg, 43% purity, 103 μmol) was dissolved in THF (15.0 mL), the reaction mixture was cooled to −70° C., DIBAL-H (206.0 μL, 206.0 μmol) was added in the reaction mixture and stirred at −70° C. for 1 hour. LCMS indicated 22% of desired product formed. The reaction mixture was quenched with 10% AcOH (2.0 mL), diluted with EtOAc (30.0 mL), washed with H2O (30.0 mL×2), saturated NaHCO3 (30.0 mL) and brine (30.0 mL), the organic phase was dried by anhydrous Na2SO4, concentrated under reduced pressure to give the product of tert-butyl N-[(3S,4S)-8-[3-(6-formyl-1,2,3,4-tetrahydro-1,5-naphthyridin-1-yl)-1-(oxan-2-yl)-1H-pyrazolo[3,4-b]pyrazin-6-yl]-3-methyl-2-oxa-8-azaspiro[4.5]decan-4-yl]carbamate (200.0 mg, crude) as a yellow oil.

Step d: Tert-butyl N-[(3S,4S)-8-[3-(6-formyl-1,2,3,4-tetrahydro-1,5-naphthyridin-1-yl)-1-(oxan-2-yl)-1H-pyrazolo[3,4-b]pyrazin-6-yl]-3-methyl-2-oxa-8-azaspiro[4.5]decan-4-yl]carbamate (200.0 mg, crude), TEA (87.5 μL, 632.0 μmol) and NH2OH HCl (8.8 mg, 126.0 μmol) were added in EtOH (10.0 mL), the reaction mixture was stirred at 15° C. for 12 hours. LCMS indicated 38% of desired product formed. The reaction mixture was concentrated under reduced pressure to afford the product of tert-butyl N-[(3S,4S)-8-(3-{6-[(1Z)-(hydroxyimino)methyl]-1,2,3,4-tetrahydro-1,5-naphthyridin-1-yl}-1-(oxan-2-yl)-1H-pyrazolo[3,4-b]pyrazin-6-yl)-3-methyl-2-oxa-8-azaspiro[4.5]decan-4-yl]carbamate (210 mg, crude) as a yellow oil, which was used in next step without further purification.

Step e: Tert-butyl N-[(3S,4S)-8-(3-{6-[(1Z)-(hydroxyimino)methyl]-1,2,3,4-tetrahydro-1,5-naphthyridin-1-yl}-1-(oxan-2-yl)-1H-pyrazolo[3,4-b]pyrazin-6-yl)-3-methyl-2-oxa-8-azaspiro[4.5]decan-4-yl]carbamate (180.0 mg, crude) was added in 4 N HCl/MeOH (10.0 mL), the reaction mixture was stirred at 15° C. for 2 hours. LCMS indicated 96% of desired product formed. The reaction mixture was concentrated under reduced pressure and purified by prep-HPLC (HCl) to afford the product of (3S,4S)-8-(3-(6-[(1Z)-(hydroxyimino)methyl]-1,2,3,4-tetrahydro-1,5-naphthyridin-1-yl}-1H-pyrazolo[3,4-b]pyrazin-6-yl)-3-methyl-2-oxa-8-azaspiro[4.5]decan-4-amine hydrochloride (20.8 mg) as a yellow solid.

Synthesis of (8S)-5-(6-[(3S,4S)-4-amino-3-methyl-2-oxa-8-azaspiro[4.5]decan-8-yl]-1H-pyrazolo[3,4-b]pyrazin-3-yl)-N-(2-methoxyethyl)-8-methyl-5,6,7,8-tetrahydro-1,5-naphthyridine-2-carboxamide hydrochloride, Compound 437

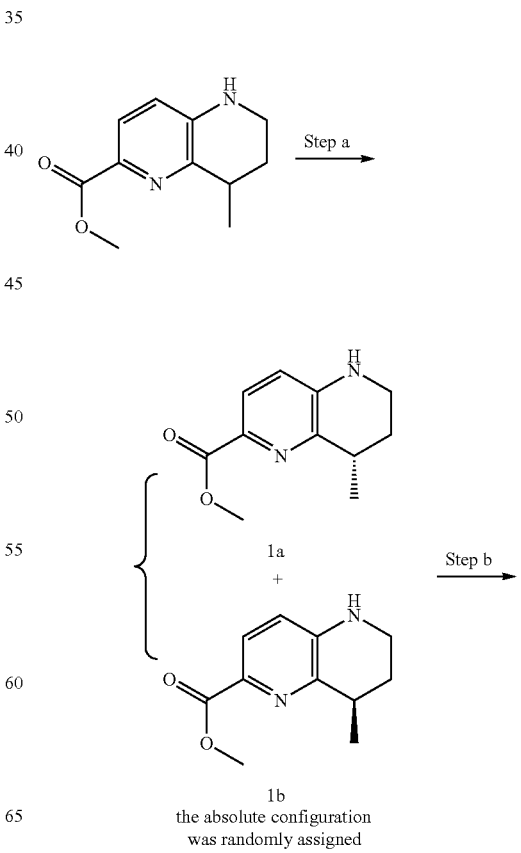

1a
+
1b
the absolute configuration was randomly assigned

457
-continued

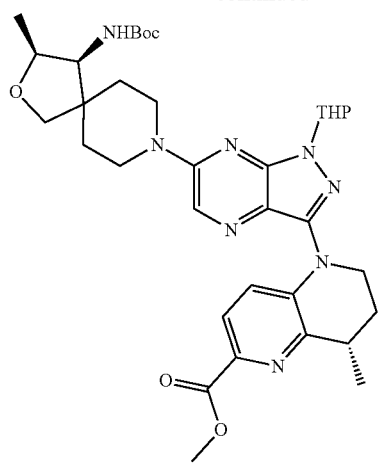

Step c →

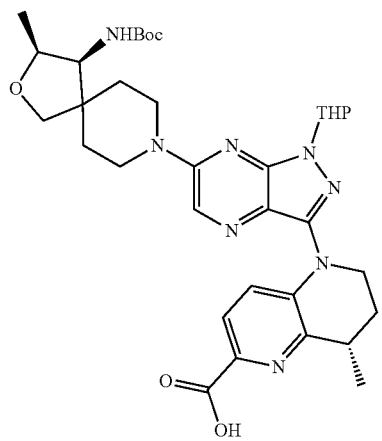

Step d →

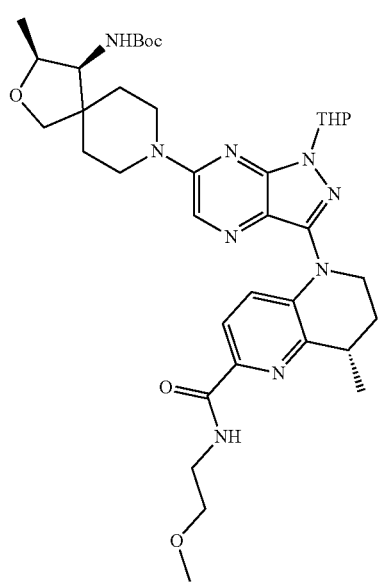

Step e →

458
-continued

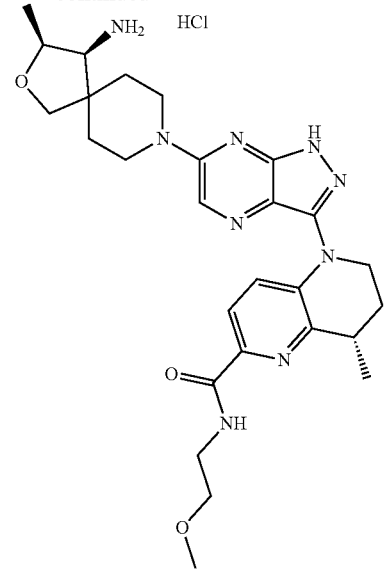

Step a: Methyl 8-methyl-5,6,7,8-tetrahydro-1,5-naphthyridine-2-carboxylate (2.0 g, 9.7 mmol) was separated by chiral SFC (Column: Phenomenex-Cellulose-2 (250 mm×50 mm, 10 um) Mobile phase: A: CO2 B: 0.1% NH3.H2O EtOH Gradient: hold 40% of B, Flow rate: 200 mL/min Column temperature: 40° C.) to afford methyl (8S)-8-methyl-5,6,7,8-tetrahydro-1,5-naphthyridine-2-carboxylate (1a, 950.0 mg, Rt=4.4 min, 47.7% yield, e.e. =99.8%) as a white solid and methyl (8R)-8-methyl-5,6,7,8-tetrahydro-1,5-naphthyridine-2-carboxylate (1b, 950.0 mg, Rt=5.7 min, 47.7% yield, e.e.=99.8%) as a white solid. In preparative SFC, peak1 is corresponding to 1a, peak 2 is corresponding to 1b.

Step b: A mixture of methyl (8S)-8-methyl-5,6,7,8-tetrahydro-1,5-naphthyridine-2-carboxylate (210.0 mg, 1.0 mmol), tert-butyl N-[(3S,4S)-8-[3-iodo-1-(oxan-2-yl)-1H-pyrazolo[3,4-b]pyrazin-6-yl]-3-methyl-2-oxa-8-azaspiro[4.5]decan-4-yl]carbamate (634.0 mg, 1.1 mmol), XantPhos-Pd-G4 (97.2 mg, 0.1 mmol) and Cs2CO3 (821.0 mg, 2.5 mmol) in toluene (20.0 mL) and the mixture was stirred at 100° C. for 12 h under N2. LCMS showed 40% of desired product formed. The combined mixture was diluted was EtOAc (200.0 mL), washed with H₂O (200.0 mL) and brine (200.0 mL). The organic phase was dried over anhydrous Na2SO4, filtered and concentrated under reduced pressure, the residue was purified by flash silica gel chromatography (Ethyl acetate in Petroleum ether=0%~80%) to afford the product of methyl (8S)-5-{6-[(3S,4S)-4-{[(tert-butoxy)carbonyl]amino}-3-methyl-2-oxa-8-azaspiro[4.5]decan-8-yl]-1-(oxan-2-yl)-1H-pyrazolo[3,4-b]pyrazin-3-yl}-8-methyl-5,6,7,8-tetrahydro-1,5-naphthyridine-2-carboxylate (1260.0 mg, 90% purity) as a yellow solid.

Step c: To a solution of methyl (8S)-5-{6-[(3S,4S)-4-{[(tert-butoxy)carbonyl]amino)-3-methyl-2-oxa-8-azaspiro[4.5]decan-8-yl]-1-(oxan-2-yl)-1H-pyrazolo[3,4-b]pyrazin-3-yl)-8-methyl-5,6,7,8-tetrahydro-1,5-naphthyridine-2-carboxylate (0.9 g, 1.3 mmol) in MeOH (10.0 mL) and H₂O (2.5 mL) was added LiOH (157.0 mg, 6.6 mmol). Then the mixture was stirred at 45° C. for 12 h. LCMS showed one peak with desired MS detected. The combined reaction mixture was concentrated under reduced pressure, diluted in H₂O (200.0 mL), adjusted to pH=5-6 by adding 1N HCl. The aqueous was extracted with EtOAc (100.0 mL×3). The combined organic layers were dried over anhydrous Na2SO4, filtered and concentrated under reduced pressure to afford the product of (8S)-5-{6-[(3S,4S)-4-{[(tert-butoxy)carbonyl]amino}-3-methyl-2-oxa-8-azaspiro[4.5]decan-8-yl]-1-(oxan-2-yl)-1H-pyrazolo[3,4-b]pyrazin-3-yl}-8-methyl-5,6,7,8-tetrahydro-1,5-naphthyridine-2-carboxylic acid (1.75 g, 97.7% purity) as a yellow solid. LCMS [M+H]+ 663.3. 1HNMR (400 MHz, CDCl3): 8.10 (s, 1H), 7.82 (d, J=8.8 Hz, 1H), 7.55-7.63 (m, 1H), 5.82 (d, J=10.4 Hz, 1H), 4.71 (d, J=10.8 Hz, 1H), 4.14-4.26 (m, 2H), 3.83-4.06 (m, 3H), 3.65-3.81 (m, 4H), 3.53-3.64 (m, 1H), 3.07-3.21 (m, 1H), 2.51-2.65 (m, 1H), 2.23-2.34 (m, 1H), 2.11-2.21 (m, 1H), 2.05 (s, 1H), 1.58-2.01 (m, 9H), 1.43-1.51 (m, 12H), 1.22 (d, J=6.0 Hz, 3H).

(8R)-5-{6-[(3S,4S)-4-{[(tert-butoxy)carbonyl]amino}-3-methyl-2-oxa-8-azaspiro[4.5]decan-8-yl]-1-(oxan-2-yl)-1H-pyrazolo[3,4-b]pyrazin-3-yl}-8-methyl-5,6,7,8-tetrahydro-1,5-naphthyridine-2-carboxylic acid was prepared by the same route, using intermediate 1b from Step a.

Step d: The mixture of (8S)-5-{6-[(3S,4S)-4-{[(tert-butoxy)carbonyl]amino}-3-methyl-2-oxa-8-azaspiro[4.5]decan-8-yl]-1-(oxan-2-yl)-1H-pyrazolo[3,4-b]pyrazin-3-yl}-8-methyl-5,6,7,8-tetrahydro-1,5-naphthyridine-2-carboxylic acid (80.0 mg, 120.0 μmol), HATU (91.2 mg, 240.0 μmol) and TEA (83.1 μL, 600.0 μmol) in DCM (5.0 mL) was stirred at 15° C. for 10 min. Then 2-methoxyethan-1-amine (18.0 mg, 240.0 μmol) was added and stirred at 15° C. for 12 hours. Yellow solution was observed. LCMS showed one peak with desired MS. The mixture was concentrated, diluted with EtOAc (100.0 mL), washed with H2O (50.0 mL×2) and brine (50.0 mL), the organic phase was dried over anhydrous Na2SO4, filtered and concentrated under reduced pressure to give tert-butyl N-[(3S,4S)-8-{3-[(4S)-6-[(2-methoxyethyl)carbamoyl]-4-methyl-1,2,3,4-tetrahydro-1,5-naphthyridin-1-yl]-1-(oxan-2-yl)-1H-pyrazolo[3,4-b]pyrazin-6-yl}-3-methyl-2-oxa-8-azaspiro[4.5]decan-4-yl]carbamate (100.0 mg, crude) as a yellow solid.

Step e: To a solution of tert-butyl N-[(3S,4S)-8-(3-[(4S)-6-[(2-methoxyethyl)carbamoyl]-4-methyl-1,2,3,4-tetrahydro-1,5-naphthyridin-1-yl]-1-(oxan-2-yl)-1H-pyrazolo[3,4-b]pyrazin-6-yl)-3-methyl-2-oxa-8-azaspiro[4.5]decan-4-yl]carbamate (100.0 mg, crude) in MeOH (2.0 mL) was added HCl/MeOH (2.0 mL). The mixture was stirred at 25° C. for 12 hours. LCMS showed one peak with desired MS detected. The mixture was concentrated under reduced pressure and purified by prep-HPLC (HCl) to afford the product of(8S)-5-{6-[(3S,4S)-4-amino-3-methyl-2-oxa-8-azaspiro[4.5]decan-8-yl]-1H-pyrazolo[3,4-b]pyrazin-3-yl}-N-(2-methoxyethyl)-8-methyl-5,6,7,8-tetrahydro-1,5-naphthyridine-2-carboxamide hydrochloride (48.2 mg, 61% yield) as a yellow solid.

The following compounds were prepared through this same route, using (8S)-5-(6-((3S,4S)-4-((tert-butoxycarbonyl)amino)-3-methyl-2-oxa-8-azaspiro[4.5]decan-8-yl)-1-(tetrahydro-2H-pyran-2-yl)-1H-pyrazolo[3,4-b]pyrazin-3-yl)-8-methyl-5,6,7,8-tetrahydro-1,5-naphthyridine-2-carboxylic acid or (8R)-5-(6-((3S,4S)-4-((tert-butoxycarbonyl)amino)-3-methyl-2-oxa-8-azaspiro[4.5]decan-8-yl)-1-(tetrahydro-2H-pyran-2-yl)-1H-pyrazolo[3,4-b]pyrazin-3-yl)-8-methyl-5,6,7,8-tetrahydro-1,5-naphthyridine-2-carboxylic acid and the corresponding commercially available amine: Compound 438, Compound 442, Compound 443, Compound 445, Compound 446, Compound 447.

Synthesis of (3S,4S)-8-{3-[(4S)-6-[(1E)-(methoxyimino)methyl]-4-methyl-1,2,3,4-tetrahydro-1,5-naphthyridin-1-yl]-1H-pyrazolo[3,4-b]pyrazin-6-yl}-3-methyl-2-oxa-8-azaspiro[4.5]decan-4-amine hydrochloride, Compound 444

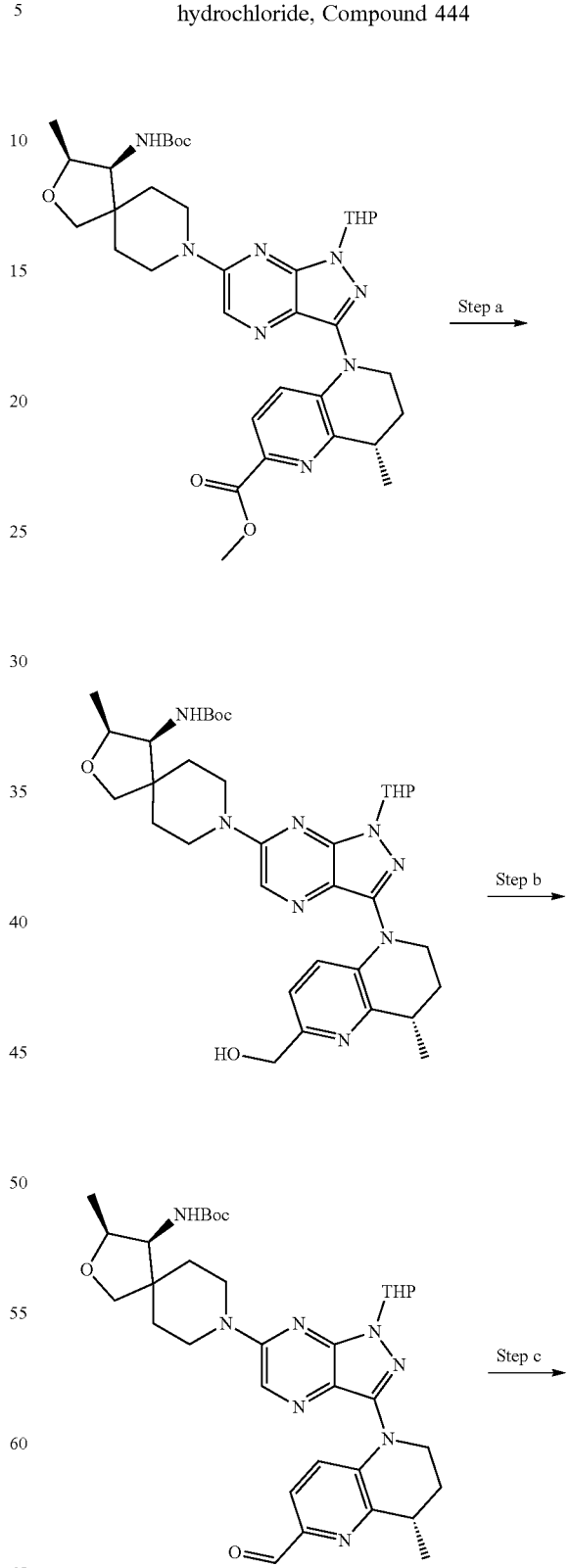

-continued

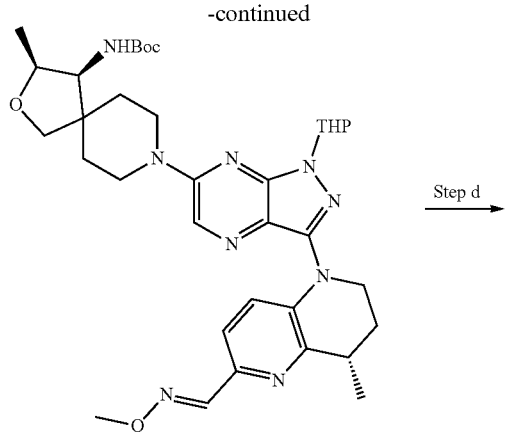

Step d

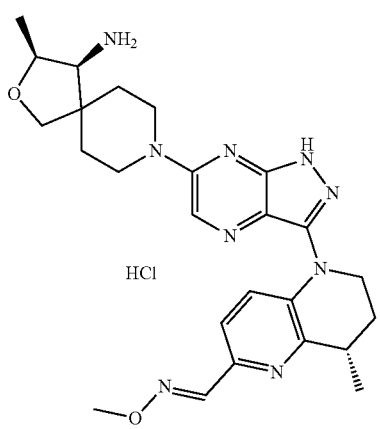

HCl

Step a: Methyl (8S)-5-{6-[(3S,4S)-4-{[(tert-butoxy)carbonyl]amino}-3-methyl-2-oxa-8-azaspiro[4.5]decan-8-yl]-1-(oxan-2-yl)-1H-pyrazolo[3,4-b]pyrazin-3-yl}-8-methyl-5,6,7,8-tetrahydro-1,5-naphthyridine-2-carboxylate (120.0 mg, 177.0 μmol) (prepared as described for compound 437) was added in THF (3.0 mL), the reaction mixture was evacuated and refilled for 3 times with N2 and cooled to −78° C., DIBAL-H (354.0 μL, 354 μmol, 1M in PhMe) was added in, the reaction mixture was stirred at −78° C. for 1 hour. LCMS indicated 43% of desired product formed. The reaction mixture was quenched with 10% CH3COOH (2.0 mL), diluted with EtOAc (30.0 mL), washed with H₂O (30.0 mL×2), saturated NaHCO₃ (30.0 mL) and brine (30.0 mL), the organic phase was dried over anhydrous Na2SO4, concentrated under reduced pressure to give the product of tert-butyl N-[(3S,4S)-8-{3-[(4S)-6-(hydroxymethyl)-4-methyl-1,2,3,4-tetrahydro-1,5-naphthyridin-1-yl]-1-(oxan-2-yl)-1H-pyrazolo[3,4-b]pyrazin-6-yl}-3-methyl-2-oxa-8-azaspiro[4.5]decan-4-yl]carbamate (120.0 mg, crude) as a yellow solid.

Step b: Tert-butyl N-[(3S,4S)-8-{3-[(4S)-6-(hydroxymethyl)-4-methyl-1,2,3,4-tetrahydro-1,5-naphthyridin-1-yl]-1-(oxan-2-yl)-1H-pyrazolo[3,4-b]pyrazin-6-yl}-3-methyl-2-oxa-8-azaspiro[4.5]decan-4-yl]carbamate (120.0 mg, crude) and Dess-Martin reagent (156.0 mg, 368.0 μmol) were added in DCM (10.0 mL), the reaction mixture was stirred at 15° C. for 0.5 hour. LCMS indicated 80% of desired product formed. The reaction mixture was washed with H₂O (5.0 mL×2), brine (5.0 mL), the organic phase was concentrated under reduced pressure to afford the product of tert-butyl N-[(3S,4S)-8-{3-[(4S)-6-formyl-4-methyl-1,2,3,4-tetrahydro-1,5-naphthyridin-1-yl]-1-(oxan-2-yl)-1H-pyrazolo[3,4-b]pyrazin-6-yl}-3-methyl-2-oxa-8-azaspiro[4.5]decan-4-yl]carbamate (150.0 mg, crude) as a yellow solid.

Step c: Tert-butyl N-[(3S,4S)-8-(3-[(4S)-6-formyl-4-methyl-1,2,3,4-tetrahydro-1,5-naphthyridin-1-yl]-1-(oxan-2-yl)-1H-pyrazolo[3,4-b]pyrazin-6-yl)-3-methyl-2-oxa-8-azaspiro[4.5]decan-4-yl]carbamate (150.0 mg, crude), MeONH2.HCl (22.7 mg, 277.0 μmol) and TEA (96.0 μL, 693.0 μmol) were added in EtOH (10.0 mL), the reaction mixture was stirred at 15° C. for 12 hours. LCMS indicated 80% of desired product formed. The reaction mixture was concentrated under reduced pressure to afford the product of tert-butyl N-[(3S,4S)-8-(3-[(4S)-6-[(1E)-(methoxyimino)methyl]-4-methyl-1,2,3,4-tetrahydro-1,5-naphthyridin-1-yl]-1-(oxan-2-yl)-1H-pyrazolo[3,4-b]pyrazin-6-yl)-3-methyl-2-oxa-8-azaspiro[4.5]decan-4-yl]carbamate (180.0 mg, crude) as a yellow solid which was used in next step without further purification.

Step d: Tert-butyl N-[(3S,4S)-8-(3-[(4S)-6-[(1E)-(methoxyimino)methyl]-4-methyl-1,2,3,4-tetrahydro-1,5-naphthyridin-1-yl]-1-(oxan-2-yl)-1H-pyrazolo[3,4-b]pyrazin-6-yl)-3-methyl-2-oxa-8-azaspiro[4.5]decan-4-yl]carbamate (100.0 mg, crude) was added in 4N HCl/MeOH (6.0 mL), the reaction mixture was stirred at 10° C. for 2 hours. LCMS indicated 95% of desired product formed. The reaction mixture was concentrated under reduced pressure and the residue was purified by prep-HPLC (HCl) to afford the product of (3S,4S)-8-{3-[(4S)-6-[(1E)-(methoxyimino)methyl]-4-methyl-1,2,3,4-tetrahydro-1,5-naphthyridin-1-yl]-1H-pyrazolo[3,4-b]pyrazin-6-yl}-3-methyl-2-oxa-8-azaspiro[4.5]decan-4-amine hydrochloride (54.1 mg) as a yellow solid.

Synthesis of (3S,4S)-8-{3-[(4R*)-6-(1H-imidazol-2-yl)-4-methyl-1,2,3,4-tetrahydro-1,5-naphthyridin-1-yl]-1H-pyrazolo[3,4-b]pyrazin-6-yl}-3-methyl-2-oxa-8-azaspiro[4.5]decan-4-amine hydrochloride, Compound 448 and Compound 449

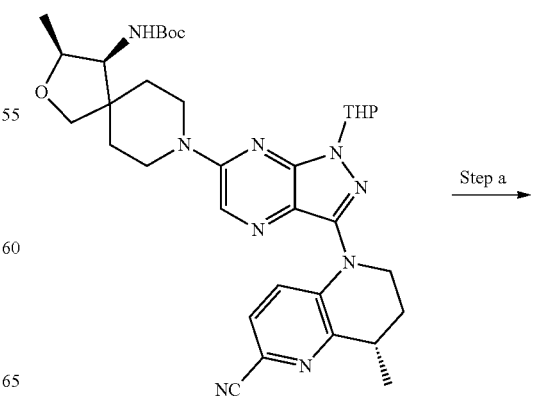

Step a

463
-continued

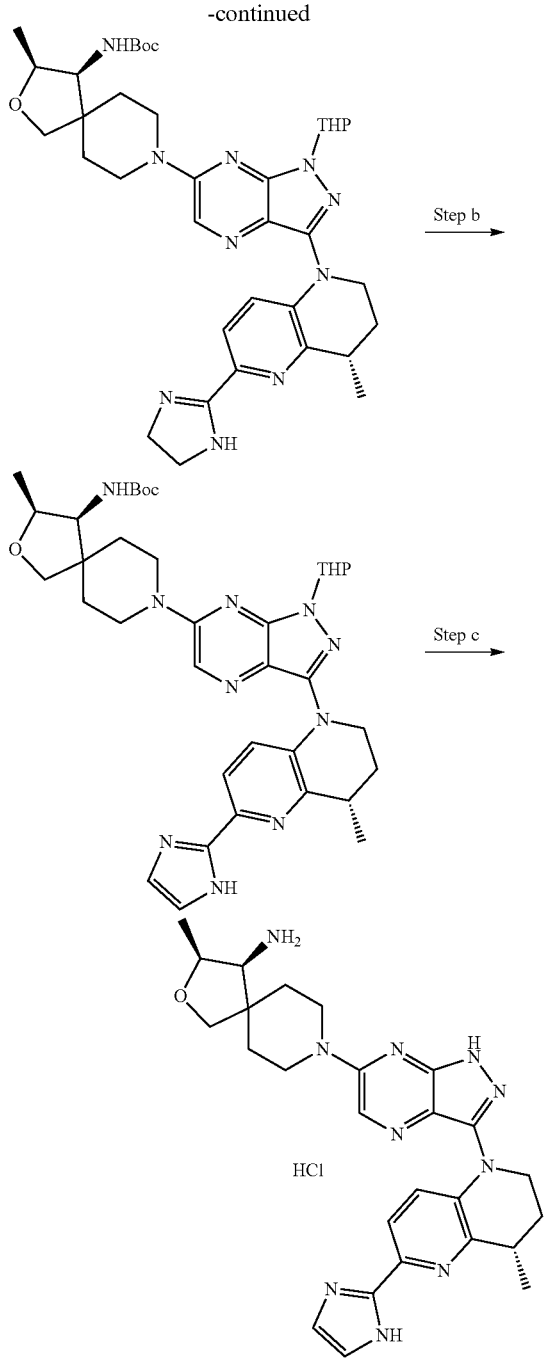

Step a: To a solution of tert-butyl N-[(3S,4S)-8-(3-[(4S)-6-cyano-4-methyl-1,2,3,4-tetrahydro-1,5-naphthyridin-1-yl]-1-(oxan-2-yl)-1H-pyrazolo[3,4-b]pyrazin-6-yl}-3-methyl-2-oxa-8-azaspiro[4.5]decan-4-yl]carbamate (150.0 mg, 232.0 μmol) (prepared as described for compound 452) and 2 (3.0 mL) was added TosOH.H2O (4.4 mg, 23.2 μmol). The mixture in sealed tube was purged with N2 for 3 min, the reaction was stirred at 120° C. for 2 hours. LCMS showed 7% starting material remained and 67% desired product formed. The reaction mixture was concentrated under reduced pressure. The residue was purified by column chromatography (Ethyl acetate/MeOH=100:0 to 100:40). The product tert-butyl N-[(3S,4S)-8-(3-[(4S)-6-(4,5-dihydro-1H-imidazol-2-yl)-4-methyl-1,2,3,4-tetrahydro-1,5-naphthyridin-1-yl]-1-(oxan-2-yl)-1H-pyrazolo[3,4-b]pyrazin-6-yl)-3-methyl-2-oxa-8-azaspiro[4.5]decan-4-yl]carbamate (130.0 mg, 189.0 μmol, 81.7% yield) was obtained as a yellow solid.

Step b: A solution of tert-butyl N-[(3S,4S)-8-{3-[(4S)-6-(4,5-dihydro-1H-imidazol-2-yl)-4-methyl-1,2,3,4-tetrahydro-1,5-naphthyridin-1-yl]-1-(oxan-2-yl)-1H-pyrazolo[3,4-b]pyrazin-6-yl}-3-methyl-2-oxa-8-azaspiro[4.5]decan-4-yl]carbamate (80.0 mg, 116.0 μmol), K2CO3 (32.0 mg, 232.0 μmol) and PhI(OAc)2 (74.7 mg, 232.0 μmol) in DMSO (2.0 mL) was stirred at 30° C. for 24 hours. LCMS showed 72.2% desired product was found at 254 nm. The reaction mixture was diluted with water (10.0 mL) and extracted with ethyl acetate (50.0 mL×2). The combined organic layers were washed with water (10.0 mL×2) and brine (10.0 mL), dried over anhydrous Na2SO4, filtered and concentrated under reduced pressure to give a residue. The residue was purified by column chromatography (Petroleum ether/Ethyl acetate=100:0 to 100:100 and Ethyl acetate/Methanol=100:0 to 100:10). The product tert-butyl N-[(3S,4S)-8-{3-[(4S)-6-(1H-imidazol-2-yl)-4-methyl-1,2,3,4-tetrahydro-1,5-naphthyridin-1-yl]-1-(oxan-2-yl)-1H-pyrazolo[3,4-b]pyrazin-6-yl}-3-methyl-2-oxa-8-azaspiro[4.5]decan-4-yl]carbamate (70.0 mg, 102.0 μmol, 88.1% yield) was obtained as a yellow solid.

Step c: A solution of tert-butyl N-[(3S,4S)-8-{3-[(4S)-6-(1H-imidazol-2-yl)-4-methyl-1,2,3,4-tetrahydro-1,5-naphthyridin-1-yl]-1-(oxan-2-yl)-1H-pyrazolo[3,4-b]pyrazin-6-yl}-3-methyl-2-oxa-8-azaspiro[4.5]decan-4-yl]carbamate (65.0 mg, 94.9 μmol) in HCl/MeOH (2.0 mL, 4N) was stirred at 10° C. for 1 hour. LCMS showed the starting material was consumed completely and 95% desired product formed. The reaction mixture was concentrated under reduced pressure. The residue was diluted with MeOH (5.0 mL). The residue was purified by prep-HPLC (HCl). The product (3S,4S)-8-{3-[(4R*)-6-(1H-imidazol-2-yl)-4-methyl-1,2,3,4-tetrahydro-1,5-naphthyridin-1-yl]-1H-pyrazolo[3,4-b]pyrazin-6-yl}-3-methyl-2-oxa-8-azaspiro[4.5]decan-4-amine hydrochloride (20.0 mg, 37.2 μmol, 39.2% yield) was obtained as a yellow solid.

Compound 449 was prepared by the same route, starting from tert-butyl N-[(3S,4S)-8-{3-[(4R)-6-cyano-4-methyl-1,2,3,4-tetrahydro-1,5-naphthyridin-1-yl]-1-(oxan-2-yl)-1H-pyrazolo[3,4-b]pyrazin-6-yl}-3-methyl-2-oxa-8-azaspiro[4.5]decan-4-yl]carbamate.

Synthesis of 3-[(8R*)-5-{6-[(3S,4S)-4-amino-3-methyl-2-oxa-8-azaspiro[4.5]decan-8-yl]-1H-pyrazolo[3,4-b]pyrazin-3-yl}-8-methyl-5,6,7,8-tetrahydro-1,5-naphthyridin-2-yl]-4,5-dihydro-1,2,4-oxadiazol-5-one, Compound 450

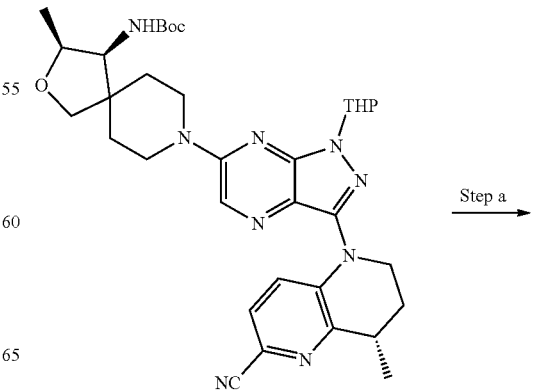

465
-continued

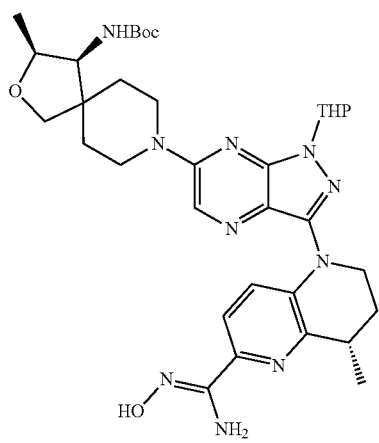

Step b →

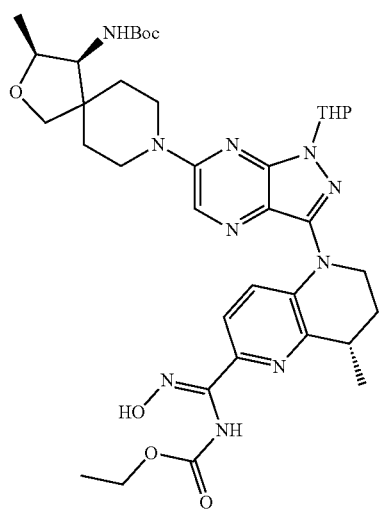

Step c →

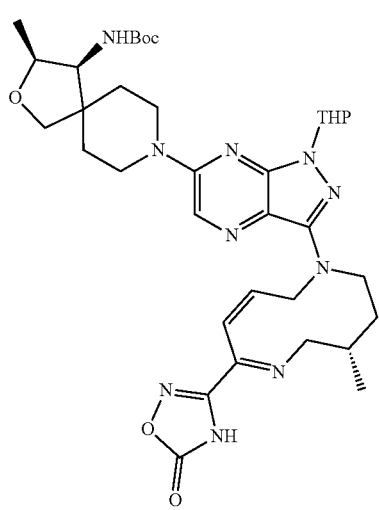

Step d →

466
-continued

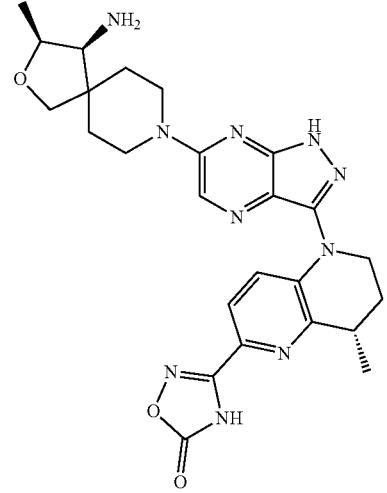

Step a: A solution of NH2OH.HCl (69.0 mg, 1.0 mmol) and TEA (278.0 μL) in EtOH (5.0 mL) was stirred at 10° C. for 15 min. To the reaction mixture was added tert-butyl N-[(3S,4S)-8-{3-[(4S)-6-cyano-4-methyl-1,2,3,4-tetrahydro-1,5-naphthyridin-1-yl]-1-(oxan-2-yl)-1H-pyrazolo[3,4-b]pyrazin-6-yl}-3-methyl-2-oxa-8-azaspiro[4.5]decan-4-yl]carbamate (130.0 mg, 201.0 μmol). The reaction mixture was stirred at 10° C. for 12 hours. LCMS showed the starting material was consumed completely and 92% desired product was formed. The reaction mixture was concentrated under reduced pressure. The residue was purified by column chromatography (DCM/MeOH=100:0 to 100:10). The product tert-butyl N-[(3S,4S)-8-{3-[(4S)-6-[(Z)—N'-hydroxycarbamimidoyl]-4-methyl-1,2,3,4-tetrahydro-1,5-naphthyridin-1-yl]-1-(oxan-2-yl)-1H-pyrazolo[3,4-b]pyrazin-6-yl}-3-methyl-2-oxa-8-azaspiro[4.5]decan-4-yl]carbamate (320 mg, crude) was obtained as a yellow solid.

Step b: To a solution of 2 (80.0 mg, crude) and TEA (32.6 μL) in THF (5.0 mL) was added solution of ClCO2Et (0.5 mL, 5.2 mmol) in DCM (0.5 mL). The reaction was stirred at 10° C. for 2 hours. LCMS showed the starting material was consumed and 84% of desired product was formed. Quenched with saturated NH4Cl (1.0 mL). The reaction mixture was concentrated under reduced pressure. The reaction mixture was diluted with water (20.0 mL) and extracted with ethyl acetate (20.0 mL×2). The combined organic layers were washed with water (20.0 mL), dried over anhydrous Na2SO4, filtered and concentrated under reduced pressure to give a residue. The residue was purified by column chromatography (Petroleum ether/Ethyl acetate=100:0 to 100:70). The product of 3 (110 mg, crude) was obtained as a yellow solid.

Step c: A solution of tert-butyl N-[(3S,4S)-8-{3-[(4S)-6-[(1Z)-[(ethoxycarbonyl)amino](hydroxyimino)methyl]-4-methyl-1,2,3,4-tetrahydro-1,5-naphthyridin-1-yl]-1-(oxan-2-yl)-1H-pyrazolo[3,4-b]pyrazin-6-yl}-3-methyl-2-oxa-8-azaspiro[4.5]decan-4-yl]carbamate (80.0 mg, crude) in xylene (5.0 mL) was stirred at 150° C. for 8 hours. LCMS showed the starting material was consumed completely and 61% desired product was formed. The reaction mixture was concentrated under reduced pressure to give the residue. The product tert-butyl N-[(3S,4S)-3-methyl-8-{3-[(4S)-4-methyl-6-(5-oxo-4,5-dihydro-1,2,4-oxadiazol-3-yl)-1,2,3,4-tetrahydro-1,5-naphthyridin-1-yl]-1-(oxan-2-yl)-1H-pyrazolo[3,4-b]pyrazin-6-yl}-2-oxa-8-azaspiro[4.5]decan-4-yl] carbamate (100 mg, crude) was obtained as a yellow solid.

Step d: A solution of tert-butyl N-[(3S,4S)-3-methyl-8-{3-[(4S)-4-methyl-6-(5-oxo-4,5-dihydro-1,2,4-oxadiazol-3-yl)-1,2,3,4-tetrahydro-1,5-naphthyridin-1-yl]-1-(oxan-2-yl)-1H-pyrazolo[3,4-b]pyrazin-6-yl}-2-oxa-8-azaspiro[4.5]decan-4-yl]carbamate (90.0 mg, crude) in TFA (2.0 mL) was stirred at 10° C. for 1 hour. LCMS showed the starting material was consumed completely and 57% desired product formed. The reaction mixture was concentrated under reduced pressure to give the residue. The residue was diluted with MeOH (3.0 mL) and adjusted to pH=8 with K2CO3 (solid). The mixture was purified by prep-HPLC (HCl). The product of 3-[(8R*)-5-{6-[(3S,4S)-4-amino-3-methyl-2-oxa-8-azaspiro[4.5]decan-8-yl]-1H-pyrazolo[3,4-b]pyrazin-3-yl}-8-methyl-5,6,7,8-tetrahydro-1,5-naphthyridin-2-yl]-4,5-dihydro-1,2,4-oxadiazol-5-one (18.0 mg, 34.7 μmol, 27.1% yield) was obtained as a yellow solid.

3-[(8R*)-5-{6-[(3S,4S)-4-amino-3-methyl-2-oxa-8-azaspiro[4.5]decan-8-yl]-1H-pyrazolo[3,4-b]pyrazin-3-yl}-8-methyl-5,6,7,8-tetrahydro-1,5-naphthyridin-2-yl]-4,5-dihydro-1,2,4-oxadiazol-5-one, compound 451, was prepared by the same route, starting from tert-butyl N-[(3S,4S)-8-{3-[(4R)-6-cyano-4-methyl-1,2,3,4-tetrahydro-1,5-naphthyridin-1-yl]-1-(oxan-2-yl)-1H-pyrazolo[3,4-b]pyrazin-6-yl}-3-methyl-2-oxa-8-azaspiro[4.5]decan-4-yl]carbamate.

Synthesis of 3S,4S)-3-methyl-8-{3-[(4S)-4-methyl-6-(4H-1,2,4-triazol-3-yl)-1,2,3,4-tetrahydro-1,5-naphthyridin-1-yl]-1H-pyrazolo[3,4-b]pyrazin-6-yl}-2-oxa-8-azaspiro[4.5]decan-4-amine and (3S,4S)-3-methyl-8-(3-[(4R)-4-methyl-6-(1-methyl-1H-pyrazol-4-yl)-1,2,3,4-tetrahydro-1,5-naphthyridin-1-yl]-1H-pyrazolo[3,4-b]pyrazin-6-yl)-2-oxa-8-azaspiro[4.5]decan-4-amine dihydrochloride, Compound 454 and Compound 452

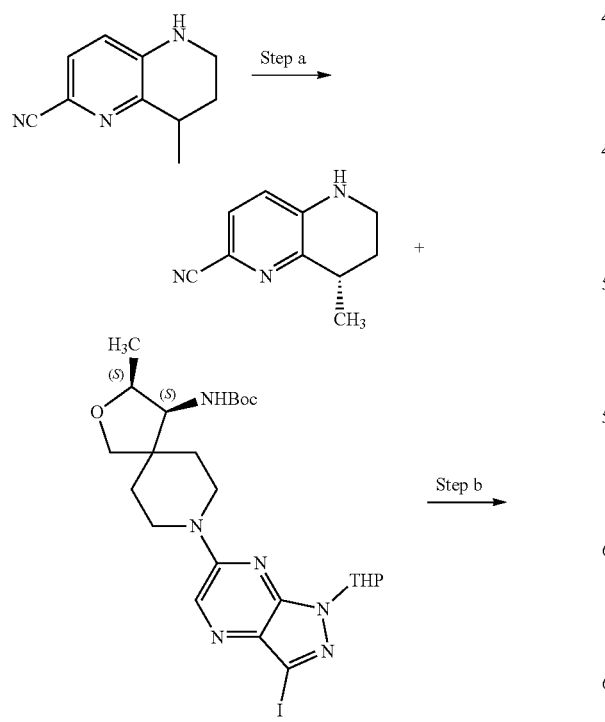

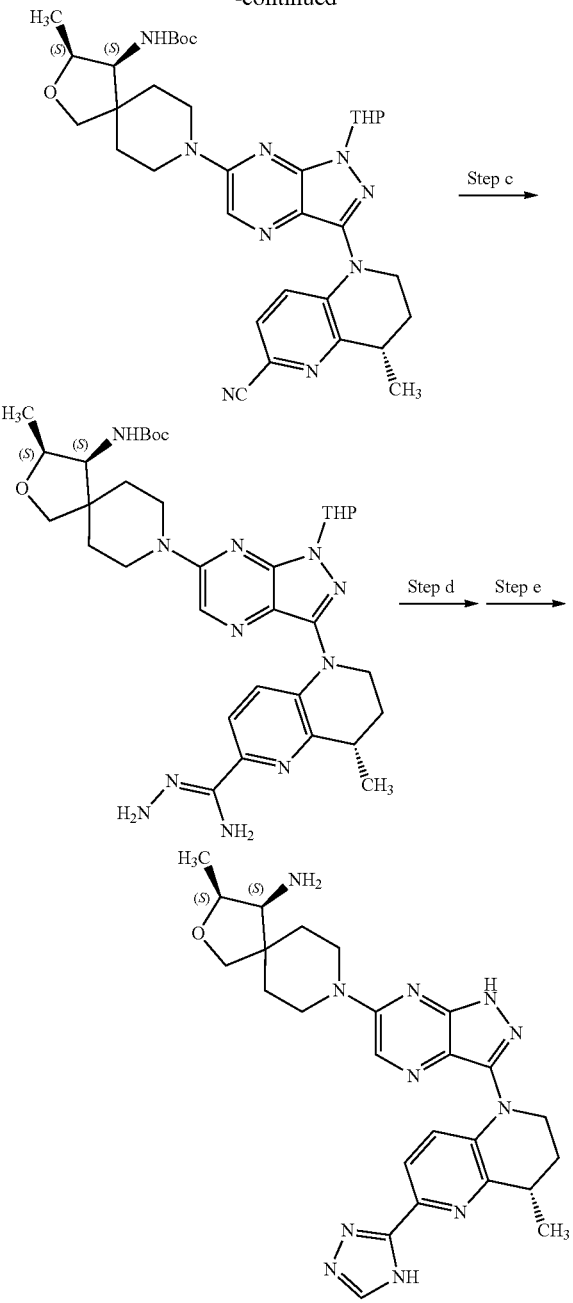

Step a: rac-8-Methyl-5,6,7,8-tetrahydro-1,5-naphthyridine-2-carbonitrile (140 mg, 808 μmol, 1.0 eq) was separated by SFC ((Column: Phenomenex-Cellulose-2 (250 mm*30 mm, 5 um). Condition: Ethanol (0.1% NH3/H2O)—begin B 30%, end B 30%; Flow rate: 60 mL/min.)) to afford (8R)-8-methyl-5,6,7,8-tetrahydro-1,5-naphthyridine-2-carbonitrile (60 mg, 43% yield) (a faster eluting isomer) and (8S)-8-methyl-5,6,7,8-tetrahydro-1,5-naphthyridine-2-carbonitrile (60 mg, 43% yield).

Step b: A mixture of tert-Butyl N-[(3S,4S)-8-[3-iodo-1-(oxan-2-yl)-1H-pyrazolo[3,4-b]pyrazin-6-yl]-3-methyl-2-oxa-8-azaspiro[4.5]decan-4-yl]carbonitrile (200 mg, 334 μmol, 1.0 eq.), (8S)-8-methyl-5,6,7,8-tetrahydro-1,5-naphthyridine-2-carbonitrile (57.8 mg, 334 μmol, 1.0 eq.), XantPhos-Pd-G4 (32.1 mg, 33.4 μmol, 0.1 eq) and Cs2CO3 (325 mg, 1.0 mmol, 3.0 eq.) in PhMe (10 mL) was evacuated and refilled 3 times with N₂ and stirred at 100° C. for 12 hours. The mixture was concentrated under reduced pressure to give a residue, which was purified by silica gel column chromatography (10-33% EtOAc/petroleum ether) to afford tert-butyl N-[(3S,4S)-8-{3-[(4S)-6-cyano-4-methyl-1,2,3,4-tetrahydro-1,5-naphthyridin-1-yl]-1-(oxan-2-yl)-1H-pyrazolo[3,4-b]pyrazin-6-yl}-3-methyl-2-oxa-8-azaspiro[4.5]decan-4-yl]carbamate (200 mg, 93% yield) as a yellow solid.

Step c: A mixture of tert-butyl N-[(3S,4S)-8-{3-[(4S)-6-cyano-4-methyl-1,2,3,4-tetrahydro-1,5-naphthyridin-1-yl]-1-(oxan-2-yl)-1H-pyrazolo[3,4-b]pyrazin-6-yl}-3-methyl-2-oxa-8-azaspiro[4.5]decan-4-yl]carbamate (140 mg, 217 µmol, 1.0 eq.) and NH₂NH₂—H₂O (551 mg, 10.8 mmol, 50 eq.) in EtOH (3 mL) was stirred at 50° C. for 30 hours. The mixture was concentrated under reduced pressure to give tert-butyl ((3S,4S)-8-(3-((S)-6-((Z)-carbamohydrazonoyl)-4-methyl-3,4-dihydro-1,5-naphthyridin-1(2H)-yl)-1-(tetrahydro-2H-pyran-2-yl)-1H-pyrazolo[3,4-b]pyrazin-6-yl)-3-methyl-2-oxa-8-azaspiro[4.5]decan-4-yl)carbamate (170 mg, crude) which was used in Step d directly without further purification.

Step d: A mixture of tert-butyl N-[(3S,4S)-8-{3-[(4S)-6-[(Z)—N-aminocarbamimidoyl]-4-methyl-1,2,3,4-tetrahydro-1,5-naphthyridin-1-yl]-1-(oxan-2-yl)-1H-pyrazolo[3,4-b]pyrazin-6-yl}-3-methyl-2-oxa-8-azaspiro[4.5]decan-4-yl]carbamate (110 mg, 86% purity, 139 µmol, 1.0 eq.) in HCOOH (3 mL) was stirred at 100° C. for 10 hours. The reaction mixture was concentrated under reduced pressure to give a residue which was dissolved in MeOH (5 mL). To this solution was added 2N NaOH (2 mL) and the mixture stirred at 100° C. for 10 hours. The reaction mixture was filtered and the filtrate concentrated under reduced pressure to give tert-butyl N-[(3S,4S)-3-methyl-8-{3-[(4S)-4-methyl-6-(4H-1,2,4-triazol-3-yl)-1,2,3,4-tetrahydro-1,5-naphthyridin-1-yl]-1H-pyrazolo[3,4-b]pyrazin-6-yl}-2-oxa-8-azaspiro[4.5]decan-4-yl]carbamate (300 mg, crude) as a yellow oil.

Step e: A mixture of tert-butyl N-[(3S,4S)-3-methyl-8-{3-[(4,S)-4-methyl-6-(4H-1,2,4-triazol-3-yl)-1,2,3,4-tetrahydro-1,5-naphthyridin-1-yl]-1H-pyrazolo[3,4-b]pyrazin-6-yl}-2-oxa-8-azaspiro[4.5]decan-4-yl]carbamate (300 mg, crude) in HCl/MeOH (5 mL, 4M) was stirred at 25° C. for 1 hour. The mixture was concentrated under reduced pressure to give a residue which was purified by prep-HPLC (acetonitrile/aq. NH₃) to afford (3S,4S)-3-methyl-8-{3-[(4S)-4-methyl-6-(4H-1,2,4-triazol-3-yl)-1,2,3,4-tetrahydro-1,5-naphthyridin-1-yl]-1H-pyrazolo[3,4-b]pyrazin-6-yl}-2-oxa-8-azaspiro[4.5]decan-4-amine (70 mg, 46% purity) as a yellow solid. The residue was re-purified by prep-HPLC (acetonitrile/aq. HCl) to afford (3S,4S)-3-methyl-8-{3-[(4S)-4-methyl-6-(4H-1,2,4-triazol-3-yl)-1,2,3,4-tetrahydro-1,5-naphthyridin-1-yl]-1H-pyrazolo[3,4-b]pyrazin-6-yl}-2-oxa-8-azaspiro[4.5]decan-4-amine (5.5 mg, HCl salt) as a yellow solid: ESMS [M+H]+=502.3; ¹H-NMR (400 MHz, methanol-d₄): δ 8.90 (s, 1H), 8.37 (s, 1H), 8.07-8.04 (d, J=8.8 Hz, 1H), 7.94-7.91 (d, J=9.2 Hz, 1H), 4.51-4.34 (m, 3H), 4.15-4.02 (m, 3H), 3.93-3.90 (m, 1H), 3.60-3.50 (m, 1H), 3.50-3.48 (m, 1H), 3.37 (m, 1H), 3.25-3.20 (m, 1H), 2.40-2.38 (m, 1H), 2.16-2.14 (m, 1H), 1.95-1.92 (m, 3H), 1.75-1.70 (m, 1H), 1.61-1.58 (d, J=6.8 Hz, 3H), 1.36-1.34 (d, J=6.8 Hz, 3H).

Steps b through Step e were similarly performed on (8R)-8-methyl-5,6,7,8-tetrahydro-1,5-naphthyridine-2-carbonitrile to afford (3S,4S)-3-methyl-8-{3-[(4R)-4-methyl-6-(1-methyl-1H-pyrazolo-4-yl)-1,2,3,4-tetrahydro-1,5-naphthyridin-1-yl]-1H-pyrazolo[3,4-b]pyrazin-6-yl}-2-oxa-8-azaspiro[4.5]decan-4-amine dihydrochloride (8.8 mg, 23% yield) as a yellow solid: ESMS [M+H]⁺=502.2; ¹H-NMR (400 MHz, methanol-d₄): δ 8.91 (s, 1H), 8.37 (s, 1H), 8.07-8.05 (d, J=8.8 Hz, 1H), 7.94-7.91 (d, J=8.8 Hz, 1H), 4.51-4.34 (m, 3H), 4.15-4.02 (m, 3H), 3.93-3.90 (m, 1H), 3.60-3.50 (m, 1H), 3.50-3.48 (m, 1H), 3.37 (m, 1H), 3.25-3.20 (m, 1H), 2.40-2.38 (m, 1H), 2.16-2.14 (m, 1H), 1.95-1.92 (m, 3H), 1.75-1.70 (m, 1H), 1.61-1.59 (d, J=7.2 Hz, 3H), 1.36-1.34 (d, J=6.4 Hz, 3H).

Synthesis of 2-(4-{6-[(3S,4S)-4-amino-3-methyl-2-oxa-8-azaspiro[4.5]decan-8-yl]-1H-pyrazolo[3,4-b]pyrazin-3-yl}-7-cyano-1,2,3,4-tetrahydroquinoxalin-1-yl)-N,N-dimethylacetamide, Compound 453

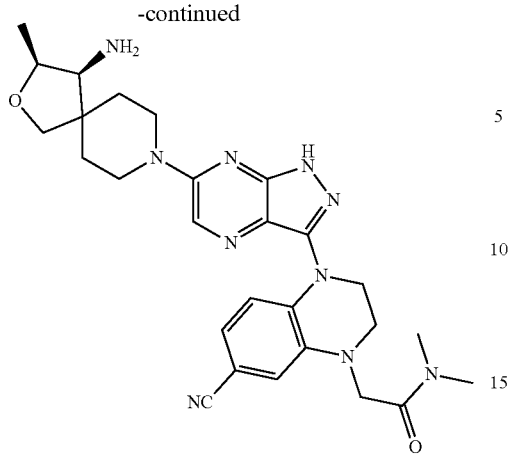

Step a: A solution of methyl 2-(4-{6-[(3S,4S)-4-{[(tert-butoxy)carbonyl]amino}-3-methyl-2-oxa-8-azaspiro[4.5]decan-8-yl]-1-(oxan-2-yl)-1H-pyrazolo[3,4-b]pyrazin-3-yl}-7-cyano-1,2,3,4-tetrahydroquinoxalin-1-yl)acetate (120.0 mg, 170.0 μmol) (prepared by conditions similar to those used for Compound 33, using CAS 1892763-41-5) and K2CO3 (93.8 mg, 680.0 μmol) in MeOH (5.0 mL) was stirred at 60° C. for 12 hours. Orange solution was observed. Desired mass ion was observed from LCMS. The mixture was concentrated in vacuum to give 2-(4-{6-[(3S,4S)-4-{[(tert-butoxy)carbonyl]amino}-3-methyl-2-oxa-8-azaspiro[4.5]decan-8-yl]-1-(oxan-2-yl)-1H-pyrazolo[3,4-b]pyrazin-3-yl}-7-cyano-1,2,3,4-tetrahydroquinoxalin-1-yl)acetic acid (120.0 mg, crude) as an orange gum. The gum was used in the next step without further purification.

Step b: A solution of 2-(4-{6-[(3S,4S)-4-{[(tert-butoxy)carbonyl]amino}-3-methyl-2-oxa-8-azaspiro[4.5]decan-8-yl]-1-(oxan-2-yl)-1H-pyrazolo[3,4-b]pyrazin-3-yl}-7-cyano-1,2,3,4-tetrahydroquinoxalin-1-yl)acetic acid (120.0 mg, 174.0 μmol), dimethylamine hydrochloride (28.3 mg, 348.0 μmol), HATU (198.0 mg, 522.0 μmol) and DIEA (93.4 μL, 522.0 μmol) in DMF (8.0 mL) was stirred at 50° C. for 1 hour. Orange solution was observed. Desired mass ion was observed from LCMS. The solution was added into H2O (50.0 mL) and then extracted with EtOAc (50.0 mL×2). The combined organic layers were washed with brine (50.0 mL), dried over anhydrous Na2SO4, filtered and concentrated in vacuum to give crude product as an orange gum. The residue was purified by flash silica gel chromatography (4 g, MeOH in Ethyl acetate from 0% to 5%) to give tert-butyl N-[(3S,4S)-8-(3-{6-cyano-4-[(dimethylcarbamoyl)methyl]-1,2,3,4-tetrahydroquinoxalin-1-yl}-1-(oxan-2-yl)-1H-pyrazolo[3,4-b]pyrazin-6-yl)-3-methyl-2-oxa-8-azaspiro[4.5]decan-4-yl]carbamate (90.0 mg, 72.5% yield) as a yellow oil.

Step c: A solution of tert-butyl N-[(3S,4S)-8-(3-{6-cyano-4-[(dimethylcarbamoyl)methyl]-1,2,3,4-tetrahydroquinoxalin-1-yl}-1-(oxan-2-yl)-1H-pyrazolo[3,4-b]pyrazin-6-yl)-3-methyl-2-oxa-8-azaspiro[4.5]decan-4-yl]carbamate (90.0 mg, 125.0 μmol) in TFA/DCM (2.0 mL/10.0 mL) was stirred at 25° C. for 1 hour. Orange solution was observed. Desired mass ion was observed from LCMS. The reaction mixture was concentrated in vacuum. The residue was diluted with THF (5.0 mL), adjusted to pH=8 with solid NaHCO3 and purified by prep-HPLC (NH3.H2O). 2-(4-{6-[(3S,4S)-4-amino-3-methyl-2-oxa-8-azaspiro[4.5]decan-8-yl]-1H-pyrazolo[3,4-b]pyrazin-3-yl}-7-cyano-1,2,3,4-tetrahydroquinoxalin-1-yl)-N,N-dimethylacetamide (12.4 mg, 18.7% yield) was obtained as a yellow solid.

Synthesis of (2R,4R)-4-amino-8-[3-(1,2,3,4-tetrahydro-1,5-naphthyridin-1-yl)-1H-pyrazolo[3,4-b]pyrazin-6-yl]-8-azaspiro[4.5]decan-2-ol, Compound 467

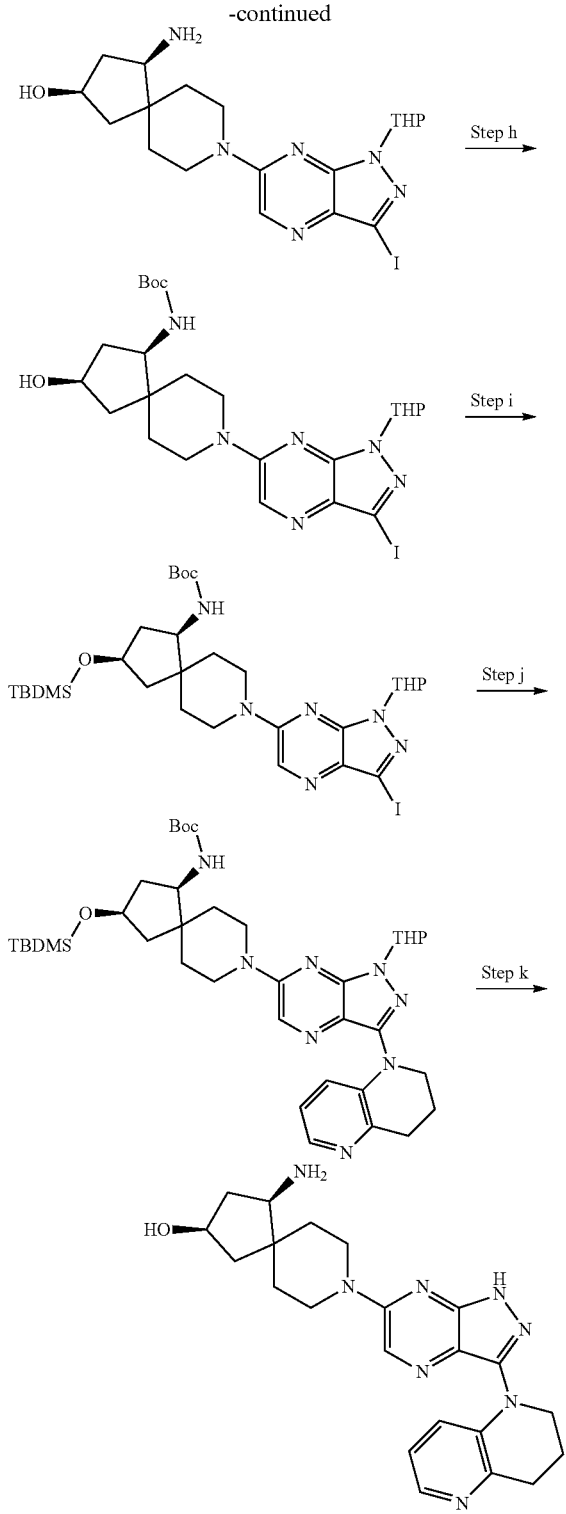

mmol, 2.70 mL, 2.00 eq), the resulting mixture was stirred at 20° C. for 16 h. Then H₂O (105 mL) was added followed by sodium perborate (13.6 g, 166.7 mmol, 5.00 eq). The resulting mixture was stirred at 20° C. for 1 h. TLC (Petroleum ether/Ethyl acetate=1/1, material Rf=0.6, product Rf=0.1) showed the reaction was completed. The reaction was filtered and the filtrate was extracted with EtOAc (200 mL*3). The combined organic phase was dried over Na2SO4 and concentrated. The residue was purified by column chromatography (SiO2, Petroleum ether/Ethyl acetate=50/1-3/1) to give tert-butyl (R)-3-hydroxy-1-oxo-8-azaspiro[4.5]decane-8-carboxylate (6.60 g, 24.5 mmol, 73.5% yield) as a white solid.

Step b: To a solution of tert-butyl (R)-3-hydroxy-1-oxo-8-azaspiro[4.5]decane-8-carboxylate (6.60 g, 24.5 mmol, 1.00 eq) in DMF (40 mL) was added TBSCl (4.62 g, 30.6 mmol, 3.75 mL, 1.25 eq) and imidazole (2.50 g, 36.8 mmol, 1.50 eq). The mixture was stirred at 20° C. for 16 hr. TLC (Petroleum ether/Ethyl acetate=3/1, material Rf=0.1, product Rf=0.4) showed the reaction was completed. The reaction was quenched with H₂O (100 mL) and extracted with EtOAc (120 mL*3). The combined organic phase was dried over Na2SO4 and concentrated. The residue was purified by column chromatography (SiO2, Petroleum ether/Ethyl acetate=20/1-5/1) to give tert-butyl (R)-3-((tert-butyldimethylsilyl)oxy)-1-oxo-8-azaspiro[4.5]decane-8-carboxylate (8.40 g, 21.9 mmol, 89.4% yield) as a white solid.

Step c: To a solution of tert-butyl (R)-3-((tert-butyldimethylsilyl)oxy)-1-oxo-8-azaspiro[4.5]decane-8-carboxylate (8.40 g, 21.9 mmol, 1.00 eq) and (R)-(+)-2-methyl-2-propanesulfinamide (5.31 g, 43.8 mmol, 2.00 eq) in 2-methyltetrahydrofuran (50 mL) was added tetraethoxytitanium (19.98 g, 87.59 mmol, 18.16 mL, 4 eq). The mixture was stirred at 65° C. for 16 hr. TLC (Petroleum ether/Ethyl acetate=1:1, material Rf=0.6, product Rf=0.3) showed the reaction was completed. The reaction was used without work up.

Step d: To a solution of tert-butyl (R,E)-3-((tert-butyldimethylsilyl)oxy)-1-(((R)-tert-butylsulfinyl)imino)-8-azaspiro[4.5]decane-8-carboxylate (10.6 g, 21.8 mmol, 1.00 eq) in MeOH (15 mL) and THF (100 mL) was added LiBH4 (1.90 g, 87.1 mmol, 4.00 eq) at −70° C. The mixture was stirred at −70° C. for 2 hr.TLC (Petroleum ether/Ethyl acetate=1/1, material Rf=0.6, product Rf=0.3) showed the reaction was completed. The reaction was quenched slowly by addition of H₂O (100 mL), diluted with EtOAc (200 mL), then filtered. the cake was washed with EtOAc (100 mL*3), the combined filtrates was separated. The organic phase was dried over Na2SO4 and concentrated. The residue was purified by column chromatography (SiO2, Petroleum ether/Ethyl acetate=10/1 to DCM/MeOH=50/1-10/1) to give tert-butyl (1R,3R)-3-((tert-butyldimethylsilyl)oxy)-1-(((R)-tert-butylsulfinyl)amino)-8-azaspiro[4.5]decane-8-carboxylate (5.40 g, crude) as a white solid.

Step e: To a solution of tert-butyl (1R,3R)-3-((tert-butyldimethylsilyl)oxy)-1-(((R)-tert-butylsulfinyl)amino)-8-azaspiro[4.5]decane-8-carboxylate (5.30 g, 10.8 mmol, 1.00 eq) in THF (30 mL) was added TBAF (1 M, 10.8 mL, 1.00 eq). The mixture was stirred at 20° C. for 1 hr. TLC (Petroleum ether/Ethyl acetate=0/1, material Rf=0.7, product Rf=0.3) showed the reaction was completed. The reaction was concentrated. The residue was purified by column chromatography (SiO₂, Petroleum ether/Ethyl acetate=10:1-0:1) to give tert-butyl (1R,3R)-1-(((R)-tert-butylsulfinyl)amino)-3-hydroxy-8-azaspiro[4.5]decane-8-carboxylate (1.30 g, 3.47 mmol, 32.0% yield) as a white solid.

Step a: A mixture of CuCl (99.0 mg, 1.00 mmol, 23.9 uL, 0.03 eq), tBuONa (96.1 mg, 1.00 mmol, 0.03 eq) and (s)-TolBINAP (679 mg, 1.00 mmol, 0.03 eq) in THF (42 mL) was stirred at 20° C. for 30 min, then a solution of BPD (9.31 g, 36.7 mmol, 1.10 eq) in THF (14 mL) was added, after 10 min, a solution of tert-butyl 1-oxo-8-azaspiro[4.5]dec-2-ene-8-carboxylate (8.38 g, 33.3 mmol, 1.00 eq) in THF (35 mL) was added, followed by MeOH (2.14 g, 66.7

Step f: A solution of tert-butyl (1R,3R)-1-(((R)-tert-butylsulfinyl)amino)-3-hydroxy-8-azaspiro[4.5]decane-8-carboxylate (0.50 g, 1.33 mmol, 1.00 eq) in HCl/dioxane (4 M, 12.5 mL, 37.5 eq) was stirred at 20° C. for 1 hr. The reaction was concentrated to give (2S,4S)-4-amino-8-azaspiro[4.5]decan-2-ol (0.34 g, crude, 2HCl) as a white solid.

Step g: To a solution of (2S,4S)-4-amino-8-azaspiro[4.5]decan-2-ol (324.0 mg, 1.33 mmol, 1.00 eq, 2HCl) in DMF (3 mL) was added DIEA (861.0 mg, 6.67 mmol, 1.16 mL, 5.00 eq) and 6-chloro-3-iodo-1-(tetrahydro-2H-pyran-2-yl)-1H-pyrazolo[3,4-b]pyrazine (485.8 mg, 1.33 mmol, 1.00 eq). The mixture was stirred at 50° C. for 4 hr. The reaction was concentrated. The residue was purified by prep-HPLC (neutral condition) to give (2R,4R)-4-amino-8-(3-iodo-1-(tetrahydro-2H-pyran-2-yl)-1H-pyrazolo[3,4-b]pyrazin-6-yl)-8-azaspiro[4.5]decan-2-ol (345.8 mg, 691.9 umol, 51.9% yield, 99.7% purity) as a yellow solid.

Step h: To a solution of (2R,4R)-4-amino-8-[3-iodo-1-(oxan-2-yl)-1H-pyrazolo[3,4-b]pyrazin-6-yl]-8-azaspiro[4.5]decan-2-ol (345 mg, 0.6922 mmol) in DCM (5 mL) was added ethylbis(propan-2-yl)amine (360 µL, 2.07 mmol) followed by di-tert-butyl dicarbonate (174 µL, 0.7614 mmol). Stirred at rt for 2 h. Concentrated and carried crude onto the next step.

Step i: To a solution of tert-butyl N-[(1R,3R)-3-hydroxy-8-[3-iodo-1-(oxan-2-yl)-1H-pyrazolo[3,4-b]pyrazin-6-yl]-8-azaspiro[4.5]decan-1-yl]carbamate (414 mg, 0.6917 mmol) in DMF (5 mL) was added 1H-imidazole (70.1 mg, 1.03 mmol) followed by tert-butyl(chloro)dimethylsilane (125 mg, 0.8300 mmol). Stirred at rt overnight. Partitioned between EtOAc and water. Extracted with EtOAc (2×), combined organic layers, washed with sat. NaHCO₃. Dried org over Na₂SO₄, filtered and concentrated. Purified by flash silica gel chromatography using EtOAc in heptanes (0-50%) to give tert-butyl N-[(1R,3R)-3-[(tert-butyldimethylsilyl)oxy]-8-[3-iodo-1-(oxan-2-yl)-1H-pyrazolo[3,4-b]pyrazin-6-yl]-8-azaspiro[4.5]decan-1-yl]carbamate (264 mg, 0.3716 mmol) as a yellow solid. Step j and Step k were performed as described in the synthesis of Compound 33 to yield the title compound.

Synthesis of (2R,4R)-4-amino-8-(3-(3,4-dihydro-1,5-naphthyridin-1(2H)-yl)-1H-pyrazolo[3,4-b]pyrazin-6-yl)-8-azaspiro[4.5]decan-2-ol, Compound 468

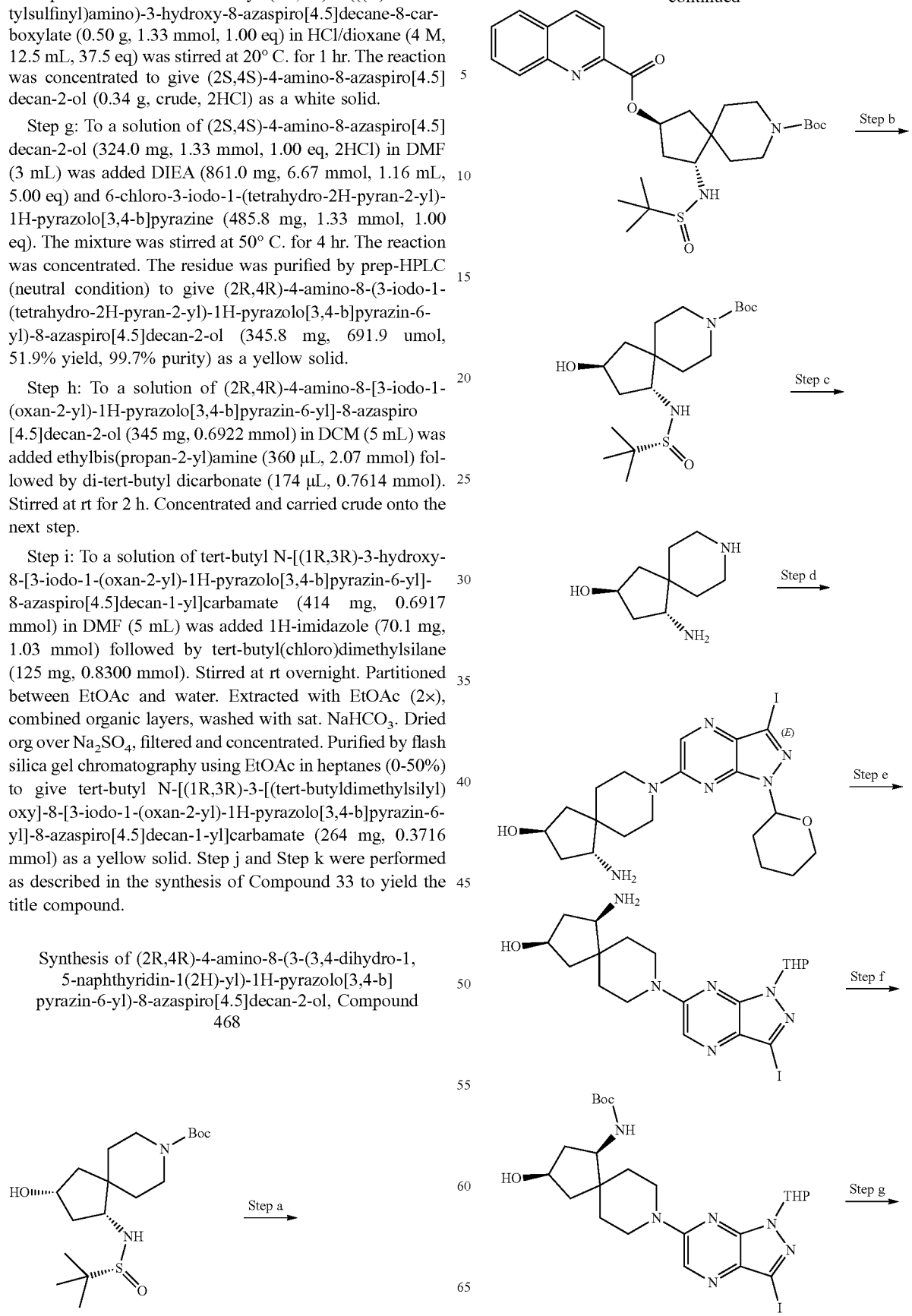

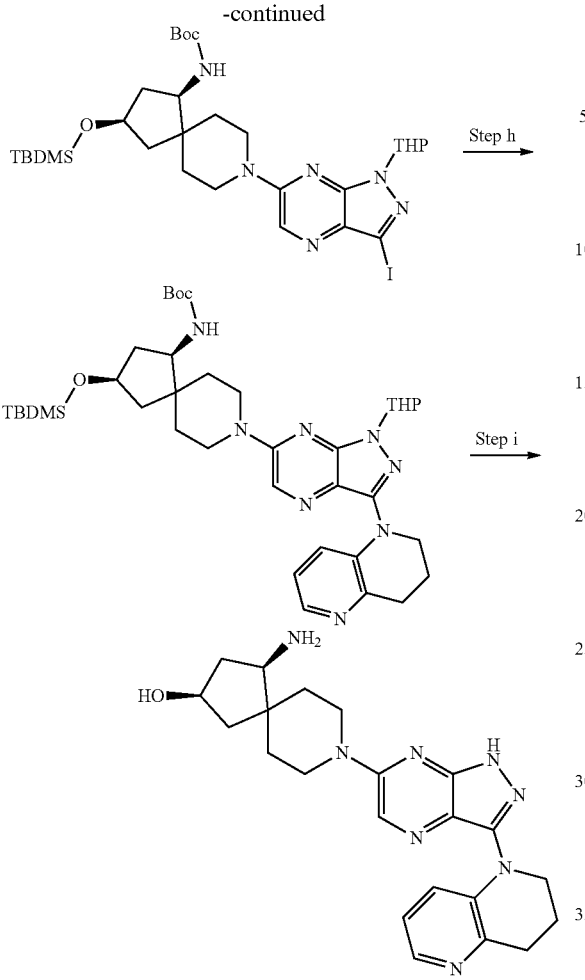

acetate=10/1-0/1) to give tert-butyl (1R,3S)-1-(((R)-tert-butylsulfinyl)amino)-3-hydroxy-8-azaspiro[4.5]decane-8-carboxylate (0.600 g, 1.60 mmol, 94.3% yield) as a white solid.

Steps c-i: Prepared as described for Compound 467 to yield the title compound.

Synthesis of 6-(4-amino-4-methyl-1-piperidyl)-N-benzyl-1H-pyrazolo[3,4-b]pyrazin-3-amine, Compound 473

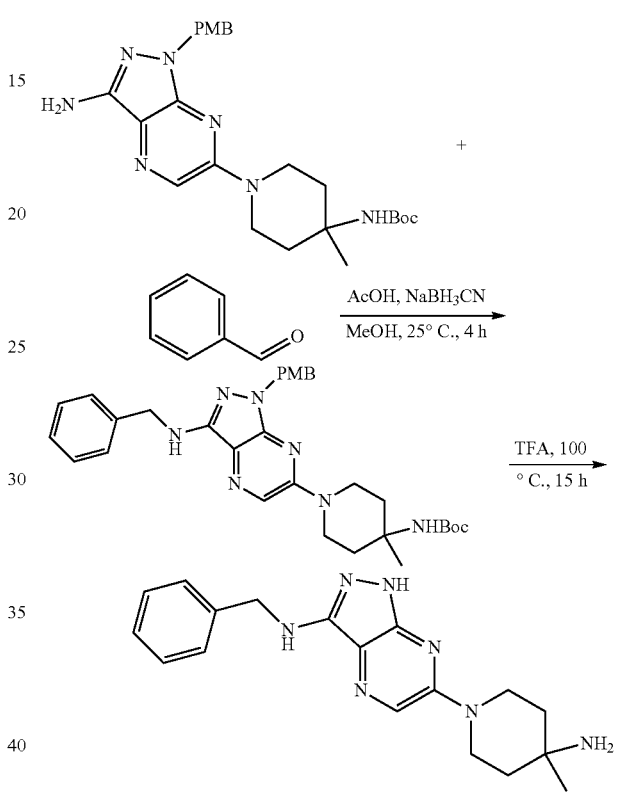

Step a: To a solution of tert-butyl (1R,3R)-1-(((R)-tert-butylsulfinyl)amino)-3-hydroxy-8-azaspiro[4.5]decane-8-carboxylate (from Compound 468 Step e, 600 mg, 1.60 mmol, 1.00 eq), quinoline-2-carboxylic acid (832.2 mg, 4.81 mmol, 3.00 eq) and PPh₃ (840.4 mg, 3.20 mmol, 2.00 eq) in THF (20 mL) was added a solution of DIAD (647.9 mg, 3.20 mmol, 623.0 uL, 2.00 eq) in THF (5 mL) The mixture was stirred at 15° C. for 10 hr. TLC (Petroleum ether/Ethyl acetate=1/1, material Rf=0.1, product Rf=0.4) showed the reaction was completed. The reaction was diluted with H₂O (100 mL) and extracted with EtOAc (100 mL*3). The combined organic phase was dried over Na₂SO₄ and concentrated. The residue was purified by column chromatography (SiO₂, Petroleum ether/Ethyl acetate=10/1-0/1) to give tert-butyl (1R,3S)-1-(((R)-tert-butylsulfinyl)amino)-3-((quinoline-2-carbonyl)oxy)-8-azaspiro[4.5]decane-8-carboxylate (0.9 g, crude) as a white solid.

Step b: To a solution of tert-butyl (1R,3S)-1-(((R)-tert-butylsulfinyl)amino)-3-((quinoline-2-carbonyl)oxy)-8-azaspiro[4.5]decane-8-carboxylate (0.900 g, 1.70 mmol, 1.00 eq) in THF (10 mL) and H₂O (10 mL) was added LiOH.H₂O (356.5 mg, 8.50 mmol, 5.00 eq). The mixture was stirred at 20° C. for 2 hr. LCMS (EW10451-19-P1A) showed the reaction was completed. The reaction was diluted with H2O (50 mL) and extracted with EtOAc (30 mL*3). The combined organic phase was dried over Na2SO4 and concentrated. The residue was purified by column chromatography (SiO2, Petroleum ether/Ethyl Step a: tert-butyl N-[1-[3-amino-1-[(4-methoxyphenyl)methyl]pyrazolo[3,4-b]pyrazin-6-yl]-4-methyl-4-piperidyl]carbamate (550.0 mg, 1.2 mmol, 1.0 eq), benzaldehyde (137.3 mg, 1.3 mmol, 1.1 eq) and AcOH (353.2 mg, 5.9 mmol, 5.0 eq) were added into MeOH (10.0 mL). The mixture was stirred at 25° C. for 1 hour. Then NaBH3CN (369.6 mg, 5.9 mmol, 5.0 eq) was added into the mixture and stirred at 25° C. for 3 hours. The mixture was diluted with EtOAc (100 mL), washed with H₂O (50 mL×2), brine (50 mL×2), dried over anhydrous Na2SO4, filtered and concentrated to give the desired product of tert-butyl N-[1-[3-(benzylamino)-1-[(4-methoxyphenyl)methyl]pyrazolo[3,4-b]pyrazin-6-yl]-4-methyl-4-piperidyl]carbamate (900.0 mg, crude) as a yellow oil, which was used in the next step without further purification.

Step b: tert-butyl N-[1-[3-(benzylamino)-1-[(4-methoxyphenyl)methyl]pyrazolo[3,4-b]pyrazin-6-yl]-4-methyl-4-piperidyl]carbamate (700.0 mg, 1.3 mmol, 1.0 eq) was added into TFA (10.0 mL) and stirred at 100° C. for 15 hours. The combined mixture was concentrated under reduced pressure and neutralized with NH3.H2O. The mixture was purified by prep-HPLC to afford the desired product of 6-(4-amino-4-methyl-1-piperidyl)-N-benzyl-1H-pyrazolo[3,4-b]pyrazin-3-amine (40.2 mg, combined) as a yellow solid.

Preparation of (S)-8-(3-((2-(trifluoromethyl)pyridin-3-yl)thio)-1H-pyrazolo[3,4-b]pyrazin-6-yl)8-azaspiro[4.5]decan-1-amine, Compound 476

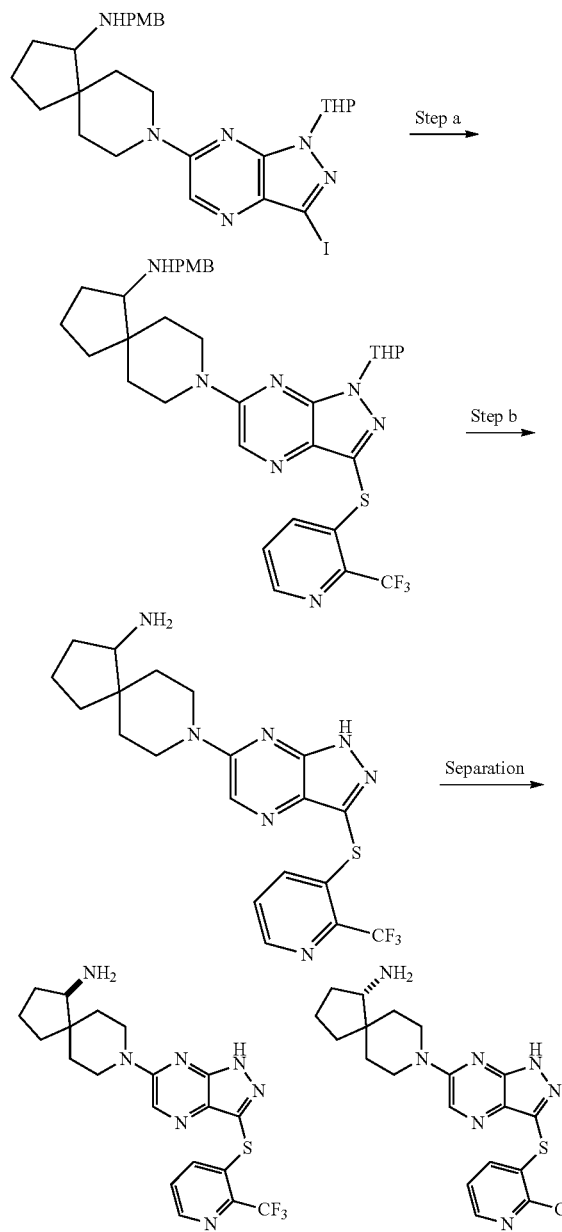

Step a: To a 5 mL vial, 8-(3-iodo-1-(tetrahydro-2H-pyran-2-yl)-1H-pyrazolo[3,4-b]pyrazin-6-yl)-N-(4-methoxybenzyl)-2-oxa-8-azaspiro[4.5]decan-1-amine (75 mg, 0.12 mmol), Pd$_2$dba$_3$ (53 mg, 0.06 mmol), XantPhos (69 mg, 0.12 mmol), 2-(trifluoromethyl)pyridine-3-thiol (66 mg, 0.36 mmol, CAS #1801693-48-0) and N,N-diisopropylethylamine (41 µL, 0.24 mmol) were successively added, followed by dioxane (0.6 mL). The resulting mixture was sealed, degassed with N$_2$ and heated under microwave irradiation at 130° C. for 90 min. After full conversion, silica gel was added and the volatiles were evaporated under reduced pressure. The crude residue was purified by flash chromatography using a gradient of ethyl acetate in hexanes (0 to 100%) to give benzyl (8-(1-(tetrahydro-2H-pyran-2-yl)-3-((2-(trifluoromethyl)pyridin-3-yl)thio)-1H-pyrazolo[3,4-b]pyrazin-6-yl)-8-azaspiro[4.5]decan-1-yl)carbamate (45 mg, 55%) as a yellow solid. MS m/z 668.2 [M+H]+.

Step b: HBr in acid acetic (33 wt %, 1.0 mL) was added dropwise to benzyl (8-(1-(tetrahydro-2H-pyran-2-yl)-3-((2-(trifluoromethyl)pyridin-3-yl)thio)-1H-pyrazolo[3,4-b]pyrazin-6-yl)-8-azaspiro[4.5]decan-1-yl)carbamate (45 mg, 0.067 mmol). The mixture was stirred for 1 hr at room temperature. Water and diethyl ether was then added. The aqueous phase was extracted three times with diethyl ether and basified with saturated solution of NaHCO$_3$. The aqueous phase was then extracted three times with dichloromethane. The combined organic extract was dried over magnesium sulfate, filtered and evaporated under vacuum. The residue was diluted in DMF and purified by C18 chromatography (0/6 to 100%/gradient of MeCN/(0.1% NH$_4$HCO$_3$ in water) to give 8-(3-((2-(trifluoromethyl)pyridin-3-yl)thio)-1H-pyrazolo[3,4-b]pyrazin-6-yl)-8-azaspiro[4.5]decan-1-amine (9 mg, 35%) as a beige solid after lyophilization. $^1$H NMR (500 MHz, DMSO) δ 8.52-8.40 (m, 1H), 8.37 (s, 1H), 7.50-7.36 (m, 2H), 4.21 (t, J=15.6 Hz, 2H), 3.16-3.02 (m, 2H), 2.76 (t, J=7.2 Hz, 1H), 1.78 (dd, J=55.9, 11.0 Hz, 2H), 1.54 (dd, J=45.7, 9.1 Hz, 4H), 1.29 (ddd, J=44.0, 38.4, 9.1 Hz, 4H). MS (ES+) m/z 450.2 (M+H)$^+$ (S)-8-(3-((2-(trifluoromethyl)pyridin-3-yl)thio)-1H-pyrazolo[3,4-b]pyrazin-6-yl)-8-azaspiro[4.5]decan-1-amine A racemic sample (9 mg) was purified by semi-preparative SFC-UV (55% CO2 and 45% MeOH+10 mMM NH4HCO2, column ChiralPak IC 250 mm×10 mm, RT=8.22 min) and provided 2.0 mg of this single enantiomer as white solid. $^1$H NMR (500 MHz, DMSO) δ 8.52-8.40 (m, 1H), 8.37 (s, 1H), 7.50-7.36 (m, 2H), 4.21 (t, J=15.6 Hz, 2H), 3.16-3.02 (m, 2H), 2.76 (t, J=7.2 Hz, 1H), 1.78 (dd, J=55.9, 11.0 Hz, 2H), 1.54 (dd, J=45.7, 9.1 Hz, 4H), 1.29 (ddd, J=44.0, 38.4, 9.1 Hz, 4H). MS (ES+) m/z 450.2 (M+H)$^+$

Preparation of 4-((6-(4-amino-4-methylpiperidin-1-yl)-1H-pyrazolo[3,4-b]pyrazin-3-yl)thio)-3-chloropyridin-2(1H)-one, Compound 477

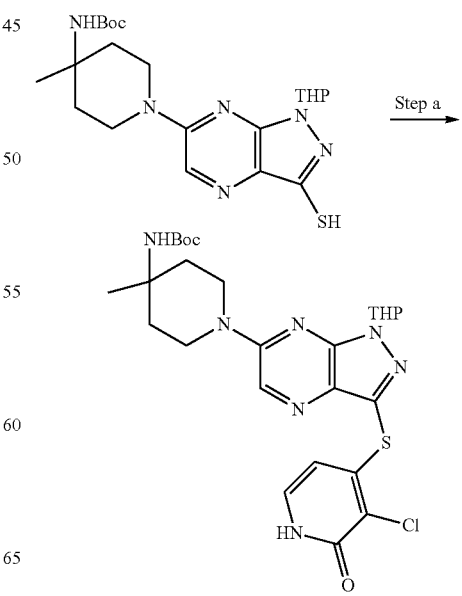

481

-continued

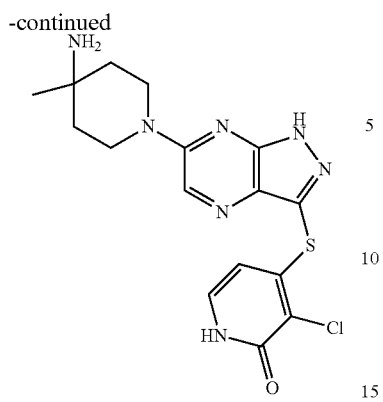

Step a: To a 5 mL vial tert-butyl (1-(3-mercapto-1-(tetrahydro-2H-pyran-2-yl)-1H-pyrazolo[3,4-b]pyrazin-6-yl)-4-methylpiperidin-4-yl)carbamate (50 mg, 0.11 mmol), Pd$_2$dba$_3$ (10 mg, 0.011 mmol), XantPhos (12 mg, 0.022 mmol), 3-chloro-4-iodopyridin-2(1H)-one (43 mg, 0.17 mmol, CAS #1227514-51-3) and N,N-diisopropylethylamine (29 µL, 0.22 mmol) were successively added, followed by dioxane (0.6 mL). The resulting mixture was sealed, degassed with N$_2$ and heated under microwave irradiation at 130° C. for 90 min. After full conversion, silica gel was added and volatiles were evaporated under reduced pressure. The crude residue was purified by flash chromatography using a gradient of methanol in dichloromethane (0 to 40%) to give tert-butyl (1-(3-((3-chloro-2-oxo-1,2-dihydropyridin-4-yl)thio)-1-(tetrahydro-2H-pyran-2-yl)-1H-pyrazolo[3,4-b]pyrazin-6-yl)-4-methylpiperidin-4-yl)carbamate (38 mg, 59%) as an yellow solid. MS m/z 576.2 [M+H]+.

Step b: HBr in acid acetic (33 wt %, 1.0 mL) was added dropwise to tert-butyl (1-(3-((3-chloro-2-oxo-1,2-dihydropyridin-4-yl)thio)-1-(tetrahydro-2H-pyran-2-yl)-1H-pyrazolo[3,4-b]pyrazin-6-yl)-4-methylpiperidin-4-yl)carbamate (30 mg, 0.052 mmol). The mixture was stirred for 1 hr at room temperature. Diethyl ether was then added and a solid crashed out. The liquid was removed and the solid was triturated with diethyl ether. The residue was diluted in water and purified by C18 chromatography (0% to 100% gradient of MeCN/(0.1% NH$_4$HCO$_3$ in water) to give 4-((6-(4-amino-4-methylpiperidin-1-yl)-1H-pyrazolo[3,4-b]pyrazin-3-yl)thio)-3-chloropyridin-2(1H)-one (9 mg, 36%) as a beige solid after lyophilization. $^1$H NMR (400 MHz, DMSO) δ 8.47 (s, 1H), 8.31 (s, 1H), 7.11 (d, J=7.1 Hz, 1H), 5.35 (d, J=7.1 Hz, 1H), 3.94-3.77 (m, 3H), 3.77-3.61 (m, 3H), 1.60 (t, J=5.5 Hz, 4H), 1.22 (s, 3H). MS (ES+) m/z 392.2 (M+H)$^+$ Synthesis of (R)-8-(3-((2-(trifluoromethyl)pyridin-3-yl)thio)-1H-pyrazolo[3,4-b]pyrazin-6-yl)-1-oxa-8-azaspiro[4.5]decan-4-amine, Compound 478

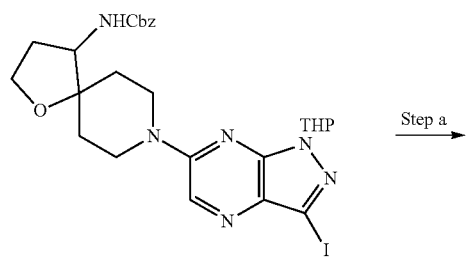

482

-continued

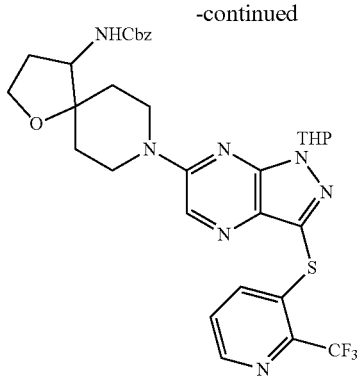

Step b

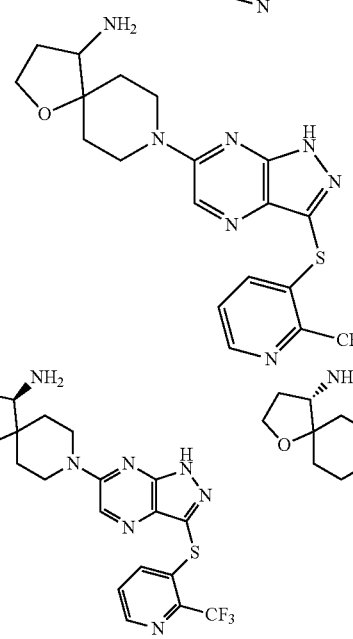

Step c

Step a: To a 5 mL vial, benzyl (8-(3-iodo-1-(tetrahydro-2H-pyran-2-yl)-1H-pyrazolo[3,4-b]pyrazin-6-yl)-1-oxa-8-azaspiro[4.5]decan-4-yl)carbamate (75 mg, 0.12 mmol), Pd2dba3 (53 mg, 0.06 mmol), XantPhos (69 mg, 0.12 mmol), 2-(trifluoromethyl)pyridine-3-thiol (66 mg, 0.36 mmol) and N,N-diisopropylethylamine (41 µL, 0.24 mmol) are successively added, followed by dioxane (0.6 mL). Resulting mixture is sealed, degassed with N2 and heated under microwave irradiation at 130° C. for 90 min. After full conversion, silica gel was added and volatiles are evaporated under reduced pressure. The crude residue is purified by flash chromatography using a gradient of ethyl acetate in hexanes (0 to 100%) to give benzyl (8-(1-(tetrahydro-2H-pyran-2-yl)-3-((2-(trifluoromethyl)pyridin-3-yl)thio)-1H-pyrazolo[3,4-b]pyrazin-6-yl)-1-oxa-8-azaspiro[4.5]decan-4-yl)carbamate (60 mg, 74%) as an yellow solid. MS m/z 656.1 [M+H]+.

Step b: HBr in acid acetic (33% wt %, 1.0 mL) was added dropwise benzyl (8-(1-(tetrahydro-2H-pyran-2-yl)-3-((2-(trifluoromethyl)pyridin-3-yl)thio)-1H-pyrazolo[3,4-b]pyrazin-6-yl)-1-oxa-8-azaspiro[4.5]decan-4-yl)carbamate (60 mg, 0.092 mmol). The mixture was stirred for 1 hr at room temperature. Diethyl ether was then added and a solid crashed out. The liquid was removed and the solid was triturated with diethyl ether. The residue was diluted in water and purified by C18 chromatography (0% to 100% gradient of MeCN/(0.1% NH4HCO3 in water) to give 8-(3-((2-

(trifluoromethyl)pyridin-3-yl)thio)-1H-pyrazolo[3,4-b] pyrazin-6-yl)-1-oxa-8-azaspiro[4.5]decan-4-amine (25 mg, 61%) as a beige solid after lyophilization. 1H NMR (500 MHz, DMSO) δ 8.49 (t, J=2.9 Hz, 1H), 8.43 (s, 1H), 7.47 (d, J=3.0 Hz, 2H), 4.38-4.16 (m, 2H), 3.80 (dd, J=13.6, 8.4 Hz, 1H), 3.68 (dd, J=15.5, 7.8 Hz, 2H), 3.18-3.13 (m, 2H), 2.16 (dd, J=12.5, 4.7 Hz, 1H), 1.62 (ddd, J=44.0, 21.1, 10.5 Hz, 4H), 1.43 (d, J=13.1 Hz, 1H). MS (ES+) m/z 452.1 (MH+)

Separation: A racemic sample (15 mg) was purified by semi-preparative SFC-UV (60% CO2 and 40% MeOH+10 mMM NH4HCO2, column ChiralPak IC 250 mm×10 mm, RT=10.14 min) to afford (R)-8-(3-((2-(trifluoromethyl)pyridin-3-yl)thio)-1H-pyrazolo[3,4-b]pyrazin-6-yl)-1-oxa-8-azaspiro[4.5]decan-4-amine (2.0 mg) as white solid.

Preparation of 1-(3-((3-chloro-2-methoxypyridin-4-yl)thio)-1H-pyrazolo[3,4-b]pyrazin-6-yl)-4-methylpiperidin-4-amine, Compound 479

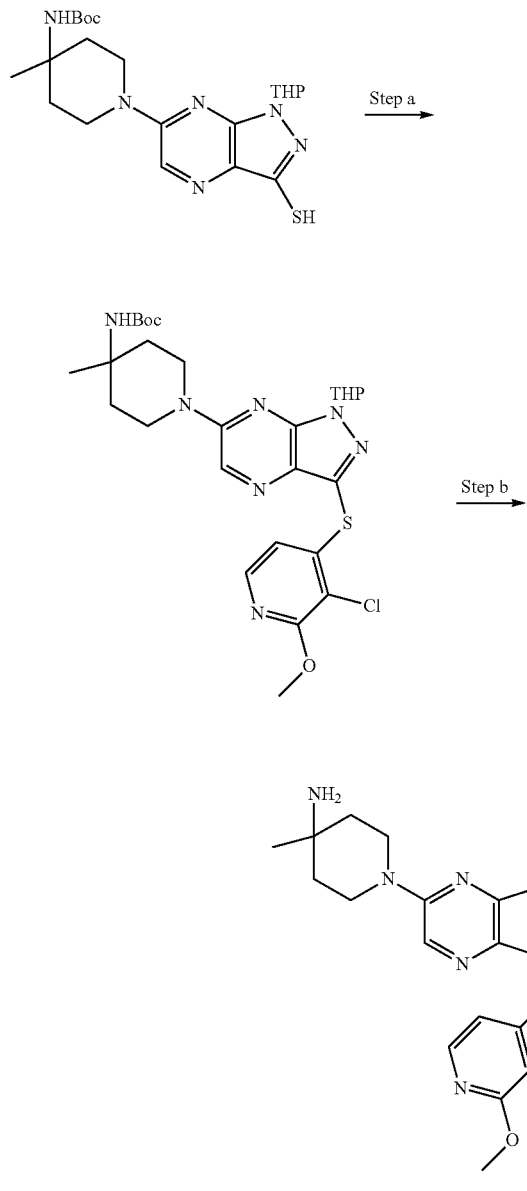

Step a: To a 5 mL vial, tert-butyl (1-(3-mercapto-1-(tetrahydro-2H-pyran-2-yl)-1H-pyrazolo[3,4-b]pyrazin-6-yl)-4-methylpiperidin-4-yl)carbamate (50 mg, 0.11 mmol), Pd₂dba; (10 mg, 0.011 mmol), XantPhos (29 mg, 0.022 mmol), 3-chloro-4-iodo-2-methoxypyridine (45 mg, 0.16 mmol, CAS #1227603-07-7) and N,N-diisopropylethylamine (29 µL, 0.22 mmol) were successively added, followed by dioxane (0.8 mL). The resulting mixture was sealed, degassed with N₂ and heated under microwave irradiation at 130° C. for 90 min. After full conversion, silica gel was added and the volatiles were evaporated under reduced pressure. The crude residue was purified by flash chromatography using a gradient of ethyl acetate in hexanes (0 to 100%) to give tert-butyl (1-(3-((3-chloro-2-methoxypyridin-4-yl)thio)-1-(tetrahydro-2H-pyran-2-yl)-1H-pyrazolo[3,4-b]pyrazin-6-yl)-4-methylpiperidin-4-yl)carbamate (30 mg, 46%) as an yellow solid. MS m/z 590.1 [M+H]⁺.

Step b: HBr in acid acetic (33 wt %, 1.0 mL) was added dropwise to tert-butyl (1-(3-((3-chloro-2-methoxypyridin-4-yl)thio)-1-(tetrahydro-2H-pyran-2-yl)-1H-pyrazolo[3,4-b] pyrazin-6-yl)-4-methylpiperidin-4-yl)carbamate (30 mg, 0.050 mmol). The mixture was stirred for 1 hr at room temperature. Diethyl ether was then added and a solid crashed out. The liquid was removed and the solid was triturated with diethyl ether. The residue was diluted in water and purified by C18 chromatography (0/a to 100% gradient of MeCN/(0.1% NH₄HCO₃ in water) to give 1-(3-((3-chloro-2-methoxypyridin-4-yl)thio)-1H-pyrazolo[3,4-b] pyrazin-6-yl)-4-methylpiperidin-4-amine (10 mg, 48%) as a white solid after lyophilization. ¹H NMR (500 MHz, DMSO) δ 8.44 (s, 1H), 7.77 (d, J=5.5 Hz, 1H), 6.19 (d, J=5.5 Hz, 1H), 3.91 (s, 3H), 3.78 (tt, J=13.9, 7.1 Hz, 4H), 1.56 (t, J=5.5 Hz, 4H), 1.19 (s, 3H). MS (ES+) m/z 406.1 (M+H)⁺

Preparation of (R)-8-(3-((2-(trifluoromethyl)pyridin-3-yl)thio)-1H-pyrazolo[3,4-b]pyrazin-6-yl)-8-azaspiro[4.5]decan-1-amine, Compound 480

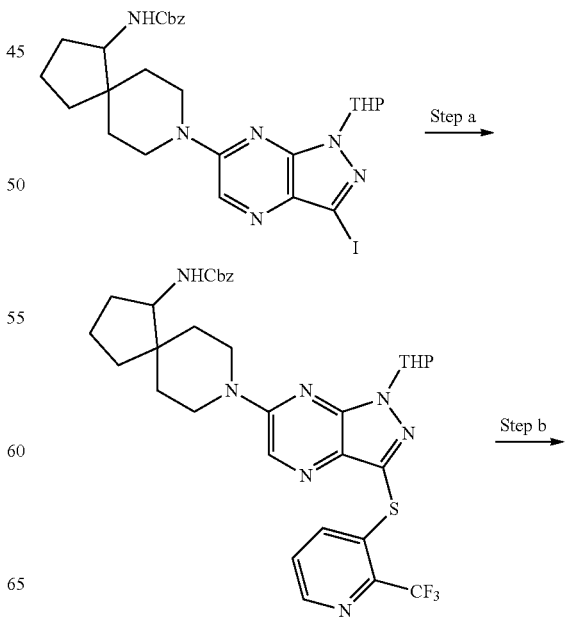

-continued

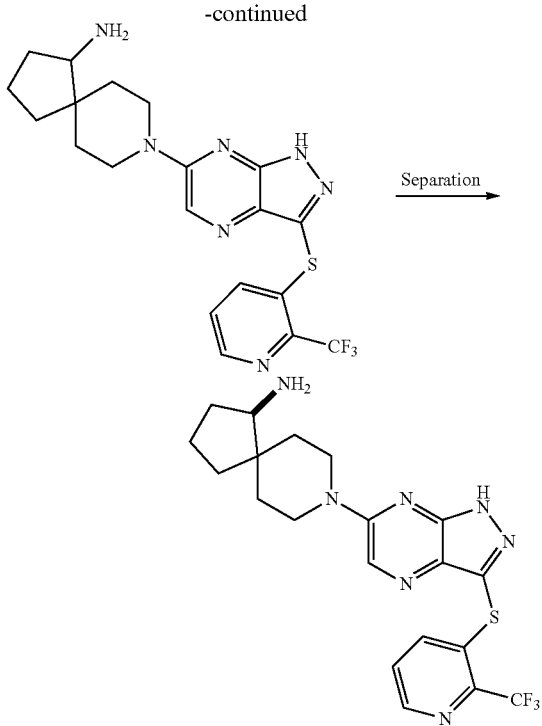

Step a: To a 5 mL vial, benzyl (8-(3-iodo-1-(tetrahydro-2H-pyran-2-yl)-1H-pyrazolo[3,4-b]pyrazin-6-yl)-8-azaspiro[4.5]decan-1-yl)carbamate (75 mg, 0.12 mmol), Pd₂dba₃ (53 mg, 0.06 mmol), XantPhos (69 mg, 0.12 mmol), 2-(trifluoromethyl)pyridine-3-thiol (66 mg, 0.36 mmol) and N,N-diisopropylethylamine (41 μL, 0.24 mmol) were successively added, followed by dioxane (0.6 mL). The resulting mixture was sealed, degassed with N₂ and heated under microwave irradiation at 130° C. for 90 min. After full conversion, silica gel was added and the volatiles were evaporated under reduced pressure. The crude residue was purified by flash chromatography using a gradient of ethyl acetate in hexanes (0 to 100%) to give benzyl (8-(1-(tetrahydro-2H-pyran-2-yl)-3-((2-(trifluoromethyl)pyridin-3-yl)thio)-1H-pyrazolo[3,4-b]pyrazin-6-yl)-8-azaspiro[4.5]decan-1-yl)carbamate (60 mg, 74%) as an yellow solid. MS m/z 656.1 [M+H]⁺.

Step b: HBr in acid acetic (33 wt %, 1.0 mL) was added dropwise benzyl (8-(1-(tetrahydro-2H-pyran-2-yl)-3-((2-(trifluoromethyl)pyridin-3-yl)thio)-1H-pyrazolo[3,4-b]pyrazin-6-yl)-8-azaspiro[4.5]decan-1-yl)carbamate (60 mg, 0.092 mmol). The mixture was stirred for 1 hr at room temperature. Diethyl ether was then added and a solid crashed out. The liquid was removed and the solid was triturated with diethyl ether. The residue was diluted in water and purified by C18 chromatography (0% to 100% gradient of MeCN/(0.1% NH₄HCO₃ in water) to give 8-(3-((2-(trifluoromethyl)pyridin-3-yl)thio)-1H-pyrazolo[3,4-b]pyrazin-6-yl)-8-azaspiro[4.5]decan-1-amine (25 mg, 61%) as a beige solid after lyophilization. ¹H NMR (500 MHz, DMSO) δ 8.49 (t, J=2.9 Hz, 1H), 8.43 (s, 1H), 7.47 (d, J=3.0 Hz, 2H), 4.38-4.16 (m, 2H), 3.80 (dd, J=13.6, 8.4 Hz, 1H), 3.68 (dd, J=15.5, 7.8 Hz, 2H), 3.18-3.13 (m, 2H), 2.16 (dd, J=12.5, 4.7 Hz, 1H), 1.62 (ddd, J=44.0, 21.1, 10.5 Hz, 4H), 1.43 (d, J=13.1 Hz, 1H). MS (ES+) m/z 452.1 (M+H)+

A racemic sample (15 mg) was purified by semi-preparative SFC-UV (60% CO2 and 40% MeOH+10 mMM NH4HCO2, column ChiralPak IC 250 mm×10 mm, RT=15.29 min) and provided 2.0 mg of this single enantiomer as white solid. ¹H NMR (500 MHz, DMSO) δ 8.49 (t, J=2.9 Hz, 1H), 8.43 (s, 1H), 7.47 (d, J=3.0 Hz, 2H), 4.38-4.16 (m, 2H), 3.80 (dd, J=13.6, 8.4 Hz, 1H), 3.68 (dd, J=15.5, 7.8 Hz, 2H), 3.18-3.13 (m, 2H), 2.16 (dd, J=12.5, 4.7 Hz, 1H), 1.62 (ddd, J=44.0, 21.1, 10.5 Hz, 4H), 1.43 (d, J=13.1 Hz, 1H). MS (ES+) m/z 452.1 (M+H)+

Preparation of 3-((6-(4-amino-4-methylpiperidin-1-yl)-1H-pyrazolo[3,4-b]pyrazin-3-yl)thio)picolinic acid and 3-((6-(4-amino-4-methylpiperidin-1-yl)-1H-pyrazolo[3,4-b]pyrazin-3-yl)thio)picolinamide, Compound 481 and 482

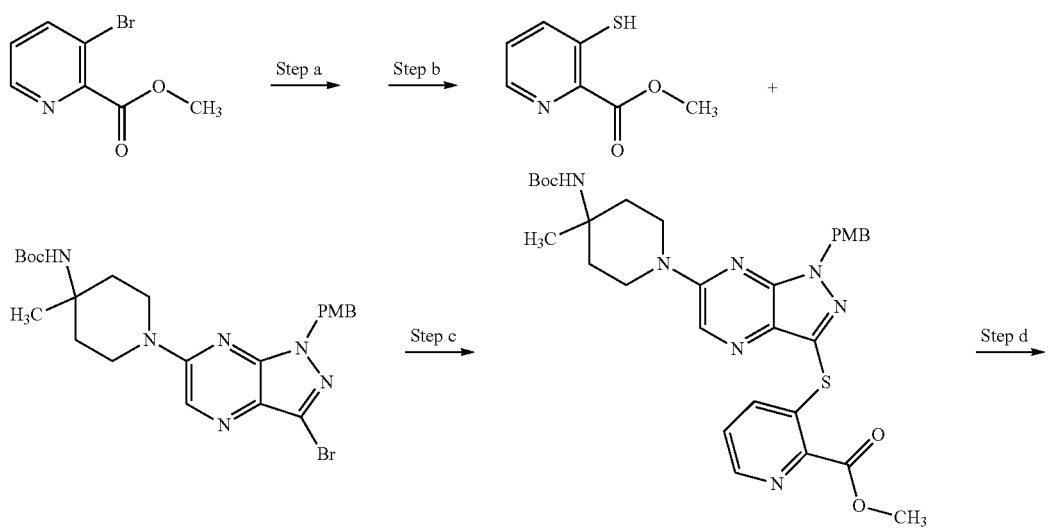

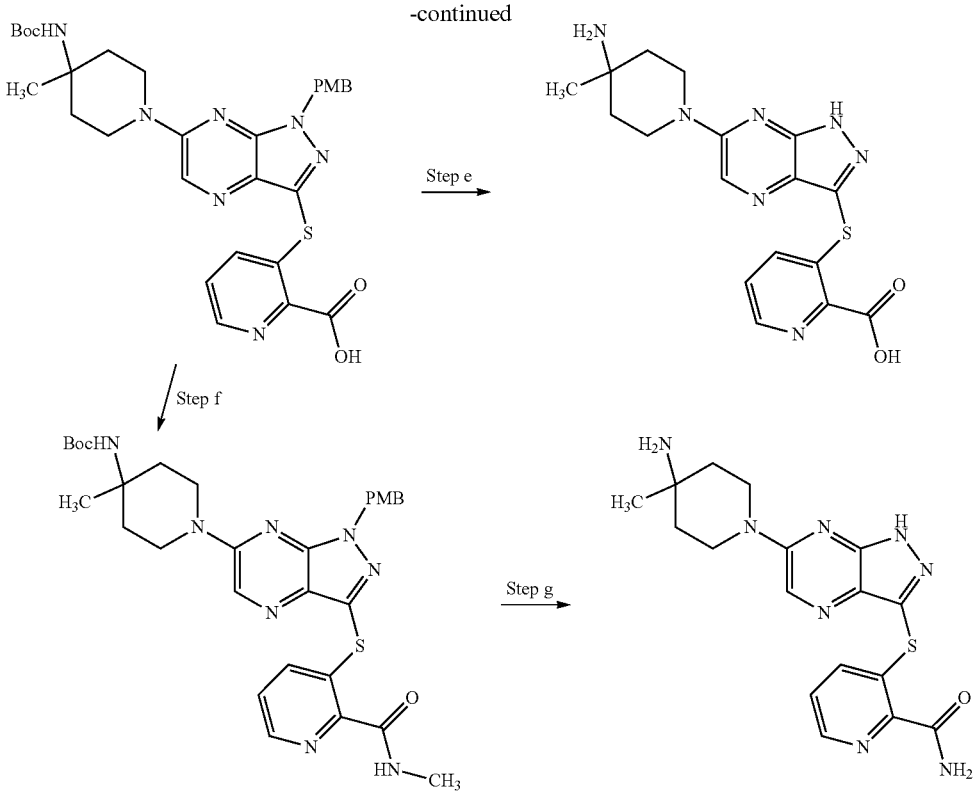

Step a: Methyl 3-bromopicolinate (3.0 g, 14 mmol), 2-ethylhexyl 3-mercaptopropanoate (3.3 g, 15 mmol, CAS #50448-95-8), XantPhos (1.6 g, 2.8 mmol), Pd$_2$(dba)$_3$ (1.3 g, 1.4 mmol), and DIPEA (7.3 mL, 42 mmol) were taken up in dioxane (150 mL). The reaction mixture was evacuated and refilled 3 times with N$_2$ followed by stirring at 100° C. for 12 hours. The volatiles were removed under reduced pressure, the residue triturated with DCM (100 mL) and H$_2$O (100 mL), and the yellow solid filtered off. The aqueous layer was extracted with DCM (100 mL×2) and the combined organics were washed with brine (100 mL), dried over anhydrous Na$_2$SO$_4$, filtered, and concentrated under reduced pressure. The residue was purified by silica gel chromatography (5-20% EtOAc/petroleum ether) to afford methyl 3-((3-((2-ethylhexyl)oxy)-3-oxopropyl)thio)picolinate (4.87 g, 97% yield) as a yellow oil.

Step b: Methyl 3-((3-((2-ethylhexyl)oxy)-3-oxopropyl)thio)picolinate (3.0 g, 8.5 mmol) was dissolved in THF (25 mL), the mixture cooled to −78° C., and t-BuOK (1M in THF, 25.4 mL) was added dropwise over 30 min under N$_2$. After addition was complete, the reaction mixture was stirred at −78° C. for 20 min. The reaction mixture was diluted with MeOH (30 mL) and EtOAc (30 mL) and the pH adjusted to 6 with 6N HCl at −78° C. The mixture was filtered and concentrated under reduced pressure to give a residue, which was purified by silica gel column chromatography (0-10% MeOH/DCM) to afford methyl 3-mercaptopicolinate (1.87 g) as a yellow solid.

Step c: tert-Butyl (1-(3-bromo-1-(4-methoxybenzyl)-1H-pyrazolo[3,4-b]pyrazin-6-yl)-4-methyl piperidin-4-yl)carbamate (0.8 g, 1.5 mmol), methyl 3-mercaptopicolinate (760 mg, 2.3 mmol, 1.5 eq), Pd$_2$(dba)$_3$ (68.6 mg, 0.07 mmol), Xantphos (86.7 mg, 0.15 mmol), and DIPEA (1.3 mL, 7.5 mmol) were taken up in dioxane (50 mL). The mixture was evacuated and refilled 3 times using N$_2$, followed by stirring at 120° C. for 12 hours. After cooling, the reaction mixture was concentrated under reduced pressure. H$_2$O (50 mL) was added followed by extraction with DCM (50 mL×3). The combined organics were washed with brine (50 mL), dried over anhydrous Na$_2$SO$_4$, filtered, concentrated under reduced pressure. The residue was purified by flash silica gel chromatography (0-100% EtOAc/petroleum ether) to afford methyl 3-((6-(4-(((tert-butoxycarbonyl)amino)-4-methylpiperidin-1-yl)-1-(4-methoxybenzyl)-1H-pyrazolo[3,4-b]pyrazin-3-yl)thio)picolinate (0.53 g, 40% yield) as a yellow oil.

Step d: Methyl 3-((6-(4-(((tert-butoxycarbonyl)amino)-4-methylpiperidin-1-yl)-1-(4-methoxybenzyl)-1H-pyrazolo[3,4-b]pyrazin-3-yl)thio)picolinate (200 mg, 0.3 mmol) and LiOH (26.8 mg, 1.1 mmol) were taken up in MeOH (10 mL) and H$_2$O (10 mL). The reaction mixture was stirred at 25° C. for 3 hours. The volatiles were then removed under reduced pressure, and the pH of the concentrate adjusted to 5-6 by by the addition of 1N HCl. The mixture was extracted with ethyl acetate (50 mL×3) and the combined organics washed with brine (50 mL), dried over anhydrous Na$_2$SO$_4$, filtered, and concentrated under reduced pressure to give 3-((6-(4-(((tert-butoxycarbonyl)amino)-4-methylpiperidin-1-yl)-1-(4-methoxybenzyl)-1H-pyrazolo[3,4-b]pyrazin-3-yl)thio)picolinic acid (160 mg, crude product) as a white solid.

Step e: 3-((6-(4-(((tert-Butoxycarbonyl)amino)-4-methylpiperidin-1-yl)-1-(4-methoxybenzyl)-1H-pyrazolo[3,4-b]pyrazin-3-yl)thio)picolinic acid (80 mg, 0.1 mmol, 1.0 eq) was taken up in TfOH (0.3 mL) and TFA (3.0 mL) and the reaction mixture as stirred at 100° C. for 15 min. The volatiles were removed under reduced pressure, the residue dissolved into MeOH (3.0 mL) and aqueous ammonia (1.0 mL) and the mixture purified by reversed phased prep.

HPLC (acetonitrile/aq. HCl) to afford the product of 3-((6-(4-amino-4-methylpiperidin-1-yl)-1H-pyrazolo[3,4-b]pyrazin-3-yl)thio)picolinic acid (8.0 mg) as a white solid: LCMS [M+H]$^+$=386.2; $^1$H-NMR (400 MHz, CD$_3$OD) δ 8.46~8.44 (m, 1H), 8.39 (s, 1H), 7.47~7.48 (m, 2H), 4.37~4.32 (m, 2H), 3.58~3.52 (m, 2H), 1.93~1.90 (m, 4H), 1.54 (s, 3H).

Step f: 3-((6-(4-((tert-Butoxycarbonyl)amino)-4-methylpiperidin-1-yl)-1-(4-methoxybenzyl)-1H-pyrazolo[3,4-b]pyrazin-3-yl)thio)picolinic acid from step d (100 mg, 0.2 mmol, 1.0 eq) and TEA (1.0 mL, 7.4 mmol, 45 eq) were taken up in DCM (5 mL), HATU (94 mg, 0.24 mmol, 1.5 eq) added, and the solution was stirred at 25° C. for 1 hr. After this time, MeNH$_2$.HCl (111 mg, 1.6 mmol, 10.0 eq) was added and the mixture was stirred at 25° C. for 12 hrs. The organics were washed with H$_2$O (20 mL×2), brine (20 mL), dried over anhydrous Na$_2$SO$_4$, filtered, and concentrated under reduced pressure. The residue was purified by prep-TLC (50% EtOAc/petroleum ether) to give tert-butyl (1-(1-(4-methoxybenzyl)-3-((2-(methylcarbamoyl)pyridin-3-yl)thio)-1H-pyrazolo[3,4-b]pyrazin-6-yl)-4-methylpiperidin-4-yl)carbamate (40 mg) as a white solid.

Step g: tert-Butyl (1-(1-(4-methoxybenzyl)-3-((2-(methylcarbamoyl)pyridin-3-yl)thio)-1H-pyrazolo[3,4-b]pyrazin-6-yl)-4-methylpiperidin-4-yl)carbamate (40 mg, 0.1 mmol, 1.0 eq) was taken up in TfOH (0.3 mL) and TFA (3.0 mL). The reaction mixture was stirred at 100° C. for 15 min and the volatiles removed under reduced pressure. NH$_3$.H$_2$O (1.0 mL) was added and the mixture was allowed to stand for 12 hrs at 20° C. On completion, the reaction mixture was concentrated under reduced pressure, and purified by reversed phase prep-HPLC (acetonitrile/aq. NH$_3$) to afford 3-((6-(4-amino-4-methylpiperidin-1-yl)-1H-pyrazolo[3,4-b]pyrazin-3-yl)thio)picolinamide (5.0 mg, 13% yield) as a white solid: LCMS [M+H]$^+$=385.0; $^1$H-NMR (400 MHz, CD$_3$OD) δ 8.35~8.33 (m, 1H), 8.31 (s, 1H), 7.22~7.21 (m, 1H), 7.16~7.15 (m, 1H), 4.00~3.94 (m, 2H), 3.80~3.74 (m, 2H), 1.29 (s, 3H).

Preparation of (S)-8-(3-((2-(trifluoromethyl)pyridin-3-yl)thio)-1H-pyrazolo[3,4-b]pyrazin-6-yl)-2-oxa-8-azaspiro[4.5]decan-4-amine, Compound 483

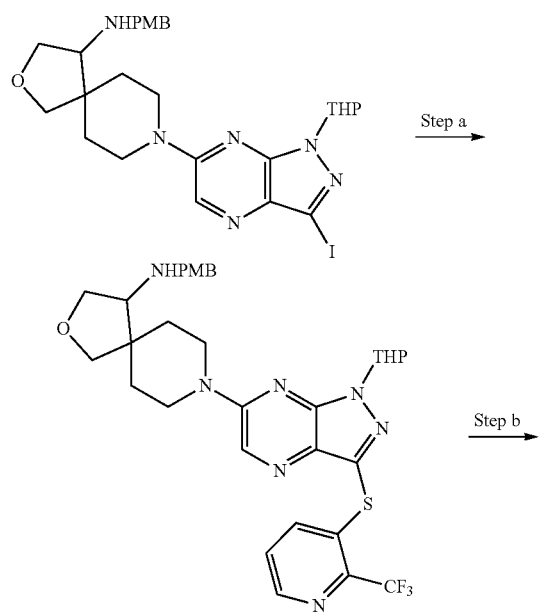

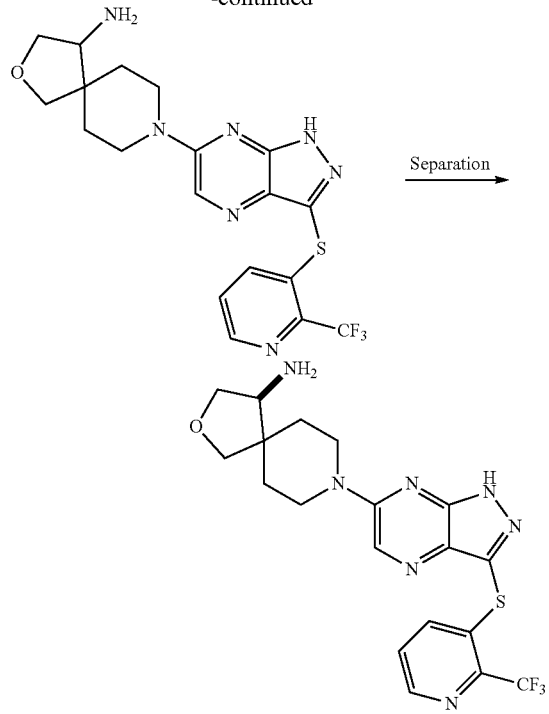

Step a: 8-(3-iodo-1-(tetrahydro-2H-pyran-2-yl)-1H-pyrazolo[3,4-b]pyrazin-6-yl)-N-(4-methoxybenzyl)-2-oxa-8-azaspiro[4.5]decan-4-amine (75 mg, 0.12 mmol), 2-(trifluoromethyl)pyridine-3-thiol (67 mg, 0.37 mmol), Pd$_2$(dba)$_3$ (36 mg, 0.06 mmol) and XantPhos (72 mg, 0.12 mmol) were all added to a nitrogen flushed microwave vial. A previously degassed (by sparging) mixture of dioxane (1 mL) and DLPEA (0.04 mL, 0.25 mmol) was added to the flushed microwave vial. The entire mixture was then heated to 110° C. for 1 hour in the microwave. The reaction was then cooled and filtered over a pad of Celite. The desired product was purified by flash chromatography (5-100% EtOAc in hexanes) to give 25 mg in 31% yield. MS m/z 656.4 [M+H]$^+$, 572.3 [M-THP+H]$^+$.

Step b: To a 10 mL round bottom flask N-(4-methoxybenzyl)-8-(1-(tetrahydro-2H-pyran-2-yl)-3-((2-(trifluoromethyl)pyridin-3-yl)thio)-1H-pyrazolo[3,4-b]pyrazin-6-yl)-2-oxa-8-azaspiro[4.5]decan-4-amine (25.0 mg, 0.04 mmol) was dissolved in trifluoroacetic acid (5 mL). The resulting mixture was then stirred for overnight at 130° C. This mixture was concentrated under vacuum and the desired product was purified using reverse phase flash chromatography with a 0-60% gradient of MeCN in 10 mM ammonium formate. This gave the desired product as a orange solid 10 mg, 58% yield post lyophilization. MS m/z 452.2 [M+H]+; 1H NMR (400 MHz, DMSO-d6) δ 8.49 (t, J=3.0 Hz, 1H), 8.44 (s, 1H), 8.15 (s, 1H), 7.48 (d, J=3.1 Hz, 2H), 4.20-4.06 (m, 2H), 3.97 (dd, J=9.0, 6.5 Hz, 1H), 3.72-3.63 (m, 2H), 3.38 (dd, J=9.1, 5.1 Hz, 2H), 3.16 (t, J=5.6 Hz, 1H), 2.53-2.52 (m, 1H), 1.73-1.56 (m, 2H), 1.52-1.42 (m, 2H).

A racemic sample (10 mg) was purified by semi-preparative SFC-UV (Lux Cellulose-4, 10×250 mm 5 um, Isocratic 40% IPA+10 mM Ammonium Formate, 10 mL/min, 150 bar, RT=12.06 min) and provided 1.0 mg of this single enantiomer as a white solid. $^1$H NMR (400 MHz, DMSO-d6) δ 8.49 (t, J=3.0 Hz, 1H), 8.44 (s, 1H), 8.15 (s, 1H), 7.48 (d, J=3.1 Hz, 2H), 4.20-4.06 (m, 2H), 3.97 (dd, J=9.0, 6.5 Hz, 1H), 3.72-3.63 (m, 2H), 3.38 (dd, J=9.1, 5.1 Hz, 2H), 3.16 (t, J=5.6 Hz, 1H), 2.53-2.52 (m, 1H), 1.73-1.56 (m, 2H), 1.52-1.42 (m, 2H). MS (ES+) m/z 452.0 (M+H)+.

Preparation of 4-((6-(4-amino-4-methylpiperidin-1-yl)-1H-pyrazolo[3,4-b]pyrazin-3-yl)thio)-3-chloro-1-methylpyridin-2(1H)-one, Compound 484

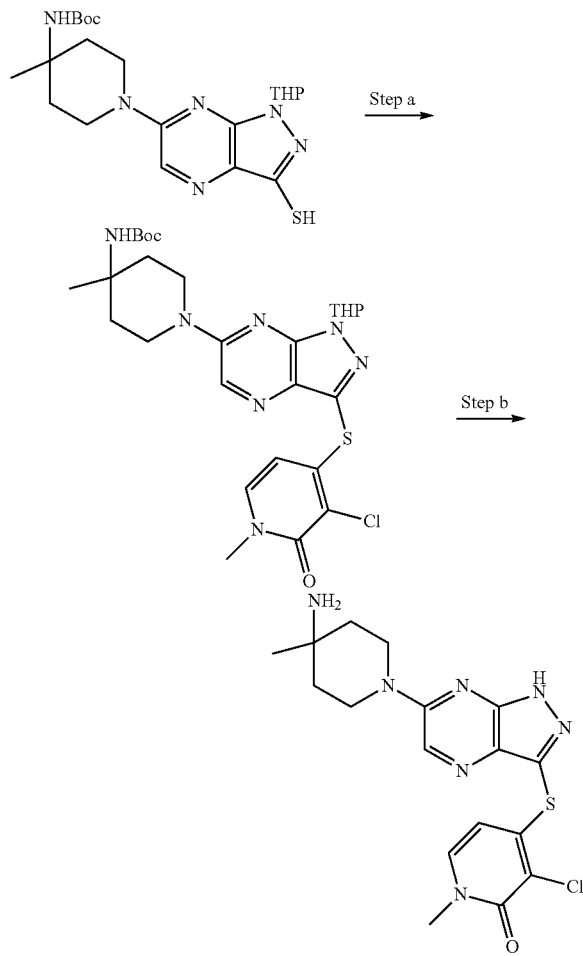

Step a: To a 5 mL vial, tert-butyl (1-(3-mercapto-1-(tetrahydro-2H-pyran-2-yl)-1H-pyrazolo[3,4-b]pyrazin-6-yl)-4-methylpiperidin-4-yl)carbamate (50 mg, 0.11 mmol), Pd₂dba₃ (53 mg, 0.06 mmol), XantPhos (58 mg, 0.11 mmol), 3-chloro-4-iodo-1-methylpyridin-2(1H)-one (CAS 889865-59-2) (45 mg, 0.16 mmol) and N,N-diisopropylethylamine (41 µL, 0.24 mmol) were successively added, followed by dioxane (0.8 mL). The resulting mixture was sealed, degassed with N₂ and heated under microwave irradiation at 130° C. for 90 min. After full conversion, silica gel was added and the volatiles were evaporated under reduced pressure. The crude residue was purified by flash chromatography using a gradient of ethyl acetate in hexanes (0 to 100%) to give tert-butyl (1-(3-((3-chloro-1-methyl-2-oxo-1,2-dihydropyridin-4-yl)thio)-1-(tetrahydro-2H-pyran-2-yl)-1H-pyrazolo[3,4-b]pyrazin-6-yl)-4-methylpiperidin-4-yl)carbamate (45 mg, 79% yield) as an yellow solid. MS m/z 590.2 [M+H]+.

Step b: HBr in acid acetic (33 wt %, 1.0 mL) was added dropwise to tert-butyl (1-(3-((3-chloro-1-methyl-2-oxo-1,2-dihydropyridin-4-yl)thio)-1-(tetrahydro-2H-pyran-2-yl)-1H-pyrazolo[3,4-b]pyrazin-6-yl)-4-methylpiperidin-4-yl)carbamate (45 mg, 0.05 mmol). The mixture was stirred for 1 hr at room temperature. Diethyl ether was then added and a solid crashed out. The liquid was removed and the solid was triturated with diethyl ether. The residue was diluted in water and purified by C18 chromatography (0% to 100% gradient of MeCN/(0.1% NH₄HCO₃ in water) to give 4-((6-(4-amino-4-methylpiperidin-1-yl)-1H-pyrazolo[3,4-b]pyrazin-3-yl)thio)-3-chloro-1-methylpyridin-2(1H)-one (15 mg, 38% yield) as a beige solid after lyophilization. ¹H NMR (500 MHz, DMSO) δ 8.46 (s, 1H), 8.35 (d, J=27.2 Hz, 1H), 7.43 (t, J=13.9 Hz, 1H), 5.41 (d, J=7.3 Hz, 1H), 4.02-3.87 (m, 2H), 3.62 (dt, J=19.2, 18.2 Hz, 2H), 1.64 (d, J=4.9 Hz, 4H), 1.23 (s, 3H). MS (ES+) m/z 406.1 (M+H)+.

Preparation of (1-(3-((2-chlorophenyl)thio)-1H-pyrazolo[3,4-b]pyrazin-6-yl)-4-fluoropiperidin-4-yl)methanamine, Compound 485

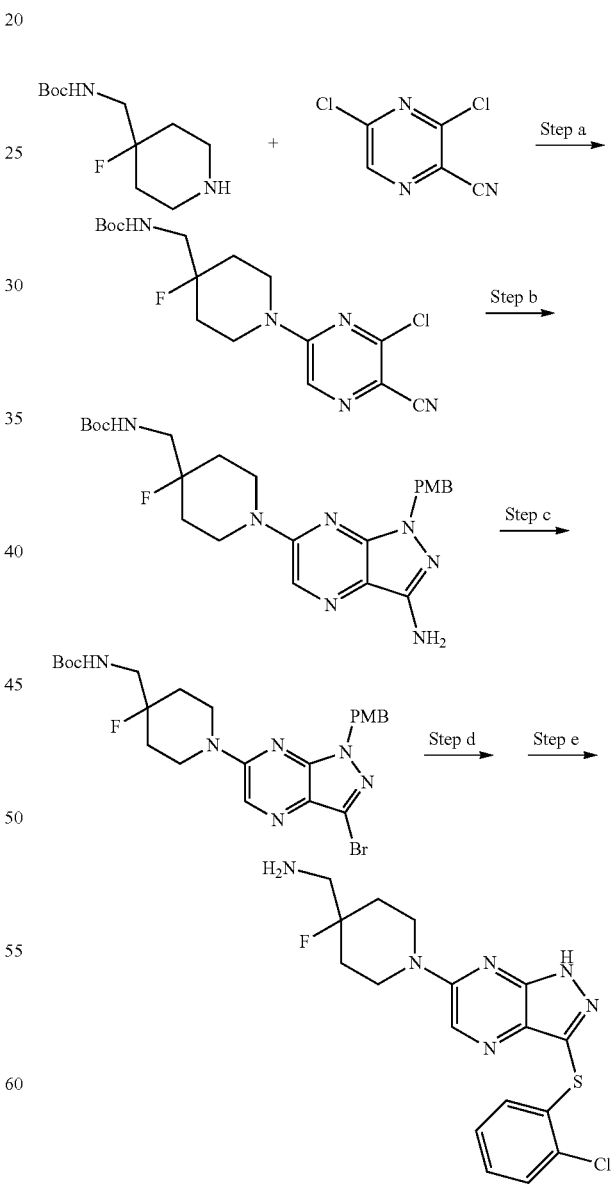

Step a: A mixture of tert-butyl ((4-fluoropiperidin-4-yl)methyl)carbamate hydrochloride (800.0 mg, 3.0 mmol, CAS

871022-62-7), 3,5-dichloropyrazine-2-carbonitrile (516.0 mg, 3.0 mmol), and DIPEA (1.9 g, 14.8 mmol) in DMF (20 mL) was stirred at 70° C. for 2 hours. After cooling, the reaction mixture was diluted with water (40 mL), extracted with ethyl acetate (50 mL×3), and the combined organic layers were washed with brine (30 mL), dried over anhydrous Na$_2$SO$_4$, filtered, concentrated under reduced pressure. The residue was purified by silica gel chromatography (15-20% EtOAc/petroleum ether) to afford tert-butyl ((1-(6-chloro-5-cyanopyrazin-2-yl)-4-fluoropiperidin-4-yl)methyl) carbamate (860 mg, 79% yield) as a yellow solid.

Step b: To a mixture of (4-methoxybenzyl)hydrazine dihydrochloride (625 mg, 2.78 mmol) and TEA (1.2 g, 11.6 mmol) in EtOH (20.0 mL) was added tert-butyl ((1-(6-chloro-5-cyanopyrazin-2-yl)-4-fluoropiperidin-4-yl)methyl) carbamate (860 mg, 2.3 mmol). The reaction mixture was stirred at 90° C. for 18 hour and cooled slowly to 20° C. The desired product, tert-butyl ((1-(3-amino-1-(4-methoxybenzyl)-1H-pyrazolo[3,4-b]pyrazin-6-yl)-4-fluoropiperidin-4-yl)methyl)carbamate (500 mg, 45% yield) was collected by filtration.

Step c: To a mixture of tert-butyl N-[[1-[3-amino-1-[(4-methoxyphenyl)methyl]pyrazolo[3,4-b]pyrazin-6-yl]-4-fluoro-4-piperidyl]methyl]carbamate (330 mg, 680 μmol, 1.0 eq) and NaNO$_2$ (56.3 mg, 816 umol, 1.2 eq) in MeCN (10 mL) at 0° C. was added HBr (1.2 g, 6.8 mmol, 47% purity, 10.0 eq) and the mixture stirred at 0° C. for 1 hour. CuBr (9.8 mg, 68.0 umol, 0.1 eq) was added at 0° C., and the mixture stirred for another 1 hour. The reaction was quenched with sat. Na$_2$SO$_3$ (8 mL) and the mixture was concentrated under reduced pressure to give a residue. The residue was dissolved into water (20 mL) and the pH adjusted 10 at 0° C. by the addition of NH$_3$.H$_2$O. The mixture was extracted with ethyl acetate (25 mL×2), and the combined organics washed with water (20 mL), brine (20 mL), dried over anhydrous Na$_2$SO$_4$, filtered, concentrated under reduced pressure, and purified by silica gel chromatography (20-50% EtOAc/petroleum ether) to afford tert-butyl N-[[1-[3-bromo-1-[(4-methoxyphenyl)methyl]pyrazolo[3,4-b]pyrazin-6-yl]-4-fluoro-4-piperidyl]methyl] carbamate (300 mg, 77/6 yield) as a white solid.

Step d: To a mixture of tert-butyl N-[[1-[3-bromo-1-[(4-methoxyphenyl)methyl]pyrazolo[3,4-b]pyrazin-6-yl]-4-fluoro-4-piperidyl]methyl]carbamate (200 mg, 364 μmol, 1.0 eq), 2-chlorobenzenethiol (79 mg, 546 umol, 1.5 eq), t-BuONa (87.5 mg, 910.0 μmol, 2.5 eq), and Xantphos (42.1 mg, 72.8 umol, 0.2 eq) in dioxane (10 mL) was added Pd$_2$(dba)$_3$ (33.3 mg, 36.4 umol, 0.1 eq) under N$_2$ atmosphere. The reaction mixture was stirred at 120° C. for 18 hours under N$_2$ atmosphere. After cooling, the reaction mixture was concentrated under reduced pressure and purified by silica gel chromatography (20-40% EtOAc/petroleum ether) to afford tert-butyl N-[[1-[3-(2-chlorophenyl)sulfanyl-1-[(4-methoxyphenyl)methyl]pyrazolo[3,4-b]pyrazin-6-yl]-4-fluoro-4-piperidyl]methyl]carbamate (100 mg) as a brown solid.

Step e: To a mixture of tert-butyl N-[[1-[3-(2-chlorophenyl)sulfanyl-1-[(4-methoxyphenyl)methyl]pyrazolo[3,4-b]pyrazin-6-yl]-4-fluoro-4-piperidyl]methyl]carbamate (100 mg, 161 μmol, 1.0 eq) in TFA (1.0 mL) was added TfOH (0.1 mL). The mixture was stirred at 90° C. for 0.25 hours, concentrated under reduced pressure to remove TFA, diluted with MeOH (2.0 mL) and the pH adjusted to 9 with 7M NH$_3$/MeOH. The mixture was filtered, concentrated under reduced pressure, and purified by reversed phase prep-HPLC to afford [1-[3-(2-chlorophenyl)sulfanyl-1H-pyrazolo[3,4-b]pyrazin-6-yl]-4-fluoro-4-piperidyl]methanamine (7.2 mg, 11% yield) as a white solid: LCMS [M+H]+=393.1; $^1$H-NMR (400 MHz, DMSO-d$_6$) δ 8.47 (s, 1H), 7.49 (d, J=7.6 Hz, 1H), 7.19-7.13 (m, 2H), 6.77 (d, J=8.0 Hz, 1H), 4.34-4.30 (m, 2H), 3.50-3.47 (m, 2H), 2.72-2.67 (m, 2H), 1.89-1.68 (m, 4H).

Preparation of 4-methyl-1-(3-(pyridin-4-ylthio)-1H-pyrazolo[3,4-b]pyrazin-6-yl)piperidin-4-amine, Compound 486

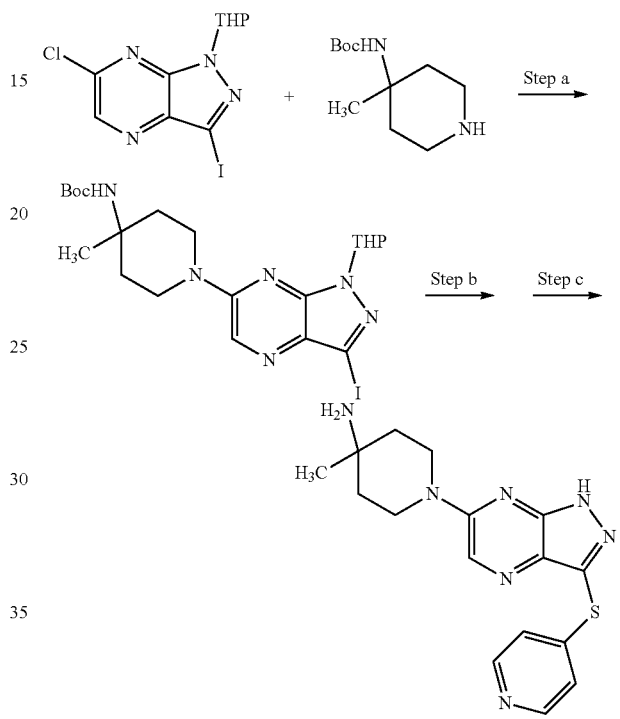

Step a: 6-Chloro-3-iodo-1-(tetrahydro-2H-pyran-2-yl)-1H-pyrazolo[3,4-b]pyrazine (400 mg, 1.1 mmol, synthesized as described above) and tert-butyl (4-methylpiperidin-4-yl)carbamate (233 mg, 1.1 mmol) taken up in DIPEA (8.0 mL) and the reaction stirred at 130° C. for 3 hours. The mixture was cooled, concentrated under reduced pressure, and purified by silica gel chromatography (0-50% EtOAc/petroleum ether) to afford tert-butyl (1-(3-iodo-1-(tetrahydro-2H-pyran-2-yl)-1H-pyrazolo[3,4-b]pyrazin-6-yl)-4-methylpiperidin-4-yl)carbamate (680 mg) as a yellow solid.

Step b: To a solution of tert-butyl N-[1-(3-iodo-1-tetrahydropyran-2-yl-pyrazolo[3,4-b]pyrazin-6-yl)-4-methyl-4-piperidyl]carbamate (200 mg, 369 umol), pyridine-4-thiol (45.1 mg, 405.6 umol), Pd$_2$(dba)$_3$ (33.8 mg, 36.9 umol), and Xantphos (21.3 mg, 36.9 umol) in dioxane (5 mL) was added DIPEA (95.3 mg, 737.4 umol). The reaction mixture was degassed and purged with N$_2$ gas 3 times, then stirred at 80° C. for 12 hours under N$_2$ atmosphere. After cooling, the mixture was concentrated under reduced pressure and purified by silica gel chromatography (0-70% EtOAc/petroleum ether) to give tert-butyl N-[4-methyl-1-[3-(4-pyridylsulfanyl)-1-tetrahydropyran-2-yl-pyrazolo[3,4-b]pyrazin-6-yl]-4-piperidyl]carbamate (180 mg, 93% yield) as a brown solid.

Step c: tert-Butyl (4-methyl-1-(3-(pyridin-4-ylthio)-1-(tetrahydro-2H-pyran-2-yl)-1H-pyrazolo[3,4-b]pyrazin-6-yl)piperidin-4-yl)carbamate (180 mg, 342 μmol) was taken up in TfOH (0.2 mL) and TFA (2.0 mL) and stirred at 90° C. for 0.5 hour. After cooling, the mixture was concentrated under reduced pressure, diluted with MeOH (5 mL), and the pH adjusted to 9 by the addition of $NH_3.H_2O$. This mixture was then purified by reversed phase prep-HPLC (acetonitrile/aq. HCl) to afford 4-methyl-1-(3-(pyridin-4-ylthio)-1H-pyrazolo[3,4-b]pyrazin-6-yl)piperidin-4-amine (60 mg, 52% yield) as a yellow solid: LCMS $[M+H]^+=342.0$; $^1$H-NMR (400 MHz, DMSO-d) δ 14.15 (br, 1H), 8.59 (d, J=6.8 Hz, 2H), 8.53 (s, 1H), 8.36 (br, 2H), 7.66 (d, J=7.2 Hz, 2H), 4.22-4.14 (m, 2H), 3.59-.3.52 (m, 2H), 1.95-1.75 (m, 4H), 1.42 (s, 3H).

Preparation of 1-(3-((6-(4-amino-4-methylpiperidin-1-yl)-1H-pyrazolo[3,4-b]pyrazin-3-yl)thio)piperidin-1-yl)ethan-1-one, Compound 488 leum ether) to afford 2-ethylhexyl 3-((6-(4-((tert-butoxycarbonyl)amino)-4-methylpiperidin-1-yl)-1-(4-methoxybenzyl)-1H-pyrazolo[3,4-b]pyrazin-3-yl)thio)propanoate (1.7 g) as a yellow oil.

Step b: 2-Ethylhexyl 3-((6-(4-((tert-butoxycarbonyl)amino)-4-methylpiperidin-1-yl)-1-(4-methoxybenzyl)-1H-pyrazolo[3,4-b]pyrazin-3-yl)thio)propanoate (700 mg, 1.0 mmol) was dissolved in THF (3 mL). The reaction mixture was cooled to −78° C., and t-BuOK (1 M in THF, 3.1 mL) was added dropwise over 30 min under $N_2$ and stirring continued at −78° C. for an additional 20 min. The reaction mixture was diluted with DCM (10 mL) and acidified to a pH of 6 with 2N HCl. The mixture was extracted with DCM (20 mL×3) and the combined organics were washed with brine (50 mL), dried over anhydrous $Na_2SO_4$, filtered, and concentrated under reduced pressure to give tert-butyl (1-(3-mercapto-1-(4-methoxybenzyl)-1H-pyrazolo[3,4-b]

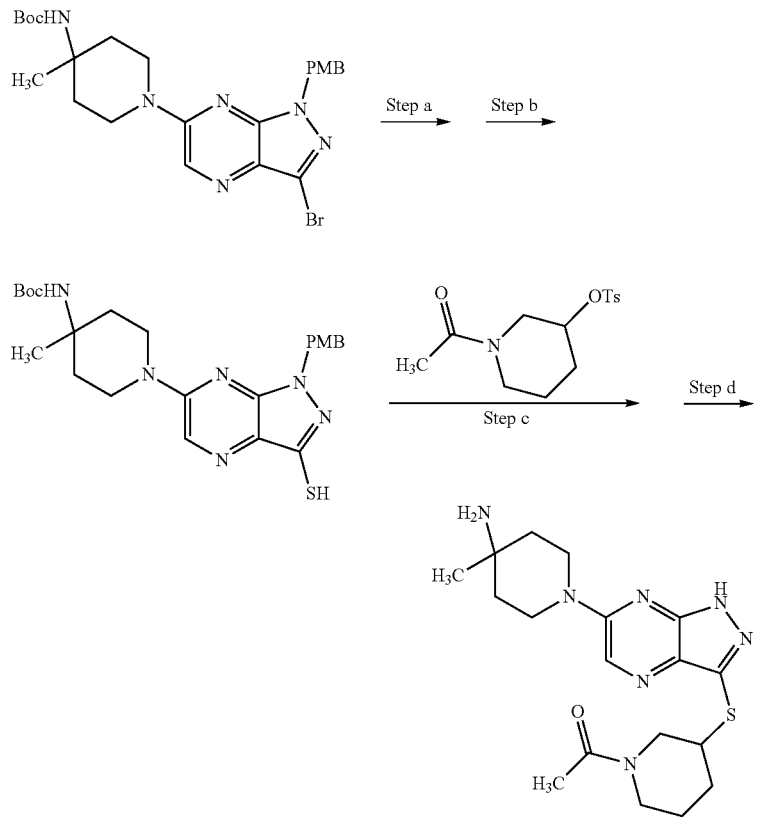

Step a: tert-Butyl (1-(3-bromo-1-(4-methoxybenzyl)-1H-pyrazolo[3,4-b]pyrazin-6-yl)-4-methylpiperidin-4-yl)carbamate (2 g, 3.7 mmol), 2-ethylhexyl 3-mercaptopropanoate (984 mg, 4.5 mmol), BrettPhos (201 mg, 0.3 mmol), BrettPhos-Pd-G3 (340 mg, 0.3 mmol), and DIPEA (1.94 mL, 11 mmol) were taken up in dioxane (25 mL). The reaction mixture was evacuated and refilled 3 times with $N_2$. The reaction mixture was stirred at 120° C. for 12 hours. After cooling, the mixture was concentrated under reduced pressure and the residue triturated with DCM (50 mL), $H_2O$ (50 mL), and the yellow solid filtered off. The aqueous layer was extracted with DCM (50 mL×2), and the combined organics were washed with brine (100 mL), dried over anhydrous $Na_2SO_4$, filtered, concentrated under reduced pressure, and purified by column chromatography (10-20% EtOAc/petropyrazin-6-yl)-4-methylpiperidin-4-yl) carbamate (300 mg, 60% yield).

Step c: To a mixture of tert-butyl N-[1-[1-[(4-methoxyphenyl)methyl]-3-sulfanyl-pyrazolo[3,4-b]pyrazin-6-yl]-4-methyl-4-piperidyl]carbamate (200 mg, 206 μmol) and (1-acetyl-3-piperidyl) 4-methylbenzenesulfonate (153 mg, 516 μmol) in DMF (10 mL) was added $K_2CO_3$ (85.6 mg, 619.1 μmol). The reaction mixture was stirred at 90° C. for 12 hours, cooled, diluted with H2O (30.0 mL), and extracted with ethyl acetate (35 mL×2). The combined organics were washed with brine (20.0 mL), dried over anhydrous $Na_2SO_4$, filtered, and concentrated under reduced pressure. The residue was purified by prep-TLC (EtOAc as eluent) to afford tert-butyl N-[1-[3-[(1-acetyl-3-piperidyl)sulfanyl]-1-[(4-methoxyphenyl)methyl]pyrazolo[3,4-b]pyrazin-6-yl]-4-methyl-4-piperidyl]carbamate (80 mg) as a colorless oil.

Step d: To a solution of tert-butyl N-[1-[3-[(1-acetyl-3-piperidyl)sulfanyl]-1-[(4-methoxyphenyl)methyl]pyrazolo[3,4-b]pyrazin-6-yl]-4-methyl-4-piperidyl]carbamate (80 mg, 131.2 μmol) in TFA (1.0 mL) was added TfOH (100 μL). The reaction mixture was stirred at 90° C. for 10 minutes, cooled, and concentrated under reduced pressure to remove TFA. The mixture was diluted with MeOH (2.0 mL) basified with 7M NH$_3$/MeOH to a pH of 9, filtered, concentrated under reduced pressure, and purified by reversed phase prep-HPLC (acetonitrile/aq. HCl) to afford 1-[3-[[6-(4-amino-4-methyl-1-piperidyl)-1H-pyrazolo[3,4-b]pyrazin-3-yl]sulfanyl]-1-piperidyl]ethanone hydrochloride (14.0 mg, 69% yield) as a yellow solid: LCMS [M+H]+=390.1; $^1$H-NMR (400 MHz, CD$_3$OD) δ 8.44 (d, J=18.8 Hz, 1H), 4.37-4.32 (m, 3H), 3.87-3.53 (m, 5H), 3.26-3.21 (m, 1H), 2.24-2.13 (m, 4H), 1.94-1.64 (m, 7H), 1.55 (s, 3H).

Preparation of 3-((6-(4-amino-4-methylpiperidin-1-yl)-1H-pyrazolo[3,4-b]pyrazin-3-yl)thio)pyridin-2(1H)-one, Compound 475

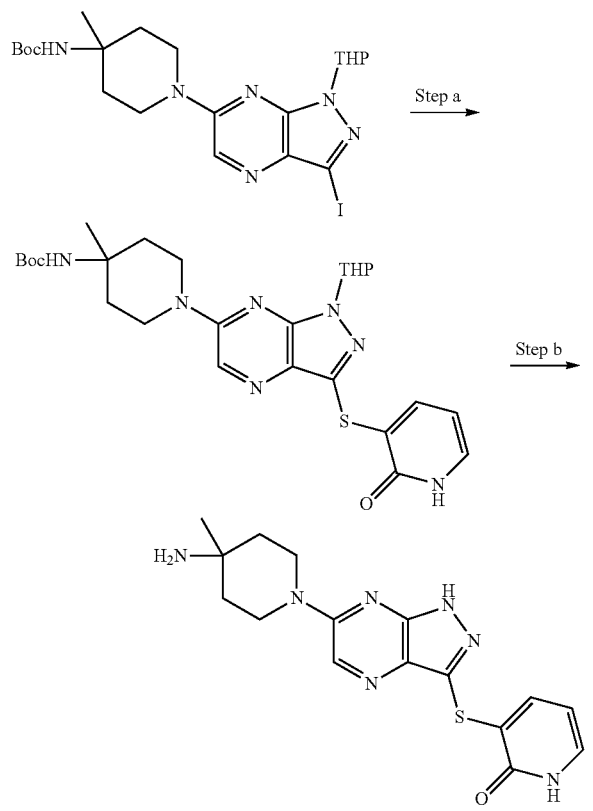

Step a: To a 5 mL vial, tert-butyl (1-(3-iodo-1-(tetrahydro-2H-pyran-2-yl)-1H-pyrazolo[3,4-b]pyrazin-6-yl)-4-methylpiperidin-4-yl)carbamate (60 mg, 0.11 mmol synthesized via Step a of Compound 486), Pd2dba3 (51 mg, 0.06 mmol), XantPhos (66 mg, 0.11 mmol), 3-mercaptopyridin-2(1H)-one (28 mg, 0.22 mmol, CAS #173278-51-8) and N,N-diisopropylethylamine (39 μL, 0.22 mmol) were successively added, followed by dioxane (0.4 mL). The resulting mixture was sealed, degassed with N2 and heated under microwave irradiation at 130° C. for 90 min. After full conversion, the volatiles were evaporated under reduced pressure. The resulting residue was purified by normal phase chromatography (0 to 20% gradient of ethyl acetate/methanol) to give tert-butyl (4-methyl-1-(3-((2-oxo-1,2-dihydropyridin-3-yl)thio)-1-(tetrahydro-2H-pyran-2-yl)-1H-pyrazolo[3,4-b]pyrazin-6-yl)piperidin-4-yl)carbamate (50 mg, 83%) as an off-white solid. MS m/z 542.5 [M+H]+.

Step b: In a 10-mL round bottomed flask, tert-butyl (4-methyl-1-(3-((2-oxo-1,2-dihydropyridin-3-yl)thio)-1-(tetrahydro-2H-pyran-2-yl)-1H-pyrazolo[3,4-b]pyrazin-6-yl)piperidin-4-yl)carbamate (50 mg, 0.09 mmol) was slowly dissolved in HCl 4 M in dioxane (1 mL), at room temperature. The resulting yellow-orange mixture was stirred at room temperature for 15 min. After this time, the volatiles were evaporated off under reduced pressure. The gummy residue was redissolved in DMF (0.8 mL), loaded on a reverse phase chromatography column and purified using a gradient of acetonitrile/0.1% formic acid in water (0 to 35%) to give 3-((6-(4-amino-4-methylpiperidin-1-yl)-1H-pyrazolo[3,4-b]pyrazin-3-yl)thio)pyridin-2(1H)-one (8 mg, 24%) as an off-white solid after lyophilization. MS m/z 358.4 [M+H]+. 1H NMR (500 MHz, DMSO) δ 8.42 (s, 1H), 8.35 (s, 1H), 7.21 (dd, J=6.5, 1.9 Hz, 1H), 6.76 (dd, J=7.1, 1.8 Hz, 1H), 6.05 (dd, J=7.0, 6.6 Hz, 1H), 3.96 (s, 2H), 3.71-3.62 (m, 2H), 1.70 (s, 4H), 1.25 (s, 3H).

Preparation of 4-((6-(4-amino-4-methylpiperidin-1-yl)-1H-pyrazolo[3,4-b]pyrazin-3-yl)thio)-3-fluoropyridin-2-amine, Compound 489

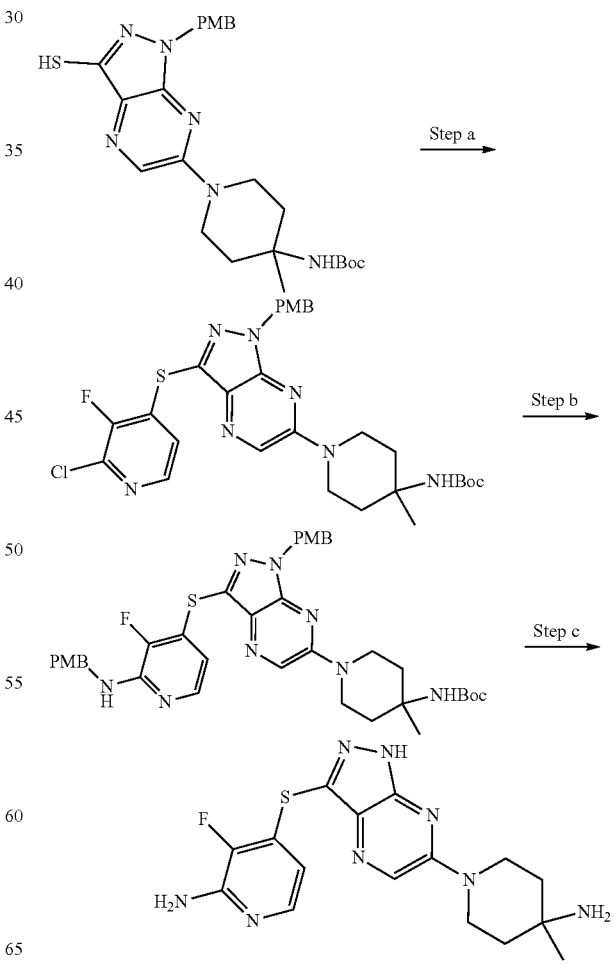

Step a: The compounds 2-chloro-3-fluoro-4-iodopyridine (106 mg, 0.4 mmol, CAS #148639-07-0), tert-butyl (1-(3-mercapto-1-(4-methoxybenzyl)-1H-pyrazolo[3,4-b]pyrazin-6-yl)-4-methylpiperidin-4-yl)carbamate (200 mg, 0.4 mmol), Pd$_2$(dba)$_3$ (37 mg, 0.04 mmol), Xantphos (47 mg, 0.08 mmol) and DIPEA (0.2 mL, 1.2 mmol) were placed into dioxane (15 mL). The reaction mixture was evacuated and refilled 3 times using N$_2$. The reaction mixture was stirred at 110° C. for 12 hours in the dark. The reaction mixture was concentrated to give a residue which was purified by flash silica gel chromatography (ethyl acetate:petroleum ether=0:100 to 30:100) to afford the product of tert-butyl (1-(3-((2-chloro-3-fluoropyridin-4-yl)thio)-1-(4-methoxybenzyl)-1H-pyrazolo[3,4-b]pyrazin-6-yl)-4-methylpiperidin-4-yl)carbamate (184 mg, 72.7% yield) as a yellow oil.

Step b: The compounds tert-butyl (1-(3-((2-chloro-3-fluoropyridin-4-yl)thio)-1-(4-methoxybenzyl)-1H-pyrazolo[3,4-b]pyrazin-6-yl)-4-methylpiperidin-4-yl)carbamate (20 mg, 0.03 mmol), PMBNH$_2$ (5 mg, 0.04 mmol), BrettPhos (2 mg, 0.003 mmol), BrettPhos-Pd-G4 (3 mg, 0.003 mmol), and t-BuONa (10 mg, 0.1 mmol) were placed into dioxane (5 mL). The reaction mixture was evacuated and refilled f3 times using N$_2$. The reaction mixture was stirred at 110° C. for 12 hours. The combined mixture was concentrated and purified by prep-TLC (ethyl acetate:petroleum ether=1:1) to afford the desired product tert-butyl (1-(3-((3-fluoro-2-((4-methoxybenzyl)amino)pyridin-4-yl)thio)-1-(4-methoxybenzyl)-1H-pyrazolo[3,4-b]pyrazin-6-yl)-4-methylpiperidin-4-yl)carbamate (40 mg) as a white solid.

Step c: The compound of tert-butyl (1-(3-((3-fluoro-2-((4-methoxybenzyl)amino)pyridin-4-yl)thio)-1-(4-methoxybenzyl)-1H-pyrazolo[3,4-b]pyrazin-6-yl)-4-methylpiperidin-4-yl)carbamate (20 mg, 0.03 mmol) was added into TfOH (3 drops) and TFA (2.0 mL). The mixture was stirred at 85° C. for 0.5 hour. The combined mixture was concentrated to give a residue which was triturated with NH$_3$/MeOH(7M, 1.0 mL), DMF (2 mL) and MeOH (2 mL). The residue was purified by prep-HPLC to afford the desired product 4-((6-(4-amino-4-methylpiperidin-1-yl)-1H-pyrazolo[3,4-b]pyrazin-3-yl)thio)-3-fluoropyridin-2-amine (6.0 mg, HCl salt) as a yellow solid. LCMS: calc. for C16H19FN8S: 374.1, found: [M+H]+ 375.0. $^1$H NMR (400 MHz, Methanol_d4): δ 8.45 (s, 1H), 7.44-7.42 (m, 1H), 6.26-6.22 (m, 1H), 4.39-4.33 (m, 2H), 3.60-3.53 (m, 2H), 1.95-1.91 (m, 4H), 1.31 (s, 3H).

Preparation of N4-[6-(4-amino-4-methyl-1-piperidyl)-1H-pyrazolo[3,4-b]pyrazin-3-yl]-N4-methylpyridine-2,4-diamine, Compound 491

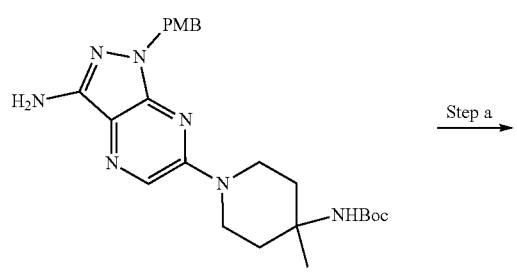

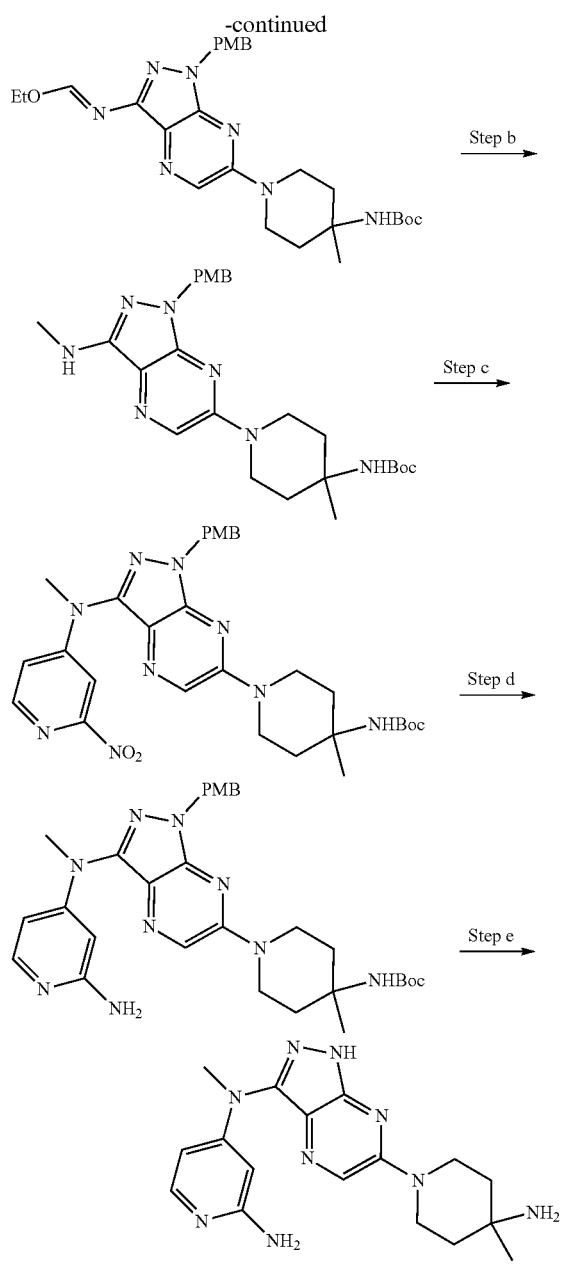

Step a: The compound of tert-butyl N-[1-[3-amino-1-[(4-methoxyphenyl)methyl]pyrazolo[3,4-b]pyrazin-6-yl]-4-methyl-4-piperidyl]carbamate (prepared as described for Compound 6) (500.0 mg, 1.1 mmol, 1.0 eq) was added into HC(OEt)$_3$ (6.2 g, 7.0 mL). The mixture was stirred at 150° C. for 4 hours. The mixture was concentrated under reduced pressure and the residue was purified by column chromatography (petroleum ether:ethyl acetate=10:1 to 1:1) to afford the desired product of ethyl (1E)-N-[6-[4-(tert-butoxycarbonylamino)-4-methyl-1-piperidyl]-1-[(4-methoxyphenyl)methyl]pyrazolo[3,4-b]pyrazin-3-yl]methanimidate (370 mg, 70% purity, 46% yield) as a yellow solid.

Step b: The compound of ethyl (1E)-N-[6-[4-(tert-butoxycarbonylamino)-4-methyl-1-piperidyl]-1-[(4-methoxyphenyl)methyl]pyrazolo[3,4-b]pyrazin-3-yl]methanimidate (340.0 mg, 454.5 umol, 1.0 eq) and NaBH$_4$ (86.0 mg, 2.3 mmol, 5.0 eq) were added into EtOH (20.0 mL) under N$_2$. The mixture was stirred at 15° C. for 15 hours and 40° C. for 20 hours. The combined reaction mixture was concentrated under reduced pressure and the residue was purified by column chromatography (petroleum ether: ethyl acetate=4:1 to 1:1) to afford the desired product of tert-butyl N-[1-[1-[(4-methoxyphenyl)methyl]-3-(methylamino)pyrazolo[3,4-b]pyrazin-6-yl]-4-methyl-4-piperidyl]carbamate (230 mg) as a yellow solid.

Step c: The compound of tert-butyl N-[1-[1-[(4-methoxyphenyl)methyl]-3-(methylamino)pyrazolo[3,4-b]pyrazin-6-yl]-4-methyl-4-piperidyl]carbamate (150.0 mg, 311.5 umol, 1.0 eq), 4-chloro-2-nitro-pyridine (59.3 mg, 373.8 umol, 1.2 eq), XPhos (14.9 mg, 31.2 umol, 0.1 eq), K₂CO₃ (129.1 mg, 934.4 umol, 3.0 eq) and Pd₂(dba)₃ (28.5 mg, 31.2 umol, 0.1 eq) were added into dioxane (10.0 mL). The mixture was stirred at 110° C. for 3 hours. The combined reaction mixture was concentrated under reduced pressure and the residue was purified by column chromatography (petroleum ether: ethyl acetate=4:1 to 1:1) to afford the desired product of tert-butyl N-[1-[1-[(4-methoxyphenyl)methyl]-3-[methyl-(2-nitro-4-pyridyl)amino]pyrazolo[3,4-b]pyrazin-6-yl]-4-methyl-4-piperidyl]carbamate (210 mg) as a green oil.

Step d: The compound of tert-butyl N-[1-[1-[(4-methoxyphenyl)methyl]-3-[methyl-(2-nitro-4-pyridyl)amino]pyrazolo[3,4-b]pyrazin-6-yl]-4-methyl-4-piperidyl]carbamate (160 mg, 265.1 umol, 1.0 eq) and 10% Pd/C (50 mg, wet) were added into MeOH (10 mL). The mixture was evacuated and refilled 3 times using H₂ gas and stirred at 15° C. for 18 hours under H₂ (15 psi). The mixture was filtered and concentrated under reduced pressure and the residue (210 mg, crude) was used in the next step directly.

Step e: The compound of tert-butyl N-[1-[3-[(2-amino-4-pyridyl)-methyl-amino]-1-[(4-methoxyphenyl)methyl]pyrazolo[3,4-b]pyrazin-6-yl]-4-methyl-4-piperidyl]carbamate (210 mg, crude) was added into the mixture of TFA (10 mL) and TfOH (0.2 mL). The mixture was stirred at 50° C. for 12 hours. The combined reaction mixture was concentrated under reduced pressure and the residue was purified by prep-HPLC (NH₃.H₂O) to afford the desired product of N4-[6-(4-amino-4-methyl-1-piperidyl)-1H-pyrazolo[3,4-b]pyrazin-3-yl]-N4-methyl-pyridine-2,4-diamine (36.3 mg) as a white solid. LCMS: calc. for $C_{17}H_{23}N_9$: 353.2, found: [M+H]+ 354.1. ¹H NMR (400 MHz, Methanol_d4): δ 8.29 (s, 1H), 7.58 (d, J=6 Hz, 1H), 6.24-6.21 (m, 1H), 6.08 (d, J=2.0 Hz, 1H), 4.01-3.97 (m, 2H), 3.77-3.70 (m, 2H), 3.48 (s, 3H), 1.74-1.68 (m, 4H), 1.31 (s, 3H).

Synthesis of 4-methyl-1-(3-(piperidin-3-ylthio)-1H-pyrazolo[3,4-b]pyrazin-6-yl)piperidin-4-amine, Compound 492

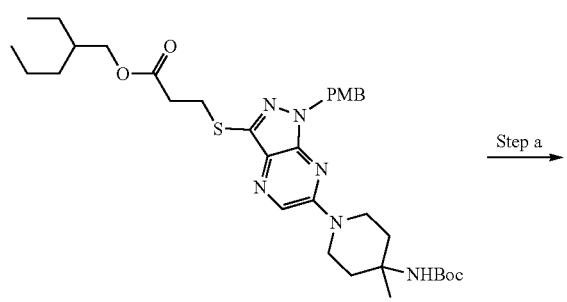

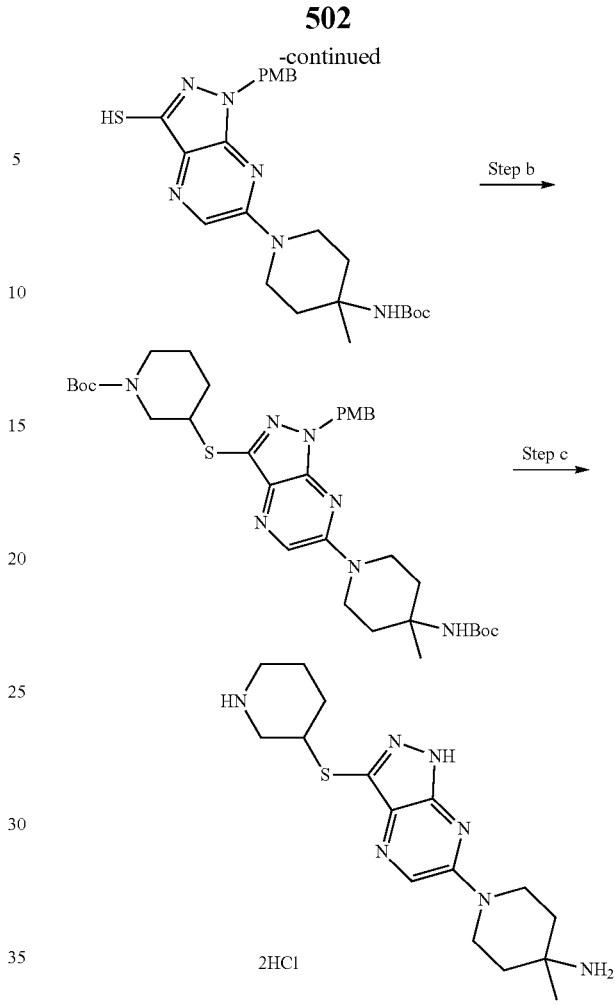

Step a: The compound of 2-ethylhexyl3-((6-(4-((tert-butoxycarbonyl)amino)-4-methylpiperidin-1-yl)-1-(4-methoxybenzyl)-1H-pyrazolo[3,4-b]pyrazin-3-yl)thio)propanoate (100 mg, 149 μmol) in THF (2 mL), the reaction was stirred at −78° C., and the solution of t-BuOK (0.5 mL, 1M in THF) was added, the reaction was stirred at −78° C. for 12 hours. LCMS showed the starting material was consumed completely and a new peak with desired MS was detected. Removal of the solvent, the crude product of tert-butyl(1-(3-mercapto-1-(4-methoxybenzyl)-1H-pyrazolo[3,4-b]pyrazin-6-yl)-4-methylpiperidin-4-yl)carbamate (74 mg, crude) was obtained as a yellow solid.

Step b: Tert-butyl(1-(3-mercapto-1-(4-methoxybenzyl)-1H-pyrazolo[3,4-b]pyrazin-6-yl)-4-methylpiperidin-4-yl)carbamate (50 mg, 103 μmol), tert-butyl 3-(tosyloxy)piperidine-1-carboxylate (40.1 mg, 113 μmol) and K2CO3 (42.7 mg, 309 μmol) were added in DMF (3 mL), The reaction was stirred at 70° C. for 12 hours. LCMS showed the starting material was consumed completely and a new peak with desired MS was detected. The reaction mixture was concentrated to give a yellow solid. The residue was purified by flash silica gel chromatography (Petroleum ether: Ethyl acetate=100:0 to 100:100). tert-butyl 3-((6-(4-((tert-butoxycarbonyl)amino)-4-methylpiperidin-1-yl)-1-(4-methoxybenzyl)-1H-pyrazolo[3,4-b]pyrazin-3-yl)thio)piperidine-1-carboxylate (40.0 mg, 59.8 μmol) was obtained as a yellow solid.

Step c: Tert-butyl 3-((6-(4-((tert-butoxycarbonyl)amino)-4-methylpiperidin-1-yl)-1-(4-methoxybenzyl)-1H-pyrazolo

[3,4-b]pyrazin-3-yl)thio)piperidine-1-carboxylate (40 mg, 59.8 μmol) were added in TFA (10 mL) and TfOH (1 mL), the reaction was stirred at 80° C. for 30 min. LCMS showed R1 was consumed completely and a new peak with desired MS was detected. The reaction mixture was concentrated to give a yellow solid. The residue was purified by prep-HPLC (HCl condition). 4-methyl-1-(3-(piperidin-3-ylthio)-1H-pyrazolo[3,4-b]pyrazin-6-yl)piperidin-4-amine (16.5 mg, 89.1% yield, 2HCl salt) was obtained as a yellow solid.

Preparation of 4-methyl-1-(3-(quinazolin-4-ylthio)-1H-pyrazolo[3,4-b]pyrazin-6-yl)piperidin-4-amine, Compound 493

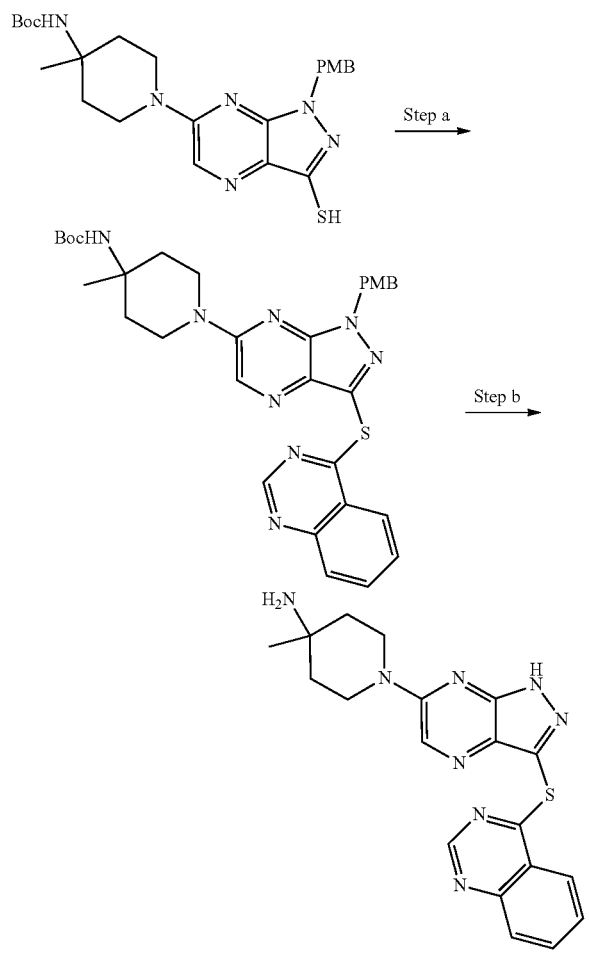

Step a: The compound of tert-butyl (1-(3-mercapto-1-(4-methoxybenzyl)-1H-pyrazolo[3,4-b]pyrazin-6-yl)-4-methylpiperidin-4-yl)carbamate (200 mg, 0.4 mmol), 4-chloroquinazoline (74 mg, 0.45 mmol) and K₂CO₃ (169 mg, 1.2 mmol) were placed into the solvent of DMF (10 mL). The reaction mixture was stirred at 80° C. for 12 hours under N₂. The mixture was concentrated and triturated with EtOAc (30 mL). The organic layers were washed with brine (30 mL), dried over anhydrous Na₂SO₄, filtered and concentrated to give a residue. The residue was purified by prep-TLC (ethyl acetate/petroleum ether=1:1) to afford the product of tert-butyl (1-(1-(4-methoxybenzyl)-3-(quinazolin-4-ylthio)-1H-pyrazolo[3,4-b]pyrazin-6-yl)-4-methylpiperidin-4-yl)carbamate (50.0 mg, 81.6 μmol) as a yellow oil.

Step b: The compound of tert-butyl (1-(1-(4-methoxybenzyl)-3-(quinazolin-4-ylthio)-1H-pyrazolo[3,4-b]pyrazin-6-yl)-4-methylpiperidin-4-yl)carbamate (50 mg, 81.6 μmol) was placed into TFA (4.0 mL). The mixture was stirred at 85° C. for 72 h. The mixture was concentrated under reduced pressure and diluted with MeOH (3.5 mL) and DMF (1 mL) and adjusted pH=9 by adding the solution of NH3/CH₃OH (7 M). The mixture was purified by prep-HPLC (NH₃.H₂O) to afford the product of 4-methyl-1-(3-(quinazolin-4-ylthio)-1H-pyrazolo[3,4-b]pyrazin-6-yl)piperidin-4-amine (3.5 mg) as a white solid. LCMS: calc. for C19H20N8S: 392.2, found: [M+H]+ 393.0. 1HNMR (400 MHz, Methanol_d4): δ 8.66 (s, 1H), 8.42~8.40 (m, 1H), 8.33 (s, 1H), 8.08~7.99 (m, 2H), 7.86~7.81 (m, 2H), 4.02~3.96 (m, 2H), 3.81~3.74 (m, 2H), 1.78~1.65 (m, 4H), 1.30 (s, 3H).

Synthesis of N4-(6-(4-amino-4-methylpiperidin-1-yl)-1H-pyrazolo[3,4-b]pyrazin-3-yl)-3-chloropyridine-2,4-diamine, Compound 494

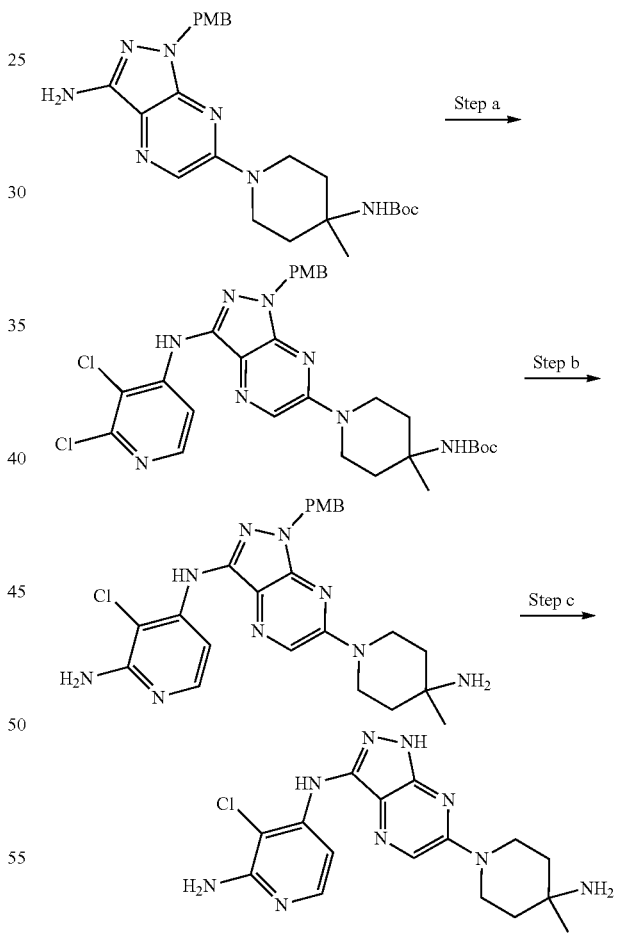

Step a: To a solution of tert-butyl (1-(3-amino-1-(4-methoxybenzyl)-1H-pyrazolo[3,4-b]pyrazin-6-yl)-4-methylpiperidin-4-yl)carbamate (500.0 mg, 1.1 mmol) and 2,3-dichloro-4-iodopyridine (290.0 mg, 1.1 mmol) in dioxane (10.0 mL) was added K2CO3 (292.0 mg, 2.1 mmol), Pd2(dba)3 (97.0 mg, 0.11 mmol) and XPhos (50.5 mg, 0.11 mmol). The reaction mixture was degassed and purged with N2 for 3 times and stirred at 100° C. for 12 hours under N2 atmosphere. LCMS showed 14% of the starting material remained and 62% of desired product formed. The reaction mixture was concentrated under reduced pressure. The residue was diluted with water (30.0 mL) and extracted with Ethyl acetate (30.0 mL×2). The combined organic layers were washed with water (30.0 mL×2), dried over anhydrous Na2SO4, filtered and concentrated under reduced pressure to give a residue. The residue was purified by column chromatography (Petroleum ether/Ethyl acetate=100:0 to 100:50). Tert-butyl (1-(3-((2,3-dichloropyridin-4-yl)amino)-1-(4-methoxybenzyl)-1H-pyrazolo[3,4-b]pyrazin-6-yl)-4-methylpiperidin-4-yl)carbamate (350.0 mg, 53.8% yield) was obtained as a light yellow solid.

Step b: A solution of tert-butyl (1-(3-((2,3-dichloropyridin-4-yl)amino)-1-(4-methoxybenzyl)-1H-pyrazolo[3,4-b]pyrazin-6-yl)-4-methylpiperidin-4-yl)carbamate (100.0 mg, 162.0 μmol) in NH3.H2O (2.0 mL) and NMP (2.0 mL) was stirred at 250° C. for 4 hours. LCMS showed the starting material was consumed completely and 83% of desired product formed. The combined mixture was diluted with ice water (10.0 mL) and extracted with EtOAc (50.0 mL×2). The combined organic layers were washed with water (10.0 mL×4), dried over anhydrous Na2SO4, filtered and concentrated under reduced pressure to give tert-butyl (1-(3-((2-amino-3-chloropyridin-4-yl)amino)-1-(4-methoxybenzyl)-1H-pyrazolo[3,4-b]pyrazin-6-yl)-4-methylpiperidin-4-yl)carbamate (350.0 mg, crude) as a brown solid.

Step c: A solution of tert-butyl (1-(3-((2-amino-3-chloropyridin-4-yl)amino)-1-(4-methoxybenzyl)-1H-pyrazolo[3,4-b]pyrazin-6-yl)-4-methylpiperidin-4-yl)carbamate (50.0 mg, 84.1 μmol) in TFA (3.0 mL) and TfOH (0.3 mL) was stirred at 85° C. for 15 min. LCMS showed most of starting material was consumed completely and one main peak with desired product was detected. The reaction mixture was concentrated under reduced pressure. The residue was diluted with MeOH (5.0 mL), adjusted pH=10 with NH3.H2O and purified by prep-HPLC (NH3.H2O). N4-(6-(4-amino-4-methylpiperidin-1-yl)-1H-pyrazolo[3,4-b]pyrazin-3-yl)-3-chloropyridine-2,4-diamine (15.0 mg, 47.7% yield) was obtained as a white solid.

Synthesis of methyl 3-[3-[[6-(4-amino-4-methyl-1-piperidyl)-1H-pyrazolo[3,4-b]pyrazin-3-yl]amino]-2-pyridyl]propanoate, Compound 495

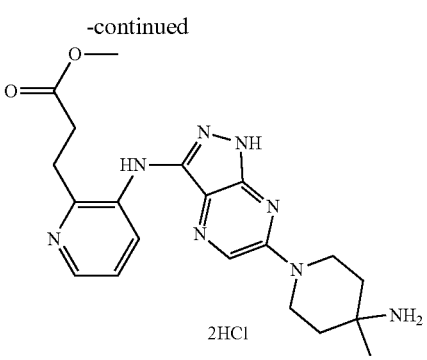

Step a: Tert-butyl (1-(3-iodo-1-(tetrahydro-2H-pyran-2-yl)-1H-pyrazolo[3,4-b]pyrazin-6-yl)-4-methylpiperidin-4-yl)carbamate (200.0 mg, 368.0 μmol), 3,4-dihydro-1,5-naphthyridin-2(1H)-one (162.0 mg, 1.1 mmol), CuI (7.0 mg, 36.8 μmol), K2CO3 (152.0 mg, 1.1 mmol) and (1S,2S)-N1,N2-dimethylcyclohexane-1,2-diamine (5.2 mg, 36.8 μmol) were added in toluene (5.0 mL), the reaction was evacuated and refilled 3 times with N2 and stirred at 110° C. for 12 hours. LCMS indicated ~65% of desired product formed. The reaction mixture was concentrated under reduced pressure to give a residue and purified by flash silica gel chromatography (Petroleum ether:EtOAc=10:0 to 10:3) to afford tert-butyl (4-methyl-1-(3-(2-oxo-3,4-dihydro-1,5-naphthyridin-1(2H)-yl)-1-(tetrahydro-2H-pyran-2-yl)-1H-pyrazolo[3,4-b]pyrazin-6-yl)piperidin-4-yl)carbamate (100.0 mg, 48.3% yield) as a yellow solid.

Step b: Tert-butyl N-[4-methyl-1-[3-(2-oxo-3,4-dihydro-1,5-naphthyridin-1-yl)-1-tetrahydropyran-2-yl-pyrazolo[3,4-b]pyrazin-6-yl]-4-piperidyl]carbamate (50.0 mg, 88.9 umol) was added in 4 M HCl/MeOH (3.0 mL), the reaction was stirred at 25° C. for 12 hours. LCMS indicated one main desired peak formed. The reaction mixture was concentrated under reduced pressure to give a residue and purified by prep-HPLC (HCl) to afford methyl 3-[3-[[6-(4-amino-4-methyl-1-piperidyl)-1H-pyrazolo[3,4-b]pyrazin-3-yl]amino]-2-pyridyl]propanoate (5.1 mg, 11.8% yield, HCl salt) as a yellow solid.

Preparation of 1-(3-(imidazo[1,2-a]pyridin-8-yl-thio)-1H-pyrazolo[3,4-b]pyrazin-6-yl)-4-methylpiperidin-4-amine hydrochloride, Compound 496

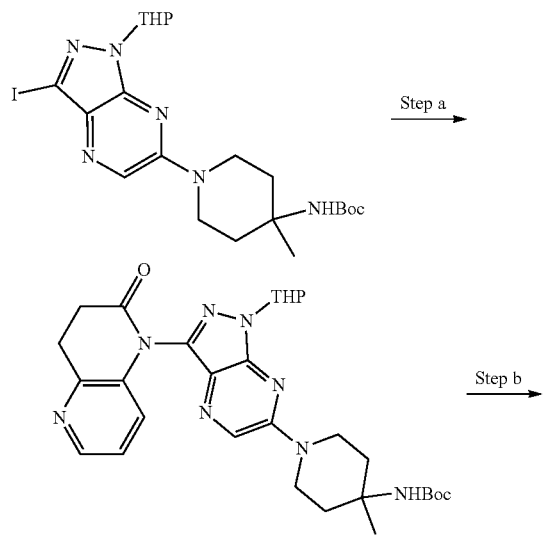

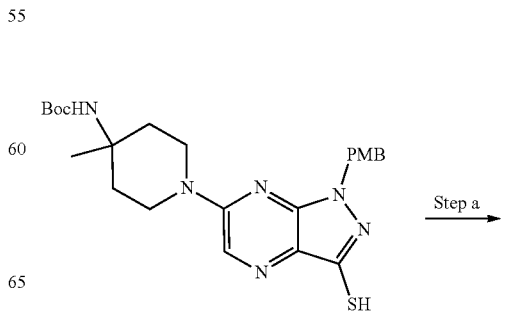

507

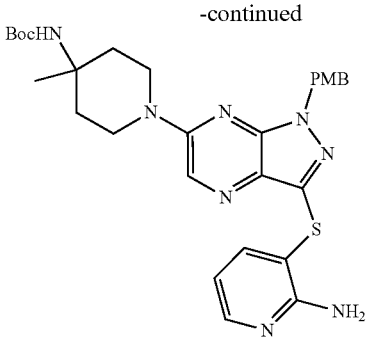

Step b →

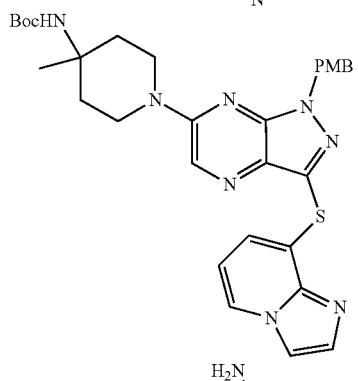

Step c →

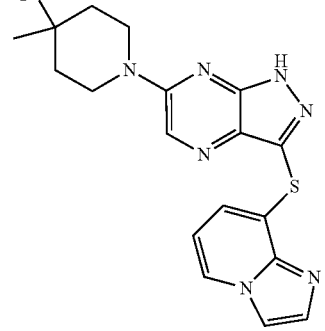

Step a: The compound of 3-iodopyridin-2-amine (195 mg, 0.9 mmol), tert-butyl (1-(3-mercapto-1-(4-methoxybenzyl)-1H-pyrazolo[3,4-b]pyrazin-6-yl)-4-methylpiperidin-4-yl)carbamate (360 mg, 0.7 mmol), Pd$_2$(dba)$_3$ (67.9 mg, 0.05 mmol), Xantphos (85 mg, 0.1 mmol) and DIPEA (0.4 mL, 2.2 mmol) were placed into dioxane (15.0 mL). The reaction mixture was evacuated and refilled 3 times using N$_2$. The reaction mixture was stirred at 110° C. for 12 hours. The mixture was concentrated to give a residue. The residue was purified by flash silica gel chromatography (petroleum ether: ethyl acetate=100:0 to 0:100) to afford the product of tert-butyl (1-(3-((2-aminopyridin-3-yl)thio)-1-(4-methoxybenzyl)-1H-pyrazolo[3,4-b]pyrazin-6-yl)-4-methylpiperidin-4-yl)carbamate (400 mg, 94% yield) as a red solid.

Step b: Tert-butyl (1-(3-((2-aminopyridin-3-yl)thio)-1-(4-methoxybenzyl)-1H-pyrazolo[3,4-b]pyrazin-6-yl)-4-methylpiperidin-4-yl)carbamate (300 mg, 0.5 mmol), 2-chloroacetaldehyde (0.1 mL, 1.0 mmol) and NaHCO$_3$ (65 mg, 0.8 mmol) were added to EtOH (10 mL), AcOH (0.2 mL) and H$_2$O (2 mL). The mixture was stirred at 110° C. for 2 h. The reaction mixture was concentrated and H$_2$O (20 mL) was added, and the mixture was extracted with dichloromethane (20 mL×3). The combined organic layers were washed with brine (20 mL), dried over anhydrous Na$_2$SO$_4$, filtered and concentrated to give a residue. The residue was purified by flash silica gel chromatography (petroleum ether: ethyl

508 acetate=100:0 to 0:100) to afford the product of tert-butyl (1-(3-(imidazo[1,2-a]pyridin-8-ylthio)-1-(4-methoxybenzyl)-1H-pyrazolo[3,4-b]pyrazin-6-yl)-4-methylpiperidin-4-yl)carbamate (300 mg, 96% yield) as a yellow solid.

Step c: The compound of tert-butyl (1-(3-(imidazo[1,2-a]pyridin-8-ylthio)-1-(4-methoxybenzyl)-1H-pyrazolo[3,4-b]pyrazin-6-yl)-4-methylpiperidin-4-yl)carbamate (250 mg, 0.4 mmol) was added into TfOH (5 mL) and TFA (0.5 mL). The mixture was stirred at 90° C. for 0.5 hour. The mixture was concentrated to give a residue which was triturated with NH$_3$/MeOH(1.0 mL, 7M), DMF (2 mL) and MeOH (2 mL). The mixture was concentrated to give a residue which was purified by prep-HPLC (HCl) to afford the desired product 1-(3-(imidazo[1,2-a]pyridin-8-ylthio)-1H-pyrazolo[3,4-b]pyrazin-6-yl)-4-methylpiperidin-4-amine hydrochloride (50.2 mg, 29% yield, HCl salt) as a yellow solid. LCMS: calc. for C18H20N8S: 380.2, found: [M+H]$^+$381.0. 1HNMR (400 MHz, DMSO_d6): δ 8.91~8.88 (m, 1H), 8.52~8.49 (m, 4H), 8.41 (s, 1H), 8.28~8.26 (m, 1H), 7.73~7.70 (m, 1H), 7.43~7.38 (m, 1H), 4.16~4.11 (m, 2H), 3.55~3.49 (m, 2H), 1.87~1.84 (m, 2H), 1.78~1.74 (m, 2H), 1.69 (s, 3H).

Preparation of 4-((6-(4-amino-4-methylpiperidin-1-yl)-1H-pyrazolo[3,4-b]pyrazin-3-yl)thio)-3-chloro-N-methylpyridin-2-amine hydrochloride, Compound 497

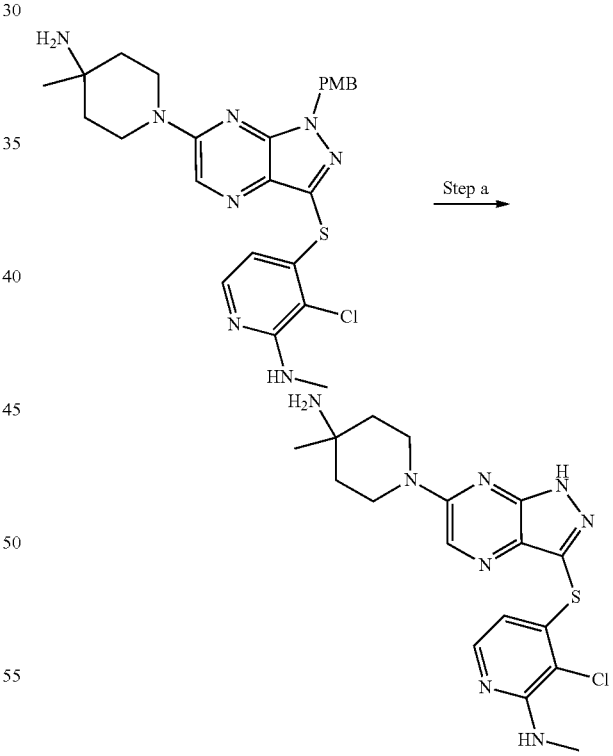

Step a: A solution of 4-((6-(4-amino-4-methylpiperidin-1-yl)-1-(4-methoxybenzyl)-1H-pyrazolo[3,4-b]pyrazin-3-yl)thio)-3-chloro-N-methylpyridin-2-amine (60 mg, 114 μmol) in TFA (5.0 mL) and TfOH (0.5 mL) was stirred at 80° C. for 20 min. The reaction mixture was concentrated under reduced pressure. The residue was diluted with MeOH (3.0 mL) and adjusted to pH=6 with 1N HCl. The residue was purified by prep-HPLC (HCl). The product of 4-((6-(4- amino-4-methylpiperidin-1-yl)-1H-pyrazolo[3,4-b]pyrazin-3-yl)thio)-3-chloro-N-methylpyridin-2-amine hydrochloride (20.0 mg, 45.3 μmol, 40% yield) was obtained as a yellow solid. LCMS: calc. for $C_{17}H_{21}ClN_8S$: 404.1, found: [M+H]$^+$ 404.9. $^1$H NMR (400 MHz, Methanol_d4): δ 8.46 (s, 1H), 7.53-7.55 (d, J=7.2 Hz, 1H), 6.20-6.22 (d, J=7.2 Hz, 1H), 4.34-4.38 (m, 3H), 3.53-3.60 (m, 2H), 3.13 (s, 3H), 1.91-1.95 (m, 4H), 1.55 (s, 3H1).

Preparation of $N^4$-(6-(4-(aminomethyl)-4-methylpiperidin-1-yl)-1H-pyrazolo[3,4-b]pyrazin-3-yl)-3-chloropyridine-2,4-diamine, Compound 498

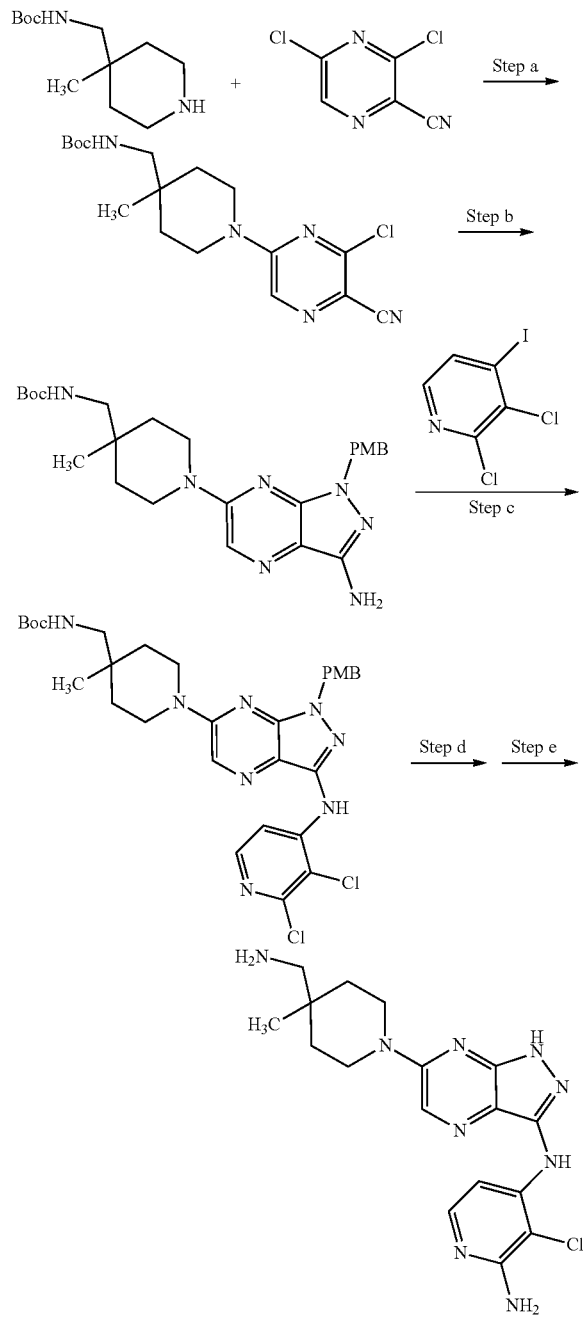

Step a: 3,5-Dichloropyrazine-2-carbonitrile (1.67 g, 9.62 mmol), tert-butyl ((4-methylpiperidin-4-yl)methyl)carbamate (2.0 g, 8.75 mmol), and Et$_3$N (2.64 g, 26.2 mmol) were taken up in THF (40.0 mL) and the reaction mixture stirred at 40° C. for 12 hrs. After cooling, the resulting suspension was diluted with saturated NH4Cl (40.0 mL) and extracted with EtOAc (50.0 mL×2). The organics were dried over anhydrous Na$_2$SO$_4$, filtered, and concentrated under reduced pressure. The residue was purified by flash silica gel chromatography (0-25% EtOAc/petroleum ether) to give tert-butyl ((1-(6-chloro-5-cyanopyrazin-2-yl)-4-methylpiperidin-4-yl)methyl)carbamate (3.0 g, 94% yield) as yellow oil.

Step b: A mixture of tert-butyl ((1-(6-chloro-5-cyanopyrazin-2-yl)-4-methylpiperidin-4-yl)methyl)carbamate (2.9 g, 7.92 mmol) and (4-methoxybenzyl)hydrazine dihydrochloride (1.32 g, 8.71 mmol) in EtOH (30 mL) was stirred at 25° C. for 2 min. Et$_3$N (1.59 g, 15.8 mmol) was added and the reaction mixture was stirred at 90° C. for 12 hrs. After cooling, the mixture was added to H$_2$O (50 mL) and extracted with EtOAc (50 mL×2). The organics were washed with saturated NH$_4$Cl (50 mL), dried over anhydrous Na$_2$SO$_4$, filtered, and concentrated under reduced pressure. The residue was purified by flash silica gel chromatography (0-80% EtOAc/petroleum ether) to give tert-butyl ((1-(3-amino-1-(4-methoxybenzyl)-1H-pyrazolo[3,4-b]pyrazin-6-yl)-4-methylpiperidin-4-yl)methyl)carbamate (2.3 g, 60/a yield) as yellow solid.

Step c: tert-butyl ((1-(3-Amino-1-(4-methoxybenzyl)-1H-pyrazolo[3,4-b]pyrazin-6-yl)-4-methylpiperidin-4-yl)methyl)carbamate (350 mg, 726 μmol), 2,3-dichloro-4-iodopyridine (238.0 mg, 871.0 μmol), K$_2$CO$_3$ (200.0 mg, 1.45 mmol), Pd$_2$(dba)$_3$ (66.4 mg, 72.6 umol), and XPhos (34.6 mg, 72.6 umol) were taken up in dioxane (5.0 mL). The reaction mixture was degassed and purged with N$_2$ three times, then stirred at 100° C. for 12 hrs. After cooling, the reaction mixture was diluted with H$_2$O (10 mL) and extracted with EtOAc (10 mL×2). The organics were washed with saturated NH$_4$Cl (10 mL), dried over anhydrous Na$_2$SO$_4$, filtered, and concentrated under reduced pressure. The residue was purified by flash silica gel chromatography (0-80% EtOAc/petroleum ether) to give tert-butyl ((1-(3-((2,3-dichloropyridin-4-yl)amino)-1-(4-methoxybenzyl)-1H-pyrazolo[3,4-b]pyrazin-6-yl)-4-methylpiperidin-4-yl)methyl)carbamate (400 mg, 88% yield) as yellow solid.

Step d: A solution of tert-butyl ((1-(3-((2,3-dichloropyridin-4-yl)amino)-1-(4-methoxybenzyl)-1H-pyrazolo[3,4-b]pyrazin-6-yl)-4-methylpiperidin-4-yl)methyl)carbamate (250 mg, 398 μmol) in NH$_3$.H$_2$O/NMP (5 mL/5 mL) was stirred in sealed vessel at 250° C. for 4 hrs. The mixture was concentrated under reduced pressure and purified by flash silica gel chromatography (0-40% MeOH/DCM) to give N-(6-(4-(aminomethyl)-4-methylpiperidin-1-yl)-1-(4-methoxybenzyl)-1H-pyrazolo[3,4-b]pyrazin-3-yl)-3-chloropyridine-2,4-diamine (90 mg) as yellow oil and recovered starting material (120 mg).

Step e: A solution of N4-(6-(4-(aminomethyl)-4-methylpiperidin-1-yl)-1-(4-methoxybenzyl)-1H-pyrazolo[3,4-b]pyrazin-3-yl)-3-chloropyridine-2,4-diamine (130 mg, 255.0 μmol) in TFA (3.0 mL) was stirred at 90° C. for 16 hrs. After this time, TfOH (0.3 mL) was added and the reaction was stirred at 25° C. for another 4 hrs. The mixture was concentrated in vacuo, the residue diluted with MeOH (5.0 mL), and the pH adjusted adjusted to 7 with NH$_3$.H$_2$O. The resulting mixture was then purified by reversed phase prep-HPLC (acetonitrile/aq. HCl) to give $N^4$-(6-(4-(aminomethyl)-4-methylpiperidin-1-yl)-1H-pyrazolo[3,4-b]pyrazin- 3-yl)-3-chloropyridine-2,4-diamine dihydrochloride (11.3 mg, 10% yield) as an orange solid: LCMS [M+H]+=388.0; ¹H-NMR (400 MHz, CD₃OD) δ 8.35 (s, 1H), 7.60 (d, J=7.2 Hz, 1H), 7.10 (d, J=7.2 Hz, 1H), 4.12-4.18 (m, 2H), 3.53-3.59 (m, 2H), 2.91 (s, 2H), 1.57-1.69 (m, 4H), 1.20 (s, 3H).

Synthesis of 6-(3-(Aminomethyl)-3-methylpyrrolidin-1-yl)-N-(2,3-dichloropyridin-4-yl)-1H-pyrazolo[3,4-b]pyrazin-3-amine, Compound 499

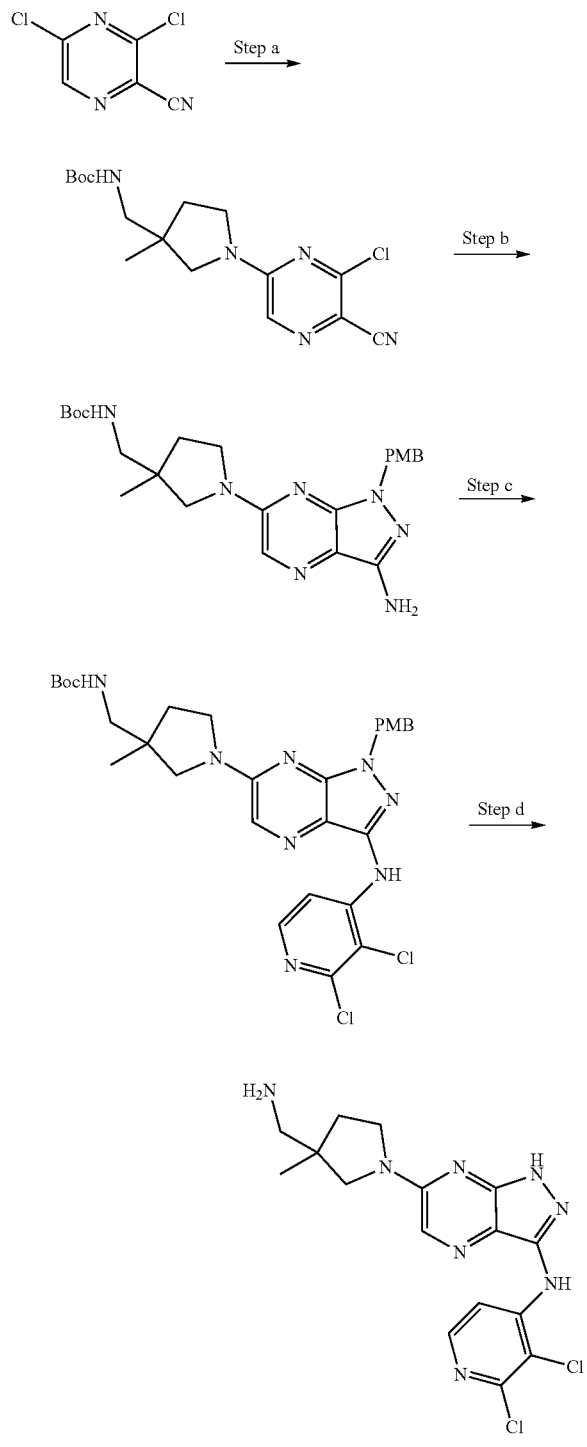

Step a: A solution of 3,5-dichloropyrazine-2-carbonitrile (300.0 mg, 1.72 mmol), tert-butyl ((3-methylpyrrolidin-3-yl)methyl)carbamate (368.0 mg, 1.72 mmol) and Et3N (521.0 mg, 5.15 mmol) in THF (5.0 mL). The reaction mixture was stirred at 40° C. for 4 h. Yellow suspension was observed. Desired mass ion was observed from LCMS. The solution was added into H₂O (10.0 mL) and then extracted with EtOAc (10.0 mL×2). The combined organic layers were washed with saturated NH4Cl (20.0 mL), dried over anhydrous Na2SO4, filtered and concentrated in vacuum to give crude product. The residue was purified by flash silica gel chromatography (Ethyl acetate in Petroleum ether from 0% to 45%) to give product (540.0 mg, 89.2% yield) as yellow gum.

Step b: A solution of tert-butyl ((1-(6-chloro-5-cyanopyrazin-2-yl)-3-methylpyrrolidin-3-yl)methyl)carbamate (490.0 mg, 1.39 mmol) and PMBNHNH2.2HCl (231.0 mg, 1.52 mmol) in EtOH (5.0 mL) was stirred at 25° C. for 3 min. Then to the reaction mixture was added Et3N (280.0 mg, 2.78 mmol) and stirred at 80° C. for 12 h. Yellow solution was observed. Desired mass ion was observed from LCMS. The solution was added into H₂O (10.0 mL) and then extracted with EtOAc (10.0 mL×2). The combined organic layers were washed with saturated NH4Cl (10.0 mL), dried over anhydrous Na2SO4, filtered and concentrated in vacuum to give crude product. The residue was purified by flash silica gel chromatography (Ethyl acetate in Petroleum ether from 0% to 80%) to give tert-butyl ((1-(3-amino-1-(4-methoxybenzyl)-1H-pyrazolo[3,4-b]pyrazin-6-yl)-3-methylpyrrolidin-3-yl)methyl)carbamate (300.0 mg, 641.0 μmol), 2,3-dichloro-4-iodopyridine (350.0 mg, 53.9% yield) as yellow oil.

Step c: A solution of tert-butyl ((1-(3-amino-1-(4-methoxybenzyl)-1H-pyrazolo[3,4-b]pyrazin-6-yl)-3-methylpyrrolidin-3-yl)methyl)carbamate (300.0 mg, 641.0 μmol), 2,3-dichloro-4-iodopyridine (210.0 mg, 769.0 μmol), Pd2(dba)3 (58.6 mg, 64.1 umol), X-Phos (30.5 mg, 64.1 umol) and K2CO3 (176.0 mg, 1.28 mmol) in dioxane (5.0 mL) was stirred at 110° C. for 12 h under N2. Orange solution was observed. Desired mass ion was observed from LCMS. The solution was added into H₂O (10.0 mL) and then extracted with EtOAc (10.0 mL×2). The combined organic layers were washed with saturated NH4Cl (10.0 mL), dried over anhydrous Na2SO4, filtered and concentrated in vacuum to give crude product. The residue was purified by flash silica gel chromatography (Ethyl acetate in Petroleum ether from 0% to 40%) to give tert-butyl ((1-(3-((2,3-dichloropyridin-4-yl)amino)-1-(4-methoxybenzyl)-1H-pyrazolo[3,4-b]pyrazin-6-yl)-3-methylpyrrolidin-3-yl)methyl)carbamate (200.0 mg, 50.8% yield) as yellow solid.

Step d: A solution of tert-butyl ((1-(3-((2,3-dichloropyridin-4-yl)amino)-1-(4-methoxybenzyl)-1H-pyrazolo[3,4-b]pyrazin-6-yl)-3-methylpyrrolidin-3-yl)methyl)carbamate (50.0 mg, 81.4 μmol) in TFA/TfOH (1 mL/0.1 mL) was stirred at 25° C. for 2 h. Brown solution was observed. Desired mass ion was observed from LCMS. The reaction mixture was concentrated in vacuum to give product. The residue was diluted with MeOH (5.0 mL), adjusted pH=7 with NH3.H2O and purified by prep-HPLC(NH3.H2O). 6-(3-(Aminomethyl)-3-methylpyrrolidin-1-yl)-N-(2,3-dichloropyridin-4-yl)-1H-pyrazolo[3,4-b]pyrazin-3-amine (2.4 mg, 7.5% Yield) was obtained as white solid.

Synthesis of 6-(4-(Aminomethyl)-4-methylpiperidin-1-yl)-N-(2,3-dichloropyridin-4-yl)-1H-pyrazolo[3,4-b]pyrazin-3-amine hydrochloride, Compound 500

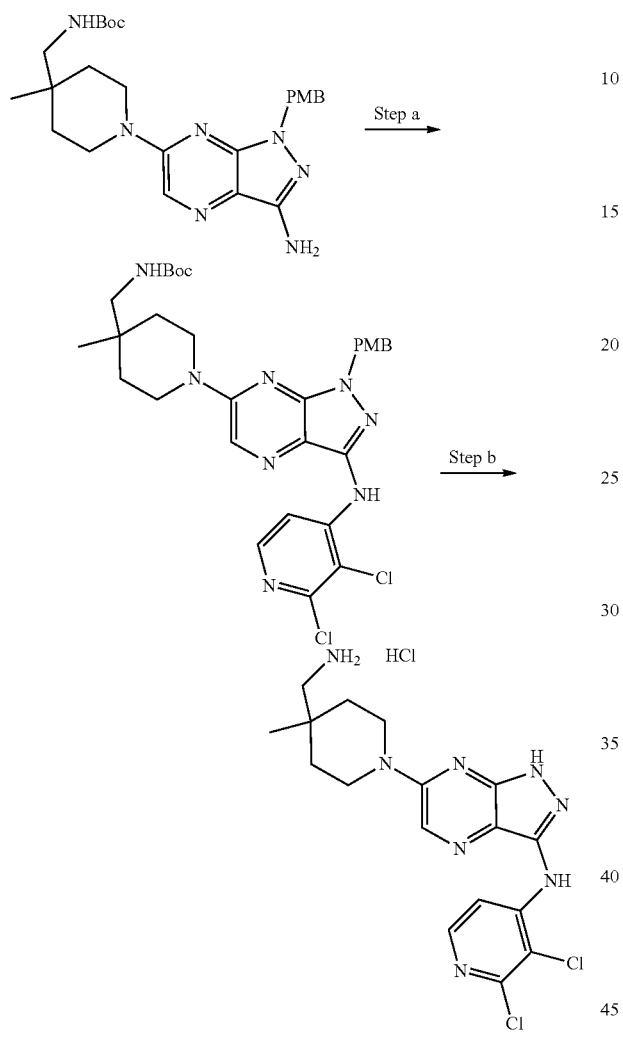

Step a: A solution of tert-butyl ((1-(3-amino-1-(4-methoxybenzyl)-1H-pyrazolo[3,4-b]pyrazin-6-yl)-4-methylpiperidin-4-yl)methyl)carbamate (150.0 mg, 311.0 µmol), 2,3-dichloro-4-iodopyridine (102.0 mg, 373.0 µmol), Pd2(dba)3 (28.3 mg, 31.0 umol), X-Phos (14.7 mg, 31.0 umol) and K2CO3 (85.9 mg, 622.0 umol) in dioxane (4.0 mL) was stirred at 110° C. for 12 h under N2. Yellow solution was observed. Desired mass ion was observed from LCMS. The solution was added into H₂O (10.0 mL) and then extracted with EtOAc (10.0 mL×2). The combined organic layers were washed with saturated NH4Cl (10.0 mL), dried over anhydrous Na2SO4, filtered and concentrated in vacuum to give crude product. The residue was purified by flash silica gel chromatography (Ethyl acetate in Petroleum ether from 0% to 40%) to give tert-butyl ((1-(3-((2,3-dichloropyridin-4-yl)amino)-1-(4-methoxybenzyl)-1H-pyrazolo[3,4-b]pyrazin-6-yl)-4-methylpiperidin-4-yl)methyl)carbamate (150.0 mg, 76.9% yield) as yellow gum.

Step b: A solution of tert-butyl ((1-(3-((2,3-dichloropyridin-4-yl)amino)-1-(4-methoxybenzyl)-1H-pyrazolo[3,4-b]pyrazin-6-yl)-4-methylpiperidin-4-yl)methyl)carbamate (150.0 mg, 239.0 µmol) in TFA/TfOH (1.0 mL/0.1 mL) was stirred at 25° C. for 12 h. Brown solution was observed. Desired mass ion was observed from LCMS. The reaction mixture was concentrated in vacuum. The residue was diluted with MeOH (5.0 mL), adjusted pH=7 with NH3.H2O and purified by prep-HPLC (HCl). 6-(4-(Aminomethyl)-4-methylpiperidin-1-yl)-N-(2,3-dichloropyridin-4-yl)-1H-pyrazolo[3,4-b]pyrazin-3-amine hydrochloride (29.4 mg, 27.7% yield) was obtained as orange solid.

Synthesis of (1-(3-((2,3-dichloropyridin-4-yl)oxy)-1-methyl-1H-pyrazolo[3,4-b]pyrazin-6-yl)-4-methylpiperidin-4-yl)methanamine, Compound 501

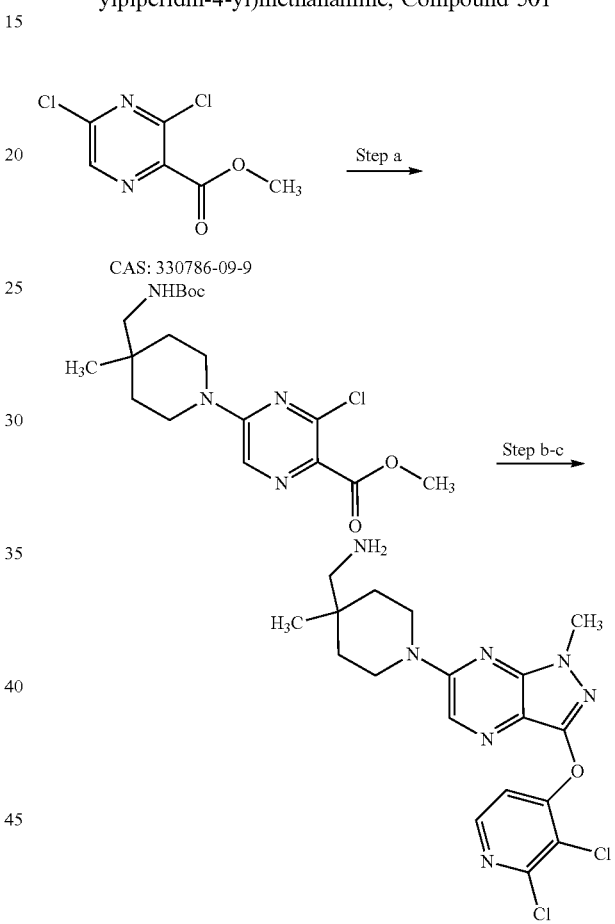

Step a: Methyl 3,5-dichloropyrazine-2-carboxylate (742 mg, 3.58 mmol) (CAS: 330786-09-9) was dissolved in DMF (7.20 mL) in a round bottom flask and cooled to 0° C. before the addition of tert-butyl ((4-methylpiperidin-4-yl)methyl)carbamate (818 mg, 3.58 mmol) (CAS: 1158759-03-5). The ice bath was removed and the reaction stirred at ambient temperature for 5 h, after which it was partitioned between EtOAc and brine. The organic layer was extracted with EtOAc (3×), the residue was dried and concentrated and purified via silica gel chromatography (10-100% EtOAc in hexanes) to yield methyl 5-(4-(((tert-butoxycarbonyl)amino)methyl)-4-methylpiperidin-1-yl)-3-chloropyrazine-2-carboxylate (1.29 g, 3.23 mmol) in 90% yield and its regioisomeric product, which was not collected. LCMS: [M+Na]+421.3.

Step b: A solution of methyl 5-(4-(((tert-butoxycarbonyl)amino)methyl)-4-methylpiperidin-1-yl)-3-chloropyrazine- 2-carboxylate (290 mg, 0.727 mmol) in EtOH (3.0 mL) was placed in a resealable vial before the addition of methylhydrazine (0.045 mL, 0.875 mmol) and triethylamine (0.303 mL, 0.727 mmol). The reaction was heated to 75° C. for 16 h before cooling to room temperature. Solvent was evaporated to yield crude tert-butyl ((4-methyl-1-(1-methyl-3-oxo-2,3-dihydro-1H-pyrazolo[3,4-b]pyrazin-6-yl)piperidin-4-yl)methyl)carbamate, which was carried on without further purification. This material was dissolved in DMF (3.6 mL) in a resealable vial and 2,3,4-trichloropyridine (160 mg, 0.873 mmol) and Cs$_2$CO$_3$ (355 mg, 1.09 mmol) were added before heating to 80° C. After 3 h, the reaction was cooled, solvent was evaporated and the residue was purified via silica gel chromatography (12-100% EtOAc in hexanes) to furnish tert-butyl ((1-(3-((2,3-dichloropyridin-4-yl)oxy)-1-methyl-1H-pyrazolo[3,4-b]pyrazin-6-yl)-4-methylpiperidin-4-yl)methyl)carbamate (200 mg, 0.383 mmol) in 53% yield over two steps. LCMS: [M+]522.3.

Step c: Tert-butyl ((1-(3-((2,3-dichloropyridin-4-yl)oxy)-1-methyl-1H-pyrazolo[3,4-b]pyrazin-6-yl)-4-methylpiperidin-4-yl)methyl)carbamate (200 mg, 0.383 mmol) in dichloromethane (3.2 mL) in a resealable vial and trifluoroacetic acid (0.48 mL, 6.36 mmol) was added. After stirring at ambient temperature for 1 h, solvent was evaporated and the residue was purified via silica gel chromatography (0-20% MeOH in dichloromethane with 0.1% NH$_3$.H$_2$O) to provide (1-(3-((2,3-dichloropyridin-4-yl)oxy)-1-methyl-1H-pyrazolo[3,4-b]pyrazin-6-yl)-4-methylpiperidin-4-yl)methanamine (84.0 mg, 0.199 mmol) in 63% yield. LCMS: [M+] 422.3.

Synthesis of 1-(3-((3-chloropyridin-2-yl)oxy)-1H-pyrazolo[3,4-b]pyrazin-6-yl)-4-methylpiperidin-4-amine dihydrochloride, Compound 502

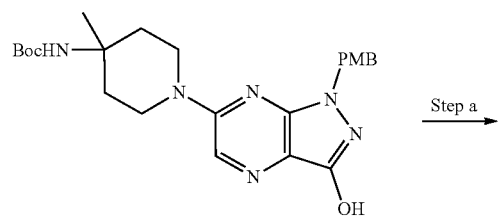

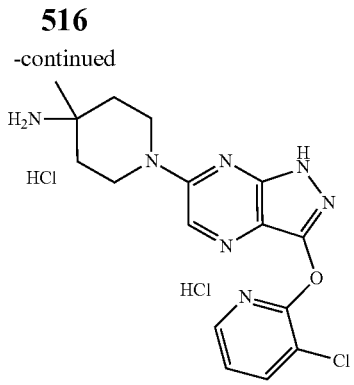

Step a: A mixture of tert-butyl (1-(3-hydroxy-1-(4-methoxybenzyl)-1H-pyrazolo[3,4-b]pyrazin-6-yl)-4-methylpiperidin-4-yl)carbamate (400 mg, 853 µmol), 2,3-dichloropyridine (251 mg, 1.7 mmol) and Cs2CO3 (831 mg, 2.6 mmol) in DMSO (15 mL) was stirred at 130° C. for 24 hours. The reaction mixture was diluted with H2O (30 mL), extracted with ethyl acetate (30 mL×2). The combined organic phase was washed with brine (15 mL), dried over anhydrous Na2SO4 and concentrated under reduced pressure. The residue was purified by column chromatography (Petroleum ether: Ethyl acetate=1:1-1:3) to afford the product of tert-butyl (1-(3-((3-chloropyridin-2-yl)oxy)-1-(4-methoxybenzyl)-1H-pyrazolo[3,4-b]pyrazin-6-yl)-4-methylpiperidin-4-yl)carbamate (100 mg, 20% yield) as a yellow oil.

Step b: A mixture of tert-butyl (1-(3-((3-chloropyridin-2-yl)oxy)-1-(4-methoxybenzyl)-1H-pyrazolo[3,4-b]pyrazin-6-yl)-4-methylpiperidin-4-yl)carbamate (100 mg, 172 µmol) in TFA (5 mL) and TfOH (0.3 mL) was stirred at 20° C. for 1.5 hours. The reaction mixture was adjusted pH=9 with NH3/MeOH (7M) and concentrated under reduced pressure to give a residue. The residue was purified by prep-HPLC (HCl) to afford the product of 1-(3-((3-chloropyridin-2-yl)oxy)-1H-pyrazolo[3,4-b]pyrazin-6-yl)-4-methylpiperidin-4-amine dihydrochloride (22 mg, 29.5% yield) as a yellow solid.

Preparation of 1-(3-((4-chloro-2-methylpyridin-3-yl)oxy)-1H-pyrazolo[3,4-b]pyrazin-6-yl)-4-methylpiperidin-4-amine, Compound 503

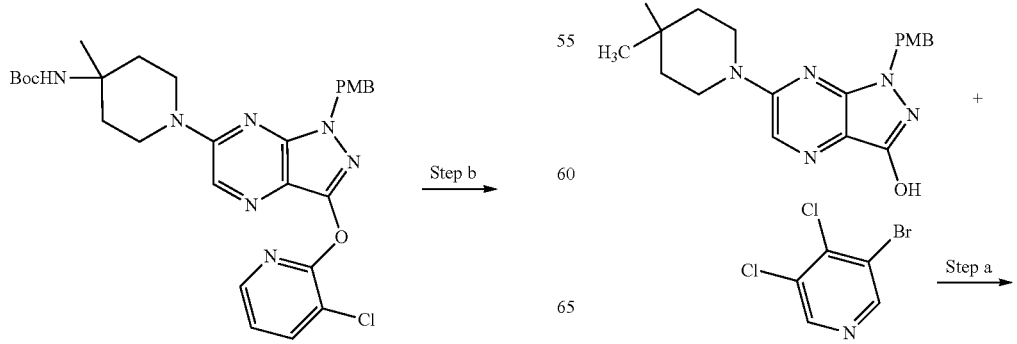

δ 9.10 (s, 1H), 8.89 (s, 1H), 8.39 (s, 1H), 4.37-4.33 (m, 2H), 3.59-3.54 (m, 2H), 1.97-1.90 (m, 4H), 1.55 (s, 3H).

Synthesis of (1-(3-((3-chloro-2-methylpyridin-4-yl)oxy)-1H-pyrazolo[3,4-b]pyrazin-6-yl)-4-methylpiperidin-4-yl)methanamine, Compound 504

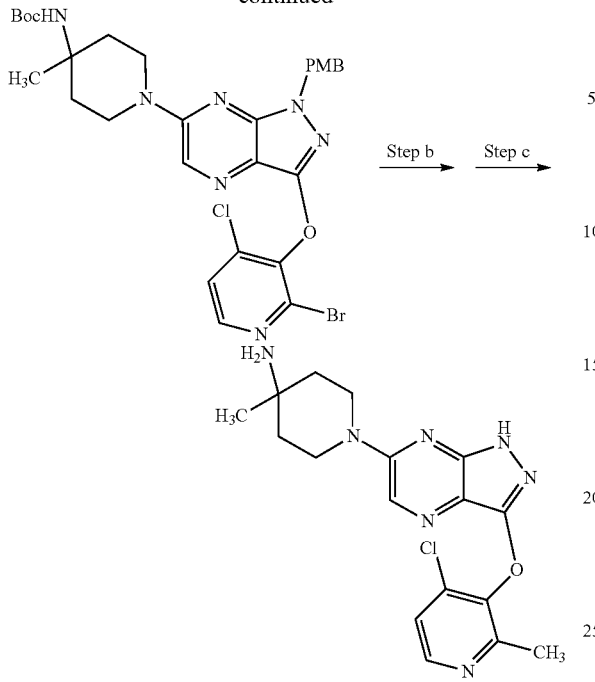

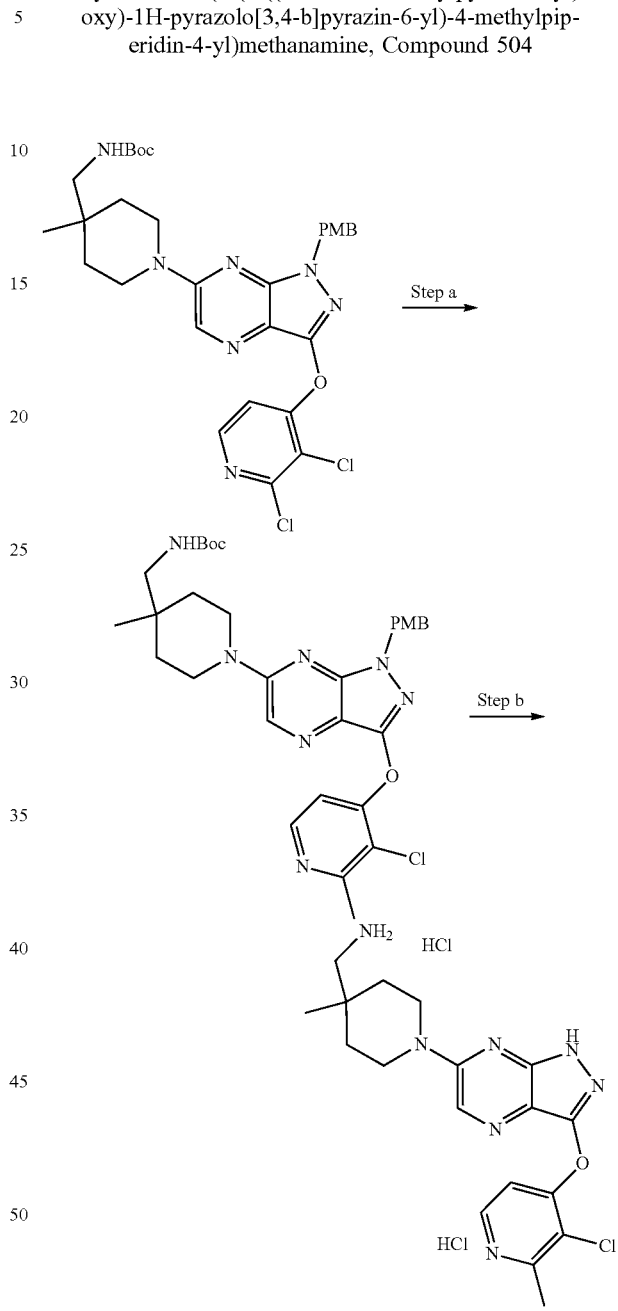

Step a: A mixture of tert-butyl (1-(3-hydroxy-1-(4-methoxybenzyl)-1H-pyrazolo[3,4-b]pyrazin-6-yl)-4-methylpiperidin-4-yl)carbamate (300 mg, 640 μmol), 3-bromo-4,5-dichloropyridine (174 mg, 768 μmol, CAS #1001056-83-2), and Cs$_2$CO$_3$ (622 mg, 1.9 mmol) in DMF (10 mL) was stirred at 80° C. for 12 hours. The reaction mixture was diluted with H$_2$O (20 mL), extracted with ethyl acetate (25 mL×2), and the organics were washed with brine (10 mL), dried over anhydrous Na$_2$SO$_4$, and concentrated under reduced pressure. The residue was purified by silica gel chromatography (50-70% EtOAc/petroleum ether) to afford tert-butyl (1-(3-((3-bromo-5-chloropyridin-4-yl)oxy)-1-(4-methoxybenzyl)-1H-pyrazolo[3,4-b]pyrazin-6-yl)-4-methylpiperidin-4-yl)carbamate (356 mg, 84% yield) as a yellow solid.

Step b: To a mixture of tert-butyl (1-(3-((3-bromo-5-chloropyridin-4-yl)oxy)-1-(4-methoxybenzyl)-1H-pyrazolo[3,4-b]pyrazin-6-yl)-4-methylpiperidin-4-yl)carbamate (300 mg, 455 μmol), methylboronic acid (32.6 mg, 546 μmol), and Cs$_2$CO$_3$ (443 mg, 1.4 mmol) in dioxane (9 mL) and H$_2$O (3 mL) was added Pd(dppf)Cl$_2$—CH$_2$Cl$_2$ (74.2 mg, 91 μmol). The reaction mixture was concentrated under reduced pressure to give a residue, which was purified by silica gel chromatography (50-70% EtOAc/petroleum ether) to afford product tert-butyl (1-(3-((3-chloro-5-methylpyridin-4-yl)oxy)-1-(4-methoxybenzyl)-1H-pyrazolo[3,4-b]pyrazin-6-yl)-4-methylpiperidin-4-yl)carbamate (170 mg, 62% yield) as a yellow oil.

Step c: A mixture of tert-butyl (1-(3-((3-chloro-5-methylpyridin-4-yl)oxy)-1-(4-methoxybenzyl)-1H-pyrazolo[3,4-b]pyrazin-6-yl)-4-methylpiperidin-4-yl)carbamate (170 mg, 286 μmol) in TFA (5 mL) and TfOH (0.3 mL) was stirred at 20° C. for 1 hour. The pH was adjusted to 9 with NH$_3$/MeOH (7M), the mixture concentrated under reduced pressure, and the residue purified by reversed phase prep-HPLC (acetonitrile/aq. HCl) to afford 1-(3-((3-chloro-5-methylpyridin-4-yl)oxy)-1H-pyrazolo[3,4-b]pyrazin-6-yl)-4-methylpiperidin-4-amine dihydrochloride (43 mg, 34% yield) as a yellow solid: LCMS [M+H]$^+$=373.9; $^1$H-NMR (400 MHz, CD$_3$OD)

Step a: The mixture of tert-butyl ((1-(3-((2,3-dichloropyridin-4-yl)oxy)-1-(4-methoxybenzyl)-1H-pyrazolo[3,4-b]pyrazin-6-yl)-4-methylpiperidin-4-yl)methyl)carbamate (300 mg, 477 μmol, 1.0 eq) (prepared as described for compound 506), 2,4,6-trimethyl-1,3,5,2,4,6-trioxatriborinane (119 mg, 954 μmol, 2.0 eq), Pd(dppf)Cl2 (70 mg, 95 μmol, 0.2 eq) and K3PO4/3H2O (380 mg, 1.4 mmol, 3.0 eq) in H2O (1 ml) and dioxane (10 mL) was evacuated and refilled for 3 times using N2 and stirred at 100° C. for 12 hours. The mixture was concentrated under reduced pressure and the residue was purified by column chromatography (Petroleum ether/Ethyl acetate=4:1~1:2) to afford tert-butyl ((1-(3-((3-chloro-2-methyl pyridin-4-yl)oxy)-1-(4-methoxybenzyl)-1H-pyrazolo[3,4-b]pyrazin-6-yl)-4-methylpiperidin-4-yl)methyl)carbamate (230 mg, 79% yield) as a yellow solid.

Step b: The mixture of tert-butyl ((1-(3-((3-chloro-2-methylpyridin-4-yl)oxy)-1-(4-methoxybenzyl)-1H-pyrazolo[3,4-b]pyrazin-6-yl)-4-methylpiperidin-4-yl)methyl)carbamate (430 mg, 707 μmol) in TFA (5 mL) and TFOH (0.25 mL) was stirred at 25° C. for 10 hours. The mixture was concentrated under reduced pressure and the residue was diluted with MeOH. The mixture was purified by pre-HPLC (HCl) to afford the desired product of (1-(3-((3-chloro-2-methylpyridin-4-yl)oxy)-1H-pyrazolo[3,4-b]pyrazin-6-yl)-4-methylpiperidin-4-yl)methanamine (153.6 mg, 2 HCl salt, 47% yield) as a yellow solid.

Synthesis of (1-(3-((1H-indol-5-yl)oxy)-1H-pyrazolo[3,4-b]pyrazin-6-yl)-4-methylpiperidin-4-yl) methanamine, Compound 505

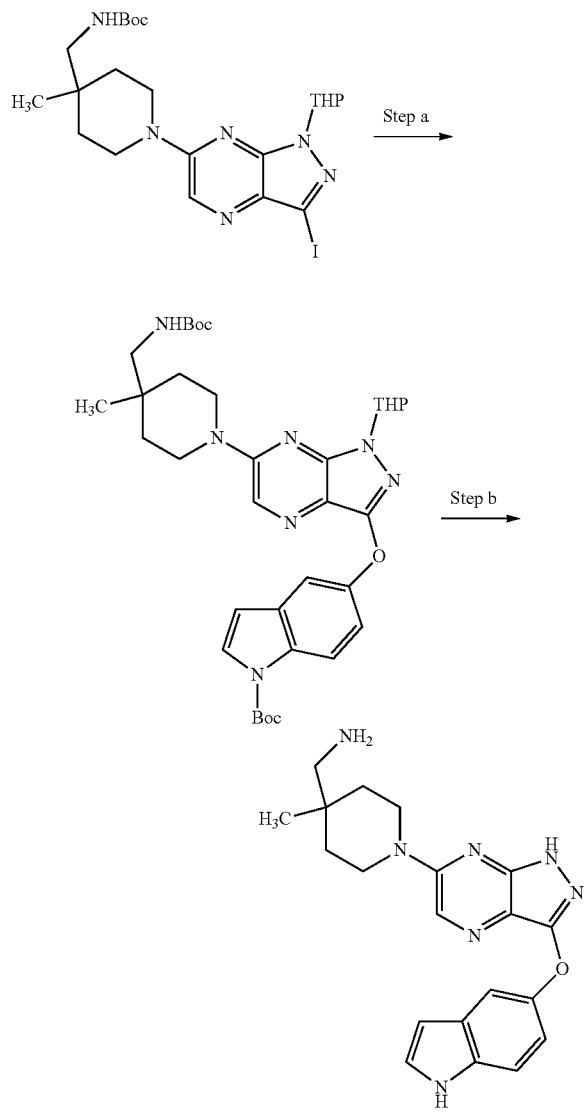

Step a: A resealable reaction vial was charged with tert-butyl ((1-(3-iodo-1-(tetrahydro-2H-pyran-2-yl)-1H-pyrazolo[3,4-b]pyrazin-6-yl)-4-methylpiperidin-4-yl) methyl)carbamate (150 mg, 0.270 mmol), tert-butyl 5-hydroxy-1H-indole-1-carboxylate (125 mg, 0.539 mmol) (CAS:434958-85-7), picolinic acid (59.7 mg, 0.485 mmol), $K_3PO_4$ (171 mg, 0.809 mmol) and CuI (51.0 mg, 0.260 mmol). The vial was evacuated and backfilled with nitrogen three times before the addition of DMSO (5.36 mL) and the mixture was sparged with nitrogen for 10 min before heating to 95° C. for 12 h. After cooling, the reaction was partitioned between EtOAc and sat. sodium bicarbonate. The organic layer was extracted with EtOAc (3×), dried and purified via silica gel chromatography (12-100/0 EtOAc in hexanes) to furnish tert-butyl 5-((6-(4-(((tert-butoxycarbonyl)amino) methyl)-4-methylpiperidin-1-yl)-1-(tetrahydro-2H-pyran-2-yl)-1H-pyrazolo[3,4-b]pyrazin-3-yl)oxy)-1H-indole-1-carboxylate (29.6 mg 0.045 mmol) in 17% yield. LCMS: [M+H]+ 622.2.

Step b: A round bottomed flask was charged with tert-butyl 5-((6-(4-(((tert-butoxycarbonyl)amino)methyl)-4-methylpiperidin-1-yl)-1-(tetrahydro-2H-pyran-2-yl)-1H-pyrazolo[3,4-b]pyrazin-3-yl)oxy)-1H-indole-1-carboxylate (29.6 mg, 0.0454 mmol) in acetonitrile (0.70 mL) and triethylsilane (0.17 mL) and cooled to 0° C. before the addition of triethylsilyl trifluoromethanesulfonate (0.019 mL, 0.088 mmol). After stirring at 0° C. for 45 min, the ice bath was removed and an additional batch of triethylsilyl trifluoromethanesulfonate (0.019 mL, 0.088 mmol) was added. The crude reaction mixture was purified directly via prep HPLC (5-40% ACN in $H_2O$ with 0.1% $CH_2OH$) to furnish (1-(3-((1H-indol-5-yl)oxy)-1H-pyrazolo[3,4-b]pyrazin-6-yl)-4-methylpiperidin-4-yl)methanamine (1.0 mg, 0.003 mmol) in 6% yield. LCMS: [M+H]+ 378.0.

Preparation of (1-(3-((3-chloro-2-(1-methyl-1H-pyrazol-4-yl)pyridin-4-yl)oxy)-1H-pyrazolo[3,4-b]pyrazin-6-yl)-4-methylpiperidin-4-yl)methanamine, Compound 506

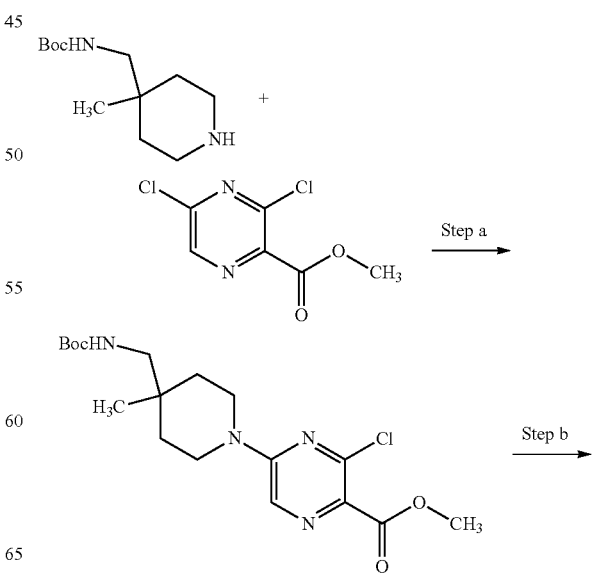

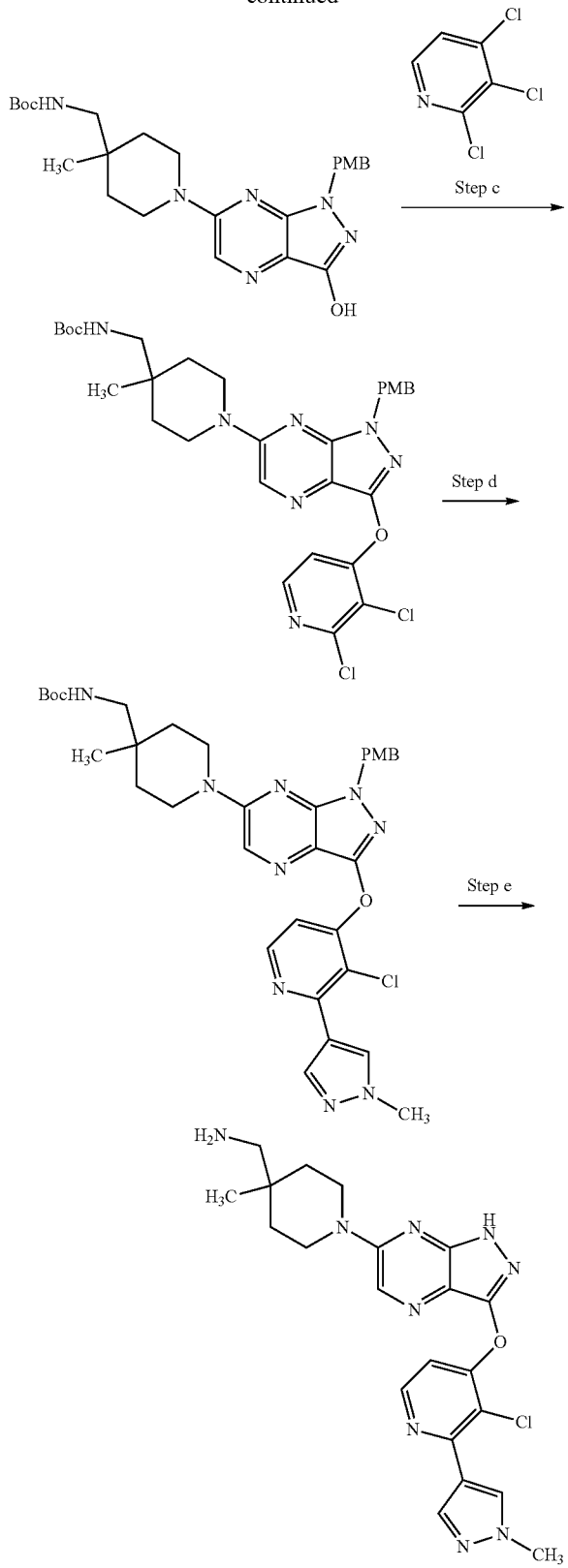

was stirred at 70° C. for 1 hour. After cooling, the mixture was diluted with H₂O (50 mL) and extracted with EtOAc (50 mL×2). The organics were washed with brine (50 mL), dried over anhydrous Na₂SO₄, filtered, and concentrated under reduced pressure. The residue was purified by column chromatography (20-50% EtOAc/petroleum ether) to afford methyl 3-(4-(((tert-butoxycarbonyl)amino)methyl)-4-methylpiperidin-1-yl)-5-chloropyrazine-2-carboxylate (1.3 g, 98% yield) as a white solid.

Step b: A mixture of methyl 5-(4-(((tert-butoxycarbonyl)amino)methyl)-4-methylpiperidin-1-yl)-3-chloropyrazine-2-carboxylate (1.3 g, 3.3 mmol, 1.0 eq), PMBNHNH₂.2HCl (878 mg, 3.9 mmol, 1.1 eq), and Et₃N (984 mg, 9.8 mmol, 3.0 eq) in EtOH (15 mL) was stirred at 80° C. for 10 hours. After cooling, the mixture was concentrated under reduced pressure and the residue was purified by column chromatography (0-10% MeOH/DCM) to afford tert-butyl ((1-(3-hydroxy-1-(4-methoxybenzyl)-1H-pyrazolo[3,4-b]pyrazin-6-yl)-4-methylpiperidin-4-yl)methyl)carbamate (2.4 g, crude) as a yellow solid.

Step c: A mixture of tert-butyl ((1-(3-hydroxy-1-(4-methoxybenzyl)-1H-pyrazolo[3,4-b]pyrazin-6-yl)-4-methylpiperidin-4-yl)methyl)carbamate (1.2 g, 2.5 mmol, 1.0 eq), 2,3,4-trichloropyridine (541 mg, 3.0 mmol, 1.2 eq), and Cs₂CO₃ (2.4 g, 7.4 mmol, 3.0 eq) in DMF (15 mL) was stirred at 70° C. for 12 hours. After cooling, the mixture was concentrated under reduced pressure and the residue was purified by column chromatography (20-50% EtOAc/petroleum ether) to afford tert-butyl ((1-(3-((2,3-dichloropyridin-4-yl)oxy)-1-(4-methoxybenzyl)-1H-pyrazolo[3,4-b]pyrazin-6-yl)-4-methylpiperidin-4-yl)methyl)carbamate (820 mg, 53% yield) as a yellow solid.

Step d: A mixture of tert-butyl ((1-(3-((2,3-dichloropyridin-4-yl)oxy)-1-(4-methoxybenzyl)-1H-pyrazolo[3,4-b]pyrazin-6-yl)-4-methylpiperidin-4-yl)methyl)carbamate (410 mg, 652 μmol, 1.0 eq), 1-methyl-4-(4,4,5,5-tetramethyl-1,3,2-dioxaborolan-2-yl)-1H-pyrazole (162 mg, 782 μmol, 1.2 eq), Pd(dppf)Cl₂ (48 mg, 65 μmol, 0.1 eq), and K₃PO₄.3H₂O (519 mg, 2.0 mmol, 3.0 eq) in H₂O (1.0 ml) and dioxane (10 mL) was evacuated and refilled 3 times using N₂, followed by stirring at 100° C. for 12 hours. After cooling, the mixture was concentrated under reduced pressure and the residue purified by flash column chromatography (20-50% EtOAc/petroleum ether) to afford tert-butyl ((1-(3-((3-chloro-2-(1-methyl-1H-pyrazol-4-yl)pyridin-4-yl)oxy)-1-(4-methoxybenzyl)-1H-pyrazolo[3,4-b]pyrazin-6-yl)-4-methylpiperidin-4-yl)methyl)carbamate (360 mg, 82% yield) as a yellow solid.

Step e: A mixture of tert-butyl ((1-(3-((3-chloro-2-(1-methyl-1H-pyrazol-4-yl)pyridin-4-yl)oxy)-1-(4-methoxybenzyl)-1H-pyrazolo[3,4-b]pyrazin-6-yl)-4-methylpiperidin-4-yl)methyl)carbamate (360 mg, 533 μmol) in TFA (10 mL) and TfOH (1 mL) was stirred at 25° C. for 1 hour. After cooling, the mixture was concentrated under reduced pressure, the residue dissolved in a minimum of MeOH, and purified by reversed phase prep-HPLC (acetonitrile/aq. HCl) to afford (1-(3-((3-chloro-2-(1-methyl-1H-pyrazol-4-yl)pyridin-4-yl)oxy)1H-pyrazolo[3,4-b]pyrazin-6-yl)-4-methylpiperidin-4-yl)methanamine (263.8 mg, 2 HCl salt) as a yellow solid: LCMS [M+H]⁺=454.0; ¹H-NMR (400 MHz, methanol-d₄) δ 8.65 (s, 1H), 8.54-8.52 (d, J=6.8 Hz, 1H), 8.39 (s, 1H), 8.26 (s, 1H), 7.52-7.50 (d, J=6.8 Hz, 1H), 4.22-4.18 (m, 2H), 4.09 (s, 3H), 3.65-3.58 (m, 2H), 2.95 (s, 2H), 1.69-1.61 (m, 4H), 1.24 (s, 3H).

Step a: A mixture of methyl 3,5-dichloropyrazine-2-carboxylate (697 mg, 3.4 mmol, 1.0 eq), tert-butyl ((4-methylpiperidin-4-yl)methyl)carbamate (770 mg, 3.4 mmol, 1.0 eq), and CsF (1.53 g, 10.1 mmol, 3.0 eq) in DMSO (10 mL)

Synthesis of 3-((6-(4-Amino-4-methylpiperidin-1-yl)-1H-pyrazolo[3,4-b]pyrazin-3-yl)oxy)pyridin-4-amine hydrochloride, Compound 507

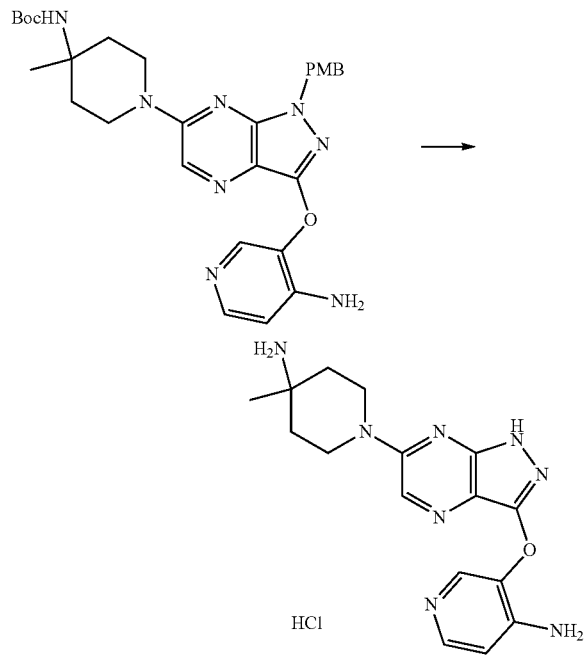

A solution of tert-butyl (1-(3-((4-aminopyridin-3-yl)oxy)-1-(4-methoxybenzyl)-1H-pyrazolo[3,4-b]pyrazin-6-yl)-4-methylpiperidin-4-yl)carbamate (300.0 mg, 535.0 μmol) (prepared as described for compound 509) in TFA/TfOH (3.0 mL/0.3 mL) was stirred at 25° C. for 3 h. Brown solution was observed. Desired mass ion was observed. The reaction mixture was concentrated in vacuum. The residue was diluted with MeOH (5.0 mL), adjusted pH=7 with NH3.H2O and purified by prep-HPLC (HCl). 3-((6-(4-Amino-4-methylpiperidin-1-yl)-1H-pyrazolo[3,4-b]pyrazin-3-yl)oxy)pyridin-4-amine hydrochloride (109.8 mg, 291 μmol, 54.2% yield) was obtained as orange solid.

Synthesis of 3-((6-(4-Amino-4-methylpiperidin-1-yl)-1H-pyrazolo[3,4-b]pyrazin-3-yl)oxy)pyridin-2-amine hydrochloride, Compound 503

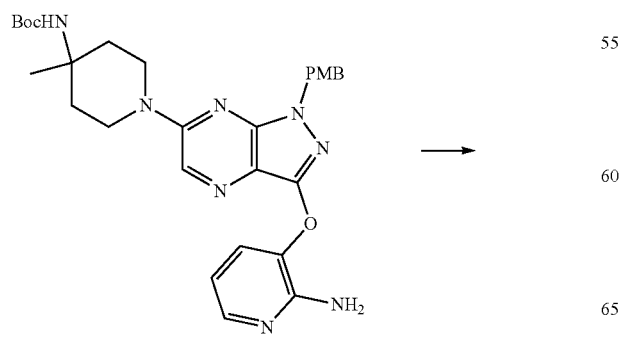

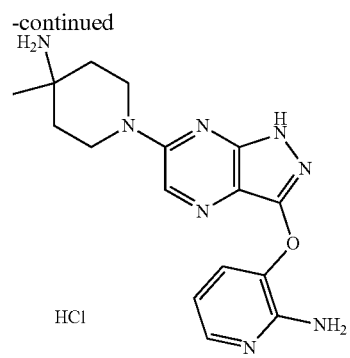

A solution of tert-butyl (1-(3-((2-aminopyridin-3-yl)oxy)-1-(4-methoxybenzyl)-1H-pyrazolo[3,4-b]pyrazin-6-yl)-4-methylpiperidin-4-yl)carbamate (200.0 mg, 356.0 μmol) (prepared as described for Compound 510) in TFA/TfOH (3.0 mL/0.3 mL) was stirred at 25° C. for 1 h. Brown solution was observed. Desired mass ion was observed from LCMS. The reaction mixture was concentrated in vacuum. The residue was diluted with MeOH (5.0 mL), adjusted pH=7 with NH3.H2O and purified by prep-HPLC (HCl). 3-((6-(4-Amino-4-methylpiperidin-1-yl)-1H-pyrazolo[3,4-b]pyrazin-3-yl)oxy)pyridin-2-amine hydrochloride (70.7 mg, 52.7% yield) was obtained as orange oil.

Synthesis of 1-(3-((4-Chloropyridin-3-yl)oxy)-1H-pyrazolo[3,4-b]pyrazin-6-yl)-4-methylpiperidin-4-amine hydrochloride, Compound 509

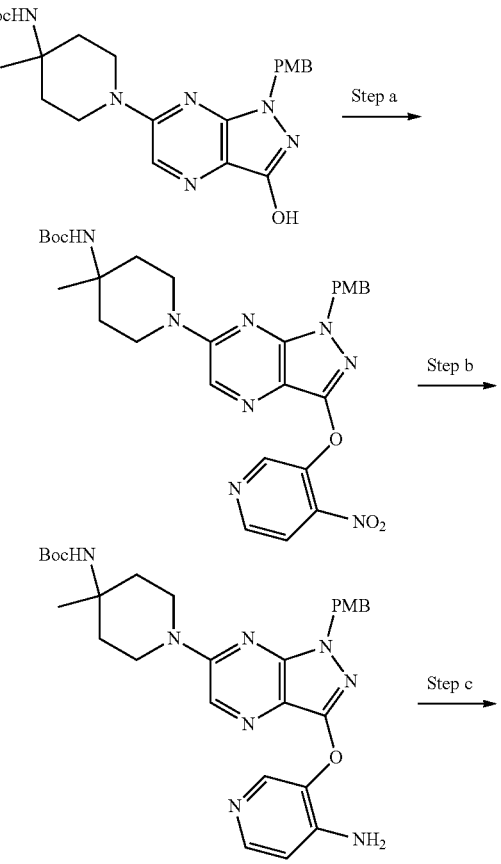

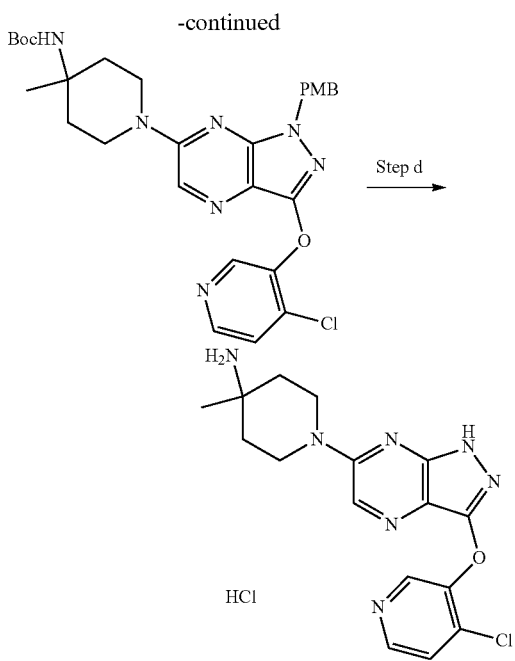

Step a: A solution of tert-butyl (1-(3-hydroxy-1-(4-methoxybenzyl)-1H-pyrazolo[3,4-b]pyrazin-6-yl)-4-methylpiperidin-4-yl)carbamate (2.0 g, 4.26 mmol), 3-fluoro-4-nitropyridine (726.0 mg, 5.11 mmol) and Cs2CO3 (2.76 g, 8.52 mmol) in DMF (20.0 mL) was stirred at 80° C. for 12 h. Orange solution was observed. Desired mass ion was observed from LCMS. The solution was added into H2O (30.0 mL) and then extracted with EtOAc (30.0 mL×2). The combined organic layers were washed with saturated NaCl (30.0 mL), dried over anhydrous Na2SO4, filtered and concentrated in vacuum to give crude product as orange gum. The residue was purified by flash silica gel chromatography (40 g, Ethyl acetate in Petroleum ether from 0% to 30%) to give tert-butyl (1-(1-(4-methoxybenzyl)-3-((4-nitropyridin-3-yl)oxy)-1H-pyrazolo[3,4-b]pyrazin-6-yl)-4-methylpiperidin-4-yl)carbamate (2.0 g, 79.6% yield) as yellow oil.

Step b: A solution of tert-butyl (1-(1-(4-methoxybenzyl)-3-((4-nitropyridin-3-yl)oxy)-1H-pyrazolo[3,4-b]pyrazin-6-yl)-4-methylpiperidin-4-yl)carbamate (2.0 g, 3.38 mmol) in THF (50.0 mL) was added Pd/C (800.0 mg, 10%). The reaction mixture was degassed and purged with H2 for three times and then the mixture was stirred at 25° C. for 12 h under H2 (15 psi). Brown suspension was observed. Desired mass ion was observed from LCMS. The reaction mixture was filtered and the filtrate was concentrated in vacuum to give tert-butyl (1-(3-((4-aminopyridin-3-yl)oxy)-1-(4-methoxybenzyl)-1H-pyrazolo[3,4-b]pyrazin-6-yl)-4-methylpiperidin-4-yl)carbamate (1.5 g, crude) as yellow oil. The oil was used in the next step without further purification.

Step c: A solution of tert-butyl (1-(3-((4-aminopyridin-3-yl)oxy)-1-(4-methoxybenzyl)-1H-pyrazolo[3,4-b]pyrazin-6-yl)-4-methylpiperidin-4-yl)carbamate (1.5 g, 2.67 mmol) in MeCN (20.0 mL) was added CuCl (1.04 g, 10.6 mmol) at 0° C. The reaction mixture was stirred at 0° C. for 30 min and the mixture was added drop-wise t-BuONO (825.0 mg, 8.01 mmol) at 0° C. The reaction mixture was stirred at 25° C. for 1.5 h. Brown solution was observed. The solution was added into H2O (20.0 mL) and then extracted with EtOAc (20.0 mL×2). The combined organic layers were washed with saturated NaCl (20.0 mL), dried over anhydrous Na2SO4, filtered and concentrated in vacuum to give crude product as brown gum. The residue was purified by flash silica gel chromatography (20 g, Ethyl acetate in Petroleum ether from 0% to 40%) to give tert-butyl (1-(3-((4-chloropyridin-3-yl)oxy)-1-(4-methoxybenzyl)-1H-pyrazolo[3,4-b]pyrazin-6-yl)-4-methylpiperidin-4-yl)carbamate (350.0 mg, 22.7% yield) as orange oil.

Step d: A solution of tert-butyl (1-(3-((4-chloropyridin-3-yl)oxy)-1-(4-methoxybenzyl)-1H-pyrazolo[3,4-b]pyrazin-6-yl)-4-methylpiperidin-4-yl)carbamate (350.0 mg, 603.0 µmol) in TFA/TfOH (3.0 ml/0.3 mL) was stirred at 25° C. for 2 h. Brown solution was observed. Desired mass ion was observed from LCMS. The reaction mixture was concentrated in vacuum. The residue was diluted with MeOH (5.0 mL), adjusted pH=7 with NH3.H2O and purified by prep-HPLC (HCl). 1-(3-((4-Chloropyridin-3-yl)oxy)-1H-pyrazolo[3,4-b]pyrazin-6-yl)-4-methylpiperidin-4-amine hydrochloride (104.5 mg, 43.6% yield) was obtained as yellow solid.

Preparation of 1-(3-((2-chloropyridin-3-yl)oxy)-1H-pyrazolo[3,4-b]pyrazin-6-yl)-4-methylpiperidin-4-amine, Compound 510

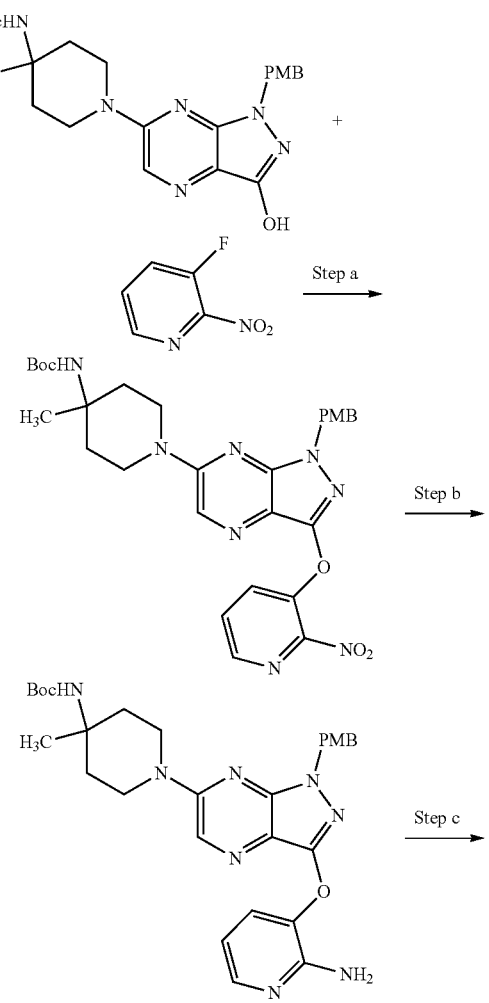

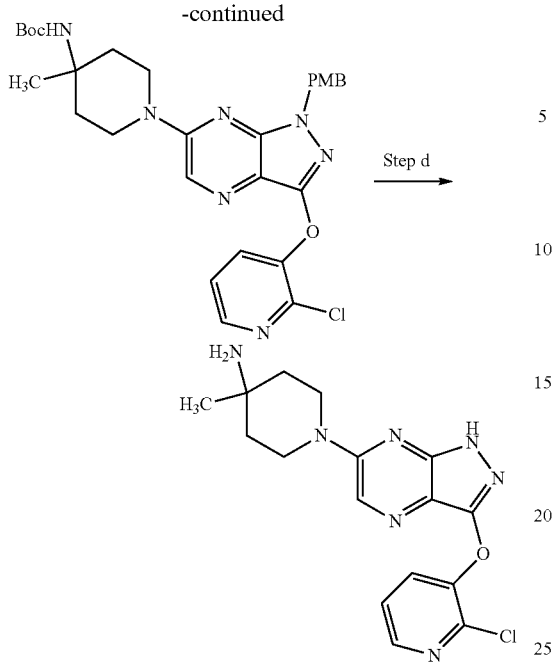

Step a: A mixture of tert-butyl (1-(3-hydroxy-1-(4-methoxybenzyl)-1H-pyrazolo[3,4-b]pyrazin-6-yl)-4-methylpiperidin-4-yl)carbamate (2.0 g, 4.26 mmol), 3-fluoro-2-nitropyridine (726.0 mg, 5.11 mmol), and Cs₂CO₃ (2.76 g, 8.52 mmol) in DMF (20 mL) was stirred at 80° C. for 12 h. After cooling, the reaction mixture was added into H₂O (30 mL) and extracted with EtOAc (30 mL×2). The organics were washed with saturated NaCl (30 mL), dried over anhydrous Na₂SO₄, filtered, and concentrated under reduced pressure, and purified by flash silica gel chromatography (0-30% EtOAc/petroleum ether) to give tert-butyl (1-(1-(4-methoxybenzyl)-3-((2-nitropyridin-3-yl)oxy)-1H-pyrazolo[3,4-b]pyrazin-6-yl)-4-methylpiperidin-4-yl)carbamate (2.0 g, 80% yield) as yellow oil.

Step b: To solution of tert-butyl (1-(1-(4-methoxybenzyl)-3-((2-nitropyridin-3-yl)oxy)-1H-pyrazolo[3,4-b]pyrazin-6-yl)-4-methylpiperidin-4-yl)carbamate (2.0 g, 3.38 mmol) in THF (50.0 mL) was added Pd/C (800.0 mg, 10%). The reaction mixture was degassed and purged with H₂ three times and then was stirred at 25° C. for 12 h under H₂ (15 psi). After replacing the atmosphere with nitrogen, the reaction was filtered and the filtrate was concentrated under reduced pressure to give tert-butyl (1-(3-((2-aminopyridin-3-yl)oxy)-1-(4-methoxybenzyl)-1H-pyrazolo[3,4-b]pyrazin-6-yl)-4-methylpiperidin-4-yl)carbamate (1.5 g, crude) as yellow oil.

Step c: To a solution of tert-butyl (1-(3-((2-aminopyridin-3-yl)oxy)-1-(4-methoxybenzyl)-1H-pyrazolo[3,4-b]pyrazin-6-yl)-4-methylpiperidin-4-yl)carbamate (1.5 g, 2.67 mmol) in MeCN (20.0 mL) was added CuCl (1.04 g, 10.6 mmol) at 0° C. The reaction mixture was stirred for 30 min, then t-BuONO (825.0 mg, 8.01 mmol) was added dropwise at 0° C. After warming to RT and stirring at 25° C. for 1.5 hrs. the solution was added into H₂O (20 mL) then extracted with EtOAc (20 mL×2). The combined organics were washed with saturated NaCl (20.0 mL), dried over anhydrous Na₂SO₄, filtered, concentrated under reduced pressure, and purified by flash silica gel chromatography (0-40% EtOAc/petroleum ether) to give tert-butyl (1-(3-((2-chloropyridin-3-yl)oxy)-1-(4-methoxybenzyl)-1H-pyrazolo[3,4-b]pyrazin-6-yl)-4-methylpiperidin-4-yl)carbamate (350 mg, 23% yield) as orange oil.

Step d: A solution of tert-butyl (1-(3-((2-chloropyridin-3-yl)oxy)-1-(4-methoxybenzyl)-1H-pyrazolo[3,4-b]pyrazin-6-yl)-4-methylpiperidin-4-yl)carbamate (350.0 mg, 603.0 μmol) in TFA/TfOH (3.0 mL/0.3 mL) was stirred at 25° C. for 2 hrs. The mixture was concentrated under reduced pressure and the residue taken up in a minimum of methanol and purified by reversed phase prep-HPLC (acetonitrile/aq. HCl) to give 1-(3-((2-chloropyridin-3-yl)oxy)-1H-pyrazolo[3,4-b]pyrazin-6-yl)-4-methylpiperidin-4-amine hydrochloride (76.1 mg, 31.9% yield) as yellow solid: LCMS [M+H]⁺=360.0; ¹H-NMR (400 MHz, DMSO-d₆) δ 12.70 (s, 1H), 8.40 (s, 1H), 8.24-8.32 (m, 4H), 7.74-7.78 (m, 1H), 7.43-7.47 (m, 1H), 4.00-4.20 (m, 2H), 3.47-3.55 (m, 2H), 1.74-1.86 (m, 4H), 1.40 (s, 3H).

Synthesis of 4-((6-(4-(aminomethyl)-4-methylpiperidin-1-yl)-1H-pyrazolo[3,4-b]pyrazin-3-yl)thio)-1-methylpyridin-2(1H)-one, Compound 511

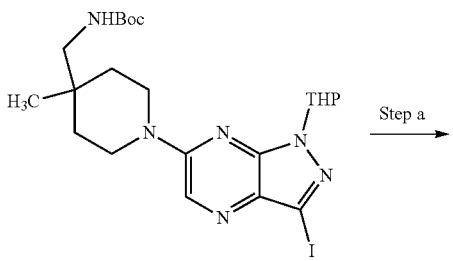

529

Step a: A resealable vial was charged with tert-butyl ((1-(3-iodo-1-(tetrahydro-2H-pyran-2-yl)-1H-pyrazolo[3,4-b]pyrazin-6-yl)-4-methylpiperidin-4-yl)methyl)carbamate (482 mg, 0.870 mmol), 2-ethylhexyl 3-mercaptopropanoate (0.290 mL, 1.30 mmol), methanesulfonato[4,5-bis(diphenylphosphino)-9,9-dimethylxanthene](2'-methylamino-1,1'-biphenyl-2-yl)palladium(II) (83.0 mg, 0.072 mmol) and Hunig's base (0.455 mL, 2.61 mmol) in dioxane (4.3 mL) and heated to 110° C. in a microwave reactor for 1 h. The reaction was cooled and partitioned between EtOAc and water. The organic layer was extracted (3×), combined organic extracts were dried, concentrated and purified via silica gel chromatography (8-50% EtOAc in hexanes) to furnish 2-ethylhexyl 3-((6-(4-(((tert-butoxycarbonyl)amino) methyl)-4-methylpiperidin-1-yl)-1-(tetrahydro-2H-pyran-2-yl)-1H-pyrazolo[3,4-b]pyrazin-3-yl)thio)propanoate, which was used directly in the next step. Following dissolution in THF (4.3 mL), the above isolated material was cooled to −78° C., and sodium tert-butoxide (1.0 M in THF, 2.61 mL, 2.61 mmol) was added dropwise over 2 min via addition funnel. Consumption of starting material was observed via TLC (50% EtOAc in Hexanes) once addition of the base was complete and the reaction was quenched by slow addition of 4M HCl in dioxane until the pH was 6. The reaction was warmed to ambient temperature and partitioned between EtOAc and water. The organic layer was washed with brine, and concentrated under reduced pressure to yield the crude residue containing tert-butyl ((1-(3-mercapto-1-(tetrahydro-2H-pyran-2-yl)-1H-pyrazolo[3,4-b]pyrazin-6-yl)-4-methylpiperidin-4-yl)methyl)carbamate which was quickly telescoped into the next reaction.

Step b: A portion of the crude residue containing tert-butyl ((1-(3-mercapto-1-(tetrahydro-2H-pyran-2-yl)-1H-pyrazolo [3,4-b]pyrazin-6-yl)-4-methylpiperidin-4-yl)methyl)carbamate (140 mg, approx. 0.290 mmol) was dissolved in dioxane (4.1 mL) and transferred to a resealable microwave vial containing 4-bromo-1-methylpyridin-2(1H)-one (81 mg, 0.435 mmol) (CAS:81971-39-3), and methanesulfonato [4,5-bis(diphenylphosphino)-9,9-dimethylxanthene](2'-methylamino-1,1'-biphenyl-2-yl)palladium(II) (28.0 mg, 0.029 mmol). Following the addition of Hunig's base (0.151 mL, 0.435 mmol) the reaction was sealed, and heated to 120° C. After 16 h, the reaction was cooled to ambient temperature, solvent was evaporated and the residue was purified via silica gel chromatography (0-10% MeOH in dichloromethane with 0.1% NH$_3$ H$_2$O) to furnish tert-butyl ((4-methyl-1-(3-((1-methyl-2-oxo-1,2-dihydropyridin-4-yl) thio)-1-(tetrahydro-2H-pyran-2-yl)-1H-pyrazolo[3,4-b] pyrazin-6-yl)piperidin-4-yl)methyl)carbamate (60.0 mg, 0.105 mmol). LCMS: [M+H]+ 570.1.

Step c: To a reaction vial containing tert-butyl ((4-methyl-1-(3-((1-methyl-2-oxo-1,2-dihydropyridin-4-yl)thio)-1-(tetrahydro-2H-pyran-2-yl)-1H-pyrazolo[3,4-b]pyrazin-6-yl) piperidin-4-yl)methyl)carbamate (60.0 mg, 0.105 mmol) in EtOH (4.0 mL) was added HCl (4.0 M in dioxane, 0.20 mL). After 45 min, additional HCl (0.20 mL) was added and the reaction stirred for another 3 h, after which solvent was evaporated and the residue was purified via prep HPLC (5-30% ACN in H$_2$O with 0.1% CH$_2$OH) to furnish 4-((6-(4-(aminomethyl)-4-methylpiperidin-1-yl)-1H-pyrazolo[3, 4-b]pyrazin-3-yl)thio)-1-methylpyridin-2(1H)-one (20.0 mg, 0.052 mmol). LCMS: [M+H]+ 386.1.

530

Preparation of (3S,4S)-8-(3-((2,3-dichloropyridin-4-yl)oxy)-1H-pyrazolo[3,4-b]pyrazin-6-yl)-3-methyl-2-oxa-8-azaspiro[4.5]decan-4-amine, Compound 512

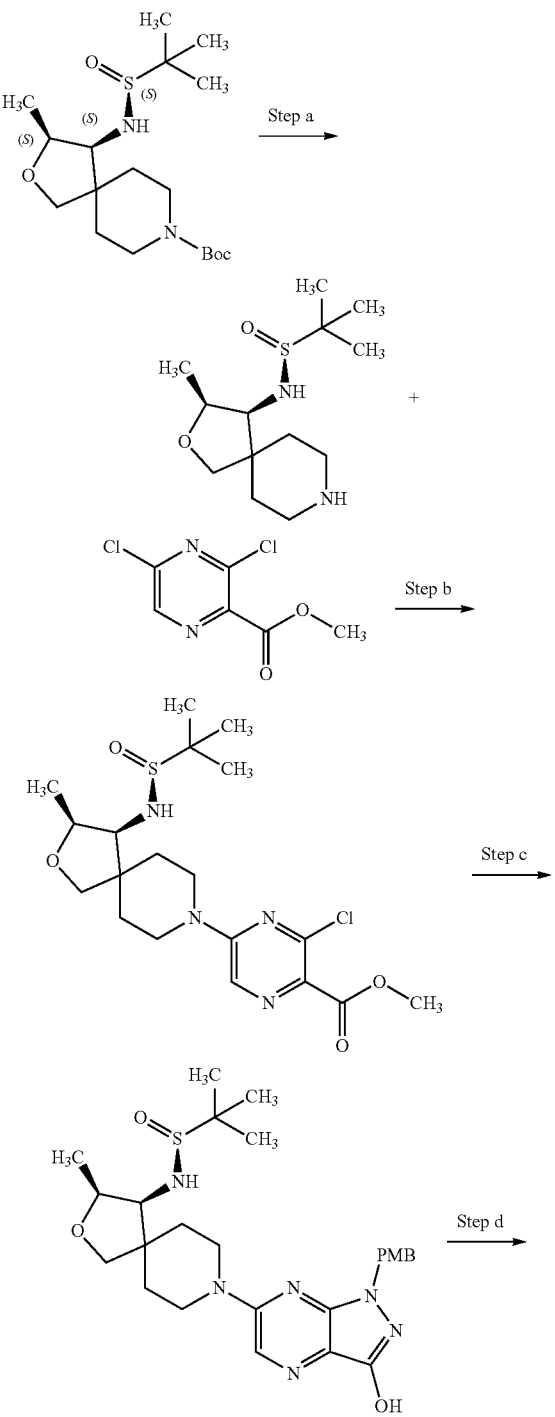

-continued

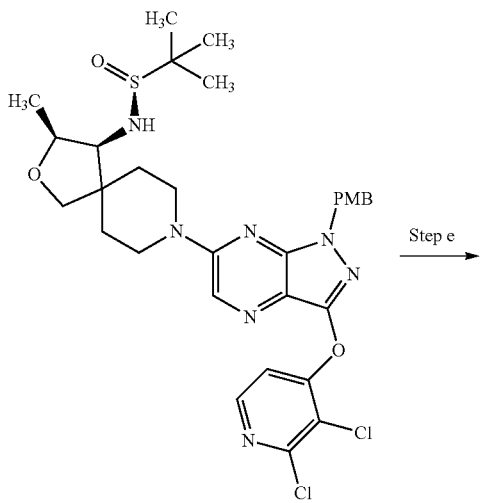

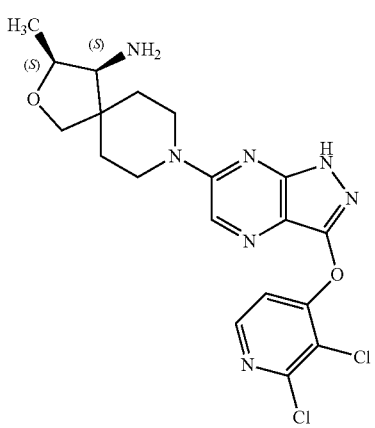

Step a: To a solution of (3S,4S)-tert-butyl 4-((S)-1,1-dimethylethylsulfinamido)-3-methyl-2-oxa-8-azaspiro[4.5]decane-8-carboxylate (350 mg, 934 μmol, CAS #2055760-00-2) in DCM (10 mL) at 0° C. was added TFA (354 μL, 4.7 mmol). The reaction mixture was stirred at 0-15° C. for 2 hrs. The mixture was concentrated under reduced pressure and THF (2.0 mL) and a drop of MeOH was added and the pH was adjusted to 8 with solid with Na₂CO₃. The mixture was concentrated under reduced pressure and purified by flash silica gel column chromatography (0-50% MeOH/DCM) to give (S)-2-methyl-N-((3S,4S)-3-methyl-2-oxa-8-azaspiro[4.5]decan-4-yl)propane-2-sulfinamide (320 mg) as a colorless oil.

Step b: To a mixture of methyl 3,5-dichloropyrazine-2-carboxylate (300 mg, 1.44 mmol) and (S)-2-methyl-N-((3S,4S)-3-methyl-2-oxa-8-azaspiro[4.5]decan-4-yl)propane-2-sulfinamide (315.0 mg, 1.15 mmol) in DMSO (9 mL) was added CsF (654 mg, 4.3 mmol). The reaction mixture was stirred at 70° C. for 2 hrs. After cooling, water (15 mL) was added and a white precipitate formed. The mixture was filtered and filter cake was dried under reduced pressure. The residue was purified by flash silica gel chromatography (0-10% MeOH/DCM) to give methyl 3-chloro-5-((3S,4S)-4-((S)-1,1-dimethylethylsulfinamido)-3-methyl-2-oxa-8-azaspiro[4.5]decan-8-yl)pyrazine-2-carboxylate (260 mg, 41% yield) as an off-white solid.

Step c: To a mixture of methyl 3-chloro-5-((3S,4S)-4-((S)-1,1-dimethylethylsulfinamido)-3-methyl-2-oxa-8-azaspiro[4.5]decan-8-yl)pyrazine-2-carboxylate (210 mg, 471 μmol) and (4-methoxybenzyl)hydrazine dihydrochloride (190 mg, 847 μmol) in EtOH (5 mL) was added Et₃N (285 mg, 2.8 mmol). The mixture was stirred at 90° C. under N₂ for 12 hrs. After cooling, the mixture was concentrated under reduced pressure and purified by flash silica gel chromatography (0-10% MeOH/DCM) to give (S)—N-((3S,4S)-8-(3-hydroxy-1-(4-methoxybenzyl)-1H-pyrazolo[3,4-b]pyrazin-6-yl)-3-methyl-2-oxa-8-azaspiro[4.5]decan-4-yl)-2-methylpropane-2-sulfinamide (220 mg) as a yellow solid.

Step d: To a mixture of (S)—N-((3S,4S)-8-(3-hydroxy-1-(4-methoxybenzyl)-1H-pyrazolo[3,4-b]pyrazin-6-yl)-3-methyl-2-oxa-8-azaspiro[4.5]decan-4-yl)-2-methylpropane-2-sulfinamide (170 mg, 321 μmol) and 2,3,4-trichloropyridine (87.7 mg, 481 μmol) in DMF (6 mL) was added cesium carbonate (313 mg, 963 μmol). The mixture was stirred at 80° C. for 12 hrs. After cooling, the mixture was poured into water (20 mL) and extracted with EtOAc (15 mL×5). The organics were washed with brine (10 mL×3), dried over anhydrous Na₂SO₄, filtered, and concentrated under reduced pressure, and purified by flash silica gel chromatography (0-100% EtOAc/petroleum ether) to give (S)—N-((3S,4S)-8-(3-((2,3-dichloropyridin-4-yl)oxy)-1-(4-methoxybenzyl)-1H-pyrazolo[3,4-b]pyrazin-6-yl)-3-methyl-2-oxa-8-azaspiro[4.5]decan-4-yl)-2-methylpropane-2-sulfinamide (150 mg, 222 μmol) as a white solid.

Step e: To a solution of (S)—N-((3S,4S)-8-(3-((2,3-dichloropyridin-4-yl)oxy)-1-(4-methoxybenzyl)-1H-pyrazolo[3,4-b]pyrazin-6-yl)-3-methyl-2-oxa-8-azaspiro[4.5]decan-4-yl)-2-methylpropane-2-sulfinamide (150 mg, 222 μmol) in TFA (1.6 mL) was added TfOH (0.2 mL). The mixture was stirred at 20° C. for 3 hrs, then concentrated under reduced pressure and the pH adjusted to 7 with a solution 7M NH₃ in MeOH. The mixture was purified by reversed phase prep-HPLC (acetonitrile/aq. HCl) to give (3S,4S)-8-(3-((2,3-dichloropyridin-4-yl)oxy)-1H-pyrazolo[3,4-b]pyrazin-6-yl)-3-methyl-2-oxa-8-azaspiro[4.5]decan-4-amine dihydrochloride (80 mg HCl salt, 69% yield) as a yellow solid: LCMS [M+H]⁺=449.9; ¹H-NMR (400 MHz, methanol-d₄) δ=8.35 (s, 1H), 8.18 (d, J=5.8 Hz, 1H), 7.11 (d, J=5.5 Hz, 1H), 4.50-4.31 (m, 3H), 4.04 (d, J=9.3 Hz, 1H), 3.91 (d, J=9.3 Hz, 1H), 3.48 (d, J=4.0 Hz, 1H), 3.30-3.22 (m, 1H), 1.94-1.87 (m, 3H), 1.79-1.75 (m, 1H), 1.35 (d, J=6.5 Hz, 3H).

Synthesis of Compound 513, Compound 514, Compound 515, and Compound 516 proceeded as exemplified for compound 511, using the following commercially available building blocks in step b.

| Compound | Name | Structure | Building Block |
|---|---|---|---|
| Compound 513 | (4-methyl-1-(3-(pyrazolo[1,5-a]pyridin-5-ylthio)-1H-pyrazolo[3,4-b]pyrazin-6-yl)piperidin-4-yl)methanamine | 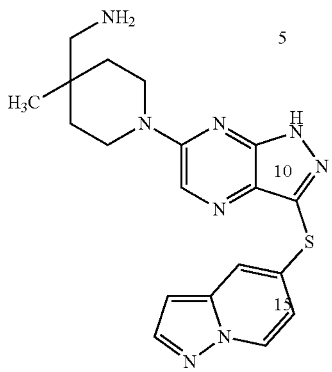 [SMILES: CC1(CN)CCN(c2cnc3c(Sc4ccn5nccc5c4)n[nH]c3n2)CC1] | CAS: 1060812-84-1 |
| Compound 514 | (1-(3-((4a,8a-dihydroisoquinolin-6-yl)thio)-1H-pyrazolo[3,4-b]pyrazin-6-yl)-4-methylpiperidin-4-yl)methanamine | 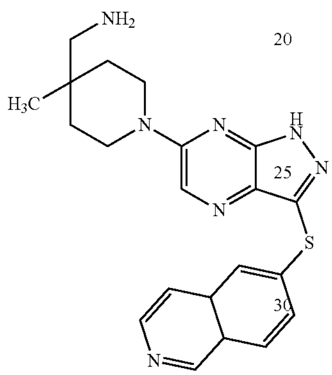 [SMILES: CC1(CN)CCN(c2cnc3c(SC4=CC5C=CN=CC5C=C4)n[nH]c3n2)CC1] | CAS: 34784-05-9 |
| Compound 515 | (1-(3-((1H-pyrrolo[2,3-b]pyridin-4-yl)thio)-1H-pyrazolo[3,4-b]pyrazin-6-yl)-4-methylpiperidin-4-yl)methanamine | 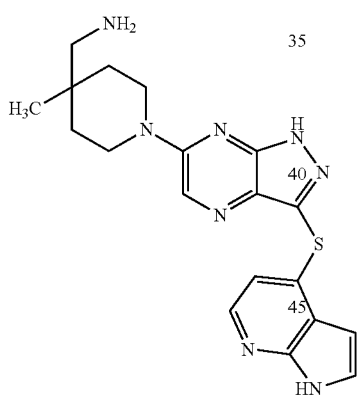 [SMILES: CC1(CN)CCN(c2cnc3c(Sc4ccnc5[nH]ccc45)n[nH]c3n2)CC1] | CAS: 1228014-35-4 |
| Compound 516 | (1-(3-((8-chloroquinolin-7-yl)thio)-1H-pyrazolo[3,4-b]pyrazin-6-yl)-4-methylpiperidin-4-yl)methanamine | 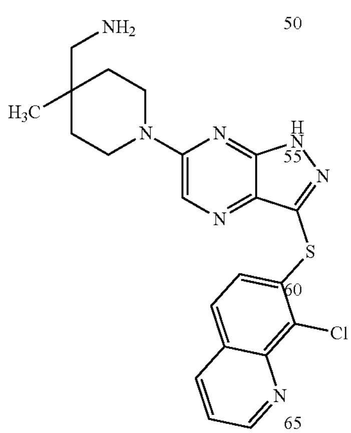 [SMILES: CC1(CN)CCN(c2cnc3c(Sc4ccc5cccnc5c4Cl)n[nH]c3n2)CC1] | CAS: 1429790-80-6 |

Preparation of (3S,4S)-8-(3-((3-chloro-2-methylpyridin-4-yl)oxy)-1H-pyrazolo[3,4-b]pyrazin-6-yl)-3-methyl-2-oxa-8-azaspiro[4.5]decan-4-amine, Compound 517

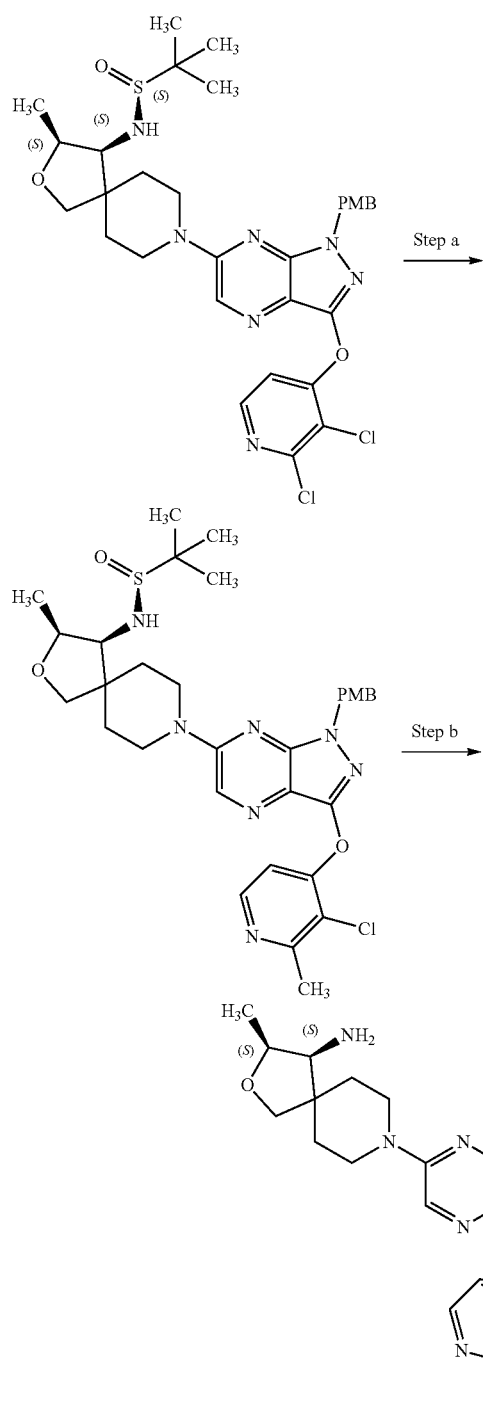

Step a: To a mixture of (S)—N-((3S,4S)-8-(3-((2,3-dichloropyridin-4-yl)oxy)-1-(4-methoxybenzyl)-1H-pyrazolo[3,4-b]pyrazin-6-yl)-3-methyl-2-oxa-8-azaspiro[4.5]decan-4-yl)-2-methylpropane-2-sulfinamide (100 mg, 148 μmol) and 2,4,6-trimethyl-1,3,5,2,4,6-trioxatriborinane (55.6 mg, 443 μmol) in dioxane (6 mL) and H₂O (2 mL) were added Pd(dppf)Cl₂ (21.6 mg, 29.6 μmol) and K₃PO₄ (93.8 mg, 443.0 μmol). The mixture was stirred at 100° C. under N₂ for 4 hrs. After cooling, the mixture was concentrated under reduced pressure and purified by flash silica gel chromatography (0-5% MeOH/DCM) to give (S)—N-((3S,4S)-8-(3-((3-chloro-2-methylpyridin-4-yl)oxy)-1-(4-methoxybenzyl)-1H-pyrazolo[3,4-b]pyrazin-6-yl)-3-methyl-2-oxa-8-azaspiro[4.5]decan-4-yl)-2-methylpropane-2-sulfinamide (80 mg) as an off-white solid.

Step b: A solution of (S)—N-((3S,4S)-8-(3-((3-chloro-2-methylpyridin-4-yl)oxy)-1-(4-methoxybenzyl)-1H-pyrazolo[3,4-b]pyrazin-6-yl)-3-methyl-2-oxa-8-azaspiro[4.5]decan-4-yl)-2-methylpropane-2-sulfinamide (80 mg, crude) in TFA (1 mL) and TfOH (0.1 mL) was stirred at 20° C. for 12 hrs. The mixture was concentrated under reduced pressure to give (S)—N-((3S,4S)-8-(3-((3-chloro-2-methylpyridin-4-yl)oxy)-1H-pyrazolo[3,4-b]pyrazin-6-yl)-3-methyl-2-oxa-8-azaspiro[4.5]decan-4-yl)-2-methylpropane-2-sulfinamide (100 mg) as a brown oil.

Step c: To a solution of (S)—N-((3S,4S)-8-(3-((3-chloro-2-methylpyridin-4-yl)oxy)-1H-pyrazolo[3,4-b]pyrazin-6-yl)-3-methyl-2-oxa-8-azaspiro[4.5]decan-4-yl)-2-methylpropane-2-sulfinamide (100 mg, 28 μmol) in MeOH (2 mL) was added 4N HCl/MeOH (1.0 mL). The mixture was stirred at 20° C. for 2 hrs, concentrated under reduced pressure, and purified by reversed phase prep-HPLC (acetonitrile/aq. HCl) to give (3S,4S)-8-(3-((3-chloro-2-methylpyridin-4-yl)oxy)-1H-pyrazolo[3,4-b]pyrazin-6-yl)-3-methyl-2-oxa-8-azaspiro[4.5]decan-4-amine dihydrochloride (11.5 mg, 12.2% yield) as a yellow solid: LCMS [M+H]⁺=430.0; ¹H-NMR (400 MHz, CD₃OD) δ=8.54 (d, J=6.8 Hz, 1H), 8.40 (s, 1H), 7.63 (d, J=6.8 Hz, 1H), 4.53-4.39 (m, 2H), 4.38-4.29 (m, 1H), 4.08-3.89 (m, 2H), 3.47 (d, J=4.0 Hz, 1H), 2.90 (s, 3H), 1.97-1.85 (m, 3H), 1.80-1.72 (m, 1H), 1.34 (d, J=6.5 Hz, 4H).

Preparation of 4-((6-(4-(aminomethyl)-4-methylpiperidin-1-yl)-1H-pyrazolo[3,4-b]pyrazin-3-yl)oxy)-5,6-dichloropyridin-2-amine hydrochloride, Compound 518

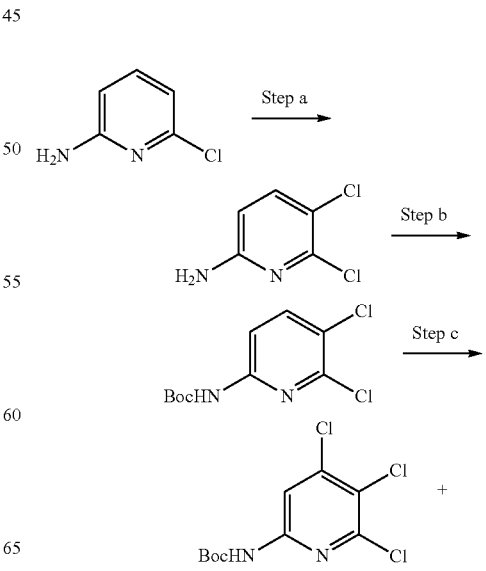

-continued

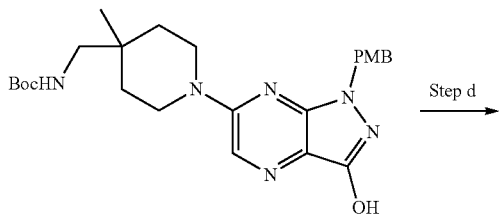

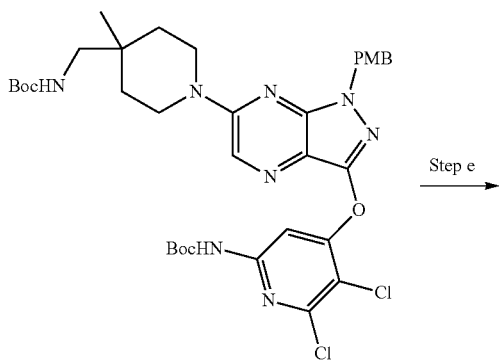

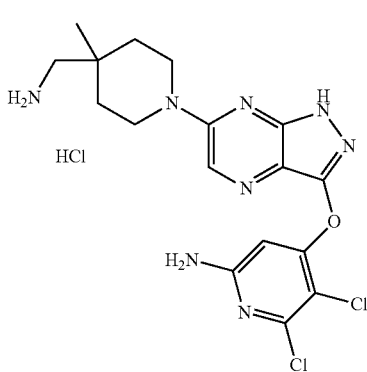

Step a: A mixture of 6-chloropyridin-2-amine (2.0 g, 15.5 mmol) and 1-chloropyrrolidine-2,5-dione (2.2 g, 16.2 mmol) in MeCN (20.0 mL) was stirred at 80° C. for 18 hours. The reaction mixture was concentrated in vacuo to give a residue, which was purified by silica gel chromatography (petroleum ether: ethyl acetate=4:1 to 2:1) to afford the product of 5,6-dichloropyridin-2-amine (2.0 g, 78% yield) as a white solid.

Step b: To a mixture of 5,6-dichloropyridin-2-amine (2.0 g, 12.3 mmol) in anhydrous THF (15 mL) was added NaHMDS (26.4 mL, 26.4 mmol) at 0° C. The reaction mixture was stirred at this temperature for 30 min, then the solution of $(Boc)_2O$ (2.85 g, 13.2 mmol) in anhydrous THF (5 mL) was added. The resulting mixture was stirred at 0° C. for 1.5 hours. The reaction mixture was quenched with sat. $NH_4Cl$, diluted with EtOAc (40 mL) and washed with $H_2O$ (30 mL×2). The organic phase was combined, washed with brine, dried over $Na_2SO_4$ and concentrated in vacuum to give a residue. The residue was purified by silica gel chromatography (petroleum ether:ethyl acetate=1:0) to afford the product of tert-butyl (5,6-dichloropyridin-2-yl)carbamate (2.3 g, 73% yield) as a colorless oil.

Step c: To a mixture of tert-butyl (5,6-dichloropyridin-2-yl)carbamate (1.0 g, 3.8 mmol) in anhydrous THF (15.0 mL) at −70° C. was added LDA (4.8 mL, 9.5 mmol) under $N_2$ atmosphere. After stirring at this temperature for 2 hours, 1-chloropyrrolidine-2,5-dione (1.0 g, 7.6 mmol) in THF (5.0 mL) was added and the resulting mixture was stirred for 2 hours at −70° C., and 10 hours at 20° C. The reaction mixture was diluted with $H_2O$ (20 mL) and extracted with ethyl acetate (25 mL×2). The combined organic phase was washed with brine, dried over anhydrous $Na_2SO_4$, filtered and concentrated in vacuo to give a residue, which was purified by silica gel chromatography (petroleum ether:ethyl acetate) to afford the product of tert-butyl (4,5,6-trichloropyridin-2-yl)carbamate (150 mg, 13% yield) as a yellow oil.

Step d: A mixture of tert-butyl ((1-(3-hydroxy-1-(4-methoxybenzyl)-1H-pyrazolo[3,4-b]pyrazin-6-yl)-4-methylpiperidin-4-yl)methyl)carbamate (202 mg, 420 μmol) (prepared as described for Compound 510, using tert-butyl ((4-methylpiperidin-4-yl)methyl)carbamate in place of tert-butyl (4-methylpiperidin-4-yl)carbamate), tert-butyl (4,5,6-trichloropyridin-2-yl)carbamate (150 mg, 504 μmol) and $Cs_2CO_3$ (410 mg, 1.3 mmol) in DMF (10 mL) was stirred at 80° C. for 48 hours. The reaction mixture was concentrated in vacuo to give a residue, which was purified by silica gel chromatography (petroleum ether: ethyl acetate=3:1 to 1:1) to afford the product of tert-butyl N-[(1-{3-[(6-([(tert-butoxy)carbonyl]amino}-2,3-dichloropyridin-4-yl)oxy]-1-[(4-methoxyphenyl)methyl]-1H-pyrazolo[3,4-b]pyrazin-6-yl}-4-methylpiperidin-4-yl)methyl]carbamate (90 mg, 28.8% yield) as a yellow oil.

Step e: A mixture of tert-butyl N-[(1-{3-[(6-{[(tert-butoxy)carbonyl]amino}-2,3-dichloropyridin-4-yl)oxy]-1-[(4-methoxyphenyl)methyl]-1H-pyrazolo[3,4-b]pyrazin-6-yl}-4-methylpiperidin-4-yl)methyl]carbamate (90 mg, 121 μmol) in TFA (5 mL) and TfOH (0.5 mL) was stirred at 30° C. for 1 hour. The reaction mixture was concentrated under reduced pressure to give a residue, which was purified by prep-HPLC (HCl) to afford the product of 4-((6-(4-(aminomethyl)-4-methylpiperidin-1-yl)-1H-pyrazolo[3,4-b]pyrazin-3-yl)oxy)-5,6-dichloropyridin-2-amine hydrochloride (9.3 mg, 16.7% yield) as a yellow solid. LCMS: calc. for $C_{17}H_{21}ClN_8O$: 422.1, found: [M+Na]+444.9 1HNMR (400 MHz, Methanol-d4): 8.34 (s, 1H), 6.24 (s, 1H), 4.19-4.15 (i, 2H), 3.61-3.55 (8, 2H), 2.93 (s, 2H), 1.70-1.60 (m, 4H), 1.23 (s, 3H).

The characterization of compounds disclosed herein is shown below in Table 1.

TABLE 1

| Cmpd. No. | Structure | ¹H-NMR | Mass Spec. (M + H)⁺ |
|---|---|---|---|
| 6 | 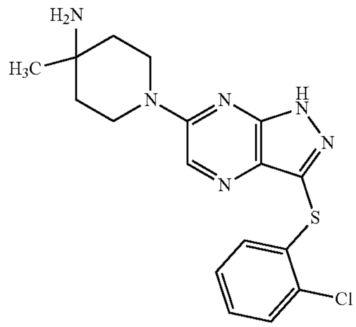 [SMILES: CC1(N)CCN(c2cnc3c(Sc4ccccc4Cl)n[nH]c3n2)CC1] | ¹H-NMR (500 MHz, DMSO) δ 8.43 (s, 1H), 8.34 (s, 1H), 7.49 (dd, J = 7.8, 1.5 Hz, 1H), 7.16 (dtd, J = 23.5, 7.4, 1.5 Hz, 2H), 6.78 (dd, J = 7.9, 1.6 Hz, 1H), 3.94-3.83 (m, 2H), 3.74-3.63 (m, 2H), 1.67-1.57 (m, 4H), 1.24 (s, 3H). | 375 |
| 7 | 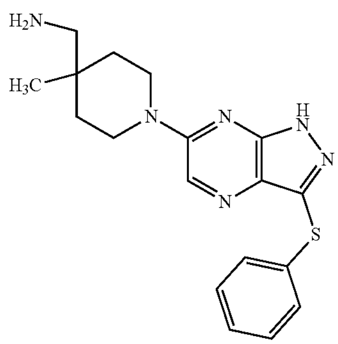 [SMILES: CC1(CN)CCN(c2cnc3c(Sc4ccccc4)n[nH]c3n2)CC1] | ¹H-NMR (500 MHz, DMSO-d₆) δ 8.38 (s, 1H), 7.29-7.21 (m, 4H), 7.20-7.16 (m, 1H), 3.97-3.86 (m, 2H), 3.53-3.41 (m, 2H), 2.41 (br 2H), 1.55-1.43 (m, 2H), 1.37-1.27 (m, 2H), 0.94 (s, 3H). | 355.3 |
| 8 | 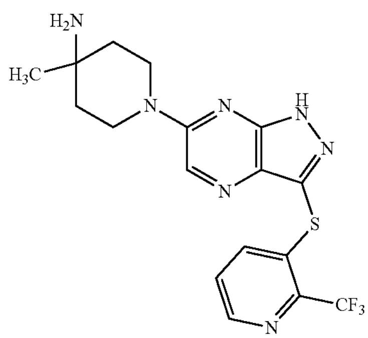 [SMILES: CC1(N)CCN(c2cnc3c(Sc4cccnc4C(F)(F)F)n[nH]c3n2)CC1] | ¹H-NMR (500 MHz, DMSO) δ 8.52-8.49 (m, 1H), 8.43 (s, 1H), 8.37 (s, 1H), 7.53-7.46 (m, 2H), 3.90-3.79 (m, 2H), 3.76-3.64 (m, 2H), 1.68-1.52 (m, 4H), 1.22 (s, 3H). | 410.2 |
| 9 | 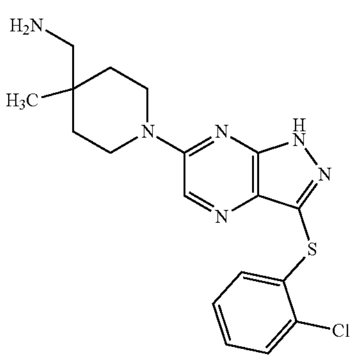 [SMILES: CC1(CN)CCN(c2cnc3c(Sc4ccccc4Cl)n[nH]c3n2)CC1] | ¹H-NMR (500 MHz, MeOD) δ 8.52 (br s, 1H), 8.30 (s, 1H), 7.42-7.37 (m, 1H), 7.17-7.09 (m, 1H), 7.09-7.02 (m, 1H), 6.83-6.76 (m, 1H), 4.20-4.10 (m, 2H), 3.62-3.51 (m, 2H), 2.90 (br s, 2H), 1.70-1.55 (m, 4H), 1.21 (s, 3H) | 389.3 |

TABLE 1-continued

| Cmpd. No. | Structure | ¹H-NMR | Mass Spec. (M + H)⁺ |
|---|---|---|---|
| 10 | 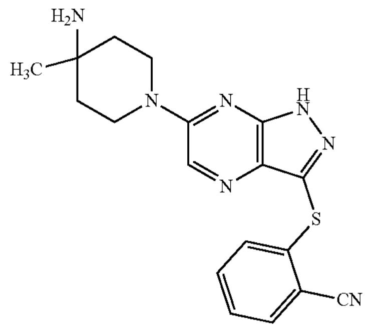 [SMILES: CC1(N)CCN(c2cnc3c(Sc4ccccc4C#N)n[nH]c3n2)CC1] | ¹H-NMR (400 MHz, CDCl₃) δ 10.08 (s, 1H), 8.85-8.79 (m, 1H), 8.34 (s, 1H), 7.61 (ddd, J = 8.1, 6.8, 1.5 Hz, 1H), 7.56-7.46 (m, 2H), 4.08-3.98 (m, 2H), 3.87-3.78 (m, 2H), 1.70 (ddd, J = 13.5, 9.4, 4.1 Hz, 2H), 1.59 (dd, J = 11.3, 6.7 Hz, 3H), 1.25 (s, 2H), 1.23 (s, 3H) | 366.3 |
| 11 | 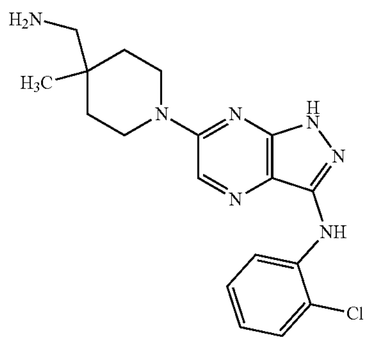 [SMILES: CC1(CN)CCN(c2cnc3c(Nc4ccccc4Cl)n[nH]c3n2)CC1] | ¹H-NMR (500 MHz, DMSO) δ 8.27 (d, J = 3.7 Hz, 1H), 8.06 (dd, J = 8.3, 1.5 Hz, 1H), 7.42 (dd, J = 8.0, 1.4 Hz, 1H), 7.29-7.20 (m, 1H), 6.91-6.81 (m, 1H), 3.94 (d, J = 13.3 Hz, 2H), 3.43 (dd, J = 21.4, 8.2 Hz, 2H), 2.55 (d, J = 15.5 Hz, 2H), 1.49 (d, J = 9.8 Hz, 2H), 1.37 (s, 2H), 0.99 (s, 3H). | 372.2 |
| 12 | 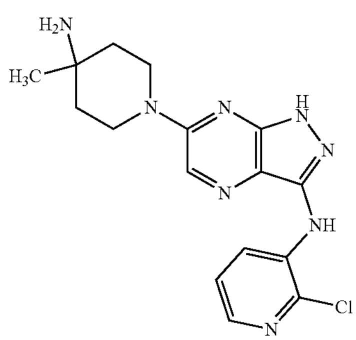 [SMILES: CC1(N)CCN(c2cnc3c(Nc4cccnc4Cl)n[nH]c3n2)CC1] | ¹H-NMR (400 MHz, CD₃OD) δ 8.69 (dd, J = 8.2, 1.6 Hz, 1H), 8.28 (s, 1H), 7.87 (dt, J = 5.9, 2.9 Hz, 1H), 7.37-7.30 (m,1H), 4.30 (dd, J = 9.7, 4.4 Hz, 2H), 3.51 (ddd, J = 14.1, 9.1, 4.8 Hz, 2H), 1.89 (h, J = 9.3 Hz, 4H), 1.51 (s, 3H). | 359.2 |
| 13 | 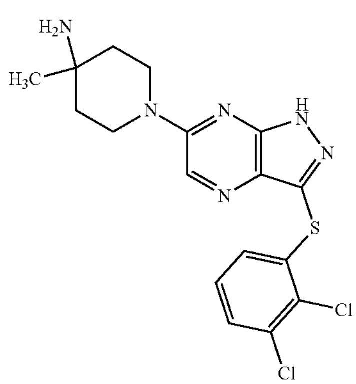 [SMILES: CC1(N)CCN(c2cnc3c(Sc4cccc(Cl)c4Cl)n[nH]c3n2)CC1] | ¹H-NMR (500 MHz, DMSO) δ 8.44 (s, 1H), 8.32 (s, 1H), 7.44 (dd, J = 8.0, 1.4 Hz, 1H), 7.21-7.06 (m, 1H), 6.70 (dd, J = 8.1, Hz, 1H), 4.02-3.87 (m, 2H), 3.71-3.59 (m, 2H), 1.74-1.59 (m, 4H), 1.27 (s, 3H). | 409.2 |

TABLE 1-continued

| Cmpd. No. | Structure | ¹H-NMR | Mass Spec. (M + H)⁺ |
|---|---|---|---|
| 14 | 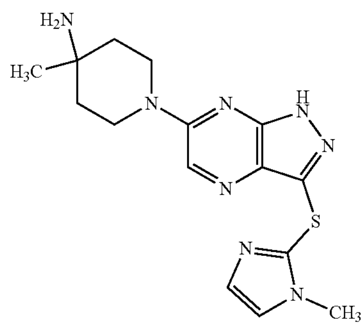 | ¹H-NMR (400 MHz, DMSO-d6) δ 8.34 (s, 1H), 7.34 (d, J = 1.2 Hz, 1H), 6.92 (d, J = 1.2 Hz, 1H), 3.81 (m, 2H), 3.73 (s, 3H), 3.65 (m, 2H), 1.45 (m, 4H), 1.09 (s, 3H). | 345.2 |
| 15 | 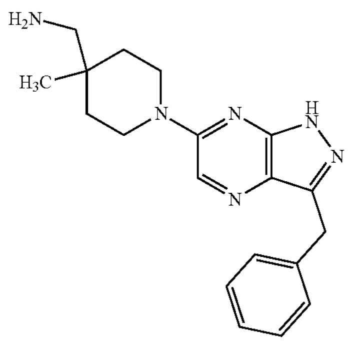 [SMILES: CC1(CN)CCN(c2cnc3c(Cc4ccccc4)n[nH]c3n2)CC1] | ¹H-NMR (500 MHz, DMSO-d6 + D₂O) δ 8.26 (s, 1H), 7.31-7.27 (m, 2H), 7.27-7.21 (m, 2H), 7.17-7.11 (m, 1H), 4.13 (s, 2H), 3.45-3.35 (m, 2H), 2.43 (s, 2H), 1.48-1.37 (m, 2H), 1.36-1.29 (m, 2H), 0.94 (s, 3H). | 337.2 |
| 16 | 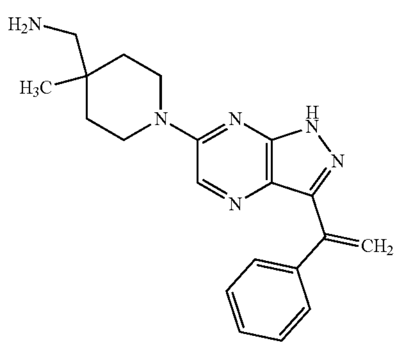 [SMILES: C=C(c1ccccc1)c1n[nH]c2nc(N3CCC(C)(CN)CC3)cnc12] | ¹H-NMR (500 MHz, DMSO) δ 8.43 (s, 1H), 8.36 (s, 1H), 7.55-7.45 (m, 2H), 7.41-7.29 (m, 3H), 6.47 (d, J = 1.7 Hz, 1H), 5.70 (d, J = 1.7 Hz, 1H), 3.96 (dt, J = 10.0, 4.5 Hz, 2H), 3.47-3.45 (m, 2H), 2.54 (s, J = 13.7 Hz, 2H), 1.52 (ddd, J = 13.4, 7.0, 3.9 Hz, 2H), 1.37 (dt, J = 13.7, 4.0 Hz, 2H), 0.99 (s, 3H). | 349.3 |
| 17 | 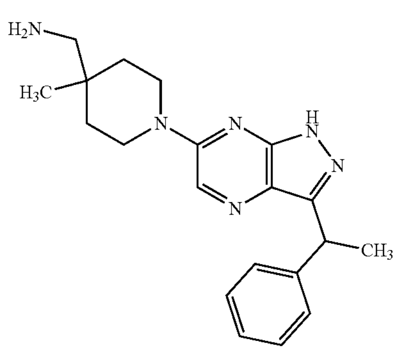 [SMILES: CC(c1ccccc1)c1n[nH]c2nc(N3CCC(C)(CN)CC3)cnc12] | ¹H-NMR (500 MHz, DMSO) δ 8.36 (s, 1H), 8.31 (s, 1H), 7.37 (dd, J = 8.2, 1.0 Hz, 2H), 7.25 (t, J = 7.6 Hz, 2H), 7.17-7.11 (m, 1H), 4.47 (q, J = 7.2 Hz, 1H), 3.96-3.87 (m, 2H), 3.43 (dd, J = 13.6, 9.7 Hz, 2H), 2.54 (s, J = 12.5 Hz, 2H), 1.72 (d, J = 7.3 Hz, 3H), 1.49 (t, J = 9.9 Hz, 2H), 1.37-1.30 (m, 2H), 0.98 (s, 3H) | 351.4 |

TABLE 1-continued

| Cmpd. No. | Structure | ¹H-NMR | Mass Spec. (M + H)⁺ |
|---|---|---|---|
| 18 | 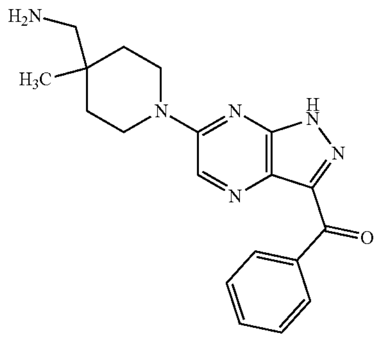 [SMILES: CC1(CN)CCN(c2cnc3c(C(=O)c4ccccc4)n[nH]c3n2)CC1] | ¹H-NMR (500 MHz, DMSO) δ 8.58 (s, 1H), 8.29 (s, 1H), 8.09 (dd, J = 8.4, 1.3 Hz, 2H), 7.70-7.63 (m, 1H), 7.55 (dd, J = 7.7 Hz, 2H), 4.01 (dt, J = 9.7, 4.6 Hz, 2H), 3.56-3.47 (m, 2H), 2.61 (s, 2H), 1.54 (ddd, J = 13.5, 9.6, 3.9 Hz, 2H), 1.48-1.34 (m, 2H), 1.03 (s, 3H) | 351.2 |
| 19 | 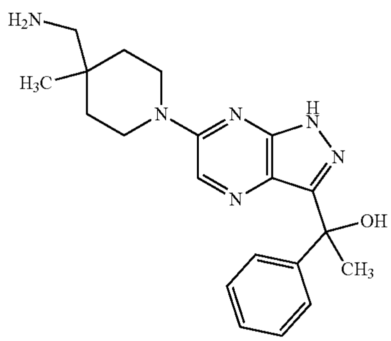 [SMILES: CC1(CN)CCN(c2cnc3c(C(C)(O)c4ccccc4)n[nH]c3n2)CC1] | ¹H-NMR (500 MHz, DMSO) δ 8.34 (s, 1H), 8.31 (s, 1H), 7.50 (dd, J = 8.3, 1.1 Hz, 2H), 7.24 (t, J = 7.7 Hz, 2H), 7.14 (t, J = 7.3 Hz, 1H), 5.61 (s, 1H), 3.91 (dd, J = 13.5, 4.9 Hz, 2H), 2.55 (s, 2H), 1.96 (s, J = 14.4 Hz, 3H), 1.54-1.42 (m, 2H), 1.34 (d, J = 13.9 Hz, 2H), 0.98 (s, J = 20.3 Hz, 3H) | 367.5 |
| 20 | 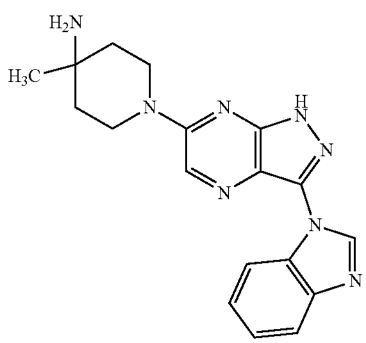 [SMILES: CC1(N)CCN(c2cnc3c(-n4cnc5ccccc54)n[nH]c3n2)CC1] | ¹H-NMR (400 MHz, DMSO-d₆) δ 9.03 (s, 1H), 8.53 (s, 1H), 8.18 (d, J = 7.5 Hz, 1H), 7.79 (d, J = 7.5 Hz, 1H), 7.37 (dtd, J = 16.4, 73, 1.2 Hz, 2H), 3.91 (dt, J = 9.9, 4.7 Hz, 2H), 3.70 (ddd, J = 13.4, 8.6, 4.7 Hz, 2H), 1.55-1.45 (m, 4H), 1.11 (s, 3H). | 349.2 |
| 21 | 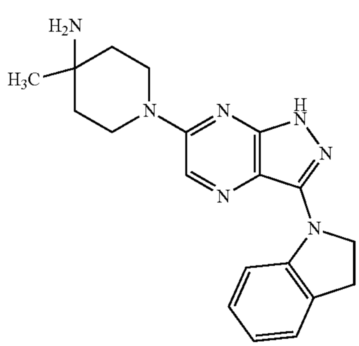 [SMILES: CC1(N)CCN(c2cnc3c(N4CCc5ccccc54)n[nH]c3n2)CC1] | ¹H-NMR (400 MHz, DMSO-d₆) δ 12.25 (s, 1H), 8.27 (s, 1H), 7.93-7.90 (d, 1H, J = 8.0 Hz), 7.20-7.17 (d, 1H, J = 7.2 Hz), 7.13-7.08 (t, 1H), 6.79-6.75 (t, 1H), 4.44-4.40 (t, 2H), 3.87-3.83 (t, 2H), 3.66-3.62 (q, 2H), 3.22-3.18 (t, 2H), 1.49-1.46 (q, 4H), 1.09 (s, 3H). | 350.1 |

TABLE 1-continued

| Cmpd. No. | Structure | ¹H-NMR | Mass Spec. (M + H)⁺ |
|---|---|---|---|
| 22 | 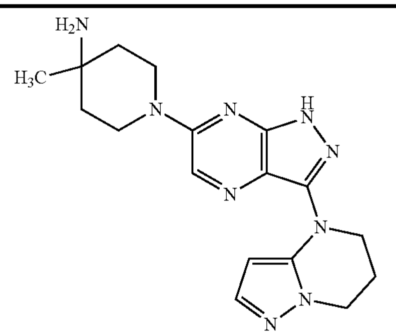 | ¹H-NMR (400 MHz, DMSO-d₆) δ = 12.33 (br s, 1H), 8.28 (s, 1H), 7.23 (d, J = 2.0 Hz, 1H), 6.34 (d, J = 2.0 Hz, 1H), 4.25-4.36 (m, 2H), 4.15 (t, J = 6.0 Hz, 2H), 3.86 (dt, J = 13.4, 4.5 Hz, 2H), 3.61 (ddd, J = 13.2, 8.9, 4.0 Hz, 2H), 2.24 (dt, J = 11.5, 5.8 Hz, 2H), 1.29-1.61 (m, 6H), 1.08 (s, 3H). | 354.2 |
| 23 | 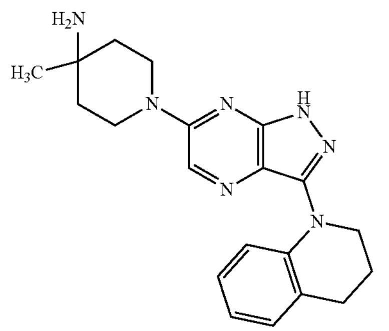 [SMILES: CC1(N)CCN(c2cnc3c(N4CCCc5ccccc54)n[nH]c3n2)CC1] | ¹H-NMR (400 MHz, DMSO-d₆) δ 8.38 (s, 3H), 8.31 (s, 1H), 7.04-7.00 (m, 2H), 6.93-6.90 (m, 1H), 6.72-6.68 (m, 1H), 4.14 (m, 2H), 3.91-3.87 (m, 2H), 3.53-3.47 (m, 2H), 2.83-2.79 (m, 2H), 2.00-1.96 (m, 2H), 1.87-1.74 (m, 4H), 1.4 (s, 3H). | 364.0 |
| 24 | 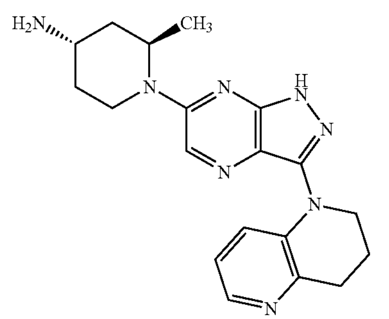 [SMILES: C[C@@H]1C[C@@H](N)CCN1c1cnc2c(N3CCCc4ncccc43)n[nH]c2n1] | ¹H-NMR (400 MHz, DMSO-d₆) δ 8.26 (s, 1H), 7.91-7.88 (m, 1H), 7.49-7.47 (m, 1H), 6.98-6.94 (m, 1H), 4.86-4.82 (m, 1H), 4.34-4.30 (m, 1H), 3.96-3.92 (m, 2H), 3.07-2.92 (m, 4H), 2.10-2.05 (m, 2H), 1.88-1.73 (m, 2H), 1.39-1.37 (m, 1H), 1.22-1.13 (m, 4H) | 365.3 |
| 25 | 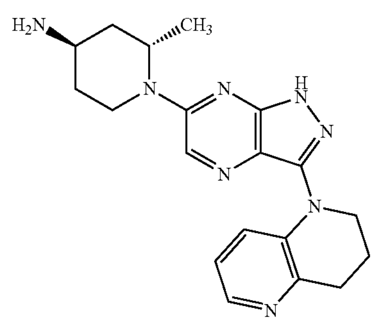 [SMILES: C[C@H]1C[C@H](N)CCN1c1cnc2c(N3CCCc4ncccc43)n[nH]c2n1] | ¹H-NMR (400 MHz, DMSO-d₆) δ 8.31 (s, 1H), 7.96-7.94 (m, 1H), 7.55-7.52 (m, 1H), 7.03-6.99 (m, 1H), 4.96-4.88 (m, 1H), 4.40-4.36 (m, 1H), 4.02-3.98 (m, 2H), 3.12-2.97 (m, 4H), 2.15-2.08 (m, 2H), 1.94-1.79 (m, 2H), 1.46-1.43 (m, 1H), 1.28-1.21 (m, 4H). | 365.3 |
| 26 | 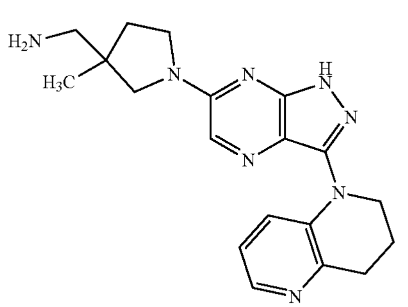 [SMILES: CC1(CN)CCN(c2cnc3c(N4CCCc5ncccc54)n[nH]c3n2)C1] | ¹H-NMR (400 MHz, DMSO-d₆) δ 12.99 (s, 1H), 8.16-8.21 (m, 3H), 8.12-8.14 (m, 1H), 8.09 (m, 1H), 7.97 (s, 1H), 7.57-7.60 (m, 1H), 4.02-4.05 (m, 2H), 3.23-3.40 (m, 2H), 2.92-2.93 (m, 2H), 2.14-2.17 (m, 1H), 2.04-2.08 (m, 1H), 1.86-1.88 (m, 1H), 1.23 (m, 1H), 1.19 (s, 3H). | 365.0 |

TABLE 1-continued

| Cmpd. No. | Structure | ¹H-NMR | Mass Spec. (M + H)⁺ |
|---|---|---|---|
| 27 | 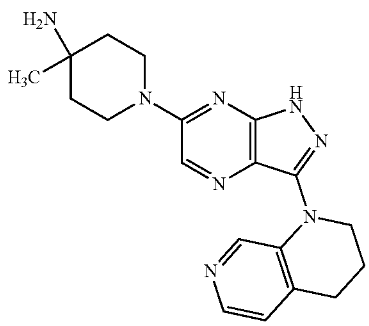 [SMILES: CC1(N)CCN(c2cnc3c(N4CCCc5ccncc54)n[nH]c3n2)CC1] | ¹H-NMR (400 MHz, DMSO-d$_6$) δ 13.04 (br, 1H), 8.76 (s, 1H), 8.42 (s, 1H), 8.34 (br, 3H), 8.22 (d, J = 5.2 Hz, 1H), 7.78-7.76 (d, J = 5.2 Hz, 1H), 4.14 (s, 4H), 3.56-3.52 (m, 2H), 3.05-3.00 (m, 2H), 2.08-2.02 (m, 2H), 1.90-1.72 (m, 4H), 1.40 (s, 3H). | 365.1 |
| 28 | 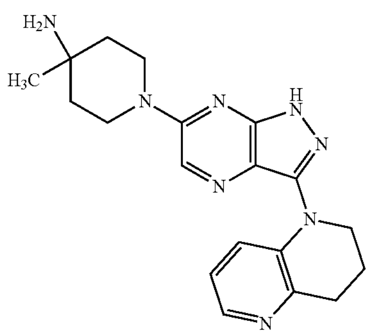 [SMILES: CC1(N)CCN(c2cnc3c(N4CCCc5ncccc54)n[nH]c3n2)CC1] | ¹H-NMR (400 MHz, DMSO-d$_6$) δ 12.57 (s, 1H), 8.29 (s, 1H), 7.89-7.91 (d, 1H), 7.47-7.50 (d, 1H), 6.94-6.98 (m, 1H), 3.93-3.97 (m, 2H), 3.84-3.89 (m, 2H), 3.58-3.65 (m, 2H), 2.92-2.96 (m, 2H), 2.05-2.09 (m, 2H), 1.44-1.52 (m, 4H), 1.09 (s, 3H). | 365.1 |
| 29 | 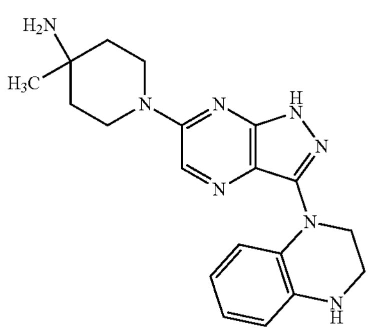 [SMILES: CC1(N)CCN(c2cnc3c(N4CCNc5ccccc54)n[nH]c3n2)CC1] | ¹H-NMR (400 MHz, DMSO-d$_6$) δ 12.88 (br, 1H), 8.40-8.33 (m, 4H), 7.41 (s, 1H), 7.38-7.31 (m, 1H), 7.29-7.26 (m, 2H), 7.16-7.12 (m, 2H), 6.93-6.85 (m, 1H), 4.18-4.10 (m, 4H), 3.65-3.45 (m, 4H), 1.88-1.72 (m, 4H), 1.40 (s, 3H). | 365.1 |
| 30 | 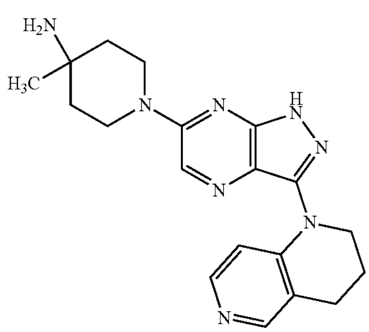 [SMILES: CC1(N)CCN(c2cnc3c(N4CCCc5cnccc54)n[nH]c3n2)CC1] | ¹H-NMR (400 MHz, DMSO-d$_6$ + TFA) δ 13.92 (br, 1H), 13.38 (br, 1H), 8.48 (s, 1H), 8.33-8.27 (m, 4H), 8.11-8.08 (m, 1H), 7.01-6.98 (m, 1H), 4.19-4.03 (m, 2H), 4.03-4.01 (m, 2H), 3.56-3.52 (m, 2H), 2.96-2.92 (m, 2H), 2.11-2.07 (m, 2H), 1.85-1.78 (m, 4H), 1.40 (s, 3H). | 365.1 |

TABLE 1-continued

| Cmpd. No. | Structure | ¹H-NMR | Mass Spec. (M + H)⁺ |
|---|---|---|---|
| 31 | 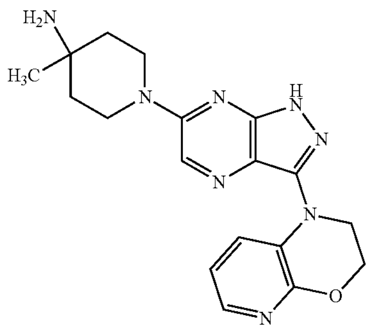 | ¹H-NMR (400 MHz, methanol-d₄) δ 8.56 (d, J = 8.0 Hz, 1H), 8.40 (s, 1H), 7.83 (d, J = 5.6 Hz, 1H), 7.40-7.33 (m, 1H), 4.95-4.85 (m, 2H), 4.50-4.40 (m, 2H), 4.38-4.30 (m, 2H), 3.70-3.50 (m, 2H), 1.98-1.92 (m, 4H), 1.56 (s, 3H). | 367.1 |
| 32 | 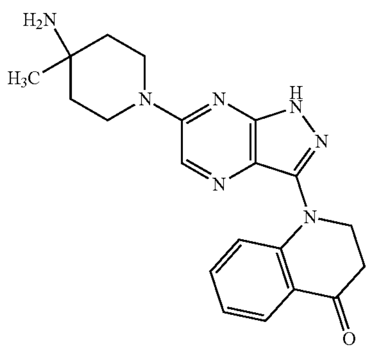 [SMILES: CC1(N)CCN(c2cnc3c(N4CCC(=O)c5ccccc54)n[nH]c3n2)CC1] | ¹H-NMR (400 MHz, DMSO-d₆) δ 12.95 (br, 1H), 8.40 (s, 1H), 8.10 (br, 3H), 7.82-7.80 (m, 1H), 7.36-7.33 (m, 1H), 7.05-7.02 (m, 1H), 6.91-6.86 (m, 1H), 4.19-4.14 (m, 4H), 3.52-3.45 (m, 2H), 2.85-2.80 (m, 2H), 1.81-1.74 (m, 4H), 1.40 (s, 3H). | 378.1 |
| 33 | 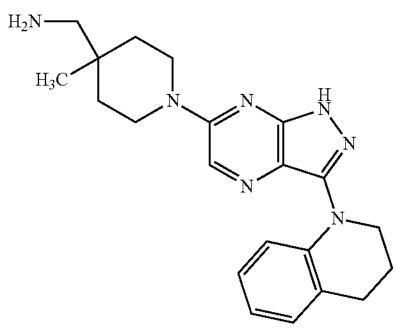 [SMILES: CC1(CN)CCN(c2cnc3c(N4CCCc5ccccc54)n[nH]c3n2)CC1] | ¹H-NMR (400 MHz, DMSO-d₆) δ 12.51 (br, 1H), 8.26 (s, 1H), 7.04-7.00 (m, 2H), 6.95-6.85 (m, 1H), 6.72-6.63 (m, 1H), 3.98-3.84 (m, 4H), 3.55-3.40 (m, 4H), 2.85-2.77 (m, 2H), 2.00-1.93 (m, 2H), 1.50-1.44 (m, 2H), 1.35-1.27 (m, 2H), 0.95 (s, 3H). | 378.1 |
| 34 | 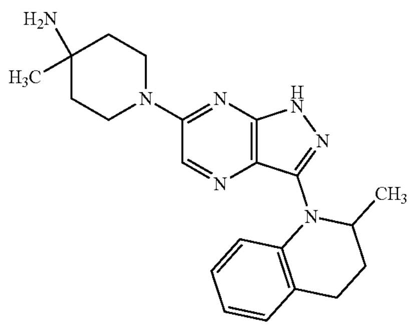 | ¹H-NMR (400 MHz, DMSO-d₆) δ 12.54 (br, 1H), 8.23 (s, 1H), 7.00-6.97 (m, 1H), 6.80-6.79 (m, 1H), 6.66-6.58 (m, 2H), 4.32-4.28 (m, 1H), 3.83-3.77 (m, 2H), 3.63-3.57 (m, 2H), 2.83-2.76 (m, 2H), 1.98-1.95 (m, 1H), 1.83-1.81 (m, 1H), 1.46-1.41 (m, 4H), 1.11 (d, J = 6.4 Hz, 3H), 1.06 (s, 3H). | 378.1 |

TABLE 1-continued

| Cmpd. No. | Structure | ¹H-NMR | Mass Spec. (M + H)⁺ |
|---|---|---|---|
| 35 | 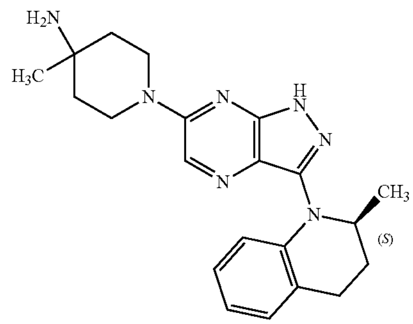 | ¹H-NMR (400 MHz, DMSO-d₆) δ 12.54 (br, 1H), 8.23 (s, 1H), 7.00-6.97 (m, 1H), 6.80-6.79 (m, 1H), 6.66-6.58 (m, 2H), 4.32-4.28 (m, 1H), 3.83-3.77 (m, 2H), 3.63-3.57 (m, 2H), 2.83-2.76 (m, 2H), 1.98-1.95 (m, 1H), 1.83-1.81 (m, 1H), 1.46-1.41 (m, 4H), 1.11 (d, J = 6.4 Hz, 3H), 1.06 (s, 3H). | 378.1 |
| 36 | 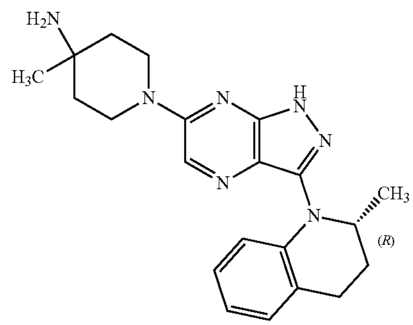 | ¹H-NMR (400 MHz, DMSO-d₆) δ 11.90 (s, 1H), 8.10 (s, 1H), 7.17-7.29 (m, 1H), 6.97-7.14 (m, 3H), 3.96-4.11 (m 2H), 3.91 (br s, 2H), 3.34-3.50 (m, 2H), 2.68-2.81 (m, 2H), 1.54-1.82 (m, 6H), 1.33 (s, 3H). | 378 |
| 37 | 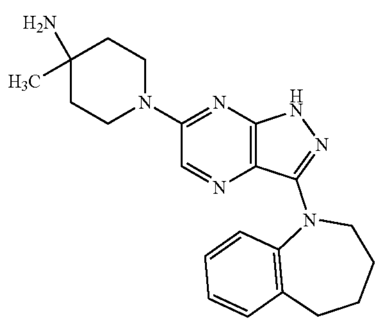 [SMILES: CC1(N)CCN(c2cnc3c(N4CCCCc5ccccc54)n[nH]c3n2)CC1] | ¹H-NMR (400 MHz, DMSO-d₆) δ 11.90 (s, 1H), 8.10 (s, 1H), 7.17-7.29 (m, 1H), 6.97-7.14 (m, 3H), 3.96-4.11 (m, 2H), 3.91 (br s, 2H), 3.34-3.50 (m, 2H), 2.68-2.81 (m, 2H), 1.54-1.82 (m, 6H), 1.33 (s, 3H). | 378 |
| 38 | 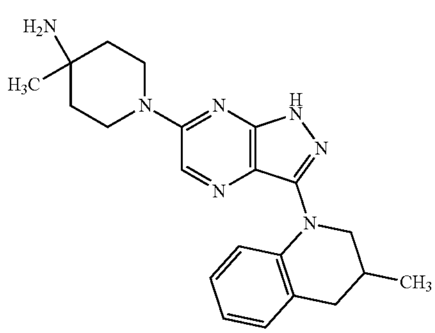 | ¹H-NMR (400 MHz, DMSO-d₆) δ 8.28 (s, 1H), 7.06-7.00 (m, 2H), 6.92-6.87 (m, 1H), 6.71-6.66 (m, 1H), 3.99-3.90 (m, 1H), 3.88-3.83 (m, 2H), 3.64-3.60 (m, 2H), 3.44-3.36 (m, 2H), 2.88-2.83 (m, 1H), 2.30-2.10 (m, 1H), 1.53-1.40 (m, 4H), 1.09 (s, 3H), 1.04 (d, J = 6.8 Hz, 3H). | 378.1 |

TABLE 1-continued

| Cmpd. No. | Structure | ¹H-NMR | Mass Spec. (M + H)⁺ |
|---|---|---|---|
| 39 | 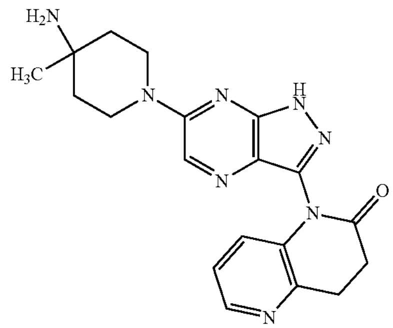 [SMILES: CC1(N)CCN(c2cnc3c(N4C(=O)CCc5ncccc54)n[nH]c3n2)CC1] | ¹H-NMR (400 MHz, DMSO-d₆) δ 13.62 (br, 1H), 8.48-8.43 (m, 4H), 7.62-7.56 (m, 1H), 7.38-7.34 (m, 1H), 4.18-4.13 (m, 4H), 3.59-3.52 (m, 4H), 3.10-3.02 (m, 2H), 1.93-1.75 (m, 4H), 1.41 (s, 3H). | 379.0 |
| 40 | 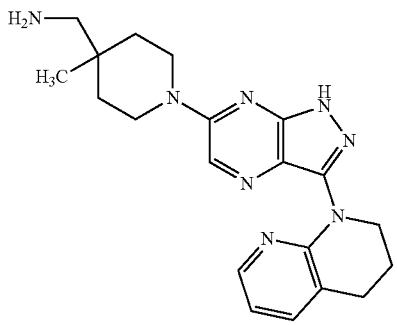 [SMILES: CC1(CN)CCN(c2cnc3c(N4CCCc5cccnc54)n[nH]c3n2)CC1] | ¹H-NMR (400 MHz, methanol-d₄) δ 8.18 (s, 1H), 7.72-7.70 (d, J = 3.6 Hz, 1H), 7.44-7.41 (d, J = 6.4 Hz, 1H), 6.73-6.69 (m, 1H), 4.1 (m, 2H), 3.92 (m, 2H), 3.54 (m, 2H), 2.95 (m, 2H), 2.60 (s, 2H), 2.16 (m, 2H), 1.58 (m, 2H), 1.50 (m, 2H), 1.10 (s, 3H). | 379.1 |
| 41 | 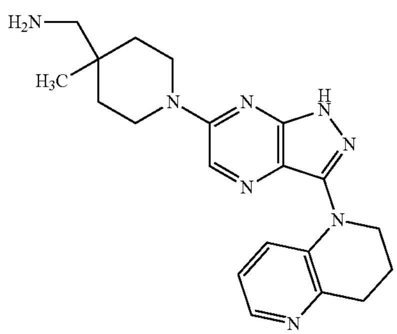 [SMILES: CC1(CN)CCN(c2cnc3c(N4CCCc5ncccc54)n[nH]c3n2)CC1] | ¹H-NMR (400 MHz, DMSO-d₆) δ 8.29 (s, 1H), 7.91-7.88 (m, 1H), 7.50-7.46 (m, 1H), 6.99-6.94 (m, 1H), 4.10-3.80 (m, 4H), 3.50-3.40 (m, 2H), 3.00-2.80 (m 2H), 2.41 (s, 2H), 2.10-2.02 (m, 2H), 1.53-1.44 (m, 2H), 1.35-1.25 (m, 2H), 0.94 (s, 3H). | 379.1 |
| 42 | 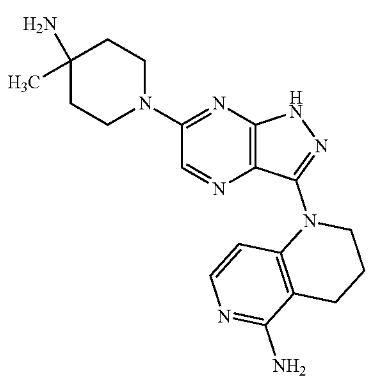 [SMILES: CC1(N)CCN(c2cnc3c(N4CCCc5c4ccnc5N)n[nH]c3n2)CC1] | ¹H-NMR (400 MHz, DMSO-d₆) δ 13.17 (s, 1H), 8.41 (s, 1H), 8.06 (br, 2H), 7.41-7.44 (d, J = 7.2, 1H), 7.29 (s, 2H), 6.19-6.22 (d, J = 7.2, 1H), 4.10-4.14 (m, 2H), 3.80-3.83 (m, 2H), 3.42-3.48 (m, 2H), 2.49-2.53 (m, 2H), 2.01-2.07 (m, 1H), 1.74 (br, 4H), 1.36 (s, 3H). | 380.1 |

TABLE 1-continued

| Cmpd. No. | Structure | ¹H-NMR | Mass Spec. (M + H)⁺ |
|---|---|---|---|
| 43 | 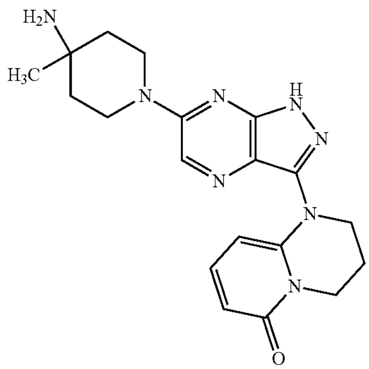 [SMILES: CC1(N)CCN(c2cnc3c(N4CCCn5c4cccc5=O)n[nH]c3n2)CC1] | ¹H-NMR (400 MHz, DMSO-d₆) δ 12.93 (br s, 1H), 9.48 (br s, 1H), 8.84 (d, J = 9.3 Hz, 1H), 8.41 (s, 1H), 8.25 (s, 1H), 3.84-4.14 (m, 4H), 3.60 (dd, J = 13.4, 6.3 Hz, 2H), 3.48-3.56(m, 2H), 1.90-2.11 (m, 2H), 1.54-1.76 (m, 4H), 1.28 (s, 3H). | 381.3 |
| 44 | 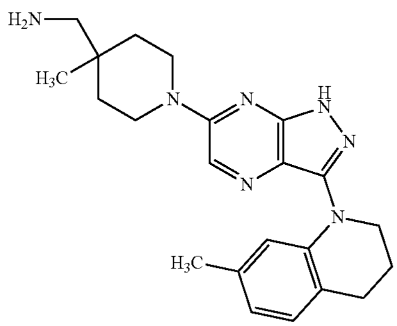 [SMILES: Cc1ccc2c(c1)N(c1n[nH]c3nc(N4CCC(C)(CN)CC4)cnc13)CCC2] | ¹H-NMR (400 MHz, DMSO-d₆) δ 12.46 (br d, J = 4.88 Hz, 1H), 8.25 (s, 1H), 6.89 (d, J = 7.57 Hz, 1H), 6.85 (s, 1H), 6.50 (br d, J = 7.32 Hz, 1H), 3.92 (td, J = 4.58, 13.55 Hz, 2H), 3.81-3.88 (m, 2H), 3.44 (ddd, J = 3.17, 9.83, 13.37 Hz, 2H), 2.75 (br t, J = 6.35 Hz, 2H), 2.06 (s, 3H), 1.94 (td, J = 6.04, 11.84 Hz, 2H), 1.42-1.56 (m, 2H), 1.29-1.38 (m, 2H), 0.97 (s, 3H). | 392.4 |
| 45 | 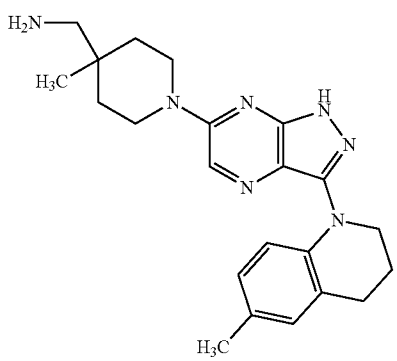 | ¹H-NMR (400 MHz, DMSO-d₆) δ 12.42 (br s, 1H), 8.25 (s, 1H), 6.75-6.84 (m, 2H), 6.60 (br d, J = 6.84 Hz, 1H), 3.89-3.97 (m, 2H), 3.79-3.84 (m, 2H), 3.44 (ddd, J = 2.93, 9.89, 13.31 Hz, 2H), 2.64-2.71 (m, 2H), 2.60 (s, 1H), 2.17 (s, 3H), 1.94-2.02 (m, 2H), 1.46-1.56 (m, 2H), 1.32-1.42 (m, 2H), 1.00 (s, 3H). | 392.4 |
| 46 | 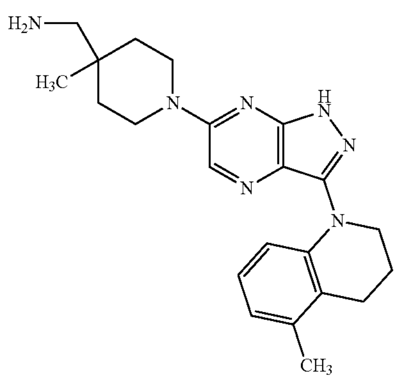 [SMILES: Cc1cccc2c1CCCN2c1n[nH]c2nc(N3CCC(C)(CN)CC3)cnc12] | ¹H-NMR (400 MHz, DMSO-d₆) δ 12.31-12.46 (m, 1H), 8.35 (s, 1H), 8.23 (s, 1H), 6.98 (d, J = 8.30 Hz, 1H), 6.83 (s, 1H), 6.71 (dd, J = 1.46, 8.30 Hz, 1H), 3.84-3.96 (m, 5H), 3.43 (ddd, J = 3.17, 9.83, 13.37 Hz, 3H), 2.75 (t, J = 6.35 Hz, 2H), 2.53 (s, 2H), 2.16 (s, 3H), 1.94 (td, J = 6.20, 11.78 Hz, 2H), 1.46-1.54 (m, 2H), 1.30-1.38 (m, 2H), 0.98 (s, 3H). | 392.3 |

TABLE 1-continued

| Cmpd. No. | Structure | ¹H-NMR | Mass Spec. (M + H)⁺ |
|---|---|---|---|
| 47 | 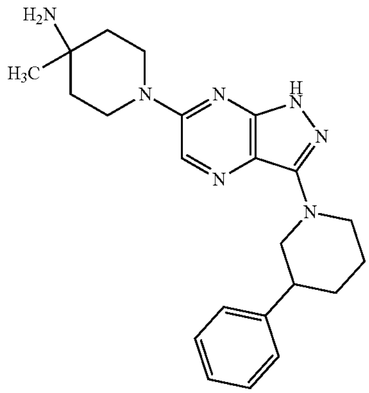 [SMILES: CC1(N)CCN(c2cnc3c(N4CCCC(c5ccccc5)C4)n[nH]c3n2)CC1] | ¹H-NMR (400 MHz, methanol-d₄) δ 8.12 (s, 1H), 7.30-7.35 (m, 4H), 7.20-7.25 (m, 1H), 4.55-4.60 (m, 1H), 4.40-4.50 (m, 1H), 3.90-4.10 (m, 2H), 3.60-3.70 (m, 2H), 2.90-2.98 (m, 3H), 2.00-2.10 (m, 1H), 1.80-1.93 (m, 2H), 1.65-1.80 (m, 5H), 1.33 (s, 3H). | 392.1 |
| 48 | 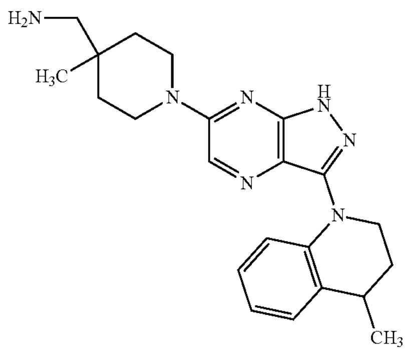 [SMILES: CC1CCN(c2n[nH]c3nc(N4CCC(C)(CN)CC4)cnc23)c2ccccc21] | ¹H-NMR (400 MHz, methanol-d₄) δ 8.17 (s, 1H), 7.15-7.18 (m, 1H), 6.89-6.94 (m, 1H), 6.74-6.81 (m, 2H), 4.07-4.11 (m, 2H), 3.91-3.94 (m, 1H), 3.85-3.87 (m, 1H), 3.50.3.57 (m, 2H), 3.03-3.05 (m, 1H), 2.62 (s, 2H), 2.02-2.25 (m, 1H), 1.83-1.86 (m, 1H), 1.57-1.61 (m, 2H), 1.49-1.54 (m, 2H), 1.38-1.41 (d, J = 7.2 Hz, 3H), 1.11 (s, 3H). | 392.1 |
| 49 | 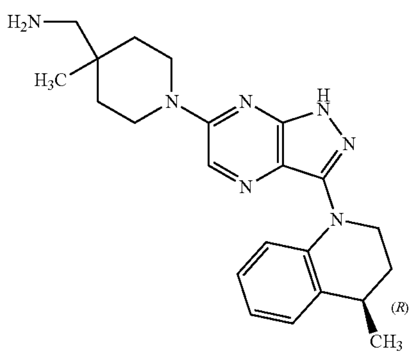 | ¹H-NMR (400 MHz, methanol-d₄) δ 8.16 (s, 1H), 7.15-7.18 (m, 1H), 6.89-6.93 (m, 1H), 6.74-6.81 (m, 2H), 4.06-4.10 (m, 2H), 3.84-3.94 (m, 1H), 3.85-3.87 (m, 1H), 3.50-3.57 (m, 2H), 3.03-3.07 (m, 1H), 2.60 (s, 2H), 2.16-2.24 (m, 1H), 1.80-1.87 (m, 1H), 1.57-1.64 (m, 2H), 1.48-1.54 (m, 2H), 1.38-1.41 (d, J = 7.2 Hz, 3H), 1.11 (s, 3H). | 392.1 |
| 50 | 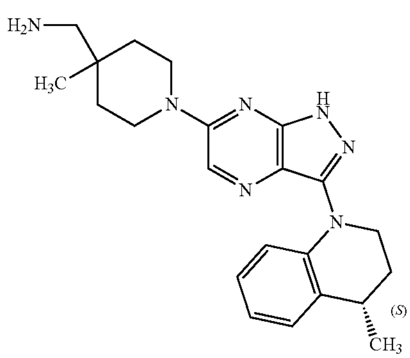 | ¹H-NMR (400 MHz, methanol-d₄) δ 8.16 (s, 1H), 7.15-7.18 (m, 1H), 6.89-6.93 (m, 1H), 6.74-6.81 (m, 2H), 4.06-4.10 (m, 2H), 3.84-3.94 (m, 1H), 3.85-3.87 (m, 1H), 3.50-3.57 (m, 2H), 3.03-3.07 (m, 1H), 2.60 (s, 2H), 2.16-2.24 (m, 1H), 1.80-1.87(m, 1H), 1.57-1.64(m, 2H), 1.48-1.54 (m, 2H), 1.38-1.41 (d, J = 7.2 Hz, 3H), 1.11 (s, 3H). | 392.1 |

TABLE 1-continued

| Cmpd. No. | Structure | ¹H-NMR | Mass Spec. (M + H)⁺ |
|---|---|---|---|
| 51 | 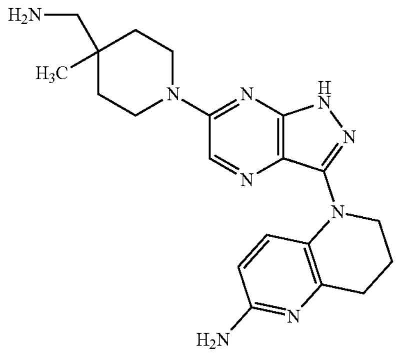 [SMILES: CC1(CN)CCN(c2cnc3c(N4CCCc5nc(N)ccc54)n[nH]c3n2)CC1] | ¹H-NMR (400 MHz, DMSO-d₆) δ 12.11 (s, 1H), 8.22(d, J = 2.4 Hz, 1H), 7.44 (d, J = 8.8 Hz, 1H), 6.81 (s, 1H), 6-19-6.22 (d, J = 8.8 Hz, 1H), 5.42 (s, 2H), 3.89-3.99 (m, 4H), 2.90-2.92 (m, 2H), 2.67-2.70 (m, 2H), 1.87-1.90 (m, 2H), 1.44-1.48 (m, 2H), 1.28-1.31 (m, 2H), 0.94 (s, 3H). | 394.0 |
| 52 | 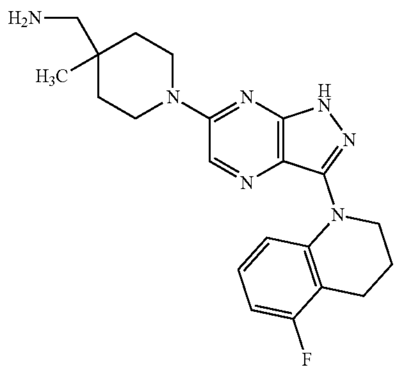 [SMILES: CC1(CN)CCN(c2cnc3c(N4CCCc5c(F)cccc54)n[nH]c3n2)CC1] | ¹H-NMR (400 MHz, DMSO-d₆) δ 8.29 (s, 1H), 6.94-6.87 (m, 1H), 6.81-6.78 (m, 1H), 6.55-6.50 (m, 1H), 3.93-3.84 (m, 4H), 3.46-3.41 (m, 2H), 2.79-2.75 (m, 2H), 2.42 (s, 2H), 2.01-1.98 (m, 2H), 1.49-1.29 (m, 2H), 0.94 (s, 3H). | 396.1 |
| 53 | 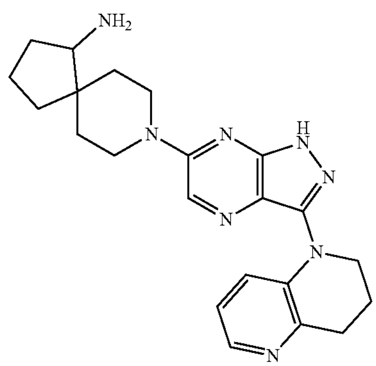 [SMILES: NC1CCCC12CCN(c1cnc3c(N4CCCc5ncccc54)n[nH]c3n1)CC2] | ¹H-NMR (400 MHz, DMSO-d₆) δ 12.54 (br d, J = 2.20 Hz, 1H), 8.28 (s, 1H), 7.88 (dd, J = 4.52, 1.34 Hz, 1H), 7.47 (dd, J = 8.42, 1.34 Hz, 1H), 6.95 (dd, J = 8.30, 4.64 Hz, 1H), 4.17-4.29 (m, 2H), 3.88-3.98 (m, 2H), 3.08-3.22 (m, 2H), 2.92 (t, J = 6.59 Hz, 2H), 2.68 (t, J = 7.32 Hz, 1H), 2.01-2.10 (m, 2H), 1.75-1.89 (m, 2H), 1.46-1.66 (m, 5H), 1.16-1.42 (m, 5H). | 405 |
| 54 | 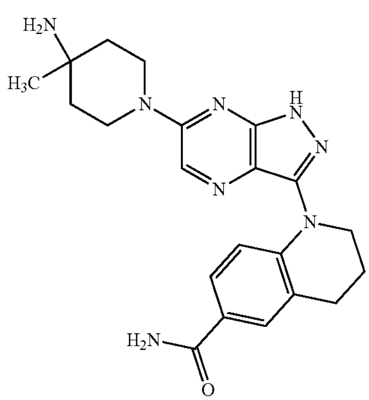 [SMILES: CC1(N)CCN(c2cnc3c(N4CCCc5cc(C(N)=O)ccc54)n[nH]c3n2)CC1] | ¹H-NMR (400 MHz, DMSO-d₆) δ 8.35 (s, 1H), 8.18 (br, 3H), 7.62-7.61 (m, 1H), 7.46-7.42 (m, 1H), 6.92-6.89 (d, J = 8.8 Hz, 1H), 4.17-4.12 (m, 2H), 3.51-3.44 (m, 2H), 2.88-2.83 (m, 2H), 2.55-2.52 (m, 1H), 2.05-2.00 (m, 2H), 1.82-1.74 (m, 4H), 1.40 (s, 3H). | 407.2 |

TABLE 1-continued

| Cmpd. No. | Structure | ¹H-NMR | Mass Spec. (M + H)⁺ |
|---|---|---|---|
| 55 | 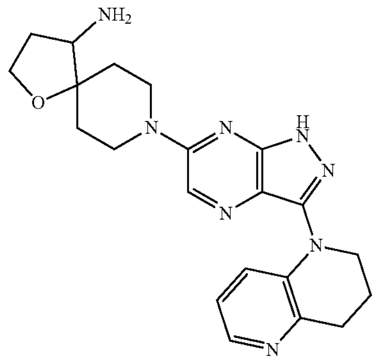 [SMILES: NC1CCOC12CCN(c1cnc3c(N4CCCc5ncccc54)n[nH]c3n1)CC2] | ¹H-NMR (400 MHz, DMSO-d₆) δ 12.56 (br s, 1H), 8.30 (s, 1H), 7.88 (dd, J = 4.64, 1.22 Hz, 1H), 7.47 (dd, J = 8.54, 1.22 Hz, 1H), 6.95 (dd, J = 8.30, 4.64 Hz, 1H), 4.19-4.32 (m, 2H), 3.90-3.97 (m, 2H), 3.80 (td, J = 8.42, 5.13 Hz, 1H), 3.68 (q, J = 7.98 Hz, 1H), 3.18-3.28 (m, 2H), 2.89-2.97 (m, 3H), 2.01-2.19 (m, 3H), 1.57-1.73 (m, 3H), 1.47-1.55 (m, 1H), 1.40 (br d, J = 13.43 Hz, 1H). | 407 |
| 56 | 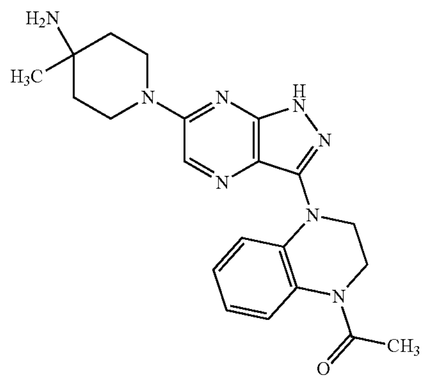 [SMILES: CC(=O)N1CCN(c2n[nH]c3nc(N4CCC(C)(N)CC4)cnc23)c2ccccc21] | ¹H-NMR (400 MHz, DMSO-d₆) δ 8.39 (br, 2H), 8.31 (s, 1H), 7.35-7.25 (m, 1H), 7.18-7.13 (m, 1H), 6.95-6.90 (m, 1H), 6.80-6.70 (m, 1H), 4.12-4.05 (m, 2H), 4.00-3.88 (m, 4H), 3.50-3.42 (m, 2H), 2.18 (s, 3H), 1.85-1.68 (m, 4H), 1.36 (s, 3H). | 407.1 |
| 57 | 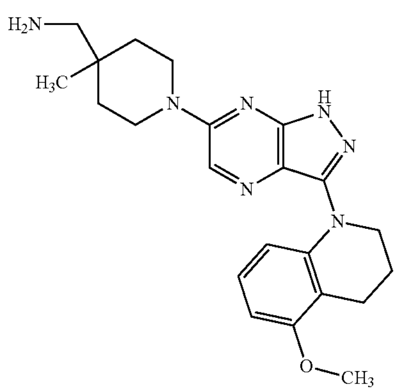 [SMILES: COc1cccc2c1CCCN2c1n[nH]c2nc(N3CCC(C)(CN)CC3)cnc12] | ¹H-NMR (400 MHz, DMSO-d₆) δ 8.30 (s, 1H), 7.87 (br, 3H), 6.89-6.84 (m, 1H), 6.66 (d, J = 8.4 Hz, 1H), 6.41 (d, J = 8.0 Hz, 1H), 4.05-3.96 (m, 2H), 3.76 (s, 3H), 3.51-3.44 (m, 2H), 2.79-2.77 (m, 2H), 2.69-2.65 (m, 2H), 2.53 (s, 2H), 1.96-1.92 (m, 2H), 1.60-1.42 (m, 4H), 1.09 (s, 3H). | 408.1 |
| 58 | 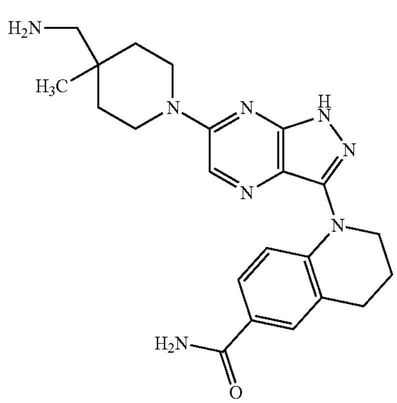 [SMILES: CC1(CN)CCN(c2cnc3c(N4CCCc5cc(C(N)=O)ccc54)n[nH]c3n2)CC1] | ¹H-NMR (400 MHz, DMSO-d₆) δ 8.32 (br, 1H), 8.10 (br, 3H), 7.61 (s, 1H), 7.44-7.42 (m, 1H), 6.92-6.90 (m, 1H), 3.96-3.88 (m, 4H), 3.51-3.46 (m, 2H), 2.90-2.72 (m, 4H), 2.12-1.90 (m, 2H), 1.65-1.40 (m, 4H), 1.09 (s, 3H). | 421.3 |

TABLE 1-continued

| Cmpd. No. | Structure | ¹H-NMR | Mass Spec. (M + H)⁺ |
|---|---|---|---|
| 59 | 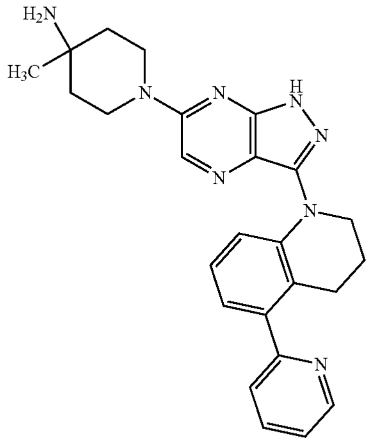 [SMILES: CC1(N)CCN(c2cnc3c(N4CCCc5c(-c6ccccn6)cccc54)n[nH]c3n2)CC1] | ¹H-NMR (400 MHz, DMSO-d$_6$) δ 12.50 (br s, 1H), 8.65 (br d, J = 4.2 Hz, 1H), 8.25 (s, 1H), 7.86 (td, J = 7.7, 1.7 Hz, 1H), 7.48 (d, J = 7.8 Hz, 1H), 7.32-7.39 (m, 1H), 6.93-7.04 (m, 2H), 6.71-6.79 (m, 1H), 3.74-3.92 (m, 4H), 3.61 (ddd, J = 13.2, 9.0, 3.9 Hz, 2H), 2.73 (t, J = 6.3 Hz, 2H), 1.89 (dt, J = 11.9, 6.1 Hz, 2H), 1.33-1.55 (m, 4H), 1.08 (s, 3H). | 441.5 |
| 60 | 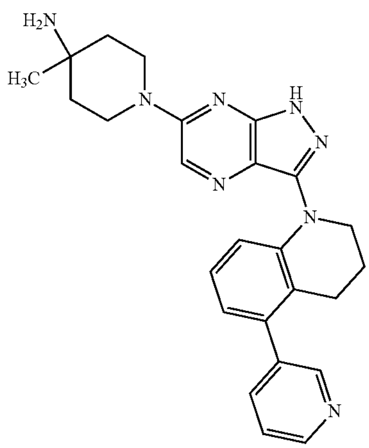 [SMILES: CC1(N)CCN(c2cnc3c(N4CCCc5c(-c6cccnc6)cccc54)n[nH]c3n2)CC1] | ¹H-NMR (400 MHz, DMSO-d$_6$) δ 12.54 (br s, 1H), 8.58 (d, J = 2.9 Hz, 2H), 8.28 (s, 1H), 7.81 (dt, J = 7.8, 1.8 Hz, 1H), 7.48 (dd, J = 7.6, 4.9 Hz, 1H), 6.94-7.08 (m, 2H), 6.60-6.69 (m, 1H), 3.75-3.93 (m, 4H), 3.62 (ddd, J = 13.2, 8.9, 4.0 Hz, 2H), 2.64 (t, J = 6.3 Hz, 2H), 1.84-2.00 (m, 2H), 1.38-1.71 (m, 6H), 1.09 (s, 3H). | 441.4 |
| 61 | 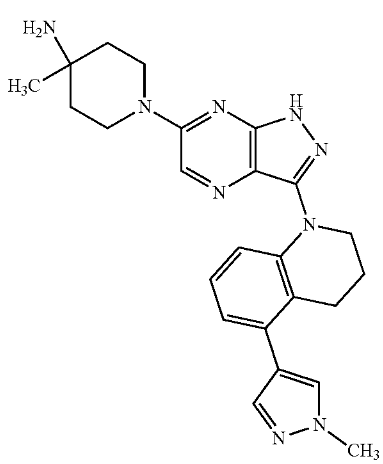 [SMILES: Cn1cc(-c2cccc3c2CCCN3c2n[nH]c3nc(N4CCC(C)(N)CC4)cnc23)cn1] | ¹H-NMR (400 MHz, DMSO-d$_6$) δ 12.48 (br s, 1H), 8.25 (s, 1H), 7.87 (s, 1H), 7.58 (s, 1H), 6.81-6.95 (m, 2H), 6.74 (dd, J = 7.1, 1.2 Hz, 1H), 3.78-3.92 (m, 6H), 3.61 (ddd, J = 13.2, 9.0, 3.9 Hz, 2H), 2.82 (t, J = 6.3 Hz, 2H), 1.93 (dt, J = 11.8, 6.2 Hz, 2H), 1.38-1.63 (m, 6H), 1.08 (s, 3H). | 444.4 |

TABLE 1-continued

| Cmpd. No. | Structure | ¹H-NMR | Mass Spec. (M + H)⁺ |
|---|---|---|---|
| 62 | 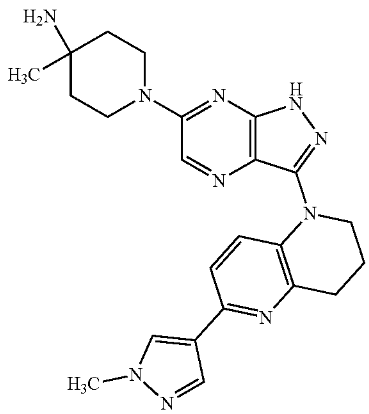 [SMILES: Cn1cc(-c2ccc3c(n2)CCCN3c2n[nH]c3nc(N4CCC(C)(N)CC4)cnc23)cn1] | ¹H-NMR (400 MHz, DMSO-d₆) δ 12.51 (br s, 1H), 8.28 (s, 1H), 8.09 (s, 1H), 7.83 (s, 1H), 7.55 (d, J = 8.5 Hz, 1H), 7.24 (d, J = 8.5 Hz, 1H), 3.94-4.02 (m, 2H), 3.86 (s, 3H), 3.78-3.85 (m, 2H), 3.66 (ddd, J = 13.1, 8.4, 4.2 Hz, 2H), 2.94 (t, J = 6.5 Hz, 2H), 2.07 (quin, J = 6.0 Hz, 2H), 1.36-1.59 (m, 4H), 1.12 (s, 3H). | 445.5 |
| 63 | 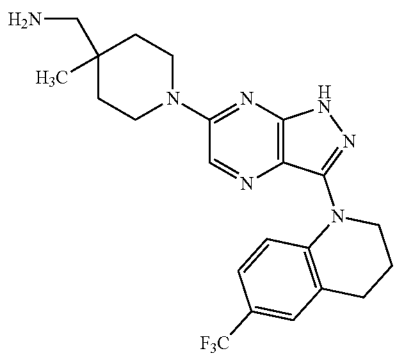 [SMILES: CC1(CN)CCN(c2cnc3c(N4CCCc5cc(C(F)(F)F)ccc54)n[nH]c3n2)CC1] | ¹H-NMR (400 MHz, DMSO-d₆) δ 8.33 (s, 1H), 7.98 (s, 3H), 7.36 (s, 1H), 7.19~7.22 (m, 1H), 6.98~7.01 (m, 1H), 3.87~4.00 (m, 4H), 3.45~3.51 (m, 2H), 2.87~2.91 (m, 2H), 2.76~2.79 (m, 2H), 2.00~2.05 (m, 2H), 1.54~1.59 (m, 2H), 1.44~1.48 (m, 2H), 1.09 (s, 3H). | 446.2 |
| 64 | 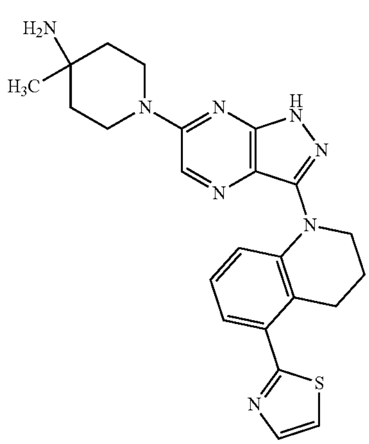 [SMILES: CC1(N)CCN(c2cnc3c(N4CCCc5c(-c6nccs6)cccc54)n[nH]c3n2)CC1] | ¹H-NMR (400 MHz, DMSO-d₆) δ 12.56 (br s, 1H), 8.27 (s, 1H), 7.97 (d, J = 3.2 Hz, 1H), 7.84 (d, J = 3.4 Hz, 1H), 6.98-7.12 (m, 3H), 3.78-3.98 (m, 4H), 3.63 (ddd, J = 13.2, 8.9, 4.0 Hz, 2H), 3.02 (t, J = 6.3 Hz, 2H), 1.96 (dt, J = 11.8, 6.2 Hz, 2H), 1.37-1.56 (m, 4H), 1.09 (s, 3H). | 447.4 |

TABLE 1-continued

| Cmpd. No. | Structure | ¹H-NMR | Mass Spec. (M + H)⁺ |
|---|---|---|---|
| 65 | 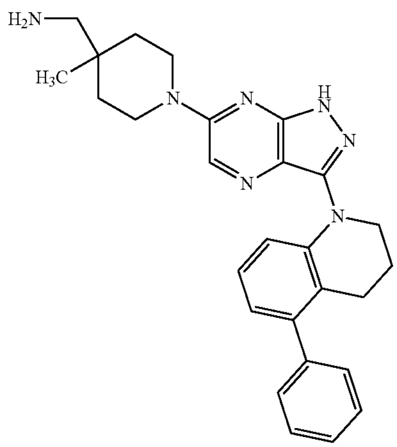 [SMILES: CC1(CN)CCN(c2cnc3c(N4CCCc5c(-c6ccccc6)cccc54)n[nH]c3n2)CC1] | ¹H-NMR (400 MHz, CDCl₃) δ 8.12 (s, 1H), 7.43-7.33 (m, 5H), 7.20-7.18 (d, J = 8.8 Hz, 1H), 7.09-7.05 (m, 1H), 6.80-6.78 (d, J = 7.2 Hz, 1H), 4.01-3.97 (m, 4H), 3.49-3.43 (m, 2H), 2.74-2.70 (m, 2H), 2.61 (s, 2H), 2.0-1.96 (m, 2H), 1.73-1.47 (m, 4H), 1.06 (s, 3H). | 454.2 |
| 66 | 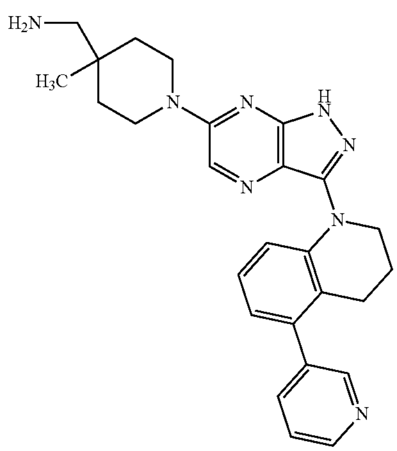 [SMILES: CC1(CN)CCN(c2cnc3c(N4CCCc5c(-c6cccnc6)cccc54)n[nH]c3n2)CC1] | ¹H-NMR (400 MHz, DMSO-d₆) δ 8.53-8.60 (m, 2H), 8.29 (s, 1H), 7.80 (td, J = 1.95, 7.81 Hz, 1H), 7.46 (dd, J = 5.00, 7.69 Hz, 1H), 6.97-7.01 (m, 2H), 6.62-6.67 (m, 1H), 3.92-4.01 (m, 2H), 3.83-3.88 (m, 2H), 3.46 (t, J = 10.01 Hz, 2H), 2.72 (s, 2H), 2.63 (t, J = 6.35 Hz, 2H), 1.90 (td, J = 6.20, 11.78 Hz, 2H), 1.49-1.58 (m, 2H), 1.37-1.45 (m, 2H), 1.05 (s, 3H) | 455.4 |
| 67 | 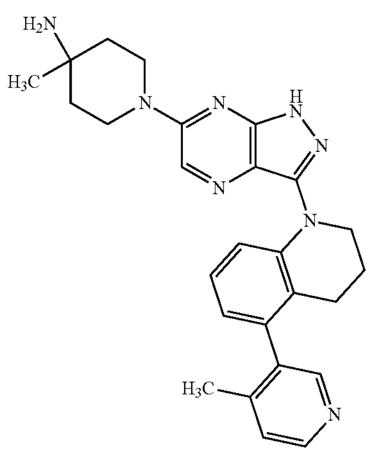 [SMILES: Cc1ccncc1-c1cccc2c1CCCN2c1n[nH]c2nc(N3CCC(C)(N)CC3)cnc12] | ¹H-NMR (400 MHz, DMSO-d₆) δ 12.54 (br s, 1H), 8.44 (d, J = 4.9 Hz, 1H), 8.29 (d, J = 5.6 Hz, 2H), 7.34 (d, J = 4.9 Hz, 1H), 6.93-7.07 (m, 2H), 6.52 (dd, J = 6.7, 1.6 Hz, 1H), 3.85 (t, J = 5.0 Hz, 4H), 3.63 (ddd, J = 13.1, 9.0, 4.0 Hz, 2H), 2.17-2.46 (m, 2H), 2.10 (s, 3H), 1.83-1.97 (m, 2H), 1.66 (br s, 2H), 1.38-1.54 (m, 4H), 1.09 (s, 3H). | 455.5 |

TABLE 1-continued

| Cmpd. No. | Structure | ¹H-NMR | Mass Spec. (M + H)⁺ |
|---|---|---|---|
| 68 | 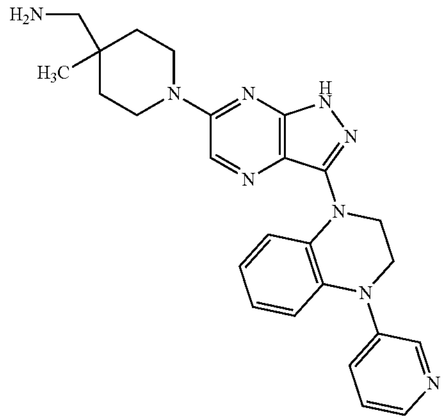 [SMILES: CC1(CN)CCN(c2cnc3c(N4CCN(c5cccnc5)c5ccccc54)n[nH]c3n2)CC1] | ¹H-NMR (400 MHz, DMSO-d₆) δ 8.53-8.52 (d, J = 2.0 Hz, 1H), 8.29 (s, 1H), 8.26-8.24 (m, 1H), 7.68-7.65 (d, J = 7.2 Hz, 1H), 7.41-7.35 (m, 1H), 7.31-7.25 (m, 1H), 6.73-6.65 (m, 2H), 6.82-6.77 (m, 1H), 4.10-4.05 (m, 2H), 3.95-3.75 (m, 4H), 2.40 (s, 1H), 1.50-1.40 (m, 2H), 1.35-1.20 (m, 4H), 0.95-0.92 (m, 3H). | 456.2 |
| 69 | 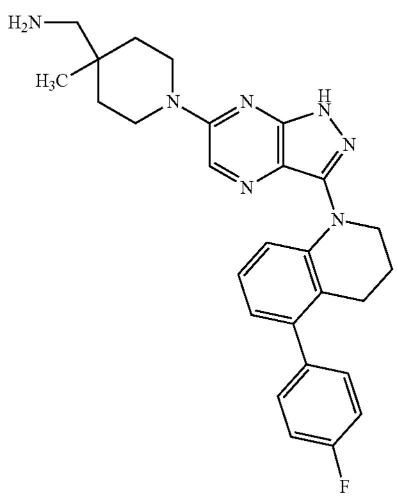 [SMILES: CC1(CN)CCN(c2cnc3c(N4CCCc5c(-c6ccc(F)cc6)cccc54)n[nH]c3n2)CC1] | ¹H-NMR (400 MHz, DMSO-d₆) δ 8.30 (s, 1H), 7.90 (br, 3H), 7.42-7.37 (m, 2H), 7.29-7.24 (m, 2H), 6.98-6.95 (m, 2H), 6.64-6.62 (m, 1H), 4.01-3.96 (m, 2H), 3.88-3.84 (m, 2H), 2.80-2.77 (m, 2H), 2.65-2.61 (m, 2H), 2.53 (s, 2H), 1.93-1.88 (m, 2H), 1.60-1.44 (m, 4H), 1.09 (s, 3H). | 472.1 |
| 70 | 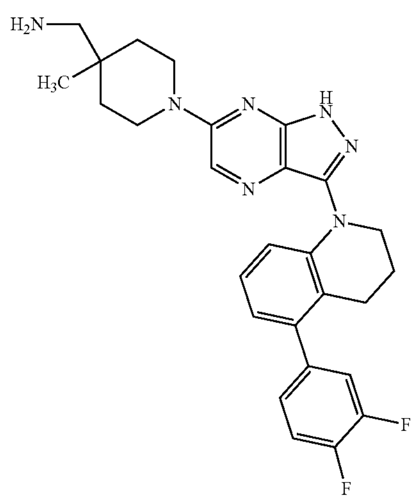 [SMILES: CC1(CN)CCN(c2cnc3c(N4CCCc5c(-c6ccc(F)c(F)c6)cccc54)n[nH]c3n2)CC1] | ¹H-NMR (400 MHz, CDCl₃) δ 8.12 (s, 1H), 7.20-7.13 (m, 3H), 7.08-7.03 (m, 2H), 6.73-6.71 (d, J = 7.2 Hz, 1H), 4.01-3.99 (m, 4H), 3.50-3.44 (m, 2H), 2.70-2.66 (m, 2H), 2.61 (s, 2H), 2.02-1.98 (m, 2H), 1.63-1.47 (m, 4H), 1.05 (s, 3H). | 490.1 |

TABLE 1-continued

| Cmpd. No. | Structure | ¹H-NMR | Mass Spec. (M + H)⁺ |
|---|---|---|---|
| 71 | 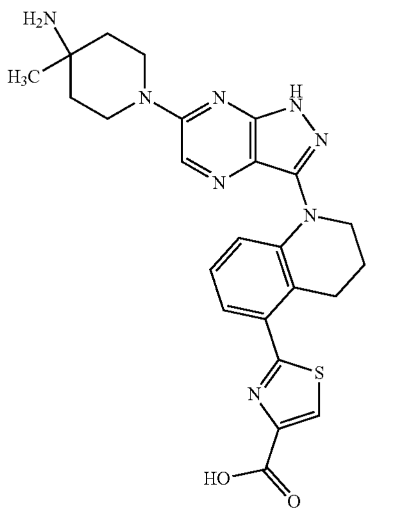 [SMILES: CC1(N)CCN(c2cnc3c(N4CCCc5c(-c6nc(C(=O)O)cs6)cccc54)n[nH]c3n2)CC1] | ND | 491.4 |
| 72 | 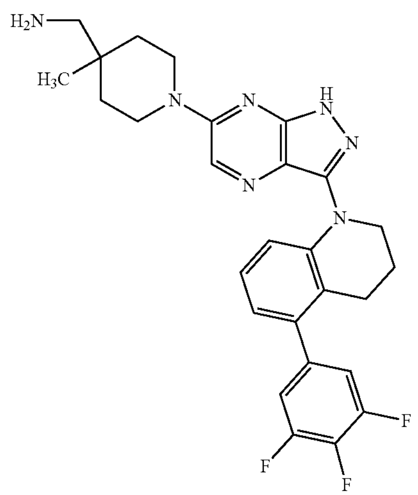 [SMILES: CC1(CN)CCN(c2cnc3c(N4CCCc5c(-c6cc(F)c(F)c(F)c6)cccc54)n[nH]c3n2)CC1] | ¹H-NMR (400 MHz, DMSO-d$_6$) δ 8.30 (s, 1H), 8.04 (br, 3H), 7.39-7.34 (m, 2H), 7.00-6.95 (m, 2H), 6.66-6.63 (m, 1H), 3.88-3.84 (m, 2H), 3.51-3.45 (m, 2H), 2.78-2.76 (m, 2H), 2.68-2.64 (m, 2H), 2.52 (s, 2H), 1.93-1.89 (m, 2H), 1.60-1.44 (m, 4H), 1.10 (s, 3H). | 508.2 |
| 73 | 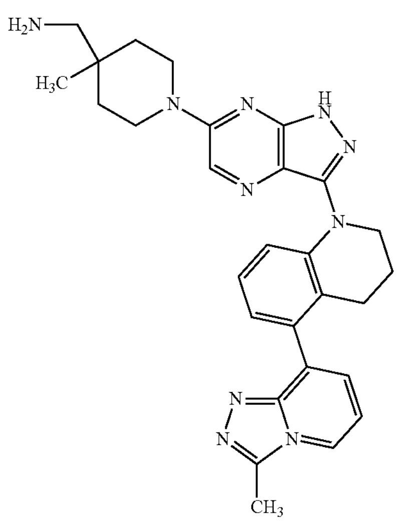 | ¹H-NMR (400 MHz, DMSO-d$_6$) δ 12.48-12.62 (m, 1H), 8.36 (d, J = 6.84 Hz, 1H), 8.26-8.30 (m, 1H), 7.21 (d, J = 6.10 Hz, 1H), 6.97-7.08 (m, 3H), 6.72 (br dd, J = 1.10, 7.20 Hz, 1H), 3.91-3.99 (m, 2H), 3.83-3.89 (m, 2H), 3.42-3.50 (m, 2H), 2.71 (s, 3H), 2.55 (m, 2H), 1.86 (td, J = 6.20, 11.78 Hz, 2H), 1.47-1.56 (m, 2H), 1.36 (br d, J = 13.92 Hz, 2H), 0.99 (s, 3H) | 509.5 |

TABLE 1-continued

| Cmpd. No. | Structure | ¹H-NMR | Mass Spec. (M + H)⁺ |
|---|---|---|---|
| 74 | 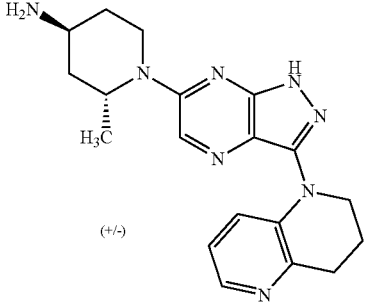 [SMILES: C[C@@H]1C[C@@H](N)CCN1c1cnc2c(N3CCCc4ncccc43)n[nH]c2n1] (+/-) | ¹H-NMR (400 MHz, DMSO_d₆) δ 8.31 (s, 1H), 7.96-7.94 (m, 1H), 7.55-7.52 (m, 1H), 7.03-6.99 (m, 1H), 4.96-4.88 (m, 1H), 4.40-4.36 (m, 1H), 4.02-3.98 (m, 2H), 3.12-2.97 (m, 4H), 2.15-2.08 (m, 2H), 1.94-1.79 (m, 2H), 1.46-1.43 (m, 1H), 1.28-1.21 (m, 4H) | 365.1 |
| 75 | 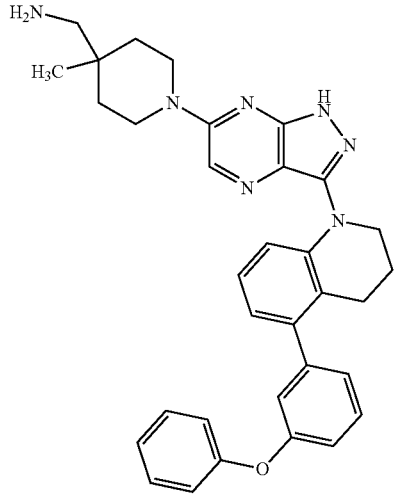 [SMILES: CC1(CN)CCN(c2cnc3c(N4CCCc5c(-c6cccc(Oc7ccccc7)c6)cccc54)n[nH]c3n2)CC1] | ¹H-NMR (400 MHz, DMSO-d₆) δ 12.51 (br s, 1H), 8.25 (s, 1H), 7.37-7.47 (m, 3H), 7.05-7.18 (m, 4H), 6.98 (dd, J = 1.71, 8.06 Hz, 1H), 6.91-6.95 (m, 2H), 6.58-6.64 (m, 1H), 3.93 (td, J = 4.58, 8.91 Hz, 2H), 3.80-3.86 (m, 2H), 3.40-3.49 (m, 2H), 2.63 (br t, J = 6.35 Hz, 2H), 2.53-2.57 (m, 2H), 1.88 (td, J = 6.20, 11.78 Hz, 2H), 1.46-1.55 (m, 2H), 1.32-1.39 (m, 2H), 0.99 (s, 3H) | 546.6 |
| 76 | 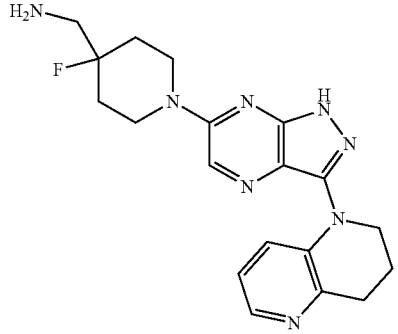 [SMILES: NCC1(F)CCN(c2cnc3c(N4CCCc5ncccc54)n[nH]c3n2)CC1] | ¹H-NMR (400 MHz, DMSO-d₆) δ 12.62 (br d, J = 4.88 Hz, 1H), 8.34 (s, 1H), 8.23 (s, 1H), 7.89 (dd, J = 1.34, 4.52 Hz, 1H), 7.47 (dd, J = 1.34, 8.42 Hz, 1H), 6.95 (dd, J = 4.52, 8.42 Hz, 1H), 4.28 (br d, J = 13.18 Hz, 2H), 3.90-3.97 (m, 2H), 3.22-3.32 (m, 4H), 2.93 (t, J = 6.47 Hz, 2H), 2.76 (br d, J = 19.78 Hz, 2H), 2.06 (td, J = 6.20, 11.78 Hz, 2H), 1.63-1.93 (m, 5H) | 383.3 |
| 77 | 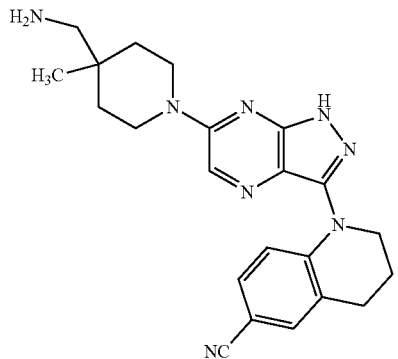 [SMILES: CC1(CN)CCN(c2cnc3c(N4CCCc5cc(C#N)ccc54)n[nH]c3n2)CC1] | ¹H-NMR (400 MHz, DMSO-d₆) δ 8.33 (s, 1H), 8.29 (s, 1H), 7.44 (d, J = 1.95 Hz, 1H), 7.27 (dd, J = 1.95, 8.79 Hz, 1H), 6.90 (d, J = 8.54 Hz, 1H), 3.95 (td, J = 4.55, 13.61 Hz, 2H), 3.85-3.91 (m, 2H), 3.46 (ddd, J = 2.93, 9.77, 13.18 Hz, 2H), 2.84 (br t, J = 6.23 Hz, 2H), 2.63 (s, 2H), 2.00 (td, J = 6.01, 11.66 Hz, 2H), 1.48-1.57 (m, 2H), 1.35-1.43 (m, 2H), 1.02 (s, 2H) | 403.4 |

TABLE 1-continued

| Cmpd. No. | Structure | ¹H-NMR | Mass Spec. (M + H)⁺ |
|---|---|---|---|
| 78 | 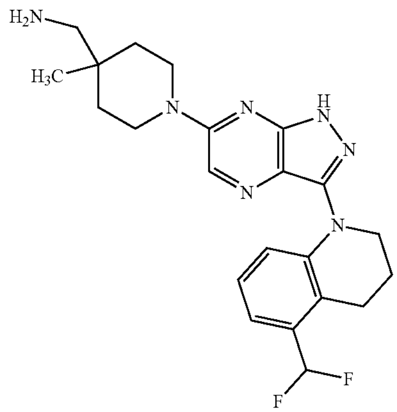 [SMILES: CC1(CN)CCN(c2cnc3c(N4CCCc5c(C(F)F)cccc54)n[nH]c3n2)CC1] | ¹H-NMR (400 MHz, DMSO-d₆) δ 0.90-0.99 (m, 1H), 0.95 (s, 2H), 1.27-1.35 (m, 2H), 1.43-1.52 (m, 2H), 3.00 (br t, J = 5.49 Hz, 2H), 3.38-3.46 (m, 2H), 3.83-3.99 (m, 4H), 4.77 (s, 2H), 6.96-7.33 (m, 5H), 7.38 (br dd, J = 12.82, 7.45 Hz, 2H), 8.20 (s, 1H), 11.90-12.00 (m, 1H) | 428.3 |
| 79 | 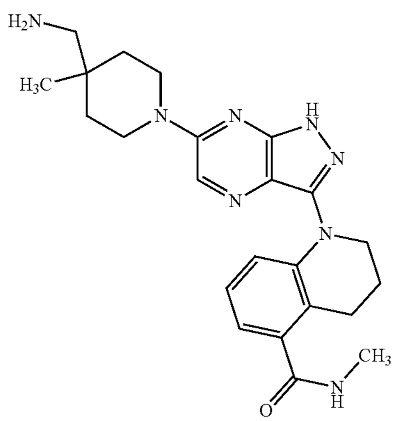 [SMILES: CNC(=O)c1cccc2c1CCCN2c1n[nH]c2nc(N3CCC(C)(CN)CC3)cnc12] | ¹H-NMR (400 MHz, DMSO-d₆) δ 8.35 (s, 1H), 7.37-7.35 (d, J = 8.0 Hz, 1H), 7.21-7.25 (m, 1H), 7.14-7.12 (d, J = 8.0 Hz, 1H), 4.25-4.16 (m, 2H), 4.14-4.12 (m, 2H), 3.67-3.60 (m, 2H), 2.95 (s, 4H), 2.93 (s, 3H), 2.12-2.02 (m, 2H), 1.70-1.62 (m, 4H), 1.24 (s, 3H) | 435.1 |
| 80 | 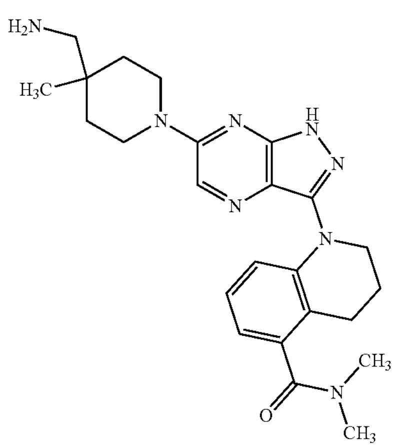 [SMILES: CN(C)C(=O)c1cccc2c1CCCN2c1n[nH]c2nc(N3CCC(C)(CN)CC3)cnc12] | ¹H-NMR (400 MHz, DMSO-d₆) δ 8.39 (s, 1H), 7.35 (d, J = 8.0 Hz, 1H), 7.25-7.29 (m, 1H), 7.00 (d, J = 8.0 Hz, 1H), 4.18-4.26 (m, 4H), 3.63-3.90 (m, 2H), 3.16 (s, 3H), 2.95 (s, 5H), 2.60-2.90 (m, 2H), 2.00-2.16 (m, 2H), 1.60-1.71 (m, 4H), 1.24 (s, 3H) | 449.2 |

TABLE 1-continued

| Cmpd. No. | Structure | ¹H-NMR | Mass Spec. (M + H)⁺ |
|---|---|---|---|
| 81 | 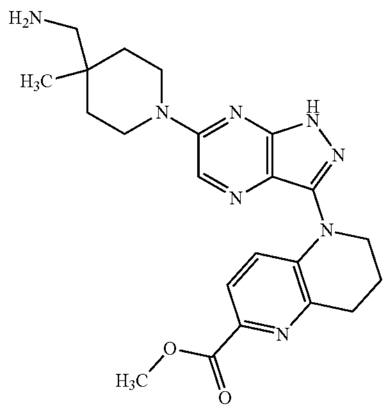 [SMILES: COC(=O)c1ccc2c(n1)CCCN2c1n[nH]c2nc(N3CCC(C)(CN)CC3)cnc12] | ¹H-NMR (400 MHz, DMSO-d₆) δ 12.68-13.00 (m, 3H), 8.32 (s, 1H), 7.66 (d, J = 8.79 Hz, 1H), 7.41 (d, J = 8.79 Hz, 1H), 3.88-4.01 (m, 4H), 3.79 (s, 2H), 3.42-3.50 (m, 2H), 2.99 (br t, J = 6.35 Hz, 2H), 2.11 (td, J = 6.07, 11.54 Hz, 2H), 1.46-1.54 (m, 2H), 1.30-1.37 (m, 2H), 0.97 (s, 2H) | 437.1 |
| 82 | 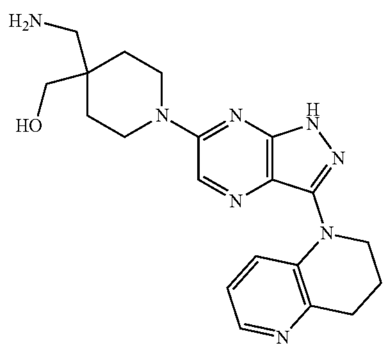 | ¹H-NMR (400 MHz, methanol-d₄) δ 8.32 (s, 1H), 8.07-8.03 (m, 2H), 7.60-7.56 (m, 1H), 4.10-4.08 (t, J = 5.6 Hz, 2H), 4.00-3.94 (m, 2H), 3.80-3.73 (m, 4H), 3.29 (t, J = 6.4 Hz, 2H), 3.12 (s, 2H), 2.33-2.30 (m, 2H), 1.77-1.69 (m, 4H) | 395.0 |
| 83 | 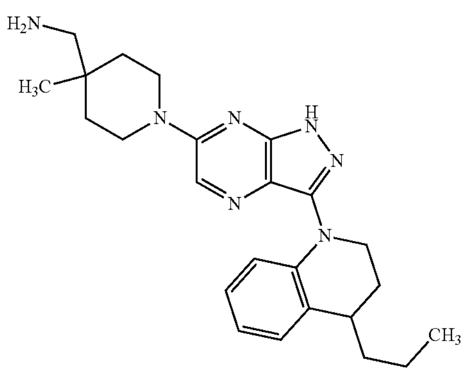 [SMILES: CCCC1CCN(c2n[nH]c3nc(N4CCC(C)(CN)CC4)cnc23)c2ccccc21] | ¹H-NMR (400 MHz, DMSO-d₆) δ 12.23-12.72 (br, 1H), 8.25 (s, 1H), 7.06 (d, J = 7.57 Hz, 1H), 6.97 (dd, J = 0.73, 8.30 Hz, 1H), 6.84-6.92 (m, 1H), 6.69 (dt, J = 1.10, 7.26 Hz, 1H), 3.86-3.98 (m, 3H), 3.77-3.85 (m, 1H), 3.44 (ddd, J = 3.05, 9.89, 13.18 Hz, 2H), 2.75-2.84 (m, 1H), 2.54 (s, 2H), 1.94-2.05 (m, 1H), 1.82-1.91 (m, 1H), 1.60-1.69 (m, 1H), 1.45-1.58 (m, 3H), 1.31-1.39 (m, 1H), 0.99 (s, 2H), 0.93 (t, J = 7.32 Hz, 3H) | 420.1 |
| 84 | 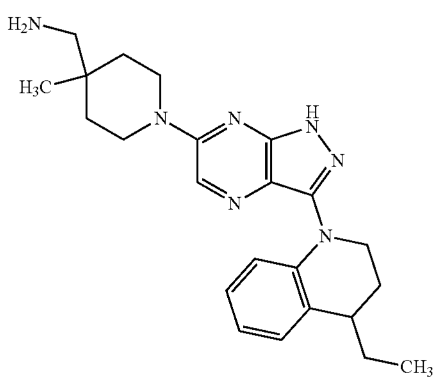 [SMILES: CCC1CCN(c2n[nH]c3nc(N4CCC(C)(CN)CC4)cnc23)c2ccccc21] | ¹H-NMR (400 MHz, DMSO-d₆) δ 12.35-12.61 (m, 1H), 8.25 (s, 1H), 7.08 (d, J = 7.32 Hz, 1H), 6.94-7.00 (m, 1H), 6.85-6.92 (m, 1H), 6.64-6.73 (m, 1H), 3.77-3.97 (m, 4H), 3.44 (ddd, J = 3.17, 9.95, 13.24 Hz, 3H), 2.65-2.74 (m, 1H), 2.53 (s, 2H), 1.94-2.05 (m, 1H), 1.83-1.93 (m, 1H), 1.74 (tt, J = 7.23, 13.40 Hz, 1H), 1.45-1.62 (m, 2H), 1.45-1.65 (m, 1H), 1.30-1.39 (m, 2H), 0.90-1.01 (m, 5H) | 406.2 |

TABLE 1-continued

| Cmpd. No. | Structure | ¹H-NMR | Mass Spec. (M + H)⁺ |
|---|---|---|---|
| 85 | 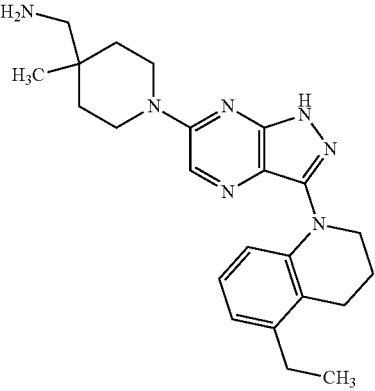 [SMILES: CCc1cccc2c1CCCN2c1n[nH]c2nc(N3CCC(C)(CN)CC3)cnc12] | ¹H-NMR (400 MHz, DMSO-d₆) δ 12.32-12.56 (m, 1H), 8.17-8.28 (m, 1H), 6.75-6.88 (m, 2H), 6.60 (dd, J = 1.71, 6.84 Hz, 1H), 3.92 (td, J = 4.55, 13.61 Hz, 2H), 3.77-3.85 (m, 2H), 3.44 (ddd, J = 3.17, 9.89, 13.31 Hz, 3H), 2.74 (t, J = 6.59 Hz, 2H), 2.51-2.60 (m, 4H), 1.93-2.02 (m, 2H), 1.45-1.55 (m, 2H), 1.30-1.39 (m, 2H), 1.15 (t, J = 7.45 Hz, 3H), 0.98 (s, 3H) | 406.1 |
| 86 | 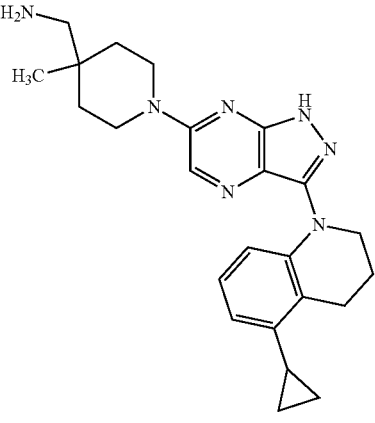 [SMILES: CC1(CN)CCN(c2cnc3c(N4CCCc5c(C6CC6)cccc54)n[nH]c3n2)CC1] | ¹H-NMR (400 MHz, DMSO-d₆) δ 12.34-12.53 (m, 1H), 8.24 (s, 1H), 6.75-6.84 (m, 2H), 6.40-6.48 (m, 1H), 3.92 (td, J = 4.61, 13.49 Hz, 3H), 3.80-3.86 (m, 3H), 3.44 (ddd, J = 3.05, 9.89, 13.18 Hz, 2H), 2.91 (t, J = 6.59 Hz, 2H), 2.54 (s, 2H), 1.97-2.04 (m, 2H), 1.85 (tt, J = 5.46, 8.33 Hz, 1H), 1.46-1.55 (m, 2H), 1.31-1.38 (m, 2H), 0.98 (s, 3H), 0.84-0.90 (m, 2H), 0.53-0.59 (m, 2H) | 418.1 |
| 87 | 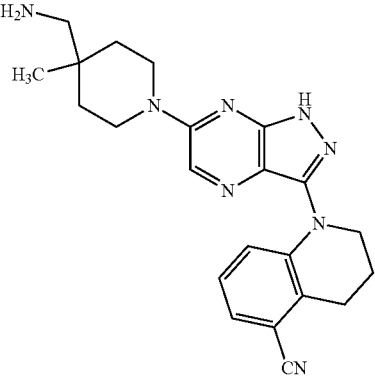 [SMILES: CC1(CN)CCN(c2cnc3c(N4CCCc5c(C#N)cccc54)n[nH]c3n2)CC1] | ¹H-NMR (400 MHz, DMSO-d₆) δ 12.48-12.82 (m, 2H), 8.29 (s, 1H), 7.25 (dd, J = 0.98, 8.30 Hz, 1H), 7.12-7.16 (m, 1H), 7.04-7.10 (m, 1H), 3.97-3.98 (m, 1H), 3.93 (td, J = 4.64, 13.67 Hz, 1H), 3.86-3.90 (m, 1H), 3.85-3.90 (m, 1H), 3.40-3.49 (m, 2H), 2.97 (t, J = 6.35 Hz, 2H), 2.55 (s, 2H), 2.04 (td, J = 6.20, 11.78 Hz, 2H), 1.45-1.55 (m, 2H), 1.31-1.39 (m, 2H), 0.99 (s, 2H) | 403.1 |
| 88 | 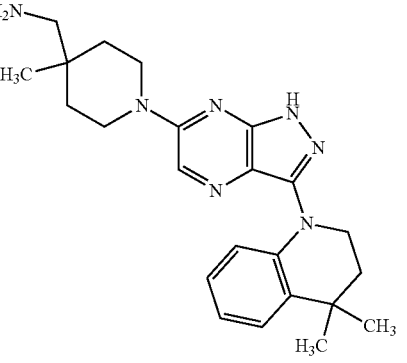 | ¹H-NMR (400 MHz, DMSO-d₆) δ 12.53 (s, 1H), 7.81 (br s, 2H), 7.23-7.29 (m, 1H), 7.13 (s, 1H), 7.01 (s, 1H), 6.90-6.95 (m, 1H), 6.86 (dt, J = 1.46, 7.69 Hz, 1H), 6.68-6.75 (m, 1H), 3.92-4.01 (m, 2H), 3.82-3.89 (m, 2H), 3.07 (dq, J = 4.88, 7.24 Hz, 1H), 2.77 (br d, J = 5.86 Hz, 2H), 1.78-1.85 (m, 2H), 1.50-1.59 (m, 2H), 1.39-1.48 (m, 2H), 1.31 (s, 4H), 1.15-1.20 (m, 1H), 1.08 (s, 2H) | 406.1 |

TABLE 1-continued

| Cmpd. No. | Structure | ¹H-NMR | Mass Spec. (M + H)+ |
|---|---|---|---|
| 89 | 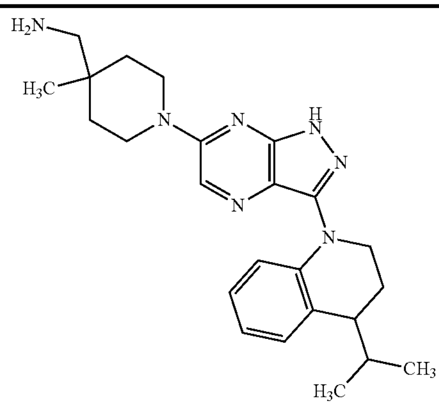 | ¹H-NMR (400 MHz, DMSO-d₆) δ 12.30-12.53 (m, 1H), 8.24 (s, 1H), 8.23 (s, 1H), 7.05 (br d, J = 7.57 Hz, 1H), 6.99 (br d, J = 7.32 Hz, 1H), 6.90-6.93 (m, 1H), 6.82-6.88 (m, 1H), 6.76 (d, J = 7.32 Hz, 1H), 6.70 (d, J = 6.84 Hz, 1H), 3.88-3.96 (m, 3H), 3.78-3.82 (m, 2H), 3.44 (ddd, J = 3.05, 9.89, 13.18 Hz, 3H), 3.11 (td, J = 6.84, 13.67 Hz, 2H), 2.79 (t, J = 6.47 Hz, 2H), 2.53-2.58 (m, 3H), 1.93-2.01 (m, 2H), 1.46-1.55 (m, 2H), 1.32-1.39 (m, 2H), 1.17 (d, J = 6.84 Hz, 5H), 0.99 (s, 3H), 0.85-0.95 (m, 2H) | 420.1 |
| 90 | 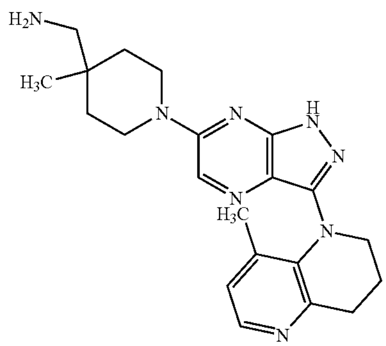 [SMILES: Cc1ccnc2c1N(c1n[nH]c3nc(N4CCC(C)(CN)CC4)cnc13)CCC2] | ¹H-NMR (400 MHz, DMSO-d₆) δ 12.10 (br s, 1H), 8.25 (s, 1H), 8.08 (d, J = 4.88 Hz, 1H), 6.97 (d, J = 4.64 Hz, 1H), 3.87-3.99 (m, 4H), 3.44 (ddd, J = 2.93, 9.83, 13.12 Hz, 2H), 2.88 (br t, J = 6.84 Hz, 2H), 2.55 (s, 2H), 1.78-1.87 (m, 5H), 1.46-1.55 (m, 2H), 1.31-1.39 (m, 2H), 0.99 (s, 3H) | 393.5 |
| 91 | 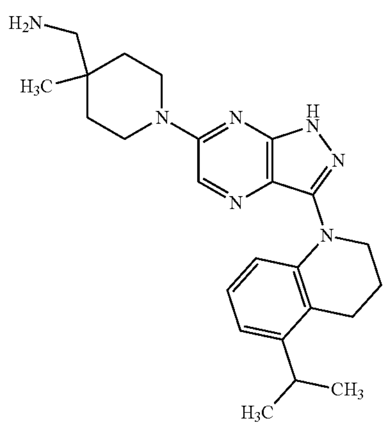 [SMILES: CC(C)c1cccc2c1CCCN2c1n[nH]c2nc(N3CCC(C)(CN)CC3)cnc12] | ¹H-NMR (400 MHz, DMSO-d₆) δ 12.30-12.51 (m, 1H), 8.24 (br s, 1H), 8.23 (s, 1H), 7.05 (br d, J = 7.57 Hz, 1H), 6.99 (br d, J = 7.57 Hz, 1H), 6.91 (br d, J = 8.54 Hz, 1H), 6.82-6.89 (m, 1H), 6.76 (d, J = 7.32 Hz, 1H), 6.70 (d, J = 6.84 Hz, 1H), 6.52 (dd, J = 2.44, 6.35 Hz, 1H), 3.89-3.96 (m, 2H), 3.78-3.83 (m, 2H), 3.39-3.48 (m, 3H), 3.11 (td, J = 6.84, 13.67 Hz, 1H), 2.79 (t, J = 6.47 Hz, 2H), 1.93-2.01 (m, 2H), 1.47-1.54 (m, 2H), 1.31-1.40 (m, 2H), 1.17 (d, J = 6.84 Hz, 4H), 0.99 (s, 2H) | 420.2 |
| 92 | 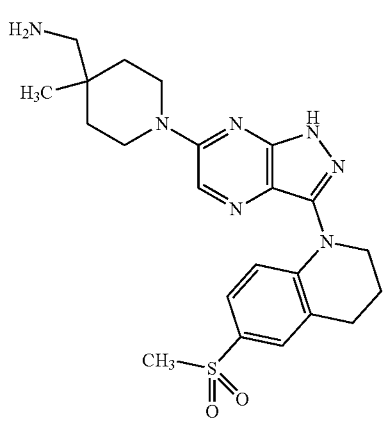 [SMILES: CC1(CN)CCN(c2cnc3c(N4CCCc5cc(S(C)(=O)=O)ccc54)n[nH]c3n2)CC1] | ¹H-NMR (400 MHz, DMSO-d₆) δ 7.54 (d, J = 1.95 Hz, 1H), 7.37 (dd, J = 2.44, 8.79 Hz, 1H), 6.94 (d, J = 9.03 Hz, 1H), 3.94 (td, J = 4.73, 13.49 Hz, 2H), 3.84-3.90 (m, 2H), 3.41-3.50 (m, 3H), 3.07 (s, 3H), 2.90 (br t, J = 6.23 Hz, 2H), 2.56 (s, 2H), 2.02 (td, J = 6.07, 11.54 Hz, 2H), 1.45-1.57 (m, 2H), 1.31-1.42 (m, 2H), 1.00 (s, 3H) | 456.1 |

TABLE 1-continued

| Cmpd. No. | Structure | ¹H-NMR | Mass Spec. (M + H)⁺ |
|---|---|---|---|
| 93 | (structure) | ¹H-NMR (400 MHz, DMSO-d₆) δ 8.32 (s, 1H) 7.53 (d, J = 1.46 Hz, 1H) 7.27 (dd, J = 8.79, 1.95 Hz, 1H) 6.88 (d, J = 8.54 Hz, 1H) 3.90-3.99 (m, 2H) 3.85-3.90 (m, 2H) 3.41-3.50 (m, 3H) 2.96-3.03 (m, 1H) 2.54 (s, 2H) 2.02-2.11 (m, 1H) 1.72-1.81 (m, 1H) 1.46-1.55 (m, 2H) 1.33-1.39 (m, 2H) 1.31 (d, J = 7.08 Hz, 3H) 0.99 (s, 2H) | 417.2 |
| 94 | (structure) | ¹H-NMR (400 MHz, DMSO-d₆) δ 8.30 (d, J = 14.65 Hz, 2H), 7.93 (dd, J = 1.34, 4.52 Hz, 1H), 7.44 (dd, J = 1.22, 8.30 Hz, 1H), 6.94 (dd, J = 4.52, 8.42 Hz, 1H), 3.87-4.00 (m, 3H), 3.45 (ddd, J = 2.93, 9.83, 13.12 Hz, 2H), 3.02 (br dd, J = 6.71, 12.82 Hz, 1H), 2.58 (s, 1H), 2.12-2.21 (m, 1H), 1.74-1.84 (m, 1H), 1.46-1.56 (m, 2H), 1.32-1.41 (m, 3H), 1.00 (s, 2H) | 393.2 |
| 95 | (structure) (+/-) | ¹H-NMR (400 MHz, CD₃OD) δ 8.25 (s, 1H), 7.98~8.05 (m, 2H), 7.54~7.58 (m, 1H), 4.79~4.90 (m, 1H), 4.17~4.34 (m, 1H), 4.16~4.17 (m, 1H), 4.06~4.09 (m, 2H), 3.53~3.54 (m, 1H), 3.26~3.33 (m, 2H), 2.30~2.35 (m, 2H), 1.97~2.00 (m, 1H), 1.87~1.91 (m, 3H), 1.46~1.48 (d, 3H) | 366.0 |
| 96 | (structure) | ¹H-NMR (400 MHz, DMSO-d₆) δ 8.38 (s, 1H), 7.29-7.35 (m, 3H), 7.21-7.25 (m, 4H), 6.99-7.03 (m, 2H), 4.31-4.35 (m, 1H), 4.24-4.27 (m, 2H), 4.07-4.14 (m, 1H), 3.60-3.68 (m, 2H), 2.95 (s, 2H), 2.38-2.45 (m, 1H), 2.24-2.31 (m, 1H), 1.62-1.72 (m, 4H), 1.24 (m, 3H) | 476.0 [M +Na]⁺ |

TABLE 1-continued

| Cmpd. No. | Structure | ¹H-NMR | Mass Spec. (M + H)⁺ |
|---|---|---|---|
| 97 | 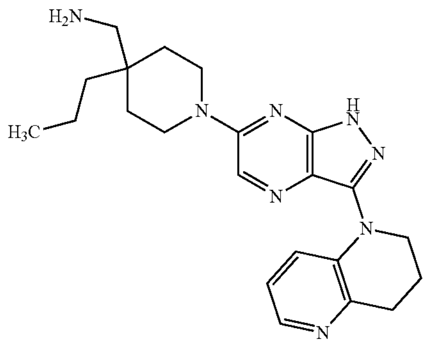 [SMILES: CCCC1(CN)CCN(c2cnc3c(N4CCCc5ncccc54)n[nH]c3n2)CC1] | ND | 407.1 |
| 98 | 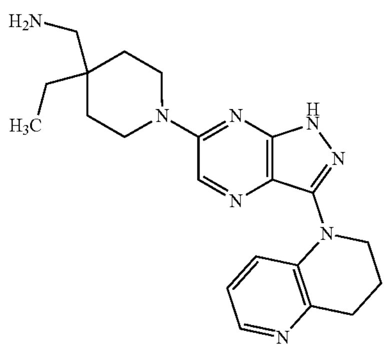 [SMILES: CCC1(CN)CCN(c2cnc3c(N4CCCc5ncccc54)n[nH]c3n2)CC1] | ¹H-NMR (400 MHz, CD₃OD) δ 8.32 (s, 1H), 8.07~8.04 (m, 2H), 7.59~7.56 (m, 1H), 4.11~3.98 (m, 2H), 3.97~3.96 (m, 2H), 3.76~3.75 (m, 2H), 3.33~3.28 (m, 4H), 2.35~2.29 (m, 2H), 1.74~1.63 (m, 6H), 0.99~0.95 (m, 3H) | 393.1 |
| 99 | 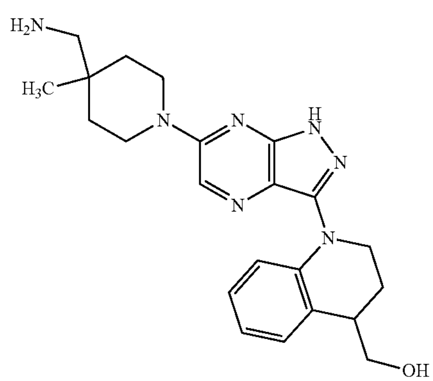 [SMILES: CC1(CN)CCN(c2cnc3c(N4CCC(CO)c5ccccc54)n[nH]c3n2)CC1] | ¹H-NMR (400 MHz, DMSO-d₆) δ 8.43 (s, 1H), 7.42-7.45 (m, 2H), 7.20-7.31 (m, 2H), 4.25-4.29 (m, 1H), 4.21-4.24 (m, 3H), 3.84-3.86 (m, 1H), 3.66-.375 (m, 3H), 3.10-3.13 (m, 1H), 2.96 (s, 2H), 2.14-2.21 (m, 2H), 1.63-1.71 (m, 4H), 1.25 (s, 3H) | 408.0 |
| 100 | 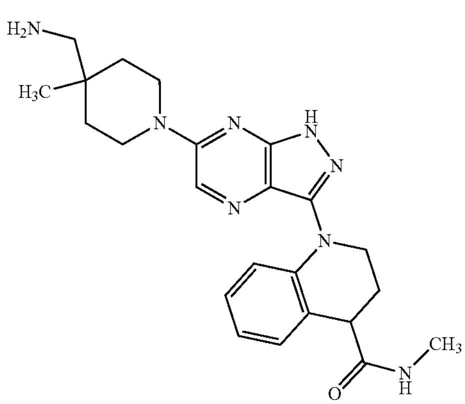 [SMILES: CNC(=O)C1CCN(c2n[nH]c3nc(N4CCC(C)(CN)CC4)cnc23)c2ccccc21] | ¹H-NMR (400 MHz, methanol-d₄) δ 8.42 (s, 1H), 7.38-7.40 (m, 1H), 7.28-7.33 (m, 2H), 7.16-7.20 (m, 1H), 4.55-4.59 (m, 1H), 4.23-4.28 (m, 2H), 4.07-4.10 (m, 1H), 3.87-3.91 (m, 1H), 3.62-3.68 (m, 2H), 2.96 (s, 2H), 2.77 (s, 3H), 2.25-2.35 (m, 2H), 1.63-1.72 (m, 4H), 1.25 (s, 3H). | 435.1 |

TABLE 1-continued

| Cmpd. No. | Structure | ¹H-NMR | Mass Spec. (M + H)⁺ |
|---|---|---|---|
| 101 | 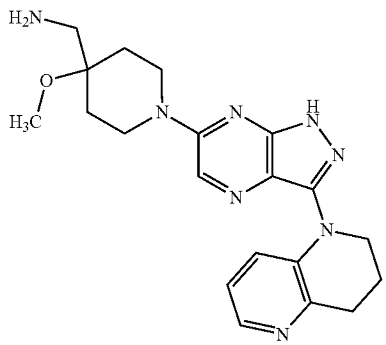 [SMILES: COC1(CN)CCN(c2cnc3c(N4CCCc5ncccc54)n[nH]c3n2)CC1] | ¹H-NMR (400 MHz, CDCl₃) δ 8.13 (s, 1H), 8.04 (d, J = 3.2 Hz, 1H), 7.59-7.63 (m, 1H), 6.93-6.98 (m, 1H), 4.14-4.19 (m, 2H), 4.05-4.09 (m, 2H), 3.33-3.42 (m, 2H), 3.26 (s, 3H), 3.05-3.10 (m, 2H), 2.73 (s, 2H), 2.15-2.23 (m, 2H), 1.94-1.99 (m, 2H), 1.52-1.58 (m, 2H) | 395.1 |
| 102 | 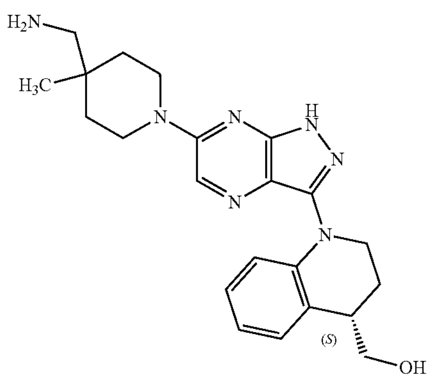 | ¹H-NMR (400 MHz, methanol-d₄) δ 8.25 (s, 1H), 7.18-7.21 (m, 1H), 6.95-7.03 (m, 1H), 6.86-6.90 (m, 1H), 4.16-4.21 (m, 2H), 3.93-4.06 (m, 2H), 3.54-3.62 (m, 2H), 2.93 (s, 2H), 2.78-2.83 (m, 1H), 2.11-2.23 (m, 1H), 1.97-2.06 (m, 2H), 1.83-1.90 (m, 1H), 1.63-1.67 (m, 4H), 1.23 (s, 3H), 1.02-1.07 (m, 3H) | 406.0 |
| 103 | 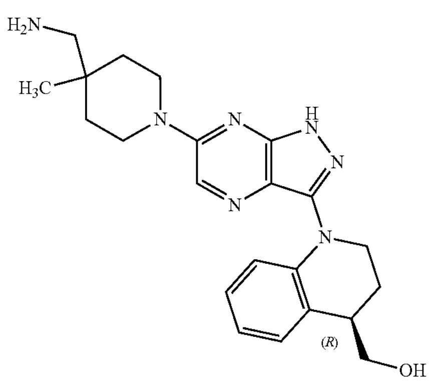 | ¹H-NMR (400 MHz, methanol-d₄) δ 8.25 (s, 1H), 7.18-7.21 (m, 1H), 6.95-7.03 (m, 1H), 6.86-6.90 (m, 1H), 4.16-4.21 (m, 2H), 3.93-4.06 (m, 2H), 3.54-3.62 (m, 2H), 2.93 (s, 2H), 2.78-2.83 (m, 1H), 2.11-2.23 (m, 1H), 1.97-2.06 (m, 2H), 1.83-1.90 (m, 1H), 1.63-1.67 (m, 4H), 1.23 (s, 3H), 1.02-1.07 (m, 3H) | 406.0 |
| 104 | 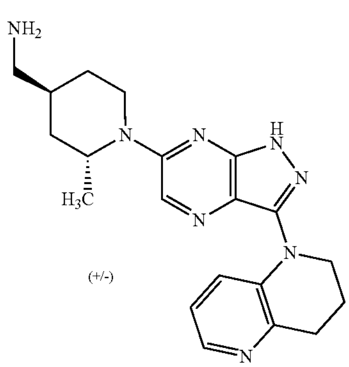 [SMILES: C[C@@H]1C[C@@H](CN)CCN1c1cnc2c(N3CCCc4ncccc43)n[nH]c2n1 ; "(+/-)"] | ¹H-NMR (400 MHz, DMSO-d₆) δ 8.23 (s, 1H), 7.16-7.19 (m, 1H), 6.96-7.00 (m, 1H), 6.90-6.93 (m, 1H), 6.82-6.86 (m, 1H), 4.16-4.20 (m, 2H), 3.92-4.00 (m, 2H), 3.53-3.61 (m, 2H), 2.93 (s, 2H), 2.78-2.82 (m, 1H), 2.12-2.20 (m, 1H), 1.96-2.06 (m, 2H), 1.83-1.90 (m, 1H), 1.63-1.67 (m, 4H), 1.23 (s, 3H), 1.03-1.07 (m, 3H) | 406.0 |

TABLE 1-continued

| Cmpd. No. | Structure | ¹H-NMR | Mass Spec. (M + H)⁺ |
|---|---|---|---|
| 106 | 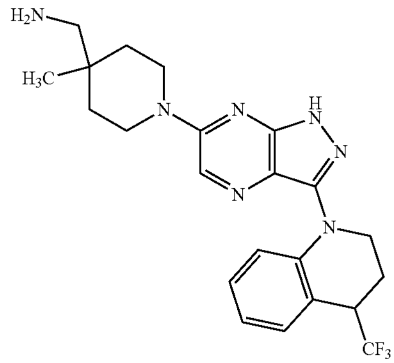 [SMILES: CC1(CN)CCN(c2cnc3c(N4CCC(C(F)(F)F)c5ccccc54)n[nH]c3n2)CC1] | ¹H-NMR (400 MHz, CD₃OD) δ 8.36 (s, 1H), 7.42-7.45 (m, 1H), 7.21-7.28 (m, 2H), 7.05-7.10 (m, 1H), 4.33-4.40 (m, 1H), 4.19-4.25 (m, 2H), 3.87-4.01 (m, 2H), 3.58-3.65 (m, 2H), 2.94 (s, 2H), 2.36-2.41 (m, 2H), 1.61-1.70 (m, 4H), 1.24 (m, 3H) | 446.0 |
| 107 | 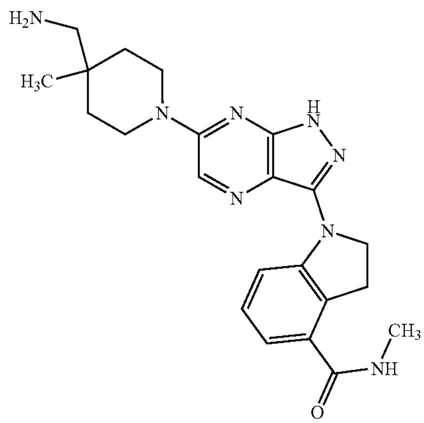 [SMILES: CNC(=O)c1cccc2c1CCN2c1n[nH]c2nc(N3CCC(C)(CN)CC3)cnc12] | ¹H-NMR (400 MHz, DMSO-d₆) δ 12.32 (br s, 1H), 8.36 (s, 1H), 8.29 (s, 1H), 8.18 (br d, J = 4.39 Hz, 1H), 8.03 (d, J = 7.81 Hz, 1H), 7.19 (t, J = 7.81 Hz, 1H), 7.03 (d, J = 7.57 Hz, 1H), 4.43 (br t, J = 8.67 Hz, 2H), 3.90-4.00 (m, 2H), 3.38-3.50 (m, 4H), 2.76 (d, J = 4.64 Hz, 3H), 2.60 (s, 2H), 1.30-1.59 (m, 4H), 1.02 (s, 3H) | 421.0 |
| 108 | 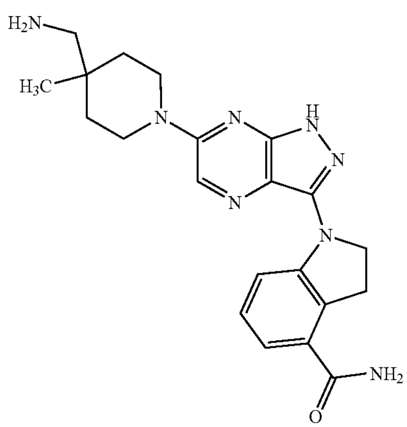 [SMILES: CC1(CN)CCN(c2cnc3c(N4CCc5c(C(N)=O)cccc54)n[nH]c3n2)CC1] | ¹H-NMR (400 MHz, DMSO-d₆) δ 12.31 (br s, 1H), 8.37 (s, 1H), 8.28 (s, 1H), 8.04 (d, J = 7.57 Hz, 1H), 7.72 (br s, 1H), 7.28 (br s, 1H), 7.15-7.21 (m, 1H), 7.07-7.14 (m, 1H), 4.43 (br t, J = 8.79 Hz, 2H), 3.90-4.00 (m, 2H), 3.41-3.51 (m, 4H), 2.58 (s, 2H), 1.30-1.58 (m, 4H), 1.01 (s, 3H). | 407.2 |
| 109 | 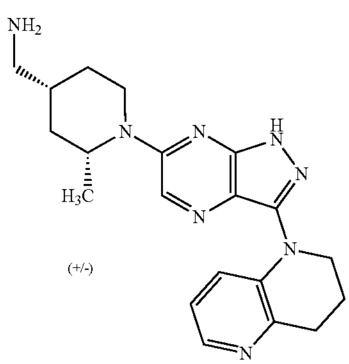 [SMILES: C[C@@H]1C[C@H](CN)CCN1c1cnc2c(N3CCCc4ncccc43)n[nH]c2n1] | ¹H-NMR (400 MHz, DMSO-d₆) δ 8.23 (s, 1H), 7.16-7.19 (m, 1H), 6.96-7.00 (m, 1H), 6.90-6.93 (m, 1H), 6.82-6.86 (m, 1H), 4.16-4.20 (m, 2H), 3.92-4.00 (m, 2H), 3.53-3.61 (m, 2H), 2.93 (s, 2H), 2.78-2.82 (m, 1H), 2.12-2.20 (m, 1H), 1.96-2.06 (m, 2H), 1.83-1.90 (m, 1H), 1.63-1.67 (m, 4H), 1.23 (s, 3H), 1.03-1.07 (m, 3H) | 406.0 |

TABLE 1-continued

| Cmpd. No. | Structure | ¹H-NMR | Mass Spec. (M + H)⁺ |
|---|---|---|---|
| 110 | 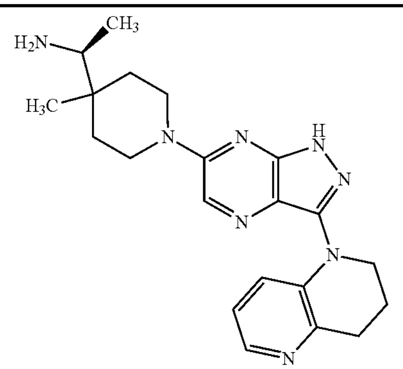 | ¹H-NMR (400 MHz, mmethanol-d₄) δ 8.27 (s, 1H), 7.95 (br, 1H), 7.60 (d, J = 8.4 Hz, 1H), 7.24-7.21 (m, 1H), 4.40-4.31 (m, 2H), 4.00 (t, J = 5.2 Hz, 2H), 3.42-3.33 (m, 2H), 3.22 (q, J = 6.8 Hz, 1H), 3.14 (t, J = 6.8 Hz, 2H), 2.28-2.22 (m, 2H), 1.69-1.62 (m, 4H), 1.32 (d, J = 6.4 Hz, 3H), 1.18 (s, 3H) | 393.0 |
| 111 | 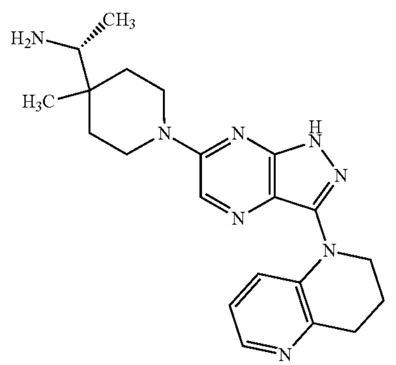 [SMILES: C[C@@H](N)C1(C)CCN(c2cnc3c(N4CCCc5ncccc54)n[nH]c3n2)CC1] | ¹H-NMR (400 MHz, methanol-d₄) δ 8.21 (s, 1H), 7.88 (d, J = 4.4 Hz, 1H), 7.32 (d, J = 8.8 Hz,1H), 7.03-6.99 (m, 1H), 4.32-4.27 (m, 2H), 3.95 (t, J = 5.2 Hz, 2H), 3.39-3.35 (m, 2H), 3.06 (t, J = 6.0 Hz, 2H), 2.73 (q, J = 6.8 Hz, 1H), 2.23-2.20 (m, 2H), 1.63-1.54(m, 4H), 1.32 (d, J = 6.8 Hz, 3H), 1.06 (s, 3H) | 393.0 |
| 112 | 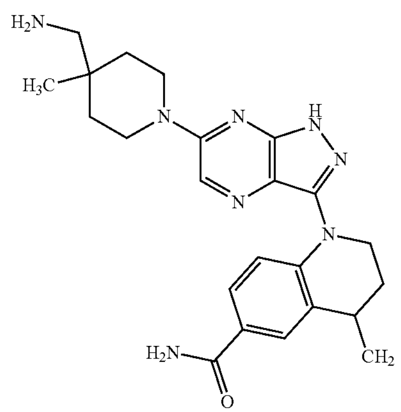 [SMILES: CC1CCN(c2n[nH]c3nc(N4CCC(C)(CN)CC4)cnc23)c2ccc(C(N)=O)cc21] | ¹H-NMR (400 MHz, DMSO-d₆) δ 12.55-12.79 (m, 1H), 8.28 (s, 1H), 7.68 (d, J = 1.71 Hz, 1H), 7.66 (br s, 1H), 7.42 (dd, J = 2.08, 8.67 Hz, 1H), 6.96 (br s, 1H), 6.87 (d, J = 8.54 Hz, 1H), 3.90-3.97 (m, 2H), 3.84-3.90 (m, 2H), 3.41-3.49 (m, 3H), 2.93-3.02 (m, 1H), 2.52-2.56 (m, 2H), 2.03-2.12 (m, 1H), 1.75 (qd, J = 6.34, 11.02 Hz, 1H), 1.46-1.55 (m, 2H), 1.31-1.39 (m, 4H), 0.98 (s, 2H) | 435.5 |
| 113 | 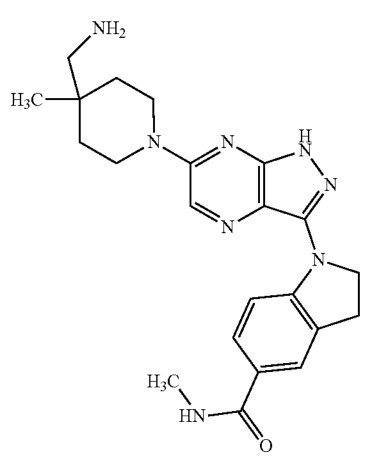 [SMILES: CNC(=O)c1ccc2c(c1)CCN2c1n[nH]c2nc(N3CCC(C)(CN)CC3)cnc12] | ¹H-NMR (400 MHz, DMSO-d₆) δ 12.39 (s, 1H), 8.52 (br d, J = 4.64 Hz, 1H), 8.32 (s, 1H), 8.16 (br d, J = 4.64 Hz, 1H), 7.86-7.98 (m, 4H), 7.63-7.71 (m, 2H), 4.48 (br t, J = 8.67 Hz, 2H), 3.93-4.03 (m, 2H), 3.41-3.54 (m, 2H), 3.23 (br t, J = 8.67 Hz, 2H), 2.72-2.81 (m, 5H), 1.51-1.60 (m, 2H), 1.40-1.49 (m, 2H), 1.09 (s, 3H) | 421.5 |

TABLE 1-continued

| Cmpd. No. | Structure | ¹H-NMR | Mass Spec. (M + H)⁺ |
|---|---|---|---|
| 114 | 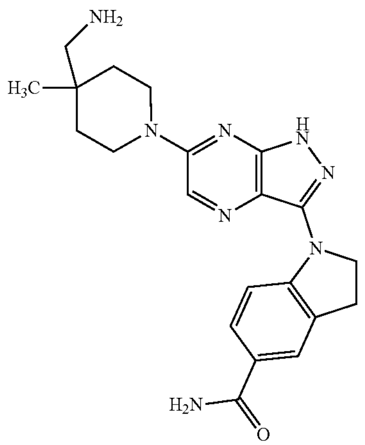 [SMILES: CC1(CN)CCN(c2cnc3c(N4CCc5cc(C(N)=O)ccc54)n[nH]c3n2)CC1] | ¹H-NMR (400 MHz, DMSO-d₆) δ 12.39 (br d, J = 7.32 Hz, 1H), 8.35 (s, 1H), 8.30 (s, 1H), 7.85-7.93 (m, 1H), 7.70 (br d, J = 4.15 Hz, 3H), 7.01 (br s, 1H), 4.48 (br t, J = 8.67 Hz, 2H), 3.90-4.01 (m, 2H), 3.42-3.52 (m, 3H), 3.23 (br t, J = 8.67 Hz, 2H), 2.58 (s, 2H), 1.46-1.58 (m, 2H), 1.32-1.43 (m, 2H), 1.01 (s, 3H) | 407 |
| 115 | 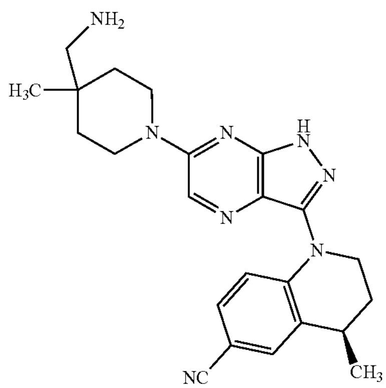 [SMILES: C[C@@H]1CCN(c2n[nH]c3nc(N4CCC(C)(CN)CC4)cnc23)c2ccc(C#N)cc21] | ¹H-NMR (400 MHz, CD₃OD) δ 8.24 (s, 1H), 7.49 (s, 1H), 7.21 (d, J = 8.8 Hz, 1H), 6.75 (d, J = 8.8 Hz, 1H), 4.11-4.06 (m, 2H), 3.98-3.86 (m, 2H), 3.60-3.52 (m, 2H), 3.10-3.06 (m,1H), 2.60 (s, 2H), 2.25-2.15 (m, 1H), 1.92-1.85 (m, 1H), 1.63-1.49 (m, 4H), 1.42 (d, J = 7.2 Hz, 3H), 1.10 (s, 3H) | 417.0 |
| 116 | 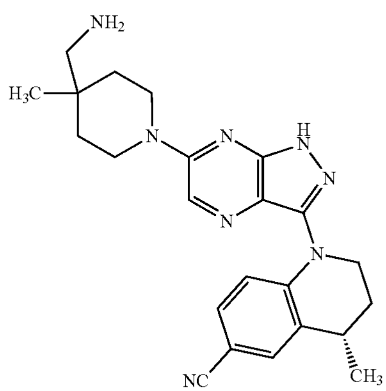 [SMILES: C[C@H]1CCN(c2n[nH]c3nc(N4CCC(C)(CN)CC4)cnc23)c2ccc(C#N)cc21] | ¹H-NMR (400 MHz, CD₃OD) δ 8.25 (s, 1H), 7.49 (s, 1H), 7.21 (d, J = 8.8 Hz, 1H), 6.75 (d, J = 8.8 Hz, 1H), 4.14-4.08 (m, 2H), 4.05-3.85 (m, 2H), 3.60-3.54 (m, 2H), 3.10-3.07 (m,1H), 2.69 (s, 2H), 2.20-2.15 (m, 1H), 1.90-1.80 (m, 1H), 1.65-1.54 (m, 4H), 1.42 (d, J = 6.8 Hz, 3H), 1.14 (s, 3H) | 417.0 |
| 117 | 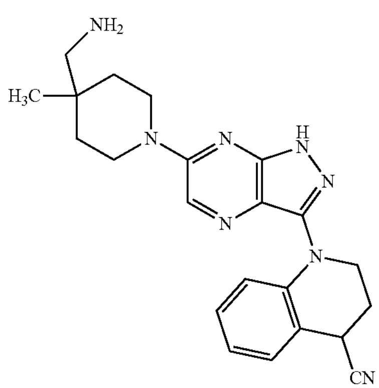 [SMILES: CC1(CN)CCN(c2cnc3c(N4CCC(C#N)c5ccccc54)n[nH]c3n2)CC1] | ¹H-NMR (400 MHz, D₂O + CD₃CN) δ 8.02 (s, 1H), 7.33 (d, J = 7.2 Hz, 1H), 7.05-7.00 (m, 1H), 6.90-6.86 (m, 1H), 6.68 (d, J = 8.4 Hz, 1H), 4.29 (t, J = 8.4 Hz, 1H), 3.95-3.89 (m, 2H), 3.84-3.80 (m, 2H), 3.43-3.37 (m, 2H), 2.88 (s, 2H), 2.35-2.30 (m, 2H), 1.54-1.50 (m, 4H), 1.10 (s, 3H) | 403.0 |

| Cmpd. No. | Structure | ¹H-NMR | Mass Spec. (M + H)⁺ |
|---|---|---|---|
| 118 | 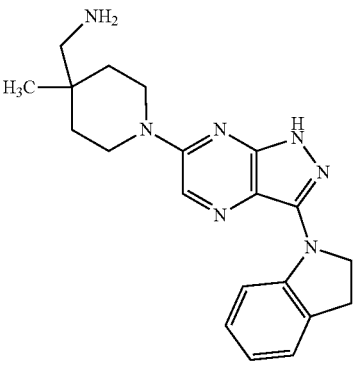 [SMILES: CC1(CN)CCN(c2cnc3c(N4CCc5ccccc54)n[nH]c3n2)CC1] | ¹H-NMR (400 MHz, DMSO-d₆) δ 12.25 (br s, 1H), 8.34 (s, 1H), 8.27 (s, 1H), 7.91 (d, J = 7.81 Hz, 1H), 7.17 (br d, J = 7.08 Hz, 1H), 7.09 (t, J = 7.69 Hz, 1H), 6.76 (t, J = 7.08 Hz, 1H), 4.41 (t, J = 8.67 Hz, 2H), 3.94 (td, J = 4.58, 13.55 Hz, 2H), 3.45 (ddd, J = 2.93, 9.95, 13.24 Hz, 3H), 3.19 (br t, J = 8.67 Hz, 2H), 1.45-1.59 (m, 2H), 1.29-1.43 (m, 2H), 1.00 (s, 3H) | 364 |
| 119 | 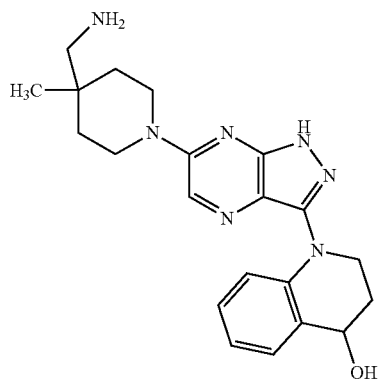 [SMILES: CC1(CN)CCN(c2cnc3c(N4CCC(O)c5ccccc54)n[nH]c3n2)CC1] | ¹H-NMR (400 MHz, CDCl₃) δ 8.11 (s, 1H), 7.39-7.20 (m, 1H), 7.19-7.09 (m, 2H), 6.89-6.85 (m, 1H), 4.89-4.86 (m, 1H), 4.11-3.98 (m, 4H), 3.50-3.45 (m, 2H), 2.61 (s, 2H), 2.23-2.16 (m, 2H), 1.51-1.47 (m, 4H), 1.06 (s, 3H) | 394.1 |
| 120 | 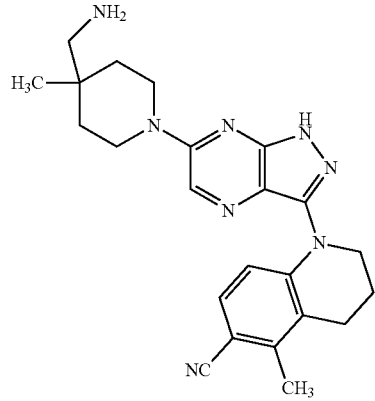 [SMILES: Cc1c(C#N)ccc2c1CCCN2c1n[nH]c2nc(N3CCC(C)(CN)CC3)cnc12] | ¹H-NMR (400 MHz, DMSO-d₆) δ 8.36 (br d, J = 3.17 Hz, 1H), 8.31 (s, 1H), 7.22 (d, J = 8.79 Hz, 1H), 6.74 (d, J = 8.79 Hz, 1H), 3.86-4.06 (m, 2H), 3.70-3.84 (m, 2H), 3.46 (ddd, J = 13.18, 9.89, 3.05 Hz, 2H), 2.75 (br t, J = 6.35 Hz, 2H), 2.60 (br s, 2H), 2.35 (s, 3H), 1.91-2.13 (m, 2H), 1.44-1.64 (m, 2H), 1.38 (br d, J = 13.67 Hz, 2H), 1.01 (s, 3H) | 417.5 |

TABLE 1-continued
| Cmpd. No. | Structure | ¹H-NMR | Mass Spec. (M + H)⁺ |
|---|---|---|---|
| 121 | 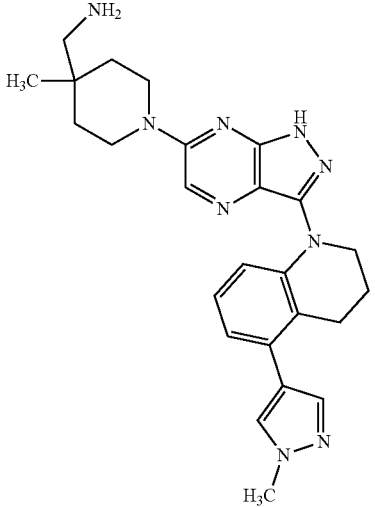 [SMILES: Cn1cc(-c2cccc3c2CCCN3c2n[nH]c3nc(N4CCC(C)(CN)CC4)cnc23)cn1] | ¹H-NMR (400 MHz, DMSO-$d_6$) δ 12.49 (br s, 1H), 8.34 (s, 1H), 8.25 (s, 1H), 7.86 (s, 1H), 6.79-6.94 (m, 2H), 6.69-6.77 (m, 1H), 3.88-3.98 (m, 1H), 3.88 (s, 3H), 3.81-3.86 (m, 1H), 3.38-3.49 (m, 4H), 2.82 (br t, J = 6.35 Hz, 2H), 1.83-1.98 (m, 2H), 1.42-1.57 (m, 2H) 1.26-1.41 (m, 2H), 0.97 (s, 3H) | 458.6 |
| 122 | 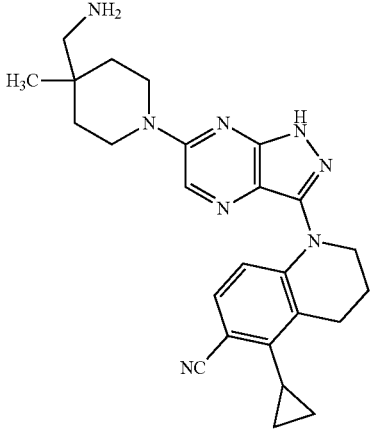 [SMILES: CC1(CN)CCN(c2cnc3c(N4CCCc5c4ccc(C#N)c5C4CC4)n[nH]c3n2)CC1] | ¹H-NMR (400 MHz, DMSO-$d_6$) δ 8.30 (s, 1H), 7.05-7.29 (m, 1H), 6.74 (d, J = 8.79 Hz, 1H), 3.88-4.00(m, 2H), 3.76-3.86 (m, 2H), 3.40-3.51 (m, 2H), 2.97 (br t, J = 6.23 Hz, 2H), 2.58 (s, 2H), 1.97-2.07 (m, 2H), 1.84-1.96 (m, 1H), 1.44-1.56 (m, 2H), 1.31-1.41 (m, 2H), 1.02-1.11 (m, 2H), 1.00 (s, 3H), 0.65-0.80 (m, 2H) | 443.6 |
| 123 | 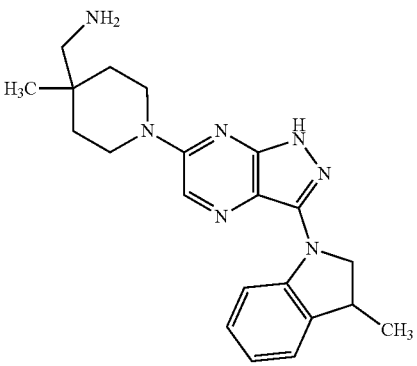 | ¹H-NMR (400 MHz, DMSO-$d_6$) δ 12.26 (br s, 1H), 8.26-8.31 (m, 2H), 7.90 (d, J = 8.06 Hz, 1H), 7.18 (br d, J = 7.32 Hz, 2H), 7.08-7.13 (m, 2H), 6.80 (t, J = 7.08 Hz, 2H), 4.63 (t, J = 9.77 Hz, 1H), 3.89-3.98 (m, 3H), 3.42-3.57 (m, 4H), 1.48-1.60 (m, 2H), 1.37-1.47 (m, 2H), 1.34 (d, J = 6.84 Hz, 3H), 1.05 (s, 3H) | 378.5 |

TABLE 1-continued

| Cmpd. No. | Structure | ¹H-NMR | Mass Spec. (M + H)⁺ |
|---|---|---|---|
| 124 | 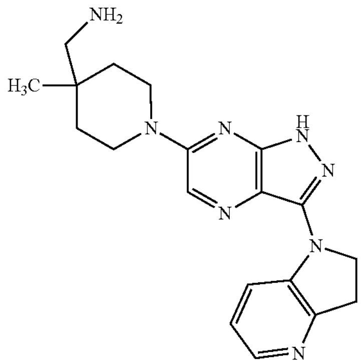 [SMILES: CC1(CN)CCN(c2cnc3c(N4CCc5ncccc54)n[nH]c3n2)CC1] | ¹H-NMR (400 MHz, DMSO-d₆) δ 12.61 (s, 1H), 8.31-8.47 (m, 2H), 8.02 (d, J = 5.37 Hz, 1H), 7.93 (br s, 3H), 7.46-7.56 (m, 1H), 4.60 (br t, J = 8.67 Hz, 2H), 3.94-4.02 (m, 2H), 3.45-3.59 (m, 4H), 2.77 (br d, J = 5.86 Hz, 2H), 1.51-1.61 (m, 2H), 1.41-1.50 (m, 2H), 1.09 (s, 3H) | 365.4 |
| 125 | 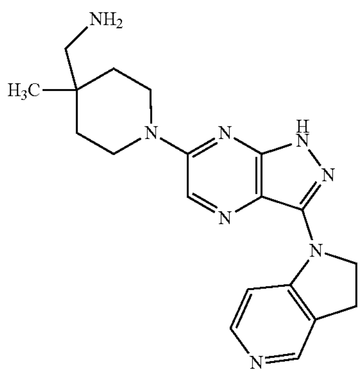 [SMILES: CC1(CN)CCN(c2cnc3c(N4CCc5cnccc54)n[nH]c3n2)CC1] | 1H NMR (400 MHz, DMSO-d₆) δ 13.81 (s, 1H), 13.05 (s, 1H), 8.38-8.49 (m, 2H), 8.34 (br s, 1H), 8.01 (br d, J = 6.84 Hz, 1H), 7.87 (br s, 2H), 4.71 (br t, J = 8.91 Hz, 2H), 3.94-4.05 (m, 3H), 3.39 (br t, J = 8.91 Hz, 2H), 2.78 (br d, J = 5.37 Hz, 2H), 1.40-1.64 (m, 4H), 1.09 (s, 3H) | 365.22 |
| 126 | 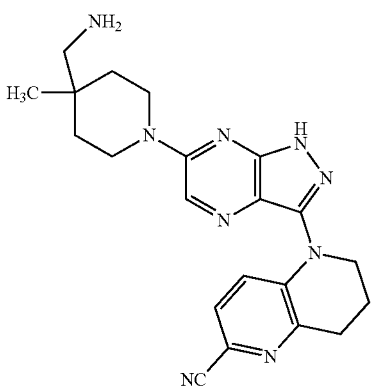 [SMILES: CC1(CN)CCN(c2cnc3c(N4CCCc5nc(C#N)ccc54)n[nH]c3n2)CC1] | ¹H-NMR (400 MHz, DMSO-d₆) δ 8.41 (s, 3H), 7.51 (d, J = 8.79 Hz, 1H), 7.40 (d, J = 8.54 Hz, 1H), 6.22-6.34 (m, 1H), 3.89-4.00 (m, 4H), 3.45 (br d, J = 3.66 Hz, 4H), 2.97 (br t, J = 6.35 Hz, 2H), 2.10 (td, J = 5.98, 11.47 Hz, 2H), 1.44-1.54 (m, 2H), 1.28-1.38 (m, 2H), 0.91-0.99 (m, 3H) | 404.5 |
| 127 | 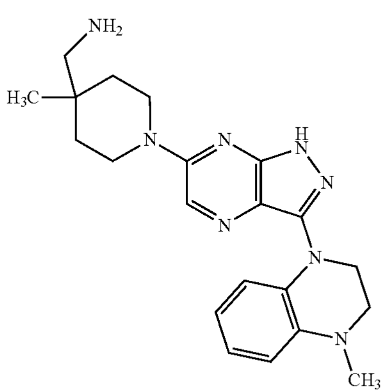 [SMILES: CN1CCN(c2n[nH]c3nc(N4CCC(C)(CN)CC4)cnc23)c2ccccc21] | ¹H-NMR (400 MHz, DMSO-d₆) δ 12.37 (br s, 1H), 8.24 (s, 1H), 7.07 (dd, J = 1.34, 7.93 Hz, 1H), 6.68-6.75 (m, 1H), 6.60-6.67 (m, 1H), 6.42-6.49 (m, 1H), 4.00-4.07 (m, 2H), 3.92 (td, J = 4.64, 13.67 Hz, 2H), 3.44 (ddd, J = 3.05, 9.83, 13.24 Hz, 3H), 3.30-3.37 (m, 3H), 2.83-2.92 (m, 3H), 2.52 (s, 1H), 1.46-1.54 (m, 2H), 1.30-1.40 (m, 2H), 0.98 (s, 1H), 0.92 (s, 1H) | 393.4 |

TABLE 1-continued

| Cmpd. No. | Structure | ¹H-NMR | Mass Spec. (M + H)⁺ |
|---|---|---|---|
| 128 | [Structure with NH₂, H₃C, piperidine, pyrazolo-pyrazine, and (S)-methyl tetrahydropyrido-pyrazine] | ¹H-NMR (400 MHz, methanol-d₄) δ 8.32 (s, 1H), 8.06-8.08 (m, 1H), 8.03-8.06 (m, 1H), 7.56-7.61 (m, 1H), 4.03-4.20 (m, 4H), 3.55-3.63 (m, 2H), 3.47-3.52 (m, 1H), 2.95 (s, 2H), 2.32-2.42 (m, 1H), 2.09-2.15 (m, 1H), 1.64-1.71 (m, 4H), 1.57-1.60 (m, 3H), 1.24 (s, 3H) | 393.3 |
| 129 | [Structure with NH₂, H₃C, piperidine, pyrazolo-pyrazine, and (R)-methyl tetrahydropyrido-pyrazine] | ¹H-NMR (400 MHz, methanol-d₄) δ 8.32 (s, 1H), 8.06-8.08 (m, 1H), 8.03-8.06 (m, 1H), 7.56-7.61 (m, 1H), 4.03-4.20 (m, 4H), 3.55-3.63 (m, 2H), 3.47-3.52 (m, 1H), 2.95 (s, 2H), 2.32-2.42 (m, 1H), 2.09-2.15 (m, 1H), 1.64-1.71 (m, 4H), 1.57-1.60 (m, 3H), 1.24 (s, 3H) | 393.3 |
| 130 | [Structure with NH₂, H₃C, piperidine, pyrazolo-pyrazine, and Cl-tetrahydroquinoline] | ¹H-NMR (400 MHz, CD₃OD) δ 8.36 (s, 1H), 7.09 (s, 3H), 4.19-4.23 (m, 2H), 4.08-4.12 (m, 2H), 3.60-3.65 (m, 2H), 2.92-2.96 (m, 4H), 2.11-2.15 (m, 2H), 1.65-1.69 (m, 4H), 1.24 (s, 3H) | 412.1 |

TABLE 1-continued

| Cmpd. No. | Structure | ¹H-NMR | Mass Spec. (M + H)⁺ |
|---|---|---|---|
| 131 | 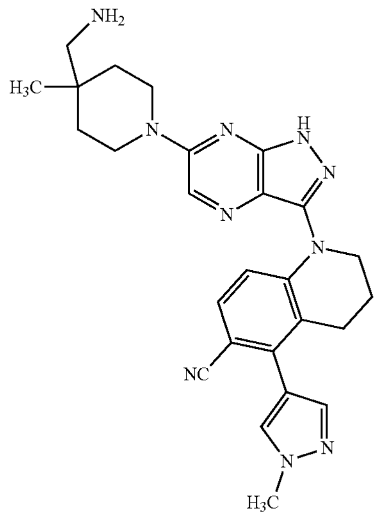 [SMILES: Cn1cc(-c2c(C#N)ccc3c2CCCN3c2n[nH]c3nc(N4CCC(C)(CN)CC4)cnc23)cn1] | ¹H-NMR (400 MHz, DMSO-d₆) δ 8.30 (s, 1H), 7.05-7.29 (m, 1H), 6.74 (d, J = 8.79 Hz, 1H), 3.88-4.00 (m, 2H), 3.76-3.86 (m, 2H), 3.40-3.51 (m, 2H), 2.97 (br t, J = 6.23 Hz, 2H), 2.58 (s, 2H), 1.97-2.07 (m, 2H), 1.84-1.96 (m, 1H), 1.44-1.56 (m, 2H), 1.31-1.41 (m, 2H), 1.02-1.11 (m, 2H), 1.00 (s, 3H), 0.65-0.80 (m, 2H) | 483.6 |
| 132 | 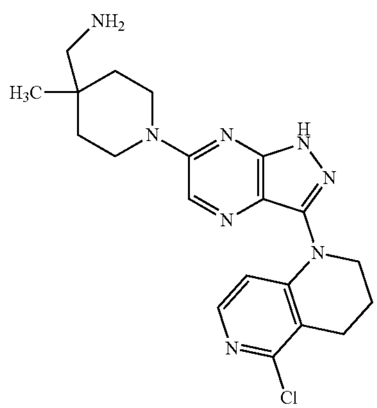 [SMILES: CC1(CN)CCN(c2cnc3c(N4CCCc5c4ccnc5Cl)n[nH]c3n2)CC1] | ¹H-NMR (400 MHz, DMSO-d₆) δ 8.35 (d, J = 1.71 Hz, 2H) 7.71 (d, J = 5.62 Hz, 1H) 6.74 (d, J = 5.86 Hz, 1H) 3.89-4.00 (m, 2H) 3.79-3.88 (m, 2H) 3.42-3.51 (m, 3H) 2.80 (br t, J = 6.47 Hz, 2H) 2.53 (s, 1H) 2.51-2.55 (m, 1H) 1.99-2.08 (m, 2H) 1.46-1.55 (m, 2H) 1.31-1.39 (m, 2H) 0.98 (s, 3H) | 413.1 |
| 133 | 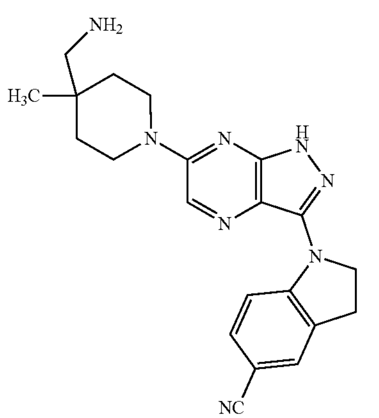 [SMILES: CC1(CN)CCN(c2cnc3c(N4CCc5cc(C#N)ccc54)n[nH]c3n2)CC1] | ¹H-NMR (400 MHz, DMSO-d6) δ 12.36-12.64 (m, 1H), 8.21-8.53 (m, 1H), 7.96 (d, J = 8.39 Hz, 1H), 7.41-7.63 (m, 2H), 4.50 (t, J = 8.85 Hz, 2H), 3.96 (dt, J = 13.65, 4.69 Hz, 2H) 3.41-3.54 (m, 2H), 3.17-3.28 (m, 2H), 2.56 (s, 2H), 1.45-1.57 (m, 2H), 1.27-1.43 (m, 2H), 0.99 (s, 3H) | 389.4 |

TABLE 1-continued

| Cmpd. No. | Structure | ¹H-NMR | Mass Spec. (M + H)⁺ |
|---|---|---|---|
| 134 | (S)-isomer structure | ¹H-NMR (400 MHz, DMSO-d6) δ 12.18-12.31 (m, 1H), 8.33 (s, 1H), 8.29 (s, 1H), 7.82 (d, J = 8.06 Hz, 1H), 7.11-7.22 (m, 1H), 7.00-7.13 (m, 1H), 6.67-6.83 (m, 1H), 5.19-5.35 (m, 1H), 3.83-4.03 (m, 2H), 3.35-3.48 (m, 3H), 2.71-2.81 (m, 1H), 2.54 (s, 2H), 1.43-1.59 (m, 2H), 1.28-1.41 (m, 2H), 1.21 (d, J = 6.10 Hz, 3H), 0.98 (s, 3H) | 378.6 |
| 135 | (R)-isomer structure | ¹H-NMR (400 MHz, DMSO-d6) δ 12.26 (br s, 1H), 8.32 (s, 1H), 8.29 (s, 1H), 7.68-7.92 (m, 1H), 7.13-7.22 (m, 1H), 7.09 (br t, J = 7.57 Hz, 1H), 6.76 (br t, J = 7.32 Hz, 1H), 5.05-5.41 (m, 1H), 3.94 (br d, J = 13.43 Hz, 2H), 3.36-3.53 (m, 3H), 2.76 (br dd, J = 15.75, 3.05 Hz, 1H), 2.54 (s, 2H), 1.44-1.56 (m, 2H), 1.28-1.41 (m, 2H), 1.21 (d, J = 6.10 Hz, 3H), 0.99 (s, 3H) | 378.6 |
| 136 | cyclopropyl-indoline structure | ¹H-NMR (400 MHz, DMSO-d6) δ 12.21 (br s, 1H), 8.28-8.37 (m, 1H), 8.16-8.28 (m, 1H), 7.72 (d, J = 7.81 Hz, 1H), 7.00 (br t, J = 7.93 Hz, 1H), 6.22-6.37 (m, 1H), 4.45 (br t, J = 8.67 Hz, 2H), 3.84-4.01 (m, 2H), 3.38-3.50 (m, 2H), 3.16-3.26 (m, 3H), 2.06 (s, 2H), 1.77-1.95 (m, 1H), 1.43-1.58 (m, 2H), 1.27-1.40 (m, 2H), 0.99 (s, 3H), 0.78-0.95 (m, 2H), 0.59-0.69 (m, 2H) | 405.6 |
| 137 | sulfonamide-piperidine structure | ND | 415.5 |

TABLE 1-continued

| Cmpd. No. | Structure | ¹H-NMR | Mass Spec. (M + H)⁺ |
|---|---|---|---|
| 138 | 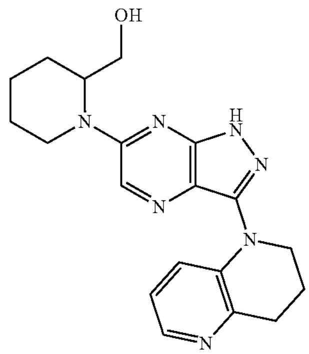 [SMILES: OCC1CCCCN1c1cnc2c(N3CCCc4ncccc43)n[nH]c2n1] | ND | 366.3 |
| 139 | 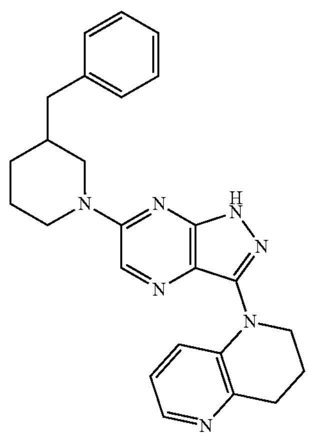 [SMILES: c1ccc(CC2CCCN(c3cnc4c(N5CCCc6ncccc65)n[nH]c4n3)C2)cc1] | ND | 426.3 |
| 140 | 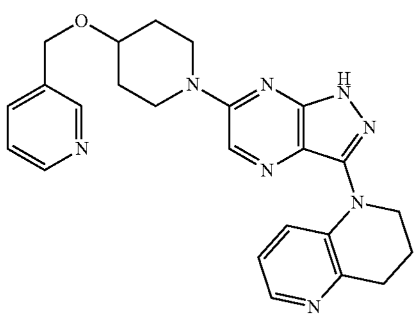 [SMILES: c1cncc(COC2CCN(c3cnc4c(N5CCCc6ncccc65)n[nH]c4n3)CC2)c1] | ND | 443.3 |
| 141 | 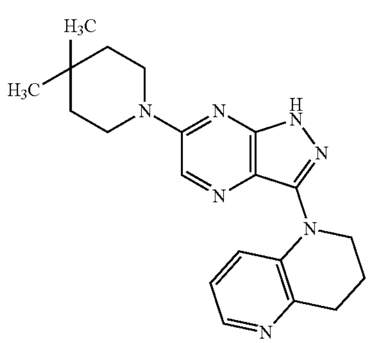 [SMILES: CC1(C)CCN(c2cnc3c(N4CCCc5ncccc54)n[nH]c3n2)CC1] | ND | 364.3 |

TABLE 1-continued

| Cmpd. No. | Structure | ¹H-NMR | Mass Spec. (M + H)⁺ |
|---|---|---|---|
| 142 | 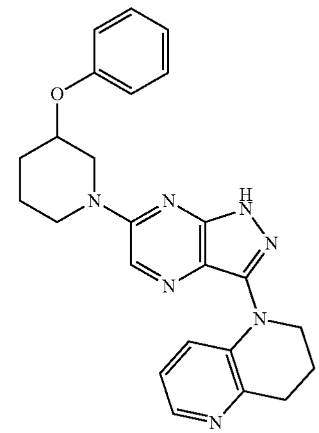 [SMILES: c1ccc(OC2CCCN(c3cnc4c(N5CCCc6ncccc65)n[nH]c4n3)C2)cc1] | ND | 428.4 |
| 143 | 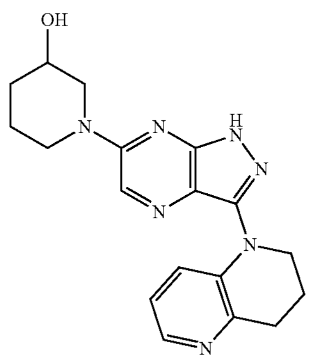 [SMILES: OC1CCCN(c2cnc3c(N4CCCc5ncccc54)n[nH]c3n2)C1] | ND | 352.2 |
| 144 | 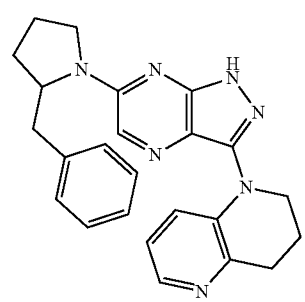 [SMILES: c1ccc(CC2CCCN2c2cnc3c(N4CCCc5ncccc54)n[nH]c3n2)cc1] | ND | 412.3 |
| 145 | 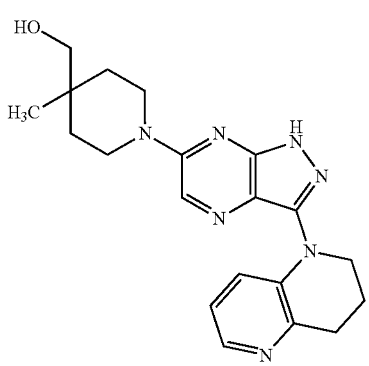 [SMILES: CC1(CO)CCN(c2cnc3c(N4CCCc5ncccc54)n[nH]c3n2)CC1] | ND | 380.3 |

TABLE 1-continued
| Cmpd. No. | Structure | ¹H-NMR | Mass Spec. (M + H)⁺ |
|---|---|---|---|
| 146 | 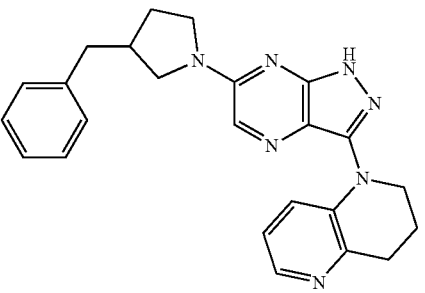 [SMILES: c1ccc(CC2CCN(c3cnc4c(N5CCCc6ncccc65)n[nH]c4n3)C2)cc1] | ND | 412.3 |
| 147 | 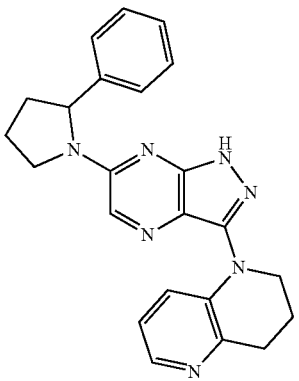 [SMILES: c1ccc(C2CCCN2c2cnc3c(N4CCCc5ncccc54)n[nH]c3n2)cc1] | ND | 398.3 |
| 148 | 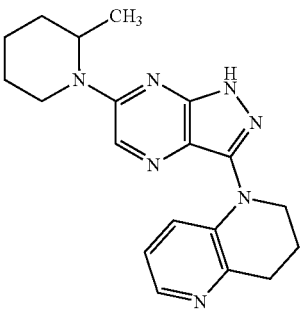 [SMILES: CC1CCCCN1c1cnc2c(N3CCCc4ncccc43)n[nH]c2n1] | ND | 350.3 |
| 149 | 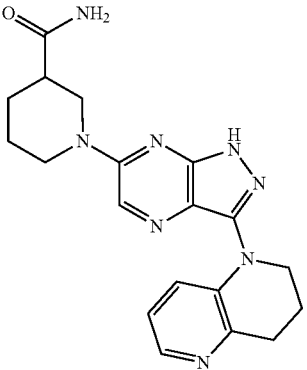 [SMILES: NC(=O)C1CCCN(c2cnc3c(N4CCCc5ncccc54)n[nH]c3n2)C1] | ND | 379.3 |

TABLE 1-continued

| Cmpd. No. | Structure | ¹H-NMR | Mass Spec. (M + H)⁺ |
|---|---|---|---|
| 150 | 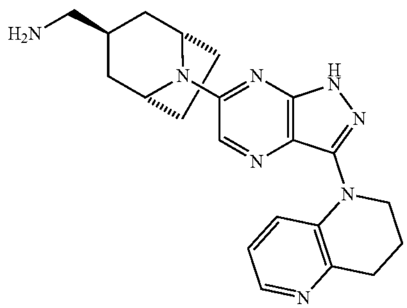 [SMILES: NC[C@@H]1C[C@H]2CC[C@@H](C1)N2c1cnc2c(N3CCCc4ncccc43)n[nH]c2n1] | ND | 391.4 |
| 151 | 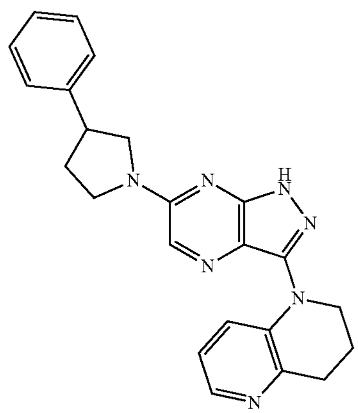 [SMILES: c1ccc(C2CCN(c3cnc4c(N5CCCc6ncccc65)n[nH]c4n3)C2)cc1] | ND | 398.3 |
| 152 | 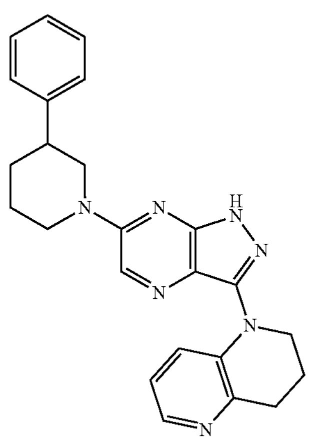 [SMILES: c1ccc(C2CCCN(c3cnc4c(N5CCCc6ncccc65)n[nH]c4n3)C2)cc1] | ND | 412.3 |
| 153 | 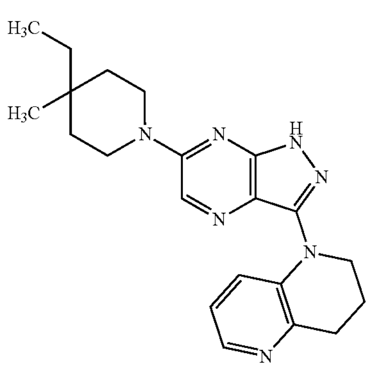 [SMILES: CCC1(C)CCN(c2cnc3c(N4CCCc5ncccc54)n[nH]c3n2)CC1] | ND | 378.3 |

TABLE 1-continued

| Cmpd. No. | Structure | ¹H-NMR | Mass Spec. (M + H)⁺ |
|---|---|---|---|
| 154 | 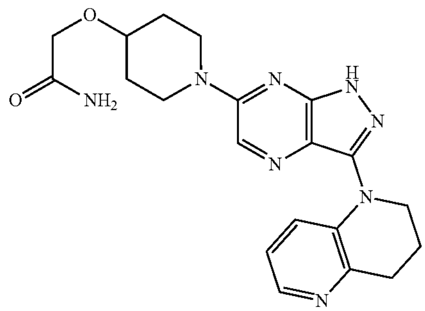 [SMILES: NC(=O)COC1CCN(c2cnc3c(N4CCCc5ncccc54)n[nH]c3n2)CC1] | ND | 410.3 |
| 155 | 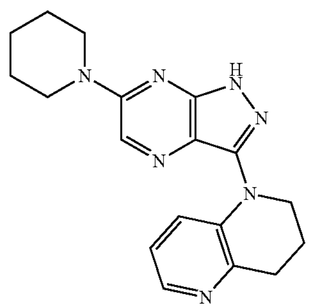 [SMILES: c1cnc2c(c1)N(c1n[nH]c3nc(N4CCCCC4)cnc13)CCC2] | ND | 336.3 |
| 156 | 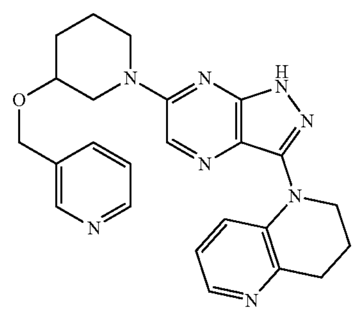 [SMILES: c1cncc(COC2CCCN(c3cnc4c(N5CCCc6ncccc65)n[nH]c4n3)C2)c1] | ND | 443.5 |
| 157 | 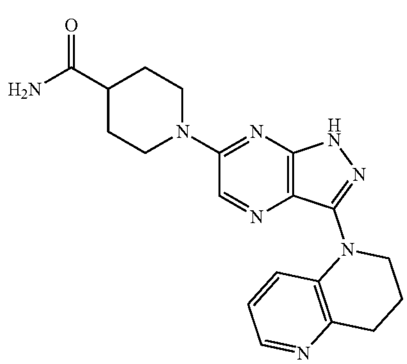 [SMILES: NC(=O)C1CCN(c2cnc3c(N4CCCc5ncccc54)n[nH]c3n2)CC1] | ND | 379.3 |

TABLE 1-continued

| Cmpd. No. | Structure | ¹H-NMR | Mass Spec. (M + H)⁺ |
|---|---|---|---|
| 158 | 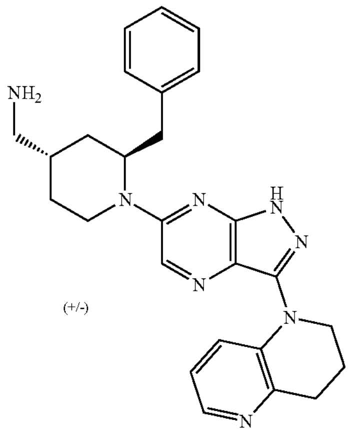 [SMILES: NC[C@H]1CCN(c2cnc3c(N4CCCc5ncccc54)n[nH]c3n2)[C@H](Cc2ccccc2)C1] | ¹H-NMR (400 MHz, methanol-d₄) δ 8.07-8.05 (m, 2H), 7.93-7.90 (d, J = 8.4 Hz, 1H), 7.60-7.57 (m, 1H), 7.32-7.30 (m, J = 7.2 Hz, 2H), 7.24-7.19 (m, 2H), 7.14-7.12 (m, 1H), 4.05-4.02 (m, 2H), 3.41-3.32 (m, 1H), 3.28-3.26 (m, 2H), 3.2-3.15 (m, 1H), 3.0-2.94 (m, 1H), 2.91-2.89 (d, J = 6.0 Hz, 2H), 2.43 (s, 1H), 2.30 (m, 2H), 2.09-2.05 (m, 1H), 1.99-1.95 (m, 1H), 1.53-1.50 (m, 1H), 1.39-1.31 (m, 3H) | 455.1 |
| 159 | 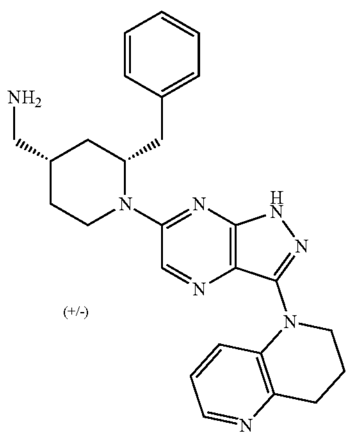 [SMILES: NC[C@H]1CCN(c2cnc3c(N4CCCc5ncccc54)n[nH]c3n2)[C@@H](Cc2ccccc2)C1] | ¹H-NMR (400 MHz, methanol-d₄) δ 8.07-8.05 (m, 2H), 7.93-7.90 (d, J = 8.8 Hz, 1H), 7.60-7.58 (m, 1H), 7.32-7.30 (m, J = 7.2 Hz, 2H), 7.30-7.19 (m, 2H), 7.14-7.10 (m, 1H), 4.05-4.02 (m, 2H), 3.45-3.38 (m, 1H), 3.30-3.26 (m, 2H), 3.2-3.15 (m, 1H), 3.0-2.94 (m, 1H), 2.91-2.89 (d, J = 6.0 Hz, 2H), 2.43 (s, 1H), 2.30 (m, 2H), 2.09-2.05 (m, 1H), 1.99-1.95 (m, 1H), 1.53-1.50 (m, 1H), 1.39-1.31 (m, 3H) | 455.2 |
| 160 | 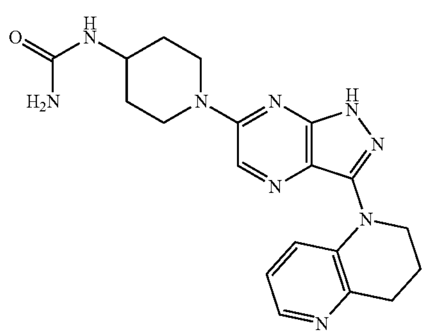 [SMILES: NC(=O)NC1CCN(c2cnc3c(N4CCCc5ncccc54)n[nH]c3n2)CC1] | ND | 394.2 |
| 161 | 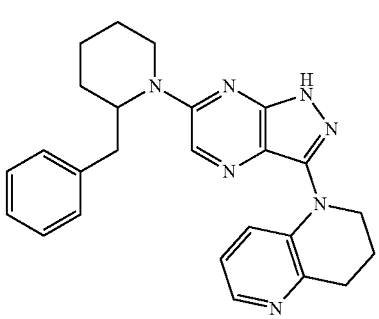 [SMILES: c1ccc(CC2CCCCN2c2cnc3c(N4CCCc5ncccc54)n[nH]c3n2)cc1] | ND | 426.2 |

TABLE 1-continued

| Cmpd. No. | Structure | ¹H-NMR | Mass Spec. (M + H)⁺ |
|---|---|---|---|
| 162 | 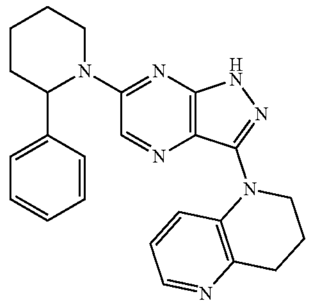 [SMILES: c1ccc(C2CCCCN2c2cnc3c(N4CCCc5ncccc54)n[nH]c3n2)cc1] | ND | 412.2 |
| 163 | 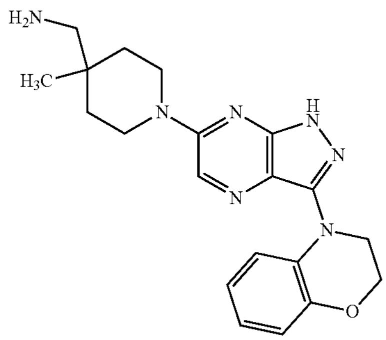 [SMILES: CC1(CN)CCN(c2cnc3c(N4CCOc5ccccc54)n[nH]c3n2)CC1] | ¹H-NMR (400 MHz, DMSO-d₆) δ 12.21 (br s, 1H), 8.28-8.37 (m, 1H), 8.16-8.28 (m, 1H), 7.72 (d, J = 7.81 Hz, 1H), 7.00 (br t, J = 7.93 Hz, 1H), 6.22-6.37 (m, 1H), 4.45 (br t, J = 8.67 Hz, 2H), 3.84-4.01 (m, 2H), 3.38-3.50 (m, 2H), 3.16-3.26 (m, 3H), 2.06 (s, 2H), 1.77-1.95 (m, 1H), 1.43-1.58 (m, 2H), 1.27-1.40 (m, 2H), 0.99 (s, 3H), 0.78-0.95 (m, 2H), 0.59-0.69 (m, 2H) | 380.4 |
| 164 | 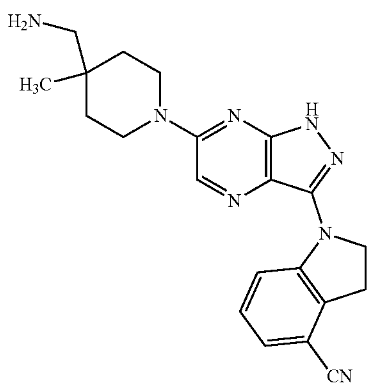 [SMILES: CC1(CN)CCN(c2cnc3c(N4CCc5c(C#N)cccc54)n[nH]c3n2)CC1] | ¹H-NMR (400 MHz, DMSO-d₆) δ 12.21 (br s, 1H), 8.28-8.37 (m, 1H), 8.16-8.28 (m, 1H), 7.72 (d, J = 7.81 Hz, 1H), 7.00 (br t, J = 7.93 Hz, 1H), 6.22-6.37 (m, 1H), 4.45 (br t, J = 8.67 Hz, 2H), 3.84-4.01 (m, 2H), 3.38-3.50 (m, 2H), 3.16-3.26 (m, 3H), 2.06 (s, 2H), 1.77-1.95 (m, 1H), 1.43-1.58 (m, 2H), 1.27-1.40 (m, 2H), 0.99 (s, 3H), 0.78-0.95 (m, 2H), 0.59-0.69 (m, 2H). | 389.4 |
| 165 | 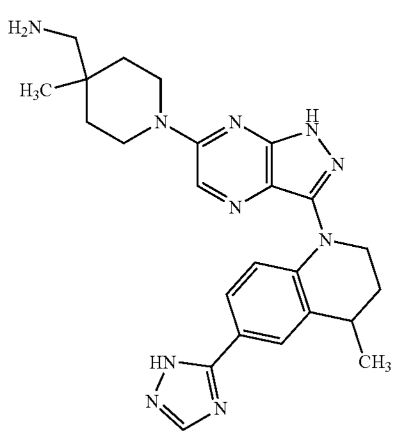 [SMILES: CC1CCN(c2n[nH]c3nc(N4CCC(C)(CN)CC4)cnc23)c2ccc(-c3ncn[nH]3)cc21] | ¹H-NMR (400 MHz, DMSO-d₆) δ 12.53-12.80 (m, 1H), 8.33 (s, 1H), 8.29 (s, 1H), 8.15 (br s, 1H), 7.79 (d, J = 1.22 Hz, 1H), 7.53 (dd, J = 1.83, 8.67 Hz, 1H), 7.02 (d, J = 8.79 Hz, 1H), 3.84-3.98 (m, 4H), 3.40-3.49 (m, 5H), 3.02 (br dd, J = 6.23, 12.33 Hz, 2H), 2.57 (s, 2H), 2.05-2.15 (m, 1H), 1.76 (qd, J = 6.47, 11.11 Hz, 1H), 1.46-1.55 (m, 2H), 1.36 (br d, J = 6.84 Hz, 4H), 1.00 (s, 3H) | 459.5 |

TABLE 1-continued

| Cmpd. No. | Structure | ¹H-NMR | Mass Spec. (M + H)⁺ |
|---|---|---|---|
| 166 | 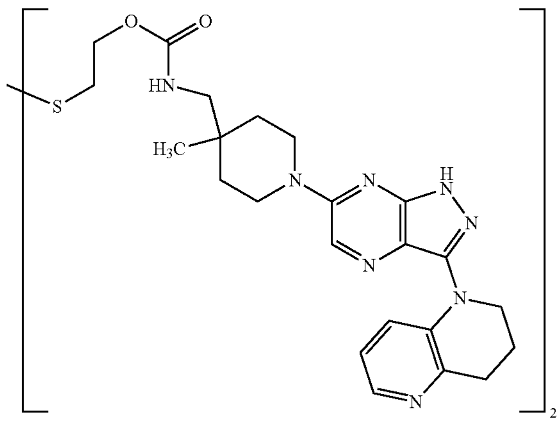 | ¹H-NMR (400 MHz, DMSO-d₆) δ 8.27 (s, 2H), 8.02-8.07 (m, 4H), 7.55-7.60 (m, 2H), 4.27-4.34 (m, 4H), 4.02-4.09 (m, 8H), 3.59-3.62 (m, 4H), 3.27-3.31 (m, 4H), 3.09 (s, 4H), 2.93-2.97 (m, 4H), 2.27-2.34 (m, 4H), 1.58-1.63 (m, 4H), 1.42-1.47 (m, 4H), 1.05 (s, 6H) | 963.6 |
| 167 | 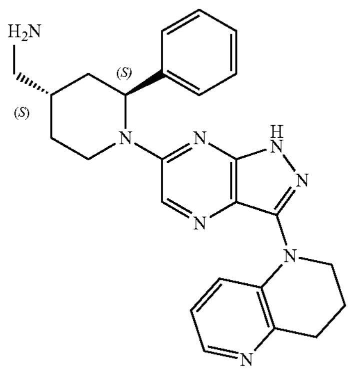 | ¹H-NMR (400 MHz, CDCl₃) δ 8.21 (s, 1H), 7.88 (dd, J = 4.8, 1.2 Hz, 1H), 7.25-7.37 (m, 6H), 6.98-7.10 (m, 1H), 6.05 (s, 1H), 3.93-3.97 (m, 2H), 3.05-3.30 (m, 1H), 3.05 (t, J = 6.6 Hz, 3H), 2.65-2.72 (m, 3H), 2.18-2.23 (m, 2H), 1.90-1.95 (m, 1H), 1.85-1.90 (m, 1H), 1.75-1.80 (m, 1H), 1.30-1.40 (m, 1H) | 441.1 |
| 168 | 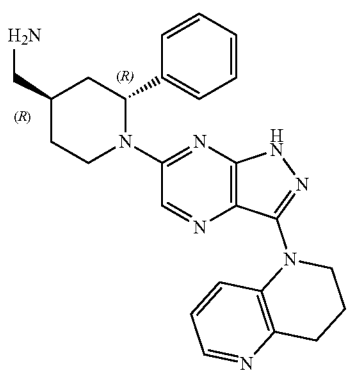 | ¹H-NMR (400 MHz, CDCl₃) δ 8.20 (s, 1H), 7.85-7.87 (m, 1H), 7.25-7.36 (m, 6H), 6.99-7.10 (m, 1H), 6.08 (s, 1H), 3.91-3.96 (m, 2H), 3.04-3.30 (m, 1H), 3.01-3.05 (m, 2H), 2.81-2.86 (m, 2H), 2.57-2.62 (m, 1H), 2.15-2.22 (m, 2H), 1.90-1.92 (m, 1H), 1.70-1.85 (m, 2H), 1.35-1.50 (m, 1H) | 441.1 |
| 169 | 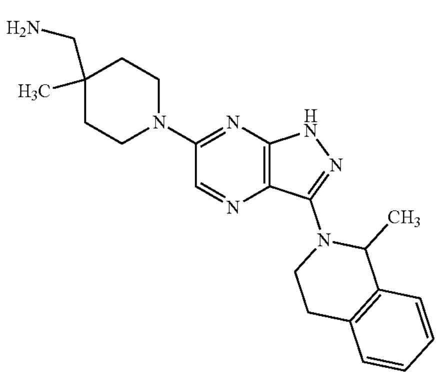 [SMILES: CC1c2ccccc2CCN1c1n[nH]c2nc(N3CCC(C)(CN)CC3)cnc12] | ¹H-NMR (400 MHz, DMSO-d6) δ 11.84 (br s, 1H) 8.33 (s, 1H) 8.18 (s, 1H) 7.07-7.22 (m, 4H) 5.66 (q, J = 6.59 Hz, 1H) 4.35-4.43 (m, 1H) 3.90 (dt, J = 13.37, 4.55 Hz, 2H) 3.36-3.48 (m, 4H) 2.92-3.04 (m, 2H) 2.74 (br d, J = 15.14 Hz, 1H) 2.59 (s, 2H) 1.45-1.54 (m, 2H) 1.31-1.43 (m, 4H) 1.00 (s, 3H) | 392.4 |

TABLE 1-continued

| Cmpd. No. | Structure | ¹H-NMR | Mass Spec. (M + H)⁺ |
|---|---|---|---|
| 170 | 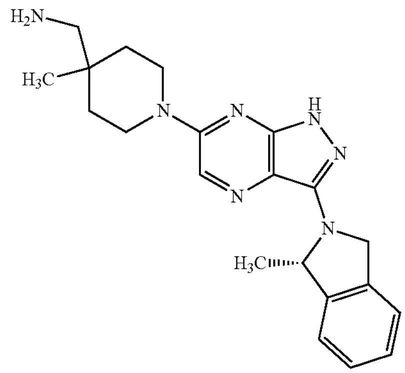 [SMILES: C[C@H]1c2ccccc2CN1c1n[nH]c2nc(N3CCC(C)(CN)CC3)cnc12] | ¹H NMR (400 MHz, DMSO-d₆) δ 11.84 (br s, 1H) 8.31 (s, 1H) 8.19 (s 1H) 7.35-7.42 (m, 2H) 7.26-7.33 (m, 2H) 5.36 (br d, J = 6.10 Hz, 1H) 4.99 (br dd, J = 14.65, 2.44 Hz, 1H) 4.80 (br d, J = 14.40 Hz, 1H) 3.92 (br d, J = 13.67 Hz, 2H) 3.38-3.48 (m, 4H) 2.59 (s, 2H) 1.46-1.56 (m, 4H) 1.33-1.41 (m, 2H) 1.00 (s, 3H) | 378.4 |
| 171 | 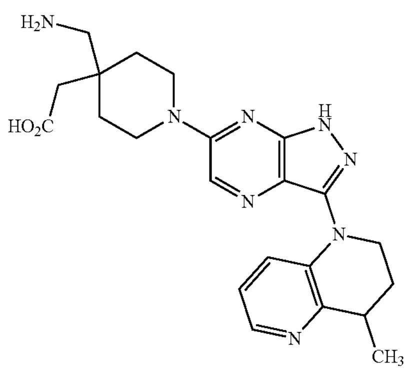 [SMILES: CC1CCN(c2n[nH]c3nc(N4CCC(CN)(CC(=O)O)CC4)cnc23)c2cccnc21] | ¹H-NMR (400 MHz, DMSO-d₆) δ 12.64 (br, 1H), 8.30 (s, 1H), 7.95-7.93 (m, 1H), 7.46-7.43 (m, 1H), 6.98-6.94 (m, 1H), 3.98-3.88 (m, 4H), 3.15-2.94 (m, 3H), 2.78 (s, 2H), 2.41 (s, 2H), 2.18-2.14 (m, 1H), 1.95-1.85 (m, 1H), 1.60-1.45 (m, 4H), 1.36 (d, J = 6.8 Hz, 3H) | 437.1 |
| 172 | 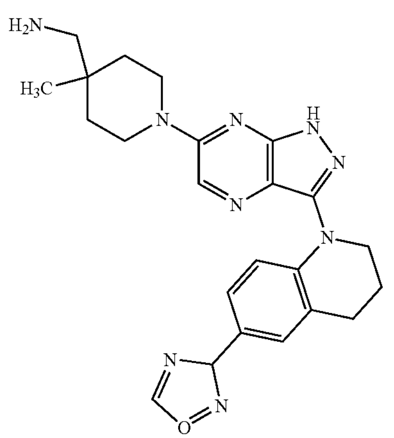 | ¹H-NMR (400 MHz, DMSO-d₆) δ 12.55-12.86 (m, 2H), 9.55 (s, 1H), 8.34 (s, 1H), 8.30 (s, 1H), 7.70 (d, J = 1.71 Hz, 1H), 7.55 (dd, J = 1.95, 8.54 Hz, 1H), 7.04 (d, J = 8.79 Hz, 1H), 3.88-3.98 (m, 4H), 3.42-3.51 (m, 6H), 2.91 (br t, J = 6.10 Hz, 2H), 2.54 (s, 2H), 1.99-2.06 (m, 2H), 1.46-1.54 (m, 2H), 1.32-1.39 (m, 2H), 0.99 (s, 3H) | 446.5 |

TABLE 1-continued

| Cmpd. No. | Structure | ¹H-NMR | Mass Spec. (M + H)⁺ |
|---|---|---|---|
| 173 | 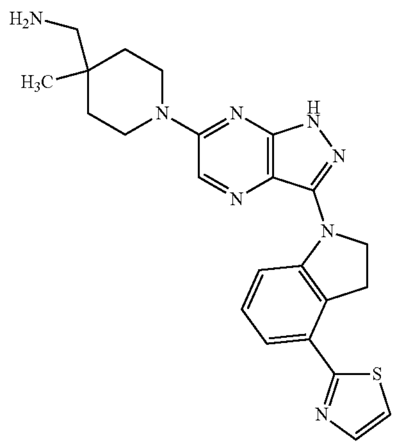 [SMILES: CC1(CN)CCN(c2cnc3c(N4CCc5c(-c6nccs6)cccc54)n[nH]c3n2)CC1] | ¹H-NMR (400 MHz, DMSO-d₆) δ 12.39 (br, 1H), 8.31 (s, 1H), 8.07-8.05 (m, 4H), 8.0-7.99 (d, J = 3.2 Hz, 1H), 7.85-7.84 (d, J = 3.2 Hz, 1H), 7.39-7.37 (d, J = 7.6 Hz, 1H), 7.30-7.25 (m, 1H), 4.56-4.51 (m, 2H), 4.0-3.96 (m, 2H), 3.58-3.55 (m, 2H), 3.51-3.45 (m, 2H), 2.78-2.76 (m, 2H), 1.61-1.44 (m, 4H), 1.1 (s, 3H) | 447.4 |
| 174 | 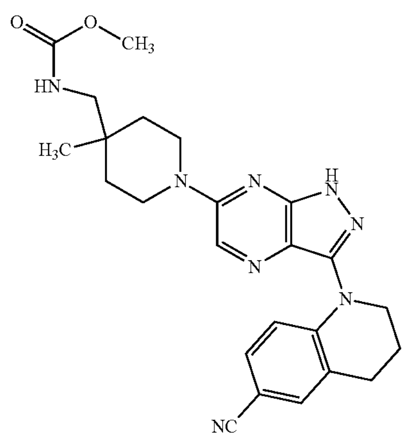 [SMILES: COC(=O)NCC1(C)CCN(c2cnc3c(N4CCCc5cc(C#N)ccc54)n[nH]c3n2)CC1] | ¹H-NMR (400 MHz, DMSO-d₆) δ 12.80 (s, 1H), 8.31 (s, 1H), 7.44 (d, J = 1.71 Hz, 1H), 7.27 (dd, J = 1.95, 8.79 Hz, 1H), 7.19 (br t, J = 6.23 Hz, 1H), 6.91 (d, J = 8.54 Hz, 1H), 5.75 (s, 1H), 3.85-3.96 (m, 4H), 3.51 (s, 3H), 3.42-3.49 (m, 2H), 3.35-3.40 (m, 1H), 2.94 (br d, J = 6.35 Hz, 2H), 2.84 (br t, J = 6.23 Hz, 2H), 1.96-2.04 (m, 2H), 1.45 (ddd, J = 3.54, 9.40, 13.18 Hz, 2H), 1.21-1.34 (m, 3H), 1.16 (br t, J = 7.08 Hz, 1H), 1.08 (t, J = 6.96 Hz, 1H), 0.93 (s, 3H) | 461.5 |
| 175 | 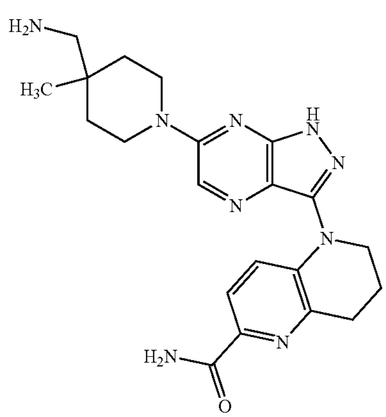 [SMILES: CC1(CN)CCN(c2cnc3c(N4CCCc5nc(C(N)=O)ccc54)n[nH]c3n2)CC1] | ¹H-NMR (400 MHz, DMSO-d₆) δ 8.31 (s, 1H), 7.69 (br d, J = 2.69 Hz, 1H), 7.55-7.64 (m, 1H), 7.39-7.53 (m, 1H), 7.21-7.34 (m, 1H), 3.81-4.05 (m, 4H), 3.45 (ddd, J = 13.31, 9.89, 3.17 Hz, 2H), 2.93-3.09 (m, 2H), 2.47 (br s, 2H), 2.00-2.16 (m, 2H), 1.39-1.57 (m, 2H), 1.21-1.38 (m, 2H), 0.86-1.00 (m, 3H). | 422.6 |

TABLE 1-continued

| Cmpd. No. | Structure | ¹H-NMR | Mass Spec. (M + H)⁺ |
|---|---|---|---|
| 176 | 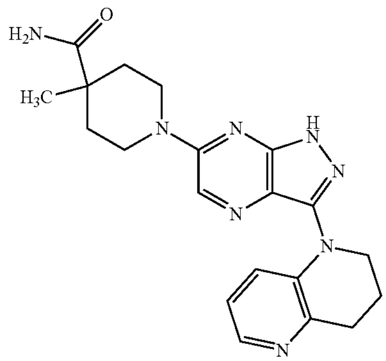 [SMILES: CC1(C(N)=O)CCN(c2cnc3c(N4CCCc5ncccc54)n[nH]c3n2)CC1] | ¹H-NMR (400 MHz, DMSO-d₆) δ 12.56 (s, 2H), 8.29 (s, 1H), 7.88 (br dd, J = 1.22, 4.39 Hz, 1H), 7.47 (br dd, J = 1.22, 8.30 Hz, 1H), 7.42 (br s, 1H), 6.95 (br dd, J = 4.52, 8.42 Hz, 2H), 4.14 (br d, J = 13.18 Hz, 2H), 3.90-3.97 (m, 2H), 3.45 (br t, J = 11.35 Hz, 2H), 2.93 (br t, J = 6.47 Hz, 2H), 2.02-2.09 (m, 2H), 1.86-1.97 (m, 2H), 1.41 (br d, J = 13.43 Hz, 2H) | 394.4 |
| 177 | 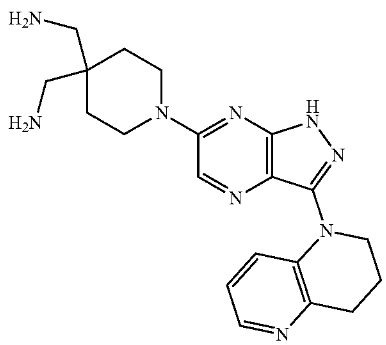 [SMILES: NCC1(CN)CCN(c2cnc3c(N4CCCc5ncccc54)n[nH]c3n2)CC1] | ¹H-NMR (400 MHz, DMSO-d₆) δ 12.99 (s, 1H), 8.39-8.41 (m, 1H), 8.20 (br s, 5H), 8.11-8.16 (m, 2H), 7.58 (dd, J = 5.56, 8.84 Hz, 1H), 3.76 (br s, 4H), 3.23 (t, J = 6.44 Hz, 2H), 3.09 (br d, J = 5.56 Hz, 3H), 2.14 (quin, J = 5.94 Hz, 2H), 1.65 (br d, J = 5.05 Hz, 4H) | 394.5 |
| 178 | 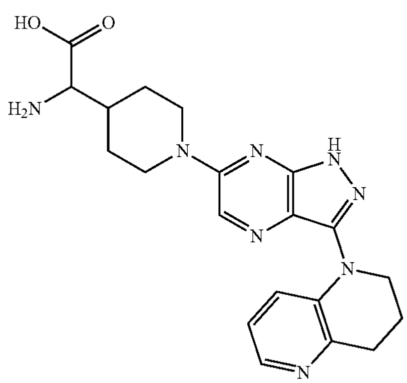 [SMILES: NC(C(=O)O)C1CCN(c2cnc3c(N4CCCc5ncccc54)n[nH]c3n2)CC1] | ¹H-NMR (400 MHz, DMSO-d₆) δ 13.02 (br s, 1H), 8.49 (br s, 3H), 8.40 (s, 1H), 8.14 (d, J = 7.6 Hz, 2H), 7.61-7.57 (m, 1H), 4.59-4.57 (m, 2H), 4.05-4.02 (m, 2H), 3.85-3.83 (m, 1H), 3.28-3.25 (m, 2H), 3.01-2.94 (m, 2H), 2.25-2.22 (m, 1H), 2.18-2.14 (m, 2H), 1.88-1.85 (m, 1H), 1.76-1.71 (m, 1H), 1.56-1.48 (m, 1H), 1.40-1.32 (m, 1H) | 409.1 |
| 179 | 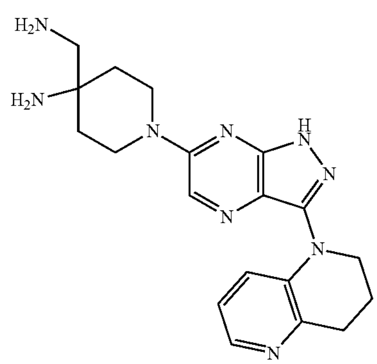 [SMILES: NCC1(N)CCN(c2cnc3c(N4CCCc5ncccc54)n[nH]c3n2)CC1] | ¹H-NMR (400 MHz, DMSO-d₆) δ 12.97 (br s, 1H), 8.80 (br s, 3H), 8.58 (br s, 3H), 8.41 (s, 1H), 8.11 (br d, J = 5.13 Hz, 1H), 7.94-8.07 (m, 1H), 7.39-7.53 (m, 2H), 3.95-4.05 (m, 4H), 3.68-3.78 (m, 2H), 3.16 (br t, J = 6.23 Hz, 2H), 2.09-2.17 (m, 2H), 1.95-2.04 (m, 2H), 1.84-1.93 (m, 2H) | 380.5 |

TABLE 1-continued

| Cmpd. No. | Structure | ¹H-NMR | Mass Spec. (M + H)⁺ |
|---|---|---|---|
| 180 | 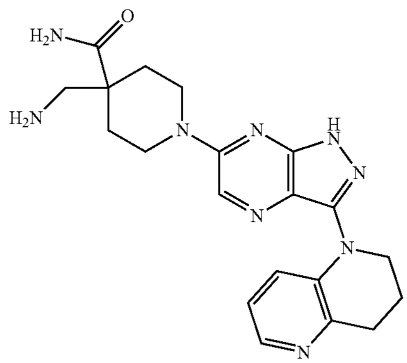 [SMILES: NCC1(C(N)=O)CCN(c2cnc3c(N4CCCc5ncccc54)n[nH]c3n2)CC1] | ¹H-NMR (400 MHz, DMSO-d₆) δ 12.55 (br s, 1H), 8.24-8.30 (m, 1H), 7.88 (dd, J = 1.34, 4.52 Hz, 1H), 7.40-7.50 (m, 2H), 6.95 (td, J = 4.27, 8.54 Hz, 2H), 6.54 (br s, 1H), 4.03-4.18 (m, 2H), 3.90-3.98 (m, 2H), 3.15-3.25 (m, 2H), 3.09-3.25 (m, 1H), 2.92 (t, J = 6.47 Hz, 2H), 2.61 (s, 2H), 1.96-2.10 (m, 4H), 1.37-1.48 (m, 2H) | 408.5 |
| 181 | 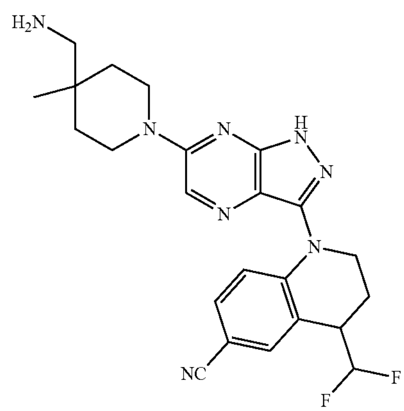 [SMILES: CC1(CN)CCN(c2cnc3c(N4CCC(C(F)F)c5cc(C#N)ccc54)n[nH]c3n2)CC1] | ¹H-NMR (400 MHz, DMSO-d₆) δ 8.37 (s, 1H), 8.30 (s, 1H), 7.60 (s, 1H), 7.36 (dd, J = 1.95, 8.79 Hz, 1H), 6.87 (d, J = 8.79 Hz, 1H), 6.36 (dt, J = 3.66, 55.91 Hz, 1H), 3.90-4.04 (m, 2H), 3.75-3.90 (m, 2H), 3.36-3.50 (m, 3H), 2.67 (br s, 2H), 2.16-2.26 (m, 1H), 2.02-2.15 (m, 1H), 1.36-1.62 (m, 4H), 1.03 (s, 3H) | 453.2 |
| 182 | 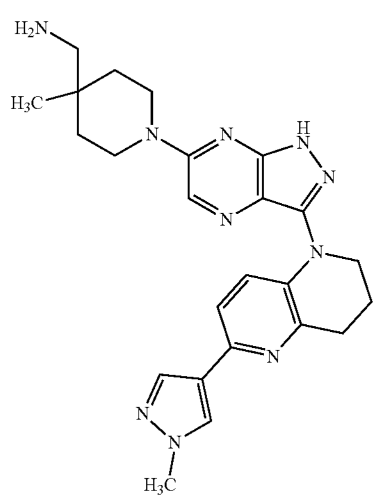 [SMILES: Cn1cc(-c2ccc3c(n2)CCCN3c2n[nH]c3nc(N4CCC(C)(CN)CC4)cnc23)cn1] | ¹H-NMR (400 MHz, DMSO-d₆) δ 8.32 (s, 1H), 8.27 (s, 1H), 8.06 (s, 1H), 7.82 (s, 1H), 7.50 (d, J = 8.54 Hz, 1H), 7.22 (d, J = 8.79 Hz, 1H), 3.91-3.99 (m, 4H), 3.83 (s, 3H), 3.39-3.48 (m, 2H), 2.92 (t, J = 6.47 Hz, 2H), 2.71 (s, 2H), 2.05 (quin, J = 5.98 Hz, 2H), 1.47-1.57 (m, 2H), 1.35-1.46 (m, 2H), 1.05 (s, 3H) | 459.3 |

TABLE 1-continued
| Cmpd. No. | Structure | ¹H-NMR | Mass Spec. (M + H)⁺ |
|---|---|---|---|
| 183 | 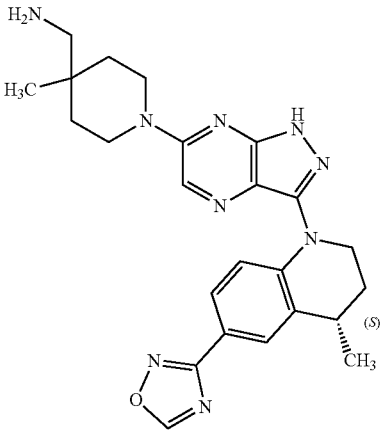 | ¹H-NMR (400 MHz, DMSO-d₆) δ 9.47 (s, 1H), 8.37 (s, 1H), 8.27 (s, 1H), 7.74-7.80 (m, 1H), 7.53 (dd, J = 1.95, 8.54 Hz, 1H), 6.94 (d, J = 8.79 Hz, 1H), 3.91-4.00 (m, 2H), 3.80-3.90 (m, 2H), 3.37-3.49 (m, 2H), 2.97-3.09 (m, 1H), 2.67 (s, 2H), 2.03-2.15 (m, 1H), 1.77 (qd, J = 6.37, 10.93 Hz, 1H), 1.45-1.55 (m, 2H), 1.36-1.44 (m, 2H), 1.33 (d, J = 7.08 Hz, 3H), 1.03 (s, 3H) | 460.3 |
| 184 | 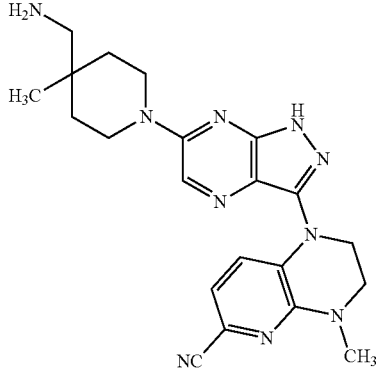 [SMILES: CN1CCN(c2n[nH]c3nc(N4CCC(C)(CN)CC4)cnc23)c2ccc(C#N)nc21] | ¹H-NMR (400 MHz, DMSO-d₆) δ 8.37 (s, 1H), 8.28 (s, 1H), 6.90-6.96 (m, 1H), 6.81-6.89 (m, 2H), 3.91-4.02 (m, 4H), 3.44 (br t, J = 10.01 Hz, 2H), 3.36-3.40 (m, 2H), 2.90 (s, 3H), 2.66 (s, 2H), 1.45-1.55 (m, 2H), 1.35-1.43 (m, 2H), 1.03 (s, 3H) | 418.3 |
| 185 | 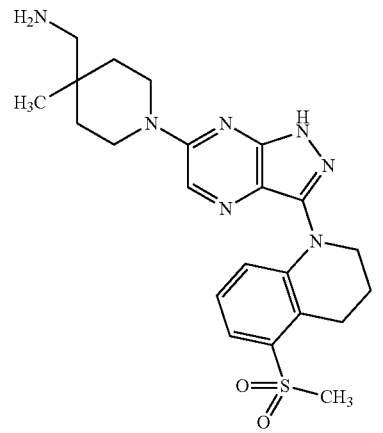 [SMILES: CC1(CN)CCN(c2cnc3c(N4CCCc5c4cccc5S(C)(=O)=O)n[nH]c3n2)CC1] | ¹H-NMR (400 MHz, DMSO-d₆) δ 8.34 (s, 1H), 8.25 (s, 1H), 7.30-7.36 (m, 1H), 7.10-7.16 (m, 2H), 3.91-3.99 (m, 2H), 3.83 (t, J = 5.74 Hz, 2H), 3.39-3.48 (m, 2H), 3.21 (s, 3H), 3.15-3.20 (m, 2H), 2.70 (s, 2H), 2.00 (quin, J = 6.29 Hz, 2H), 1.45-1.55 (m, 2H), 1.37-1.45 (m, 2H), 1.04 (s, 3H) | 456.2 |

TABLE 1-continued

| Cmpd. No. | Structure | ¹H-NMR | Mass Spec. (M + H)⁺ |
|---|---|---|---|
| 186 | 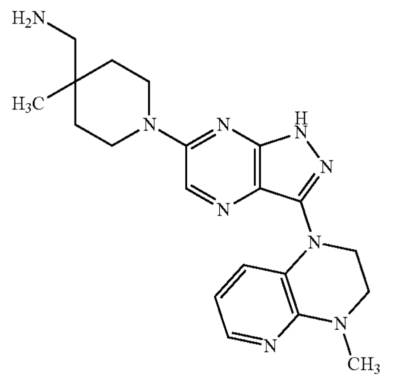 [SMILES: CN1CCN(c2n[nH]c3nc(N4CCC(C)(CN)CC4)cnc23)c2cccnc21] | ¹H-NMR (400 MHz, DMSO-d₆) δ 8.27 (s, 1H), 8.03-8.16 (m, 1H), 7.51-7.62 (m, 1H), 7.36 (br d, J = 7.81 Hz, 1H), 6.40-6.51 (m, 1H), 4.01-4.09 (m, 2H), 3.91-4.01 (m, 2H), 3.50-3.57 (m, 2H), 3.42 (br s, 2H), 3.00-3.14 (m, 3H), 2.71-2.80 (m, 2H), 1.48-1.59 (m, 2H), 1.38-1.48 (m, 2H), 1.07 (s, 3H) | 394.5 |
| 187 | 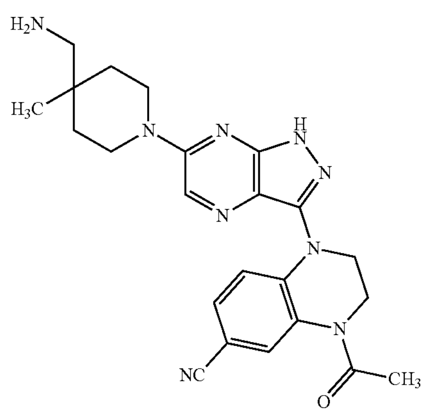 [SMILES: CC(=O)N1CCN(c2n[nH]c3nc(N4CCC(C)(CN)CC4)cnc23)c2ccc(C#N)cc21] | ND | 446.5 |
| 188 | 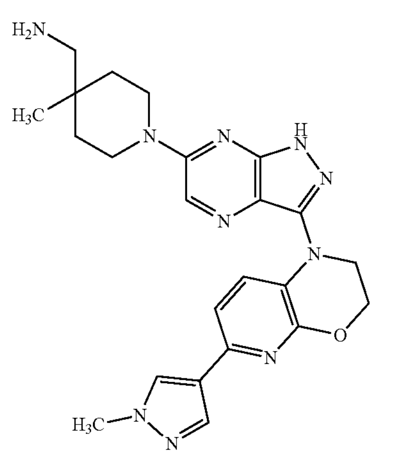 [SMILES: Cn1cc(-c2ccc3c(n2)OCCN3c2n[nH]c3nc(N4CCC(C)(CN)CC4)cnc23)cn1] | ND | 461.6 |

TABLE 1-continued

| Cmpd. No. | Structure | ¹H-NMR | Mass Spec. (M + H)⁺ |
|---|---|---|---|
| 189 | 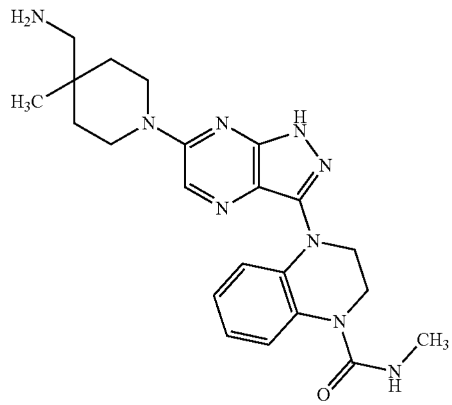 [SMILES: CNC(=O)N1CCN(c2n[nH]c3nc(N4CCC(C)(CN)CC4)cnc23)c2ccccc21] | ¹H-NMR (400 MHz, DMSO-d₆) δ 8.39 (s, 1H), 8.25 (s, 1H), 7.31 (br d, J = 7.93 Hz, 1H), 7.13 (br d, J = 8.24 Hz, 1H), 6.81-6.89 (m, 1H), 6.72-6.79 (m, 1H), 3.87-4.01 (m, 4H), 3.77 (br t, J = 4.96 Hz, 2H), 3.52 (br s, 2H), 3.35-3.47 (m, 2H), 2.63 (s, 3H), 1.45-1.53 (m, 2H), 1.29-1.44 (m, 2H), 1.02 (s, 3H) | 436.5 |
| 190 | 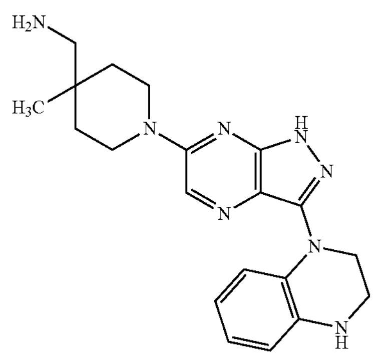 [SMILES: CC1(CN)CCN(c2cnc3c(N4CCNc5ccccc54)n[nH]c3n2)CC1] | ¹H-NMR (400 MHz, DMSO-d₆) δ 8.35 (s, 1H) 8.18 (s, 1H) 6.94-7.03 (m, 1H) 6.58-6.65 (m, 1H) 6.52 (dd, J = 7.93, 1.37 Hz, 1H) 6.32-6.40 (m, 1H) 3.93 (dt, J = 13.65, 4.46 Hz, 2H) 3.86-3.89 (m, 2H) 3.40 (ddd, J = 13.38, 9.95, 3.20 Hz, 2H) 3.25-3.34 (m, 2H) 2.69 (s, 2H) 1.44-1.52 (m, 2H) 1.35-1.43 (m, 2H) 1.03 (s, 3H) | 379.4 |
| 191 | 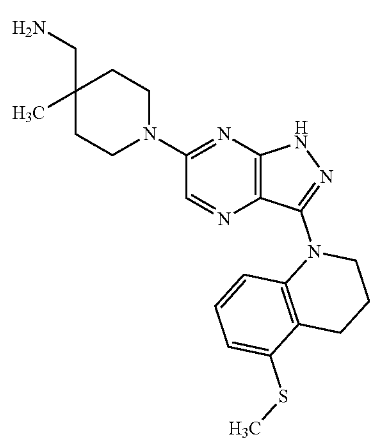 [SMILES: CSc1cccc2c1CCCN2c1n[nH]c2nc(N3CCC(C)(CN)CC3)cnc12] | ¹H-NMR (400 MHz, CD₃OD) δ 8.41 (s, 1H), 7.20~7.24 (m, 1H), 7.06~7.13 (m, 2H), 4.21~4.27 (m, 4H), 3.63~3.68 (m, 2H), 2.95 (s, 2H), 2.82~2.86 (m, 2H), 2.51 (m, 3H), 2.11~2.15 (m, 2H), 1.66~1.70 (m, 4H), 1.24 (s, 3H) | 424.2 |

TABLE 1-continued

| Cmpd. No. | Structure | ¹H-NMR | Mass Spec. (M + H)⁺ |
|---|---|---|---|
| 192 | 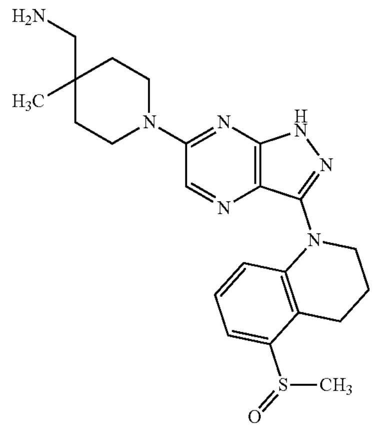 [SMILES: CS(=O)c1cccc2c1CCCN2c1n[nH]c2nc(N3CCC(C)(CN)CC3)cnc12] | ND | 440.2 |
| 193 | 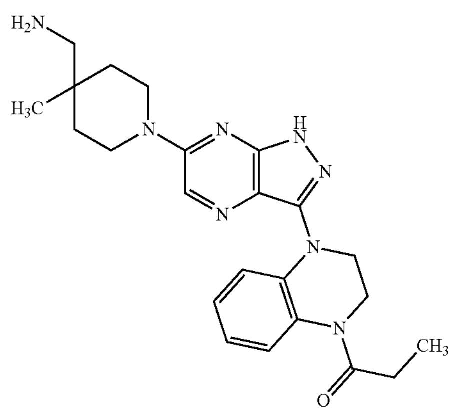 [SMILES: CCC(=O)N1CCN(c2n[nH]c3nc(N4CCC(C)(CN)CC4)cnc23)c2ccccc21] | ¹H-NMR (500 MHz, DMSO-d₆) δ 8.34 (s, 1H) 8.20 (s, 1H) 7.31 (br d, J = 5.19 Hz, 1H) 7.01 (br d, J = 8.08 Hz, 1H) 6.93 (br s, 1H) 6.74-6.83 (m, 1H) 3.40 (ddd, J = 13.35, 9.91, 3.13 Hz, 2H) 2.63 (s, 2H) 2.49-2.55 (m, 8H) 1.43-1.49 (m, 2H) 1.34-1.41 (m, 2H) 0.89-1.07 (m, 6H) | 435.6 |
| 194 | 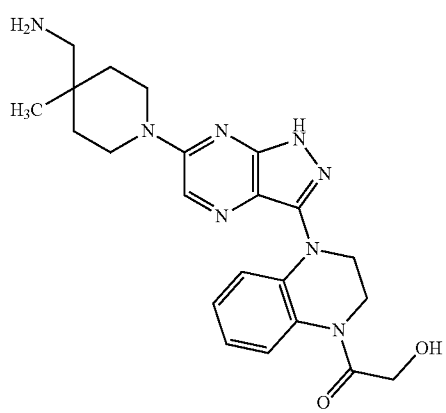 [SMILES: CC1(CN)CCN(c2cnc3c(N4CCN(C(=O)CO)c5ccccc54)n[nH]c3n2)CC1] | ND | 437.5 |

TABLE 1-continued
| Cmpd. No. | Structure | ¹H-NMR | Mass Spec. (M + H)⁺ |
|---|---|---|---|
| 195 | 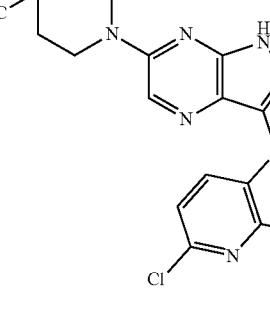 | ¹H-NMR (400 MHz, DMSO-d₆) δ 8.36 (s, 1H) 8.22 (s, 1H) 7.16-7.38 (m, 1H) 6.41 (d, J = 8.06 Hz, 1H) 3.84-4.05 (m, 4H) 3.48-3.55 (m, 2H) 3.31-3.47(m, 2H) 3.02 (s, 3H) 2.53-2.80 (m, 2H) 1.30-1.58 (m, 4H) 0.91-1.14 (m, 3H) | 428.5 |
| 196 | 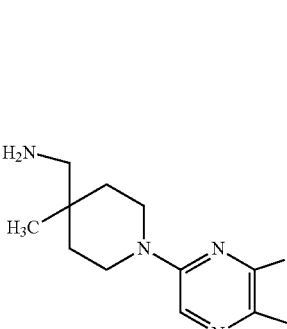 | ¹H-NMR (400 MHz, DMSO-d₆) δ 12.78 (s, 1H), 8.36 (s, 1H), 8.03 (br, 3H),7.85-7.87 (d, J = 3.2 Hz, 1H), 7.73-7.75 (d, J = 8.8 Hz, 1H), 7.68-7.70 (d, J = 3.2 Hz, 1H), 7.55-7.58 (d, J = 8.4 Hz, 2H), 3.94-4.09 (m, 4H), 3.47-3.52 (m, 2H), 3.07-3.14 (m, 1H), 3.77-3.80 (m, 2H), 2.21-2.28 (m, 1H), 1.83-1.91 (m, 1H), 1.63-1.61 (m, 2H), 1.43-1.48 (m, 5H), 1.10 (s, 3H) | 476.2 |
| 197 | 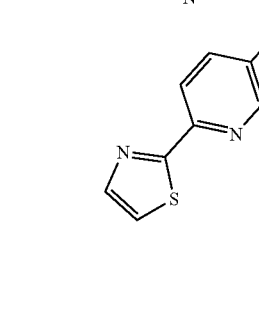 | ¹H-NMR (400 MHz, DMSO-d₆) δ 12.77 (s, 1H), 8.36 (s, 1H), 7.93 (br, 3H), 7.84-7.86 (d, J = 3.6 Hz, 1H), 7.72-7.75 (d, J = 8.8 Hz, 1H), 7.67-7.69 (d, J = 3.6 Hz, 1H), 7.55-7.58 (d, J = 8.4 Hz, 2H), 3.94-4.09 (m, 4H), 3.47-3.52 (m, 2H), 3.07-3.14 (m, 1H), 3.77-3.80 (m, 2H), 2.21-2.28 (m, 1H), 1.83-1.91 (m, 1H), 1.63-1.61 (m, 2H), 1.43-1.48 (m, 5H), 1.10 (s, 3H) | 476.0 |

TABLE 1-continued

| Cmpd. No. | Structure | ¹H-NMR | Mass Spec. (M + H)⁺ |
|---|---|---|---|
| 198 | 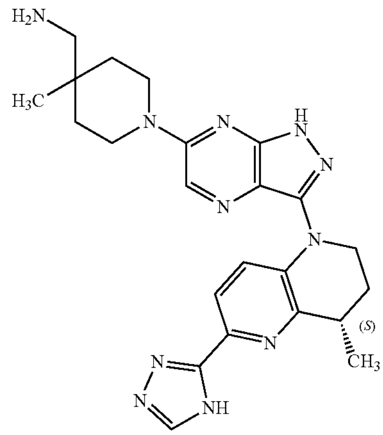 | ¹H-NMR (400 MHz, CD₃OD) δ 8.24 (s, 1H), 8.13 (s, 1H), 7.66~7.69 (m, 1H), 7.31~7.34 (m, 1H), 3.97~4.13 (m, 4H), 3.50~3.66 (m, 3H), 2.66 (s, 2H), 2.30~2.38 (m, 1H), 1.95~2.06 (m, 1H), 1.30~1.66 (m, 7H), 1.13 (s, 3H) | 460.2 |
| 199 | 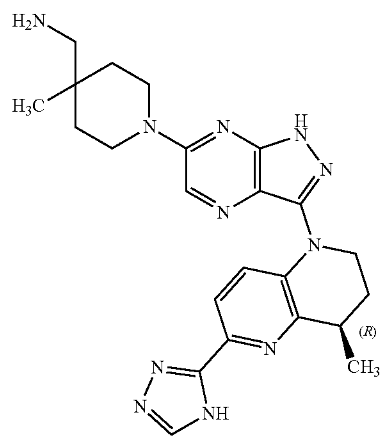 | ¹H-NMR (400 MHz, CD₃OD) δ 8.90 (s, 1H), 8.34 (s, 1H), 8.05~8.08 (m, 1H), 7.90~7.93 (m, 1H), 4.08~4.21 (m, 4H), 3.57~3.63 (m, 3H), 2.95 (s, 2H), 2.36~2.41 (m, 1H), 2.11~2.16 (m, 1H), 1.57-1.69 (m, 7H), 1.24 (s, 3H) | 460.2 |
| 200 | 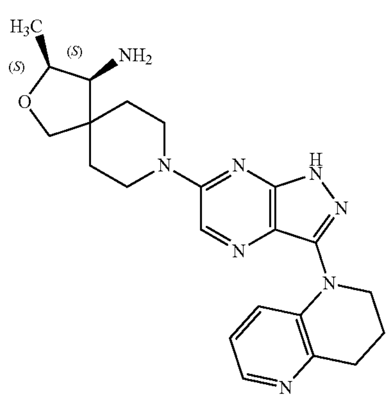 | ¹H NMR (400 MHz, CD₃OD) δ 8.24 (s, 1H), 7.88 (d, J = 4.8 Hz, 1H), 7.33 (d, J = 8.4 Hz, 1H), 7.23-7.00 (m, 1H), 4.28-4.19 (m, 3H), 3.97-3.91 (m, 3H), 3.76 (d, J = 8.8 Hz, 1H), 3.48-3.40 (m 2H), 3.08-3.04 (m, 3H), 2.23-2.20 (m, 2H), 1.88-1.73 (m, 4H), 1.25 (d, J = 6.4 Hz, 3H). | 421.3 |

TABLE 1-continued

| Cmpd. No. | Structure | ¹H-NMR | Mass Spec. (M + H)⁺ |
|---|---|---|---|
| 201 | 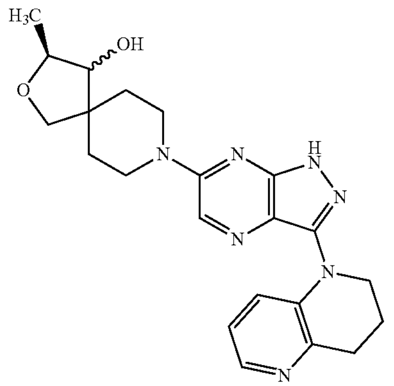 [SMILES: C[C@@H]1OCC2(CCN(c3cnc4c(N5CCCc6ncccc65)n[nH]c4n3)CC2)C1O] | ¹H-NMR (400 MHz, DMSO-d₆) δ 12.59 (s, 1H), 8.30 (s, 1H), 7.89 (d, J = 4.8 Hz, 1H), 7.48 (d, J = 7.2 Hz, 1H), 6.98-6.95 (m, 1H), 4.83 (d, J = 6.0 Hz, 1H), 4.08-3.52 (m, 11H), 2.94 (t, J = 6.4 Hz, 2H), 1.59-1.24 (m, 4H), 1.10 (d, J = 6.0 Hz, 3H) | 422.0 |
| 202 | 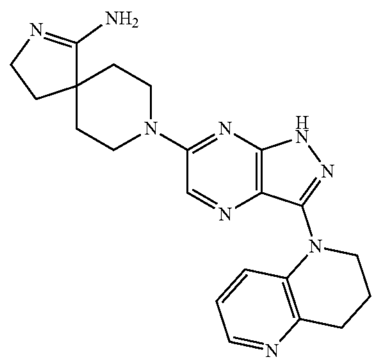 [SMILES: NC1=NCCC12CCN(c1cnc3c(N4CCCc5ncccc54)n[nH]c3n1)CC2] | ¹H-NMR (400 MHz, CD₃OD) δ 8.38 (s, 1H), 8.08~8.06 (m, 2H), 7.61~7.57 (m, 1H), 4.73~4.70 (m, 2H), 4.12~4.09 (m, 2H), 3.78~3.74 (m, 2H), 3.31~3.20 (m, 4H), 2.46~2.43 (m, 4H), 2.32~2.30 (m, 2H), 189~1.86 (m, 2H) | 404.0 |
| 203 | 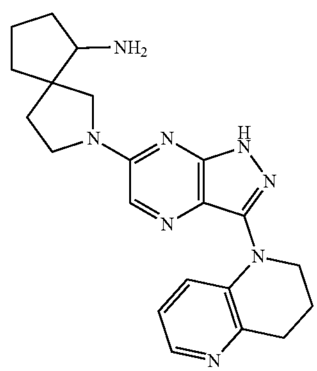 [SMILES: NC1CCCC12CCN(c1cnc3c(N4CCCc5ncccc54)n[nH]c3n1)C2] | ¹H-NMR (400 MHz, CDCl₃) δ 11.65 (br, 1H), 8.03 (d, J = 3.6 Hz, 1H), 7.90 (s, 1H), 7.54 (d, J = 7.6 Hz, 1H), 6.90-6.96 (m, 1H), 3.95-4.10 (m, 2H), 3.60-3.90 (m, 3H), 3.40-3.50 (m, 1H), 3.00-3.20 (m, 3H), 1.95-2.25 (m, 4H), 1.75-1.90 (m, 3H), 1.40-1.70 (m, 4H) | 391.2 |
| 204 | 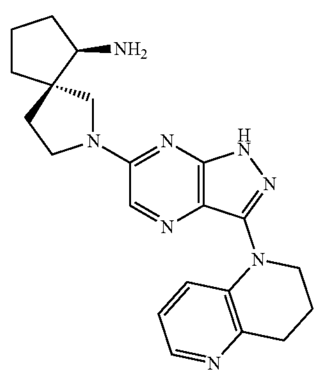 [SMILES: N[C@@H]1CCC[C@]12CCN(c1cnc3c(N4CCCc5ncccc54)n[nH]c3n1)C2] | ¹H-NMR (400 MHz, CDCl₃) δ 8.03 (d, J = 4.4 Hz, 1H), 7.86 (s, 1H), 7.61 (d, J = 8.0 Hz, 1H), 6.90-6.96 (m, 1H), 4.04-4.10 (m, 2H), 3.60-3.90 (m, 2H), 3.35-3.55 (m, 2H), 3.00-3.25 (m, 3H), 1.95-2.25 (m, 4H), 1.60-1.90 (m, 4H), 1.25-1.55 (m, 2H) | 391.2 |

TABLE 1-continued

| Cmpd. No. | Structure | ¹H-NMR | Mass Spec. (M + H)⁺ |
|---|---|---|---|
| 205 | 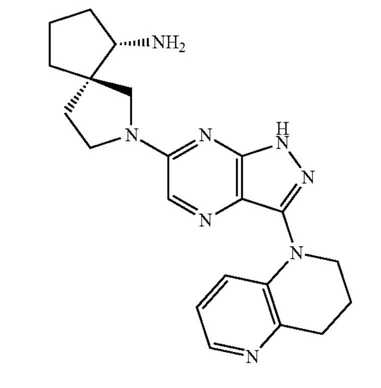 [SMILES: N[C@H]1CCC[C@@]12CCN(c1cnc3c(N4CCCc5ncccc54)n[nH]c3n1)C2] | ¹HNMR (400 MHz, CDCl₃) δ 11.14 (br, 1H), 8.03 (d, J = 4.4 Hz, 1H), 7.86 (s, 1H), 7.61 (d, J = 8.0 Hz, 1H), 6.91-6.96 (m, 1H), 4.00-4.10 (m, 2H), 3.75-3.85 (m, 1H), 3.60-3.70 (m, 1H), 3.40-3.55 (m, 2H), 3.15-3.25 (m, 1H), 3.10-3.10 (m, 2H), 1.95-2.25 (m, 4H), 1.60-1.90 (m, 4H), 1.25-1.55 (m, 2H) | 391.2 |
| 206 | 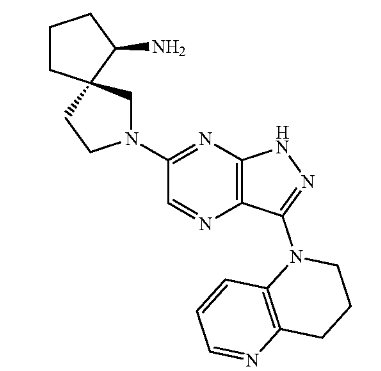 [SMILES: N[C@@H]1CCC[C@@]12CCN(c1cnc3c(N4CCCc5ncccc54)n[nH]c3n1)C2] | ¹H-NMR (400 MHz, CDCl₃) δ 11.65 (br, 1H), 8.03 (d, J = 3.6 Hz, 1H), 7.90 (s, 1H), 7.54 (d, J = 7.6 Hz, 1H), 6.90-6.96 (m, 1H), 3.95-4.10 (m, 2H), 3.60-3.90 (m, 3H), 3.40-3.50 (m, 1H), 3.00-3.20 (m, 3H), 1.95-2.25 (m, 4H), 1.75-1.90 (m, 3H), 1.40-1.70 (m, 4H) | 391.2 |
| 207 | 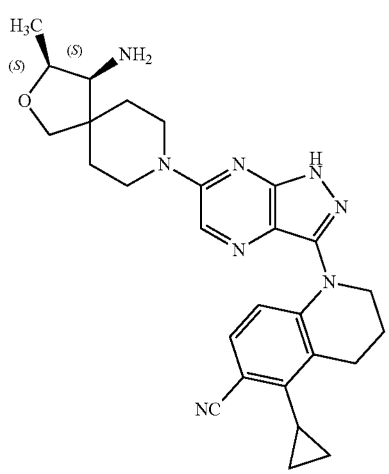 | ¹H-NMR (500 MHz, DMSO-d6) δ 12.79 (s, 1H), 8.31 (s, 1H), 7.19 (d, J = 8.69 Hz, 1H), 6.69-6.81 (m, 1H), 4.01-4.11 (m, 1H), 3.86-4.00 (m, 2H), 3.77-3.85 (m, 2H), 3.67 (d, J = 8.54 Hz, 1H), 3.46-3.54 (m, 2H), 3.38-3.46 (m, 1H), 2.97 (br t, J = 6.33 Hz, 2H), 2.90 (d, J = 5.19 Hz, 1H), 1.97-2.09 (m, 2H), 1.91 (ddd, J = 14.19, 8.39, 5.80 Hz, 1H), 1.76 (ddd, J = 13.19, 9.38, 3.51 Hz, 1H), 1.65 (ddd, J = 13.16, 9.27, 3.66 Hz, 1H), 1.43-1.58 (m, 2H), 0.99-1.13 (m, 5H), 0.65-0.78 (m, 2H) | 485.6 |

TABLE 1-continued

| Cmpd. No. | Structure | ¹H-NMR | Mass Spec. (M + H)⁺ |
|---|---|---|---|
| 208 | 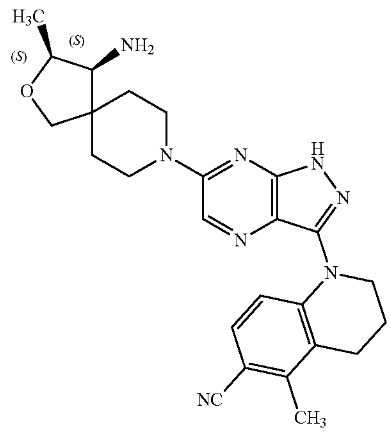 | ¹H-NMR (400 MHz, DMSO-d6) δ 12.62-12.88 (m, 1H), 8.32 (s, 1H), 8.23 (s, 1H), 7.22 (d, J = 8.79 Hz, 1H), 6.60-6.87 (m, 1H), 4.03-4.14 (m, 1H), 3.90-4.02 (m, 2H), 3.75-3.87 (m, 2H), 3.61-3.73 (m, 1H), 3.26-3.55 (m, 3H), 2.94 (d, J = 5.13 Hz, 1H), 2.75 (br t, J = 6.35 Hz, 2H), 2.36 (s, 3H), 1.92-2.14 (m, 2H), 1.76 (ddd, J = 13.18, 9.52, 3.42 Hz, 1H), 1.62-1.70 (m, 1H), 1.44-1.61 (m, 2H), 1.08 (d, J = 6.59 Hz, 3H) | 459.6 |
| 209 | 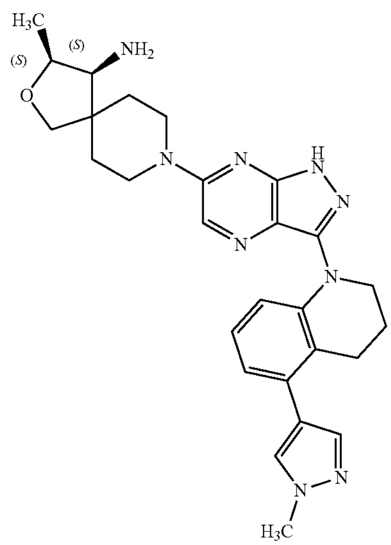 | ¹H-NMR (400 MHz, DMSO-d6) δ 12.50 (br s, 1H), 8.26 (s, 1H), 7.86 (s, 1H), 7.58 (s, 1H), 6.80-6.95 (m, 2H), 6.68-6.78 (m, 1H), 4.01-4.14 (m, 1H), 3.92 (td, J = 9.22, 4.03 Hz, 2H), 3.88 (s, 3H), 3.80-3.86 (m, 2H), 3.68 (br d, J = 8.30 Hz, 2H), 3.43-3.53 (m, 2H), 2.92 (br d, J = 5.13 Hz, 1H), 2.74-2.86 (m, 2H), 1.86-1.99 (m, 2H), 1.71-1.82 (m, 1H), 1.59-1.69 (m, 1H), 1.40-1.59 (m, 2H), 1.07 (d, J = 6.35 Hz, 3H) | 500.6 |
| 210 | 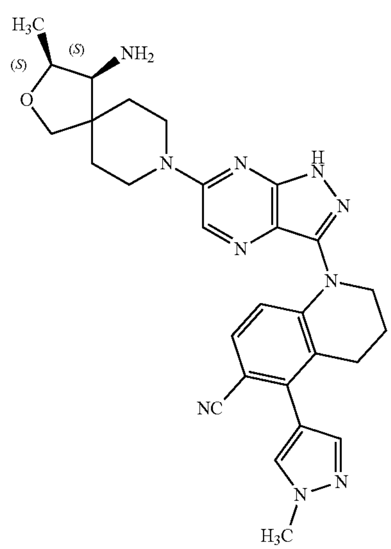 | ¹H-NMR (400 MHz, DMSO-d6) δ 12.76-12.89 (m, 1H), 8.33 (s, 1H), 7.93 (s, 1H), 7.54-7.62 (m, 1H), 7.27-7.38 (m, 1H), 6.80 (d, J = 8.79 Hz, 1H), 3.99-4.15 (m, 1H), 3.89-3.95 (m, 5H), 3.76-3.85 (m, 2H), 3.62-3.71 (m, 2H), 3.38-3.57 (m, 2H), 2.86-2.98 (m, 1H), 2.64-2.75 (m, 2H), 1.86-1.99 (m, 2H), 1.71-1.83 (m, 1H), 1.61-1.71 (m, 1H), 1.44-1.59 (m, 2H), 1.02-1.14 (m, 3H) | 525.8 |

TABLE 1-continued

| Cmpd. No. | Structure | ¹H-NMR | Mass Spec. (M + H)⁺ |
|---|---|---|---|
| 211 | 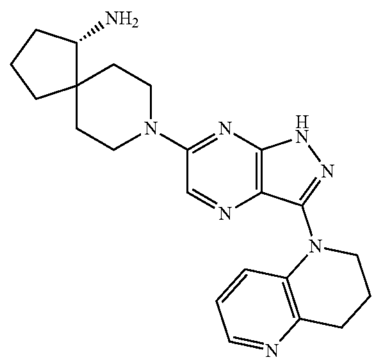 [SMILES: N[C@H]1CCCC12CCN(c1cnc3c(N4CCCc5ncccc54)n[nH]c3n1)CC2] | ¹H-NMR (400 MHz, CDCl₃) δ 12.54 (br s, 1H), 8.28 (s, 1H), 7.88 (dd, J = 1.34, 4.52 Hz, 1H), 7.47 (dd, J = 1.22, 8.30 Hz, 1H), 6.95 (dd, J = 4.64, 8.30 Hz, 1H), 4.15-4.29 (m, 2H), 3.89-3.98 (m, 2H), 3.09-3.23 (m, 2H), 2.93 (t, J = 6.47 Hz, 2H), 2.64-2.72 (m, 1H), 2.02-2.10 (m, 2H), 1.75-1.90 (m, 2H), 1.46-1.65 (m, 4H), 1.16-1.42 (m, 4H) | 405.3 |
| 212 | 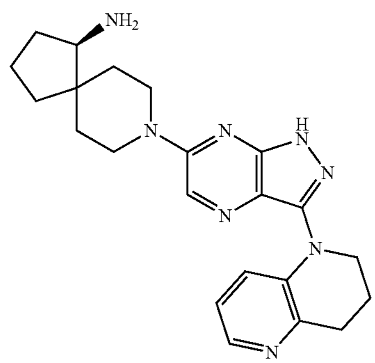 [SMILES: N[C@@H]1CCCC12CCN(c1cnc3c(N4CCCc5ncccc54)n[nH]c3n1)CC2] | ¹H-NMR (400 MHz, DMSO-d6) δ 12.54 (br s, 1H), 8.28 (s, 1H), 7.88 (dd, J = 1.22, 4.39 Hz, 1H), 7.47 (dd, J = 1.22, 8.30 Hz, 1H), 6.95 (dd, J = 4.52, 8.42 Hz, 1H), 4.17-4.28 (m, 2H), 3.90-3.97 (m, 2H), 3.08-3.22 (m, 2H), 2.92 (t, J = 6.47 Hz, 2H), 2.63-2.71 (m, 1H), 2.06 (td, J = 6.20, 11.78 Hz, 2H), 1.75-1.88 (m, 2H), 1.46-1.68 (m, 4H), 1.15-1.43 (m, 4H) | 405.3 |
| 213 | 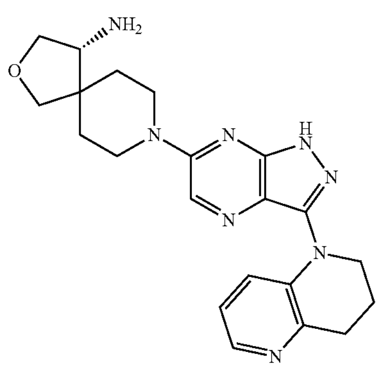 [SMILES: N[C@H]1COCC12CCN(c1cnc3c(N4CCCc5ncccc54)n[nH]c3n1)CC2] | ¹H-NMR (400 MHz, DMSO-d6) δ 12.51-12.61 (m, 1H), 8.30 (s, 1H), 7.89 (dd, J = 1.22, 4.64 Hz, 1H), 7.47 (dd, J = 1.22, 8.30 Hz, 1H), 6.95 (dd, J = 4.64, 8.30 Hz, 1H) 4.04-4.17 (m 2H) 3.90-3.99 (m, 3H), 3.71 (d, J = 8.54 Hz, 1H), 3.59 (d, J = 8.54 Hz, 1H), 3.24-3.30 (m, 2H), 3.03 (br t, J = 6.23 Hz, 1H), 2.93 (t, J = 6.47 Hz, 2H), 2.06 (td, 1 = 6.20, 11.78 Hz, 2H), 1.53-1.74 (m, 3H), 1.42 (br dd, J = 4.52, 8.18 Hz, 2H) | 407.2 |
| 214 | 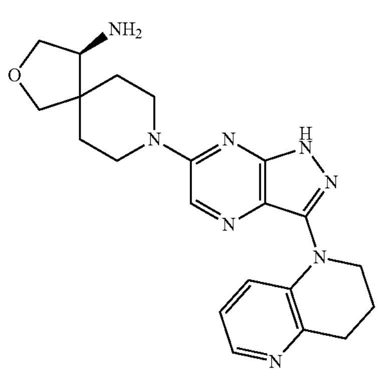 [SMILES: N[C@@H]1COCC12CCN(c1cnc3c(N4CCCc5ncccc54)n[nH]c3n1)CC2] | ¹H-NMR (400 MHz, DMSO-d6) δ 8.37 (s, 1H), 8.10 (dd, J = 1.10, 5.49 Hz, 1H), 8.02 (d, J = 8.06 Hz, 1H), 7.51 (dd, J = 5.49, 8.67 Hz, 1H), 4.14-4.29 (m, 2H), 4.08 (dd, J = 5.98, 10.38 Hz, 1H), 3.97-4.03 (m, 2H), 3.83-3.89 (m, 1H), 3.75-3.81 (m, 1H), 3.69 (dd, J = 3.17, 10.50 Hz, 1H), 3.47-3.51 (m, 1H), 3.18-3.36 (m, 2H), 3.15 (t, J = 6.47 Hz, 2H), 2.09-2.17 (m, 2H), 1.57-1.76 (m, 4H) | 407.2 |

TABLE 1-continued

| Cmpd. No. | Structure | ¹H-NMR | Mass Spec. (M + H)⁺ |
|---|---|---|---|
| 215 | 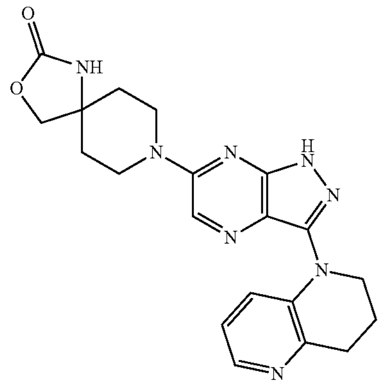 [SMILES: O=C1NC2(CCN(c3cnc4c(N5CCCc6ncccc65)n[nH]c4n3)CC2)CO1] | ND | 407.3 |
| 216 | 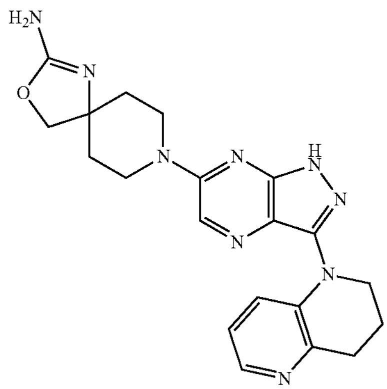 [SMILES: NC1=NC2(CCN(c3cnc4c(N5CCCc6ncccc65)n[nH]c4n3)CC2)CO1] | ¹H-NMR (400 MHz, methanol-d₄) δ 8.34 (s, 1H), 8.03 (d, J = 3.2 Hz, 1H), 8.01 (s, 1H), 7.55-7.52 (m, 1H), 4.72 (s, 2H), 4.13-4.05 (m, 4H), 3.72-3.67 (m, 2H), 3.25 (t, J = 6.4 Hz, 2H), 2.31-2.26 (m, 2H), 2.05-2.00 (m, 2H) | 406.0 |
| 217 | 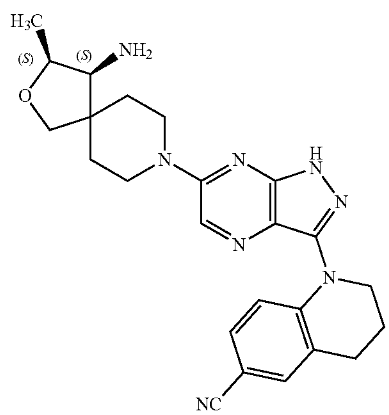 | ¹H-NMR (400 MHz, DMSO-d₆) δ 12.83 (br s, 1H), 8.33 (s, 1H), 8.27 (s, 1H), 7.44 (d, J = 1.71 Hz, 1H), 7.27 (dd, J = 1.95, 8.79 Hz, 1H), 6.90 (d, J = 8.79 Hz, 1H), 4.06 (quin, J = 6.10 Hz, 1H), 3.90-3.98 (m, 2H), 3.83-3.90 (m, 2H), 3.68 (d, J = 8.54 Hz, 1H), 3.38-3.53 (m, 3H), 3.27 (br s, 4H), 2.91 (d, J = 5.13 Hz, 1H), 2.84 (br t, J = 6.23 Hz, 2H), 2.00 (td, J = 6.01, 11.66 Hz, 2H), 1.76 (ddd, J = 3.42, 9.58, 13.12 Hz, 1H), 1.61-1.69 (m, 1H), 1.44-1.58 (m, 2H), 1.07 (d, J = 6.59 Hz, 2H) | |
| 218 | 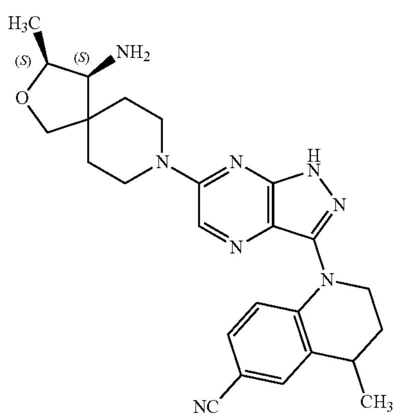 | ¹H-NMR (400 MHz, DMSO-d₆) δ 12.84 (br s, 1H), 8.33 (s, 1H), 7.53 (d, J = 1.46 Hz, 1H), 7.27 (dd, J = 1.95, 8.79 Hz, 1H), 6.88 (d, J = 8.79 Hz, 1H), 4.06 (td, J = 6.13, 11.90 Hz, 1H), 3.83-3.99 (m, 3H), 3.67 (d, J = 8.54 Hz, 1H), 3.38-3.55 (m, 3H), 3.30 (br s, 5H), 3.00 (br dd, J = 6.23, 12.08 Hz, 1H), 2.91 (d, J = 5.13 Hz, 1H), 2.00-2.11 (m, 1H), 1.72-1.83 (m, 2H), 1.65 (ddd, J = 3.66, 9.22, 13.00 Hz, 1H), 1.43-1.59 (m, 2H), 1.31 (d, J = 6.84 Hz, 2H), 1.07 (d, J = 6.59 Hz, 2H) | 459.3 |

TABLE 1-continued

| Cmpd. No. | Structure | ¹H-NMR | Mass Spec. (M + H)⁺ |
|---|---|---|---|
| 219 | 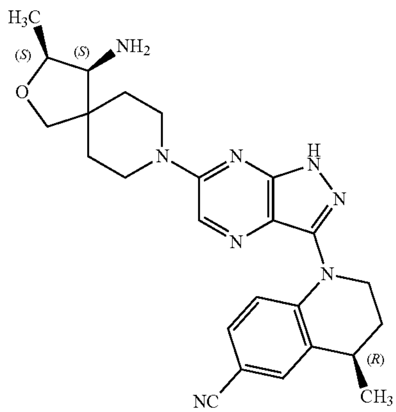 | ¹H-NMR (500 MHz, DMSO-d₆) δ 12.84 (br s, 1H), 8.33 (s, 1H), 7.53 (d, J = 1.53 Hz, 1H), 7.27 (dd, J = 1.98, 8.69 Hz, 1H), 6.88 (d, J = 8.69 Hz, 1H), 4.02-4.09 (m, 1H), 3.82-3.98 (m, 4H), 3.67 (d, J = 8.54 Hz, 1H), 3.40-3.55 (m, 3H), 2.96-3.03 (m, 1H), 2.89 (d, J = 5.03 Hz, 1H), 2.02-2.12 (m, 1H), 1.73-1.82 (m, 2H), 1.65 (ddd, J = 3.66, 9.11, 13.16 Hz, 1H), 1.44-1.57 (m, 3H), 1.31 (d, J = 6.86 Hz, 3H), 1.07 (d, J = 6.41 Hz, 3H) | 459.6 |
| 220 | 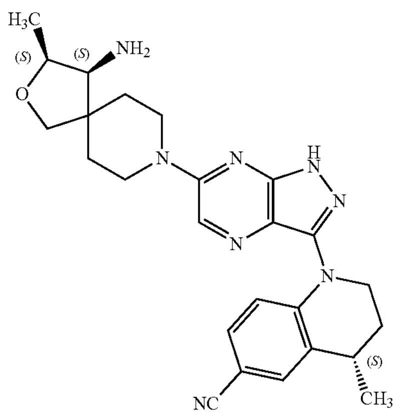 | ¹H-NMR (400 MHz, DMSO-d₆) δ 8.33 (s, 1H), 8.15 (s, 1H), 7.51 (d, J = 1.46 Hz, 1H), 7.26 (dd, J = 1.95, 8.54 Hz, 1H), 6.82 (d, J = 8.79 Hz, 1H), 4.12-4.26 (m, 3H), 3.79-3.90 (m, 3H), 3.64 (br d, J = 9.03 Hz, 1H), 3.22-3.30 (m, 2H), 3.15-3.22 (m, 1H), 2.99 (qd, J = 6.30, 12.12 Hz, 1H), 2.00-2.09 (m, 1H), 1.63-1.80 (m, 4H), 1.54 (br d, J = 13.43 Hz, 1H), 1.30 (d, J = 7.08 Hz, 3H), 1.16 (d, J = 6.59 Hz, 3H) | 459.6 |
| 221 | 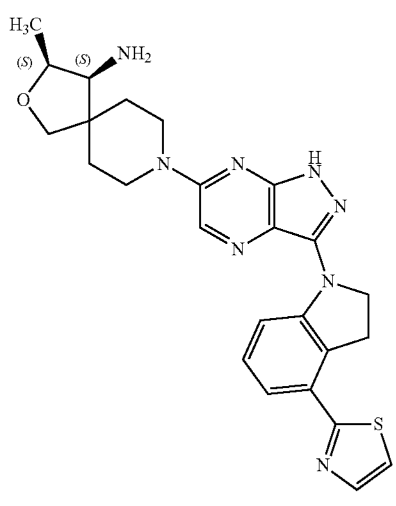 | ¹H-NMR (400 MHz, DMSO-d₆) δ 12.35 (s, 1H), 8.31 (s, 1H), 8.05 (d, J = 7.57 Hz, 1H), 7.98 (d, J = 3.42 Hz, 1H), 7.84 (d, J = 3.17 Hz, 1H), 7.37 (d, J = 7.32 Hz, 1H), 7.24-7.30 (m, 1H), 4.54 (br t, J = 8.67 Hz, 2H), 4.07-4.11 (m, 1H), 3.95-4.06 (m, 2H), 3.72 (br d, J = 8.54 Hz, 1H), 3.51-3.60 (m, 3H), 3.38-3.48 (m, 3H), 3.00 (br d, J = 5.13 Hz, 1H), 1.64-1.81 (m, 3H), 1.48-1.61 (m, 2H), 1.10 (d, J = 6.59 Hz, 2H), 1.04 (br d, J = 3.66 Hz, 1H) | 489.5 |

TABLE 1-continued

| Cmpd. No. | Structure | ¹H-NMR | Mass Spec. (M + H)⁺ |
|---|---|---|---|
| 222 | 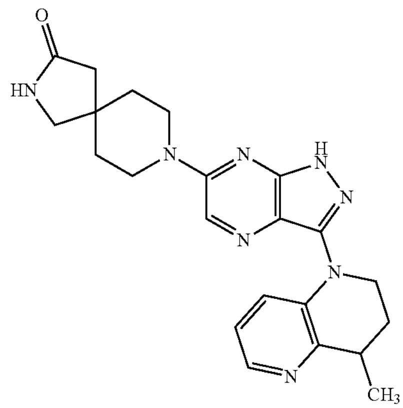 [SMILES: CC1CCN(c2n[nH]c3nc(N4CCC5(CC4)CNC(=O)C5)cnc23)c2cccnc21] | ¹H-NMR (400 MHz, CD₃OD) δ 8.12 (s, 1H), 7.80-7.78 (m, 1H), 7.22-7.19 (m, 1H), 6.91-6.86 (m, 1H), 3.88-3.77(m 4H), 3.70-3.55 (m, 2H), 3.20 (s, 2H), 3.10-2.95 (m, 1H), 2.24 (s, 2H), 2.19-2.14 (m, 1H), 1.87-1.83 (m, 1H), 1.70-1.65 (m, 4H), 1.33 (d, J = 7.2 Hz, 3H) | 419.1 |
| 223 | 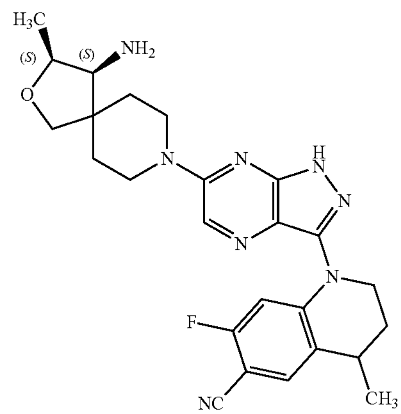 | ¹H-NMR (400 MHz, CDCl₃) δ 8.32 (s, 1H), 7.44 (d, J = 7.6 Hz, 1H), 6.52 (d, J = 12.8 Hz, 1H), 4.37-4.54 (m, 2H), 4.29-4.37 (m, 1H), 3.87-4.08 (m, 4H), 3.45 (d, J = 12.8 Hz, 1H), 3.21-3.29 (m, 1H), 3.01-3.12 (m, 1H), 2.14-2.26 (m, 1H), 1.83-1.96(m, 4H), 1.72-1.80 (m, 1H), 1.41 (d, J = 7.2 Hz, 3H), 1.34 (d, J = 6.4 Hz, 3H) | 477.1 |
| 224 | 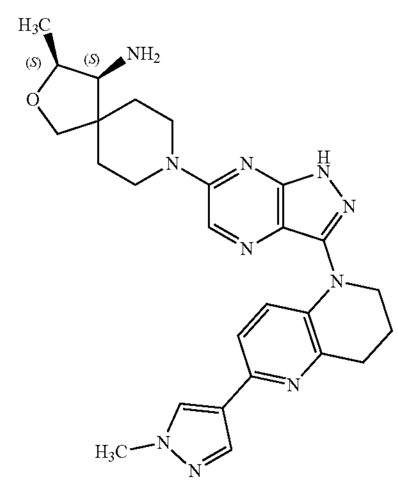 | ¹H-NMR (400 MHz, DMSO-d₆) δ 13.01-13.02 (s, 1H), 8.42 (s, 1H), 8.32 (s, 3H), 8.19-8.22 (m, 1H), 7.95-7.98 (m, 2H), 7.27-7.28 (m, 1H), 4.23-4.44 (m, 3H), 4.06-4.21 (m, 2H), 4.04-4.06 (m, 3H), 3.96-4.04 (m, 1H), 3.67-3.70 (m, 1H), 3.35-3.39 (m, 3H), 3.15-3.23 (m, 2H), 3.13-3.17 (m, 2H), 1.79-1.89 (m, 3H), 1.61-1.73 (m, 2H), 1.24-1.26 (m, 3H) | 501.6 |

TABLE 1-continued

| Cmpd. No. | Structure | ¹H-NMR | Mass Spec. (M + H)⁺ |
|---|---|---|---|
| 225 | 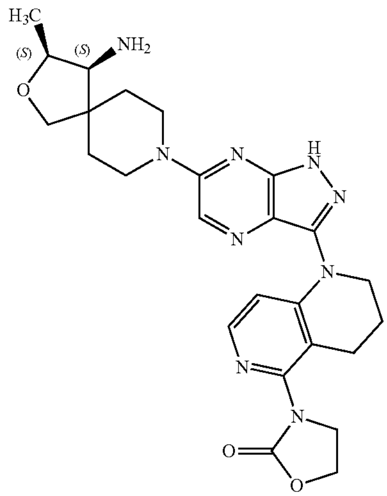 | ¹H-NMR (400 MHz, DMSO-d₆) δ 12.97 (br s, 1H), 8.35 (s, 1H), 7.79 (d, J = 5.62 Hz, 1H), 6.69 (d, J = 5.86 Hz, 1H), 4.47 (t, J = 7.81 Hz, 2H), 4.03-4.10 (m, 3H), 3.83-3.99 (m, 5H), 3.67 (br d, J = 8.54 Hz, 2H), 3.48 (br d, J = 8.30 Hz, 4H), 2.90 (d, J = 5.13 Hz, 1H), 2.71 (br t, J = 6.23 Hz, 2H), 1.95-2.02 (m, 2H), 1.72-1.82 (m, 1H), 1.61-1.70 (m, 1H), 1.44-1.58 (m, 2H), 1.22 (br s, 1H), 1.07 (d, J = 6.35 Hz, 3H) | 506.3 |
| 226 | 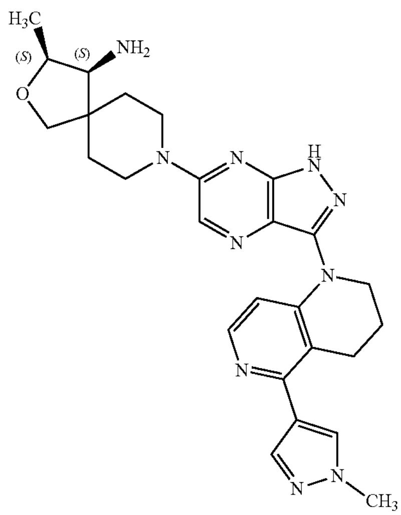 | ¹H-NMR (400 MHz, DMSO-d₆) δ 12.76-12.90 (m, 1H), 8.34 (s, 1H), 8.08 (s, 1H), 7.85-7.92 (m, 1H), 7.76-7.86 (m, 1H), 6.50-6.71 (m, 1H), 4.00-4.14 (m, 1H), 3.92-4.00 (m, 2H), 3.88-3.90 (m, 3H), 3.79-3.86 (m, 2H), 3.67 (br d, J = 8.54 Hz, 1H), 3.37-3.59 (m, 4H), 2.84-2.98 (m, 2H), 1.94-2.12 (m, 2H), 1.71-1.81 (m, 1H), 1.60-1.71 (m, 1H), 1.42-1.57 (m, 2H), 1.02-1.12 (m, 3H) | 501.6 |
| 227 | 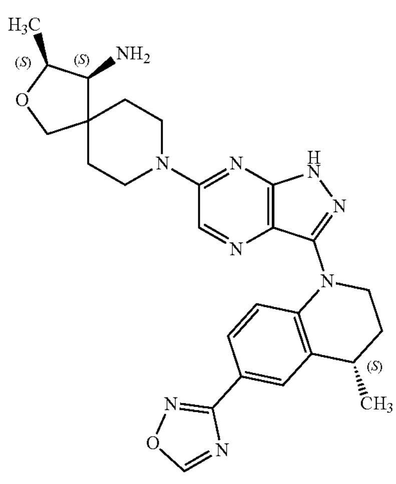 | ¹H-NMR (400 MHz, DMSO-d₆) δ 12.78 (br s, 1H), 9.56 (s, 1H), 8.35 (s, 1H), 8.14 (s, 1H), 7.79 (d, J = 1.71 Hz, 1H), 7.56 (dd, J = 1.95, 8.79 Hz, 1H), 7.01 (d, J = 8.79 Hz, 1H), 4.08-4.26 (m, 3H), 3.81-3.98 (m, 3H), 3.63 (d, J = 8.79 Hz, 1H), 3.30 (br d, J = 10.74 Hz, 2H), 3.25 (br s, 2H), 3.06 (qd, J = 6.38, 12.36 Hz, 1H), 2.06-2.17 (m, 1H), 1.70-1.85 (m, 3H), 1.51-1.69 (m, 2H), 1.35 (d, J = 6.84 Hz, 3H), 1.17 (d, J = 6.35 Hz, 3H) | 502.6 |

TABLE 1-continued

| Cmpd. No. | Structure | ¹H-NMR | Mass Spec. (M + H)⁺ |
|---|---|---|---|
| 228 | 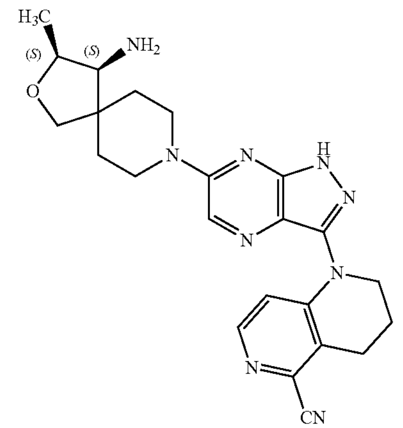 | ¹H-NMR (400 MHz, DMSO-d₆) δ 12.88-13.12 (m, 1H), 8.37 (s, 1H), 8.01 (br d, J = 5.86 Hz, 1H), 6.92-7.04 (m, 1H), 4.00-4.13 (m, 1H), 3.84-4.00 (m, 2H), 3.59-3.76 (m, 1H), 3.38-3.56 (m, 5H), 2.96-3.10 (m, 2H), 2.81-2.93 (m, 1H), 1.96-2.22 (m, 2H), 1.71-1.84 (m, 1H), 1.61-1.70 (m, 1H), 1.42-1.57 (m, 2H), 0.96-1.17 (m, 3H). | 446.6 |
| 229 | 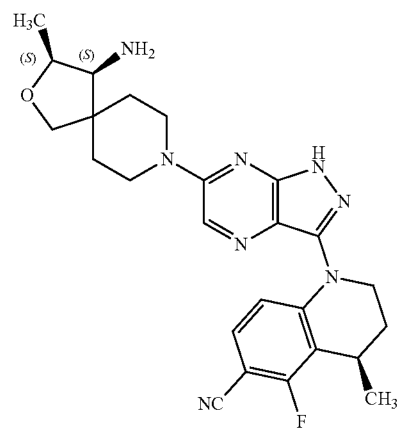 | ¹H-NMR (400 MHz, CDCl₃) δ 8.20 (s, 1H), 7.15 (d, J = 8.8 Hz, 1H), 6.81 (d, J = 8.8 Hz, 1H), 4.20-4.30 (m, 1H), 3.88-4.18 (m, 4H), 3.74 (d, J = 8.8 Hz, 1H), 3.45-3.56 (m, 1H), 3.31-3.44 (m, 2H), 3.08-3.23 (m, 1H), 2.21-2.28 (m, 2H), 1.97-2.09 (m, 2H), 1.85-(m, 2H), 1.75-1.84 (m, 2H), 1.36 (d, J = 7.2 Hz, 3H), 1.25 (d, J = 6.0 Hz, 3H) | 477.2 |
| 230 | 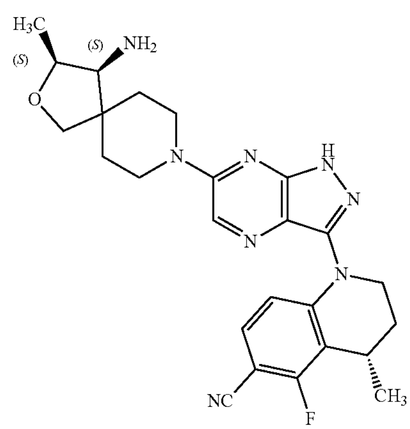 | ¹H-NMR (400 MHz, CDCl₃) δ 8.18 (s, 1H), 7.12-7.17 (m, 1H), 6.83 (d, J = 9.2 Hz, 1H), 4.20-4.30 (m, 1H), 3.88-4.18 (m, 4H), 3.74 (d, J = 8.8 Hz, 1H), 3.45-3.56 (m, 1H), 3.31-3.44 (m, 2H), 3.08-3.23 (m, 1H), 2.21-2.28 (m, 2H), 1.97-2.09 (m, 2H), 1.85-1.95 (m, 2H), 1.75-1.84 (m, 2H), 1.36 (d, J = 7.2 Hz, 3H), 1.25 (d, J = 6.0 Hz, 3H) | 477.2 |

TABLE 1-continued

| Cmpd. No. | Structure | ¹H-NMR | Mass Spec. (M + H)⁺ |
|---|---|---|---|
| 231 | 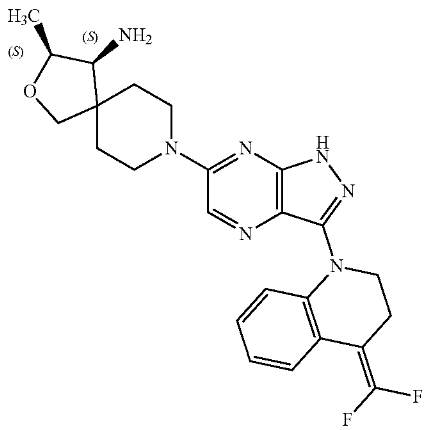 | ¹H-NMR (400 MHz, DMSO-d₆) δ 12.63 (br s, 1H), 8.29 (s, 1H), 8.24 (s, 1H), 7.44 (br d, J = 8.06 Hz, 1H), 6.92-7.04 (m, 2H), 6.78-6.86 (m, 1H), 4.02-4.13 (m, 1H), 3.84-4.01 (m, 4H), 3.68 (d, J = 8.54 Hz, 1H), 3.41-3.53 (m, 3H), 2.92 (d, J = 5.13 Hz, 1H), 2.67 (td, J = 2.93, 5.86 Hz, 2H), 1.76 (ddd, J = 3.54, 9.52, 13.06 Hz, 1H), 1.59-1.69 (m, 1H), 1.42-1.58 (m, 2H), 1.08 (d, J = 6.59 Hz, 3H) | 468.2 |
| 232 | 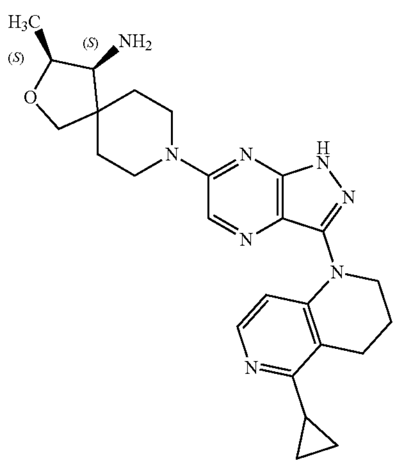 | ND | 461.6 |
| 233 | 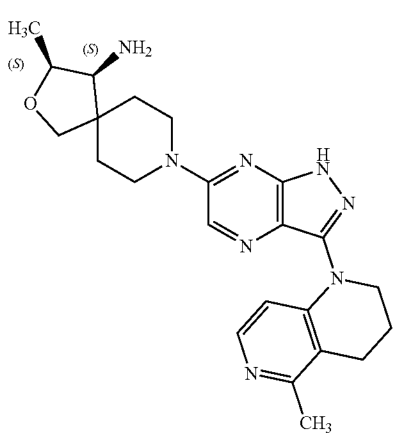 | ¹H-NMR (400 MHz, DMSO-d₆) δ 8.46 (br s, 1H), 7.85-8.00 (m, 1H), 6.74-6.88 (m, 1H), 4.15-4.43 (m, 3H), 3.81-3.99 (m, 2H), 3.61-3.75 (m, 1H), 3.33-3.47 (m, 1H), 3.19-3.28 (m, 2H), 2.74-2.90 (m, 3H), 2.50-2.60 (m, 3H), 1.98-2.20 (m, 2H), 1.65-1.83 (m, 3H), 1.59 (br d, J = 12.45 Hz, 1H), 1.14-1.30 (m, 3H) | 435.5 |

TABLE 1-continued

| Cmpd. No. | Structure | ¹H-NMR | Mass Spec. (M + H)⁺ |
|---|---|---|---|
| 234 | 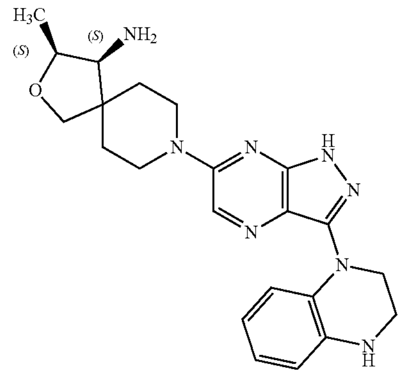 | ¹H-NMR (400 MHz, DMSO-d₆) δ 12.28 (br s, 1H), 8.11-8.34 (m, 2H), 7.13 (dd, J = 1.22, 8.06 Hz, 1H), 6.58-6.69 (m, 1H), 6.48-6.57 (m, 1H), 6.30-6.44 (m, 1H), 5.72-5.87 (m, 1H), 4.07 (td, J = 6.10, 11.72 Hz, 1H), 3.91-4.02 (m, 3H), 3.70 (br d, J = 8.30 Hz, 1H), 3.51 (br d, J = 8.54 Hz, 2H), 3.42 (d, J = 13.43 Hz, 3H), 2.96 (br s, 1H), 1.70-1.81 (m, 1H), 1.62-1.70 (m, 1H), 1.46-1.59 (m, 2H), 1.09 (d, J = 6.35 Hz, 3H) | 421.3 |
| 235 | 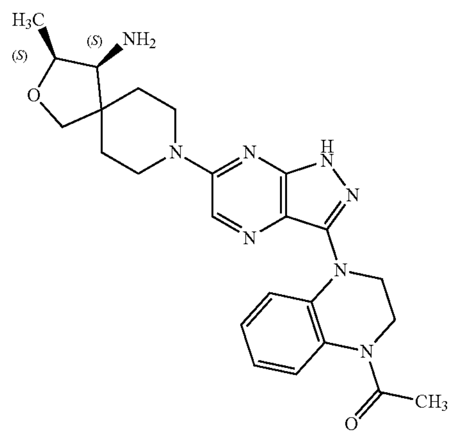 | ¹H-NMR (400 MHz, DMSO-d₆) δ 12.65 (br s, 1H), 8.30 (s, 1H), 8.21 (s, 1H), 7.26-7.45 (m, 1H), 7.19 (br d, J = 8.06 Hz, 1H), 6.95 (br s, 1H), 6.78 (br t, J = 7.45 Hz, 1H), 3.88-4.13 (m, 6H), 3.69 (br d, J = 8.54 Hz, 1H), 3.43-3.53 (m, 3H), 2.93 (d, J = 5.13 Hz, 1H), 2.21 (s, 3H), 1.76 (ddd, J = 3.30, 9.46, 13.12 Hz, 1H), 1.61-1.71 (m, 1H), 1.43-1.59 (m, 2H), 1.08 (d, J = 6.59 Hz, 3H) | 463.3 |
| 236 | 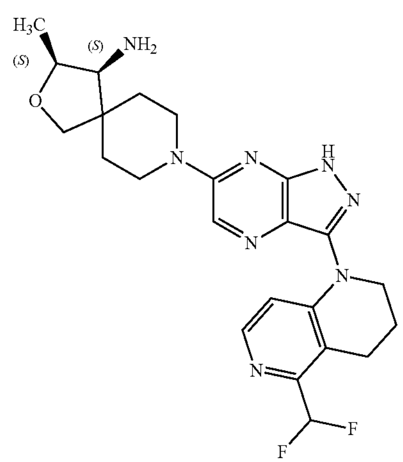 | ¹H-NMR (400 MHz, methanol-d₄) δ 8.30 (s, 1H), 7.90-7.92 (m, 1H), 6.64-6.93 (m, 2H), 4.16-4.28 (m, 3H), 3.89-3.94 (m, 3H), 3.73-3.76 (m, 1H), 3.41-3.51 (m, 2H), 3.07-3.10 (m, 2H), 3.03-3.05 (m, 1H), 2.18-2.23 (m, 2H), 1.69-1.92 (m, 4H), 1.23-1.25 (m, 3H) | 471.4 |

TABLE 1-continued

| Cmpd. No. | Structure | ¹H-NMR | Mass Spec. (M + H)⁺ |
|---|---|---|---|
| 237 | 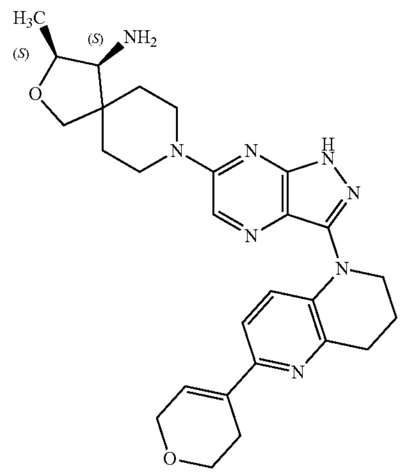 | ¹H-NMR (400 MHz, DMSO-d₆) δ 8.28 (s, 1H), 8.26 (s, 1H), 7.43 (d, J = 8.79 Hz, 1H), 7.12 (d J = 8.54 Hz, 1H), 6.46 (br s, 1H), 4.20 (br d, J = 2.69 Hz, 2H), 4.01-4.15 (m, 3H), 3.88-3.95 (m, 2H), 3.73-3.81 (m, 3H), 3.58 (d, J = 8.79 Hz, 1H), 3.18-3.36 (m, 2H), 3.10 (d, J = 4.88 Hz, 1H), 2.90 (t, J = 6.35 Hz, 2H), 2.45 (br d, J = 1.22 Hz, 2H), 2.04 (quin, J = 5.98 Hz, 2H), 1.58-1.78 (m, 3H), 1.52 (br d, J = 13.43 Hz, 1H), 1.12 (d, J = 6.35 Hz, 3H) | 503.3 |
| 238 | 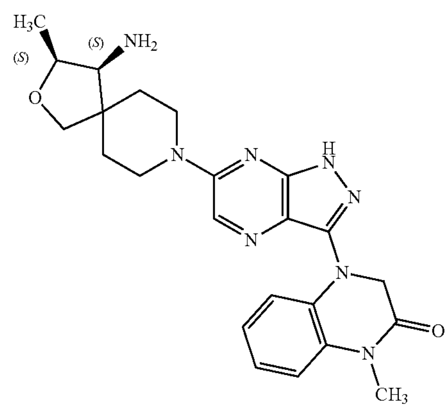 | ¹H-NMR (400 MHz, DMSO-d₆) δ 12.59 (br s, 1H), 8.27 (s, 1H), 8.25 (s, 1H), 7.16-7.22 (m, 1H), 7.12 (dd, J = 1.39, 7.96 Hz, 1H), 7.02 (dt, J = 1.39, 7.64 Hz, 1H), 6.90-6.97 (m, 1H), 4.47 (s, 2H), 4.03-4.11 (m, 1H), 3.90-4.01 (m, 2H), 3.69 (d, J = 8.59 Hz, 1H), 3.36-3.52 (m, 6H), 3.34 (s, 3H), 2.94 (d, J = 5.05 Hz, 1H), 1.76 (ddd, J = 3.41, 9.60, 13.26 Hz, 1H), 1.61-1.70 (m, 1H), 1.44-1.58 (m, 2H), 1.08 (d, J = 6.57 Hz, 3H) | 449.2 |
| 239 | 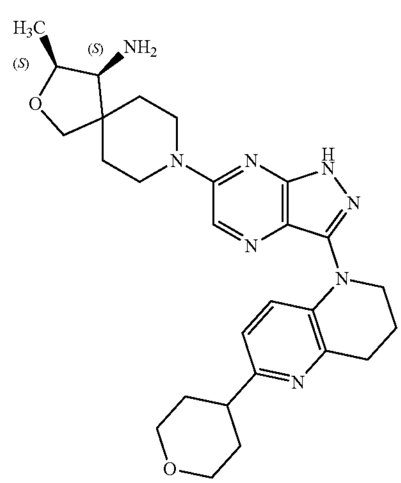 | ¹H-NMR (400 MHz, DMSO-d₆) δ 12.50 (br s, 1H), 8.29 (s, 1H), 8.17 (s, 1H), 7.49 (d, J = 8.54 Hz, 1H), 6.86 (d, J = 8.54 Hz, 1H), 3.99-4.16 (m, 4H), 3.88-3.98 (m, 5H), 3.76 (d, J = 8.79 Hz, 1H), 3.56 (d, J = 8.79 Hz, 1H), 3.34-3.46 (m, 5H), 3.29 (br s, 1H), 3.08 (d, J = 5.13 Hz, 1H), 2.90 (t, J = 6.47 Hz, 2H), 2.71-2.82 (m, 1H), 2.00-2.09 (m, 2H), 1.65-1.81 (m, 6H), 1.56-1.64 (m, 1H), 1.51 (br d, J = 13.92 Hz, 1H), 1.12 (d, J = 6.35 Hz, 3H) | 505.3 |

TABLE 1-continued

| Cmpd. No. | Structure | ¹H-NMR | Mass Spec. (M + H)⁺ |
|---|---|---|---|
| 240 | 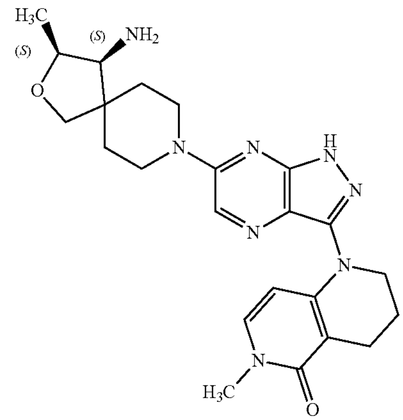 | ¹H-NMR (400 MHz, DMSO-d₆) δ 12.77 (s, 1H), 8.35 (s, 1H), 8.24 (s, 1H), 7.19 (d, J = 7.57 Hz, 1H), 5.85 (d, J = 7.57 Hz, 1H), 4.06 (quin, J = 6.04 Hz, 1H), 3.89-4.00 (m, 2H), 3.71-3.78 (m, 2H), 3.68 (d, J = 8.30 Hz, 1H), 3.39-3.55 (m, 4H), 3.29 (s, 3H), 2.92 (d, J = 5.13 Hz, 1H), 1.92 (quin, J = 5.68 Hz, 2H), 1.76 (ddd, J = 3.42, 9.58, 13.12 Hz, 1H), 1.61-1.69 (m, 1H), 1.43-1.59 (m, 2H), 1.08 (d, J = 6.35 Hz, 3H) | 451.3 |
| 241 | 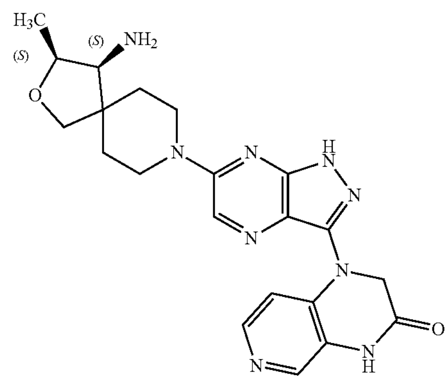 | ¹H-NMR (400 MHz, DMSO-d₆) δ 13.36 (s, 1H), 11.44 (s, 1H), 8.49 (s, 1H), 8.10-8.20 (m, 4H), 8.07 (s, 1H), 7.43 (d, J = 6.84 Hz, 1H), 7.30 (s, 1H), 7.17 (s, 1H), 7.04 (s, 1H), 4.78 (s, 2H), 4.17-4.39 (m, 4H), 3.92 (br d, J = 9.03 Hz, 2H), 3.63-3.72 (m, 11H), 3.43-3.52 (m, 9H), 1.69-1.87 (m, 4H), 1.61 (br d, J = 12.94 Hz, 1H), 1.23 (d, J = 6.59 Hz, 4H) | 436.2 |
| 242 | 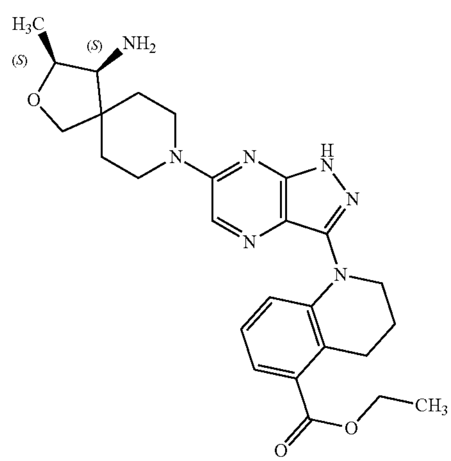 | ¹H-NMR (400 MHz, DMSO-d₆) δ 12.43-12.62 (m, 1H), 8.17-8.30 (m, 1H), 7.06-7.17 (m, 1H), 6.88-7.06 (m, 1H), 6.45-6.63 (m, 1H), 4.15-4.40 (m, 2H), 4.05 (br dd, J = 11.96, 5.86 Hz, 1H), 3.92 (br d, J = 5.37 Hz, 2H), 3.78-3.87 (m, 2H), 3.59-3.71 (m, 1H), 3.43-3.51 (m, 1H), 3.40 (br d, J = 13.43 Hz, 2H), 2.94-3.12 (m, 2H), 2.85-2.93 (m, 1H), 1.89-2.04 (m, 2H), 1.70-1.83 (m, 1H), 1.59-1.69 (m, 1H), 1.41-1.58 (m, 2H), 1.25-1.35 (m, 3H), 0.98-1.10 (m, 3H) | 464.6 |

TABLE 1-continued
| Cmpd. No. | Structure | ¹H-NMR | Mass Spec. (M + H)⁺ |
|---|---|---|---|
| 243 | 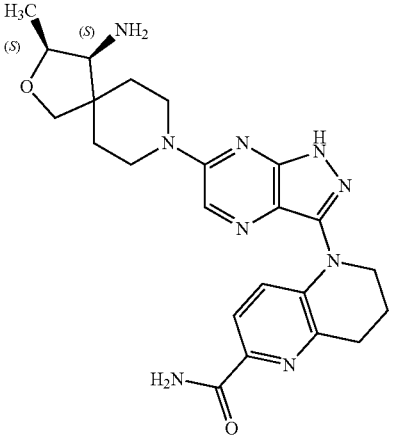 | ¹H-NMR (400 MHz, DMSO-d₆) δ 8.34 (s, 1H), 7.72 (s, 1H), 7.64-7.60 (m, 1H), 7.53-7.47 (m, 1H), 7.29 (s, 1H), 4.12-4.06 (m, 1H), 4.05-3.92 (m, 2H), 3.72-3.67 (m, 2H), 3.53-3.49 (m, 2H), 3.03-2.99 (m, 2H), 2.96-2.94 (m, 1H), 2.14-2.10 (m, 2H), 1.80-1.45 (m, 4H), 1.25-1.20 (m, 2H), 1.12-1.08 (m, 3H) | 464.5 |
| 244 | 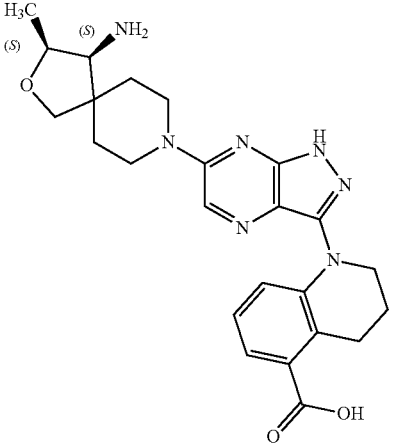 | ¹H-NMR (400 MHz, DMSO-d₆) δ 12.41-12.56 (m, 1H), 8.16-8.29 (m, 1H), 6.99-7.12 (m, 1H), 6.84-6.97 (m, 1H), 6.51-6.63 (m, 1H), 4.07 (ddd, J = 17.82, 11.72, 6.59 Hz, 1H), 3.86-4.00 (m, 2H), 3.78-3.86 (m, 2H), 3.60-3.74 (m, 1H), 3.44-3.54 (m, 1H), 2.96-3.13 (m, 2H), 2.84-2.89 (m, 1H), 2.53-2.63 (m, 2H), 1.83-1.99 (m, 2H), 1.68-1.82(m, 1H), 1.59-1.68 (m, 1H), 1.40-1.59 (m, 2H), 0.91-1.12 (m, 3H) | 492.6 |
| 245 | 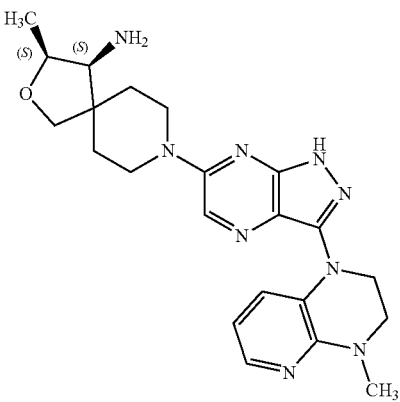 | ¹H-NMR (400 MHz, DMSO-d₆) δ 12.38 (br s, 1H), 8.25 (s, 1H), 7.07 (dd, J = 1.22, 8.06 Hz, 1H), 6.68-6.74 (m, 1H), 6.63 (dd, J = 0.98, 8.06 Hz, 1H), 6.43-6.49 (m, 1H), 4.00-4.11 (m, 3H), 3.90-4.00 (m, 2H), 3.69 (d, J = 8.54 Hz, 1H), 3.50 (br d, J = 8.54 Hz, 2H), 3.31-3.35 (m, 6H), 2.94 (d, J = 5.13 Hz, 1H), 2.87 (s, 2H), 1.72-1.80 (m, 1H), 1.62-1.70 (m, 1H), 1.45-1.58 (m, 2H), 1.08 (d, J = 6.35 Hz, 3H) | 435.5 |

TABLE 1-continued

| Cmpd. No. | Structure | ¹H-NMR | Mass Spec. (M + H)⁺ |
|---|---|---|---|
| 246 | 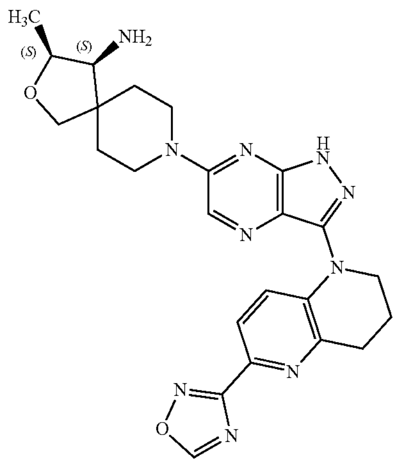 | ¹H-NMR (400 MHz, DMSO-d₆) δ 12.78 (br s, 1H), 9.61 (s, 1H), 8.34 (s, 1H), 7.69 (d, J = 8.54 Hz, 1H), 7.55 (d, J = 8.79 Hz, 1H), 4.07 (td, J = 6.23, 11.96 Hz, 1H), 3.91-4.02 (m, 4H), 3.69 (d, J = 8.54 Hz, 1H), 3.43-3.56 (m, 5H), 3.03 (br t, J = 6.47 Hz, 2H), 2.94 (d, J = 5.13 Hz, 1H), 2.09-2.19 (m, 2H), 1.72-1.80 (m, 1H), 1.63-1.70 (m, 1H), 1.45-1.59 (m, 2H), 1.08 (d, J = 6.35 Hz, 3H) | 489.5 |
| 247 | 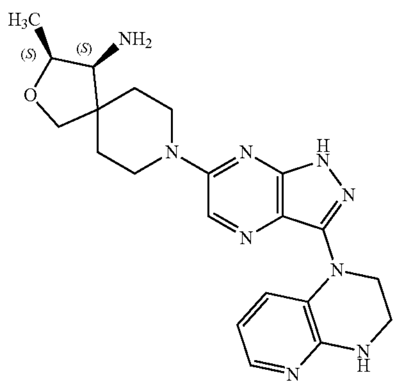 | ND | 422.5 |
| 248 | 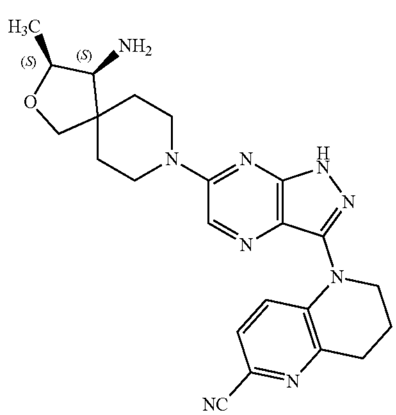 | ¹H-NMR (400 MHz, DMSO-d₆) δ 12.95 (br s, 1H), 8.33-8.43 (m, 1H), 7.52 (br d, J = 8.79 Hz, 1H), 7.36-7.45 (m, 1H), 4.12-4.35 (m, 3H), 3.93-4.05 (m, 2H), 3.85-3.93 (m, 1H), 3.68 (br d, J = 9.03 Hz, 1H), 3.33-3.40 (m, 1H), 3.10-3.25 (m, 2H), 2.90-3.06 (m, 2H), 2.02-2.16 (m, 2H), 1.65-1.85 (m, 3H), 1.48-1.61 (m, 1H), 1.21 (br d, J = 6.10 Hz, 3H) | 446.6 |

TABLE 1-continued

| Cmpd. No. | Structure | ¹H-NMR | Mass Spec. (M + H)⁺ |
|---|---|---|---|
| 249 | 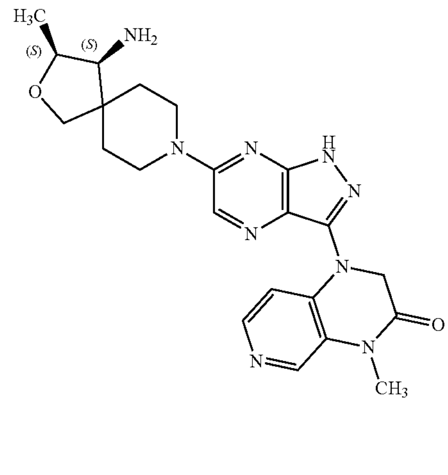 | ¹H-NMR (400 MHz, DMSO-d₆) δ 8.43-8.47 (m, 1H), 8.37 (s, 1H), 8.15 (d, J = 6.84 Hz, 1H), 7.36 (d, J = 6.59 Hz, 1H), 4.82 (s, 2H), 4.28 (dd, J = 26.49, 13.79 Hz, 2H), 4.17-4.23 (m, 1H), 3.90 (d, J = 9.28 Hz, 1H), 3.70 (d, J = 9.28 Hz, 1H), 3.36-3.40 (m, 4H), 3.14-3.27 (m, 2H), 1.70-1.81 (m, 3H), 1.59 (br d, J = 13.18 Hz, 1H), 1.21 (d, J = 6.59 Hz, 3H) | 440.2 |
| 250 | 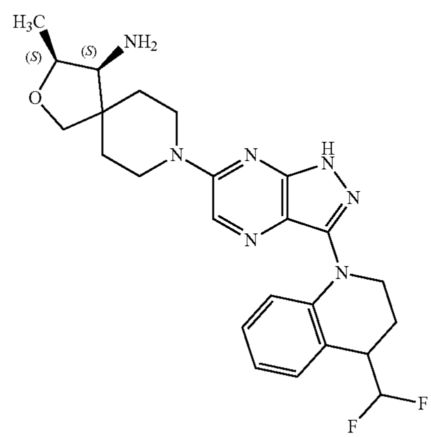 | ¹H-NMR (400 MHz, DMSO-d₆) δ 8.28 (s, 1H), 8.20 (s, 1H), 7.22 (d, J = 7.57 Hz, 1H), 6.92-7.04 (m, 2H), 6.75 (ddd, J = 2.32, 5.98, 7.81 Hz, 1H), 6.13-6.50 (m, 1H), 4.03-4.20 (m, 3H), 3.76-3.90 (m, 3H), 3.60 (d, J = 8.79 Hz, 1H), 3.20-3.46 (m, 3H), 3.16 (d, J = 4.88 Hz, 1H), 2.01-2.20 (m, 2H), 1.59-1.79 (m, 3H), 1.53 (br d, J = 13.43 Hz, 1H), 1.14 (d, J = 6.59 Hz, 3H) | 470.3 |
| 251 | 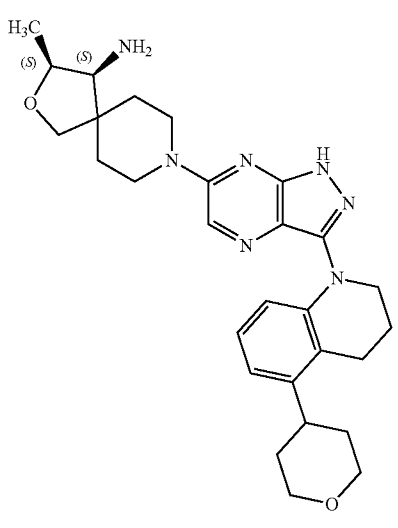 | ¹H-NMR (400 MHz, DMSO-d₆) δ 12.50 (br s, 1H), 8.26 (s, 1H), 6.97-7.05 (m, 2H), 6.88-6.94 (m, 1H), 6.64-6.72 (m, 1H), 3.90-4.11 (m, 4H), 3.79-3.89 (m, 2H), 3.66-3.78 (m, 2H), 3.47-3.51 (m, 2H), 3.45 (br s, 3H), 3.11-3.26 (m, 3H), 2.94 (d, J = 5.13 Hz, 1H), 2.53-2.60 (m, 1H), 2.10-2.21 (m, 1H), 1.59-1.91 (m, 5H), 1.33-1.59 (m, 4H), 1.24 (dq, J = 4.39, 12.21 Hz, 1H), 1.08 (d, J = 6.35 Hz, 2H) | 504.6 |

TABLE 1-continued

| Cmpd. No. | Structure | ¹H-NMR | Mass Spec. (M + H)⁺ |
|---|---|---|---|
| 252 | 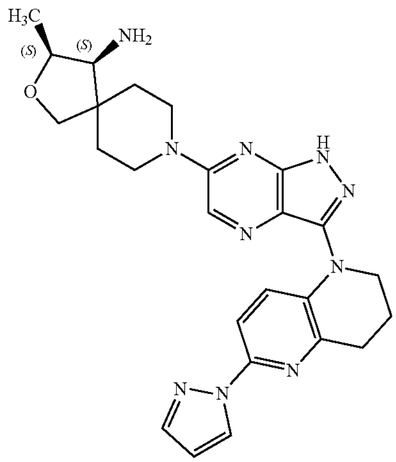 | ¹H-NMR (400 MHz, DMSO-d₆) δ 12.67 (s, 1H), 8.47 (s, 1H), 8.36 (s, 1H), 8.18 (s, 3H), 7.79~7.81 (m, 1H), 7.72 (s, 1H), 7.56~7.54 (m, 1H), 6.51 (s, 1H), 4.23~4.01 (m, 3H), 4.13~3.93 (m, 3H), 3.70~3.68 (m, 1H), 3.58~3.56 (m, 1H), 3.19~3.17 (m, 2H), 3.01~2.99 (m, 2H), 2.12~2.10 (m, 2H), 1.72~1.70 (m, 4H), 1.25~1.23 (m, 3H) | 487.1 |
| 253 | 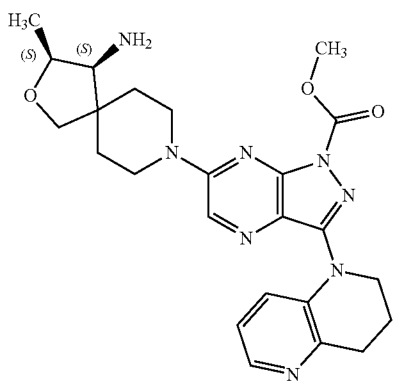 | ¹H-NMR (400 MHz, DMSO-d₆) δ 8.48-8.51 (m, 2H), 8.28-8.30 (m, 4H), 7.66-7.70 (m, 1H), 4.44-4.48 (m, 1H), 4.34-4.38 (m, 1H), 4.20-4.23 (m, 1H), 4.16-4.17 (m, 2H), 3.95-3.99 (m, 3H), 3.70-3.76 (m, 2H), 3.39-3.46 (m, 1H), 3.25-3.38 (m, 3H), 2.11-2.17 (m, 2H), 1.64-1.87 (m, 4H), 1.24-1.26 (m, 3H) | 479.6 |
| 254 | 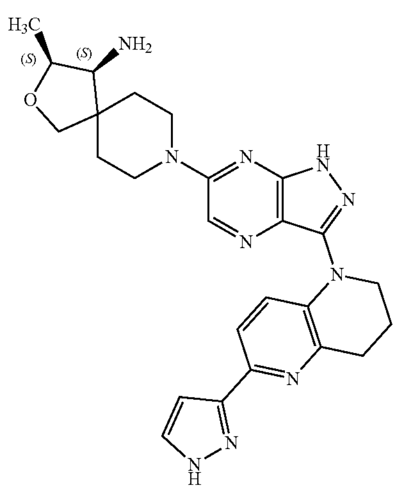 | ¹H-NMR (400 MHz, methanol-d₄) δ 8.36 (s, 1H), 8.13 (d, J = 8.8 Hz, 1H), 7.95 (d, J = 9.2 Hz, 1H), 7.89 (d, J = 2.4 Hz, 1H), 7.02 (d, J = 2.4 Hz, 1H), 4.52-4.31 (m, 3H), 4.14-4.11 (m, 2H), 4.03 (d, J = 9.2 Hz, 1H), 3.92 (d, J = 9.2 Hz, 1H), 3.48 (d, J = 4.0 Hz, 1H), 3.39-3.34 (m, 3H), 3.27-3.24 (m, 1H), 2.36-2.28 (m, 2H), 1.94-1.88 (m, 3H), 1.79-1.76 (m, 1H), 1.35 (d, J = 6.4 Hz, 3H) | 487.2 |

TABLE 1-continued
| Cmpd. No. | Structure | ¹H-NMR | Mass Spec. (M + H)⁺ |
|---|---|---|---|
| 255 | 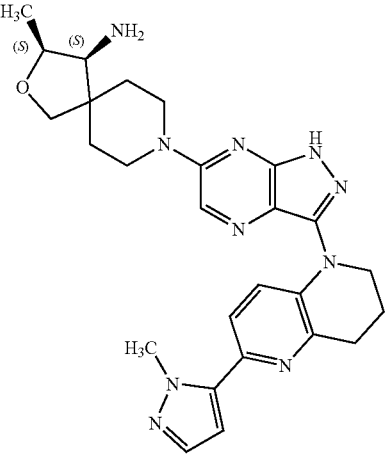 | ¹H-NMR (400 MHz, DMSO-d₆) δ 8.41 (s, 1H), 8.31 (s, 3H), 7.91-7.94 (m, 1H), 7.55-7.61 (m, 2H), 6.69-6.70 (s, 1H), 4.23-4.27 (m, 2H), 4.20-4.22 (m, 4H), 4.04-4.06 (m, 4H), 4.02-4.04 (m, 1H), 3.67-3.69 (m, 1H), 3.35-3.38 (m, 1H), 3.16-3.22 (m, 4H), 2.14-2.18 (m, 2H), 1.64-1.84 (m, 4H), 1.23-1.26 (m, 3H) | 501.6 |
| 256 | 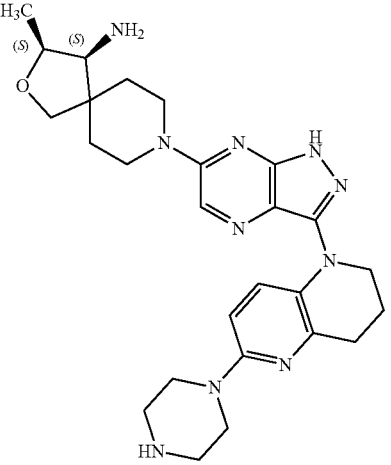 | ¹H-NMR (400 MHz, DMSO-d₆) δ 12.60 (br, 1H), 9.63 (br, 2H), 8.34 (s, 1H), 8.29 (br, 3H), 8.06-8.03 (d, J = 9.2 Hz, 1H), 7.11-7.07 (d, J = 10.0 Hz, 1H), 4.24-4.00 (m, 4H), 4.00-3.89 (m, 4H), 3.69-3.67 (m, 1H), 3.32-3.3 (m, 1H), 3.24-3.09 (m, 9H), 2.02-2.00 (m, 3H), 1.99-1.60 (m, 4H), 1.26-1.24 (d, J = 6.8 Hz, 3H) | 505.2 |
| 257 | 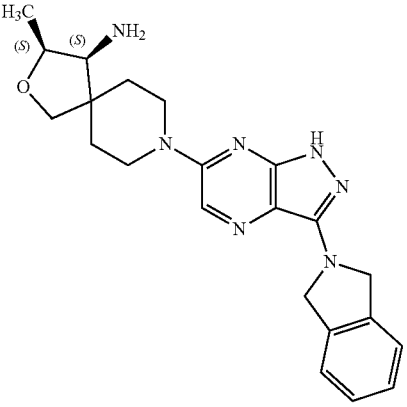 | ND | 408 |

TABLE 1-continued

| Cmpd. No. | Structure | ¹H-NMR | Mass Spec. (M + H)⁺ |
|---|---|---|---|
| 258 | 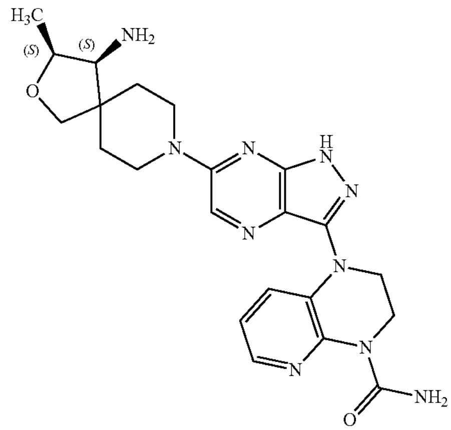 | ¹H-NMR (400 MHz, DMSO-d₆) δ 12.81 (s, 1H), 8.39 (s, 1H), 8.22 (d, 3H), 7.80-7.88 (m, 2H), 7.00-7.03 (m, 1H), 4.21-4.35 (m, 3H), 4.05 (s, 4H), 3.93-3.96 (m, 1H), 3.67-3.71 (m, 1H), 3.30-3.40 (m, 1H), 3.15-3.20 (m, 2H), 1.60-1.85 (m, 4H), 1.24 (s, 3H) | 465.5 |
| 259 | 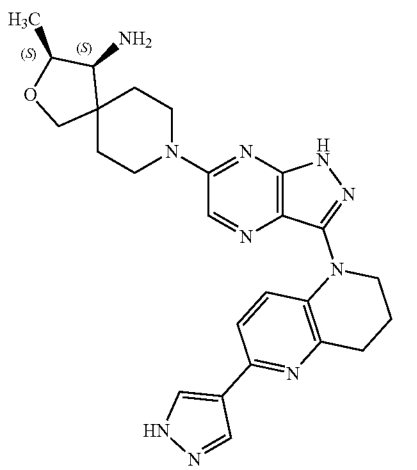 | ¹H-NMR (400 MHz, methanol-d₄) δ 8.34 (s, 2H), 8.33 (s, 1H), 8.10 (d, J = 9.2 Hz, 1H), 7.79 (d, J = 9.2 Hz, 1H), 4.49-4.29 (m, 3H), 4.11-4.08 (m, 2H), 4.02 (d, J = 9.6 Hz, 1H), 3.92 (d, J = 9.2 Hz, 1H), 3.46 (d, J = 4.0 Hz, 1H), 3.35-3.33 (m, 3H), 3.27-3.22 (m, 1H), 2.33-2.27 (m, 2H), 1.93-1.87 (m, 3H), 1.78-1.74 (m, 1H), 1.33 (d, J = 6.4 Hz, 3H) | 487.2 |
| 260 | 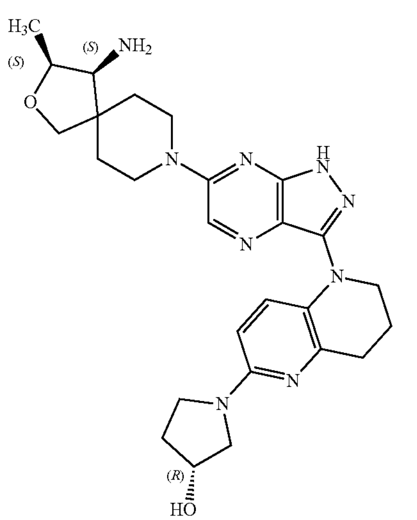 | ¹H-NMR (400 MHz, DMSO-d₆) δ 12.06 (br, 1H), 8.30~8.34 (m, 4H), 8.00~8.03 (m, 1H), 6.88~6.91 (m, 1H), 4.47 (s, 1H), 4.20~4.26 (m, 4H), 3.94~4.02 (m, 3H), 3.66~3.70 (m, 3H), 3.47~3.51 (m, 1H), 3.35~3.40 (m, 1H), 3.12~3.21 (m, 2H), 3.02~3.08 (m, 2H), 1.92~2.10 (m, 4H), 1.78~1.84 (m, 2H), 1.60~1.72 (m, 2H), 1.24~1.27 (m, 3H) | 506.2 |

TABLE 1-continued

| Cmpd. No. | Structure | ¹H-NMR | Mass Spec. (M + H)⁺ |
|---|---|---|---|
| 261 | 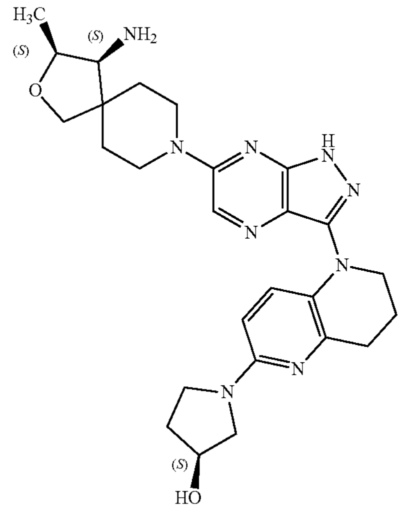 | ¹H-NMR (400 MHz, DMSO-d₆) δ 12.59 (br, 1H), 8.34 (s, 1H), 8.31 (br, 1H), 8.01 (d, J = 9.6 Hz, 1H), 6.89 (d, J = 9.6 Hz, 1H), 4.48 (s, 1H), 4.40-4.30 (m, 2H), 4.25-4.18 (m, 2H), 4.00-3.90 (m, 2H), 3.70-3.60 (m, 4H), 3.50-3.45 (m, 1H), 3.40-3.35 (m, 1H), 3.20-3.10 (m, 2H), 3.09-3.00 (m, 2H), 2.10-1.86 (m, 4H), 1.85-1.73 (m, 2H), 1.71-7.60 (m, 2H), 1.25 (d, J = 6.4 Hz, 3H) | 506.2 |
| 262 | 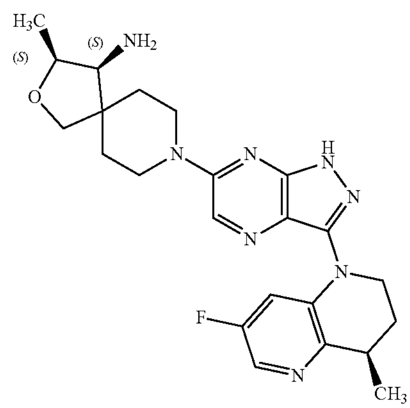 | ¹H-NMR (400 MHz, CD₃OD) δ 8.22 (s, 1H), 8.21(s,1H), 8.06-8.07 (m, 1H), 4.20-4.34 (m, 3H), 4.02-4.05 (m, 1H), 3.93-4.03 (m, 2H), 3.90-3.93 (m, 1H), 3.48-3.49 (m, 2H), 3.33-3.35 (m, 1H), 3.33-3.34 (m, 1H), 2.14-2.15 (m, 1H), 1.94-1.95 (m, 1H),1.92-.1.94 (m, 3H), 1.91-1.92 (m, 1H), 1.79-1.89 (m, 3H), 1.57 (s, 3H) | 453.5 |
| 263 | 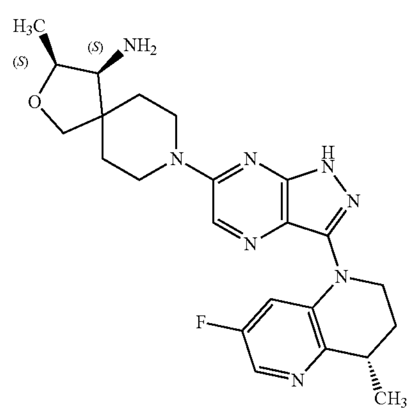 | ¹H-NMR (400 MHz, DMSO-d₆) δ 12.97 (s, 1H), 8.41 (s, 1H), 8.30 (s, 2H), 8.17-8.18 (m, 1H), 7.81-7.85 (m, 1H), 4.21-4.23(m, 1H), 4.09-4.21 (m, 2H), 4.02-4.08 (m, 1H), 3.99-4.07 (m, 2H), 3.67-3.69 (m, 1H), 3.30-3.38 (m, 2H), 3.14-3.22 (m, 2H), 2.16-2.20 (m, 1H), 1.82-1.92 (m, 3H), 1.68-1.83 (m, 2H), 1.25-1.65 (m, 3H), 1.24-1.25 (s, 3H) | 453.5 |

TABLE 1-continued

| Cmpd. No. | Structure | ¹H-NMR | Mass Spec. (M + H)⁺ |
|---|---|---|---|
| 264 | 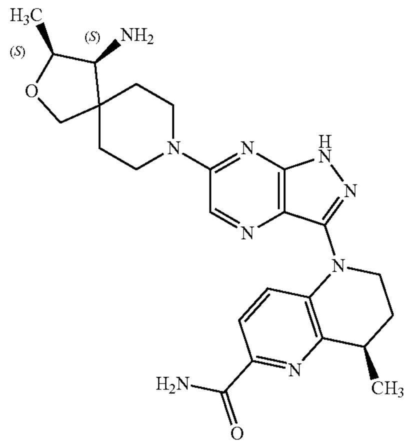 | ¹H-NMR (400 MHz, DMSO-d₆) δ 12.78 (br, 1H), 8.34 (s, 1H), 7.73 (d, J = 2.8 Hz, 1H), 7.61 (d, J = 8.8 Hz, 1H), 7.45 (d, J = 8.4 Hz, 1H), 7.31 (d, J = 2.8 Hz, 1H), 4.06-4.14 (m, 1H), 3.89-4.05 (m, 4H), 3.71 (d, J = 8.4 Hz, 1H), 3.45-3.55 (m, 3H), 3.02-3.20 (m, 2H), 2.96 (d, J = 4.8 Hz, 1H), 2.15-2.28 (m, 1H), 1.61-2.03 (m, 4H), 1.46-1.61 (m, 2H), 1.42 (d, J = 6.8 Hz, 3H), 1.09 (d, J = 6.4 Hz, 3H) | 478.5 |
| 265 | 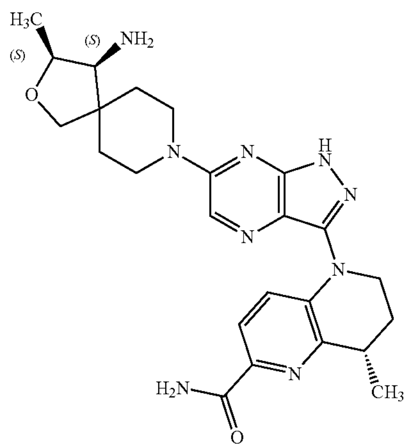 | ¹H-NMR (400 MHz, methanol-d₄) δ 8.36 (s, 1H), 7.99 (s, 2H), 4.27-4.53 (m, 3H), 4.14-4.22 (m, 1H), 3.99-4.12 (m, 2H), 3.90 (d, J = 9.2 Hz, 1H), 3.64-3.75 (m, 1H), 3.48 (d, J = 4.0 Hz, 1H), 3.32-3.39 (m, 1H), 3.20-3.2 (m, 1H), 2.98 (s, 3H), 2.29-2.41 (m, 1H), 2.10-2.19 (m, 1H), 1.85-1.98 (m, 3H), 1.71-1.80 (m, 1H), 1.55 (d, J = 6.8 Hz, 3H), 1.33 (d, J = 6.4 Hz, 3H) | 478.5 |
| 266 | 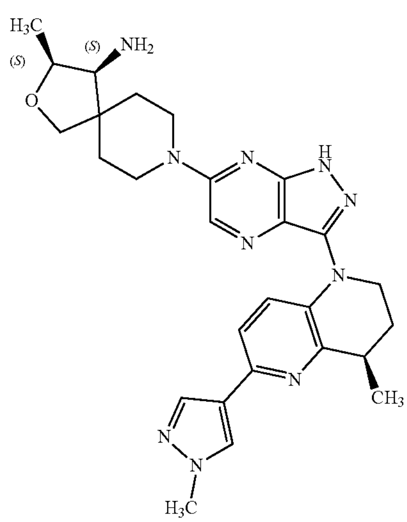 | ¹H-NMR (400 MHz, CDCl₃) δ 8.05 (s, 1H), 7.78 (s, 1H), 7.77 (s, 1H), 7.60-7.57 (d, J = 8.8 Hz, 1H), 7.08-7.05 (d, J = 8.4 Hz, 1H), 4.13-3.92 (m, 4H), 3.86 (s, 3H), 3.77-3.74 (m, 1H), 3.65-3.62 (m, 1H), 3.33 (m, 2H), 3.08-3.06 (m, 1H), 2.94-2.92 (m, 1H), 2.20-2.10 (m, 1H), 1.86-1.42 (m, 6H), 1.43-1.40 (d, J = 7.2 Hz, 1H), 1.19-1.16 (d, J = 7.2 Hz, 1H) | 515.2 |

TABLE 1-continued

| Cmpd. No. | Structure | ¹H-NMR | Mass Spec. (M + H)⁺ |
|---|---|---|---|
| 267 | 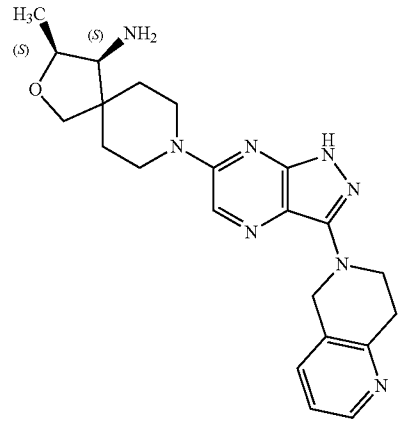 | ND | 421.3 |
| 268 | 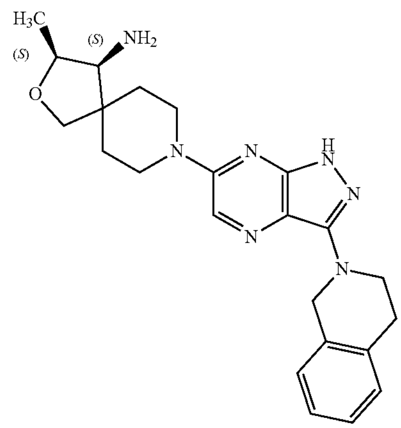 | ND | 420.3 |
| 269 | 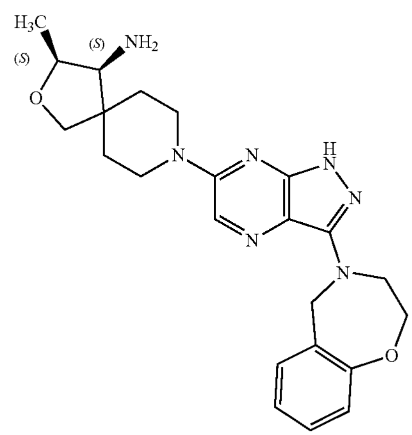 | ND | 436.2 |

TABLE 1-continued

| Cmpd. No. | Structure | ¹H-NMR | Mass Spec. (M + H)⁺ |
|---|---|---|---|
| 270 | 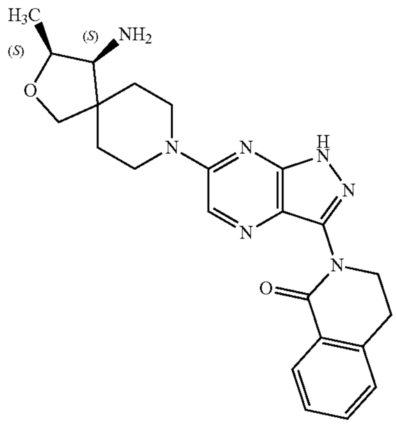 | ND | 434.2 |
| 271 | 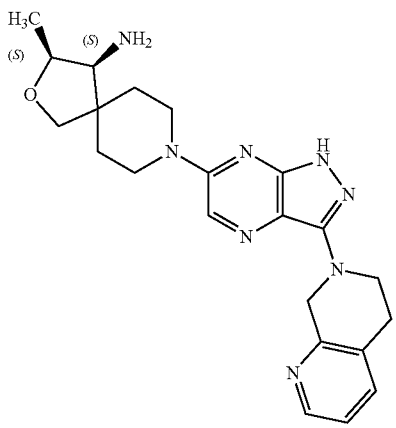 | ND | 421.2 |
| 272 | 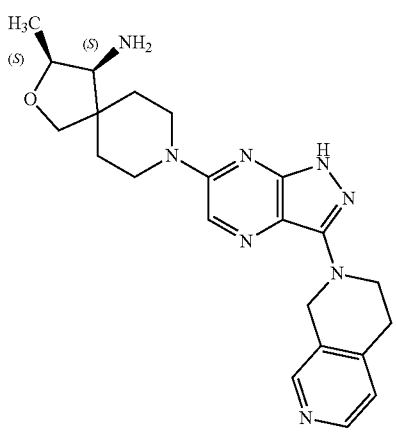 | ND | 421.2 |

TABLE 1-continued

| Cmpd. No. | Structure | ¹H-NMR | Mass Spec. (M + H)⁺ |
|---|---|---|---|
| 273 | 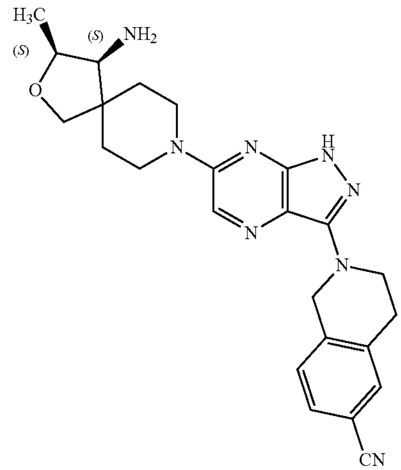 | ND | 445.2 |
| 274 | 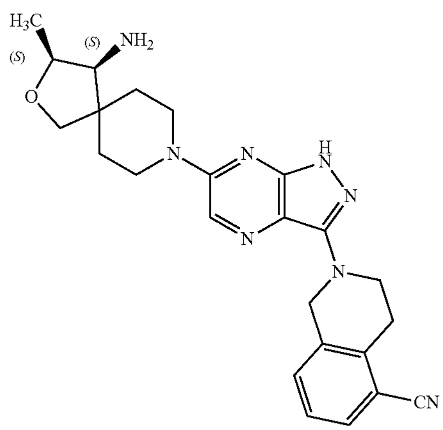 | ND | 445.2 |
| 275 | 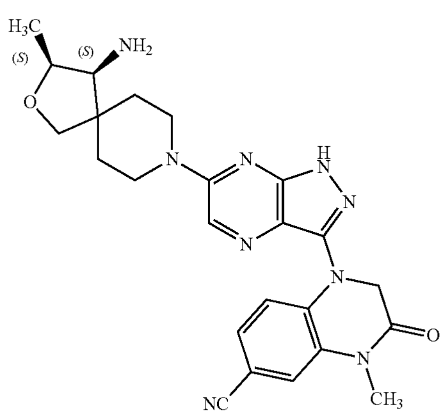 | ¹H-NMR (400 MHz, DMSO-d₆) δ 8.31 (s, 1H), 7.60 (d, J = 1.71 Hz, 1H), 7.35 (dd, J = 1.71, 8.54 Hz, 1H), 7.13 (d, J = 8.54 Hz, 1H), 4.53 (s, 2H), 4.15-4.34 (m, 3H), 3.89 (d, J = 9.28 Hz, 1H), 3.69 (br d, J = 9.03 Hz, 1H), 3.62-3.62 (m, 1H), 3.36 (s, 3H), 3.10-3.21 (m, 2H), 1.66-1.80 (m, 3H), 1.57 (br d, J = 12.94 Hz, 1H), 1.19(d, J = 6.59 Hz, 3H) | 474.2 |

TABLE 1-continued

| Cmpd. No. | Structure | ¹H-NMR | Mass Spec. (M + H)⁺ |
|---|---|---|---|
| 276 | 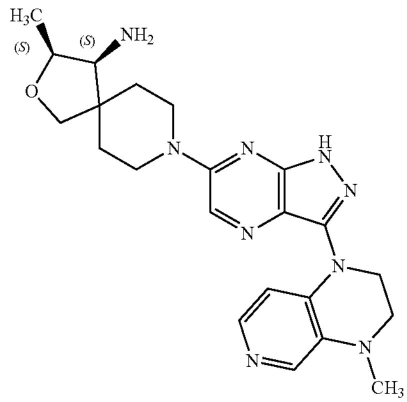 | ¹H-NMR (400 MHz, DMSO-d₆) δ 12.80 (br s, 1H), 8.36 (s, 1H), 8.14 (s, 1H), 7.79 (s, 1H), 7.53-7.68 (m, 1H), 6.86-7.01 (m, 1H), 3.99-4.23 (m, 4H), 3.75-3.89 (m, 2H), 3.57-3.65 (m, 2H), 3.31-3.36 (m, 2H), 3.19 (br d, J = 5.13 Hz, 2H), 2.91 (s, 3H), 1.69-1.83 (m, 2H), 1.60-1.69 (m, 1H), 1.43-1.60 (m, 1H), 1.15 (d, J = 6.35 Hz, 3H) | 436.5 |
| 277 | 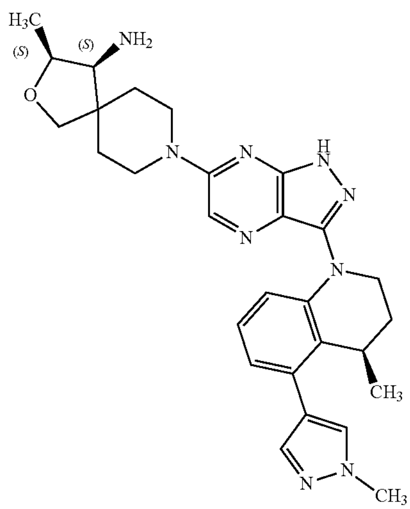 | ¹H-NMR (400 MHz, DMSO-d₆) δ 8.31 (s, 1H), 8.24 (br, 3H), 7.87 (s, 1H), 7.56 (s, 1H), 6.92-6.88 (m, 1H), 6.83-6.81 (m, 1H), 6.69-6.66 (m, 1H), 4.30-4.20 (m, 3H), 4.03-3.91 (m, 2H), 3.91 (s, 3H), 3.80-3.65 (m, 2H), 3.40-3.25 (m, 2H), 3.21-3.10 (m, 2H), 1.91-1.87 (m, 2H), 1.85-1.76 (m, 2H), 1.75-1.55 (m, 2H), 1.25 (d, J = 6.4 Hz, 3H), 1.14 (d, J = 6.8 Hz, 3H) | 514.2 |
| 278 | 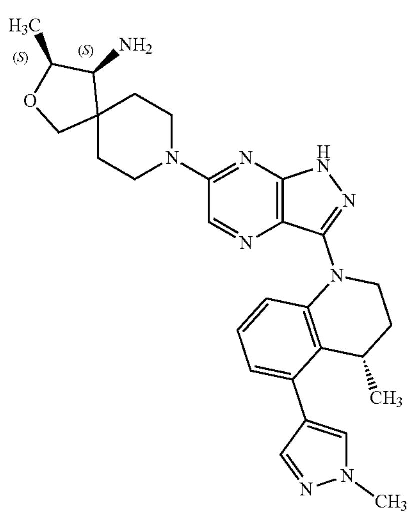 | ¹H-NMR (400 MHz, DMSO-d₆) δ 8.31 (s, 1H), 8.23 (br, 3H), 7.86 (s, 1H), 7.56 (s, 1H), 6.92-6.88 (m, 1H), 6.83-6.81 (m, 1H), 6.68-6.66 (m, 1H), 4.33-4.25 (m, 1H), 4.23-4.20 (m, 2H), 4.05-3.95 (m, 2H), 3.88 (s, 3H), 3.75-3.67 (m, 2H), 3.40-3.26 (m, 2H), 3.22-3.10 (m, 2H), 1.91-1.85 (m, 2H), 1.80-1.72 (m, 2H), 1.72-1.58 (m, 2H), 1.25 (d, J = 6.4 Hz, 3H), 1.14 (d, J = 6.8 Hz, 3H) | 514.2 |

TABLE 1-continued

| Cmpd. No. | Structure | ¹H-NMR | Mass Spec. (M + H)⁺ |
|---|---|---|---|
| 279 | 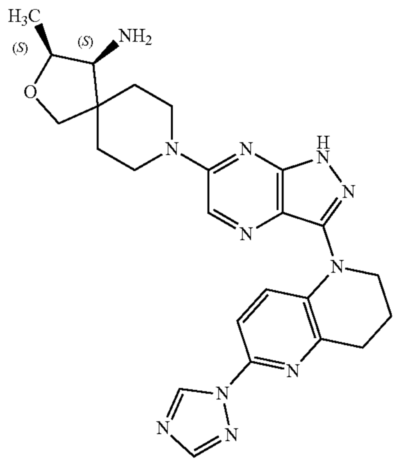 | ¹H-NMR (400 MHz, CD₃OD) δ 9.97 (s, 1H), 8.68 (s, 1H), 8.32 (s, 1H), 7.63 (s, 1H), 4.39-4.32 (m, 3H), 4.07-4.02 (m, 3H), 3.92 (d, J = 9.2 Hz, 1H), 3.47 (s, 1H), 3.26 (s, 1H), 3.16-3.12 (m, 2H), 2.26 (t, J = 5.6 Hz, 2H), 193-1.78 (m, 4H), 1.35 (d, J = 6.8 Hz, 3H) | 488.1 |
| 280 | 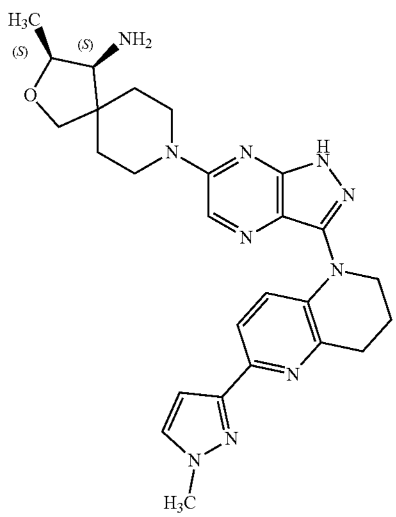 | ¹H-NMR (400 MHz, DMSO-d₆) δ 13.01-13.02 (s, 1H), 8.42 (s, 1H), 8.32 (s, 3H), 8.19-8.22 (m, 1H), 7.95-7.98 (m, 2H), 7.27-7.28 (m, 1H), 4.23-4.44 (m, 3H), 4.06-4.21 (m, 2H), 4.04-4.06 (m, 3H), 3.96-4.04 (m, 1H), 3.67-3.70 (m, 1H), 3.35-3.39 (m, 3H), 3.15-3.23 (m, 2H), 3.13-3.17 (m, 2H), 1.79-1.89 (m, 3H), 1.61-1.73 (m, 2H), 1.24-1.26 (m, 3H) | 501.6 |
| 281 | 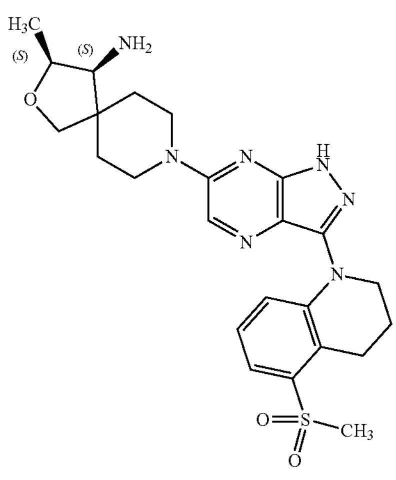 | ¹H-NMR (400 MHz, DMSO-d₆) δ 12.65 (br, 1H), 8.28 (s, 1H), 7.35 (d, J = 7.2 Hz, 1H), 7.10-7.21 (m, 2H), 4.01-4.11 (m, 1H), 3.89-3.99 (m, 2H), 3.83-3.88 (m, 2H), 3.68 (d, J = 8.4 Hz, 1H), 3.45-3.55 (m, 3H), 3.24 (s, 3H), 3.19-3.23 (m, 2H), 2.90 (d, J = 5.2 Hz, 1H), 1.96-2.08 (m, 2H), 1.71-1.82 (m, 1H), 1.60-1.70 (m, 1H), 1.44-1.59 (m, 2H), 2.90 (d, J = 6.8 Hz, 3H) | 498.5 |

TABLE 1-continued
| Cmpd. No. | Structure | ¹H-NMR | Mass Spec. (M + H)⁺ |
|---|---|---|---|
| 282 | 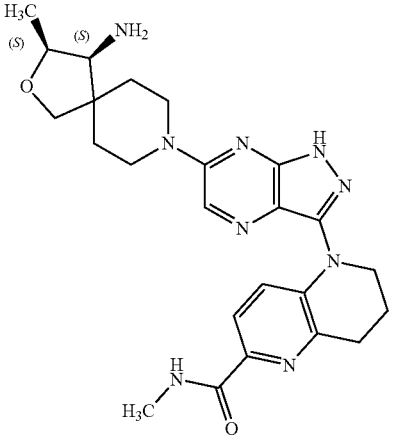 | ¹H-NMR (400 MHz, DMSO-d$_6$) δ 12.79 (s, 1H), 8.37 (s, 1H), 7.86 (br s, 2H), 7.56-7.67 (m, 1H), 7.42-7.53 (m, 1H), 4.16-4.36 (m, 3H), 3.93-4.03 (m, 1H), 3.83-3.91 (m, 1H), 3.62-3.78 (m, 2H), 3.14-3.25 (m, 2H), 2.95-3.05 (m, 1H), 2.71-2.90 (m, 3H), 2.50-2.56 (m, 2H), 2.01-2.19 (m, 2H), 1.66-1.85 (m, 3H), 1.49-1.65 (m, 1H), 1.12-1.28 (m, 3H) | 478.6 |
| 283 | 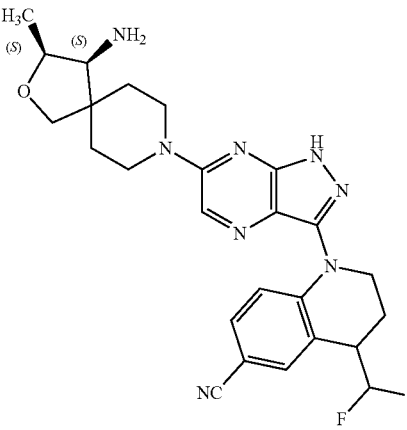 | ¹H-NMR (400 MHz, DMSO-d$_6$) δ 8.30-8.38 (m, 1H), 8.18 (s, 1H), 7.61 (s, 1H), 7.37 (dd, J = 1.95, 8.79 Hz, 1H), 6.90 (d, J = 8.79 Hz, 1H), 6.38 (dt, J = 3.66, 55.91 Hz, 1H), 4.05-4.20 (m, 3H), 3.75-3.95 (m, 3H), 3.60 (d, J = 8.79 Hz, 1H), 3.29 (dt, J = 10.62, 13.98 Hz, 2H), 3.15 (br d, J = 4.88 Hz, 1H), 2.16-2.26 (m, 1H), 2.02-2.15 (m, 1H), 1.59-1.80 (m, 3H), 1.53 (br d, J = 13.92 Hz, 1H), 1.13 (d, J = 6.59 Hz, 3H) | 495.2 |
| 284 | 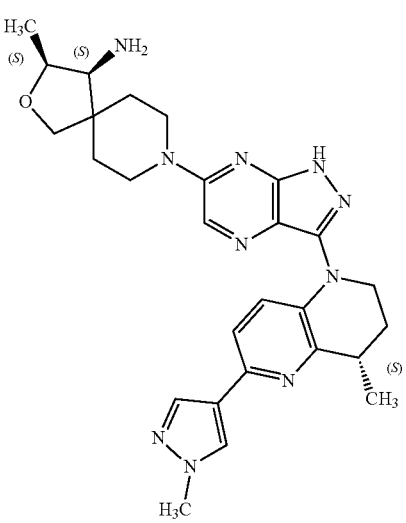 | ¹H-NMR (400 MHz, methanol-d$_4$) δ 8.37 (s, 1H), 8.35 (s, 1H), 8.13 (s, 1H), 8.10-8.07 (d, J = 9.2 Hz, 1H), 7.76-7.73 (d, J = 9.2 Hz, 1H), 4.51-4.32 (m, 4H), 4.19 (m, 2H), 4.05-4.00 (s, 3H), 3.93-3.91 (m, 1H), 3.60 (m, 1H), 3.45 (m, 1H), 3.30-3.26 (m, 2H), 2.36 (m, 1H), 2.16 (m, 1H), 1.96-1.93 (m, 3H), 1.79 (m, 1H), 1.60-1.57 (d, J = 7.2 Hz, 3H), 1.36-1.34 (d, J = 6.4 Hz, 3H) | 515.2 |

TABLE 1-continued

| Cmpd. No. | Structure | ¹H-NMR | Mass Spec. (M + H)⁺ |
|---|---|---|---|
| 285 | 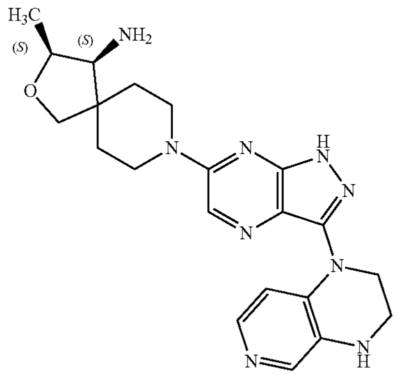 | ¹H-NMR (400 MHz, DMSO-d₆) δ 8.42 (s, 1H), 7.78 (s, 1H), 7.68-7.74 (m, 1H), 7.03-7.23 (m, 1H), 4.12-4.37 (m, 3H), 4.00-4.10 (m, 2H), 3.83-3.94 (m, 1H), 3.64-3.77 (m, 1H), 3.48 (br t, J = 4.52 Hz, 2H), 3.28-3.38 (m, 1H), 3.06-3.25 (m, 2H), 1.69-1.83 (m, 2H), 1.45-1.69 (m, 2H), 1.20 (d, J = 6.35 Hz, 3H) | 422.6 |
| 286 | 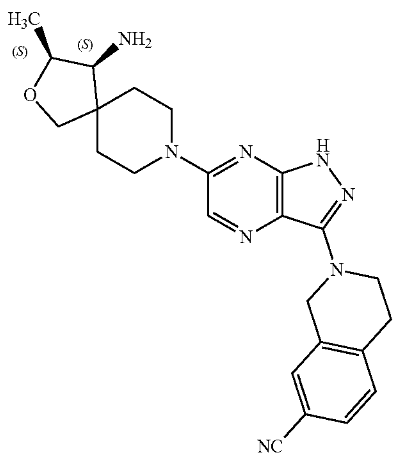 | ND | 445.2 |
| 287 | 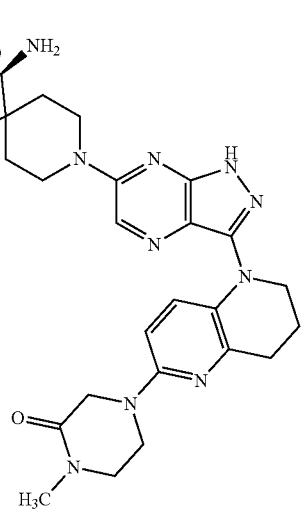 | ¹H-NMR (400 MHz, DMSO-d₆) δ 8.30-8.39 (s, 1H), 8.06 (m, 1H), 7.12-7.19 (m, 1H), 4.45-4.49 (m, 1H), 4.33-4.41 (m, 2H), 4.27-4.33 (m, 1H), 3.99-4.06 (m, 3H), 3.85-3.99 (m, 3H), 3.65-3.71 (m, 2H), 3.48 (s, 1H), 3.32-3.33 (m, 1H), 3.28 (m, 1H), 3.22-3.23 (m, 1H), 3.16-3.22 (m, 2H) 3.04-3.13 (m, 3H) | 532.6 |

TABLE 1-continued

| Cmpd. No. | Structure | ¹H-NMR | Mass Spec. (M + H)⁺ |
|---|---|---|---|
| 288 | 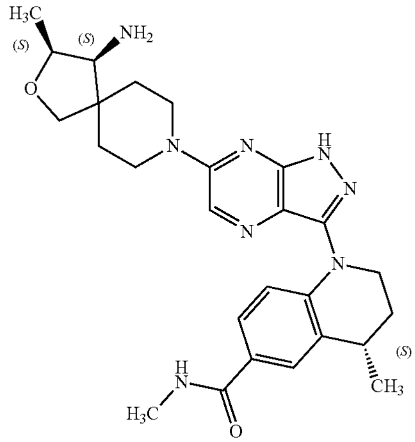 | ¹H-NMR (400 MHz, methanol-d₄) δ 8.39 (s, 1H), 7.79 (s, 1H), 7.59-7.56 (d, J = 8.8 Hz, 1H), 7.17-7.14 (d, J = 8.4 Hz, 1H), 4.51-4.35 (m, 2H), 4.34 (m, 1H), 4.16-3.91 (m, 4H), 3.50-3.49 (m, 1H), 3.41-3.89 (m, 2H), 3.11-3.08 (m, 1H), 2.94 (s, 3H), 2.25 (m, 1H), 1.95-1.80 (m, 5H), 1.46-1.44 (d, J = 7.2 Hz, 3H), 1.36-1.34 (d, J = 6.0 Hz, 1H) | 491.5 |
| 289 | 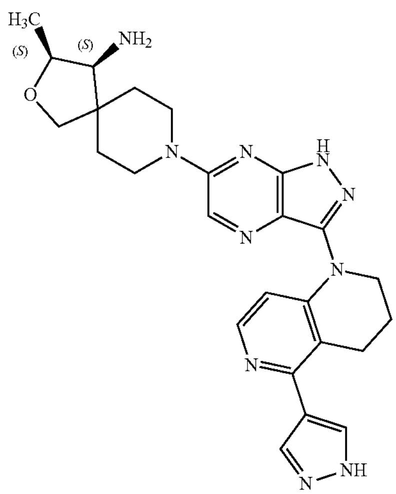 | ¹H-NMR (400 MHz, methanol-d₄) δ 8.43 (s, 1H), 8.22 (s, 2H), 7.93 (d, J = 7.2 Hz, 1H), 6.87 (d, J = 7.2 Hz, 1H), 4.52-4.32 (m, 3H), 4.09-4.04 (m, 3H), 3.92 (d, J = 9.2 Hz, 1H), 3.50 (d, J = 4.0 Hz, 1H), 3.39-3.34 (m, 1H), 3.29-3.25 (m, 1H), 3.08 (t, J = 6.0 Hz, 2H), 2.26-2.20 (m, 2H), 1.97-1.90 (m, 3H), 1.81-1.78 (m, 1H), 1.36 (d, J = 6.4 Hz, 3H) | 487.1 |
| 290 | 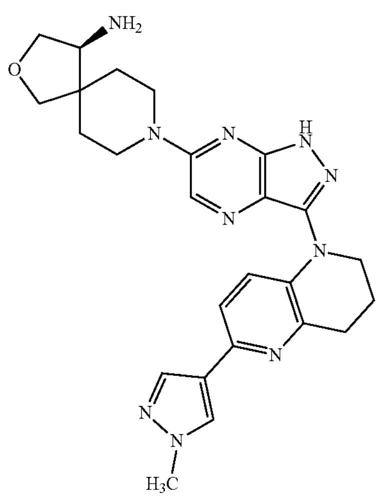 [SMILES: Cn1cc(-c2ccc3c(n2)CCCN3c2n[nH]c3nc(N4CCC5(CC4)COC[C@H]5N)cnc23)cn1] | ¹H-NMR (400 MHz, DMSO-d₆) δ 8.29-8.41 (m, 2H), 8.25 (s, 2H), 7.99 (s, 2H), 7.83 (br d, J = 8.79 Hz, 2H), 7.50 (br d, J = 8.79 Hz, 1H), 4.20-4.28 (m, 1H), 4.17 (br d, J = 13.92 Hz, 1H), 4.07 (dd, J = 6.10, 10.50 Hz, 2H), 3.93-4.02 (m, 3H), 3.88 (s, 2H), 3.85 (br d, J = 9.28 Hz, 1H), 3.68 (dd, J = 3.17, 10.50 Hz, 1H), 3.50 (br dd, J = 3.42, 5.86 Hz, 1H), 3.29 (br t, J = 10.62 Hz, 1H), 3.14-3.23 (m, 1H), 2.98-3.14 (m, 4H), 2.09 (td, J = 6.07, 11.54 Hz, 4H), 1.54-1.80 (m, 8H) | 487.3 |

TABLE 1-continued

| Cmpd. No. | Structure | ¹H-NMR | Mass Spec. (M + H)⁺ |
|---|---|---|---|
| 291 | 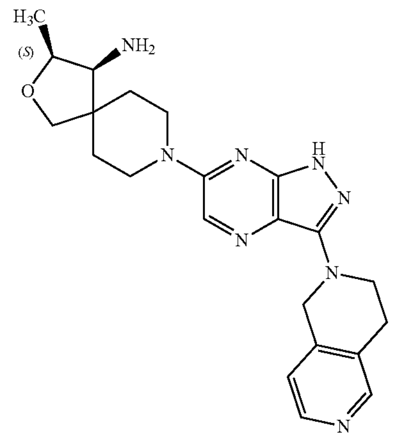 | ND | 421.2 |
| 292 | 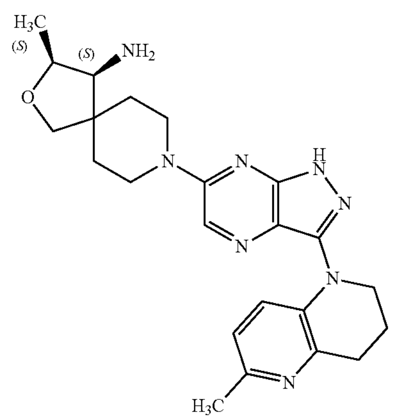 | ¹H-NMR (400 MHz, DMSO-d₆) δ 12.48 (br, 1H), 8.27 (s, 1H), 7.46 (d, J = 8.4 Hz, 1H), 6.83 (d, J = 8.4 Hz, 1H), 4.00-4.11 (m, 1H), 3.86-4.00 (m, 4H), 3.67 (d, J = 8.8 Hz, 1H), 3.46-3.58 (m, 1H), 2.81-2.95 (m, 3H), 2.32 (s, 3H), 1.89-2.12 (m, 3H), 1.71-1.82(m, 1H), 1.59-1.70 (m, 1H), 1.41-1.58 (m, 3H), 1.07 (d, J = 6.4 Hz, 3H) | 435.5 |
| 293 | 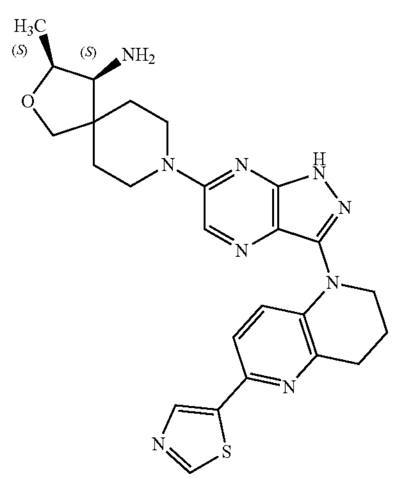 | ¹H-NMR (400 MHz, DMSO-d₆) δ 8.39 (s, 1H), 8.15 (br, 3H), 7.86 (d, J = 3.2 Hz, 1H), 7.76 (d, J = 8.8 Hz, 1H), 7.70 (d, J = 3.2 Hz, 1H), 7.60 (d, J = 8.8 Hz 1H), 4.32-4.26 (m, 2H), 4.24-4.20 (m, 2H), 4.04-4.00 (m, 2H), 3.96-3.93 (m, 1H), 3.40-3.38 (m, 1H), 3.21-3.18 (m, 2H), 3.05-3.01 (m, 2H), 2.17-2.12 (m, 2H), 1.85-1.72 (m, 2H), 1.63-1.59 (m, 2H), 1.24 (d, J = 6.4 Hz, 3H) | 504.1 |

TABLE 1-continued
| Cmpd. No. | Structure | ¹H-NMR | Mass Spec. (M + H)⁺ |
|---|---|---|---|
| 294 | 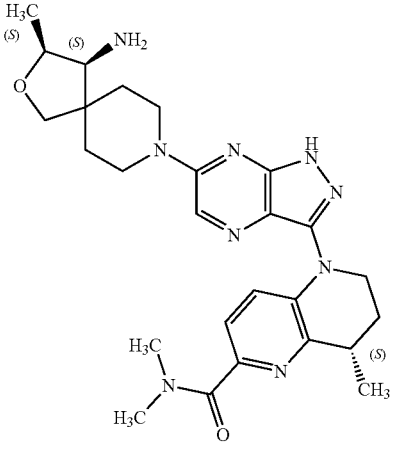 | ¹H-NMR (400 MHz, DMSO-d₆) δ 8.35 (s, 1H), 8.30 (br, 3H), 7.22 (s, 1H), 7.02-6.99 (d, J = 8.4 Hz, 1H), 6.95-6.92 (d, J = 8.4 Hz, 1H), 4.26-4.21 (m, 2H), 3.91-3.88 (m, 3H), 3.68-3.66 (m, 1H), 3.35-3.30 (m, 1H), 3.17-3.15 (m, 2H), 2.30-2.97 (m, 1H), 2.95 (s, 6H), 2.09-2.07 (m, 2H), 1.82-1.64 (m, 5H), 1.32-1.30 (d, J = 6.8 Hz, 3H), 1.26-1.24 (d, J = 6.4 Hz, 3H) | 505.6 |
| 295 | 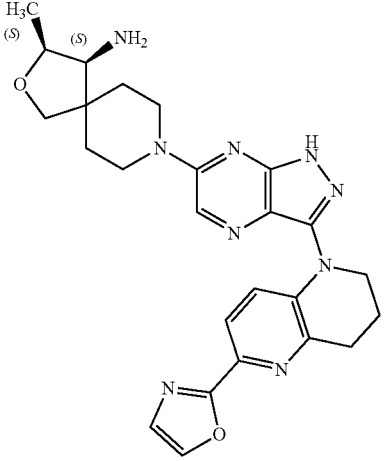 | ¹H-NMR (400 MHz, DMSO-d₆) δ 8.34 (s, 1H), 8.15 (s, 1H), 7.69 (d, J = 8.4 Hz, 1H), 7.56 (d, J = 8.8 Hz, 1H), 7.33 (s, 1H), 4.10-4.04 (m, 1H), 4.01-3.95 (m, 4H), 3.69 (d, J = 8.4 Hz, 1H), 3.55-3.45 (m, 1H), 3.03 (t, J = 6.4 Hz, 2H), 2.90 (d, J = 5.2 Hz, 1H), 2.16-2.10 (m, 2H), 2.03-1.98 (m, 1H), 1.80-1.75 (m, 1H), 1.70-1.63 (m, 1H), 1.57-1.49 (m, 1H), 1.08 (d, J = 6.4 Hz, 3H) | 488.1 |
| 296 | 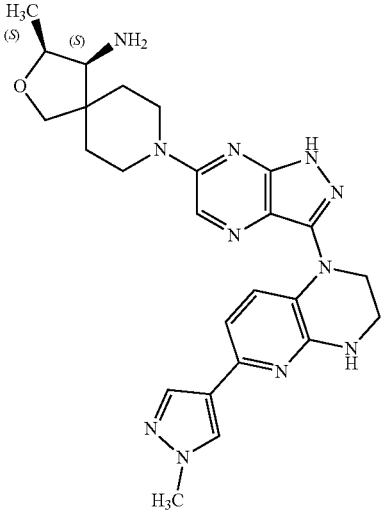 | ¹H-NMR (400 MHz, DMSO-d₆) δ 14.68 (s, 1H), 12.80 (s, 1H), 8.86 (s, 1H), 8.55 (s, 1H), 8.37 (s, 1H), 8.34 (s, 2H), 8.25 (s, 1H), 7.87 (d, J = 8.4 Hz, 1H), 7.02 (d, J = 8.4 Hz, 1H), 4.35-4.19 (m, 3H), 4.15-4.13(m, 2H), 3.96 (d, J = 9.2 Hz, 1H), 3.91 (s, 3H), 3.78-3.73 (m, 2H), 3.68 (d, J = 9.2 Hz, 1H), 3.38-3.35 (m, 1H), 3.21-3.13 (m, 2H), 1.87-1.78 (m, 2H), 1.72-1.62 (m, 2H), 1.25 (d, J = 6.8 Hz, 3H) | 502.2 |

TABLE 1-continued
| Cmpd. No. | Structure | ¹H-NMR | Mass Spec. (M + H)⁺ |
|---|---|---|---|
| 297 | 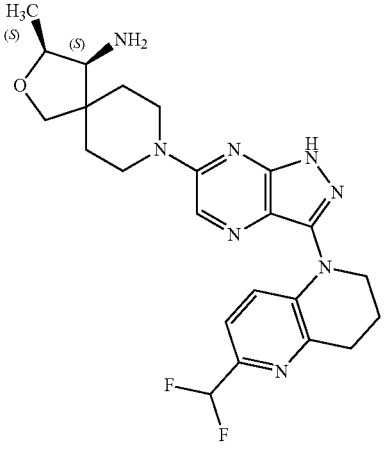 | ¹H-NMR (400 MHz, DMSO-d₆) δ 12.85 (br, 1H), 8.40 (s, 1H), 8.20~8.29 (m, 3H), 7.54~7.60 (m, 1H), 7.29~7.33 (m, 1H), 6.69~6.98 (m, 1H), 4.20~4.31 (m, 3H), 3.94~4.00 (m, 3H), 3.67~3.70 (m, 1H), 3.35~3.39 (m, 1H), 3.09~3.22 (m, 2H), 2.97~3.04 (m, 2H), 2.05~2.15 (m, 2H), 1.77~1.86 (m, 2H), 1.60~1.77 (m, 2H), 1.20-1.26 (m, 3H) | 471.5 |
| 298 | 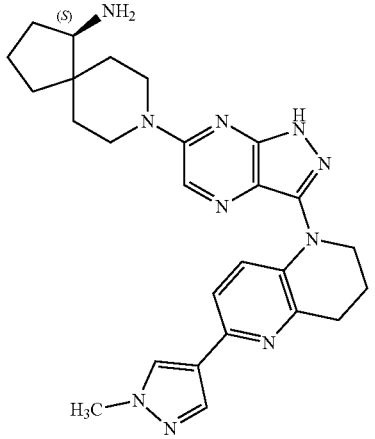 | ¹H-NMR (400 MHz, DMSO-d6) δ 8.33 (s, 1H), 8.29 (s, 1H), 8.06 (s, 1H), 7.82 (s, 1H), 7.51 (d, J = 8.54 Hz, 1H), 7.23 (d, J = 8.54 Hz, 1H), 4.28 (br dd, J = 14.53, 18.92 Hz, 2H), 3.92-3.98 (m, 2H), 3.83 (s, 3H), 3.15 (br t, J = 11.47 Hz, 2H), 3.01 (br t, J = 6.84 Hz, 1H), 2.93 (t, J = 6.47 Hz, 2H), 2.03-2.10 (m, 2H), 2.00 (br dd, J = 5.86, 12.45 Hz, 1H), 1.75-1.84 (m, 1H), 1.49-1.72 (m, 6H), 1.37 (br dd, J = 13.43, 21.48 Hz, 2H) | 485.3 |
| 299 | 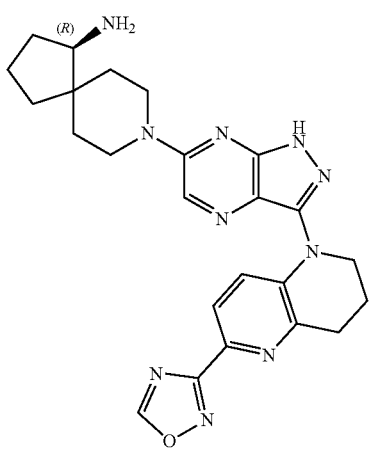 | ¹H-NMR (400 MHz, DMSO-d₆) δ 9.48 (s, 1H), 8.31 (s, 1H), 8.17 (s, 1H), 7.78 (d, J = 1.46 Hz, 1H), 7.54 (dd, J = 1.95, 8.79 Hz, 1H), 6.95 (d, J = 8.79 Hz, 1H), 4.11-4.25 (m, 2H), 4.03 (dd, J = 6.10, 10.01 Hz, 1H), 3.65-3.93 (m, 5H), 3.37 (dd, J = 4.15, 5.62 Hz, 1H), 3.16-3.33 (m, 2H), 3.00-3.09 (m, 1H), 2.03-2.14 (m, 1H), 1.73-1.81 (m, 1H), 1.68 (q, J = 9.93 Hz, 2H), 1.53-1.61 (m, 2H), 1.34 (d, J = 7.08 Hz, 3H) | 488.3 |

TABLE 1-continued

| Cmpd. No. | Structure | ¹H-NMR | Mass Spec. (M + H)⁺ |
|---|---|---|---|
| 300 | 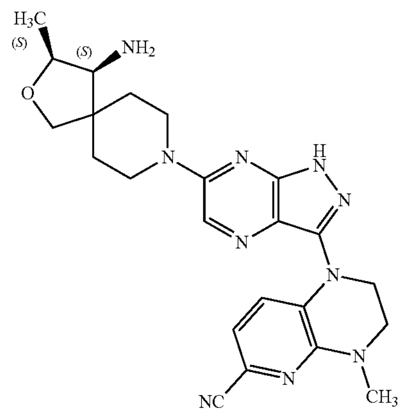 | ¹H-NMR (400 MHz, DMSO-d₆) δ 8.29 (s, 1H), 8.27 (s, 1H), 6.91-6.96 (m, 1H), 6.83-6.89 (m, 2H), 3.96-4.13 (m, 5H), 3.73 (d, J = 8.54 Hz, 1H), 3.55 (s, 1H), 3.28-3.42 (m, 4H), 3.01 (d, J = 5.13 Hz, 1H), 2.90 (s, 3H), 1.63-1.76 (m, 2H), 1.54-1.62 (m, 1H), 1.50 (br d, J = 14.16 Hz, 1H), 1.10 (d, J = 6.35 Hz, 3H) | 460.3 |
| 301 | 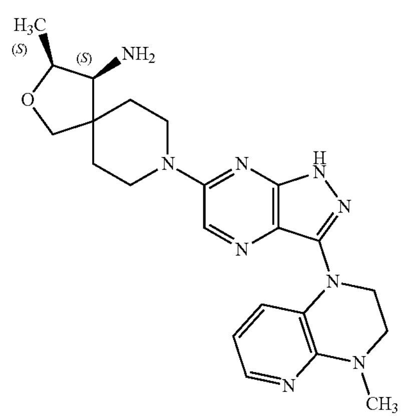 | ¹H-NMR (400 MHz, DMSO-d₆) δ 8.30 (br s, 1H), 7.51-7.64 (m, 1H), 7.27-7.42 (m, 1H), 6.38-6.58 (m, 1H), 4.15-4.40 (m, 3H), 3.97-4.12 (m, 2H), 3.81-3.97 (m, 1H), 3.62-3.76 (m, 1H), 3.46-3.51 (m, 2H), 3.14-3.25 (m, 1H), 2.99-3.13 (m, 2H), 1.66-1.84 (m, 2H), 1.46-1.66 (m, 2H), 1.09-1.27 (m, 3H) | 436.6 |
| 302 | 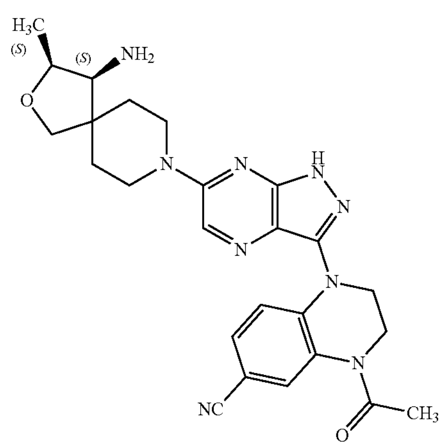 | ¹H-NMR (400 MHz, DMSO-d₆) δ 8.28 (s, 1H), 6.97-7.14 (m, 1H), 6.83 (d, J = 1.95 Hz, 1H), 6.76 (dd, J = 8.54, 1.95 Hz, 1H), 3.86-4.14 (m, 4H), 3.66-3.78 (m, 2H), 3.49-3.56 (m, 3H), 3.34-3.43 (m, 2H), 2.93-3.03 (m, 1H), 2.17-2.30 (m, 3H), 1.62-1.82 (m, 2H), 1.41-1.59 (m, 2H), 1.09 (d, J = 6.35 Hz, 3H) | 488.5 |

TABLE 1-continued

| Cmpd. No. | Structure | ¹H-NMR | Mass Spec. (M + H)⁺ |
|---|---|---|---|
| 303 | 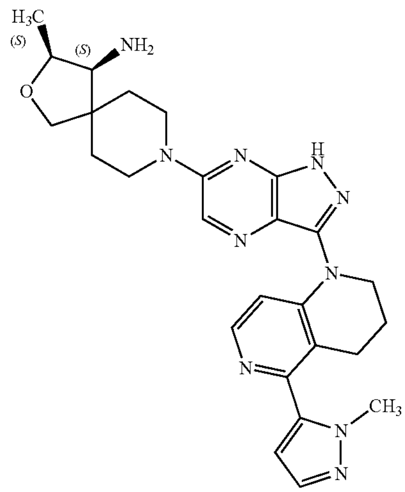 | ¹H-NMR (400 MHz, DMSO-d₆) δ 13.41-13.47 (br, 1H), 8.51 (s, 1H), 8.28-8.30 (s, 3H), 8.14-8.16 (m, 1H), 7.68-7.69 (m, 1H), 7.04-7.06 (m, 1H), 6.74-6.75 (s, 1H), 4.00-4.38(m 3H), 3.97(m 2H), 3.94-3.96 (m, 2H), 3.82 (s, 3H), 3.39-3.53 (m, 2H), 3.23-3.38 (m, 2H), 2.65-2.68 (m, 2H), 2.04-2.06 (m, 2H), 1.83-1.86 (m, 4H), 1.24-1.25 (m, 3H) | 501.6 |
| 304 | 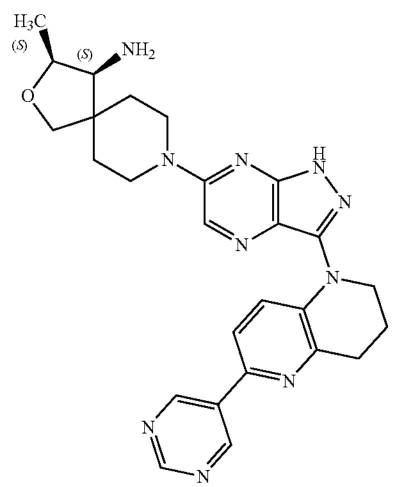 | ¹H-NMR (400 MHz, DMSO-d₆) δ 9.35 (s, 2H), 9.23 (s, 1H), 8.40 (s, 1H), 8.24 (m, 3H), 7.85 (m, 2H), 4.21-4.32 (m, 3H), 4.03-4.06 (m, 2H), 3.96-4.03 (m, 3H), 3.38-3.39 (m, 1H), 3.20-3.21 (m, 3H), 3.18 (s, 1H), 2.15-2.18 (s, 2H), 1.60-1.85 (m, 4H), 1.23-1.26 (m, 3H) | 499.6 |
| 305 | 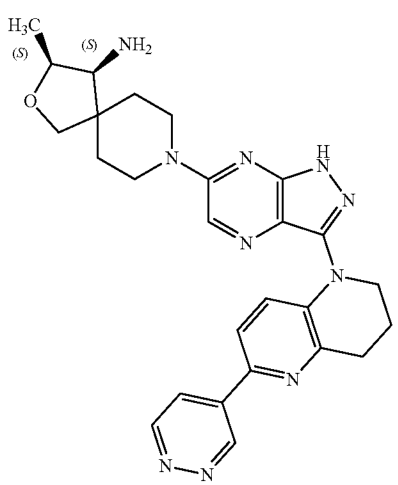 | ¹H-NMR (400 MHz, DMSO-d₆) δ 12.78 (s, 1H), 9.81 (s, 1H), 9.21 (d, J = 5.6 Hz, 1H), 8.34 (s, 1H), 8.13 (dd, J = 5.6, 2.4 Hz, 1H), 7.87 (d, J = 8.8 Hz, 1H), 7.59 (d, J = 8.8 Hz, 1H), 4.05-4.12 (m, 1H), 3.90-4.04 (m, 4H), 3.70 (d, J = 8.4 Hz, 1H), 3.48-3.57 (m, 4H), 3.07 (t, J = 6.2 Hz, 2H), 2.94 (d, J = 4.8 Hz, 1H), 2.30-2.35 (m, 1H), 2.10-2.20 (m, 2H), 1.73-1.82(m, 1H), 1.62-1.71 (m, 1H), 1.44-1.61 (m, 2H), 1.09 (d, J = 6.4 Hz, 3H) | 499.2 |

TABLE 1-continued

| Cmpd. No. | Structure | ¹H-NMR | Mass Spec. (M + H)⁺ |
|---|---|---|---|
| 306 | 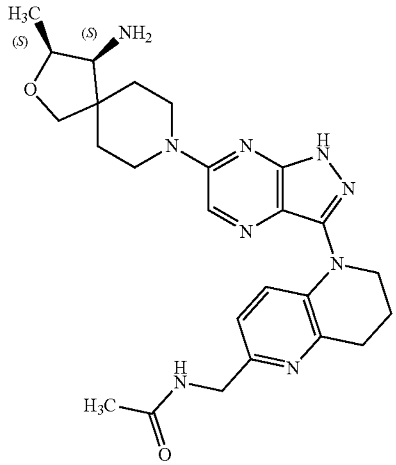 | ¹H-NMR (400 MHz, methanol-d₄) δ 8.40 (s, 1H), 8.09-8.06 (d, J = 8.0 Hz, 1H), 7.54-7.51 (d, J = 8.0 Hz, 1H), 4.59 (s, 2H), 4.51-4.34 (m, 3H), 4.10-4.03 (m, 3H), 3.92-3.88 (m, 1H), 3.52 (m, 1H), 3.33-3.32 (m, 2H), 3.32-3.30 (m, 2H), 2.31 (m, 2H), 2.06 (s, 3H), 1.98-1.94 (m, 3H), 1.81-1.78 (m, 1H), 1.36-1.34 (d, J = 6.4 Hz, 3H) | 492.6 |
| 307 | 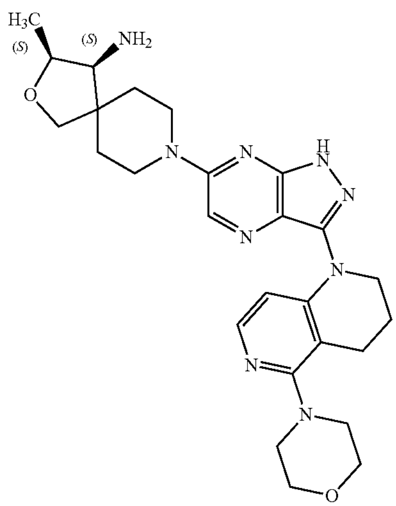 | ¹H-NMR (400 MHz, DMSO-d₆) δ 13.33 (br, 1H), 8.46 (s, 1H), 8.30 (br, 3H), 7.70 (d, J = 7.2 Hz, 1H), 6.62 (d, J = 7.2 Hz, 1H), 4.37-4.21 (m, 3H), 3.96-3.91 (m, 2H), 3.80-3.75 (m, 4H), 3.74-3.66 (m, 2H), 3.41-3.35 (m, 1H), 3.34-3.29 (m, 4H), 3.23-3.15 (m, 2H), 2.82-2.75 (m, 2H), 2.07-2.00 (m, 2H), 1.85-1.60 (m, 4H), 1.25 (d, J = 6.0 Hz, 3H) | 506.2 |
| 308 | 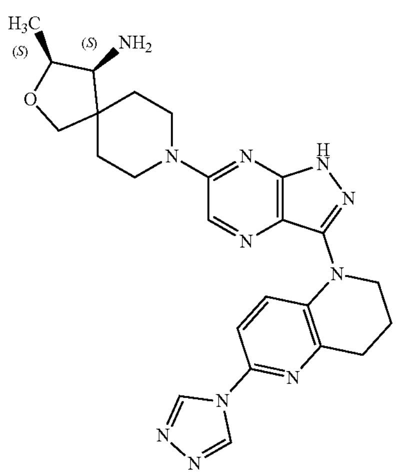 | ¹-HNMR (400 MHz, CD₃OD) δ 10.11 (s, 2H), 8.40 (br, 1H), 7.67 (d, J = 8.8 Hz, 1H), 7.57 (d, J = 8.8 Hz, 1H), 4.31-4.48 (m, 3H), 4.01-4.08 (m, 3H), 3.92 (d, J = 8.8 Hz, 1H), 3.49 (d, J = 4.0 Hz, 1H), 3.26-3.40 (m, 2H), 3.12-3.17 (m, 2H), 2.20-2.35 (m, 2H), 1.90-1.96 (m, 3H), 1.75-1.80 (m, 1H), 1.35 (d, J = 6.8 Hz, 3H) | 488.2 |

TABLE 1-continued

| Cmpd. No. | Structure | ¹H-NMR | Mass Spec. (M + H)⁺ |
|---|---|---|---|
| 309 | 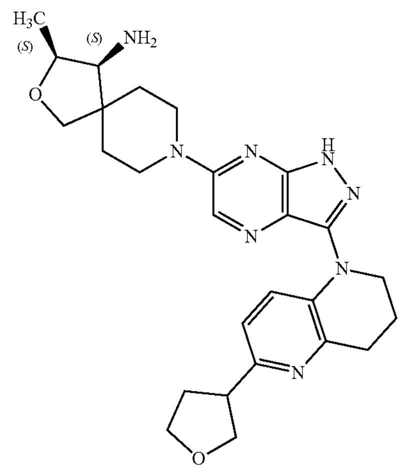 | ¹H-NMR (400 MHz, DMSO-d₆) δ 12.91 (br, 1H), 8.36 (s, 1H), 8.21 (s, 3H), 8.10 (d, J = 9.2 Hz, 1H), 7.48 (d, J = 9.2 Hz, 1H), 4.31-4.17 (m, 3H), 4.01-3.86 (m, 6H), 3.78-3.69 (m, 3H), 3.35-3.32 (m, 1H), 3.25-3.11 (m, 4H), 2.39-2.33 (m, 1H), 2.11-1.98 (m, 3H), 1.82-1.57 (m, 4H), 1.21 (d, J = 6.8 Hz, 3H) | 491.2 |
| 310 | 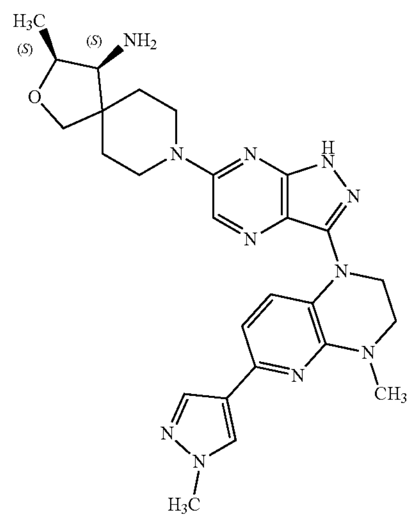 | ¹H-NMR (500 MHz, DMSO-d₆) δ 12.79 (br, 1H), 8.36-8.31 (m, 5H), 7.96 (s, 1H), 7.62 (d, J = 8.0 Hz, 1H), 6.87 (d, J = 8.4 Hz, 1H), 4.26-4.12 (m, 6H), 3.95 (d, J = 9.2 Hz, 1H), 3.91 (s, 3H), 3.76 (br, 2H), 3.68 (d, J = 9.2 Hz, 1H), 3.38 (s, 3H), 1.85-1.62 (m, 4H), 1.25 (d, J = 6.8 Hz, 3H) | 516.1 |
| 311 | 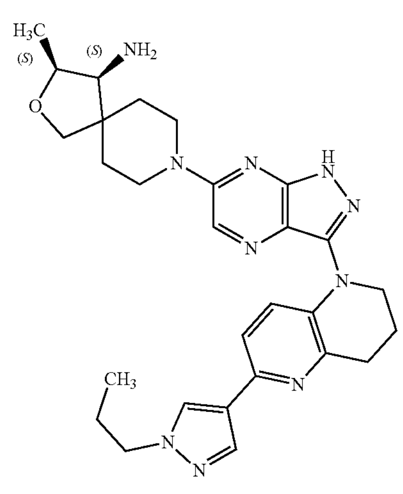 | ¹H-NMR (400 MHz, DMSO-d₆) δ 12.95 (s, 1H), 8.79 (s, 1H), 8.35-8.41 (m, 2H), 8.18-8.25 (m, 3H), 7.82-7.84 (m, 1H), 4.14-4.35 (m, 5H), 4.05-4.07 (m, 2H), 3.93-4.00 (m, 1H), 3.68-3.70 (m, 1H), 3.34-3.38 (m, 3H), 3.16-3.23 (m, 2H), 2.14-2.16 (m, 2H), 1.61-1.89 (m, 6H), 1.24-1.26 (m, 3H), 0.85-0.89 (m, 3H) | 529.7 |

TABLE 1-continued
| Cmpd. No. | Structure | ¹H-NMR | Mass Spec. (M + H)⁺ |
|---|---|---|---|
| 312 | 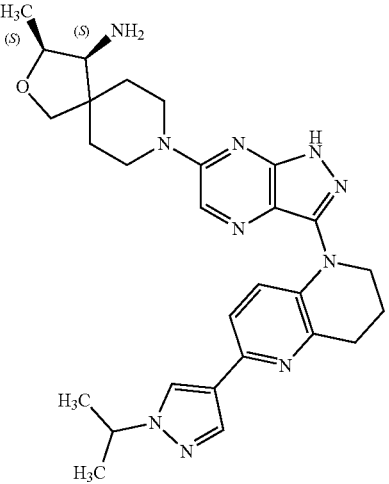 | ¹H-NMR (400 MHz, DMSO-d$_6$) δ 12.95 (s, 1H), 8.94 (s, 1H), 8.38-8.40 (m, 2H), 8.25-8.30 (m, 2H), 8.19-8.21 (s, 1H), 7.85-7.87 (m, 1H), 4.55-4.59 (m, 4H), 4.18-4.36 (m, 3H), 4.02-4.12 (m, 2H), 3.95 (m, 1H), 3.65-3.73 (m, 1H), 3.30-3.45 (m, 3H), 3.10-3.25 (m, 2H), 2.08-2.20 (m, 2H), 1.57-1.97 (m, 3H), 1.46-1.55 (m, 6H), 1.19-1.30 (m, 3H) | 529.6 |
| 313 | 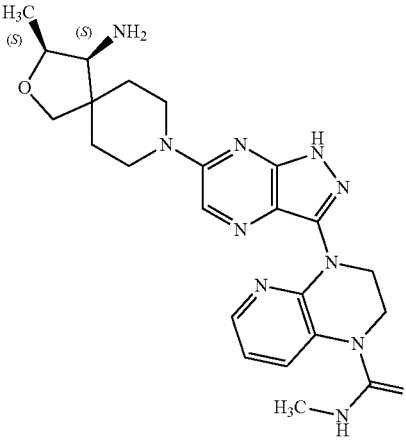 | ¹H-NMR (400 MHz, CD$_3$OD) δ 8.49 (s, 1H), 8.40~8.32 (m, 1H), 8.12~7.98 (m, 1H), 7.60~7.52 (m, 1H), 4.58~4.48 (m, 2H), 4.38~4.32 (m, 1H), 4.15~4.10 (m, 2H), 4.02~3.88 (m, 2H), 3.75~3.48 (m, 4H), 3.46~3.42 (m, 1H), 2.88 (s, 3H), 1.95~1.72 (m, 4H), 1.35~1.27 (m, 3H) | 479.2 |
| 314 | 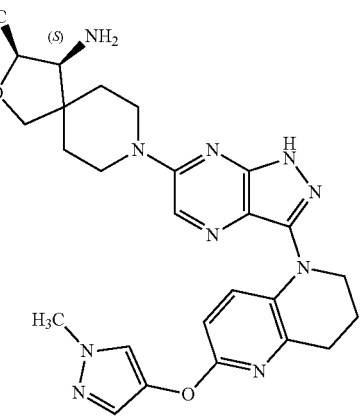 | ¹H-NMR (400 MHz, DMSO-d$_6$) δ 8.33 (s, 1H), 8.25 (br s, 3H), 7.84 (s, 1H), 7.76 (d, J = 9.2 Hz, 1H), 7.42 (s, 1H), 6.68 d, J = 8.8 Hz, 1H), 4.30-4.23 (m, 3H), 4.01-3.98 (m, 2H), 3.96-3.94 (m, 1H), 3.81 (s, 3H), 3.69-3.67 (m, 1H), 3.38-3.35 (m, 1H), 3.20-3.13 (m, 2H), 2.87-2.84 (m, 2H), 2.04-1.98 (m, 2H), 1.84-1.77 (m, 2H), 1.71-1.68 (m, 1H), 1.63-1.60 (m, 1H), 1.25 (d, J = 6.4 Hz, 3H) | 517.3 |

TABLE 1-continued

| Cmpd. No. | Structure | ¹H-NMR | Mass Spec. (M + H)⁺ |
|---|---|---|---|
| 315 | 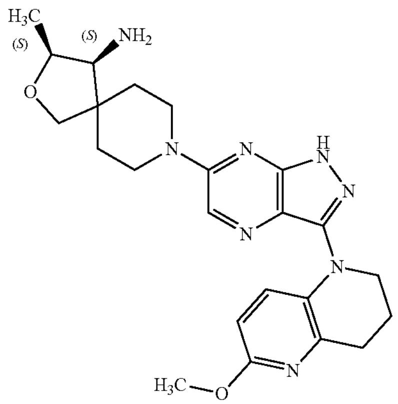 | ¹HNMR (400 MHz, DMSO-d₆) δ 12.52 (br s, 1H), 8.33 (s, 1H), 8.26 (br, 3H), 7.89 (d, J = 9.2 Hz, 1H), 6.25 (d, J = 9.2 Hz, 1H), 4.33-4.30 (m, 1H), 4.25-4.18 (m, 2H), 4.02-4.00 (m, 3H), 3.96-3.93 (m, 3H), 3.69-3.67 (m, 1H), 3.37-3.35 (m, 1H), 3.20-3.12 (m, 2H), 2.94-2.90 (m, 2H), 2.03-1.97 (m, 2H), 1.84-1.78 (m, 2H), 1.71-1.68 (m, 1H), 1.63-1.60 (m, 1H), 1.25 (d, J = 6.8 Hz, 3H) | 451.1 |
| 316 | 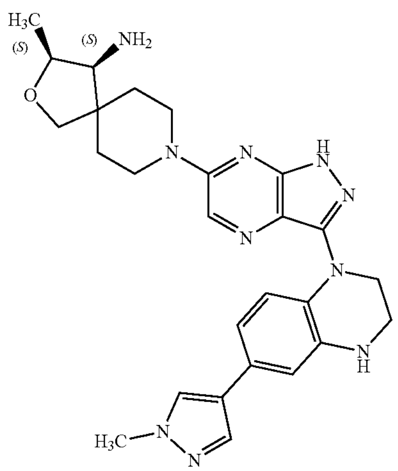 | ¹H-NMR (400 MHz, CD₃OD) δ 8.35 (s, 1H), 8.10 (s, 1H), 7.98 (s, 1H), 7.48-7.42 (m, 2H), 7.27 (d, J = 8.8 Hz, 1H), 4.51-4.27 (m, 5H), 4.05-3.91 (m, 5H), 3.84-3.82 (m, 2H), 3.48 (d, J = 4.4 Hz, 1H), 3.27-3.27 (m, 2H), 1.94-1.76 (m, 4H), 1.35 (d, J = 6.4 Hz, 3H) | 501.2 |
| 317 | 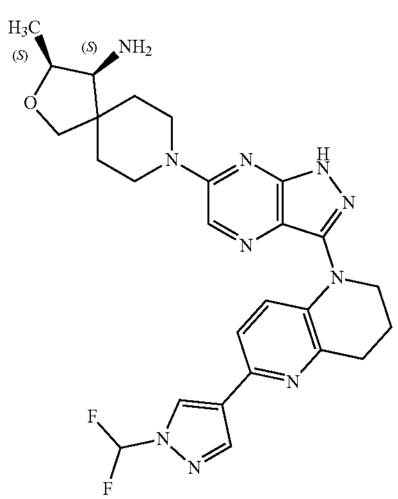 | ¹H-NMR (400 MHz, DMSO-d₆) δ 12.95 (br, 1H), 9.21 (s, 1H), 8.61 (s, 1H), 8.40 (s, 1H), 8.27 (br, 3H), 8.12-7.82 (m, 3H), 4.35-4.20 (m, 3H), 4.15-4.00 (m, 2H), 3.97-3.92 (m, 1H), 3.71-3.67 (m, 2H), 3.40-3.30 (m, 2H), 3.24-3.12 (m, 2H), 2.20-2.11 (m, 2H), 1.87-1.77 (m, 2H), 1.75-1.57 (m, 2H), 1.25 (d, J = 6.4 Hz, 3H) | 537.1 |

TABLE 1-continued

| Cmpd. No. | Structure | ¹H-NMR | Mass Spec. (M + H)⁺ |
|---|---|---|---|
| 318 | 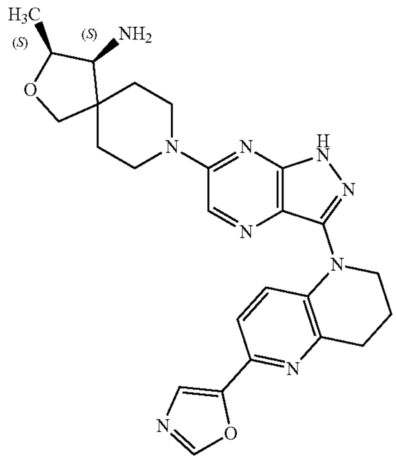 | ¹H-NMR (400 MHz, DMSO-d$_6$) δ 12.7 (s, 1H), 8.39 (s, 1H), 8.33 (s, 1H), 7.50-7.60 (m, 1H), 7.52 (s, 1H), 7.37-7.40 (m, 1H), 4.04-4.10 (m, 1H), 3.95-4.01 (m, 4H), 3.68-3.71 (m, 1H), 3.49-3.53 (m, 2H), 2.98-3.01 (m, 2H), 2.93-2.94 (m, 1H), 2.10-2.14 (m, 2H), 1.47-1.80 (m, 5H), 1.08-1.10 (m, 3H) | 488.2 |
| 319 | 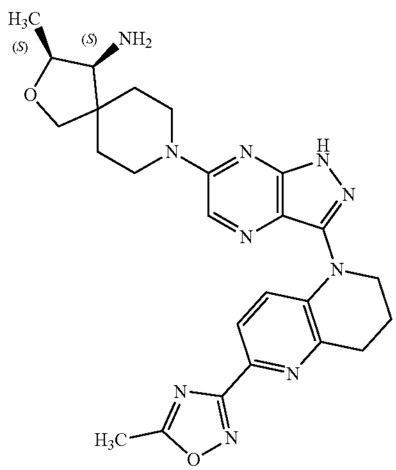 | ¹H-NMR (400 MHz, DMSO-d$_6$) δ 12.77 (br s, 1H), 8.34 (s, 1H), 7.61-7.66 (m, 1H), 7.54 (d, J = 8.54 Hz, 1H), 4.07 (quin, J = 6.10 Hz, 1H), 3.90-4.02 (m, 4H), 3.69 (d, J = 8.54 Hz, 1H), 3.47-3.54 (m, 3H), 3.44 (d, J = 3.42 Hz, 2H), 3.02 (br t, J = 6.35 Hz, 2H), 2.94 (d, J = 4.88 Hz, 1H), 2.57-2.67 (m, 3H), 2.12 (quin, J = 5.98 Hz, 2H), 1.76 (ddd, J = 3.66, 9.58, 13.12 Hz, 1H), 1.63-1.71 (m, 1H), 1.44-1.59 (m, 2H), 1.08 (d, J = 6.35 Hz, 3H) | 503.6 |
| 320 | 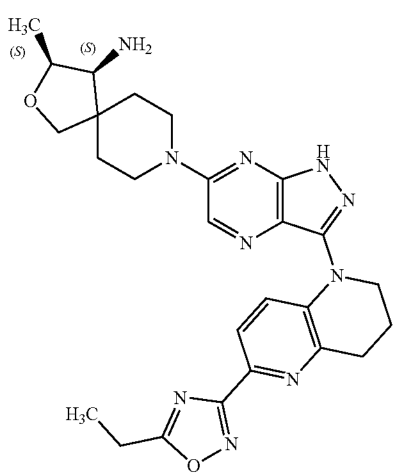 | ¹H-NMR (400 MHz, DMSO-d$_6$) δ 12.77 (br s, 1H), 8.33 (s, 1H), 8.25 (s, 1H), 7.60-7.68 (m, 1H), 7.54 (d, J = 8.54 Hz, 1H), 4.06 (td, J = 6.23, 11.96 Hz, 1H), 3.89-4.01 (m, 4H), 3.68 (d, J = 8.54 Hz, 1H), 3.41-3.55 (m, 4H), 3.35-3.56 (m, 2H), 2.99-3.05 (m, 2H), 2.97 (d, J = 7.57 Hz, 1H), 2.90-2.95 (m, 1H), 2.12 (quin, J = 5.98 Hz, 2H), 1.76 (ddd, J = 3.42, 9.46, 13.00 Hz, 1H), 1.62-1.69 (m, 1H), 1.45-1.58 (m, 2H), 1.32 (t, J = 7.57 Hz, 2H), 1.08 (d, J = 6.35 Hz, 2H) | 517.6 |

TABLE 1-continued
| Cmpd. No. | Structure | ¹H-NMR | Mass Spec. (M + H)+ |
|---|---|---|---|
| 321 | 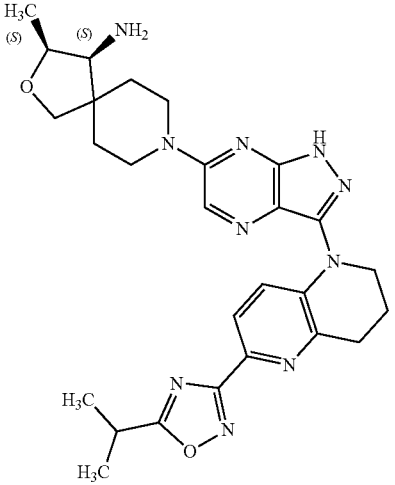 | ¹H-NMR (400 MHz, DMSO-d$_6$) δ 12.77 (br s, 1H), 8.33 (s, 1H), 7.64 (d, J = 8.69 Hz, 1H), 7.54 (d, J = 8.69 Hz, 1H), 4.06 (quin, J = 6.06 Hz, 1H), 3.90-4.02 (m, 4H), 3.68 (d, J = 8.54 Hz, 1H), 3.47-3.54 (m, 2H), 3.43 (ddd, J = 2.97, 9.65, 13.16 Hz, 1H), 3.28-3.35 (m, 3H), 3.02 (br t, J = 6.41 Hz, 2H), 2.91 (d, J = 5.19 Hz, 1H), 2.09-2.15 (m, 2H), 1.76 (ddd, J = 3.43, 9.50, 13.16 Hz, 1H), 1.66 (ddd, J = 3.74, 9.30, 13.19 Hz, 1H), 1.46-1.59 (m, 2H), 1.36 (d, J = 7.02 Hz, 6H), 1.07 (d, J = 6.41 Hz, 3H) | 531.5 |
| 322 | 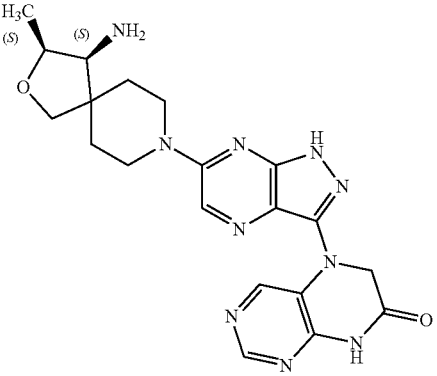 | ¹H-NMR (400 MHz, DMSO-d$_6$) δ 8.61 (s, 1H), 8.37-8.42 (m, 1H), 8.30 (s, 1H), 4.66 (s, 2H), 4.02-4.09 (m, 1H), 3.89-4.00 (m, 2H), 3.67 (d, J = 8.69 Hz, 1H), 3.36-3.45 (m, 2H), 2.89 (d, J = 5.03 Hz, 1H), 1.74 (ddd, J = 3.66, 9.61, 13.27 Hz, 1H), 1.65 (ddd, J = 3.66, 9.38, 13.19 Hz, 1H), 1.51-1.57 (m, 1H), 1.44-1.51 (m, 1H), 1.06 (d, J = 6.41 Hz, 3H) | 437.2 |
| 323 | 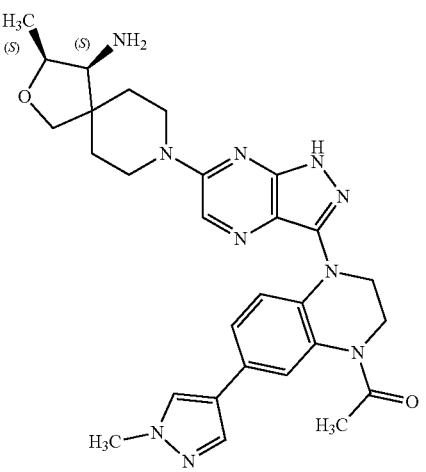 | ¹H-NMR (400 MHz, DMSO-d$_6$) δ 8.33-8.42 (m, 1H), 8.24-8.32 (m, 1H), 7.96-8.06 (m, 1H), 7.75 (br s, 1H), 7.20-7.26 (m, 1H), 7.16 (br d, J = 6.84 Hz, 1H), 3.99-4.13 (m, 3H), 3.95 (br d, J = 5.13 Hz, 4H), 3.82 (s, 3H), 3.60-3.74 (m, 2H), 3.45-3.55 (m, 2H), 2.90 (br d, J = 4.88 Hz, 1H), 2.25 (s, 3H), 1.62-1.80 (m, 2H), 1.42-1.58 (m, 2H), 1.07 (d, J = 6.35 Hz, 3H) | 543.5 |

TABLE 1-continued

| Cmpd. No. | Structure | ¹H-NMR | Mass Spec. (M + H)⁺ |
|---|---|---|---|
| 324 | 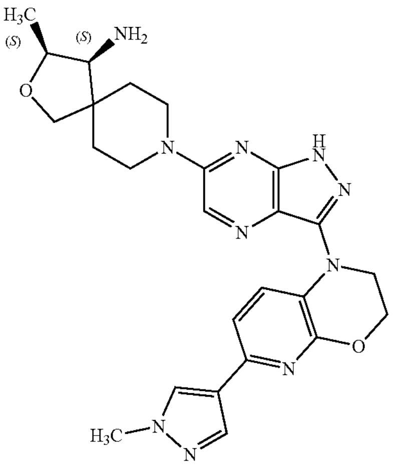 | ND | 503.6 |
| 325 | 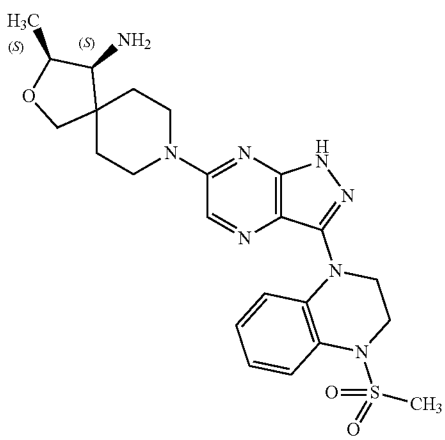 | ¹H-NMR (400 MHz, DMSO-d₆) δ 8.29 (s, 1H), 8.25 (s, 1H), 7.42 (dd, J = 1.22, 8.06 Hz, 1H), 7.06 (dd, J = 1.22, 8.30 Hz, 1H), 6.92-6.99 (m, 1H), 6.75-6.81 (m, 1H), 4.05-4.12 (m, 1H), 3.95-4.04 (m, 4H), 3.84-3.91 (m, 2H), 3.71 (d, J = 8.79 Hz, 1H), 3.52 (d, J = 8.54 Hz, 1H), 3.30-3.42 (m, 2H), 3.04 (s, 3H), 2.98 (d, J = 5.13 Hz, 1H), 1.62-1.78 (m, 2H), 1.44-1.60 (m, 2H), 1.09 (d, J = 6.35 Hz, 3H) | 499.2 |
| 326 | 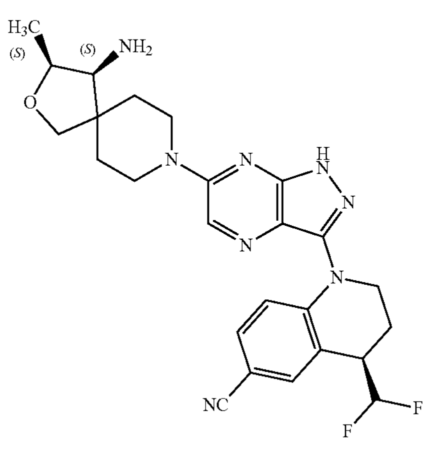 | ¹H-NMR (400 MHz, DMSO-d₆) δ 12.90 (br s, 1H), 8.35 (s, 1H), 7.63 (s, 1H), 7.38 (dd, J = 1.95, 8.79 Hz, 1H), 6.95 (d, J = 8.79 Hz, 1H), 6.25-6.59 (m, 1H), 4.06 (quin, J = 6.04 Hz, 1H), 3.81-4.00 (m, 4H), 3.65-3.73 (m, 1H), 3.39-3.56 (m, 5H), 2.93 (d, J = 5.13 Hz, 1H), 2.17-2.25 (m, 1H), 2.03-2.16 (m, 1H), 1.76 (ddd, J = 3.42, 9.58, 13.12 Hz, 1H), 1.60-1.70 (m, 1H), 1.43-1.60 (m, 2H), 1.08 (d, J = 6.35 Hz, 3H) | 495.2 |

TABLE 1-continued

| Cmpd. No. | Structure | ¹H-NMR | Mass Spec. (M + H)⁺ |
|---|---|---|---|
| 327 | 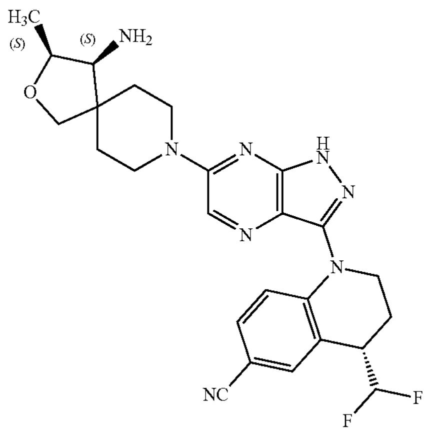 | ¹H-NMR (400 MHz, DMSO-d₆) δ 12.90 (br s, 1H), 8.35 (s, 1H), 7.63 (s, 1H), 7.38 (dd, J = 2.08, 8.91 Hz, 1H), 6.95 (d, J = 8.79 Hz, 1H), 6.26-6.58 (m, 1H), 4.06 (quin, J = 6.10 Hz, 1H), 3.80-4.01 (m, 4H), 3.68 (d, J = 8.54 Hz, 1H), 3.41-3.57 (m, 4H), 3.40-3.60 (m, 1H), 2.93 (d, J = 5.13 Hz, 1H), 2.17-2.26 (m, 1H), 2.05-2.15 (m, 1H), 1.76 (ddd, J = 3.42, 9.58, 13.12 Hz, 1H), 1.60-1.71 (m, 1H), 1.45-1.58 (m, 2H), 1.08 (d, J = 6.59 Hz, 3H) | 495.2 |
| 328 | 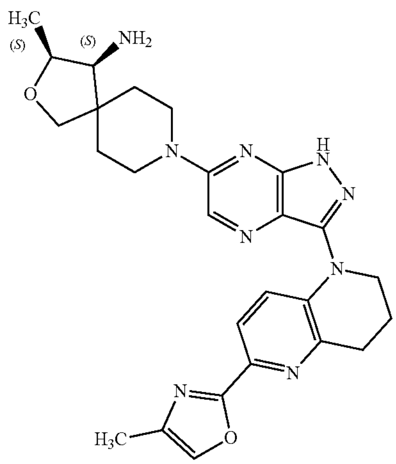 | ¹H-NMR (400 MHz, CD₃OD) δ 8.37 (s, 1H), 8.06-8.00 (m, 2H), 7.96 (s, 1H), 4.51-4.35 (m, 3H), 4.14 (t, J = 5.8 Hz, 2H), 4.04 (d, J = 9.2 Hz, 1H), 3.92 (d, J = 8.8 Hz, 1H), 3.49 (d, J = 4.0 Hz, 1H), 3.40-3.27 (m, 4H), 2.38-2.32 (m, 5H), 1.95-1.76 (m, 4H), 1.35 (d, J = 6.4 Hz, 3H) | 502.3 |
| 329 | 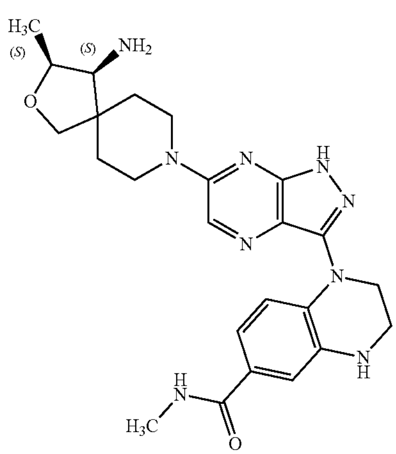 | ¹H-NMR (400 MHz, DMSO-d₆) δ 12.7 (s, 1H), 8.36 (s, 1H), 8.10-8.19 (m, 4H), 7.37 (s, 1H), 7.16-7.19 (m, 2H), 4.30-4.36 (m, 1H), 4.20-4.26 (m, 2H), 4.06-4.07 (m, 2H), 3.92-3.95 (m, 2H), 3.65-3.71 (m, 1H), 3.14-3.23 (m, 2H), 2.73-2.75 (m, 3H), 1.97-2.03 (m, 1H), 1.77-1.80 (m, 2H), 1.69-1.73 (m, 1H), 1.59-1.63 (m, 1H), 1.24 (s, 3H) | 478.6 |

TABLE 1-continued

| Cmpd. No. | Structure | ¹H-NMR | Mass Spec. (M + H)⁺ |
|---|---|---|---|
| 330 | 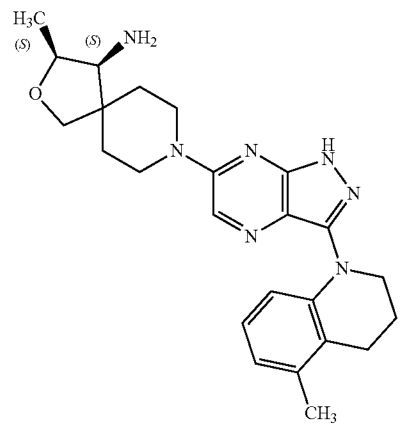 | ¹H-NMR (400 MHz, methanol-d₄) δ 8.42 (s, 1H), 7.11-7.19 (m, 2H), 7.01-7.10 (m, 1H), 4.46-4.57 (m, 2H), 4.32-4.36 (m, 1H), 4.26-4.30 (m, 2H), 4.03-4.06 (m, 1H), 3.90-3.94 (m, 1H), 3.49-3.51 (m, 1H), 3.34-3.42 (m, 2H), 2.81-2.85 (m, 2H), 2.30 (s, 3H), 2.11-2.15 (m, 2H), 1.89-1.99 (m, 3H), 1.77-1.82 (m, 1H), 1.34-1.36 (m, 3H) | 434.5 |
| 331 | 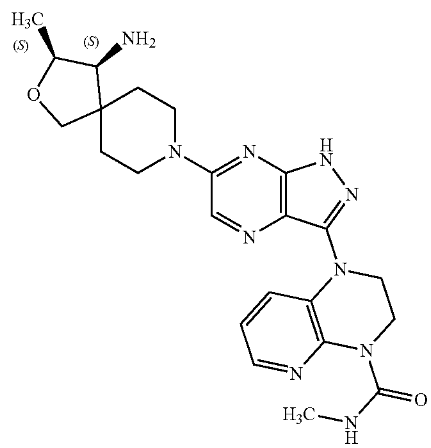 | ¹H-NMR (400 MHz, CD₃OD) δ 8.49 (s, 1H), 8.40~8.32 (m, 1H), 8.12~7.98 (m, 1H), 7.60~7.52 (m, 1H), 4.58~4.48 (m, 2H), 4.38~4.32 (m, 1H), 4.15~4.10 (m, 2H), 4.02~3.88 (m, 2H), 3.75~3.48 (m, 4H), 3.46~3.42 (m, 1H), 2.88 (s, 3H), 1.95~1.72 (m, 4H), 1.35~1.27 (m, 3H) | 479.2 |
| 332 | 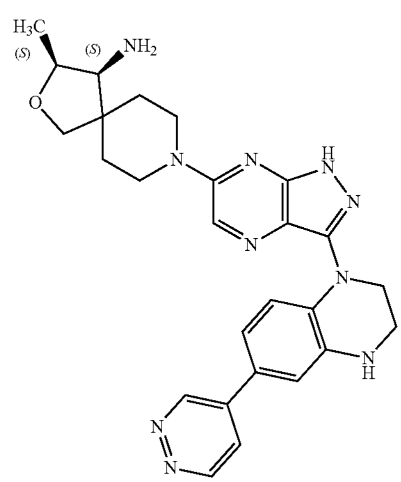 | ¹H-NMR (400 MHz, CD₃OD) δ 9.85 (s, 1H), 9.48 (s, 1H), 8.66~8.58 (m, 1H), 8.41~8.36 (m, 1H), 7.75~7.62 (m, 2H), 7.32~7.25 (m, 1H), 4.55~4.42 (m, 4H), 4.25~4.21 (m, 2H), 4.08~4.05 (m, 1H), 3.98~3.96 (m, 1H), 3.75~3.62 (m, 2H), 3.52~3.48 (m, 1H), 3.24~3.21 (m, 1H), 1.98~1.90 (m, 3H), 1.82~1.78 (m, 1H), 1.41~1.38 (m, 3H) | 499.1 |

| Cmpd. No. | Structure | ¹H-NMR | Mass Spec. (M + H)⁺ |
|---|---|---|---|
| 333 | 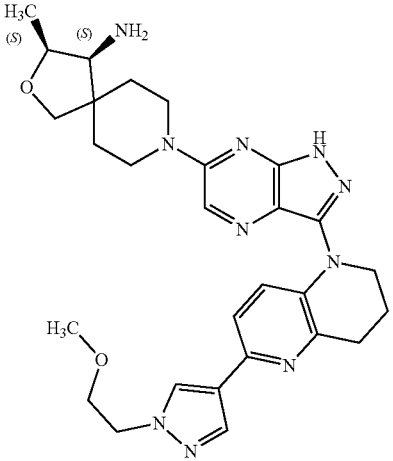 | ¹H-NMR (400 MHz, DMSO-d₆) δ 12.96 (s, 1H), 8.84 (s, 1H), 8.44 (s, 1H), 8.38-8.41 (m, 1H), 8.28-8.38 (m, 2H), 8.16-8.22 (m, 1H), 7.82-7.90 (m, 1H), 4.30-4.39 (m, 3H), 4.17-4.29 (m, 2H), 4.01-4.09 (m, 2H), 3.92-4.00 (m, 2H), 3.64-3.75 (m, 6H), 3.32-3.45 (m, 3H), 3.07-3.23 (m, 2H), 2.08-2.20 (m, 2H), 1.78-1.92 (m, 2H), 1.58-1.75 (m, 2H), 1.18-1.33 (m, 3H) | 545.1 |
| 334 | 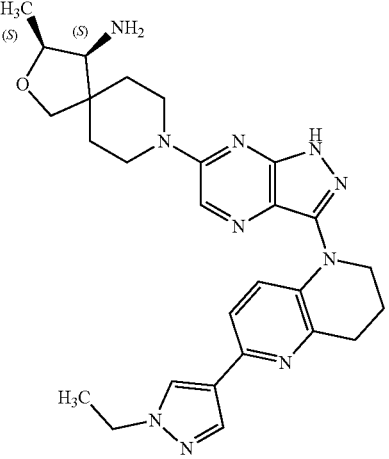 | ¹H-NMR (400 MHz, CD₃OD) δ 8.45 (s, 1H), 8.34 (s, 1H), 8.09-8.16 (m, 2H), 7.75-7.78 (m, 1H), 4.30-4.55 (m, 2H), 4.28-4.30 (m, 3H), 4.12-4.20 (m, 2H), 4.00-4.05 (m, 1H), 3.88-3.95 (m, 1H), 3.43-3.55 (m, 1H), 3.37-3.43 (m, 2H), 3.20-3.30 (m, 2H), 2.25-2.35 (m, 2H), 1.85-2.00 (m, 3H), 1.34-1.36 (m, 3H) | 515.6 |
| 335 | 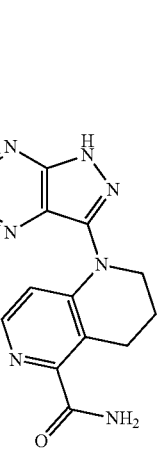 | ¹H-NMR (400 MHz, methanol-d₄) δ 8.42 (s, 1H), 7.96-7.99 (m, 1H), 6.98-7.01 (m, 1H), 4.40-4.52 (m, 2H), 4.33-4.37 (m, 1H), 4.08-4.12 (m, 2H), 4.02-4.05 (m, 1H), 3.91-3.94 (m, 1H), 3.48-3.50 (m, 1H), 3.36-3.48 (m, 2H), 3.07-3.11 (m, 2H), 2.23-2.29 (m, 2H), 1.88-1.95 (m, 3H), 1.76-1.80 (m, 1H), 1.34-1.36 (m, 3H) | 464 |

TABLE 1-continued

| Cmpd. No. | Structure | ¹H-NMR | Mass Spec. (M + H)⁺ |
|---|---|---|---|
| 336 | 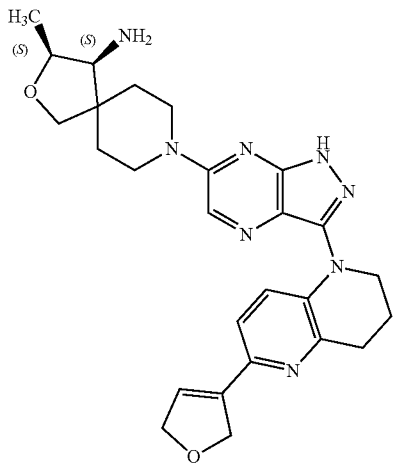 | ¹H-NMR (400 MHz, methanol-d₄) δ 8.34 (s, 1H), 8.04 (d, J = 9.2 Hz, 1H), 7.47 (d, J = 9.2 Hz, 1H), 7.01-7.00 (m, 1H), 5.04-5.02 (m, 2H), 4.94-4.93 (m, 2H), 4.50-4.31 (m, 3H), 4.13-4.10 (m, 2H), 4.03 (d, J = 9.2 Hz, 1H), 3.92 (d, J = 9.2 Hz, 1H), 3.48 (d, J = 4.0 Hz, 1H), 3.38-3.35 (m, 3H), 3.28-3.22 (m, 1H), 2.35-2.29 (m, 2H), 1.94-1.88 (m, 3H), 1.79-1.76 (m, 1H), 1.35 (d, J = 6.8 Hz, 3H) | 489.1 |
| 337 | 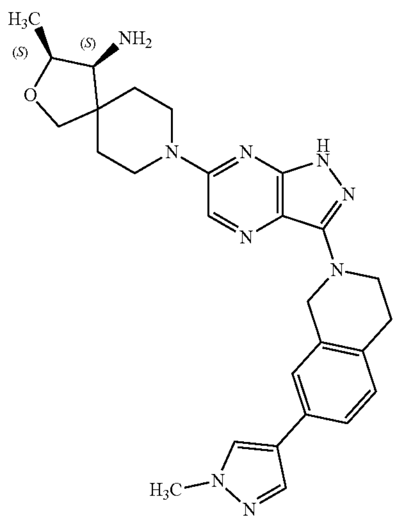 | ND | 500.3 |
| 338 | 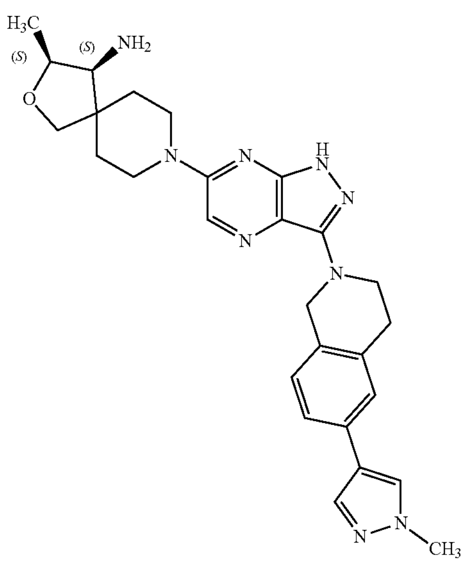 | ND | 500.3 |

TABLE 1-continued

| Cmpd. No. | Structure | ¹H-NMR | Mass Spec. (M + H)⁺ |
|---|---|---|---|
| 339 | (R) | ¹H-NMR (400 MHz, DMSO-d₆) δ 12.86 (s, 1H), 8.39 (s, 1H), 8.09 (d, J = 4.58 Hz, 1H), 7.88-8.01 (m, 4H), 7.40 (br dd, J = 5.34, 8.24 Hz, 1H), 4.23-4.41 (m, 2H), 3.96-4.06 (m, 2H), 3.39 (br d, J = 5.49 Hz, 1H), 3.08-3.18 (m, 3H), 2.93-3.02 (m, 1H), 2.17-2.22 (m, 1H), 2.12 (quin, J = 5.99 Hz, 2H), 1.94-2.06 (m, 2H), 1.84 (br d, J = 12.20 Hz, 1H), 1.51-1.75 (m, 4H) | 391.4 |
| 340 | (S) | ¹H-NMR (400 MHz, DMSO-d₆) δ 12.86 (s, 1H), 8.38 (s, 1H), 8.09 (d, J = 4.58 Hz, 1H), 7.88-8.00 (m, 4H), 7.40 (br dd, J = 5.26, 8.16 Hz, 1H), 4.37 (br d, J = 13.73 Hz, 1H), 4.27 (br d, J = 13.58 Hz, 1H), 3.95-4.04 (m, 2H), 3.39 (br d, J = 5.34 Hz, 2H), 3.08-3.15 (m, 3H), 2.94-3.02 (m, 1H), 2.16-2.24 (m, 1H), 2.08-2.15 (m, 2H), 1.93-2.06 (m, 3H), 1.84 (br d, J = 12.35 Hz, 1H), 1.54-1.74 (m, 5H) | 391.2 |
| 341 | 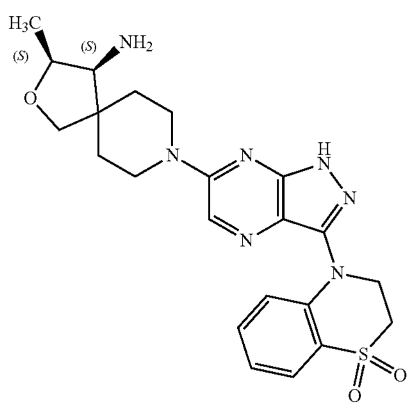 | ¹H-NMR (400 MHz, DMSO-d₆) δ 8.34 (br s, 1H), 8.30 (br dd, J = 10.98, 3.36 Hz, 1H), 7.66-7.72 (m, 1H), 7.30 (br t, J = 7.86 Hz, 1H), 6.97 (t, J = 7.55 Hz, 1H), 6.82-6.91 (m, 1H), 4.29-4.39 (m, 2H), 4.06-4.14 (m, 1H), 4.03 (br s, 1H), 3.47-3.76 (m, 5H), 3.23-3.46 (m, 2H), 3.00 (br s, 1H), 1.45-1.80 (m, 4H), 1.09 (br d, J = 6.10 Hz, 3H) | 470.5 |
| 342 | 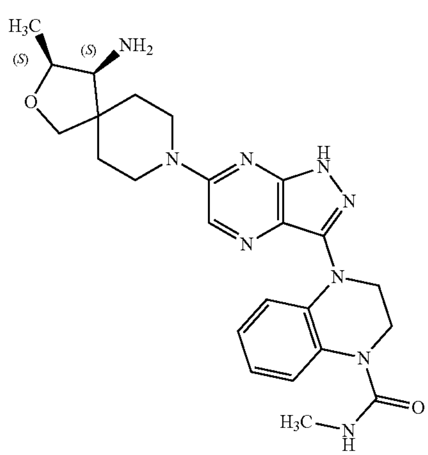 | ¹H-NMR (400 MHz, DMSO-d₆) δ 8.33 (s, 1H), 8.25 (s, 1H), 7.25-7.34 (m, 1H), 7.12 (br d, J = 8.24 Hz, 1H), 6.81-6.91 (m, 1H), 6.70-6.78 (m, 1H), 6.56 (q, J = 4.27 Hz, 1H), 4.07 (quin, J = 6.10 Hz, 1H), 3.93-4.04 (m, 2H), 3.85-3.94 (m, 2H), 3.77 (br t, J = 5.26 Hz, 2H), 3.70 (d, J = 8.69 Hz, 1H), 3.52 (br d, J = 8.54 Hz, 1H), 3.27-3.46 (m, 2H), 2.95 (br d, J = 5.03 Hz, 1H), 2.59-2.67 (m, 3H), 1.73 (ddd, J = 13.19, 9.84, 3.66 Hz, 1H), 1.62-1.69 (m, 1H), 1.53-1.60 (m, 1H), 1.45-.52 (m, 1H), 1.08 (d, J = 6.41 Hz, 3H) | 478.6 |

TABLE 1-continued

| Cmpd. No. | Structure | ¹H-NMR | Mass Spec. (M + H)⁺ |
|---|---|---|---|
| 343 | 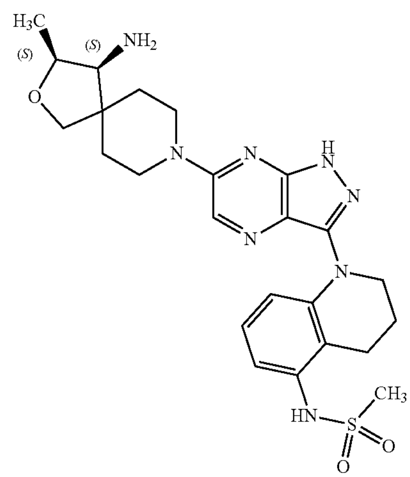 | ¹H-NMR (500 MHz, DMSO-d₆) δ 12.53 (br s, 1H), 8.26 (s, 1H), 8.25 (s, 1H), 6.82-6.93 (m, 2H), 6.72 (dd, J = 1.37, 7.32 Hz, 1H), 4.02-4.11 (m, 1H), 3.88-3.98 (m, 2H), 3.77-3.84 (m, 2H), 3.65-3.71 (m, 1H), 3.39-3.53 (m, 4H), 2.99 (s, 3H), 2.91 (d, J = 5.03 Hz, 1H), 2.84 (t, J = 6.41 Hz, 2H), 1.94 (quin, J = 6.06 Hz, 2H), 1.76 (ddd, J = 3.66, 9.50, 13.23 Hz, 1H), 1.65 (ddd, J = 3.74, 9.34, 13.16 Hz, 1H), 1.45-1.60 (m, 2H), 1.07 (d, J = 6.41 Hz, 3H) | 513.2 |
| 344 | 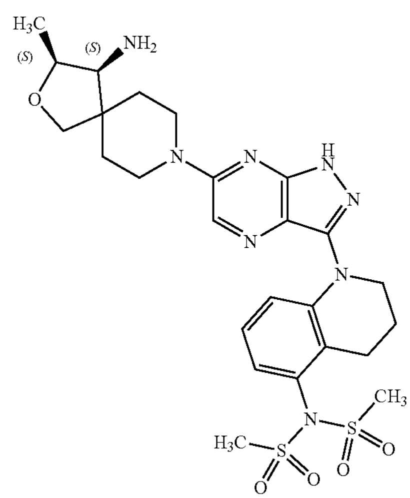 | ¹H-NMR (400 MHz, DMSO-d₆) δ 12.63 (br s, 1H), 8.29 (s, 1H), 8.28 (s, 1H), 7.03-7.08 (m, 1H), 6.98 (t, J = 8.08 Hz, 1H), 6.84 (d, J = 6.86 Hz, 1H), 4.06 (quin, J = 6.06 Hz, 1H), 3.89-3.99 (m, 2H), 3.82-3.87 (m, 2H), 3.68 (d, J = 8.39 Hz, 1H), 3.53 (s, 6H), 3.38-3.50 (m, 4H), 2.91 (d, J = 5.19 Hz, 1H), 2.86 (t, J = 6.25 Hz, 2H), 1.97 (quin, J = 6.02 Hz, 2H), 1.76 (ddd, J = 3.51, 9.42, 13.16 Hz, 1H), 1.66 (ddd, J = 3.66, 9.27, 13.16 Hz, 1H), 1.45-1.59 (m, 2H), 1.07 (d, J = 6.41 Hz, 3H) | 591.2 |
| 345 | 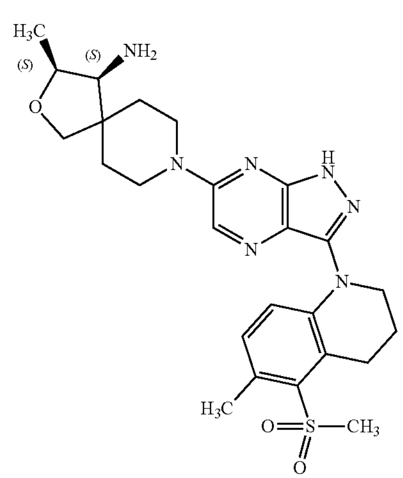 | ¹H-NMR (400 MHz, DMSO-d₆) δ 8.28 (s, 1H), 8.20 (s, 1H), 7.04 (d, J = 8.54 Hz, 1H), 6.95 (d, J = 8.54 Hz, 1H), 3.96-4.15 (m, 3H), 3.70-3.80 (m, 3H), 3.54 (s, 1H), 3.30-3.38 (m, 1H), 3.24-3.30 (m, 1H), 3.20 (s, 3H), 3.15-3.19 (m, 2H), 3.03 (d, J = 5.03 Hz, 1H), 2.49 (s, 3H), 1.93 (quin, J = 6.22 Hz, 2H), 1.62-1.76 (m, 2H), 1.54-1.62 (m, 1H), 1.50 (br d, J = 13.88 Hz, 1H), 1.10 (d, J = 6.56 Hz, 3H) | 512.2 |

TABLE 1-continued

| Cmpd. No. | Structure | ¹H-NMR | Mass Spec. (M + H)⁺ |
|---|---|---|---|
| 346 | 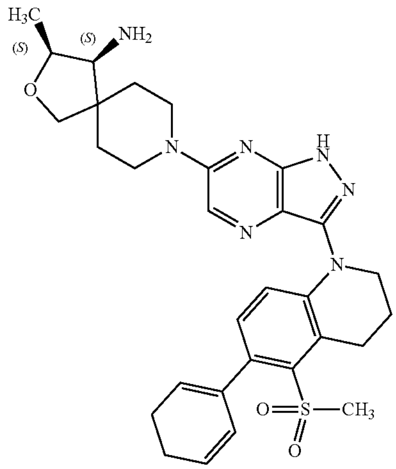 | ¹H-NMR (400 MHz, DMSO-d₆) δ 8.35 (s, 1H), 8.24 (s, 1H), 7.16-7.36 (m, 5H), 7.09 (d, J = 8.54 Hz, 1H), 6.82 (d, J = 8.54 Hz, 1H), 4.03-4.10 (m, 1H), 3.92-4.02 (m, 2H), 3.83 (t, J = 6.18 Hz, 2H), 3.69 (d, J = 8.69 Hz, 1H), 3.51 (br d, J = 8.69 Hz, 1H), 3.41 (ddd, J = 3.13, 9.80, 13.31 Hz, 1H), 3.30-3.37 (m, 1H), 3.25 (br t, J = 6.10 Hz, 2H), 3.09 (s, 3H), 2.93 (d, J = 5.19 Hz, 1H), 1.99-2.07 (m, 2H), 1.73 (ddd, J = 3.58, 9.88, 13.23 Hz, 1H), 1.60-1.68 (m, 1H), 1.52-1.58(m, 1H), 1.44-1.51 (m, 1H), 1.07 (d, J = 6.41 Hz, 3H) | 574.3 |
| 347 | 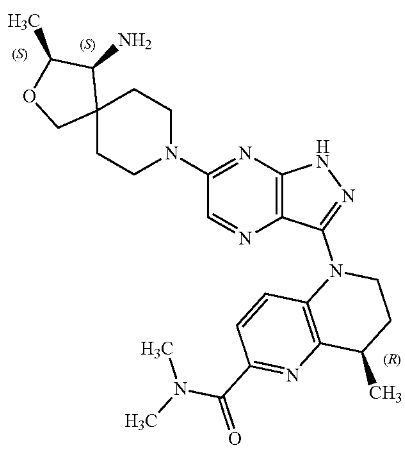 | ¹H-NMR (400 MHz, DMSO-d₆) δ 12.88 (br, 1H), 8.38 (s, 1H), 8.25 (br, 3H), 7.62 (d, J = 8.8 Hz, 1H), 7.36 (d, J = 8.8 Hz, 1H), 4.28-4.40 (m, 1H), 4.16-4.27 (m, 2H), 3.97-4.06 (m, 3H), 3.31-3.43 (m, 1H), 3.15-3.26 (m, 3H), 3.11 (s, 3H), 2.99 (s, 3H), 2.15-2.27 (m, 1H), 1.94-2.06 (m, 1H), 1.75-1.93 (m, 3H), 1.67-1.74 (m, 1H), 1.56-1.66 (m, 1H), 1.39 (d, J = 6.8 Hz, 3H), 1.25 (d, J = 6.4 Hz, 3H) | 506.3 |
| 348 | 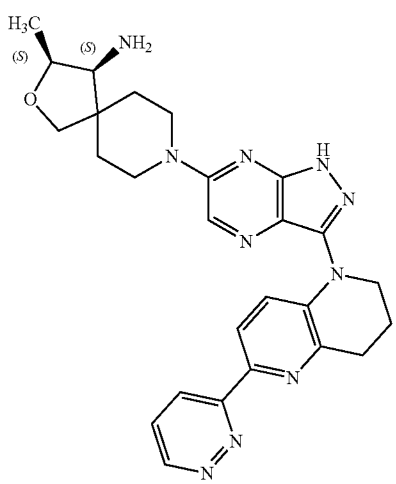 | ¹H-NMR (400 MHz, DMSO-d₆) δ 10.02 (s, 1H), 9.49 (d, J = 6.0 Hz, 1H), 8.73 (dd, J = 6.0, 2.2 Hz, 1H), 8.26-8.47 (m, 3H), 8.14 (d, J = 8.8 Hz, 1H), 7.57 (d, J = 8.8 Hz, 1H), 4.14-4.42 (m, 3H), 4.01-4.10 (m, 2H), 3.96 (d, J = 9.2 Hz, 1H), 3.68 (d, J = 9.2 Hz, 1H), 3.31-3.42 (m, 1H), 3.07-3.26 (m, 4H), 2.12-2.24 (m, 2H), 1.92-2.05 (m, 1H), 1.78-1.90 (m, 2H), 1.58-1.75 (m, 2H), 1.25 (d, J = 6.4 Hz, 3H) | 499.3 |

US 11,591,336 B2
TABLE 1-continued
| Cmpd. No. | Structure | ¹H-NMR | Mass Spec. (M + H)⁺ |
|---|---|---|---|
| 349 | 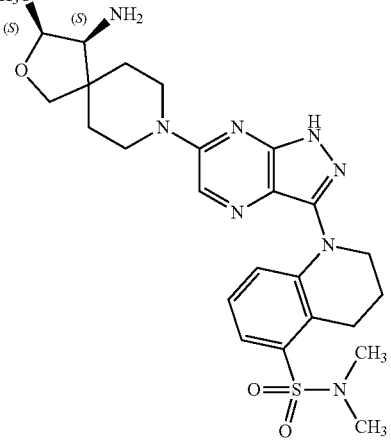 | ¹H-NMR (400 MHz, DMSO-d₆) δ 12.74 (br s, 1H), 8.33 (s, 1H), 8.18 (s, 3H), 7.21-7.16 (m, 2H), 7.13-7.09 (m, 1H), 4.33-4.29 (m, 3H), 3.95-3.93 (m, 1H), 3.87-3.84 (m, 2H), 3.70-3.68 (m, 1H), 3.39-3.34 (m, 1H) 3.18-3.12 (m, 4H), 2.79 (s, 6H), 2.00-1.98 (m, 2H), 1.81-1.78 (m, 2H), 1.76-1.72 (m, 1H), 1.66-1.62(m, 1H) 1.24 (d, J = 6.4 Hz, 3H) | 427.1 |
| 350 | 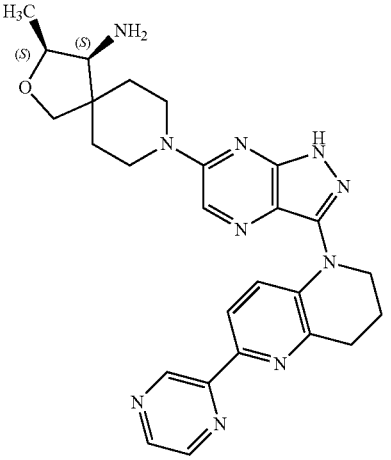 | ¹H-NMR (400 MHz, DMSO-d₆) δ 12.85 (br s, 1H), 9.45 (d, J = 1.2 Hz, 1H), 8.66 (d, J = 2.0 Hz, 1H), 8.60 (d, J = 2.4 Hz, 1H), 8.40 (s, 1H), 8.14 (br, s, 3H), 8.02 (d, J = 8.8 Hz, 1H), 7.71 (d, J = 8.8 Hz, 1H), 4.35-4.22 (m, 3H), 4.06-4.03 (m, 2H), 3.95-3.93 (m, 1H), 3.71-3.69 (m, 1H), 3.41-3.39 (m, 1H), 3.23-3.12 (m, 4H), 2.18-2.17 (m, 2H), 1.81-1.74 (m, 3H), 1.72-1.68 (m, 1H), 1.24 (d, J = 6.8 Hz, 3H) | 499.1 |
| 351 | 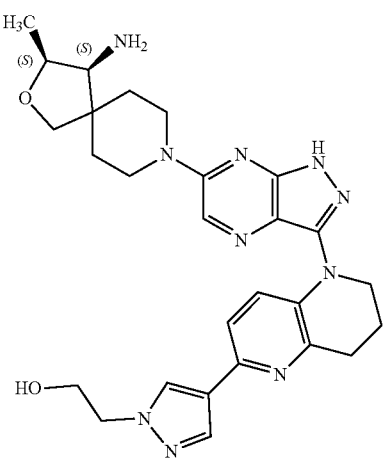 | ¹H-NMR (400 MHz, DMSO-d₆) δ 12.86 (br, 1H), 8.55 (br, 1H), 8.40 (s, 1H), 8.22 (s, 1H), 8.14-8.00 (m, 4H), 7.70 (s, 1H), 4.31-4.21 (m, 7H), 4.08-4.02 (m, 2H), 3.94 (d, J = 9.2 Hz, 1H), 3.81-3.77 (m, 2H), 3.71 (d, J = 9.2 Hz, 1H), 3.56 (s, 1H), 3.28-3.13 (m, 2H), 2.20-2.10 (m, 2H), 1.87-1.57 (m, 4H), 1.23 (d, J = 6.4 Hz, 3H) | 531.1 |

TABLE 1-continued

| Cmpd. No. | Structure | ¹H-NMR | Mass Spec. (M + H)⁺ |
|---|---|---|---|
| 352 | 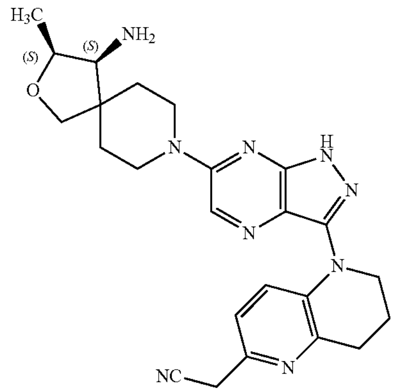 | ¹H-NMR (400 MHz, CD₃OD) δ 8.24 (s, 1H), 7.32~7.28 (m, 1H), 7.14~7.10 (m, 1H), 4.32~4.24 (m, 3H), 3.96~3.92 (m, 2H), 3.88~3.80 (m, 2H), 3.75~3.71 (m, 1H), 3.58~3.48 (m, 3H), 3.21~3.18 (m, 3H), 2.26~2.20 (m 2H), 1.82~1.70 (m, 4H), 1.26~1.22 (m, 3H) | 460.1 |
| 353 | 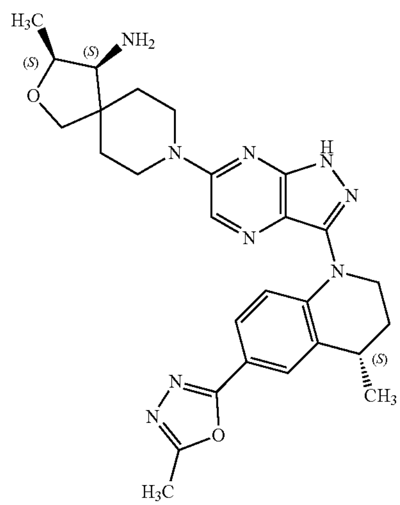 | ¹H-NMR (400 MHz, methanol-d₄) δ 8.25 (s, 1H), 7.83 (s, 1H), 7.56-7.53 (m, 1H), 6.85-6.82 (d, J = 8.8 Hz, 1H), 4.28-4.19 (m, 3H), 3.99-3.89 (m, 3H), 3.76-3.74 (m, 1H), 3.51-3.33 (m, 2H), 3.10-3.03 (m, 2H), 2.59 (s, 3H), 2.24 (m, 1H), 1.93-1.72 (m, 5H), 1.48-1.45 (d, J = 7.2 Hz, 3H), 1.25-1.23 (d, J = 6.8 Hz, 3H) | 516.2 |
| 354 | 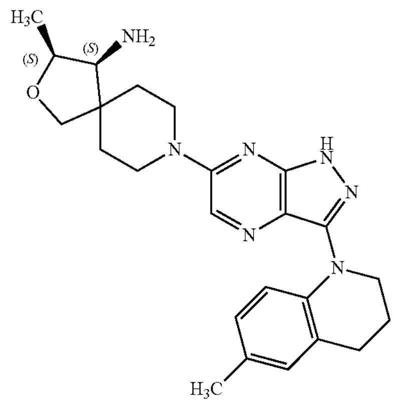 | ¹H-NMR (400 MHz, methanol-d₄) δ 8.40 (s, 1H), 7.22-7.25 (m, 1H), 7.08 (s, 1H), 7.02-7.05 (m, 1H), 4.46-4.57 (m, 2H), 4.31-4.35 (m, 1H), 4.23-4.27 (m, 2H), 4.02-4.06 (m, 1H), 3.90-3.93 (m, 1H), 3.49-3.51 (m, 1H), 3.35-3.43 (m, 2H), 2.85-2.89 (m, 2H), 2.33 (s, 3H), 2.05-2.12 (m, 2H), 1.88-1.98 (m, 3H), 1.77-1.81 (m, 1H), 1.34-1.36, (m, 3H) | 434.2 |

TABLE 1-continued

| Cmpd. No. | Structure | ¹H-NMR | Mass Spec. (M + H)⁺ |
|---|---|---|---|
| 355 | 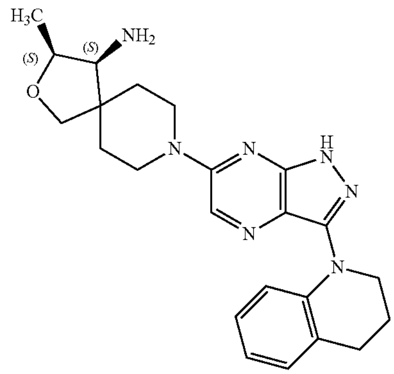 | ¹H-NMR (400 MHz, methanol-d₄) δ 8.40 (s, 1H), 7.22-7.29 (m, 2H), 7.15-7.20 (m, 1H), 7.05-7.10 (m, 1H), 4.45-4.56 (m, 2H), 4.30-4.37 (m, 1H), 4.20-4.23 (m, 2H), 4.02-4.06 (m, 1H), 3.91-3.94 (m, 1H), 3.48-3.50 (m, 1H), 3.34-3.40 (m, 2H), 2.89-2.94 (m, 2H), 2.08-2.15 (m, 2H), 1.88-2.00 (m, 3H), 1.77-1.81 (m, 1H), 1.34-1.36 (m, 3H) | 420.0 |
| 356 | 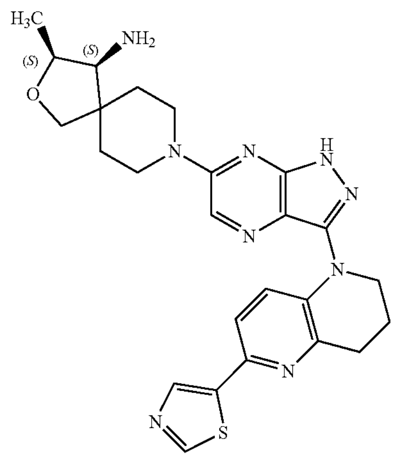 | ¹H-NMR (400 MHz, methanol-d₄) δ 9.44 (s, 1H), 8.61 (s, 1H), 8.36 (s, 1H), 8.01-8.04 (m, 1H), 7.78-7.82 (m, 1H), 4.33-4.51 (m, 3H), 4.12-4.16 (m, 2H), 4.03-4.06 (m, 1H), 3.90-3.93 (m, 1H), 3.49-3.51(m, 1H), 3.33-3.38 (m, 2H), 3.24-3.29 (m, 1H), 2.32-2.36 (m, 2H), 1.90-1.95 (m, 3H), 1.76-1.81 (m, 1H), 1.34-1.37 (m, 3H) | 504.2 |
| 357 | 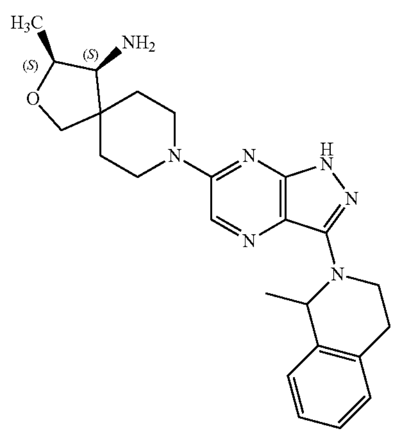 | ND | 434.2 |

TABLE 1-continued
| Cmpd. No. | Structure | ¹H-NMR | Mass Spec. (M + H)⁺ |
|---|---|---|---|
| 358 | 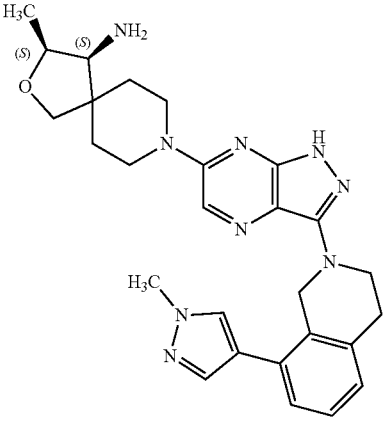 | ND | 500.2 |
| 359 | 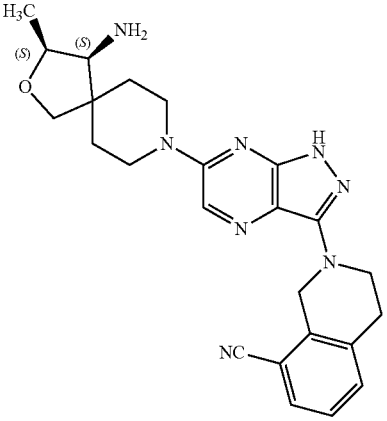 | ND | 445.2 |
| 360 | 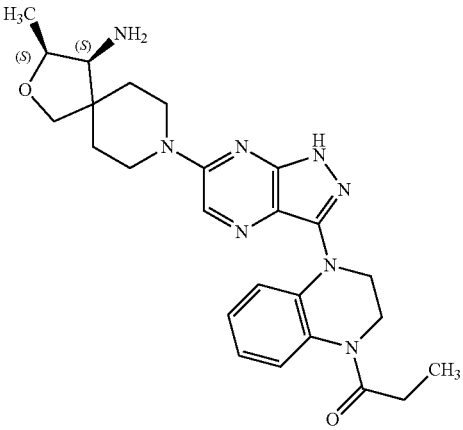 | ¹H-NMR (500 MHz, DMSO-d₆) δ 8.36 (s, 1H) 8.23 (s, 1H) 7.22-7.45 (m, 1H) 7.07 (br d, J = 8.08 Hz, 1H) 6.93 (br t, J = 6.71 Hz, 1H) 6.70-6.84 (m, 1H) 4.03-4.12 (m, 1H) 3.86-4.02 (m, 5H) 3.67-3.73 (m, 2H) 3.52 (br d, J = 8.69 Hz, 1H) 3.24-3.42 (m, 2H) 2.94 (br d, J = 5.03 Hz, 1H) 2.50-2.57 (m, 2H) 1.59-1.75 (m, 2H) 1.43-1.58 (m, 2H) 1.07 (d, J = 6.56 Hz, 3H) 1.00 (br t, J = 7.32 Hz, 3H) | 477.6 |

TABLE 1-continued

| Cmpd. No. | Structure | ¹H-NMR | Mass Spec. (M + H)⁺ |
|---|---|---|---|
| 361 | 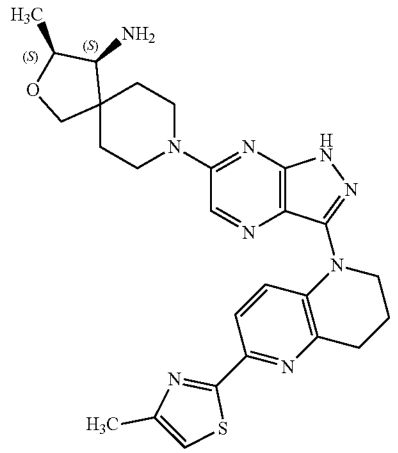 | ¹H-NMR (400 MHz, DMSO-d₆) δ 8.33 (s, 1H), 7.68 (d, J = 8.79 Hz, 1H), 7.57 (d, J = 8.79 Hz, 1H), 7.20 (s, 1H), 4.07 (td, J = 6.23, 11.96 Hz, 2H), 3.90-4.01 (m, 4H), 3.69 (br d, J = 8.54 Hz, 1H), 3.50 (br d, J = 8.54 Hz, 2H), 3.38-3.47 (m, 2H), 2.99 (br t, J = 6.47 Hz, 2H), 2.93 (br d, J = 4.88 Hz, 1H), 2.37 (s, 3H), 2.07-2.15 (m, 2H), 1.72-1.81 (m, 2H), 1.62-1.70 (m, 2H), 1.45-1.60 (m, 3H), 1.08 (d, J = 6.35 Hz, 3H) | 518.5 |
| 362 | 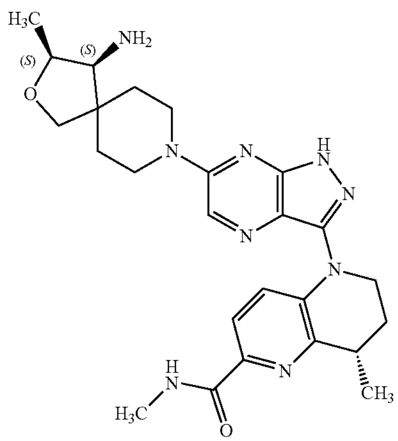 | ¹H-NMR (400 MHz, CD₃OD) δ 8.35 (s, 1H), 7.92-7.96 (m, 2H), 4.26-4.52 (m, 3H), 3.98-4.21 (m, 3H), 3.90 (d, J = 9.2 Hz, 1H), 3.59-3.69 (m, 1H), 3.46 (d, J = 3.6 Hz, 1H), 3.18-3.28 (m, 2H), 2.98 (s, 3H), 2.21-2.41 (m, 1H), 2.08-2.18 (m, 1H), 1.84-1.96 (m, 3H), 1.70-1.80 (m, 1H), 1.54 (d, J = 6.8 Hz, 3H), 1.33 (d, J = 6.4 Hz, 3H) | 492.3 |
| 363 | 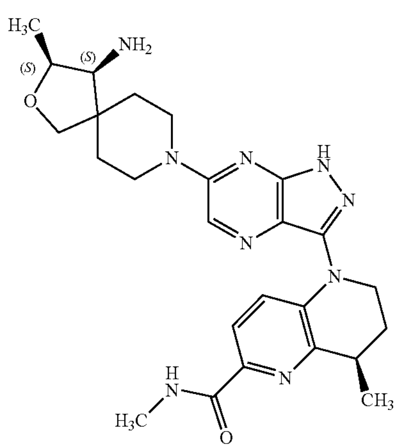 | ¹HNMR (400 MHz, methanol-d₄) δ 8.36 (s, 1H), 7.99 (s, 2H), 4.27-4.53 (m, 3H), 4.14-4.22 (m, 1H), 3.99-4.12 (m, 2H), 3.90 (d, J = 9.2 Hz, 1H), 3.64-3.75 (m, 1H), 3.48 (d, J = 4.0 Hz, 1H), 3.32-3.39 (m, 1H), 3.20-3.2 (m, 1H), 2.98 (s, 3H), 2.29-2.41 (m, 1H), 2.10-2.19 (m, 1H), 1.85-1.98 (m, 3H), 1.71-1.80 (m, 1H), 1.55 (d, J = 6.8 Hz, 3H), 1.33 (d, J = 6.4 Hz, 3H) | 492.3 |

TABLE 1-continued
| Cmpd. No. | Structure | ¹H-NMR | Mass Spec. (M + H)⁺ |
|---|---|---|---|
| 364 | 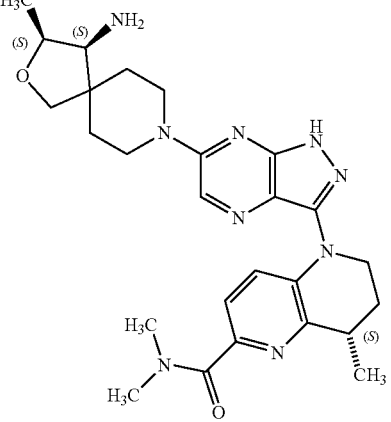 | ¹H-NMR (400 MHz, CD₃OD) δ 8.35 (s, 1H), 8.00 (d, J = 8.8 Hz, 1H), 7.69 (d, J = 8.4 Hz, 1H), 4.26-4.54 (m, 3H), 4.13-4.22 (m, 1H), 3.98-4.12 (m, 2H), 3.90 (d, J = 9.2 Hz, 1H), 3.51-3.62 (m, 1H), 3.44-3.50 (m, 1H), 3.27-3.30 (m, 3H), 3.20-3.27 (m, 1H), 3.15 (s, 6H), 2.30-2.43 (m, 1H), 2.10-2.28 (m, 1H), 1.83-2.08 (m, 4H), 1.71-1.81 (m, 1H), 1.56 (d, J = 7.2 Hz, 3H), 1.33 (d, J = 6.0 Hz, 3H) | 506.5 |
| 365 | 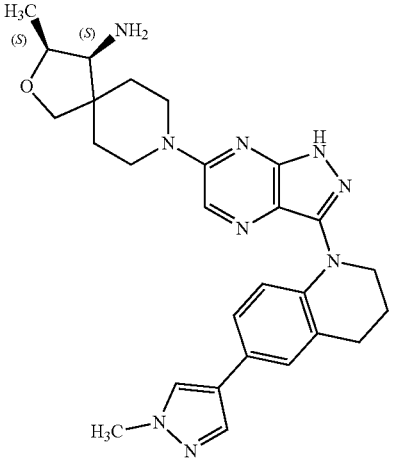 | ¹H-NMR (400 MHz, DMSO-d₆) δ 8.30 (s, 1H), 8.09 (s, 1H), 8.00 (s, 1H), 7.18-7.44 (m, 3H), 4.31-4.47 (m, 2H), 4.17-4.28 (m, 1H), 4.07-4.15 (m, 2H), 3.87-3.98 (m, 4H), 3.73-3.85 (m, 1H), 3.36-3.42 (m, 1H), 3.22-3.32 (m, 2H), 2.78-2.88 (m, 2H), 1.98-2.08 (m, 2H), 1.77-1.88 (m, 3H), 1.63-1.74 (m, 1H), 1.23-1.25 (m, 3H) | 500.3 |
| 366 | 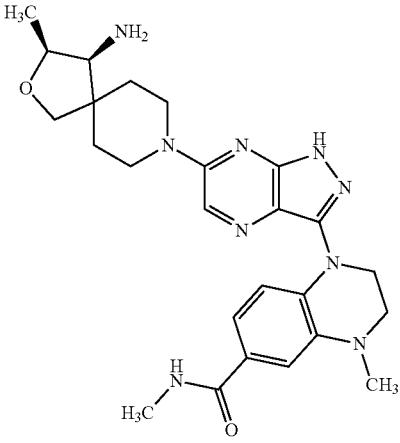 [SMILES: CNC(=O)c1ccc2c(c1)N(C)CCN2c1n[nH]c2nc(N3CCC4(CC3)CO[C@@H](C)[C@H]4N)cnc12] | ¹H-NMR (400 MHz, DMSO-d₆) δ 12.63 (br, 1H), 8.33 (s, 1H), 8.03-8.13 (m, 4H), 7.13 (s, 1H), 7.02 (s, 2H), 4.20-4.33 (m, 3H), 4.04-4.07 (m, 2H), 3.91-3.94 (m, 1H), 3.69-3.71 (m, 1H), 3.14-3.22 (m, 2H), 2.95 (s, 3H), 2.74-2.75 (d, J = 3.6 Hz 3H), 1.98-2.03 (m, 2H), 1.69-1.80 (m, 4H), 1.57-1.61 (m, 1H), 1.24 (s, 3H) | 491.8 |

TABLE 1-continued

| Cmpd. No. | Structure | ¹H-NMR | Mass Spec. (M + H)⁺ |
|---|---|---|---|
| 367 | 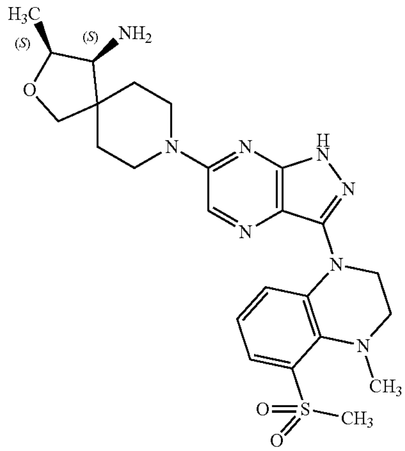 | ¹H-NMR (400 MHz, DMSO-d₆) 8.37 (s, 1H), 8.26 (br, 3H), 7.38 (d, J = 8.0 Hz, 1H), 7.29 (d, J = 8.0 Hz, 1H), 7.04-7.10 (m, 1H), 4.20-4.35 (m, 3H), 4.02-4.08 (m, 2H), 3.95 (d, J = 9.2 Hz, 1H), 3.68 (d, J = 9.2 Hz, 1H), 3.30-3.40 (m, 4H), 3.14-3.25 (m, 4H), 2.86 (s, 3H), 1.60-1.86 (m, 4H), 1.25 (d, J = 6.4 Hz, 3H) | 535.5 [M+ Na]⁺ |
| 368 | 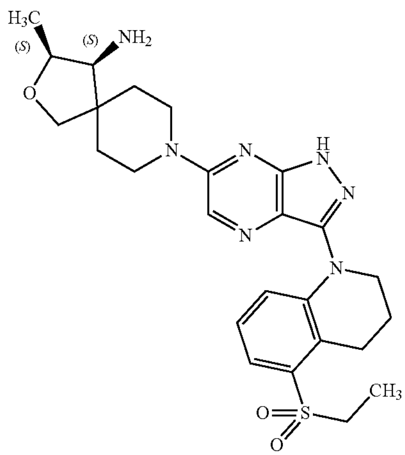 | ¹H-NMR (400 MHz, DMSO-d₆) δ 8.33 (s, 1H), 8.25 (br s, 3H), 7.33-7.31 (m, 1H), 7.22-7.13 (m, 2H), 4.25-4.20 (m, 3H), 3.96-3.94 (m, 1H), 3.88-3.85 (m, 2H), 3.69-3.67 (m, 1H), 3.37-3.29 (m, 3H), 3.22-3.13 (m, 4H), 2.05-1.99 (m, 2H), 1.84-1.77 (m, 2H), 1.72-1.68 (m, 1H), 1.63-1.60(m, 1H), 1.25 (d, J = 6.4 Hz, 3H), 1.15 (t, J – 7.2 Hz, 3H) | 534.1 [M+ Na]⁺ |
| 369 | 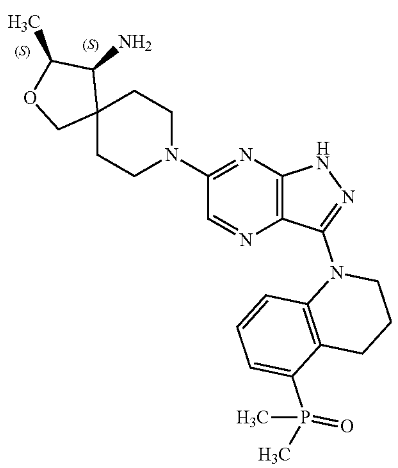 | ¹H-NMR (400 MHz, DMSO-d₆) δ 8.30 (s, 1H), 8.10-8.25 (s, 3H), 6.99-7.15 (m, 3H), 4.15-4.35 (m, 3H), 3.90-4.00 (m,1H), 3.84-3.87 (m, 2H), 3.36-3.43 (m, 1H), 3.10-3.28 (m, 4H), 1.94-2.05 (m, 2H), 1.55-1.87 (m, 10H), 1.23-1.28 (m, 3H) | 496.6 |

TABLE 1-continued

| Cmpd. No. | Structure | ¹H-NMR | Mass Spec. (M + H)⁺ |
|---|---|---|---|
| 370 | 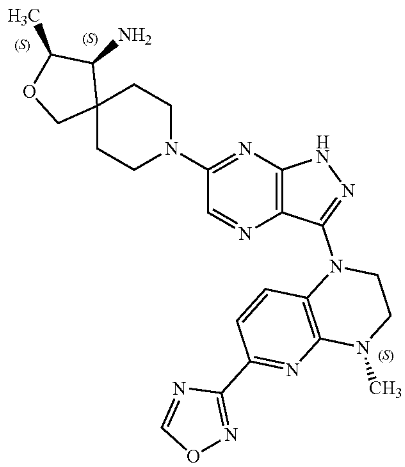 | ¹H-NMR (400 MHz, methanol-d₄) δ 9.28 (s, 1H), 8.27 (s, 1H), 7.74-7.76 (m, 1H), 7.33-7.35 (m, 1H), 4.18-4.31 (m, 3H), 3.98-4.03 (m, 2H), 3.91-3.94 (m, 1H), 3.76-3.78 (m, 1H), 3.36-3.51 (m, 3H), 3.28-3.30 (m, 1H), 3.09-3.10 (m, 1H), 2.30-2.38 (m, 1H), 2.00-2.05 (m, 1H), 1.81-1.88 (m, 2H), 1.69-1.80 (m, 1H), 1.50-1.52 (m, 3H), 1.24-1.27 (m, 3H) | 503.3 |
| 371 | 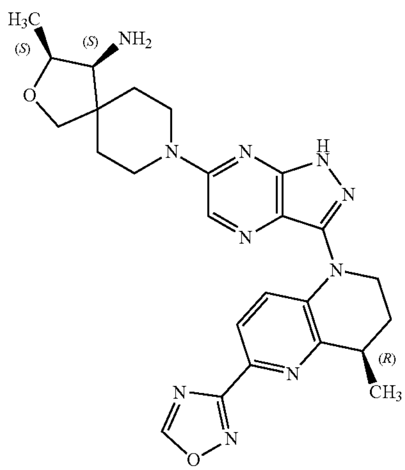 | ¹H-NMR (400 MHz, DMSO-d₆) δ 9.28 (s, 1H), 8.27 (s, 1H), 7.74-7.76 (m, 1H), 7.33-7.35 (m, 1H), 4.18-4.31 (m, 3H), 3.98-4.03 (m, 2H), 3.91-3.94 (m, 1H), 3.76-3.78 (m, 1H), 3.36-3.51 (m, 3H), 3.28-3.30 (m, 1H), 3.09-3.10 (m, 1H), 2.30-2.38 (m, 1H), 2.00-2.05 (m, 1H), 1.81-1.88 (m, 2H), 1.69-1.80 (m, 1H), 1.50-1.52 (m, 3H), 1.24-1.27 (m, 3H) | 503.3 |
| 372 | 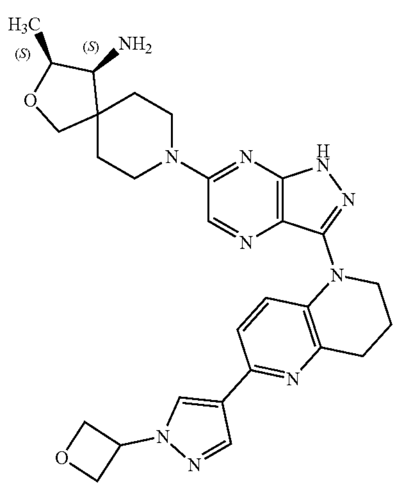 | ¹H-NMR (400 MHz, methanol-d₄) δ 8.21 (s, 2H), 8.04 (s, 1H), 7.38 (d, J = 8.4 Hz, 1H), 7.27 (d, J = 8.4 Hz, 1H), 5.64-5.59 (m, 1H), 5.11-5.05 (m, 4H), 4.28-4.16 (m, 3H), 4.00-3.96 (m, 2H), 3.92-3.88 (m, 1H), 3.76-3.73 (m, 1H), 3.50-3.35 (m, 3H), 3.10-3.03 (m, 3H), 2.23-2.20 (m, 2H), 1.92-1.71 (m, 4H), 1.25-1.23 (m, 3H) | 543.1 |

TABLE 1-continued

| Cmpd. No. | Structure | ¹H-NMR | Mass Spec. (M + H)⁺ |
|---|---|---|---|
| 373 | 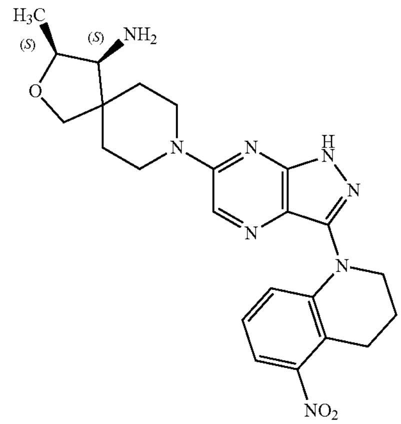 | ¹H-NMR (400 MHz, DMSO-d₆) δ 8.29 (s, 1H), 8.25 (s, 1H), 7.22 (dd, J = 1.46, 7.57 Hz, 1H), 7.06-7.16 (m, 2H), 3.98-4.13 (m, 3H), 3.81-3.86 (m, 2H), 3.74 (d, J = 8.54 Hz, 1H), 3.54 (d, J = 8.79 Hz, 1H), 3.28-3.42 (m, 2H), 3.02 (d, J = 4.88 Hz, 1H), 2.90 (t, J = 6.47 Hz, 2H), 1.96 (quin, J = 5.98 Hz, 2H), 1.63-1.77 (m, 2H), 1.55-1.62 (m, 1H), 1.50 (br d, J = 14.65 Hz, 1H), 1.10 (d, J = 6.35 Hz, 3H) | 465.5 |
| 374 | 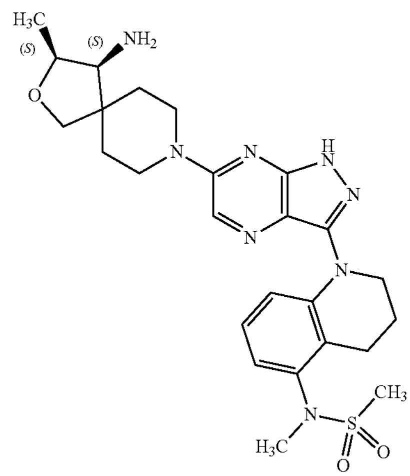 | ¹H-NMR (400 MHz, DMSO-d6) δ 8.26 (s, 2H), 6.88-6.99 (m, 2H), 6.83 (dd, J = 1.10, 7.45 Hz, 1H), 3.97-4.14 (m, 3H), 3.81-3.89 (m, 1H), 3.71-3.80 (m, 2H), 3.53-3.60 (m, 2H), 3.25-3.40 (m, 2H), 3.11 (s, 3H), 3.03 (s, 3H), 2.85-2.95 (m, 1H), 2.74-2.83 (m, 1H), 1.88-2.00 (m, 2H), 1.63-1.78 (m, 2H), 1.56-1.62 (m, 1H), 1.51 (br d, J = 13.67 Hz, 1H), 1.10 (d, J = 6.35 Hz, 3H) | 527.3 |
| 375 | 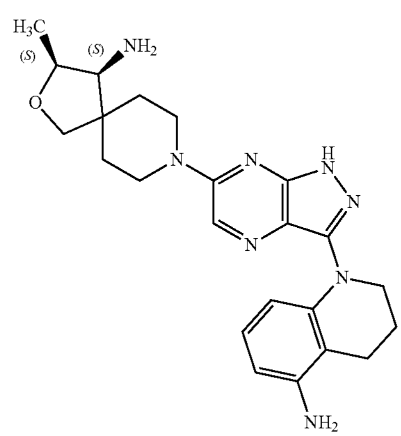 | ¹H-NMR (400 MHz, DMSO-d₆) δ 8.30 (s, 1H), 8.22 (s, 1H), 6.58 (t, J = 8.06 Hz, 1H), 6.13 (dd, J = 8.06, 12.94 Hz, 2H), 4.00-4.17 (m, 3H), 3.71-3.81 (m, 3H), 3.58 (d, J = 8.79 Hz, 1H), 3.18-3.35 (m, 2H), 3.05-3.11 (m, 1H), 2.42-2.47 (m, 2H), 1.89-2.00 (m, 2H), 1.57-1.77 (m, 3H), 1.51 (br d, J = 13.67 Hz, 1H), 1.11 (d, J = 6.59 Hz, 3H) | 435.3 |

| Cmpd. No. | Structure | ¹H-NMR | Mass Spec. (M + H)⁺ |
|---|---|---|---|
| 376 | 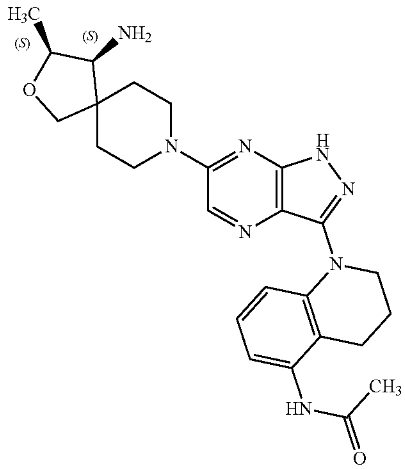 | ¹H-NMR (400 MHz, DMSO-d₆) δ 8.28 (s, 1H), 8.24 (s, 1H), 6.81-6.88 (m, 1H), 6.70-6.78 (m, 2H), 4.01-4.15 (m, 3H), 3.73-3.82 (m, 3H), 3.51-3.57 (m, 1H), 3.22-3.36 (m, 2H), 3.06-3.10 (m, 1H), 2.64 (br t, J = 6.47 Hz, 2H), 2.03 (s, 3H), 1.92 (quin, J = 5.98 Hz, 2H), 1.65-1.77 (m, 2H), 1.56-1.63 (m, 1H), 1.51 (br d, J = 13.67 Hz, 1H), 1.11 (d, J = 6.35 Hz, 3H) | 477.3 |
| 377 | 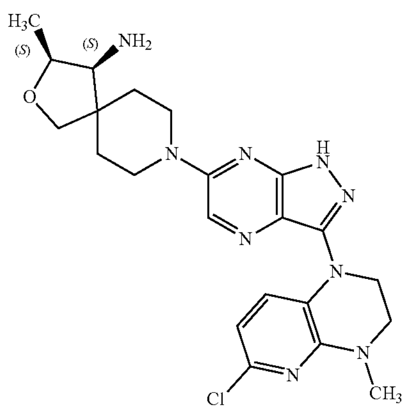 | ¹H-NMR (400 MHz, DMSO-d₆) δ 8.34 (s, 1H) 8.20 (s, 1H) 7.18-7.30 (m, 1H) 6.40 (d, J = 8.06 Hz, 1H) 3.92-4.14 (m, 5H) 3.72 (d, J = 8.79 Hz, 1H) 3.51-3.57 (m, 1H) 3.50 (br t, J = 4.76 Hz, 2H) 3.18-3.40 (m, 2H) 3.01 (s, 3H) 2.98 (br d, J = 4.88 Hz, 1H) 1.43-1.75 (m, 4H) 1.08 (d, J = 6.35 Hz, 3H) | 470.5 |
| 378 | 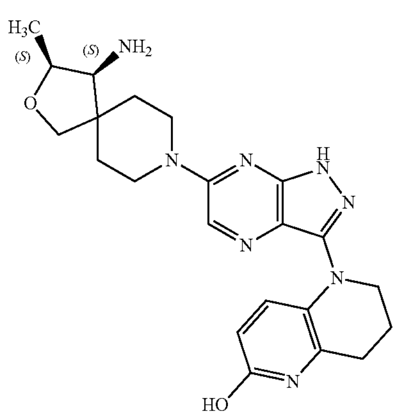 | ¹H-NMR (400 MHz, DMSO-d₆) δ 8.25 (s, 1H), 8.23 (s, 1H), 7.40-7.49 (m, 1H), 6.11 (d, J = 9.52 Hz, 1H), 3.99-4.14 (m, 3H), 3.94 (td, J = 2.44, 4.88 Hz, 2H), 3.76 (d, J = 8.79 Hz, 1H), 3.57 (s, 1H), 3.29 (td, J = 10.50, 21.00 Hz, 2H), 3.06 (d, J = 4.88 Hz, 1H), 2.57 (br t, J = 6.59 Hz, 2H), 1.55-1.78 (m, 5H), 1.50 (br d, J = 13.67 Hz, 1H), 1.11 (d, J = 6.59 Hz, 3H) | 437.2 |

TABLE 1-continued

| Cmpd. No. | Structure | ¹H-NMR | Mass Spec. (M + H)⁺ |
|---|---|---|---|
| 379 | 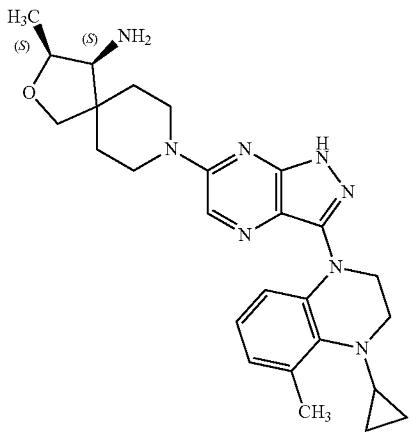 | ¹H-NMR (400 MHz, DMSO-d₆) δ 8.33 (s, 1H), 8.11-8.26 (m, 1H) 6.68-6.76 (m, 1H) 6.65 (t, J = 7.69 Hz, 1H) 6.52-6.61 (m, 1H) 3.98-4.15 (m, 4H) 3.70-3.79 (m, 1H) 3.50-3.65 (m, 1H) 3.14-3.39 (m, 4H) 2.95-3.07 (m, 1H) 2.22-2.26 (m, 3H) 2.21-2.27 (m, 2H) 2.16-2.18 (m, 1H), 1.45-1.75 (m, 4H), 1.01-1.15 (m, 2H) 0.45-0.57 (m, 2H) | 475.6 |
| 380 | 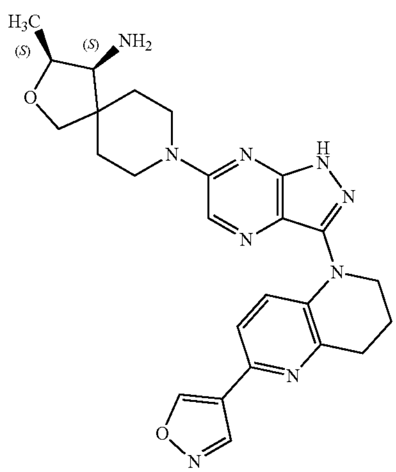 | ¹H-NMR (400 MHz, CDCl₃) δ 8.74 (s, 1H), 8.64 (s, 1H), 8.06 (s, 1H), 7.62-7.59 (d, J = 8.4 Hz, 1H), 7.09-7.06 (d, J = 8.4 Hz, 1H), 4.13-3.93 (m, 5H), 3.78-3.75 (m, 1H), 3.65-3.62 (m, 1H), 3.45-3.25 (m, 2H), 3.03-2.93 (m, 3H), 2.16-2.12 (m, 2H), 1.74-1.71 (m, 1H), 1.70-1.66 (m, 3H), 1.19-1.17 (d, J = 6.4 Hz, 3H) | 488.2 |
| 381 | 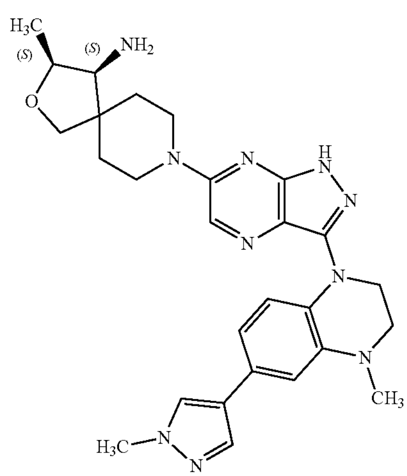 | ¹H-NMR (400 MHz, CD₃OD) δ 8.41-8.30 (m, 3H), 7.48 (s, 1H), 7.30 (s, 1H), 4.54-4.34 (m, 6H), 4.09-4.03 (m, 4H), 3.92 (d, J = 9.2 Hz, 1H), 3.80 (s, 2H), 3.50 (d, J = 3.6 Hz, 1H), 1.96-1.78 (m, 4H), 1.35 (d, J = 6.4 Hz, 3H) | 514.1 |

TABLE 1-continued

| Cmpd. No. | Structure | ¹H-NMR | Mass Spec. (M + H)⁺ |
|---|---|---|---|
| 382 | 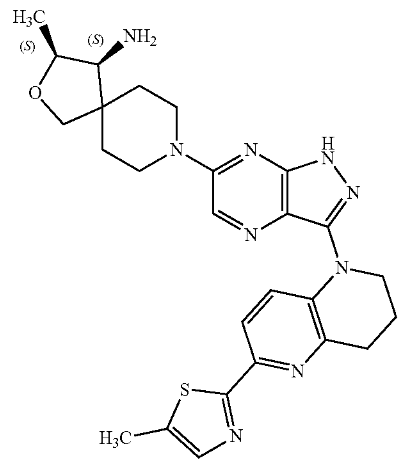 | ¹H-NMR (400 MHz, methanol-d₄) δ 8.25 (s, 1H), 7.67-7.64 (d, J = 8.8 Hz, 1H), 7.46 (s, 1H), 7.33-7.30 (d, J = 8.8 Hz, 1H), 4.28-4.00 (m, 3H), 3.99-3.89 (m, 3H), 3.76-3.74 (m, 1H), 3.51-3.33 (m, 1H), 3.12-3.04 (m, 3H), 2.52 (s, 3H), 2.26-2.21 (m, 2H), 1.86-1.72 (m, 5H), 1.25-1.23 (d, J = 6.4 Hz, 3H) | 518.0 |
| 383 | 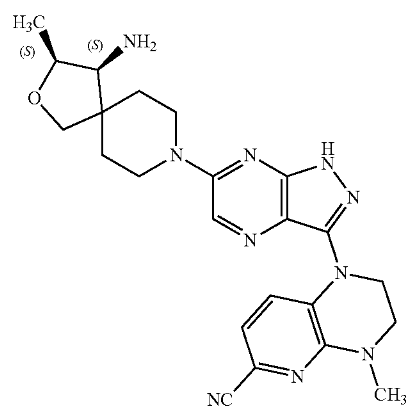 | ¹H-NMR (400 MHz, DMSO-d₆) δ 8.34 (s, 1H), 7.32 (d, J = 8.0 Hz, 1H), 7.05-7.02 (m, 1H), 4.10-4.06 (m, 3H), 3.95-3.87 (m, 2H), 3.68 (d, J = 8.4 Hz, 1H), 3.62-3.60 (m, 2H), 3.55-3.48 (m, 3H), 3.09 (s, 3H), 2.91 (d, J = 5.2 Hz, 1H), 1.78-1.64 (m, 2H), 1.56-1.48 (m, 2H), 1.08 (d, J = 6.4 Hz, 3H) | 461.1 |
| 384 | 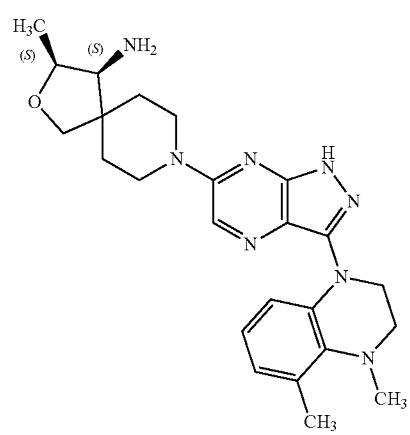 | ¹H-NMR (400 MHz, DMSO-d₆) δ 12.96 (br, 1H), 8.39 (s, 1H), 8.28 (br, 3H), 7.03-7.08 (m, 2H), 6.71-6.75 (m, 1H), 4.20-4.35 (m, 5H), 3.95 (d, J = 9.2 Hz, 1H), 3.60-3.70 (m, 2H), 3.35-3.39 (m, 2H), 3.14-3.25 (m, 5H), 2.57 (s, 3H), 1.60-1.86 (m, 4H), 1.25 (d, J = 6.8 Hz, 3H) | 449.1 |

TABLE 1-continued

| Cmpd. No. | Structure | ¹H-NMR | Mass Spec. (M + H)⁺ |
|---|---|---|---|
| 385 | 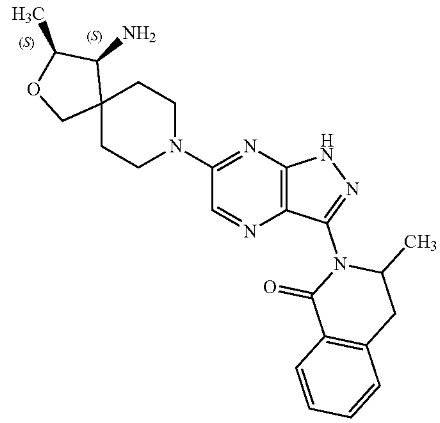 | | 448.2 |
| 386 | 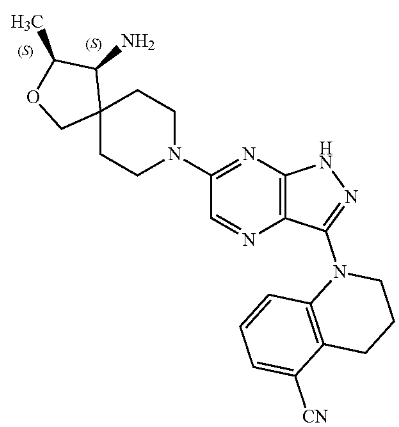 | ¹H-NMR (400 MHz, DMSO-d₆) δ 12.67 (br s, 1H), 8.30 (s, 1H), 8.24 (s, 1H), 7.22-7.28 (m, 1H), 7.11-7.17 (m, 1H), 7.04-7.10 (m, 1H), 4.06 (quin, J = 6.10 Hz, 1H), 3.90-4.01 (m, 2H), 3.84-3.90 (m, 2H), 3.69 (d, J = 8.54 Hz, 1H), 3.47-3.52 (m, 1H), 3.35-3.47 (m, 2H), 2.90-3.01 (m, 3H), 2.04 (quin, J = 6.04 Hz, 2H), 1.76 (ddd, J = 3.30, 9.52, 13.06 Hz, 1H), 1.61-1.70 (m, 1H), 1.44-1.58 (m, 2H), 1.08 (d, J = 6.35 Hz, 3H) | 445.3 |
| 387 | 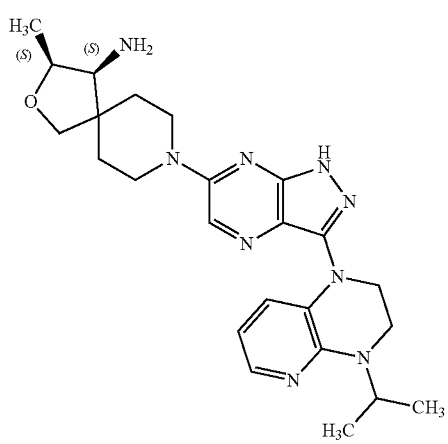 | ¹H-NMR (400 MHz, DMSO-d₆) δ 8.35 (s, 1H), 8.22 (s, 1H), 7.57 (dd, J = 1.46, 4.88 Hz, 1H), 7.24 (dd, J = 1.46, 7.81 Hz, 1H), 6.37 (dd, J = 4.88, 7.57 Hz, 1H), 4.98-5.09 (m, 1H), 3.96-4.14 (m, 3H), 3.88-3.96 (m, 2H), 3.72 (d, J = 8.79 Hz, 1H), 3.53 (d, J = 8.54 Hz, 1H), 3.38-3.46 (m, 2H), 3.22-3.38 (m, 2H), 2.98 (d, J = 4.88 Hz, 1H), 1.60-1.76 (m, 2H), 1.43-1.60 (m, 2H), 0.92-1.30 (m, 9H) | 464.3 |

TABLE 1-continued
| Cmpd. No. | Structure | ¹H-NMR | Mass Spec. (M + H)⁺ |
|---|---|---|---|
| 388 | 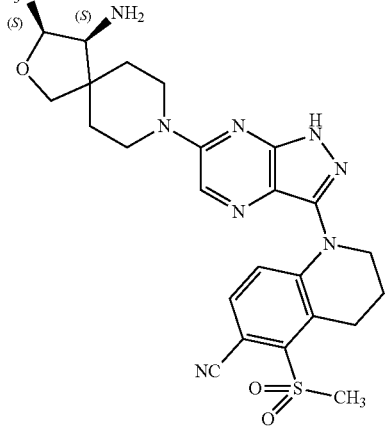 | ¹H-NMR (400 MHz, DMSO-d₆) δ 8.34 (s, 1H), 8.30 (s, 1H), 7.46 (d, J = 8.30 Hz, 1H), 6.61 (d, J = 8.54 Hz, 1H), 4.07-4.16 (m, 1H), 3.97-4.07 (m, 2H), 3.73 (br d, J = 8.79 Hz, 1H), 3.66-3.66 (m, 3H), 3.54 (br d, J = 8.79 Hz, 1H), 3.29-3.44 (m, 2H), 3.19-3.27 (m, 2H), 2.93-3.00 (m, 2H), 1.78-1.86 (m, 2H), 1.63-1.78 (m, 2H), 1.48-1.63 (m, 2H), 1.09 (d, J = 6.59 Hz, 3H) | 523.2 |
| 389 | 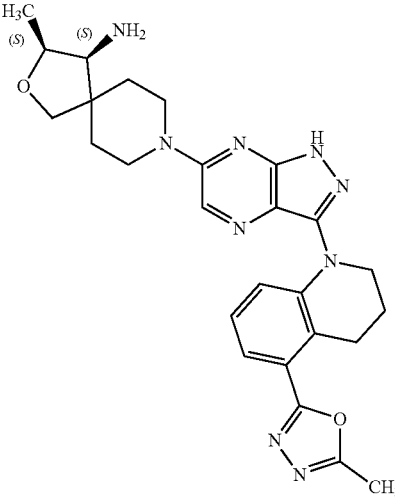 | ¹H-NMR (400 MHz, Methanol-d₄) δ 8.21 (s, 1H), 7.34-7.31 (d, J = 7.2 Hz, 1H), 7.11-7.07 (m, 1H), 7.02-6.99 (d, J = 8.4 Hz, 1H), 4.28-4.24 (m, 3H), 3.93-3.89 (m, 3H), 3.76-3.73 (m, 1H), 3.34-3.32 (m, 2H), 3.25-3.21 (m, 2H), 3.05-3.03 (m, 1H), 2.65 (s, 3H), 2.16-2.12 (m, 2H), 1.89-1.71 (m, 4H), 1.25-1.23 (d, J = 6.4 Hz, 3H) | 502.3 |
| 390 | 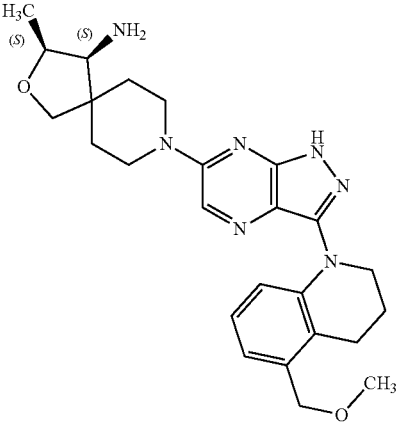 | ¹H-NMR (400 MHz, methanol-d₄) δ 8.48 (s, 1H), 7.48~7.46 (m, 1H), 7.29~7.24 (m, 2H), 4.52~4.35 (m, 4H), 3.34~3.30 (m, 3H), 4.07~4.05 (m, 1H), 3.92~3.90 (m, 1H), 3.54~3.50 (m, 1H), 3.44~3.40 (m, 3H), 3.36 (s, 2H), 2.94~2.90 (m, 2H), 2.15~2.13 (m, 2H), 2.10~2.06 (m, 2H), 1.95~1.86 (m, 3H), 1.83~1.80 (m, 1H), 1.37~1.35 (m, 3H) | 464.4 |

TABLE 1-continued

| Cmpd. No. | Structure | $^1$H-NMR | Mass Spec. $(M + H)^+$ |
|---|---|---|---|
| 391 | 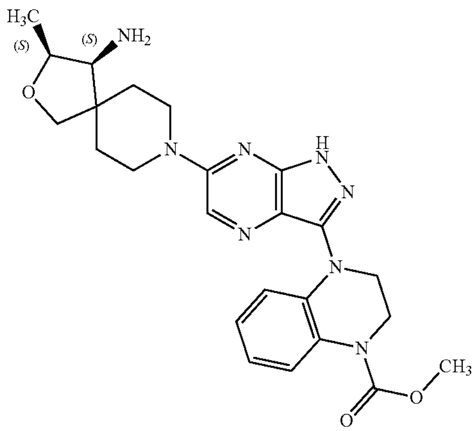 | $^1$H-NMR (400 MHz, DMSO-d$_6$) δ 12.58-12.71 (m, 1H), 8.25-8.35 (m, 1H), 7.53 (br d, J = 7.81 Hz, 1H), 7.11 (br dd, J = 1.22, 8.30 Hz, 1H), 6.82-6.91 (m, 1H), 6.72-6.79 (m, 1H), 4.08 (td, J = 6.23, 11.96 Hz, 1H), 3.93-4.04 (m, 3H), 3.86-3.93 (m, 1H), 3.67-3.78 (m, 4H), 3.52 (br d, J = 8.54 Hz, 1H), 3.35-3.48 (m, 4H), 3.00 (br d, J = 4.64 Hz, 1H), 1.63-1.80 (m, 2H), 1.46-1.61 (m, 2H), 1.05-1.14 (m, 3H) | 479.5 |
| 392 | 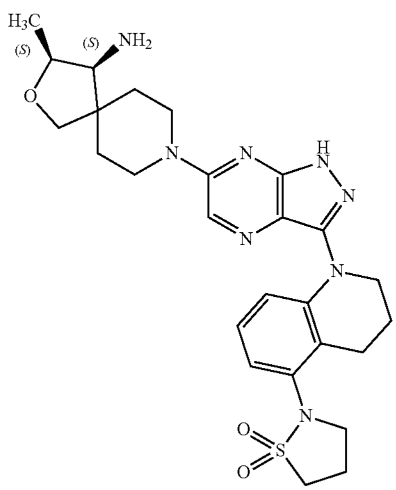 | $^1$H-NMR (400 MHz, DMSO-d$_6$) δ 8.31 (s, 1H), 8.25 (s, 1H), 6.92 (td, J = 7.60, 15.32 Hz, 2H), 6.79 (dd, J = 1.22, 7.57 Hz, 1H), 4.08 (td, J = 6.23, 11.96 Hz, 1H), 3.99 (br t, J = 12.57 Hz, 2H), 3.77-3.83 (m, 2H), 3.71 (br d, J = 8.54 Hz, 1H), 3.58 (br t, J = 6.71 Hz, 2H), 3.28-3.44 (m, 4H), 2.97 (br d, J = 5.13 Hz, 1H), 2.85 (br t, J = 6.47 Hz, 2H), 2.35-2.44 (m, 2H), 1.88-1.96 (m, 2H), 1.61-1.78 (m, 3H), 1.45-1.64 (m, 2H), 1.02-1.15 (m, 3H) | 539.3 |
| 393 | 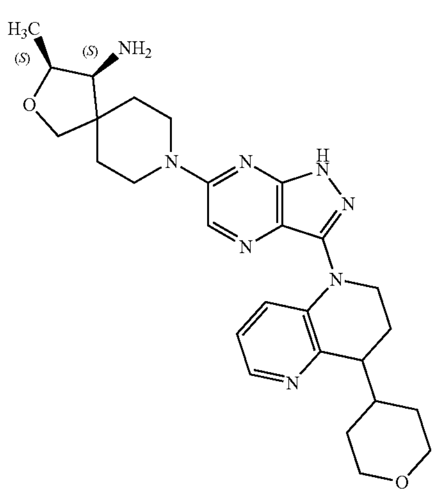 | $^1$H-NMR (400 MHz, DMSO-d$_6$) δ 8.35 (s, 1H), 7.66 (dd, J = 1.10, 7.93 Hz, 1H), 7.53 (dd, J = 1.22, 6.10 Hz, 1H), 6.78 (dd, J = 6.35, 7.81 Hz, 1H), 4.40-4.50 (m, 1H), 4.30 (br d, J = 13.92 Hz, 1H), 4.15-4.26 (m, 2H), 4.05 (br t, J = 4.64 Hz, 2H), 3.97 (br dd, J = 3.54, 10.86 Hz, 2H), 3.90 (d, J = 9.03 Hz, 1H), 3.74 (br t, J = 4.76 Hz, 2H), 3.66-3.72 (m, 1H), 3.50-3.57 (m, 2H), 3.10-3.27 (m, 2H), 1.88 (dq, J = 4.27, 11.92 Hz, 2H), 1.67-1.82 (m, 5H), 1.59 (br d, J = 13.18 Hz, 1H), 1.21 (d, J = 6.59 Hz, 3H) | 506.3 |

TABLE 1-continued
| Cmpd. No. | Structure | ¹H-NMR | Mass Spec. (M + H)⁺ |
|---|---|---|---|
| 394 | 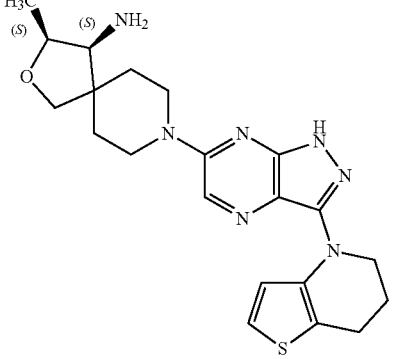 | ¹H-NMR (400 MHz, CD₃OD) δ 8.49 (s, 1H), 7.38 (d, J = 5.6 Hz, 1H), 7.22 (d, J = 5.6 Hz, 1H), 4.32-4.57 (m, 5H), 4.05 (d, J = 9.6 Hz, 1H), 3.92 (d, J = 9.6 Hz, 1H), 3.52 (d, J = 4.0 Hz, 1H), 3.30-3.40 (m, 2H), 2.96-3.01 (m, 2H), 2.17-2.22 (m, 2H), 1.78-1.97 (m, 4H), 1.36 (d, J = 6.4 Hz, 3H) | 426.0 |
| 395 | 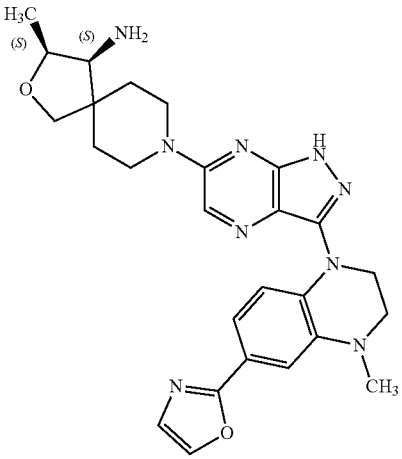 | ¹H-NMR (400 MHz, CD₃OD) δ 8.36 (s, 1H), 8.20 (s, 1H), 7.67 (s, 1H), 7.55 (d, J = 1.6 Hz, 1H), 7.49-7.47 (m, 1H), 7.14 (d, J = 8.4 Hz, 1H), 4.50-4.39 (m, 2H), 4.35-4.29 (m, 1H), 4.27-4.25 (m, 2H), 4.03-4.01 (m, 1H), 3.91-3.89 (m, 1H), 3.66-3.63 (m, 2H), 3.48-3.47 (m, 1H), 3.39-3.35 (m, 1H), 3.27-3.24 (m, 1H), 3.19 (s, 3H), 1.93-1.87 (m, 3H), 1.78-1.75 (m, 1H), 1.33 (d, J = 6.8 Hz, 3H) | 502.3 |
| 396 | 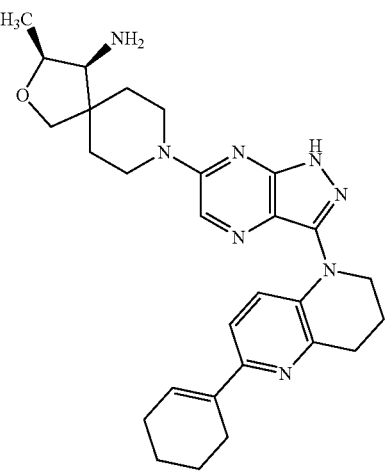 [SMILES: C[C@@H]1OCC2(CCN(c3cnc4c(N5CCCc6nc(C7=CCCCC7)ccc65)n[nH]c4n3)CC2)[C@@H]1N] | ¹H-NMR (400 MHz, CD₃OD) δ 8.34 (s, 1H), 7.95-8.14 (m, 1H), 7-44-7.64 (s, 1H), 6.50-6.68 (s, 1H), 4.24-4.58 (m, 3H), 3.98-4.17 (m, 3H), 3.86-3.97 (m, 1H), 3.42-3.55 (s, 1H), 3.20-3.33 (m, 4H), 2.20-2.58 (m, 6H), 1.68-2.00 (m, 8H), 1.33-1.38 (m, 3H) | 501.3 |

TABLE 1-continued
| Cmpd. No. | Structure | ¹H-NMR | Mass Spec. (M + H)⁺ |
|---|---|---|---|
| 397 | 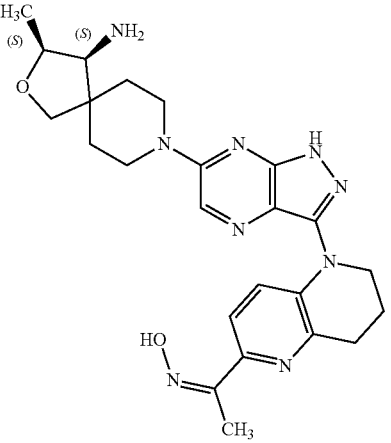 | ¹H-NMR (400 MHz, CD₃OD) δ 8.22 (s, 1H), 7.35-7.46 (m, 1H), 7.21-7.30 (m, 1H), 4.10-4.33 (m, 3H), 3.85-4.07 (m, 3H), 3.67-3.82 (m, 1H), 3.35-3.53 (m, 2H), 2.98-3.13 (m, 3H), 2.18-2.30 (m, 5H), 1.68-1.95 (m, 4H), 1.18-1.28 (m, | 478.3 |
| 398 | 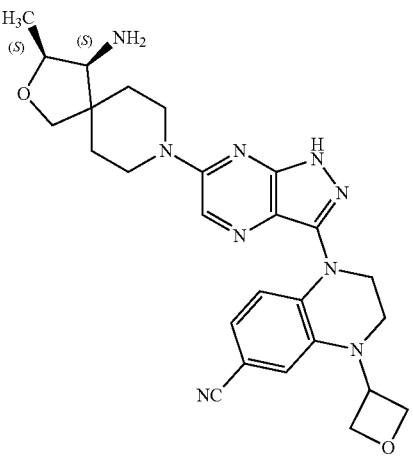 | ¹H-NMR (400 MHz, methanol-d₄) δ 8.13 (s, 1H), 6.81-6.85 (m, 1H), 6.73-6.77 (m, 1H), 6.33-6.35 (m, 1H), 4.86-4.96 (m, 2H), 4.68-4.72 (m, 2H), 4.55-4.60 (m, 1H), 4.02-4.18 (m, 5H), 3.78-3.80 (m, 1H), 3.62-3.66 (m, 1H), 3.29-3.33 (m, 2H), 3.24-3.27 (m, 2H), 2.93-2.95 (m, 1H), 1.61-1.80 (m, 4H), 1.12-1.40 (m, 3H) | 502.2 |
| 399 | 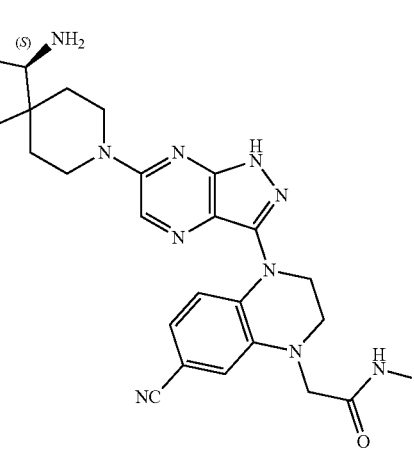 | ¹H-NMR (400 MHz, methanol-d₄) δ 8.24 (s, 1H), 6.85-6.90 (m, 2H), 6.68 (s, 1H), 4.15-4.30 (m, 3H), 4.07-4.09 (m, 2H), 3.99 (s, 2H), 3.89-3.92 (m, 1H), 3.73-3.76 (m, 1H), 3.62-3.66 (m, 2H), 3.39-3.53 (m, 2H), 3.03-3.05 (m, 1H), 2.82,(s, 3H), 1.72-1.91 (m, 4H), 1.23-1.25 (m, 3H) | 517.1 |

TABLE 1-continued

| Cmpd. No. | Structure | ¹H-NMR | Mass Spec. (M + H)⁺ |
|---|---|---|---|
| 400 | 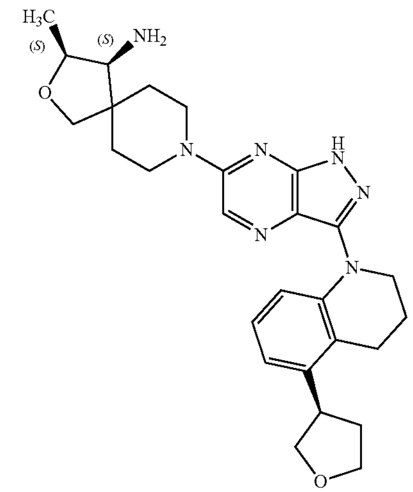 | ¹H-NMR (400 MHz, DMSO-d₆) δ 8.30 (s, 1H), 8.17 (br, 3H), 6.87-6.91 (m, 1H), 6.80-6.83 (m, 1H), 6.73-6.76 (m, 1H), 4.28-4.33 (m, 1H), 4.18-4.25 (m, 2H), 3.99-4.04 (m, 1H), 3.89-3.95 (m, 3H), 3.67-3.70 (m, 2H), 3.52-3.63 (m, 2H), 3.36-3.40 (m, 1H), 3.12-3.20 (m, 2H), 2.76-2.88 (m, 2H), 2.24-2.31 (m, 1H), 1.97-2.01 (m, 2H), 1.86-1.94 (m, 1H), 1.77-1.85 (m, 2H), 1.68-1.72 (m, 1H), 1.58-1.62 (m, 1H), 1.23-1.25 (d, J = 6.4 Hz, 3H) | 490.1 |
| 401 | 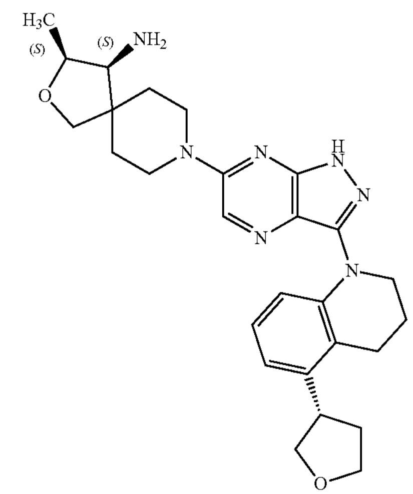 | ¹H-NMR (400 MHz, DMSO-d₆) δ 8.30 (s, 1H), 8.18 (br, 3H), 6.86-6.91 (m, 1H), 6.80-6.83 (m, 1H), 6.73-6.76 (m, 1H), 4.28-4.33 (m, 1H), 4.18-4.25 (m, 2H), 3.99-4.04 (m, 2H), 3.77-3.8 (m, 4H), 3.67-3.70 (m, 1H), 3.50-3.63 (m, 2H), 3.36-3.39 (m, 1H), 3.12-3.20 (m, 2H), 2.76-2.90 (m, 2H), 2.24-2.31 (m, 1H), 1.97-2.02 (m, 2H), 1.86-1.94 (m, 1H), 1.77-1.85 (m, 2H), 1.68-1.72 (m, 1H), 1.58-1.62 (m, 1H), 1.23-1.25 (d, J = 6.4 Hz, 3H) | 490.1 |
| 402 | 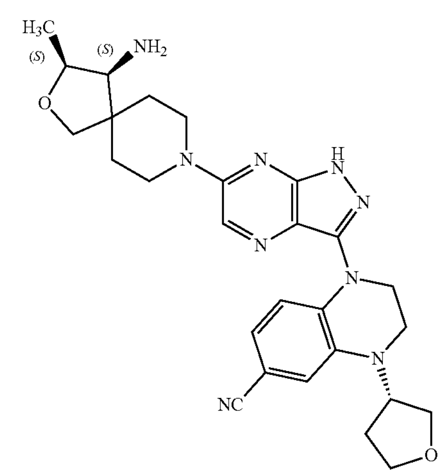 | ¹H-NMR (400 MHz, methanol-d₄) δ 8.22 (s, 1H), 7.07 (s, 1H), 6.85-6.82 (m, 2H), 4.16-3.90 (m, 7H), 3.89-3.72 (m, 4H), 3.6-3.3 (m, 5H), 3.04-3.02 (m, 1H), 2.4-2.3 (m, 1H), 2.0-1.6 (m, 5H), 1.25-1.23 (d, J = 6.8 Hz, 3H) | 516.3 |

TABLE 1-continued

| Cmpd. No. | Structure | ¹H-NMR | Mass Spec. (M + H)⁺ |
|---|---|---|---|
| 403 | 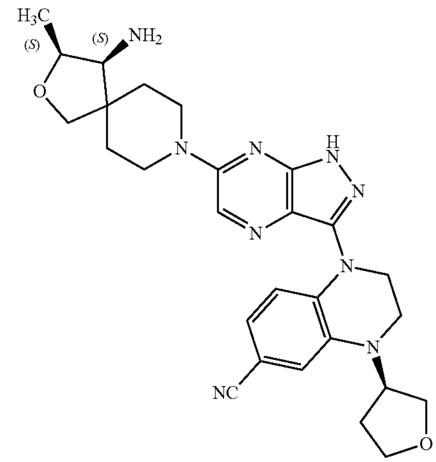 | ¹H-NMR (400 MHz, methanol-d₄) δ 8.22 (s, 1H), 7.07 (s, 1H), 6.85-6.82 (d, J = 8.4 Hz, 2H), 4.16-3.90 (m, 7H), 3.89-3.72 (m, 4H), 3.6-3.3 (m, 5H), 3.04-3.02 (m, 1H), 2.4-2.3 (m, 1H), 2.0-1.6 (m, 5H), 1.25-1.23 (d, J = 6.8 Hz, 3H) | 516.3 |
| 404 | 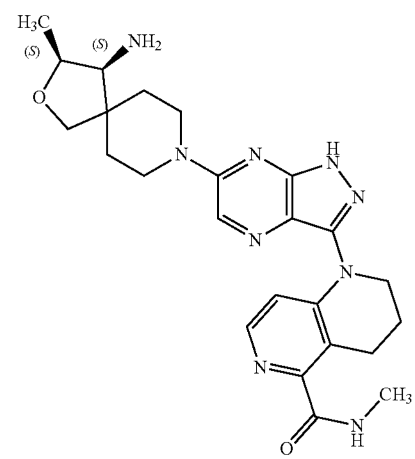 | ¹H-NMR (400 MHz, DMSO-d₆) δ 13.43 (s, 1H), 9.20 (s, 1H), 8.49 (s, 1H), 8.25 (br, 3H), 8.07 (d, 1H, J = 6.8 Hz), 6.99 (d, 1H, J = 7.2 Hz), 4.30-4.19 (m, 3H), 4.03-3.93 (m, 3H), 3.69 (d, 1H, J = 9.2 Hz), 3.40-3.17 (m, 3H), 2.91-2.85 (m, 5H), 2.12-2.05 (m, 2H), 1.83-1.61 (m, 4H), 1.25 (d, 3H, J = 6.8 Hz) | 478.1 |
| 405 | 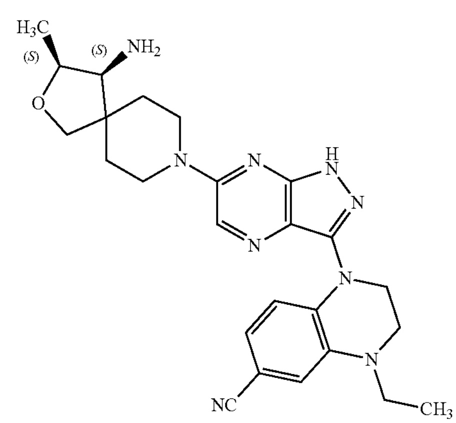 | ¹H-NMR (400 MHz, methanol-d₄) δ 8.22 (s, 1H), 6.93 (d, 1H, J = 1.6 Hz), 6.85-6.77 (m, 2H), 4.30-4.15 (m, 3H), 4.03-3.98 (m, 2H), 3.91 (d, 1H, J = 8.8 Hz), 3.52 (d, 1H, J = 8.8 Hz), 3.56-3.38 (m, 6H), 3.05 (d, 1H, J = 5.2 Hz), 1.92-1.68 (m, 4H), 1.26-1.20 (m, 6H) | 474.3 |

TABLE 1-continued

| Cmpd. No. | Structure | ¹H-NMR | Mass Spec. (M + H)⁺ |
|---|---|---|---|
| 406 | 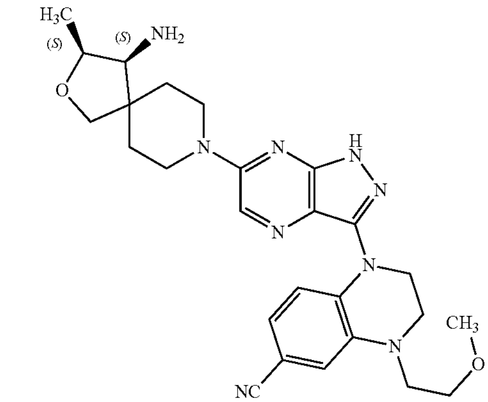 | ¹H-NMR (400 MHz, methanol-d₄) δ 8.20 (s, 1H), 6.95 (d, 1H, J = 1.6 Hz), 6.86 (d, 1H, J = 8 Hz), 6.80-6.77 (m, 1H), 4.28-4.13 (m, 3H), 3.99-3.95 (m, 2H), 3.89 (d, 1H, J = 8.8 Hz), 3.74 (d, 1H, J = 8.8 Hz), 3.69-3.66 (m, 2H), 3.63-3.57 (m, 4H), 3.50-3.42 (m, 2H), 3.40 (s, 3H), 3.03 (d, 1H, J = 5.2 Hz), 1.88-1.67 (m, 4H), 1.24 (d, 3H, J = 6.4 Hz) | 504.3 |
| 407 | 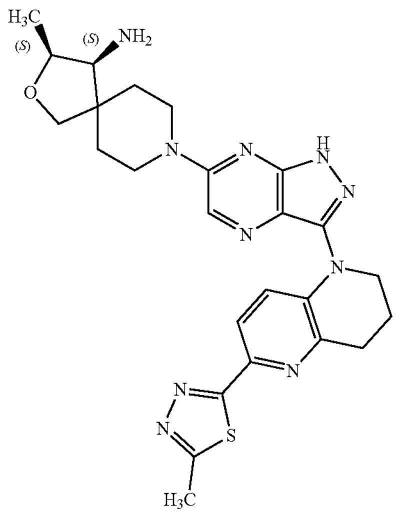 | ¹H-NMR (400 MHz, DMSO-d₆) δ 12.77 (s, 1H), 8.34 (s, 1H), 7.80 (br d, J = 8.79 Hz, 1H), 7.57 (br d, J = 8.79 Hz, 1H), 4.06 (td, J = 6.13, 11.90 Hz, 1H), 3.88-4.01 (m, 3H), 3.68 (br d, J = 8.30 Hz, 1H), 3.38-3.57 (m, 3H), 3.21 (s, 1H), 3.00 (br t, J = 6.47 Hz, 1H), 2.91 (br d, J = 5.13 Hz, 1H), 2.71 (s, 1H), 2.63-2.68 (m, 1H), 2.58-2.67 (m, 1H), 2.29-2.40 (m, 2H), 2.11 (dt, J = 5.98, 11.78 Hz, 2H), 1.60-1.83 (m, 3H), 1.45-1.58 (m, 2H), 1.07 (br d, J = 6.35 Hz, 3H) | 519.5 |
| 408 | 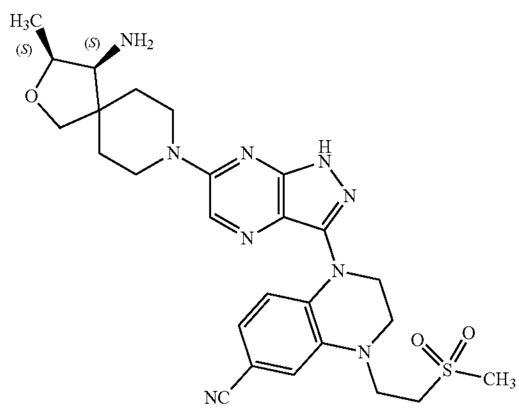 | ¹H-NMR (400 MHz, methanol-d₄) δ 8.28 (s, 1H), 7.06 (s, 1H), 6.95 (d, J = 8.4 Hz, 1H), 6.88 (d, J = 8.0 Hz, 1H), 4.25-4.50 (m, 3H), 3.95-4.15 (m, 3H), 3.85-4.14 (m, 3H), 3.55-3.65 (m, 2H), 3.51 (t, J = 6.6 Hz, 2H), 3.45 (d, J = 4.0 Hz, 1H), 3.20-3.30 (m, 2H), 3.06 (s, 3H), 1.80-1.95 (m, 3H), 1.70-1.80 (m, 1H), 1.33 (d, J = 6.0 Hz, 3H) | 552.3 |

TABLE 1-continued

| Cmpd. No. | Structure | ¹H-NMR | Mass Spec. (M + H)⁺ |
|---|---|---|---|
| 409 | 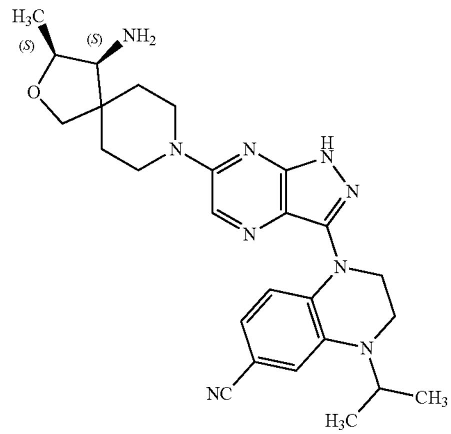 | ¹H-NMR (400 MHz, methanol-d₄) δ 8.34 (s, 1H), 7.31 (s, 1H), 6.95-7.10 (m, 2H), 4.35-4.52 (m, 2H), 4.25-4.35 (m, 1H), 4.10-4.25 (m, 3H), 4.01 (d, J = 9.2 Hz, 1H), 3.90 (d, J = 9.2 Hz, 1H), 3.55-3.70 (m, 2H), 3.43-3.50 (m, 1H), 3.20-3.30 (m, 2H), 1.83-1.98 (m, 3H), 1.72-1.81 (m, 1H), 1.30-1.41 (m, 9H) | 488.3 |
| 410 | 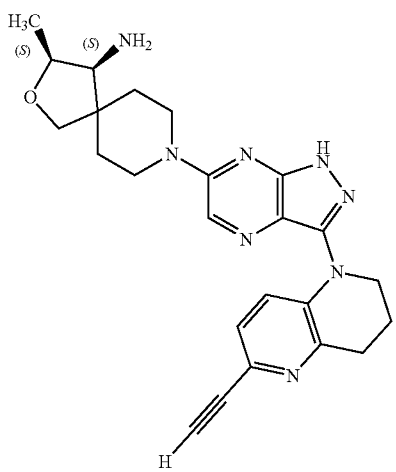 | ¹H NMR (400 MHz, DMSO-d₆) δ 8.34 (s, 1H), 8.29 (s, 1H), 7.38 (d, J = 8.54 Hz, 1H), 7.12 (d, J = 8.54 Hz, 1H), 4.02-4.11 (m, 1H), 3.88-3.98 (m, 4H), 3.68 (d, J = 8.54 Hz, 1H), 3.50 (s, 1H), 3.33-3.42 (m, 1H), 3.08-3.19 (m, 1H), 2.87-2.95 (m, 3H), 2.06 (quin, J = 5.98 Hz, 2H), 1.74 (ddd, J = 3.17, 9.58, 13.12 Hz, 1H), 1.61-1.69 (m, 1H), 1.44-1.59 (m, 3H), 1.25-1.36 (m, 1H), 1.07 (d, J = 6.35 Hz, 3H), 0.91 (t, J = 7.32 Hz, 1H) | 445.3 |
| 411 | 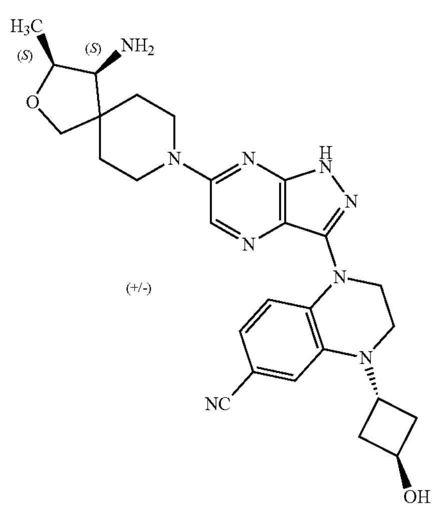 | ¹H-NMR (400 MHz, DMSO-d₆) δ 12.77 (s, 1H), 8.32 (s, 1H), 6.97-7.00 (m, 1H), 6.89-6.93 (m, 1H), 6.83-6.85 (m, 1H), 5.14-5.17 (m, 1H), 4.02-4.11 (m, 3H), 3.89-3.97 (m, 3H), 3.67-3.71 (m, 1H), 3.40-3.54 (m, 5H), 2.91-2.93 (m, 1H), 2.67-2.72 (m, 2H), 1.86-1.94 (m, 2H), 1.75-1.80 (m, 1H), 1.64-1.70 (m, 1H), 1.47-1.58 (m, 3H), 1.08-1.10 (d, J = 6.0 Hz, 3H) | 538.1 [M+ Na]⁺ |

TABLE 1-continued
| Cmpd. No. | Structure | ¹H-NMR | Mass Spec. (M + H)⁺ |
|---|---|---|---|
| 412 | 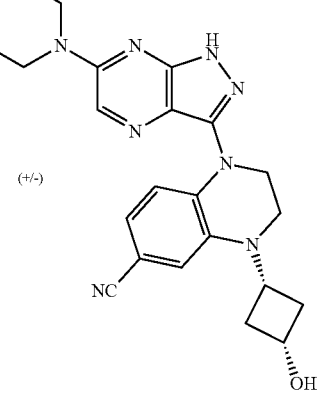 | ¹H-NMR (400 MHz, DMSO-d₆) δ 12.77 (s, 1H), 8.32 (s, 1H), 6.97-7.00 (m, 1H), 6.89-6.93 (m, 1H), 6.83-6.85 (m, 1H), 5.14-5.17 (m, 1H), 4.02-4.11 (m, 3H), 3.89-3.97 (m, 3H), 3.67-3.71 (m, 1H), 3.40-3.54 (m, 5H), 2.91-2.93 (m, 1H), 2.67-2.72 (m, 2H), 1.86-1.94 (m, 2H), 1.75-1.80 (m, 1H), 1.64-1.70 (m, 1H), 1.47-1.58 (m, 3H), 1.08-1.10 (d, J = 6.0 Hz, 3H) | 538.1 [M+Na]⁺ |
| 413 | 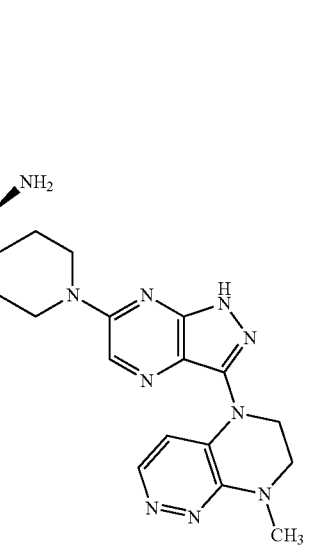 | ¹H-NMR (400 MHz, CD₃OD) δ 8.42 (s, 1H), 8.31~8.34 (m, 1H), 7.31~7.33 (m, 1H), 4.40~4.52 (m, 2H), 4.31~4.37 (m, 3H), 4.02~4.05 (m, 1H), 3.90~3.93 (m, 1H), 3.81~3.83 (m, 2H), 3.48~3.50 (m, 1H), 3.30~3.35 (m, 1H), 3.25~3.28 (m, 4H), 1.89~1.96 (m, 3H), 1.76~1.80 (m, 1H), 1.34~1.36 (m, 3H) | 437.1 |
| 414 | 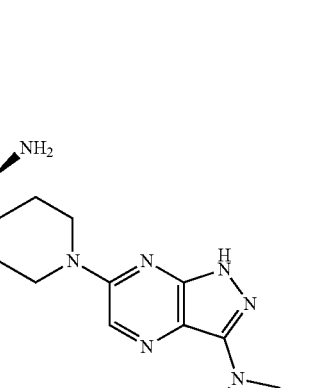 | ¹H-NMR (400 MHz, CD₃OD + DMSO-d₆) δ 9.16 (s, 1H), 8.62 (s, 1H), 8.38 (s, 1H), 4.33~4.51 (m, 5H), 4.04~4.07(m, 1H), 3.89~3.92 (m, 3H), 3.49~3.51 (m, 1H), 3.41 (s, 3H), 3.24~3.28 (m, 2H), 1.90~1.98 (m, 3H), 1.76~1.81 (m, 1H), 1.35~1.38 (m, 3H) | 437.2 |

TABLE 1-continued

| Cmpd. No. | Structure | ¹H-NMR | Mass Spec. (M + H)⁺ |
|---|---|---|---|
| 415 | 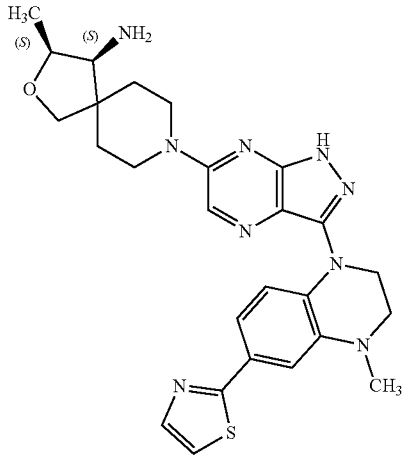 | ¹H-NMR (400 MHz, CD₃OD) δ 8.33 (s, 1H), 8.10 (d, J = 4.0 Hz, 1H), 7.89 (s, 1H), 7.29 (s, 1H), 7.04 (s, 1H), 4.51-4.32 (m, 5H), 4.05-3.91 (m, 2H), 3.59 (s, 1H), 3.48 (d, J = 4.0 Hz, 1H), 3.26-3.15 (m, 5H), 193-1.76 (m, 4H), 1.35 (d, J = 6.4 Hz, 3H) | 518.0 |
| 416 | 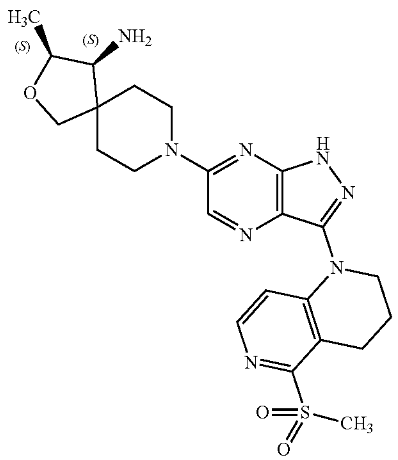 | ¹H-NMR (400 MHz, CD₃OD) δ 8.43 (s, 1H), 8.07 (d, J = 7.2 Hz, 1H), 7.17 (d, J = 6.8 Hz, 1H), 4.49-4.34 (m, 3H), 4.15 (t, J = 5.6 Hz, 2H), 4.05-3.93 (m, 2H), 3.53-3.29 (m, 8H), 2.35-2.31 (m, 2H), 1.95-1.77 (m, 4H),1.35 (d, J = 6.4 Hz, 3H) | 521.1 [M+ Na]⁺ |
| 417 | 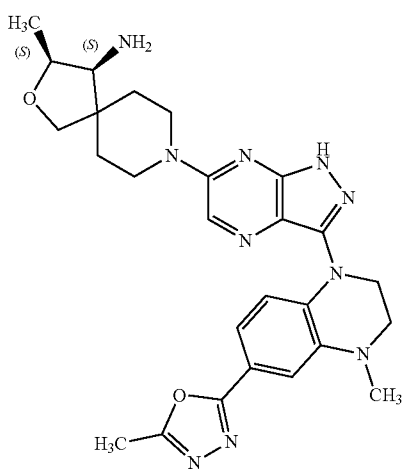 | ¹H-NMR (400 MHz, CD₃OD) δ 8.23 (s, 1H), 7.28 (d, J = 2.0 Hz, 1H), 7.19-7.17 (m, 1H), 6.92 (d, J = 8.4 Hz, 1H), 4.63-4.08 (m, 5H), 3.92 (d, J = 8.8 Hz, 1H), 3.76 (d, J = 8.8 Hz, 1H), 3.51-3.49 (m, 4H), 3.10-3.06 (m, 4H), 2.60 (s, 3H), 1.88-1.73 (m, 4H), 1.25 (d, J = 6.8 Hz, 3H) | 515.8 |

TABLE 1-continued

| Cmpd. No. | Structure | ¹H-NMR | Mass Spec. (M + H)⁺ |
|---|---|---|---|
| 418 | 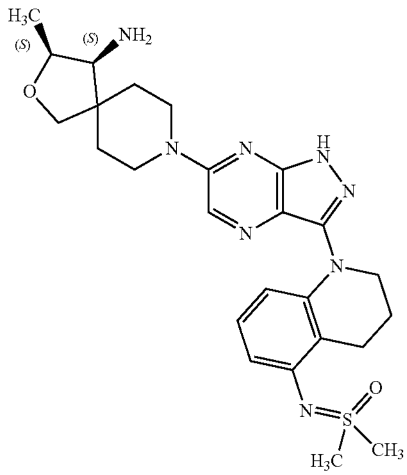 | ¹H-NMR (400 MHz, CD₃OD) δ 8.43 (s, 1H), 7.18-7.33 (m, 3H), 4.45-4.58 (m, 2H), 4.30-4.38 (m, 1H), 4.16-4.20 (m, 2H), 4.05 (d, J = 9.2 Hz, 1H), 3.91 (d, J = 9.2 Hz, 1H), 3.77 (s, 6H), 3.52 (d, J = 4.0 Hz, 1H), 3.33-3.40 (m, 2H), 2.93-2.98 (m, 2H), 2.08-2.18 (m, 2H), 1.78-1.97 (m, 4H), 1.36 (d, J = 6.4 Hz, 3H) | 511.1 |
| 419 | 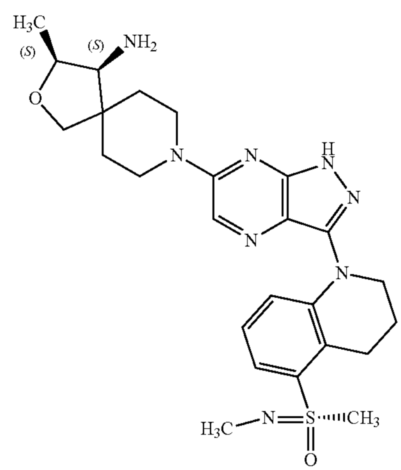 | ¹H-NMR (400 MHz, CD₃OD) δ 8.54 (s, 1H), 8.21 (s, 1H), 7.50-7.47 (m, 1H), 7.18-7.14 (m, 1H), 7.08-7.06 (m, 1H), 4.36-4.28 (m, 3H), 3.99-3.84 (m, 4H), 3.53-3.45 (m, 1H), 3.4-3.36 (m-1H), 3.3-3.28 (m, 2H), 3.24 (s, 3H), 3.18-3.10 (m, 1H), 2.65 (s, 3H), 2.23-2.06 (m, 2H), 1.91-1.85 (m, 3H), 1.75-1.71 (m, 1H), 1.30 (d, J = 6.4 Hz, 3H) | 533.1 [M+ Na]⁺ |
| 420 | 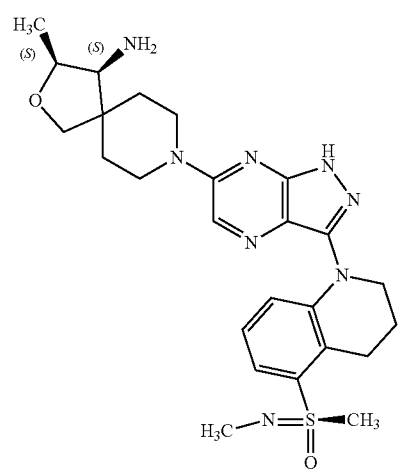 | ¹H-NMR (400 MHz, CD₃OD) δ 8.47 (s, 1H), 8.22 (s, 1H), 7.49-7.48 (m, 1H), 7.18-7.14 (m, 1H), 7.09-7.07 (m, 1H), 4.44-4.29 (m, 3H), 4.03-3.85 (m, 4H), 3.52-3.45 (m, 1H), 3.43-3.42 (m, 1H), 3.30-3.24 (m, 5H), 3.18-3.11 (m, 1H), 2.65 (s, 3H), 2.24-2.06 (m, 2H), 1.96-1.85 (m, 3H), 1.77-1.73 (m, 1H), 1.33 (d, J = 6.8 Hz, 3H) | 533.1 [M+ Na]⁺ |

TABLE 1-continued

| Cmpd. No. | Structure | ¹H-NMR | Mass Spec. (M + H)⁺ |
|---|---|---|---|
| 421 | 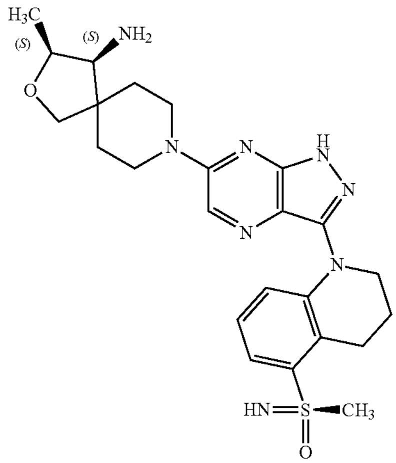 | ¹H-NMR (400 MHz, CD₃OD) δ 8.31 (s, 1H), 7.72 (d, J = 8.0 Hz, 1H), 7.47-7.38 (m, 2H), 4.51-4.40 (m, 2H), 4.35-4.32 (m, 1H), 4.05-3.98 (m, 6H), 3.92-3.90 (m-1H), 3.49-3.48 (m, 1H), 3.43-3.36 (m, 2H), 3.29-3.22 (m, 2H), 2.23-2.22 (m, 2H), 1.94-1.90 (m, 3H), 1.79-1.76 (m, 1H), 1.35 (d, J = 6.4 Hz, 3H) | 519.1 [M+ Na]⁺ |
| 422 | 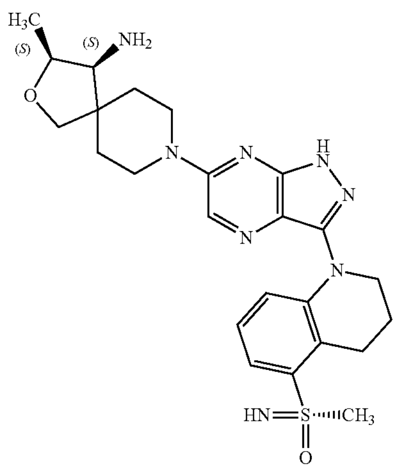 | ¹H-NMR (400 MHz, CD₃OD) δ 8.29 (s, 1H), 7.69-7.66 (m, 1H), 7.40-7.34 (m, 2H), 4.50-4.31 (m, 3H), 4.04-3.90 (m, 7H), 3.49-3.48 (m, 1H), 3.43-3.36 (m, 2H), 3.30-3.21 (m, 2H), 2.28-2.18 (m, 2H), 1.93-1.88 (m, 3H), 1.79-1.76 (m 1H), 1.35 (d, J = 6.4 Hz, 3H) | 519.1 [M+ Na]⁺ |
| 423 | 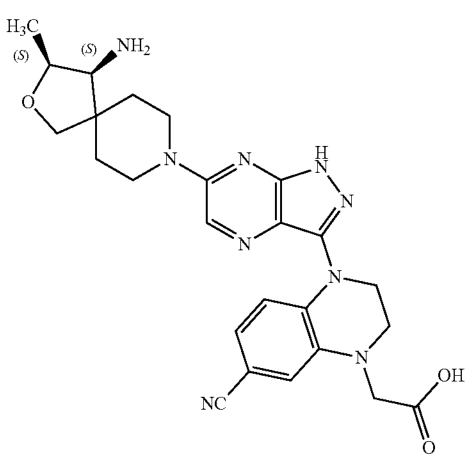 | ¹H-NMR (400 MHz, methanol-d₄) δ 8.14 (s, 1H), 6.90-6.95 (m, 1H), 6.72-6.76 (m, 2H), 4.27-4.30 (m, 3H), 4.00-4.05 (m, 2H), 3.95-3.98 (m, 1H), 3.87 (s, 2H), 3.82-3.84 (m, 1H), 3.61-3.65 (m, 2H), 3.29-3.31 (m, 2H), 3.15-3.24 (m, 1H), 1.82-1.90 (m, 3H), 1.68-1.73 (m, 1H), 1.30-1.33 (m, 3H) | 504.3 |

TABLE 1-continued

| Cmpd. No. | Structure | ¹H-NMR | Mass Spec. (M + H)⁺ |
|---|---|---|---|
| 424 | 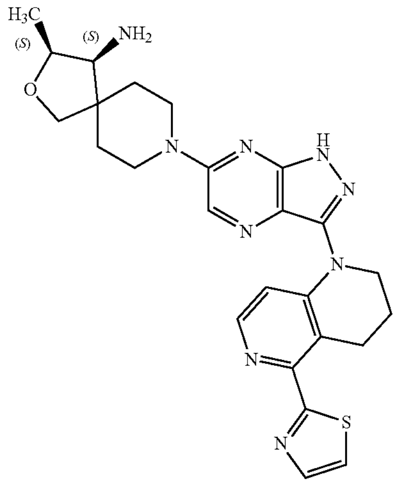 | ¹H-NMR (400 MHz, CD₃OD) δ 8.30 (s, 1H), 7.97-7.93 (m, 2H), 7.69-7.68 (m, 1H), 6.68-6.66 (m, 1H), 4.27-4.17 (m, 3H), 3.94-3.90 (m,, 3H), 3.76-3.74 (m, 1H), 3.54-3.43 (m, 2H), 3.39-3.37 (m, 2H), 3.05-3.04 (m, 1H), 2.23-2.16 (m, 2H), 1.91-1.81 (m, 2H), 1.76-1.69 (m, 2H), 1.24 (d, J = 6.4 Hz, 3H) | 504.1 |
| 425 | 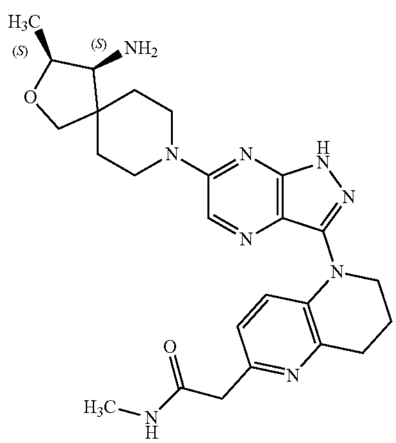 | ¹H-NMR (400 MHz, CD₃OD) δ 8.24 (s, 1H), 7.37~7.31 (m, 1H), 7.02~6.90 (m, 1H), 4.26~4.17 (m, 3H), 3.96~3.91 (m, 3H), 3.74 (t, J = 6.4 Hz, 1H), 3.59 (s, 2H), 3.51~3.42 (m, 2H), 3.08~2.98 (m, 3H), 2.75 (s, 3H), 2.25~2.20 (m, 2H), 1.86~1.68 (m, 4H), 1.27~1.21 (m, 3H) | 492.2 |
| 426 | 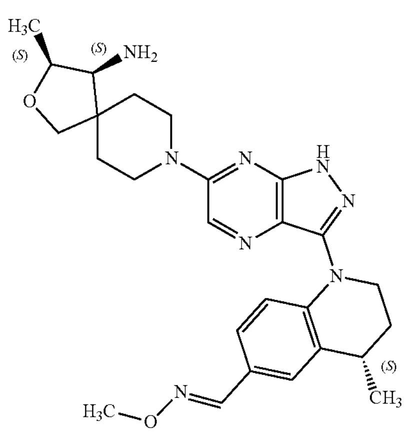 | ¹H-NMR (500 MHz, DMSO-d₆) δ 8.27 (s, 1H), 8.02 (s, 1H), 7.48 (br dd, J = 1.91, 8.77 Hz, 1H), 7.35 (d, J = 1.53 Hz, 1H), 7.20 (s, 1H), 7.12 (dd, J = 1.83, 8.69 Hz, 1H), 6.88 (d, J = 8.69 Hz, 1H), 4.02-4.09 (m, 1H), 3.89-3.97 (m, 2H), 3.82-3.87 (m, 2H), 3.80 (s, 3H), 3.67 (d, J = 8.54 Hz, 1H), 3.49 (s, 1H), 3.39 (ddd, J = 3.13, 9.76, 13.19 Hz, 1H), 2.93-3.01 (m, 1H), 2.87 (d, J = 5.19 Hz, 1H), 2.01-2.11 (m, 1H), 1.70-1.79 (m, 2H), 1.64 (ddd, J = 3.74, 9.38, 13.27 Hz, 1H), 1.43-1.56 (m, 2H), 1.30 (d, J = 7.02 Hz, 3H), 1.06 (d, J = 6.41 Hz, 3H) | 491.3 |

TABLE 1-continued

| Cmpd. No. | Structure | ¹H-NMR | Mass Spec. (M + H)⁺ |
|---|---|---|---|
| 427 | 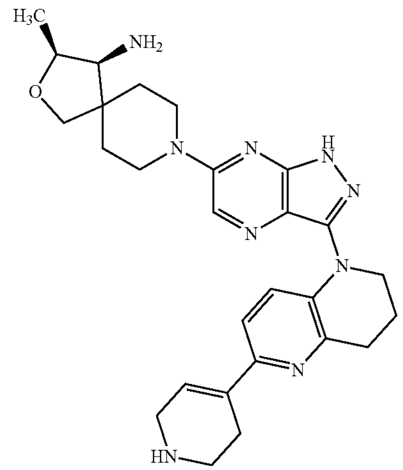 [SMILES: C[C@@H]1OCC2(CCN(c3cnc4c(N5CCCc6nc(C7=CCNCC7)ccc65)n[nH]c4n3)CC2)[C@@H]1N] | ¹H-NMR (400 MHz, CD₃OD) δ 8.36 (s, 1H), 8.01-8.18 (m, 1H), 7.60-7.74 (m, 1H), 6.53-6.68 (m, 1H), 4.33-4.51(m, 3H), 3.90-4.13 (m, 6H), 3.48-3.56 (m, 3H), 3.37-3.41 (m, 2H), 3.24-3.35 (m, 2H), 2.85-2.95 (m, 2H), 2.31-2.34 (m, 2H), 1.85-1.98 (m, 3H), 1.76-1.80 (m, 1H), 1.34-1.37 (m, 3H) | 502.3 |
| 428 | 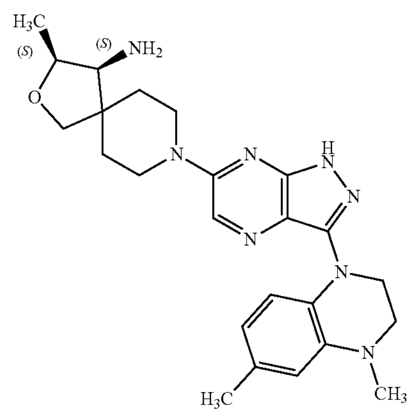 | ND | 448.3 |
| 429 | 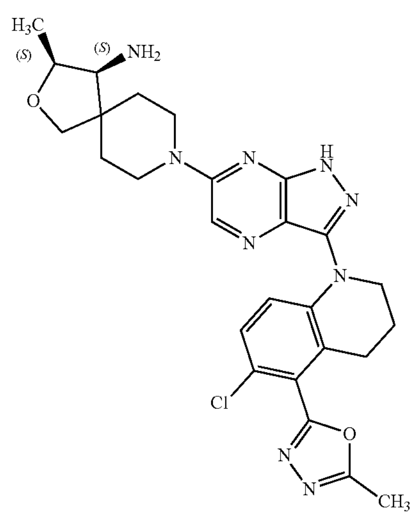 | ¹H-NMR (400 MHz, DMSO-d₆) δ 8.27 (s, 1H), 7.08-7.25 (m, 2H), 3.91-4.13 (m, 3H), 3.78-3.86 (m, 2H), 3.70 (br d, J = 8.54 Hz, 1H), 3.51 (br d, J = 8.79 Hz, 1H), 3.30-3.47 (m, 2H), 2.93 (br d, J = 5.13 Hz, 1H), 2.56-2.61 (m, 2H), 2.52-2.58 (m, 2H), 1.91 (td, J = 6.07, 11.54 Hz, 2H), 1.61-1.79 (m, 2H), 1.43-1.61 (m, 2H), 1.07 (d, J = 6.35 Hz, 3H) | 536.2 |

TABLE 1-continued

| Cmpd. No. | Structure | ¹H-NMR | Mass Spec. (M + H)⁺ |
|---|---|---|---|
| 430 | 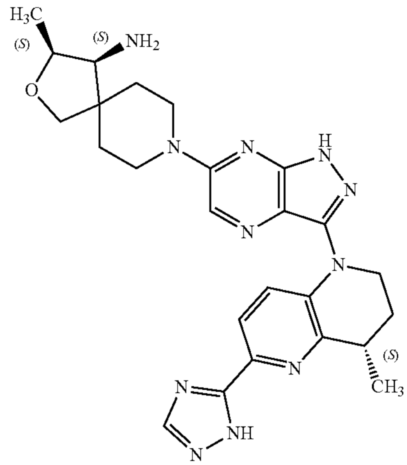 | ¹H-NMR (400 MHz, CD₃OD) δ 8.44 (s, 1H), 8.13-8.11 (m, 1H), 7.98-7.96 (m, 1H), 7.91-7.90 (m, 1H), 7.06 (s, 1H), 4.51-4.40 (m, 3H), 4.25-4.20 (m, 1H), 4.12-4.10 (m, 2H), 3.92-3.88 (m, 1H), 3.75-3.72 (m, 1H), 3.52-3.48 (m, 1H), 3.42-3.40 (m, 1H), 3.28-3.22 (m, 1H), 2.41-2.26 (m, 1H), 2.21-2.19 (m, 1H), 1.98-1.92 (m, 3H), 1.81-1.78 (m, 1H), 1.59 (d, J = 5.2 Hz, 3H), 1.36 (d, J = 6.4 Hz, 3H) | 501.1 |
| 431 | 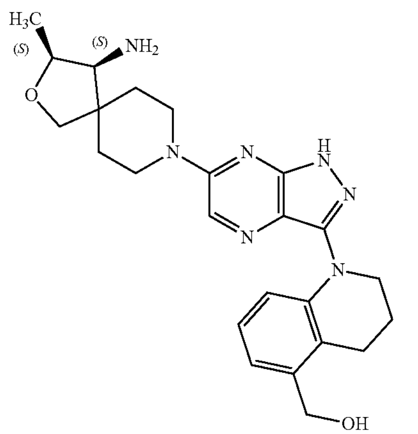 | ¹H-NMR (400 MHz, CD₃OD) δ 8.16 (s, 1H), 6.98-6.78 (m, 2H), 6.77-6.76 (m, 1H), 4.66 (s, 2H), 4.26-2.23 (m, 3H), 3.92-3.86 (m, 3H), 3.76-3.74 (m, 1H), 3.49-3.40 (m, 2H), 3.12-3.10 (m, 1H), 2.92-2.88 (m, 2H), 2.20-2.02 (m, 2H), 1.88-1.62 (m, 4H), 1.25-1.23 (m, 3H) | 450.2 |
| 432 | 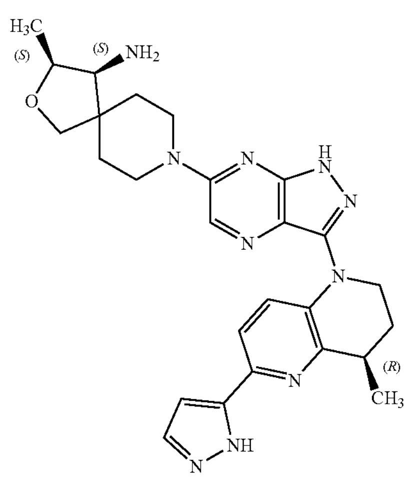 | ¹H-NMR (400 MHz, CD₃OD) δ 8.38 (s, 1H), 8.13~8.10 (m, 1H), 7.98~7.96 (m, 1H), 7.90~7.88 (m, 1H), 7.05 (s, 1H), 4.51~4.35 (m, 3H), 4.34~4.33 (m, 1H), 4.18~4.06 (m, 2H), 3.92~3.90 (m, 1H), 3.70~3.51 (m, 1H), 3.49~3.46 (m, 1H), 3.36~3.34 (m, 1H), 3.29~2.26 (m, 1H), 2.39~2.38 (m, 1H), 2.17~2.16 (m, 1H), 1.94~1.90 (m, 3H), 1.80~1.77 (m, 1H), 1.58 (d, J = 6.8 Hz, 3H), 1.35 (d, J = 6.4 Hz, 3H) | 501.2 |

TABLE 1-continued
| Cmpd. No. | Structure | ¹H-NMR | Mass Spec. (M + H)⁺ |
|---|---|---|---|
| 433 | 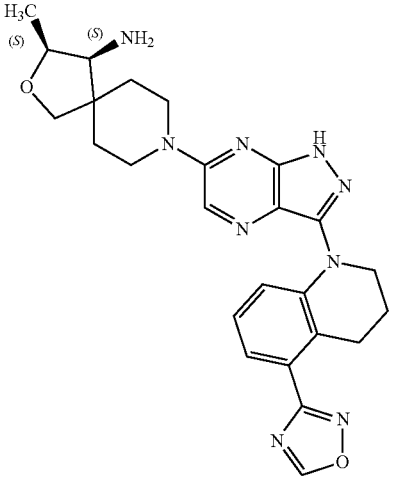 | ¹H-NMR (400 MHz, methanol-d₄) δ 9.18 (s, 1H), 8.09 (s, 1H), 7.24-7.26 (m, 1H), 6.93-6.99 (m, 1H), 6.85-6.88 (m, 1H), 4.08-4.18 (m, 3H), 3.77-3.81 (m, 3H), 3.63-3.66 (m, 1H), 3.30-3.38 (m, 2H), 3.03-3.06 (m, 2H), 2.95-2.97 (m, 1H), 1.95-2.04 (m, 2H), 1.72-1.77 (m, 2H), 1.57-1.70 (m, 2H), 1.12-1.14 (m, 3H) | 488.2 |
| 434 | 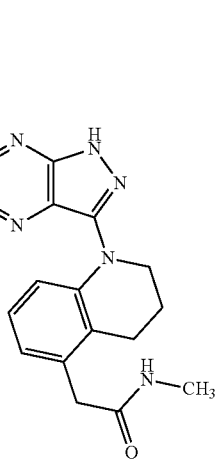 | ¹H-NMR (400 MHz, CD₃OD) δ 8.46 (s, 1H), 7.12-7.37 (m, 3H), 4.47-4.60 (m, 2H), 4.28-4.37 (m, 3H), 4.05 (d, J = 9.2 Hz, 1H), 3.92 (d, J = 9.2 Hz, 1H), 3.64 (s, 2H), 3.51 (d, J = 4.0 Hz, 1H), 3.35-3.44 (m, 2H), 2.82-2.90 (m, 2H), 2.77 (s, 3H), 2.05-2.15 (m, 2H), 1.78-1.98 (m, 4H), 1.35 (d, J = 6.4 Hz, 3H) | 513.1 [M+ Na]⁺ |
| 435 | 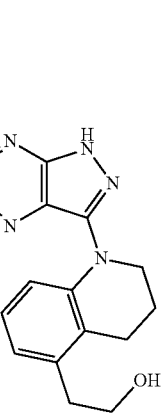 | ¹H-NMR (400 MHz, CD₃OD) δ 8.30 (s, 1H), 7.14-6.96 (m, 3H), 4.33-4.45 (m, 2H), 4.13-4.25 (m, 3H), 3.91 (d, J = 9.2 Hz, 1H), 3.79 (d, J = 9.2 Hz, 1H), 3.65 (t, J = 7.2 Hz, 2H), 3.37 (d, J = 4.0 Hz, 1H), 3.20-3.32 (m, 2H), 2.76-2.81 (m, 4H), 1.95-2.03 (m, 2H), 1.65-1.83 (m, 4H), 1.23 (d, J = 6.8 Hz, 3H) | 464.1 |

TABLE 1-continued
| Cmpd. No. | Structure | ¹H-NMR | Mass Spec. (M + H)⁺ |
|---|---|---|---|
| 436 | 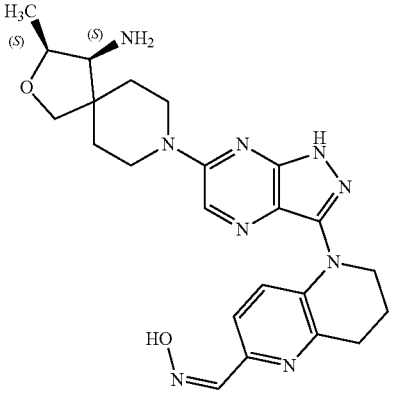 | ¹H-NMR (400 MHz, methanol-$d_4$) δ 8.36 (s, 1H), 8.21 (s, 1H), 8.04 (d, J = 8.8 Hz, 1H), 7.79 (d, J = 9.2 Hz, 1H), 4.50-4.28 (m, 3H), 4.13-4.10 (m, 2H), 4.37 (d, J = 8.8 Hz, 1H), 3.92 (d, J = 9.2 Hz, 1H), 3.49 (d, J = 3.6 Hz, 1H), 3.31-3.23 (m, 4H), 2.34-2.31 (m, 2H), 1.93-1.89 (m, 3H), 1.80-1.76 (m, 1H), 1.35 (d, J = 6.4 Hz, 3H) | 464.1 |
| 437 | 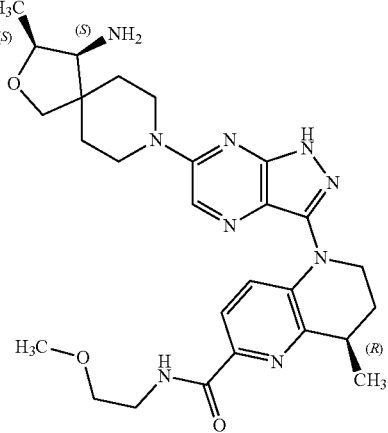 | ¹H-NMR (400 MHz, CD₃OD) δ 8.37 (s, 1H), 7.92-8.10 (m, 2H), 4.33-4.51 (m, 3H), 3.92-4.16 (m, 3H), 3.90-3.93 (m, 1H), 3.59-3.66 (m, 5H), 3.49-3.50 (m, 1H), 3.24-3.34 (m, 5H), 2.32-2.41 (m, 1H), 2.12-2.17 (m, 1H), 1.94 (s, 3H), 1.76-1.80 (m, 1H), 1.55-1.63 (m, 3H), 1.34-1.37 (m, 3H) | 536.3 |
| 438 | 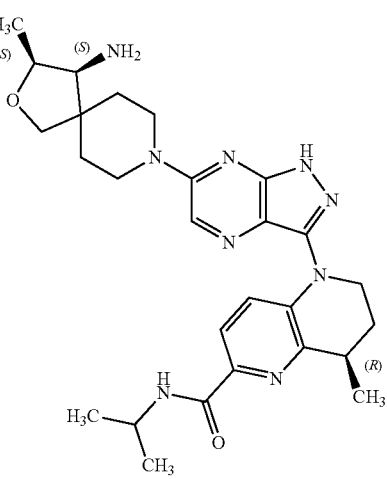 | ¹H-NMR (400 MHz, CD₃OD) δ 8.37 (s, 1H), 8.02-8.11 (m, 1H), 7.92-8.01 (m, 1H), 4.18-4.48 (m, 5H), 4.09-4.17 (m, 2H), 3.90-3.93 (m, 1H), 3.65-3.78 (m, 1H), 3.45-3.56 (m, 1H), 3.33-3.38 (m, 1H), 3.20-3.30 (m, 1H), 3.32-2.42 (m, 2.14-2.19 (m, 1H), 1.92-1.98 (m, 3H), 1.74-1.81 (m, 1H), 1.53-1.62 (m, 3H), 1.29-1.40 (m, 9H) | 520.3 |

TABLE 1-continued

| Cmpd. No. | Structure | ¹H-NMR | Mass Spec. (M + H)⁺ |
|---|---|---|---|
| 439 | 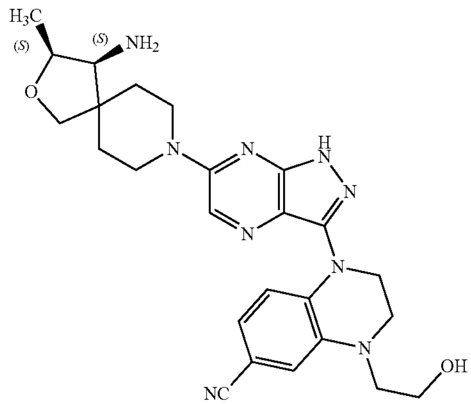 | ¹H-NMR (400 MHz, methanol-d₄) δ 8.22(s, 1H), 6.98 (d, 1H, J = 1.6 Hz), 6.87-6.85 (m, 1H), 6.81-6.78 (m, 1H), 4.28-4.14 (m, 3H), 4.00-3.98 (m, 2H), 3.91 (d, 1H, J = 8.8 Hz), 3.84-3.81 (m, 2H), 3.75 (d, 1H, J = 8.4 Hz), 3.66-3.63 (m, 2H), 3.56-3.52 (m, 2H), 3.49-3.37 (m, 2H), 3.05 (d, 1H, J = 5.2 Hz), 1.92-1.68 (m, 4H), 1.24 (d, 3H, J = 6.8 Hz) | 490.3 |
| 440 | 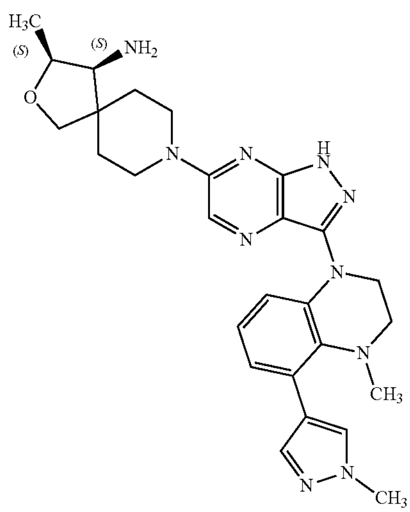 | ¹H-NMR (400 MHz, CD₃OD) δ 8.40 (s, 1H), 8.25 (s, 1H), 8.08 (s, 1H), 7.28-7.24 (m, 1H), 7.13 (d, J = 8.0 Hz, 1H), 6.94 (d, J = 7.2 Hz, 1H), 4.49-4.35 (m, 5H), 4.13 (s, 3H), 4.05 (d, J = 9.2 Hz, 1H), 3.93-3.88 (m, 3H), 3.50 (d, J = 4.0 Hz, 1H), 3.36 (m, 1H), 3.30 (m, 1H), 3.26 (m, 3H), 1.95-1.91 (m, 3H), 1.81-1.78 (m, 1H), 1.35 (d, J = 6.4 Hz, 3H) | 515.3 |
| 441 | 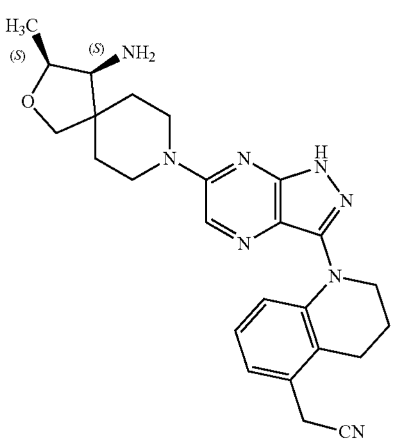 | ¹H-NMR (400 MHz, CDCl₃) δ 8.04 (s, 1H), 7.10 (d, J = 8.8 Hz, 1H), 6.93-6.99 (m, 1H), 6.84 (d, J = 8.8 Hz, 1H), 4.10-4.15 (m, 1H), 3.86-3.96 (m, 4H), 3.75 (d, J = 8.8 Hz, 1H), 3.63 (d, J = 8.8 Hz, 1H), 3.58 (s, 2H), 3.32-3.50 (m, 2H), 2.94 (d, J = 4.4 Hz, 1H), 2.73 (t, J = 6.4 Hz, 1H), 2.03-2.10 (m, 2H), 1.80-1.89 (m, 1H), 1.63-1.73 (m, 3H), 1.18 (d, J = 7.0 Hz, 3H) | 459.3 |

| Cmpd. No. | Structure | ¹H-NMR | Mass Spec. (M + H)⁺ |
|---|---|---|---|
| 442 | 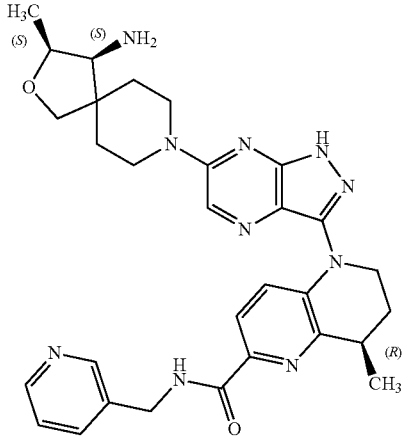 | ¹H-NMR (400 MHz, CD₃OD) δ 8.94 (s, 1H), 8.82 (d, J = 5.6 Hz, 1H), 8.71 (d, J = 7.6 Hz, 1H), 8.34 (s, 1H), 8.05-8.19 (m, 1H), 7.93 (d, J = 8.8 Hz, 1H), 7.67 (d, J = 8.8 Hz, 1H), 4.85 (s, 2H), 4.28-4.54 (m, 3H), 3.98-4.13 (m, 3H), 3.92 (d, J = 9.2 Hz, 1H), 3.74 (d, J = 10.8 Hz, 1H), 3.42-3.53 (m, 2H), 3.12-3.25 (m, 1H), 2.26-2.43 (m, 1H), 2.01-2.18 (m, 1H), 1.84-1.99 (m, 3H), 1.71-1.82 (m, 1H), 1.56 (d, J = 6.8 Hz, 3H), 1.35 (d, J = 7.6 Hz, 3H) | 469.3 |
| 443 | 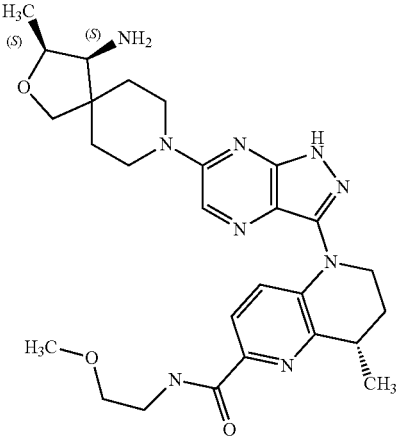 | ¹H-NMR (400 MHz, methanol-d₄) 8.35 (s, 1H), 7.98 (d, J = 8.8 Hz, 1H), 7.90 (d, J = 8.8 Hz, 1H), 4.29-4.51 (m, 3H), 4.00-4.20 (m, 3H), 3.90 (d, J = 9.2 Hz, 1H), 3.56-3.66 (m, 5H), 3.47 (d, J = 4.0 Hz, 1H), 3.38 (s, 3H), 3.32-3.35 (m, 1H), 3.21-3.28 (m, 1H), 2.29-2.41 (m, 1H), 2.08-2.18 (m, 1H), 1.86-1.97 (m, 3H), 1.73-1.81 (m, 1H), 1.55 (d, J = 7.2 Hz, 3H), 1.33 (d, J = 6.4 Hz, 3H) | 536.3 |
| 444 | 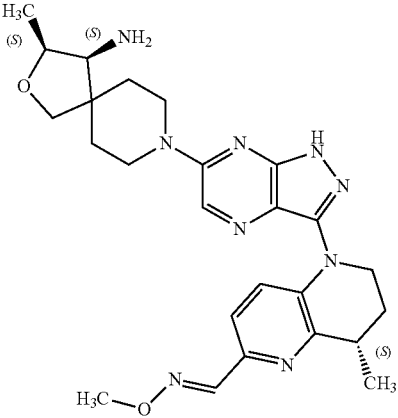 | ¹H-NMR (400 MHz, DMSO-d₆) δ 8.39 (s, 1H), 8.25-8.18 (m, 4H), 7.69 (d, J = 8.8 Hz, 1H), 7.56 (d, J = 8.8 Hz, 1H), 4.24-4.22 (m, 3H), 4.04-3.95 (m, 6H), 3.71-3.68 (m, 1H), 3.40-3.36 (m, 1H), 3.28-3.15 (m, 3H), 2.25-2.18 (m, 1H), 1.94-1.89(m, 1H), 1.84-1.59 (m, 4H), 1.40 (d, J = 7.2 Hz, 3H), 1.24 (d, J = 6.4 Hz, 3H) | 492.3 |

TABLE 1-continued

| Cmpd. No. | Structure | ¹H-NMR | Mass Spec. (M + H)⁺ |
|---|---|---|---|
| 445 | 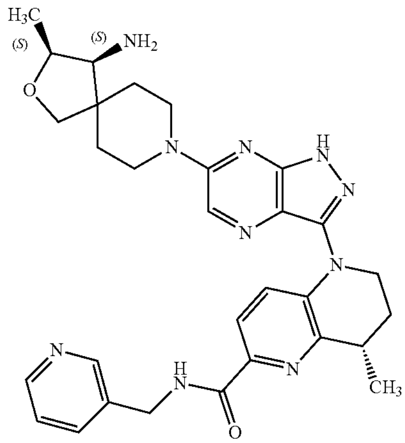 | ¹H-NMR (400 MHz, CD₃OD) δ 8.94 (s, 1H), 8.82 (d, J = 5.6 Hz, 1H), 8.71 (d, J = 7.6 Hz, 1H), 8.34 (s, 1H), 8.05-8.19 (m, 1H), 7.93 (d, J = 8.8 Hz, 1H), 7.67 (d, J = 8.8 Hz, 1H), 4.85 (s, 2H), 4.28-4.54 ( m, 3H), 3.98-4.13 (m, 3H), 3.92 (d, J = 9.2 Hz, 1H), 3.74 (d, J = 10.8 Hz, 1H), 3.42-3.53 (m, 2H), 3.12-3.25 (m, 1H), 2.26-2.43 (m, 1H), 2.01-2.18 (m, 1H), 1.84-1.99 (m, 3H), 1.71-1.82 (m, 1H), 1.56 (d, J = 6.8 Hz, 3H), 1.35 (d, J = 7.6 Hz, 3H) | 569.3 |
| 446 | 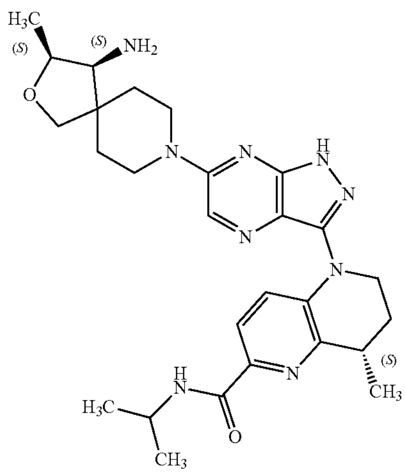 | ¹H-NMR (400 MHz, CD₃OD) δ 8.35 (s, 1H), 8.05-8.02 (m, 1H), 7.99-7.96 (m, 1H), 4.49-4.31 (m, 3H), 4.26-4.16 (m, 2H), 4.11-4.07 (m, 1H), 4.05-4.00 (m, 1H), 3.91-3.89 (m, 1H), 3.69-3.66 (m, 1H), 3.47-3.46 (m, 1H), 3.29-3.23 (m, 2H), 2.39-2.31 (m, 1H), 2.16-2.12 (m, 1H), 1.93-1.87 (m, 3H), 1.78-1.74 (m, 1H), 1.55 (d, J = 7.2 Hz, 3H), 1.33 (d, J = 6.8 Hz, 3H), 1.28 (d, J = 6.4 Hz, 6H) | 520.3 |
| 447 | 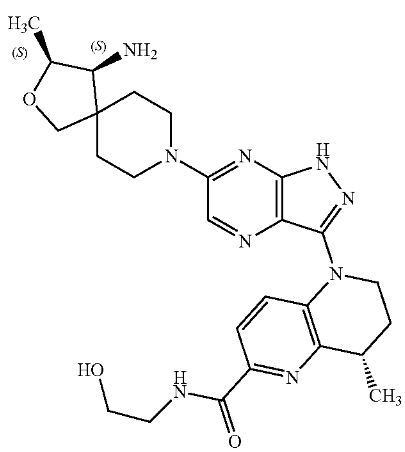 | ¹H-NMR (400 MHz, CD₃OD) δ 8.37 (s, 1H), 7.96-8.04 (m, 2H), 4.32-4.51 (m, 3H), 4.02-4.21 (m, 3H), 3.90-3.93 (m, 1H), 3.67-3.77 (m, 3H), 3.56-3.60 (m, 2H), 3.48-3.50 (m, 1H), 3.24-3.28 (m, 2H), 2.33-2.41 (m, 1H), 2.13-2.18 (m, 1H), 1.89-1.94 (m, 3H), 1.76-1.80 (m, 1H), 1.56-1.58 (m, 3H), 1.34-1.36 (m, 3H) | 522.1 |

TABLE 1-continued

| Cmpd. No. | Structure | ¹H-NMR | Mass Spec. (M + H)⁺ |
|---|---|---|---|
| 448 | 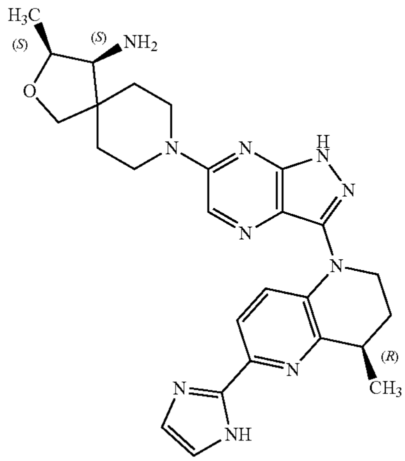 | ¹H-NMR (400 MHz, CD$_3$OD): δ 8.34 (s, 1H), 7.67-7.70 (d, J = 8.8 Hz, 1H), 7.58 (s, 2H), 7.41-7.44 (d, J = 8.8 Hz, 1H), 4.32-4.51 (m, 3H), 4.02-4.10 (m, 3H), 3.90-3.94 (m, 1H), 3.48-3.50 (m, 1H), 3.34-3.36 (m, 1H), 3.21-3.28 (m, 2H), 2.33-2.41 (m, 1H), 2.01-2.05 (m, 1H), 1.89-1.94 (m, 3H), 1.76-1.79 (m, 1H), 1.56-1.59 (m, 3H), 1.34-1.36 (m, 3H) | 501.3 |
| 449 | 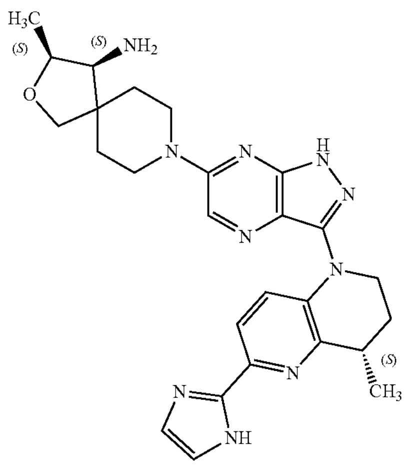 | ¹H-NMR (400 MHz, CD$_3$OD): δ 8.34 (s, 1H), 7.68-7.71 (d, J = 8.8 Hz, 1H), 7.58 (s, 2H), 7.41-7.44 (d, J = 8.8 Hz, 1H), 4.32-4.51 (m, 3H), 4.02-4.10 (m, 3H), 3.90-3.94 (m, 1H), 3.48-3.50 (m, 1H), 3.34-3.36 (m, 1H), 3.21-3.28 (m, 2H), 2.33-2.41 (m, 1H), 2.01-2.05 (m, 1H), 1.89-1.94 (m, 3H), 1.76-1.79 (m, 1H), 1.56-1.59 (m, 3H), 1.34-1.36 (m, 3H) | 501.3 |
| 450 | 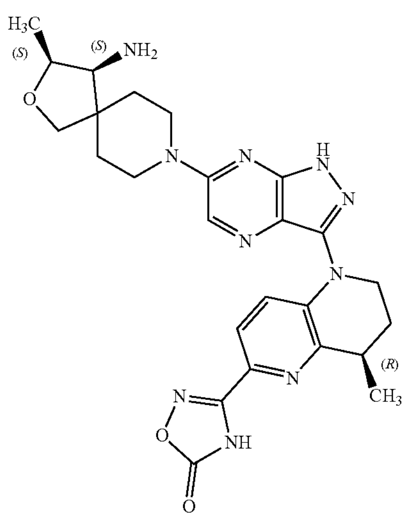 | ¹H-NMR (400 MHz, CDCl$_3$ + CD$_3$OD): δ 8.07 (s, 1H), 7.53-7.60 (d, J = 8.4 Hz, 1H), 7.37-7.40 (d, J = 8.8 Hz, 1H), 4.13-4.16 (m, 1H), 3.93-4.01 (m, 3H), 3.75-3.78 (m, 1H), 3.64-3.67 (m, 1H), 3.41-3.46 (m, 1H), 3.33-3.35 (m, 2H), 3.05-3.10 (m, 1H), 2.92-2.94 (m, 1H), 1.82-1.95 (m, 3H), 1.66-1.70 (m, 3H), 1.39-1.41 (m, 3H), 1.19-1.20 (m, 3H) | 519.3 |

TABLE 1-continued

| Cmpd. No. | Structure | ¹H-NMR | Mass Spec. (M + H)⁺ |
|---|---|---|---|
| 451 | 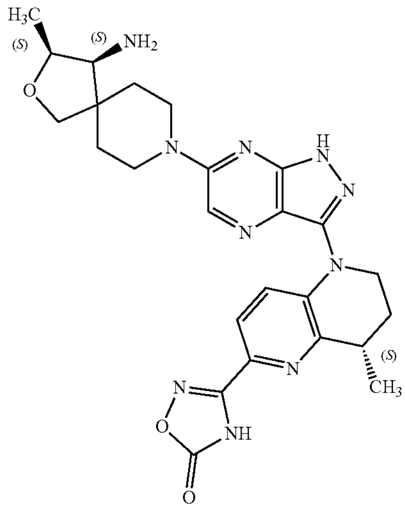 | ¹H-NMR (400 MHz, CDCl₃ + CD₃OD): δ 8.07 (s, 1H), 7.53-7.60 (d, J = 8.4 Hz, 1H), 7.37-7.40 (d, J = 8.8 Hz, 1H), 4.13-4.16 (m, 1H), 3.93-4.01 (m, 3H), 3.75-3.78 (m, 1H), 3.64-3.67 (m, 1H), 3.41-3.46 (m, 1H), 3.33-3.35 (m, 2H), 3.05-3.10 (m, 1H), 2.92-2.94 (m, 1H), 1.82-1.95 (m, 3H), 1.66-1.70 (m, 3H), 1.39-1.41 (m, 3H), 1.19-1.20 (m, 3H) | 519.3 |
| 452 | 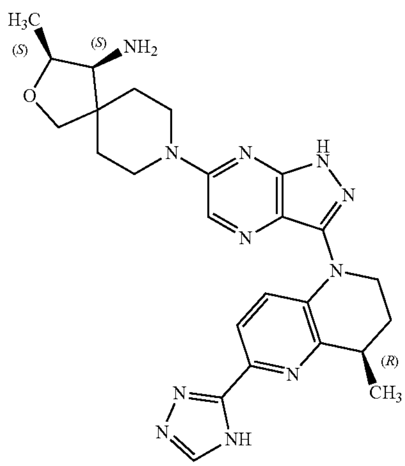 | ¹H-NMR (400 MHz, methanol-d₄): δ 8.91 (s, 1H), 8.37 (s, 1H), 8.07-8.05 (d, J = 8.8 Hz, 1H), 7.94-7.91 (d, J = 8.8 Hz, 1H), 4.51-4.34 (m, 3H), 4.15-4.02 (m, 3H), 3.93-3.90 (m, 1H), 3.60-3.50 (m, 1H), 3.50-3.48 (m, 1H), 3.37 (m, 1H), 3.25-3.20 (m, 1H), 2.40-2.38 (m, 1H), 2.16-2.14 (m, 1H), 1.95-1.92 (m, 3H), 1.75-1.70 (m, 1H), 1.61-1.59 (d, J = 7.2 Hz, 3H), 1.36-1.34 (d, J = 6.4 Hz, 3H) | 502.2 |
| 453 | 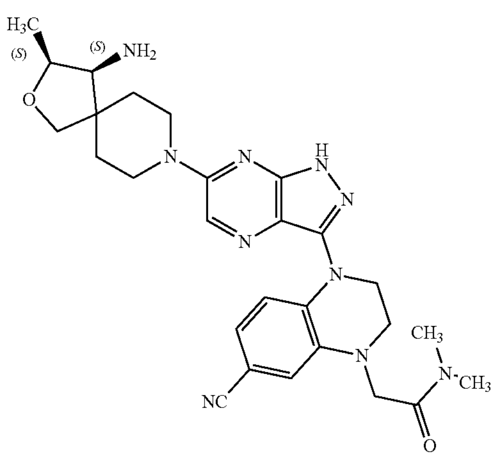 | ¹H-NMR (400 MHz, methanol-d₄) δ 8.22 (s, 1H), 6.91-6.94 (m, 1H), 6.81-6.84 (m, 1H), 6.70-6.72 (m, 1H), 4.34 (s, 2H), 4.24-4.28 (m, 1H), 4.14-4.23 (m, 2H), 4.06-4.09 (m, 2H), 3.89-3.92 (m, 1H), 3.73-3.77 (m, 1H), 3.61-3.64 (m, 2H), 3.37-3.52 (m, 2H), 3.16 (s, 3H), 3.04-3.06 (m, 1H), 3.01 (s, 3H), 1.68-1.91 (m, 4H), 1.23-1.25 (m, 3H) | 531.3 |

TABLE 1-continued

| Cmpd. No. | Structure | ¹H-NMR | Mass Spec. (M + H)⁺ |
|---|---|---|---|
| 454 | 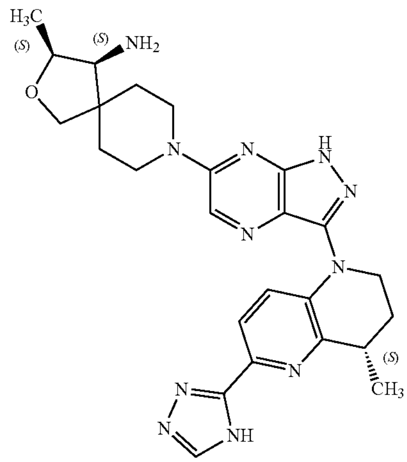 | ¹H-NMR (400 MHz, methanol-d₄) δ 8.90 (s, 1H), 8.37 (s,1H), 8.07-8.04 (d, J = 8.8 Hz, 1H), 7.94-7.91 (d, J = 9.2 Hz, 1H), 4.51-4.34 (m, 3H), 4.15-4.02 (m, 3H), 3.93-3.90 (m, 1H), 3.60-3.50 (m, 1H), 3.50-3.48 (m, 1H), 3.37 (m, 1H), 3.25-3.20 (m, 1H), 2.40-2.38 (m, 1H), 2.16-2.14 (m, 1H), 1.95-1.92 (m, 3H), 1.75-1.70 (m, 1H), 1.61-1.58 (d, J = 6.8 Hz, 3H), 1.36-1.34 (d, J = 6.8 Hz, 3H) | 502.3 |
| 455 | 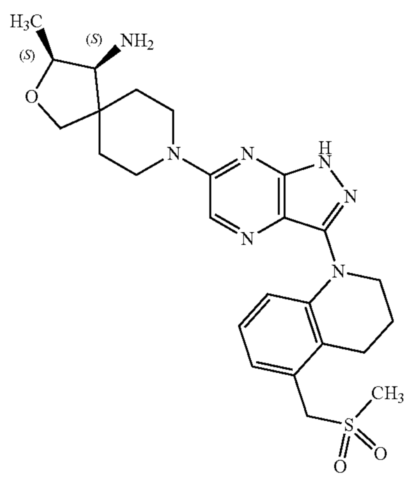 | ¹H-NMR (400 MHz, DMSO-d₆) δ 8.24 (s, 1H) 6.85-6.97 (m, 2H) 6.78 (dd, J = 6.10, 2.69 Hz, 1H) 4.48 (s, 2H) 3.98-4.17 (m, 4H) 3.69-3.88 (m, 4H) 3.56 (br d, J = 8.79 Hz, 1H) 3.20-3.39 (m, 3H) 3.02-3.09 (m, 1H) 2.98 (s, 3H) 2.89 (br t, J = 6.47 Hz, 2H) 1.94 (quin, J = 5.98 Hz, 2H) 1.47-1.80 (m, 5H) 1.11 (d, J = 6.35 Hz, 4H) | 512.2 |
| 456 | 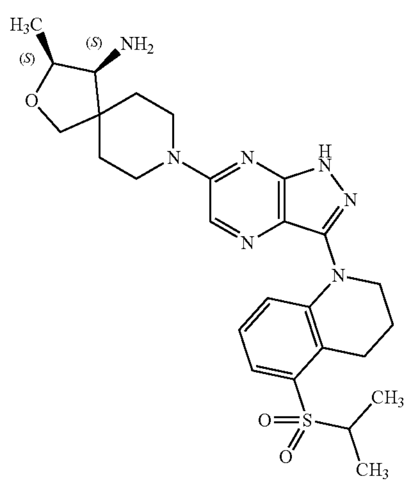 | ¹H-NMR (400 MHz, DMSO-d₆) δ 8.16-8.32 (m, 1H) 7.28 (dd, J = 7.32, 1.46 Hz, 1H) 7.10-7.21 (m, 2H) 4.06-4.22 (m, 3H) 3.76-3.90 (m, 3H) 3.47-3.66 (m, 2H) 3.14-3.37 (m, 6H) 1.94-2.05 (m, 2H) 1.61-1.78 (m, 3H) 1.53 (br d, J = 13.43 Hz, 1H) 1.11-1.23 (m, 9H) | 526.3 |

| Cmpd. No. | Structure | ¹H-NMR | Mass Spec. (M + H)⁺ |
|---|---|---|---|
| 457 | 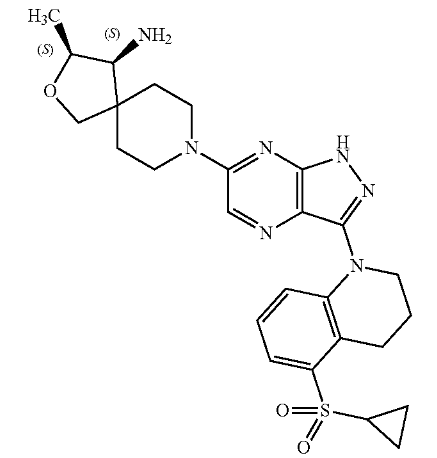 | ¹H-NMR (400 MHz, DMSO-d₆) δ 8.22-8.29 (m, 1H) 7.21-7.31 (m, 1H) 7.05-7.16 (m, 2H) 4.04-4.20 (m, 3H) 3.69-3.89 (m, 4H) 3.18-3.32 (m, 4H) 3.15 (br d, J = 4.88 Hz, 1H) 2.90-3.13 (m, 1H) 1.95-2.06 (m, 2H) 1.59-1.76 (m, 3H) 1.52 (br d, J = 13.18 Hz, 1H) 0.98-1.25 (m, 8H) | 524.2 |
| 458 | 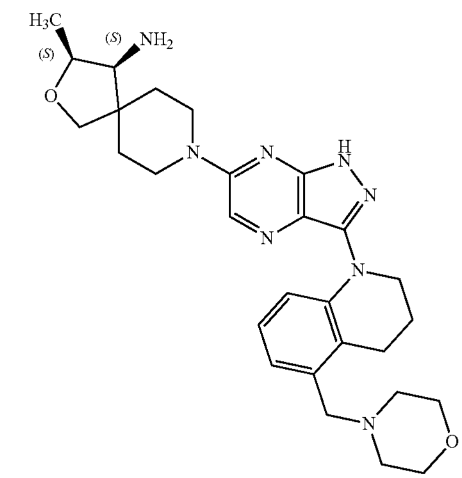 | ¹H-NMR (400 MHz, DMSO-d₆) δ 8.23 (s, 1H) 6.76-6.91 (m, 2H) 6.67 (dd, J = 6.10, 2.44 Hz, 1H) 4.02-4.12 (m, 1H) 3.96 (td, J = 9.09, 5.00 Hz, 2H) 3.74-3.84 (m, 2H) 3.69 (d, J = 8.54 Hz, 1H) 3.25-3.47 (m, 4H) 2.81-2.97 (m, 3H) 2.24-2.39(m, 4H) 1.89-2.01 (m, 2H) 1.60-1.82 (m, 2H) 1.42-1.58 (m, 2H) 1.07 (d, J = 6.35 Hz, 3H) | 519.3 |
| 459 | 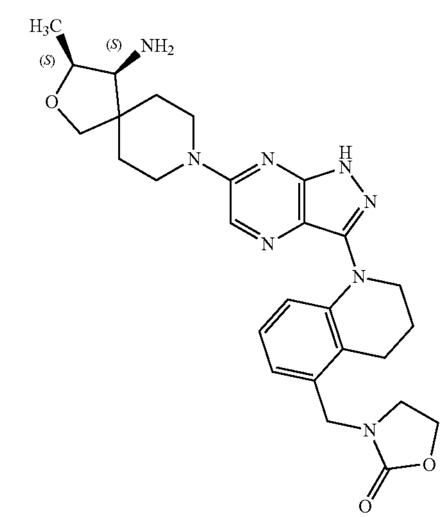 | ¹H-NMR (400 MHz, DMSO-d₆) δ 8.22 (s, 1H) 6.83-6.96 (m, 2H) 6.60 (s, 1H) 4.23-4.35 (m, 5H) 4.05 (quin, J = 6.04 Hz, 1H) 3.92 (br dd, J = 11.11, 6.71 Hz, 3H) 3.64-3.84 (m, 4H) 3.33-3.52 (m, 6H) 2.86 (d, J = 5.13 Hz, 1H) 1.91-2.03 (m, 2H) 1.59-1.76 (m, 3 H) 1.36-1.59 (m, 2H) 1.05 (d, J = 6.35 Hz, 4H) | 519.3 |

TABLE 1-continued

| Cmpd. No. | Structure | ¹H-NMR | Mass Spec. (M + H)⁺ |
|---|---|---|---|
| 460 | 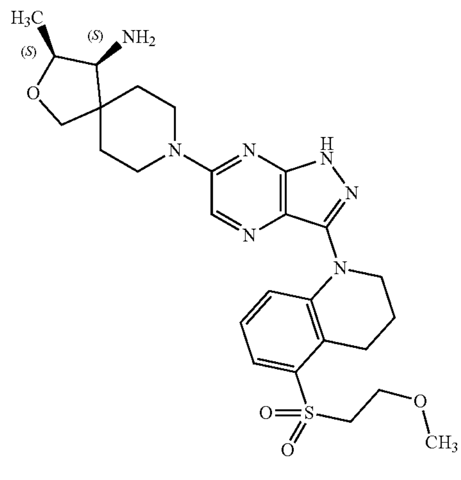 | ¹H-NMR (400 MHz, DMSO-d₆) δ 8.28 (s, 1H) 7.30 (dd, J = 7.08, 1.71 Hz, 1H) 7.08-7.20 (m, 2H) 4.08-4.27 (m, 4H) 3.77-3.91 (m, 4H) 3.61-3.72 (m, 4H) 3.55-3.59 (m, 2H) 3.20-3.30 (m, 3H) 3.14-3.20 (m, 3H) 3.12 (s, 3H) 1.99 (quin, J = 6.04 Hz, 2H) 1.63-1.82 (m, 4H) 1.54 (br d, J = 13.18 Hz, 1H) 1.16 (d, J = 6.35 Hz, 4H) | 542.3 |
| 461 | 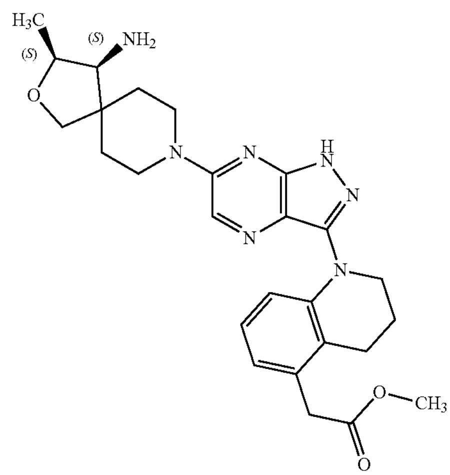 | ¹H-NMR (400 MHz, DMSO-d₆) δ 8.17-8.32 (m, 1H) 6.79-6.89 (m, 2H) 6.62 (dd, J = 5.25, 3.30 Hz, 1H) 4.00-4.21 (m, 3H) 3.76-3.89 (m, 3H) 3.60-3.67 (m, 5H) 3.19-3.35 (m, 2H) 3.12 (d, J = 4.88 Hz, 1H) 2.66 (t, J = 6.47 Hz, 2H) 1.94 (quin, J = 6.04 Hz, 2H) 1.58-1.78 (m, 3H) 1.52 (br d, J = 13.43 Hz, 1H) 1.13 (d, J = 6.59 Hz, 3H) | 492.3 |
| 462 | 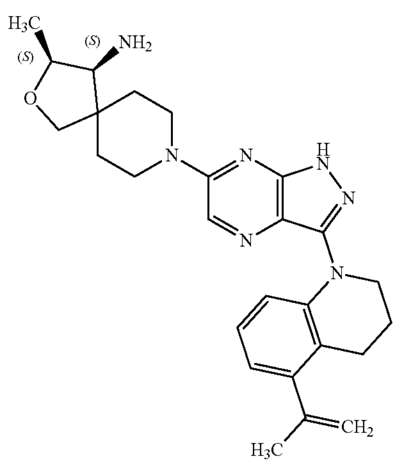 | ¹H-NMR (400 MHz, DMSO-d₆) δ 8.26 (s, 1H), 6.74-6.90 (m, 2H), 6.52 (dd, J = 1.34, 7.20 Hz, 1H), 5.18 (s, 1H), 4.79 (d, J = 0.98 Hz, 1H), 4.06-4.25 (m, 3H), 3.76-3.88 (m, 3H), 3.63 (d, J = 8.79 Hz, 1H), 3.16-3.30 (m, 3H), 2.73 (t, J = 6.35 Hz, 2H), 1.98 (s, 3H), 1.92 (quin, J = 6.10 Hz, 2H), 1.60-1.79 (m, 3H), 1.53 (br d, J = 12.94 Hz, 1H), 1.15 (d, J = 6.35 Hz, 3H) | ND |

TABLE 1-continued

| Cmpd. No. | Structure | ¹H-NMR | Mass Spec. (M + H)⁺ |
|---|---|---|---|
| 463 | 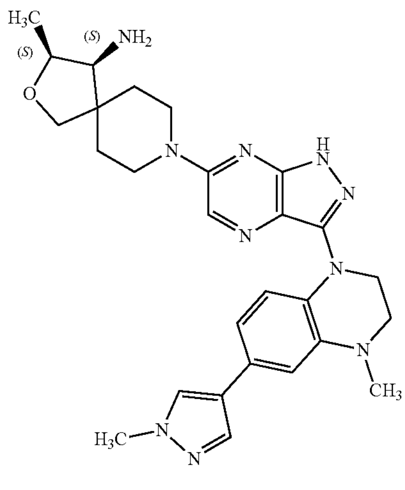 | ¹H-NMR (400 MHz, CD₃OD) δ 8.35 (s, 1H), 8.10 (s, 1H), 7.98 (s, 1H), 7.48-7.42 (m, 2H), 7.27 (d, J = 8.8 Hz, 1H), 4.51-4.27 (m, 5H), 4.05-3.91 (m, 5H), 3.84-3.82 (m, 2H), 3.48 (d, J = 4.4 Hz, 1H), 3.27-3.27 (m, 2H), 1.94-1.76 (m, 4H), 1.35 (d, J = 6.4 Hz, 3H) | 514.2 |
| 464 | 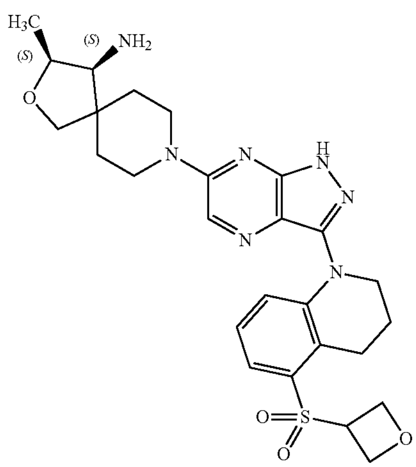 | ¹H-NMR (400 MHz, DMSO-d₆) δ 8.24 (s, 1H), 7.29 (dd, J = 2.08, 6.71 Hz, 1H), 7.04-7.19 (m, 2H), 4.90-5.08 (m, 1H), 4.79 (t, J = 7.45 Hz, 2H), 4.69 (t, J = 6.35 Hz, 2H), 4.04 (quin, J = 6.04 Hz, 1H), 3.85-3.97 (m, 2H), 3.81 (t, J = 5.86 Hz, 2H), 3.66 (d, J = 8.54 Hz, 1H), 3.29-3.50 (m, 3H), 3.11 (t, J = 6.35 Hz, 2H), 2.86 (d, J = 5.37 Hz, 1H), 1.98 (quin, J = 6.04 Hz, 2H), 1.72 (ddd, J = 3.54, 9.52, 13.06 Hz, 1H), 1.58-1.66 (m, 1H), 1.43-1.56 (m, 2H), 1.05 (d, J = 6.59 Hz, 3H) | |
| 465 | 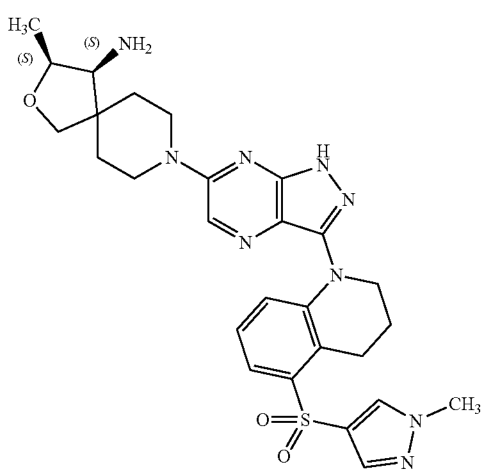 | ¹H-NMR (400 MHz, DMSO-d₆) δ 8.42 (s, 1H), 8.24 (s, 1H), 7.88 (s, 1H), 7.40 (dd, J = 2.44, 6.59 Hz, 1H), 7.05-7.17 (m, 2H), 4.05-4.20 (m, 3H), 3.87 (s, 3H), 3.70-3.83 (m, 3H), 3.60 (br d, J = 8.79 Hz, 2H), 3.14-3.32 (m, 3H), 3.07 (t, J = 6.35 Hz, 2H), 1.86-1.96 (m, 2H), 1.58-1.76 (m, 3H), 1.52 (br d, J = 13.67 Hz, 1H), 1.14 (d, J = 6.59 Hz, 3H) | 564.3 |

TABLE 1-continued

| Cmpd. No. | Structure | ¹H-NMR | Mass Spec. (M + H)⁺ |
|---|---|---|---|
| 466 | 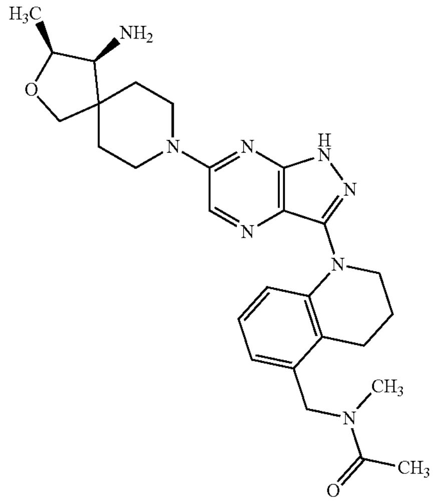 [SMILES: CC(=O)N(C)Cc1cccc2c1CCCN2c1n[nH]c2nc(N3CCC4(CC3)CO[C@@H](C)[C@H]4N)cnc12] | ¹H-NMR (400 MHz, DMSO-d₆) δ 8.18-8.26 (m, 1H), 6.77-6.98 (m, 2H), 6.41 (dd, J = 6.96, 47.00 Hz, 1H), 4.36-4.57 (m, 2H), 3.99-4.19 (m, 3H), 3.68-3.86 (m, 3H), 3.56 (s,1H), 3.18-3.39 (m, 2H), 3.06 (br d, J = 4.64 Hz, 1H), 2.90 (s, 2H), 2.81 (s, 1H), 2.59-2.77 (m, 2H), 2.08 (s, 2H), 1.89-2.09 (m, 2H), 1.42-1.76 (m, 5H), 1.11 (d, J = 6.59 Hz, 3H) | 505.4 |
| 467 | 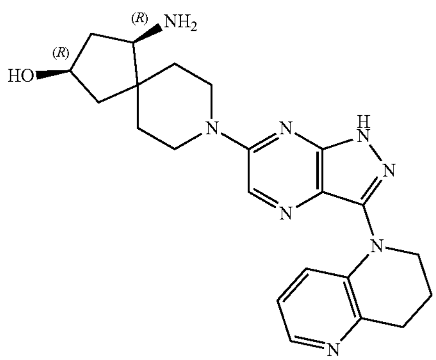 | ¹H-NMR (400 MHz, DMSO-d₆) δ 12.45-12.66 (m, 1H), 8.28 (s, 1H), 7.88 (dd, J = 1.34, 4.52 Hz, 1H), 7.47 (dd, J = 1.22, 8.30 Hz, 1H), 6.95 (dd, J = 4.52, 8.42 Hz, 1H), 4.17-4.34 (m, 2H), 4.08 (td, J = 6.16, 12.09 Hz, 1H), 3.88-3.99 (m, 2H), 3.03-3.20 (m, 2H), 2.92 (t, J = 6.47 Hz, 2H), 2.58-2.68 (m, 1H), 1.99-2.18 (m, 3H), 1.67-1.74 (m, 2H), 1.46-1.66 (m, 3H), 1.34 (ddd, J = 5.86, 8.67, 13.06 Hz, 1H), 1.15 (br d, J = 12.70 Hz, 1H) | 421.2 |
| 468 | 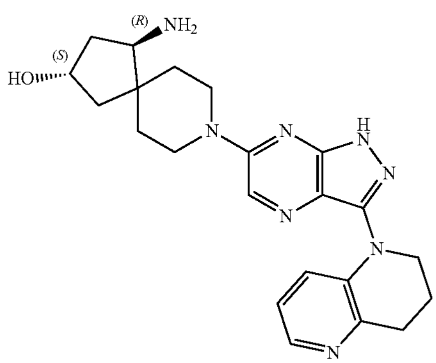 | ¹H-NMR (400 MHz, DMSO-d₆) δ 12.54 (br s, 1H), 8.28 (s, 1H), 7.88 (dd, J = 1.34, 4.52 Hz, 1H), 7.47 (dd, J = 1.34, 8.42 Hz, 1H), 6.95 (dd, J = 4.64, 8.30 Hz, 1H), 4.45 (d, J = 4.15 Hz, 1H), 4.23-4.33 (m, 2H), 4.14 (td, J = 3.42, 6.84 Hz, 1H), 3.90-3.96 (m, 2H), 3.02-3.15 (m, 2H), 2.92 (t, J = 6.59 Hz, 3H), 2.13 (br dd, J = 7.32, 13.67 Hz, 1H), 2.01-2.09 (m, 2H), 1.47-1.77 (m, 5H), 1.28-1.38 (m, 2H), 1.17 (br d, J = 13.18 Hz, 1H) | 421.3 |

TABLE 1-continued

| Cmpd. No. | Structure | ¹H-NMR | Mass Spec. (M + H)+ |
|---|---|---|---|
| 469 | 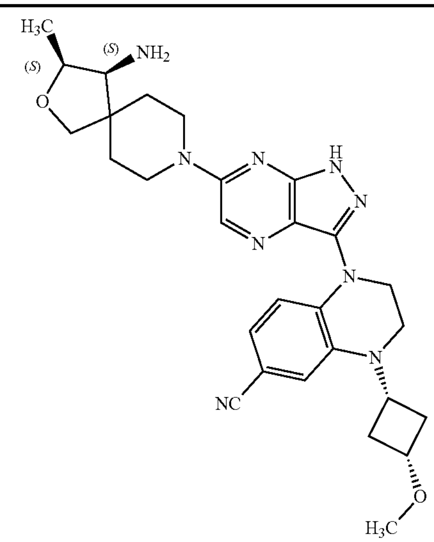 | ¹H-NMR (400 MHz, DMSO-d₆) δ 12.76 (s, 1H), 8.31 (s, 1H), 6.97-7.02 (m, 1H), 6.93 (br dd, J = 1.71, 8.54 Hz, 1H), 6.72 (br d, J = 1.71 Hz, 1H), 4.09-4.18 (m, 1H), 4.02-4.09 (m, 2H), 3.95 (dt, J = 3.30, 6.41 Hz, 2H), 3.68 (br d, J = 8.54 Hz, 1H), 3.49 (br d, J = 8.54 Hz, 1H), 3.37-3.47 (m, 2H), 3.16-3.23 (m, 2H), 2.93 (br d, J = 5.13 Hz, 1H), 2.28-2.41 (m, 4H), 1.72-1.79 (m, 1H), 1.62-1.69 (m, 1H), 1.44-1.59 (m, 3H), 1.00-1.15 (m, 3H) | 530.3 |
| 470 | 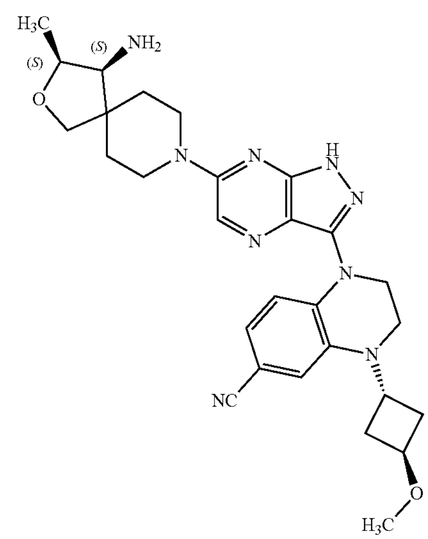 | ¹H-NMR (400 MHz, DMSO-d₆) ☐ 12.75 (s, 1H), 8.31 (s, 1H), 6.95-7.01 (m, 1H), 6.91 (br dd, J = 1.68, 8.39 Hz, 1H), 6.86 (d, J = 1.68 Hz, 1H), 4.00-4.11 (m, 3H), 3.90-4.00 (m, 2H), 3.59-3.74 (m, 3H), 3.45-3.52 (m, 2H), 3.38-3.44 (m, 1H), 3.14-3.20 (m, 2H), 3.19 (s, 1H), 2.93 (br d, J = 5.03 Hz, 1H), 2.65-2.72 (m, 2H), 1.83-1.95 (m, 2H), 1.76 (ddd, J = 3.51, 9.42, 13.31 Hz, 1H), 1.66 (ddd, J = 3.58, 9.11, 13.08 Hz, 1H), 1.46-1.57 (m, 2H), 1.01-1.12 (m, 3H) | 530.2 |
| 471 | 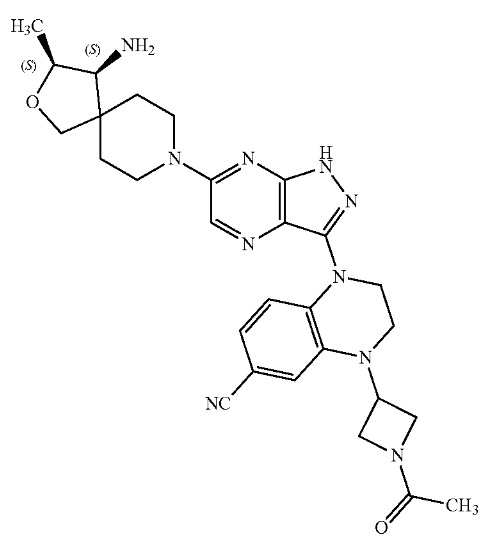 | ¹H-NMR (400 MHz, DMSO-d6) δ 12.81 (br s, 1H), 8.19 (s, 1H), 6.97-7.04 (m, 2H), 6.74 (d, J = 0.98 Hz, 1H), 4.46-4.52 (m, 1H), 4.38-4.45 (m, 1H), 4.14-4.21 (m, 2H), 4.05-4.13 (m, 3H), 3.95-4.04 (m, 2H), 3.92 (br dd, J = 5.25, 10.13 Hz, 1H), 3.71 (d, J = 8.54 Hz, 1H), 3.52 (d, J = 8.54 Hz, 1H), 3.35-3.49 (m, 4H), 3.26-3.34 (m, 2H), 2.98 (d, J = 5.13 Hz, 1H), 1.80 (s, 3H), 1.64-1.78 (m, 2H), 1.46-1.60 (m, 2H), 1.09 (d, J = 6.35 Hz, 3H) | 543.3 |

TABLE 1-continued

| Cmpd. No. | Structure | ¹H-NMR | Mass Spec. (M + H)⁺ |
|---|---|---|---|
| 473 | 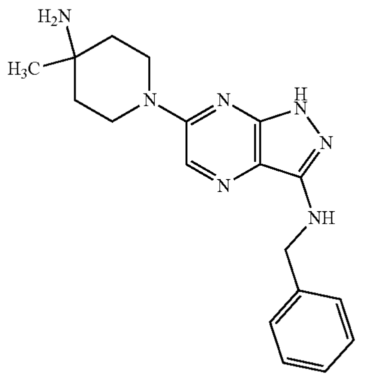 [SMILES: CC1(N)CCN(c2cnc3c(NCc4ccccc4)n[nH]c3n2)CC1] | ¹HNMR(400 MHz, DMSO-d₆): δ 11.51 (br, 1H), 8.11 (s, 1H), 7.38-7.35 (m, 2H), 7.30-7.25 (m, 2H), 7.21-7.18 (m, 1H), 6.48 (m, 1H), 4.48-4.45 (m, 2H), 3.81-3.75 (m, 2H), 3.62-3.57 (m, 2H), 1.46-1.41 (m, 4H), 1.08 (s, 3H) | 338.1 |
| 474 | 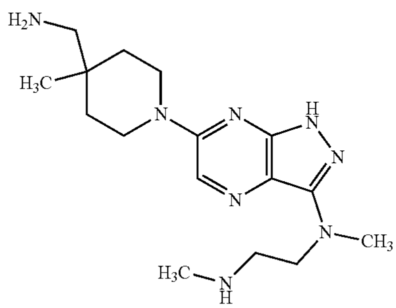 [SMILES: CNCCN(C)c1n[nH]c2nc(N3CCC(C)(CN)CC3)cnc12] | | |
| 475 | 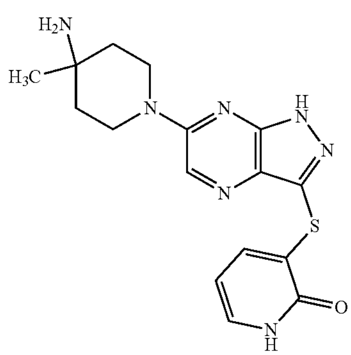 [SMILES: CC1(N)CCN(c2cnc3c(Sc4ccc[nH]c4=O)n[nH]c3n2)CC1] | ¹H NMR (500 MHz, DMSO) δ 8.42 (s, 1H), 8.35 (s, 1H), 7.21 (dd, J = 6.5, 1.9 Hz, 1H), 6.76 (dd, J = 7.1, 1.8 Hz, 1H), 6.05 (dd, J = 7.0, 6.6 Hz, 1H), 3.96 (s, 2H), 3.71-3.62 (m, 2H), 1.70 (s, 4H), 1.25 (s, 3H) | 358.4 |
| 476 | 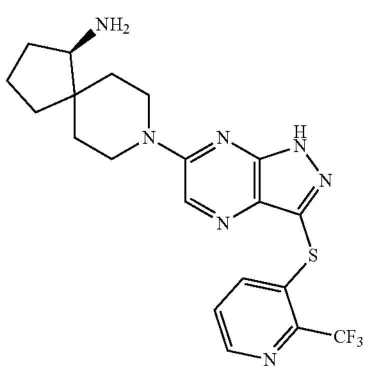 [SMILES: N[C@@H]1CCCC12CCN(c1cnc3c(Sc4cccnc4C(F)(F)F)n[nH]c3n1)CC2] | ¹H NMR (500 MHz, DMSO) δ 8.52-8.40 (m, 1H), 8.37 (s, 1H), 7.50-7.36 (m, 2H), 4.21 (t, J = 15.6 Hz, 2H), 3.16-3.02 (m,2H), 2.76 (t, J = 7.2 Hz, 1H), 1.78 (dd, J = 55.9, 11.0 Hz, 2H), 1.54 (dd, J = 45.7, 9.1 Hz, 4H), 1.29 (ddd, J = 44.0, 38.4, 9.1 Hz, 4H) | 450.2 |

TABLE 1-continued

| Cmpd. No. | Structure | ¹H-NMR | Mass Spec. (M + H)⁺ |
|---|---|---|---|
| 477 | 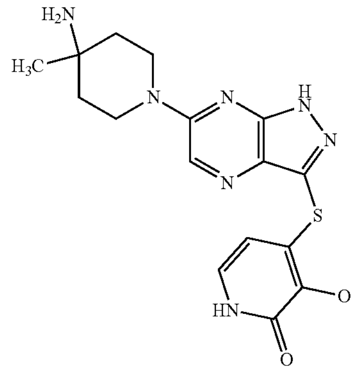 [SMILES: CC1(N)CCN(c2cnc3c(Sc4cc[nH]c(=O)c4O)n[nH]c3n2)CC1] | ¹H-NMR (400 MHz, DMSO) δ 8.47 (s, 1H), 8.31 (s, 1H), 7.11 (d, J = 7.1 Hz, 1H), 5.35 (d, J = 7.1 Hz, 1H), 3.94-3.77 (m, 3H), 3.77-3.61 (m, 3H), 1.60 (t, J = 5.5 Hz, 4H), 1.22 (s, 3H) | 392.2 |
| 478 | 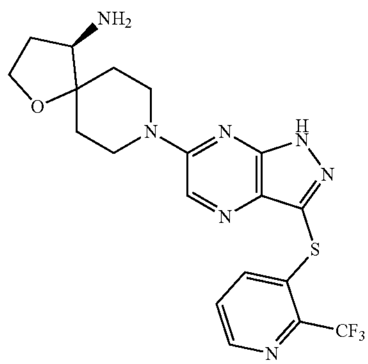 | ¹H NMR (500 MHz, DMSO) δ 8.49 (t, J = 2.9 Hz, 1H), 8.43 (s, 1H), 7.47 (d, J = 3.0 Hz, 2H), 4.38-4.16 (m, 2H), 3.80 (dd, J = 13.6, 8.4 Hz, 1H), 3.68 (dd, J = 15.5, 7.8 Hz, 2H), 3.18-3.13 (m, 2H), 2.16 (dd, J = 12.5, 4.7 Hz, 1H), 1.62 (ddd, J = 44.0, 21.1, 10.5 Hz, 4H), 1.43 (d, J = 13.1 Hz, 1H) | 452.1 |
| 479 | 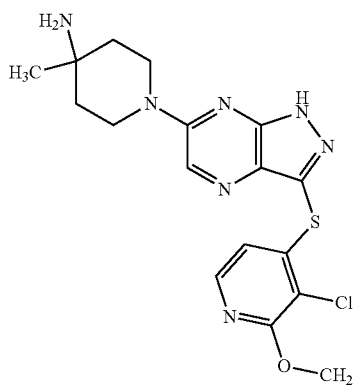 [SMILES: COc1nccc(Sc2n[nH]c3nc(N4CCC(C)(N)CC4)cnc23)c1Cl] | ¹H NMR (500 MHz, DMSO) δ 8.44 (s,1H), 7.77 (d, J = 5.5 Hz, 1H), 6.19 (d, J = 5.5 Hz, 1H), 3.91 (s, 3H), 3.78 (tt, J = 13.9, 7.1 Hz, 4H), 1.56 (t, J = 5.5 Hz, 4H), 1.19 (s, 3H) | 406.1 |
| 480 | 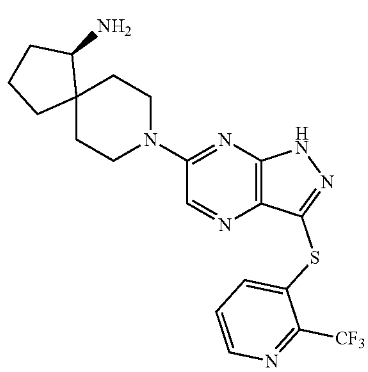 [SMILES: N[C@@H]1CCCC12CCN(c1cnc3c(Sc4cccnc4C(F)(F)F)n[nH]c3n1)CC2] | ¹H NMR (500 MHz, DMSO) δ 8.52-8.40 (m, 1H), 8.37 (s, 1H), 7.50-7.36 (m, 2H), 4.21 (t, J = 15.6 Hz, 2H), 3.16-3.02 (m, 2H), 2.76 (t, J = 7.2 Hz, 1H), 1.78 (dd, J = 55.9, 11.0 Hz, 2H), 1.54 (dd, J = 45.7, 9.1 Hz, 4H), 1.29 (ddd, J = 44.0, 38.4, 9.1 Hz, 4H) | 450.2 |

TABLE 1-continued

| Cmpd. No. | Structure | ¹H-NMR | Mass Spec. (M + H)⁺ |
|---|---|---|---|
| 481 | 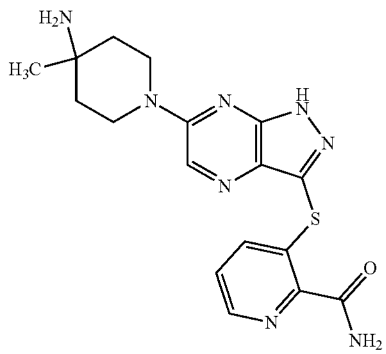 [SMILES: CC1(N)CCN(c2cnc3c(Sc4cccnc4C(N)=O)n[nH]c3n2)CC1] | ¹H-NMR (400 MHz, CD₃OD) δ 8.35~8.33 (m, 1H), 8.31 (s, 1H), 7.22~7.21 (m, 1H), 7.16~7.15 (m, 1H), 4.00~3.94 (m, 2H), 3.80~3.74 (m, 2H), 1.29 (s, 3H) | 385.0 |
| 482 | 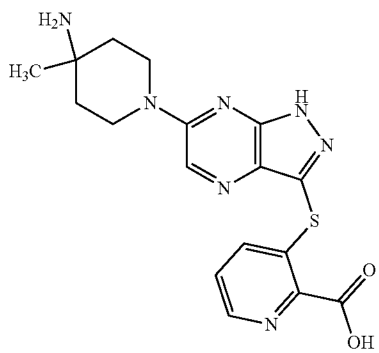 [SMILES: CC1(N)CCN(c2cnc3c(Sc4cccnc4C(=O)O)n[nH]c3n2)CC1] | ¹H-NMR (400 MHz, CD₃OD) δ 8.46~8.44 (m, 1H), 8.39 (s, 1H), 7.47~7.48 (m, 2H), 4.37~4.32 (m, 2H), 3.58~3.52 (m, 2H), 1.93~1.90 (m, 4H), 1.54 (s, 3H) | 386.2 |
| 483 | 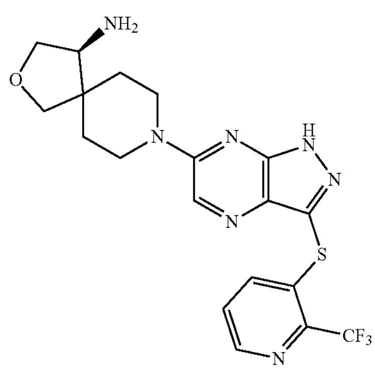 [SMILES: N[C@@H]1COCC12CCN(c1cnc3c(Sc4cccnc4C(F)(F)F)n[nH]c3n1)CC2] | ¹H NMR (400 MHz, DMSO-d6) δ 8.49 (t, J = 3.0 Hz, 1H), 8.44 (s, 1H), 8.15 (s, 1H), 7.48 (d, J = 3.1 Hz, 2H), 4.20-4.06 (m, 2H), 3.97 (dd, J = 9.0, 6.5 Hz, 1H), 3.72-3.63 (m, 2H), 3.38 (dd, J = 9.1, 5.1 Hz, 2H), 3.16 (t, J = 5.6 Hz, 1H), 2.53-2.52 (m, 1H), 1.73-1.56 (m, 2H), 1.52-1.42 (m, 2H) | 452.0 |
| 484 | 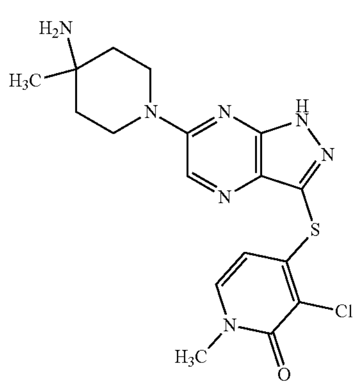 [SMILES: Cn1ccc(Sc2n[nH]c3nc(N4CCC(C)(N)CC4)cnc23)c(Cl)c1=O] | ¹H NMR (500 MHz, DMSO) δ 8.46 (s, 1H), 8.35 (d, J = 27.2 Hz, 1H), 7.43 (t, J = 13.9 Hz, 1H), 5.41 (d, J = 7.3 Hz, 1H), 4.02-3.87 (m, 2H), 3.62 (dt, J = 19.2, 18.2 Hz, 2H), 1.64 (d, J = 4.9 Hz, 4H), 1.23 (s, 3H) | 406.1 |

TABLE 1-continued

| Cmpd. No. | Structure | ¹H-NMR | Mass Spec. (M + H)⁺ |
|---|---|---|---|
| 485 | 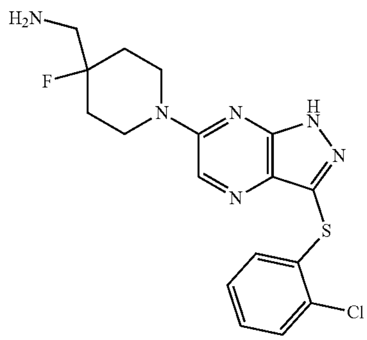 [SMILES: NCC1(F)CCN(c2cnc3c(Sc4ccccc4Cl)n[nH]c3n2)CC1] | ¹H-NMR (400 MHz, DMSO-d₆) δ 8.47 (s, 1H), 7.49 (d, 1 = 7.6 Hz, 1H), 7.19~7.13 (m, 2H), 6.77 (d, J = 8.0 Hz, 1H), 4.34~4.30 (m, 2H), 3.50~3.47 (m, 2H), 2.72~2.67 (m, 2H), 1.89~1.68 (m, 4H) | 393.1 |
| 486 | 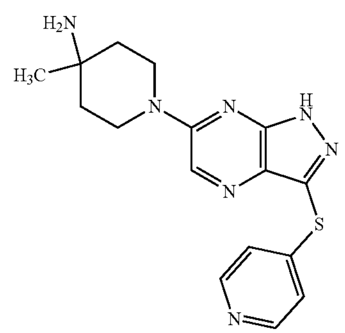 [SMILES: CC1(N)CCN(c2cnc3c(Sc4ccncc4)n[nH]c3n2)CC1] | ¹H-NMR (400 MHz, DMSO-d₆) δ 14.15 (br, 1H), 8.59 (d, J = 6.8 Hz, 2H), 8.53 (s, 1H), 8.36 (br, 2H), 7.66 (d, 1 = 7.2 Hz, 2H), 4.22-4.14 (m, 2H), 3.59-.3.52 (m, 2H), 1.95-1.75 (m, 4H), 1.42 (s, 3H) | 342.0 |
| 488 | 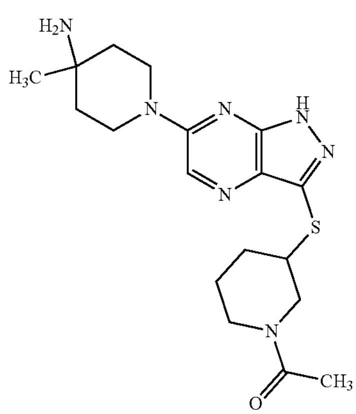 [SMILES: CC(=O)N1CCCC(Sc2n[nH]c3nc(N4CCC(C)(N)CC4)cnc23)C1] | ¹H-NMR (400 MHz, CD₃OD) δ 8.44 (d, J = 18.8 Hz, 1H), 4.37~4.32 (m, 3H), 3.87~3.53 (m, 5H), 3.26~3.21 (m, 1H), 2.24~2.13 (m, 4H), 1.94~1.64 (m, 7H), 1.55 (s, 3H) | 390.1 |
| 489 | 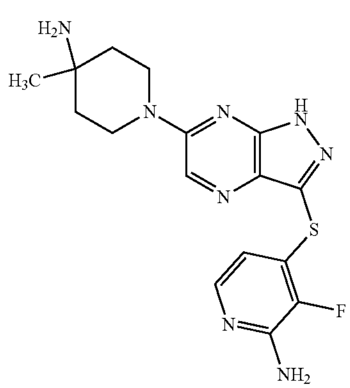 [SMILES: CC1(N)CCN(c2cnc3c(Sc4ccnc(N)c4F)n[nH]c3n2)CC1] | ¹H-NMR (400 MHz, methanol-d₄) δ 8.45 (s, 1H), 7.44~7.42 (m, 1H), 6.26~6.22 (m, 1H), 4.39~4.33 (m, 2H), 3.60~3.53 (m, 2H), 1.95~1.91 (m, 4H), 1.31 (s, 3H) | 375.0 |

TABLE 1-continued

| Cmpd. No. | Structure | ¹H-NMR | Mass Spec. (M + H)⁺ |
|---|---|---|---|
| 491 | 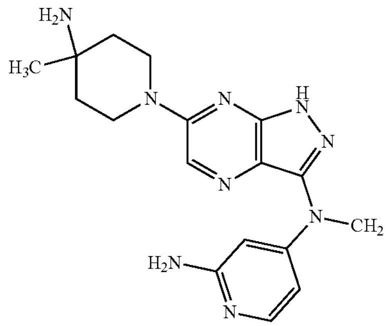 | ¹H-NMR (400 MHz, methanol-d₄) δ 8.29 (s, 1H), 7.58 (d, J = 6 Hz, 1H), 6.24-6.21 (m, 1H), 6.08 (d, J = 2.0 Hz, 1H), 4.01-3.97 (m, 2H), 3.77-3.70 (m, 2H), 3.48 (s, 3H), 1.74-1.68 (m, 4H), 1.31 (s, 3H) | 354.1 |
| 492 | 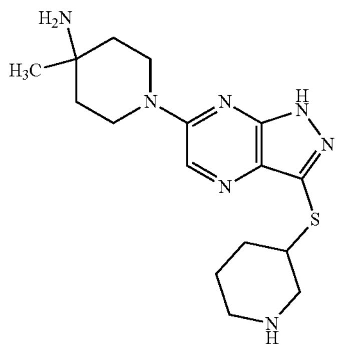 [SMILES: CC1(N)CCN(c2cnc3c(SC4CCCNC4)n[nH]c3n2)CC1] | ¹H-NMR (400 MHz, DMSO-d₆) δ 13.45 (s, 1H), 8.73-8.97 (m, 2H), 8.45 (s, 1H), 8.45 (br, 3H), 4.13-4.18 (m, 2H), 3.58-3.66 (m, 1H), 3.43-3.55 (m, 2H), 2.94-2.98 (m, 1H), 2.90-3.01 (m, 1H), 2.73-2.88 (m, 1H), 2.07-2.09 (m, 1H), 1.65-1.90 (m, 6H), 1.60-1.63 (m, 1H), 1.39 (s, 1H) | 348.1 |
| 493 | 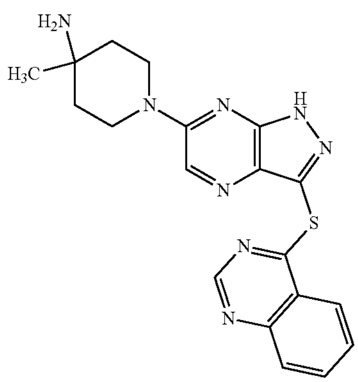 [SMILES: CC1(N)CCN(c2cnc3c(Sc4ncnc5ccccc45)n[nH]c3n2)CC1] | ¹H-NMR (400 MHz, CD₃OD) δ 8.00 (d, J = 6.0 Hz, 1H), 7.96 (s, 1H), 7.90 (d, J = 6.0 Hz, 1H), 3.70-3.76 (m, 2H), 3.52-3.57 (m, 1H), 3.32-3.43 (m, 1H), 2.75 (s, 2H), 2.00-2.10 (m, 1H), 1.85-1.90 (m, 1H), 1.21 (s, 3H) | 406.9 |
| 494 | 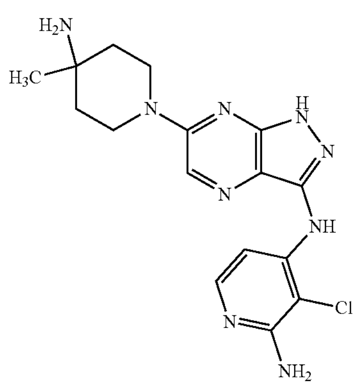 [SMILES: CC1(N)CCN(c2cnc3c(Nc4ccnc(N)c4Cl)n[nH]c3n2)CC1] | ¹H-NMR (400 MHz, DMSO-d₆) δ 8.31 (s, 1H), 7.77 (s, 1H), 7.61-7.64 (d, J = 5.6 Hz, 1H), 6.93-6.95 (d, J = 5.6 Hz, 1H), 5.97 (s, 2H), 3.81-3.87 (m, 2H), 3.61-3.66 (m, 2H), 1.41-1.52 (m, 4H), 1.09 (s, 3H) | 374.0 |

TABLE 1-continued

| Cmpd. No. | Structure | ¹H-NMR | Mass Spec. (M + H)⁺ |
|---|---|---|---|
| 495 | 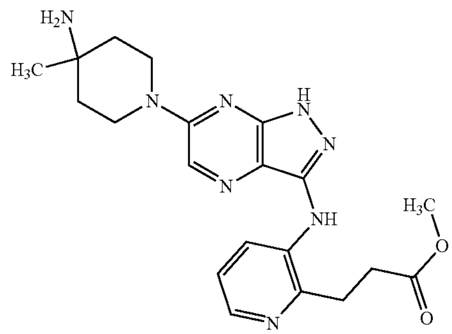 [SMILES: COC(=O)CCc1ncccc1Nc1n[nH]c2nc(N3CCC(C)(N)CC3)cnc12] | ¹H-NMR (400 MHz, methanol-d₄) δ 9.03 (d, J = 8.8 Hz, 1H), 8.38 (s, 1H), 8.23 (d, J = 5.2 Hz, 1H), 7.84-7.80 (m, 1H), 4.38-4.32 (,, 2H), 3.70 (s, 3H), 3.60-3.48 (m, 4H), 3.03-2.97 (m, 2H), 2.00-1.80 (m, 4H), 1.56 (s, 3H) | 411.3 |
| 496 | 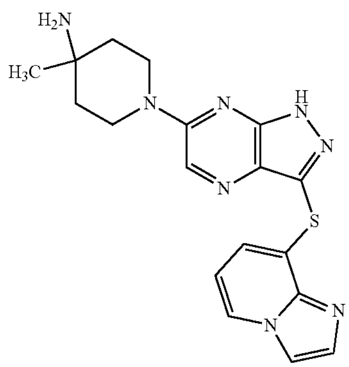 [SMILES: CC1(N)CCN(c2cnc3c(Sc4cccn5ccnc45)n[nH]c3n2)CC1] | ¹H-NMR (400 MHz, DMSO-d₆) δ 8.91~8.88 (m, 1H), 8.52~8.49 (m, 4H), 8.41 (s, 1H), 8.28~8.26 (m, 1H), 7.73~7.70 (m, 1H), 7.43~7.38 (m, 1H), 4.16~4.11 (m, 2H), 3.55~3.49 (m, 2H), 1.87~1.84 (m, 2H), 1.78~1.74 (m, 2H), 1.69 (s, 3H) | 380.0 |
| 497 | 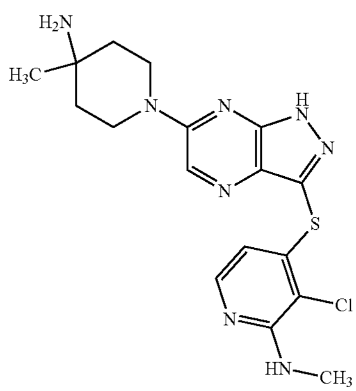 [SMILES: CNc1nccc(Sc2n[nH]c3nc(N4CCC(C)(N)CC4)cnc23)c1Cl] | ¹H-NMR (400 MHz, methanol-d₄) δ 8.46 (s, 1H), 7.53-7.55 (d, J = 7.2 Hz, 1H), 6.20-6.22 (d, J = 7.2 Hz, 1H), 4.34-4.38 (m, 3H), 3.53-3.60 (m, 2H), 3.13 (s, 3H), 1.91-1.95 (m, 4H), 1.55 (s, 3H) | 404.9 |
| 498 | 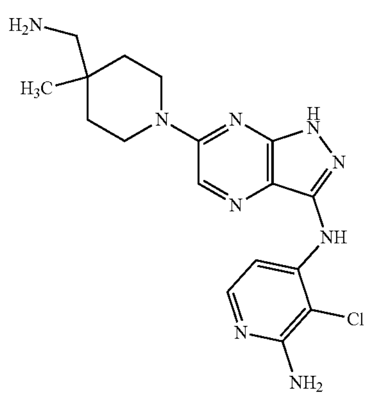 [SMILES: CC1(CN)CCN(c2cnc3c(Nc4ccnc(N)c4Cl)n[nH]c3n2)CC1] | ¹H-NMR (400 MHz, CD₃OD) δ 8.35 (s, 1H), 7.60 (d, J = 7.2 Hz, 1H), 7.10 (d, J = 7.2 Hz, 1H), 4.12-4.18 (m, 2H), 3.53-3.59 (m, 2H), 2.91 (s, 2H), 1.57-1.69 (m, 4H), 1.20 (s, 3H) | 388.0 |

TABLE 1-continued

| Cmpd. No. | Structure | ¹H-NMR | Mass Spec. (M + H)⁺ |
|---|---|---|---|
| 499 | 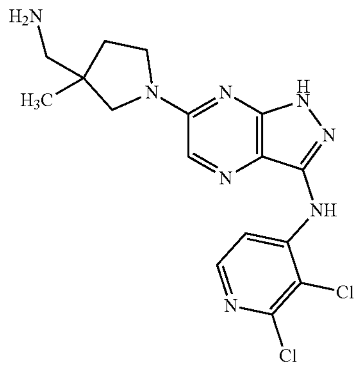 [SMILES: CC1(CN)CCN(c2cnc3c(Nc4ccnc(Cl)c4Cl)n[nH]c3n2)C1] | ¹H-NMR (400 MHz, CD₃OD) δ 8.40 (s, 1H), 8.20 (d, J = 7.2 Hz, 1H), 7.92-7.90 (d, J = 7.2 Hz, 1H), 4.16-4.22 (m, 2H), 3.58-3.65 (m, 2H), 2.95 (s, 2H), 1.60-1.75 (m, 4H), 1.24 (s, 3H) | 392.9 |
| 500 | 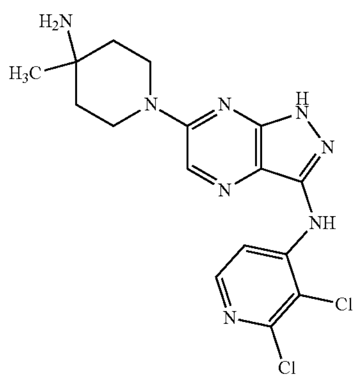 [SMILES: CC1(N)CCN(c2cnc3c(Nc4ccnc(Cl)c4Cl)n[nH]c3n2)CC1] | ¹H-NMR (400 MHz, methanol-d₄) δ 8.40 (s, 1H), 8.20 (d, J = 7.2 Hz, 1H), 7.92-7.90 (d, J = 7.2 Hz, 1H), 4.16-4.22 (m, 2H), 3.58-3.65 (m, 2H), 2.95 (s, 2H), 1.60-1.75 (m, 4H), 1.24 (s, 3H) | 406.9 |
| 501 | 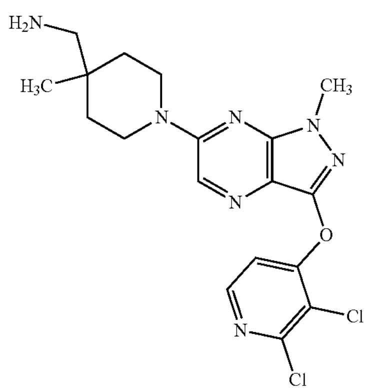 [SMILES: Cn1nc(Oc2ccnc(Cl)c2Cl)c2ncc(N3CCC(C)(CN)CC3)nc21] | ¹H NMR (400 MHz, DMSO-d6) δ ppm 8.39 (s, 1H), 8.24 (d, J = 5.61 Hz, 1H), 7.12-7.30 (m, 1H), 4.02 (dt, J = 13.43, 4.76 Hz, 2H), 3.79 (s, 3H), 3.45-3.58 (m, 2H), 2.53 (s, 2H), 1.51 (ddd, J = 13.37, 9.70, 3.78 Hz, 2H), 1.30-1.42 (m, 2H), 0.98 (s, 3H) | 422.2 |
| 502 | 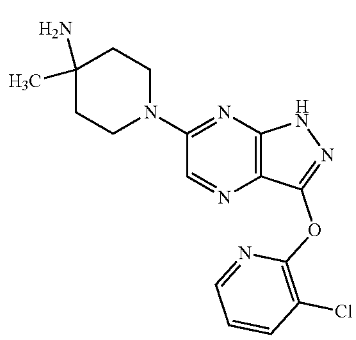 [SMILES: CC1(N)CCN(c2cnc3c(Oc4ncccc4Cl)n[nH]c3n2)CC1] | ¹H-NMR (400 MHz, CD₃OD) δ 8.30 (s, 1H), 8.01-7.96 (m, 2H), 7.21-7.18 (m, 1H), 4.36-4.30 (m, 2H), 3.57-3.50 (m, 2H), 1.93-1.89 (m, 4H), 1.54 (s, 3H) | 360.1 |

TABLE 1-continued

| Cmpd. No. | Structure | ¹H-NMR | Mass Spec. (M + H)⁺ |
|---|---|---|---|
| 503 | 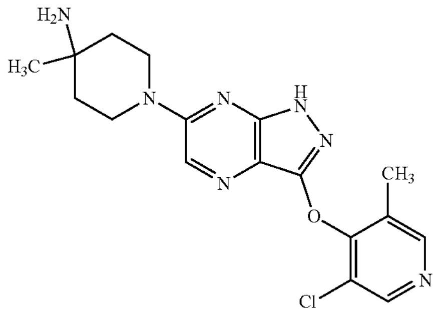 [SMILES: Cc1cncc(Cl)c1Oc1n[nH]c2nc(N3CCC(C)(N)CC3)cnc12] | ¹H-NMR (400 MHz, CD₃OD) δ 9.10 (s, 1H), 8.89 (s, 1H), 8.39 (s, 1H), 4.37-4.33 (m, 2H), 3.59-3.54 (m, 2H), 1.97-1.90 (m, 4H), 1.55 (s, 3H) | 373.9 |
| 504 | 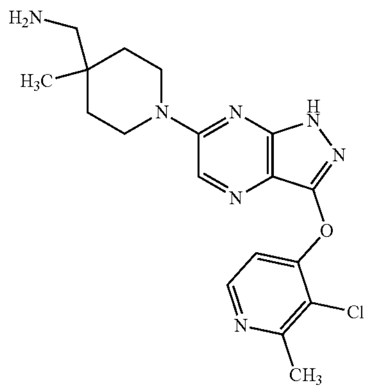 [SMILES: Cc1nccc(Oc2n[nH]c3nc(N4CCC(C)(CN)CC4)cnc23)c1Cl] | ¹H-NMR (400 MHz, CD₃OD) δ 8.57-8.54 (d, J = 6.8 Hz, 1H), 8.38 (s, 1H), 7.63-7.61 (d, J = 6.8 Hz, 1H), 4.22-4.16 (m, 2H), 3.63-3.58 (m, 2H), 2.95 (s, 2H), 2.91 (s, 3H), 1.69-1.63 (m, 4H), 1.24 (s, 3H) | 387.9 |
| 505 | 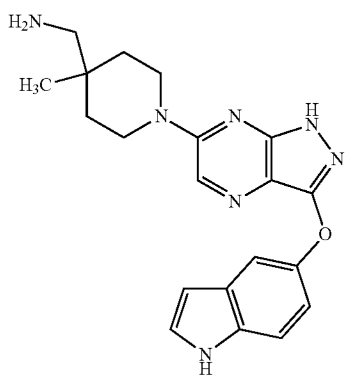 [SMILES: CC1(CN)CCN(c2cnc3c(Oc4ccc5[nH]ccc5c4)n[nH]c3n2)CC1] | ¹H-NMR (400 MHz, DMSO-d₆) δ ppm 12.32 (s, 1H), 11.08 (br s, 1H), 8.27 (s, 1H), 7.27-7.40 (m, 2H), 7.26 (br d, J = 2.20 Hz, 1H), 6.94 (br dd, J = 8.79, 2.20 Hz, 1H), 6.23-6.41 (m, 1H), 3.80-4.00 (m, 2H), 1.27-1.56 (m, 4H), 0.85-1.01 (m, 3H) | |
| 506 | 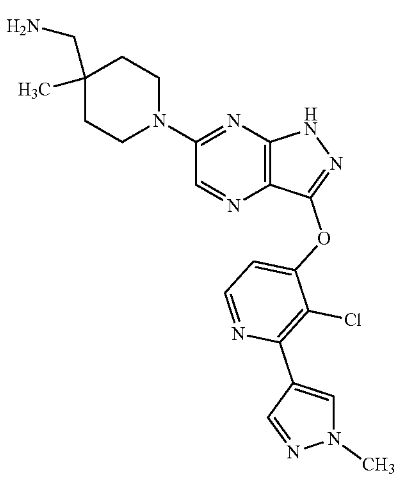 [SMILES: Cn1cc(-c2nccc(Oc3n[nH]c4nc(N5CCC(C)(CN)CC5)cnc34)c2Cl)cn1] | ¹H-NMR (400 MHz, methanol-d₄) δ 8.65 (s, 1H), 8.54-8.52 (d, J = 6.8 Hz, 1H), 8.39 (s, 1H), 8.26 (s, 1H), 7.52-7.50 (d, 1 = 6.8 Hz, 1H), 4.22-4.18 (m, 2H), 4.09 (s, 3H), 3.65-3.58 (m, 2H), 2.95 (s, 2H), 1.69-1.61 (m, 4H), 1.24 (s, 3H) | 454.0 |

TABLE 1-continued

| Cmpd. No. | Structure | ¹H-NMR | Mass Spec. (M + H)⁺ |
|---|---|---|---|
| 507 | 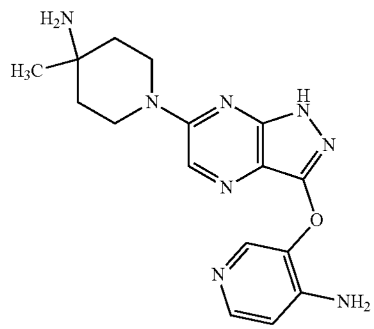 [SMILES: CC1(N)CCN(c2cnc3c(Oc4cnccc4N)n[nH]c3n2)CC1] | ¹H-NMR (400 MHz, CD₃OD) δ 8.63 (s, 1H), 8.45 (s, 1H), 8.04 (d, J = 8.0 Hz, 1H), 7.09 (d, J = 8.0 Hz, 1H), 4.29-4.43 (m, 2H), 3.53-3.63 (m, 2H), 1.93-1.97 (m, 4H), 1.54 (s, 3H) | 340.9 |
| 508 | 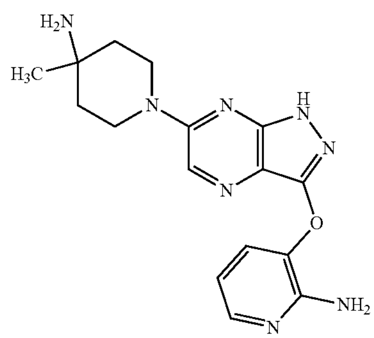 [SMILES: CC1(N)CCN(c2cnc3c(Oc4cccnc4N)n[nH]c3n2)CC1] | ¹H-NMR (400 MHz, CD₃OD) δ 8.40 (s, 1H), 8.08 (d, J = 8.0 Hz, 1H), 7.67 (d, J = 8.0 Hz, 1H), 6.87-6.92 (m, 1H), 4.32-4.36 (m, 2H), 3.52-3.60 (m, 2H), 1.90-2.05 (m, 4H), 1.54 (s, 3H) | 340.0 |
| 509 | 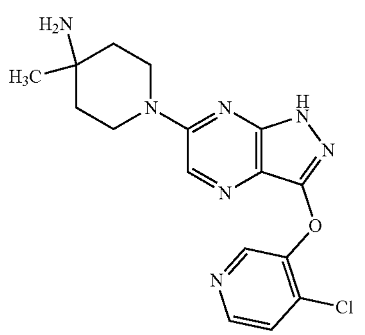 [SMILES: CC1(N)CCN(c2cnc3c(Oc4cnccc4Cl)n[nH]c3n2)CC1] | ¹H-NMR (400 MHz, DMSO-d₆) δ 12.65 (s, 1H), 8.64 (s, 1H), 8.45 (d, J = 5.2 Hz, 1H), 8.41 (s, 1H), 8.33 (s, 3H), 7.80 (d, J = 5.2 Hz, 1H), 4.11-4.16 (m, 2H), 3.48-3.57 (m, 2H), 1.72-1.88 (m, 4H), 1.40 (s, 3H) | 359.9 |
| 510 | 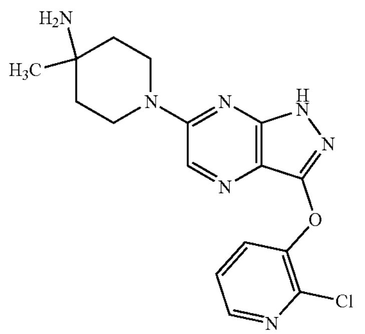 [SMILES: CC1(N)CCN(c2cnc3c(Oc4cccnc4Cl)n[nH]c3n2)CC1] | ¹H-NMR (400 MHz, DMSO-d₆) δ 12.70 (s, 1H), 8.40 (s, 1H), 8.24-8.32 (m, 4H), 7.74-7.78 (m, 1H), 7.43-7.47 (m, 1H), 4.00-4.20 (m, 2H), 3.47-3.55 (m, 2H), 1.74-1.86 (m, 4H), 1.40 (s, 3H) | 360.0 |

TABLE 1-continued

| Cmpd. No. | Structure | ¹H-NMR | Mass Spec. (M + H)⁺ |
|---|---|---|---|
| 511 | 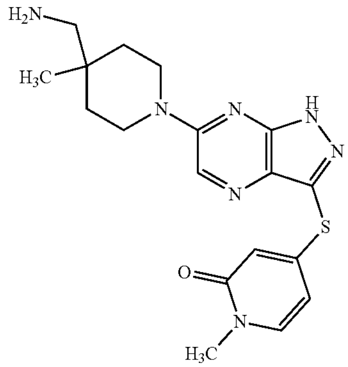 [SMILES: Cn1ccc(Sc2n[nH]c3nc(N4CCC(C)(CN)CC4)cnc23)cc1=O] | ¹H-NMR (400 MHz, DMSO-d₆) δ ppm 8.45 (s, 1H), 8.32 (s, 1H), 7.55 (d, J = 7.32 Hz, 1H), 5.99-6.07 (m, 1H), 5.78 (d, J = 1.95 Hz, 1H), 3.97 (dt, J = 13.43, 4.52 Hz, 2H), 3.42-3.56 (m, 2H), 3.31 (s, 3H), 2.58 (s, 2H), 1.45-1.61 (m, 2H), 1.31-1.43 (m, 2H), 1.00 (s, 3H) | |
| 512 | 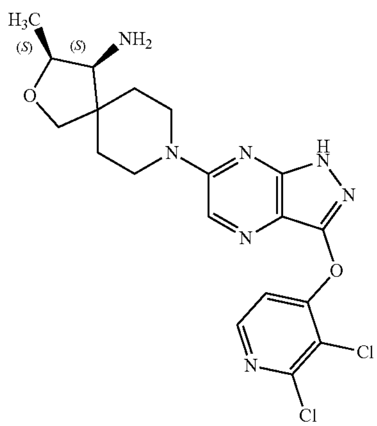 | ¹H-NMR (400MHz, methanol-d₄) δ = 8.35 (s, 1H), 8.18 (d, J = 5.8 Hz, 1H), 7.11 (d, J = 5.5 Hz, 1H), 4.50-4.31 (m, 3H), 4.04 (d, J = 9.3 Hz, 1H), 3.91 (d, J = 9.3 Hz, 1H), 3.48 (d, J = 4.0 Hz, 1H), 3.30-3.22 (m, 1H), 1.94-1.87 (m, 3H), 1.79-1.75 (m, 1H), 1.35 (d, J = 6.5 Hz, 3H) | 449.9 |
| 513 | 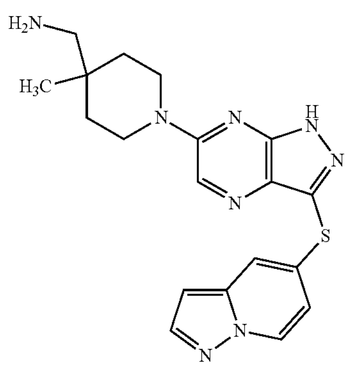 [SMILES: CC1(CN)CCN(c2cnc3c(Sc4ccn5nccc5c4)n[nH]c3n2)CC1] | ¹H-NMR (400 MHz, DMSO-d₆) δ ppm 8.48-8.58 (m, 1H), 8.40 (s, 1H), 8.34 (s, 1H), 7.93 (d, J = 1.95 Hz, 1H), 7.45 (d, J = 1.71 Hz, 1H), 6.66 (dd, J = 7.32, 1.95 Hz, 1H), 6.45 (d, J = 1.95 Hz, 1H), 3.95 (dt, J = 13.43, 4.52 Hz, 2H), 3.41-3.52 (m, 2H), 2.53 (s, 2H), 1.44-1.56 (m, 2H), 1.28-1.41 (m, 2H), 0.98 (s, 3H) | |
| 514 | 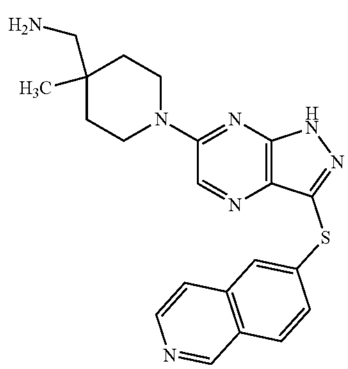 [SMILES: CC1(CN)CCN(c2cnc3c(Sc4ccc5cnccc5c4)n[nH]c3n2)CC1] | ¹H-NMR (400 MHz, DMSO-d₆) δ ppm 9.09-9.31 (m, 1H), 8.42 (d, J = 5.61 Hz, 1H), 8.38 (s, 1H), 8.34 (s, 1H), 7.99 (d, J = 8.79 Hz, 1H), 7.68 (s, 1H), 7.65 (d, J = 5.86 Hz, 1H), 7.44 (dd, J = 8.54, 1.71 Hz, 1H), 3.95 (dt, J = 13.49, 4.61 Hz, 2H), 3.47 (ddd, J = 13.31, 9.77, 3.05 Hz, 2H), 2.57 (s, 2H), 1.46-1.59 (m, 2H), 1.28-1.43 (m, 2H), 0.99 (s, 3H) | |

TABLE 1-continued

| Cmpd. No. | Structure | ¹H-NMR | Mass Spec. (M + H)⁺ |
|---|---|---|---|
| 515 | 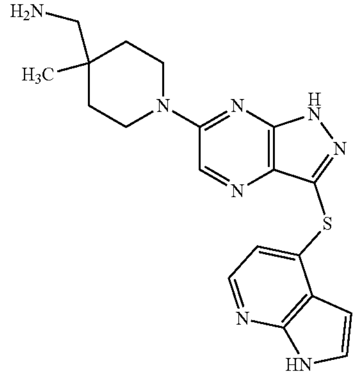 [SMILES: CC1(CN)CCN(c2cnc3c(Sc4ccnc5[nH]ccc45)n[nH]c3n2)CC1] | ¹H-NMR (400 MHz, DMSO-d₆) δ ppm 11.77 (br s, 1H), 8.38 (s, 1H), 8.32 (s, 1H), 7.94 (d, J = 5.13 Hz, 1H), 7.38-7.50 (m, 1H), 6.51 (d, J = 5.13 Hz, 1H), 6.35 (d, J = 3.42 Hz, 1H), 3.87-4.05 (m, 2H), 3.38-3.54 (m, 2H), 2.60 (s, 2H), 1.45-1.59 (m, 2H), 1.32-1.43 (m, 2H), 1.01 (s, 3H) | |
| 516 | 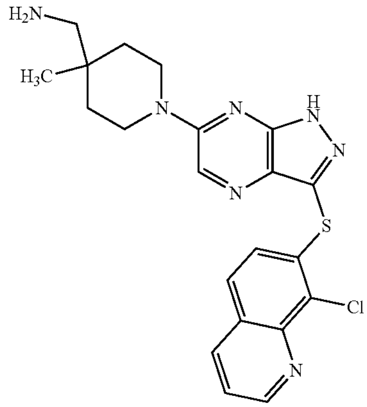 [SMILES: CC1(CN)CCN(c2cnc3c(Sc4ccc5cccnc5c4Cl)n[nH]c3n2)CC1] | ¹H-NMR (400 MHz, DMSO-d₆) δ ppm 8.99 (br dd, J = 4.27, 1.59 Hz, 1H), 8.40 (s, 1H), 8.30-8.37 (m, 2H), 7.73 (d, J = 8.79 Hz, 1H), 7.57 (dd, J = 8.30, 4.15 Hz, 1H), 6.91 (d, J = 8.79 Hz, 1H), 3.96 (dt, J = 13.61, 4.55 Hz, 2H), 3.39-3.58 (m, 2H), 2.54 (s, 2H), 1.43-1.62 (m, 2H), 1.27-1.41 (m, 2H), 0.99 (s, 3H) | |
| 517 | 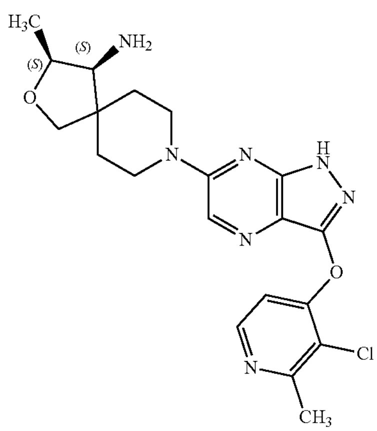 | ¹H-NMR (400 MHz, CD₃OD) δ = 8.54 (d, J = 6.8 Hz, 1H), 8.40 (s, 1H), 7.63 (d, J = 6.8 Hz, 1H), 4.53-4.39 (m, 2H), 4.38-4.29 (m, 1H), 4.08-3.89 (m, 2H), 3.47 (d, J = 4.0 Hz, 1H), 2.90 (s, 3H), 1.97-1.85 (m, 3H), 1.80-1.72 (m, 1H), 1.34 (d, J = 6.5 Hz, 4H) | 430.0 |
| 518 | 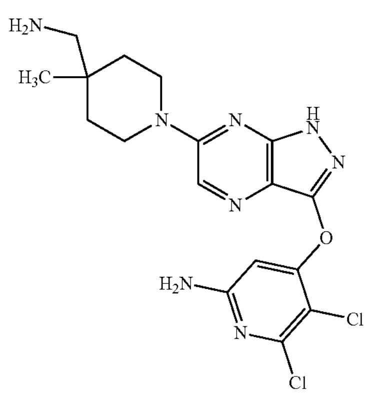 [SMILES: CC1(CN)CCN(c2cnc3c(Oc4cc(N)nc(Cl)c4Cl)n[nH]c3n2)CC1] | ¹HNMR (400 MHz, Methanol-d4): δ 8.34 (s, 1H), 6.24 (s, 1H), 4.19-4.15 (m, 2H), 3.61-3.55 (m, 2H), 2.93 (s, 2H), 1.70-1.60 (m, 4H), 1.23 (s, 3H) | 444.9 |

TABLE 1-continued
| Cmpd. No. | Structure | ¹H-NMR | Mass Spec. (M + H)⁺ |
|---|---|---|---|
| 519 | 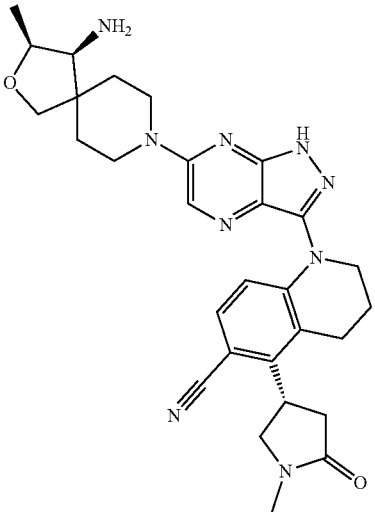 [SMILES: C[C@@H]1OCC2(CCN(c3cnc4c(N5CCCc6c5ccc(C#N)c6[C@@H]5CC(=O)N(C)C5)n[nH]c4n3)CC2)[C@@H]1N] | 1HNMR (400 MHz, MeOD-d4): δ 8.21 (s, 1H), 7.24 (d, J = 8.8 Hz, 1H), 6.61 (d, J = 8.8 Hz, 1H), 4.33-4.12 (m, 4H), 3.91-3.80 (m, 4H), 3.74-3.69 (m, 2H), 3.49-3.35 (m, 2H), 3.01 (d, J = 4.8 Hz, 1H), 2.96-2.86 (m, 6H), 2.78-2.71 (m, 1H), 2.17-2.11 (m, 2H), 1.88-1.65 (m, 4H), 1.21 (d, J = 6.8 Hz, 3H) | 542.5 |
| 520 | 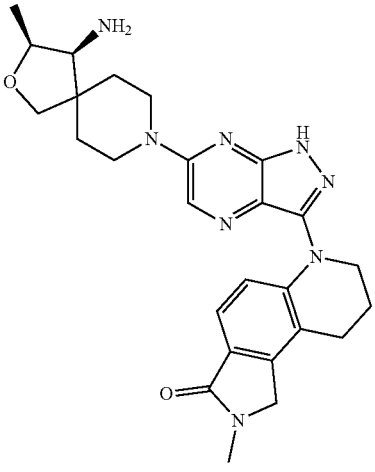 [SMILES: C[C@@H]1OCC2(CCN(c3cnc4c(N5CCCc6c5ccc5c6CN(C)C5=O)n[nH]c4n3)CC2)[C@@H]1N] | 1HNMR (400 MHz, Methanol-d4): δ 8.20 (s, 1H), 7.25 (d, J = 8.8 Hz, 1H), 6.87 (d, J = 8.4 Hz, 1H), 4.39-4.29 (m, 4H), 4.24-4.19 (m, 1H), 3.93-3.90 (m, 3H), 3.80 (d, J = 9.2 Hz, 1H), 3.35 (d, J = 4.0 Hz, 1H), 3.27-3.24 (m, 1H), 3.17-3.12 (m, 1H), 3.09 (s, 3H), 2.79-2.75 (m, 2H), 2.11-2.05 (m, 2H), 1.82-1.75 (m, 3H), 1.67-1.63 (m, 1H), 1.23 (d, J = 6.4 Hz, 3H) | 489.2 |
| 521 | 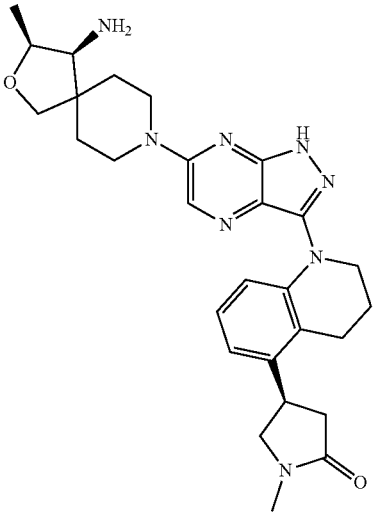 [SMILES: C[C@@H]1OCC2(CCN(c3cnc4c(N5CCCc6c([C@H]7CC(=O)N(C)C7)cccc65)n[nH]c4n3)CC2)[C@@H]1N] | 1HNMR (400 MHz, Methanol-d4): δ 8.34 (s, 1H), 7.16-7.12 (m, 1H), 7.06 (d, J = 7.6 Hz, 1H), 7.00 (d, J = 7.6 Hz, 1H), 4.53-4.43 (m, 2H), 4.37-4.31 (m, 1H), 4.16-4.02 (m, 3H), 3.98-3.87 (m, 3H), 3.51-3.48 (m, 2H), 3.39-3.36 (m, 1H), 3.30-3.27 (m, 1H), 2.93-2.85 (m, 6H), 2.50-2.44 (m, 1H), 2.17-2.11 (m, 2H), 1.93-1.87 (m, 3H), 1.79-1.76 (m, 1H), 1.35 (d, J = 6.4 Hz, 3H) | 517.2 |

TABLE 1-continued

| Cmpd. No. | Structure | ¹H-NMR | Mass Spec. (M + H)⁺ |
|---|---|---|---|
| 522 | 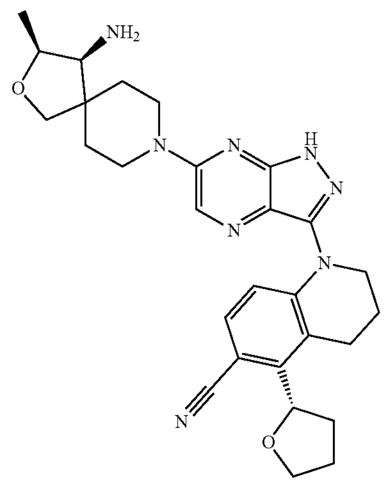 [SMILES: C[C@@H]1OCC2(CCN(c3cnc4c(N5CCCc6c5ccc(C#N)c6[C@@H]5CCCO5)n[nH]c4n3)CC2)[C@@H]1N] | 1HNMR (400 MHz, CD3OD): δ 8.24 (s, 1H), 7.24~7.26 (m, 1H), 6.65~6.68 (m, 1H), 5.28~5.32 (m, 1H), 4.18~4.30 (m, 4H), 3.84~3.98 (m, 4H), 3.74~3.76 (m, 1H), 3.39~3.51 (m, 2H), 2.97-3.05 (m, 2H), 2.83~2.88 (m, 1H), 2.44~2.48 (m, 1H), 2.12~2.23 (m, 4H), 1.68~1.90(m, 5H), 1.23~1.25 (m, 3H) | 515.3 |
| 523 | 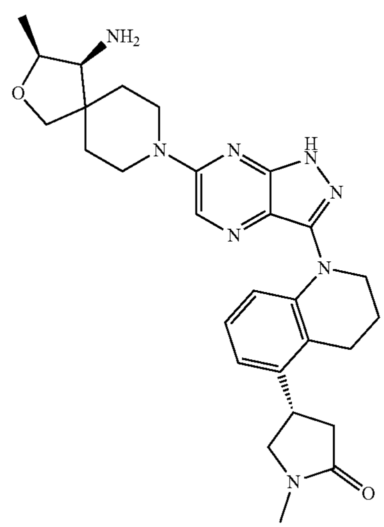 [SMILES: C[C@@H]1OCC2(CCN(c3cnc4c(N5CCCc6c([C@@H]7CC(=O)N(C)C7)cccc65)n[nH]c4n3)CC2)[C@@H]1N] | ¹HNMR (400 MHz, Methanol-d₄): δ 8.41 (s, 1H), 7.23-7.21 (m, 2H), 7.13-7.10 (m, 1H), 4.56-4.46 (m, 2H), 4.37-4.31 (m, 1H), 4.28-4.15 (m, 2H), 4.04 (d, J = 9.2 Hz, 1H), 3.99-3.88 (m, 3H), 3.52-3.48 2H), 3.43-3.37 (m, 1H), 3.31-3.29 (m, 1H), 2.94-2.86 (m, 6H), 2.50-2.44(m, 1H), 2.17-2.11 (m, 2H), 1.95-1.89 (m, 3H), 1.80-1.75 (m, 1H), 1.35 (d, J = 6.8 Hz, 3H) | 517.1 |
| 524 | 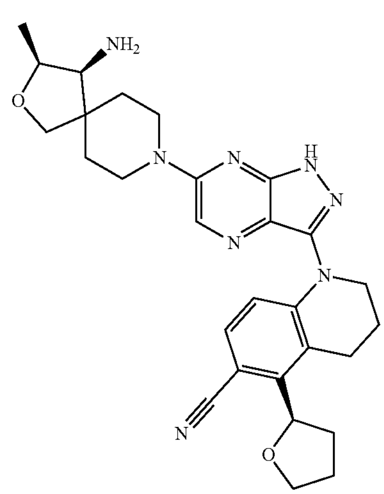 [SMILES: C[C@@H]1OCC2(CCN(c3cnc4c(N5CCCc6c5ccc(C#N)c6[C@H]5CCCO5)n[nH]c4n3)CC2)[C@@H]1N] | 1HNMR (400 MHz, CD3OD): δ 8.11 (s, 1H), 7.11~7.14 (m, 1H), 6.52~6.55 (m, 1H), 5.15~5.19 (m, 1H), 4.02~4.19 (m, 4H), 3.71~3.86 (m, 4H), 3.61~3.63 (m, 1H), 3.28~3.39 (m, 2H), 2.84~2.92 (m, 2H), 2.70~2.75 (m, 1H), 2.31~2.35 (m, 1H), 2.00~2.10 (m, 4H), 1.67~1.78(m, 3H), 1.58~1.63 (m, 2H), 1.11~1.12 (m, 3H) | 515.3 |

TABLE 1-continued

| Cmpd. No. | Structure | ¹H-NMR | Mass Spec. (M + H)⁺ |
|---|---|---|---|
| 525 | 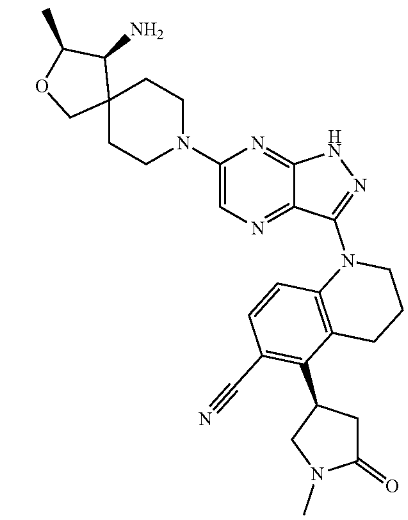 [SMILES: C[C@@H]1OCC2(CCN(c3cnc4c(N5CCCc6c5ccc(C#N)c6[C@H]5CC(=O)N(C)C5)n[nH]c4n3)CC2)[C@@H]1N] | 1HNMR (400 MHz, MeOD-d4): δ 8.21 (s, 1H), 7.24 (d, J = 8.8 Hz, 1H), 6.62 (d, J = 8.8 Hz, 1H), 4.33-4.15 (m, 4H), 3.91-3.81 (m, 4H), 3.74-3.69 (m, 2H), 3.49-3.35 (m, 2H), 3.01 (d, J = 4.8 Hz, 1H), 2.96-2.86 (m, 6H), 2.78-2.72 (m, 1H), 2.17-2.11 (m, 2H), 1.87-1.65 (m, 4H), 1.21 (d, J = 6.0 Hz, 3H) | 542.3 |
| 526 | 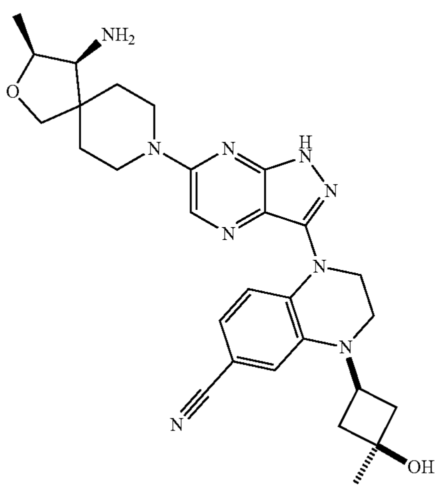 | 1H NMR (400 MHz, DMSO-d6) Shift 12.76 (br s, 1H), 8.31 (s, 1H), 6.94-6.99 (m, 1H), 6.87-6.92 (m, 1H), 6.84 (d, J = 1.71 Hz, 1H), 4.92-5.14 (m, 1H), 4.00-4.10 (m, 3H), 3.90-3.99 (m, 2H), 3.69 (d, J = 8.54 Hz, 1H), 3.53-3.62 (m, 2H), 3.49 (br d, J = 8.54 Hz, 2H), 3.41 (ddd, J = 2.93, 9.95, 13.24 Hz, 2H), 3.25-3.32 (m, 2H), 2.93 (d, J = 5.13 Hz, 1H), 2.36-2.45 (m, 2H), 2.05-2.14 (m, 2H), 1.76 (ddd, J = 3.30, 9.52, 13.06 Hz, 1H), 1.61-1.70 (m, 1H), 1.45-1.59 (m, 2H), 1.33 (s, 3H), 1.08 (d, J = 6.59 Hz, 3H) | 530.2 |
| 527 | 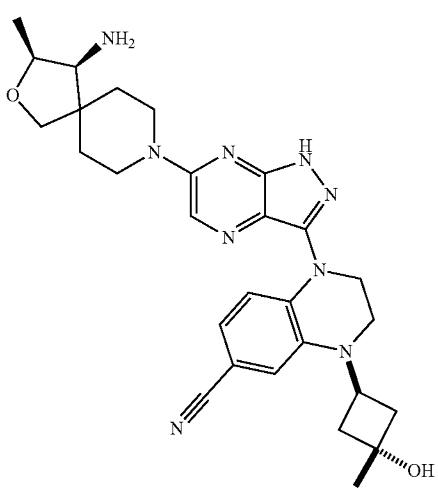 | 1H NMR (400 MHz, DMSO-d6) Shift 12.77 (br s, 1H), 8.31 (s, 1H), 6.96-7.01 (m, 1H), 6.89-6.94 (m, 1H), 6.69 (d, J = 1.71 Hz, 1H), 4.83-5.06 (m, 1H), 4.01-4.10 (m, 4H), 3.91-4.01 (m, 2H), 3.69 (d, J = 8.54 Hz, 1H), 3.50 (br d, J = 8.54 Hz, 2H), 3.36-3.48 (m, 2H), 3.26 (t, J = 5.13 Hz, 2H), 2.94 (d, J = 5.13 Hz, 1H), 2.30-2.38 (m, 2H), 2.03-2.11 (m, 2H), 1.72-1.80 (m, 1H), 1.62-1.71 (m, 1H), 1.46-1.59 (m, 2H), 1.27 (s, 3H), 1.08 (d, J = 6.35 Hz, 3H) | 530.3 |

| Cmpd. No. | Structure | ¹H-NMR | Mass Spec. (M + H)⁺ |
|---|---|---|---|
| 528 | 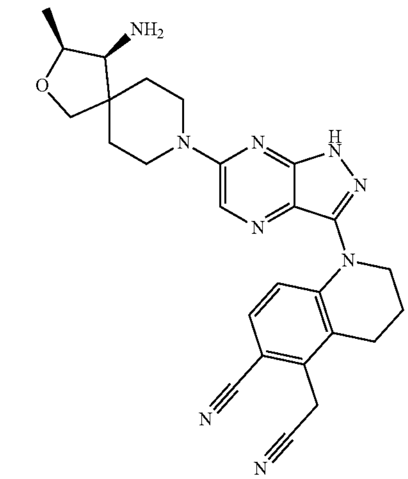 [SMILES: C[C@@H]1OCC2(CCN(c3cnc4c(N5CCCc6c5ccc(C#N)c6CC#N)n[nH]c4n3)CC2)[C@@H]1N] | 1H NMR (400 MHz, DMSO-d6) Shift 12.89 (br s, 1H), 8.33 (s, 1H), 7.36 (d, J = 8.79 Hz, 1H), 6.86 (d, J = 8.79 Hz, 1H), 4.03-4.10 (m, 3H), 3.91-4.01 (m, 2H), 3.81-3.88 (m, 2H), 3.69 (d, J = 8.54 Hz, 1H), 3.49 (br d, J = 8.79 Hz, 2H), 3.38-3.46 (m, 4H), 2.93 (d, J = 5.13 Hz, 1H), 2.89 (br t, J = 6.35 Hz, 2H), 2.53 (s, 1H), 2.03-2.10 (m, 2H), 1.72-1.81 (m, 1H), 1.62-1.70 (m, 1H), 1.46-1.59 (m, 2H), 1.08 (d, J = 6.59 Hz, 3H) | 484.2 |
| 529 | 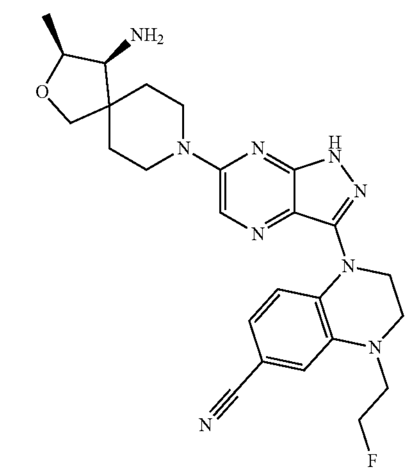 [SMILES: C[C@@H]1OCC2(CCN(c3cnc4c(N5CCN(CCF)c6cc(C#N)ccc65)n[nH]c4n3)CC2)[C@@H]1N] | 1H NMR (400 MHz, DMSO-d6) Shift 12.69 (s, 1H), 8.30 (s, 1H), 6.96-7.06 (m, 2H), 6.84 (dd, J = 1.71, 8.30 Hz, 1H), 4.74 (br t, J = 4.64 Hz, 1H), 4.62 (br t, J = 4.76 Hz, 1H), 4.06 (td, J = 6.23, 11.96 Hz, 1H), 3.88-4.00 (m, 3H), 3.75 (br t, J = 4.64 Hz, 1H), 3.68 (br d, J = 8.54 Hz, 2H), 3.34-3.57 (m, 6H), 2.91 (d, J = 5.13 Hz, 1H), 1.76 (ddd, J = 3.30, 9.34, 13.00 Hz, 1H), 1.61-1.70 (m, 1H), 1.44-1.59 (m, 2H), 1.07 (d, J = 6.35 Hz, 3H) | 492.2 |
| 530 | 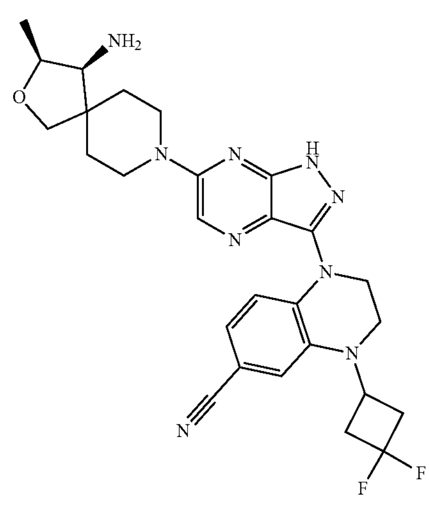 [SMILES: C[C@@H]1OCC2(CCN(c3cnc4c(N5CCN(C6CC(F)(F)C6)c6cc(C#N)ccc65)n[nH]c4n3)CC2)[C@@H]1N] | 1H NMR (500 MHz, DMSO-d6) Shift 12.78 (br s, 1H), 8.31 (s, 1H), 6.96-7.04 (m, 2H), 6.89 (d, J = 1.30 Hz, 1H), 4.03-4.10 (m, 3H), 3.89-3.99 (m, 3H), 3.67 (d, J = 8.56 Hz, 1H), 3.47-3.53 (m, 2H), 3.43 (ddd, J = 3.11, 9.59, 13.23 Hz, 2H), 3.31 (br s, 3H), 3.06-3.14 (m, 2H), 2.90 (d, J = 5.19 Hz, 1H), 2.69-2.82 (m, 2H), 1.76 (ddd, J = 3.37, 9.47, 13.10 Hz, 1H), 1.65 (ddd, J = 3.50, 9.34, 13.10 Hz, 1H), 1.44-1.58 (m, 2H), 1.07 (d, J = 6.48 Hz, 3H) | 536.2 |

TABLE 1-continued

| Cmpd. No. | Structure | ¹H-NMR | Mass Spec. (M + H)⁺ |
|---|---|---|---|
| 531 | 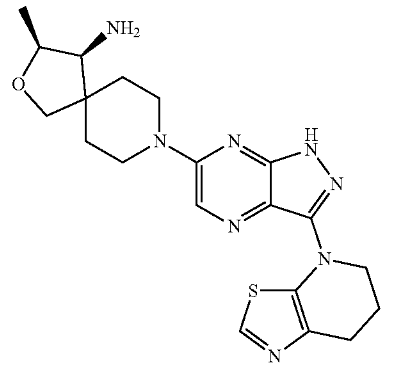 [SMILES: C[C@@H]1OCC2(CCN(c3cnc4c(N5CCCc6ncsc65)n[nH]c4n3)CC2)[C@@H]1N] | 1HNMR (400 MHz, CD3OD): 9.26 (s, 1H), 8.31 (s, 1H), 4.70-4.73 (m, 2H), 4.30-4.50 (m, 3H), 4.04 (d, J = 9.6 Hz, 1H), 3.92 (d, J = 9.6 Hz, 1H), 3.48 (d, J = 4.0 Hz, 1H), 3.20-3.35 (m, 2H), 3.12 (t, J = 6.4 Hz, 2H), 2.30-2.38 (m, 2H), 1.86-1.95 (m, 3H), 1.70-1.80 (m, 1H), 1.35 (d, J = 6.4 Hz, 3H) | 427.2 |
| 532 | 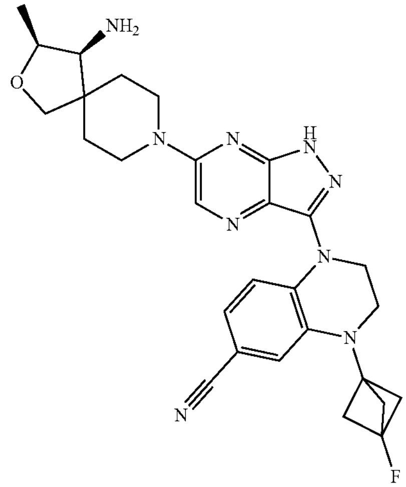 [SMILES: C[C@@H]1OCC2(CCN(c3cnc4c(N5CCN(C67CC(F)(C6)C7)c6cc(C#N)ccc65)n[nH]c4n3)CC2)[C@@H]1N] | 1H NMR (500 MHz, DMSO-d6) Shift 12.76 (s, 1H), 8.27-8.35 (m, 1H), 7.15 (d, J = 1.82 Hz, 1H), 7.03-7.08 (m, 1H), 6.96-7.02 (m, 1H), 4.02-4.09 (m, 1H), 3.85-3.99 (m, 4H), 3.67 (d, J = 8.56 Hz, 1H), 3.37-3.54 (m, 6H), 2.89 (d, J = 5.19 Hz, 1H), 2.50 (d, J = 2.07 Hz, 6H), 1.76 (ddd, J = 3.63, 9.40, 13.16 Hz, 1H), 1.64 (ddd, J = 3.76, 9.21, 13.23 Hz, 1H), 1.44-1.56 (m, 3H), 1.07 (d, J = 6.22 Hz, 3H) | 530.4 |

SHP2 Allosteric Inhibition Assay

SHP2 is allosterically activated through binding of bis-tyrosyl-phorphorylated peptides to its Src Homology 2 (SH2) domains. The latter activation step leads to the release of the auto-inhibitory interface of SHP2, which in turn renders the SHP2 protein tyrosine phosphatase (PTP) active and available for substrate recognition and reaction catalysis. The catalytic activity of SHP2 was monitored using the surrogate substrate DiFMUP in a prompt fluorescence assay format.

The inhibition of SHP2 by compounds of the disclosure (concentrations varying from 0.003-100 μM) was monitored using an assay in which 0.25 nM of SHP2 was incubated with of 0.5 μM of peptide IRS1_pY1172(dPEG8)pY1222 (sequence: H2N-LN(pY)IDLDLV(dPEG8)LST(pY)AS-INFQK-amide) After 30-60 minutes incubation at 25° C., the surrogate substrate DiFMUP (Invitrogen, cat #D6567, 100 μM final) was added to the reaction and the conversion of DiFMUP to 6,8-difluoro-7-hydroxyl-4-methyl coumarin (DiFMU) was monitored continuously for 10 minutes with excitation at 355 nm and emission at 460 nm using a microplate reader (PolarStar, BMG). The inhibitor dose response curves were analyzed using normalized $IC_{50}$ regression curve fitting with control based normalization. $IC_{50}$ results for compounds of the disclosure are shown in examples and Table 2. In Table 2, A means an $IC_{50}$ of less than 1 μM; B means an $IC_{50}$ equal to 1 μM but less than 10 μM; and C means an $IC_{50}$ of 10 μM or more.

TABLE 2

SHP2 IC₅₀ Assay Results

| Cmpd. No. | IC₅₀ | Cmpd. No. | IC₅₀ | Cmpd. No. | IC₅₀ | Cmpd. No. | IC₅₀ |
|---|---|---|---|---|---|---|---|
| 6 | A | 127 | A | 247 | A | 367 | A |
| 7 | A | 128 | A | 248 | A | 368 | A |
| 8 | A | 129 | A | 249 | A | 369 | A |
| 9 | A | 130 | A | 250 | A | 370 | A |
| 10 | A | 131 | A | 251 | A | 371 | A |
| 11 | A | 132 | A | 252 | A | 372 | A |
| 12 | B | 133 | A | 253 | A | 373 | A |
| 13 | A | 134 | A | 254 | A | 374 | A |
| 14 | C | 135 | A | 255 | A | 375 | A |
| 15 | B | 136 | A | 256 | A | 376 | A |
| 16 | A | 137 | A | 257 | A | 377 | A |
| 17 | B | 138 | A | 258 | A | 378 | A |
| 18 | B | 139 | A | 259 | A | 379 | A |
| 19 | B | 140 | C | 260 | A | 380 | A |
| 20 | B | 141 | C | 261 | A | 381 | A |
| 21 | A | 142 | C | 262 | A | 382 | A |
| 22 | A | 143 | C | 263 | A | 383 | A |
| 23 | A | 144 | C | 264 | A | 384 | A |
| 24 | A | 145 | C | 265 | A | 385 | C |
| 25 | A | 146 | C | 266 | A | 386 | A |
| 26 | A | 147 | C | 267 | A | 387 | A |
| 27 | C | 148 | C | 268 | A | 388 | B |
| 28 | A | 149 | C | 269 | A | 389 | A |
| 29 | B | 150 | A | 270 | A | 390 | A |
| 30 | B | 151 | C | 271 | A | 391 | A |
| 31 | A | 152 | C | 272 | A | 392 | A |

TABLE 2-continued

SHP2 IC$_{50}$ Assay Results

| Cmpd. No. | IC$_{50}$ | Cmpd. No. | IC$_{50}$ | Cmpd. No. | IC$_{50}$ | Cmpd. No. | IC$_{50}$ | Cmpd. No. | IC$_{50}$ | Cmpd. No. | IC$_{50}$ | Cmpd. No. | IC$_{50}$ | Cmpd. No. | IC$_{50}$ |
|---|---|---|---|---|---|---|---|---|---|---|---|---|---|---|---|
| 32 | A | 153 | C | 273 | A | 393 | A | 108 | A | 228 | A | 348 | A | 468 | A |
| 33 | A | 154 | C | 274 | A | 394 | A | 109 | B | 229 | A | 349 | A | 469 | A |
| 34 | A | 155 | C | 275 | A | 395 | A | 110 | A | 230 | A | 350 | A | 470 | A |
| 35 | A | 156 | C | 276 | A | 396 | A | 111 | A | 231 | A | 351 | A | 471 | A |
| 36 | B | 157 | B | 277 | A | 397 | A | 112 | A | 232 | A | 352 | A | 472 | B |
| 37 | A | 158 | C | 278 | A | 398 | A | 113 | A | 233 | A | 353 | A | 473 | B |
| 38 | B | 159 | B | 279 | A | 399 | A | 114 | A | 234 | A | 354 | A | 474 | C |
| 39 | B | 160 | C | 280 | A | 400 | A | 115 | A | 235 | A | 355 | A | 475 | B |
| 40 | B | 161 | C | 281 | A | 401 | A | 116 | A | 236 | A | 356 | A | 476 | A |
| 41 | A | 162 | C | 282 | A | 402 | A | 117 | A | 237 | A | 357 | A | 477 | A |
| 42 | B | 163 | A | 283 | A | 403 | A | 118 | A | 238 | A | 358 | C | 478 |   |
| 43 | C | 164 | A | 284 | A | 404 | A | 119 | A | 239 | A | 359 | B | 479 | A |
| 44 | B | 165 | A | 285 | A | 405 | A | 120 | A | 240 | A | 360 | A | 480 | A |
| 45 | A | 166 | A | 286 | A | 406 | A | 121 | A | 241 | A | 361 | A | 481 | A |
| 46 | A | 167 | B | 287 | A | 407 | A | 122 | A | 242 | A | 362 | A | 482 | A |
| 47 | B | 168 | B | 288 | A | 408 | A | 123 | A | 243 | A | 363 | A | 483 | A |
| 48 | A | 169 | A | 289 | A | 409 | A | 124 | A | 244 | A | 364 | A | 484 | A |
| 49 | A | 170 | A | 290 | A | 410 | A | 125 | B | 245 | A | 365 | A | 485 | A |
| 50 | A | 171 | B | 291 | A | 411 | A | 126 | A | 246 | A | 366 | A | 486 | A |
| 51 | A | 172 | A | 292 | A | 412 | A |   |   |   |   |   |   |   |   |
| 52 | A | 173 | A | 293 | A | 413 | A | Cmpd No. | IC$_{50}$ |   |   |   |   |   |   |
| 53 | A | 174 | C | 294 | A | 414 | B |   |   |   |   |   |   |   |   |
| 54 | A | 175 | A | 295 | A | 415 | A |   |   |   |   |   |   |   |   |
| 55 | A | 176 | A | 296 | A | 416 | A | 487 | C |   |   |   |   |   |   |
| 56 | A | 177 | A | 297 | A | 417 | A | 488 | C |   |   |   |   |   |   |
| 57 | A | 178 | B | 298 | A | 418 | A | 489 | A |   |   |   |   |   |   |
| 58 | A | 179 | A | 299 | A | 419 | A | 490 | C |   |   |   |   |   |   |
| 59 | A | 180 | A | 300 | A | 420 | A | 491 | B |   |   |   |   |   |   |
| 60 | A | 181 | A | 301 | A | 421 | A | 492 | C |   |   |   |   |   |   |
| 61 | A | 182 | A | 302 | A | 422 | A | 493 | A |   |   |   |   |   |   |
| 62 | A | 183 | A | 303 | A | 423 | A | 494 | A |   |   |   |   |   |   |
| 63 | A | 184 | A | 304 | A | 424 | A | 495 | B |   |   |   |   |   |   |
| 64 | A | 185 | A | 305 | A | 425 | A | 496 | A |   |   |   |   |   |   |
| 65 | A | 186 | A | 306 | A | 426 | A | 497 | A |   |   |   |   |   |   |
| 66 | A | 187 | A | 307 | A | 427 | A | 498 | A |   |   |   |   |   |   |
| 67 | A | 188 | A | 308 | A | 428 | A | 499 | A |   |   |   |   |   |   |
| 68 | A | 189 | A | 309 | A | 429 | A | 500 | A |   |   |   |   |   |   |
| 69 | A | 190 | A | 310 | A | 430 | A | 501 | C |   |   |   |   |   |   |
| 70 | A | 191 | A | 311 | A | 431 | A | 502 | A |   |   |   |   |   |   |
| 71 | A | 192 | A | 312 | A | 432 | A | 503 | B |   |   |   |   |   |   |
| 72 | A | 193 | A | 313 | B | 433 | A | 504 | A |   |   |   |   |   |   |
| 73 | A | 194 | A | 314 | A | 434 | A | 505 | B |   |   |   |   |   |   |
| 74 | A | 195 | A | 315 | A | 435 | A | 506 | A |   |   |   |   |   |   |
| 75 | A | 196 | A | 316 | A | 436 | A | 507 | C |   |   |   |   |   |   |
| 76 | A | 197 | A | 317 | A | 437 | A | 508 | B |   |   |   |   |   |   |
| 77 | A | 198 | A | 318 | A | 438 | A | 509 | B |   |   |   |   |   |   |
| 78 | A | 199 | A | 319 | A | 439 | A | 510 | A |   |   |   |   |   |   |
| 79 | A | 200 | A | 320 | A | 440 | A | 511 | A |   |   |   |   |   |   |
| 80 | A | 201 | C | 321 | A | 441 | A | 512 | A |   |   |   |   |   |   |
| 81 | A | 202 | A | 322 | B | 442 | A | 513 | A |   |   |   |   |   |   |
| 82 | A | 203 | B | 323 | A | 443 | A | 514 | A |   |   |   |   |   |   |
| 83 | A | 204 | B | 324 | A | 444 | A | 515 | A |   |   |   |   |   |   |
| 84 | A | 205 | B | 325 | A | 445 | A | 516 | A |   |   |   |   |   |   |
| 85 | A | 206 | B | 326 | A | 446 | A | 517 | A |   |   |   |   |   |   |
| 86 | A | 207 | A | 327 | A | 447 | A | 518 | A |   |   |   |   |   |   |
| 87 | A | 208 | A | 328 | A | 448 | A | 519 | A |   |   |   |   |   |   |
| 88 | A | 209 | A | 329 | A | 449 | A | 510 | A |   |   |   |   |   |   |
| 89 | A | 210 | B | 330 | A | 450 | A | 521 | A |   |   |   |   |   |   |
| 90 | B | 211 | A | 331 | A | 451 | A | 522 | A |   |   |   |   |   |   |
| 91 | A | 212 | A | 332 | A | 452 | A | 523 | A |   |   |   |   |   |   |
| 92 | A | 213 | A | 333 | A | 453 | A | 524 | A |   |   |   |   |   |   |
| 93 | A | 214 | A | 334 | A | 454 | A | 525 | A |   |   |   |   |   |   |
| 94 | A | 215 | B | 335 | A | 455 | A | 526 | A |   |   |   |   |   |   |
| 95 | C | 216 | A | 336 | A | 456 | A | 527 | A |   |   |   |   |   |   |
| 96 | A | 217 | A | 337 | A | 457 | A | 528 | A |   |   |   |   |   |   |
| 97 | A | 218 | A | 338 | A | 458 | A | 529 | A |   |   |   |   |   |   |
| 98 | A | 219 | A | 339 | A | 459 | A | 530 | A |   |   |   |   |   |   |
| 99 | A | 220 | A | 340 | A | 460 | A | 531 | A |   |   |   |   |   |   |
| 100 | A | 221 | A | 341 | A | 461 | A | 532 | A |   |   |   |   |   |   |
| 101 | A | 222 | B | 342 | A | 462 | A |   |   |   |   |   |   |   |   |
| 102 | A | 223 | A | 343 | A | 463 | A |   |   |   |   |   |   |   |   |
| 103 | A | 224 | A | 344 | A | 464 | A |   |   |   |   |   |   |   |   |
| 104 | A | 225 | A | 345 | A | 465 | A |   |   |   |   |   |   |   |   |
| 106 | A | 226 | A | 346 | A | 466 | A |   |   |   |   |   |   |   |   |
| 107 | A | 227 | A | 347 | A | 467 | A |   |   |   |   |   |   |   |   |

INCORPORATION BY REFERENCE

All publications and patents mentioned herein are hereby incorporated by reference in their entirety for all purposes as if each individual publication or patent was specifically and individually incorporated by reference. In case of conflict, the present application, including any definitions herein, will control.

EQUIVALENTS

While specific embodiments of the subject disclosure have been discussed, the above specification is illustrative and not restrictive. Many variations of the present disclosure will become apparent to those skilled in the art upon review of this specification. The full scope of the disclosure should be determined by reference to the claims, along with their full scope of equivalents, and the specification, along with such variations.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in this specification and attached claims are approximations that may vary depending upon the desired properties sought to be obtained by the present disclosure.

What is claimed is:
1. A compound of Formula (I):

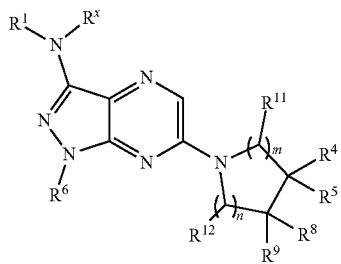

or a pharmaceutically acceptable salt or stereoisomer thereof,
wherein:
$R^x$ and $R^1$ together with the nitrogen atom to which they are attached, form a monocyclic, bicyclic, or tricyclic nitrogen-containing ring system selected from the group consisting of:
(a) a 4- to 7-membered heterocyclyl;
(b) a monocyclic 5- to 7-membered heteroaryl;
(c) a bicyclic 8- to 14-membered heteroaryl; and
(d) a tricyclic 11- to 15-membered heteroaryl;
  wherein the 4- to 7-membered heterocyclyl, monocyclic 5- to 7-membered heteroaryl, bicyclic 8- to 14-membered heteroaryl, or tricyclic 11- to 15-membered heteroaryl is optionally substituted with one or more substituents independently selected from the group consisting of halogen, CN, $NO_2$, $C_{1-3}$ haloalkyl, $C_{1-6}$ alkylene-S(O)$_w$—$C_{1-3}$ alkyl, C(NOR$^a$)H, C(NOR$^a$)C$_{1-3}$ alkyl, C(O)R$^{10}$, C(O)N(R$^{10}$)$_2$, C(O)OR$^{10}$, N(R$^{10}$)$_2$, NR$^a$C(O)R$^{10}$, NR$^a$S(O)$_w$R$^{10}$, NR$^a$S(O)(NR$^a$)C$_{1-3}$ alkyl, N=[S(O)(C$_{1-3}$ alkyl)$_2$], N[S(O)$_2$C$_{1-3}$ alkyl]$_2$, OR$^{10}$, =O, OS(O)$^w$R$^{10}$, P(O)(R$^{10}$)$_2$, S(O)$^w$R$^{10}$, S(O)$_w$N(R$^{10}$)$_2$, heterocyclyl, heteroaryl, and R$^{10}$;
  wherein each heterocyclyl substituent is optionally and independently substituted with one, two, or three substituents independently selected from the group consisting of halogen, $C_{1-3}$ alkyl, $C_{1-3}$ haloalkyl, and =O;
  wherein when $R^{10}$ is phenyl, each phenyl substituent is optionally and independently substituted with one, two, or three substituents independently selected from the group consisting of halogen, $C_{1-3}$ alkyl, $C_{1-3}$ haloalkyl, and O-phenyl; and
  wherein each heteroaryl substituent is optionally and independently substituted with one, two, or three substituents independently selected from the group consisting of halogen, $C_{1-3}$ alkyl, $C_{1-3}$ haloalkyl, $C_{1-3}$ alkylOH, $C_{1-3}$ alkylOC$_{1-3}$ alkyl, and C(O)N(R$^{10}$)$_2$;
$R^4$ is hydrogen, halogen, CN, $C_{1-6}$ alkyl, $C_{1-6}$ alkylN(R$^6$)$_2$, $C_{1-6}$ alkylOR$^6$, C(O)N(R$^6$)$_2$, N(R$^6$)$_2$, OH, or OC$_{1-6}$ alkyl, wherein the $C_{1-6}$ alkyl, $C_{1-6}$ alkylN(R$^6$)$_2$, $C_{1-6}$ alkylOR$^6$, or OC$_{1-6}$ alkyl is optionally substituted with one or more substituents independently selected from the group consisting of halogen, $NH_2$, OH, and =O;
$R^5$ is hydrogen, halogen, CN, $C_{1-6}$ alkyl, $C_{1-6}$ alkylN(R$^6$)$_2$, $C_{1-6}$ alkylOR$^6$, C(O)N(R$^6$)$_2$, N(R$^6$)$_2$, OH, or OC$_{1-6}$ alkyl, wherein the $C_{1-6}$ alkyl, $C_{1-6}$ alkylN(R$^6$)$_2$, $C_{1-6}$ alkylOR$^6$, or OC$_{1-6}$ alkyl is optionally substituted with one or more substituents independently selected from the group consisting of halogen, $NH_2$, OH, and =O; or
$R^4$ and $R^5$, together with the carbon atom to which they are attached, form a saturated or partially unsaturated 3- to 7-membered carbocyclic or heterocyclic ring, wherein the 3- to 7-membered carbocyclic or heterocyclic ring is optionally substituted with one or more substituents independently selected from the group consisting of halogen, CN, $C_{1-6}$ alkyl, N(R$^6$)$_2$, OH, OC$_{1-6}$ alkyl, and =O;
$R^8$ is hydrogen, halogen, CN, $C_{1-6}$ alkyl, $C_{1-6}$ alkylN(R$^6$)$_2$, $C_{1-6}$ alkylOR$^6$, C(O)NH$_2$, N(R$^6$)$_2$, or OR$^6$: or
$R^4$ and $R^8$, together with the carbon atoms to which they are attached, form a 3- to 7-membered carbocyclic or heterocyclic ring, wherein the 3- to 7-membered carbocyclic or heterocyclic ring is optionally substituted with one or more substituents independently selected from the group consisting of halogen, CN, $C_{1-6}$ alkyl, N(R$^6$)$_2$, OH, OC$_{1-6}$ alkyl, and =O;
$R^9$ is hydrogen, halogen, CN, $C_{1-6}$ alkyl, $C_{1-6}$ alkylN(R$^6$)$_2$, $C_{1-6}$ alkylOR$^6$, C(O)NH$_2$, N(R$^6$)$_2$, or OR$^6$;
each $R^{10}$ is independently hydrogen, $C_{1-6}$ alkyl, $C_{2-6}$ heteroalkyl, $C_{2-6}$ alkenyl, $C_{2-6}$ alkynyl, P(O)(R$^{20}$)$_2$, $C_{3-6}$ cycloalkyl, $C_{5-6}$ cycloalkenyl, heterocycloalkyl, aryl, or heteroaryl, wherein each $C_{1-6}$ alkyl, $C_{2-6}$ heteroalkyl, $C_{2-6}$ alkenyl, $C_{2-6}$ alkynyl, $C_{3-6}$ cycloalkyl, $C_{5-6}$ cycloalkenyl, heterocycloalkyl, aryl, and heteroaryl is optionally and independently substituted with one or more substituents independently selected from the group consisting of halogen, CN, $C_{1-6}$ alkyl, $C_{1-6}$ haloalkyl, C(NR$^a$)R$^b$, C(O)R$^{20}$, NR$^a$R$^b$, NR$^a$C(O)R$^{20}$, OH, and OC$_{1-6}$ alkyl;
each $R^{11}$ is independently hydrogen, halogen, CN, $C_{1-6}$ alkyl, $C_{1-6}$ alkylN(R$^6$)$_2$, $C_{1-6}$ alkylOR$^6$, arylalkylene, heteroarylalkylene, C(O)N(R$^6$)$_2$, C(O)OH, N(R$^6$)$_2$, OH, OC$_{1-6}$ alkyl, aryl, or heteroaryl, wherein each $C_{1-6}$ alkyl, $C_{1-6}$ alkylN(R$^6$)$_2$, $C_{1-6}$ alkylOR$^6$, arylalkylene, heteroarylalkylene, OC$_{1-6}$ alkyl, aryl, and heteroaryl is optionally and independently substituted with one or more substituents independently selected from the group consisting of halogen, $NH_2$, and OH; or
$R^{11}$ and $R^{12}$, together with the carbon atoms to which they are attached, form a 5- to 7-membered carbocyclic or heterocyclic ring;

each $R^{12}$ is independently hydrogen, halogen, CN, $C_{1-6}$ alkyl, $C_{1-6}$ alkylN($R^6$)$_2$, $C_{1-6}$ alkylOR$^6$, arylalkylene, heteroarylalkylene, C(O)N($R^6$)$_2$, C(O)OH, N($R^6$)$_2$, OH, OC$_{1-6}$ alkyl, aryl, or heteroaryl, wherein each $C_{1-6}$ alkyl, $C_{1-6}$ alkylN($R^6$)$_2$, $C_{1-6}$ alkylOR$^6$, arylalkylene, heteroarylalkylene, OC$_{1-6}$ alkyl, aryl, and heteroaryl is optionally and independently substituted with one or more substituents independently selected from the group consisting of halogen, NH$_2$, and OH: or $R^4$ and $R^{12}$, together with the carbon atoms to which they are attached, form a 5- to 7-membered carbocyclic or heterocyclic ring: or $R^{11}$ and $R^{12}$, together with the carbon atoms to which they are attached, form a 5- to 7-membered heterocyclic ring;

each $R^6$ is independently hydrogen, $C_{1-6}$ alkyl, C(O)OC$_{1-4}$ alkyl, or phenyl;

each $R^{20}$ is independently hydrogen, halogen, $C_{1-6}$ alkyl, NR$^a$R$^b$, OH, or OC$_{1-6}$ alkyl;

each $R^a$ is independently hydrogen or $C_{1-6}$ alkyl, wherein each $C_{1-6}$ alkyl is optionally and independently substituted with one or more substituents independently selected from the group consisting of halogen, CN, OH, and =O;

each $R^b$ is independently hydrogen or $C_{1-6}$ alkyl, wherein each $C_{1-6}$ alkyl is optionally and independently substituted with one or more substituents independently selected from the group consisting of halogen, CN, OH, and =O; or each $R^a$ and $R^b$, together with the nitrogen atom to which they are attached, independently forms a monocyclic 4- to 6-membered heterocyclic ring, wherein each 4- to 6-membered heterocyclic ring optionally and independently contains one additional heteroatom selected from the group consisting of nitrogen, oxygen, and sulfur, and further wherein each 4- to 6-membered heterocyclic ring is optionally and independently substituted with one or more substituents independently selected from the group consisting of halogen, CN, OH, and =O;

m is 0, 1, 2, or 3;
n is 0, 1, 2, or 3; and
each w is independently 0, 1, or 2;
with the proviso that the sum of m and n is 2, 3, or 4.

2. The compound of claim 1, or a pharmaceutically acceptable salt or stereoisomer thereof, wherein R$^x$ and R$^1$, together with the nitrogen atom to which they are attached, form an optionally substituted, monocyclic, bicyclic, or tricyclic nitrogen-containing ring system selected from the group consisting of:

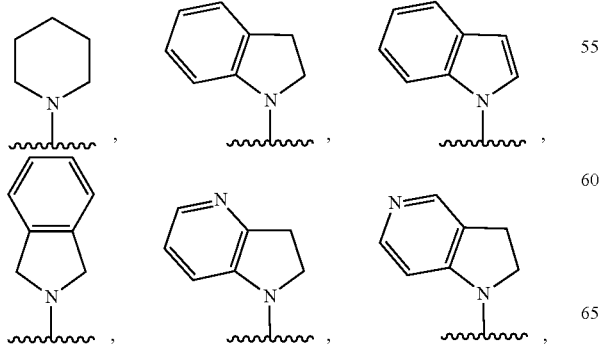

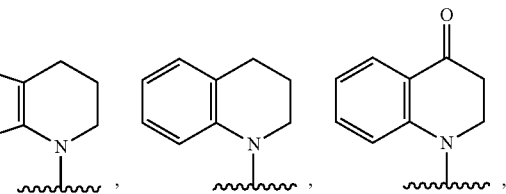

-continued

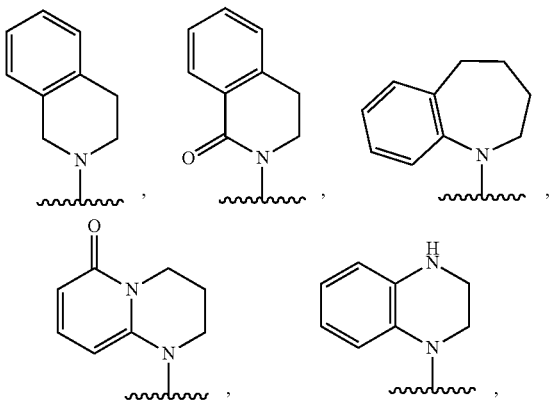

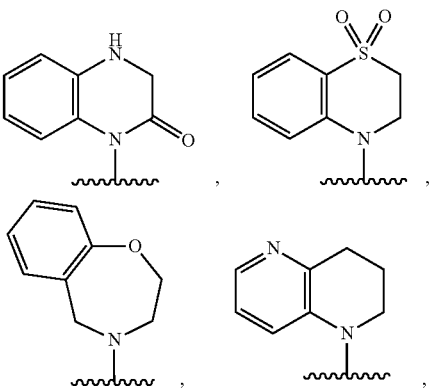

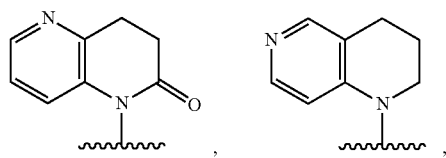

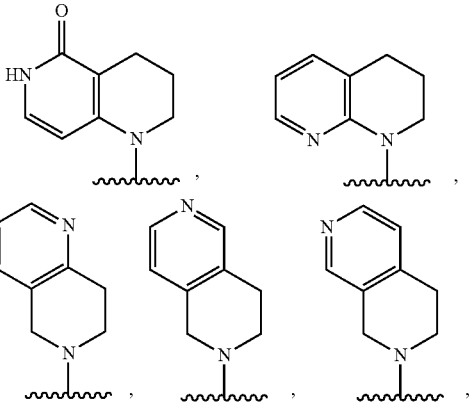

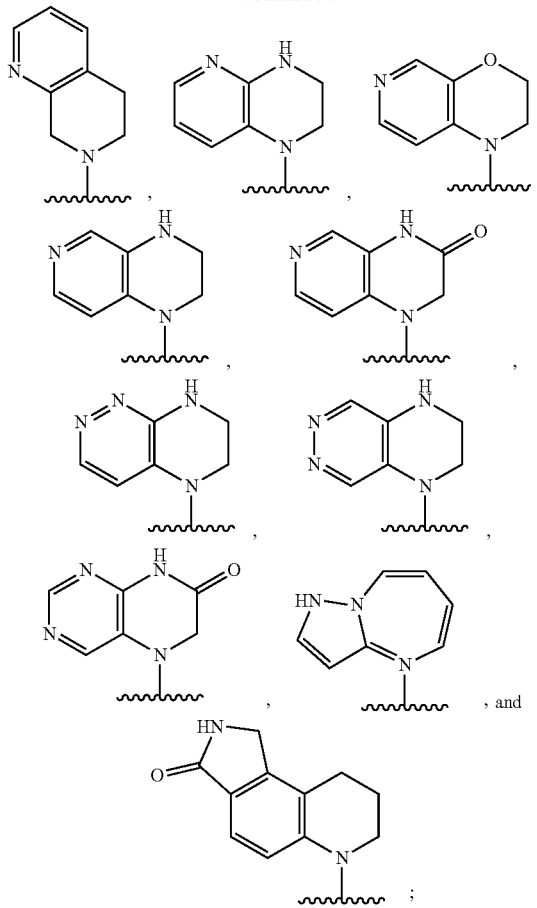

wherein the optionally substituted, monocyclic, bicyclic, or tricyclic nitrogen-containing ring system is optionally further substituted with one or more substituents independently selected from the group consisting of F, Cl, CN, $C_{1-4}$ alkyl, $CH_2C(O)NH_2$, $CH_2C(O)NHC_{1-4}$ alkyl, $CH_2C(O)N(C_{1-4}$ alkyl$)_2$, $CH_2C(O)OH$, $CH_2C(O)OC_{1-4}$ alkyl, $CH_2NH_2$, $CH_2NHC_{1-4}$ alkyl, $CH_2N(C_{1-4}$ alkyl$)_2$, $CH_2NHC(O)C_{1-4}$ alkyl, $C_{2-6}$ alkenyl, $C_{2-4}$ alkynyl, $C(NOH)H$, $C(NOCH_3)H$, $C(NOH)CH_3$, $C(O)NH_2$, $C(O)NHC_{1-4}$ alkyl, $C(O)N(C_{1-4}$ alkyl$)_2$, $C(O)OH$, $C(O)OC_{1-4}$ alkyl, $NH_2$, $NHC_{1-4}$ alkyl, $N(C_{1-4}$ alkyl$)_2$, $NHC(O)C_{1-4}$ alkyl, $OC_{1-4}$ alkyl, $S(O)_2C_{1-4}$ alkyl, $C_{3-6}$ cycloalkyl, $C_{5-6}$ cycloalkenyl, heterocyclyl, phenyl, and heteroaryl;
wherein each $C_{1-4}$ alkyl substituent is optionally and independently substituted with one or more substituents independently selected from the group consisting of F, CN, OH, and $OC_{1-2}$ alkyl;
wherein each $C_{3-6}$ cycloalkyl substituent is optionally and independently substituted with one or more substituents independently selected from the group consisting of F, CN, OH, and $OC_{1-2}$ alkyl;
wherein each heterocyclyl substituent is optionally and independently substituted with one, two, or three substituents independently selected from the group consisting of halogen, $C_{1-3}$ alkyl, $C_{1-3}$ haloalkyl, and =O; and
wherein each heteroaryl substituent is optionally and independently substituted with one, two, or three substituents independently selected from the group consisting of halogen, $C_{1-3}$ alkyl, $C_{1-3}$ haloalkyl, $C_{1-3}$ alkylOH, $C_{1-3}$ alkylOC$_{1-3}$ alkyl, and $C(O)N(R^{10})_2$.

3. The compound of claim 2, or a pharmaceutically acceptable salt or stereoisomer thereof, wherein each heterocyclyl substituent is independently selected from the group consisting of pyrrolidin-1-yl, pyrrolidin-2-on-4-yl, tetrahydrofuran-2-yl, tetrahydrofuran-3-yl, 2,5-dihydrofuran-3-yl, 1,2,4-oxadiazol-5-on-3-yl, piperidin-1-yl, piperidin-4-yl, 1,2,3,6-tetrahydropyridin-4-yl, tetrahydropyran-2-yl, piperazin-1-yl, piperazin-3-on-1-yl, and morpholin-4-yl:
wherein each heterocyclyl substituent is optionally and independently substituted with one, two, or three independently selected $C_{1-2}$ alkyl substituents; and
wherein each $C_{1-2}$ alkyl substituent is optionally and independently substituted with one, two, or three fluoro substituents, one or two OH substituents, or one or two $OC_{1-2}$ alkyl substituents.

4. The compound of claim 2, or a pharmaceutically acceptable salt or stereoisomer thereof, wherein each heteroaryl substituent is independently selected from the group consisting of pyrazol-1-yl, pyrazol-3-yl, pyrazol-4-yl, imidazol-2-yl, isoxazol-5-yl, oxazol-2-yl, oxazol-5-yl, thiazol-2-yl, thiazol-5-yl, 1,2,4-triazol-1-yl, 1,2,4-triazol-3-yl, 1,3,4-triazol-2-yl, 1,2,4-oxadiazol-3-yl, 1,3,4-oxadiazol-2-yl, 1,3,4-thiadiazol-2-yl, pyrid-2-yl, pyrid-3-yl, and pyrid-4-yl;
wherein each heteroaryl substituent is optionally and independently substituted with one $C_{1-2}$ alkyl substituent; and
wherein the $C_{1-2}$ alkyl substituent is optionally substituted with one, two, or three fluoro substituents, one or two OH substituents, or one or two $OC_{1-2}$ alkyl substituents.

5. The compound of claim 1, or a pharmaceutically acceptable salt or stereoisomer thereof, wherein $R^x$ and $R^1$, together with the nitrogen atom to which they are attached, form 1,2,3,4-tetrahydroquinolinyl;
wherein the 1,2,3,4-tetrahydroquinolinyl is optionally substituted with one, two, or three substituents independently selected from the group consisting of halogen, $C_{1-3}$ alkyl, $C_{1-3}$ haloalkyl, $C(O)N(R^{10})_2$, and heteroaryl; and
wherein each heteroaryl substituent is optionally and independently substituted with one, two, or three substituents independently selected from the group consisting of halogen, $C_{1-3}$ alkyl, $C_{1-3}$ haloalkyl, $C_{1-3}$ alkylOH, $C_{1-3}$ alkylOC$_{1-3}$ alkyl, and $C(O)N(R^{10})_2$.

6. The compound of claim 1, or a pharmaceutically acceptable salt or stereoisomer thereof, wherein $R^x$ and $R^1$, together with the nitrogen atom to which they are attached, form 1,2,3,4-tetrahydro-1,5-naphthyridinyl:
wherein the 1,2,3,4-tetrahydro-1,5-naphthyridinyl is optionally substituted with one, two, or three substituents independently selected from the group consisting of halogen, $C_{1-3}$ alkyl, $C_{1-3}$ haloalkyl, $C(O)N(R^{10})_2$, and heteroaryl; and
wherein each heteroaryl substituent is optionally and independently substituted with one, two, or three substituents independently selected from the group consisting of halogen, $C_{1-3}$ alkyl, $C_{1-3}$ haloalkyl, $C_{1-3}$ alkylOH, $C_{1-3}$ alkylOC$_{1-3}$ alkyl, and $C(O)N(R^{10})_2$.

7. The compound of claim 1, or a pharmaceutically acceptable salt or stereoisomer thereof, wherein:
$R^4$ is hydrogen, halogen, CN, $C_{1-3}$ alkyl, $C_{1-3}$ alkylC(O)OH, $C_{1-3}$ alkylN(R^6)$_2$, $C_{1-3}$ alkylOR$^6$, $C(O)NH_2$, N(R$^6$)$_2$, OH, or $OC_{1-3}$ alkyl, wherein the $C_{1-3}$ alkyl, $C_{1-3}$ alkylN(R$^6$)$_2$, $C_{1-3}$ alkylOR$^6$, or $OC_{1-3}$ alkyl is optionally substituted with one or more substituents independently selected from the group consisting of halogen, $NH_2$, and OH;

$R^5$ is hydrogen, halogen, CN, $C_{1-3}$ alkyl, $C_{1-3}$ alkylC(O)OH, $C_{1-3}$ alkylN$(R^6)_2$, $C_{1-3}$ alkylOR$^6$, C(O)NH$_2$, N$(R^6)_2$, OH, or OC$_{1-3}$ alkyl, wherein the $C_{1-3}$ alkyl, $C_{1-3}$ alkylN$(R^6)_2$, $C_{1-3}$ alkylOR$^6$, or OC$_{1-3}$ alkyl is optionally substituted with one or more substituents independently selected from the group consisting of halogen, $NH_2$, and OH; or $R^4$ and $R^5$, together with the carbon atom to which they are attached, form a saturated or partially unsaturated 3- to 7-membered carbocyclic or heterocyclic ring, wherein the 3- to 7-membered carbocyclic or heterocyclic ring is optionally substituted with one or more substituents independently selected from the group consisting of halogen, CN, $C_{1-6}$ alkyl, N$(R^6)_2$, OH, OC$_{1-6}$ alkyl, and =O; or $R^4$ and $R^8$, together with the carbon atoms to which they are attached, form a 3- to 7-membered carbocyclic or heterocyclic ring; and each $R^6$ is independently hydrogen or $C_{1-3}$ alkyl.

8. The compound of claim 1, or a pharmaceutically acceptable salt or stereoisomer thereof, wherein

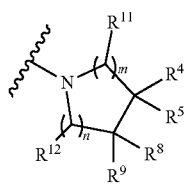

is selected from the group consisting of:

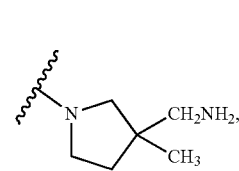 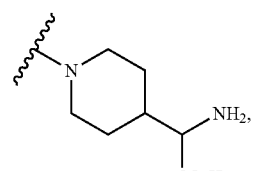

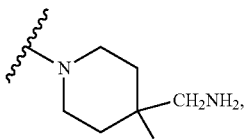 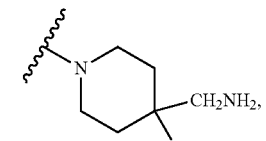

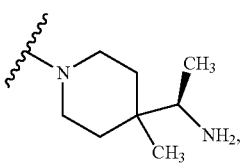 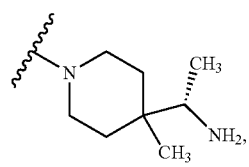

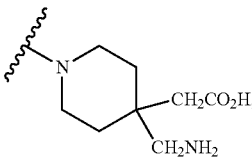 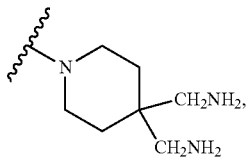

-continued

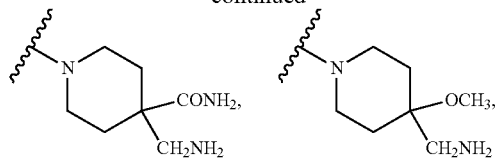

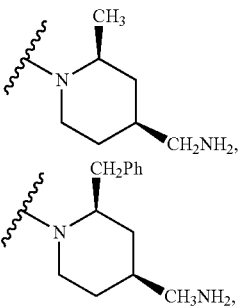 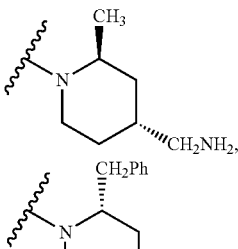

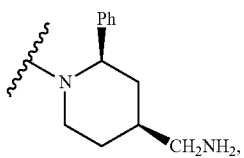 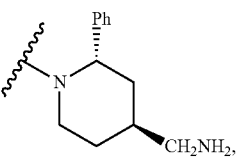

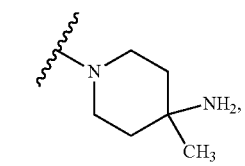 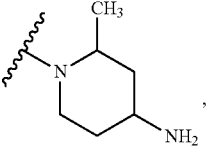

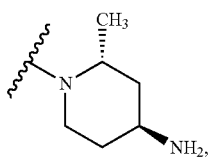 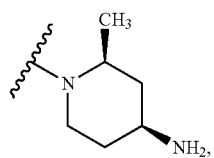

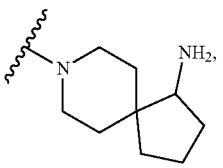 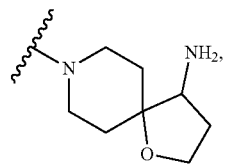

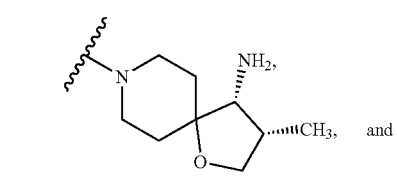

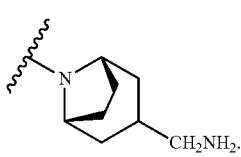

9. The compound of claim 1, or a pharmaceutically acceptable salt or stereoisomer thereof, wherein

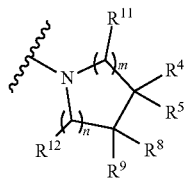

is selected from the group consisting of:

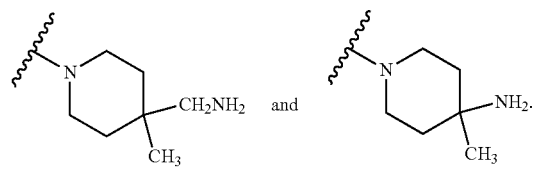

10. The compound of claim 1, or a pharmaceutically acceptable salt or stereoisomer thereof, wherein

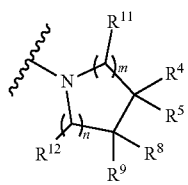

is:

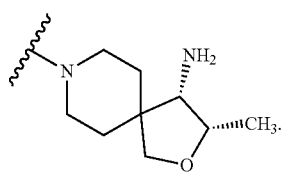 [SMILES: *N1CCC2(CC1)CO[C@@H](C)[C@H]2N]

11. The compound of claim 1, or a pharmaceutically acceptable salt or stereoisomer thereof, wherein:
m is 1 or 2; and
n is 1.

12. A pharmaceutical composition comprising a pharmaceutically acceptable carrier and the compound of claim 1, or a pharmaceutically acceptable salt or stereoisomer thereof.

13. A method for inhibiting Src homology region 2-containing protein tyrosine phosphatase 2 activity in a subject, wherein the method comprises administering to the subject in need thereof a therapeutically effective amount of the compound of claim 1, or a pharmaceutically acceptable salt or stereoisomer thereof.

14. The method of claim 13, wherein the subject is a human.

15. The method of claim 13, wherein the subject has a disorder selected from the group consisting of acute myeloid leukemia, breast cancer, colorectal cancer, diabetes, juvenile leukemia, lung cancer, melanoma, neutropenia, and Noonan syndrome.

16. The method of claim 15, wherein the lung cancer is non-small cell lung cancer (NSCLC).

17. The method of claim 13, wherein the method further comprises administering to the subject in need thereof a therapeutically effective amount of an antibody, an antibody-drug conjugate, an immunomodulator, or a histone deacetylase inhibitor.

18. A compound of Formula (II):

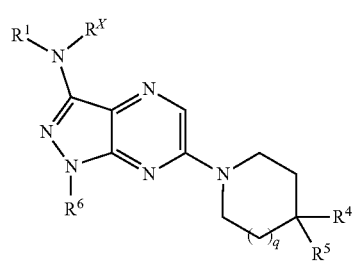

(II)

or a pharmaceutically acceptable salt or stereoisomer thereof,
wherein:
$R^x$ and $R^1$, together with the nitrogen atom to which they are attached, form a monocyclic, bicyclic, or tricyclic nitrogen-containing ring system selected from the group consisting of:
(a) a 4- to 7-membered heterocyclyl;
(b) a monocyclic 5- to 7-membered heteroaryl;
(c) a bicyclic 8- to 14-membered heteroaryl; and
(d) a tricyclic 11- to 15-membered heteroaryl;
wherein the 4- to 7-membered heterocyclyl, monocyclic 5- to 7-membered heteroaryl, bicyclic 8- to 14-membered heteroaryl, or tricyclic 11- to 15-membered heteroaryl is optionally substituted with one or more substituents independently selected from the group consisting of halogen, CN, $NO_2$, $C_{1-3}$ haloalkyl, $C_{1-6}$ alkylene-S(O)$_w$—$C_{1-3}$ alkyl, C(NOR$^a$)H, C(NOR$^a$)C$_{1-3}$ alkyl, C(O)R$^{10}$, C(O)N(R$^{10}$)$_2$, C(O)OR$^{10}$, N(R$^{10}$)$_2$, NR$^a$C(O)R$^{10}$, NR$^a$S(O)$_w$R$^{10}$, NR$^a$S(O)(NR$^a$)C$_{1-3}$ alkyl, N[S(O)$_2$C$_{1-3}$ alkyl]$_2$, OR$^{10}$, =O, OS(O)$_w$R$^{10}$, P(O)(R$^{10}$)$_2$, S(O)$_w$R$^{10}$, S(O)$_w$N(R$^{10}$)$_2$, heterocyclyl, heteroaryl, and R$^{10}$;
wherein each heterocyclyl substituent is optionally and independently substituted with one, two, or three substituents independently selected from the group consisting of halogen, $C_{1-3}$ alkyl, $C_{1-3}$ haloalkyl, and =O;
wherein each heteroaryl substituent is optionally and independently substituted with one, two, or three substituents independently selected from the group consisting of halogen, $C_{1-3}$ alkyl, $C_{1-3}$ haloalkyl, $C_{1-3}$ alkylOH, $C_{1-3}$ alkylOC$_{1-3}$ alkyl, and C(O)N(R$^{10}$)$_2$; and
wherein when R$^{10}$ is phenyl, each phenyl substituent is optionally and independently substituted with one, two, or three substituents independently selected from the group consisting of halogen, $C_{1-3}$ alkyl, $C_{1-3}$ haloalkyl, and O-phenyl;
R$^4$ is hydrogen, halogen, CN, $C_{1-6}$ alkyl, $C_{1-6}$ alkylN(R$^6$)$_2$, $C_{1-6}$ alkylOR$^6$, C(O)N(R$^6$)$_2$, N(R$^6$)$_2$, OH, or OC$_{1-6}$ alkyl, wherein the $C_{1-6}$ alkyl, $C_{1-6}$ alkylN(R$^6$)$_2$, $C_{1-6}$ alkylOR$^6$, or OC$_{1-6}$ alkyl is optionally substituted with one or more substituents independently selected from the group consisting of halogen, $NH_2$, OH, and =O;

R[5] is hydrogen, halogen, CN, $C_{1-6}$ alkyl, $C_{1-6}$ alkylN(R[6])$_2$, $C_{1-6}$ alkylOR[6], C(O)N(R[6])$_2$, N(R[6])$_2$, OH, or OC$_{1-6}$ alkyl, wherein the $C_{1-6}$ alkyl, $C_{1-6}$ alkylN(R[6])$_2$, $C_{1-6}$ alkylOR[6], or OC$_{1-6}$ alkyl is optionally substituted with one or more substituents independently selected from the group consisting of halogen, NH$_2$, OH, and =O; or R[4] and R[5], together with the carbon atom to which they are attached, form a saturated or partially unsaturated 3- to 7-membered carbocyclic or heterocyclic ring, wherein the 3- to 7-membered carbocyclic or heterocyclic ring is optionally substituted with one or more substituents independently selected from the group consisting of halogen, CN, $C_{1-6}$alkyl, N(R[6])$_2$, OH, OC$_{1-6}$ alkyl, and =O;

each R[6] is independently hydrogen, $C_{1-6}$ alkyl, C(O)OC$_{1-6}$ alkyl, or phenyl;

each R[10] is independently hydrogen, $C_{1-6}$ alkyl, $C_{2-6}$ heteroalkyl, $C_{2-6}$ alkenyl, $C_{2-6}$ alkynyl, P(O)(R[20])$_2$, $C_{3-6}$ cycloalkyl, $C_{5-6}$ cycloalkenyl, heterocycloalkyl, aryl, or heteroaryl, wherein each $C_{1-6}$ alkyl, $C_{2-6}$ heteroalkyl, $C_{2-6}$ alkenyl, $C_{2-6}$ alkynyl, $C_{3-6}$ cycloalkyl, $C_{5-6}$ cycloalkenyl, heterocycloalkyl, aryl, and heteroaryl is optionally and independently substituted with one or more substituents independently selected from the group consisting of halogen, CN, $C_{1-6}$ alkyl, $C_{1-6}$ haloalkyl, C(NR[a])R[b], C(O)R[20], NR[a]R[b], NR[a]C(O)R[20], OH, and OC$_{1-6}$ alkyl;

each R[20] is independently hydrogen, halogen, $C_{1-6}$ alkyl, NR[a]R[b], OH, or OC$_{1-6}$ alkyl;

each R[a] is independently hydrogen or $C_{1-6}$ alkyl, wherein each $C_{1-6}$ alkyl is optionally and independently substituted with one or more substituents independently selected from the group consisting of halogen, CN, OH, and =O;

each R[b] is independently hydrogen or $C_{1-6}$ alkyl, wherein each $C_{1-6}$ alkyl is optionally and independently substituted with one or more substituents independently selected from the group consisting of halogen, CN, OH, and =O; or each R[a] and R[b], together with the nitrogen atom to which they are attached, independently forms a monocyclic 4- to 6-membered heterocyclic ring, wherein each 4- to 6-membered heterocyclic ring optionally and independently contains one additional heteroatom selected from the group consisting of nitrogen, oxygen, and sulfur, and further wherein each 4- to 6-membered heterocyclic ring is optionally and independently substituted with one or more substituents independently selected from the group consisting of halogen, CN, OH, and =O;

q is 0 or 1; and each w is independently 0, 1, or 2.

19. The compound of claim 18, or a pharmaceutically acceptable salt or stereoisomer thereof, wherein R[x] and R[1], together with the nitrogen atom to which they are attached, form an optionally substituted, monocyclic, bicyclic, or tricyclic nitrogen-containing ring system selected from the group consisting of:

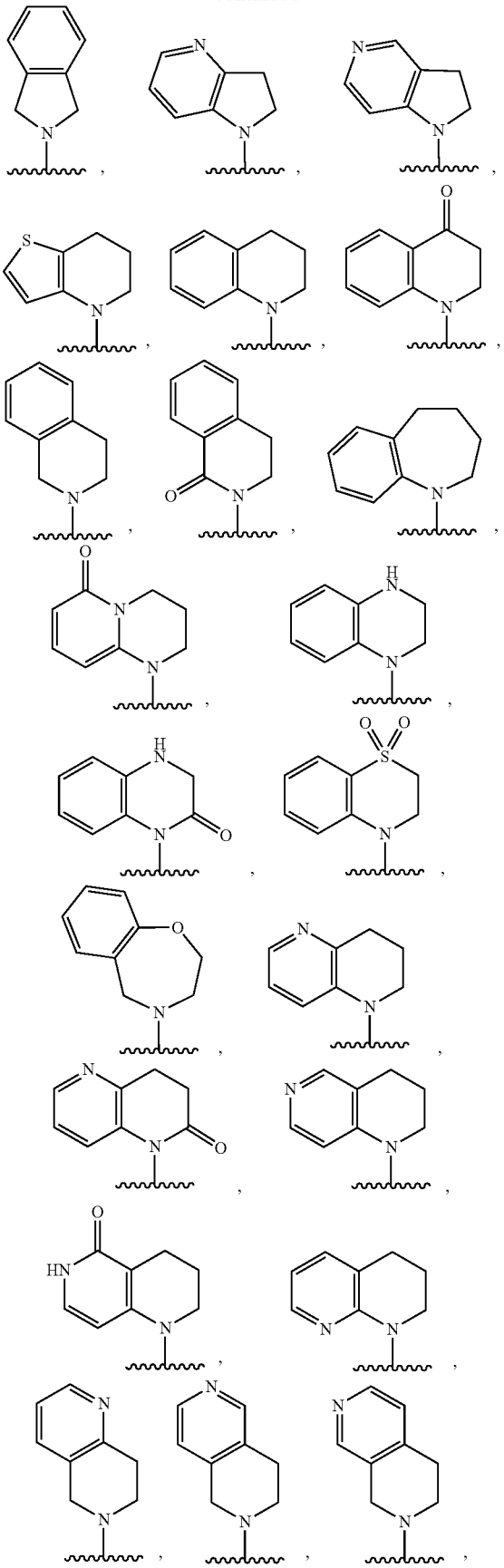

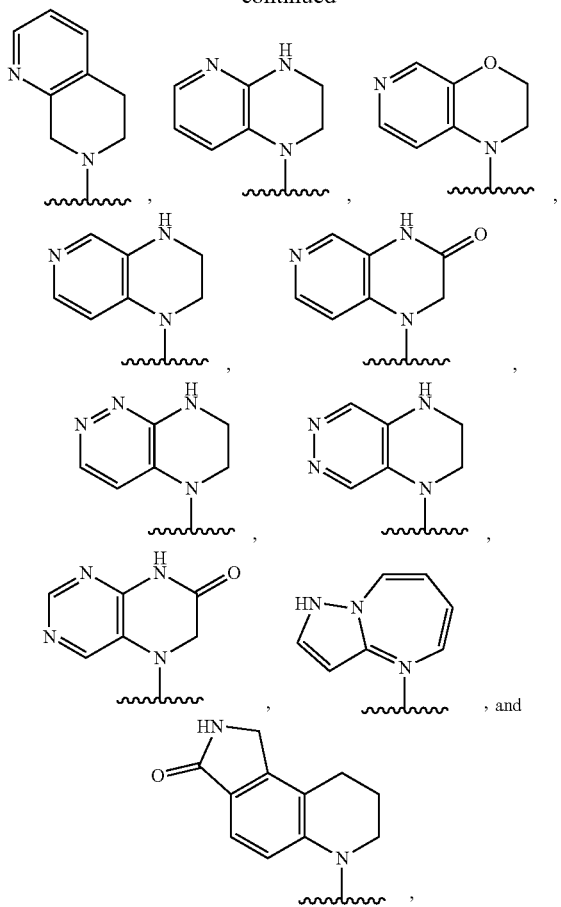

wherein the optionally substituted, monocyclic, bicyclic, or tricyclic nitrogen-containing ring system is optionally further substituted with one or more substituents independently selected from the group consisting of F, Cl, CN, $C_{1-4}$ alkyl, $CH_2C(O)NH_2$, $CH_2C(O)NHC_{1-4}$ alkyl, $CH_2C(O)N(C_{1-4}$ alkyl$)_2$, $CH_2C(O)OH$, $CH_2C(O)C_{1-4}$ alkyl, $CH_2NH_2$, $CH_2NHC_{1-4}$ alkyl, $CH_2N(C_{1-4}$ alkyl$)_2$, $CH_2NHC(O)C_{1-4}$ alkyl, $C_{2-6}$ alkenyl, $C_{2-4}$ alkynyl, $C(NOH)H$, $C(NOCH_3)H$, $C(NOH)CH_3$, $C(O)NH_2$, $C(O)NHC_{1-4}$ alkyl, $C(O)N(C_{1-4}$ alkyl$)_2$, $C(O)OH$, $C(O)OC_{1-4}$ alkyl, $NH_2$, $NHC_{1-4}$ alkyl, $N(C_{1-4}$ alkyl$)_2$, $NHC(O)C_{1-4}$ alkyl, $OC_{1-4}$ alkyl, $S(O)_2C_{1-4}$ alkyl, $C_{3-6}$ cycloalkyl, $C_{5-6}$ cycloalkenyl, heterocyclyl, phenyl, and heteroaryl;
wherein each $C_{1-4}$ alkyl substituent is optionally and independently substituted with one or more substituents independently selected from the group consisting of F, CN, OH, and $OC_{1-2}$ alkyl;
wherein each $C_{3-6}$ cycloalkyl substituent is optionally and independently substituted with one or more substituents independently selected from the group consisting of F, CN, OH, and $OC_{1-2}$ alkyl;
wherein each heterocyclyl substituent is optionally and independently substituted with one, two, or three substituents independently selected from the group consisting of halogen, $C_{1-3}$ alkyl, $C_{1-3}$ haloalkyl, and =O; and
wherein each heteroaryl substituent is optionally and independently substituted with one, two, or three substituents independently selected from the group consisting of halogen, $C_{1-3}$ alkyl, $C_{1-3}$ haloalkyl, $C_{1-3}$ alkylOH, $C_{1-3}$ alkylOC$_{1-3}$ alkyl, and $C(O)N(R^{10})_2$.

20. The compound of claim 19, or a pharmaceutically acceptable salt or stereoisomer thereof, wherein each heterocyclyl substituent is independently selected from the group consisting of pyrrolidin-1-yl, pyrrolidin-2-on-4-yl, tetrahydrofuran-2-yl, tetrahydrofuran-3-yl, 2,5-dihydrofuran-3-yl, 1,2,4-oxadiazol-5-on-3-yl, piperidin-1-yl, piperidin-4-yl, 1,2,3,6-tetrahydropyridin-4-yl, tetrahydropyran-2-yl, piperazin-1-yl, piperazin-3-on-1-yl, and morpholin-4-yl;
wherein each heterocyclyl substituent is optionally and independently substituted with one, two, or three independently selected $C_{1-2}$ alkyl substituents; and
wherein each $C_{1-2}$ alkyl substituent is optionally and independently substituted with one, two, or three fluoro substituents, one or two OH substituents, or one or two $OC_{1-2}$ alkyl substituents.

21. The compound of claim 19, or a pharmaceutically acceptable salt or stereoisomer thereof, wherein each heteroaryl substituent is independently selected from the group consisting of pyrazol-1-yl, pyrazol-3-yl, pyrazol-4-yl, imidazol-2-yl, isoxazol-5-yl, oxazol-2-yl, oxazol-5-yl, thiazol-2-yl, thiazol-5-yl, 1,2,4-triazol-1-yl, 1,2,4-triazol-3-yl, 1,3,4-triazol-2-yl, 1,2,4-oxadiazol-3-yl, 1,3,4-oxadiazol-2-yl, 1,3,4-thiadiazol-2-yl, pyrid-2-yl, pyrid-3-yl, and pyrid-4-yl:
wherein each heteroaryl substituent is optionally and independently substituted with one $C_{1-2}$ alkyl substituent; and
wherein the $C_{1-2}$ alkyl substituent is optionally substituted with one, two, or three fluoro substituents, one or two OH substituents, or one or two $OC_{1-2}$ alkyl substituents.

22. The compound of claim 18, or a pharmaceutically acceptable salt or stereoisomer thereof, wherein $R^x$ and $R^1$, together with the nitrogen atom to which they are attached, form 1,2,3,4-tetrahydroquinolinyl;
wherein the 1,2,3,4-tetrahydroquinolinyl is optionally substituted with one, two, or three substituents independently selected from the group consisting of halogen, $C_{1-3}$ alkyl, $C_{1-3}$ haloalkyl, $C(O)N(R^{10})_2$, and heteroaryl; and
wherein each heteroaryl substituent is optionally and independently substituted with one, two, or three substituents independently selected from the group consisting of halogen, $C_{1-3}$ alkyl, $C_{1-3}$ haloalkyl, $C_{1-3}$ alkylOH, $C_{1-3}$ alkylOC$_{1-3}$ alkyl, and $C(O)N(R^{10})_2$.

23. The compound of claim 18, or a pharmaceutically acceptable salt or stereoisomer thereof, wherein $R^x$ and $R^1$, together with the nitrogen atom to which they are attached, form 1,2,3,4-tetrahydro-1,5-naphthyridinyl:
wherein the 1,2,3,4-tetrahydro-1,5-naphthyridinyl is optionally substituted with one, two, or three substituents independently selected from the group consisting of halogen, $C_{1-3}$ alkyl, $C_{1-3}$ haloalkyl, $C(O)N(R^{10})_2$, and heteroaryl; and
wherein each heteroaryl substituent is optionally and independently substituted with one, two, or three substituents independently selected from the group consisting of halogen, $C_{1-3}$ alkyl, $C_{1-3}$ haloalkyl, $C_{1-3}$ alkylOH, $C_{1-3}$ alkylOC$_{1-3}$ alkyl, and $C(O)N(R^{10})_2$.

24. The compound of claim 18, or a pharmaceutically acceptable salt or stereoisomer thereof, wherein:
$R^4$ is hydrogen, halogen, $C_{1-3}$ alkyl, $N(R^6)_2$, OH, or $OC_{1-3}$ alkyl, wherein the $C_{1-3}$ alkyl is optionally substituted with one or more substituents independently selected from the group consisting of halogen, $NH_2$, and OH; and $R^5$ is hydrogen, halogen, $C_{1-3}$ alkyl, $N(R^6)_2$, OH, or $OC_{1-3}$ alkyl, wherein the $C_{1-3}$ alkyl is optionally substituted with one or more substituents independently selected from the group consisting of halogen, $NH_2$, and OH.

25. The compound of claim 18, or a pharmaceutically acceptable salt or stereoisomer thereof, wherein:
$R^4$ is F, $CH_3$, $CH_2NH_2$, $CH_2NHCH_3$, $CH_2OH$, $NH_2$, or $OCH_3$; and
$R^3$ is F, $CH_3$, $CH_2NH_2$, $CH_2NHCH_3$, $CH_2OH$, $NH_2$, or $OCH_3$.

26. The compound of claim 18, or a pharmaceutically acceptable salt or stereoisomer thereof, wherein $R^4$ and $R^5$, together with the carbon atom to which they are attached, form an optionally substituted, saturated or partially unsaturated, 3- to 7-membered carbocyclic or heterocyclic ring selected from the group consisting of:

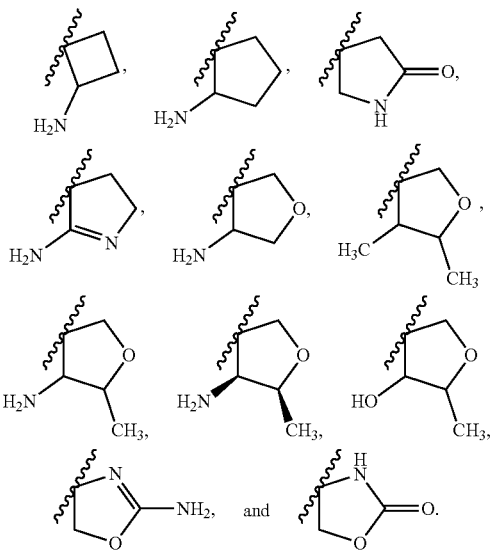

27. The compound of claim 18, or a pharmaceutically acceptable salt or stereoisomer thereof, wherein q is 1.

28. A compound of Formula (III):

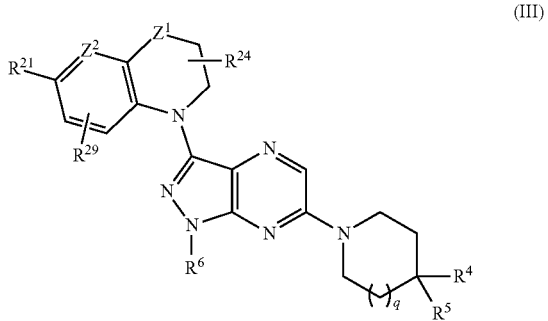

(III)

or a pharmaceutically acceptable salt or stereoisomer thereof,
wherein:
$Z^1$ is $-C(R^{23})_2-$, $-C(O)-$, $-NR^{61}-$, or $-O-$;
$Z^2$ is $CR^{22}$ or N;
$R^{21}$ is hydrogen, halogen, CN, $C_{1-6}$ alkyl, $C_{2-6}$ alkenyl, $C_{2-6}$ alkynyl, $C(O)N(R^6)_2$, $N(R^6)_2$, OH, $OC_{1-6}$ alkyl, $C_{3-6}$ cycloalkyl, heterocycloalkyl, phenyl, or heteroaryl, wherein the $C_{1-6}$ alkyl, $C_{2-6}$ alkenyl, $C_{2-6}$ alkynyl, $OC_{1-6}$ alkyl, $C_{3-6}$ cycloalkyl, heterocycloalkyl, phenyl, or heteroaryl is optionally substituted with one or more substituents independently selected from the group consisting of halogen, $C_{1-3}$ alkyl, $C_{1-3}$ haloalkyl, $C(O)R^{26}$, $C(O)N(R^6)_2$, $C(O)OR^{26}$, $N(R^6)_2$, and $OC_{1-3}$ alkyl, and further wherein each $C_{1-3}$ alkyl substituent is optionally and independently substituted with one, two, or three substituents independently selected from the group consisting of OH and $OCH_3$;
$R^{22}$ is hydrogen, halogen, CN, $C_{1-6}$ alkyl, $C(O)N(R^6)_2$, $N(R^6)_2$, OH, $OC_{1-6}$ alkyl, $C_{3-6}$ cycloalkyl, heterocycloalkyl, phenyl, or heteroaryl, wherein the $C_{1-6}$ alkyl, $OC_{1-6}$ alkyl, $C_{3-6}$ cycloalkyl, heterocycloalkyl, phenyl, or heteroaryl is optionally substituted with one or more substituents independently selected from the group consisting of halogen, CN, $C_{1-3}$ alkyl, $C_{1-3}$ haloalkyl, $C(O)R^{26}$, $C(O)N(R^6)_2$, $C(O)OR^{26}$, $N(R^6)_2$, OH, $OC_{1-3}$ alkyl, and =O, and further wherein each $C_{1-3}$ alkyl substituent is optionally and independently substituted with one, two, or three substituents independently selected from the group consisting of OH and $OCH_3$;
each $R^{23}$ is independently hydrogen, halogen, or $C_{1-6}$ alkyl;
$R^{24}$ is hydrogen, halogen, or $C_{1-6}$ alkyl;
each $R^{26}$ is independently hydrogen or $C_{1-3}$ alkyl;
$R^{29}$ is hydrogen, halogen, $C_{1-6}$ alkyl, $C(O)N(R^6)_2$, $N(R^6)_2$, $OC_{1-6}$ alkyl, $C_{3-6}$ cycloalkyl, heterocycloalkyl, phenyl, or heteroaryl, wherein the $C_{1-6}$ alkyl, $OC_{1-6}$ alkyl, $C_{3-6}$ cycloalkyl, heterocycloalkyl, phenyl, or heteroaryl is optionally substituted with one or more substituents independently selected from the group consisting of halogen, $C_{1-3}$ alkyl, $C_{1-3}$ haloalkyl, $C(O)R^{26}$, $C(O)N(R^6)_2$, $C(O)OR^{26}$, and $N(R^6)_2$, and further wherein each $C_{1-3}$ alkyl substituent is optionally and independently substituted with one, two, or three substituents independently selected from the group consisting of OH and $OCH_3$;
$R^4$ is hydrogen, halogen, CN, $C_{1-6}$ alkyl, $C(O)N(R^6)_2$, or $N(R^6)_2$, wherein the $C_{1-6}$ alkyl is optionally substituted with one or more substituents independently selected from the group consisting of halogen, $N(R^6)_2$, OH, and =O;
$R^5$ is hydrogen, halogen, CN, $C_{1-6}$ alkyl, $C(O)N(R^6)_2$, or $N(R^6)_2$, wherein the $C_{1-6}$ alkyl is optionally substituted with one or more substituents independently selected from the group consisting of halogen, $N(R^6)_2$, OH, and =O; or
$R^4$ and $R^5$, together with the carbon atom to which they are attached, form a 4- to 6-membered carbocyclic or heterocyclic ring, wherein the 4- to 6-membered carbocyclic or heterocyclic ring is optionally substituted with one or two substituents independently selected from the group consisting of halogen, CN, $C_{1-6}$ alkyl, $C(O)N(R^6)_2$, $N(R^6)_2$, $OC_{1-6}$ alkyl, and =O;
each $R^6$ is independently hydrogen, $C_{1-6}$ alkyl, $C(O)OC_{1-6}$ alkyl, or phenyl;
$R^{61}$ is hydrogen, $C_{1-6}$ alkyl, $C(O)C_{1-6}$ alkyl, $C_{3-6}$ cycloalkyl, or phenyl, wherein the $C_{1-6}$ alkyl is optionally substituted with one or two independently selected halogen substituents, and further wherein the $C_{3-6}$ cycloalkyl is optionally substituted with one or two substituents independently selected from the group consisting of $C_{1-2}$ alkyl and OH; and
q is 0 or 1.

29. The compound of claim 28, or a pharmaceutically acceptable salt or stereoisomer thereof, wherein $Z^1$ is —C($R^{23}$)$_2$—.

30. The compound of claim 29, or a pharmaceutically acceptable salt or stereoisomer thereof, wherein each $R^{23}$ is independently hydrogen.

31. The compound of claim 29, or a pharmaceutically acceptable salt or stereoisomer thereof, wherein each $R^{23}$ is independently $CH_3$.

32. The compound of claim 28, or a pharmaceutically acceptable salt or stereoisomer thereof, wherein $Z^2$ is CH.

33. The compound of claim 28, or a pharmaceutically acceptable salt or stereoisomer thereof, wherein $Z^2$ is N.

34. The compound of claim 28, or a pharmaceutically acceptable salt or stereoisomer thereof, wherein $R^{21}$ is hydrogen, halogen, CN, $CF_3$, C(O)N($R^6$)$_2$, N($R^6$)$_2$, phenyl, or heteroaryl.

35. The compound of claim 28, or a pharmaceutically acceptable salt or stereoisomer thereof, wherein $R^{21}$ is hydrogen.

36. The compound of claim 28, or a pharmaceutically acceptable salt or stereoisomer thereof, wherein $R^{21}$ is C(O)NHCH$_3$.

37. The compound of claim 28, or a pharmaceutically acceptable salt or stereoisomer thereof, wherein $R^{21}$ is optionally substituted heteroaryl.

38. The compound of claim 37, or a pharmaceutically acceptable salt or stereoisomer thereof, wherein the optionally substituted heteroaryl is selected from the group consisting of:

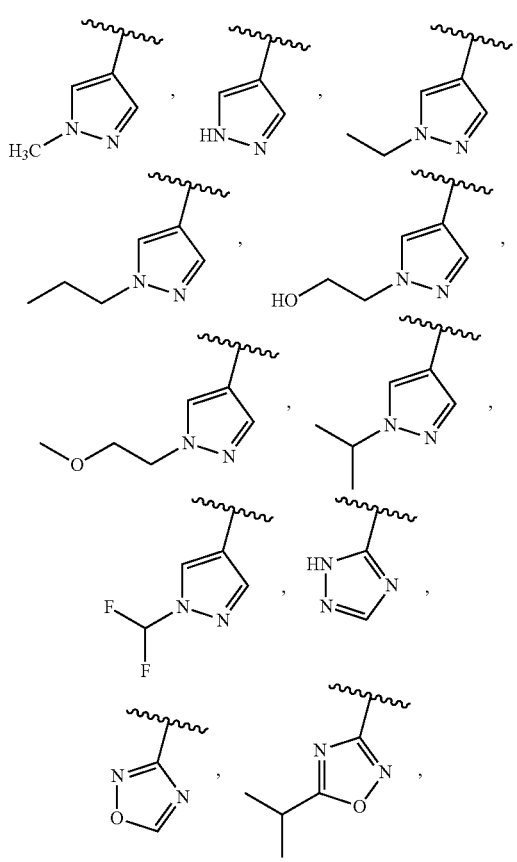

-continued

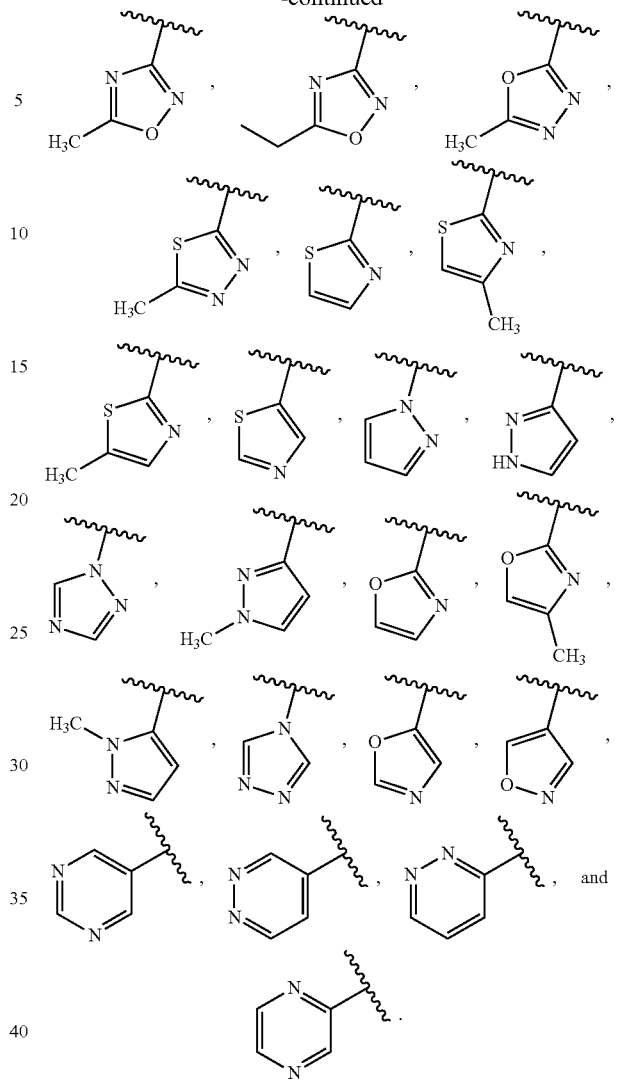

39. The compound of claim 28, or a pharmaceutically acceptable salt or stereoisomer thereof, wherein:
$R^{21}$ is hydrogen; and
$R^{24}$ is hydrogen.

40. The compound of claim 28, or a pharmaceutically acceptable salt or stereoisomer thereof, wherein:
$R^4$ is hydrogen, halogen, $C_{1-3}$ alkyl, or N($R^6$)$_2$, wherein the $C_{1-3}$ alkyl is optionally substituted with one or more substituents independently selected from the group consisting of halogen, N($R^6$)$_2$, and OH; and
$R^5$ is hydrogen, halogen, $C_{1-3}$ alkyl, or N($R^6$)$_2$, wherein the $C_{1-3}$ alkyl is optionally substituted with one or more substituents independently selected from the group consisting of halogen, N($R^6$)$_2$, and OH.

41. The compound of claim 28, or a pharmaceutically acceptable salt or stereoisomer thereof, wherein:
$R^4$ is F, $CH_3$, $CH_2NH_2$, $CH_2NHCH_3$, $CH_2OH$, or $NH_2$; and
$R^5$ is F, $CH_3$, $CH_2NH_2$, $CH_2NHCH_3$, $CH_2OH$, or $NH_2$.

42. The compound of claim 28, or a pharmaceutically acceptable salt or stereoisomer thereof, wherein $R^4$ and $R^5$, together with the carbon atom to which they are attached, form an optionally substituted 4- to 6-membered carbocyclic or heterocyclic ring selected from the group consisting of:

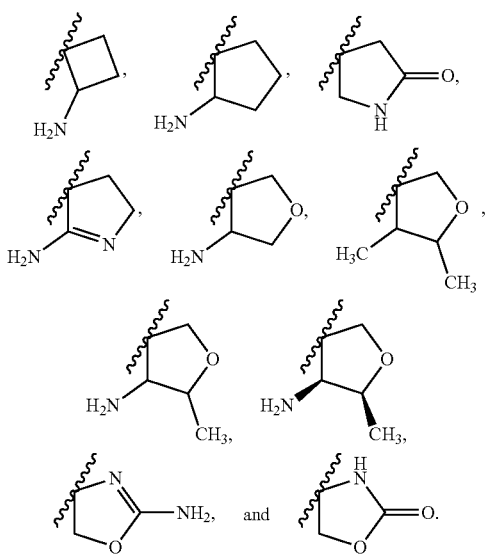

43. The compound of claim 28, or a pharmaceutically acceptable salt or stereoisomer thereof, wherein q is 1.

44. A compound of Formula (IV):

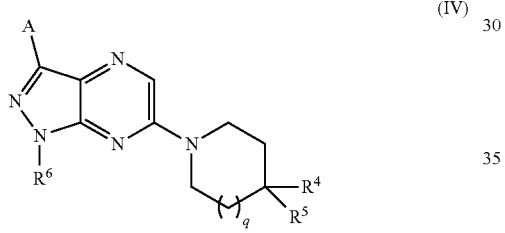

or a pharmaceutically acceptable salt or stereoisomer thereof,
wherein:
A is selected from the group consisting of:

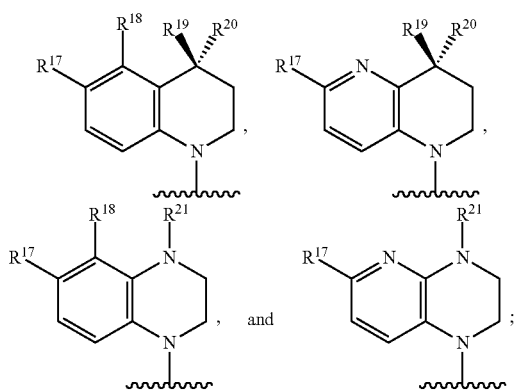

wherein:
$R^{17}$ is hydrogen, F, Cl, CN, $CHF_2$, $CF_3$, $CH_2C(O)NH_2$, $CH_2C(O)NHC_{1-4}$ alkyl, $CH_2C(O)NHC_{1-4}$ alkyl-heteroaryl, $CH_2C(O)N(C_{1-4}$ alkyl$)_2$, $CH_2C(O)OH$, $CH_2C(O)OC_{1-4}$ alkyl, $CH_2NH_2$, $CH_2NHC_{1-4}$ alkyl, $CH_2N(C_{1-4}$ alkyl$)_2$, $CH_2NHC(O)C_{1-4}$ alkyl, $CH_2S(O)_2C_{1-4}$ alkyl, $C_{1-4}$ alkyl, $C_{2-4}$ alkenyl, $C_{2-4}$ alkynyl, $C(NOH)H$, $C(NOH)C_{1-4}$ alkyl, $C(NOC_{1-4}$ alkyl)H, $C(O)NH_2$, $C(O)NHC_{1-4}$ alkyl, $C(O)NHC_{1-4}$ alkyl-heteroaryl, $C(O)N(C_{1-4}$ alkyl$)_2$, $C(O)OH$, $C(O)OC_{1-4}$ alkyl, $NH_2$, $NHC_{1-4}$ alkyl, $N(C_{1-4}$ alkyl$)_2$, $NHC(O)C_{1-4}$ alkyl, $OC_{1-4}$ alkyl, Oheteroaryl, $S(O)_2C_{1-4}$ alkyl, $C_{3-6}$ cycloalkyl, $C_{5-6}$ cycloalkenyl, heterocyclyl, phenyl, or O-heteroaryl;
  wherein the $C_{1-4}$ alkyl, $C_{2-4}$ alkenyl, $C_{2-4}$ alkynyl, $C_{3-6}$ cycloalkyl, or $C_{5-6}$ cycloalkenyl is optionally substituted with one, two, or three F substituents, one or two CN substituents, one or two $C_{1-2}$ alkyl substituents, one or two OH substituents, or one or two $OC_{1-2}$ alkyl substituents;
  wherein the heterocyclyl is optionally substituted with one or more substituents independently selected from the group consisting of $C_{1-2}$ alkyl and OH;
  wherein the O-heteroaryl or heteroaryl is optionally substituted with one or more independently selected $C_{1-2}$ alkyl substituents; and
  wherein each $C_{1-2}$ alkyl substituent of the heterocyclyl, O-heteroaryl, or heteroaryl is optionally and independently substituted with one, two, or three F substituents, one or two OH substituents, or one or two $OC_{1-2}$ alkyl substituents:
$R^{18}$ is hydrogen, F, Cl, CN, $NO_2$, $CH_2C(O)NH_2$, $CH_2C(O)NHC_{1-4}$ alkyl, $CH_2C(O)N(C_{1-4}$ alkyl$)_2$, $CH_2C(O)OH$, $CH_2C(O)OC_{1-4}$ alkyl, $CH_2SC_{1-4}$ alkyl, $CH_2S(O)C_{1-4}$ alkyl, $CH_2S(O)_2C_{1-4}$ alkyl, $C_{1-4}$ alkyl, $C_{2-4}$ alkenyl, $C_{2-4}$ alkynyl, $C(O)NH_2$, $C(O)NHC_{1-4}$ alkyl, $C(O)N(C_{1-4}$ alkyl$)_2$, $C(O)OH$, $C(O)OC_{1-4}$ alkyl, $NH_2$, $NHC(O)C_{1-4}$ alkyl, $NHS(O)_2C_{1-4}$ alkyl, $N(C_{1-4}$ alkyl$)S(O)_2C_{1-4}$ alkyl, $N=[S(O)(C_{1-4}$ alkyl$)_2]$, $N[S(O)_2C_{1-4}$ alkyl$]_2$, $OC_{1-4}$ alkyl, $SC_{1-4}$ alkyl, $S(O)C_{1-4}$ alkyl, $S(O)(NH)C_{1-4}$ alkyl, $S(O)_2C_{1-4}$ alkyl, $S(O)_2C_{3-4}$ cycloalkyl, $S(O)_2$heteroaryl, $C_{3-4}$ cycloalkyl, heterocyclyl, phenyl, or heteroaryl;
  wherein the $C_{1-4}$ alkyl, $C_{2-4}$ alkenyl, $C_{2-4}$ alkynyl, or $C_{3-4}$ cycloalkyl is optionally substituted with one, two, or three F substituents, one or two CN substituents, one or two $C_{1-2}$ alkyl substituents, one or two OH substituents, or one or two $OC_{1-2}$ alkyl substituents;
  wherein the heterocyclyl, phenyl, or heteroaryl is optionally substituted with one or more substituents independently selected from the group consisting of F, $C_{1-2}$ alkyl, $C(O)NH_2$, $C(O)NHC_{1-4}$ alkyl, $C(O)N(C_{1-4}$ alkyl$)_2$, $C(O)OH$, $C(O)OC_{1-4}$ alkyl, and cyclopropyl; and
  wherein each $C_{1-2}$ alkyl substituent of the heterocyclyl, phenyl, or heteroaryl is optionally and independently substituted with one, two, or three F substituents, one or two OH substituents, or one or two $OC_{1-2}$ alkyl substituents:
$R^{19}$ is hydrogen or $C_{1-4}$ alkyl, wherein the $C_{1-4}$ alkyl is optionally substituted with one, two, or three F substituents, one or two CN substituents, one or two $C_{1-2}$ alkyl substituents, one or two OH substituents, or one or two $OC_{1-2}$ alkyl substituents;
$R^{20}$ is hydrogen or $C_{1-4}$ alkyl, wherein the $C_{1-4}$ alkyl is optionally substituted with one, two, or three F substituents, one or two CN substituents, one or two $C_{1-2}$ alkyl substituents, one or two OH substituents, or one or two $OC_{1-2}$ alkyl substituents; or R$^{19}$ and R$^{20}$ together with the carbon atom to which they are attached, form C$_{2-4}$ alkenyl, wherein the C$_{2-4}$ alkenyl is optionally substituted with one or two F substituents;

R$^{21}$ is hydrogen, (CH$_2$)$_{1-4}$C(O)NH$_2$, (CH$_2$)$_{1-4}$C(O)NHC$_{1-4}$ alkyl, (CH$_2$)$_{1-4}$C(O)N(C$_{1-4}$ alkyl)$_2$, (CH$_2$)$_{1-4}$C(O)OC$_{1-4}$ alkyl, (CH$_2$)$_{1-4}$S(O)$_2$C$_{1-4}$ alkyl, C$_{1-4}$ alkyl, C(O)NH$_2$, C(O)NHC$_{1-4}$ alkyl, C(O)N(C$_{1-4}$ alkyl)$_2$, C(O)OC$_{1-4}$ alkyl, S(O)$_2$C$_{1-4}$ alkyl, C$_{3-4}$ cycloalkyl, or heterocyclyl;
  wherein the C$_{1-4}$ alkyl or C$_{3-4}$ cycloalkyl is optionally substituted with one, two, or three F substituents, one or two CN substituents, one or two C$_{1-2}$ alkyl substituents, one or two OH substituents, or one or two OC$_{1-2}$ alkyl substituents;

R$^4$ is hydrogen, halogen, CN, C$_{1-6}$ alkyl, C(O)N(R$^6$)$_2$, or N(R$^6$)$_2$, wherein the C$_{1-6}$ alkyl is optionally substituted with one or more substituents independently selected from the group consisting of halogen, N(R$^6$)$_2$, OH, and =O;

R$^5$ is hydrogen, halogen, CN, C$_{1-6}$ alkyl, C(O)N(R$^6$)$_2$, or N(R$^6$)$_2$, wherein the C$_{1-6}$ alkyl is optionally substituted with one or more substituents independently selected from the group consisting of halogen, N(R$^6$)$_2$, OH, and =O; or R$^4$ and R$^5$, together with the carbon atom to which they are attached, form a 4- to 6-membered carbocyclic or heterocyclic ring, wherein the 4- to 6-membered carbocyclic or heterocyclic ring is optionally substituted with one or two substituents independently selected from the group consisting of halogen, CN, C$_{1-6}$ alkyl, C(O)N(R$^6$)$_2$, N(R$^6$)$_2$, OC$_{1-6}$ alkyl, and =O;

each R$^6$ is independently hydrogen, C$_{1-6}$ alkyl, C(O)OC$_{1-4}$ alkyl, or phenyl; and q is 0 or 1.

45. The compound of claim 44, or a pharmaceutically acceptable salt or stereoisomer thereof, wherein R$^{17}$ is pyrrolidin-1-yl, tetrahydrofuran-3-yl, 2,5-dihydrofuran-3-yl, 1,2,4-oxadiazol-5-on-3-yl, piperidin-1-yl, piperidin-4-yl, 1,2,3,6-tetrahydropyridin-4-yl, tetrahydropyran-2-yl, piperazin-1-yl, piperazin-3-on-1-yl, or morpholin-4-yl;
  wherein R$^{17}$ is optionally substituted with one or more substituents independently selected from the group consisting of C$_{1-2}$ alkyl and OH; and
  wherein each C$_{1-2}$ alkyl substituent of R$^{17}$ is optionally and independently substituted with one, two, or three F substituents, one or two OH substituents, or one or two OC$_{1-2}$ alkyl substituents.

46. The compound of claim 44, or a pharmaceutically acceptable salt thereof, wherein A is a stereoisomer selected from the group consisting of:

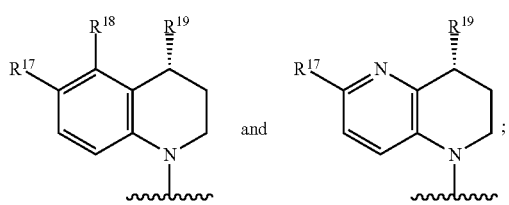

wherein:
R$^{19}$ is CH$_3$ or CHF$_2$.

47. The compound of claim 44, or a pharmaceutically acceptable salt thereof, wherein A is a stereoisomer selected from the group consisting of:

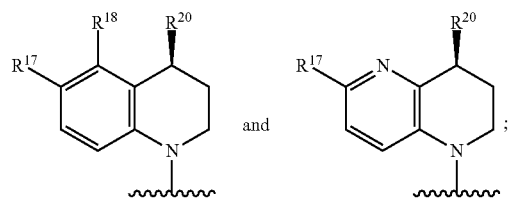

wherein:
R$^{20}$ is CH$_3$ or CHF$_2$.

48. The compound of claim 44, or a pharmaceutically acceptable salt or stereoisomer thereof, wherein R$^{17}$ is pyrazol-1-yl, pyrazol-3-yl, pyrazol-4-yl, imidazol-2-yl, isoxazol-5-yl, oxazol-2-yl, oxazol-5-yl, thiazol-2-yl, thiazol-5-yl, 1,2,4-triazol-1-yl, 1,2,4-triazol-3-yl, 1,3,4-triazol-2-yl, 1,2,4-oxadiazol-3-yl, 1,3,4-oxadiazol-2-yl, 1,3,4-thiadiazol-2-yl, pyrid-2-yl, pyrid-3-yl, or pyrid-4-yl;
  wherein R$^{17}$ is optionally substituted with one or more independently selected C$_{1-2}$ alkyl substituents; and
  wherein each C$_{1-2}$ alkyl substituent of R$^{17}$ is optionally and independently substituted with one, two, or three F substituents, one or two OH substituents, or one or two OC$_{1-2}$ alkyl substituents.

49. The compound of claim 44, or a pharmaceutically acceptable salt or stereoisomer thereof, wherein R$^{18}$ is pyrroldin-2-on-4-yl, oxiranyl, tetrahydrofuranyl, oxazolidin-2-on-3-yl, isothiazolidin-2-yl-1,1-dioxide, tetrahydropyranyl, or morpholinyl;
  wherein R$^{18}$ is optionally substituted with one or more substituents independently selected from the group consisting of F, C$_{1-2}$ alkyl, C(O)NH$_2$, C(O)NHC$_{1-4}$ alkyl, C(O)N(C$_{1-4}$ alkyl)$_2$, C(O)OH, C(O)OC$_{1-4}$ alkyl, and cyclopropyl; and
  wherein each C$_{1-2}$ alkyl substituent of R$^{18}$ is optionally and independently substituted with one, two, or three F substituents, one or two OH substituents, or one or two OC$_{1-2}$ alkyl substituents.

50. The compound of claim 44, or a pharmaceutically acceptable salt or stereoisomer thereof, wherein R$^{18}$ is phenyl, pyrazol-3-yl, pyrazol-4-yl, thiazol-2-yl, 1,2,4-oxadiazol-3-yl, 1,3,4-oxadiazol-2-yl, pyrid-2-yl, pyrid-3-yl, or pyrid-4-yl;
  wherein R$^{18}$ is optionally substituted with one or more substituents independently selected from the group consisting of F, C$_{1-2}$ alkyl, C(O)NH$_2$, C(O)NHC$_{1-4}$ alkyl, C(O)N(C$_{1-4}$ alkyl)$_2$, C(O)OH, C(O)OC$_{1-4}$ alkyl, and cyclopropyl; and
  wherein each C$_{1-2}$ alkyl substituent of R$^{18}$ is optionally and independently substituted with one, two, or three F substituents, one or two OH substituents, or one or two OC$_{1-2}$ alkyl substituents.

51. The compound of claim 44, or a pharmaceutically acceptable salt thereof, wherein:
  R$^4$ is hydrogen, halogen, C$_{1-3}$ alkyl, or N(R$^6$)$_2$, wherein the C$_{1-3}$ alkyl is optionally substituted with one or more substituents independently selected from the group consisting of halogen, N(R$^6$)$_2$, and OH; and
  R$^5$ is hydrogen, halogen, C$_{1-3}$ alkyl, or N(R$^6$)$_2$, wherein the C$_{1-3}$ alkyl is optionally substituted with one or more substituents independently selected from the group consisting of halogen, N(R$^6$)$_2$, and OH.

52. The compound of claim 44, or a pharmaceutically acceptable salt or stereoisomer thereof, wherein:

R$^4$ is F, CH$_3$, CH$_2$NH$_2$, CH$_2$NHCH$_3$, CH$_2$OH, or NH$_2$; and

R$^3$ is F, CH$_3$, CH$_2$NH$_2$, CH$_2$NHCH$_3$, CH$_2$OH, or NH$_2$.

53. The compound of claim 44, or a pharmaceutically acceptable salt or stereoisomer thereof, wherein R$^4$ and R$^5$, together with the carbon atom to which they are attached, form an optionally substituted 4- to 6-membered carbocyclic or heterocyclic ring selected from the group consisting of:

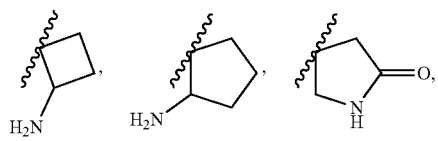

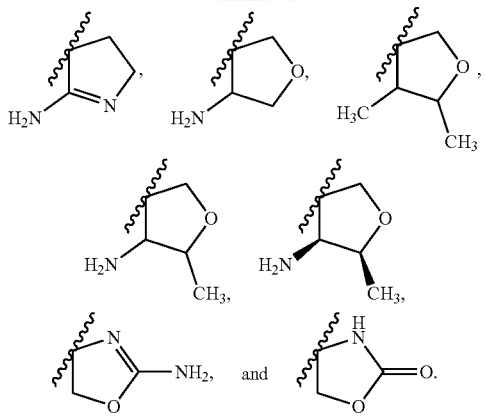

54. The compound of claim 44, or a pharmaceutically acceptable salt or stereoisomer thereof, wherein q is 1.

* * * * *

UNITED STATES PATENT AND TRADEMARK OFFICE
CERTIFICATE OF CORRECTION

Page 1 of 2

PATENT NO. : 11,591,336 B2
APPLICATION NO. : 16/616361
DATED : February 28, 2023
INVENTOR(S) : Taylor et al.

It is certified that error appears in the above-identified patent and that said Letters Patent is hereby corrected as shown below:

In the Claims

At Claim 1, Column 857, Line 63, "OS(O)"R$^{10}$" should read --OS(O)$_w$R$^{10}$--, therefor.
At Claim 1, Column 857, Line 64, "S(O)"R$^{10}$" should read --S(O)$_w$R$^{10}$--, therefor.
At Claim 1, Column 858, Line 65, "R$^{11}$ and R$^{12}$" should read --R$^8$ and R$^{11}$--, therefor.
At Claim 1, Column 859, Line 9, ":" should read --;--, therefor.
At Claim 1, Column 859, Line 12, ":" should read --;--, therefor.
At Claim 3, Column 862, Line 10, ":" should read --;--, therefor.
At Claim 6, Column 862, Line 51, ":" should read --;--, therefor.

At Claim 8, Column 864, Lines 15-20, " 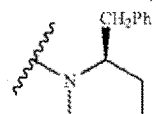 " should read -- 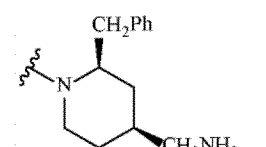 --, therefor.

At Claim 8, Column 864, Lines 15-20, " 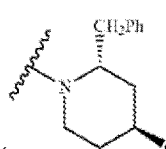 " should read -- 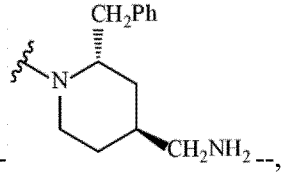 --, therefor.

At Claim 8, Column 864, Lines 21-28, " 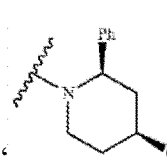 " should read -- 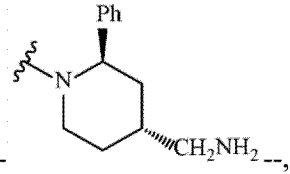 --, therefor.

Signed and Sealed this
Fourteenth Day of November, 2023

Katherine Kelly Vidal
*Director of the United States Patent and Trademark Office*

CERTIFICATE OF CORRECTION (continued)

At Claim 8, Column 864, Lines 37-43, " 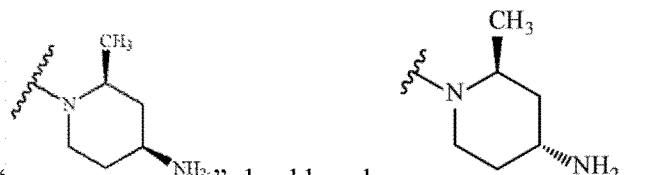 " should read -- -- , therefor.

At Claim 19, Column 869, Lines 43-44, "CH$_2$C(O)C$_{1-4}$ alkyl" should read --CH$_2$C(O)OC$_{1-4}$ alkyl--, therefor.

At Claim 21, Column 870, Line 26, ":" should read --;--, therefor.

At Claim 21, Column 870, Line 32, "OC$_{12}$" should read --OC$_{1-2}$--, therefor.

At Claim 23, Column 870, Line 50, ":" should read --;--, therefor.

At Claim 25, Column 871, Line 9, "R$^3$" should read --R$^5$--, therefor.

At Claim 28, Column 872, Lines 58-59, "C(O)OC$_{1-6}$ alkyl" should read --C(O)OC$_{1-4}$ alkyl--, therefor.

At Claim 39, Column 874, Line 46, "R$^{21}$" should read --R$^{22}$--, therefor.

At Claim 44, Column 876, Line 6, "Oheteroaryl" should read --O-heteroaryl--, therefor.

At Claim 44, Column 876, Lines 7-8, "O-heteroaryl" should read --heteroaryl--, therefor.

At Claim 44, Column 876, Line 26, ":" should read --;--, therefor.

At Claim 44, Column 876, Line 57, ":" should read --;--, therefor.

At Claim 44, Column 877, Line 1, "R$^{20}$ together" should read --R$^{20}$, together--, therefor.

At Claim 52, Column 879, Line 6, "R$^3$" should read --R$^5$--, therefor.